(12) United States Patent
Allen et al.

(10) Patent No.: US 9,718,803 B2
(45) Date of Patent: *Aug. 1, 2017

(54) UNSATURATED NITROGEN HETEROCYCLIC COMPOUNDS USEFUL AS PDE10 INHIBITORS

(71) Applicant: AMGEN INC., Thousand Oaks, CA (US)

(72) Inventors: Jennifer R. Allen, Newbury Park, CA (US); Jian J. Chen, Camarillo, CA (US); Michael J. Frohn, Thousand Oaks, CA (US); Essa Hu Harrington, Camarillo, CA (US); Qingyian Liu, Camarillo, CA (US); Alexander J. Pickrell, Westlake Village, CA (US); Shannon Rumfelt, Camarillo, CA (US); Robert M. Rzasa, Ventura, CA (US); Wenge Zhong, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/973,491

(22) Filed: Dec. 17, 2015

(65) Prior Publication Data

US 2016/0102075 A1    Apr. 14, 2016

Related U.S. Application Data

(63) Continuation of application No. 14/242,432, filed on Apr. 1, 2014, now abandoned, which is a continuation of application No. 13/105,860, filed on May 11, 2011, now Pat. No. 8,957,073.

(60) Provisional application No. 61/334,525, filed on May 13, 2010.

(51) Int. Cl.

| | | |
|---|---|---|
| C07D 401/14 | (2006.01) |
| A61K 31/497 | (2006.01) |
| C07D 403/14 | (2006.01) |
| C07D 405/14 | (2006.01) |
| C07D 409/14 | (2006.01) |
| C07D 413/14 | (2006.01) |
| C07D 417/14 | (2006.01) |
| C07D 471/04 | (2006.01) |
| C07D 471/08 | (2006.01) |
| C07D 487/04 | (2006.01) |
| C07D 491/08 | (2006.01) |
| C07D 487/08 | (2006.01) |
| C07D 487/10 | (2006.01) |
| C07D 491/107 | (2006.01) |
| C07C 53/18 | (2006.01) |
| C07D 491/056 | (2006.01) |
| C07D 513/04 | (2006.01) |

(52) U.S. Cl.
CPC ........... *C07D 401/14* (2013.01); *C07C 53/18* (2013.01); *C07D 403/14* (2013.01); *C07D 405/14* (2013.01); *C07D 409/14* (2013.01); *C07D 413/14* (2013.01); *C07D 417/14* (2013.01); *C07D 471/04* (2013.01); *C07D 471/08* (2013.01); *C07D 487/04* (2013.01); *C07D 487/08* (2013.01); *C07D 487/10* (2013.01); *C07D 491/056* (2013.01); *C07D 491/08* (2013.01); *C07D 491/107* (2013.01); *C07D 513/04* (2013.01)

(58) Field of Classification Search
CPC   C07D 401/14; C07D 403/14; A61K 31/4709; A61K 31/497
USPC ................ 544/284, 405; 514/255.05, 266.22
See application file for complete search history.

(56) References Cited

U.S. PATENT DOCUMENTS

| | | | |
|---|---|---|---|
| 4,107,288 A | 8/1978 | Oppenheim et al. | |
| 5,145,684 A | 9/1992 | Liversidge et al. | |
| 8,691,986 B2 | 4/2014 | Allen et al. | |
| 9,303,028 B2 * | 4/2016 | Allen .................... | C07D 401/14 |
| 2006/0019975 A1 | 1/2006 | Humphrey et al. | |
| 2007/0072908 A1 | 3/2007 | Yamamoto et al. | |
| 2007/0149513 A1* | 6/2007 | Chen .................... | C07D 207/38 |
| | | | 514/227.5 |

(Continued)

FOREIGN PATENT DOCUMENTS

| | | |
|---|---|---|
| EP | 0 039 051 A2 | 4/1981 |
| WO | WO 03/040107 A1 | 5/2003 |

(Continued)

OTHER PUBLICATIONS

Berge, et al "Pharmaceutical Salts", *JPharmaSci*, 66:1 (1977).

(Continued)

*Primary Examiner* — Deepak Rao
(74) *Attorney, Agent, or Firm* — Elsa D. Lemoine

(57) ABSTRACT

Unsaturated nitrogen heterocyclic compounds of formula (I):

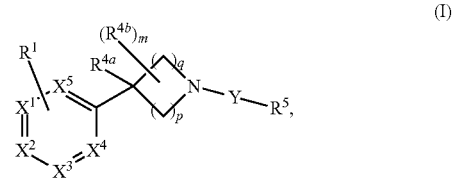

as defined in the specification, compositions containing them, and processes for preparing such compounds. Provided herein also are methods of treating disorders or diseases treatable by inhibition of PDE10, such as obesity, Huntington's Disease, non-insulin dependent diabetes, schizophrenia, bipolar disorder, obsessive-compulsive disorder, and the like.

19 Claims, No Drawings

(56) References Cited

U.S. PATENT DOCUMENTS

| | | |
|---|---|---|
| 2011/0306588 A1 | 12/2011 | Allen et al. |
| 2011/0306590 A1 | 12/2011 | Allen et al. |
| 2011/0306591 A1 | 12/2011 | Allen et al. |

FOREIGN PATENT DOCUMENTS

| | | |
|---|---|---|
| WO | WO 2004/035549 A1 | 4/2004 |
| WO | WO 2005/051390 A1 | 6/2005 |
| WO | WO 2005/012485 A2 | 10/2005 |
| WO | WO 2005/116009 A1 | 12/2005 |
| WO | WO 2007/085954 A2 | 8/2007 |
| WO | WO 2009/081197 A1 | 7/2009 |
| WO | WO 2010/007120 A1 | 1/2010 |
| WO | WO 2010/008739 A2 | 1/2010 |
| WO | WO 2010/091409 A1 | 8/2010 |
| WO | WO 2010/130424 A1 | 11/2010 |
| WO | WO 2011/028947 A2 | 3/2011 |
| WO | WO 2011/034078 A1 | 3/2011 |

OTHER PUBLICATIONS

Bundgaard, et al., "A Novel Solution-Stable, Water-Soluble Prodrug Type for Drugs Containing a Hydroxyl or an NH-Acidic Group", *JMedChem*, 32:12, 2503-2507, (1989).

Celen, et al., "Preclinical Evaluation of $^{18}$F-JNJ41510417 as a Radioligand for PET Imaging of Phosphodiesterase-10A in the Brain," J Nuclear Med., 51(10):1584-1591, (2010).

Fujishige, et al., "Cloning and Characterization of a Novel Human Phosphodiesterase That Hydrolyzes Both cAMP and cGMP (PDE10A)", *Jour Biol Chem*, 274:26, 18438-18445, (1999).

Giedd, et al., "MRI Assessment of Children With Obsessive-Compulsive Disorder or Tics Associated with Streptococcal Infection", *AmJPsych*, 157:281-283, (2000).

Loughney, et al., "Isolation and characterization of PDE10A, a novel human 3', 5'—cyclic nucleotide phosphodiesterase", *Gene*, 234: 109-117, (1999).

Obeso, et al, "The origin of motor fluctuations in Parkinson's disease", Neurology, 62(Suppl 1): S17-S30 (2004).

Saxena, et al., "Neuroimaging and frontal-subcortical circuitry in obsessive-compulsive disorder", BrJPsychSuppl, 173(Suppl. 35):26-37, (1998).

Solderling, et al., "Isolation and characterization of a dual-substrate phosphodiesterase gene family: PDE10A", *Proc. Natl. Acad. Sci*, 96: 7071-7076, (1999).

Svensson, et al., "The Design and Bioactivation of Presystemically Stable Prodrugs", *Drug Metabolism Rev.*, 19(2), 165-194 (1988).

\* cited by examiner

UNSATURATED NITROGEN HETEROCYCLIC COMPOUNDS USEFUL AS PDE10 INHIBITORS

CROSS-REFERENCE TO RELATED APPLICATIONS

This application is a continuation application of U.S. Non Provisional application Ser. No. 14/242,432, filed Apr. 1, 2014, which claims the priority benefit of U.S. Non Provisional application Ser. No. 13/105,860, filed May 11, 2011, now U.S. Pat. No. 8,957,073, which claims the priority benefit of U.S. Provisional Application No. 61/334,525, filed May 13, 2010, all of which are hereby incorporated by reference in their entirety.

FIELD OF THE INVENTION

Provided herein are certain unsaturated nitrogen heterocyclic compounds that are PDE10 inhibitors, pharmaceutical compositions containing such compounds, and processes for preparing such compounds. Provided herein also are methods of treating disorders or diseases treatable by inhibition of PDE10, such as obesity, Huntington's disease, non-insulin dependent diabetes, schizophrenia, bipolar disorder, obsessive-compulsive disorder, and the like.

BACKGROUND

Neurotransmitters and hormones, as well as other types of extracellular signals such as light and odors, create intracellular signals by altering the amounts of cyclic nucleotide monophosphates (cAMP and cGMP) within cells. These intracellular messengers alter the functions of many intracellular proteins. Cyclic AMP regulates the activity of cAMP-dependent protein kinase (PKA). PKA phosphorylates and regulates the function of many types of proteins, including ion channels, enzymes, and transcription factors. Downstream mediators of cGMP signaling also include kinases and ion channels. In addition to actions mediated by kinases, cAMP and cGMP bind directly to some cell proteins and directly regulate their activities.

Cyclic nucleotides are produced from the actions of adenylyl cyclase and guanylyl cyclase, which convert ATP to cAMP and GTP to cGMP. Extracellular signals, often through the actions of G protein-coupled receptors, regulate the activities of the cyclases. Alternatively, the amount of cAMP and cGMP may be altered by regulating the activities of the enzymes that degrade cyclic nucleotides. Cell homeostasis is maintained by the rapid degradation of cyclic nucleotides after stimulus-induced increases. The enzymes that degrade cyclic nucleotides are called 3',5'-cyclic nucleotide-specific phosphodiesterases (PDEs).

Eleven PDE gene families (PDE1-PDE11) have been identified based on their distinct amino acid sequences, catalytic and regulatory characteristics, and sensitivity to small molecule inhibitors. These families are coded for by 21 genes; and further multiple splice variants are transcribed from many of these genes. Expression patterns of each of the gene families are distinct. PDEs differ with respect to their affinity for cAMP and cGMP. Activities of different PDEs are regulated by different signals. For example, PDE1 is stimulated by $Ca^{2+}$/calmodulin. PDE2 activity is stimulated by cGMP. PDE3 is inhibited by cGMP. PDE4 is cAMP specific and is specifically inhibited by rolipram. PDE5 is cGMP-specific. PDE6 is expressed in retina.

PDE10 sequences were identified by using bioinformatics and sequence information from other PDE gene families (Fujishige et al., *J. Biol. Chem.* 274:18438-18445, 1999; Loughney et al., *Gene* 234:109-117, 1999; Soderling et al., *Proc. Natl. Acad. Sci. USA* 96:7071-7076, 1999). The PDE10 gene family is distinguished based on its amino acid sequence, functional properties and tissue distribution. The human PDE10 gene is large, over 200 kilobases, with up to 24 exons coding for each of the splice variants. The amino acid sequence is characterized by two GAF domains (which bind cGMP), a catalytic region, and alternatively spliced N and C termini. Numerous splice variants are possible because at least three alternative exons encode N termini and two exons encode C-termini. PDE10A1 is a 779 amino acid protein that hydrolyzes both cAMP and cGMP. The $K_m$ values for cAMP and cGMP are 0.05 and 3.0 micromolar, respectively. In addition to human variants, several variants with high homology have been isolated from both rat and mouse tissues and sequence banks.

PDE10 RNA transcripts were initially detected in human testis and brain. Subsequent immunohistochemical analysis revealed that the highest levels of PDE10 are expressed in the basal ganglia. Specifically, striatal neurons in the olfactory tubercle, caudate nucleus and nucleus accumbens are enriched in PDE10. Western blots did not reveal the expression of PDE10 in other brain tissues, although immunoprecipitation of the PDE10 complex was possible in hippocampal and cortical tissues. This suggests that the expression level of PDE10 in these other tissues is 100-fold less than in striatal neurons. Expression in hippocampus is limited to the cell bodies, whereas PDE10 is expressed in terminals, dendrites and axons of striatal neurons.

The tissue distribution of PDE10 indicates that PDE10 inhibitors can be used to raise levels of cAMP and/or cGMP within cells that express the PDE10 enzyme, for example, in neurons that comprise the basal ganglia and therefore would be useful in treating a variety of neuropsychiatric conditions involving the basal ganglia such as obesity, non-insulin dependent diabetes, schizophrenia, bipolar disorder, obsessive compulsive disorder, and the like.

Noninvasive, nuclear imaging techniques can be used to obtain basic and diagnostic information about the physiology and biochemistry of a variety of living subjects including experimental animals, normal humans and patients. These techniques rely on the use of sophisticated imaging instrumentation that is capable of detecting radiation emitted from radiotracers administered to such living subjects. The information obtained can be reconstructed to provide planar and tomographic images that reveal distribution of the radiotracer as a function of time. Use of appropriately designed radiotracers can result in images which contain information on the structure, function and most importantly, the physiology and biochemistry of the subject. Much of this information cannot be obtained by other means. The radiotracers used in these studies are designed to have defined behaviors in vivo which permit the determination of specific information concerning the physiology or biochemistry of the subject or the effects that various diseases or drugs have on the physiology or biochemistry of the subject. Currently, radiotracers are available for obtaining useful information concerning such things as cardiac function, myocardial blood flow, lung perfusion, liver function, brain blood flow, regional brain glucose and oxygen metabolism.

Compounds of the invention can be labeled with either positron or gamma emitting radionuclides. For imaging, the most commonly used positron emitting (PET) radionuclides are $^{11}$C, $^{18}$F, $^{15}$O, $^{13}$N, $^{76}$Br, $^{77}$Br, $^{123}$I, or $^{125}$I, wherein $^{11}$C, $^{18}$F, $^{123}$I, or $^{125}$I are preferred, all of which are accelerator produced. In the two decades, one of the most active areas of nuclear medicine research has been the development of receptor imaging radiotracers. These tracers bind with high affinity and specificity to selective receptors and neuroreceptors. For example, Johnson and Johnson has synthesized and evaluated $^{18}$F-JNJ41510417 as a selective and high-affinity radioligand for in vivo brain imaging of PDE10A using PET (The Journal Of Nuclear Medicine; Vol. 51; No. 10; October 2010).

SUMMARY OF THE INVENTION

The present invention comprises a new class of unsaturated nitrogen heterocyclic compounds useful in the treatment of diseases, such as PDE10-mediated diseases and other maladies, such as schizophrenia, Huntington's disease, bipolar disorder, or obsessive-compulsive disorder. Accordingly, the invention also comprises pharmaceutical compositions comprising the compounds, methods for the treatment of PDE10-mediated diseases and other maladies, such as schizophrenia, Huntington's disease, bipolar disorder, or obsessive-compulsive disorder, using the compounds and compositions of the invention, and intermediates and processes useful for the preparation of the compounds of the invention.

Another aspect of the invention comprises a new class of unsaturated nitrogen heterocyclic compounds radiolabeled with a positron emitting radionuclide selected from $^{11}$C, $^{18}$F, $^{15}$O, $^{13}$N, $^{76}$Br, $^{77}$Br, $^{123}$I, or $^{125}$I, a radiopharmaceutical composition comprising the radiolabelled compound, a method for the diagnostic imaging of PDE10 receptors in a mammal, including human, or tissues bearing PDE10 receptors in a mammal, including human brain, which comprises administering to a mammal in need of such diagnostic imaging an effective amount of the radiolabeled compound, and a method for the detection or quantification of PDE10 receptors in mammalian tissue, including human tissue, which comprises contacting such mammalian tissue in which such detection or quantification is desired with an effective amount of the radiolabeled compound.

The compounds of the invention are represented by the following general structure:

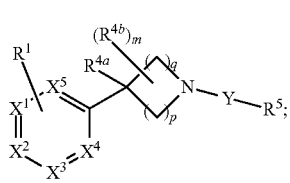

(I)

or a pharmaceutically acceptable salt thereof, wherein m, p, q, R$^1$, R$^{4a}$, R$^{4b}$, R$^5$, Y, X$^1$, X$^2$, X$^3$, X$^4$, and X$^5$ are defined below.

The compounds of the invention are represented by the following general structure:

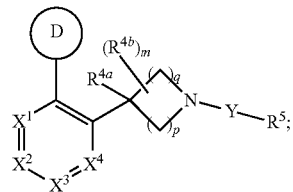

(II)

or a pharmaceutically acceptable salt thereof, wherein m, p, q, R$^{4a}$, R$^{4b}$, R$^5$, Y, X$^1$, X$^2$, X$^3$, and X$^4$ are defined below.

The compounds of the invention are represented by the following general structure:

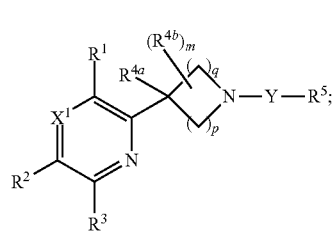

(III)

or a pharmaceutically acceptable salt thereof, wherein m, p, q, R$^1$, R$^2$, R$^3$, R$^{4a}$, R$^{4b}$, R$^5$, Y, and X$^1$ are defined below.

Other compounds of the invention are represented by the following general structure:

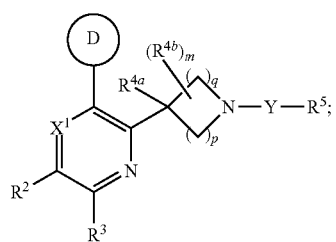

(IV)

or a pharmaceutically acceptable salt thereof, wherein m, p, q, Ring D, R$^2$, R$^3$, R$^{4a}$, R$^{4b}$, R$^5$, Y, and X$^1$ are defined below.

DETAILED DESCRIPTION OF THE INVENTION

One aspect of the current invention relates to compounds having the general structure of formula (I):

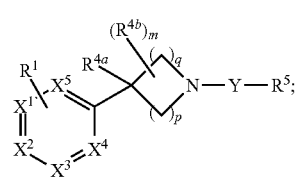

(I)

or a pharmaceutically acceptable salt thereof, wherein:
X$^1$ is N or CR$^6$;
X$^2$ is N or CR$^2$;
X$^3$ is N or CR$^3$;

$X^4$ is N or $CR^6$;
$X^5$ is N or $CR^6$;
wherein 1 to 2 of $X^1$, $X^2$, $X^3$, $X^4$ and $X^5$ are N;
$R^1$ is halo, $C_{1-8}$alk, $C_{1-4}$haloalk, —$OR^c$, —$N(R^a)C(\!=\!O)R^b$, —$C(\!=\!O)R^a$, —$C(\!=\!O)R^c$, —$C(\!=\!O)$—O—$R^a$, —$NR^aR^c$, —$N(R^c)C(\!=\!O)R^b$, —$N(R^a)C(\!=\!O)R^c$, —$C(\!=\!O)NR^aR^b$, —$C(\!=\!O)NR^aR^c$, or $C_{0-4}$alk-$L^1$; wherein said $C_{1-8}$alk group is substituted by 0, 1, 2 or 3 groups which are halo, $C_{1-3}$haloalk, —OH, —$OC_{1-4}$alk, —$NH_2$, —$NHC_{1-4}$alk, —$OC(\!=\!O)C_{1-4}$alk, or —$N(C_{1-4}$alk$)C_{1-4}$alk;

Y is a $C_{0-4}$alk, —$C(\!=\!O)$, SO, or $SO_2$;

each $R^2$ and $R^3$ is independently $R^1$, H, halo, CN, OH, —$OC_{1-4}$alk, $C_{1-4}$alk, $C_{1-4}$haloalk, —$C_{1-6}$alkOR$^a$, —$C(\!=\!O)C_{1-4}$alk, —$C(\!=\!O)NR^aR^a$, —$C_{0-4}$alkNH—$C(\!=\!O)R^a$, or $R^c$;

or alternatively the ring containing $X^1$, $X^2$, $X^3$, $X^4$ and $X^5$ can be fused to ring A, ring B, or ring C; having the formula:

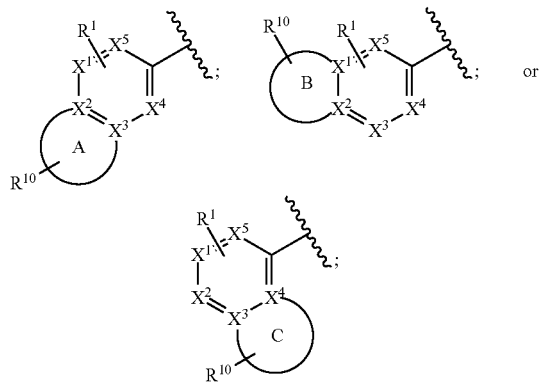

wherein said ring A, ring B, or ring C is a fused 4- to 6-membered-saturated, -partially saturated, or -unsaturated- carbocyclic or -heterocyclic ring containing 0, 1, 2, or 3 heteroatoms; and is substituted by 0, 1, or 2 $R^{10}$ groups;

$R^{4a}$ is H, OH, halo, $C_{1-4}$alk, or $C_{1-4}$haloalk;

$R^{4b}$ is halo, CN, OH, $OC_{1-4}$alk, $C_{1-4}$alk, $C_{1-4}$haloalk, or oxo;

$R^5$ is —$C_{1-6}$alkOR$^a$, 5- to 6-membered heteroaryl, unsaturated 9- to 10-membered bicyclo-heterocyclic ring, or 11- to 15-membered tricyclo-heterocyclic ring; $R^5$ ring is substituted by 0, 1, 2, 3, or 4 $R^8$ groups;

$R^6$ is independently $R^1$, H, halo, CN, OH, $OC_{1-4}$alk, $C_{1-4}$alk or $C_{1-4}$haloalk;

m is 0, 1, 2, 3, or 4;

each of p and q is independently 0, 1, 2, 3, 4, 5, or 6; wherein the sum of p and q is 2 to 6;

the ring containing p and q contains 0, 1, or 2 double bonds;

$R^a$ is independently H or $R^b$;

$R^b$ is independently phenyl, benzyl, or $C_{1-6}$alk, wherein said phenyl, benzyl, and $C_{1-6}$alk are substituted by 0, 1, 2 or 3 substituents which are, independently, halo, $C_{1-4}$alk, $C_{1-3}$haloalk, —OH, —$OC_{1-4}$alk, —$NH_2$, —$NHC_{1-4}$alk, —$OC(\!=\!O)C_{1-4}$alk, or —$N(C_{1-4}$alk$)C_{1-4}$alk;

$R^c$ is $C_{0-4}$alk-$L^2$;

each $L^1$ is independently a carbon-linked or nitrogen-linked saturated, partially-saturated or unsaturated 3-, 4-, 5-, 6-, or 7-membered monocyclic ring or a saturated, partially-saturated or unsaturated 6-, 7-, 8-, 9-, 10-, 11-, or 12-membered bicyclic ring, said ring contains 0, 1, 2, 3, or 4 N atoms and 0, 1, or 2 atoms which are O or S; $L^1$ is independently substituted by 0, 1, 2 or 3 $R^9$ groups;

each $L^2$ is independently a carbon-linked or nitrogen-linked saturated, partially-saturated or unsaturated 3-, 4-, 5-, 6-, or 7-membered monocyclic ring or a saturated, partially-saturated or unsaturated 6-, 7-, 8-, 9-, 10-, 11-, or 12-membered bicyclic ring, said ring contains 0, 1, 2, 3, or 4 N atoms and 0, 1, or 2 atoms which are O or S; $L^2$ is independently substituted by 0, 1, 2 or 3 $R^{11}$ groups;

$R^8$ is halo, CN, OH, $OC_{1-4}$alk, $C_{1-4}$alk, $C_{1-4}$haloalk, $OC_{1-4}$haloalk, —$C(\!=\!O)R^b$, —$C(\!=\!O)R^c$, —$C(\!=\!O)NHR^b$, —$C(\!=\!O)NHR^c$, —$S(\!=\!O)_2R^b$, —$S(\!=\!O)_2R^c$, —$S(\!=\!O)_2NR^aR^a$, $R^b$, $R^c$, $NO_2$, $OR^b$, or $OR^c$;

$R^9$ is halo, $C_{1-6}$alk, $C_{1-4}$haloalk, —$OR^a$, —$OC_{1-4}$haloalk, CN, —$C(\!=\!O)R^b$, —$C(\!=\!O)OR^a$, —$C(\!=\!O)NR^aR^a$, —$C(\!=\!NR^a)NR^aR^a$, —$OC(\!=\!O)R^b$, —$OC(\!=\!O)NR^aR^a$, —$OC_{1-6}$alkNR$^aR^a$, —$OC_{1-6}$alkOR$^a$, —$SR^a$, —$S(\!=\!O)R^b$, —$S(\!=\!O)_2R^b$, —$S(\!=\!O)_2NR^aR^a$, —$NR^aR^a$, —$N(R^a)C(\!=\!O)R^b$, —$N(R^a)C(\!=\!O)OR^b$, —$N(R^a)C(\!=\!O)NR^aR^a$, —$N(R^a)C(\!=\!NR^a)NR^aR^a$, —$N(R^a)S(\!=\!O)_2R^b$, —$N(R^a)S(\!=\!O)_2NR^aR^a$, —$NR^aC_{1-6}$alkNR$^aR^a$, —$NR^aC_{1-6}$alkOR$^a$, —$C_{1-6}$alkNR$^aR^a$, —$C_{1-6}$alkOR$^a$, —$C_{1-6}$alkN(R$^a$)C($=$O)R$^b$, —$C_{1-6}$alkOC($=$O)R$^b$, —$C_{1-6}$alkC($=$O)NR$^aR^a$, —$C_{1-6}$alkC($=$O)OR$^a$, oxo, or $R^c$;

$R^{10}$ is oxo, $C_{1-6}$alk, $C_{1-3}$haloalk, —OH, —$OC_{1-4}$alk, —$NH_2$, —$NHC_{1-4}$alk, —$OC(\!=\!O)C_{1-4}$alk, or —$N(C_{1-4}$alk$)C_{1-4}$alk; and $R^{11}$ is halo, $C_{1-6}$alk, $C_{1-4}$haloalk, —$OR^a$, —$OC_{1-4}$haloalk, CN, —$C(\!=\!O)R^b$, —$C(\!=\!O)OR^a$, —$C(\!=\!O)NR^aR^a$, —$C(\!=\!NR^a)NR^aR^a$, —$OC(\!=\!O)R^b$, —$OC(\!=\!O)NR^aR^a$, —$OC_{1-6}$alkNR$^aR^a$, —$OC_{1-6}$alkOR$^a$, —$SR^a$, —$S(\!=\!O)R^b$, —$S(\!=\!O)_2R^b$, —$S(\!=\!O)_2NR^aR^a$, —$NR^aR^a$, —$N(R^a)C(\!=\!O)R^b$, —$N(R^a)C(\!=\!O)OR^b$, —$N(R^a)C(\!=\!O)NR^aR^a$, —$N(R^a)C(\!=\!NR^a)NR^aR^a$, —$N(R^a)S(\!=\!O)_2R^b$, —$N(R^a)S(\!=\!O)_2NR^aR^a$, —$NR^aC_{1-6}$alkNR$^aR^a$, —$NR^aC_{1-6}$alkOR$^a$, —$C_{1-6}$alkNR$^aR^a$, —$C_{1-6}$alkOR$^a$, —$C_{1-6}$alkN(R$^a$)C($=$O)R$^b$, —$C_{1-6}$alkOC($=$O)R$^b$, —$C_{1-6}$alkC($=$O)NR$^aR^a$, —$C_{1-6}$alkC($=$O)OR$^a$, or oxo.

In one embodiment of the compound of formula (I), (II), (III), or (IV), or a pharmaceutically acceptable salt thereof, the group

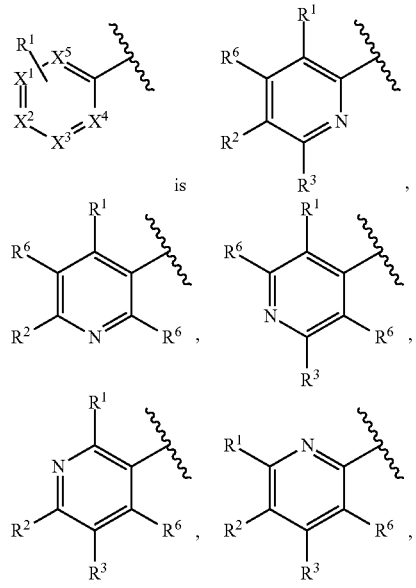

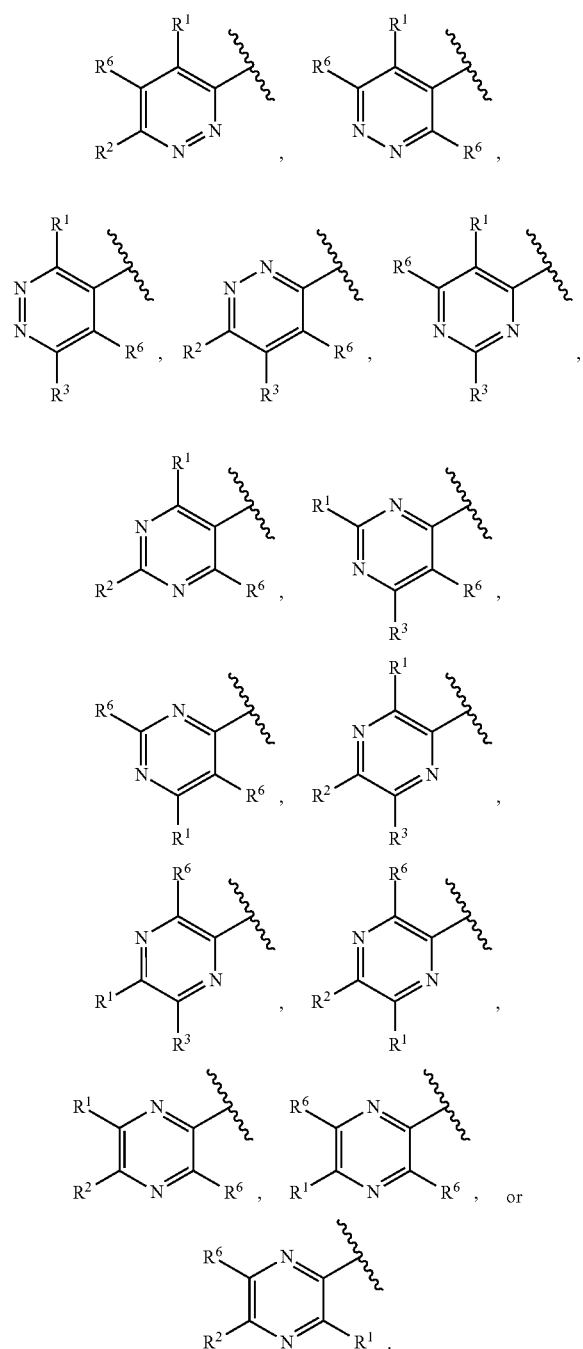
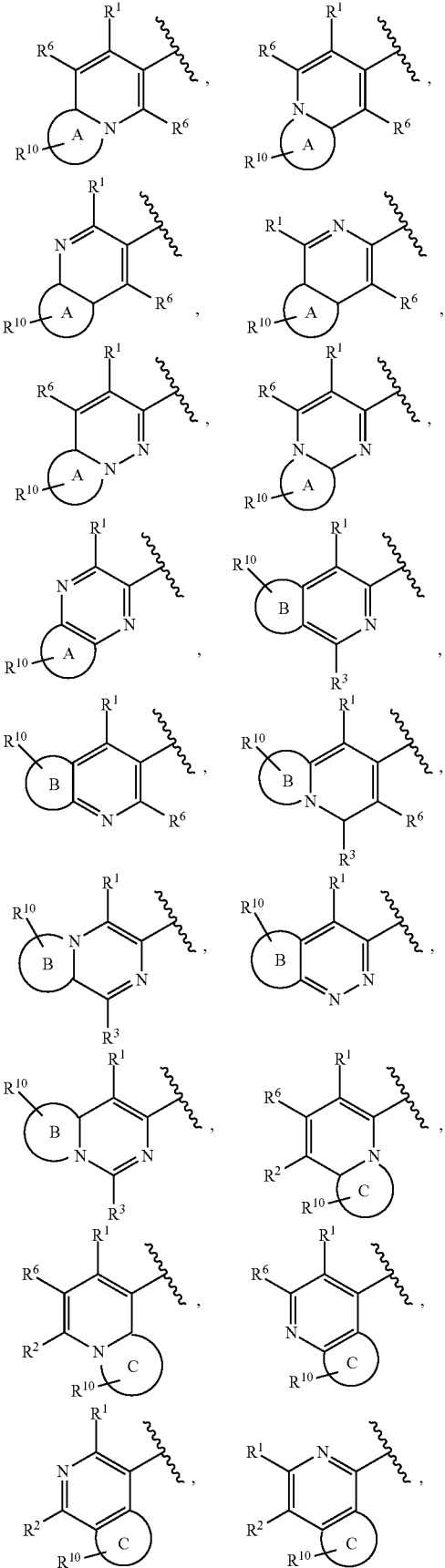
In another embodiment of the compound of formula (I), (II), (III), or (IV), or a pharmaceutically acceptable salt thereof, the group
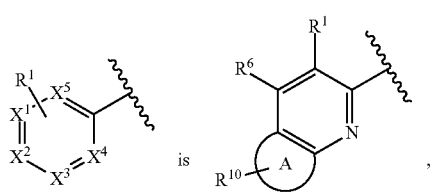

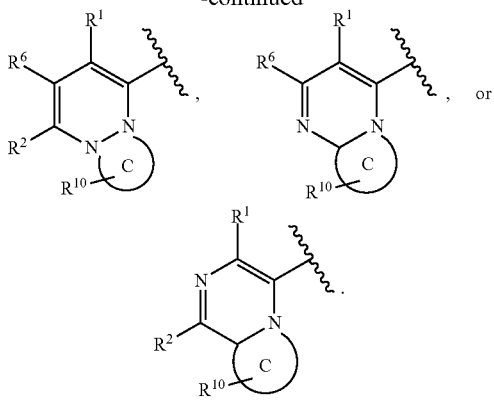

In another embodiment of the compound of formula (I), (II), (III), or (IV), or a pharmaceutically acceptable salt thereof, each of said Ring A, Ring B, and Ring C is a fused 4- to 6-membered-saturated, -partially saturated, or -unsaturated-carbocyclic which are fused phenyl, cyclobutyl, cyclopentyl, or cyclohexyl; said Ring A, Ring B, and Ring C is substituted by 0, 1, or 2 $R^{10}$ groups which are oxo, $C_{1-6}$alk, $C_{1-3}$haloalk, —OH, —O$C_{1-4}$alk, —NH$_2$, —N$_{1-4}$alk, —OC(=O)$C_{1-4}$alk, or —N($C_{1-4}$alk)$C_4$alk.

In another embodiment of the compound of formula (I), (II), (III), or (IV), or a pharmaceutically acceptable salt thereof, each of said Ring A, Ring B, and Ring C is a fused 5-membered-saturated, -partially saturated, or -unsaturated-heterocyclic ring which are fused furanyl, thiophenyl, pyrrolyl, pyrrolinyl, pyrrolidinyl, dioxolanyl, oxazolyl, thiazolyl, isothiazolyl, imidazolyl, imidazolinyl, imidazolidinyl, pyrazolyl, pyrazolinyl, pyrazolidinyl, isoxazolyl, or isothiazolyl; said Ring A, Ring B, and Ring C is substituted by 0, 1, or 2 $R^{10}$ groups which are oxo, $C_{1-6}$alk, $C_{1-3}$haloalk, —OH, —O$C_{1-4}$alk, —NH$_2$, —NH$C_{1-4}$alk, —OC(=O)$C_{1-4}$alk, or —N($C_{1-4}$alk)$C_{1-4}$alk.

In another embodiment of the compound of formula (I), (II), (III), or (IV), or a pharmaceutically acceptable salt thereof, each of said Ring A, Ring B, and Ring C is a fused 6-membered-saturated, -partially saturated, or -unsaturated-heterocyclic ring which are fused pyranyl, pyridinyl, piperidinyl, dioxanyl, morpholinyl, dithianyl, thiomorpholinyl, pyridazinyl, pyrazinyl, or piperazinyl; said Ring A, Ring B, and Ring C is substituted by 0, 1, or 2 $R^{10}$ groups which are oxo, $C_{1-6}$alk, $C_{1-3}$haloalk, —OH, —O$C_{1-4}$alk, —NH$_2$, —NH$C_{1-4}$alk, —OC(=O)$C_{1-4}$alk, or —N($C_{1-4}$alk)$C_{1-4}$alk.

In another embodiment of the compound of formula (I), (II), (III), or (IV), or a pharmaceutically acceptable salt thereof, each of p and q is independently 1.

In another embodiment of the compound of formula (I), (II), (III), or (IV), or a pharmaceutically acceptable salt thereof, each of p and q is independently 2.

In another embodiment of the compound of formula (I), (II), (III), or (IV), or a pharmaceutically acceptable salt thereof, the ring containing p and q contains 0 or 1 double bond.

In another embodiment of the compound of formula (I), (II), (III), or (IV), or a pharmaceutically acceptable salt thereof, wherein the sum of p and q is 3; and the ring containing p and q contains 0 or 1 double bond.

In another embodiment of the compound of formula (I), (II), (III), or (IV), or a pharmaceutically acceptable salt thereof, $R^{4b}$ is oxo and m is 1.

In another embodiment of the compound of formula (I), (II), (III), or (IV), or a pharmaceutically acceptable salt thereof, $R^5$ is unsaturated 10-membered bicyclo-heterocyclic ring; wherein each $R^5$ ring is substituted by 0, 1, or 2 $R^8$ groups.

In another embodiment of the compound of formula (I), (II), (III), or (IV), or a pharmaceutically acceptable salt thereof, the group

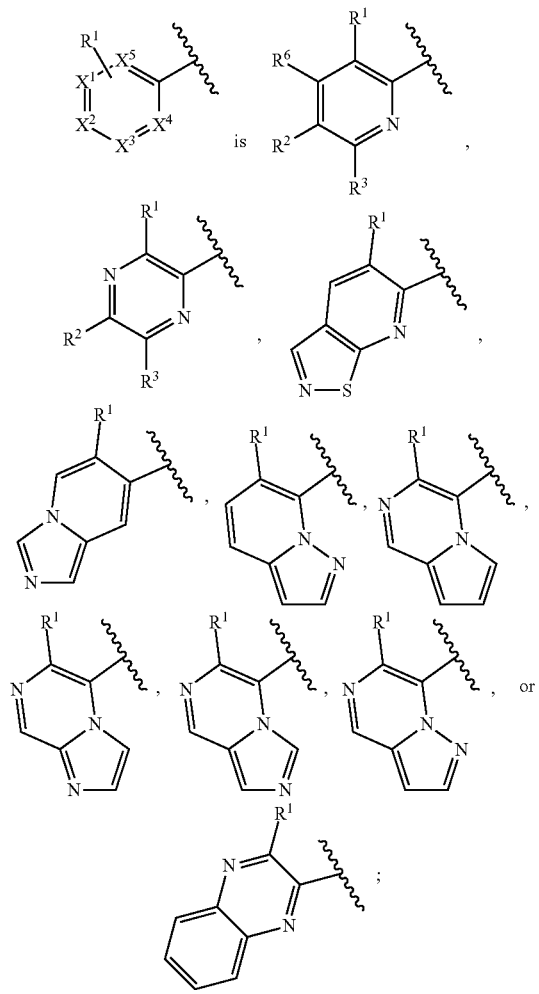

wherein each

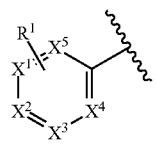

is substituted by 0, 1, or 2 $R^{10}$ groups.

In another embodiment of the compound of formula (I), (II), (III), or (IV), or a pharmaceutically acceptable salt thereof, m is 1 or 2.

In another embodiment of the compound of formula (I), (II), (III), or (IV), or a pharmaceutically acceptable salt thereof, m is 0.

In another embodiment of the compound of formula (I), (II), (III), or (IV), or a pharmaceutically acceptable salt thereof, $R^1$ is —$NR^aR^c$, —$OR^c$ or —$C_{0-4}$alk-$L^1$.

In another embodiment of the compound of formula (I), (II), (III), or (IV), or a pharmaceutically acceptable salt thereof, $L^1$ is a carbon-linked-saturated or partially-saturated 3-, 4-, 5-, 6-, or 7-membered monocyclic ring, wherein each said ring contains 0, 1, or 2 N atoms and 0 or 1 O atoms, and wherein each said $L^1$ is substituted by 0, 1 or 2 $R^9$ groups which are F, Cl, Br, $C_{1-6}$alk, —$OR^a$, CN, —$C(=O)R^b$, $C(=O)OR^a$, —$C(=O)NR^aR^a$, —$SR^a$, —$S(=O)R^b$, —$S(=O)_2R^b$, —$NR^aR^a$, —$N(R^a)C(=O)R^b$, —$N(R^a)C(=O)OR^b$, —$C_{1-6}$alkOR$^a$, —$C_{1-6}$alkN(R$^a$)C(=O)R$^b$, —$C_{1-6}$alkOC(=O) R$^b$, —$C_{1-6}$alkC(=O)NR$^a$R$^a$, —$C_{1-6}$alkC(=O)OR$^a$, oxo, or $R^c$.

In another embodiment of the compound of formula (I), (II), (III), or (IV), or a pharmaceutically acceptable salt thereof, $L^1$ is a carbon-linked-saturated or partially-saturated 5- to 6-membered monocyclic ring, wherein each said ring contains 0, 1, or 2 N atoms and 0 or 1 O atoms, and wherein each said $L^1$ is substituted by 0, 1 or 2 $R^9$ groups which are F, Cl, Br, $C_{1-6}$alk, —$OR^a$, CN, —$C(=O)R^b$, $C(=O)OR^a$, —$C(=O)NR^aR^a$, —$SR^a$, —$S(=O)R^b$, —$S(=O)_2R^b$, —$NR^aR^a$, —$N(R^a)C(=O)R^b$, —$N(R^a)C(=O)OR^b$, —$C_{1-6}$alkOR$^a$, —$C_{1-6}$alkN(R$^a$)C(=O)R$^b$, —$C_{1-6}$alkOC(=O) R$^b$, —$C_{1-6}$alkC(=O)NR$^a$R$^a$, —$C_{1-6}$alkC(=O)OR$^a$, oxo, or $R^c$.

In another embodiment of the compound of formula (I), (II), (III), or (IV), or a pharmaceutically acceptable salt thereof, $L^1$ is a carbon-linked-unsaturated 5- to 6-membered monocyclic ring, wherein each said ring contains 0, 1, or 2 N atoms and 0 or 1 O atoms, and wherein each said $L^1$ is substituted by 0, 1 or 2 $R^9$ groups which are F, Cl, Br, $C_{1-6}$alk, —$OR^a$, CN, —$C(=O)R^b$, $C(=O)OR^a$, —$C(=O)NR^aR^a$, —$SR^a$, —$S(=O)R^b$, —$S(=O)_2R^b$, —$NR^aR^a$, —$N(R^a)C(=O)R^b$, —$N(R^a)C(=O)OR^b$, —$C_{1-6}$alkOR$^a$, —$C_{1-6}$alkN(R$^a$)C(=O)R$^b$, —$C_{1-6}$alkOC(=O) R$^b$, —$C_{1-6}$alkC(=O)NR$^a$R$^a$, —$C_{1-6}$alkC(=O)OR$^a$, oxo, or $R^c$.

In another embodiment of the compound of formula (I), (II), (III), or (IV), or a pharmaceutically acceptable salt thereof, $L^1$ is a carbon-linked-saturated, partially-saturated or unsaturated 6-, 7-, 8-, 9-, or 10-membered bicyclic ring, wherein each said ring contains 0, 1, or 2 N atoms and 0 or 1 O atoms, and wherein each said $L^1$ is substituted by 0, 1 or 2 $R^9$ groups which are F, Cl, Br, $C_{1-6}$alk, —$OR^a$, CN, —$C(=O)R^b$, $C(=O)OR^a$, —$C(=O)NR^aR^a$, —$SR^a$, —$S(=O)R^b$, —$S(=O)_2R^b$, —$NR^aR^a$, —$N(R^a)C(=O)R^b$, —$N(R^a)C(=O)OR^b$, —$C_{1-6}$alkOR$^a$, —$C_{1-6}$alkN(R$^a$)C(=O)R$^b$, —$C_{1-6}$alkOC(=O) R$^b$, —$C_{1-6}$alkC(=O)NR$^a$R$^a$, —$C_{1-6}$alkC(=O)OR$^a$, oxo, or $R^c$.

In another embodiment of the compound of formula (I), (II), (III), or (IV), or a pharmaceutically acceptable salt thereof, $L^1$ is a nitrogen-linked saturated, partially-saturated or unsaturated 4-, 5-, 6-, or 7-membered monocyclic ring, wherein said ring contains 0, 1, 2, 3, or 4 N atoms and 0 or 1 O atoms, and wherein each said $L^1$ is substituted by 0, 1 or 2 $R^9$ groups which are F, Cl, Br, $C_{1-6}$alk, —$OR^a$, CN, —$C(=O)R^b$, $C(=O)OR^a$, —$C(=O)NR^aR^a$, —$SR^a$, —$S(=O)R^b$, —$S(=O)_2R^b$, —$NR^aR^a$, —$N(R^a)C(=O)R^b$, —$N(R^a)C(=O)OR^b$, —$C_{1-6}$alkOR$^a$, —$C_{1-6}$alkN(R$^a$)C(=O)R$^b$, —$C_{1-6}$alkOC(=O) R$^b$, —$C_{1-6}$alkC(=O)NR$^a$R$^a$, —$C_{1-6}$alkC(=O)OR$^a$, oxo, or $R^c$.

In another embodiment of the compound of formula (I), (II), (III), or (IV), or a pharmaceutically acceptable salt thereof, $L^1$ is a nitrogen-linked saturated, partially-saturated or unsaturated 6-, 7-, 8-, 9-, 10-, 11-, or 12-membered bicyclic ring, wherein each said ring contains 0, 1, or 2 N atoms and 0 or 1 O atoms, and wherein each said $L^1$ is substituted by 0, 1 or 2 $R^9$ groups which are F, Cl, Br, $C_{1-6}$alk, —$OR^a$, CN, —$C(=O)R^b$, $C(=O)OR^a$, —$C(=O)NR^aR^a$, —$SR^a$, —$S(=O)R^b$, —$S(=O)_2R^b$, —$NR^aR^a$, —$N(R^a)C(=O)R^b$, —$N(R^a)C(=O)OR^b$, —$C_{1-6}$alkOR$^a$, —$C_{1-6}$alkN(R$^a$)C(=O)R$^b$, —$C_{1-6}$alkOC(=O) R$^b$, —$C_{1-6}$alkC(=O)NR$^a$R$^a$, —$C_{1-6}$alkC(=O)OR$^a$, oxo, or $R^c$.

In another embodiment of the compound of formula (I), (II), (III), or (IV), or a pharmaceutically acceptable salt thereof, $L^1$ is -3-azabicyclo[3.1.0]hexanyl, azetidinyl, indolyl, phenyl, 2-pyridyl, 3-pyridyl, 4-pyridyl, pyrazolyl, piperazinonyl, piperidinyl, pyrrolidinyl, dihydropyranyl, tetrahydropyridinyl, octahydropyrrolo[3,4-c]pyrrolyl, tetrahydroisoquinolinyl, which are substituted by 0, 1 or 2 $R^9$ groups which are F, Cl, Br, $C_{1-6}$alk, —$OR^a$, CN, —$C(=O)R^b$, $C(=O)OR^a$, —$C(=O)NR^aR^a$, —$SR^a$, —$S(=O)R^b$, —$S(=O)_2R^b$, —$NR^aR^a$, —$N(R^a)C(=O)R^b$, —$N(R^a)C(=O)OR^b$, —$C_{1-6}$alkOR$^a$, —$C_{1-6}$alkN(R$^a$)C(=O)R$^b$, —$C_{1-6}$alkOC(=O) R$^b$, —$C_{1-6}$alkC(=O)NR$^a$R$^a$, —$C_{1-6}$alkC(=O)OR$^a$, oxo, or $R^c$.

In another embodiment of the compound of formula (I), (II), (III), or (IV), or a pharmaceutically acceptable salt thereof, $R^1$ is selected from the group consisting of: Cl; Br; —C≡C—CH$_3$; —NH—CH(CH$_3$)$_2$; —NHCH$_2$CH$_2$OCH$_3$; —NHCH$_2$CH$_2$OH;

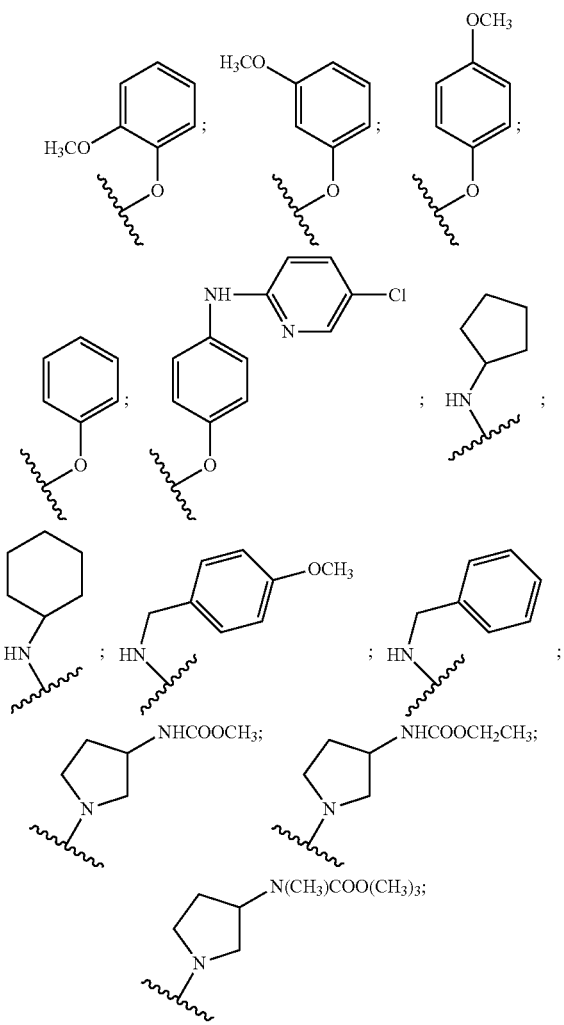

-continued
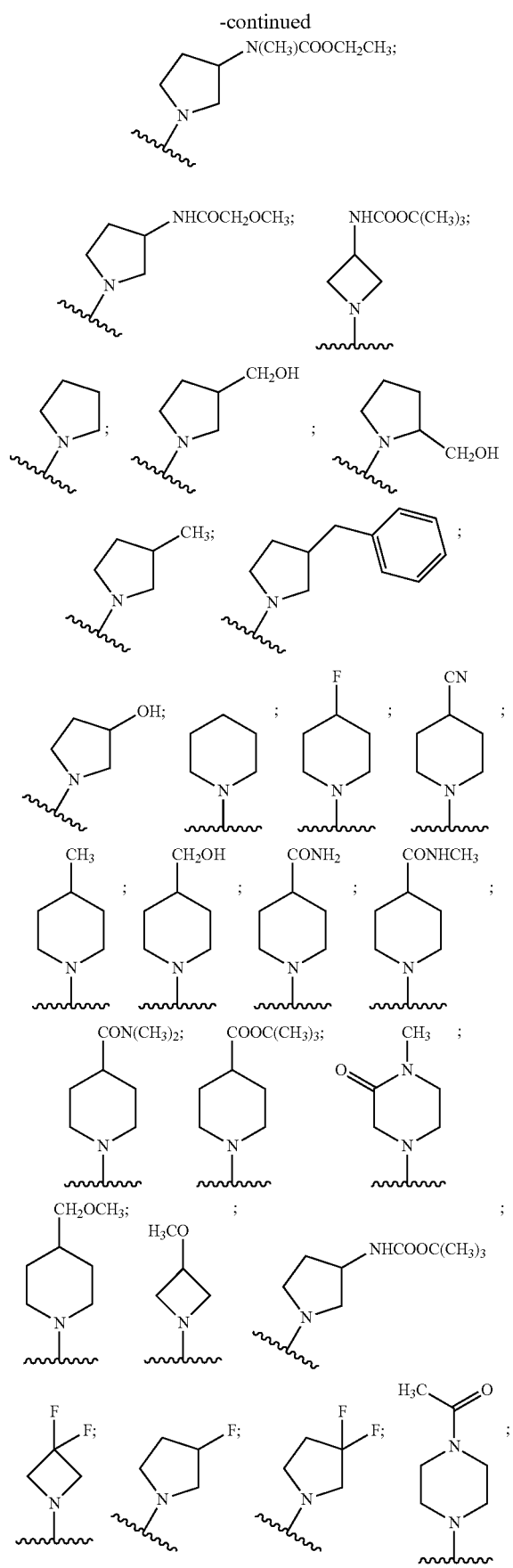
-continued
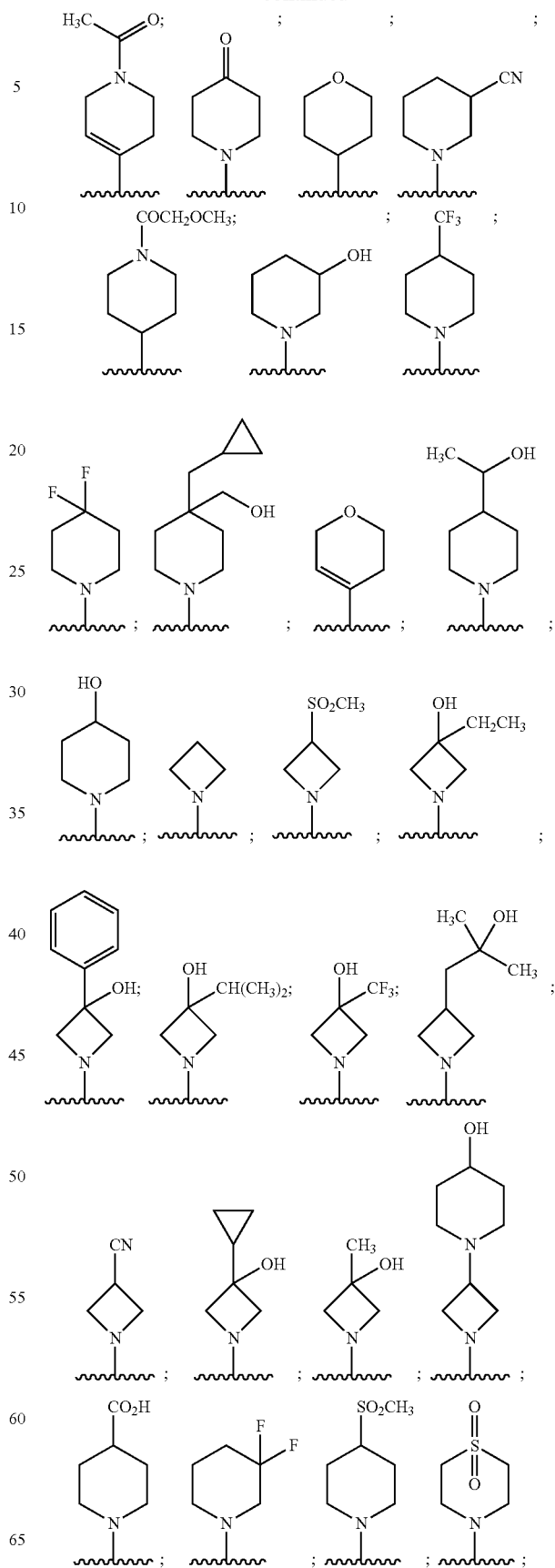

-continued
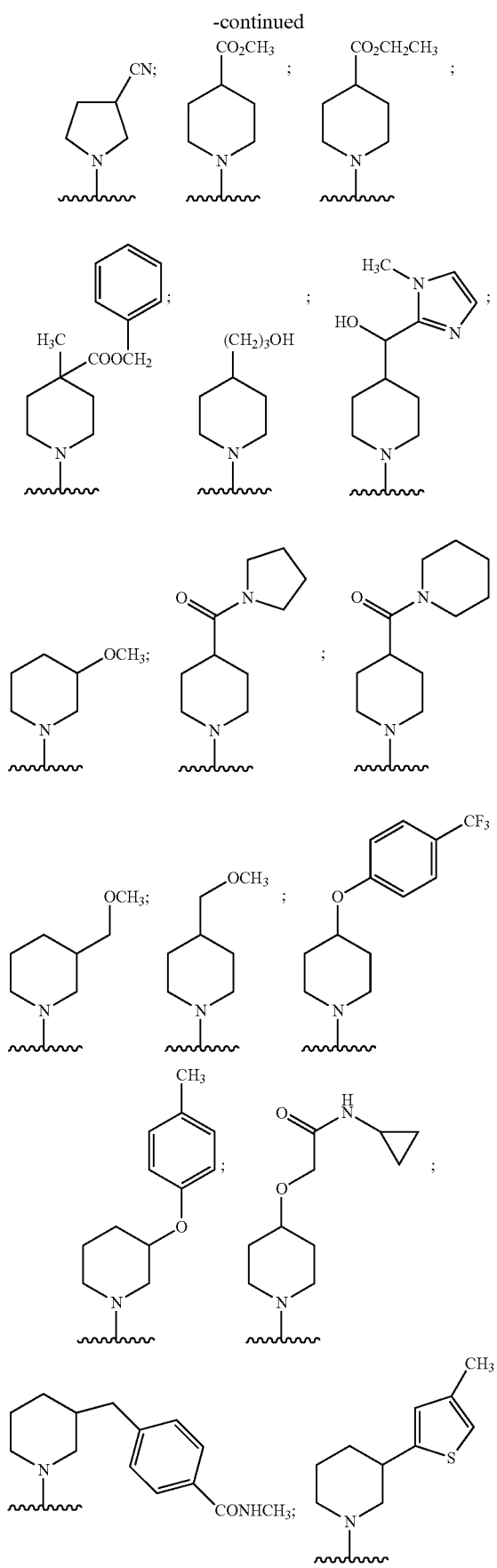
-continued
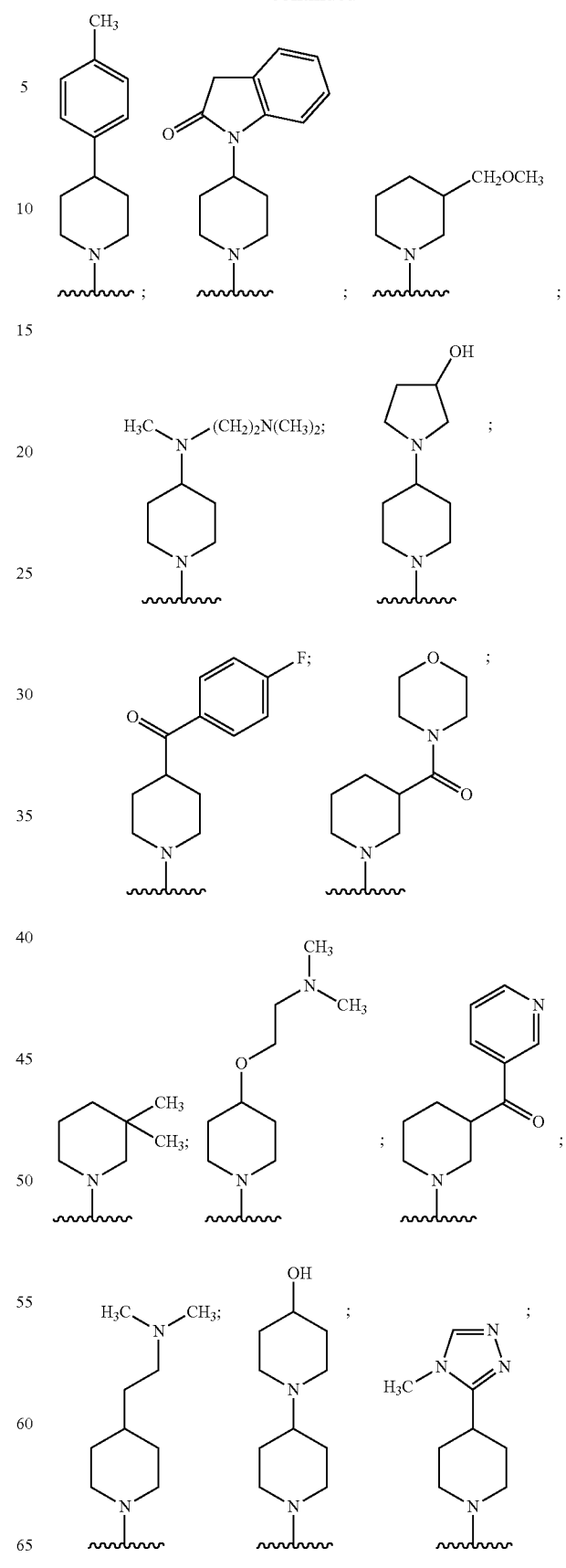

-continued
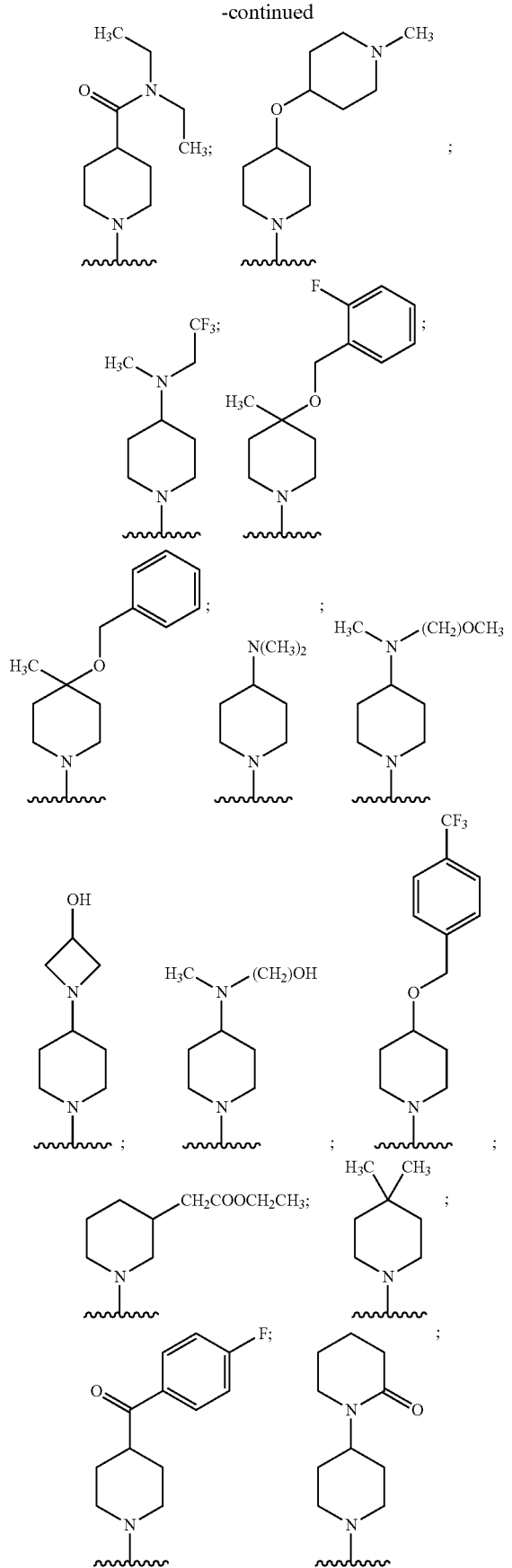
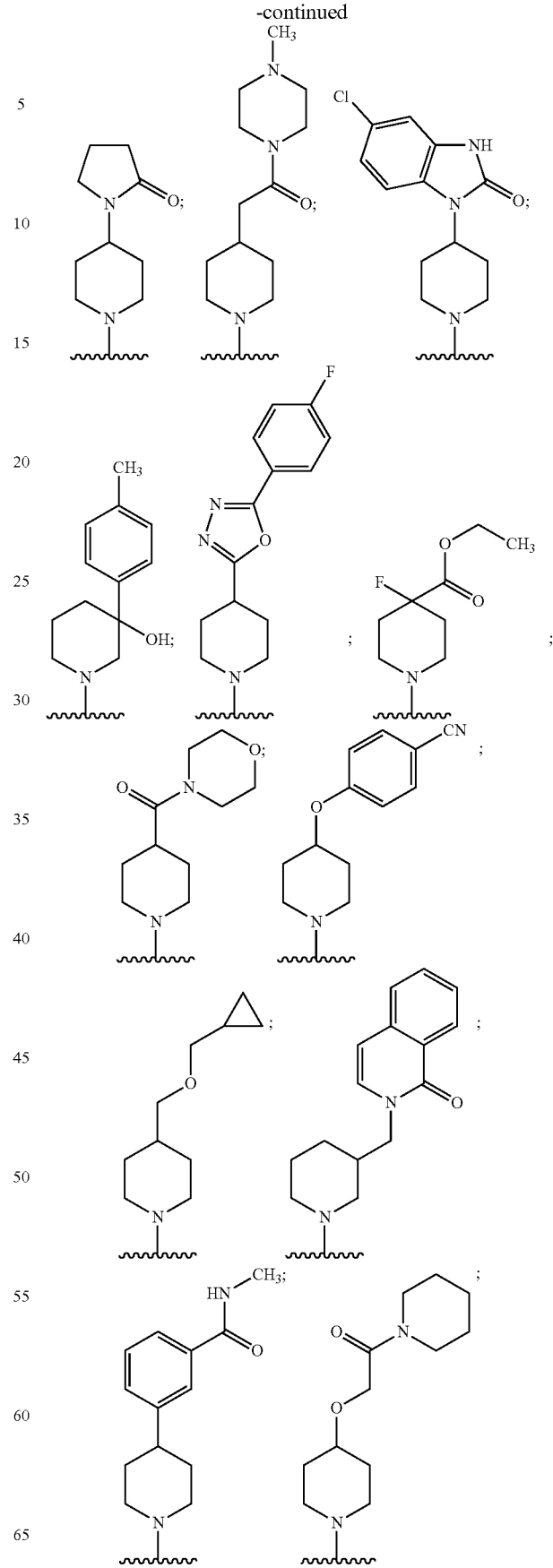

19
-continued
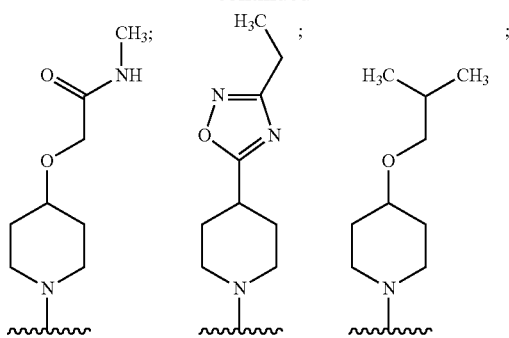
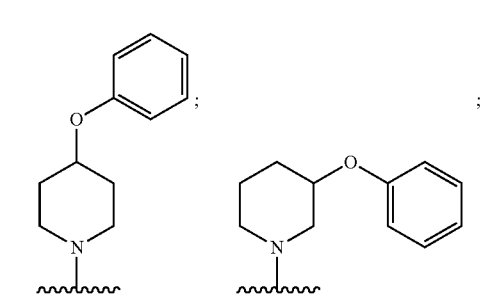
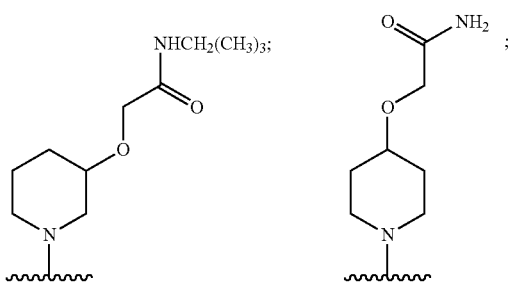
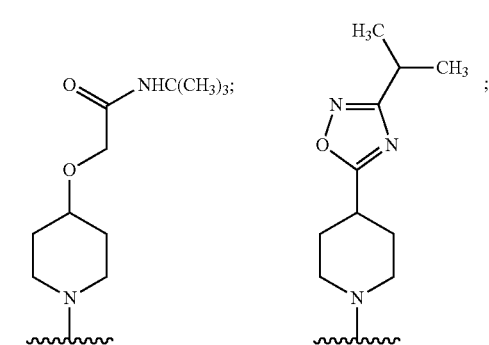
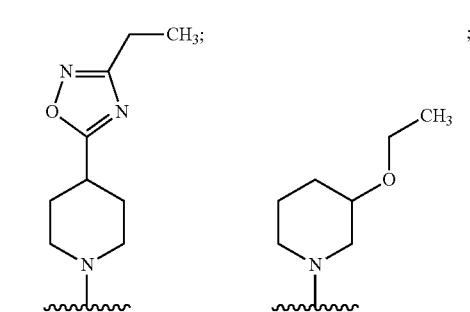
20
-continued
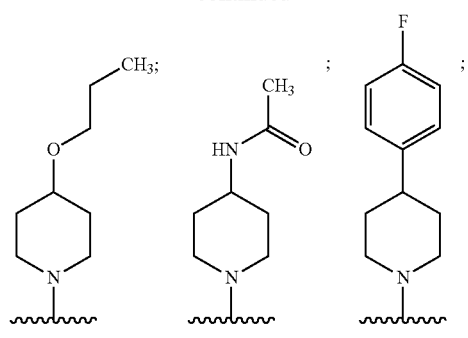
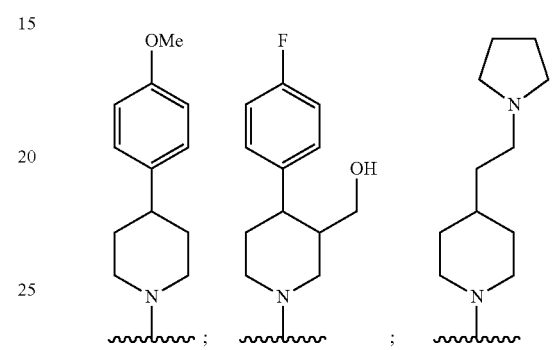
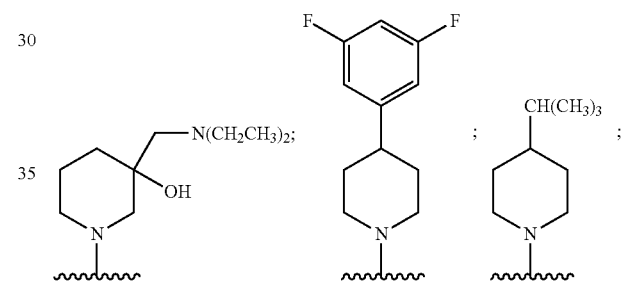
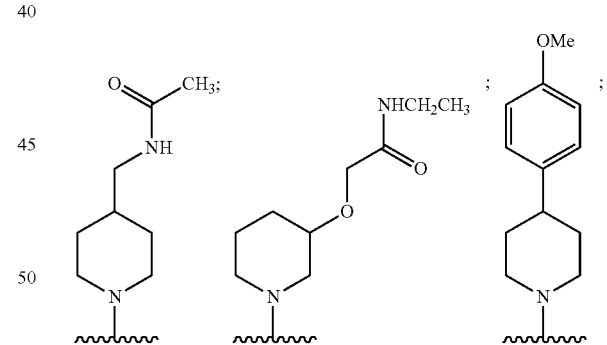
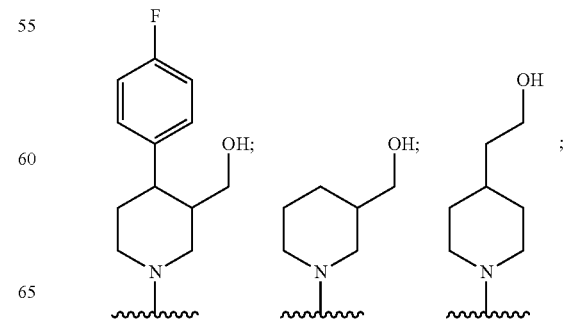

-continued
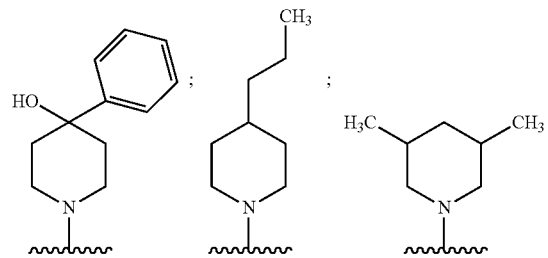
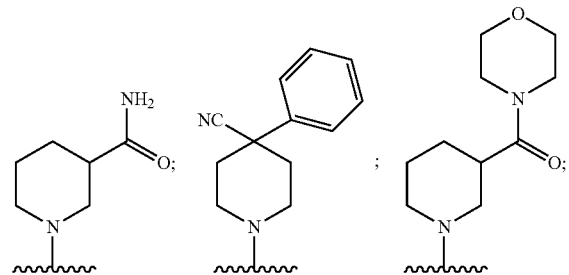
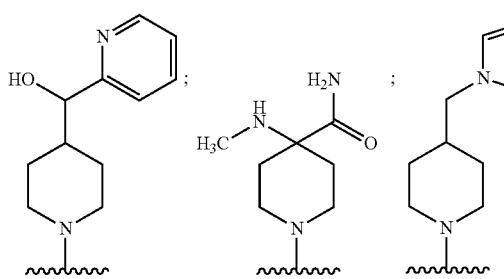
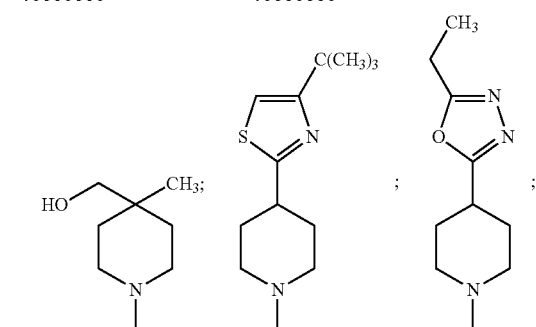
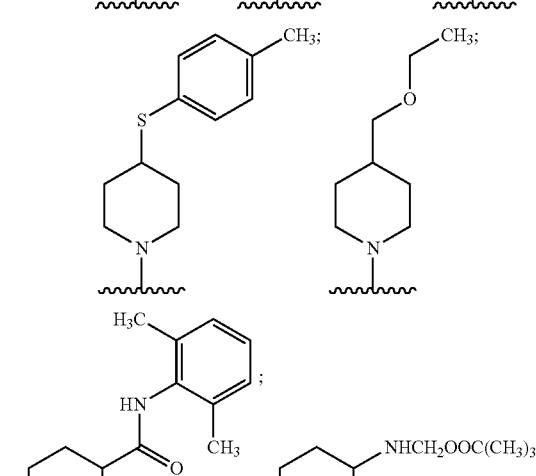
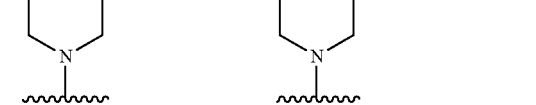
-continued
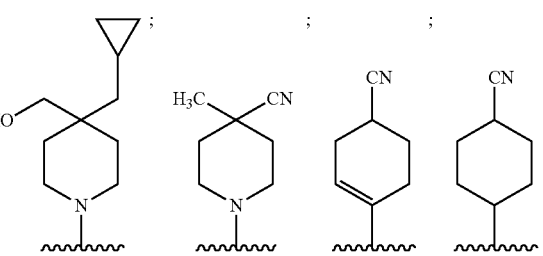
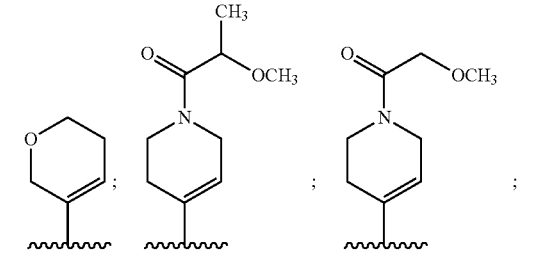
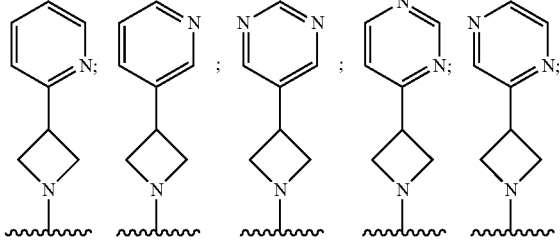
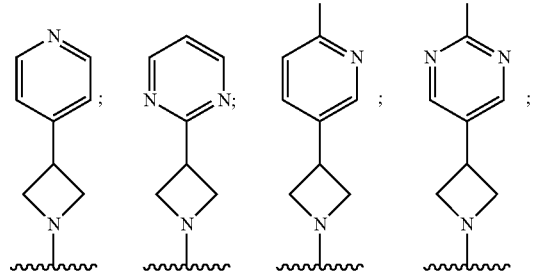
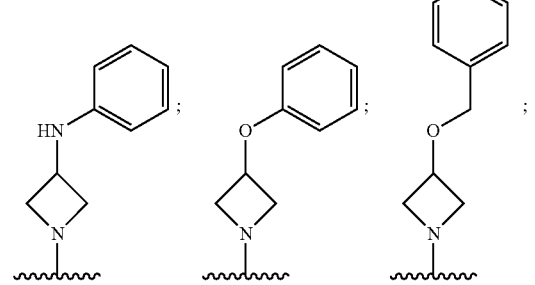
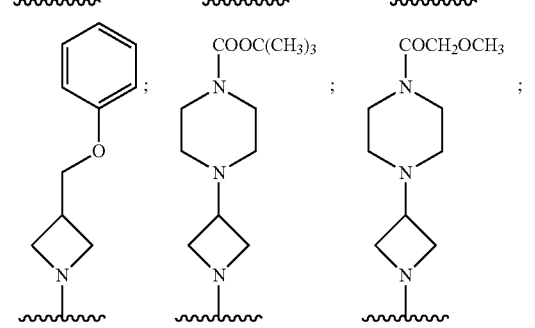

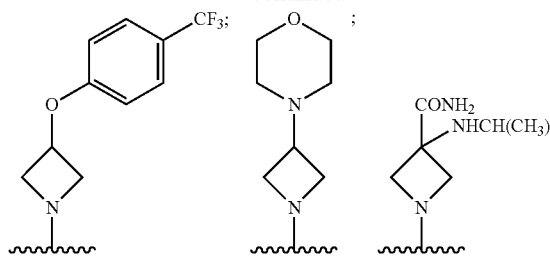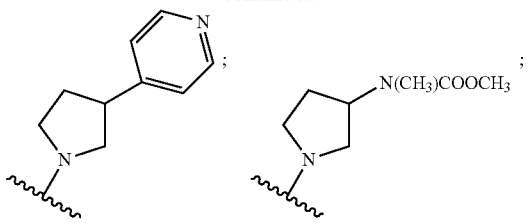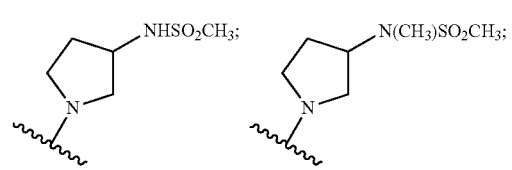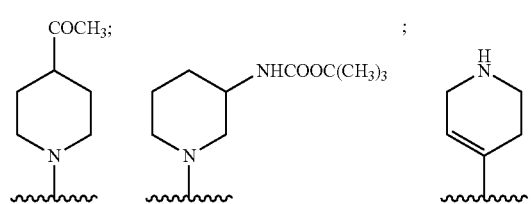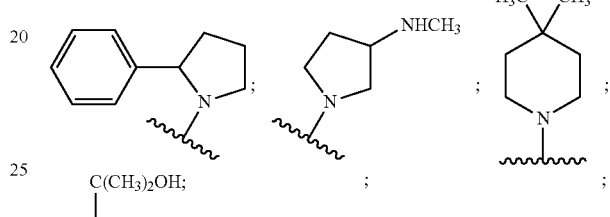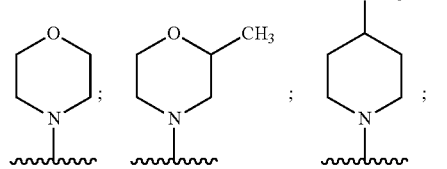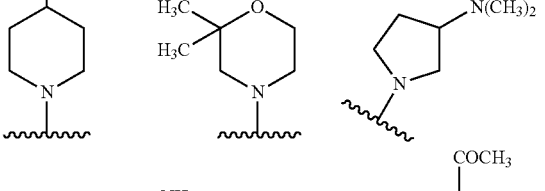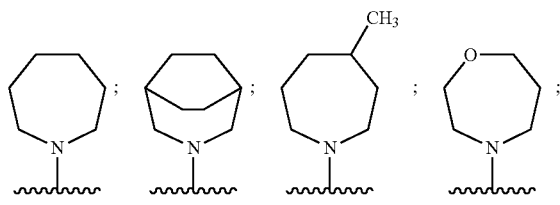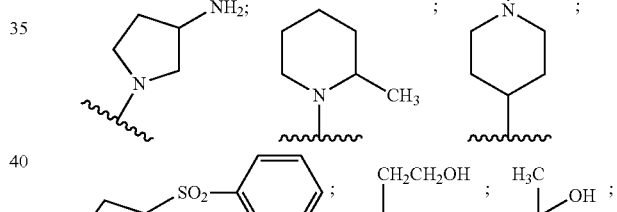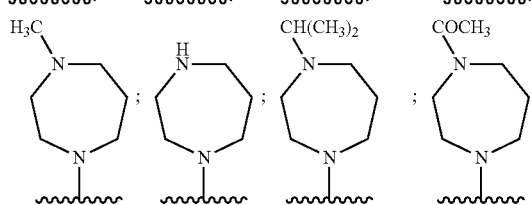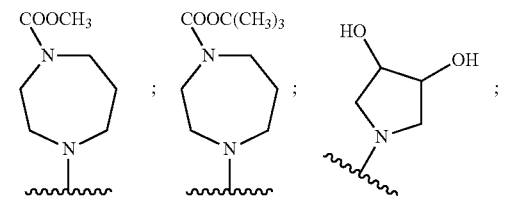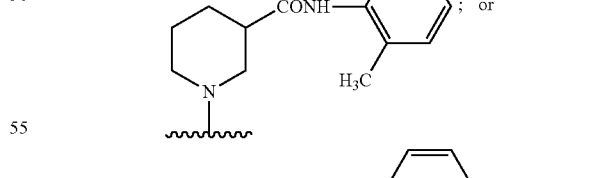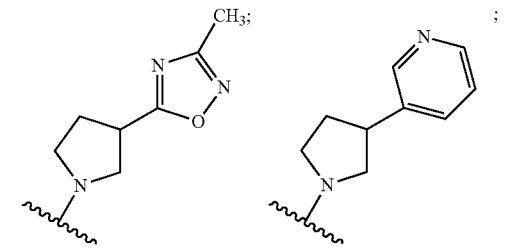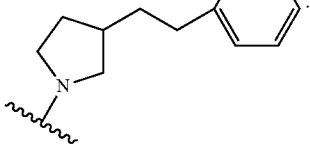
In another embodiment of the compound of formula (I), (II), (III), or (IV), or a pharmaceutically acceptable salt thereof, $R^1$ is selected from the group consisting of:

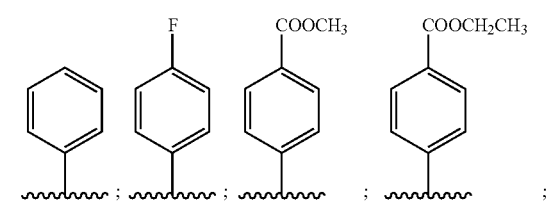
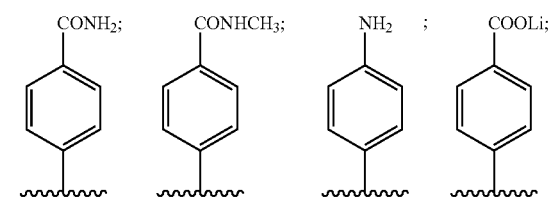
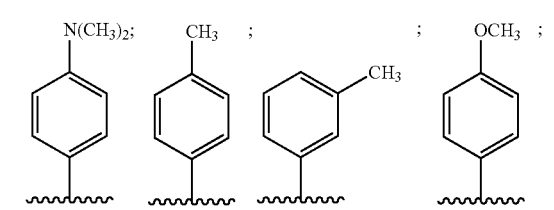
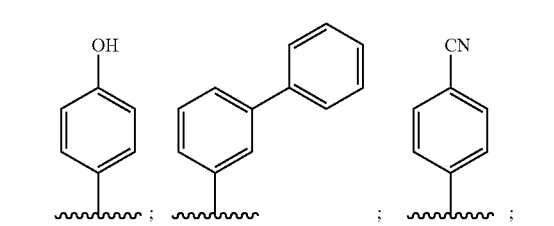
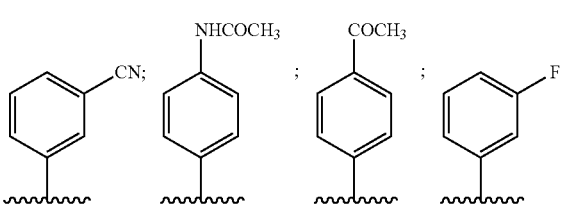
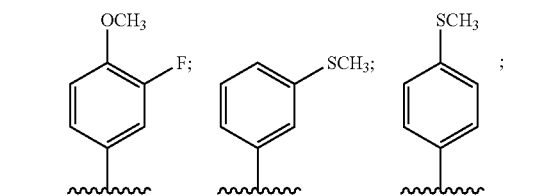
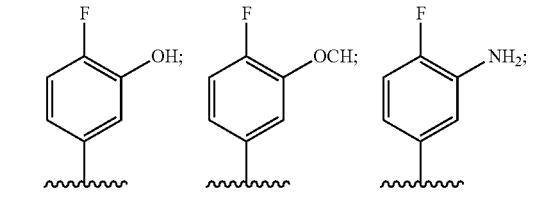
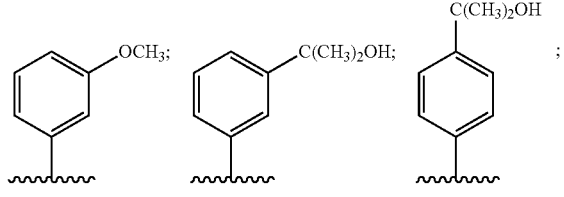
-continued
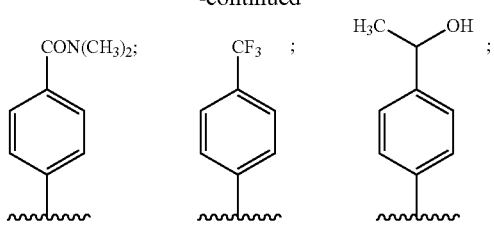
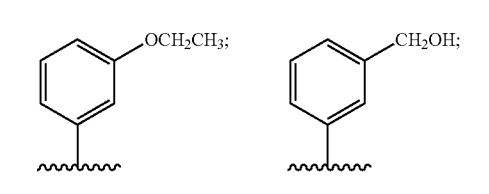
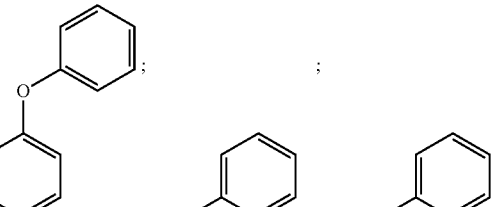
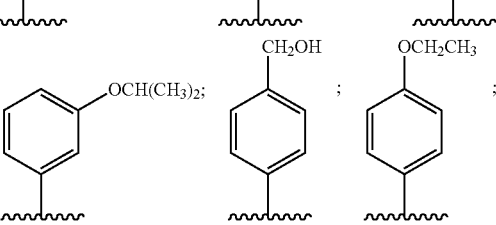
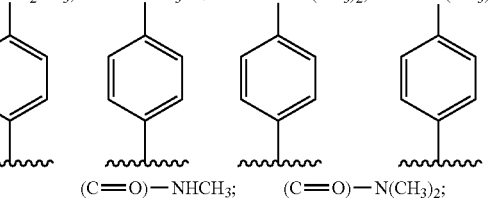
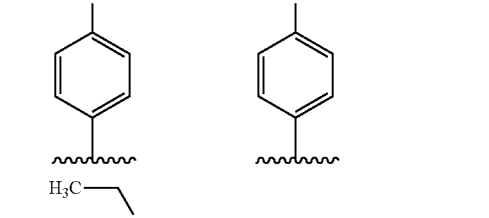
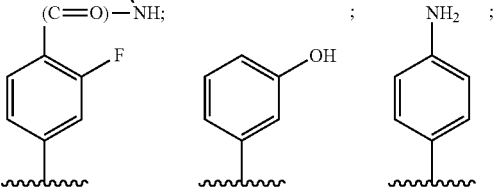
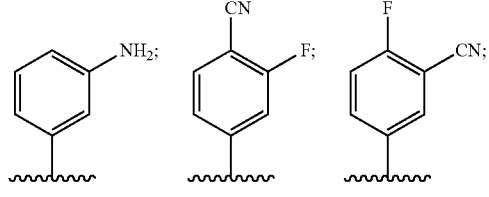

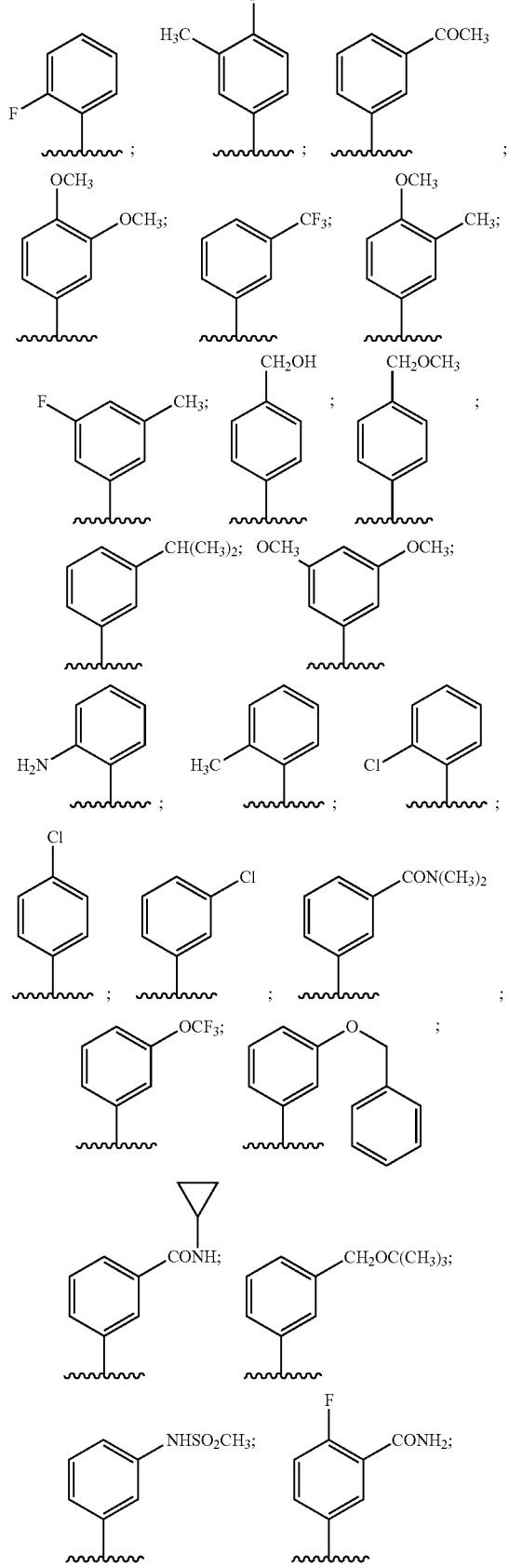
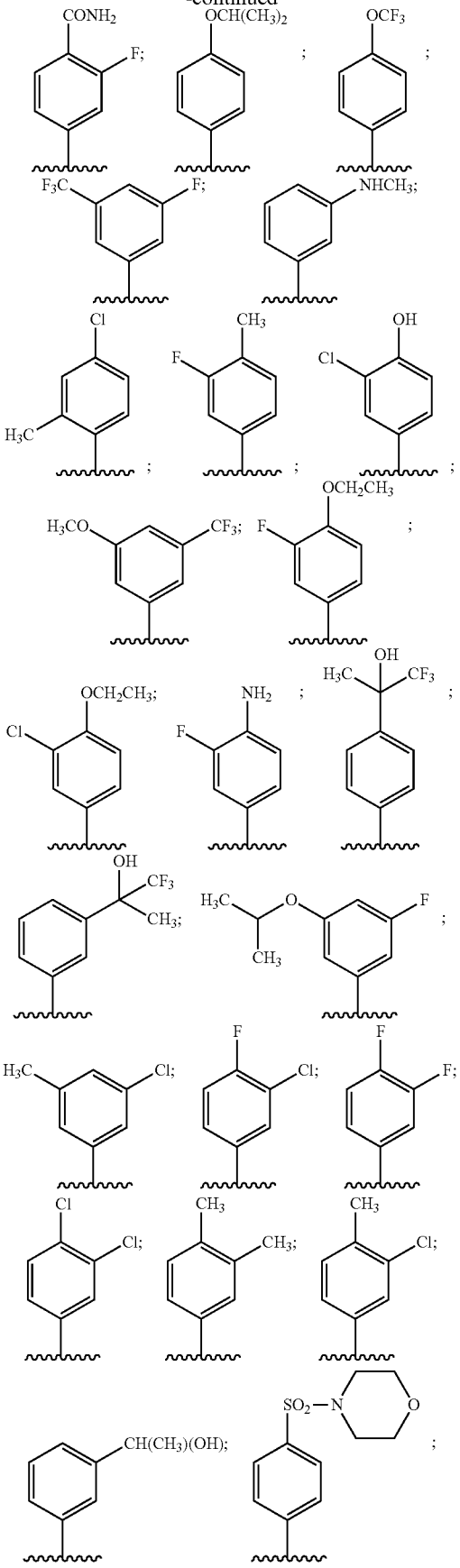

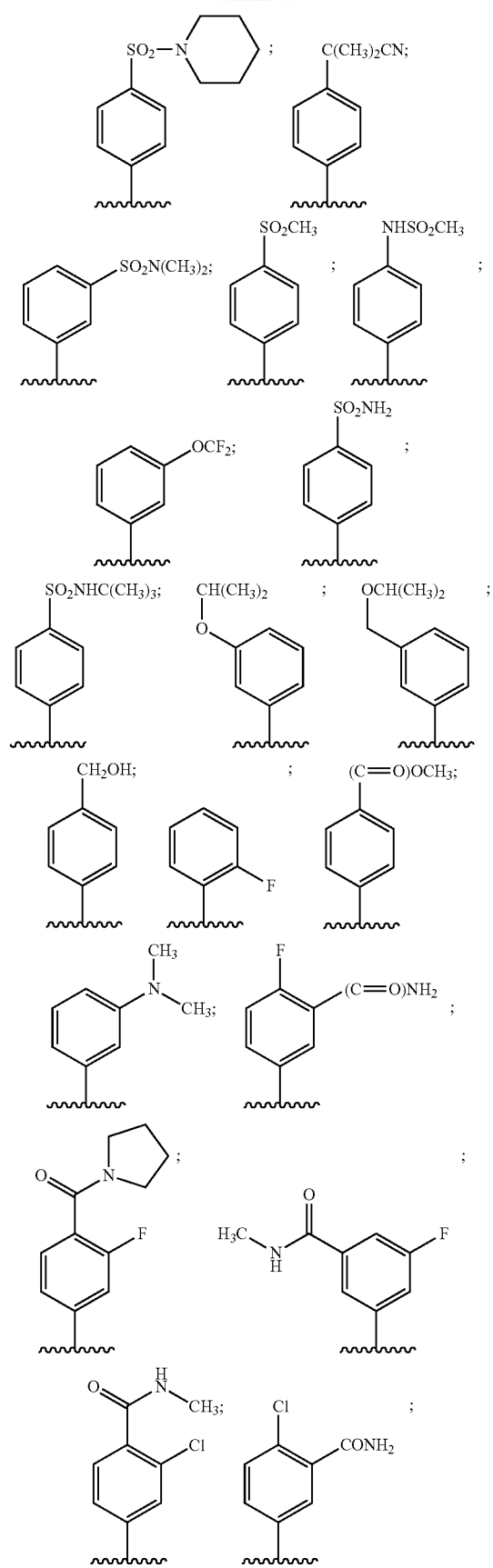
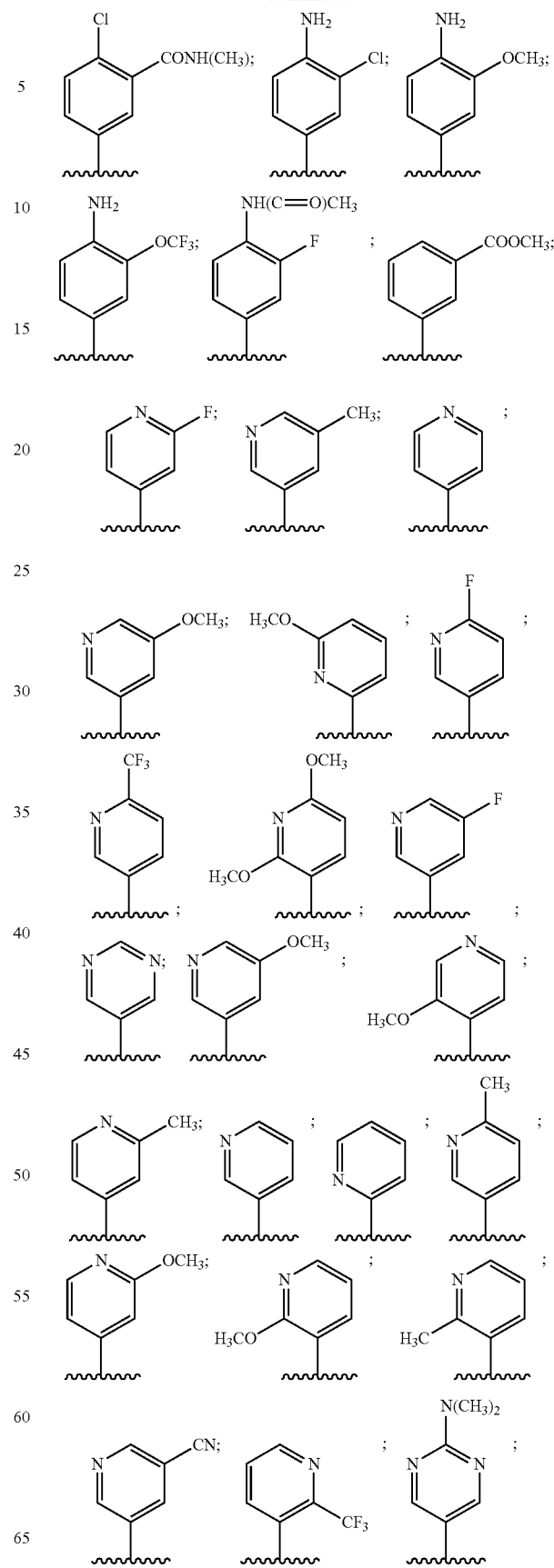

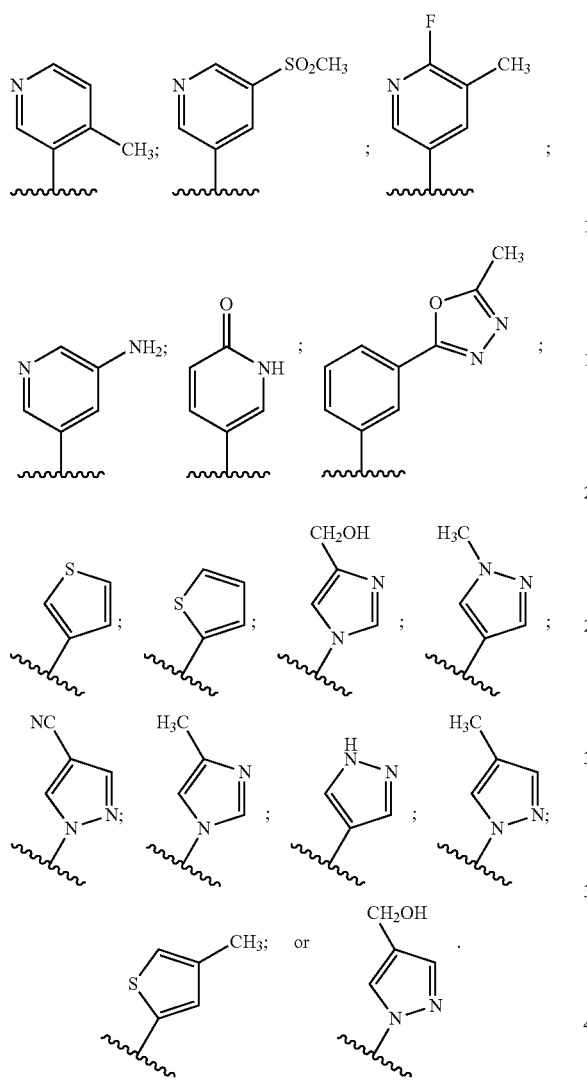
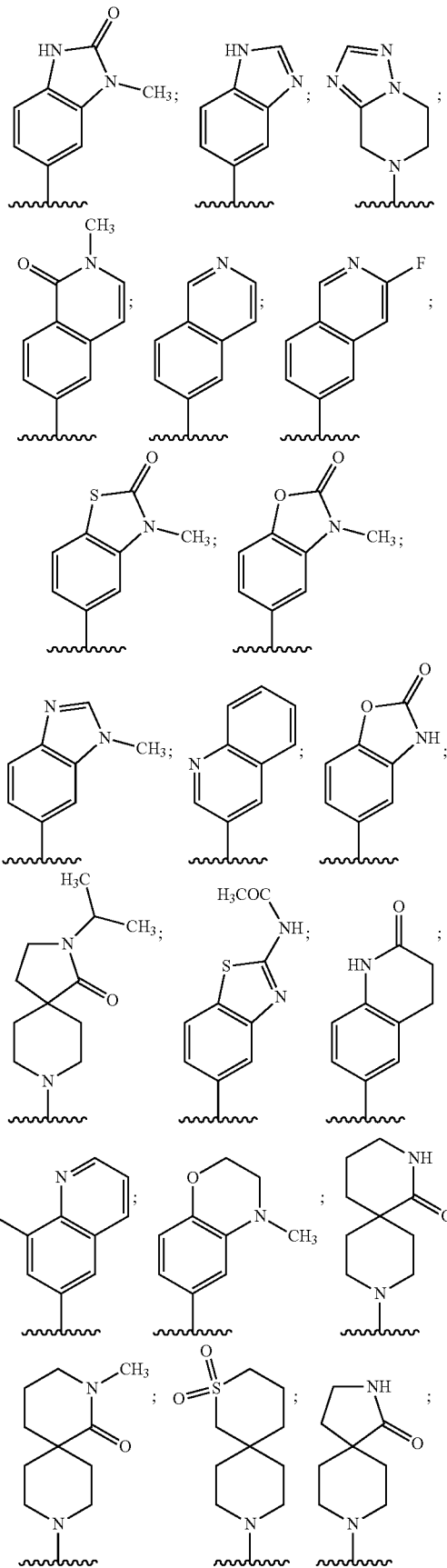
In another embodiment of the compound of formula (I), (II), (III), or (IV), or a pharmaceutically acceptable salt thereof, R[1] is selected from the group consisting of:
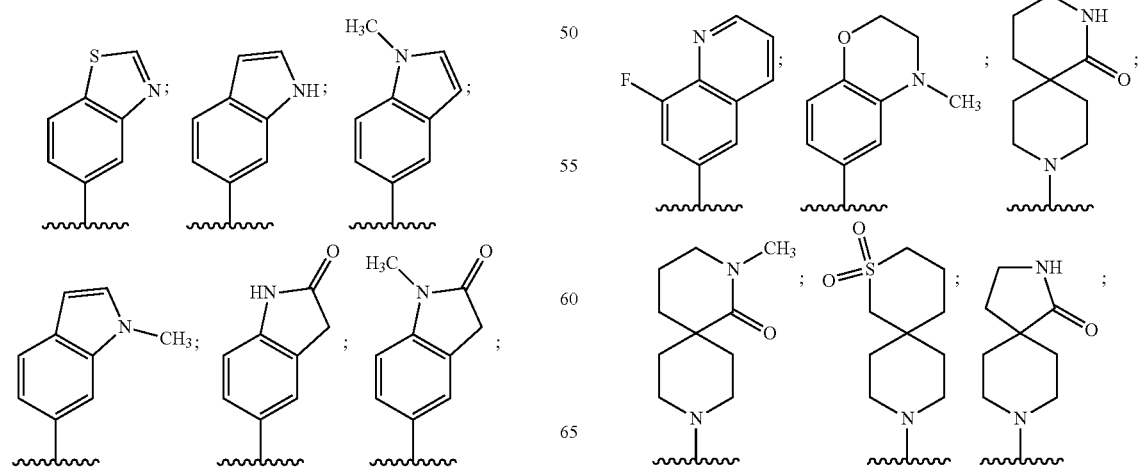

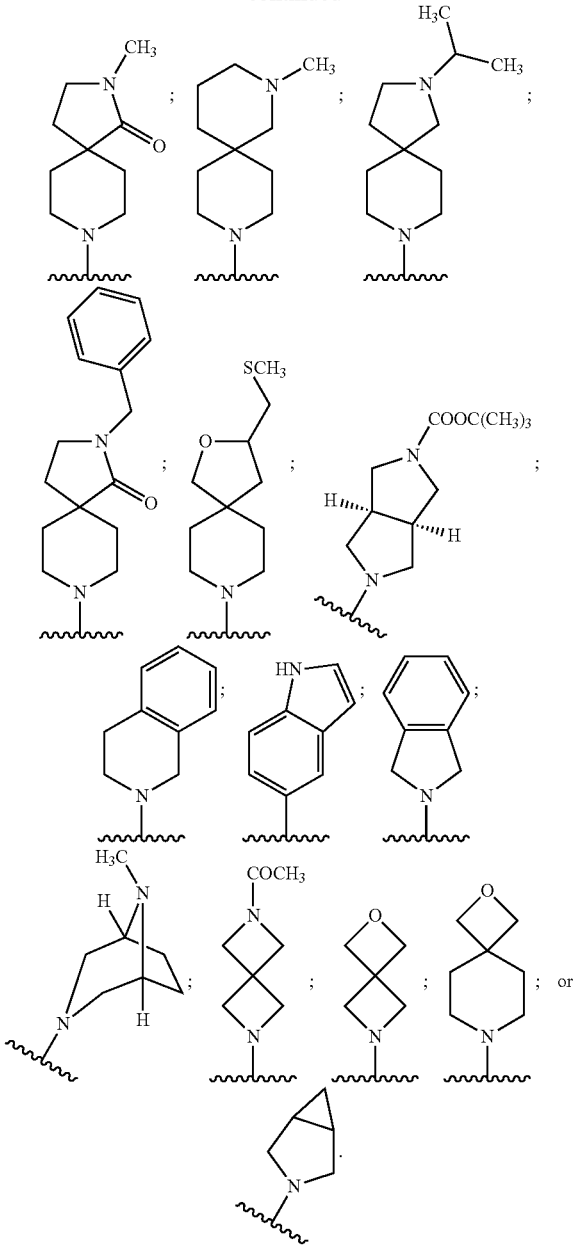

In another embodiment of the compound of formula (I), (II), (III), or (IV), or a pharmaceutically acceptable salt thereof, each $R^2$ and $R^3$ is independently H, F, Cl, Br, CN, OH, $OC_{1-4}$alk, $C_{1-4}$alk or $C_{1-4}$haloalk.

In another embodiment of the compound of formula (I), (II), (III), or (IV), or a pharmaceutically acceptable salt thereof, $R^6$ is H, F, or $C_{1-4}$alk.

In another embodiment of the compound of formula (I), (II), (III), or (IV), or a pharmaceutically acceptable salt thereof, $R^{4a}$ is H, F, OH, or methyl.

In another embodiment of the compound of formula (I), (II), (III), or (IV), or a pharmaceutically acceptable salt thereof, $R^{4b}$ is oxo and m is 1

In another embodiment of the compound of formula (I), (II), (III), or (IV), or a pharmaceutically acceptable salt thereof, $R^{4a}$ is H and m is 0.

In another embodiment of the compound of formula (I), (II), (III), or (IV), or a pharmaceutically acceptable salt thereof, $R^5$ is pyridinyl.

In another embodiment of the compound of formula (I), (II), (III), or (IV), or a pharmaceutically acceptable salt thereof, $R^5$ is unsaturated 9- to 10-membered bicyclo-heterocyclic ring.

In another embodiment of the compound of formula (I), (II), (III), or (IV), or a pharmaceutically acceptable salt thereof, $R^5$ is 11- to 15-membered tricyclo-heterocyclic ring.

In another embodiment of the compound of formula (I), (II), (III), or (IV), or a pharmaceutically acceptable salt thereof, the group —Y—$R^5$ is:

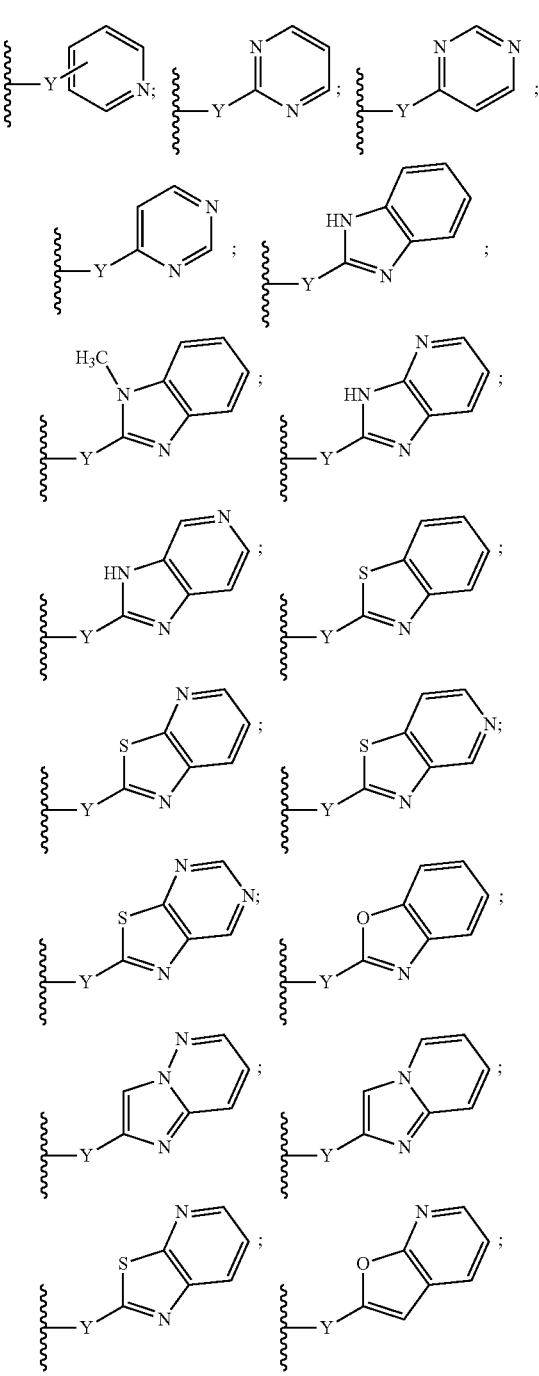

wherein each R⁵ is substituted by 1 or 2 R⁸ groups.

In another embodiment of the compound of formula (I), (II), (III), or (IV), or a pharmaceutically acceptable salt thereof, the group —Y—R$^5$ is:
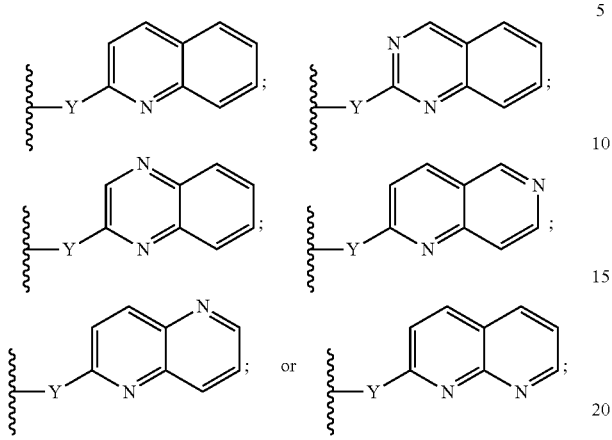
wherein each R$^5$ is substituted by 1 or 2 R$^8$ groups.
In another embodiment of the compound of formula (I), (II), (III), or (IV), or a pharmaceutically acceptable salt thereof, the group —Y—R$^5$ is:
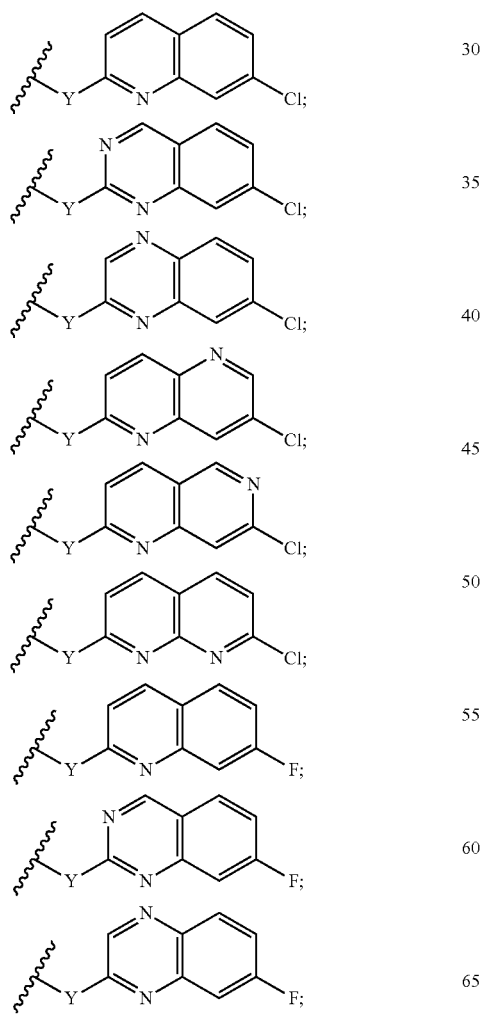
-continued
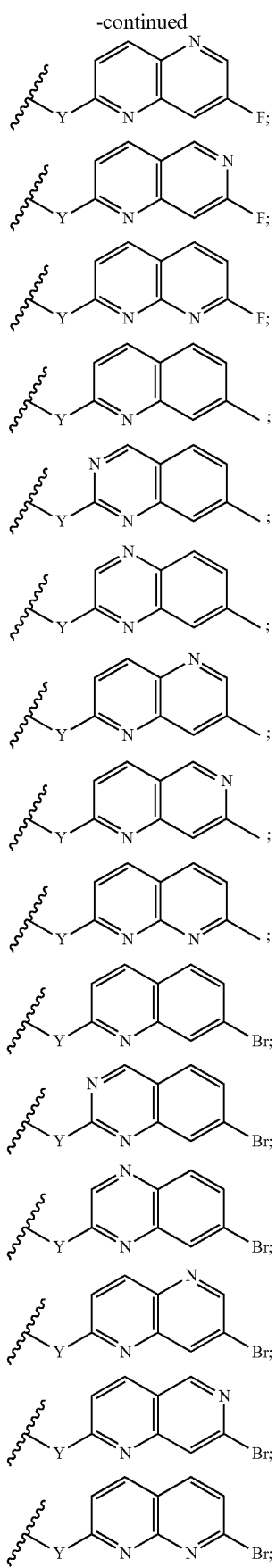

-continued

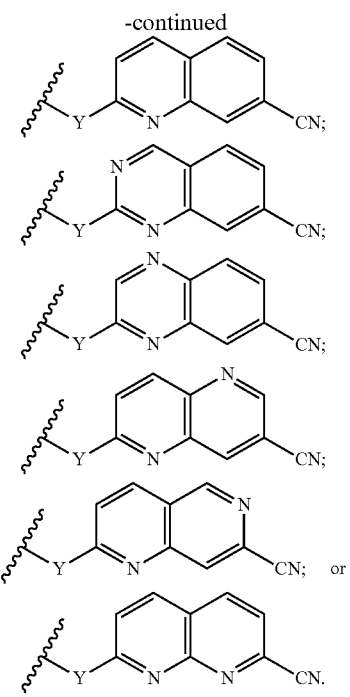

In another embodiment of the compound of formula (I), (II), (III), or (IV), or a pharmaceutically acceptable salt thereof, Y is a bond or —C(=O).

In another embodiment of the compound of formula (I), (II), (III), or (IV), or a pharmaceutically acceptable salt thereof, Y is a bond.

In another embodiment of the compound of formula (I), (II), (III), or (IV), or a pharmaceutically acceptable salt thereof, $R^8$ is independently F, Br, Cl, $CF_3$, methyl, methoxy, or CN.

In another embodiment of the compound of formula (I), (II), (III), or (IV), or a pharmaceutically acceptable salt thereof, $R^a$ is H or $C_{1-6}$alk substituted by 0 or 1 —OH, —$OC_{1-4}$alk, —OC(=O)$C_{1-4}$alk, or —N($C_{1-4}$alk)$C_{1-4}$alk.

In another embodiment of the compound of formula (I), (II), (III), or (IV), or a pharmaceutically acceptable salt thereof, $R^c$ is a $C_{0-4}$alk-carbon-linked saturated, partially-saturated or unsaturated 3-, 4-5-, or 6-membered monocyclic ring containing 0, 1, or 2 N atoms and 0 or 1 atom which are O or S, which is substituted by 0 or 1 $R^{11}$ groups which are F, $C_{1-6}$alk, $C_{1-4}$haloalk, or —$OR^a$.

In another embodiment of the compound of formula (I), (II), (III), or (IV), or a pharmaceutically acceptable salt thereof, $R^c$ is pyridyl, phenyl, or 1,2,4-oxadiazolyl.

Another aspect of the current invention relates to compounds having the general structure of formula (II):

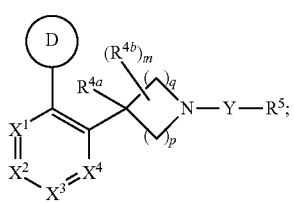

(II)

or a pharmaceutically acceptable salt thereof, wherein:
Ring D is -$L^1$;
$X^1$ is N or $CR^6$;
$X^2$ is N or $CR^2$;
$X^3$ is N or $CR^3$;
$X^4$ is N or $CR^6$;
wherein 1 to 2 of $X^1$, $X^2$, $X^3$, and $X^4$ are N;
Y is a $C_{0-4}$alk, —C(=O), SO, or $SO_2$;
each $R^2$ and $R^3$ is independently H, halo, CN, OH, —$OC_{1-4}$alk, $C_{1-4}$alk, $C_{1-4}$haloalk, —$C_{1-6}$alk$OR^a$, —C(=O)$C_{1-4}$alk, —C(=O)$NR^aR^a$, —$C_{0-4}$alkNH—C(=O)$R^a$, or $R^c$;
or alternatively the ring containing $X^1$, $X^2$, $X^3$, $X^4$ and $X^5$ can be fused to ring A, ring B, or ring C; having the formula:

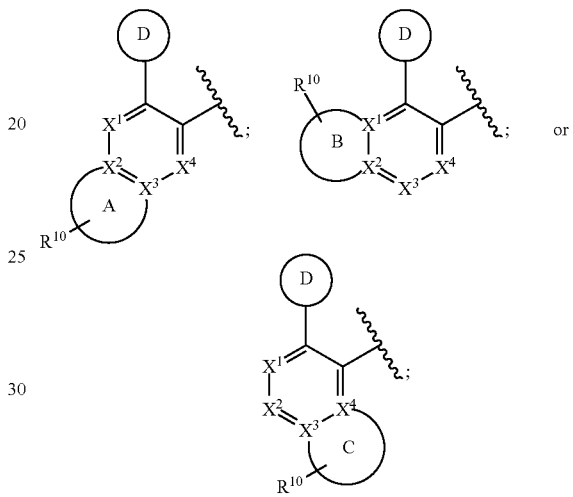

wherein each said ring A, ring B, or ring C is a fused 4- to 6-membered-saturated, -partially saturated, or -unsaturated-carbocyclic or -heterocyclic ring containing 0, 1, 2, or 3 heteroatoms; and is substituted by 0, 1, or 2 $R^{10}$ groups;
$R^{4a}$ is H, OH, halo, $C_{1-4}$alk, or $C_{1-4}$haloalk;
$R^{4b}$ is halo, CN, OH, $OC_{1-4}$alk, $C_{1-4}$alk, $C_{1-4}$haloalk, or oxo;
$R^5$ is pyridinyl or unsaturated 9- to 10-membered bicyclo-heterocyclic ring; wherein each $R^5$ is substituted by 0, 1, 2 or 3 $R^8$ groups;
$R^6$ is independently H, halo, CN, OH, $OC_{1-4}$alk, $C_{1-4}$alk or $C_{1-4}$haloalk;
m is 0, 1, 2, 3, or 4;
each of p and q is independently 0, 1, 2, 3, 4, 5, or 6;
wherein the sum of p and q is 2 to 6;
the ring containing p and q contains 0, 1, or 2 double bonds;
$R^a$ is independently H or $R^b$;
$R^b$ is independently phenyl, benzyl, or $C_{1-6}$alk, wherein said phenyl, benzyl, or $C_{1-6}$alk substituted by 0, 1, 2 or 3 substituents which are, independently, halo, $C_{1-4}$alk, $C_{1-3}$haloalk, —OH, —$OC_{1-4}$alk, —$NH_2$, —$NHC_{1-4}$alk, —OC(=O)$C_{1-4}$alk, or —N($C_{1-4}$alk)$C_{1-4}$alk;
$R^c$ is $C_{0-4}$alk-$L^2$;
each $L^1$ is independently a carbon-linked or nitrogen-linked saturated, partially-saturated or unsaturated 3-, 4-, 5-, 6-, or 7-membered monocyclic ring or a saturated, partially-saturated or unsaturated 6-, 7-, 8-, 9-, 10-, 11-, or 12-membered bicyclic ring, wherein each said ring contains 0, 1, 2, 3, or 4 N atoms and 0, 1, or 2 atoms which are O or S; wherein each $L^1$ is independently substituted by 0, 1, 2 or 3 $R^9$ groups;

each L² is independently a carbon-linked or nitrogen-linked saturated, partially-saturated or unsaturated 3-, 4-, 5-, 6-, or 7-membered monocyclic ring or a saturated, partially-saturated or unsaturated 6-, 7-, 8-, 9-, 10-, 11-, or 12-membered bicyclic ring, wherein each said ring contains 0, 1, 2, 3, or 4 N atoms and 0, 1, or 2 atoms which are O or S; wherein each L² is independently substituted by 0, 1, 2 or 3 R¹¹ groups;

R⁸ is halo, CN, OH, OC₁₋₄alk, C₁₋₄alk, C₁₋₄haloalk, OC₁₋₄haloalk, —C(=O)Rᵇ, —C(=O)Rᶜ, —C(=O)NHRᵇ, —C(=O)NHRᶜ, —S(=O)₂Rᵇ, —S(=O)₂R, —S(=O)₂NRᵃRᵃ, Rᵇ, Rᶜ, NO₂, ORᵇ, or ORᶜ;

R⁹ is F, Cl, Br, C₁₋₆alk, C₁₋₄haloalk, —ORᵃ, —OC₁₋₄haloalk, CN, —C(=O)Rᵇ, —C(=O)ORᵃ, —C(=O)NRᵃRᵃ, —C(=NRᵃ)NRᵃRᵃ, —OC(=O)Rᵇ, —OC(=O)NRᵃRᵃ, —OC₁₋₆alkNRᵃRᵃ, —OC₁₋₆alkORᵃ, —SRᵃ, —S(=O)Rᵇ, —S(=O)₂Rᵇ, —S(=O)₂NRᵃRᵃ, —NRᵃRᵃ, —N(Rᵃ)C(=O)Rᵇ, —N(Rᵃ)C(=O)ORᵇ, —N(Rᵃ)C(=O)NRᵃRᵃ, —N(Rᵃ)C(=NRᵃ)NRᵃRᵃ, —N(Rᵃ)S(=O)₂Rᵇ, —N(Rᵃ)S(=O)₂NRᵃRᵃ, —NRᵃC₁₋₆alkNRᵃRᵃ, —NRᵃC₁₋₆alkORᵃ, —C₁₋₆alkNRᵃRᵃ, —C₁₋₆alkORᵃ, —C₁₋₆alkN(Rᵃ)C(=O)Rᵇ, —C₁₋₆alkOC(=O)Rᵇ, —C₁₋₆alkC(=O)NRᵃRᵃ, —C₁₋₆alkC(=O)ORᵃ, oxo, or Rᶜ;

R¹⁰ is oxo, C₁₋₆alk, C₁₋₃haloalk, —OH, —OC₁₋₄alk, —NH₂, —NHC₁₋₄alk, —OC(=O)C₁₋₄alk, or —N(C₁₋₄alk)C₁₋₄alk; and R¹¹ is F, Cl, Br, C₁₋₆alk, C₁₋₄haloalk, —ORᵃ, —OC₁₋₄haloalk, CN, —C(=O)Rᵇ, —C(=O)ORᵃ, —C(=O)NRᵃRᵃ, —C(=NRᵃ)NRᵃRᵃ, —OC(=O)Rᵇ, —OC(=O)NRᵃRᵃ, —OC₁₋₆alkNRᵃRᵃ, —OC₁₋₆alkORᵃ, —SRᵃ, —S(=O)Rᵇ, —S(=O)₂Rᵇ, —S(=O)₂NRᵃRᵃ, —NRᵃRᵃ, —N(Rᵃ)C(=O)Rᵇ, —N(Rᵃ)C(=O)ORᵇ, —N(Rᵃ)C(=O)NRᵃRᵃ, —N(Rᵃ)C(=NRᵃ)NRᵃRᵃ, —N(Rᵃ)S(=O)₂Rᵇ, —N(Rᵃ)S(=O)₂NRᵃRᵃ, —NRᵃC₁₋₆alkNRᵃRᵃ, —NRᵃC₁₋₆alkORᵃ, —C₁₋₆alkNRᵃRᵃ, —C₁₋₆alkORᵃ, —C₁₋₆alkN(Rᵃ)C(=O)Rᵇ, —C₁₋₆alkOC(=O)Rᵇ, —C₁₋₆alkC(=O)NRᵃRᵃ, —C₁₋₆alkC(=O)ORᵃ, or oxo.

In another embodiment of the compound of formula (I), (II), (III), or (IV), or a pharmaceutically acceptable salt thereof, the group

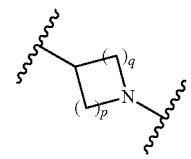

is azetidinyl, pyrrolidinyl, piperidinyl, or azepanyl.

In another embodiment of the compound of formula (I), (II), (III), or (IV), or a pharmaceutically acceptable salt thereof, the compound of formula (II) has the formula:

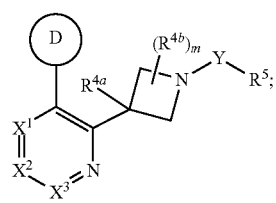

(IIa)

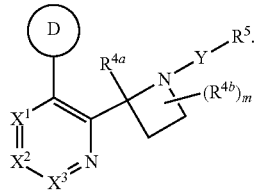

(IIb)

In another embodiment of the compound of formula (I), (II), (III), or (IV), or a pharmaceutically acceptable salt thereof, the compound of formula (II) has the formula:

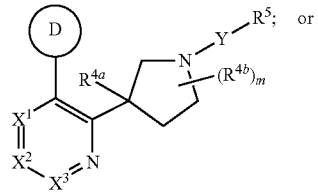

(IIc)

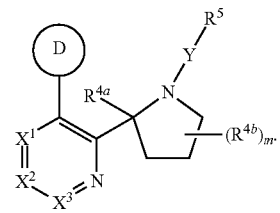

(IId)

In another embodiment of the compound of formula (I), (II), (III), or (IV), or a pharmaceutically acceptable salt thereof, the compound of formula (II) has the formula:

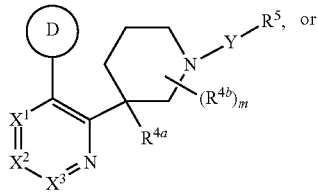

(IIe)

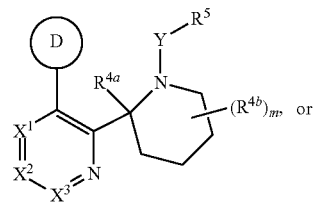

(IIf)

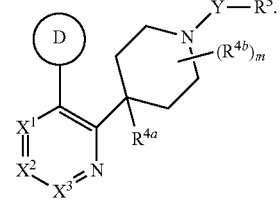

(IIg)

In another embodiment of the compound of formula (IIg), R⁴ᵇ is oxo; m is 1; and R⁵ is unsaturated 10-membered bicyclo-heterocyclic ring; wherein each $R^5$ ring is substituted by 0, 1, or 2 $R^8$ groups.

In another embodiment of the compound of formula (IIg), said compound has the formula

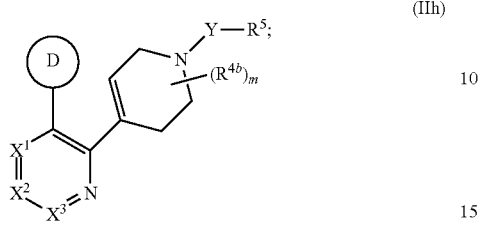

(IIh)

wherein m is 0; and $R^5$ is unsaturated 10-membered bicyclo-heterocyclic ring; wherein each $R^5$ ring is substituted by 0, 1, or 2 $R^8$ groups.

In another embodiment of any of the compound of the formula (IIa), (IIb), (IIc), (IId), (IIe), (IIf), and (IIg), the group —Y—$R^5$ is:

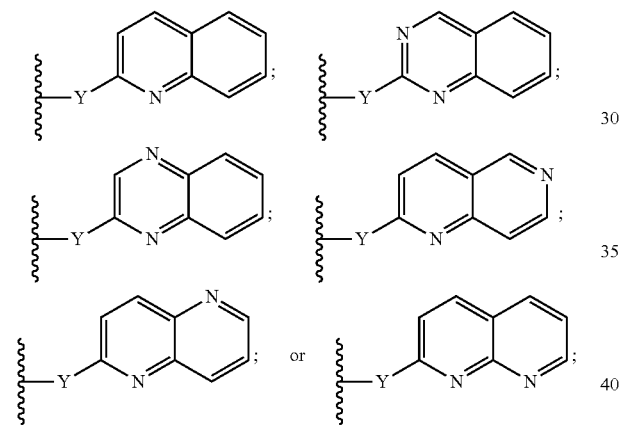

Y is a bond; wherein each $R^5$ is substituted by 1 or 2 $R^8$ groups; and $R^8$ is independently F, Cl, Br, methyl, ethyl, isopropyl, methoxy, CN, $CF_3$, OH, or $OCF_3$.

In another embodiment of any of the compound of the formula (IIa), (IIb), (IIc), (IId), (IIe), (IIf), and (IIg), or a pharmaceutically acceptable salt thereof, the group —Y—$R^5$ is:

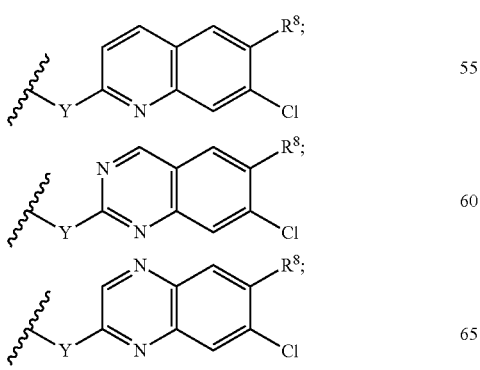

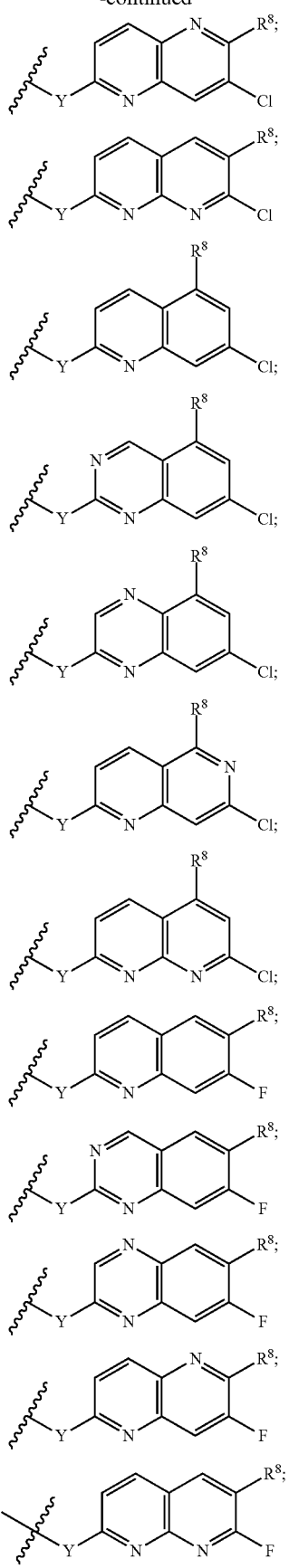

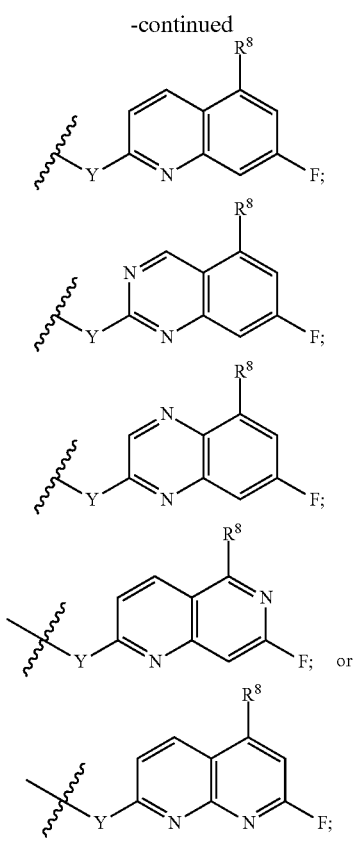

Y is a bond; wherein $R^8$ is independently F, Cl, Br, methyl, ethyl, isopropyl, methoxy, CN, $CF_3$, OH, or $OCF_3$.

Another aspect of the current invention relates to compounds having the general structure of formula (III):

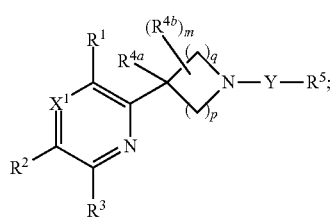
(III)

or a pharmaceutically-acceptable salt thereof, wherein:
$X^1$ is N or $CR^6$;
$R^1$ is F, Cl, Br, I, $C_{1-8}$alk, $C_{1-4}$haloalk, $—OR^a$, $—OR^c$, $—N(R^a)C(=O)R^b$, $—C(=O)R^a$, $—C(=O)R^c$, $—C(=O)—O—R^a$, $—NR^aR^c$, $—N(R^c)C(=O)R^b$, $—N(R^a)C(=O)R^c$, $—C(=O)NR^aR^b$, $—C(=O)NR^aR^c$, or $C_{0-4}$alk-$L^1$; wherein said $C_{1-8}$alk group is substituted by 0, 1, 2 or 3 groups selected from halo, $C_{1-3}$haloalk, $—OH$, $—OC_{1-4}$alk, $—NH_2$, $—NHC_{1-4}$alk, $—OC(=O)C_{1-4}$alk, or $—N(C_{1-4}$alk)$C_{1-4}$alk;
Y is a $C_{0-4}$alk, $—C(=O)$, SO, or $SO_2$;
each of $R^2$, $R^3$, $R^{4b}$, $R^6$ and $R^8$ is independently H, F, Cl, Br, I, CN, OH, $OC_{1-4}$alk, $C_{1-4}$alk or $C_{1-4}$haloalk;
or alternatively $R^2$ and $R^3$ can form an optionally substituted 5- to 6-membered-saturated, -partially saturated, or -unsaturated-heterocyclic ring fused to the ring containing $X^1$;

$R^{4a}$ is H, $C_{1-4}$alk, or $C_{1-4}$haloalk;
$R^5$ is pyridinyl or unsaturated 9- or 10-membered bicycloheterocyclic ring;
wherein each $R^5$ is substituted by 0, 1, 2 or 3 $R^8$ groups; and is not substituted by oxo;
m is 1, 2, 3, or 4;
each of p and q is independently 0, 1, 2, 3, 4, 5, or 6; wherein the sum of p and q is 2 to 6;
$R^a$ is independently H or $R^b$;
$R^b$ is independently phenyl, benzyl, or $C_{1-6}$alk, wherein said phenyl, benzyl, and $C_{1-6}$alk are being substituted by 0, 1, 2 or 3 substituents selected from halo, $C_{1-4}$alk, $C_{1-3}$haloalk, $—OH$, $—OC_{1-4}$alk, $—NH_2$, $—NHC_{1-4}$alk, $—OC(=O)C_{1-4}$alk, or $—N(C_{1-4}$alk)$C_{1-4}$alk;
$R^c$ is $C_{0-4}$alk-$L^2$; and
each of L and $L^2$ is independently a carbon-linked or nitrogen-linked saturated, partially-saturated or unsaturated 3-, 4-, 5-, 6-, or 7-membered monocyclic ring or a saturated, partially-saturated or unsaturated 8-, 9-, 10-, 11-, or 12-membered bicyclic ring, wherein each said ring contains 0, 1, 2, 3, or 4 N atoms and 0, 1, or 2 atoms selected from O and S; wherein each $L^1$ and $L^2$ is independently substituted by 0, 1, 2 or 3 $R^9$ groups selected from F, Cl, Br, $C_{1-6}$alk, $C_{1-4}$haloalk, $—OR^a$, $—OC_{1-4}$haloalk, CN, $—C(=O)R^b$, $—C(=O)OR^a$, $—C(=O)NR^aR^a$, $—C(=NR^a)NR^aR^a$, $—OC(=O)R^b$, $—OC(=O)NR^aR^a$, $—OC_{2-6}$alkNR$^a$R$^a$, $—OC_{2-6}$alkOR$^a$, $—SR^a$, $—S(=O)R^b$, $—S(=O)_2R^b$, $—S(=O)_2NR^aR^a$, $—NR^aR^a$, $—N(R^a)C(=O)R^b$, $—N(R^a)C(=O)OR^a$, $—N(R^a)C(=O)NR^aR^a$, $—N(R^a)C(=NR^a)NR^aR^a$, $—N(R^a)S(=O)_2R^b$, $—N(R^a)S(=O)_2NR^aR^a$, $—NR^aC_{2-6}$alkNR$^a$R$^a$, $—NR^aC_{2-6}$alkOR$^a$, $—C_{1-6}$alkNR$^a$R$^a$, $—C_{1-6}$alkOR$^a$, $—C_{1-6}$alkN(R$^a$)C(=O)R$^b$, $—C_{1-6}$alkOC(=O)R$^b$, $—C_{1-6}$alkC(=O)NR$^a$R$^a$, $—C_{1-6}$alkC(=O)OR$^a$ or oxo;
with the proviso that: when all $X^1$, $X^2$, and $X^3$ are $CR^3$; each of p and q is 2; and $R^3$ is methyl; then $R^1$ is F, Cl, Br, I, $C_{1-8}$alk, $C_{1-4}$haloalk, $—OR^a$, $—OR^c$, $—N(R^a)C(=O)R^b$, $—NR^aR^c$, $—N(R^c)C(=O)R^b$, $—N(R^a)C(=O)R^c$, or $C_{0-4}$alk-$L^1$; wherein said $C_{1-8}$alk group is substituted by 0, 1, 2 or 3 groups selected from halo, $C_{1-3}$haloalk, $—OH$, $—OC_{1-4}$alk, $—NH_2$, $—NHC_{1-4}$alk, $—OC(=O)C_{1-4}$alk, or $—N(C_{1-4}$alk)$C_{1-4}$alk.

In another embodiment of the compound of formula (I), (II), (III), or (IV), or a pharmaceutically acceptable salt thereof, $R^5$ is not substituted by oxo.

In another embodiment of the compound of formula (I), (II), (III), or (IV), or a pharmaceutically acceptable salt thereof, the group:

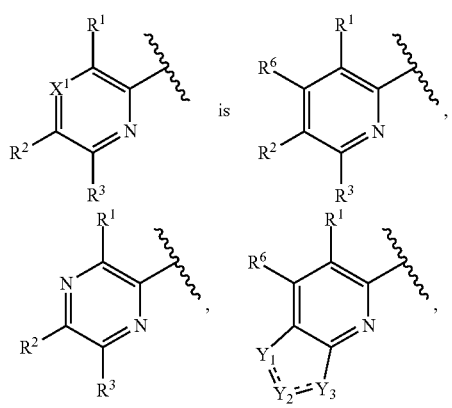

-continued

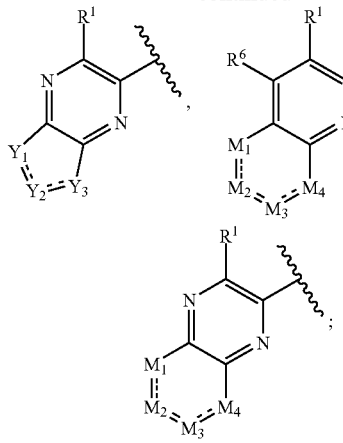

wherein each of $Y_1$, $Y_2$, $Y_3$, $M_1$, $M_2$, $M_3$, and $M_4$ is independently $CR^{10}$ or a heteroatom selected from S, O, or $NR^{11}$; wherein no more than of $Y_1$, $Y_2$, $Y_3$, $M_1$, $M_2$, $M_3$, and $M_4$ are N; and wherein $R^{10}$ is H, halo, $C_{1-4}$alk, $C_{1-3}$haloalk, —OH, —$OC_{1-4}$alk, —$NH_2$, —$NHC_{1-4}$alk, —$OC(=O)C_{1-4}$alk, or —$N(C_{1-4}alk)C_{1-4}$alk; and $R^1$ is H, $C_{1-4}$alk, or $C_{1-3}$haloalk.

In another embodiment of the compound of formula (I), (II), (III), or (IV), or a pharmaceutically acceptable salt thereof, the group

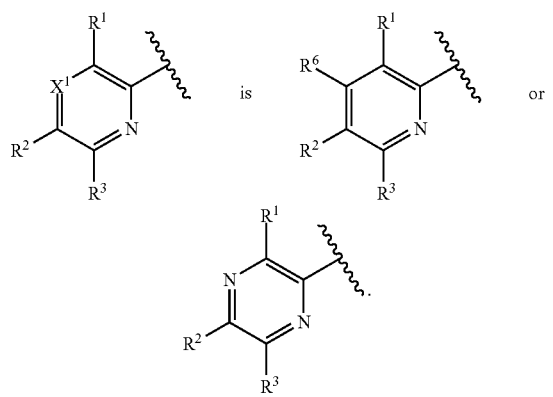

In another embodiment of the compound of formula (I), (II), (III), or (IV), or a pharmaceutically acceptable salt thereof, the group

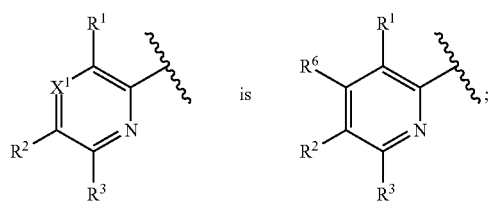

each of p and q is 2; $R^5$ is unsaturated 9-membered bicyclo-heterocyclic ring; and Y is $C_{0-4}$alk; and $R^1$ is $C_{0-4}$alk-$L^1$.

In another embodiment of the compound of formula (I), (II), (III), or (IV), or a pharmaceutically acceptable salt thereof, the group

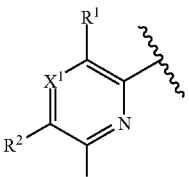 is 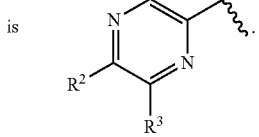.

In another embodiment of the compound of formula (I), (II), (III), or (IV), or a pharmaceutically acceptable salt thereof, m is 1 or 2.

In another embodiment of the compound of formula (I), (II), (III), or (IV), or a pharmaceutically acceptable salt thereof, p is 0, 1, or 2.

In another embodiment of the compound of formula (I), (II), (III), or (IV), or a pharmaceutically acceptable salt thereof, q is 0, 1, or 2.

In another embodiment of the compound of formula (I), (II), (III), or (IV), or a pharmaceutically acceptable salt thereof, $R^1$ is F, Cl, Br, I, —$OR^a$, —C(=O)—O—$R^a$, —C(=O)$NR^aR^b$, —$OR^c$, or —C(=O)$NR^aR^c$.

In another embodiment of the compound of formula (I), (II), (III), or (IV), or a pharmaceutically acceptable salt thereof, $R^1$ is a saturated, partially-saturated or unsaturated 4-, 5-, 6-, or 7-membered monocyclic ring, wherein each said ring contains 0, 1, 2, or 3 N atoms and 0, 1, or 2 O atoms, and wherein each said ring is substituted by 0, 1, 2 or 3 $R^9$ groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —$NR^aR^a$, $SR^a$, or oxo.

In another embodiment of the compound of formula (I), (II), (III), or (IV), or a pharmaceutically acceptable salt thereof, $R^1$ is a saturated or partially-saturated 5- to 6-membered monocyclic ring, wherein each said ring contains 0, 1, 2, or 3 N atoms and 0, 1, or 2 O atoms, and wherein each said ring is substituted by 0, 1, 2 or 3 $R^9$ groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —$NR^aR^a$, $SR^a$, or oxo.

In another embodiment of the compound of formula (I), (II), (III), or (IV), or a pharmaceutically acceptable salt thereof, $R^1$ is a saturated, partially-saturated or unsaturated 8-, 9-, 10-, 11-, or 12-membered bicyclic ring, wherein each said ring contains 0, 1, 2, or 3 N atoms and 0, 1, or 2 O atoms, and wherein each said ring is substituted by 0, 1, 2 or 3 $R^9$ groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —$NR^aR^a$, $SR^a$, or oxo.

In another embodiment of the compound of formula (I), (II), (III), or (IV), or a pharmaceutically acceptable salt thereof, $R^1$ is a nitrogen-linked saturated, partially-saturated or unsaturated 4-, 5-, 6-, or 7-membered monocyclic ring wherein each said ring contains 0, 1, 2, 3, or 4 N atoms and 0, 1, or 2 atoms selected from O and S; substituted by 0, 1, 2 or 3 $R^9$ groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —$NR^aR^a$, $SR^a$, or oxo.

In another embodiment of the compound of formula (I), (II), (III), or (IV), or a pharmaceutically acceptable salt thereof, $R^1$ is cyclohexyl, cyclopentyl, cyclopentenyl, cyclohexenyl, cycloheptyl, azetidinyl, phenyl, 2-pyridyl, 3-pyridyl, pyrazolyl, morpholinyl, pyrimidyl, piperazinyl, piperidinyl, dihydropyranyl, tetrahydropyranyl, tetrahydrofuranyl, tetrahydropyridinyl, tetrahydrothiopyranyl, oxaspiro[3.5]nonyl, azepanyl, oxepanyl, or quinolinyl, all of which are substituted by 0, 1, 2 or 3 $R^9$ groups selected from F, Cl, Br, $C_{1-6}$alk, $C_{1-4}$haloalk, —$OR^a$, CN, —C(=O)$R^b$, —C(=O)$OR^a$, —$SR^a$, or oxo.

In another embodiment of the compound of formula (I), (II), (III), or (IV), or a pharmaceutically acceptable salt thereof, $R^1$ is:

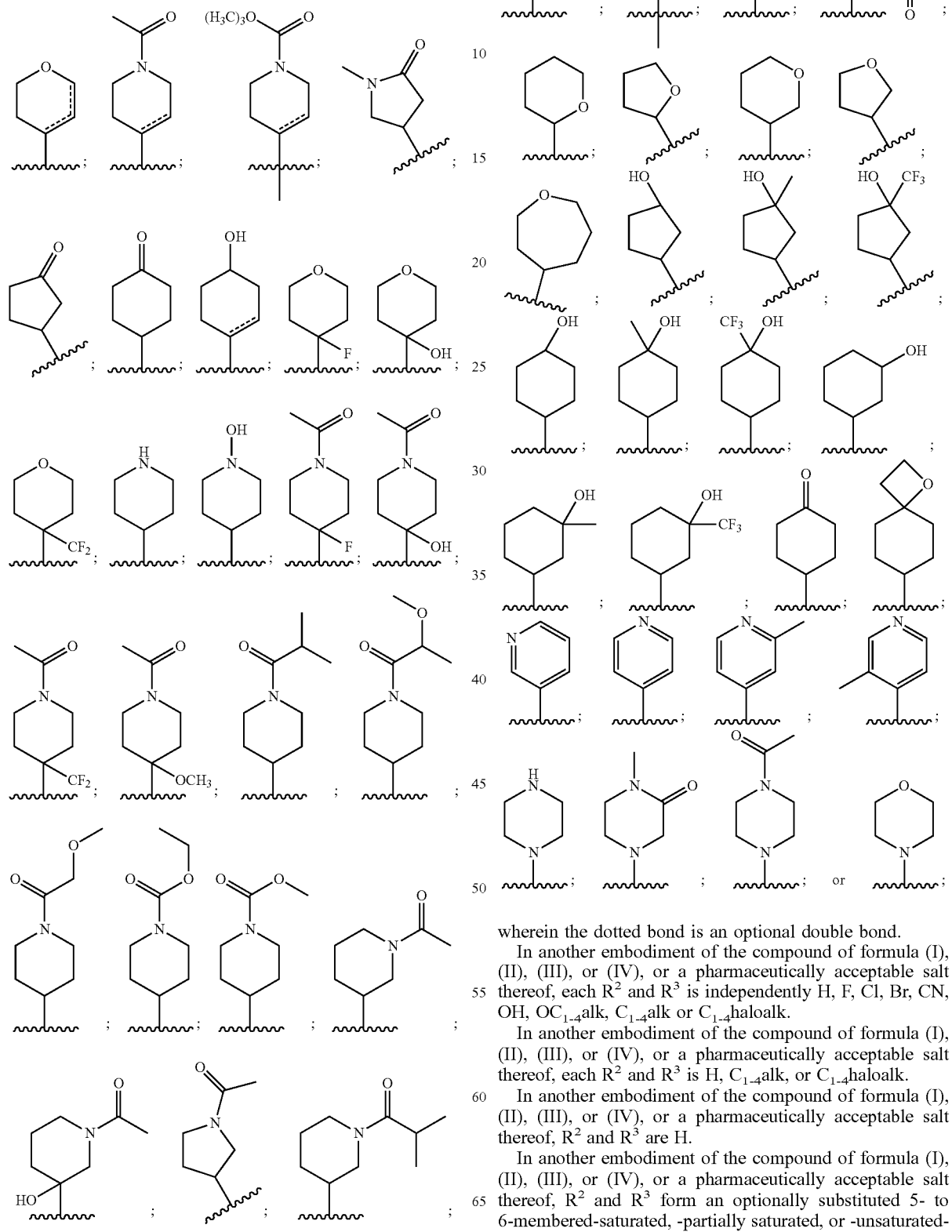

wherein the dotted bond is an optional double bond.

In another embodiment of the compound of formula (I), (II), (III), or (IV), or a pharmaceutically acceptable salt thereof, each $R^2$ and $R^3$ is independently H, F, Cl, Br, CN, OH, $OC_{1-4}$alk, $C_{1-4}$alk or $C_{1-4}$haloalk.

In another embodiment of the compound of formula (I), (II), (III), or (IV), or a pharmaceutically acceptable salt thereof, each $R^2$ and $R^3$ is H, $C_{1-4}$alk, or $C_{1-4}$haloalk.

In another embodiment of the compound of formula (I), (II), (III), or (IV), or a pharmaceutically acceptable salt thereof, $R^2$ and $R^3$ are H.

In another embodiment of the compound of formula (I), (II), (III), or (IV), or a pharmaceutically acceptable salt thereof, $R^2$ and $R^3$ form an optionally substituted 5- to 6-membered-saturated, -partially saturated, or -unsaturated-heterocyclic ring fused to the ring containing $X^1$.

In another embodiment of the compound of formula (I), (II), (III), or (IV), or a pharmaceutically acceptable salt thereof, $X^1$ is N.

In another embodiment of the compound of formula (I), (II), (III), or (IV), or a pharmaceutically acceptable salt thereof, $X^1$ is $CR^6$; wherein $R^6$ is H, F, Cl, Br, I, $OC_{1-4}$alk, or $C_{1-4}$alk.

In another embodiment of the compound of formula (I), (II), (III), or (IV), or a pharmaceutically acceptable salt thereof, $R^6$ is H or $C_{1-4}$alk.

In another embodiment of the compound of formula (I), (II), (III), or (IV), or a pharmaceutically acceptable salt thereof, $R^{4a}$ is H or $C_{1-4}$alk.

In another embodiment of the compound of formula (I), (II), (III), or (IV), or a pharmaceutically acceptable salt thereof, $R^{4b}$ is independently H, F, CN, $OC_{1-4}$alk, $C_{1-4}$alk or $C_{1-4}$haloalk.

In another embodiment of the compound of formula (I), (II), (III), or (IV), or a pharmaceutically acceptable salt thereof, each of $R^{4a}$ and $R^{4b}$ is H.

In another embodiment of the compound of formula (I), (II), (III), or (IV), or a pharmaceutically acceptable salt thereof, $R^5$ is pyridinyl.

In another embodiment of the compound of formula (I), (II), (III), or (IV), or a pharmaceutically acceptable salt thereof, $R^5$ is unsaturated 9- or 10-membered bicyclo-heterocyclic ring; wherein the ring is aromatic.

In another embodiment of the compound of formula (I), (II), (III), or (IV), or a pharmaceutically acceptable salt thereof, $R^5$ is unsaturated 9-membered bicyclo-heterocyclic ring; wherein the ring is aromatic.

In another embodiment of the compound of formula (I), (II), (III), or (IV), or a pharmaceutically acceptable salt thereof, $R^5$ is unsaturated 10-membered bicyclo-heterocyclic ring; wherein the ring is aromatic.

In another embodiment of the compound of formula (I), (II), (III), or (IV), or a pharmaceutically acceptable salt thereof, the group —Y—$R^5$ is:

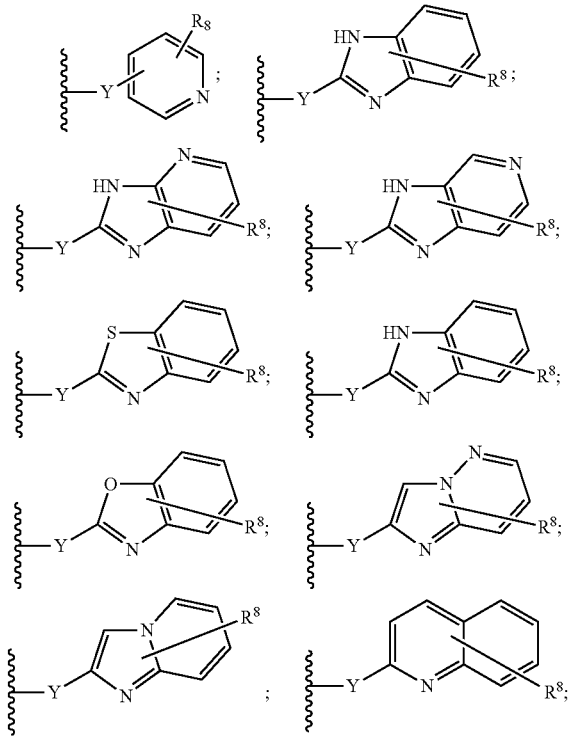

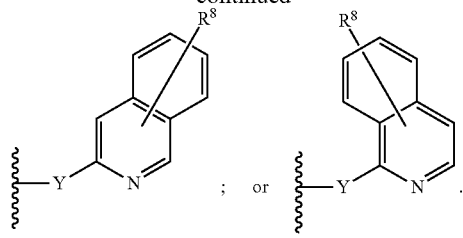

In another embodiment of the compound of formula (I), (II), (III), or (IV), or a pharmaceutically acceptable salt thereof, the group —Y—$R^5$ is:

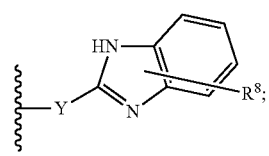

and Y is C(=O).

In another embodiment of the compound of formula (I), (II), (III), or (IV), or a pharmaceutically acceptable salt thereof, Y is —C(=O).

In another embodiment of the compound of formula (I), (II), (III), or (IV), or a pharmaceutically acceptable salt thereof, Y is a bond or $C_{1-3}$alk.

In another embodiment of the compound of formula (I), (II), (III), or (IV), or a pharmaceutically acceptable salt thereof, $R^5$ is:

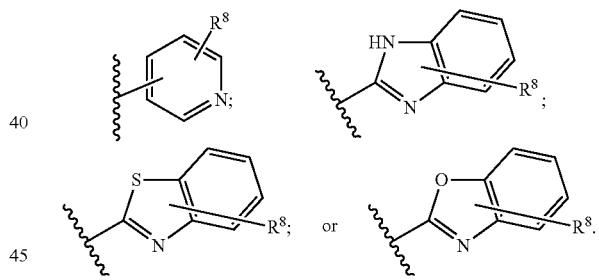

In another embodiment of the compound of formula (I), (II), (III), or (IV), or a pharmaceutically acceptable salt thereof, $R^8$ is independently H, F, CN, $OC_{1-4}$alk, $C_{1-4}$alk or $C_{1-4}$haloalk.

In another embodiment of the compound of formula (I), (II), (III), or (IV), or a pharmaceutically acceptable salt thereof, $R^8$ is H.

In another embodiment of the compound of formula (I), (II), (III), or (IV), or a pharmaceutically acceptable salt thereof, $R^a$ is H or $C_{1-6}$alk substituted by 0 or 1 —OH, —$OC_{1-4}$alk, —OC(=O)$C_{1-4}$alk, or —N($C_{1-4}$alk)$C_{1-4}$alk.

In another embodiment of the compound of formula (I), (II), (III), or (IV), or a pharmaceutically acceptable salt thereof, $R^c$ is a carbon-linked saturated, partially-saturated or unsaturated 3-, 4-5-, or 6-membered monocyclic ring containing 0 or 1 N atom and 0 or 1 atom selected from O and S, which is substituted by 0 or 1 $R^9$ groups selected from F, $C_{1-6}$alk, $C_{1-4}$haloalk, or —$OR^a$.

In another embodiment of the compound of formula (I), (II), (III), or (IV), or a pharmaceutically acceptable salt thereof, $R^c$ is a nitrogen-linked saturated, partially-saturated, or unsaturated 4-, 5-, 6- or 7-membered ring heterocycle containing the linking nitrogen and 0, 1 or 2 additional nitrogen atoms and containing 0 or 1 sulfur or oxygen atom, the heterocycle being substituted by 0, 1, 2 or 3 $R^9$ groups selected from F, Cl, Br, $C_{1-4}$alk, $C_{1-4}$haloalk, $-OC_{1-4}$alk, $-NH_2$, $-NHC_{1-4}$alk, $-N(C_{1-4}$alk$)C_{1-4}$alk, or oxo.

In another embodiment of the compound of formula (I), (II), (III), or (IV), or a pharmaceutically acceptable salt thereof, $R^c$ is a $C_{0-4}$alk-saturated, partially-saturated or unsaturated 3-, 5-, or 6-membered monocyclic ring containing 0 or 1 N atom and 0 or 1 atom selected from O and S, which is substituted by 0 or 1 $R^9$ groups selected from F, $C_{1-6}$alk, $C_{1-4}$haloalk, or $-OR^a$.

In another embodiment of the compound of formula (I), (II), (III), or (IV), or a pharmaceutically acceptable salt thereof, the compound has the following formula (IIIa):

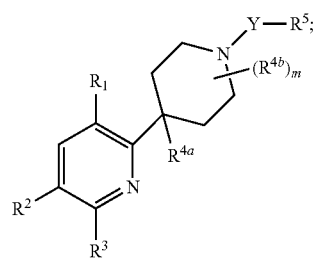

(IIIa)

wherein $R^1$ is F, Cl, Br, I, $C_{1-8}$alk, $C_{1-4}$haloalk, $-OR^a$, $-OR^c$, $-N(R^a)C(=O)R^b$, $-NR^aR^c$, $-N(R^c)C(=O)R^b$, $-N(R^a)C(=O)R^c$, or $C_{0-4}$alk-$L^1$; wherein said $C_{1-8}$alk group is substituted by 0, 1, 2 or 3 groups selected from halo, $C_{1-3}$haloalk, $-OH$, $-OC_{1-4}$alk, $-NH_2$, $-NHC_{1-4}$alk, $-OC(=O)C_{1-4}$alk, or $-N(C_{1-4}$alk$)C_{1-4}$alk; and $R^3$ is not methyl.

Another aspect of the current invention relates to compounds having the general structure of formula (IV):

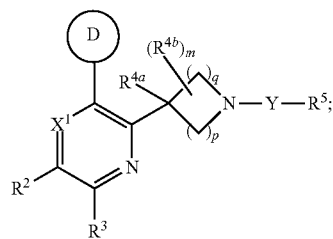

(IV)

or any pharmaceutically-acceptable salt thereof, wherein:
Ring D is -$L^1$;
$X^1$ is N or $CR^6$;
Y is a $C_{0-4}$alk, $-C(=O)$, SO, or $SO_2$;
each of $R^2$, $R^3$, $R^{4b}$, $R^6$ and $R^8$ is independently H, F, Cl, Br, I, CN, OH, $OC_{1-4}$alk, $C_{1-4}$alk or $C_{1-4}$haloalk;
or alternatively $R^2$ and $R^3$ can form an optionally substituted 5- to 6-membered-saturated, -partially saturated, or -unsaturated-heterocyclic ring fused to the ring containing $X^1$;
$R^{4a}$ is H, $C_{1-4}$alk, or $C_{1-4}$haloalk;
$R^5$ is pyridinyl or unsaturated 9- or 10-membered bicyclo-heterocyclic ring; wherein each $R^5$ is substituted by 0, 1, 2 or 3 $R^8$ groups; and is not substituted by oxo;

m is 1, 2, 3, or 4;
each of p and q is independently 0, 1, 2, 3, 4, 5, or 6; wherein the sum of p and q is 2 to 6;
$R^a$ is independently H or $R^b$;
$R^b$ is independently phenyl, benzyl, or $C_{1-6}$alk, wherein said phenyl, benzyl, and $C_{1-6}$alk are being substituted by 0, 1, 2 or 3 substituents selected from halo, $C_{1-4}$alk, $C_{1-3}$haloalk, $-OH$, $-OC_{1-4}$alk, $-NH_2$, $-NHC_{1-4}$alk, $-OC(=O)C_{1-4}$alk, and $-N(C_{1-4}$alk$)C_{1-4}$alk; and
each of L and $L^2$ is independently a carbon-linked or nitrogen-linked saturated, partially-saturated or unsaturated 3-, 4-, 5-, 6-, or 7-membered monocyclic ring or a saturated, partially-saturated or unsaturated 8-, 9-, 10-, 11-, or 12-membered bicyclic ring, wherein each said ring contains 0, 1, 2, 3, or 4 N atoms and 0, 1, or 2 atoms selected from O and S; wherein each $L^1$ and $L^2$ is independently substituted by 0, 1, 2 or 3 $R^9$ groups selected from F, Cl, Br, $C_{1-6}$alk, $C_{1-4}$haloalk, $-OR^a$, $-OC_{1-4}$haloalk, CN, $-C(=O)R^b$, $-C(=O)OR^a$, $-C(=O)NR^aR^a$, $-C(=NR^a)NR^aR^a$, $-OC(=O)R^b$, $-OC(=O)NR^aR^a$, $-OC_{2-6}$alkNR$^aR^a$, $-OC_{2-6}$alkOR$^a$, $-SR^a$, $-S(=O)R^b$, $-S(=O)_2R^b$, $-S(=O)_2NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-N(R^a)S(=O)_2NR^aR^a$, $-NR^aC_{2-6}$alkNR$^aR^a$, $-NR^aC_{2-6}$alkOR$^a$, $-C_{1-6}$alkNR$^aR^a$, $-C_{1-6}$alkOR$^a$, $-C_{1-6}$alkN(R$^a$)C(=O)R$^b$, $-C_{1-6}$alkOC(=O)R$^b$, $-C_{1-6}$alkC(=O)NR$^aR^a$, $-C_{1-6}$alkC(=O)OR$^a$ and oxo.

In another embodiment of the compound of formula (I), (II), (III), or (IV), or a pharmaceutically acceptable salt thereof, the group

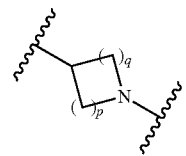

is azetidinyl, pyrrolidinyl, piperidinyl, or azepanyl; wherein each group is not substituted by oxo.

In another embodiment of the compound of formula (I), (II), (III), or (IV), or a pharmaceutically acceptable salt thereof, the group

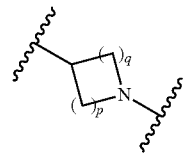

is azetidinyl; which is not substituted by oxo.

In another embodiment of the compound of formula (I), (II), (III), or (IV), or a pharmaceutically acceptable salt thereof, the group

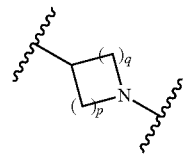

is pyrrolidinyl; which is not substituted by oxo.

In another embodiment of the compound of formula (I), (II), (III), or (IV), or a pharmaceutically acceptable salt thereof, the group

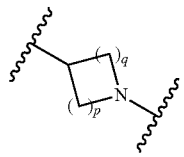

is piperidinyl; which is not substituted by oxo.

In another embodiment of the compound of formula (I), (II), (III), or (IV), or a pharmaceutically acceptable salt thereof, the group

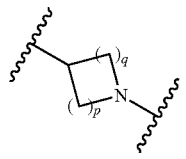

is azepanyl; which is not substituted by oxo.

In another embodiment of the compound of formula (I), (II), (III), or (IV), or a pharmaceutically acceptable salt thereof, the group

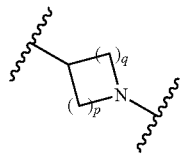

is azetidinyl or piperidinyl; which is not substituted by oxo; and Y is —C(=O), SO, or SO$_2$.

In another embodiment of the compound of formula (I), (II), (III), or (IV), or a pharmaceutically acceptable salt thereof, the group

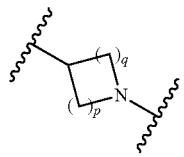

is azetidinyl; which is not substituted by oxo; and Y is —C(=O), SO, or SO$_2$.

In another embodiment of the compound of formula (I), (II), (III), or (IV), or a pharmaceutically acceptable salt thereof, ring D is a carbon-linked saturated, partially-saturated or unsaturated 4-, 5-, 6-, or 7-membered monocyclic ring, wherein each said ring contains 0, 1, 2, 3, or 4 N atoms and 0, 1, or 2 atoms selected from O and S; independently substituted by 0, 1, 2 or 3 R$^9$ groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$ and oxo.

In another embodiment of the compound of formula (I), (II), (III), or (IV), or a pharmaceutically acceptable salt thereof, ring D is a carbon-linked-saturated, partially-saturated or unsaturated 8-, 9-, 10-, 11-, or 12-membered bicyclic ring, wherein each said ring contains 0, 1, 2, 3, or 4 N atoms and 0, 1, or 2 atoms selected from O and S; independently substituted by 0, 1, 2 or 3 R$^9$ groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$ and oxo.

In another embodiment of the compound of formula (I), (II), (III), or (IV), or a pharmaceutically acceptable salt thereof, ring D is a nitrogen-linked saturated, partially-saturated or unsaturated 4-, 5-, 6-, or 7-membered monocyclic ring, wherein each said ring contains 0, 1, 2, 3, or 4 N atoms and 0, 1, or 2 atoms selected from O and S; independently substituted by 0, 1, 2 or 3 R$^9$ groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$ and oxo.

In another embodiment of the compound of formula (I), (II), (III), or (IV), or a pharmaceutically acceptable salt thereof, ring D is a nitrogen-linked-saturated, partially-saturated or unsaturated 8-, 9-, 10-, 11-, or 12-membered bicyclic ring, wherein each said ring contains 0, 1, 2, 3, or 4 N atoms and 0, 1, or 2 atoms selected from O and S; independently substituted by 0, 1, 2 or 3 R$^9$ groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$ and oxo.

In another embodiment of the compound of formula (I), (II), (III), or (IV), or a pharmaceutically acceptable salt thereof, ring D is cyclohexyl, cyclopentyl, cyclopentenyl, cyclohexenyl, or cycloheptyl.

In another embodiment of the compound of formula (I), (II), (III), or (IV), or a pharmaceutically acceptable salt thereof, ring D is azetidinyl, phenyl, 2-pyridyl, 3-pyridyl, pyrazolyl, morpholinyl, pyrimidyl, piperazinyl, piperidinyl, dihydropyranyl, tetrahydropyranyl, tetrahydrofuranyl, tetrahydropyridinyl, or tetrahydrothiopyranyl.

In another embodiment of the compound of formula (I), (II), (III), or (IV), or a pharmaceutically acceptable salt thereof, ring D is oxaspiro[3.5]nonyl, azepanyl, oxepanyl, or quinolinyl.

In another embodiment of the compound of formula (I), (II), (III), or (IV), or a pharmaceutically acceptable salt thereof, ring D is cyclohexyl, cyclopentyl, cyclopentenyl, cyclohexenyl, cycloheptyl, azetidinyl, phenyl, 2-pyridyl, 3-pyridyl, pyrazolyl, morpholinyl, pyrimidyl, piperazinyl, piperidinyl, dihydropyranyl, tetrahydropyranyl, tetrahydrofuranyl, tetrahydropyridinyl, tetrahydrothiopyranyl, oxaspiro[3.5]nonyl, azepanyl, oxepanyl, or quinolinyl, all of which are substituted by 0, 1, 2 or 3 $R^9$ groups selected from F, Cl, Br, $C_{1-6}$alk, $C_{1-4}$haloalk, —$OR^a$, CN, —C(=O)$R^b$, —C(=O)$OR^a$, —$NR^aR^a$, —$SR^a$, and oxo.

Another aspect of the invention relates to a compound of formula (IV) having the formula:

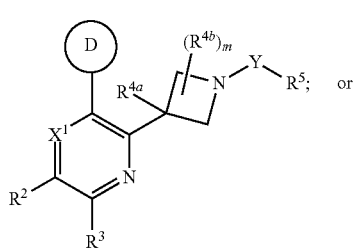
(IVa)

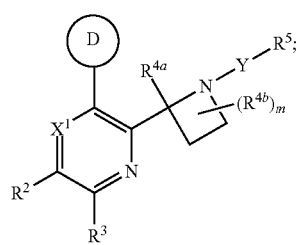
(IVb)

wherein m, Ring D, $R^2$, $R^3$, $R^{4a}$, $R^{4b}$, $R^5$, Y, and $X^1$ are defined above.

Another aspect of the invention relates to a compound having the formula:

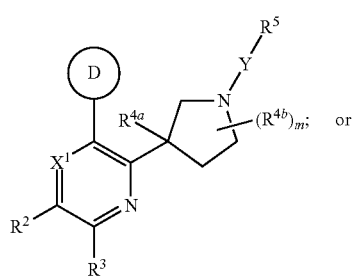
(IVc)

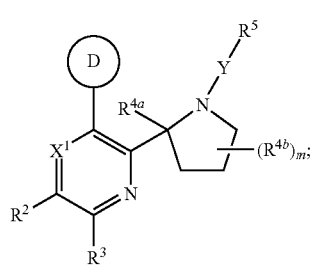
(IVd)

wherein m, Ring D, $R^2$, $R^3$, $R^{4a}$, $R^{4b}$, $R^5$, Y, and $X^1$ are defined above.

Another aspect of the invention relates to a compound having the formula:

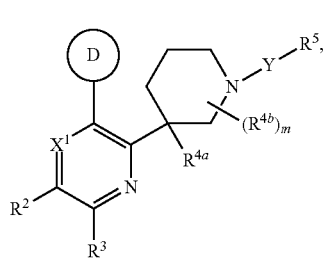
(IVe)

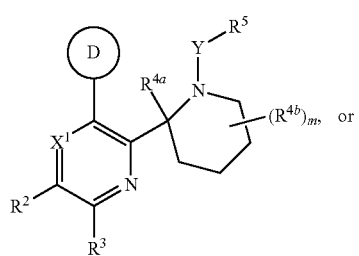
(IVf)

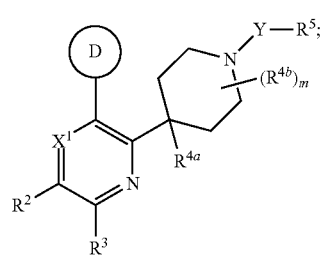
(IVg)

wherein m, Ring D, $R^2$, $R^3$, $R^{4a}$, $R^{4b}$, $R^5$, Y, and $X^1$ are defined above.

Another aspect of the invention relates to a method of treating conditions that may be treated with PDE10 inhibitors comprising the step of administering to a patient in need thereof a therapeutically effective amount of any one of the above compounds, or a pharmaceutically acceptable salt thereof.

In one embodiment of the method, said conditions is psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, or compulsions with pallidal disease.

In another embodiment of the method, said condition is schizophrenia, Huntington's disease, bipolar disorder, or obsessive-compulsive disorder.

In another embodiment of the method, said condition is schizophrenia.

Another aspect of the invention relates to a pharmaceutical composition comprising any one of the above compounds, or a pharmaceutically acceptable salt thereof, and a pharmaceutically-acceptable excipient.

Another aspect of the invention relates to the use of any one of the above compounds, or a pharmaceutically acceptable salt thereof, as a medicament.

Another aspect of the invention relates to the use of any one of the above compounds, or a pharmaceutically acceptable salt thereof in the manufacture of a medicament for the treatment of schizophrenia, bipolar disorder, or obsessive-compulsive disorder.

Another aspect of the invention relates to a compound, or a pharmaceutically acceptable salt thereof, which is tabulated below:

| Chemical Structure | Chemical Name |
|---|---|
| 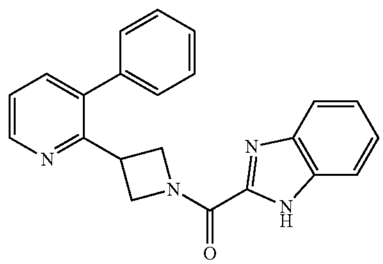 [SMILES: O=C(c1nc2ccccc2[nH]1)N1CC(c2ncccc2-c2ccccc2)C1] | (1H-Benzoimidazol-2-yl)-[3-(3-phenyl-pyridin-2-yl)-azetidin-1-yl]-methanone |
| 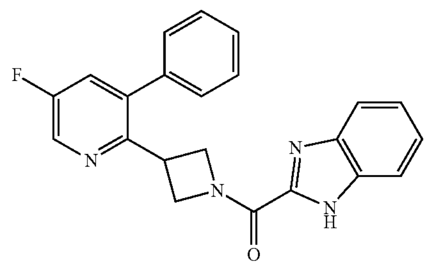 [SMILES: O=C(c1nc2ccccc2[nH]1)N1CC(c2ncc(F)cc2-c2ccccc2)C1] | (1H-Benzoimidazol-2-yl)-[3-(5-fluoro-3-phenyl-pyridin-2-yl)-azetidin-1-yl]-methanone |
| 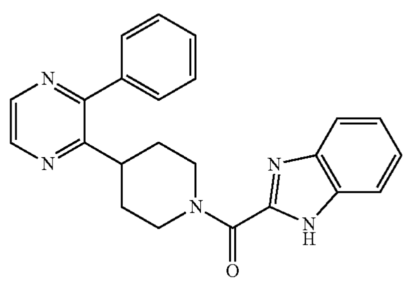 [SMILES: O=C(c1nc2ccccc2[nH]1)N1CCC(c2nccnc2-c2ccccc2)CC1] | (1H-benzoimidazol-2-yl)-[4-(3-phenyl-pyrazin-2-yl)-piperidin-1-yl]-methanone |
| 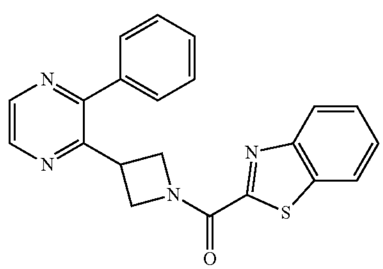 [SMILES: O=C(c1nc2ccccc2s1)N1CC(c2nccnc2-c2ccccc2)C1] | Benzothiazol-2-yl-[3-(3-phenyl-pyrazin-2-yl)-azetidin-1-yl]-methanone |
| 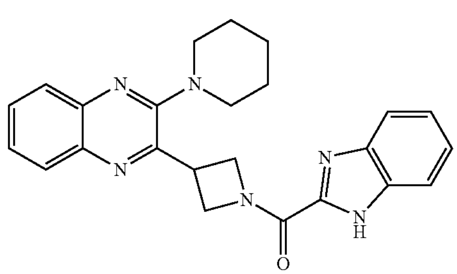 [SMILES: O=C(c1nc2ccccc2[nH]1)N1CC(c2nc3ccccc3nc2N2CCCCC2)C1] | (1H-Benzoimidazol-2-yl)-[3-(3-piperidin-1-yl-quinoxalin-2-yl)-azetidin-1-yl]-methanone |

| Chemical Structure | Chemical Name |
|---|---|
| 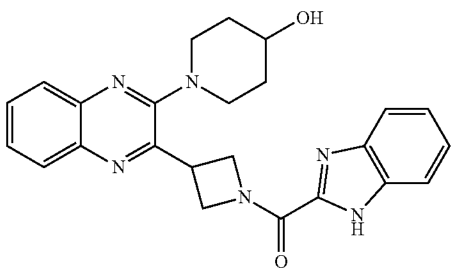 [SMILES: O=C(c1nc2ccccc2[nH]1)N1CC(c2nc3ccccc3nc2N2CCC(O)CC2)C1] | (1H-Benzoimidazol-2-yl)-{3-[3-(4-hydroxy-piperidin-1-yl)-quinoxalin-2-yl]-azetidin-1-yl}-methanone |
| 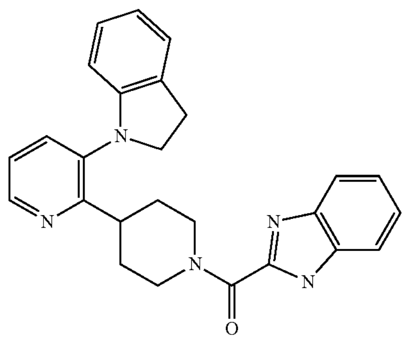 [SMILES: O=C(c1nc2ccccc2[nH]1)N1CCC(c2ncccc2N2CCc3ccccc32)CC1] | (1H-Benzoimidazol-2-yl)-[3-(2,3-dihydro-indol-1-yl)-3',4',5',6'-tetrahydro-2'H-[2,4']bipyridinyl-1'-yl]-methanone |
| 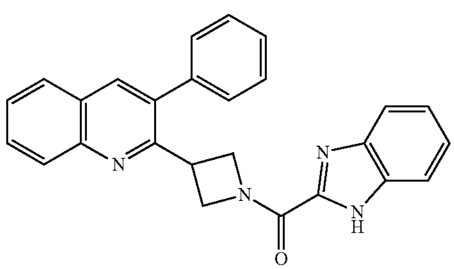 [SMILES: O=C(c1nc2ccccc2[nH]1)N1CC(c2nc3ccccc3cc2-c2ccccc2)C1] | (1H-Benzoimidazol-2-yl)-[3-(3-phenyl-quinolin-2-yl)-azetidin-1-yl]-methanone |
| 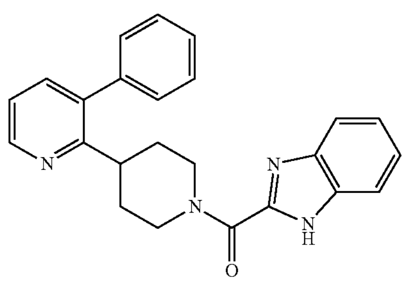 [SMILES: O=C(c1nc2ccccc2[nH]1)N1CCC(c2ncccc2-c2ccccc2)CC1] | (1H-Benzoimidazol-2-yl)-(3-phenyl 3',4',5',6'-tetrahydro-2'H-[2,4']bipyridinyl-1'-yl)-methanone |
| 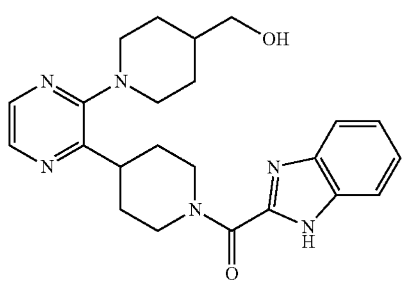 [SMILES: O=C(c1nc2ccccc2[nH]1)N1CCC(c2nccnc2N2CCC(CO)CC2)CC1] | (1H-Benzoimidazol-2-yl)-{4-[3-(4-hydroxymethyl-piperidin-1-yl)-pyrazin-2-yl]-piperidin-1-yl}-methanone |

| Chemical Structure | Chemical Name |
|---|---|
| 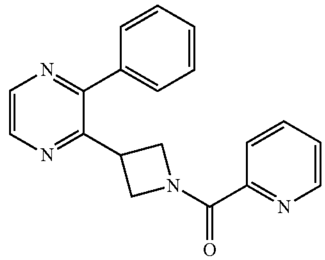 [SMILES: O=C(c1ccccn1)N1CC(c2nccnc2-c2ccccc2)C1] | (3-(3-phenylpyrazin-2-yl)azetidin-1-yl)(pyridin-2-yl)methanone |
| 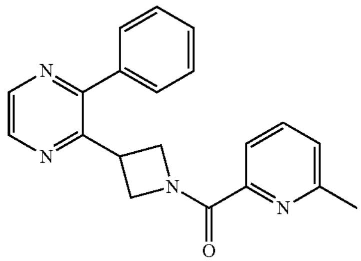 [SMILES: Cc1cccc(C(=O)N2CC(c3nccnc3-c3ccccc3)C2)n1] | (6-methylpyridin-2-yl)(3-(3-phenylpyrazin-2-yl)azetidin-1-yl)methanone |
| 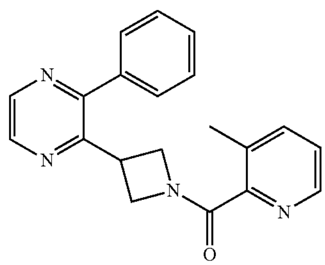 [SMILES: Cc1cccnc1C(=O)N1CC(c2nccnc2-c2ccccc2)C1] | (3-methylpyridin-2-yl)(3-(3-phenylpyrazin-2-yl)azetidin-1-yl)methanone |
| 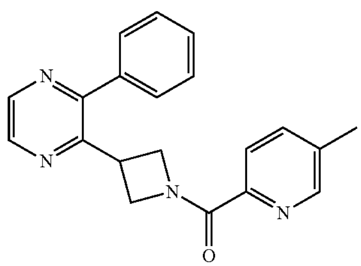 [SMILES: Cc1ccc(C(=O)N2CC(c3nccnc3-c3ccccc3)C2)nc1] | (5-methylpyridin-2-yl)(3-(3-phenylpyrazin-2-yl)azetidin-1-yl)methanone |
| 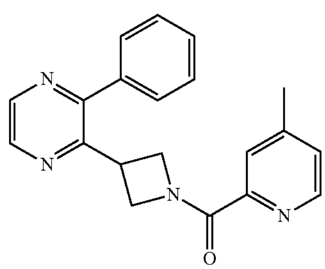 [SMILES: Cc1ccnc(C(=O)N2CC(c3nccnc3-c3ccccc3)C2)c1] | (4-methylpyridin-2-yl)(3-(3-phenylpyrazin-2-yl)azetidin-1-yl)methanone |
| 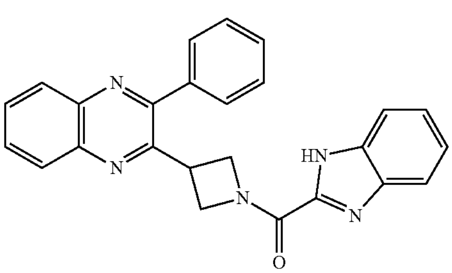 [SMILES: O=C(c1nc2ccccc2[nH]1)N1CC(c2nc3ccccc3nc2-c2ccccc2)C1] | (1H-Benzoimidazol-2-yl)-[3-(3-phenyl-quinoxalin-2-yl)-azetidin-1-yl]-methanone |

| Chemical Structure | Chemical Name |
| --- | --- |
| 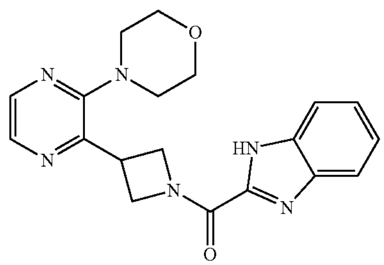 [SMILES: O=C(c1nc2ccccc2[nH]1)N1CC(c2nccnc2N2CCOCC2)C1] | (1H-Benzoimidazol-2-yl)-[3-(3-morpholin-4-yl-pyrazin-2-yl)-azetidin-1-yl]-methanone |
| 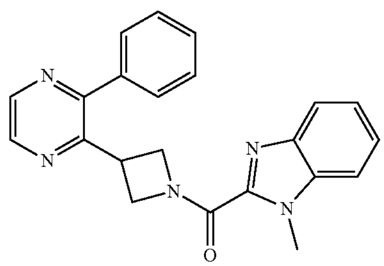 [SMILES: Cn1c(C(=O)N2CC(c3nccnc3-c3ccccc3)C2)nc2ccccc21] | (1-Methyl-1H-benzoimidazol-2-yl)-[3-(3-phenyl-pyrazin-2-yl)-azetidin-1-yl]-methanone |
| 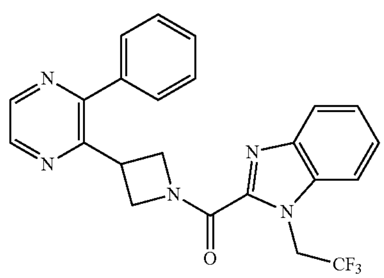 [SMILES: O=C(c1nc2ccccc2n1CC(F)(F)F)N1CC(c2nccnc2-c2ccccc2)C1] | [3-(3-Phenyl-pyrazin-2-yl)-azetidin-1-yl]-[1-(2,2,2-trifluoro-ethyl)-1H-benzoimidazol-2-yl]-methanone |
| 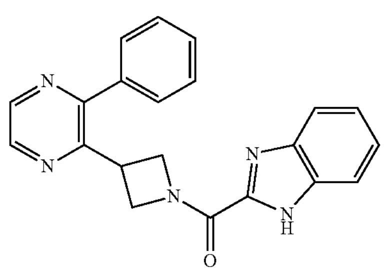 [SMILES: O=C(c1nc2ccccc2[nH]1)N1CC(c2nccnc2-c2ccccc2)C1] | (1H-Benzoimidazol-2-yl)-[3-(3-phenyl-pyrazin-2-yl)-azetidin-1-yl]-methanone |
| 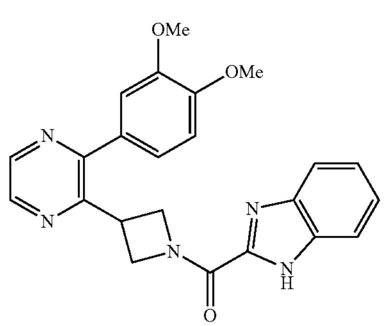 [SMILES: COc1ccc(-c2nccnc2C2CN(C(=O)c3nc4ccccc4[nH]3)C2)cc1OC] | (1H-Benzoimidazol-2-yl)-{3-[3-(3,4-dimethoxy-phenyl)-pyrazin-2-yl]-azetidin-1-yl}-methanone |

| Chemical Structure | Chemical Name |
| --- | --- |
| 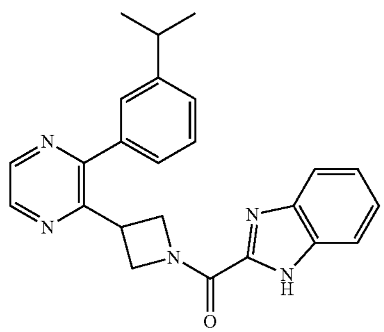 [SMILES: CC(C)c1cccc(-c2nccnc2C2CN(C(=O)c3nc4ccccc4[nH]3)C2)c1] | (1H-Benzoimidazol-2-yl)-{3-[3-(3-isopropyl-phenyl)-pyrazin-2-yl]-azetidin-1-yl}-methanone |
| 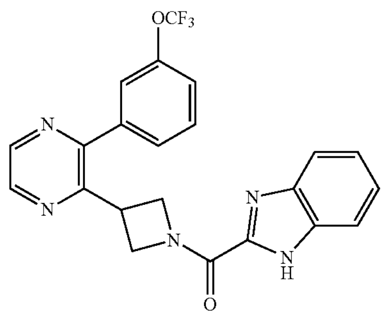 [SMILES: O=C(c1nc2ccccc2[nH]1)N1CC(c2nccnc2-c2cccc(OC(F)(F)F)c2)C1] | (1H-Benzoimidazol-2-yl)-{3-[3-(3-trifluoromethoxy-phenyl)-pyrazin-2-yl]-azetidin-1-yl}-methanone |
| 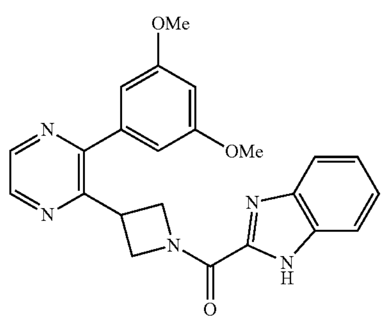 [SMILES: COc1cc(OC)cc(-c2nccnc2C2CN(C(=O)c3nc4ccccc4[nH]3)C2)c1] | 1H-Benzoimidazol-2-yl)-{3-[3-(3,5-dimethoxy-phenyl)-pyrazin-2-yl]-azetidin-1-yl}-methanone |
| 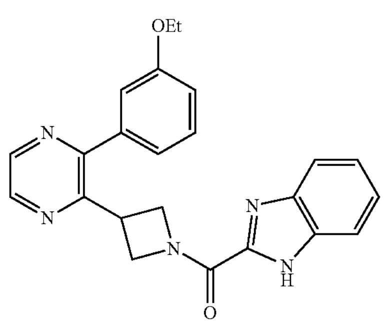 [SMILES: CCOc1cccc(-c2nccnc2C2CN(C(=O)c3nc4ccccc4[nH]3)C2)c1] | (1H-Benzoimidazol-2-yl)-{3-[3-(3-ethoxy-phenyl)-pyrazin-2-yl]-azetidin-1-yl}-methanone |

| Chemical Structure | Chemical Name |
|---|---|
| 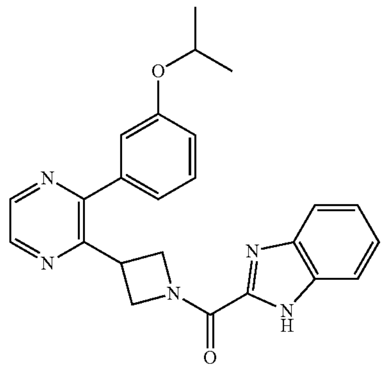 [SMILES: CC(C)Oc1cccc(-c2nccnc2C2CN(C(=O)c3nc4ccccc4[nH]3)C2)c1] | (1H-Benzoimidazol-2-yl)-{3-[3-(3-isopropoxy-phenyl)-pyrazin-2-yl]-azetidin-1-yl}-methanone |
| 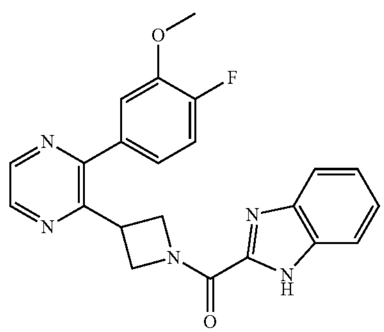 [SMILES: COc1cc(-c2nccnc2C2CN(C(=O)c3nc4ccccc4[nH]3)C2)ccc1F] | (1H-Benzoimidazol-2-yl)-{3-[3-(3-fluoro-5-methoxy-phenyl)-pyrazin-2-yl]-azetidin-1-yl}-methanone |
| 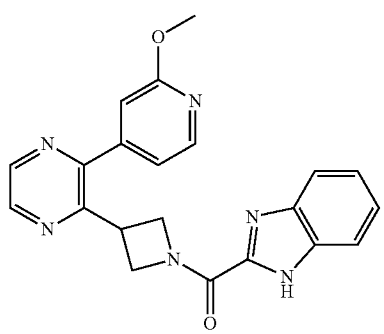 [SMILES: COc1cc(-c2nccnc2C2CN(C(=O)c3nc4ccccc4[nH]3)C2)ccn1] | (1H-Benzoimidazol-2-yl)-{3-[3-(2-methoxy-pyridin-4-yl)-pyrazin-2-yl]-azetidin-1-yl}-methanone |
| 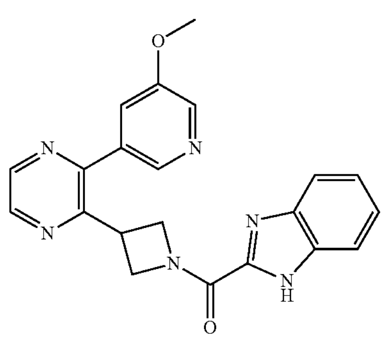 [SMILES: COc1cncc(-c2nccnc2C2CN(C(=O)c3nc4ccccc4[nH]3)C2)c1] | (1H-Benzoimidazol-2-yl)-{3-[3-(5-methoxy-pyridin-3-yl)-pyrazin-2-yl]-azetidin-1-yl}-methanone |

| Chemical Structure | Chemical Name |
| --- | --- |
| 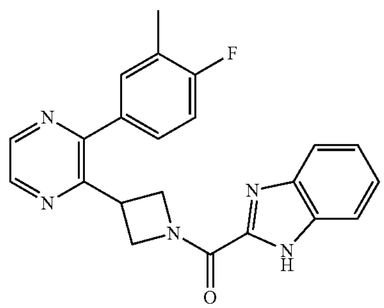 [SMILES: Cc1cc(-c2nccnc2C2CN(C(=O)c3nc4ccccc4[nH]3)C2)ccc1F] | (1H-benzo[d]imidazol-2-yl)(3-(3-(4-fluoro-3-methylphenyl)pyrazin-2-yl)azetidin-1-yl)methanone |
| 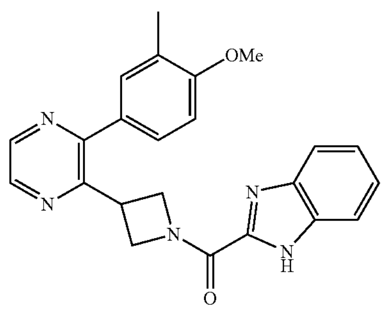 [SMILES: COc1ccc(-c2nccnc2C2CN(C(=O)c3nc4ccccc4[nH]3)C2)cc1C] | (1H-Benzoimidazol-2-yl)-{3-[3-(4-methoxy-3-methyl-phenyl)-pyrazin-2-yl]-azetidin-1-yl}-methanone |
| 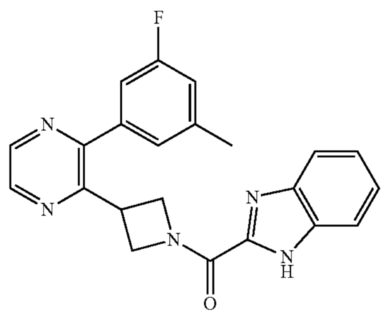 [SMILES: Cc1cc(F)cc(-c2nccnc2C2CN(C(=O)c3nc4ccccc4[nH]3)C2)c1] | (1H-Benzoimidazol-2-yl)-{3-[3-(3-fluoro-5-methyl-phenyl)-pyrazin-2-yl]-azetidin-1-yl}-methanone |
| 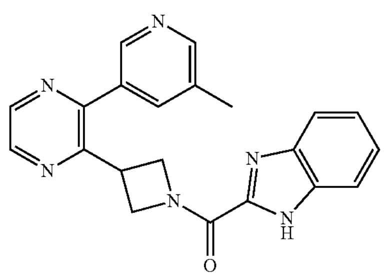 [SMILES: Cc1cncc(-c2nccnc2C2CN(C(=O)c3nc4ccccc4[nH]3)C2)c1] | (1H-Benzoimidazol-2-yl)-{3-[3-(5-methyl-pyridin-3-yl)-pyrazin-2-yl]-azetidin-1-yl}-methanone |
| 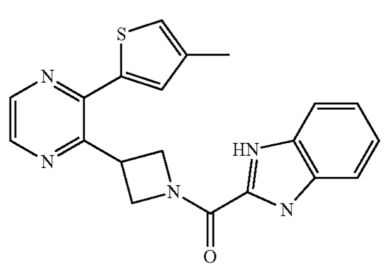 [SMILES: Cc1csc(-c2nccnc2C2CN(C(=O)c3nc4ccccc4[nH]3)C2)c1] | (1H-Benzoimidazol-2-yl)-{3-[3-(4-methyl-thiophen-2-yl)-pyrazin-2-yl]-azetidin-1-yl}-methanone |

| Chemical Structure | Chemical Name |
|---|---|
| 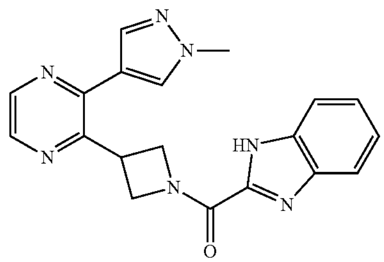 [SMILES: Cn1cc(-c2nccnc2C2CN(C(=O)c3nc4ccccc4[nH]3)C2)cn1] | (1H-Benzoimidazol-2-yl)-{3-[3-(1-methyl-1H-pyrazol-4-yl)-pyrazin-2-yl]-azetidin-1-yl}-methanone |
| 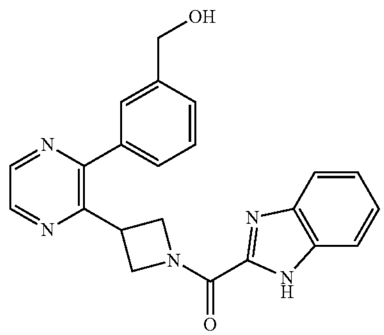 [SMILES: O=C(c1nc2ccccc2[nH]1)N1CC(c2nccnc2-c2cccc(CO)c2)C1] | (1H-Benzoimidazol-2-yl)-{3-[3-(3-hydroxymethyl-phenyl)-pyrazin-2-yl]-azetidin-1-yl}-methanone |
| 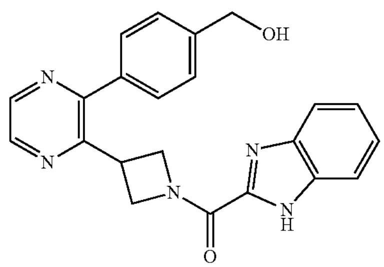 [SMILES: O=C(c1nc2ccccc2[nH]1)N1CC(c2nccnc2-c2ccc(CO)cc2)C1] | (1H-Benzoimidazol-2-yl)-{3-[3-(4-hydroxymethyl-phenyl)-pyrazin-2-yl]-azetidin-1-yl}-methanone |
| 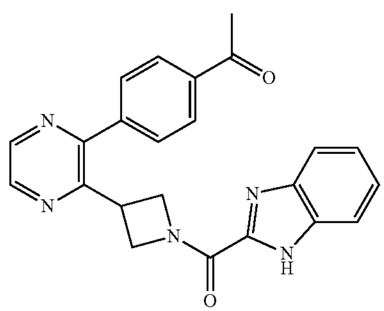 [SMILES: CC(=O)c1ccc(-c2nccnc2C2CN(C(=O)c3nc4ccccc4[nH]3)C2)cc1] | 1-(4-{3-[1-(1H-Benzoimidazole-2-carbonyl)-azetidin-3-yl]-pyrazin-2-yl}-phenyl)-ethanone |
| 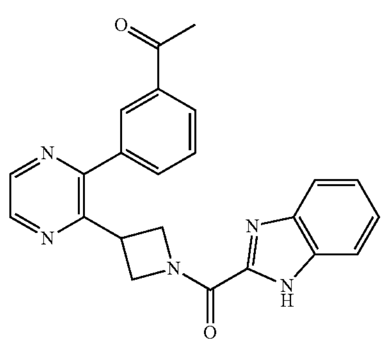 [SMILES: CC(=O)c1cccc(-c2nccnc2C2CN(C(=O)c3nc4ccccc4[nH]3)C2)c1] | 1-(3-{3-[1-(1H-Benzoimidazole-2-carbonyl)-azetidin-3-yl]-pyrazin-2-yl}-phenyl)-ethanone |

| Chemical Structure | Chemical Name |
|---|---|
| 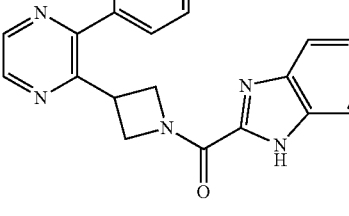 | (1H-Benzoimidazol-2-yl)-{3-[3-(3-methoxymethyl-phenyl)-pyrazin-2-yl]-azetidin-1-yl}-methanone |
| 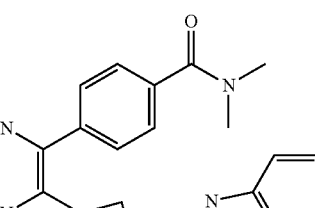 | 4-{3-[1-(1H-Benzoimidazole-2-carbonyl)-azetidin-3-yl]-pyrazin-2-yl}-N,N-dimethyl-benzamide |
| 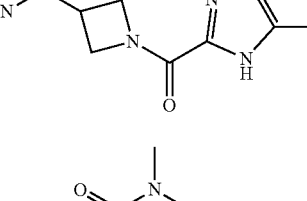 | 3-{3-[1-(1H-Benzoimidazole-2-carbonyl)-azetidin-3-yl]-pyrazin-2-yl}-N,N-dimethyl-benzamide |
| 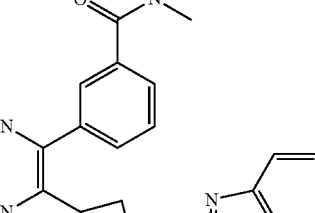 | (1H-benzo[d]imidazol-2-yl)(3-(3-(pyridin-4-yl)pyrazin-2-yl)azetidin-1-yl)methanone |
| 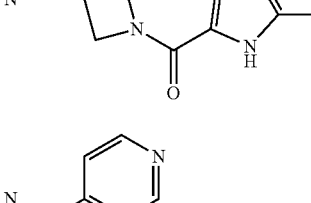 | (7-chloro-1H-benzo[d]imidazol-2-yl)(3-(3-(pyridin-3-yl)pyrazin-2-yl)azetidin-1-yl)methanone |

| Chemical Structure | Chemical Name |
| --- | --- |
| 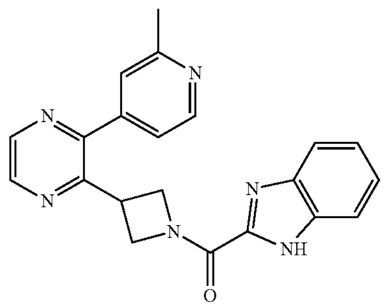 [SMILES: Cc1cc(-c2nccnc2C2CN(C(=O)c3nc4ccccc4[nH]3)C2)ccn1] | (1H-benzo[d]imidazol-2-yl)(3-(3-(2-methylpyridin-4-yl)pyrazin-2-yl)azetidin-1-yl)methanone |
| 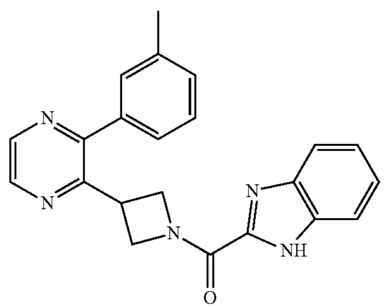 | (1H-benzo[d]imidazol-2-yl)(3-(3-(m-tolyl)pyrazin-2-yl)azetidin-1-yl)methanone |
| 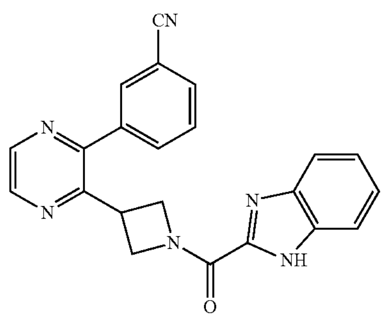 [SMILES: N#Cc1cccc(-c2nccnc2C2CN(C(=O)c3nc4ccccc4[nH]3)C2)c1] | 3-(3-(1-(1H-benzo[d]imidazole-2-carbonyl)azetidin-3-yl)pyrazin-2-yl)benzonitrile |
| 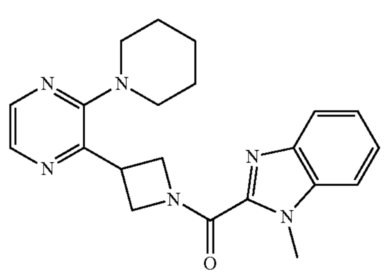 [SMILES: Cn1c(C(=O)N2CC(c3nccnc3N3CCCCC3)C2)nc2ccccc21] | (1-Methyl-1H-benzoimidazol-2-yl)-[3-(3-piperidin-1-yl-pyrazin-2-yl)-azetidin-1-yl]-methanone |
| 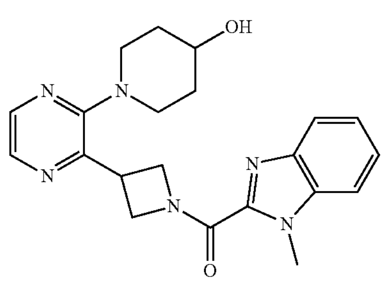 [SMILES: Cn1c(C(=O)N2CC(c3nccnc3N3CCC(O)CC3)C2)nc2ccccc21] | {3-[3-(4-Hydroxy-piperidin-1-yl)-pyrazin-2-yl]-azetidin-1-yl}-(1-methyl-1H-benzoimidazol-2-yl)-methanone |

| Chemical Structure | Chemical Name |
|---|---|
| 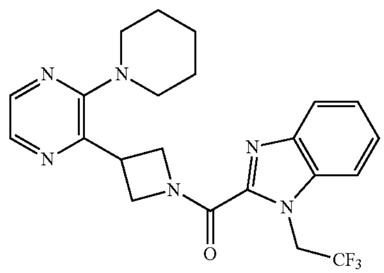 [SMILES: O=C(c1nc2ccccc2n1CC(F)(F)F)N1CC(c2nccnc2N2CCCCC2)C1] | [3-(3-Piperidin-1-yl-pyrazin-2-yl)-azetidin-1-yl]-[1-(2,2,2-trifluoro-ethyl)-1H-benzoimidazol-2-yl]-methanone |
| 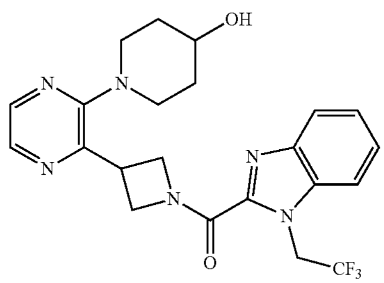 [SMILES: O=C(c1nc2ccccc2n1CC(F)(F)F)N1CC(c2nccnc2N2CCC(O)CC2)C1] | {3-[3-(4-Hydroxy-piperidin-1-yl)-pyrazin-2-yl]-azetidin-1-yl}-[1-(2,2,2-trifluoro-ethyl)-1H-benzoimidazol-2-yl]-methanone |
| 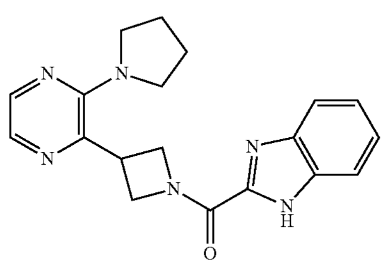 [SMILES: O=C(c1nc2ccccc2[nH]1)N1CC(c2nccnc2N2CCCC2)C1] | (1H-Benzoimidazol-2-yl))-[3-(3-pyrrolidin-1-yl-pyrazin-2-yl)-azetidin-1-yl]-methanone |
| 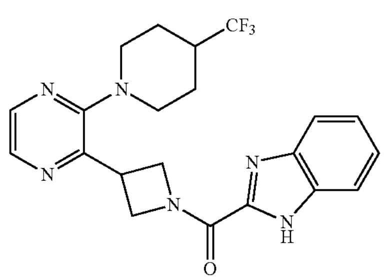 [SMILES: O=C(c1nc2ccccc2[nH]1)N1CC(c2nccnc2N2CCC(C(F)(F)F)CC2)C1] | (1H-Benzoimidazol-2-yl)-{3-[3-(4-trifluoromethyl-piperidin-1-yl)-pyrazin-2-yl]-azetidin-1-yl}-methanone |
| 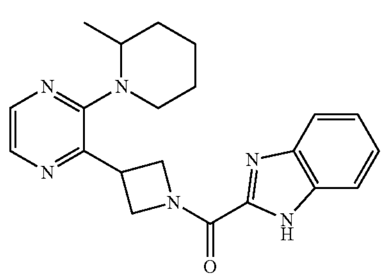 [SMILES: CC1CCCCN1c1nccnc1C1CN(C(=O)c2nc3ccccc3[nH]2)C1] | (R & S)-(1H-Benzoimidazol-2-yl)-{3-[3-(2-methyl-piperidin-1-yl)-pyrazin-2-yl]-azetidin-1-yl}-methanone |

| Chemical Structure | Chemical Name |
| --- | --- |
| 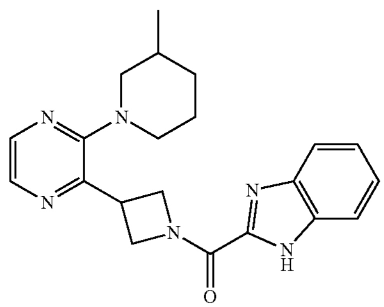 [SMILES: CC1CCCN(c2nccnc2C2CN(C(=O)c3nc4ccccc4[nH]3)C2)C1] | (1H-Benzoimidazol-2-yl)-{3-[3-(3-methyl-piperidin-1-yl)-pyrazin-2-yl]-azetidin-1-yl}-methanone |
| 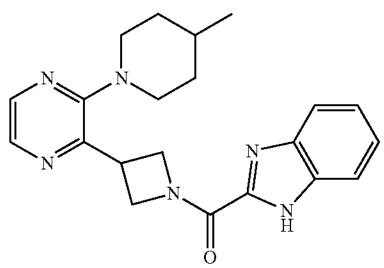 [SMILES: CC1CCN(c2nccnc2C2CN(C(=O)c3nc4ccccc4[nH]3)C2)CC1] | (1H-Benzoimidazol-2-yl)-{3-[3-(4-methyl-piperidin-1-yl)-pyrazin-2-yl]-azetidin-1-yl}-methanone |
| 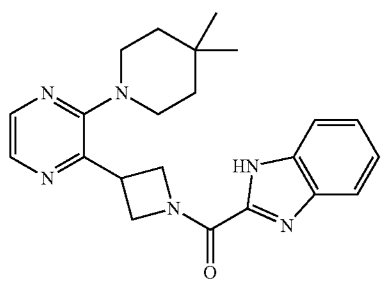 [SMILES: CC1(C)CCN(c2nccnc2C2CN(C(=O)c3nc4ccccc4[nH]3)C2)CC1] | (1H-Benzoimidazol-2-yl)-{3-[3-(4,4-dimethyl-piperidin-1-yl)-pyrazin-2-yl]-azetidin-1-yl}-methanone |
| 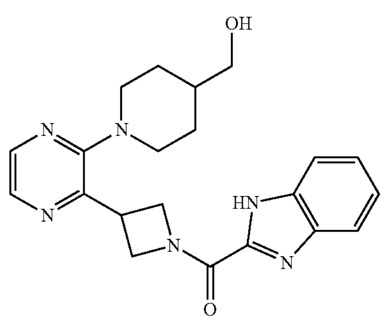 [SMILES: O=C(c1nc2ccccc2[nH]1)N1CC(c2nccnc2N2CCC(CO)CC2)C1] | (1H-Benzoimidazol-2-yl)-{3-[3-(4-hydroxymethyl-piperidin-1-yl)-pyrazin-2-yl]-azetidin-1-yl}-methanone |
| 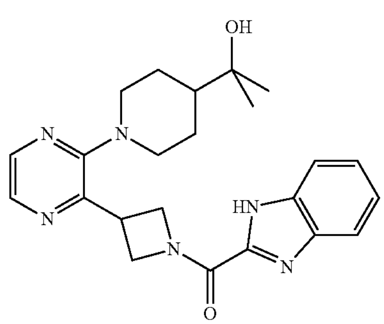 [SMILES: CC(C)(O)C1CCN(c2nccnc2C2CN(C(=O)c3nc4ccccc4[nH]3)C2)CC1] | (1H-Benzoimidazol-2-yl)-(3-{3-[4-(1-hydroxy-1-methyl-ethyl)-piperidin-1-yl]-pyrazin-2-yl}-azetidin-1-yl)-methanone |

-continued

| Chemical Structure | Chemical Name |
|---|---|
| 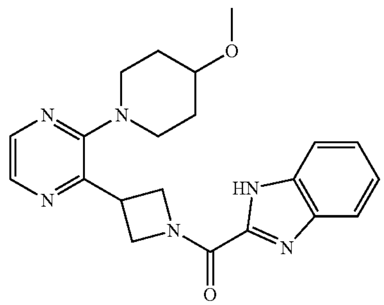 [SMILES: COC1CCN(c2nccnc2C2CN(C(=O)c3nc4ccccc4[nH]3)C2)CC1] | (1H-Benzoimidazol-2-yl)-(3-{3-[4-(1-hydroxy-1-methyl-ethyl)-piperidin-1-yl]-pyrazin-2-yl}-azetidin-1-yl)-methanone |
| 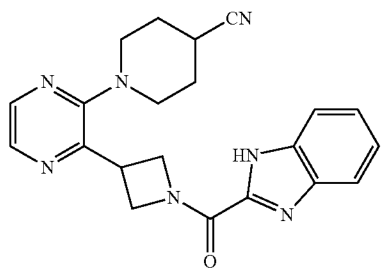 [SMILES: N#CC1CCN(c2nccnc2C2CN(C(=O)c3nc4ccccc4[nH]3)C2)CC1] | 1-{3-[1-(1H-Benzoimidazole-2-carbonyl)-azetidin-3-yl]-pyrazin-2-yl}-piperidine-4-carbonitrile |
| 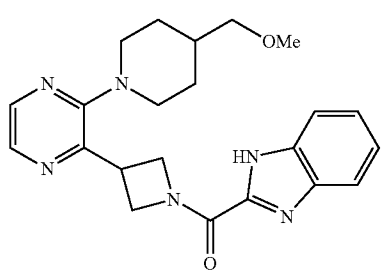 [SMILES: COCC1CCN(c2nccnc2C2CN(C(=O)c3nc4ccccc4[nH]3)C2)CC1] | (1H-Benzoimidazol-2-yl)-{3-[3-(4-methoxymethyl-piperidin-1-yl)-pyrazin-2-yl]-azetidin-1-yl}-methanone |
| 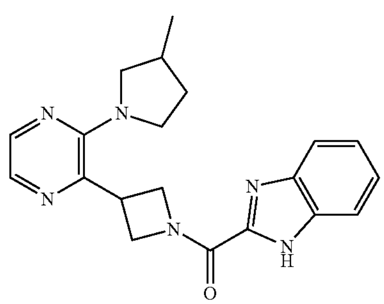 [SMILES: CC1CCN(c2nccnc2C2CN(C(=O)c3nc4ccccc4[nH]3)C2)C1] | (R & S)-(1H-Benzoimidazol-2-yl)-{3-[3-(3-methyl-pyrrolidin-1-yl)-pyrazin-2-yl]-azetidin-1-yl}-methanone |
| 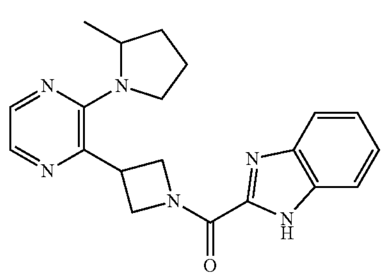 [SMILES: CC1CCCN1c1nccnc1C1CN(C(=O)c2nc3ccccc3[nH]2)C1] | (R & S)-(1H-Benzoimidazol-2-yl)-{3-[3-(2-methyl-pyrrolidin-1-yl)-pyrazin-2-yl]-azetidin-1-yl}-methanone |

| Chemical Structure | Chemical Name |
|---|---|
| 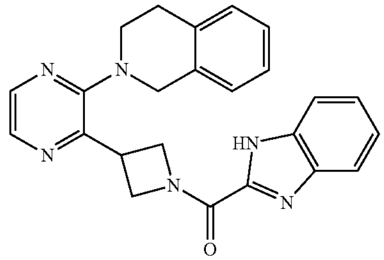 [SMILES: O=C(c1nc2ccccc2[nH]1)N1CC(c2nccnc2N2CCc3ccccc3C2)C1] | (1H-Benzoimidazol-2-yl)-{3-[3-(3,4-dihydro-1H-isoquinolin-2-yl)-pyrazin-2-yl]-azetidin-1-yl}-methanone |
| | (1H-Benzoimidazol-2-yl)-{3-[3-(1,3-dihydro-isoindol-2-yl)-pyrazin-2-yl]-azetidin-1-yl}-methanone |
| 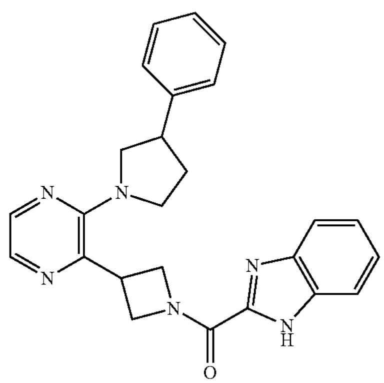 [SMILES: O=C(c1nc2ccccc2[nH]1)N1CC(c2nccnc2N2CCC(c3ccccc3)C2)C1] | (R & S)-(1H-Benzoimidazol-2-yl)-{3-[3-(3-phenyl-pyrrolidin-1-yl)-pyrazin-2-yl]-azetidin-1-yl}-methanone |
| 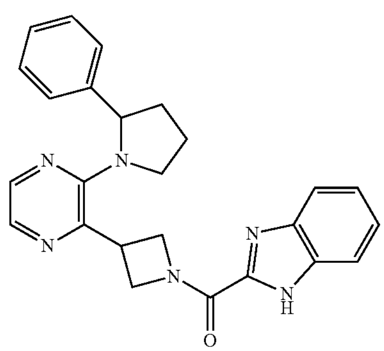 [SMILES: O=C(c1nc2ccccc2[nH]1)N1CC(c2nccnc2N2CCCC2c2ccccc2)C1] | (R & S)-(1H-Benzoimidazol-2-yl)-{3-[3-(2-phenyl-pyrrolidin-1-yl)-pyrazin-2-yl]-azetidin-1-yl}-methanone |
| 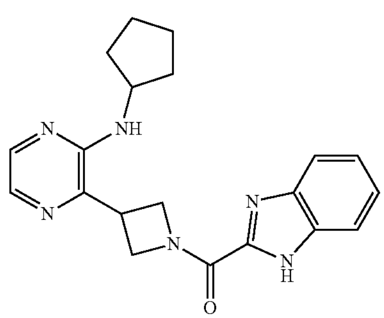 [SMILES: O=C(c1nc2ccccc2[nH]1)N1CC(c2nccnc2NC2CCCC2)C1] | (1H-Benzoimidazol-2-yl)-[3-(3-cyclopentylamino-pyrazin-2-yl)-azetidin-1-yl]-methanone |

| Chemical Structure | Chemical Name |
| --- | --- |
| 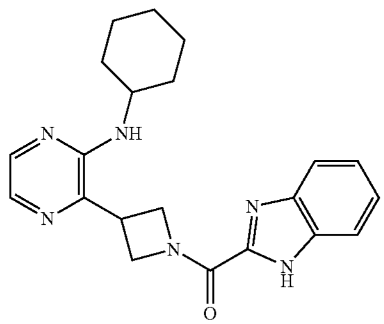 [SMILES: O=C(c1nc2ccccc2[nH]1)N1CC(c2nccnc2NC2CCCCC2)C1] | (1H-Benzoimidazol-2-yl)-[3-(3-cyclohexylamino-pyrazin-2-yl)-azetidin-1-yl]-methanone |
| 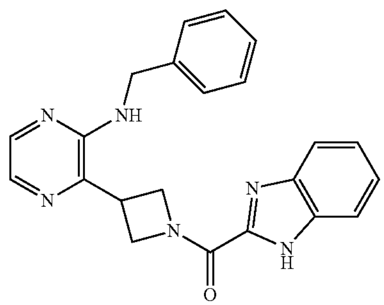 [SMILES: O=C(c1nc2ccccc2[nH]1)N1CC(c2nccnc2NCc2ccccc2)C1] | (1H-Benzoimidazol-2-yl)-[3-(3-benzylamino-pyrazin-2-yl)-azetidin-1-yl]-methanone |
| 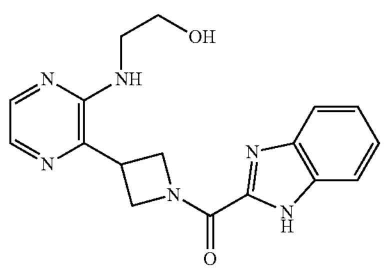 [SMILES: O=C(c1nc2ccccc2[nH]1)N1CC(c2nccnc2NCCO)C1] | (1H-Benzoimidazol-2-yl)-{3-[3-(2-hydroxy-ethylamino)-pyrazin-2-yl]-azetidin-1-yl}-methanone |
| 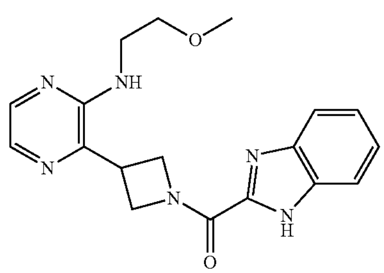 [SMILES: COCCNc1nccnc1C1CN(C(=O)c2nc3ccccc3[nH]2)C1] | (1H-benzo[d]imidazol-2-yl)(3-(3-((2-methoxyethyl)amino)pyrazin-2-yl)azetidin-1-yl)methanone |
| 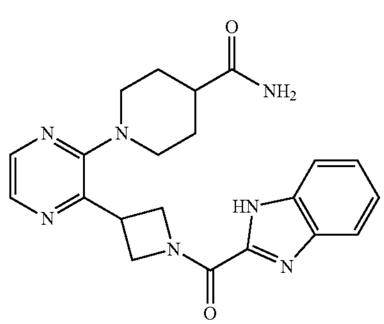 [SMILES: NC(=O)C1CCN(c2nccnc2C2CN(C(=O)c3nc4ccccc4[nH]3)C2)CC1] | 1-{3-[1-(1H-Benzoimidazole-2-carbonyl)-azetidin-3-yl]-pyrazin-2-yl}-piperidine-4-carboxylic acid amide |

| Chemical Structure | Chemical Name |
| --- | --- |
| 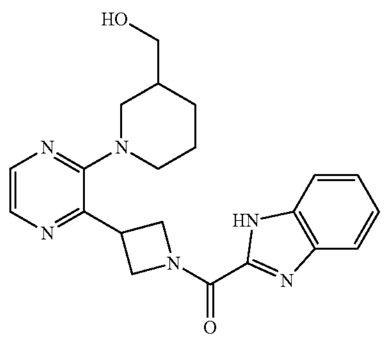 [SMILES: O=C(c1nc2ccccc2[nH]1)N1CC(c2nccnc2N2CCCC(CO)C2)C1] | (R & S)-(1H-Benzoimidazol-2-yl)-{3-[3-(3-hydroxymethyl-piperidin-1-yl)-pyrazin-2-yl]-azetidin-1-yl}-methanone |
| 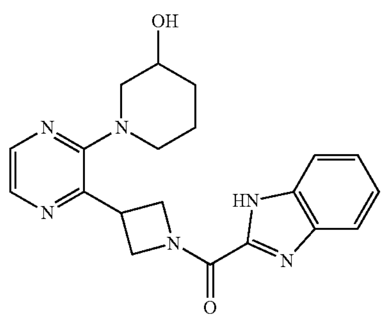 | (1H-Benzoimidazol-2-yl)-{3-[3-(3-hydroxy-piperidin-1-yl)-pyrazin-2-yl]-azetidin-1-yl}-methanone |
| 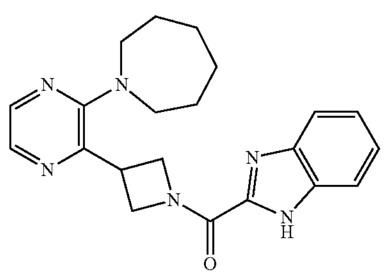 [SMILES: O=C(c1nc2ccccc2[nH]1)N1CC(c2nccnc2N2CCCCCC2)C1] | [3-(3-Azepan-1-yl-pyrazin-2-yl)-azetidin-1-yl]-(1H-benzoimidazol-2-yl)-methanone |
| 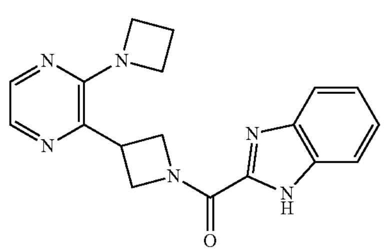 [SMILES: O=C(c1nc2ccccc2[nH]1)N1CC(c2nccnc2N2CCC2)C1] | [3-(3-Azetidin-1-yl-pyrazin-2-yl)-azetidin-1-yl]-(1H-benzoimidazol-2-yl)-methanone |
| 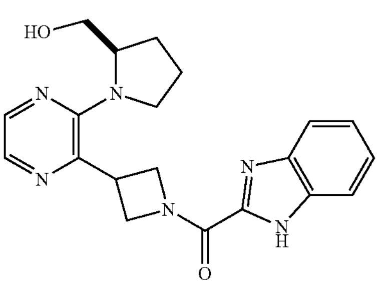 [SMILES: O=C(c1nc2ccccc2[nH]1)N1CC(c2nccnc2N2CCC[C@@H]2CO)C1] | (R)-(1H-Benzoimidazol-2-yl)-{3-[3-(2-hydroxymethyl-pyrrolidin-1-yl)-pyrazin-2-yl]-azetidin-1-yl}-methanone |

| Chemical Structure | Chemical Name |
|---|---|
| 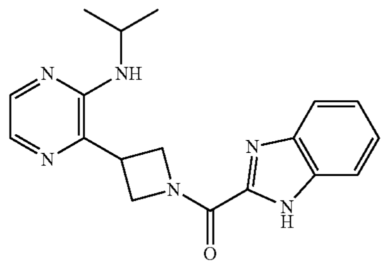 [SMILES: CC(C)Nc1nccnc1C1CN(C(=O)c2nc3ccccc3[nH]2)C1] | (1H-Benzoimidazol-2-yl)-[3-(3-isopropylamino-pyrazin-2-yl)-azetidin-1-yl]-methanone |
| 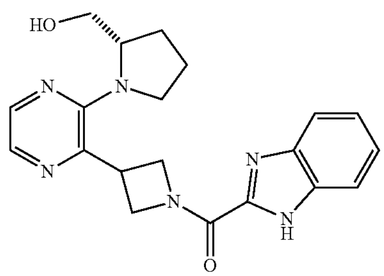 [SMILES: O=C(c1nc2ccccc2[nH]1)N1CC(c2nccnc2N2CCC[C@H]2CO)C1] | (S)-(1H-Benzoimidazol-2-yl)-{3-[3-(2-hydroxymethyl-pyrrolidin-1-yl)-pyrazin-2-yl]-azetidin-1-yl}-methanone |
| 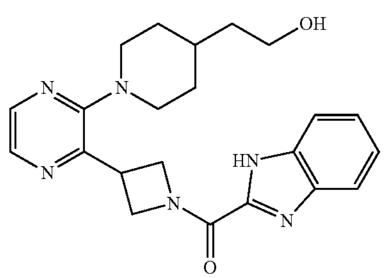 [SMILES: O=C(c1nc2ccccc2[nH]1)N1CC(c2nccnc2N2CCC(CCO)CC2)C1] | (1H-Benzoimidazol-2-yl)-(3-{3-[4-2-hydroxy-ethyl)-piperidin-1-yl]-pyrazin-2-yl}-azetidin-1-yl)-methanone |
| 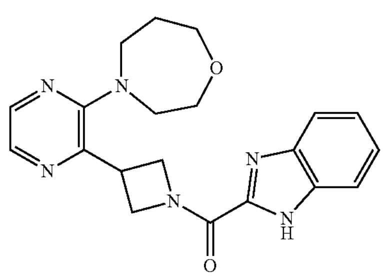 [SMILES: O=C(c1nc2ccccc2[nH]1)N1CC(c2nccnc2N2CCCOCC2)C1] | (1H-Benzoimidazol-2-yl)-[3-(3-[1,4]oxazepan-4-yl-pyrazin-2-yl)-azetidin-1-yl]-methanone |
| 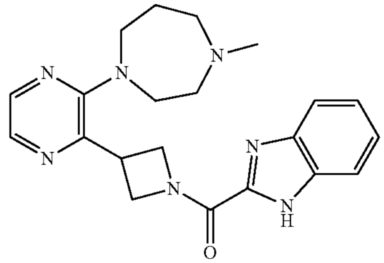 [SMILES: CN1CCCN(c2nccnc2C2CN(C(=O)c3nc4ccccc4[nH]3)C2)CC1] | (1H-Benzoimidazol-2-yl)-{3-[3-(4-methyl-[1,4]diazepan-1-yl)-pyrazin-2-yl]-azetidin-1-yl}-methanone |

| Chemical Structure | Chemical Name |
| --- | --- |
| 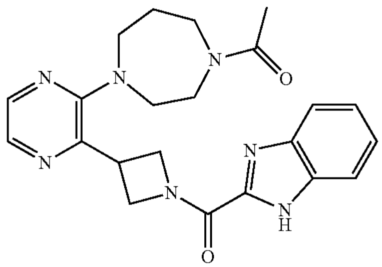 [SMILES: CC(=O)N1CCCN(c2nccnc2C2CN(C(=O)c3nc4ccccc4[nH]3)C2)CC1] | 1-(4-{3-[1-(1H-Benzoimidazole-2-carbonyl)-azetidin-3-yl]-pyrazin-2-yl}-[1,4]diazepan-1-yl)-ethanone |
| 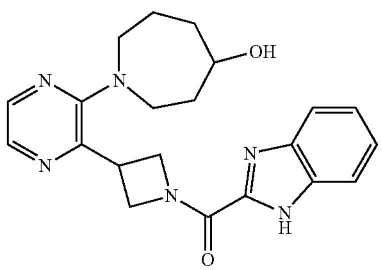 [SMILES: O=C(c1nc2ccccc2[nH]1)N1CC(c2nccnc2N2CCCC(O)CC2)C1] | (1H-Benzoimidazol-2-yl)-{3-[3-(4-hydroxy-azepan-1-yl)-pyrazin-2-yl]-azetidin-1-yl}-methanone |
| 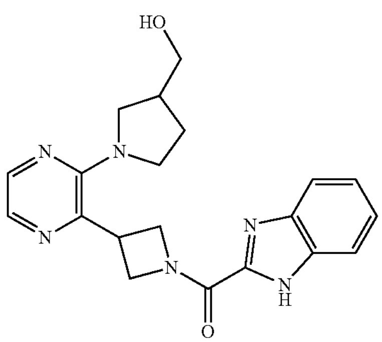 [SMILES: O=C(c1nc2ccccc2[nH]1)N1CC(c2nccnc2N2CCC(CO)C2)C1] | (R & S)-(1H-Benzoimidazol-2-yl)-{3-[3-(3-hydroxymethyl-pyrrolidin-1-yl)-pyrazin-2-yl]-azetidin-1-yl}-methanone |
| 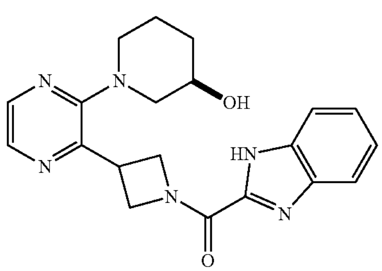 [SMILES: O=C(c1nc2ccccc2[nH]1)N1CC(c2nccnc2N2CCC[C@@H](O)C2)C1] | (R)-(1H-Benzoimidazol-2-yl)-{3-[3-(3-hydroxy-piperidin-1-yl)-pyrazin-2-yl]-azetidin-1-yl}-methanone |
| 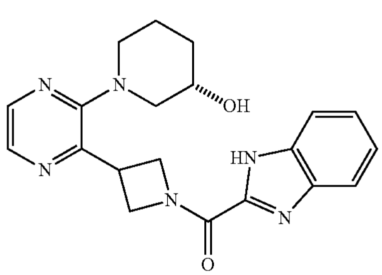 [SMILES: O=C(c1nc2ccccc2[nH]1)N1CC(c2nccnc2N2CCC[C@H](O)C2)C1] | (S)-(1H-Benzoimidazol-2-yl)-{3-[3-(3-hydroxy-piperidin-1-yl)-pyrazin-2-yl]-azetidin-1-yl}-methanone |

| Chemical Structure | Chemical Name |
|---|---|
| 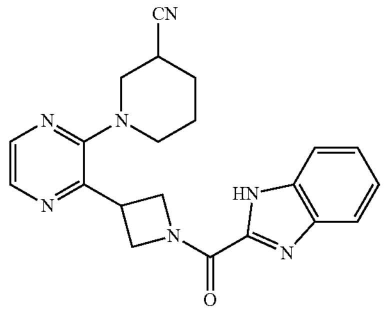 | (R & S)-1-{3-[1-(1H-Benzoimidazole-2-carbonyl)-azetidin-3-yl]-pyrazin-2-yl}-piperidine-3-carbonitrile |
| 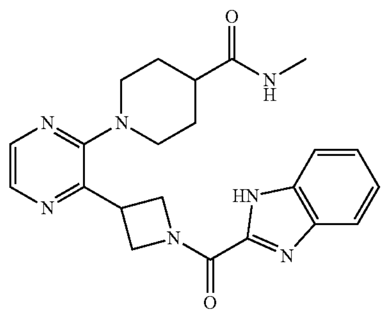 [SMILES: CNC(=O)C1CCN(c2nccnc2C2CN(C(=O)c3nc4ccccc4[nH]3)C2)CC1] | 1-{3-[1-(1H-Benzoimidazole-2-carbonyl)-azetidin-3-yl]-pyrazin-2-yl}-piperidine-4-carboxylic acid methylamide |
| 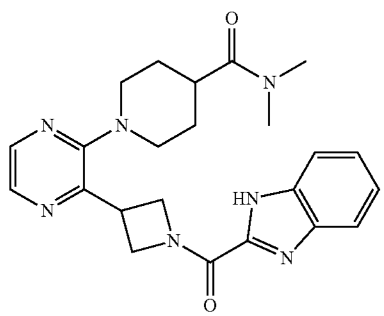 [SMILES: CN(C)C(=O)C1CCN(c2nccnc2C2CN(C(=O)c3nc4ccccc4[nH]3)C2)CC1] | 1-{3-[1-(1H-Benzoimidazole-2-carbonyl)-azetidin-3-yl]-pyrazin-2-yl}-piperidine-4-carboxylic acid dimethylamide |
| 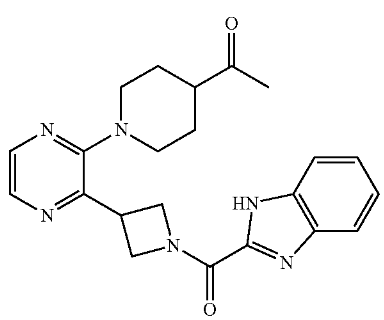 | 1-(1-(3-(1-(1H-benzo[d]imidazole-2-carbonyl)azetidin-3-yl)pyrazin-2-yl)piperidin-4-yl)ethanone |
| 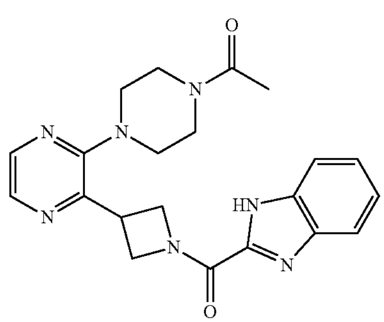 [SMILES: CC(=O)N1CCN(c2nccnc2C2CN(C(=O)c3nc4ccccc4[nH]3)C2)CC1] | 1-(4-(3-(1-(1H-benzo[d]imidazole-2-carbonyl)azetidin-3-yl)pyrazin-2-yl)piperazin-1-yl)ethanone |

| Chemical Structure | Chemical Name |
|---|---|
| 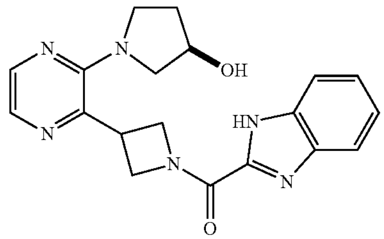 [SMILES: O=C(c1nc2ccccc2[nH]1)N1CC(c2nccnc2N2CC[C@@H](O)C2)C1] | (R)-(1H-benzo[d]imidazol-2-yl)(3-(3-(3-hydroxypyrrolidin-1-yl)pyrazin-2-yl)azetidin-1-yl)methanone |
| 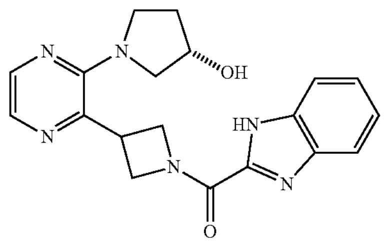 [SMILES: O=C(c1nc2ccccc2[nH]1)N1CC(c2nccnc2N2CC[C@H](O)C2)C1] | (S)-(1H-benzo[d]imidazol-2-yl)(3-(3-(3-hydroxypyrrolidin-1-yl)pyrazin-2-yl)azetidin-1-yl)methanone |
| 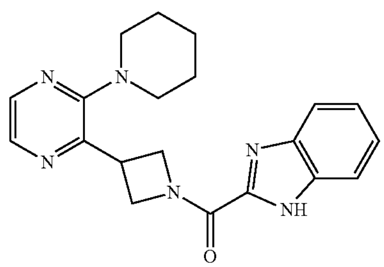 [SMILES: O=C(c1nc2ccccc2[nH]1)N1CC(c2nccnc2N2CCCCC2)C1] | (1H-benzo[d]imidazol-2-yl)(3-(3-(piperidin-1-yl)pyrazin-2-yl)azetidin-1-yl)methanone |
| 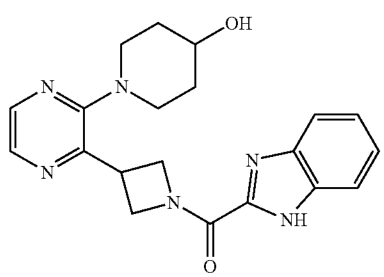 [SMILES: O=C(c1nc2ccccc2[nH]1)N1CC(c2nccnc2N2CCC(O)CC2)C1] | (1H-benzo[d]imidazol-2-yl)(3-(3-(4-hydroxypiperidin-1-yl)pyrazin-2-yl)azetidin-1-yl)methanone |
| 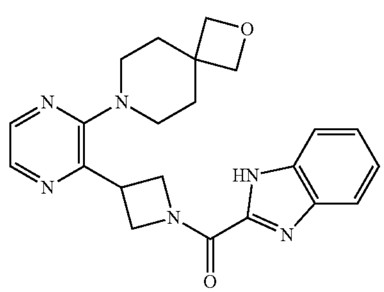 [SMILES: O=C(c1nc2ccccc2[nH]1)N1CC(c2nccnc2N2CCC3(CC2)COC3)C1] | (1H-Benzoimidazol-2-yl)-{3-[3-(2-oxa-7-aza-spiro[3.5]non-7-yl)-pyrazin-2-yl]-azetidin-1-yl}-methanone |
| 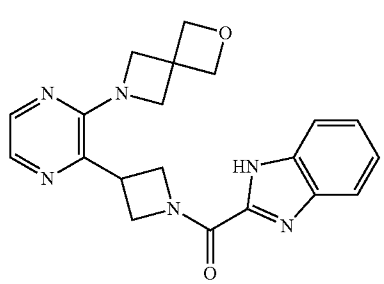 [SMILES: O=C(c1nc2ccccc2[nH]1)N1CC(c2nccnc2N2CC3(COC3)C2)C1] | (1H-Benzoimidazol-2-yl)-{3-[3-(2-oxa-6-aza-spiro[3.3]hept-6-yl)-pyrazin-2-yl]-azetidin-1-yl}-methanone |

| Chemical Structure | Chemical Name |
|---|---|
| 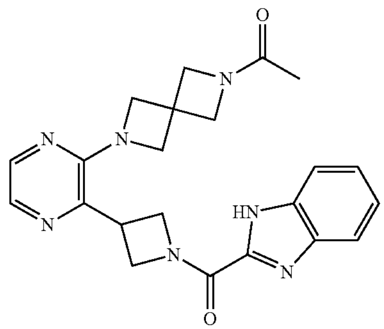 [SMILES: CC(=O)N1CC2(C1)CN(c1nccnc1C1CN(C(=O)c3nc4ccccc4[nH]3)C1)C2] | 1-(6-{3-[1-(1H-Benzoimidazole-2-carbonyl)-azetidin-3-yl]-pyrazin-2-yl}-2,6-diaza-spiro[3.3]hept-2-yl)-ethanone |
| 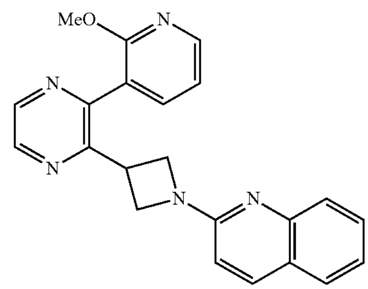 [SMILES: COc1ncccc1-c1nccnc1C1CN(c2ccc3ccccc3n2)C1] | 2-(3-(3-(2-methoxypyridin-3-yl)pyrazin-2-yl)azetidin-1-yl)quinoline |
| 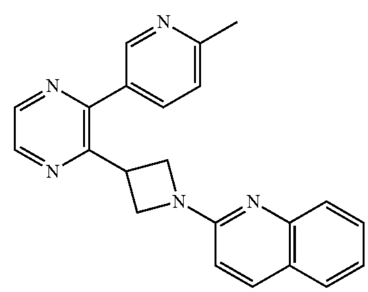 [SMILES: Cc1ccc(-c2nccnc2C2CN(c3ccc4ccccc4n3)C2)cn1] | 2-(3-(3-(6-methylpyridin-3-yl)pyrazin-2-yl)azetidin-1-yl)quinoline |
| 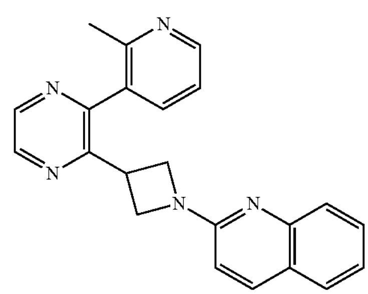 [SMILES: Cc1ncccc1-c1nccnc1C1CN(c2ccc3ccccc3n2)C1] | 2-(3-(3-(2-methylpyridin-3-yl)pyrazin-2-yl)azetidin-1-yl)quinoline |
| 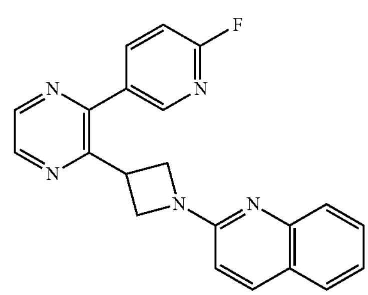 [SMILES: Fc1ccc(-c2nccnc2C2CN(c3ccc4ccccc4n3)C2)cn1] | 2-(3-(3-(6-fluoropyridin-3-yl)pyrazin-2-yl)azetidin-1-yl)quinoline |

| Chemical Structure | Chemical Name |
| --- | --- |
| 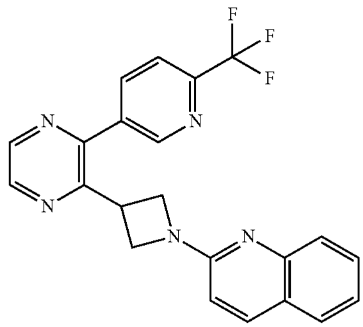 [SMILES: FC(F)(F)c1ccc(-c2nccnc2C2CN(c3ccc4ccccc4n3)C2)cn1] | 2-(3-(3-(6-(trifluoromethyl)pyridin-3-yl)pyrazin-2-yl)azetidin-1-yl)quinoline |
| 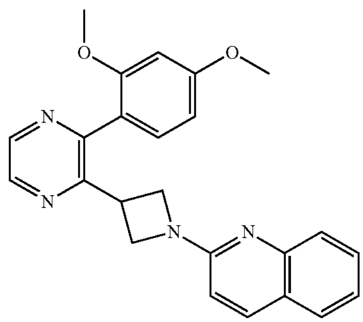 [SMILES: COc1ccc(-c2nccnc2C2CN(c3ccc4ccccc4n3)C2)c(OC)c1] | 2-(3-(3-(2,6-dimethoxypyridin-3-yl)pyrazin-2-yl)azetidin-1-yl)quinoline |
| 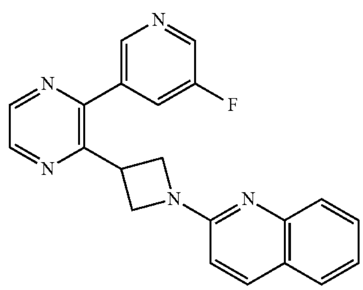 [SMILES: Fc1cncc(-c2nccnc2C2CN(c3ccc4ccccc4n3)C2)c1] | 2-(3-(3-(5-fluoropyridin-3-yl)pyrazin-2-yl)azetidin-1-yl)quinoline |
| 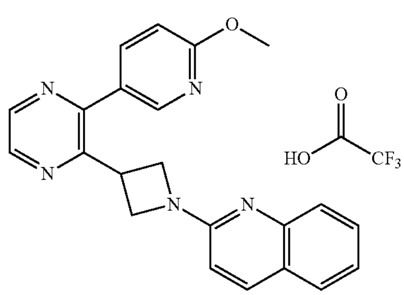 | 2-(3-(3-(6-methoxypyridin-3-yl)pyrazin-2-yl)azetidin-1-yl)quinoline 2,2,2-trifluoroacetate |
| 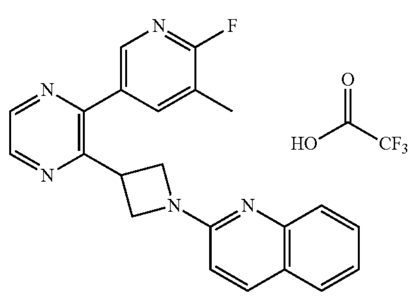 [SMILES: Cc1cc(-c2nccnc2C2CN(c3ccc4ccccc4n3)C2)cnc1F ; O=C(O)C(F)(F)F] | 2-(3-(3-(6-fluoro-5-methylpyridin-3-yl)pyrazin-2-yl)azetidin-1-yl)quinoline 2,2,2-trifluoroacetate |

| Chemical Structure | Chemical Name |
|---|---|
| 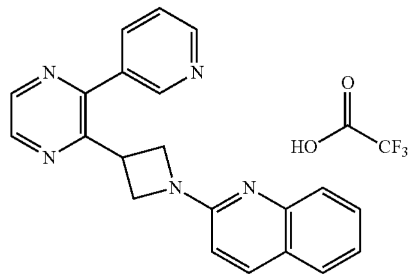 | 2-(3-(3-(pyridin-3-yl)pyrazin-2-yl)azetidin-1-yl)quinoline 2,2,2-trifluoroacetate |
| 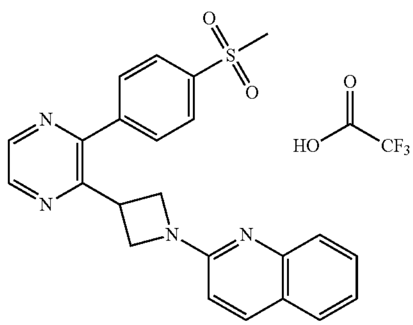 [SMILES: CS(=O)(=O)c1ccc(-c2nccnc2C2CN(c3ccc4ccccc4n3)C2)cc1 ; O=C(O)C(F)(F)F] | 2-(3-(3-(4-(methylsulfonyl)phenyl)pyrazin-2-yl)azetidin-1-yl)quinoline 2,2,2-trifluoroacetate |
| 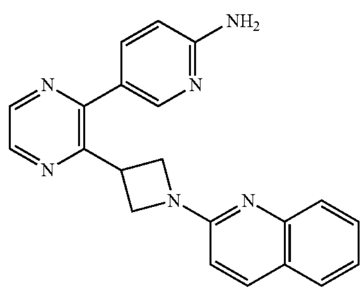 [SMILES: Nc1ccc(-c2nccnc2C2CN(c3ccc4ccccc4n3)C2)cn1] | 5-(3-(1-(quinolin-2-yl)azetidin-3-yl)pyrazin-2-yl)pyridin-2-amine |
| 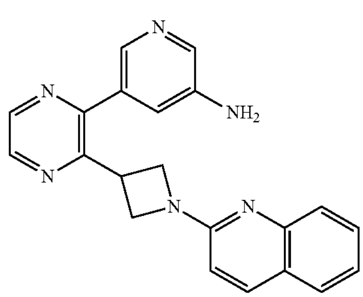 [SMILES: Nc1cncc(-c2nccnc2C2CN(c3ccc4ccccc4n3)C2)c1] | 5-(3-(1-(quinolin-2-yl)azetidin-3-yl)pyrazin-2-yl)pyridin-3-amine |
| 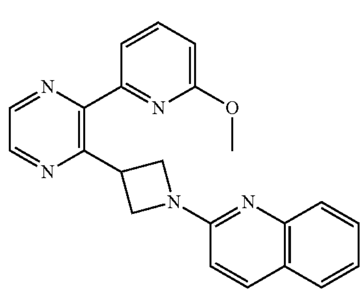 [SMILES: COc1cccc(-c2nccnc2C2CN(c3ccc4ccccc4n3)C2)n1] | 2-(3-(3-(6-methoxypyridin-2-yl)pyrazin-2-yl)azetidin-1-yl)quinoline |

| Chemical Structure | Chemical Name |
|---|---|
| 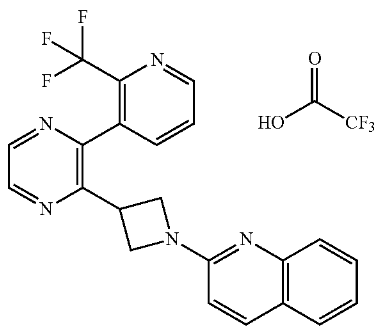 [SMILES: FC(F)(F)c1ncccc1-c1nccnc1C1CN(c2ccc3ccccc3n2)C1 ; O=C(O)C(F)(F)F] | 2-(3-(3-(2-(trifluoromethyl)pyridin-3-yl)pyrazin-2-yl)azetidin-1-yl)quinoline 2,2,2-trifluoroacetate |
| 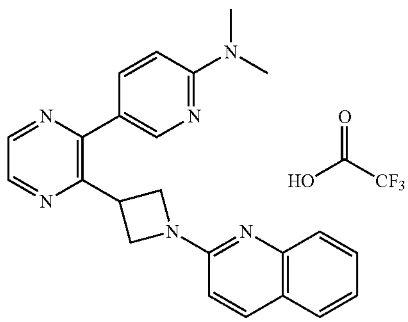 | N,N-dimethyl-5-(3-(1-(quinolin-2-yl)azetidin-3-yl)pyrazin-2-yl)pyrimidin-2-amine 2,2,2-trifluoroacetate |
| 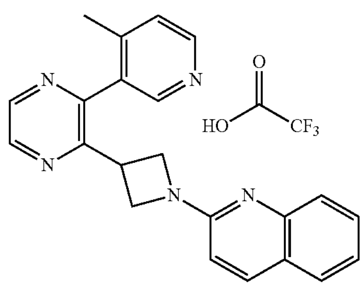 | 2-(3-(3-(4-methylpyridin-3-yl)pyrazin-2-yl)azetidin-1-yl)quinoline 2,2,2-trifluoroacetate |
| 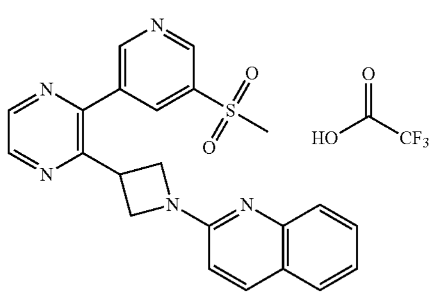 [SMILES: CS(=O)(=O)c1cncc(-c2nccnc2C2CN(c3ccc4ccccc4n3)C2)c1 ; O=C(O)C(F)(F)F] | 2-(3-(3-(5-(methylsulfonyl)pyridin-3-yl)pyrazin-2-yl)azetidin-1-yl)quinoline 2,2,2-trifluoroacetate |
| 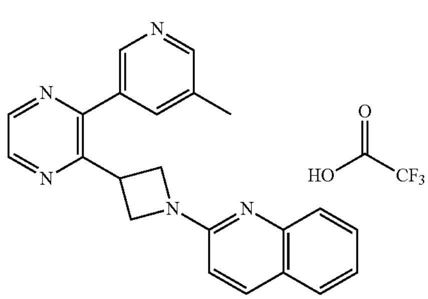 | 2-(3-(3-(5-methylpyridin-3-yl)pyrazin-2-yl)azetidin-1-yl)quinoline 2,2,2-trifluoroacetate |

| Chemical Structure | Chemical Name |
|---|---|
| 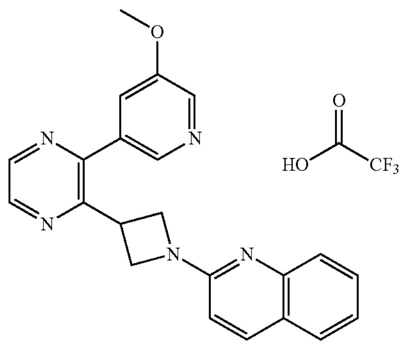 [SMILES: COc1cncc(-c2nccnc2C2CN(c3ccc4ccccc4n3)C2)c1 ; O=C(O)C(F)(F)F] | 2-(3-(3-(5-methoxypyridin-3-yl)pyrazin-2-yl)azetidin-1-yl)quinoline 2,2,2-trifluoroacetate |
| 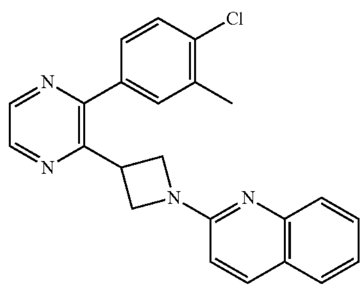 | 2-(3-(3-(4-chloro-3-methylphenyl)pyrazin-2-yl)azetidin-1-yl)quinoline |
| 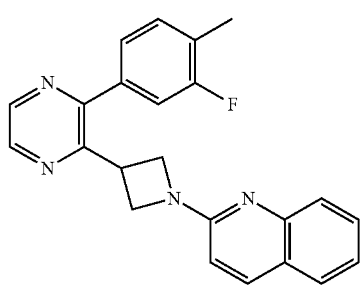 | 2-(3-(3-(3-fluoro-4-methylphenyl)pyrazin-2-yl)azetidin-1-yl)quinoline |
| 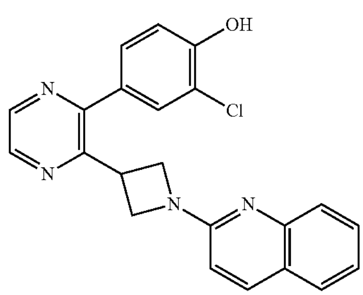 [SMILES: Oc1ccc(-c2nccnc2C2CN(c3ccc4ccccc4n3)C2)cc1Cl] | 2-chloro-4-(3-(1-(quinolin-2-yl)azetidin-3-yl)pyrazin-2-yl)phenol |
| 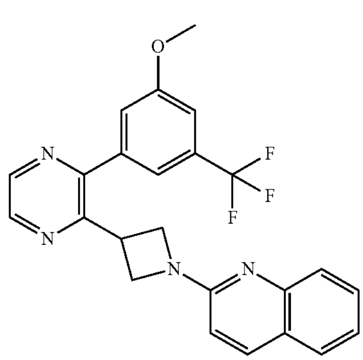 [SMILES: COc1cc(-c2nccnc2C2CN(c3ccc4ccccc4n3)C2)cc(C(F)(F)F)c1] | 2-(3-(3-(3-methoxy-5-(trifluoromethyl)phenyl)pyrazin-2-yl)azetidin-1-yl)quinoline |

| Chemical Structure | Chemical Name |
|---|---|
| 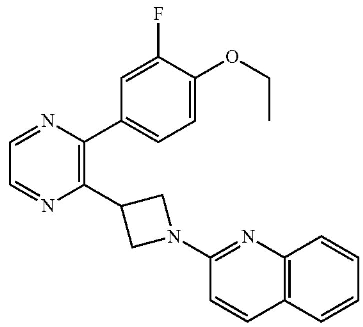 [SMILES: CCOc1ccc(-c2nccnc2C2CN(c3ccc4ccccc4n3)C2)cc1F] | 2-(3-(3-(4-ethoxy-3-fluorophenyl)pyrazin-2-yl)azetidin-1-yl)quinoline |
| 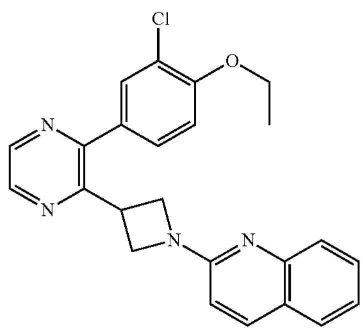 [SMILES: CCOc1ccc(-c2nccnc2C2CN(c3ccc4ccccc4n3)C2)cc1Cl] | 2-(3-(3-(3-chloro-4-ethoxyphenyl)pyrazin-2-yl)azetidin-1-yl)quinoline |
| 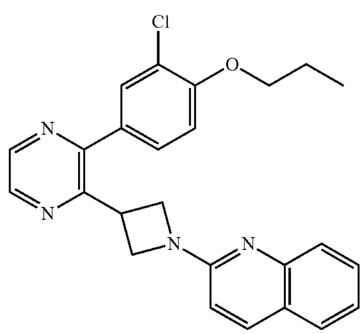 [SMILES: CCCOc1ccc(-c2nccnc2C2CN(c3ccc4ccccc4n3)C2)cc1Cl] | 2-(3-(3-(3-chloro-4-propoxyphenyl)pyrazin-2-yl)azetidin-1-yl)quinoline |
| 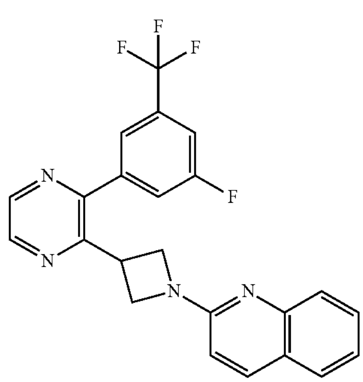 [SMILES: Fc1cc(-c2nccnc2C2CN(c3ccc4ccccc4n3)C2)cc(C(F)(F)F)c1] | 2-(3-(3-(3-fluoro-5-(trifluoromethyl)phenyl)pyrazin-2-yl)azetidin-1-yl)quinoline |

| Chemical Structure | Chemical Name |
|---|---|
| 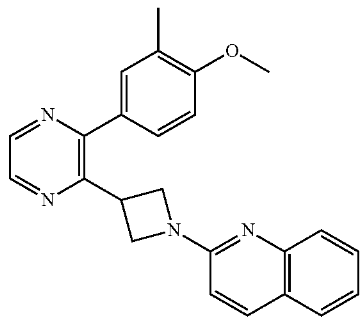 [SMILES: COc1ccc(-c2nccnc2C2CN(c3ccc4ccccc4n3)C2)cc1C] | 2-(3-(3-(4-methoxy-3-methylphenyl)pyrazin-2-yl)azetidin-1-yl)quinoline |
| 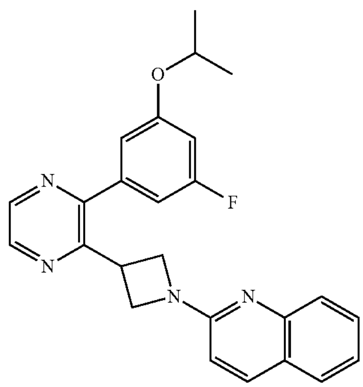 [SMILES: CC(C)Oc1cc(F)cc(-c2nccnc2C2CN(c3ccc4ccccc4n3)C2)c1] | 2-(3-(3-(3-fluoro-5-isopropoxyphenyl)pyrazin-2-yl)azetidin-1-yl)quinoline |
| 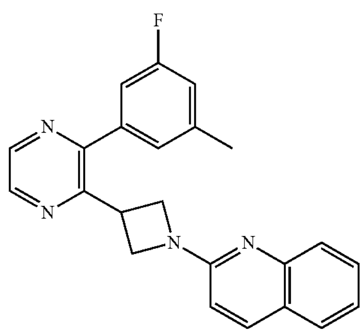 [SMILES: Cc1cc(F)cc(-c2nccnc2C2CN(c3ccc4ccccc4n3)C2)c1] | 2-(3-(3-(3-fluoro-5-methylphenyl)pyrazin-2-yl)azetidin-1-yl)quinoline |
| 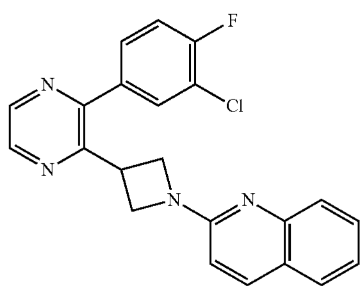 | 2-(3-(3-(3-chloro-4-fluorophenyl)pyrazin-2-yl)azetidin-1-yl)quinoline |

| Chemical Structure | Chemical Name |
| --- | --- |
| 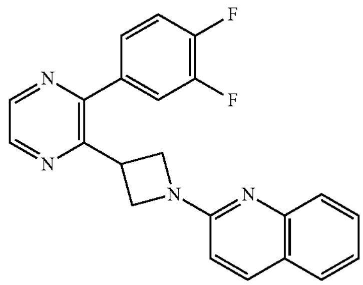 | 2-(3-(3-(3,4-difluorophenyl)pyrazin-2-yl)azetidin-1-yl)quinoline |
| 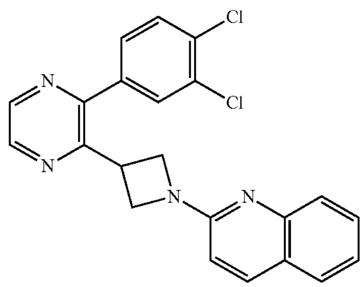 | 2-(3-(3-(3,4-dichlorophenyl)pyrazin-2-yl)azetidin-1-yl)quinoline |
| 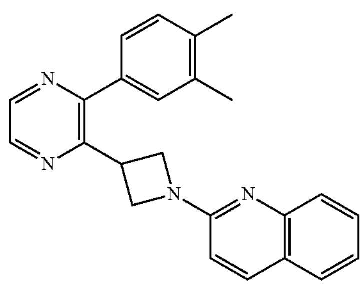 | 2-(3-(3-(3,4-dimethylphenyl)pyrazin-2-yl)azetidin-1-yl)quinoline |
| 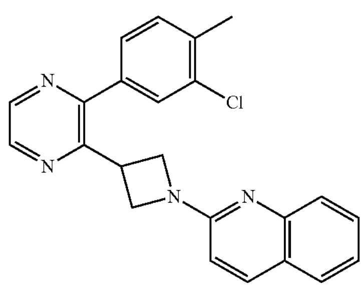 | 2-(3-(3-(3-chloro-4-methylphenyl)pyrazin-2-yl)azetidin-1-yl)quinoline |
| 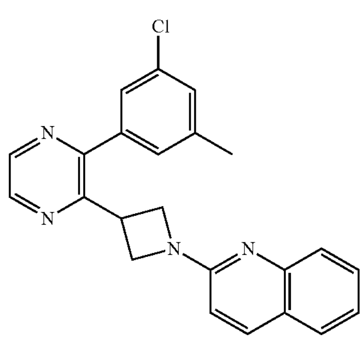 | 2-(3-(3-(3-chloro-5-methylphenyl)pyrazin-2-yl)azetidin-1-yl)quinoline |

| Chemical Structure | Chemical Name |
|---|---|
| 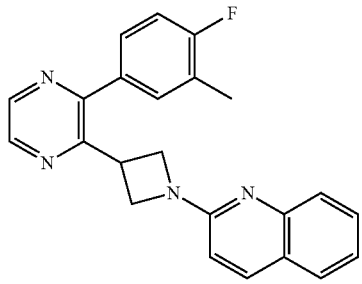 | 2-(3-(3-(4-fluoro-3-methylphenyl)pyrazin-2-yl)azetidin-1-yl)quinoline |
| 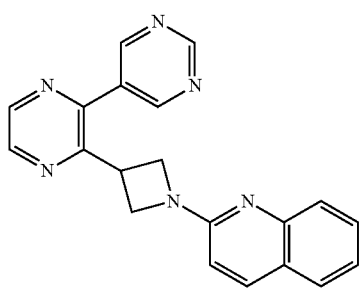 | 2-(3-(3-(pyrimidin-5-yl)pyrazin-2-yl)azetidin-1-yl)quinoline |
| 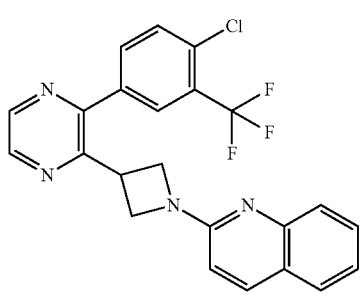 [SMILES: FC(F)(F)c1cc(-c2nccnc2C2CN(c3ccc4ccccc4n3)C2)ccc1Cl] | 2-(3-(3-(4-chloro-3-(trifluoromethyl)phenyl)pyrazin-2-yl)azetidin-1-yl)quinoline |
| 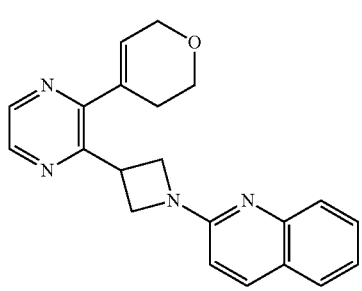 | 2-(3-(3-(3,6-dihydro-2H-pyran-4-yl)pyrazin-2-yl)azetidin-1-yl)quinoline |
| 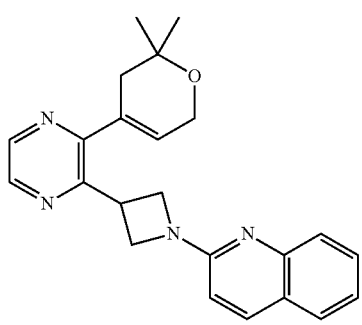 [SMILES: CC1(C)CC(c2nccnc2C2CN(c3ccc4ccccc4n3)C2)=CCO1] | 2-(3-(3-(2,2-dimethyl-3,6-dihydro-2H-pyran-4-yl)pyrazin-2-yl)azetidin-1-yl)quinoline and 2-(3-(3-(6,6-dimethyl-3,6-dihydro-2H-pyran-4-yl)pyrazin-2-yl)azetidin-1-yl)quinoline |

| Chemical Structure | Chemical Name |
|---|---|
| 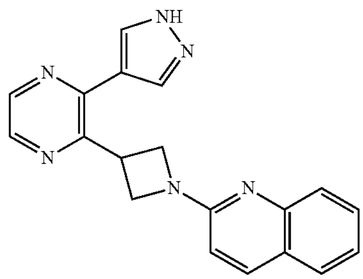 [SMILES: c1ccc2nc(N3CC(c4nccnc4-c4cn[nH]c4)C3)ccc2c1] | 2-(3-(3-(1H-pyrazol-4-yl)pyrazin-2-yl)azetidin-1-yl)quinoline |
| 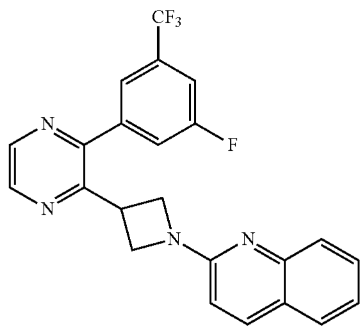 [SMILES: Fc1cc(-c2nccnc2C2CN(c3ccc4ccccc4n3)C2)cc(C(F)(F)F)c1] | 2-(3-(3-(3-fluoro-5-(trifluoromethyl)phenyl)pyrazin-2-yl)azetidin-1-yl)quinoline |
| 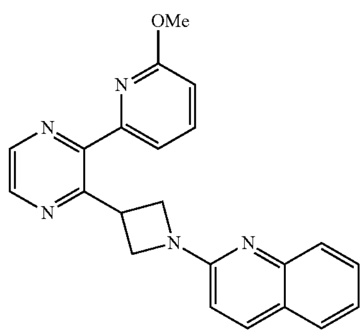 [SMILES: COc1cccc(-c2nccnc2C2CN(c3ccc4ccccc4n3)C2)n1] | 2-(3-(3-(6-methoxypyridin-2-yl)pyrazin-2-yl)azetidin-1-yl)quinoline |
| 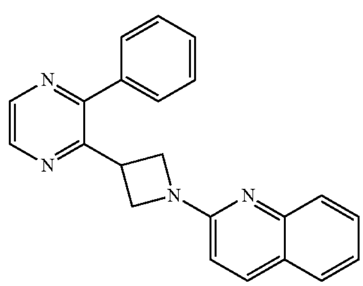 | 2-(3-(3-phenylpyrazin-2-yl)azetidin-1-yl)quinoline |
| 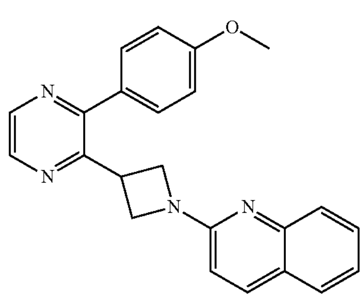 [SMILES: COc1ccc(-c2nccnc2C2CN(c3ccc4ccccc4n3)C2)cc1] | 2-(3-(3-(4-methoxyphenyl)pyrazin-2-yl)azetidin-1-yl)quinoline |

| Chemical Structure | Chemical Name |
| --- | --- |
| 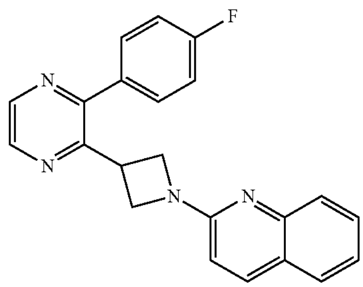 [SMILES: Fc1ccc(-c2nccnc2C2CN(c3ccc4ccccc4n3)C2)cc1] | 2-(3-(3-(4-fluorophenyl)pyrazin-2-yl)azetidin-1-yl)quinoline |
| 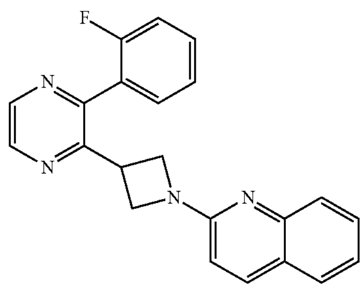 [SMILES: Fc1ccccc1-c1nccnc1C1CN(c2ccc3ccccc3n2)C1] | 2-(3-(3-(2-fluorophenyl)pyrazin-2-yl)azetidin-1-yl)quinoline |
| 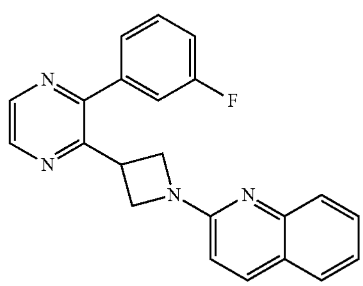 [SMILES: Fc1cccc(-c2nccnc2C2CN(c3ccc4ccccc4n3)C2)c1] | 2-(3-(3-(3-fluorophenyl)pyrazin-2-yl)azetidin-1-yl)quinoline |
| 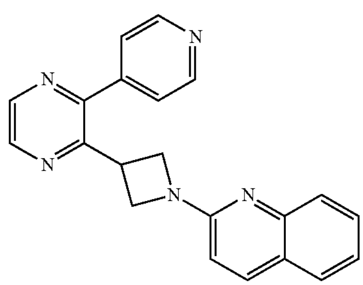 | 2-(3-(3-(pyridin-4-yl)pyrazin-2-yl)azetidin-1-yl)quinoline |
| 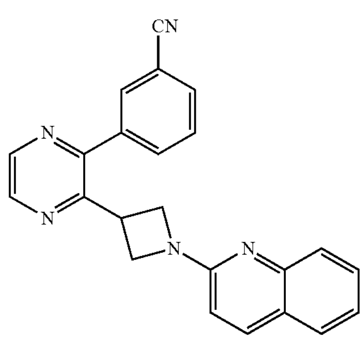 [SMILES: N#Cc1cccc(-c2nccnc2C2CN(c3ccc4ccccc4n3)C2)c1] | 3-(3-(1-(quinolin-2-yl)azetidin-3-yl)pyrazin-2-yl)benzonitrile |

| Chemical Structure | Chemical Name |
|---|---|
| 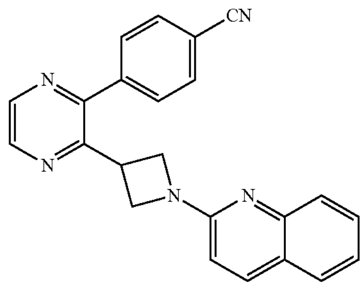 | 4-(3-(1-(quinolin-2-yl)azetidin-3-yl)pyrazin-2-yl)benzonitrile |
| 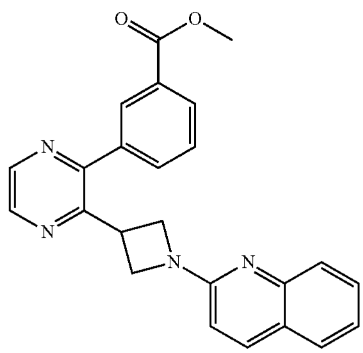 [SMILES: COC(=O)c1cccc(-c2nccnc2C2CN(c3ccc4ccccc4n3)C2)c1] | methyl 3-(3-(1-(quinolin-2-yl)azetidin-3-yl)pyrazin-2-yl)benzoate |
| 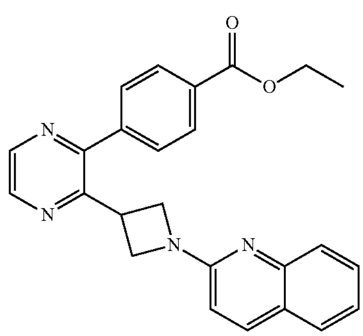 [SMILES: CCOC(=O)c1ccc(-c2nccnc2C2CN(c3ccc4ccccc4n3)C2)cc1] | ethyl 4-(3-(1-(quinolin-2-yl)azetidin-3-yl)pyrazin-2-yl)benzoate |
| 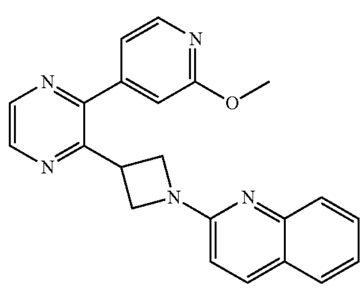 [SMILES: COc1cc(-c2nccnc2C2CN(c3ccc4ccccc4n3)C2)ccn1] | 2-(3-(3-(2-methoxypyridin-4-yl)pyrazin-2-yl)azetidin-1-yl)quinoline |
| 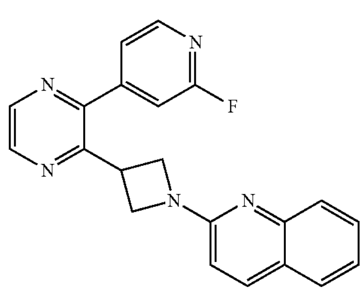 | 2-(3-(3-(2-fluoropyridin-4-yl)pyrazin-2-yl)azetidin-1-yl)quinoline |

| Chemical Structure | Chemical Name |
|---|---|
| 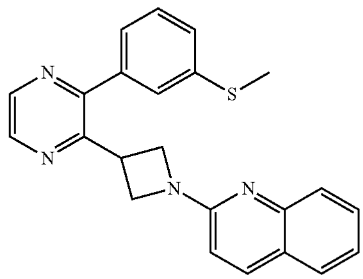 [SMILES: CSc1cccc(-c2nccnc2C2CN(c3ccc4ccccc4n3)C2)c1] | 2-(3-(3-(3-(methylthio)phenyl)pyrazin-2-yl)azetidin-1-yl)quinoline |
| 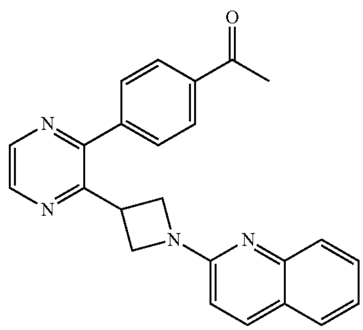 [SMILES: CC(=O)c1ccc(-c2nccnc2C2CN(c3ccc4ccccc4n3)C2)cc1] | 1-(4-(3-(1-(quinolin-2-yl)azetidin-3-yl)pyrazin-2-yl)phenyl)ethanone |
| 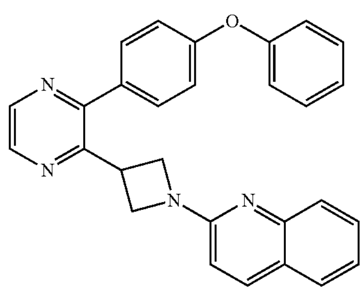 [SMILES: c1ccc(Oc2ccc(-c3nccnc3C3CN(c4ccc5ccccc5n4)C3)cc2)cc1] | 2-(3-(3-(4-phenoxyphenyl)pyrazin-2-yl)azetidin-1-yl)quinoline |
| 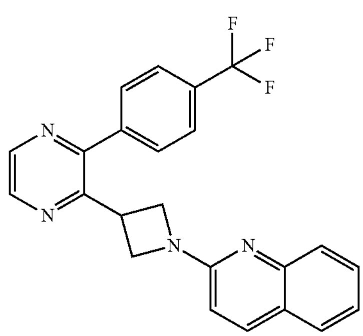 [SMILES: FC(F)(F)c1ccc(-c2nccnc2C2CN(c3ccc4ccccc4n3)C2)cc1] | 2-(3-(3-(4-(trifluoromethyl)phenyl)pyrazin-2-yl)azetidin-1-yl)quinoline |
| 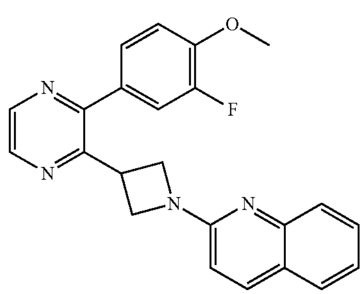 [SMILES: COc1ccc(-c2nccnc2C2CN(c3ccc4ccccc4n3)C2)cc1F] | 2-(3-(3-(3-fluoro-4-methoxyphenyl)pyrazin-2-yl)azetidin-1-yl)quinoline |

| Chemical Structure | Chemical Name |
|---|---|
| 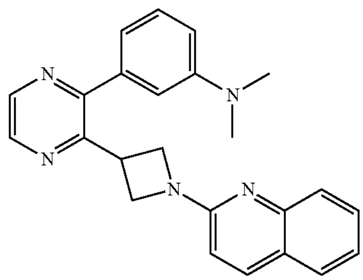 [SMILES: CN(C)c1cccc(-c2nccnc2C2CN(c3ccc4ccccc4n3)C2)c1] | N,N-dimethyl-3-(3-(1-(quinolin-2-yl)azetidin-3-yl)pyrazin-2-yl)aniline |
| 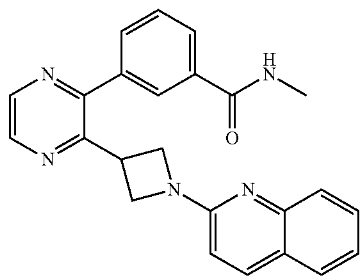 | N-methyl-3-(3-(1-(quinolin-2-yl)azetidin-3-yl)pyrazin-2-yl)benzamide |
| 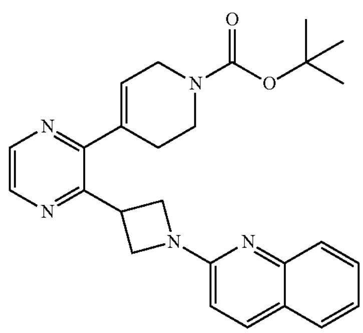 [SMILES: CC(C)(C)OC(=O)N1CC=C(c2nccnc2C2CN(c3ccc4ccccc4n3)C2)CC1] | tert-butyl 4-(3-(1-(quinolin-2-yl)azetidin-3-yl)pyrazin-2-yl)-5,6-dihydropyridine-1(2H)-carboxylate |
| 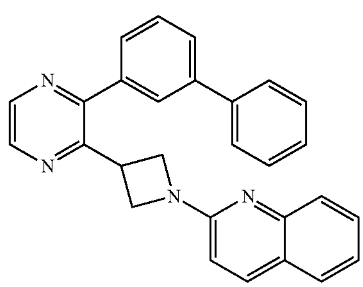 [SMILES: c1ccc(-c2cccc(-c3nccnc3C3CN(c4ccc5ccccc5n4)C3)c2)cc1] | 2-(3-(3-([1,1'-biphenyl]-3-yl)pyrazin-2-yl)azetidin-1-yl)quinoline |
| 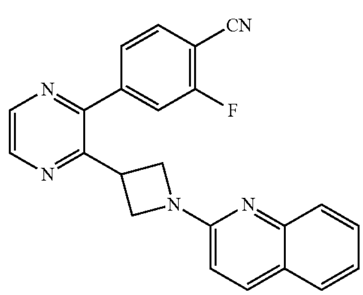 [SMILES: N#Cc1ccc(-c2nccnc2C2CN(c3ccc4ccccc4n3)C2)cc1F] | 2-fluoro-4-(3-(1-(quinolin-2-yl)azetidin-3-yl)pyrazin-2-yl)benzonitrile |

| Chemical Structure | Chemical Name |
|---|---|
| 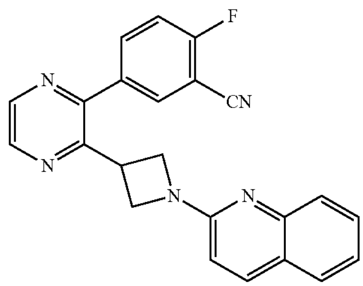 [SMILES: N#Cc1cc(-c2nccnc2C2CN(c3ccc4ccccc4n3)C2)ccc1F] | 2-fluoro-5-(3-(1-(quinolin-2-yl)azetidin-3-yl)pyrazin-2-yl)benzonitrile |
| 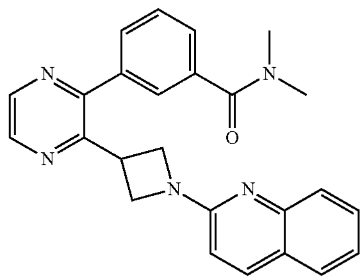 [SMILES: CN(C)C(=O)c1cccc(-c2nccnc2C2CN(c3ccc4ccccc4n3)C2)c1] | N,N-dimethyl-3-(3-(1-(quinolin-2-yl)azetidin-3-yl)pyrazin-2-yl)benzamide |
| 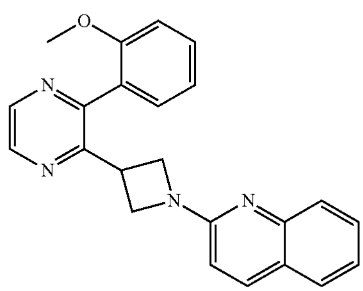 [SMILES: COc1ccccc1-c1nccnc1C1CN(c2ccc3ccccc3n2)C1] | 2-(3-(3-(2-methoxyphenyl)pyrazin-2-yl)azetidin-1-yl)quinoline |
| 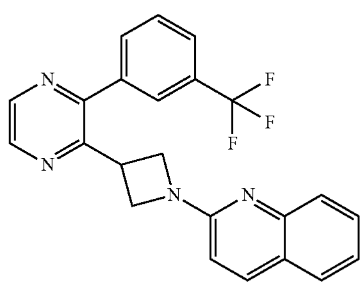 [SMILES: FC(F)(F)c1cccc(-c2nccnc2C2CN(c3ccc4ccccc4n3)C2)c1] | 2-(3-(3-(3-(trifluoromethyl)phenyl)pyrazin-2-yl)azetidin-1-yl)quinoline |
| 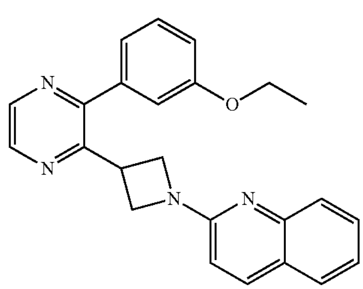 [SMILES: CCOc1cccc(-c2nccnc2C2CN(c3ccc4ccccc4n3)C2)c1] | 2-(3-(3-(3-ethoxyphenyl)pyrazin-2-yl)azetidin-1-yl)quinoline |

-continued

| Chemical Structure | Chemical Name |
|---|---|
| 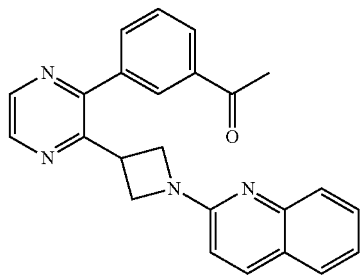 [SMILES: CC(=O)c1cccc(-c2nccnc2C2CN(c3ccc4ccccc4n3)C2)c1] | 1-(3-(3-(1-(quinolin-2-yl)azetidin-3-yl)pyrazin-2-yl)phenyl)ethanone |
| 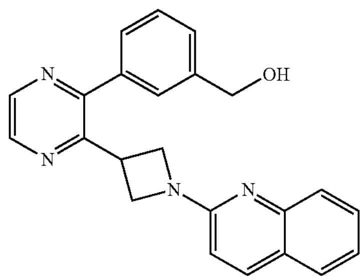 [SMILES: OCc1cccc(-c2nccnc2C2CN(c3ccc4ccccc4n3)C2)c1] | (3-(3-(1-(quinolin-2-yl)azetidin-3-yl)pyrazin-2-yl)phenyl)methanol |
| 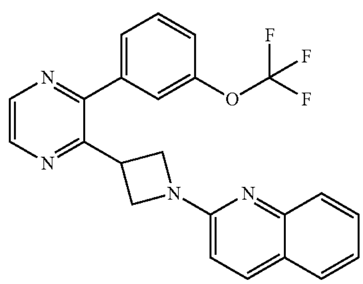 [SMILES: FC(F)(F)Oc1cccc(-c2nccnc2C2CN(c3ccc4ccccc4n3)C2)c1] | 2-(3-(3-(3-(trifluoromethoxy)phenyl)pyrazin-2-yl)azetidin-1-yl)quinoline |
| 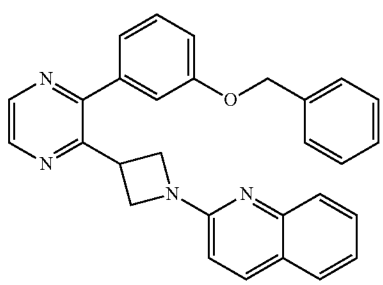 [SMILES: c1ccc(COc2cccc(-c3nccnc3C3CN(c4ccc5ccccc5n4)C3)c2)cc1] | 2-(3-(3-(3-(benzyloxy)phenyl)pyrazin-2-yl)azetidin-1-yl)quinoline |
| 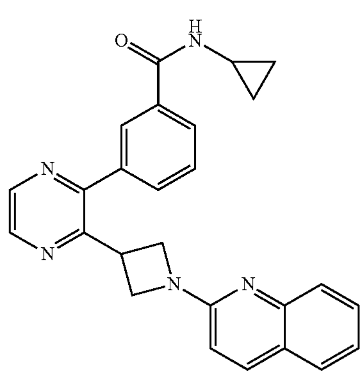 [SMILES: O=C(NC1CC1)c1cccc(-c2nccnc2C2CN(c3ccc4ccccc4n3)C2)c1] | N-cyclopropyl-3-(3-(1-(quinolin-2-yl)azetidin-3-yl)pyrazin-2-yl)benzamide |

| Chemical Structure | Chemical Name |
|---|---|
| 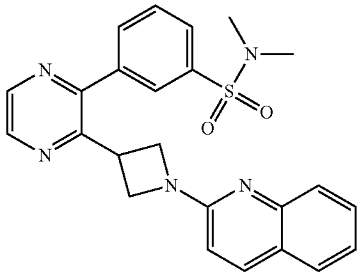 [SMILES: CN(C)S(=O)(=O)c1cccc(-c2nccnc2C2CN(c3ccc4ccccc4n3)C2)c1] | N,N-dimethyl-3-(3-(1-(quinolin-2-yl)azetidin-3-yl)pyrazin-2-yl)benzenesulfonamide |
| 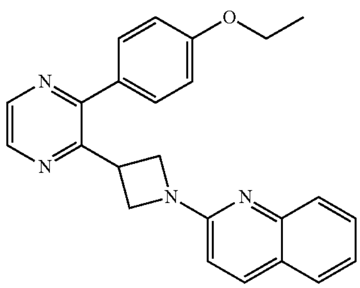 [SMILES: CCOc1ccc(-c2nccnc2C2CN(c3ccc4ccccc4n3)C2)cc1] | 2-(3-(3-(4-ethoxyphenyl)pyrazin-2-yl)azetidin-1-yl)quinoline |
| 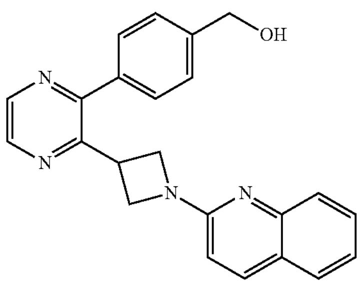 [SMILES: OCc1ccc(-c2nccnc2C2CN(c3ccc4ccccc4n3)C2)cc1] | (4-(3-(1-(quinolin-2-yl)azetidin-3-yl)pyrazin-2-yl)phenyl)methanol |
| 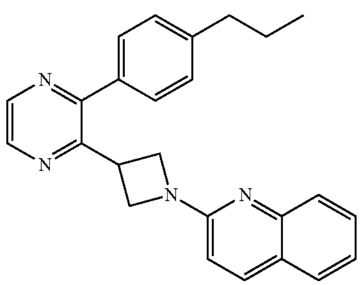 [SMILES: CCCc1ccc(-c2nccnc2C2CN(c3ccc4ccccc4n3)C2)cc1] | 2-(3-(3-(4-propylphenyl)pyrazin-2-yl)azetidin-1-yl)quinoline |
| 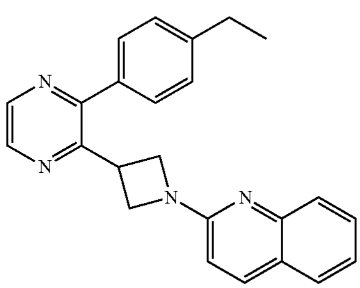 [SMILES: CCc1ccc(-c2nccnc2C2CN(c3ccc4ccccc4n3)C2)cc1] | 2-(3-(3-(4-ethylphenyl)pyrazin-2-yl)azetidin-1-yl)quinoline |

| Chemical Structure | Chemical Name |
|---|---|
| 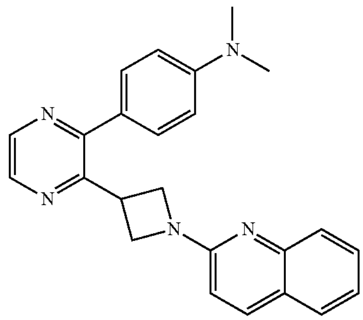 [SMILES: CN(C)c1ccc(-c2nccnc2C2CN(c3ccc4ccccc4n3)C2)cc1] | N,N-dimethyl-4-(3-(1-(quinolin-2-yl)azetidin-3-yl)pyrazin-2-yl)aniline |
| 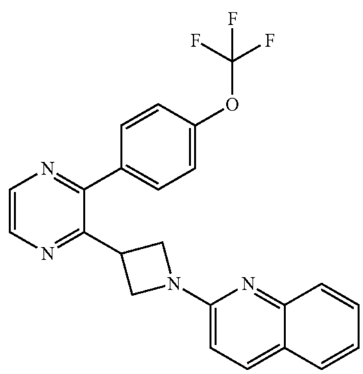 [SMILES: FC(F)(F)Oc1ccc(-c2nccnc2C2CN(c3ccc4ccccc4n3)C2)cc1] | 2-(3-(3-(4-(trifluoromethoxy)phenyl)pyrazin-2-yl)azetidin-1-yl)quinoline |
| 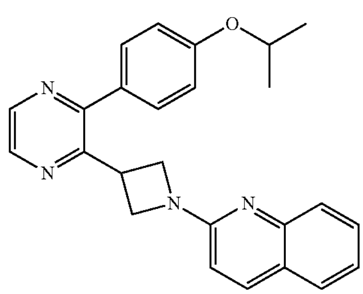 [SMILES: CC(C)Oc1ccc(-c2nccnc2C2CN(c3ccc4ccccc4n3)C2)cc1] | 2-(3-(3-(4-isopropoxyphenyl)pyrazin-2-yl)azetidin-1-yl)quinoline |
| 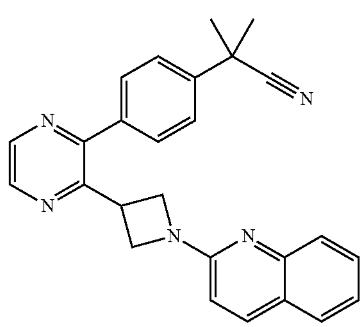 [SMILES: CC(C)(C#N)c1ccc(-c2nccnc2C2CN(c3ccc4ccccc4n3)C2)cc1] | 2-methyl-2-(4-(3-(1-(quinolin-2-yl)azetidin-3-yl)pyrazin-2-yl)phenyl)propanenitrile |

| Chemical Structure | Chemical Name |
|---|---|
| 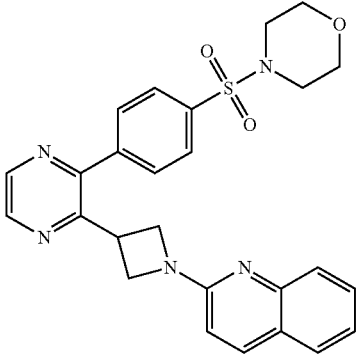 | 4-((4-(3-(1-(quinolin-2-yl)azetidin-3-yl)pyrazin-2-yl)phenyl)sulfonyl)morpholine |
| 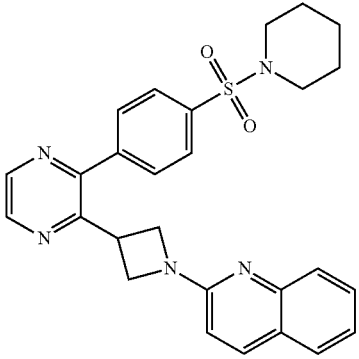 [SMILES: O=S(=O)(c1ccc(-c2nccnc2C2CN(c3ccc4ccccc4n3)C2)cc1)N1CCCCC1] | 2-(3-(3-(4-(piperidin-1-yl sulfonyl)phenyl)pyrazin-2-yl)azetidin-1-yl)quinoline |
| 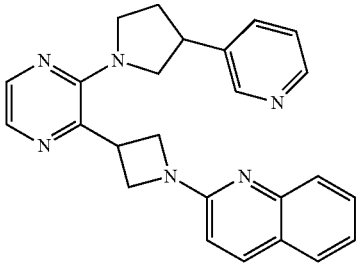 [SMILES: c1cncc(C2CCN(c3nccnc3C3CN(c4ccc5ccccc5n4)C3)C2)c1] | (R- & S-)-2-(3-(3-(3-(pyridin-3-yl)pyrrolidin-1-yl)pyrazin-2-yl)azetidin-1-yl)quinoline |
| 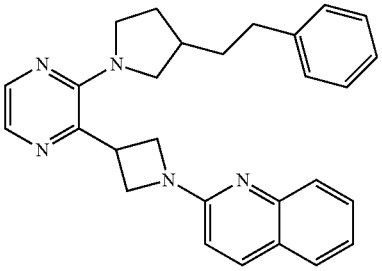 [SMILES: c1ccc(CCC2CCN(c3nccnc3C3CN(c4ccc5ccccc5n4)C3)C2)cc1] | (R- & S-)-2-(3-(3-(3-phenethylpyrrolidin-1-yl)pyrazin-2-yl)azetidin-1-yl)quinoline |

| Chemical Structure | Chemical Name |
|---|---|
| 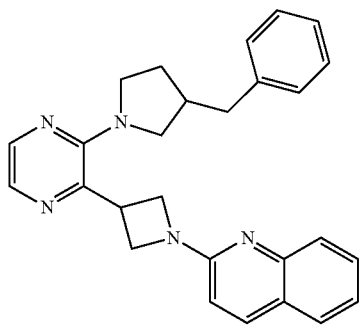 [SMILES: c1ccc(CC2CCN(c3nccnc3C3CN(c4ccc5ccccc5n4)C3)C2)cc1] | (R- & S-)-2-(3-(3-(3-benzylpyrrolidin-1-yl)pyrazin-2-yl)azetidin-1-yl)quinoline |
| 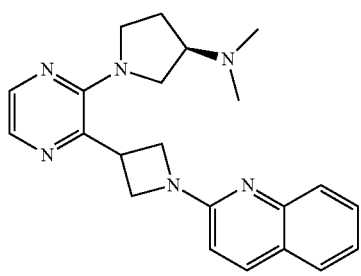 [SMILES: CN(C)[C@@H]1CCN(c2nccnc2C2CN(c3ccc4ccccc4n3)C2)C1] | (R)-N,N-dimethyl-1-(3-(1-(quinolin-2-yl)azetidin-3-yl)pyrazin-2-yl)pyrrolidin-3-amine |
| 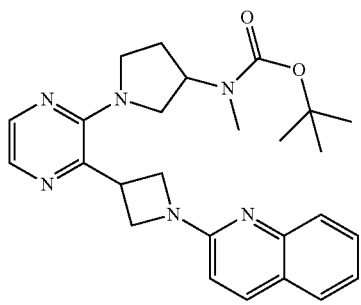 [SMILES: CN(C(=O)OC(C)(C)C)C1CCN(c2nccnc2C2CN(c3ccc4ccccc4n3)C2)C1] | (R- & S-)-tert-butyl methyl(1-(3-(1-(quinolin-2-yl)azetidin-3-yl)pyrazin-2-yl)pyrrolidin-3-yl)carbamate |
| 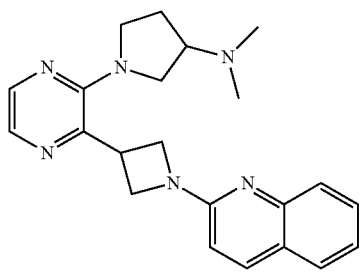 [SMILES: CN(C)C1CCN(c2nccnc2C2CN(c3ccc4ccccc4n3)C2)C1] | (R- & S-)-N,N-dimethyl-1-(3-(1-(quinolin-2-yl)azetidin-3-yl)pyrazin-2-yl)pyrrolidin-3-amine |
| 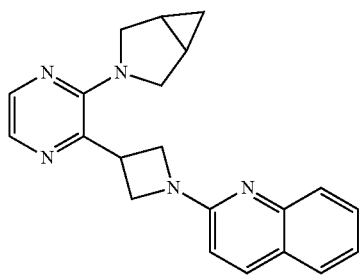 [SMILES: c1ccc2nc(N3CC(c4nccnc4N4CC5CC5C4)C3)ccc2c1] | 2-(3-(3-(3-azabicyclo[3.1.0]hexan-3-yl)pyrazin-2-yl)azetidin-1-yl)quinoline |

| Chemical Structure | Chemical Name |
|---|---|
| 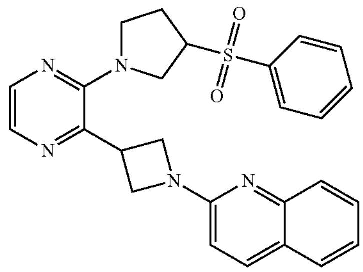 [SMILES: O=S(=O)(c1ccccc1)C1CCN(c2nccnc2C2CN(c3ccc4ccccc4n3)C2)C1] | (R- & S-)-2-(3-(3-(3-(phenylsulfonyl)pyrrolidin-1-yl)pyrazin-2-yl)azetidin-1-yl)quinoline |
| 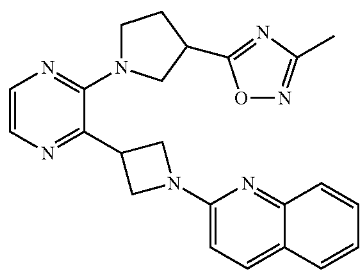 [SMILES: Cc1noc(C2CCN(c3nccnc3C3CN(c4ccc5ccccc5n4)C3)C2)n1] | (R- & S-)-3-methyl-5-(1-(3-(1-(quinolin-2-yl)azetidin-3-yl)pyrazin-2-yl)pyrrolidin-3-yl)-1,2,4-oxadiazole |
| 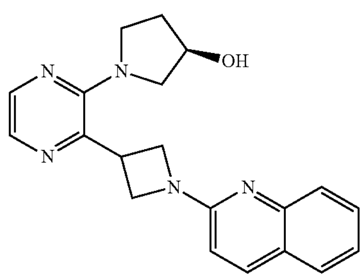 [SMILES: O[C@@H]1CCN(c2nccnc2C2CN(c3ccc4ccccc4n3)C2)C1] | (R)-1-(3-(1-(quinolin-2-yl)azetidin-3-yl)pyrazin-2-yl)pyrrolidin-3-ol |
| 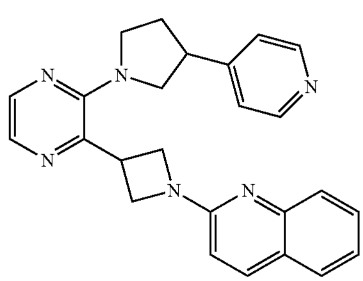 [SMILES: c1ccc2nc(N3CC(c4nccnc4N4CCC(c5ccncc5)C4)C3)ccc2c1] | (R- & S-)-2-(3-(3-(3-(pyridin-4-yl)pyrrolidin-1-yl)pyrazin-2-yl)azetidin-1-yl)quinoline |
| 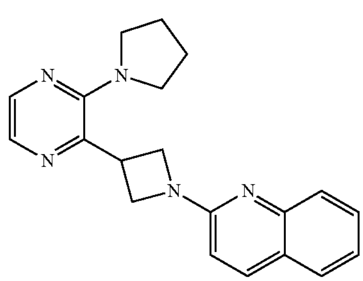 [SMILES: c1ccc2nc(N3CC(c4nccnc4N4CCCC4)C3)ccc2c1] | 2-(3-(3-(pyrrolidin-1-yl)pyrazin-2-yl)azetidin-1-yl)quinoline |

| Chemical Structure | Chemical Name |
|---|---|
| 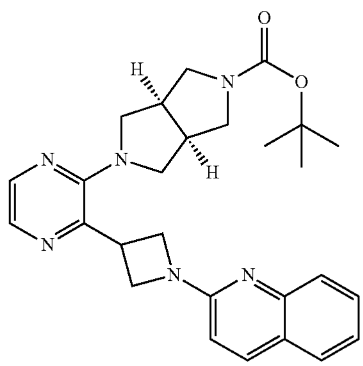 [SMILES: CC(C)(C)OC(=O)N1C[C@@H]2CN(c3nccnc3C3CN(c4ccc5ccccc5n4)C3)C[C@@H]2C1] | (3aR,6aS)-tert-butyl 5-(3-(1-(quinolin-2-yl)azetidin-3-yl)pyrazin-2-yl)hexahydropyrrolo[3,4-c]pyrrole-2(1H)-carboxylate |
| 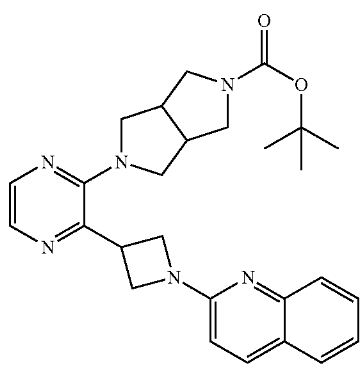 [SMILES: CC(C)(C)OC(=O)N1CC2CN(c3nccnc3C3CN(c4ccc5ccccc5n4)C3)CC2C1] | tert-butyl 5-(3-(1-(quinolin-2-yl)azetidin-3-yl)pyrazin-2-yl)hexahydropyrrolo[3,4-c]pyrrole-2(1H)-carboxylate |
| 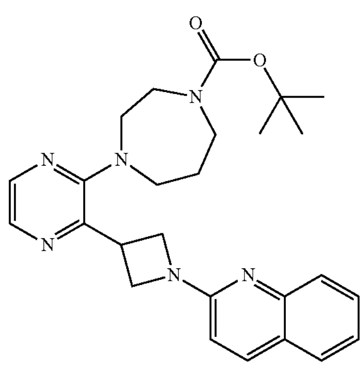 [SMILES: CC(C)(C)OC(=O)N1CCCN(c2nccnc2C2CN(c3ccc4ccccc4n3)C2)CC1] | tert-butyl 4-(3-(1-(quinolin-2-yl)azetidin-3-yl)pyrazin-2-yl)-1,4-diazepane-1-carboxylate |
| 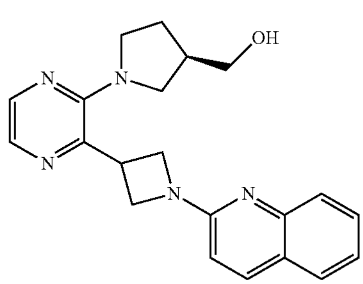 [SMILES: OC[C@@H]1CCN(c2nccnc2C2CN(c3ccc4ccccc4n3)C2)C1] | (R)-(1-(3-(1-(quinolin-2-yl)azetidin-3-yl)pyrazin-2-yl)pyrrolidin-3-yl)methanol |

| Chemical Structure | Chemical Name |
|---|---|
| 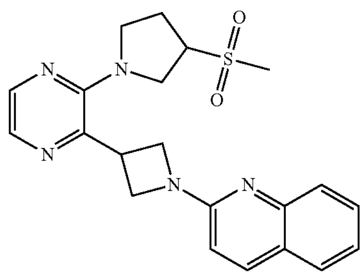 [SMILES: CS(=O)(=O)C1CCN(c2nccnc2C2CN(c3ccc4ccccc4n3)C2)C1] | (R- & S-)-2-(3-(3-(3-(methylsulfonyl)pyrrolidin-1-yl)pyrazin-2-yl)azetidin-1-yl)quinoline |
| 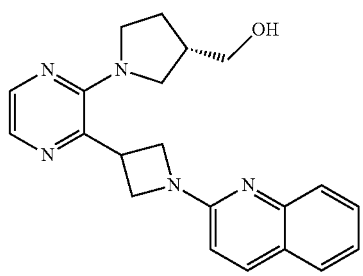 [SMILES: OC[C@H]1CCN(c2nccnc2C2CN(c3ccc4ccccc4n3)C2)C1] | (S)-(1-(3-(1-(quinolin-2-yl)azetidin-3-yl)pyrazin-2-yl)pyrrolidin-3-yl)methanol |
| 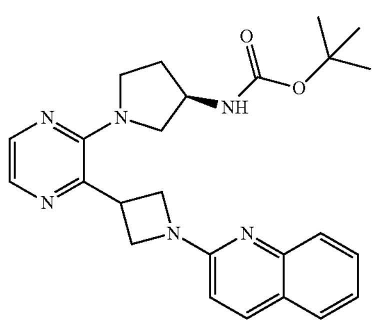 [SMILES: CC(C)(C)OC(=O)N[C@@H]1CCN(c2nccnc2C2CN(c3ccc4ccccc4n3)C2)C1] | (R)-tert-butyl 1-(3-(1-(quinolin-2-yl)azetidin-3-yl)pyrazin-2-yl)pyrrolidin-3-ylcarbamate |
| 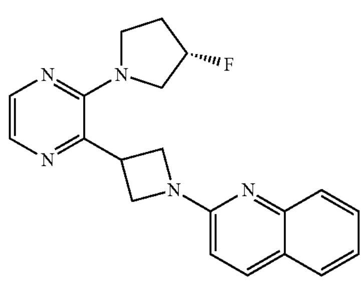 | (S)-2-(3-(3-(3-fluoropyrrolidin-1-yl)pyrazin-2-yl)azetidin-1-yl)quinoline |
| 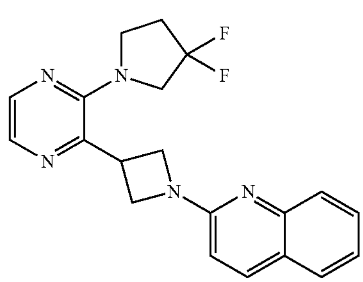 [SMILES: FC1(F)CCN(c2nccnc2C2CN(c3ccc4ccccc4n3)C2)C1] | 2-(3-(3-(3,3-difluoropyrrolidin-1-yl)pyrazin-2-yl)azetidin-1-yl)quinoline |

| Chemical Structure | Chemical Name |
|---|---|
| 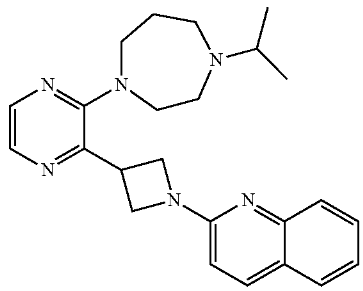 [SMILES: CC(C)N1CCCN(c2nccnc2C2CN(c3ccc4ccccc4n3)C2)CC1] | 2-(3-(3-(4-isopropyl-1,4-diazepan-1-yl)pyrazin-2-yl)azetidin-1-yl)quinoline |
| 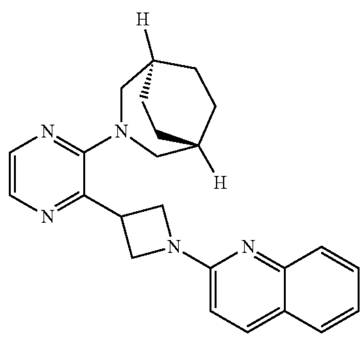 [SMILES: c1ccc2nc(N3CC(c4nccnc4N4C[C@H]5CC[C@@H](CC5)C4)C3)ccc2c1] | (1R,5R)-3-(3-(1-(quinolin-2-yl)azetidin-3-yl)pyrazin-2-yl)-3-azabicyclo[3.2.2]nonane |
| 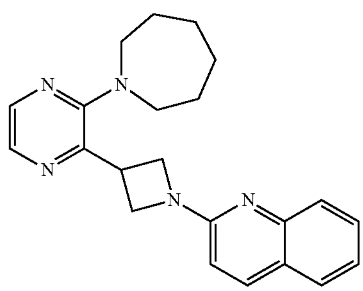 [SMILES: c1ccc2nc(N3CC(c4nccnc4N4CCCCCC4)C3)ccc2c1] | 2-(3-(3-(azepan-1-yl)pyrazin-2-yl)azetidin-1-yl)quinoline |
| 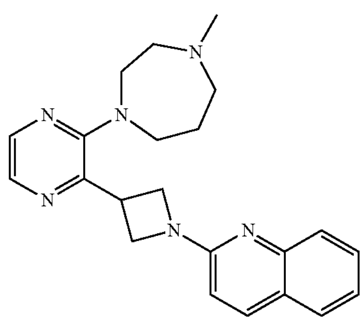 [SMILES: CN1CCCN(c2nccnc2C2CN(c3ccc4ccccc4n3)C2)CC1] | 2-(3-(3-(4-methyl-1,4-diazepan-1-yl)pyrazin-2-yl)azetidin-1-yl)quinoline |
| 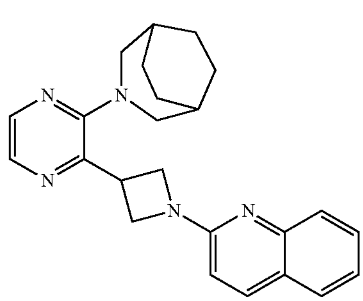 [SMILES: c1ccc2nc(N3CC(c4nccnc4N4CC5CCC(CC5)C4)C3)ccc2c1] | 3-(3-(1-(quinolin-2-yl)azetidin-3-yl)pyrazin-2-yl)-3-azabicyclo[3.2.2]nonane |

| Chemical Structure | Chemical Name |
| --- | --- |
| 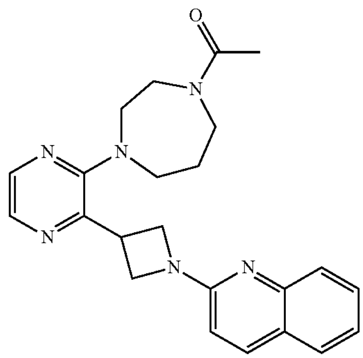 [SMILES: CC(=O)N1CCCN(c2nccnc2C2CN(c3ccc4ccccc4n3)C2)CC1] | 1-(4-(3-(1-(quinolin-2-yl)azetidin-3-yl)pyrazin-2-yl)-1,4-diazepan-1-yl)ethanone |
| 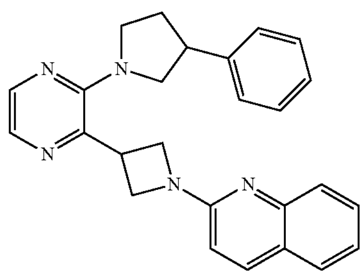 | (R- & S-)-2-(3-(3-(3-phenylpyrrolidin-1-yl)pyrazin-2-yl)azetidin-1-yl)quinoline |
| 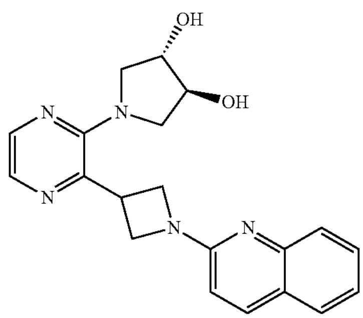 [SMILES: O[C@H]1CN(c2nccnc2C2CN(c3ccc4ccccc4n3)C2)C[C@@H]1O] | (3S,4S)-1-(3-(1-(quinolin-2-yl)azetidin-3-yl)pyrazin-2-yl)pyrrolidine-3,4-diol |
| 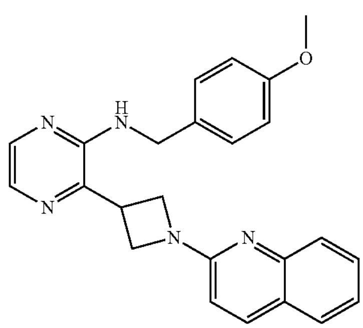 [SMILES: COc1ccc(CNc2nccnc2C2CN(c3ccc4ccccc4n3)C2)cc1] | N-(4-methoxybenzyl)-3-(1-(quinolin-2-yl)azetidin-3-yl)pyrazin-2-amine |
| 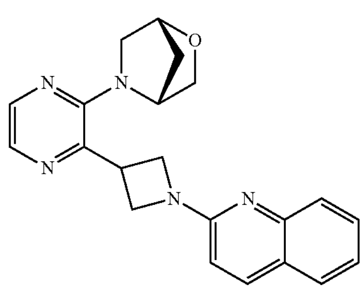 [SMILES: c1ccc2nc(N3CC(c4nccnc4N4C[C@H]5C[C@@H]4CO5)C3)ccc2c1] | (1R,4R)-5-(3-(1-(quinolin-2-yl)azetidin-3-yl)pyrazin-2-yl)-2-oxa-5-azabicyclo[2.2.1]heptane |

| Chemical Structure | Chemical Name |
|---|---|
| 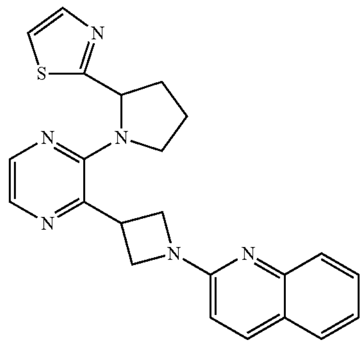 [SMILES: c1ccc2nc(N3CC(c4nccnc4N4CCCC4c4nccs4)C3)ccc2c1] | (R- & S-)-2-(1-(3-(1-(quinolin-2-yl)azetidin-3-yl)pyrazin-2-yl)pyrrolidin-3-yl)thiazole |
| 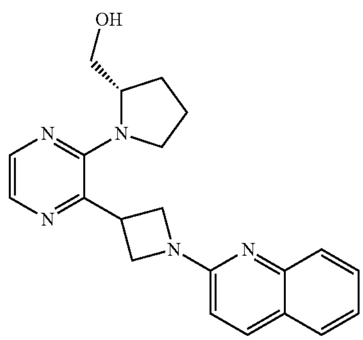 [SMILES: OC[C@@H]1CCCN1c1nccnc1C1CN(c2ccc3ccccc3n2)C1] | (S)-(1-(3-(1-(quinolin-2-yl)azetidin-3-yl)pyrazin-2-yl)pyrrolidin-2-yl)methanol |
| 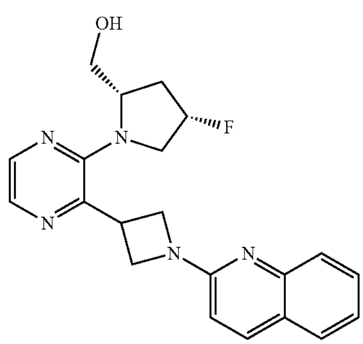 [SMILES: OC[C@@H]1C[C@H](F)CN1c1nccnc1C1CN(c2ccc3ccccc3n2)C1] | ((2S,4S)-4-fluoro-1-(3-(1-(quinolin-2-yl)azetidin-3-yl)pyrazin-2-yl)pyrrolidin-2-yl)methanol |
| 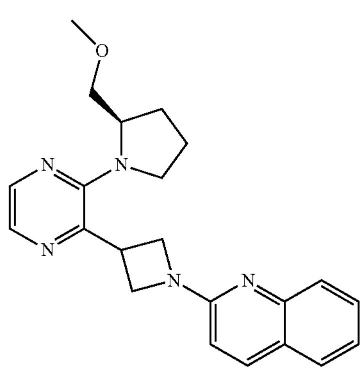 [SMILES: COC[C@H]1CCCN1c1nccnc1C1CN(c2ccc3ccccc3n2)C1] | (R)-2-(3-(3-(2-(methoxymethyl)pyrrolidin-1-yl)pyrazin-2-yl)azetidin-1-yl)quinoline |

| Chemical Structure | Chemical Name |
|---|---|
| 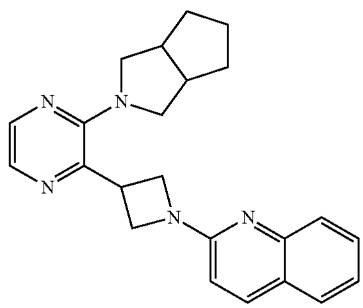 [SMILES: c1ccc2nc(N3CC(c4nccnc4N4CC5CCCC5C4)C3)ccc2c1] | 2-(3-(3-(hexahydrocyclopenta[c]pyrrol-2(1H)-yl)pyrazin-2-yl)azetidin-1-yl)quinoline |
| 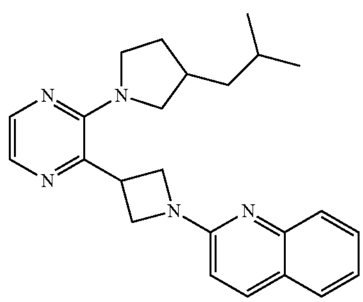 [SMILES: CC(C)CC1CCN(c2nccnc2C2CN(c3ccc4ccccc4n3)C2)C1] | (R- & S-)-2-(3-(3-(3-isobutylpyrrolidin-1-yl)pyrazin-2-yl)azetidin-1-yl)quinoline |
| 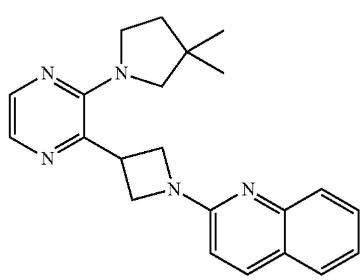 [SMILES: CC1(C)CCN(c2nccnc2C2CN(c3ccc4ccccc4n3)C2)C1] | 2-(3-(3-(3,3-dimethylpyrrolidin-1-yl)pyrazin-2-yl)azetidin-1-yl)quinoline |
| 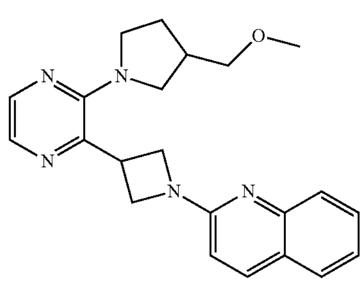 [SMILES: COCC1CCN(c2nccnc2C2CN(c3ccc4ccccc4n3)C2)C1] | (R- & S-)-2-(3-(3-(3-(methoxymethyl)pyrrolidin-1-yl)pyrazin-2-yl)azetidin-1-yl)quinoline |
| 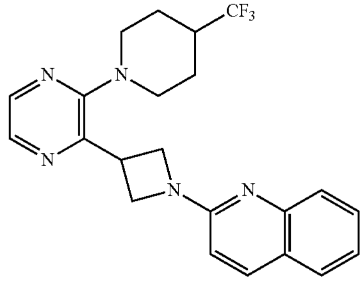 | 2-(3-(3-(4-(trifluoromethyl)piperidin-1-yl)pyrazin-2-yl)azetidin-1-yl)quinoline |

| Chemical Structure | Chemical Name |
|---|---|
| 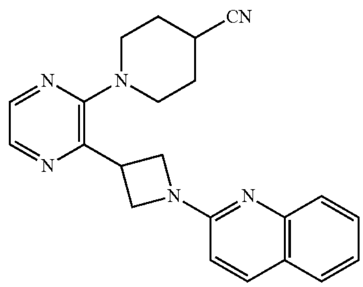 | 1-(3-(1-(quinolin-2-yl)azetidin-3-yl)pyrazin-2-yl)piperidine-4-carbonitrile |
| 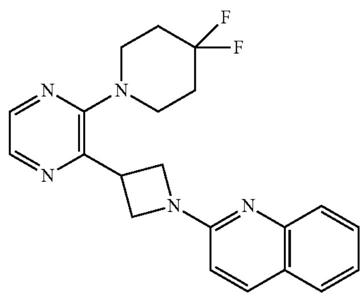 [SMILES: FC1(F)CCN(c2nccnc2C2CN(c3ccc4ccccc4n3)C2)CC1] | 2-(3-(3-(4,4-difluoropiperidin-1-yl)pyrazin-2-yl)azetidin-1-yl)quinoline |
| 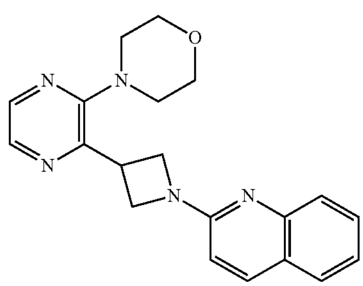 [SMILES: c1ccc2nc(N3CC(c4nccnc4N4CCOCC4)C3)ccc2c1] | 4-(3-(1-(quinolin-2-yl)azetidin-3-yl)pyrazin-2-yl)morpholine |
| 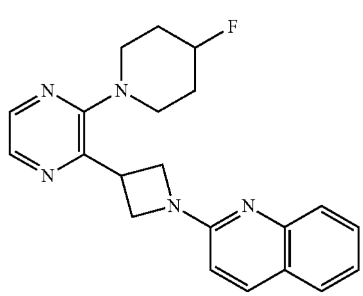 [SMILES: FC1CCN(c2nccnc2C2CN(c3ccc4ccccc4n3)C2)CC1] | 2-(3-(3-(4-fluoropiperidin-1-yl)pyrazin-2-yl)azetidin-1-yl)quinoline |
| 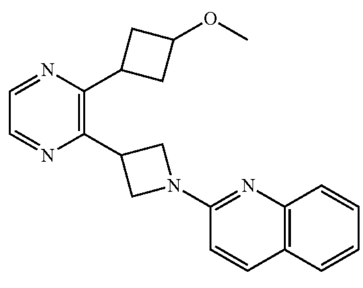 | 2-(3-(3-(3-methoxyazetidin-1-yl)pyrazin-2-yl)azetidin-1-yl)quinoline |

| Chemical Structure | Chemical Name |
|---|---|
| 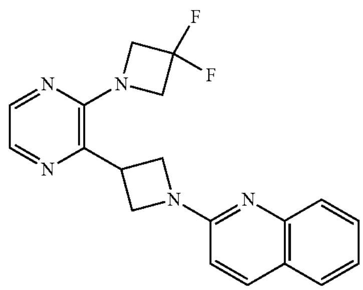 [SMILES: FC1(F)CN(c2nccnc2C2CN(c3ccc4ccccc4n3)C2)C1] | 2-(3-(3-(3,3-difluoroazetidin-1-yl)pyrazin-2-yl)azetidin-1-yl)quinoline |
| 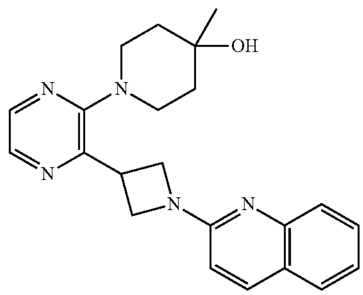 [SMILES: CC1(O)CCN(c2nccnc2C2CN(c3ccc4ccccc4n3)C2)CC1] | 4-methyl-1-(3-(1-(quinolin-2-yl)azetidin-3-yl)pyrazin-2-yl)piperidin-4-ol |
| 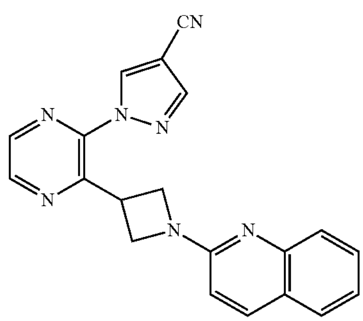 [SMILES: N#Cc1cnn(-c2nccnc2C2CN(c3ccc4ccccc4n3)C2)c1] | 1-(3-(1-(quinolin-2-yl)azetidin-3-yl)pyrazin-2-yl)-1H-pyrazole-4-carbonitrile |
| 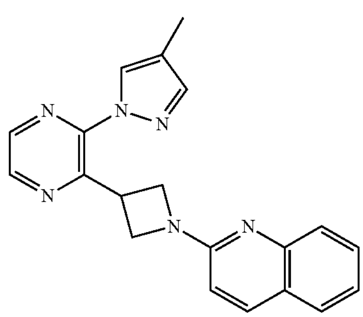 [SMILES: Cc1cnn(-c2nccnc2C2CN(c3ccc4ccccc4n3)C2)c1] | 2-(3-(3-(4-methyl-1H-pyrazol-1-yl)pyrazin-2-yl)azetidin-1-yl)quinoline |
| 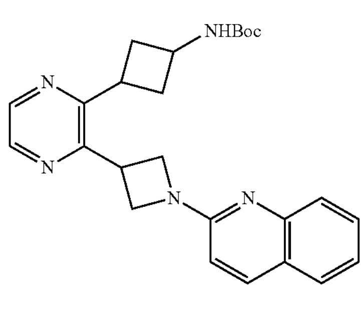 | tert-butyl(1-(3-(1-(quinolin-2-yl)azetidin-3-yl)pyrazin-2-yl)azetidin-3-yl)carbamate |

| Chemical Structure | Chemical Name |
|---|---|
| 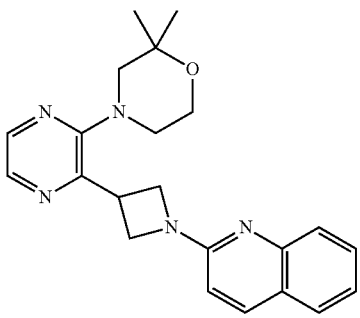 [SMILES: CC1(C)CN(c2nccnc2C2CN(c3ccc4ccccc4n3)C2)CCO1] | 2,2-dimethyl-4-(3-(1-(quinolin-2-yl)azetidin-3-yl)pyrazin-2-yl)morpholine |
| 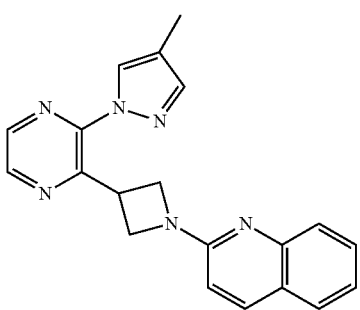 [SMILES: Cc1cnn(-c2nccnc2C2CN(c3ccc4ccccc4n3)C2)c1] | 2-(3-(3-(4-methyl-1H-imidazol-1-yl)pyrazin-2-yl)azetidin-1-yl)quinoline |
| 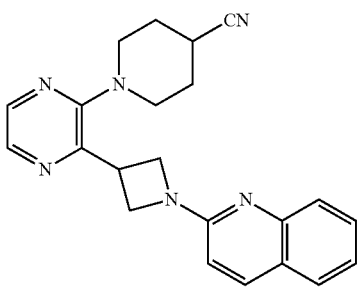 | 1-(3-(1-(quinazolin-2-yl)azetidin-3-yl)pyrazin-2-yl)piperidine-4-carbonitrile |
| 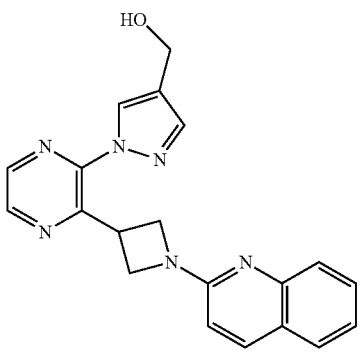 [SMILES: OCc1cnn(-c2nccnc2C2CN(c3ccc4ccccc4n3)C2)c1] | (1-(3-(1-(quinolin-2-yl)azetidin-3-yl)pyrazin-2-yl)-1H-pyrazol-4-yl)methanol |

| Chemical Structure | Chemical Name |
|---|---|
| 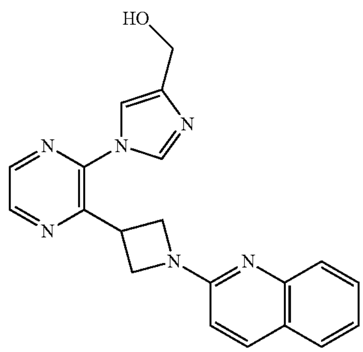 [SMILES: OCc1cn(-c2nccnc2C2CN(c3ccc4ccccc4n3)C2)cn1] | (1-(3-(1-(quinolin-2-yl)azetidin-3-yl)pyrazin-2-yl)-1H-imidazol-4-yl)methanol |
| 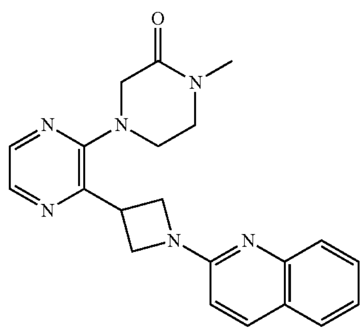 [SMILES: CN1CCN(c2nccnc2C2CN(c3ccc4ccccc4n3)C2)CC1=O] | 1-methyl-4-(3-(1-(quinolin-2-yl)azetidin-3-yl)pyrazin-2-yl)piperazin-2-one |
| 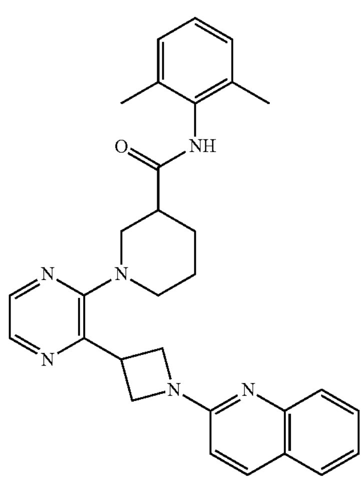 [SMILES: Cc1cccc(C)c1NC(=O)C1CCCN(c2nccnc2C2CN(c3ccc4ccccc4n3)C2)C1] | N-(2,6-dimethylphenyl)-1-(3-(1-(quinolin-2-yl)azetidin-3-yl)pyrazin-2-yl)piperidine-3-carboxamide |
| 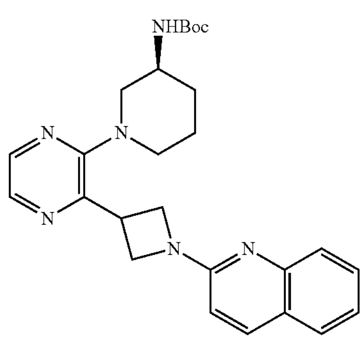 [SMILES: CC(C)(C)OC(=O)N[C@H]1CCCN(c2nccnc2C2CN(c3ccc4ccccc4n3)C2)C1] | (S)-tert-butyl (1-(3-(1-(quinolin-2-yl)azetidin-3-yl)pyrazin-2-yl)piperidin-3-yl)carbamate |

| Chemical Structure | Chemical Name |
|---|---|
| 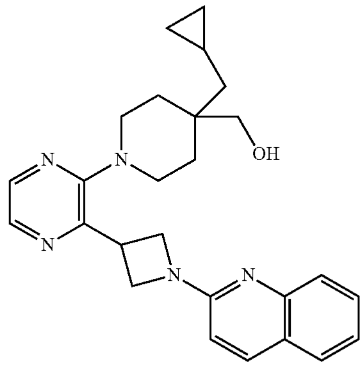 [SMILES: OCC1(CC2CC2)CCN(c2nccnc2C2CN(c3ccc4ccccc4n3)C2)CC1] | (4-(cyclopropylmethyl)-1-(3-(1-(quinolin-2-yl)azetidin-3-yl)pyrazin-2-yl)piperidin-4-yl)methanol |
| 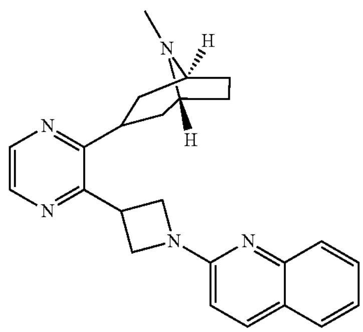 [SMILES: CN1[C@@H]2CC[C@H]1CC(c1nccnc1C1CN(c3ccc4ccccc4n3)C1)C2] | 2-(3-(3-((1R,5S)-8-methyl-3,8-diazabicyclo[3.2.1]octan-3-yl)pyrazin-2-yl)azetidin-1-yl)quinoline |
| 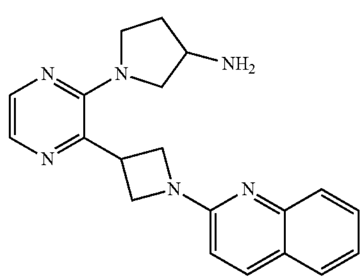 [SMILES: NC1CCN(c2nccnc2C2CN(c3ccc4ccccc4n3)C2)C1] | 1-(3-(1-(quinolin-2-yl)azetidin-3-yl)pyrazin-2-yl)pyrrolidin-3-amine |
| 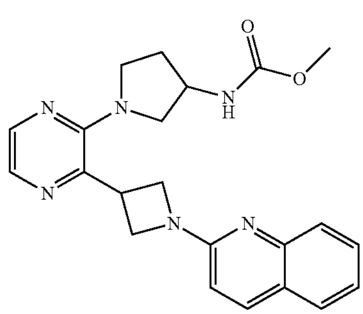 [SMILES: COC(=O)NC1CCN(c2nccnc2C2CN(c3ccc4ccccc4n3)C2)C1] | (R- & S-)-methyl (1-(3-(1-(quinolin-2-yl)azetidin-3-yl)pyrazin-2-yl)pyrrolidin-3-yl)carbamate |
| 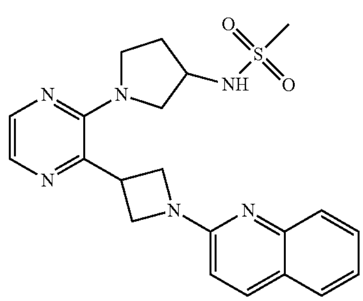 [SMILES: CS(=O)(=O)NC1CCN(c2nccnc2C2CN(c3ccc4ccccc4n3)C2)C1] | (R- & S-)-N-(1-(3-(1-(quinolin-2-yl)azetidin-3-yl)pyrazin-2-yl)pyrrolidin-3-yl)methanesulfonamide |

US 9,718,803 B2

-continued

| Chemical Structure | Chemical Name |
|---|---|
| 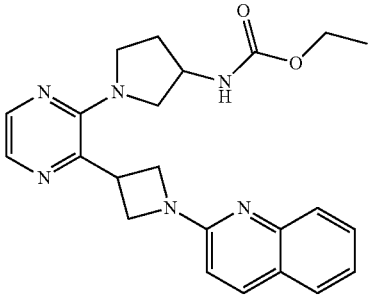 [SMILES: CCOC(=O)NC1CCN(c2nccnc2C2CN(c3ccc4ccccc4n3)C2)C1] | (R- & S-)-ethyl (1-(3-(1-(quinolin-2-yl)azetidin-3-yl)pyrazin-2-yl)pyrrolidin-3-yl)carbamate |
| 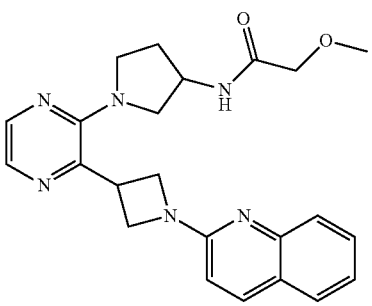 [SMILES: COCC(=O)NC1CCN(c2nccnc2C2CN(c3ccc4ccccc4n3)C2)C1] | (R- & S-)-2-methoxy-N-(1-(3-(1-(quinolin-2-yl)azetidin-3-yl)pyrazin-2-yl)pyrrolidin-3-yl)acetamide |
| 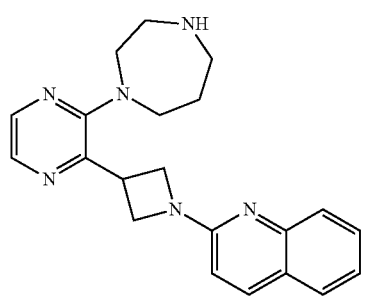 [SMILES: c1ccc2nc(N3CC(c4nccnc4N4CCCNCC4)C3)ccc2c1] | 2-(3-(3-(1,4-Diazepan-1-yl)pyrazin-2-yl)azetidin-1-yl)quinoline |
| 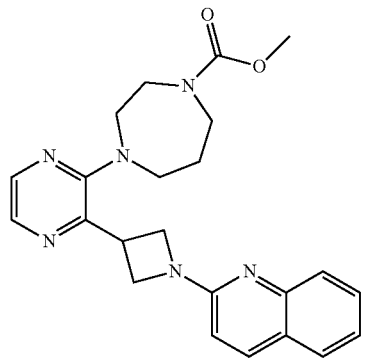 [SMILES: COC(=O)N1CCCN(c2nccnc2C2CN(c3ccc4ccccc4n3)C2)CC1] | Methyl 4-(3-(1-(quinolin-2-yl)azetidin-3-yl)pyrazin-2-yl)-1,4-diazepane-1-carboxylate |
| 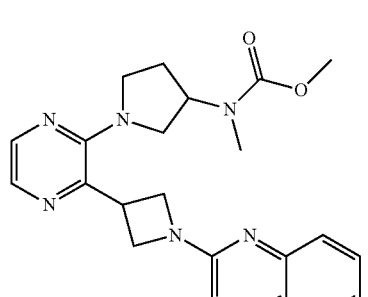 | methyl methyl(1-(3-(1-(quinolin-2-yl)azetidin-3-yl)pyrazin-2-yl)pyrrolidin-3-yl)carbamate |

-continued

| Chemical Structure | Chemical Name |
|---|---|
| 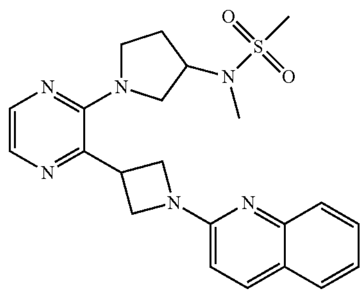 [SMILES: CN(C1CCN(c2nccnc2C2CN(c3ccc4ccccc4n3)C2)C1)S(C)(=O)=O] | N-methyl-N-(1-(3-(1-(quinolin-2-yl)azetidin-3-yl)pyrazin-2-yl)pyrrolidin-3-yl)methanesulfonamide |
| 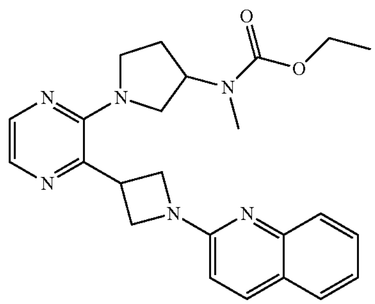 [SMILES: CCOC(=O)N(C)C1CCN(c2nccnc2C2CN(c3ccc4ccccc4n3)C2)C1] | Ethyl methyl(1-(3-(1-(quinolin-2-yl)azetidin-3-yl)pyrazin-2-yl)pyrrolidin-3-yl)carbamate |
| 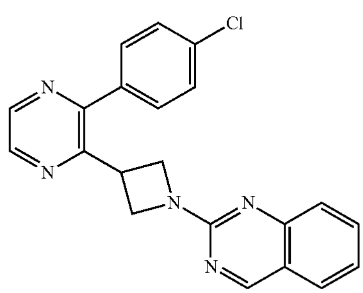 [SMILES: Clc1ccc(-c2nccnc2C2CN(c3ncc4ccccc4n3)C2)cc1] | 2-(3-(3-(4-chlorophenyl)pyrazin-2-yl)azetidin-1-yl)quinazoline |
| 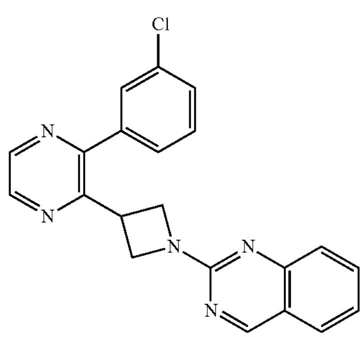 [SMILES: Clc1cccc(-c2nccnc2C2CN(c3ncc4ccccc4n3)C2)c1] | 2-(3-(3-(3-chlorophenyl)pyrazin-2-yl)azetidin-1-yl)quinazoline |
| 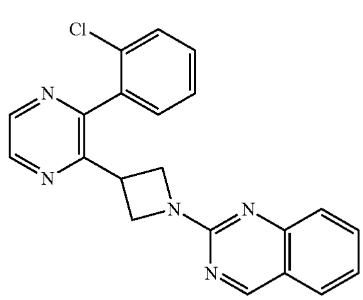 [SMILES: Clc1ccccc1-c1nccnc1C1CN(c2ncc3ccccc3n2)C1] | 2-(3-(3-(2-chlorophenyl)pyrazin-2-yl)azetidin-1-yl)quinazoline |

| Chemical Structure | Chemical Name |
| --- | --- |
| 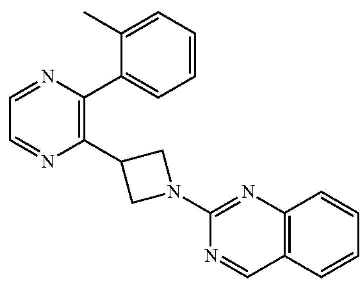 [SMILES: Cc1ccccc1-c1nccnc1C1CN(c2ncc3ccccc3n2)C1] | 2-(3-(3-(o-tolyl)pyrazin-2-yl)azetidin-1-yl)quinazoline |
| 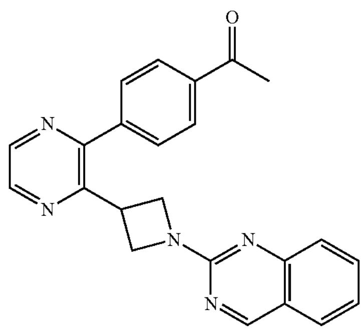 [SMILES: CC(=O)c1ccc(-c2nccnc2C2CN(c3ncc4ccccc4n3)C2)cc1] | 1-(4-(3-(1-(quinazolin-2-yl)azetidin-3-yl)pyrazin-2-yl)phenyl)ethanone |
| 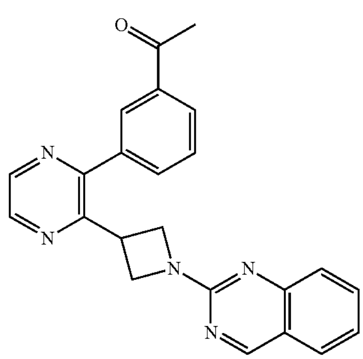 [SMILES: CC(=O)c1cccc(-c2nccnc2C2CN(c3ncc4ccccc4n3)C2)c1] | 1-(3-(3-(1-(quinazolin-2-yl)azetidin-3-yl)pyrazin-2-yl)phenyl)ethanone |
| 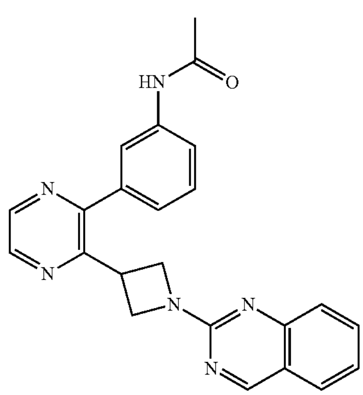 [SMILES: CC(=O)Nc1cccc(-c2nccnc2C2CN(c3ncc4ccccc4n3)C2)c1] | N-(3-(3-(1-(quinazolin-2-yl)azetidin-3-yl)pyrazin-2-yl)phenyl)acetamide |

| Chemical Structure | Chemical Name |
|---|---|
| 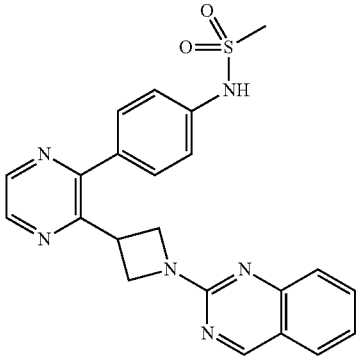 [SMILES: CS(=O)(=O)Nc1ccc(-c2nccnc2C2CN(c3ncc4ccccc4n3)C2)cc1] | N-(4-(3-(1-(quinazolin-2-yl)azetidin-3-yl)pyrazin-2-yl)phenyl)methanesulfonamide |
| 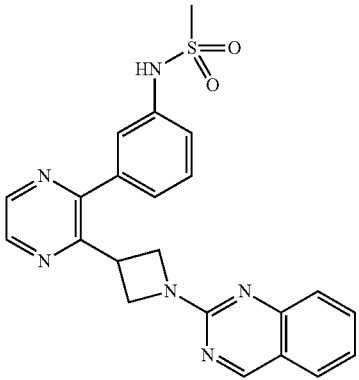 [SMILES: CS(=O)(=O)Nc1cccc(-c2nccnc2C2CN(c3ncc4ccccc4n3)C2)c1] | N-(3-(3-(1-(quinazolin-2-yl)azetidin-3-yl)pyrazin-2-yl)phenyl)methanesulfonamide |
| 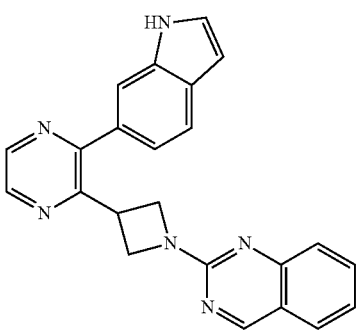 [SMILES: c1ccc2nc(N3CC(c4nccnc4-c4ccc5cc[nH]c5c4)C3)ncc2c1] | 2-(3-(3-(1H-indol-6-yl)pyrazin-2-yl)azetidin-1-yl)quinazoline |
| 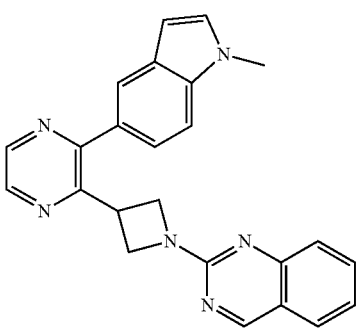 [SMILES: Cn1ccc2cc(-c3nccnc3C3CN(c4ncc5ccccc5n4)C3)ccc21] | 2-(3-(3-(1-methyl-1H-indol-5-yl)pyrazin-2-yl)azetidin-1-yl)quinazoline |

| Chemical Structure | Chemical Name |
|---|---|
| 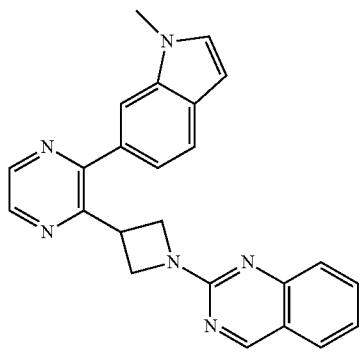 [SMILES: Cn1ccc2ccc(-c3nccnc3C3CN(c4ncc5ccccc5n4)C3)cc21] | 2-(3-(3-(1-methyl-1H-indol-6-yl)pyrazin-2-yl)azetidin-1-yl)quinazoline |
| 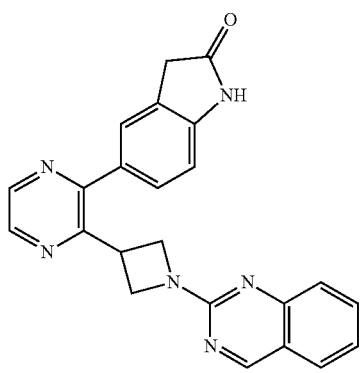 [SMILES: O=C1Cc2cc(-c3nccnc3C3CN(c4ncc5ccccc5n4)C3)ccc2N1] | 5-(3-(1-(quinazolin-2-yl)azetidin-3-yl)pyrazin-2-yl)indolin-2-one |
| 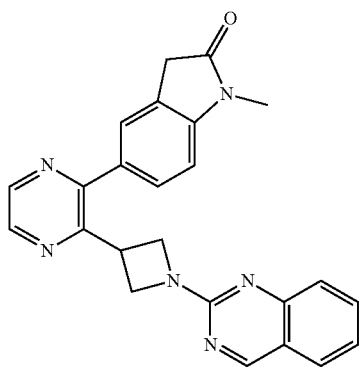 [SMILES: CN1C(=O)Cc2cc(-c3nccnc3C3CN(c4ncc5ccccc5n4)C3)ccc21] | 1-methyl-5-(3-(1-(quinazolin-2-yl)azetidin-3-yl)pyrazin-2-yl)indolin-2-one |
| 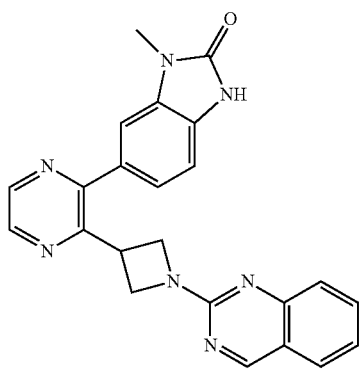 [SMILES: Cn1c(=O)[nH]c2ccc(-c3nccnc3C3CN(c4ncc5ccccc5n4)C3)cc21] | 1-methyl-6-(3-(1-(quinazolin-2-yl)azetidin-3-yl)pyrazin-2-yl)-1H-benzo[d]imidazol-2(3H)-one |

-continued
| Chemical Structure | Chemical Name |
|---|---|
| 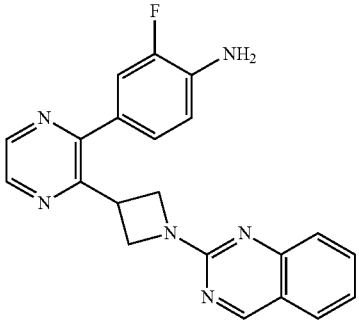 [SMILES: Nc1ccc(-c2nccnc2C2CN(c3ncc4ccccc4n3)C2)cc1F] | 2-fluoro-4-(3-(1-(quinazolin-2-yl)azetidin-3-yl)pyrazin-2-yl)aniline |
| 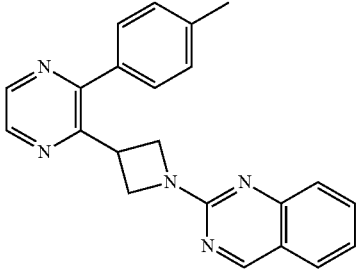 | 2-(3-(3-(p-tolyl)pyrazin-2-yl)azetidin-1-yl)quinazoline |
| 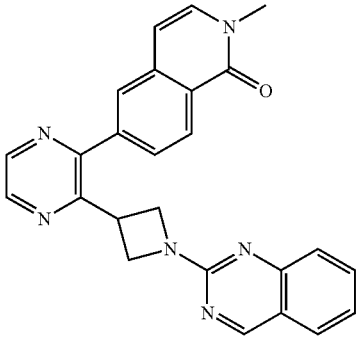 [SMILES: Cn1ccc2cc(-c3nccnc3C3CN(c4ncc5ccccc5n4)C3)ccc2c1=O] | 2-methyl-6-(3-(1-(quinazolin-2-yl)azetidin-3-yl)pyrazin-2-yl)isoquinolin-1(2H)-one |
| 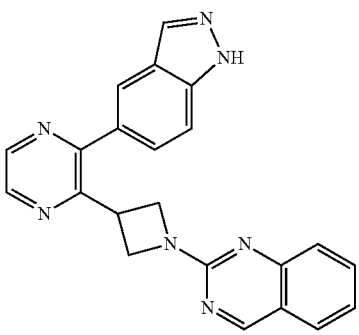 [SMILES: c1ccc2nc(N3CC(c4nccnc4-c4ccc5[nH]ncc5c4)C3)ncc2c1] | 2-(3-(3-(1H-indazol-5-yl)pyrazin-2-yl)azetidin-1-yl)quinazoline |

-continued

| Chemical Structure | Chemical Name |
|---|---|
| 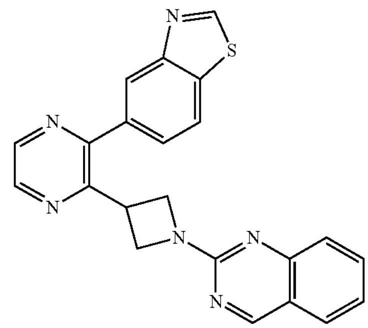 [SMILES: c1ccc2nc(N3CC(c4nccnc4-c4ccc5scnc5c4)C3)ncc2c1] | 5-(3-(1-(quinazolin-2-yl)azetidin-3-yl)pyrazin-2-yl)benzo[d]thiazole |
| 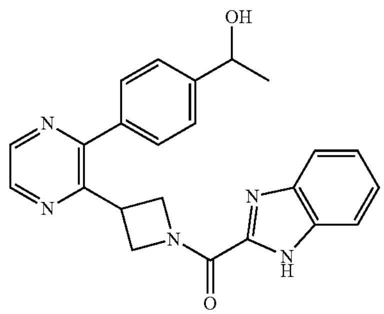 [SMILES: CC(O)c1ccc(-c2nccnc2C2CN(C(=O)c3nc4ccccc4[nH]3)C2)cc1] | (R & S)-(1H-Benzoimidazol-2-yl)-(3-{3-[4-(1-hydroxy-ethyl)-phenyl]-pyrazin-2-yl}-azetidin-1-yl)-methanone |
| 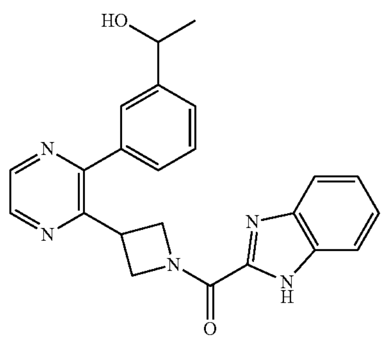 [SMILES: CC(O)c1cccc(-c2nccnc2C2CN(C(=O)c3nc4ccccc4[nH]3)C2)c1] | (R & S)-(1H-Benzoimidazol-2-yl)-(3-{3-[3-(1-hydroxy-ethyl)-phenyl]-pyrazin-2-yl}-azetidin-1-yl)-methanone |
| 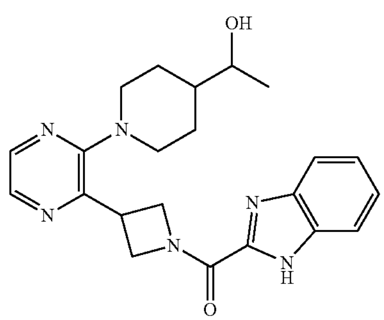 [SMILES: CC(O)C1CCN(c2nccnc2C2CN(C(=O)c3nc4ccccc4[nH]3)C2)CC1] | (R & S)-(1H-Benzoimidazol-2-yl)-(3-{3-[4-(1-hydroxy-ethyl)-piperidin-1-yl]-pyrazin-2-yl}-azetidin-1-yl)-methanone |
| 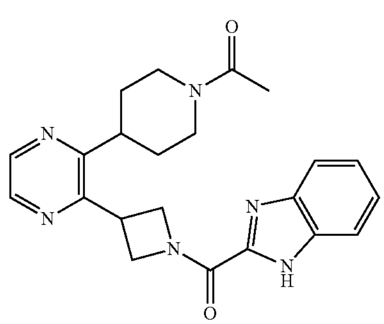 [SMILES: CC(=O)N1CCC(c2nccnc2C2CN(C(=O)c3nc4ccccc4[nH]3)C2)CC1] | 1-(4-{3-[1-(1H-Benzoimidazole-2-carbonyl)-azetidin-3-yl]-pyrazin-2-yl}-piperidin-1-yl)-ethanone |

-continued

| Chemical Structure | Chemical Name |
|---|---|
| 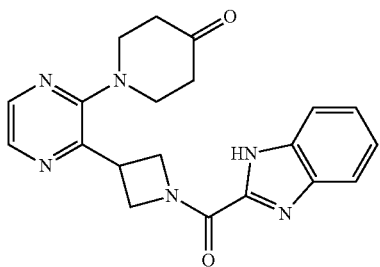 [SMILES: O=C1CCN(c2nccnc2C2CN(C(=O)c3nc4ccccc4[nH]3)C2)CC1] | 1-{3-[1-(1H-Benzoimidazole-2-carbonyl)-azetidin-3-yl]-pyrazin-2-yl}-piperidin-4-one |
| 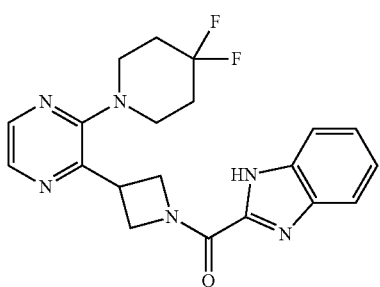 [SMILES: O=C(c1nc2ccccc2[nH]1)N1CC(c2nccnc2N2CCC(F)(F)CC2)C1] | (1H-Benzoimidazol-2-yl)-{3-[3-(4,4-difluoro-piperidin-1-yl)-pyrazin-2-yl]-azetidin-1-yl}-methanone |
| 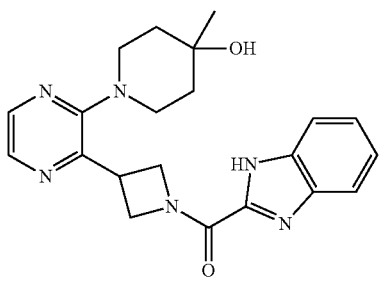 [SMILES: CC1(O)CCN(c2nccnc2C2CN(C(=O)c3nc4ccccc4[nH]3)C2)CC1] | (1H-Benzoimidazol-2-yl)-{3-[3-(4-hydroxy-4-methyl-piperidin-1-yl)-pyrazin-2-yl]-azetidin-1-yl}-methanone |
| 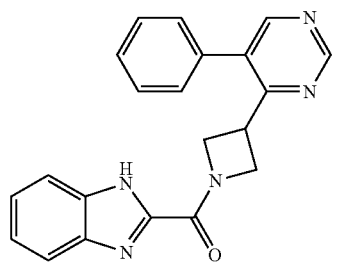 [SMILES: O=C(c1nc2ccccc2[nH]1)N1CC(c2ncncc2-c2ccccc2)C1] | (1H-Benzoimidazol-2-yl)-[3-(5-phenyl-pyrimidin-4-yl)-azetidin-1-yl]-methanone |
| 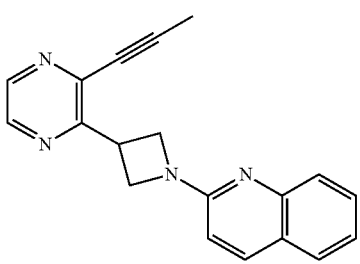 [SMILES: CC#Cc1nccnc1C1CN(c2ccc3ccccc3n2)C1] | 2-(3-(3-(prop-1-yn-1-yl)pyrazin-2-yl)azetidin-1-yl)quinoline |

| Chemical Structure | Chemical Name |
|---|---|
| 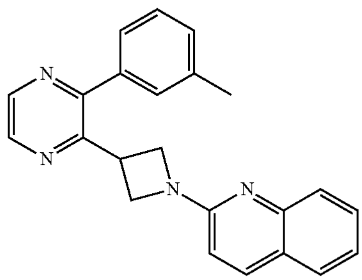 | 2-[3-(3-m-Tolyl-pyrazin-2-yl)-azetidin-1-yl]-quinoline |
| 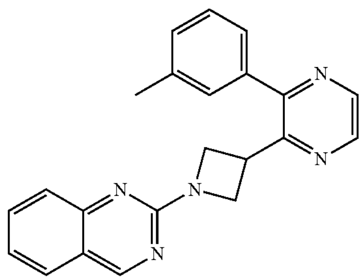 [SMILES: Cc1cccc(-c2nccnc2C2CN(c3ncc4ccccc4n3)C2)c1] | 2-[3-(3-m-Tolyl-pyrazin-2-yl)-azetidin-1-yl]-quinazoline |
| 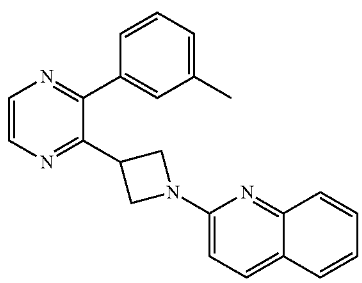 [SMILES: Cc1cccc(-c2nccnc2C2CN(c3ccc4ccccc4n3)C2)c1] | 2-[3-(3-m-Tolyl-pyrazin-2-yl)-azetidin-1-yl]-quinoxaline |
| 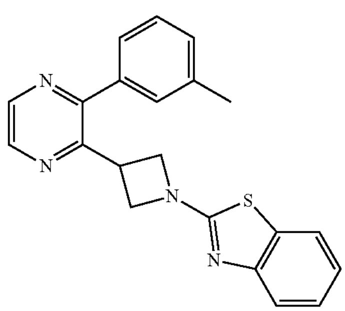 [SMILES: Cc1cccc(-c2nccnc2C2CN(c3nc4ccccc4s3)C2)c1] | 2-[3-(3-m-Tolyl-pyrazin-2-yl)-azetidin-1-yl]-benzothiazole |
| 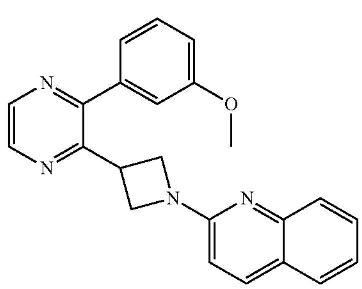 | 2-{3-[3-(3-Methoxy-phenyl)-pyrazin-2-yl]-azetidin-1-yl}-quinoline |

-continued

| Chemical Structure | Chemical Name |
|---|---|
| 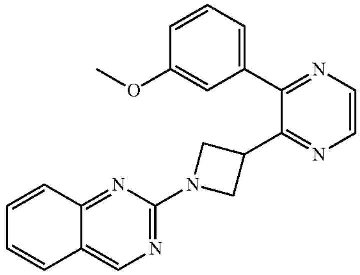 [SMILES: COc1cccc(-c2nccnc2C2CN(c3ncc4ccccc4n3)C2)c1] | 2-{3-[3-(3-Methoxy-phenyl)-pyrazin-2-yl]-azetidin-1-yl}-quinazoline |
| 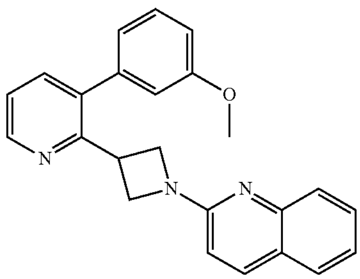 [SMILES: COc1cccc(-c2cccnc2C2CN(c3ccc4ccccc4n3)C2)c1] | 2-{3-[3-(3-Methoxy-phenyl)-pyridin-2-yl]-azetidin-1-yl}-quinoline |
| 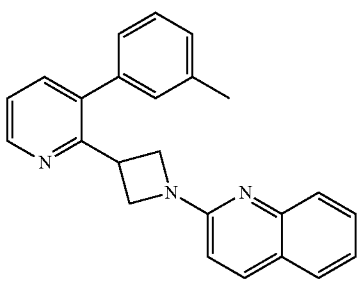 [SMILES: Cc1cccc(-c2cccnc2C2CN(c3ccc4ccccc4n3)C2)c1] | 2-[3-(3-m-Tolyl-pyridin-2-yl)-azetidin-1-yl]-quinoline |
| 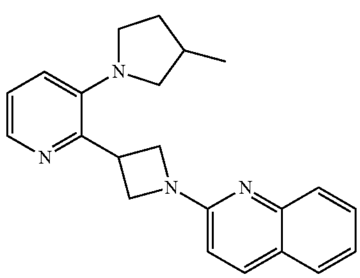 [SMILES: CC1CCN(c2cccnc2C2CN(c3ccc4ccccc4n3)C2)C1] | (R & S)-2-{3-[3-(3-Methyl-pyrrolidin-1-yl)-pyridin-2-yl]-azetidin-1-yl}-quinoline |
| 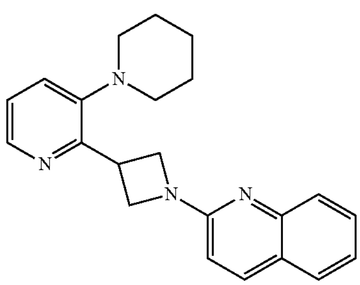 [SMILES: c1cnc(C2CN(c3ccc4ccccc4n3)C2)c(N2CCCCC2)c1] | 4-Methyl-2'-(1-quinolin-2-yl-azetidin-3-yl)-3,4,5,6-tetrahydro-2H-[1,3']bipyridinyl |

| Chemical Structure | Chemical Name |
| --- | --- |
| 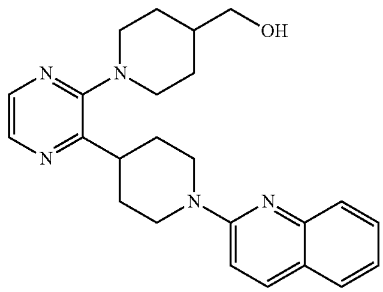 [SMILES: OCC1CCN(c2nccnc2C2CCN(c3ccc4ccccc4n3)CC2)CC1] | {1-[3-(1-Quinolin-2-yl-piperidin-4-yl)-pyrazin-2-yl]-piperidin-4-yl}-methanol |
| 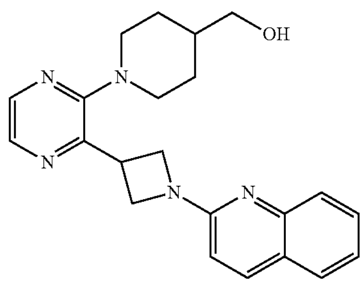 [SMILES: OCC1CCN(c2nccnc2C2CN(c3ccc4ccccc4n3)C2)CC1] | {1-[3-(1-Quinolin-2-yl-azetidin-3-yl)-pyrazin-2-yl]-piperidin-4-yl}-methanol |
| 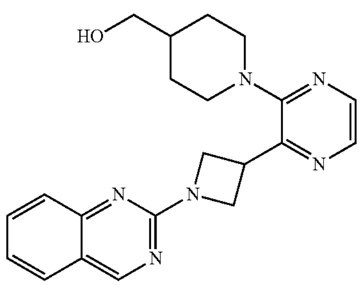 [SMILES: OCC1CCN(c2nccnc2C2CN(c3ncc4ccccc4n3)C2)CC1] | {1-[3-(1-Quinazolin-2-yl-azetidin-3-yl)-pyrazin-2-yl]-piperidin-4-yl}-methanol |
| 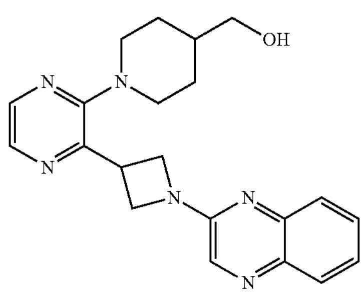 [SMILES: OCC1CCN(c2nccnc2C2CN(c3cnc4ccccc4n3)C2)CC1] | 4-[3-(1-Quinolin-2-yl-azetidin-3-yl)-pyrazin-2-yl]-phenylamine |
| 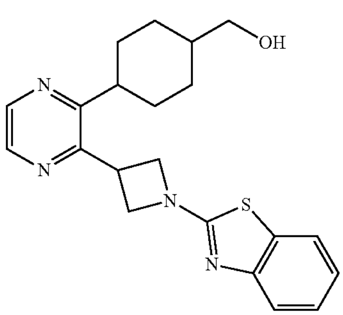 [SMILES: OCC1CCC(c2nccnc2C2CN(c3nc4ccccc4s3)C2)CC1] | {1-[3-(1-Benzothiazol-2-yl-azetidin-3-yl)-pyrazin-2-yl]-piperidin-4-yl}-methanol |

-continued

| Chemical Structure | Chemical Name |
|---|---|
| 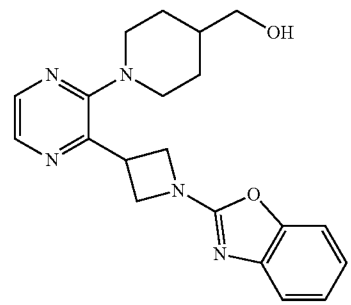 [SMILES: OCC1CCN(c2nccnc2C2CN(c3nc4ccccc4o3)C2)CC1] | {1-[3-(1-Benzooxazol-2-yl-azetidin-3-yl)-pyrazin-2-yl]-piperidin-4-yl}-methanol |
| 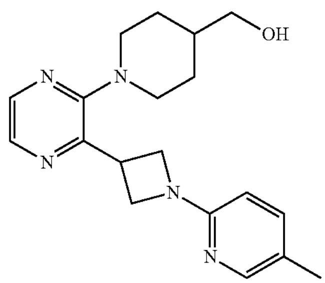 [SMILES: Cc1ccc(N2CC(c3nccnc3N3CCC(CO)CC3)C2)nc1] | (1-{3-[1-(5-Methyl-pyridin-2-yl)-azetidin-3-yl]-pyrazin-2-yl}-piperidin-4-yl)-methanol |
| 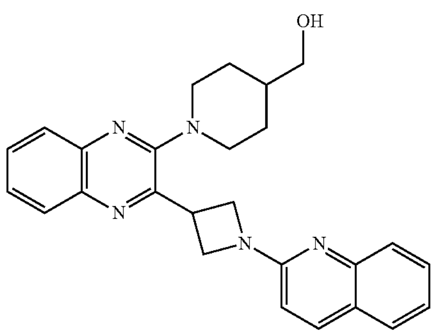 [SMILES: OCC1CCN(c2nc3ccccc3nc2C2CN(c3ccc4ccccc4n3)C2)CC1] | 2-(4-benzylpiperidin-1-yl)-3-(1-(quinolin-2-yl)azetidin-3-yl)quinoxaline |
| 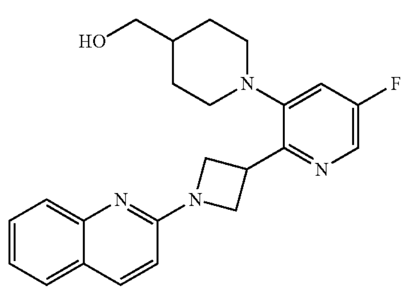 [SMILES: OCC1CCN(c2cc(F)cnc2C2CN(c3ccc4ccccc4n3)C2)CC1] | [5'-Fluoro-2'-(1-quinolin-2-yl-azetidin-3-yl)-3,4,5,6-tetrahydro-2H-[1,3']bipyridinyl-4-yl]-methanol |
| 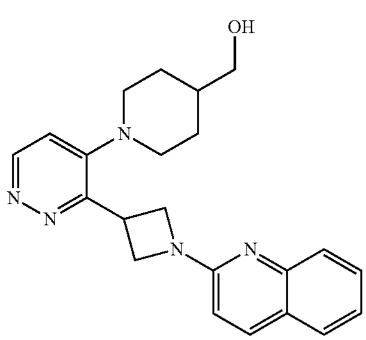 [SMILES: OCC1CCN(c2ccnnc2C2CN(c3ccc4ccccc4n3)C2)CC1] | {1-[3-(1-Quinolin-2-yl-azetidin-3-yl)-pyridazin-4-yl]-piperidin-4-yl}-methanol |

| Chemical Structure | Chemical Name |
|---|---|
| 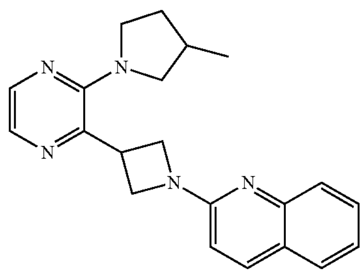 [SMILES: CC1CCN(c2nccnc2C2CN(c3ccc4ccccc4n3)C2)C1] | (R & S)-2-(3-(3-(3-methylpyrrolidin-1-yl)pyrazin-2-yl)azetidin-1-yl)quinoline |
| 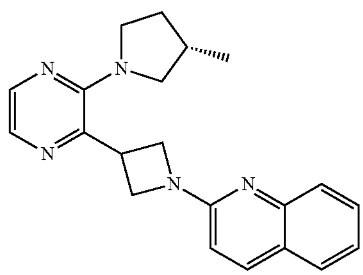 | (S or R)-2-(3-(3-(3-methylpyrrolidin-1-yl)pyrazin-2-yl)azetidin-1-yl)quinoline |
| 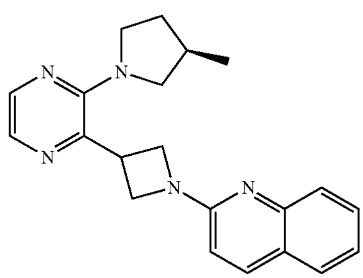 [SMILES: C[C@@H]1CCN(c2nccnc2C2CN(c3ccc4ccccc4n3)C2)C1] | (R or S)-2-(3-(3-(3-methylpyrrolidin-1-yl)pyrazin-2-yl)azetidin-1-yl)quinoline |
| 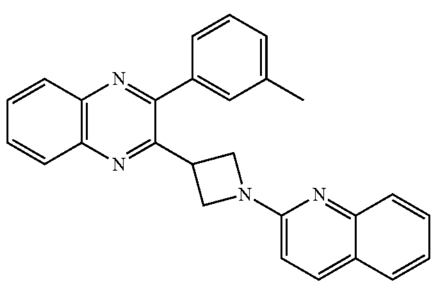 [SMILES: Cc1cccc(-c2nc3ccccc3nc2C2CN(c3ccc4ccccc4n3)C2)c1] | 2-(1-Quinolin-2-yl-azetidin-3-yl)-3-m-tolyl-quinoxaline |
| 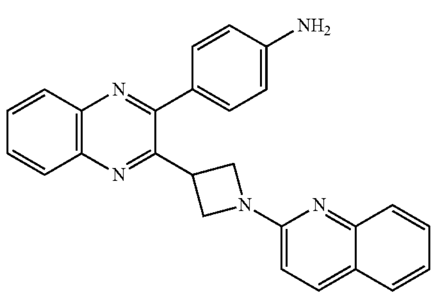 [SMILES: Nc1ccc(-c2nc3ccccc3nc2C2CN(c3ccc4ccccc4n3)C2)cc1] | 4-[3-(1-Quinolin-2-yl-azetidin-3-yl)-quinoxalin-2-yl]-phenylamine |

| Chemical Structure | Chemical Name |
|---|---|
| 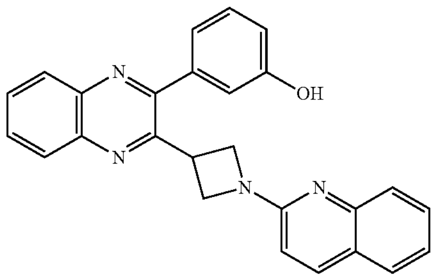 [SMILES: Oc1cccc(-c2nc3ccccc3nc2C2CN(c3ccc4ccccc4n3)C2)c1] | 3-[3-(1-Quinolin-2-yl-azetidin-3-yl)-quinoxalin-2-yl]-phenol |
| 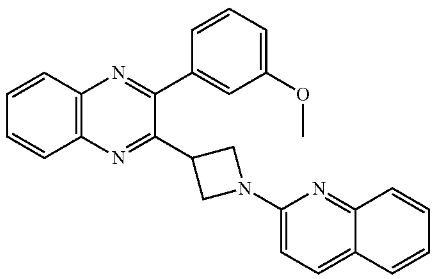 [SMILES: COc1cccc(-c2nc3ccccc3nc2C2CN(c3ccc4ccccc4n3)C2)c1] | 2-(3-Methoxy-phenyl)-3-(1-quinolin-2-yl-azetidin-3-yl)-quinoxaline |
| 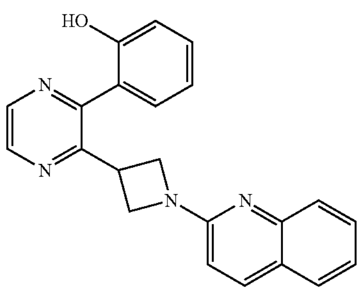 [SMILES: Oc1ccccc1-c1nccnc1C1CN(c2ccc3ccccc3n2)C1] | 2-[3-(1-Quinolin-2-yl-azetidin-3-yl)-pyrazin-2-yl]-phenol |
| 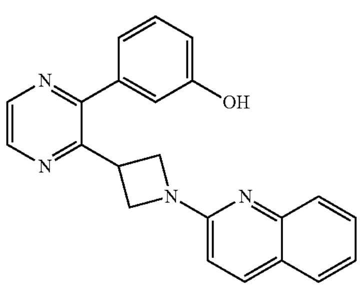 [SMILES: Oc1cccc(-c2nccnc2C2CN(c3ccc4ccccc4n3)C2)c1] | 3-[3-(1-Quinolin-2-yl-azetidin-3-yl)-pyrazin-2-yl]-phenol |
| 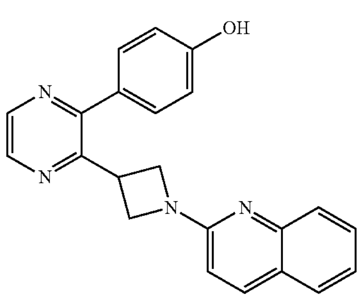 [SMILES: Oc1ccc(-c2nccnc2C2CN(c3ccc4ccccc4n3)C2)cc1] | 4-[3-(1-Quinolin-2-yl-azetidin-3-yl)-pyrazin-2-yl]-phenol |

| Chemical Structure | Chemical Name |
|---|---|
| 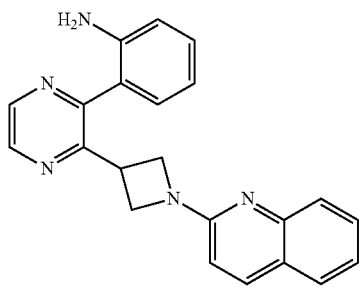 | 2-[3-(1-Quinolin-2-yl-azetidin-3-yl)-pyrazin-2-yl]-phenylamine |
| 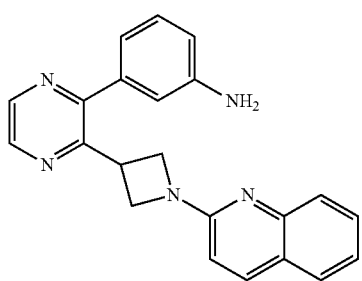 | 3-[3-(1-Quinolin-2-yl-azetidin-3-yl)-pyrazin-2-yl]-phenylamine |
| 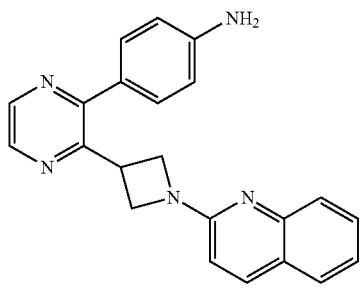 [SMILES: Nc1ccc(-c2nccnc2C2CN(c3ccc4ccccc4n3)C2)cc1] | 4-[3-(1-Quinolin-2-yl-azetidin-3-yl)-pyrazin-2-yl]-phenylamine |
| 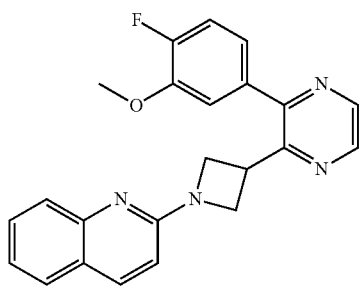 [SMILES: COc1cc(-c2nccnc2C2CN(c3ccc4ccccc4n3)C2)ccc1F] | 2-{3-[3-(4-Fluoro-3-methoxy-phenyl)-pyrazin-2-yl]-azetidin-1-yl}-quinoline |
| 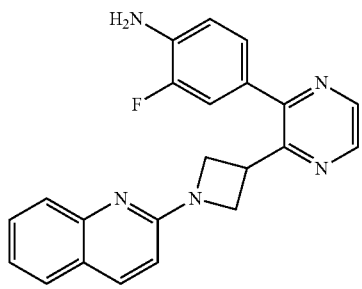 [SMILES: Nc1ccc(-c2nccnc2C2CN(c3ccc4ccccc4n3)C2)cc1F] | 2-Fluoro-4-[3-(1-quinolin-2-yl-azetidin-3-yl)-pyrazin-2-yl]-phenylamine |

| Chemical Structure | Chemical Name |
|---|---|
| 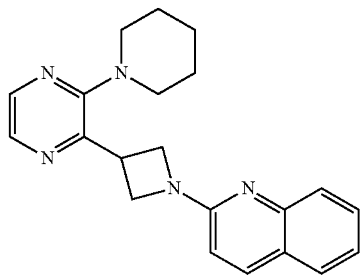 [SMILES: c1ccc2nc(N3CC(c4nccnc4N4CCCCC4)C3)ccc2c1] | 2-[3-(3-Piperidin-1-yl-pyrazin-2-yl)-azetidin-1-yl]-quinoline |
| 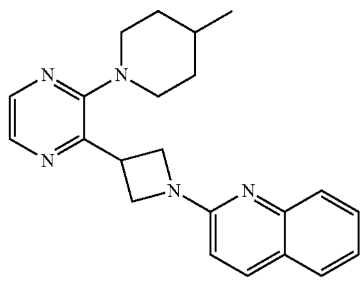 [SMILES: CC1CCN(c2nccnc2C2CN(c3ccc4ccccc4n3)C2)CC1] | 2-{3-[3-(4-Methyl-piperidin-1-yl)-pyrazin-2-yl]-azetidin-1-yl}-quinoline |
| 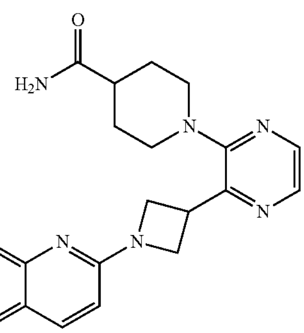 | 1-[3-(1-Quinolin-2-yl-azetidin-3-yl)-pyrazin-2-yl]-piperidine-4-carboxylic acid amide |
| 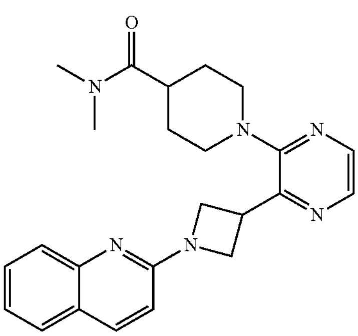 [SMILES: CN(C)C(=O)C1CCN(c2nccnc2C2CN(c3ccc4ccccc4n3)C2)CC1] | 1-[3-(1-Quinolin-2-yl-azetidin-3-yl)-pyrazin-2-yl]-piperidine-4-carboxylic acid dimethylamide |
| 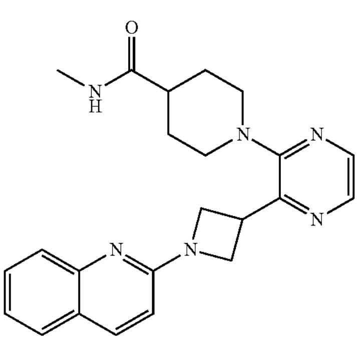 [SMILES: CNC(=O)C1CCN(c2nccnc2C2CN(c3ccc4ccccc4n3)C2)CC1] | 1-[3-(1-Quinolin-2-yl-azetidin-3-yl)-pyrazin-2-yl]-piperidine-4-carboxylic acid methylamide |

| Chemical Structure | Chemical Name |
|---|---|
| 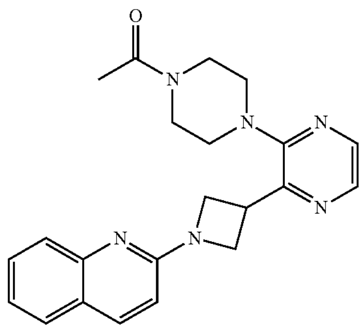 [SMILES: CC(=O)N1CCN(c2nccnc2C2CN(c3ccc4ccccc4n3)C2)CC1] | 1-[3'-(1-Quinolin-2-yl-azetidin-3-yl)-2,3,5,6-tetrahydro-[1,2']bipyrazinyl-4-yl]-ethanone |
| 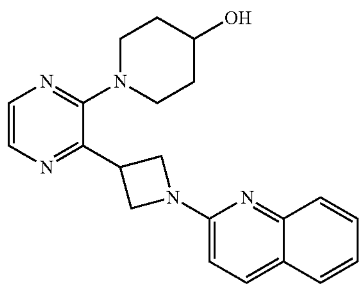 [SMILES: OC1CCN(c2nccnc2C2CN(c3ccc4ccccc4n3)C2)CC1] | 1-[3-(1-Quinolin-2-yl-azetidin-3-yl)-pyrazin-2-yl]-piperidin-4-ol |
| 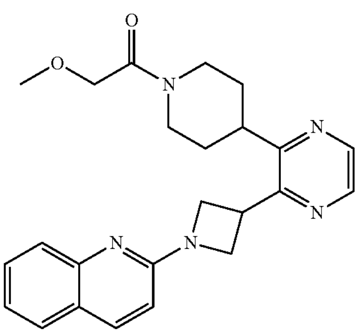 [SMILES: COCC(=O)N1CCC(c2nccnc2C2CN(c3ccc4ccccc4n3)C2)CC1] | 2-Methoxy-1-{4-[3-(1-quinolin-2-yl-azetidin-3-yl)-pyrazin-2-yl]-piperidin-1-yl}-ethanone |
| 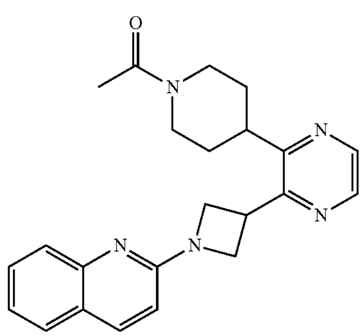 | 1-{4-[3-(1-Quinolin-2-yl-azetidin-3-yl)-pyrazin-2-yl]-piperidin-1-yl}-ethanone |
| 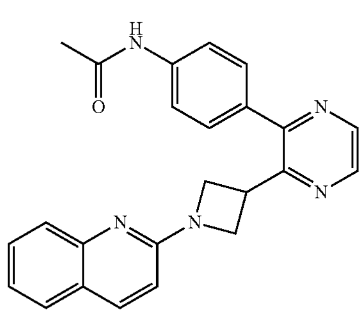 [SMILES: CC(=O)Nc1ccc(-c2nccnc2C2CN(c3ccc4ccccc4n3)C2)cc1] | N-{4-[3-(1-Quinolin-2-yl-azetidin-3-yl)-pyrazin-2-yl]-phenyl}-acetamide |

| Chemical Structure | Chemical Name |
|---|---|
| 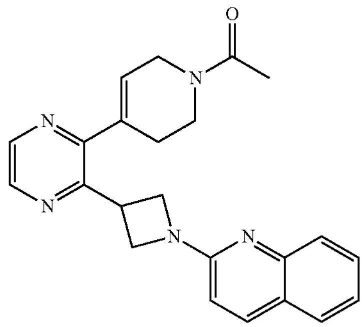 [SMILES: CC(=O)N1CC=C(c2nccnc2C2CN(c3ccc4ccccc4n3)C2)CC1] | 1-(4-(3-(1-(quinolin-2-yl)azetidin-3-yl)pyrazin-2-yl)-5,6-dihydropyridin-1(2H)-yl)ethanone |
| 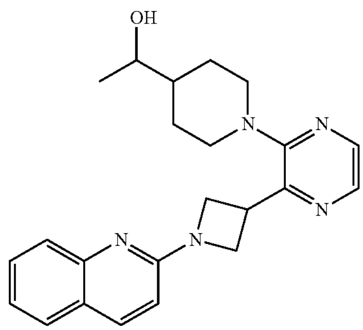 [SMILES: CC(O)C1CCN(c2nccnc2C2CN(c3ccc4ccccc4n3)C2)CC1] | (R & S)-1-{1-[3-(1-Quinolin-2-yl-azetidin-3-yl)-pyrazin-2-yl]-piperidin-4-yl}-ethanol |
| 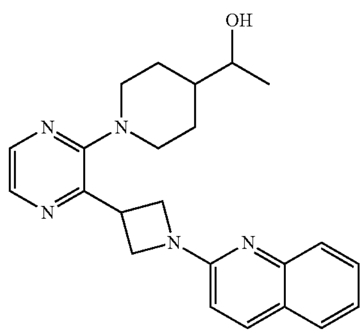 [SMILES: CC(O)C1CCN(c2nccnc2C2CN(c3ccc4ccccc4n3)C2)CC1] | (R or S, absolute stereospecificity not determined)-1-{1-[3-(1-Quinolin-2-yl-azetidin-3-yl)-pyrazin-2-yl]-piperidin-4-yl}-ethanol |
| 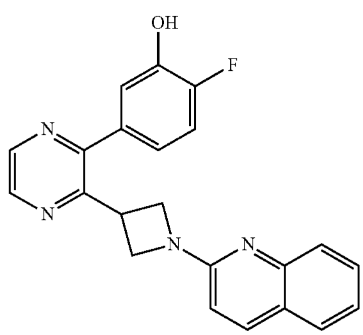 | 2-fluoro-5-(3-(1-(quinolin-2-yl)azetidin-3-yl)pyrazin-2-yl)phenol |
| 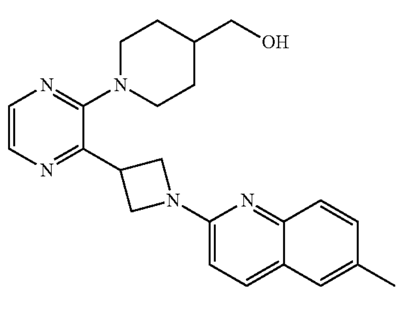 [SMILES: Cc1ccc2nc(N3CC(c4nccnc4N4CCC(CO)CC4)C3)ccc2c1] | (1-{3-[1-(6-Methyl-quinolin-2-yl)-azetidin-3-yl]-pyrazin-2-yl}-piperidin-4-yl)-methanol |

| Chemical Structure | Chemical Name |
| --- | --- |
| 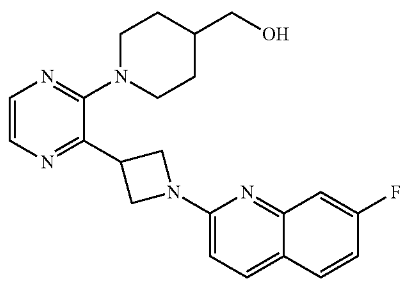 [SMILES: OCC1CCN(c2nccnc2C2CN(c3ccc4ccc(F)cc4n3)C2)CC1] | (1-{3-[1-(7-Fluoro-quinolin-2-yl)-azetidin-3-yl]-pyrazin-2-yl}-piperidin-4-yl)-methanol |
| 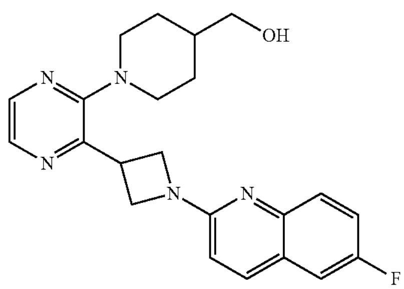 [SMILES: OCC1CCN(c2nccnc2C2CN(c3ccc4cc(F)ccc4n3)C2)CC1] | (1-{3-[1-(6-Fluoro-quinolin-2-yl)-azetidin-3-yl]-pyrazin-2-yl}-piperidin-4-yl)-methanol |
| 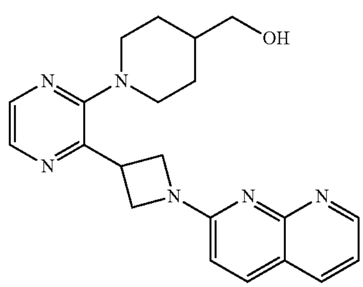 [SMILES: OCC1CCN(c2nccnc2C2CN(c3ccc4cccnc4n3)C2)CC1] | {1-[3-(1-[1,8]Naphthyridin-2-yl-azetidin-3-yl)-pyrazin-2-yl]-piperidin-4-yl}-methanol |
| 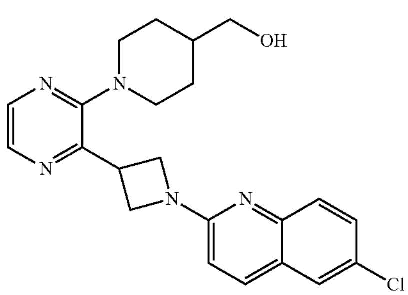 [SMILES: OCC1CCN(c2nccnc2C2CN(c3ccc4cc(Cl)ccc4n3)C2)CC1] | (1-{3-[1-(6-Chloro-quinolin-2-yl)-azetidin-3-yl]-pyrazin-2-yl}-piperidin-4-yl)-methanol |
| 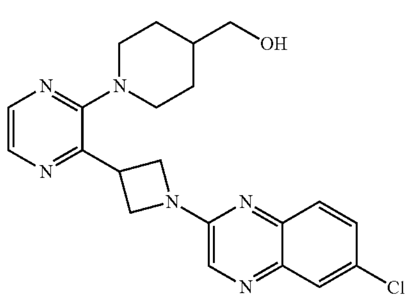 | (1-{3-[1-(6-Chloro-quinoxalin-2-yl)-azetidin-3-yl]-pyrazin-2-yl}-piperidin-4-yl)-methanol |

| Chemical Structure | Chemical Name |
|---|---|
| 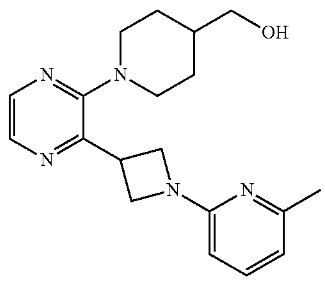 [SMILES: Cc1cccc(N2CC(c3nccnc3N3CCC(CO)CC3)C2)n1] | (1-{3-[1-(6-Methyl-pyridin-2-yl)-azetidin-3-yl]-pyrazin-2-yl}-piperidin-4-yl)-methanol |
| 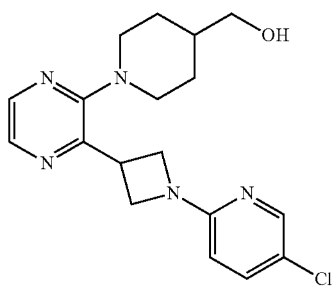 [SMILES: OCC1CCN(c2nccnc2C2CN(c3ccc(Cl)cn3)C2)CC1] | (1-{3-[1-(5-Chloro-pyridin-2-yl)-azetidin-3-yl]-pyrazin-2-yl}-piperidin-4-yl)-methanol |
| 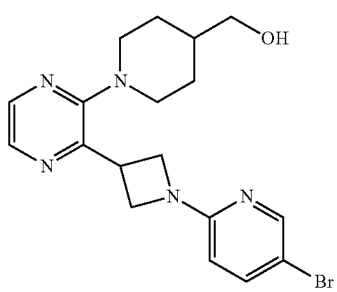 [SMILES: OCC1CCN(c2nccnc2C2CN(c3ccc(Br)cn3)C2)CC1] | (1-(3-(1-(5-bromopyridin-2-yl)azetidin-3-yl)pyrazin-2-yl)piperidin-4-yl)methanol |
| 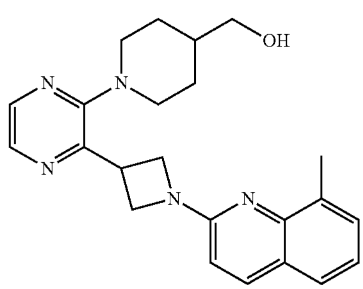 [SMILES: Cc1cccc2ccc(N3CC(c4nccnc4N4CCC(CO)CC4)C3)nc12] | (1-(3-(1-(8-methylquinolin-2-yl)azetidin-3-yl)pyrazin-2-yl)piperidin-4-yl)methanol |
| 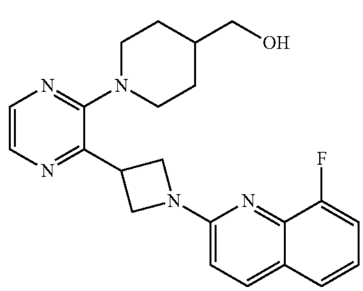 [SMILES: OCC1CCN(c2nccnc2C2CN(c3ccc4cccc(F)c4n3)C2)CC1] | (1-{3-[1-(8-Fluoro-quinolin-2-yl)-azetidin-3-yl]-pyrazin-2-yl}-piperidin-4-yl)-methanol |

| Chemical Structure | Chemical Name |
|---|---|
| 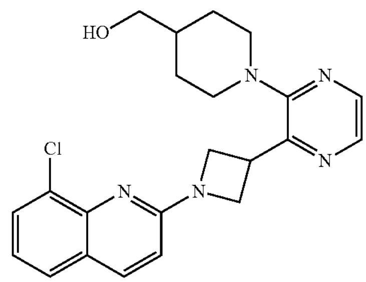 [SMILES: OCC1CCN(c2nccnc2C2CN(c3ccc4cccc(Cl)c4n3)C2)CC1] | (1-(3-(1-(8-chloroquinolin-2-yl)azetidin-3-yl)pyrazin-2-yl)piperidin-4-yl)methanol |
| 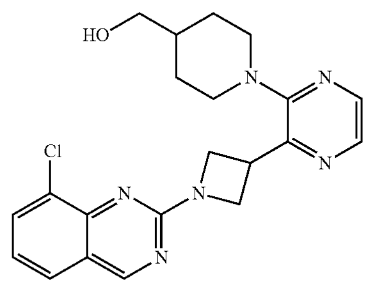 [SMILES: OCC1CCN(c2nccnc2C2CN(c3ncc4cccc(Cl)c4n3)C2)CC1] | (1-{3-[1-(8-Chloro-quinazolin-2-yl)-azetidin-3-yl]-pyrazin-2-yl}-piperidin-4-yl)-methanol |
| 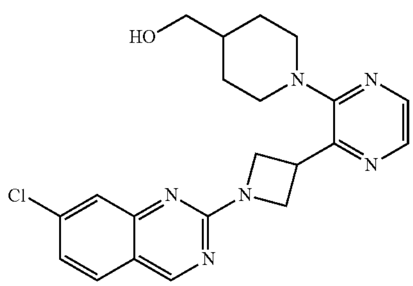 [SMILES: OCC1CCN(c2nccnc2C2CN(c3ncc4ccc(Cl)cc4n3)C2)CC1] | (1-{3-[1-(7-Chloro-quinazolin-2-yl)-azetidin-3-yl]-pyrazin-2-yl}-piperidin-4-yl)-methanol |
| 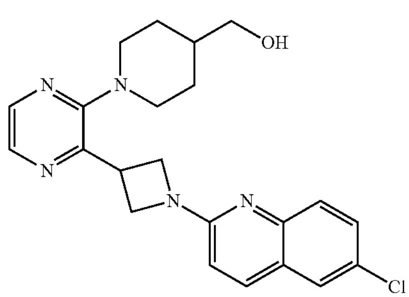 [SMILES: OCC1CCN(c2nccnc2C2CN(c3ccc4cc(Cl)ccc4n3)C2)CC1] | (1-{3-[1-(6-Chloro-quinazolin-2-yl)-azetidin-3-yl]-pyrazin-2-yl}-piperidin-4-yl)-methanol |
| 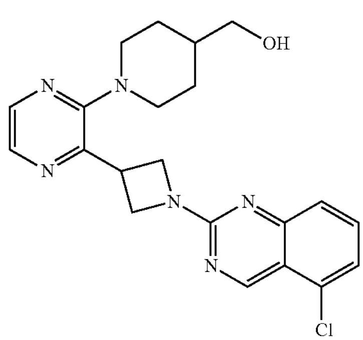 [SMILES: OCC1CCN(c2nccnc2C2CN(c3ncc4c(Cl)cccc4n3)C2)CC1] | (1-{3-[1-(5-Chloro-quinazolin-2-yl)-azetidin-3-yl]-pyrazin-2-yl}-piperidin-4-yl)-methanol |

-continued
| Chemical Structure | Chemical Name |
|---|---|
| 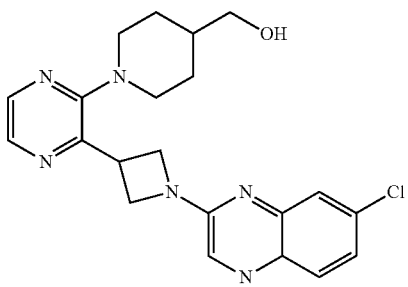 [SMILES: OCC1CCN(c2nccnc2C2CN(C3=CNC4C=CC(Cl)=CC4=N3)C2)CC1] | (1-{3-[1-(7-Chloro-quinoxalin-2-yl)-azetidin-3-yl]-pyrazin-2-yl}-piperidin-4-yl)-methanol |
| 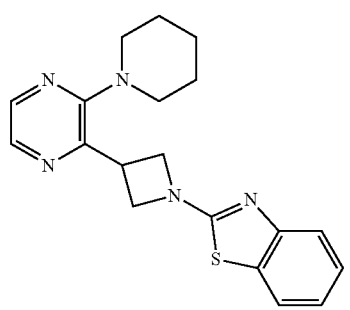 [SMILES: c1ccc2sc(N3CC(c4nccnc4N4CCCCC4)C3)nc2c1] | 2-[3-(3-Piperidin-1-yl-pyrazin-2-yl)-azetidin-1-yl]-benzothiazole |
| 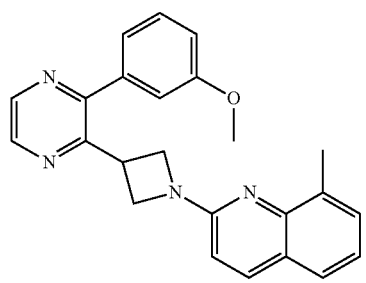 [SMILES: COc1cccc(-c2nccnc2C2CN(c3ccc4cccc(C)c4n3)C2)c1] | 2-(3-(3-(3-methoxyphenyl)pyrazin-2-yl)azetidin-1-yl)-8-methylquinoline |
| 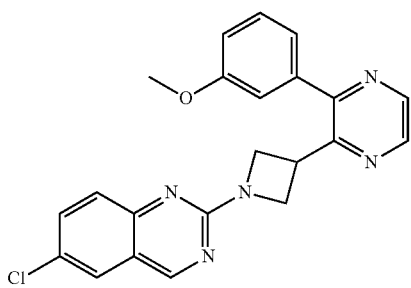 [SMILES: COc1cccc(-c2nccnc2C2CN(c3ncc4cc(Cl)ccc4n3)C2)c1] | 6-Chloro-2-{3-[3-(3-methoxy-phenyl)-pyrazin-2-yl]-azetidin-1-yl}-quinazoline |
| 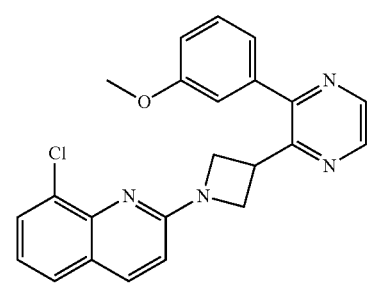 [SMILES: COc1cccc(-c2nccnc2C2CN(c3ccc4cccc(Cl)c4n3)C2)c1] | 8-Chloro-2-{3-[3-(3-methoxy-phenyl)-pyrazin-2-yl]-azetidin-1-yl}-quinoline |

| Chemical Structure | Chemical Name |
|---|---|
| 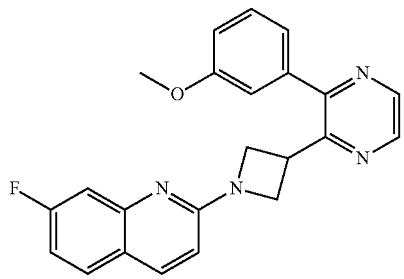 [SMILES: COc1cccc(-c2nccnc2C2CN(c3ccc4ccc(F)cc4n3)C2)c1] | 7-Fluoro-2-{3-[3-(3-methoxy-phenyl)-pyrazin-2-yl]-azetidin-1-yl}-quinoline |
| 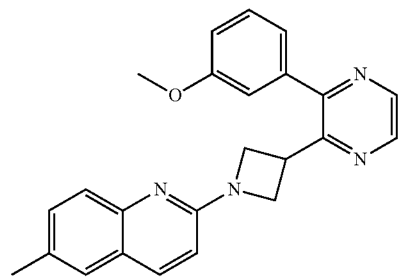 [SMILES: COc1cccc(-c2nccnc2C2CN(c3ccc4cc(C)ccc4n3)C2)c1] | 2-{3-[3-(3-Methoxy-phenyl)-pyrazin-2-yl]-azetidin-1-yl}-6-methyl-quinoline |
| 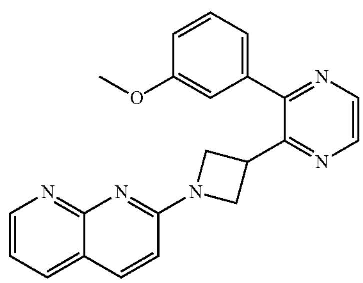 [SMILES: COc1cccc(-c2nccnc2C2CN(c3ccc4cccnc4n3)C2)c1] | 2-{3-[3-(3-Methoxy-phenyl)-pyrazin-2-yl]-azetidin-1-yl}-[1,8]naphthyridine |
| 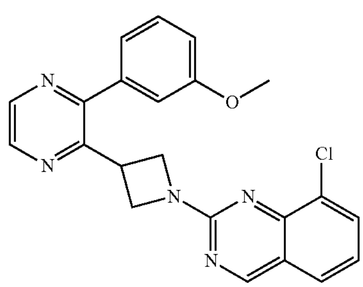 [SMILES: COc1cccc(-c2nccnc2C2CN(c3ncc4cccc(Cl)c4n3)C2)c1] | 8-Chloro-2-{3-[3-(3-methoxy-phenyl)-pyrazin-2-yl]-azetidin-1-yl}-quinazoline |
| 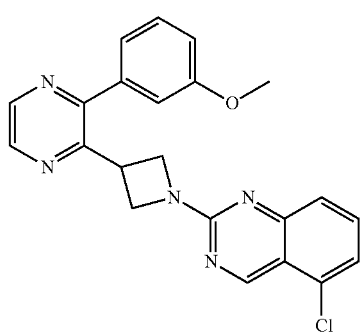 [SMILES: COc1cccc(-c2nccnc2C2CN(c3ncc4c(Cl)cccc4n3)C2)c1] | 5-Chloro-2-{3-[3-(3-methoxy-phenyl)-pyrazin-2-yl]-azetidin-1-yl}-quinazoline |

| Chemical Structure | Chemical Name |
|---|---|
| 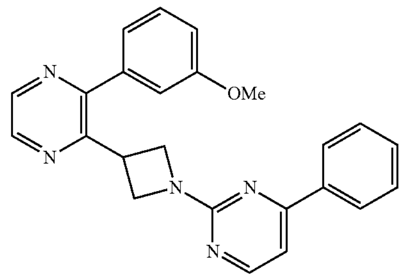 [SMILES: COc1cccc(-c2nccnc2C2CN(c3nccc(-c4ccccc4)n3)C2)c1] | 2-(3-(3-(3-methoxyphenyl)pyrazin-2-yl)azetidin-1-yl)-4-phenylpyrimidine |
| 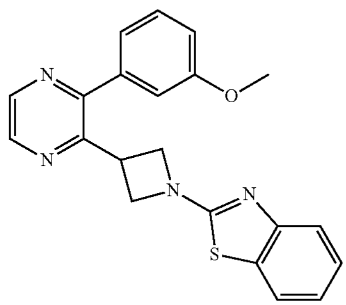 [SMILES: COc1cccc(-c2nccnc2C2CN(c3nc4ccccc4s3)C2)c1] | 2-(3-(3-(3-methoxyphenyl)pyrazin-2-yl)azetidin-1-yl)benzo[d]thiazole |
| 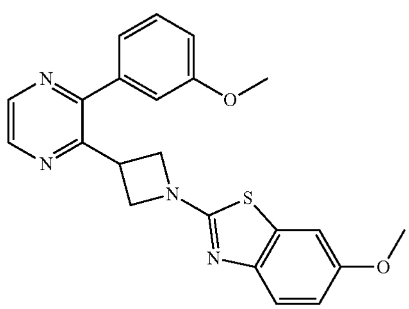 [SMILES: COc1cccc(-c2nccnc2C2CN(c3nc4ccc(OC)cc4s3)C2)c1] | 6-methoxy-2-(3-(3-(3-methoxyphenyl)pyrazin-2-yl)azetidin-1-yl)benzo[d]thiazole |
| 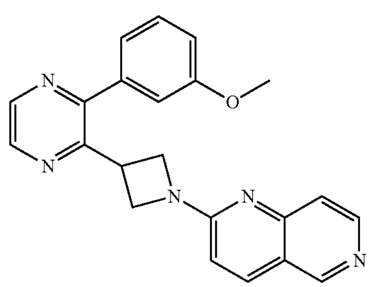 [SMILES: COc1cccc(-c2nccnc2C2CN(c3ccc4cnccc4n3)C2)c1] | 2-(3-(3-(3-methoxyphenyl)pyrazin-2-yl)azetidin-1-yl)-1,6-naphthyridine |
| 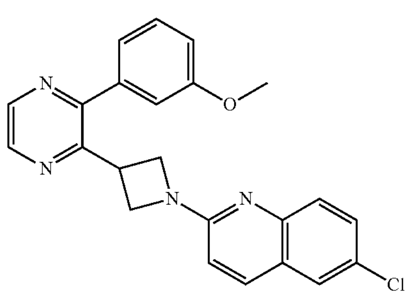 [SMILES: COc1cccc(-c2nccnc2C2CN(c3ccc4cc(Cl)ccc4n3)C2)c1] | 6-chloro-2-(3-(3-(3-methoxyphenyl)pyrazin-2-yl)azetidin-1-yl)quinoline |

| Chemical Structure | Chemical Name |
| --- | --- |
| 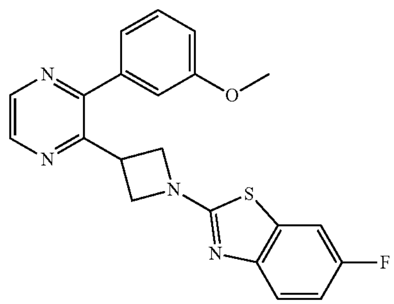 [SMILES: COc1cccc(-c2nccnc2C2CN(c3nc4ccc(F)cc4s3)C2)c1] | 6-fluoro-2-(3-(3-(3-methoxyphenyl)pyrazin-2-yl)azetidin-1-yl)benzo[d]thiazole |
| 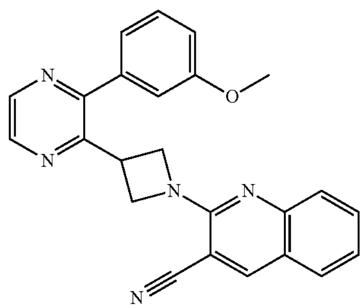 [SMILES: COc1cccc(-c2nccnc2C2CN(c3nc4ccccc4cc3C#N)C2)c1] | 2-(3-(3-(3-methoxyphenyl)pyrazin-2-yl)azetidin-1-yl)quinoline-3-carbonitrile |
| 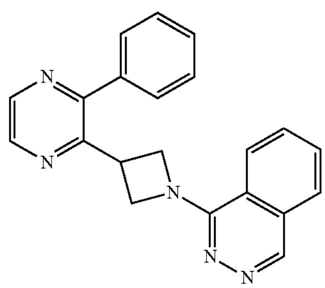 [SMILES: c1ccc(-c2nccnc2C2CN(c3nncc4ccccc34)C2)cc1] | 1-[3-(3-Phenyl-pyrazin-2-yl)-azetidin-1-yl]-phthalazine |
| 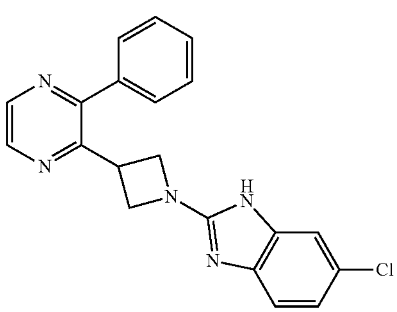 [SMILES: Clc1ccc2nc(N3CC(c4nccnc4-c4ccccc4)C3)[nH]c2c1] | 6-chloro-2-(3-(3-phenylpyrazin-2-yl)azetidin-1-yl)-1H-benzo[d]imidazole |
| 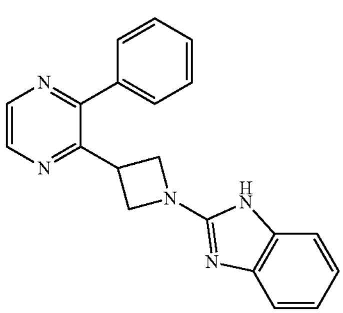 [SMILES: c1ccc(-c2nccnc2C2CN(c3nc4ccccc4[nH]3)C2)cc1] | 2-(3-(3-phenylpyrazin-2-yl)azetidin-1-yl)-1H-benzo[d]imidazole |

| Chemical Structure | Chemical Name |
|---|---|
| 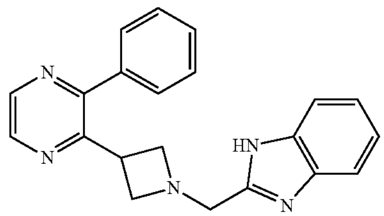 [SMILES: c1ccc(-c2nccnc2C2CN(Cc3nc4ccccc4[nH]3)C2)cc1] | 2-((3-(3-phenylpyrazin-2-yl)azetidin-1-yl)methyl)-1H-benzo[d]imidazole |
| 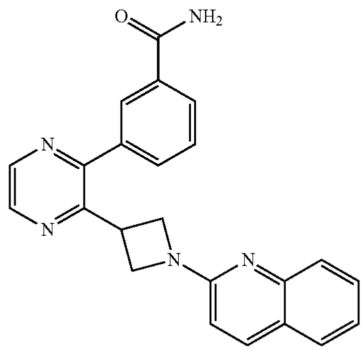 [SMILES: NC(=O)c1cccc(-c2nccnc2C2CN(c3ccc4ccccc4n3)C2)c1] | 3-(3-(1-(quinolin-2-yl)azetidin-3-yl)pyrazin-2-yl)benzamide |
| 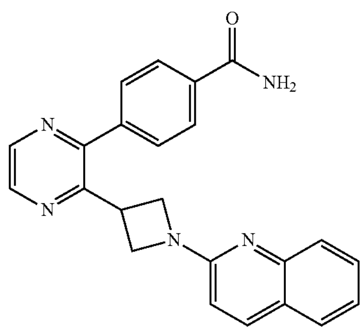 [SMILES: NC(=O)c1ccc(-c2nccnc2C2CN(c3ccc4ccccc4n3)C2)cc1] | 4-(3-(1-(quinolin-2-yl)azetidin-3-yl)pyrazin-2-yl)benzamide |
| 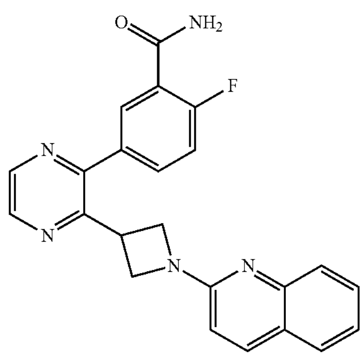 [SMILES: NC(=O)c1cc(-c2nccnc2C2CN(c3ccc4ccccc4n3)C2)ccc1F] | 2-fluoro-5-(3-(1-(quinolin-2-yl)azetidin-3-yl)pyrazin-2-yl)benzamide |
| 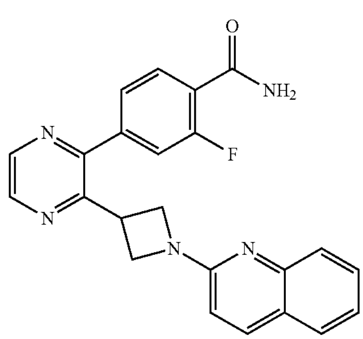 [SMILES: NC(=O)c1ccc(-c2nccnc2C2CN(c3ccc4ccccc4n3)C2)cc1F] | 2-fluoro-4-(3-(1-(quinolin-2-yl)azetidin-3-yl)pyrazin-2-yl)benzamide |

| Chemical Structure | Chemical Name |
|---|---|
| 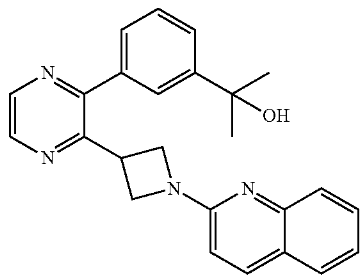 [SMILES: CC(C)(O)c1cccc(-c2nccnc2C2CN(c3ccc4ccccc4n3)C2)c1] | 2-(3-(3-(1-(quinolin-2-yl)azetidin-3-yl)pyrazin-2-yl)phenyl)propan-2-ol |
| 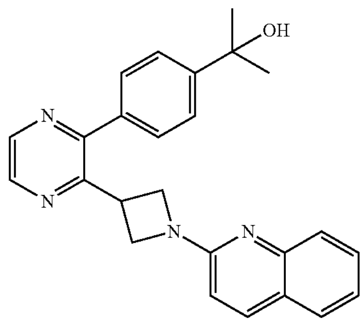 [SMILES: CC(C)(O)c1ccc(-c2nccnc2C2CN(c3ccc4ccccc4n3)C2)cc1] | 2-(4-(3-(1-(quinolin-2-yl)azetidin-3-yl)pyrazin-2-yl)phenyl)propan-2-ol |
| 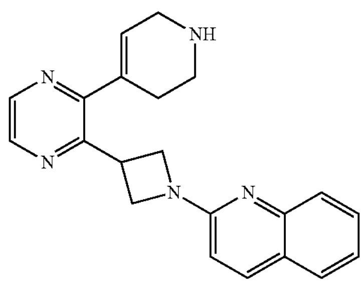 [SMILES: C1=C(c2nccnc2C2CN(c3ccc4ccccc4n3)C2)CCNC1] | 2-(3-(3-(1,2,3,6-tetrahydropyridin-4-yl)pyrazin-2-yl)azetidin-1-yl)quinoline |
| 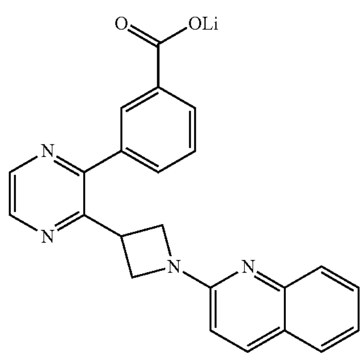 | lithium 3-(3-(1-(quinolin-2-yl)azetidin-3-yl)pyrazin-2-yl)benzoate |
| 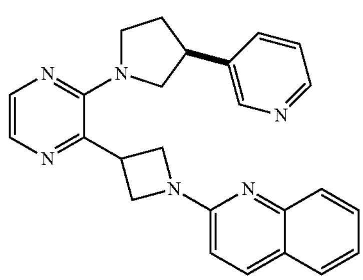 [SMILES: c1cncc([C@@H]2CCN(c3nccnc3C3CN(c4ccc5ccccc5n4)C3)C2)c1] | (S or R)-2-(3-(3-(3-(pyridin-3-yl)pyrrolidin-1-yl)pyrazin-2-yl)azetidin-1-yl)quinoline |

| Chemical Structure | Chemical Name |
|---|---|
| 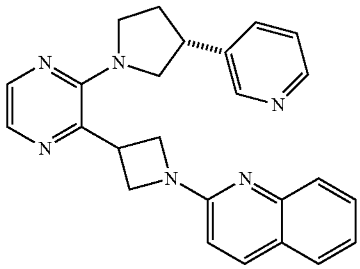 [SMILES: c1cncc([C@H]2CCN(c3nccnc3C3CN(c4ccc5ccccc5n4)C3)C2)c1] | (R or S)-2-(3-(3-(3-(pyridin-3-yl)pyrrolidin-1-yl)pyrazin-2-yl)azetidin-1-yl)quinoline |
| 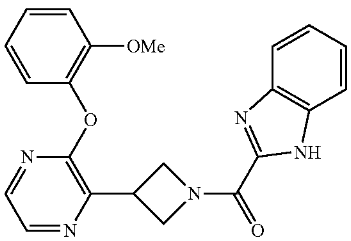 [SMILES: COc1ccccc1Oc1nccnc1C1CN(C(=O)c2nc3ccccc3[nH]2)C1] | (1H-Benzoimidazol-2-yl)-{3-[3-(2-methoxy-phenoxy)-pyrazin-2-yl]-azetidin-1-yl}-methanone |
| 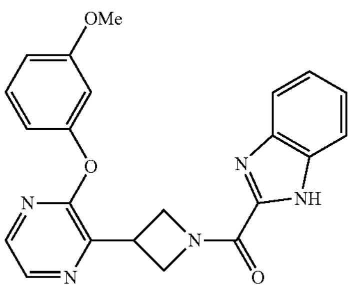 [SMILES: COc1cccc(Oc2nccnc2C2CN(C(=O)c3nc4ccccc4[nH]3)C2)c1] | (1H-Benzoimidazol-2-yl)-{3-[3-(3-methoxy-phenoxy)-pyrazin-2-yl]-azetidin-1-yl}-methanone |
| 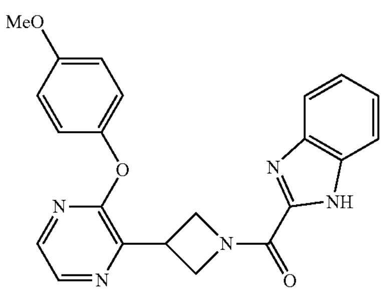 [SMILES: COc1ccc(Oc2nccnc2C2CN(C(=O)c3nc4ccccc4[nH]3)C2)cc1] | (1H-benzoimidazol-2-yl)-{3-[3-(4-methoxy-phenoxy)-pyrazin-2-yl]-azetidin-1-yl}-methanone |
| 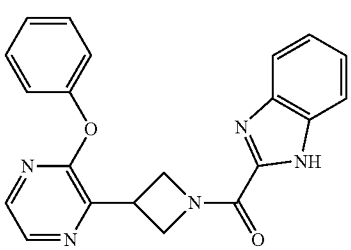 [SMILES: O=C(c1nc2ccccc2[nH]1)N1CC(c2nccnc2Oc2ccccc2)C1] | (1H-Benzoimidazol-2-yl)-[3-(3-phenoxy-pyrazin-2-yl)-azetidin-1-yl]-methanone |
| 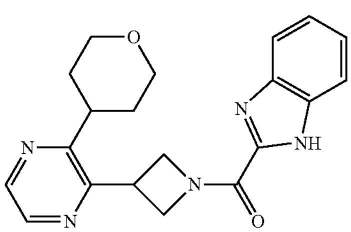 [SMILES: O=C(c1nc2ccccc2[nH]1)N1CC(c2nccnc2C2CCOCC2)C1] | (1H-benzoimidazol-2-yl)-{3-[3-(tetrahydro-pyran-4-yl)-pyrazin-2-yl]-azetidin-1-yl}-methanone |

| Chemical Structure | Chemical Name |
|---|---|
| 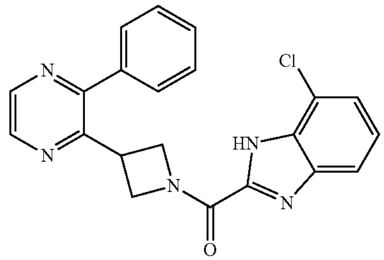 | (7-Chloro-1H-benzoimidazol-2-yl)-[3-(3-phenyl-pyrazin-2-yl)-azetidin-1-yl]-methanone |
| 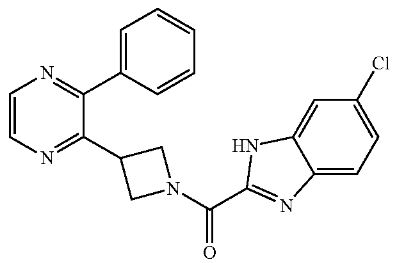 [SMILES: O=C(c1nc2ccc(Cl)cc2[nH]1)N1CC(c2nccnc2-c2ccccc2)C1] | (6-Chloro-1H-benzoimidazol-2-yl)-[3-(3-phenyl-pyrazin-2-yl)-azetidin-1-yl]-methanone |
| 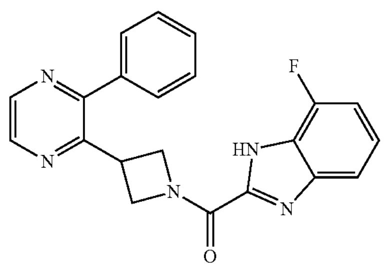 [SMILES: O=C(c1nc2cccc(F)c2[nH]1)N1CC(c2nccnc2-c2ccccc2)C1] | (7-Fluoro-1H-benzoimidazol-2-yl)-[3-(3-phenyl-pyrazin-2-yl)-azetidin-1-yl]-methanone |
| 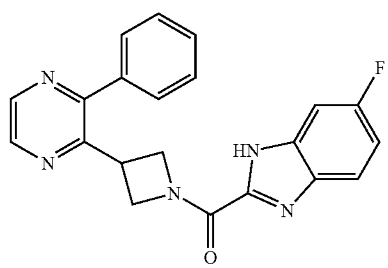 [SMILES: O=C(c1nc2ccc(F)cc2[nH]1)N1CC(c2nccnc2-c2ccccc2)C1] | (6-Fluoro-1H-benzoimidazol-2-yl)-[3-(3-phenyl-pyrazin-2-yl)-azetidin-1-yl]-methanone |
| | (6-methyl-1H-benzoimidazol-2-yl)-[3-(3-phenyl-pyrazin-2-yl)-azetidin-1-yl]-methanone |
| | (6-methyl-1H-benzoimidazol-2-yl)-[3-(3-phenyl-pyrazin-2-yl)-azetidin-1-yl]-methanone |

-continued
| Chemical Structure | Chemical Name |
|---|---|
| 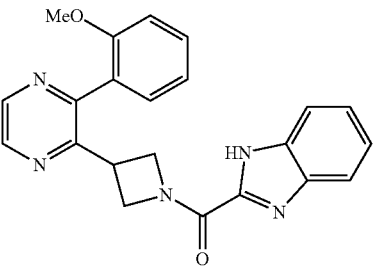 [SMILES: COc1ccccc1-c1nccnc1C1CN(C(=O)c2nc3ccccc3[nH]2)C1] | (1H-benzoimidazol-2-yl)-{3-[3-(2-methoxy-phenyl)-pyrazin-2-yl]-azetidin-1-yl}-methanone |
| 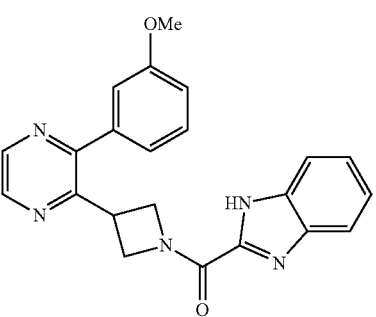 [SMILES: COc1cccc(-c2nccnc2C2CN(C(=O)c3nc4ccccc4[nH]3)C2)c1] | (1H-benzoimidazol-2-yl)-{3-[3-(3-methoxy-phenyl)-pyrazin-2-yl]-azetidin-1-yl}-methanone |
| 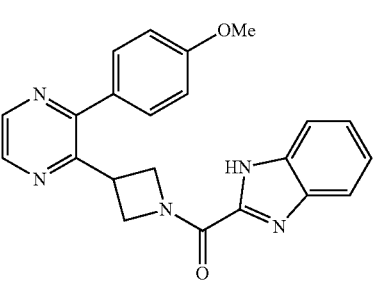 [SMILES: COc1ccc(-c2nccnc2C2CN(C(=O)c3nc4ccccc4[nH]3)C2)cc1] | (1H-Benzoimidazol-2-yl)-{3-[3-(4-methoxy-phenyl)-pyrazin-2-yl]-azetidin-1-yl}-methanone |
| 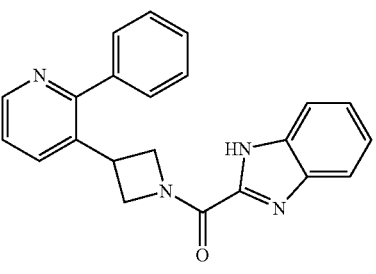 [SMILES: O=C(c1nc2ccccc2[nH]1)N1CC(c2cccnc2-c2ccccc2)C1] | (1H-benzoimidazol-2-yl)-[3-(2-phenyl-pyridin-3-yl)-azetidin-1-yl]-methanone |
| 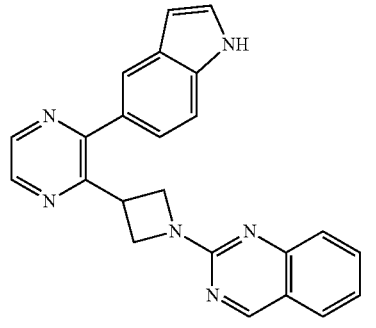 | 2-(3-(3-(1H-indol-5-yl)pyrazin-2-yl)azetidin-1-yl)quinazoline |

Another aspect of the invention relates to the compounds of Examples 36.1 to 36.190 as listed in Table 36 below, or a pharmaceutically acceptable salt thereof.

Yet another aspect of the current invention relates to any compound of the present invention, or a pharmaceutically-acceptable salt thereof, radiolabeled with a positron emitting radionuclide selected from $^{11}$C, $^{18}$F, $^{15}$O, $^{13}$N, $^{76}$Br, $^{77}$Br, $^{123}$I, or $^{125}$I.

Yet another aspect of the current invention relates to a radiopharmaceutical composition comprising any compound of the present invention, or a pharmaceutically-acceptable salt thereof, radiolabeled with a positron emitting radionuclide selected from $^{11}$C, $^{18}$F, $^{15}$O, $^{13}$N, $^{76}$Br, $^{77}$Br, $^{123}$I, or $^{125}$I, and at least one pharmaceutically acceptable carrier or excipient.

Yet another aspect of the current invention relates to a method for the diagnostic imaging of PDE10 receptors in a mammal, including human, or tissues bearing PDE10 receptors in a mammal, including human brain, which comprises administering to a mammal in need of such diagnostic imaging an effective amount of any compound of the present invention, or a pharmaceutically-acceptable salt thereof, radiolabeled with a positron emitting radionuclide selected from $^{11}$C, $^{18}$F, $^{15}$O, $^{13}$N, $^{76}$Br, $^{77}$Br, $^{123}$I, or $^{125}$I.

Yet another aspect of the current invention relates to a method for the diagnostic imaging of PDE10 receptors in a mammal, including human, or tissues bearing PDE10 receptors in a mammal, including human brain, which comprises administering to a mammal in need of such diagnostic imaging an effective amount of any compound of the present invention, or a pharmaceutically-acceptable salt thereof, radiolabeled with a positron emitting radionuclide selected from $^{11}$C, $^{18}$F, $^{15}$O, $^{13}$N, $^{76}$Br, $^{77}$Br, $^{123}$I, or $^{125}$I.

Yet another aspect of the current invention relates to a method for the detection or quantification of PDE10 receptors in mammalian tissue, including human tissue, which comprises contacting such mammalian tissue in which such detection or quantification is desired with an effective amount of any compound of the present invention, or a pharmaceutically-acceptable salt thereof, radiolabeled with a positron emitting radionuclide selected from $^{11}$C, $^{18}$F, $^{15}$O, $^{13}$N, $^{76}$Br, $^{77}$Br, $^{123}$I, or $^{125}$I.

The compounds of this invention may have in general several asymmetric centers and are typically depicted in the form of racemic mixtures. This invention is intended to encompass racemic mixtures, other racemic mixtures and separate enantiomers and diastereomers.

The present invention includes all pharmaceutically acceptable isotopically-labelled compounds of the present invention wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^2$H and $^3$H, carbon, such as $^{11}$C, $^{13}$C and $^{14}$C, chlorine, such as $^{38}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of the present invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Specific embodiments of the present invention include the compounds exemplified in the Examples below and their pharmaceutically acceptable salts, complexes, solvates, polymorphs, stereoisomers, metabolites, prodrugs, and other derivatives thereof, Unless otherwise specified, the following definitions apply to terms found in the specification and claims:

The term "$C_{\alpha-\beta}$alk" means an alkyl group comprising a minimum of a and a maximum of β carbon atoms in a branched, cyclical or linear relationship or any combination of the three, wherein α and β represent integers. The alkyl groups described in this section may also contain one or two double or triple bonds. A designation of $C_0$alk indicates a direct bond. Examples of $C_{1-6}$alkyl include, but are not limited to the following:

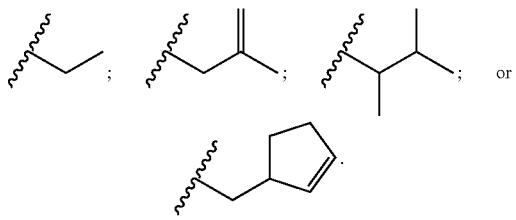

The term "benzo group", alone or in combination, means the divalent radical $C_4H_4$=, one representation of which is —CH=CH—CH=CH—, that when vicinally attached to another ring forms a benzene-like ring—for example tetrahydronaphthylene, indole and the like.

The terms "oxo" and "thioxo" represent the groups =O (as in carbonyl) and =S (as in thiocarbonyl), respectively.

The term "halo" or "halogen" means a halogen atoms selected from F, Cl, Br or I.

The term "$C_{\alpha-\beta}$haloalk" means an alk group, as described above, wherein one or more hydrogen atom of the alk group is replaced by F, Cl, Br or I.

The term "carbon-linked" means a substituent is linked to another group through a carbon atom. Examples of "carbon-linked" substituents include, but are not limited to the following:

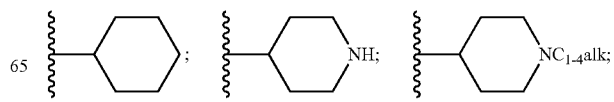

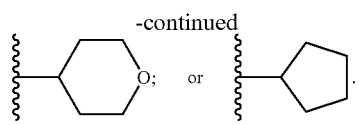

The term "nitrogen-linked" means a substituent is linked to another group through a nitrogen atom. Examples of "nitrogen-linked" substituents include, but are not limited to the following:

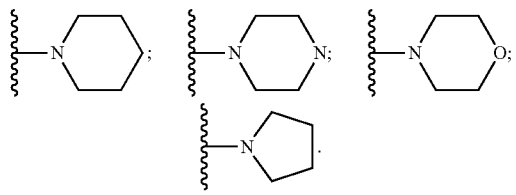

The group $N(R^a)R^a$ and the like include substituents where the two $R^a$ groups together form a ring, optionally including a N, O or S atom, and include groups such as:

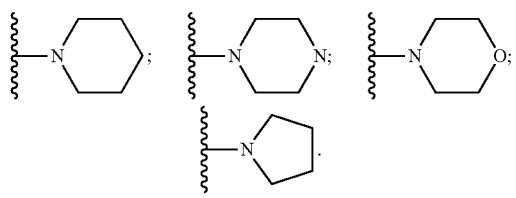

The group $N(C_{\alpha\text{-}\beta}alk) C_{\alpha\text{-}\beta}alk$, wherein $\alpha$ and $\beta$ are as defined above, include substituents where the two $C_{\alpha\text{-}\beta}alk$ groups together form a ring, optionally including a N, O or S atom, and include groups such as:

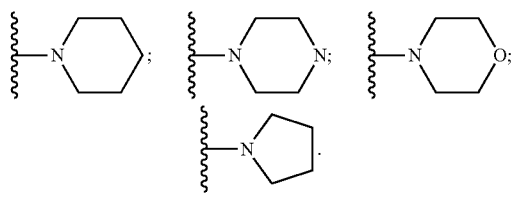

The term "carbocyclyl" means a ring comprising by itself or in combination with other terms, represents, unless otherwise stated, cyclic version of "$C_{\alpha\text{-}\beta}alk$". Thus, the term "carbocyclyl" is meant to be included in the terms "$C_{\alpha\text{-}\beta}alk$". Examples of carbocycle include cyclopentyl, cyclohexyl, or partially unsaturated ring such as 1-cyclohexenyl, 3-cyclohexenyl, cycloheptyl, cyclobutylene, cyclohexylene and the like. Unless otherwise stated, carbocycle can include fully saturated ring such as phenyl or naphthyl.

The term "heteroatom" means N, O and S.

The term "heterocyclyl" means a ring comprising at least one carbon atom and at least one other atom selected from N, O and S. "Heterocyclyl" includes aromatic heterocyclic ring which is commonly known as heteroaryl. Thus, the term "heteroaryl" is meant to be included in the terms "heterocyclyl". Examples of heterocycles that may be found in the claims include, but are not limited to, the following:

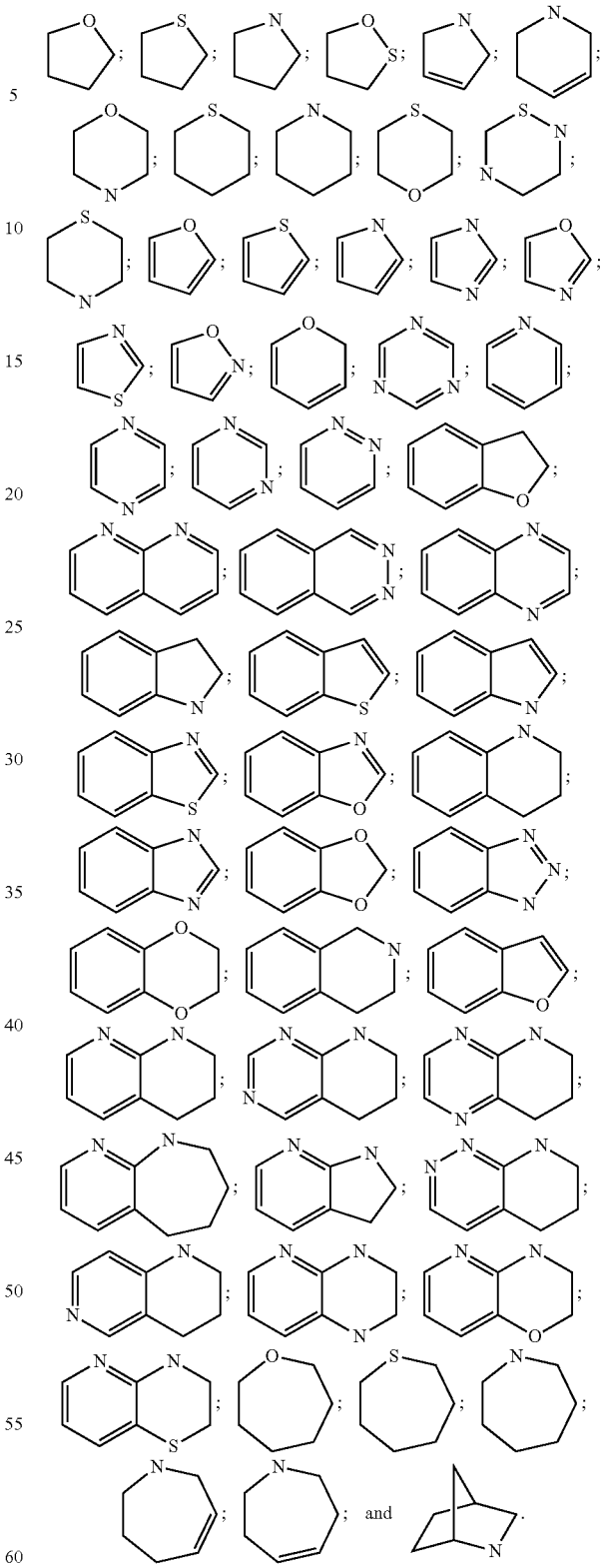

The term "pharmaceutically acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," and Berge et al., J. Pharm. Sci. 66:1 (1977).

The term "saturated, partially-saturated or unsaturated" includes substituents saturated with hydrogens, substituents completely unsaturated with hydrogens and substituents partially saturated with hydrogens.

Representative examples of "saturated, partially-saturated or unsaturated" five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyndazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-(3 oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

The term "monocyclic" means a group having a single saturated, partially-saturated, or unsaturated ring system. Typically a monocyclic ring system can have from 3- to 8 atoms in the ring system. The term includes, but is not limited to, cyclopropyl, cyclopropyl, cyclobutyl, cyclopentyl, cyclohexyl, cycloheptyl, phenyl, and the like.

The term "bicyclic" means a group having two interconnected saturated, partially-saturated, or unsaturated rings that include stable bridged, fused, or spiro rings. The bicyclic ring may be attached at any carbon or heteroatom which affords a stable group. Typically a bicyclic ring system can have from 6- to 14 atoms in the ring system. The term includes, but is not limited to, benzimidazole, naphthyl, bicyclo[3.1.0]hexane, bicyclo[4.1.0]heptane, spiro[2.4]heptane, spiro[2.5]octane, bicyclo[4.4.0]decane, bicyclo[4.3.0]nonane, bicyclo[3.3.1]nonane, bicyclo[3.2.1]octane, spiro[4.5]decane, spiro[3.5]nonane, norbornane, bicyclo[2.1.0]pentane, bicyclo[3.3.0]octane, bicyclo[2.2.2]octane, bicyclo[3.3.3]undecane, and the like.

The term "tricyclic" means a group having three interconnected saturated, partially-saturated, or unsaturated rings that include stable bridged, fused, or spiro rings. Typically a tricyclic ring system can have from 11 to 18 ring atoms in the ring system. The term includes, but is not limited to, adamantyl, tricyclo[5.2.1.0.sup.2,6]decane, and the like.

Exemplary bicyclic rings consisting of two fused partially saturated, fully saturated or fully unsaturated five and/or six membered rings, optionally having one to four heteroatoms, are indolizinyl, indolyl, isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)pyridinyl, pyrido(3,2-b)pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "substituted" means that a hydrogen atom on a molecule or group is replaced with a group or atom. Typical substitutents include: halogen, $C_{1-8}$alkyl, hydroxyl, $C_{1-8}$alkoxy, —$NR^xR^x$, nitro, cyano, halo or perhalo $C_{1-8}$alkyl, $C_{2-8}$alkenyl, $C_{2-8}$alkynyl, —$SR^x$, —$S(=O)_2R^x$, —$C(=O)OR^x$, —$C(=O)R^x$, wherein each $R^x$ is independently hydrogen or $C_1$-$C_8$ alkyl. It is noted that when the substituent is —$NR^xR^x$, the $R^x$ groups may be joined together with the nitrogen atom to form a ring.

A group or atom that replaces a hydrogen atom is also called a substituent.

Any particular molecule or group can have one or more substituent depending on the number of hydrogen atoms that can be replaced.

The symbol "-" represents a covalent bond and can also be used in a radical group to indicate the point of attachment to another group. In chemical structures, the symbol is commonly used to represent a methyl group in a molecule.

The term "leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

The term "protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, isobutoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

The term "silyl protecting groups" means silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted aromatic heterocyclyl groups (Y'=O, S, NR), and the like, which are illustrated in the following examples:

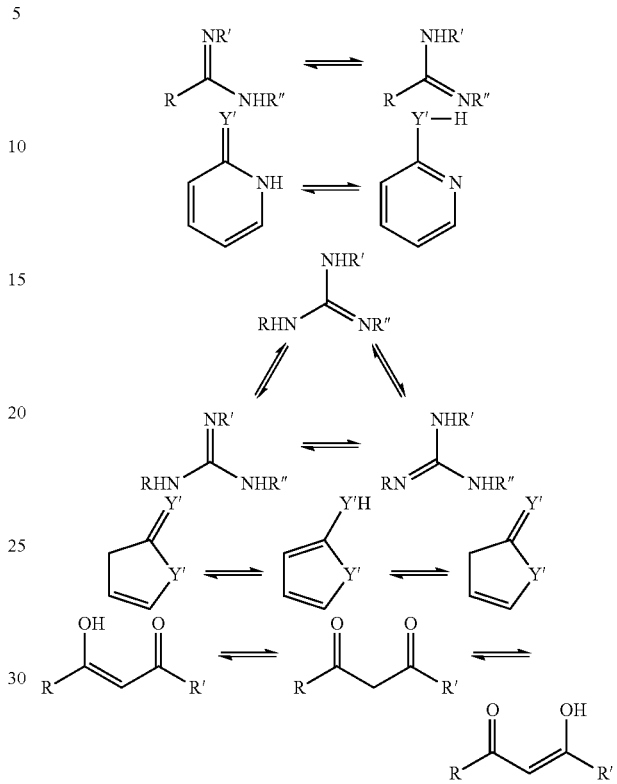

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The term "therapeutically effective amount" means an amount of a compound that ameliorates, attenuates or eliminates one or more symptom of a particular disease or condition, or prevents or delays the onset of one of more symptom of a particular disease or condition.

The term "patient" means animals, such as dogs, cats, cows, horses, sheep and humans. Particular patients are mammals. The term patient includes males and females.

The term "pharmaceutically acceptable" means that the referenced substance, such as a compound of Formula I, or a salt of a compound of Formula I, or a formulation containing a compound of Formula I, or a particular excipent, are suitable for administration to a patient.

The terms "treating", "treat" or "treatment" and the like include preventative (e.g., prophylactic) and palliative treatment.

The term "excipient" means any pharmaceutically acceptable additive, carrier, diluent, adjuvant, or other ingredient, other than the active pharmaceutical ingredient (API), which is typically included for formulation and/or administration to a patient.

Utility and Methods of Use

Provided herein are methods for treating a disorder or disease by inhibiting PDE10 enzyme. The methods, in general, comprises the step of administering a therapeutically effective amount of a compounds of the present invention, or an individual stereoisomer, a mixture of stereoisomers, or a pharmaceutically acceptable salt or solvate thereof, to a patient in need thereof to treat the disorder or disease.

In certain embodiments, this invention provides a use of a compound as described herein in the manufacture of a medicament for treating a disorder or disease treatable by inhibition of PDE10.

The compounds of the present invention inhibit PDE10 enzyme activity, and hence raise the levels of cAMP or cGMP within cells that express PDE10. Accordingly, inhibition of PDE10 enzyme activity would be useful in the treatment of diseases caused by deficient amounts of cAMP or cGMP in cells. PDE10 inhibitors would also be of benefit in cases wherein raising the amount of cAMP or cGMP above normal levels results in a therapeutic effect. Inhibitors of PDE10 may be used to treat disorders of the peripheral and central nervous system, cardiovascular diseases, cancer, gastro-enterological diseases, endocrinological diseases and urological diseases.

Indications that may be treated with PDE10 inhibitors, either alone or in combination with other drugs, include, but are not limited to, those diseases thought to be mediated in part by the basal ganglia, prefrontal cortex, and hippocampus. These indications include psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Psychoses are disorders that affect an individual's perception of reality. Psychoses are characterized by delusions and hallucinations. The compounds of the present invention are suitable for use in treating patients suffering from all forms of psychoses, including, but not limited to, schizophrenia, late-onset schizophrenia, schizoaffective disorders, prodromal schizophrenia, and bipolar disorders. Treatment can be for the positive symptoms of schizophrenia as well as for the cognitive deficits and negative symptoms. Other indications for PDE10 inhibitors include psychoses resulting from drug abuse (including amphetamines and PCP), encephalitis, alcoholism, epilepsy, Lupus, sarcoidosis, brain tumors, multiple sclerosis, dementia with Lewy bodies, or hypoglycemia. Other psychiatric disorders, like posttraumatic stress disorder (PTSD), and schizoid personality can also be treated with PDE10 inhibitors.

Obsessive-compulsive disorder (OCD) has been linked to deficits in the frontal-striatal neuronal pathways (Saxena et al., Br. J. Psychiatry Suppl, 35:26-37, 1998). Neurons in these pathways project to striatal neurons that express PDE10. PDE10 inhibitors cause cAMP to be elevated in these neurons; elevations in cAMP result in an increase in CREB phosphorylation and thereby improve the functional state of these neurons. The compounds of the present invention are therefore suitable for use in the indication of OCD. OCD may result, in some cases, from streptococcal infections that cause autoimmune reactions in the basal ganglia (Giedd et al., Am J Psychiatry. 157:281-283, 2000). Because PDE10 inhibitors may serve a neuroprotective role, administration of PDE10 inhibitors may prevent the damage to the basal ganglia after repeated streptococcal infections and thereby prevent the development of OCD.

In the brain, the level of cAMP or cGMP within neurons is believed to be related to the quality of memory, especially long term memory. Without wishing to be bound to any particular mechanism, it is proposed that, since PDE10 degrades cAMP or cGMP, the level of this enzyme affects memory in animals, for example, in humans. A compound that inhibits cAMP phosphodiesterase (PDE) can thereby increase intracellular levels of cAMP, which in turn activate a protein kinase that phosphorylates a transcription factor (cAMP response binding protein). The phosphorylated transcription factor then binds to a DNA promoter sequence to activate genes that are important in long term memory. The more active such genes are, the better is long-term memory. Thus, by inhibiting a phosphodiesterase, long term memory can be enhanced.

Dementias are diseases that include memory loss and additional intellectual impairment separate from memory. The compounds of the present invention are suitable for use in treating patients suffering from memory impairment in all forms of dementia. Dementias are classified according to their cause and include: neurodegenerative dementias (e.g., Alzheimer's, Parkinson's disease, Huntington's disease, Pick's disease), vascular (e.g., infarcts, hemorrhage, cardiac disorders), mixed vascular and Alzheimer's, bacterial meningitis, Creutzfeld-Jacob Disease, multiple sclerosis, traumatic (e.g., subdural hematoma or traumatic brain injury), infectious (e.g., HIV), genetic (down syndrome), toxic (e.g., heavy metals, alcohol, some medications), metabolic (e.g., vitamin B12 or folate deficiency), CNS hypoxia, Cushing's disease, psychiatric (e.g., depression and schizophrenia), and hydrocephalus.

The condition of memory impairment is manifested by impairment of the ability to learn new information and/or the inability to recall previously learned information. The present invention includes methods for dealing with memory loss separate from dementia, including mild cognitive impairment (MCI) and age-related cognitive decline. The present invention includes methods of treatment for memory impairment as a result of disease. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. The compounds of the present invention are suitable for use in the treatment of memory impairment due to, for example, Alzheimer's disease, multiple sclerosis, amylolaterosclerosis (ALS), multiple systems atrophy (MSA), schizophrenia, Parkinson's disease, Huntington's disease, Pick's disease, Creutzfeld-Jakob disease, depression, aging, head trauma, stroke, spinal cord injury, CNS hypoxia, cerebral senility, diabetes associated cognitive impairment, memory deficits from early exposure of anesthetic agents, multiinfarct dementia and other neurological conditions including acute neuronal diseases, as well as HIV and cardiovascular diseases.

The compounds of the present invention are also suitable for use in the treatment of a class of disorders known as polyglutamine-repeat diseases. These diseases share a common pathogenic mutation. The expansion of a CAG repeat, which encodes the amino acid glutamine, within the genome leads to production of a mutant protein having an expanded polyglutamine region. For example, Huntington's disease has been linked to a mutation of the protein huntingtin. In individuals who do not have Huntington's disease, huntingtin has a polyglutamine region containing about 8 to 31 glutamine residues. For individuals who have Huntington's disease, huntingtin has a polyglutamine region with over 37 glutamine residues. Aside from Huntington's disease (HD), other known polyglutamine-repeat diseases and the associated proteins include dentatorubral-pallidoluysian atrophy, DRPLA (atrophin-1); spinocerebellar ataxia type-1 (ataxin-1); spinocerebellar ataxia type-2 (ataxin-2); spinocerebellar ataxia type-3 (also called Machado-Joseph disease or MJD) (ataxin-3); spinocerebellar ataxia type-6 (alpha 1a-voltage dependent calcium channel); spinocerebellar ataxia type-7 (ataxin-7); and spinal and bulbar muscular atrophy (SBMA, also know as Kennedy disease).

The basal ganglia are important for regulating the function of motor neurons; disorders of the basal ganglia result in movement disorders. Most prominent among the movement disorders related to basal ganglia function is Parkinson's disease (Obeso et al., Neurology. 62(1 Suppl 1):S17-30, 2004). Other movement disorders related to dysfunction of the basal ganglia include tardive dyskinesia, progressive supranuclear palsy and cerebral palsy, corticobasal degeneration, multiple system atrophy, Wilson disease, dystonia, tics, and chorea. The compounds of the invention are also suitable for use to treat movement disorders related to dysfunction of basal ganglia neurons.

PDE10 inhibitors are useful in raising cAMP or cGMP levels and prevent neurons from undergoing apoptosis. PDE10 inhibitors may be anti-inflammatory by raising cAMP in glial cells. The combination of anti-apoptotic and anti-inflammatory properties, as well as positive effects on synaptic plasticity and neurogenesis, make these compounds useful to treat neurodegeneration resulting from any disease or injury, including stroke, spinal cord injury, Alzheimer's disease, multiple sclerosis, amylolaterosclerosis (ALS), and multiple systems atrophy (MSA).

Autoimmune diseases or infectious diseases that affect the basal ganglia may result in disorders of the basal ganglia including ADHD, OCD, tics, Tourette's disease, Sydenham chorea. In addition, any insult to the brain can potentially damage the basal ganglia including strokes, metabolic abnormalities, liver disease, multiple sclerosis, infections, tumors, drug overdoses or side effects, and head trauma. Accordingly, the compounds of the invention can be used to stop disease progression or restore damaged circuits in the brain by a combination of effects including increased synaptic plasticity, neurogenesis, anti-inflammatory, nerve cell regeneration and decreased apoptosis.

The growth of some cancer cells is inhibited by cAMP and cGMP. Upon transformation, cells may become cancerous by expressing PDE10 and reducing the amount of cAMP or cGMP within cells. In these types of cancer cells, inhibition of PDE10 activity inhibits cell growth by raising cAMP. In some cases, PDE10 may be expressed in the transformed, cancerous cell but not in the parent cell line. In transformed renal carcinoma cells, PDE10 is expressed and PDE10 inhibitors reduce the growth rate of the cells in culture. Similarly, breast cancer cells are inhibited by administration of PDE10 inhibitors. Many other types of cancer cells may also be sensitive to growth arrest by inhibition of PDE10. Therefore, compounds disclosed in this invention can be used to stop the growth of cancer cells that express PDE10.

The compounds of the invention are also suitable for use in the treatment of diabetes and related disorders such as obesity, by focusing on regulation of the cAMP signaling system. By inhibiting PDE-10, especially PDE-10A, intracellular levels of cAMP are increased, thereby increasing the release of insulin-containing secretory granules and, therefore, increasing insulin secretion. See, for example, WO 2005/012485. The compounds of Formula (I) can also be used to treat diseases disclosed in US Patent application publication No. 2006/019975.

Testing

The PDE10 inhibitory activities of the compounds of the present invention can be tested, for example, using the in vitro and in vivo assays described in the Biological Examples below.

Administration and Pharmaceutical Compositions

In general, the compounds of this invention can be administered in a therapeutically effective amount by any of the accepted modes of administration for agents that serve similar utilities. The actual amount of a compound of this invention, i.e., the active ingredient, depends upon numerous factors, such as the severity of the disease to be treated, the age and relative health of the subject, the potency of the compound used, the route and form of administration, and other factors.

Therapeutically effective amounts of compounds of formula (I) may range from approximately 0.1-1000 mg per day; preferably 0.5 to 250 mg/day, more preferably 3.5 mg to 70 mg per day.

In general, compounds of this invention can be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors, such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area, i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, a compounds of the present invention in combination with at least one pharmaceutically acceptable excipient. Acceptable excipients are non-toxic, aid administration, and do not adversely affect the therapeutic benefit of the compounds of the present invention. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, Gennaro, A. R. (Mack Publishing Company, 18th ed., 1995).

The level of the compound in a formulation can vary within the full range employed by those skilled in the art. Typically, the formulation contains, on a weight percent (wt %) basis, from about 0.01-99.99 wt % of a compounds of the present invention based on the total formulation, with the balance being one or more suitable pharmaceutical excipients. Preferably, the compound is present at a level of about 1-80 wt %.

The compounds can be administered as the sole active agent or in combination with other pharmaceutical agents such as other agents used in the treatment of psychoses, especially schizophrenia and bipolar disorder, obsessive-compulsive disorder, Parkinson's disease, Alzheimer's disease, cognitive impairment and/or memory loss, e.g., nicotinic α-7 agonists, PDE4 inhibitors, other PDE10 inhibitors, calcium channel blockers, muscarinic m1 and m2 modulators, adenosine receptor modulators, ampakines, NMDA-R modulators, mGluR modulators, dopamine modulators, serotonin modulators, canabinoid modulators, and cholinesterase inhibitors (e.g., donepezil, rivastigimine, and galanthanamine). In such combinations, each active ingredient can be administered either in accordance with their usual dosage range or a dose below their usual dosage range, and can be administered either simultaneously or sequentially.

Drugs suitable in combination with the compounds of the present invention include, but are not limited to, other suitable schizophrenia drugs such as Clozaril, Zyprexa, Risperidone, and Seroquel; bipolar disorder drugs, including, but not limited to, Lithium, Zyprexa, and Depakote; Parkinson's disease drugs, including, but not limited to, Levodopa, Parlodel, Permax, Mirapex, Tasmar, Contan, Kemadin, Artane, and Cogentin; agents used in the treatment of Alzheimer's disease, including, but not limited to, Reminyl, Cognex, Aricept, Exelon, Akatinol, Neotropin, Eldepryl, Estrogen and Cliquinol; agents used in the treatment of dementia, including, but not limited to, Thioridazine, Haloperidol, Risperidone, Cognex, Aricept, and Exelon; agents used in the treatment of epilepsy, including, but not limited to, Dilantin, Luminol, Tegretol, Depakote, Depakene, Zarontin, Neurontin, Barbita, Solfeton, and Felbatol; agents used in the treatment of multiple sclerosis, including, but not limited to, Detrol, Ditropan XL, OxyContin, Betaseron, Avonex, Azothioprine, Methotrexate, and Copaxone; agents used in the treatment of Huntington's disease, including, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone; agents useful in the treatment of diabetes, including, but not limited to, PPAR ligands (e.g. agonists, antagonists, such as Rosiglitazone, Troglitazone and Pioglitazone), insulin secretagogues (e.g., sulfonylurea drugs, such as Glyburide, Glimepiride, Chlorpropamide, Tolbutamide, and Glipizide, and non-sulfonyl secretagogues), c-glucosidase inhibitors (such as Acarbose, Miglitol, and Voglibose), insulin sensitizers (such as the PPAR-γ agonists, e.g., the glitazones; biguanides, PTP-1B inhibitors, DPP-IV inhibitors, and 11beta-HSD inhibitors), hepatic glucose output lowering compounds (such as glucagon antagonists and metaformin, e.g., Glucophage and Glucophage XR), insulin and insulin derivatives (both long and short acting forms and formulations of insulin); and anti-obesity drugs, including, but not limited to, β-3 agonists, CB-1 agonists, neuropeptide Y5 inhibitors, Ciliary Neurotrophic Factor and derivatives (e.g., Axokine), appetite suppressants (e.g., Sibutramine), and lipase inhibitors (e.g., Orlistat).

EXPERIMENTAL

Unless otherwise noted, all materials were purchased from Sinopharm Chemical Reagent Co., Ltd and used without further purification. All microwave assisted reactions were conducted with a Initiator Synthesizer® from Biotage®. All compounds showed NMR spectra consistent with their assigned structures. Melting points were determined on a Buchi apparatus and are uncorrected. Mass spectral data was determined by electrospray ionization technique. All examples were purified to >90% purity as determined by high-performance liquid chromatography. Unless otherwise stated, reactions were run at room temperature.

The following abbreviations are commonly used:
Ac the group $CH_3$—(CO)—
AcOH or HOAc acetic acid
$Ac_2O$ acetic anhydride
BINAP 2,2'-bis(diphenylphosphino)-1,1'-binaphthalene
BnO Benzyloxy
$Boc_2O$ di-tert-butyl dicarbonate
BTEA-Cl benzyltriethylammonium chloride
Bz Benzyl group
Cbz carboxylic acid benzyl ester
CDI 1,1'-carbonyldiimidazole
d Day
DCM Dichloromethane
DIAD $(CH_3)_2CHOOCN\!=\!NCOOCH(CH_3)_2$
DIEA N,N-diisopropylethylamine
Diox Dioxane
DIPEA diisopropylethyl amine
DMA Dimethylamine
DMAP 4-(dimethylamino)pyridine
DME Dimethoxyethane
DMF N,N-dimethylformamide
Dess-Martin Periodinane 1,1,1-Tris(acetyloxy)-1,1-dihydro-1,2-benziodoxol-3-(1H)-one DMSO dimethyl sulfoxide
DPPA diphenyl phosphoryl azide
EDCI N-(3-Dimethylaminopropyl)-N'-ethylcarbodiimide hydrochloride
ESI-MS electrospray ionization mass spectrometry
$Et_2O$ diethyl ether
EtOAc ethyl acetate
EtOH ethyl alcohol
$Et_3N$ triethyl amine
g Grams
h hour or hours
HATU O-(7-Azobenzotriazol-1-yl)-1,1,3,3-tetramethyluronium hexafluorophosphate
HBTU 2-(1H-Benzotriazole-1-yl)-1,1,3,3-tetramethylaminium hexafluorophosphate
HCl Hydrochloric acid
HPLC high pressure liquid chromatography
IPA isopropyl alcohol
i $Pr_2NEt$ Diisopropylethylamine
i PrOH Isopropyl alcohol
ISCO in-situ chemical oxidation
Lawesson reagent 4-Methoxyphenylthiophosphoric cyclic di(thioanhydride), LR, 2,4-Bis(4-methoxyphenyl)-2,4-dithioxo-1,3,2,4-dithiadiphosphetane, 2,4-Bis-(4-methoxyphenyl)-1,3-dithia-2,4-diphosphetane 2,4-disulfide
LCMS liquid chromatography mass spectrometry
LDA Lithium diisopropyl amide
LiHMDS Lithium bis(trimethylsilyl)amide
Me Methyl
MeCN Acetonitrile
MeI Iodomethane
MeOH methyl alcohol
MeOD deuteurated methyl alcohol
mg Milligrams
min Min
mL Milliliters
Mo—$(CO)_6$ molybdenum hexacarbonyl
MTBE methyl tert-butyl ether
NBS N-bromosuccinimide
NMP 1-methyl-2-pyrrolidinone
NMR nuclear magnetic resonance
NOESY nuclear Overhauser effect spectroscopy
Pd(dppf)$Cl_2$ [1,1'-Bis(diphenylphosphino)ferrocene]dichloropalladium(II), complex with dichloromethane
PMBCl 1-(chloromethyl)-4-methoxybenzene
PTSA p-toluenesulfonic acid
Py pyridine
RT RT
sat. saturated
t-bu tert-butyl group
TFA trifluoroacetic acid
THF tetrahydrofuran
TLC thin layer chromatography
TMSCl Trimethylsilyl chloride
TBDPS Tert-Butylchlorodiphenyl
Tol Toluene
TsCl 4-toluenesulfonyl chloride ($CH_3C_6H_4SO_2Cl$)
Xantphos 4,5-bis(diphenylphosphino)-9,9-dimethylxanthene General Schemes In general, the compounds of the formula I can be prepared according to the following General Schemes A to H, wherein m, p, q, $R^1$, $R^{4a}$, $R^{4b}$, $R^5$, Y, $X^1$, $X^2$, $X^3$, $X^4$, and $X^5$ are defined herein.

GENERAL SCHEME A:

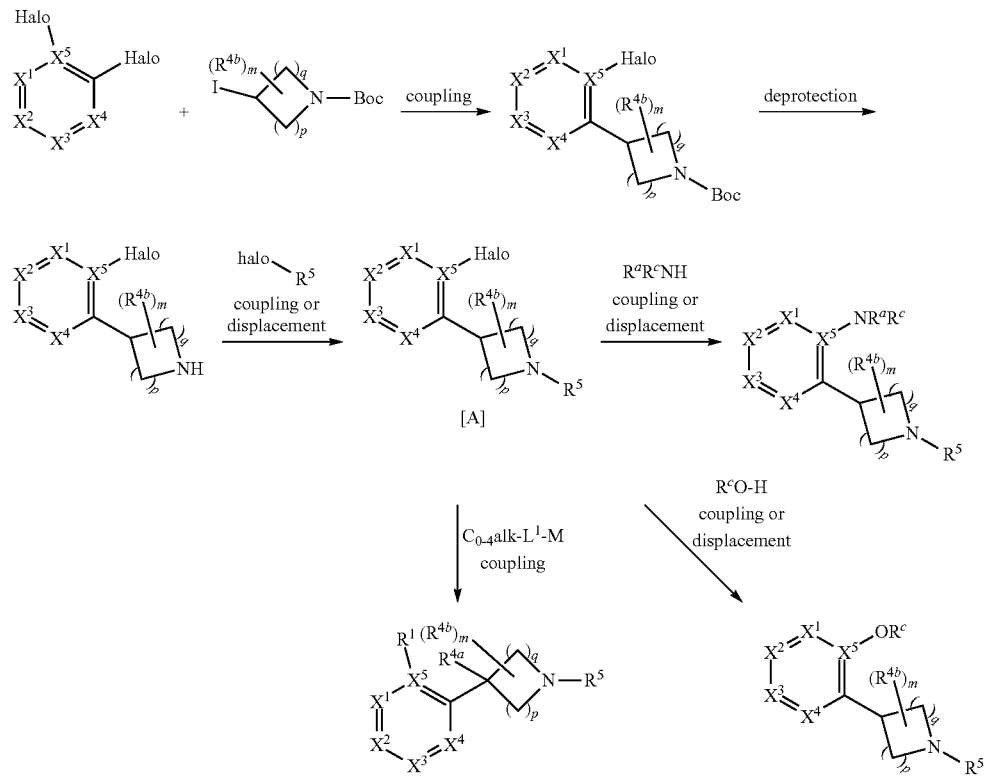

M = metal

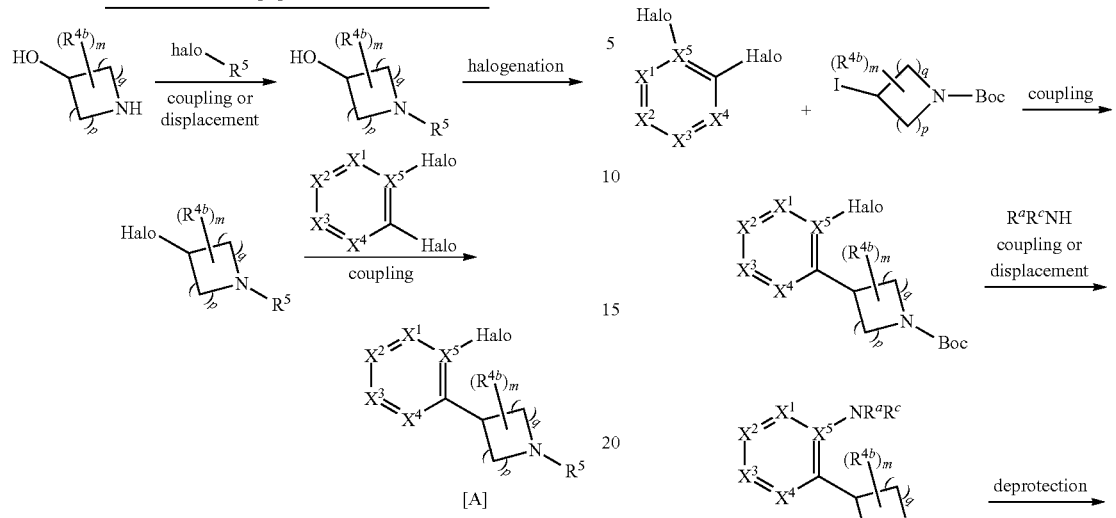
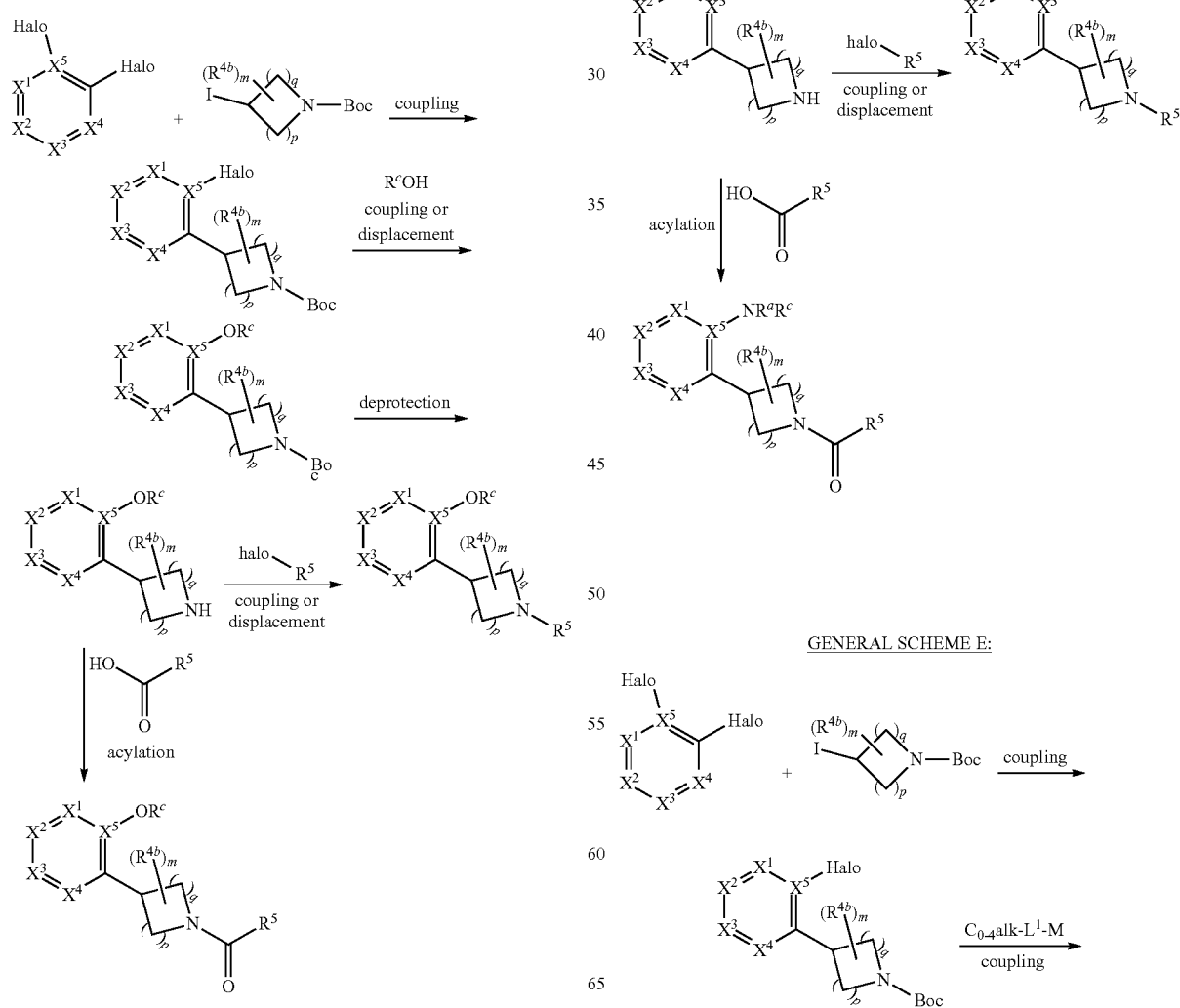

241
-continued
242
-continued
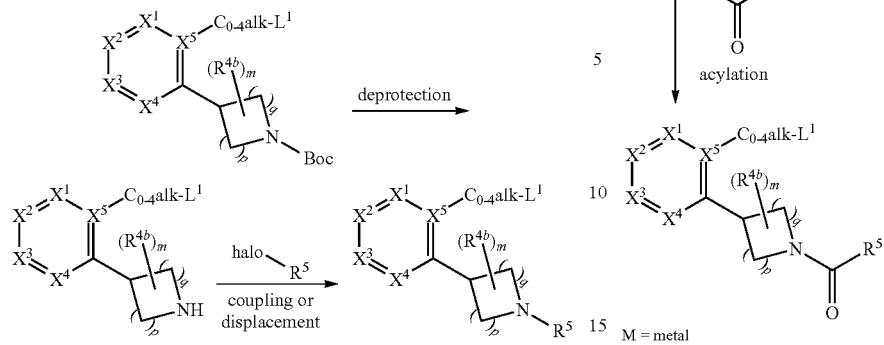
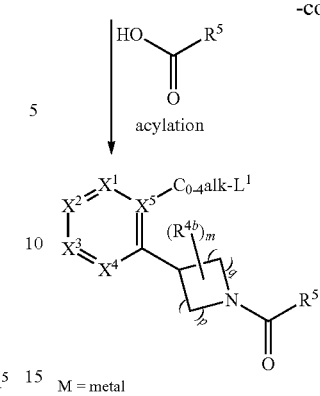
GENERAL SCHEME F:
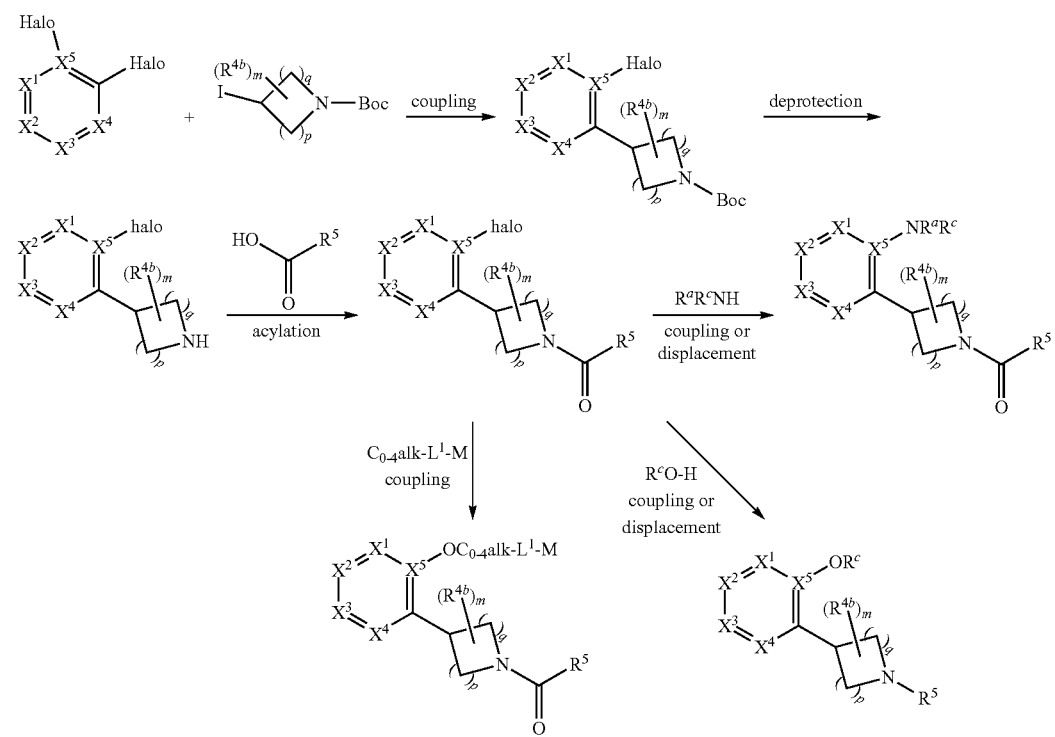
GENERAL SCHEME G:
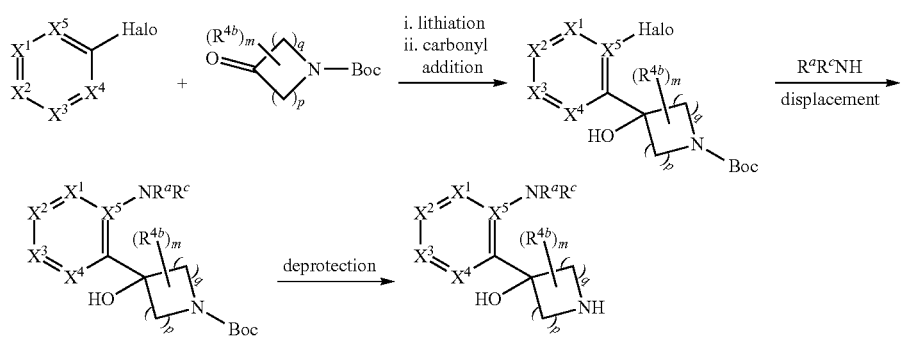

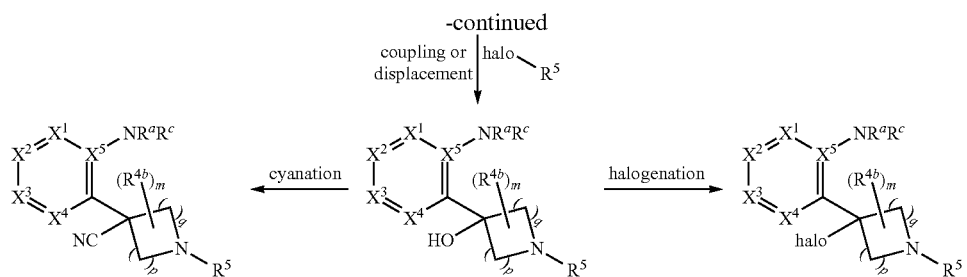
GENERAL SCHEME H:
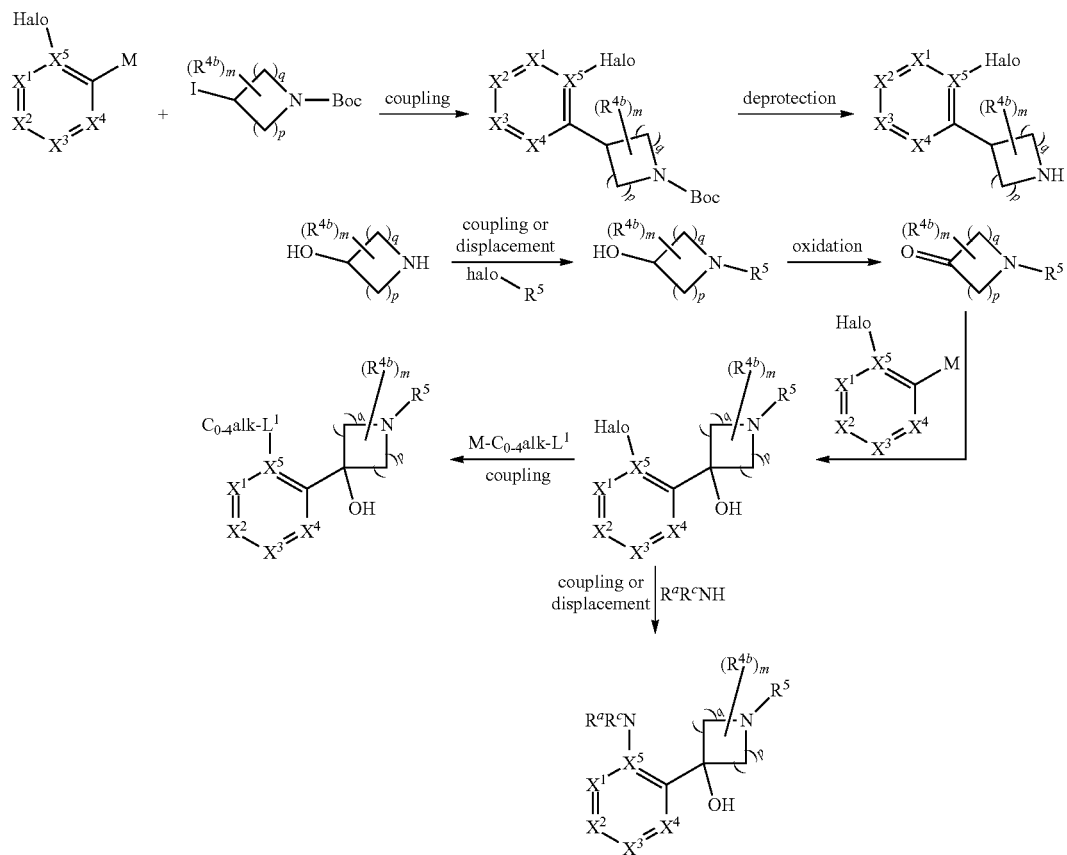
Preparation 1
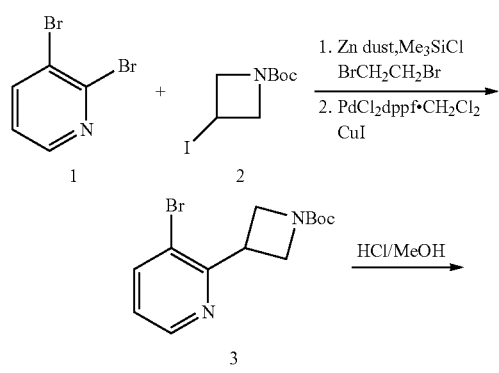

Zinc Dust Preactivation Procedure

Zinc dust (Acros) was slowly added to a well stirred solution of aqueous 2N HCl. The material was allowed to stir for 30 min at which point it was filtered, washed with water, EtOH, and diethyl ether. The material was dried using a rotavapor.

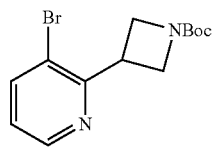

3

Step 1: Tert-Butyl 3-(3-Bromopyridin-2-Yl)Azetidine-1-Carboxylate (3)

A 5 L 3-neck round bottom flask fitted with a magnetic stirrer under nitrogen was charged with zinc dust (138 g, preactivated according to the above Preparation 1, 2.11 mol, 2 eq.) and DMA (370 mL, anhydrous). 1,2-dibromoethane (13 mL, 0.158 mol, 0.15 eq, Aldrich) was then added over 5 min, followed by TMSCl (20 mL, 0.158 mol, 0.15 eq, Acros) over 5 min. The reaction mixture was stirred for 20 min at RT. A solution of N-Boc-3-iodoazetidine (2) (448 g, 1.583 mol, 1.5 eq, CNH Technologies) in DMA (925 mL, anhydrous) was added over 25 min keeping the internal temperature below 65° C. using a water bath. The suspension was stirred for 1 h at RT at which point it was degassed with nitrogen. Stirring was stopped and the suspension was allowed to stand. A 12 L 3-neck round bottom flask fitted with a mechanical stirrer was charged with 2,3-dibromopyridine (1) (250 g, 1.055 mol, 1.0 eq, Frontier Scientific), PdCl$_2$dppf·CH$_2$Cl$_2$ (25.8 g, 31.65 mmol, 0.03 eq, Aldrich), CuI (12.5 g, 65.41 mmol, 0.062 eq, Aldrich), and DMA (925 mL, anhydrous). The solution was degassed with nitrogen. The clear zinc reagent solution above the residual solid zinc was poured into the 12 L flask under nitrogen. The brown solution was degassed with nitrogen and heated to 80° C. for 17 h at which point LCMS indicated complete conversion of 2,3-dibromopyridine (1). The reaction mixture was transferred to brine (2 L) in 22 L separatory funnel. Water (2 L) and EtOAc (4 L) were added and the layers were separated. The aqueous layer was extracted with EtOAc (2×3 L). The combined organics were washed with water (3×3 L) and brine (2 L), dried over sodium sulfate and evaporated. The resulting residue was purified by column chromatography (eluting with hexanes/ethyl acetate=9:1 to 5:1) to obtain 289 g of impure tert-butyl 3-(3-bromopyridin-2-yl)azetidine-1-carboxylate (3) which was distilled under high vacuum to remove the impurity (N-Boc-azetidine) to give 281 g of pure tert-butyl 3-(3-bromopyridin-2-yl)azetidine-1-carboxylate. Yield: 85%.

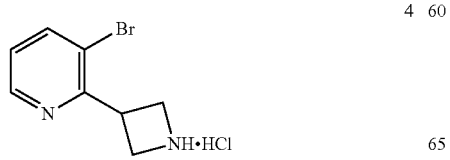

4

Step 2: 2-(Azetidin-3-Yl)-3-Bromopyridine Hydrochloride (4)

To a solution of tert-butyl 3-(3-bromopyridin-2-yl)azetidine-1-carboxylate (3) (266 g, 0.849 mol, 1 eq.) in methanol (6 L) was added concentrated HCl (350 mL, 4.2 mol, 4.95 eq.) and the resulting mixture was stirred at RT for 92 hrs. The mixture was concentrated and dried using a rotavapor to obtain 230 g of 2-(azetidin-3-yl)-3-bromopyridine hydrochloride (4).

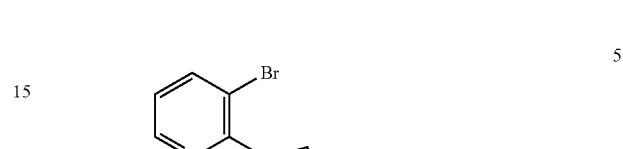

5

Step 3: 2-(3-(3-Bromopyridin-2-Yl)Azetidin-1-Yl)Quinoline (5)

A mixture of 2-(azetidin-3-yl)-3-bromopyridine hydrochloride (4) (221 g, 0.886 mol), 2-chloroquinoline (133.5 g, 0.816 mol, 0.92 eq., Combi-Blocks) and cesium carbonate (866 g, 2.658 mol, 3 eq.) in anhydrous DMF (7 L) was heated to 110° C. and stirred for 16 hrs. After cooling to RT, the mixture was transferred to 50 L separatory funnel and diluted with water (14 L). The precipitated solid was filtered, stirred in water (4 L), filtered and dried to obtain 222 g of 2-(3-(3-bromopyridin-2-yl)azetidin-1-yl)quinoline. Yield: 80% over two steps.

$^1$H NMR (300 MHz, d$_6$-DMSO) δ ppm 8.58 (d, J=4.8 Hz, 1H), 8.11 (d, J=8.1 Hz, 1H), 8.04 (d, J=9.0 Hz, 1H), 7.71 (d, J=8.1 Hz, 1H), 7.65-7.50 (m, 2H), 7.35-7.15 (m, 2H), 6.81 (d, J=9.0 Hz, 1H), 4.55-4.30 (m, 5H). HPLC purity: >98% (215 nm and 254 nm)

LCMS: m/z: 340.1 for $^{79}$Br (M+1), Calcd. for C$_{17}$H$_{14}$$^{79}$BrN$_3$: 339.04; 342.1 for $^{81}$Br (M+1), Calcd. for C$_{17}$H$_{14}$$^{81}$BrN$_3$: 341.04.

Preparation 2

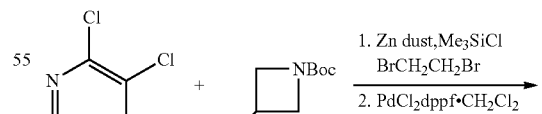

247

-continued

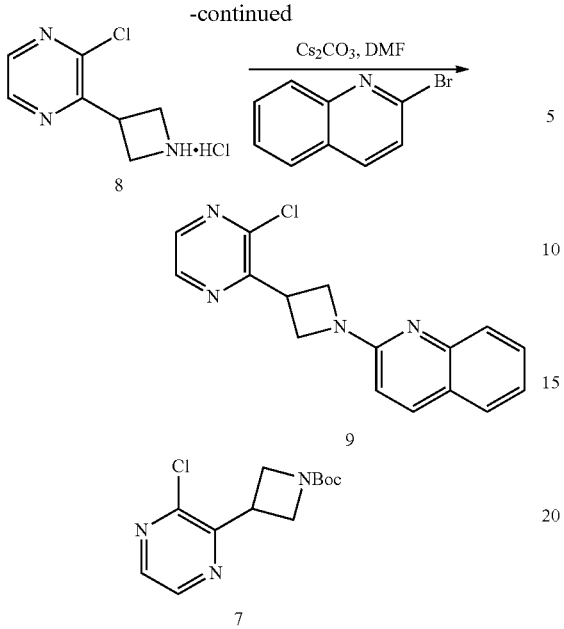

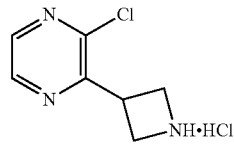

Step 1: Tert-Butyl 3-(3-Chloropyrazin-2-Yl)Azetidine-1-Carboxylate (7)

A 12 L 3-neck round bottom flask fitted with a magnetic stirrer under nitrogen was charged with zinc dust (745 g, preactivated according to the above Preparation 1, 11.4 mol, 2 eq.) and DMA (2 L, anhydrous). 1,2-dibromoethane (71 mL, 0.855 mol, 0.15 eq, Aldrich) was then added over 10 min, followed by TMSCl (108 mL, 0.855 mol, 0.15 eq, Acros) over 20 min. The reaction mixture was stirred for 25 min at RT. A solution of N-Boc-3-iodoazetidine (2) (2420 g, 8.55 mol, 1.5 eq, CNH Technologies) in DMA (5 L, anhydrous) was added via a 2 L addition funnel over 2 h keeping the internal temperature below 65° C. using a water bath. The suspension was stirred for 1 h at RT at which point it was degassed with nitrogen. Stirring was stopped and the suspension was allowed to stand. A 22 L 3-neck round bottom flask fitted with a mechanical stirrer was charged with 2,3-dichloropyrazine (6) (850 g, 5.70 mol, 1.0 eq, AK Scientific), PdCl$_2$dppf-CH$_2$Cl$_2$ (140 g, 171 mmol, 0.03 eq, Aldrich), CuI (67.3 g, 353 mmol, 0.062 eq, Aldrich), and DMA (5 L, anhydrous). The solution was degassed with nitrogen. The clear zinc reagent solution above the residual solid zinc was poured into the 22 L flask under nitrogen. The brown solution was degassed with nitrogen and heated to 80° C. for 16 h at which point LCMS indicated complete conversion of 2,3-dichloropyrazine (6). The reaction mixture was transferred to brine (8 L) in 50 L separatory funnel. Water (8 L) and EtOAc (15 L) were added and the layers were separated. The aqueous layer was extracted with EtOAc (2×10 L). The combined organics were washed with water (3×10 L) and brine (5 L), dried over sodium sulfate and evaporated. The resulting residue was purified by column chromatography (eluting with hexanes/ethyl acetate=10:1) to obtain 536 g of pure tert-butyl 3-(3-chloropyrazin-2-yl)azetidine-1-carboxylate (7) and 121 g of mixed fractions. The impure material was distilled under high vacuum to remove the impurity (N-Boc-azetidine) to give 81 g of pure tert-butyl 3-(3-chloropyrazin-2-yl)azetidine-1-carboxylate (7).

Total: 617 g, Yield: 40%.

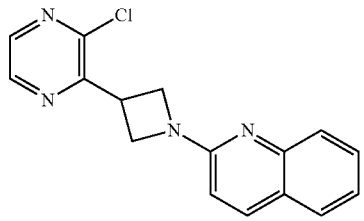

Step 2: 2-(Azetidin-3-Yl)-3-Chloropyrazine Hydrochloride (8)

To a solution of tert-butyl 3-(3-chloropyrazin-2-yl)azetidine-1-carboxylate (7) (300 g, 1.112 mol, 1 eq.) in methanol (6 L) was added concentrated HCl (400 mL, 4.8 mol, 4.3 eq.) and the resulting mixture was stirred at RT for 112 h. The mixture was concentrated and dried on rotavapor to obtain 230 g of 2-(azetidin-3-yl)-3-chloropyrazine hydrochloride (8).

Step 3: 2-(3-(3-Chloropyrazin-2-Yl)Azetidin-1-Yl)Quinoline (9)

A mixture of 2-(azetidin-3-yl)-3-chloropyrazine hydrochloride (8) (163 g, 0.79 mol), 2-bromoquinoline (164 g, 0.79 mol, 1 eq., Combi-Blocks) and cesium carbonate (772 g, 2.37 mol, 3 eq., Aldrich) in anhydrous DMF (6.5 L) was heated to 110° C. and stirred for 19 h. After cooling to RT, the mixture was transferred to 50 L separatory funnel and diluted with water (13 L). Then it was extracted with ethyl acetate (20 L×2) and the organic extracts were combined, washed with water (8 L), brine (8 L), dried and concentrated. The resulting residue was purified by column chromatography (eluting with hexanes/ethyl acetate=9:1 to 3:1). All fractions containing desired compound were combined and concentrated. The obtained solid was triturated with MTBE (250 mL), washed with MTBE (100 mL×2) and dried to obtain 100 g of 2-(3-(3-chloropyrazin-2-yl)azetidin-1-yl)quinoline (9) with >99% purity. The mother liquor was concentrated and purified by column chromatography and trituration with MTBE again to give 4.5 g of 2-(3-(3-chloropyrazin-2-yl)azetidin-1-yl)quinoline (9) with >99% purity. Yield: 45% for two steps.

$^1$H NMR (300 MHz, d$_6$-DMSO) δ ppm 8.67 (d, J=2.4 Hz, 1H), 8.44 (d, J=2.4 Hz, 1H), 8.04 (d, J=9.6 Hz, 1H), 7.72 (d, J=8.4 Hz, 1H), 7.65-7.50 (m, 2H), 7.23 (t, J=7.35 Hz, 2H), 6.79 (d, J=9.0 Hz, 1H), 4.60-4.30 (m, 5H). HPLC purity: >99% (215 nm and 254 nm) LCMS: m/z: 297.1 (M+1), Calcd. for C$_{16}$H$_{13}$ClN$_4$: 296.08.

Preparation 3

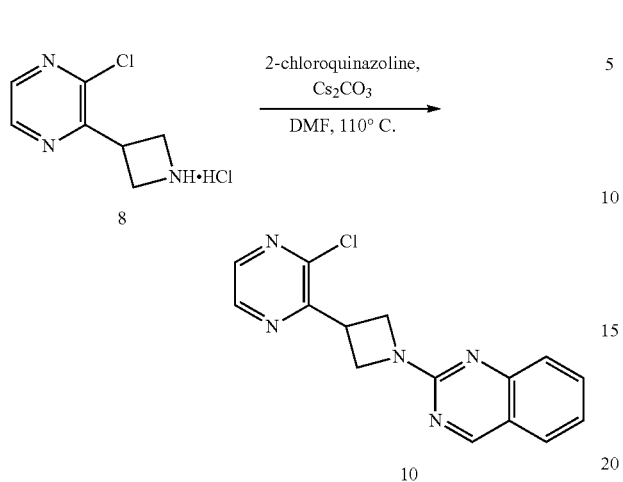

2-(3-(3-Chloropyrazin-2-Yl)Azetidin-1-Yl)Quinazoline (10)

2-(Azetidin-3-yl)-3-chloropyrazine hydrochloride (8) (1.50 g, 7.28 mmol), 2-chloroquinazoline (1.20 g, 7.28 mmol, Parkway Scientific), and cesium carbonate (5.22 g, 16.0 mmol, Fluka) were mixed in DMF (30 mL) in a round bottom flask under a nitrogen atmosphere. The mixture was stirred at 110° C. for 17 h. The reaction mixture was cooled to RT, diluted with water, and extracted with EtOAc (2×). The combined organic extracts were washed with saturated sodium chloride, dried over magnesium sulfate, filtered, and concentrated in vacuo. The resulting crude mixture was purified via silica gel flash column chromatography eluting with 0% to 100% EtOAc in hexanes to give 1.02 g (47%) of a yellow amorphous solid.

$^1$H NMR (400 MHz, CHLOROFORM-d) δ ppm 4.41-4.50 (m, 1H) 4.58-4.63 (m, 2H) 4.65-4.72 (m, 2H) 7.22-7.28 (m, 1H) 7.61-7.72 (m, 3H) 8.28 (d, J=2.35 Hz, 1H) 8.51 (d, J=2.35 Hz, 1H) 9.04 (s, 1H). ESI (M+1) 298.1; calc for $C_{15}H_{12}ClN_5$ 297.

Preparation 4

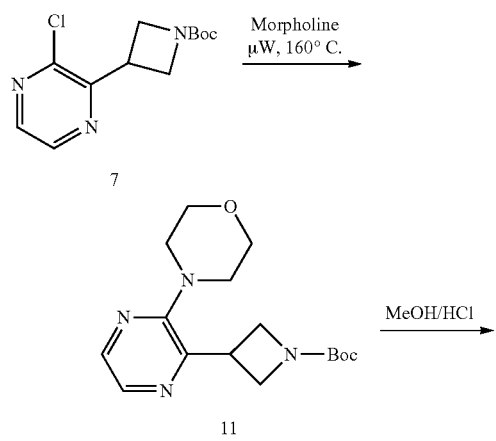

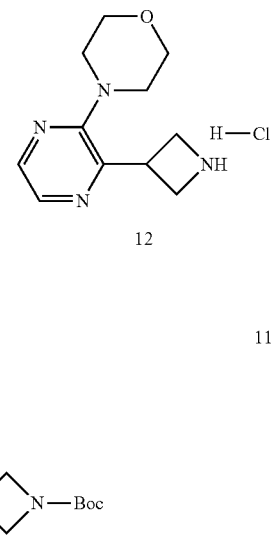

Step 1. 3-(3-Morpholin-4-Yl-Pyrazin-2-Yl)-Azetidine-1-Carboxylic Acid Tert-Butyl Ester (11)

A mixture of 3-(3-chloro-pyrazin-2-yl)-azetidine-1-carboxylic acid tert-butyl ester (7) (269 mg, 1.0 mmol) in morpholine was heated by microwave at 160° C. for 2 h. The mixture was concentrated to give the crude compound and which was purified by column chromatography to afford pure product (11) (300 mg, yield 94%) as solid. ESI-MS (M+1): 321 calc. for $C_{16}H_{24}N_4O_3$ 320.

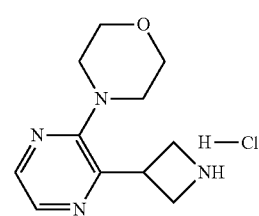

Step 2. 4-(3-Azetidin-3-Yl-Pyrazin-2-Yl)-Morpholine Hydrochloride (12)

To a solution of 4 N HCl/MeOH (10 mL) was added compound (11) (300 mg, 0.90 mmol) at 0° C. and the resulting mixture was stirred at RT for 1 h. The mixture was concentrated under reduced pressure to give (12) (200 mg, yield 100%), which was used directly for the next step without further purification. ESI-MS (M+1): 221 calc. for $C_{11}H_{16}N_4O$ 220.

The following Table 1 lists compounds of Preparation P4.1 to P4.4, which were made analogously to Preparation 4 by using the appropriate materials.

TABLE 1
PREPARATION P4.1 TO P4.4
| Prep. # | Structure | Chemical Name | ESI-MS (M + 1) |
|---|---|---|---|
| P4.1 | 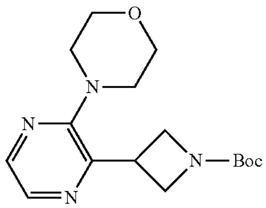 [SMILES: CC(C)(C)OC(=O)N1CC(c2nccnc2N2CCOCC2)C1] | tert-butyl 3-(3-morpholinopyrazin-2-yl)azetidine-1-carboxylate | 321 |
| P4.2 | 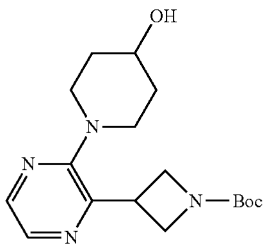 [SMILES: CC(C)(C)OC(=O)N1CC(c2nccnc2N2CCC(O)CC2)C1] | tert-butyl 3-(3-(4-hydroxypiperidin-1-yl)pyrazin-2-yl)azetidine-1-carboxylate | 335 |
| P4.3 | 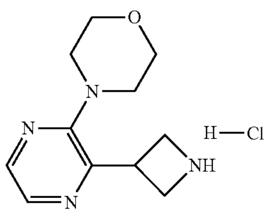 | 4-(3-azetidin-3-yl-pyrazin-2-yl)-morpholine hydrochloride | 221 |
| P4.4 | 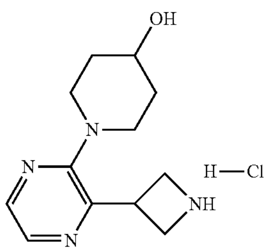 | 1-(3-(azetidin-3-yl)pyrazin-2-yl)piperidin-4-ol hydrochloride | 235 |
Preparation 5
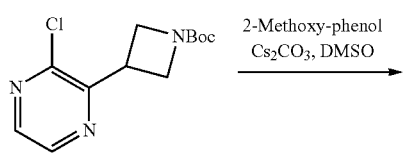
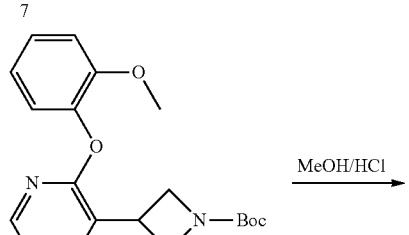
-continued
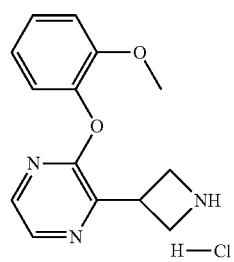
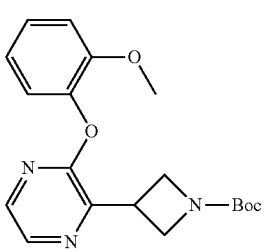

Step 1. 3-[3-(2-Methoxy-Phenoxy)-Pyrazin-2-Yl]-Azetidine-1-Carboxylic Acid Tert-Butyl Ester (13)

A mixture of 3-(3-chloro-pyrazin-2-yl)-azetidine-1-carboxylic acid tert-butyl ester (7) (100 mg, 0.37 mmol), 2-methoxy-phenol (47 mg, 0.37 mmol) and $Cs_2CO_3$ (242 mg, 0.74 mmol) in DMSO (10 mL) was stirred at 90° C. overnight. The mixture was diluted with water and extracted with EtOAc. The organic layer was washed with brine, dried over $Na_2SO_4$ and concentrated to give the crude compound, which was purified by column chromatography to afford pure product (13) (80 mg, 0.22 mmol, yield 61%) as solid. ESI-MS (M+1): 358 calc. for $C_{19}H_{23}N_3O_4$ 357.

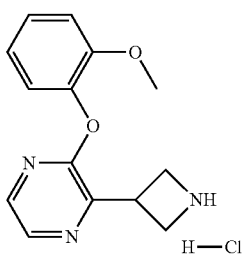

14

Step 2. 2-Azetidin-3-Yl-3-(2-Methoxy-Phenoxy)-Pyrazine Hydrochloride (14)

To a solution of 4 N HCl/MeOH (10 mL) was added compound (13) (80 mg, 0.22 mmol) at 0° C. The resulting mixture was stirred at RT for 1 h. The mixture was concentrated under reduced pressure to give (14) (65 mg, yield 100%), which was used for the next step without further purification. ESI-MS (M+1): 258 calc. for $C_{14}H_{15}N_3O_2$ 257.

The following Table 2 lists compounds of Preparation P5.1 to P5.8, which were made analogous to Preparation 5 by using the appropriate materials.

TABLE 2

| Ex. # | Structure | Chemical Name | ESI-MS (M + 1) |
|---|---|---|---|
| P5.1 | | 3-[3-(2-methoxy-phenoxy)-pyrazin-2-yl]-azetidine-1-carboxylic acid tert-butyl ester | 358 |
| P5.2 | | tert-butyl 3-(3-(3-methoxyphenoxy)pyrazin-2-yl)azetidine-1-carboxylate | 358 |
| P5.3 | 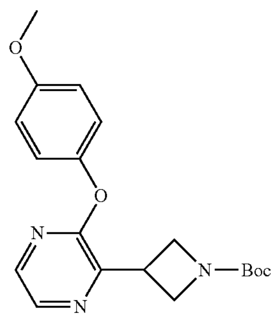 | tert-butyl 3-(3-(4-methoxy-phenoxy)pyrazin-2-yl)azetidine-1-carboxylate | 358 |
| P5.4 | 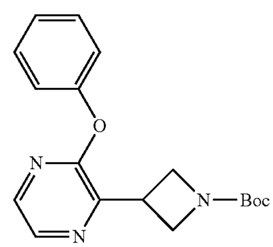 | tert-butyl 3-(3-phenoxypyrazin-2-yl)azetidine-1-carboxylate | 328 |
| P5.5 | 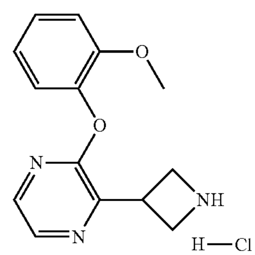 | 2-azetidin-3-yl-3-(2-methoxy-phenoxy)-pyrazine hydrochloride | 258 |
| P5.6 | 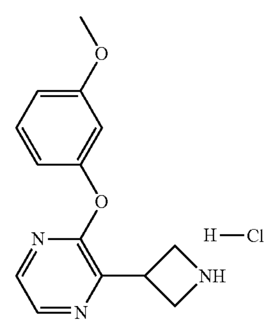 | 2-(azetidin-3-yl)-3-(3-methoxy-phenoxy)pyrazine hydrochloride | 258 |
| P5.7 | 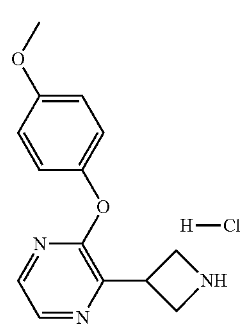 | 2-(azetidin-3-yl)-3-(4-methoxy phenoxy)pyrazine hydrochloride | 258 |

TABLE 2-continued

PREPARATION P5.1 TO P5.8

| Ex. # | Structure | Chemical Name | ESI-MS (M + 1) |
|---|---|---|---|
| P5.8 | 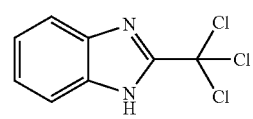 | 2-(azetidin-3-yl)-3-phenoxy-pyrazine hydrochloride | 228 |

Preparation 6

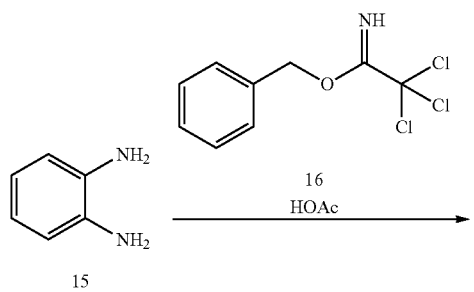

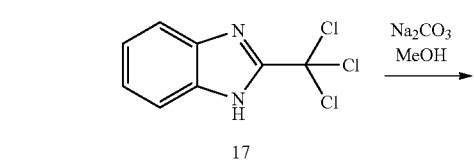

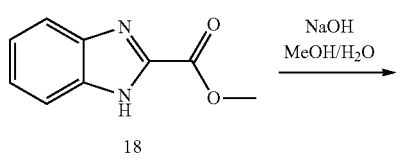

Step 1. 2-Trichloromethyl-1H-Benzoimidazole (17)

2,2,2-trichloro-acetimidic acid benzyl ester (16) (2.3 g, 9.22 mmol, Alfa Aesar) was added to a solution of Benzene-1,2-diamine (15) (1.0 g, 9.2 mmol) in acetic acid (30 mL), the solution was stirred at RT for 1 h. $H_2O$ (20 mL) was added to the mixture and the suspension was filtered. The filter cake was washed with water and dried under vacuum to afford compound (17) (1.90 g yield 88%) which was used directly for the next step without further purification. ESI-MS (M+1): 235 calc. for $C_9H_5Cl_3N_2$ 234.

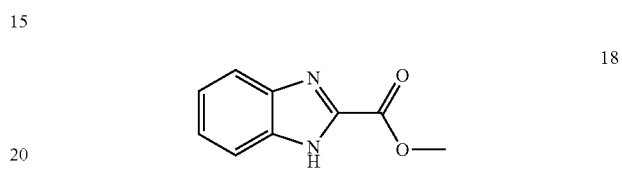

Step 2. 1H-Benzoimidazole-2-Carboxylic Acid Methyl Ester (18)

$Na_2CO_3$ (0.64 g, 6.07 mmoi) was added to a solution of (17) (1.9 g, 6.07 mmol) in 20 mL MeOH. The reaction mixture was heated to reflux for 14 h and then cooled to RT. 1N HCl was added to the solution and the reaction mixture was stirred for 0.5 hour. The mixture was extracted with EA. The organic phase was washed with brine, dried over $Na_2SO_4$ and evaporated to give the title compound (0.89 g, yield 83%). ESI-MS (M+1): 177 calc. for $C_9H_8N_2O_2$ 176.

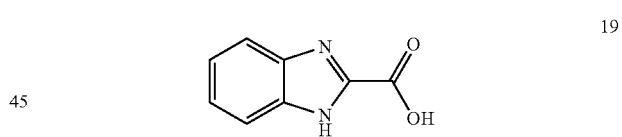

Step 3. 1H-Benzoimidazole-2-Carboxylic Acid (19)

A mixture of 1H-benzoimidazole-2-carboxylic acid methyl ester (18) (0.89 g, 5.1 mmol) in 2 N aq. NaOH (10 mL) and MeOH (10 mL) was stirred at RT for 18 h. The mixture was acidified to pH=4 with 1 N aqueous HCl. The mixture was extracted with EtOAc. The organic layer was washed with brine, dried over $Na_2SO_4$ and evaporated to obtain compound (19) as a brown solid (0.67 g, yield 80%). ESI-MS (M+1): 163 calc. for $C_8H_6N_2O_2$ 162.

The following Table 3 lists compounds of Preparation P6.1 to P6.18, which were made analogous to Preparation 6 by using the appropriate materials.

TABLE 3

| | PREPARATION P6.1 TO P6.18 | | |
|---|---|---|---|
| Ex. # | Structure | Chemical Name | ESI-MS (M + 1) |
| P6.1 | | 4-chloro-2-(trichloromethyl)-1H-benzo[d]imidazole | 268 |
| P6.2 | | 5-chloro-2-(trichloromethyl)-1H-benzo[d]imidazole | 268 |
| P6.3 | | 4-fluoro-2-(trichloromethyl)-1H-benzo[d]imidazole | 252 |
| P6.4 | | 5-fluoro-2-(trichloromethyl)-1H-benzo[d]imidazole | 252 |
| P6.5 | | 4-methyl-2-(trichloromethyl)-1H-benzo[d]imidazole | 249 |
| P6.6 | | 5-methyl-2-(trichloromethyl)-1H-benzo[d]imidazole | 249 |
| P6.7 | | methyl 4-chloro-1H-benzo[d]imidazole-2-carboxylate | 211 |
| P6.8 | | methyl 5-chloro-1H-benzo[d]imidazole-2-carboxylate | 211 |
| P6.9 | | methyl 4-fluoro-1H-benzo[d]imidazole-2-carboxylate | 195 |
| P6.10 | | methyl 5-fluoro-1H-benzo[d]imidazole-2-carboxylate | 195 |

TABLE 3-continued

PREPARATION P6.1 TO P6.18

| Ex. # | Structure | Chemical Name | ESI-MS (M + 1) |
|---|---|---|---|
| P6.11 | 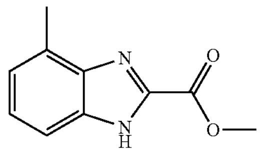 | methyl 4-methyl-1H-benzo[d]imidazole-2-carboxylate | 191 |
| P6.12 | 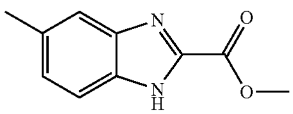 | methyl 5-methyl-1H-benzo[d]imidazole-2-carboxylate | 191 |
| P6.13 | 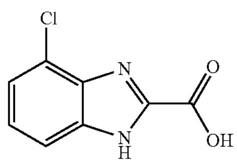 [SMILES: O=C(O)c1nc2c(Cl)cccc2[nH]1] | 4-chloro-1H-benzo[d]imidazole-2-carboxylic acid | 197 |
| P6.14 | 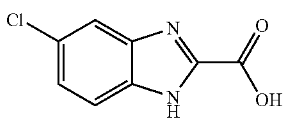 [SMILES: O=C(O)c1nc2cc(Cl)ccc2[nH]1] | 5-chloro-1H-benzo[d]imidazole-2-carboxylic acid | 197 |
| P6.15 | 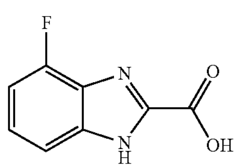 [SMILES: O=C(O)c1nc2c(F)cccc2[nH]1] | 4-fluoro-1H-benzo[d]imidazole-2-carboxylic acid | 181 |
| P6.16 | 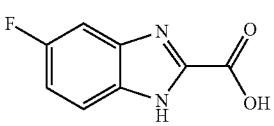 [SMILES: O=C(O)c1nc2cc(F)ccc2[nH]1] | 5-fluoro-1H-benzo[d]imidazole-2-carboxylic acid | 181 |
| P6.17 | 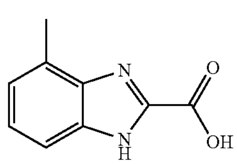 | 4-methyl-1H-benzo[d]imidazole-2-carboxylic acid | 177 |
| P6.18 | 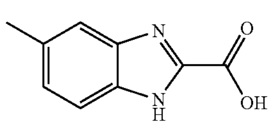 | 5-methyl-1H-benzo[d]imidazole-2-carboxylic acid | 177 |

Preparation 7

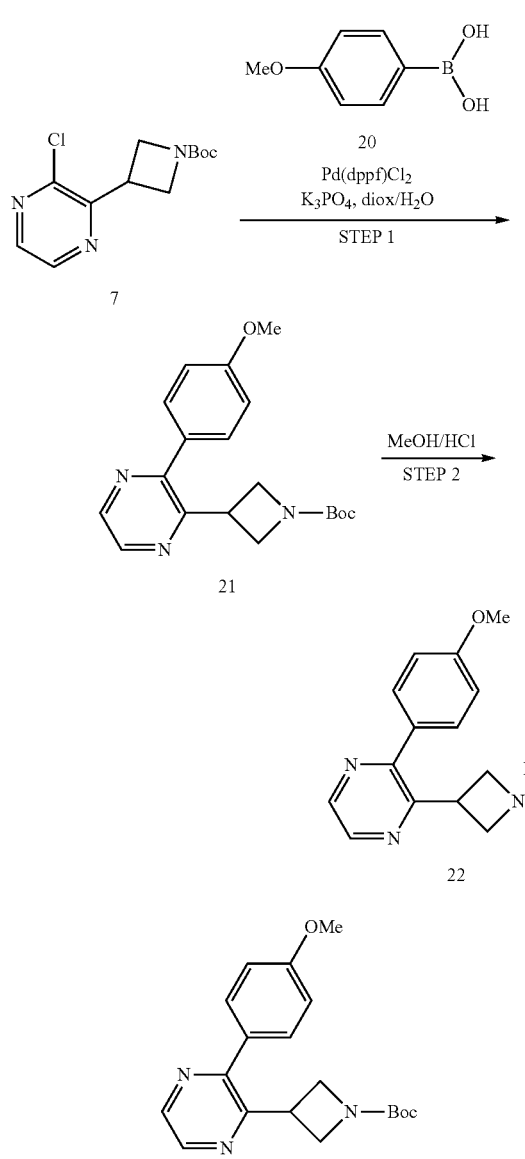

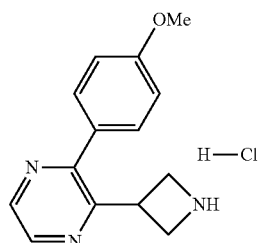

Step 2. 2-Azetidin-3-Yl-3-(4-Methoxy-Phenyl)-Pyrazine Hydrochloride (22)

To a solution of 4 N HCl in MeOH (10 mL) was added (21) (120 mg, 0.35 mmol) at 0° C. and the resulting mixture was stirred at RT for 1 h. The mixture was concentrated under reduced pressure to give 2-azetidin-3-yl-3-(4-methoxy-phenyl)-pyrazine (22) (95 mg, yield 100%) which was used for the next step without further purification. ESI-MS (M+1): 242 calc. for $C_{14}H_{15}N_3O$ 241.

The following Table 4 lists compounds of Preparation P7.1 to P7.6, which were made analogous to Preparation 7 by using the appropriate materials.

TABLE 4

PREPARATION P7.1 TO P7.6

| Ex. # | Structure | Chemical Name | ESI-MS (M + 1) |
|---|---|---|---|
| P7.1 | 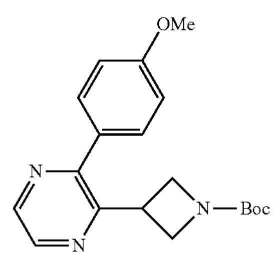 [SMILES: COc1ccc(-c2nccnc2C2CN(C(=O)OC(C)(C)C)C2)cc1] | tert-butyl 3-(3-(4-methoxyphenyl)pyrazin-2-yl)azetidine-1-carboxylate | 342 |
| P7.2 | 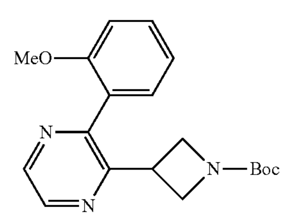 [SMILES: COc1ccccc1-c1nccnc1C1CN(C(=O)OC(C)(C)C)C1] | tert-butyl 3-(3-(2-methoxyphenyl)pyrazin-2-yl)azetidine-1-carboxylate | 342 |
| P7.3 | 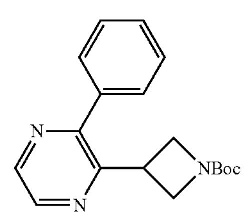 [SMILES: CC(C)(C)OC(=O)N1CC(c2nccnc2-c2ccccc2)C1] | tert-butyl 3-(3-phenylpyrazin-2-yl)azetidine-1-carboxylate | 312 |

Step 1. 3-[3-(4-Methoxy-Phenyl)-Pyrazin-2-Yl]-Azetidine-1-Carboxylic Acid Tert-Butyl Ester (21)

To a solution of 3-(3-chloro-pyrazin-2-yl)-azetidine-1-carboxylic acid tert-butyl ester (7) (100 mg, 0.37 mmol, as prepared in the above Preparation 2) in dioxane (8 mL) was added a solution of $Na_2CO_3$ (78 mg, 0.64 mmol) in 0.5 mL water, followed by additional of 4-methoxybenzeneboronic acid (20) (49 mg 0.40 mmol) and Pd(dppf)Cl$_2$ (8 mg). The resulting mixture was heated to reflux overnight under $N_2$ atmosphere. TLC showed that the starting material was consumed completely. The solution was filtered and the filtrate was concentrated to give the residue which was purified by column chromatography on silica gel to give the product compound (21) (120 mg, yield 96%) as solid. ESI-MS (M+1): 342 calc. for $C_{19}H_{23}N_3O_3$ 341.

TABLE 4-continued

PREPARATION P7.1 TO P7.6

| Ex. # | Structure | Chemical Name | ESI-MS (M + 1) |
|---|---|---|---|
| P7.4 | 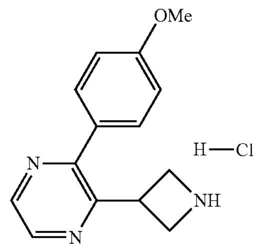 | 2-(azetidin-3-yl)-3-(4-methoxyphenyl)pyrazine hydrochloride | 242 |
| P7.5 | 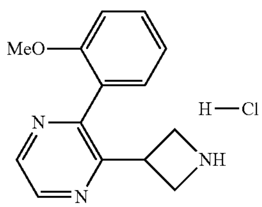 | 2-(azetidin-3-yl)-3-(2-methoxyphenyl)pyrazine hydrochloride | 242 |
| P7.6 | 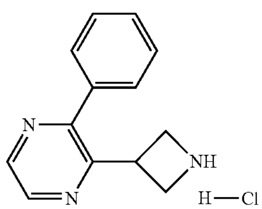 | 2-(azetidin-3-yl)-3-phenylpyrazine hydrochloride | 212 |

Preparation 8

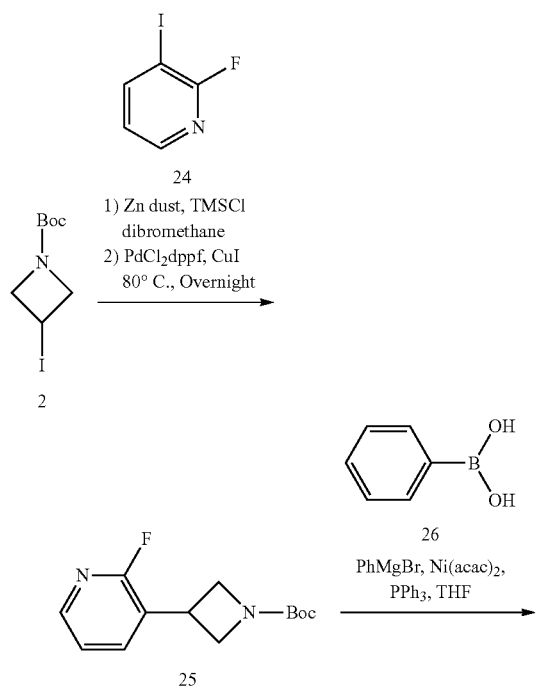

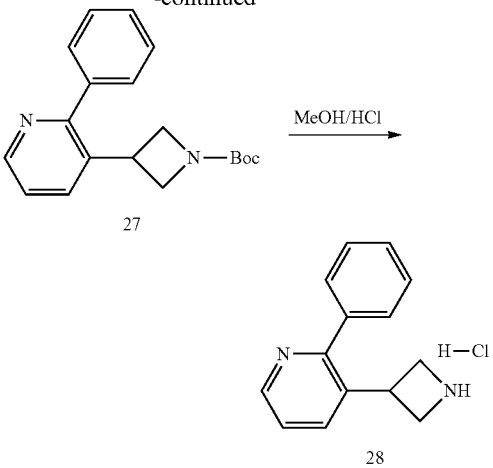

Step 1. Tert-Butyl 3-(2-Fluoropyridin-3-Yl)Azetidine-1-Carboxylate (25)

To a 2 L 3 necked round bottomed flask fitted with a mechanical stirrer, under nitrogen atmosphere was placed Zinc dust, which was preactivated according to above Preparation 2, (51.2 g, 0.78 mol, 1.94 eq) and dimethyl acetamide (162 mL). To the above suspension, 1,2-dibromoethane (12.14 g, 0.0646 mol, 0.16 eq) was added dropwise at RT (exotherm and bubbling were observed), followed by dropwise addition of TMSCl (6.99 g, 0.0646 mol, 0.16 eq). A vigorous reaction (exotherm to 55° C.) was observed. To this, a solution of N-Boc-3-iodoazetidine (2) (182.88 g, 0.646 mol, 1.6 eq) in dimethyl acetamide (378 mL) was added dropwise using an addition funnel (exotherm to 50° C. was observed). The suspension was stirred for 1.5 h at RT and was then degassed with nitrogen for 15 min. Stirring was stopped and suspension was allowed to stand under nitrogen. To a 5 L 3 necked round bottomed flask, fitted with mechanical stirrer, flushed with nitrogen were placed 3-iodo-2-fluoropyridine (24) (90 g, 0.404 mol, 1.0 eq), PdCl$_2$dppf.CH$_2$Cl$_2$ (9.88 g, 0.012 mol, 0.03 eq), CuI (4.76 g, 0.025 mol, 0.062 eq) and dimethyl acetamide (396 mL). The red colored suspension was degassed with nitrogen for 15 min.

The Zinc reagent solution in 2 L flask was cannulated into 5 L round bottomed flask. The resulting reaction mixture was degassed again with nitrogen for 15 min with stirring and heated to 80° C. for overnight under nitrogen. LCMS indicates completion of reaction. The reaction was cooled to RT and quenched by addition of brine solution (1 L). To this EtOAc (1 L) and water (1 L) were added and layers were separated. The aqueous layer was extracted with EtOAc (2×2 L). The combined EtOAc layers were washed with water (2 L), brine (1 L), dried (Na$_2$SO$_4$), filtered, and evaporated. The crude was purified by column chromatography to give 52 g of tert-butyl 3-(2-fluoropyridin-3-yl)azetidine-1-carboxylate (25) (yield: 51%) as an oil, which solidified on standing.

$^1$HNMR (300 MHz CDCl$_3$): 8.13 (doublet, J=4.8 Hz, 1H), 7.83-7.76 (dt, 1H), 7.28-7.20 (dt, 1H), 4.35 (t, J=8.7 Hz, 2H), 4.05-3.88 (m, 3H), 1.46 (s, 9H). LC-MS: 253 (M+1); calcd for C$_{13}$H$_{17}$FN$_2$O$_2$:252.28

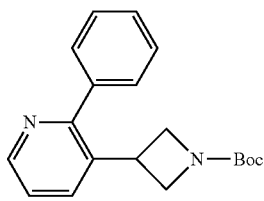

27

Step 2. 3-(2-Phenyl-Pyridin-3-Yl)-Azetidine-1-Carboxylic Acid Tert-Butyl Ester (27)

To a solution of 3-(2-fluoro-pyridin-3-yl)-azetidine-1-carboxylic acid tert-butyl ester (25) (200 mg, 0.80 mmol), Ni(acac)$_2$ (20 mg, 0.08 mmol), DPPF (32 mg, 0.08 mmol) in THF (10 mL) was added PhMgBr (1 M, 0.8 mL, 0.80 mmol). The resulting mixture was heated to reflux overnight under N$_2$ atmosphere. TLC showed that the staring material was consumed completely. The solution was filtered and the filtrate was concentrated to give the residue, The crude compound was purified by column chromatography on silica gel to give the product 3compound (27) (180 mg, yield 78%) as solid. ESI-MS (M+1): 311 calc. for C$_{19}$H$_{22}$N$_2$O$_2$ 310.

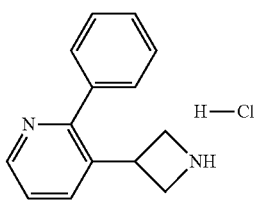

28

Step 3. 3-Azetidin-3-Yl-2-Phenyl-Pyridine Hydrochloride (28)

To a solution of 4 M HCl in MeOH (10 mL) was added 3-(2-phenyl-pyridin-3-yl)-azetidine-1-carboxylic acid tert-butyl ester (27) (180 mg, 0.58 mmol) at 0° C. and the resulting mixture was stirred at RT for 1 h. The mixture was concentrated under reduced pressure to give 3-azetidin-3-yl-2-phenyl-pyridine hydrochloride (28) (120 mg, yield 94%) which was used for the next step without further purification. ESI-MS (M+1): 211 calc. for C$_{14}$H$_{14}$N$_2$ 210.

Preparation 9

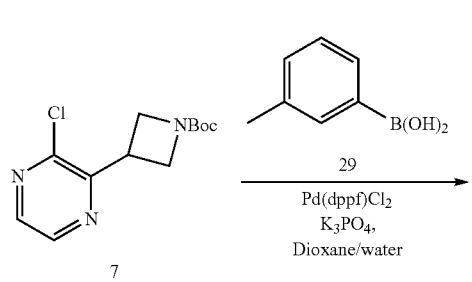

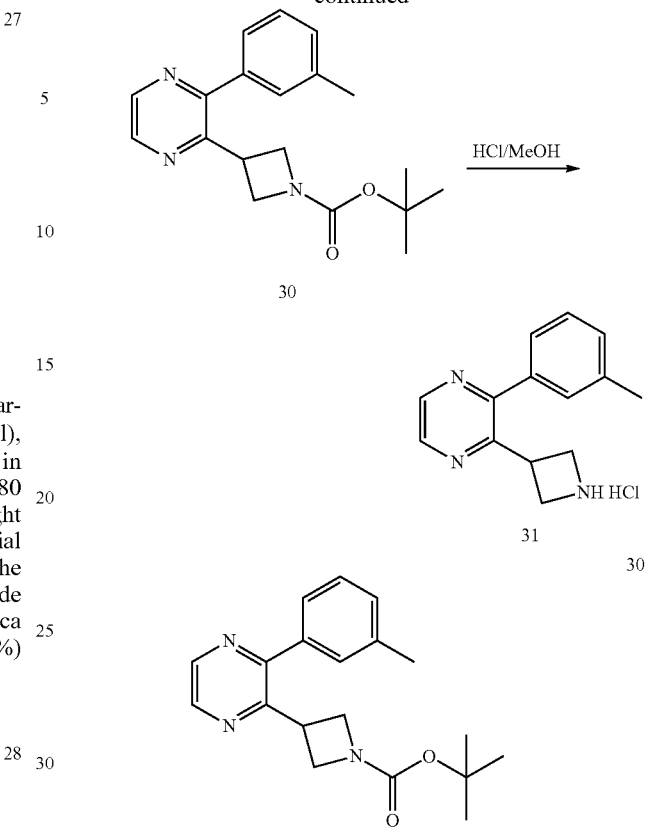

Step 1. 3-(3-M-Tolyl-Pyrazin-2-Yl)-Azetidine-1-Carboxylic Acid Tert-Butyl Ester (30)

To a solution of 3-(3-chloro-pyrazin-2-yl)-azetidine-1-carboxylic acid tert-butyl ester (7) (540 mg, 2.0 mmol, Preparation 2), 3-methyl-phenylboronic acid (78) (299.2 mg, 2.2 mmol), K$_3$PO$_4$ (818 mg, 4.0 mmol), in dioxane (20 mL) and water (4 mL) was added Pd(dppf)Cl$_2$ (73.2 mg, 0.1 mmol) then the reaction mixture was stirred at 90° C. under nitrogen atmosphere overnight. The reaction mixture was filtered through CELITE® and washed with EtOAc (50 mL). The filtrate was concentrated and the crude product was purified by silica gel column to give 3-(3-m-tolyl-pyrazin-2-yl)-azetidine-1-carboxylic acid tert-butyl ester (30) (597 mg, 1.84 mmol, yield 91.85%).

ESI-MS (M+1): 326 calc. for C$_{19}$H$_{23}$N$_3$O$_2$ 325.

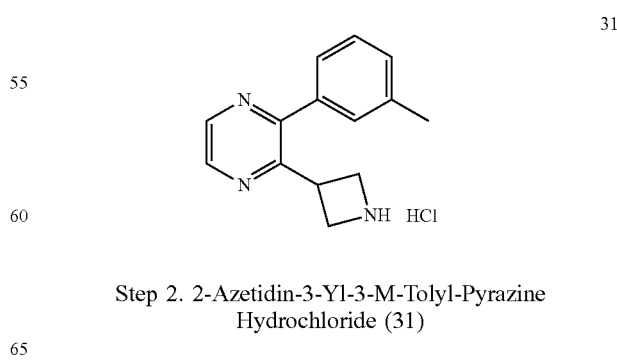

Step 2. 2-Azetidin-3-Yl-3-M-Tolyl-Pyrazine Hydrochloride (31)

A solution of 3-(3-m-tolyl-pyrazin-2-yl)-azetidine-1-carboxylic acid tert-butyl ester (30) (325 mg, 1.0 mmol) in 4N HCl/MeOH (20 mL) was stirred at RT for 30 min. The reaction mixture was concentrated to give (31) (260 mg, 0.99 mmol, yield 99.24%).

ESI-MS (M+1): 226 calc. for $C_{14}H_{15}N_3$ 225.

Preparation 10

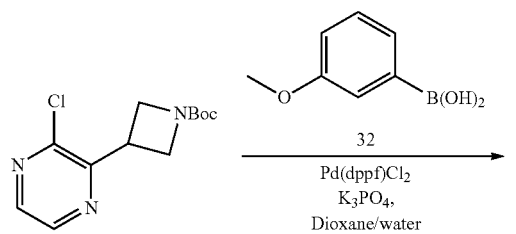

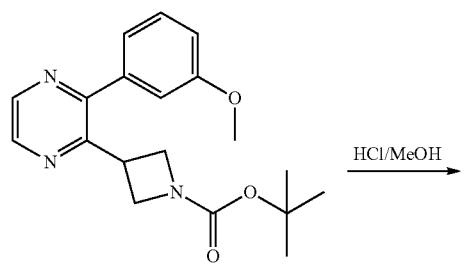

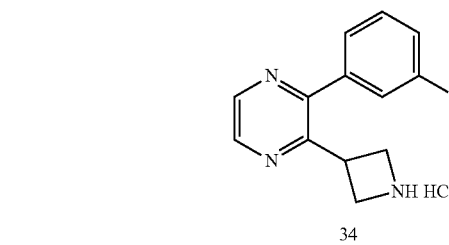

Step 1. 3-[3-(3-Methoxy-Phenyl)-Pyrazin-2-Yl]-Azetidine-1-Carboxylic Acid Tert-Butyl Ester (33)

To a solution of 3-(3-chloro-pyrazin-2-yl)-azetidine-1-carboxylic acid tert-butyl ester (7) (540 mg, 2.0 mmol, Preparation 2), 3-methoxy-phenylboronic acid (29) (334.4 mg, 2.2 mmol), $K_3PO_4$ (818 mg, 4.0 mmol), in dioxane (20 mL) and water (4 mL) was added Pd(dppf)Cl$_2$ (73.2 mg, 0.1 mmol) then the reaction mixture was stirred at 90° C. under nitrogen atmosphere overnight. The reaction mixture was filtered through CELITE® and washed with EtOAc (50 mL). The filtrate was concentrated and the crude product was purified by silica gel column to give compound (33) (627.4 mg, 1.84 mmol, yield 91.85%).

ESI-MS (M+1): 342 calc. for $C_{19}H_{23}N_3O_3$ 341.

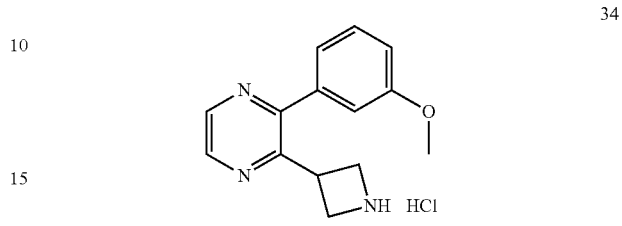

Step 2. 2-Azetidin-3-Yl-3-(3-Methoxy-Phenyl)-Pyrazine Hydrochloride (34)

A solution of (33) (341 mg, 1.0 mmol) in 4N HCl/MeOH (20 mL) was stirred at RT for 30 min. The reaction mixture was concentrated to give (34) (260 mg, 0.99 mmol, yield 99.24%).

ESI-MS (M+1): 242 calc. for $C_{14}H_{15}N_3O$ 241.

Preparation 11

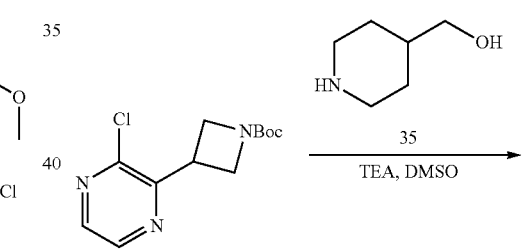

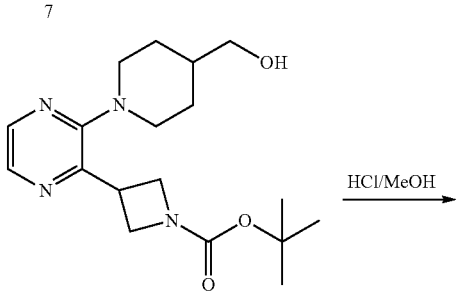

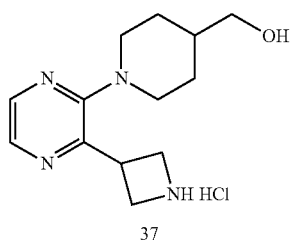

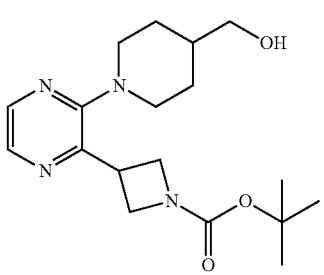

Step 1. 3-[3-(4-Hydroxymethyl-Piperidin-1-Yl)-Pyrazin-2-Yl]-Azetidine-1-Carboxylic Acid Tert-Butyl Ester (36)

To a solution of compound (7) (540 mg, 2 mmol, Preparation 2) and 4-amino-2-methyl-butan-1-ol (230 mg, 2 mmol) in DMSO (20 mL) was added $Et_3N$ (404 mg, 4 mmol). The reaction mixture was stirred at 110° C. overnight. The reaction mixture was diluted with water, extracted with EtOAc (50 mL×3). The combined organic extracts were washed with water (30 mL) and brine (30 mL), dried over $Na_2SO_4$ and filtered. The filtrate was evaporated in vacuo and the residue was purified by flash column chromatography (EtOAc: Petrol ether=3:1) on silica gel to give (36). (557 mg, 1.6 mmol, yield 80%)₀

ESI-MS (M+1): 349 calc. for $C_{18}H_{28}N_4O_3$ 348.

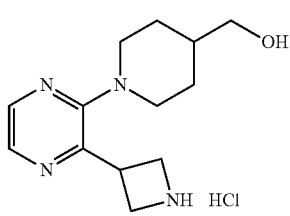

Step 2. [1-(3-Azetidin-3T-Yl-Pyrazin-2-Yl)-Piperidin-4-Yl]-Methanol Hydrochloride (37)

A solution of (36) (557 mg, 1.6 mmol) in 4N HCl/MeOH (20 mL) was stirred at RT for 30 min. The reaction mixture was concentrated to give (37) (450 mg, 1.58 mmol, yield 98%).

ESI-MS (M+1): 249 calc. for $C_{13}H_{20}N_4O$ 248.

Preparation 12

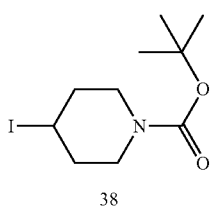

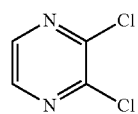

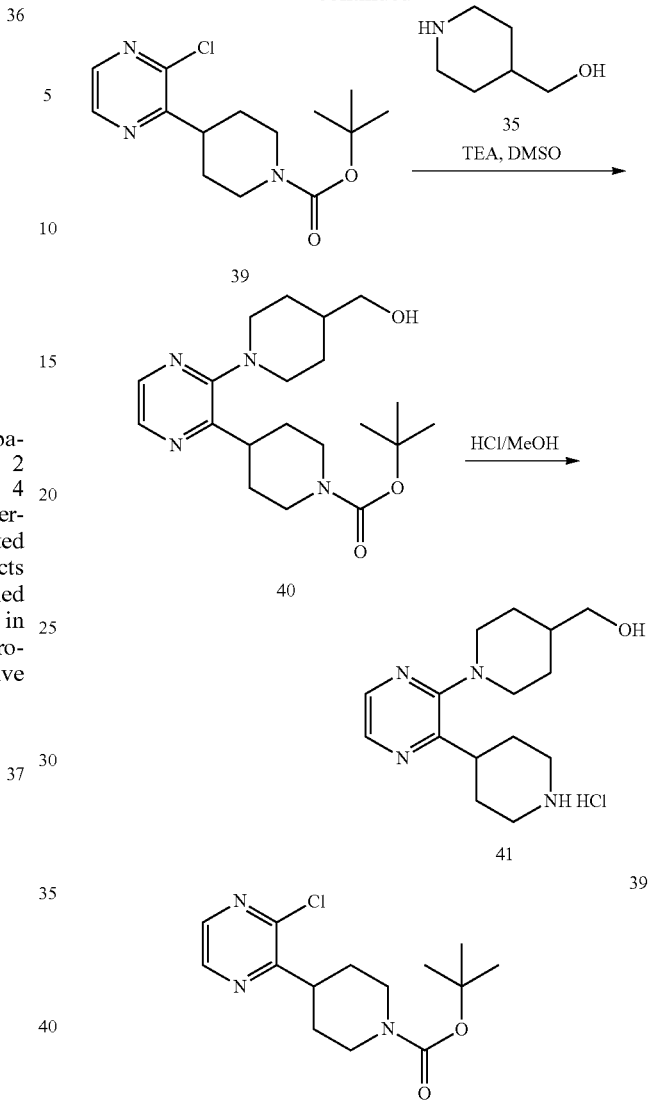

Step 1. 4-(3-Chloro-Pyrazin-2-Yl)-Piperidine-1-Carboxylic Acid Tert-Butyl Ester (39)

A 100 mL 3-neck round bottom flask fitted with a magnetic stirrer and flushed with nitrogen was charged with zinc dust (813 mg, preactivated according to the above Preparation 1, 12.7 mmol, 2.0 eq.) and DMA (10 mL, anhydrous). 1,2-dibromoethane (236 mg, 1.27 mmol, 0.2 eq) was added slowly, followed by TMSCl (137 mg, 1.27 mmol, 0.2 eq). The reaction was stirred for 15 min at RT. A solution of 4-iodo-piperidine-1-carboxylic acid tert-butyl ester (38) (2.95 g, 9.5 mmol, 1.5 eq) in DMA (10 mL, anhydrous) was added dropwise. The suspension was stirred for 1 h at RT.

A 100 mL 3-neck round bottom flask fitted with a mechanical stirrer was charged with 2,3-dichloro-pyrazine (6) (0.95 g, 6.4 mmol, 1.0 eq), Pd(dppf)Cl₂ (446 mg, 0.64 mmol, 0.1 eq), cuprous iodide (121 mg, 0.64 mmol, 0.1 eq), and DMA (20 mL, anhydrous). The dark solution was degassed for 15 min. The clear zinc reagent solution above the residual solid zinc was transferred to the above 100 mL flask by cannulation. The dark solution was degassed and heated to 80° C. for 16 h. The reaction was diluted with brine and extracted with EtOAc (3×100 mL). The combined organics were washed with water (2×100 mL) and brine (100 mL), followed by drying over sodium sulfate. The solution was concentrated and the residue was purified by flash column chromatography on silica gel (PE:EAOAc=2:1) to give the title compound (39) (0.95 g, 3.2 mmol, 50% yield) as a light yellow solid.

ESI-MS (M+1): 298 calc. for $C_{14}H_{20}ClN_3O_2$ 297.

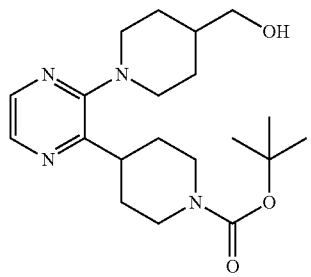

40

Step 2. 4-[3-(4-Hydroxymethyl-Piperidin-1-Yl)-Pyrazin-2-Yl]-Piperidine-1-Carboxylic Acid Tert-Butyl Ester (40)

To a solution of 4-(3-chloro-pyrazin-2-yl)-piperidine-1-carboxylic acid tert-butyl ester (39) (297 mg, 1 mmol) and piperidin-4-yl-methanol (35) (126.5 mg, 1.1 mmol) in DMSO (6 mL) was added Et$_3$N (202 mg, 2 mmol). The reaction mixture was stirred at 100° C. overnight. The reaction mixture was diluted with water, extracted with EtOAc (30 mL×3). The combined organic extracts were washed with water (30 mL) and brine (30 mL), dried over Na$_2$SO$_4$ and filtered. The filtrate was evaporated in vacuo and the residue was purified by flash column chromatography on silica gel to give compound (40) (302 mg, 0.8 mmol, yield 80.32%).

ESI-MS (M+1): 377 calc. for $C_{20}H_{32}N_4O_3$ 376.

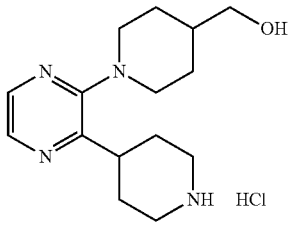

41

Step 3. [1-(3-Piperidin-4-Yl-Pyrazin-2-Yl)-Piperidin-4-Yl]-Methanol Hydrochloride (41)

A solution of 4-[3-(4-hydroxymethyl-piperidin-1-yl)-pyrazin-2-yl]-piperidine-1-carboxylic acid tert-butyl ester (40) (376 mg, 1 mmol) in 4N HCl/MeOH (20 mL) was stirred at RT for 30 min. The reaction mixture was concentrated to give (41) (308 mg, 0.98 mmol, yield 98.72%).

ESI-MS (M+1): 277 calc. for $C_{15}H_{24}N_4O$ 276.

Preparation 13

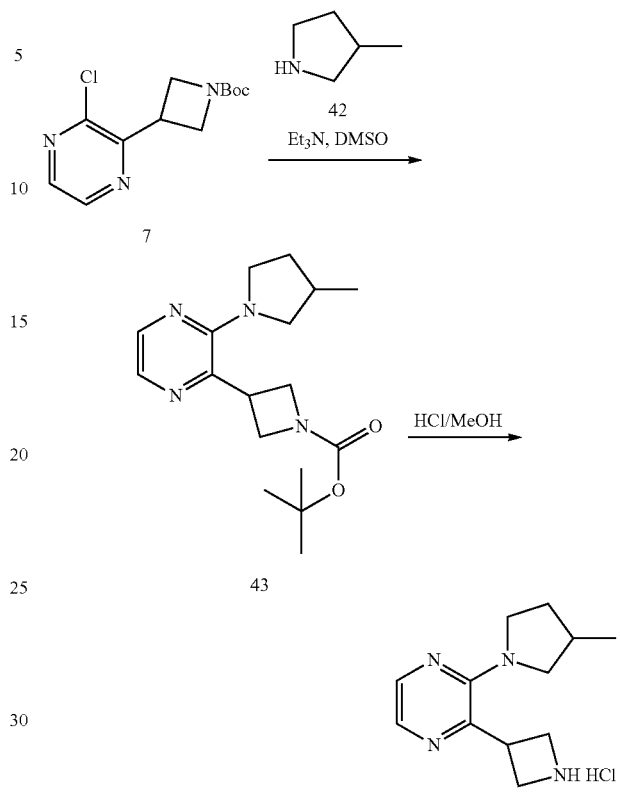

Step 1. 3-[3-(3-Methyl-Pyrrolidin-1-Yl)-Pyrazin-2-Yl]-Azetidine-1-Carboxylic Acid Tert-Butyl Ester (43)

To a solution of 3-(3-chloro-pyrazin-2-yl)-azetidine-1-carboxylic acid tert-butyl ester (7) (200 mg, 0.74 mmol, Preparation 2) and 3-methyl-pyrrolidine (42) (69.2 mg, 0.84 mmol) in DMSO (5 mL) was added Et$_3$N (149.5 mg, 1.48 mmol). The reaction mixture was stirred at 100° C. overnight. The reaction mixture was diluted with water, extracted with EtOAc (30 mL×3). The combined organic extracts were washed with water (30 mL) and brine (30 mL), dried over Na$_2$SO$_4$ and filtered. The filtrate was evaporated in vacuo and the residue was purified by flash column chromatography on silica gel to give 3-[3-(3-methyl-pyrrolidin-1-yl)-pyrazin-2-yl]-azetidine-1-carboxylic acid tert-butyl ester (43) (194 mg, 0.56 mmol, yield 75.99%)$_o$ ESI-MS (M+1): 319 calc. for $C_{17}H_{26}N_4O_2$ 318

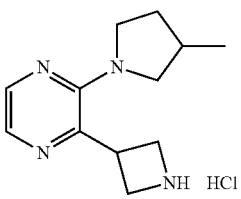

Step 2. 2-Azetidin-3-Yl-3-(3-Methyl-Pyrrolidin-1-Yl)-Pyrazine Hydrochloride (44)

A solution of 3-[3-(3-methyl-pyrrolidin-1-yl)-pyrazin-2-yl]-azetidine-1-carboxylic acid tert-butyl ester (43) (191 mg, 0.6 mmol) in 4N HCl/MeOH (13 mL) was stirred at RT for 30 min. The reaction mixture was concentrated to give 2-azetidin-3-yl-3-(3-methyl-pyrrolidin-1-yl)-pyrazine hydrochloride (44)
(150 mg, 0.59 mmol, yield 99%).
ESI-MS (M+1): 219 calc. for $C_{12}H_{18}N_4$ 218.

Preparation 14

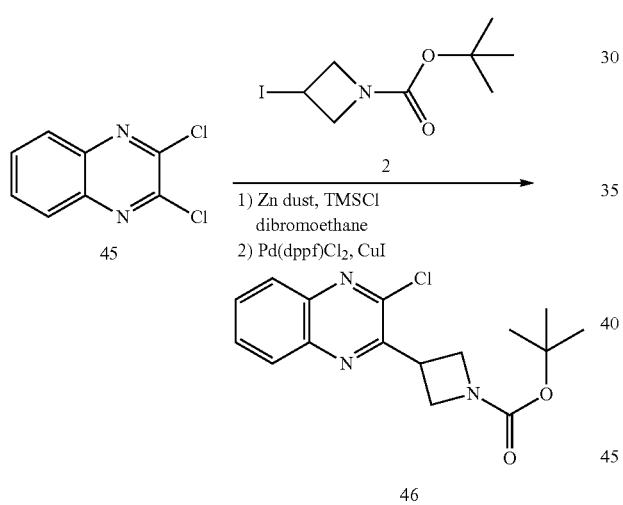

3-(3-Chloro-Quinoxalin-2-Yl)-Azetidine-1-Carboxylic Acid Tert-Butyl Ester (46)

A 100 mL 3-neck round bottom flask fitted with a magnetic stirrer and flushed with nitrogen was charged with zinc dust (1.3 g, preactivated according to the above Preparation 1, 20 mmol, 2.0 eq.) and DMA (10 mL, anhydrous). 1,2-Dibromoethane (400 mg, 2.0 mmol, 0.2 eq) was added slowly, followed by TMSCl (240 mg, 2.0 mmol, 0.2 eq). The reaction was stirred for 15 min at RT. A solution of N-Boc-3-iodoazetidine (2) (4 g, 16 mmol, 1.6 eq) in DMA (10 mL, anhydrous) was added dropwise. The suspension was stirred for 1 h at RT.
A 100 mL 3-neck round bottom flask fitted with a mechanical stirrer was charged with 2,3-dichloro-quinoxaline (44) (2 g, 10 mmol, 1.0 eq), Pd(dppf)Cl$_2$ (800 mg, 1.0 mmol, 0.1 eq), cuprous iodide (200 mg, 1.0 mmol, 0.1 eq), and DMA (20 mL, anhydrous). The dark solution was degassed for 15 min. The clear zinc reagent solution above the residual solid zinc was transferred to the above 100 mL flask by cannulation. The dark solution was degassed and heated to 80° C. for 16 h. The reaction was diluted with brine and extracted with EtOAc (3×100 mL). The combined organics were washed with water (2×100 mL) and brine (100 mL), followed by drying over sodium sulfate. The solution was concentrated and the residue was purified by flash column chromatography (PE:EAOAc=2:1) provides 3-(3-chloro-quinoxalin-2-yl)-azetidine-1-carboxylic acid tert-butyl ester (46) (1.43 g, 4.5 mmol, 45% yield) as a light yellow solid.
ESI-MS (M+1): 320 calc. for $C_{16}H_{18}ClN_3O_2$ 319.

Preparation 15

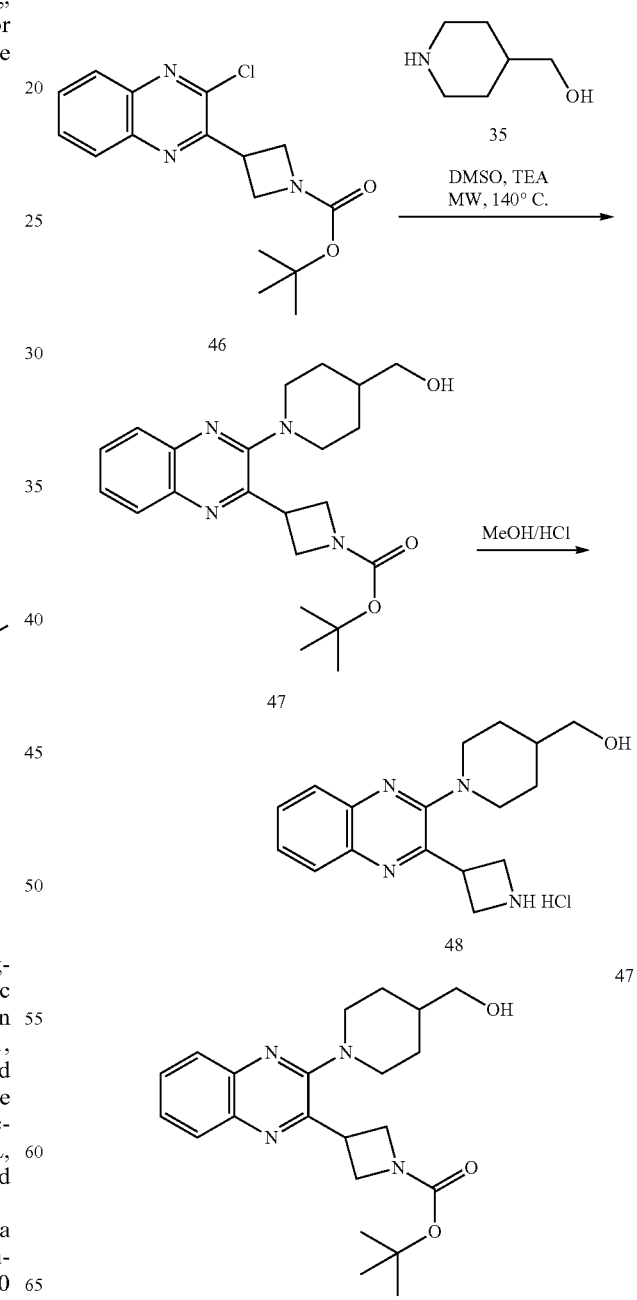

Step 1. 3-[3-(4-Hydroxymethyl-Piperidin-1-Yl)-Quinoxalin-2-Yl]-Azetidine-1-Carboxylic Acid Tert-Butyl Ester (47)

To a solution of 3-(3-chloro-quinoxalin-2-yl)-azetidine-1-carboxylic acid tert-butyl ester (46) (638 mg, 2 mmol, Preparation 14) and piperidin-4-yl-methanol (253 mg, 2.2 mmol) in DMSO (10 mL) was added Et$_3$N (404 mg, 4 mmol). The reaction mixture was stirred at 140° C. in microwave heating for 4 h. The reaction mixture was diluted with water, extracted with EtOAc (30 mL×3). The combined organic extracts were washed with water (30 mL) and brine (30 mL), dried over Na$_2$SO$_4$ and filtered. The filtrate was evaporated in vacuo and the residue was purified by flash column chromatography on silica gel to give (47) (670 mg, 1.68 mmol, yield 84.15%). ESI-MS (M+1): 399 calc. for C$_{17}$H$_{22}$N$_4$O 398.

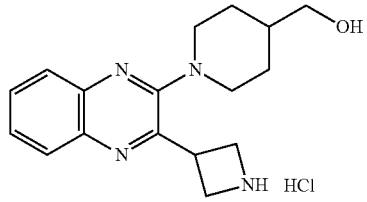

48

Step 2. [1-(3-Azetidin-3-Yl-Quinoxalin-2-Yl)-Piperidin-4-Yl]-Methanol Hydrochloride (48)

A solution of (47) (670 mg, 1.68 mmol) in 4N HCl/MeOH (25 mL) was stirred at RT for 30 min. The reaction mixture was concentrated to give [1-(3-azetidin-3-yl-quinoxalin-2-yl)-piperidin-4-yl]-methanol hydrochloride (48) (560 mg, 1.67 mmol, yield 99%).

ESI-MS (M+1): 299 calc. for C$_{17}$H$_{22}$N$_4$O 298.

Preparation 16

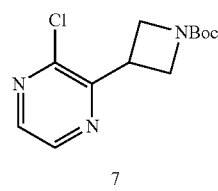

7

HCl/MeOH →

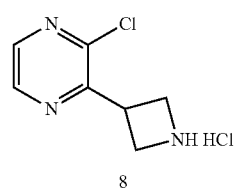 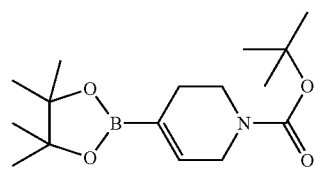

8

49

Pd(dppf)Cl$_2$, K$_3$PO$_4$
Dioxane/water →

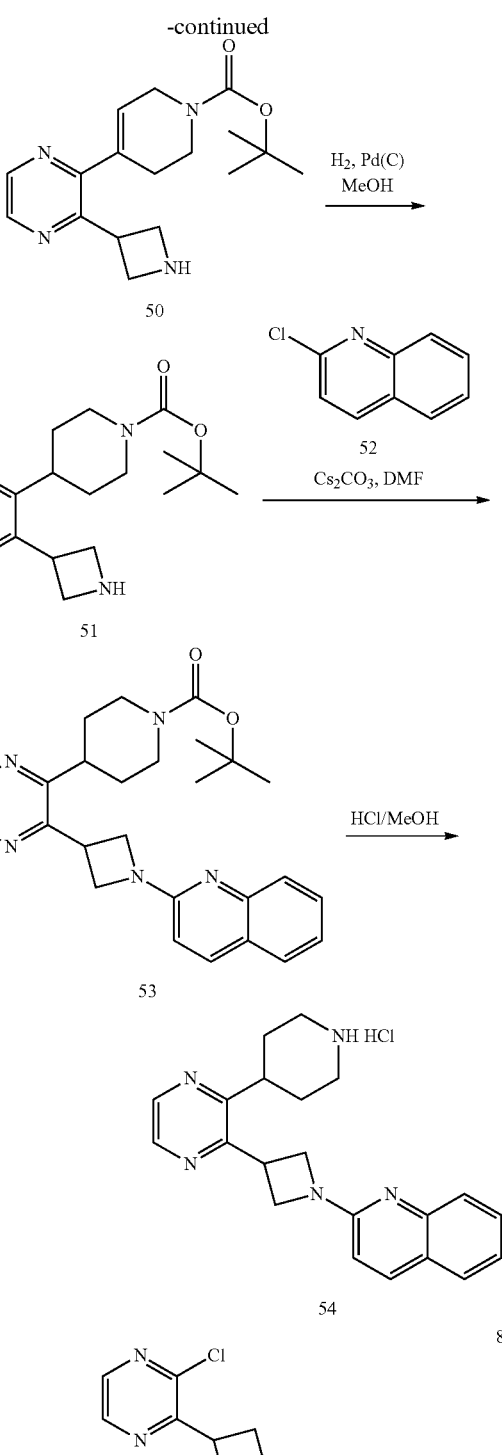

Step 1. 2-Azetidin-3-Yl-3-Chloro-Pyrazine Hydrochloride (8)

A solution of compound (7) (540 mg, 2.0 mmol) in 2N HCl/MeOH (20 mL) was stirred at RT for 30 min according to Preparation 2. The reaction mixture was concentrated to give compound (8) (440 mg, 1.99 mmol, yield 99.7%).

ESI-MS (M+1): 170 calc. for C$_7$H$_8$ClN$_3$ 169.

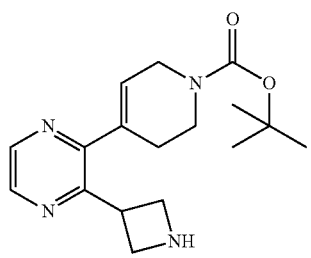

50

Step 2. 4-(3-Azetidin-3-Yl-Pyrazin-2-Yl)-3,6-Dihydro-2H-Pyridine-1-Carboxylic Acid Tert-Butyl Ester (50)

To a solution of (8) (442 mg, 2.0 mmol), 4-phenylboronic acid-3,6-dihydro-2H-pyridine-1-carboxylic acid tert-butyl ester (49) (679.8 mg, 2.2 mmol), $K_3PO_4$ (818 mg, 4.0 mmol) in dioxane (20 mL) and water (4 mL) was added Pd(dppf)$Cl_2$ (73.2 mg, 0.1 mmol) then the reaction mixture was stirred at 90° C. under nitrogen atmosphere overnight. The reaction mixture was filtered through CELITE® and washed with EtOAc (50 mL). The filtrate was concentrated and the crude product was purified by silica gel column to give (50) (540 mg, 1.7 mmol, yield 85%).

ESI-MS (M+1): 317 calc. for $C_{17}H_{24}N_4O_2$ 316.

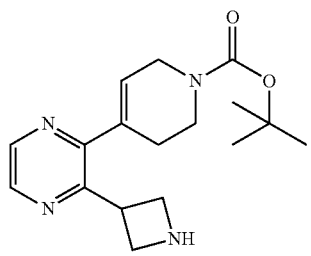

51

Step 3. 4-(3-Azetidin-3-Yl-Pyrazin-2-Yl)-Piperidine-1-Carboxylic Acid Tert-Butyl Ester (51)

To a solution of 4-(3-azetidin-3-yl-pyrazin-2-yl)-3,6-dihydro-2H-pyridine-1-carboxylic acid tert-butyl ester (50) (540 mg, 1.7 mmol) in MeOH was added Pd/C (10%, 0.5 g) under nitrogen. The reaction was stirred under hydrogen (30 psi) at RT for 6 h. Filtered to remove Pd/C and concentrated to dryness to give 4-(3-azetidin-3-yl-pyrazin-2-yl)-piperidine-1-carboxylic acid tert-butyl ester (51) (502 mg, 1.58 mmol yield 92.9%).

ESI-MS (M+1): 319 calc. for $C_{17}H_{26}N_4O_2$ 318.

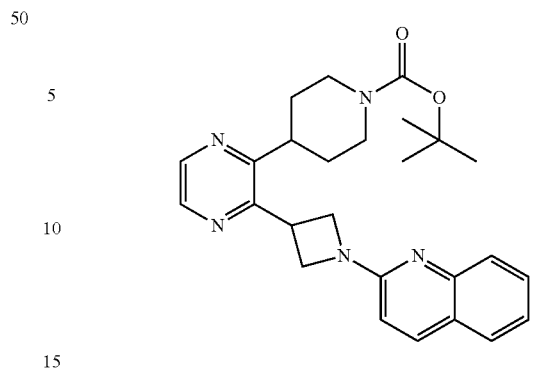

53

Step 4. 4-[3-(1-Quinolin-2-Yl-Azetidin-3-Yl)-Pyrazin-2-Yl]-Piperidine-1-Carboxylic Acid Tert-Butyl Ester (53)

To a solution of (51) (318 mg, 1 mmol) and 2-chloroquinoline (52) (163 mg, 1 mmol) in DMF was added $Cs_2CO_3$ (650 mg, 2 mmol). The reaction mixture was stirred at 100° C. overnight. The reaction mixture was diluted with water, extracted with EtOAc (3×20 mL). The combined organic extracts were washed with water (20 mL) and brine (20 mL), dried over $Na_2SO_4$ and filtered. The filtrate was evaporated in vacuo and the residue was purified by flash column chromatography on silica gel to give (53) (346 mg, 0.78 mmol, yield 77.8%).

ESI-MS (M+1): 446 calc. for $C_{26}H_{31}N_5O_2$ 445.

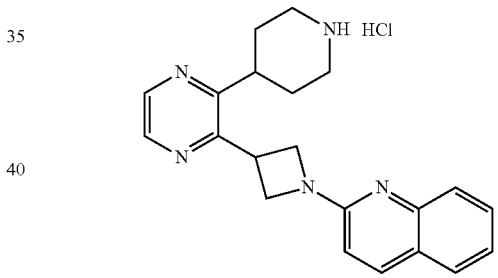

54

Step 5. 2-[3-(3-Piperidin-4-Yl-Pyrazin-2-Yl)-Azetidin-1-Yl]-Quinoline Hydrochloride (54)

A solution of 4-[3-(1-quinolin-2-yl-azetidin-3-yl)-pyrazin-2-yl]-piperidine-1-carboxylic acid tert-butyl ester (53) (346 mg, 0.78 mmol) in 4N HCl/MeOH (20 mL) was stirred at RT for 30 min. The reaction mixture was concentrated to give the product (54) (294 mg, 0.77 mmol, yield 98.9%).

ESI-MS (M+1): 346 calc. for $C_{21}H_{23}N_5$ 345.

Preparation 17

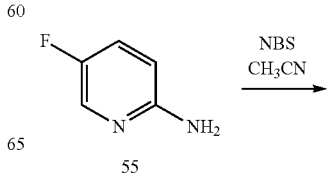

55

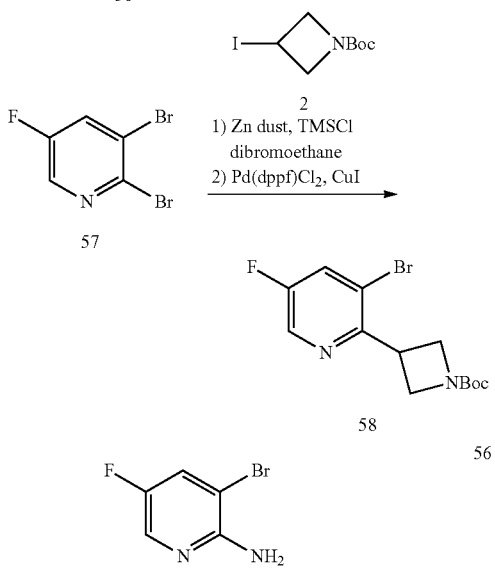

Step 1. 3-Bromo-5-Fluoro-Pyridin-2-Ylamine (56)

NBS (10 g, 56.2 mmol) was added slowly to a solution of 5-fluoro-pyridin-2-ylamine (55) (12.4 g, 56.2 mmol) in MeCN (200 mL). The reaction mixture was stirred at RT overnight. After completion, the solution was filtered and the filtrate was concentrated to obtain a residue, which was purified by silica gel chromatography (10% to 20% EtOAc in petroleum ether) to give 3-bromo-5-fluoro-pyridin-2-ylamine (56) (5.2 g, 27.2 mmol, 31% yield) as a yellow solid.

ESI-MS (M+1): 191 calc. for $C_5H_4BrFN_2$ 190.

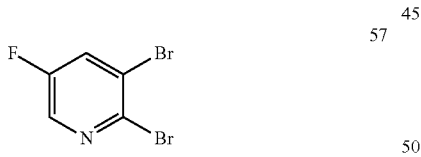

Step 2. 2,3-Dibromo-5-Fluoro-Pyridine (57)

At 60° C., 3-bromo-5-fluoro-pyridin-2-ylamine (56) (1.91 g, 0.01 mol) was dissolved in 48% hydrobromic acid (30 mL). After cooling to −5° C., bromine (3.24 g, 0.02 mol) was added dropwise over 5 min. A solution of sodium nitrite (1.01 g, 0.02 mol) in water (3 mL) was then added at a rate to keep the temperature of the reaction mixture between −5° C. and 0° C. When finished, the temperature was allowed to reach 25° C. The bromine was reduced with an excess of solid sodium sulfite, and the reaction mixture was extracted with EtOAc (3×50 mL). The combined organic extracts were washed with water (30 mL), brine (30 mL), dried over $Na_2SO_4$ and filtered. The filtrate was evaporated in vacuo and the residue was purified by flash column chromatography on silica gel (10% to 20% EtOAc in petroleum ether) to give 2,3-dibromo-5-fluoro-pyridine (57) (1.27 g, 5.0 mmol, 50% yield) as a yellow solid.

ESI-MS (M+1): 254 calc. for $C_5H_2Br_2FN$ 253.

Step 3. 3-(3-Bromo-5-Fluoro-Pyridin-2-Yl)-Azetidine-1-Carboxylic Acid Tert-Butyl Ester (58)

A 100 mL 3-neck round bottom flask fitted with a magnetic stirrer and flushed with nitrogen was charged with zinc dust (813 mg, preactivated according to the above Preparation 1, 12.7 mmol) and DMA (10 mL, anhydrous). 1,2-dibromoethane (236 mg, 1.27 mmol) was added slowly, followed by TMSCl (137 mg, 1.27 mmol). The reaction was stirred for 15 min at RT. A solution of N-Boc-3-iodoazetidine (2) (2.7 g, 9.5 mmol) in DMA (10 mL, anhydrous) was added dropwise. The suspension was stirred for 1 h at RT.

A 100 mL 3-neck round bottom flask fitted with a mechanical stirrer was charged with 2,3-dibromo-pyridine (57) (1.62 g, 6.4 mmol), Pd(dppf)Cl$_2$ (446 mg, 0.64 mmol, 0.1 eq), cuprous iodide (121 mg, 0.64 mmol), and DMA (20 mL, anhydrous). The dark solution was degassed for 15 min. The clear zinc reagent solution above the residual solid zinc was transferred to the above 100 mL flask by cannulation. The dark solution was degassed and heated to 80° C. for 16 h. The reaction was diluted with brine and extracted with EtOAc (3×100 mL). The combined organics were washed with water (2×100 mL) and brine (100 mL), followed by drying over sodium sulfate. The solution was concentrated and the residue was purified by flash column chromatography (PE:EtOAc=2:1) provided the title compound (58) (860 mg, 2.6 mmol, 40% yield) as a light yellow solid.

ESI-MS (M+1): 331 calc. for $C_{13}H_{16}BrFN_2O_2$ 330.

Preparation 18

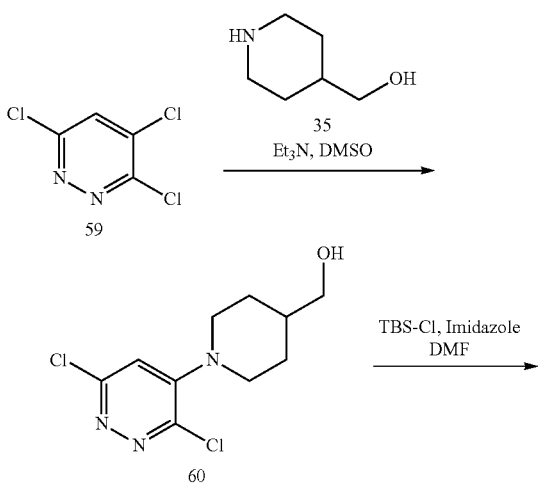

-continued

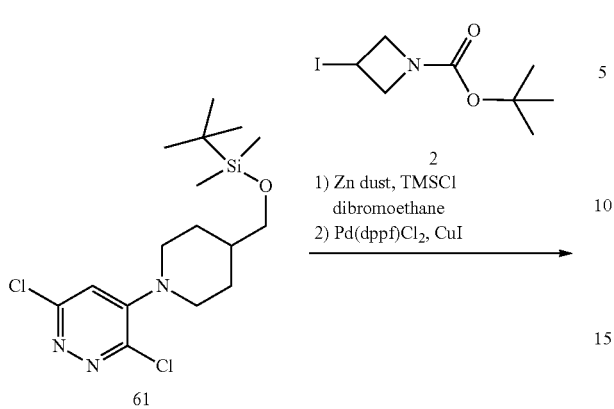

61

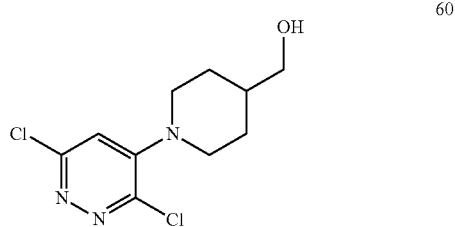

2

1) Zn dust, TMSCl
dibromoethane
2) Pd(dppf)Cl₂, CuI

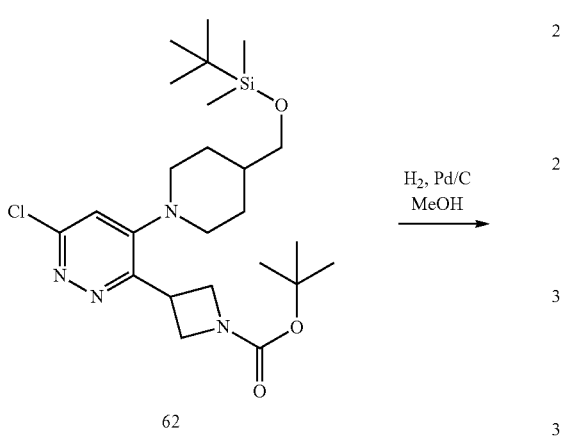

62

H₂, Pd/C
MeOH

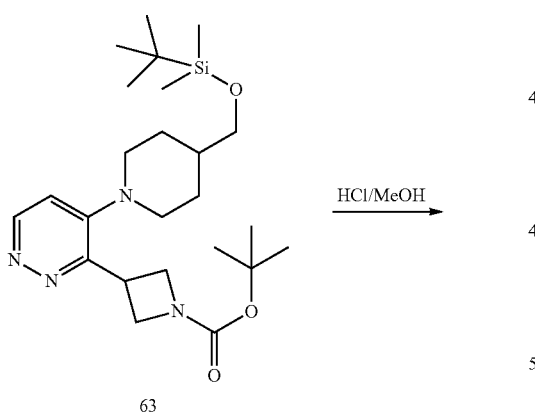

63

HCl/MeOH

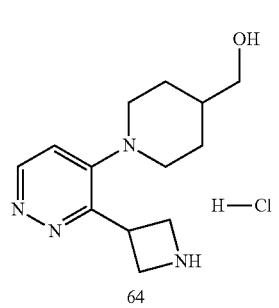

64

-continued

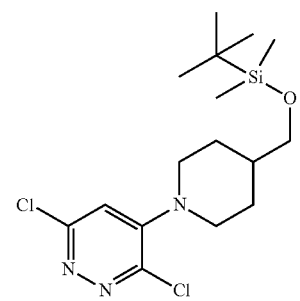

60

Step 1. [1-(3,6-Dichloro-Pyridazin-4-Yl)-Piperidin-4-Yl]-Methanol (60)

To a solution of 3,4,6-trichloro-pyridazine (59) (364 mg, 2 mmol) and piperidin-4-yl-methanol (35) (253 mg, 2.2 mmol) in DMSO (5 mL) was added Et₃N (404 mg, 4 mmol). The reaction mixture was stirred at 100° C. overnight. The reaction mixture was diluted with water, extracted with EtOAc (30 mL×3). The combined organic extracts were washed with water (30 mL) and brine (30 mL), dried over Na₂SO₄ and filtered. The filtrate was evaporated in vacuo and the residue was purified by flash column chromatography on silica gel to give [1-(3,6-dichloro-pyridazin-4-yl)-piperidin-4-yl]-methanol (60) (292.3 mg, 1.12 mmol, yield 75.99%).

ESI-MS (M+1): 262 calc. for $C_{10}H_{13}Cl_2N_3O$ 261.

Step 2. 4-[4-(Tert-Butyl-Dimethyl-Silanyloxymethyl)-Piperidin-1-Yl]-3,6-Dichloro-Pyridazine (61)

[1-(3,6-dichloro-pyridazin-4-yl)-piperidin-4-yl]-methanol (60) (1.83 g, 7 mol) upon treatment with TBSCl (2.1 g, 14 mmol) and imidazole (2.38 g, 35 mmol) in DMF (15 mL) stirred at RT for 3 h, The reaction mixture was diluted with water, extracted with EtOAc (40 mL×3). The combined organic extracts were washed with water (20 mL) and brine (20 mL), dried over Na₂SO₄ and filtered. The filtrate was evaporated in vacuo and the residue was purified by flash column chromatography on silica gel to give 4-[4-(tert-butyl-dimethyl-silanyloxymethyl)-piperidin-1-yl]-3,6-dichloro-pyridazine (61) (2.55 g, 6.8 mmol, 99% yield) ESI-MS (M+1): 376 calc. for $C_{16}H_{27}Cl_2N_3OSi$ 375.

62

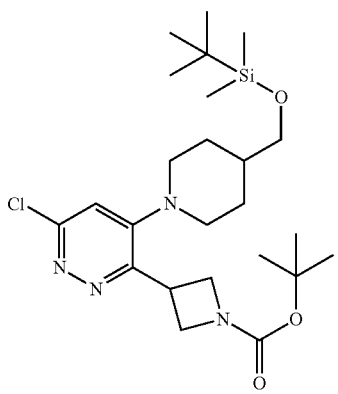

Step 3. 3-{4-[4-(Tert-Butyl-Dimethyl-Silanyloxymethyl)-Piperidin-1-Yl]-6-Chloro-Pyridazin-3-Yl}-Azetidine-1-Carboxylic Acid Tert-Butyl Ester (62)

A 100 mL 3-neck round bottom flask fitted with a magnetic stirrer and flushed with nitrogen was charged with zinc dust (813 mg, preactivated according to the above Preparation 1, 12.7 mmol) and DMA (10 mL, anhydrous). 1,2-dibromoethane (236 mg, 1.27 mmol) was added slowly, followed by TMSCl (137 mg, 1.27 mmol). The reaction was stirred for 15 min at RT. A solution of N-Boc-3-iodoazetidine (2) (2.7 g, 9.5 mmol) in DMA (10 mL, anhydrous) was added dropwise. The suspension was stirred for 1 h at RT.

A 100 mL 3-neck round bottom flask fitted with a mechanical stirrer was charged with 4-[4-(tert-butyl-dimethyl-silanyloxymethyl)-piperidin-1-yl]-3,6-dichloro-pyridazine (61) (2.4 g, 6.4 mmol), Pd(dppf)Cl$_2$ (446 mg, 0.64 mmol), cuprous iodide (121 mg, 0.64 mmol), and DMA (20 mL, anhydrous). The dark solution was degassed for 15 min. The clear zinc reagent solution above the residual solid zinc was transferred to the above 100 mL flask by cannulation. The dark solution was degassed and heated to 80° C. for 16 h. The reaction was diluted with brine and extracted with EtOAc (3×100 mL). The combined organics were washed with water (2×100 mL) and brine (100 mL), followed by drying over sodium sulfate. The solution was concentrated and the residue was purified by flash column chromatography (PE:EAOAc=2:1) provides the title compound (62) (1.25 g, 2.5 mmol, 39% yield) as a light yellow solid.

ESI-MS (M+1): 497 calc. for C$_{24}$H$_{41}$ClN$_4$O$_3$Si 496.

63

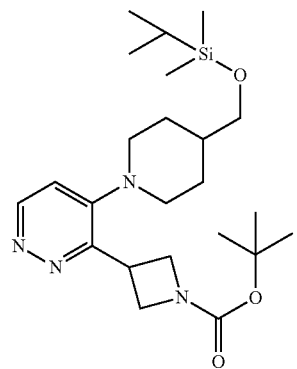

Step 4. 3-{4-[4-(Tert-Butyl-Dimethyl-Silanyloxymethyl)-Piperidin-1-Yl]-Pyridazin-3-Yl}-Azetidine-1-Carboxylic Acid Tert-Butyl Ester (63)

To a solution of 3-{4-[4-(tert-butyl-dimethyl-silanyloxymethyl)-piperidin-1-yl]-6-chloro-pyridazin-3-yl}-azetidine-1-carboxylic acid tert-butyl ester (62) (843 mg, 1.7 mmol) in MeOH was added Pd/C (10%, 0.5 g) under nitrogen. The reaction was stirred under hydrogen at RT for 6 h, filtered to remove Pd/C and concentrated to dryness to give 3-{4-[4-(tert-butyl-dimethyl-silanyloxymethyl)-piperidin-1-yl]-pyridazin-3-yl}-azetidine-1-carboxylic acid tert-butyl ester (63) (730 mg, 1.58 mmol yield 92.9%).

ESI-MS (M+1): 463 calc. for C$_{24}$H$_{42}$N$_4$O$_3$Si 462.

64

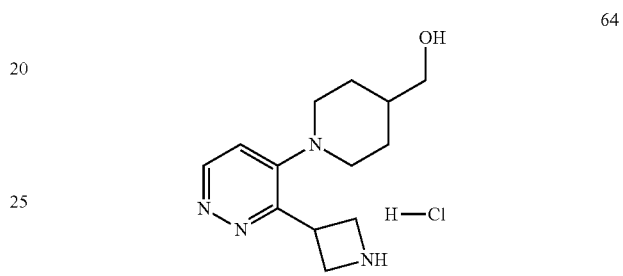

Step 5. [1-(3-Azetidin-3-Yl-Pyridazin-4-Yl)-Piperidin-4-Yl]-Methanol Hydrochloride (64)

A mixture of 3-{4-[4-(tert-butyl-dimethyl-silanyloxymethyl)-piperidin-1-yl]-pyridazin-3-yl}-azetidine-1-carboxylic acid tert-butyl ester (63) (730 mg, 1.58 mmol) in 4 M HCl/MeOH solution (20 mL) was stirred at RT for 30 min. Then the solvent was evaporated at 40° C. to give [1-(3-azetidin-3-yl-pyridazin-4-yl)-piperidin-4-yl]-methanol hydrochloride (64) (387 mg, 1.56 mmol, 98% yield) as a yellow solid.

ESI-MS (M+1): 249 calc. for C$_{13}$H$_{20}$N$_4$O 248.

Preparation 19

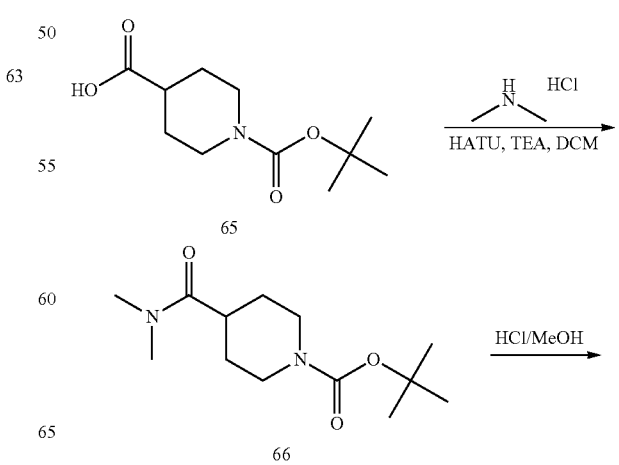

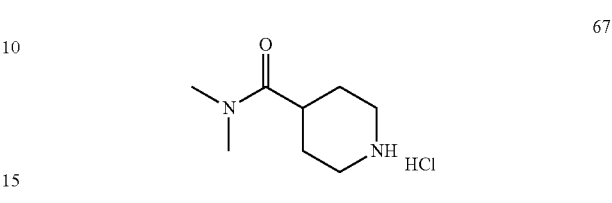

Step 1. 4-Dimethylcarbamoyl-Piperidine-1-Carboxylic Acid Tert-Butyl Ester (66)

To a mixture of piperidine-1,4-dicarboxylic acid mono-tert-butyl ester (65) (229 mg, 1 mmol, AalenChem) in DCM (5 mL) was added TEA (202 mg, 2 mmol) and HATU (414 mg, 1.2 mmol). The reaction mixture was stirred for 5 min and dimethylamine hydrochloride (81 mg, 1 mmol) was added. The reaction mixture was stirred at RT overnight. The mixture was diluted with water (10 mL), and extracted with EtOAc (2×20 mL). The combined organic extracts were washed with water (5 mL) and brine (5 mL), dried over Na$_2$SO$_4$, and filtered. The filtrate was evaporated in vacuo and the residue was purified by column chromatography to give 4-dimethylcarbamoyl-piperidine-1-carboxylic acid tert-butyl ester (66) (220 mg, 0.85 mmol, 85% yield) as a light yellow oil.

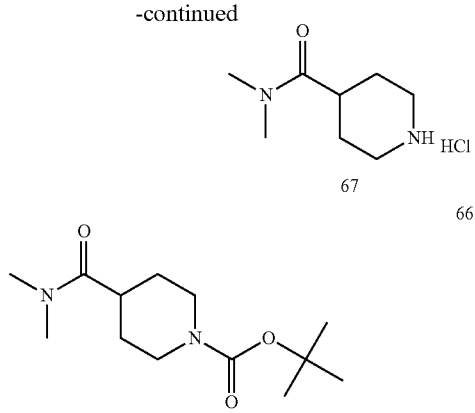

Step 2. Piperidine-4-Carboxylic Acid Dimethylamide Hydrochloride (67)

A solution of 4-dimethylcarbamoyl-piperidine-1-carboxylic acid tert-butyl ester (66) (220 mg, 0.85 mmol) in 4N HCl/MeOH (20 mL) was stirred at RT for 30 min. The reaction mixture was concentrated to give the product piperidine-4-carboxylic acid dimethylamide hydrochloride (67) (163 mg, 0.85 mmol, yield 99.9%).

ELSD-MS (M+1): 157 calc. for C$_8$H$_{16}$N$_2$O 156.

The following Table 5 lists compounds of Preparation P19.1 to P19.4, which were made analogous to Preparation 19 by using the appropriate materials.

TABLE 5

| PREPARATION P19.1 TO P19.4 | | | |
|---|---|---|---|
| Ex. # | Chemical Structure | Chemical Name | ESI-MS (M + 1) |
| P19.1 | | 4-Dimethylcarbamoyl-piperidine-1-carboxylic acid tert-butyl ester | 257 |
| P19.2 | | 4-methylcarbamoyl-piperidine-1-carboxylic acid tert-butyl ester | 243 |
| P19.3 | | Piperidine-4-carboxylic acid dimethylamide hydrochloride | 157 |

TABLE 5-continued

PREPARATION P19.1 TO P19.4

| Ex. # | Chemical Structure | Chemical Name | ESI-MS (M + 1) |
|---|---|---|---|
| P19.4 |  | Piperidine-4-carboxylic acid methylamide hydrochloride | 143 |

Preparation 20

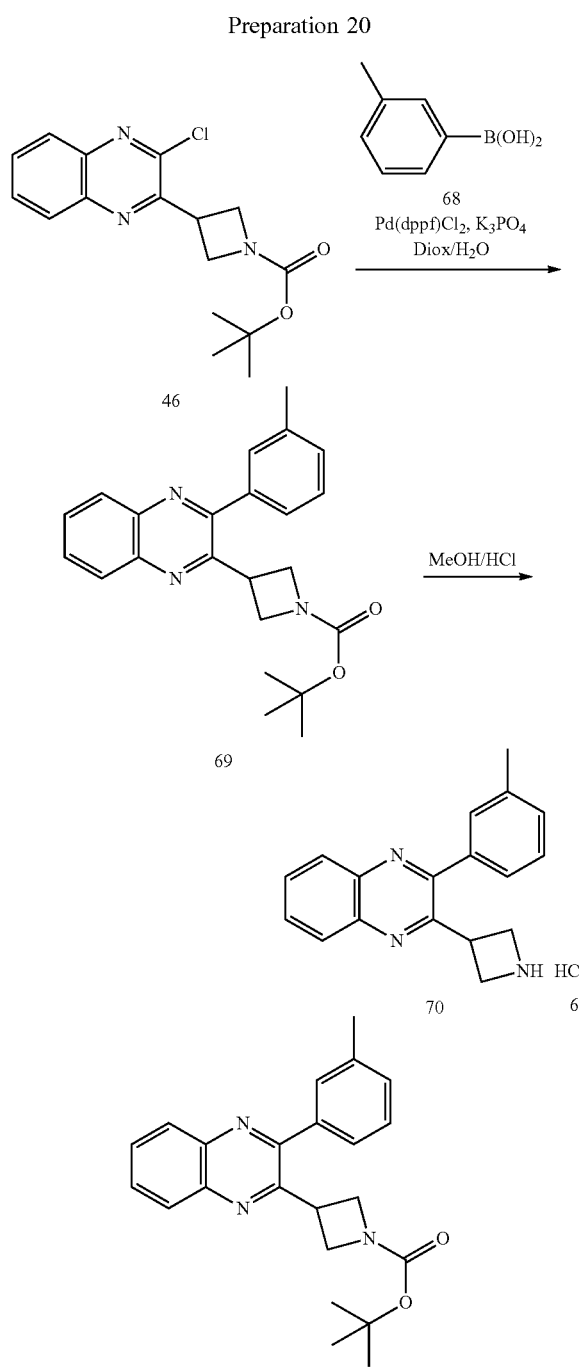

Step 1. 3-(3-M-Tolyl-Quinoxalin-2-Yl)-Azetidine-1-Carboxylic Acid Tert-Butyl Ester To a solution of 3-(3-chloro-quinoxalin-2-yl)-azetidine-1-carboxylic acid tert-butyl ester (46) (639 mg, 2.0 mmol, as prepared in the above Preparation 14), 3-methyl-phenylboronic acid (68) (299.2 mg, 2.2 mmol), $K_3PO_4$ (818 mg, 4.0 mmol) in dioxane (20 mL) and water (4 mL) was added Pd(dppf)Cl$_2$ (73.2 mg, 0.1 mmol) then the reaction mixture was stirred at 90° C. under nitrogen atmosphere overnight. The reaction mixture was filtered through CELITE® and washed with EtOAc (50 mL). The filtrate was concentrated and the crude product was purified by silica gel column to give 3-(3-m-tolyl-quinoxalin-2-yl)-azetidine-1-carboxylic acid tert-butyl ester (69) (637 mg, 1.7 mmol, yield 85%).

ESI-MS (M+1): 376 calc. for $C_{23}H_{25}N_3O_2$ 375.

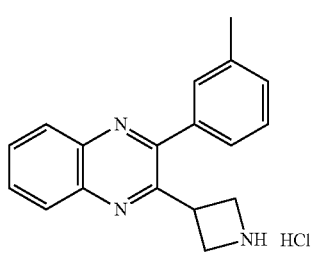

70

Step 2. 2-Azetidin-3-Yl-3-M-Tolyl-Quinoxaline Hydrochloride (70)

A solution of 3-(3-m-tolyl-quinoxalin-2-yl)-azetidine-1-carboxylic acid tert-butyl ester (69) (637 mg, 1.7 mmol) in 4N HCl/MeOH (25 mL) was stirred at RT for 30 min. The reaction mixture was concentrated to give 2-azetidin-3-yl-3-m-tolyl-quinoxaline hydrochloride (70) (523 mg, 1.68 mmol, yield 98.8%).

ESI-MS (M+1): 276 calc. for $C_{18}H_{17}N_3$ 275.

The following Table 6 lists compounds of Preparation P20.1 to P20.10, which were made analogous to Preparation 20 by using the appropriate materials.

TABLE 6

PREPARATION P20.1 TO P20.10

| Ex. # | Chemical Structure | Chemical Name | ESI-MS (M + 1) |
|---|---|---|---|
| P20.1 | 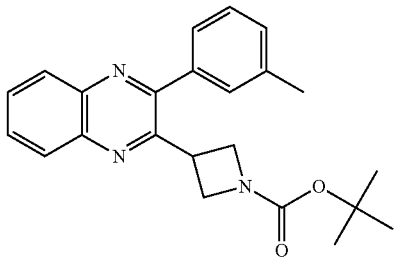 [SMILES: Cc1cccc(-c2nc3ccccc3nc2C2CN(C(=O)OC(C)(C)C)C2)c1] | 3-(3-m-Tolyl-quinoxalin-2-yl)-azetidine-1-carboxylic acid tert-butyl ester | 376 |
| P20.2 | 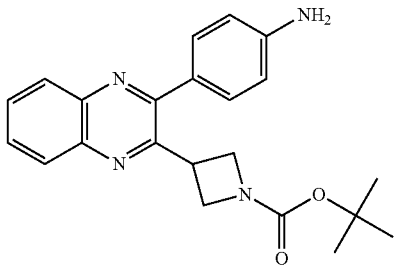 [SMILES: CC(C)(C)OC(=O)N1CC(c2nc3ccccc3nc2-c2ccc(N)cc2)C1] | tert-butyl 3-(3-(4-aminophenyl)quinoxalin-2-yl)azetidine-1-carboxylate | 376 |
| P20.3 | 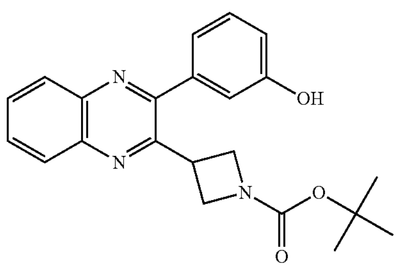 [SMILES: CC(C)(C)OC(=O)N1CC(c2nc3ccccc3nc2-c2cccc(O)c2)C1] | tert-butyl 3-(3-(3-hydroxyphenyl)quinoxalin-2-yl)azetidine-1-carboxylate | 378 |
| P20.4 | 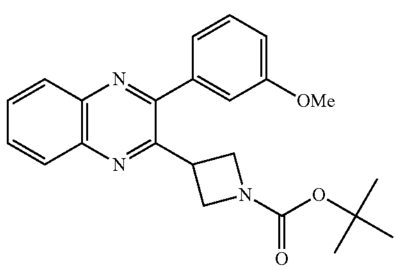 [SMILES: COc1cccc(-c2nc3ccccc3nc2C2CN(C(=O)OC(C)(C)C)C2)c1] | tert-butyl 3-(3-(3-methoxyphenyl)quinoxalin-2-yl)azetidine-1-carboxylate | 392 |
| P20.5 | 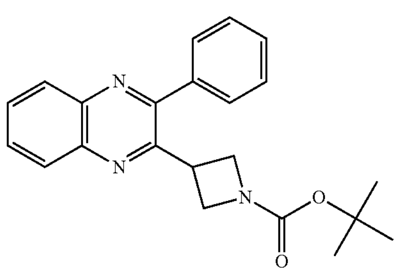 [SMILES: CC(C)(C)OC(=O)N1CC(c2nc3ccccc3nc2-c2ccccc2)C1] | tert-butyl 3-(3-phenylquinoxalin-2-yl)azetidine-1-carboxylate | 362 |
| P20.6 | 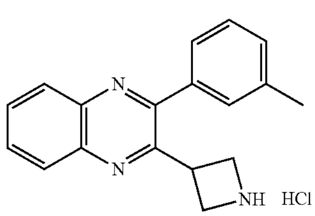 [SMILES: Cc1cccc(-c2nc3ccccc3nc2C2CNC2)c1 ; Cl] | 2-Azetidin-3-yl-3-m-tolyl-quinoxaline hydrochloride | 276 |

TABLE 6-continued
PREPARATION P20.1 TO P20.10
| Ex. # | Chemical Structure | Chemical Name | ESI-MS (M + 1) |
|---|---|---|---|
| P20.7 | 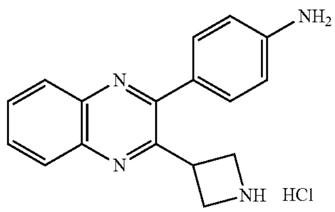 [SMILES: Nc1ccc(-c2nc3ccccc3nc2C2CNC2)cc1 ; Cl] | 4-(3-(azetidin-3-yl)quinoxalin-2-yl)aniline hydrochloride | 277 |
| P20.8 | 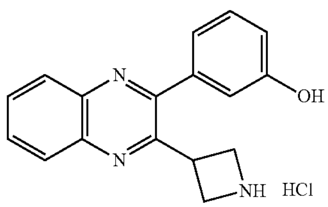 [SMILES: Oc1cccc(-c2nc3ccccc3nc2C2CNC2)c1 ; Cl] | 3-(3-(azetidin-3-yl)quinoxalin-2-yl)phenol hydrochloride | 278 |
| P20.9 | 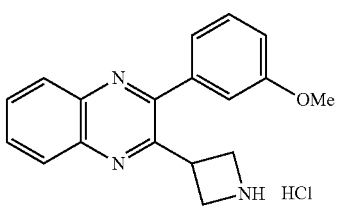 [SMILES: COc1cccc(-c2nc3ccccc3nc2C2CNC2)c1 ; Cl] | 2-(azetidin-3-yl)-3-(3-methoxyphenyl)quinoxaline hydrochloride | 292 |
| P20.10 | 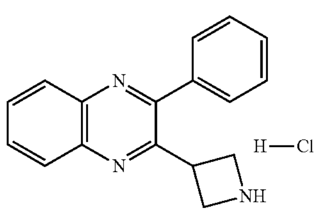 | 2-(azetidin-3-yl)-3-phenylquinoxaline hydrochloride | 262 |
Preparation 21
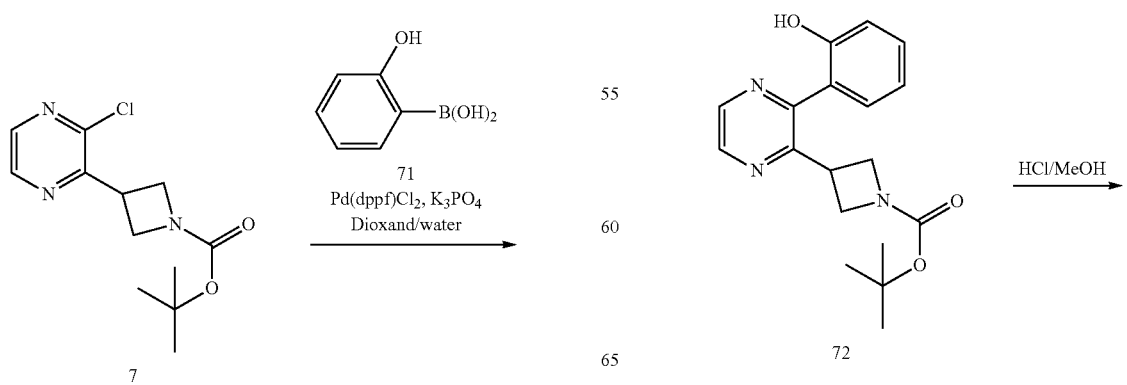

-continued

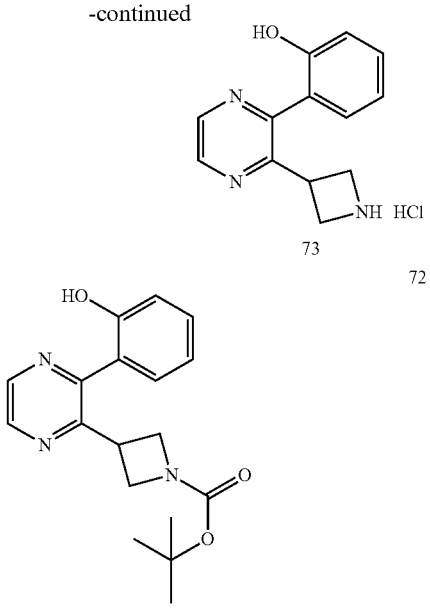

Step 1. 3-[3-(2-Hydroxy-Phenyl)-Pyrazin-2-Yl]-Azetidine-1-Carboxylic Acid Tert-Butyl Ester (72)

To a solution of 3-(3-chloro-pyrazin-2-yl)-azetidine-1-carboxylic acid tert-butyl ester (7) (540 mg, 2.0 mmol, see Preparation 2), 2-hydroxy-phenylboronic acid (71) (303.6 mg, 2.2 mmol), $K_3PO_4$ (818 mg, 4.0 mmol), in dioxane (20 mL) and water (4 mL) was added Pd(dppf)Cl$_2$ (73.2 mg, 0.1 mmol) then the reaction mixture was stirred at 90° C. under nitrogen atmosphere overnight. The reaction mixture was filtered through CELITE® and washed with EtOAc (50 mL). The filtrate was concentrated and the crude product was purified by silica gel column to give (72) (601.7 mg, 1.84 mmol, yield 91.85%).

ESI-MS (M+1): 328 calc. for $C_{18}H_{21}N_3O_3$ 327.

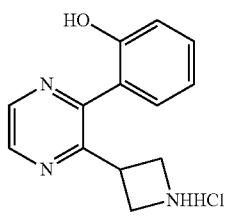

Step 2. 2-(3-Azetidin-3-Yl-Pyrazin-2-Yl)-Phenol Hydrochloride (73)

A solution of 3-[3-(2-hydroxy-phenyl)-pyrazin-2-yl]-azetidine-1-carboxylic acid tert-butyl ester (72) (325 mg, 1.0 mmol) in 4N HCl/MeOH (20 mL) was stirred at RT for 30 min. The reaction mixture was concentrated to give (74) (274.3 mg, 0.99 mmol, yield 99.24%).

ESI-MS (M+1): 228 calc. for $C_{13}H_{13}N_3O$ 227.

The following Table 7 lists compounds of Preparation P21.1 to P21.8, which were made analogous to Preparation 21 by using the appropriate materials.

TABLE 7

PREPARATION P21.1 TO P21.8

| Ex. # | Chemical Structure | Chemical Name | ESI-MS (M + 1) |
|---|---|---|---|
| P21.1 | 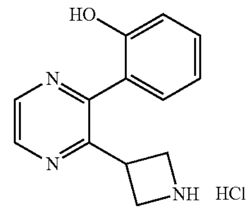 [SMILES: Oc1ccccc1-c1nccnc1C1CNC1 ; Cl] | 2-(3-(azetidin-3-yl)pyrazin-2-yl)phenol hydrochloride | 228 |
| P21.2 | 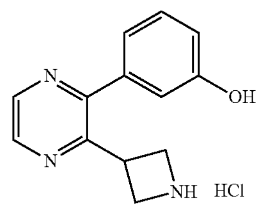 [SMILES: Oc1cccc(-c2nccnc2C2CNC2)c1 ; Cl] | 3-(3-(azetidin-3-yl)pyrazin-2-yl)phenol hydrochloride | 228 |
| P21.3 | 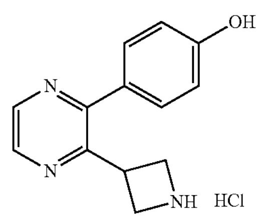 [SMILES: Oc1ccc(-c2nccnc2C2CNC2)cc1 ; Cl] | 4-(3-(azetidin-3-yl)pyrazin-2-yl)phenol hydrochloride | 228 |
| P21.4 | 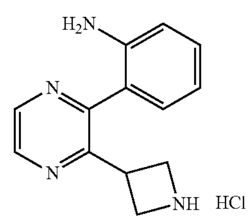 [SMILES: Nc1ccccc1-c1nccnc1C1CNC1 ; Cl] | 2-(3-(azetidin-3-yl)pyrazin-2-yl)aniline hydrochloride | 226 |
| P21.5 | 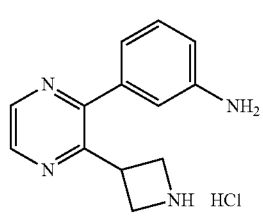 [SMILES: Nc1cccc(-c2nccnc2C2CNC2)c1 ; Cl] | 3-(3-(azetidin-3-yl)pyrazin-2-yl)aniline hydrochloride | 226 |
| P21.6 | 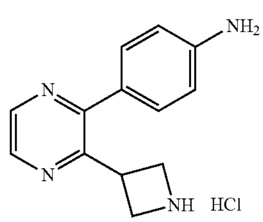 [SMILES: Nc1ccc(-c2nccnc2C2CNC2)cc1 ; Cl] | 4-(3-(azetidin-3-yl)pyrazin-2-yl)aniline hydrochloride | 226 |

TABLE 7-continued

PREPARATION P21.1 TO P21.8

| Ex. # | Chemical Structure | Chemical Name | ESI-MS (M + 1) |
|---|---|---|---|
| P21.7 | 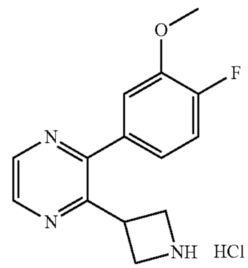 [SMILES: COc1cc(-c2nccnc2C2CNC2)ccc1F ; Cl] | 2-(azetidin-3-yl)-3-(4-fluoro-3-methoxyphenyl)pyrazine hydrochloride | 260 |
| P21.8 | 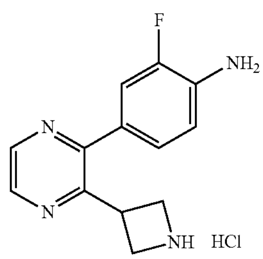 [SMILES: Nc1ccc(-c2nccnc2C2CNC2)cc1F ; Cl] | 4-(3-(azetidin-3-yl)pyrazin-2-yl)-2-fluoroaniline hydrochloride | 245 |

Preparation 22

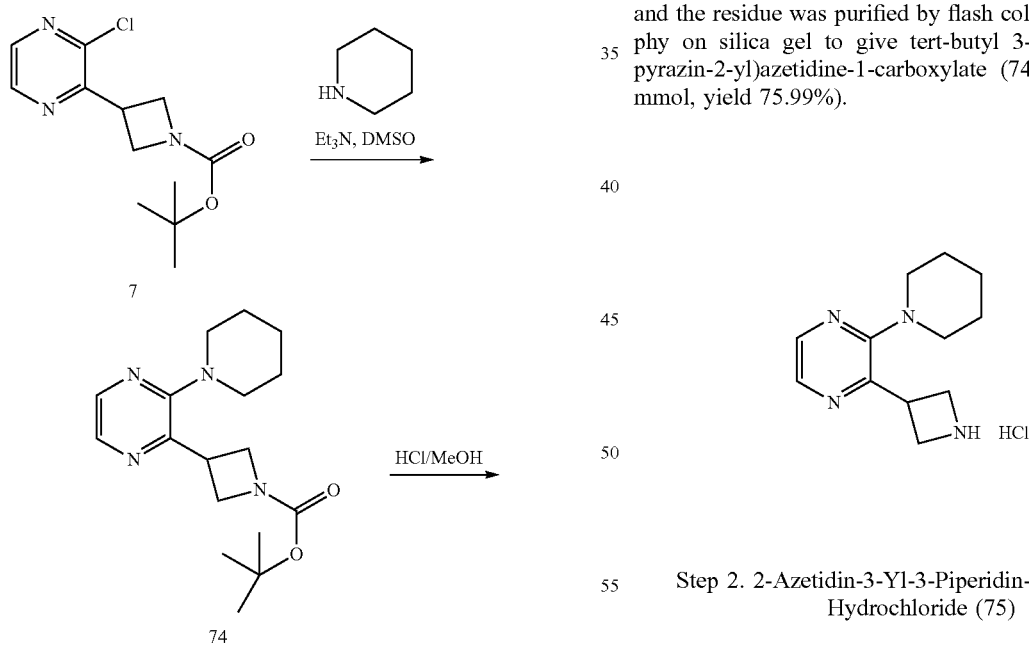

Step 1. Tert-Butyl 3-(3-(Piperidin-1-Yl)Pyrazin-2-Yl)Azetidine-1-Carboxylate (74)

To a solution of 3-(3-chloro-pyrazin-2-yl)-azetidine-1-carboxylic acid tert-butyl ester (7) (200 mg, 0.74 mmol, see Preparation 2) and piperidine (69.2 mg, 0.84 mmol) in DMSO (5 mL) was added Et$_3$N (149.5 mg, 1.48 mmol). The reaction mixture was stirred at 100° C. overnight. The reaction mixture was diluted with water, extracted with EtOAc (30 mL×3). The combined organic extracts were washed with water (30 mL) and brine (30 mL), dried over Na$_2$SO$_4$ and filtered. The filtrate was evaporated in vacuo and the residue was purified by flash column chromatography on silica gel to give tert-butyl 3-(3-(piperidin-1-yl)pyrazin-2-yl)azetidine-1-carboxylate (74). (194 mg, 0.56 mmol, yield 75.99%).

Step 2. 2-Azetidin-3-Yl-3-Piperidin-1-Yl-Pyrazine Hydrochloride (75)

A solution of 3-(3-piperidin-1-yl-pyrazin-2-yl)-azetidine-1-carboxylic acid tert-butyl ester (74) (191 mg, 0.6 mmol) in 4N HCl/MeOH (13 mL) was stirred at RT for 30 min. The reaction mixture was concentrated to give (75) (150 mg, 0.59 mmol, yield 99%). ESI-MS (M+1): 219 calc. for C$_{12}$H$_{18}$N$_4$218.

The following Table 8 lists compounds of Preparation P22.1 to P22.12, which were made analogous to Preparation 22 by using the appropriate materials.

TABLE 8

PREPARATION P22.1 TO P22.12

| Ex. # | Chemical Structure | Chemical Name | ESI-MS (M + 1) |
|---|---|---|---|
| P22.1 | 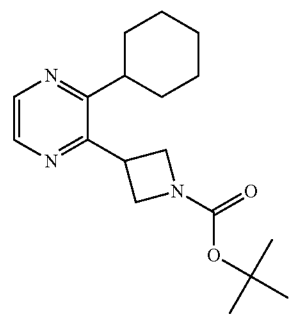 [SMILES: CC(C)(C)OC(=O)N1CC(c2nccnc2C2CCCCC2)C1] | tert-butyl 3-(3-(piperidin-1-yl)pyrazin-2-yl)azetidine-1-carboxylate | 319 |
| P22.2 | 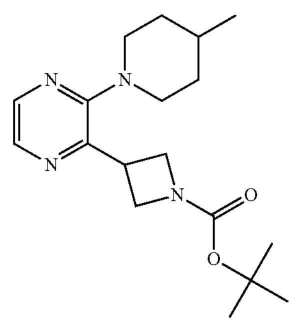 [SMILES: CC1CCN(c2nccnc2C2CN(C(=O)OC(C)(C)C)C2)CC1] | tert-butyl 3-(3-(4-methylpiperidin-1-yl)pyrazin-2-yl)azetidine-1-carboxylate | 333 |
| P22.3 | 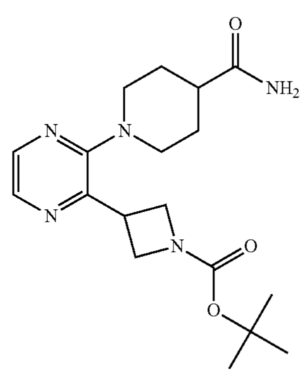 [SMILES: CC(C)(C)OC(=O)N1CC(c2nccnc2N2CCC(C(N)=O)CC2)C1] | tert-butyl 3-(3-(4-carbamoylpiperidin-1-yl)pyrazin-2-yl)azetidine-1-carboxylate | 362 |
| P22.4 | 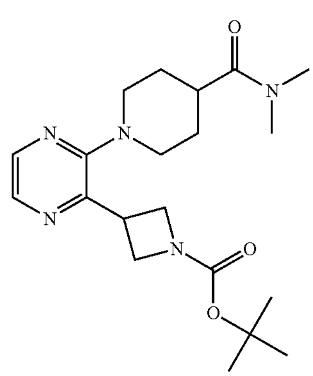 [SMILES: CN(C)C(=O)C1CCN(c2nccnc2C2CN(C(=O)OC(C)(C)C)C2)CC1] | tert-butyl 3-(3-(4-(dimethylcarbamoyl)piperidin-1-yl)pyrazin-2-yl)azetidine-1-carboxylate | 390 |

TABLE 8-continued

PREPARATION P22.1 TO P22.12

| Ex. # | Chemical Structure | Chemical Name | ESI-MS (M + 1) |
|---|---|---|---|
| P22.5 | 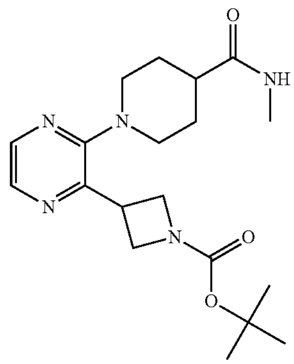 [SMILES: CNC(=O)C1CCN(c2nccnc2C2CN(C(=O)OC(C)(C)C)C2)CC1] | tert-butyl 3-(3-(4-(methylcarbamoyl)piperidin-1-yl)pyrazin-2-yl)azetidine-1-carboxylate | 376 |
| P22.6 | 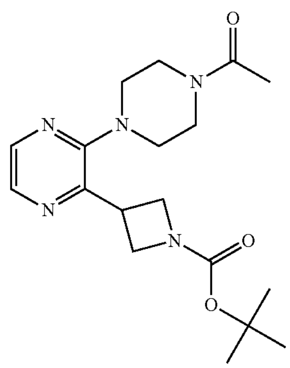 [SMILES: CC(=O)N1CCN(c2nccnc2C2CN(C(=O)OC(C)(C)C)C2)CC1] | tert-butyl 3-(3-(4-acetylpiperazin-1-yl)pyrazin-2-yl)azetidine-1-carboxylate | 362 |
| P22.7 | 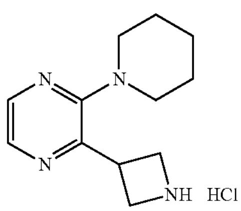 [SMILES: c1cnc(N2CCCCC2)c(C2CNC2)n1 ; Cl] | 2-(azetidin-3-yl)-3-(piperidin-1-yl)pyrazine hydrochloride | 219 |
| P22.8 | 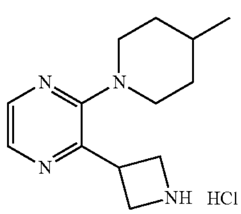 [SMILES: CC1CCN(c2nccnc2C2CNC2)CC1 ; Cl] | 2-(azetidin-3-yl)-3-(4-methylpiperidin-1-yl)pyrazine hydrochloride | 233 |
| P22.9 | 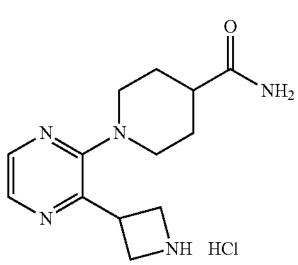 [SMILES: NC(=O)C1CCN(c2nccnc2C2CNC2)CC1 ; Cl] | 1-(3-(azetidin-3-yl)pyrazin-2-yl)piperidine-4-carboxamide hydrochloride | 262 |

TABLE 8-continued
PREPARATION P22.1 TO P22.12
| Ex. # | Chemical Structure | Chemical Name | ESI-MS (M + 1) |
|---|---|---|---|
| P22.10 | 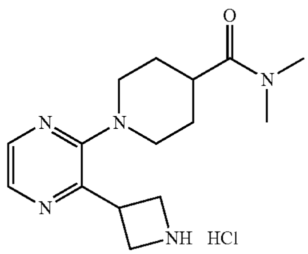 [SMILES: CN(C)C(=O)C1CCN(c2nccnc2C2CNC2)CC1 ; Cl] | 1-(3-(azetidin-3-yl)pyrazin-2-yl)-N,N-dimethylpiperidine-4-carboxamide hydrochloride | 290 |
| P22.11 | 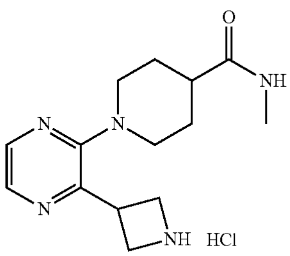 [SMILES: CNC(=O)C1CCN(c2nccnc2C2CNC2)CC1 ; Cl] | 1-(3-(azetidin-3-yl)pyrazin-2-yl)-N-methylpiperidine-4-carboxamide hydrochloride | 276 |
| P22.12 | 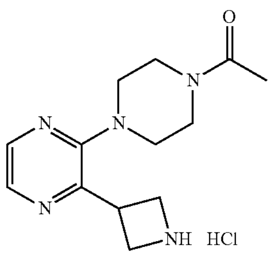 [SMILES: CC(=O)N1CCN(c2nccnc2C2CNC2)CC1 ; Cl] | 1-(4-(3-(azetidin-3-yl)pyrazin-2-yl)piperazin-1-yl)ethanone hydrochloride | 262 |
Preparation 23
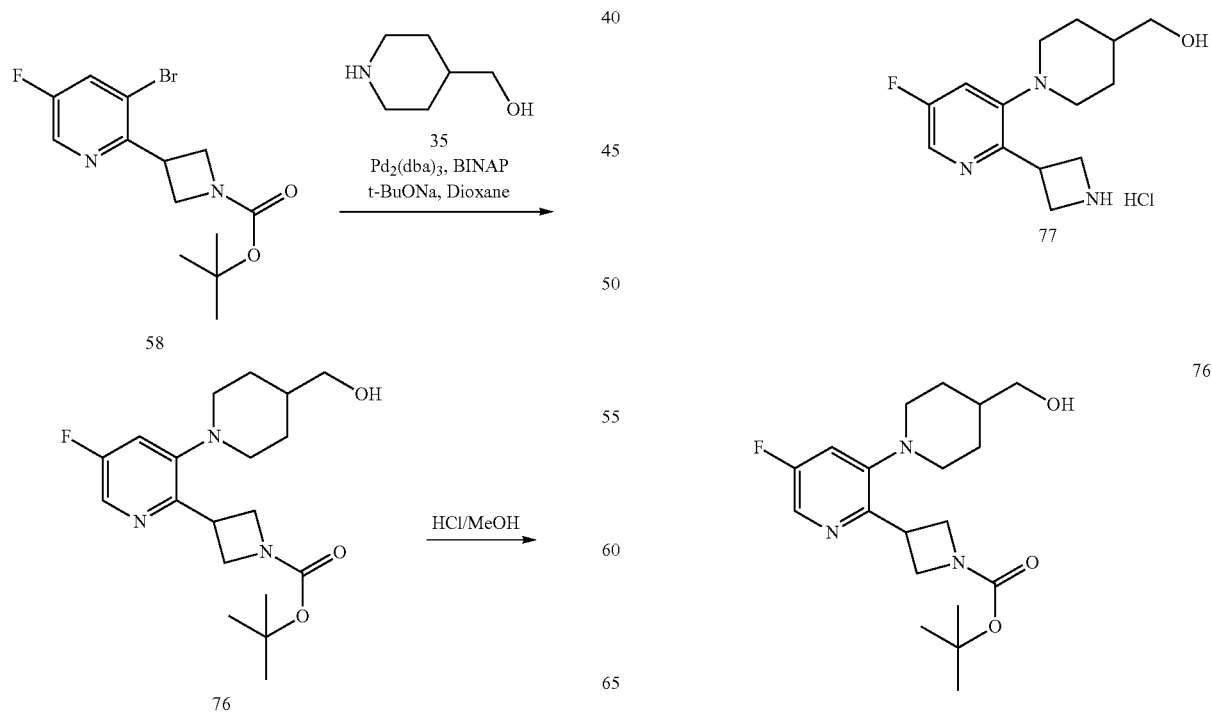

Step 1. 3-(5'-Fluoro-4-Hydroxymethyl-3,4,5,6-Tetrahydro-2H-[1,3']Bipyridinyl-2'-Yl)-Azetidine-1-Carboxylic Acid Tert-Butyl Ester (76)

To a solution of 3-(3-bromo-5-fluoro-pyridin-2-yl)-azetidine-1-carboxylic acid tert-butyl ester (58) (660 mg, 2 mmol, Preparation 17) and piperidin-4-yl-methanol (35) (230 mg, 2 mmol) in DMSO (20 mL) was added Et₃N (404 mg, 4 mmol). The reaction mixture was stirred at 100° C. overnight. The reaction mixture was diluted with water, extracted with EtOAc (50 mL×3). The combined organic extracts were washed with water (30 mL) and brine (30 mL), dried over Na₂SO₄ and filtered. The filtrate was evaporated in vacuo and the residue was purified by flash column chromatography (EtOAc:PE=3:1) on silica gel to give (76) (490 mg, 1.34 mmol, yield 67%). ESI-MS (M+1): 366 calc. for $C_{19}H_{28}FN_3O_3$ 365.

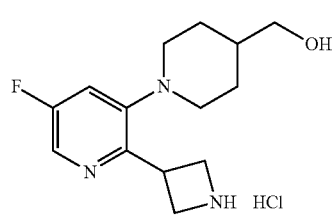

77

Step 2. (2'-Azetidin-3-Yl-5'-Fluoro-3,4,5,6-Tetrahydro-2H-[1,3']Bipyridinyl-4-Yl)-Methanol Hydrochloride (77)

A mixture of 3-(5'-fluoro-4-hydroxymethyl-3,4,5,6-tetrahydro-2H-[1,3']bipyridinyl-2'-yl)-azetidine-1-carboxylic acid tert-butyl ester (76) (490 mg, 1.34 mmol) in 4 M HCl/MeOH solution (10 mL) was stirred at RT for 30 min. Then the solvent was evaporated at 40° C. to give (77) (392 mg, 1.3 mmol, 98% yield) as a yellow solid. ESI-MS (M+1): 266 calc. for $C_{14}H_{20}FN_3O$ 265.

Preparation 24

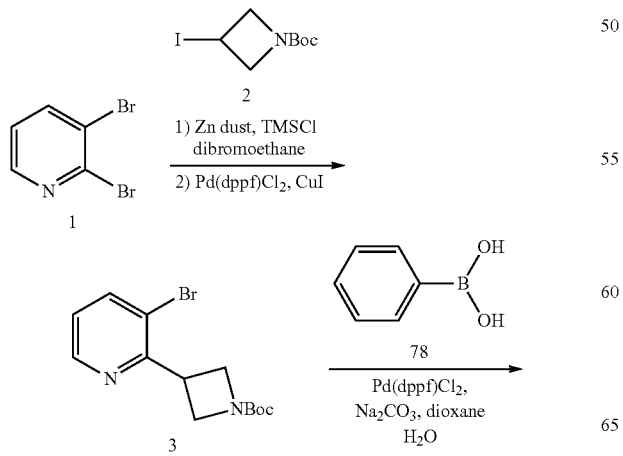

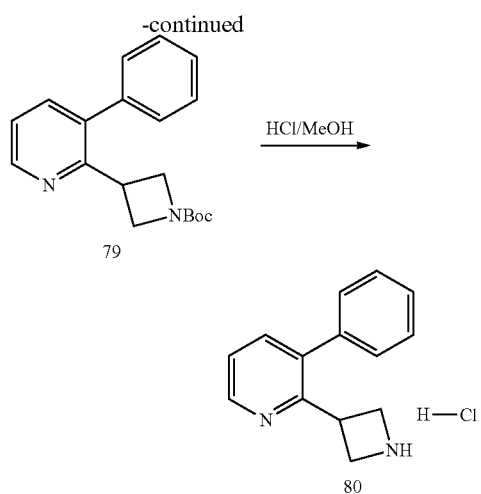

Step 1. 3-(3-Bromo-Pyridin-2-Yl)-Azetidine-1-Carboxylic Acid Tert-Butyl Ester (3)

A 100 mL 3-neck round bottom flask fitted with a magnetic stirrer and flushed with nitrogen was charged with zinc dust (813 mg, preactivated according to the above Preparation 1, 12.7 mmol, 2.0 eq.) and DMA (10 mL, anhydrous). 1,2-Dibromoethane (236 mg, 1.27 mmol, 0.2 eq) was added slowly, followed by TMSCl (137 mg, 1.27 mmol, 0.2 eq). The reaction was stirred for 15 min at RT. A solution of N-Boc-3-iodoazetidine (2) (2.7 g, 9.5 mmol, 1.5 eq) in DMA (10 mL, anhydrous) was added dropwise. The suspension was stirred for 1 h at RT.

A 100 mL 3-neck round bottom flask fitted with a mechanical stirrer was charged with 2,3-dibromo-pyridine (1) (1.5 g, 6.4 mmol, 1.0 eq), PdCl₂(dppf) (446 mg, 0.64 mmol, 0.1 eq), CuI (121 mg, 0.64 mmol, 0.1 eq), and DMA (20 mL, anhydrous). The dark solution was degassed for 15 min. The clear zinc reagent solution above the residual solid zinc was transferred to the above 100 mL flask by cannulation. The dark solution was degassed and heated to 80° C. for 16 h. The reaction was diluted with brine and extracted with EtOAc (3×100 mL). The combined organics were washed with water (2×100 mL) and brine (100 mL), followed by drying over sodium sulfate. The solution was concentrated and the residue was purified by flash column chromatography (PE:EtOAc=2:1) provides the title compound (3) (600 mg, 31% yield) as a light yellow solid.

ESI-MS (M+1): 313 calc. for $C_{13}H_{17}BrN_2O_2$ 312.

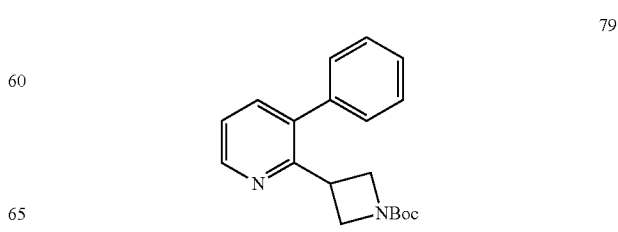

Step 2. 3-(3-Phenyl-Pyridin-2-Yl)-Azetidine-1-Carboxylic Acid Tert-Butyl Ester (79)

To a stirred solution of 3-(3-bromo-pyridin-2-yl)-azetidine-1-carboxylic acid tert-butyl ester (3) (150 mg, 0.48 mmol) in dioxane (10 mL) was added phenylboronic acid (78) (87 mg, 0.71 mmol), Na₂CO₃ (152 mg, 1.4 mmol) and H₂O (2 mL). The reaction mixture was degassed with N₂ and then PdCl₂(dppf) (35 mg, 0.05 mmol) was added. The reaction mixture was stirred at 80° C. for 12 h. The reaction mixture was left to reach RT and filtered through a pad of CELITE® and the filter cake was washed with CH₂Cl₂ (20 mL×3). The combined filtrates were evaporated in vacuo and the residue was purified by column chromatography ((EtOAc:Petrol ether=3:1) to give the desired compound (79) (130 mg, 87% yield). ESI-MS (M+1): 311 calc. for $C_{19}H_{22}N_2O_2$ 310.

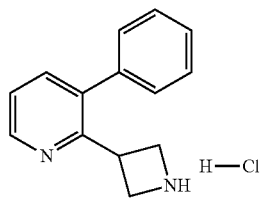

80

Step 3. 2-Azetidin-3-Yl-3-Phenyl-Pyridine Hydrochloride

A mixture of 3-(3-phenyl-pyridin-2-yl)-azetidine-1-carboxylic acid tert-butyl ester (79) (130 mg, 0.60 mmol) in HCl/MeOH solution (5 mL) was stirred at RT for 30 min. Then the solvent was evaporated at 40° C. to give 2-Azetidin-3-yl-3-phenyl-pyridine hydrochloride (80) (100 mg, 100% yield) as a yellow solid.

ESI-MS (M+1): 211 calc. for $C_{14}H_{14}N_2$ 210.

Preparation 25

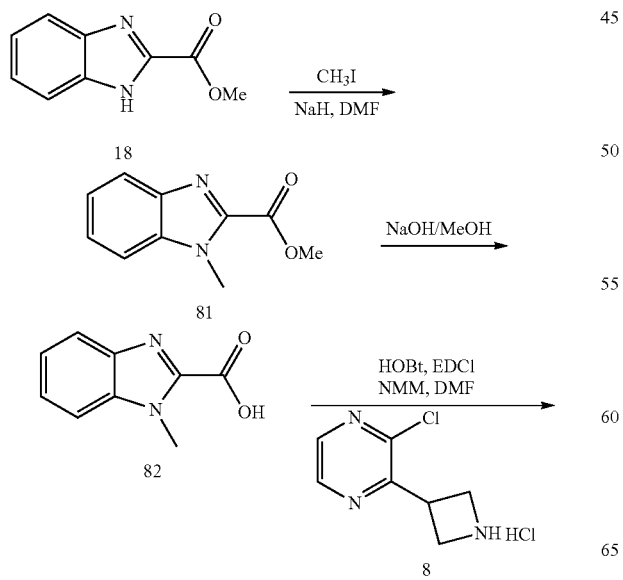

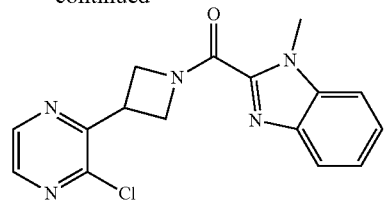

83

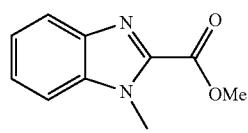

81

Step 1. 1-Methyl-1H-Benzoimidazole-2-Carboxylic Acid Methyl Ester (81)

To a solution of 1H-benzoimidazole-2-carboxylic acid methyl ester (18) (177 mg, 1.0 mmol) in dry DMF (5 mL) was added sodium hydride (applied as 60% dispersion in oil, 62 mg, 1.5 mmol)) at 0° C. under N₂ atmosphere. After 0.5 h, iodomethane (284 mg, 2.0 mmol) was added slowly. The reaction mixture was stirred at RT for 4 h. The reaction was diluted with brine at 0° C. and extracted with EtOAc (3×20 mL). The combined organics were washed with water (2×15 mL), brine (20 mL), dried over sodium sulfate and filtered. The filtrate was concentrated and purified by flash column chromatography to provide the title compound (81) (180 mg, 90% yield) as a light yellow solid.

ESI-MS (M+1): 191 calc. for C10H10N2O2 190.

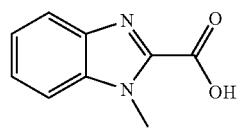

82

Step 2. 1-Methyl-1H-Benzoimidazole-2-Carboxylic Acid (82)

A mixture of 1-methyl-1H-benzoimidazole-2-carboxylic acid methyl ester (81) (190 mg, 1.0 mmol) and NaOH (80 mg, 2.0 mmol) in MeOH/H₂O (1:1, 20 mL) was stirred at 50° C. for 1 h. The mixture was concentrated, then diluted with water (15 mL), adjusted pH=2 with concentrated HCl. Then the precipitate was formed and filtered, washed with water and dried to give 1-methyl-1H-benzoimidazole-2-carboxylic acid (82) (176 mg, 1.0 mmol, yield 100%) ESI-MS (M+1): 177 calc. for $C_9H_8N_2O_2$ 176.

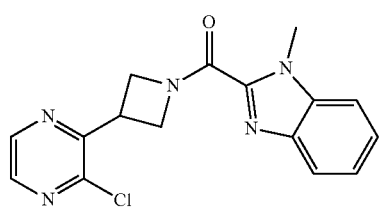

83

Step 3. [3-(3-Chloro-Pyrazin-2-Yl)-Azetidin-1-Yl]-(1-Methyl-1H-Benzoimidazol-2-Yl)-Methanone (83)

A mixture of 1-methyl-1H-benzoimidazole-2-carboxylic acid (82) (176 mg, 1.0 mmol), 2-Azetidin-3-yl-3-chloropyrazine hydrochloride (8) (169 mg, 1.0 mmol), HOBt (151 mg, 1.2 mmol), EDCI (231 mg, 1.2 mmol) and N-methylmorpholine (NMM) (300 mg, 3.0 mmol) in DMF (5 mL) was stirred at RT for 24 h. The mixture was diluted with water (20 mL), and filtered. The filter cake was washed with water and dried in vacuo to provide [3-(3-chloro-pyrazin-2-yl)-azetidin-1-yl]-(1-methyl-1H-benzoimidazol-2-yl)-methanone (83) (300 mg, yield 90%).

ESI-MS (M+1): 328 calc. for $C_{16}H_{14}ClN_5O$ 327.

Preparation 26

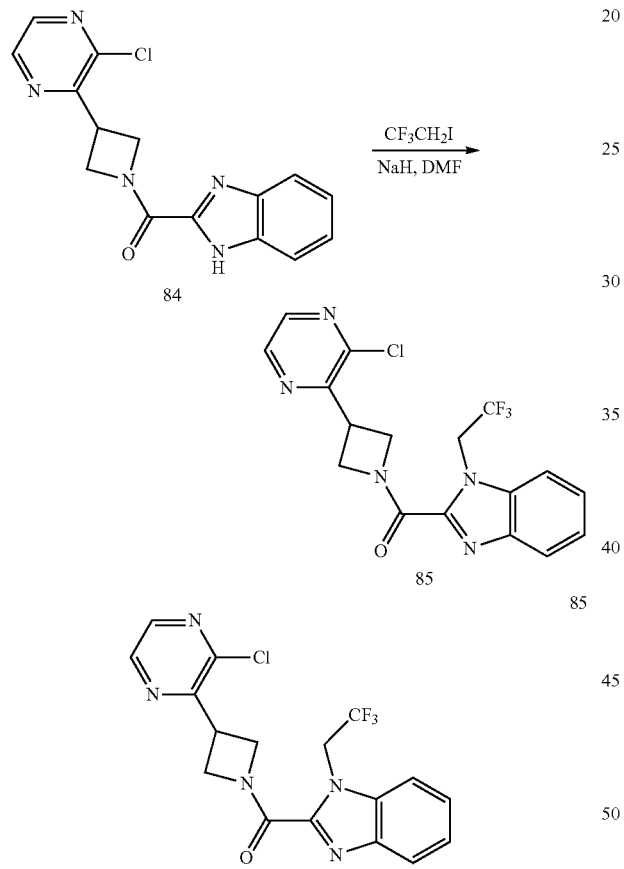

[3-(3-Chloro-Pyrazin-2-Yl)-Azetidin-1-Yl]-[1-(2,2,2-Trifluoro-Ethyl)-1H-Benzoimidazol-2-Yl]-Methanone (85)

To a solution of (1H-benzoimidazol-2-yl)-[3-(3-chloro-pyrazin-2-yl)-azetidin-1-yl]-methanone (84), as prepared in Preparation 36 below, (314 mg, 1.0 mmol) in dry DMF (10 mL) was added sodium hydride (applied as 60% dispersion in oil, 62 mg, 1.5 mmol)) at 0° C. under $N_2$ atmosphere. After 0.5 h, 1,1,1-Trifluoro-2-iodo-ethane (418 mg, 2.0 mmol) was added slowly. The reaction mixture was stirred at RT for 4 h. The reaction was quenched with water (10 mL) at 0° C. and extracted with EtOAc (3×20 mL). The combined organics were washed with water (2×15 mL), brine (20 mL), dried over sodium sulfate and filtered. The filtrate was concentrated and the residue was purified by flash column chromatography to provide (85) (355 mg, 0.90 mmol, 90% yield) as white solid.

ESI-MS (M+1): 396 calc. for $C_{17}H_{13}ClF_3N_5O$ 395.

Preparation 27

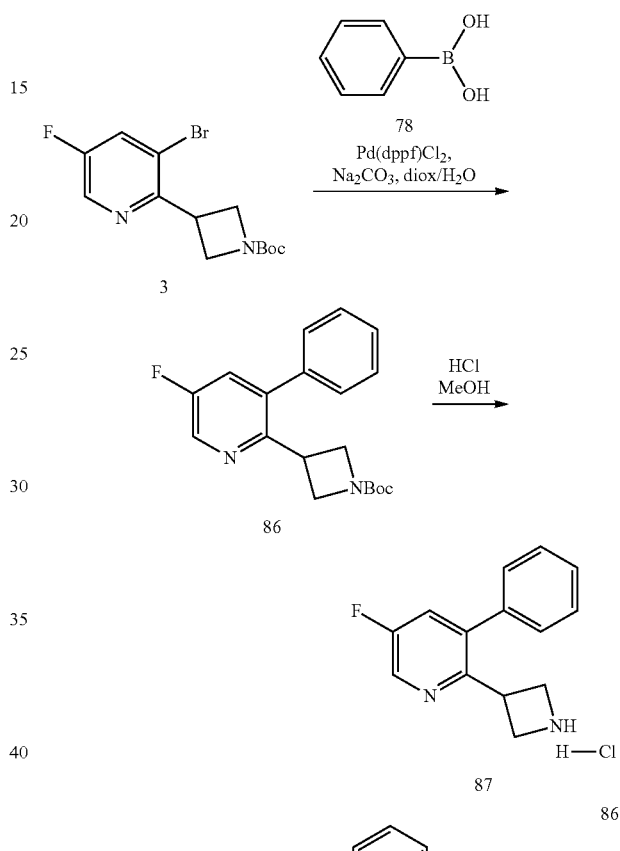

Step 1. 3-(3-Phenyl-Pyridin-2-Yl)-Azetidine-1-Carboxylic Acid Tert-Butyl Ester (86)

To a stirred solution of 3-(3-bromo-pyridin-2-yl)-azetidine-1-carboxylic acid tert-butyl ester (3) (158 mg, 0.48 mmol) in dioxane (10 mL) was added phenylboronic acid (78) (87 mg, 0.71 mmol), $Na_2CO_3$ (152 mg, 1.4 mmol) and $H_2O$ (2 mL). The reaction mixture was degassed with $N_2$ and then $PdCl_2$(dppf) (35 mg, 0.05 mmol) was added. The reaction mixture was stirred at 80° C. for 12 h. The reaction mixture was left to reach RT and filtered through a pad of CELITE® and the filter cake was washed with $CH_2Cl_2$ (20 mL×3). The combined filtrates were evaporated in vacuo and the residue was purified by column chromatography ((EtOAc:Petrol ether=3:1) to give 3-(3-phenyl-pyridin-2-yl)-azetidine-1-carboxylic acid tert-butyl ester (125 mg, 0.38 mmol, 80% yield).

ESI-MS (M+1): 329 calc. for $C_{19}H_{21}FN_2O_2$ 328.

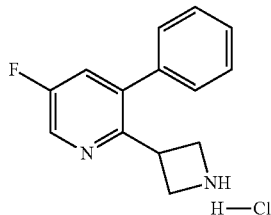

87

Step 2. 2-Azetidin-3-Yl-5-Fluoro-3-Phenyl-Pyridine Hydrochloride (87)

A mixture of 3-(3-phenyl-pyridin-2-yl)-azetidine-1-carboxylic acid tert-butyl ester (86) (125 mg, 0.38 mmol) in 4 M HCl/MeOH solution (10 mL) was stirred at RT for 30 min. Then the solvent was evaporated at 40° C. to give 2-azetidin-3-yl-5-fluoro-3-phenyl-pyridine hydrochloride (87) (100 mg, 0.38 mmol, 100% yield) as a yellow solid.

ESI-MS (M+1): 229 calc. for $C_{14}H_{13}FN_2$ 228.

Preparation 28

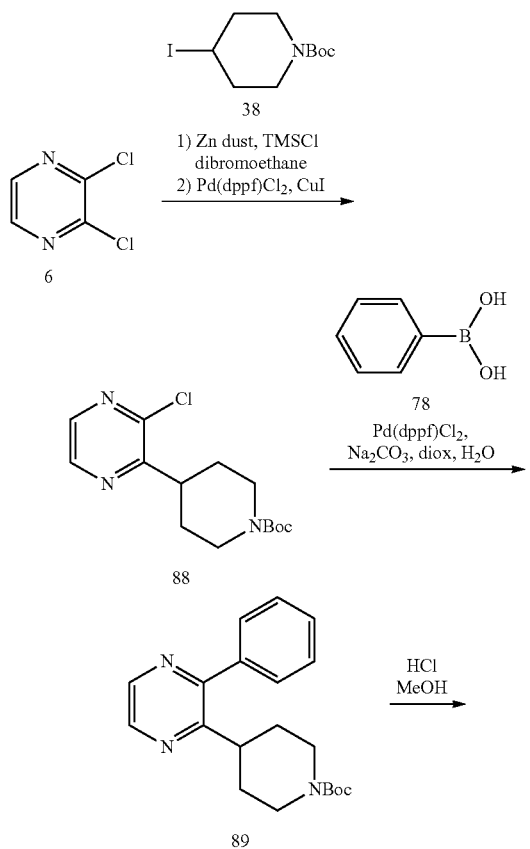

Step 1. 4-(3-Chloro-Pyrazin-2-Yl)-Piperidine-1-Carboxylic Acid Tert-Butyl Ester (88)

A 100 mL 3-neck round bottom flask fitted with a magnetic stirrer and flushed with nitrogen was charged with zinc dust (813 mg, preactivated according to the above Preparation 1, 12.7 mmol, 2.0 eq.) and DMA (10 mL, anhydrous). 1,2-dibromoethane (236 mg, 1.27 mmol, 0.2 eq) was added slowly, followed by TMSCl (137 mg, 1.27 mmol, 0.2 eq). The reaction was stirred for 15 min at RT. A solution of 4-iodo-piperidine-1-carboxylic acid tert-butyl ester (38) (2.95 g, 9.5 mmol, 1.5 eq) in DMA (10 mL, anhydrous) was added dropwise. The suspension was stirred for 1 h at RT.

A 100 mL 3-neck round bottom flask fitted with a mechanical stirrer was charged with 2,3-dichloro-pyrazine (6) (0.95 g, 6.4 mmol, 1.0 eq), PdCl$_2$(dppf) (446 mg, 0.64 mmol, 0.1 eq), CuI (121 mg, 0.64 mmol, 0.1 eq), and DMA (20 mL, anhydrous). The dark solution was degassed for 15 min. The clear zinc reagent solution above the residual solid zinc was transferred to the above 100 mL flask by cannulation. The dark solution was degassed and heated to 80° C. for 16 h. The reaction was diluted with brine and extracted with EtOAc (3×100 mL). The combined organics were washed with water (2×100 mL) and brine (100 mL), followed by drying over sodium sulfate. The solution was concentrated and the residue was purified by flash column chromatography (PE:EA=2:1) provides the title compound (88) (0.95 g, 3.2 mmol, 50% yield) as a light yellow solid.

ESI-MS (M+1): 298 calc. for $C_{14}H_{20}ClN_3O_2$ 297.

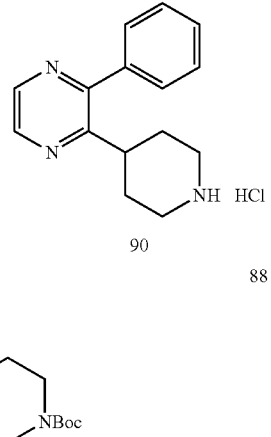

Step 4. 4-(3-Phenyl-Pyrazin-2-Yl)-Piperidine-1-Carboxylic Acid Tert-Butyl Ester (89)

To a stirred solution of (88) (142 mg, 0.48 mmol) in dioxane (10 mL) was added phenylboronic acid (78) (87 mg, 0.71 mmol), Na$_2$CO$_3$ (152 mg, 1.4 mmol) and H$_2$O (2 mL). The reaction mixture was degassed with N$_2$ and then PdCl$_2$(dppf) (35 mg, 0.05 mmol) was added. The reaction mixture was stirred at 80° C. for 12 h. The reaction mixture was left to reach RT and filtered through a pad of CELITE® and the filter cake was washed with CH$_2$Cl$_2$ (20 mL×3). The combined filtrates were evaporated in vacuo and the residue was purified by column chromatography ((EtOAc:Petrol ether=1:1) to give 4-(3-Phenyl-pyrazin-2-yl)-piperidine-1-carboxylic acid tert-butyl ester (89) (128 mg, 0.38 mmol, 80% yield).

ESI-MS (M+1): 340 calc. for C$_{20}$H$_{25}$N$_3$O$_2$ 339.

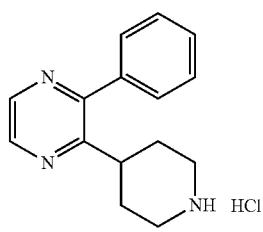

89

Step 4. 2-Phenyl-3-Piperidin-4-Yl-Pyrazine Hydrochloride (90)

A mixture of 4-(3-Phenyl-pyrazin-2-yl)-piperidine-1-carboxylic acid tert-butyl ester (89) (128 mg, 0.38 mmol) in 4 M HCl/MeOH solution (10 mL) was stirred at RT. for 30 min. Then the solvent was evaporated at 40° C. to give 2-phenyl-3-piperidin-4-yl-pyrazine hydrochloride (90) (105 mg, 0.38 mmol, 100% yield) as a yellow solid.

ESI-MS (M+1): 240 calc. for C$_{15}$H$_{17}$N$_3$ 239.

Preparation 29

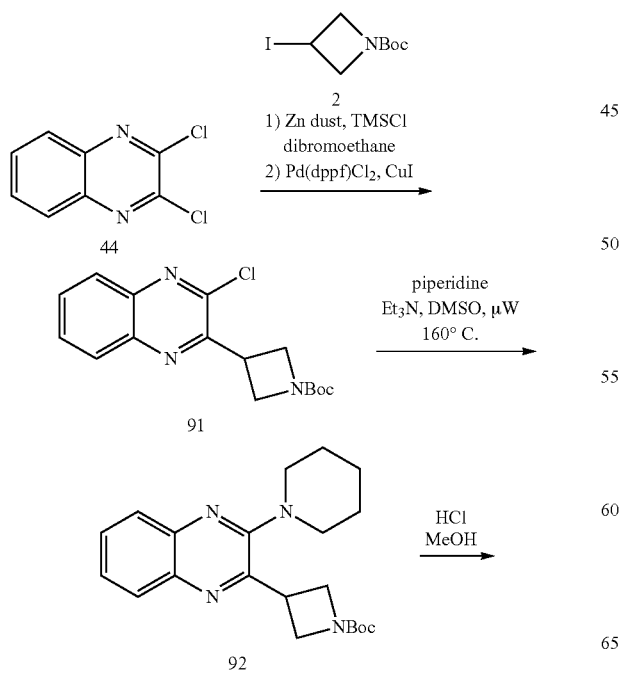

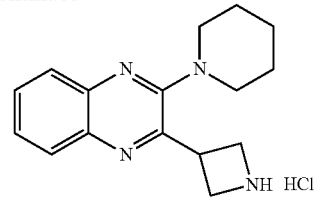

93

91

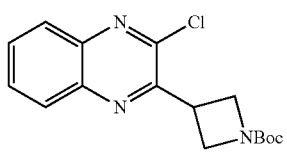

Step 1. 3-(3-Chloro-Quinoxalin-2-Yl)-Azetidine-1-Carboxylic Acid Tert-Butyl Ester (91)

A 100 mL 3-neck round bottom flask fitted with a magnetic stirrer and flushed with nitrogen was charged with zinc dust (1.3 g, preactivated according to the above Preparation 1, 20 mmol, 2.0 eq.) and DMA (10 mL, anhydrous). 1,2-dibromoethane (400 mg, 2.0 mmol, 0.2 eq) was added slowly, followed by TMSCl (240 mg, 2.0 mmol, 0.2 eq). The reaction was stirred for 15 min at RT. A solution of N-Boc-3-iodoazetidine (2) (4 g, 16 mmol, 1.6 eq) in DMA (10 mL, anhydrous) was added dropwise. The suspension was stirred for 1 h at RT.

A 100 mL 3-neck round bottom flask fitted with a mechanical stirrer was charged with 2,3-Dichloro-quinoxaline (44) (2 g, 10 mmol, 1.0 eq), PdCl$_2$(dppf) (800 mg, 1.0 mmol, 0.1 eq), CuI (200 mg, 1.0 mmol, 0.1 eq), and DMA (20 mL, anhydrous). The dark solution was degassed for 15 min. The clear zinc reagent solution above the residual solid zinc was transferred to the above 100 mL flask by cannulation. The dark solution was degassed and heated to 80° C. for 16 h. The reaction was diluted with brine and extracted with EtOAc (3×100 mL). The combined organics were washed with water (2×100 mL) and brine (100 mL), followed by drying over sodium sulfate. The solution was concentrated and the residue was purified by flash column chromatography (PE:EA=2:1) provides 3-(3-Chloro-quinoxalin-2-yl)-azetidine-1-carboxylic acid tert-butyl ester (91) (1.43 g, 4.5 mmol, 45% yield) as a light yellow solid.

ESI-MS (M+1): 320 calc. for C$_{16}$H$_{18}$ClN$_3$O$_2$ 319.

92

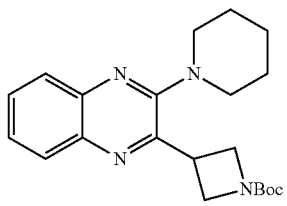 [SMILES: CC(C)(C)OC(=O)N1CC(c2nc3ccccc3nc2N2CCCCC2)C1]

Step 2. 3-(3-Piperidin-1-Yl-Quinoxalin-2-Yl)-Azetidine-1-Carb Oxylic Acid Tert-Butyl Ester (92)

To a mixture of 3-(3-chloro-quinoxalin-2-yl)-azetidine-1-carboxylic acid tert-butyl ester (91) (0.16 g, 0.50 mmol) and piperidine (0.085 g, 1.0 mmol) was added triethylamine (0.10 g, 1.0 mmol) and DMSO (3 mL). The solution was heated to 160° C. in microwave for 2 h. Then the mixture was diluted with water (10 mL) and extracted with EtOAc (2×20 mL). The combined organic extracts were washed with water (10 mL) and brine (10 mL), dried over $Na_2SO_4$ and filtered. The filtrate was evaporated in vacuo and the residue was purified by flash column chromatography on silica gel (20% to 50% EtOAc in petroleum ether) to give 3-(3-piperidin-1-yl-quinoxalin-2-yl)-azetidine-1-carboxylic acid tert-butyl ester (92) (0.16 g, 0.90 mmol, 90% yield) as a white solid. ESI-MS (M+1): 369 calc. for $C_{21}H_{28}N_4O_2$ 368.

Step 3.
2-Azetidin-3-Yl-3-Piperidin-1-Yl-Quinoxaline Hydrochloride (93)

A mixture of 3-(3-piperidin-1-yl-quinoxalin-2-yl)-azetidine-1-carboxylic acid tert-butyl ester (92) (139 mg, 0.38 mmol) in 4 M HCl/MeOH solution (10 mL) was stirred at RT for 30 min. Then the solvent was evaporated at 40° C. to give 2-azetidin-3-yl-3-piperidin-1-yl-quinoxaline hydrochloride (93) (115 mg, 0.38 mmol, 100% yield) as a yellow solid. ESI-MS (M+1): 269 calc. for $C_{16}H_{20}N_4$ 269.

93

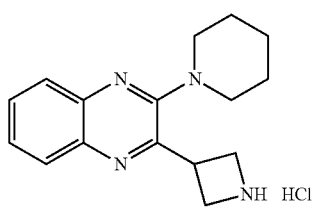

The following Table 9 lists compounds of Preparation P29.1 to P29.4, which were made analogous to Preparation 29 by using the appropriate materials.

TABLE 9

| | PREPARATION P29.1 TO P29.4 | | |
|---|---|---|---|
| Ex. # | Structure | Chemical Name | ESI-MS (M + 1) |
| P29.1 | | 3-(3-Piperidin-1-yl-quinoxalin-2-yl)-azetidine-1-carboxylic acid tert-butyl ester | 369 |
| P29.2 | | tert-butyl 3-(3-(4-hydroxypiperidin-1-yl)quinoxalin-2-yl)azetidine-1-carboxylate | 385 |
| P29.3 | | 2-Azetidin-3-yl-3-piperidin-1-yl-quinoxaline hydrochloride | 269 |
| P29.4 | | 1-(3-(azetidin-3-yl)quinoxalin-2-yl)piperidin-4-ol hydrochloride | 285 |

Preparation 30

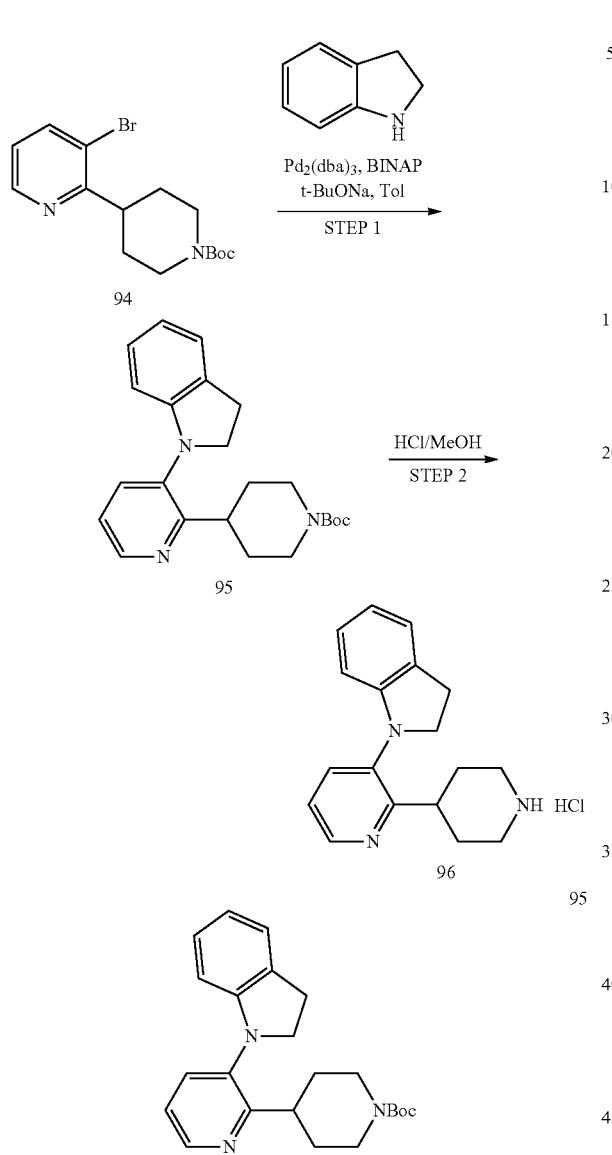

Step 1. 3-(2,3-Dihydro-Indol-1-Yl)-3',4',5',6'-Tetrahydro-2'H-[2,4']Bipyridinyl-1'-Carboxylic Acid Tert-Butyl Ester (95)

A mixture of 3-bromo-3',4',5',6'-tetrahydro-2'H-[2,4']bipyridinyl-1'-carboxylic acid tert-butyl ester (94) (280 mg, 0.82 mmol), 2,3-dihydro-1H-indole (97 mg, 0.82 mmol), Pd$_2$(dba)$_3$ (37 mg, 0.04 mmol), BINAP (24 mg, 0.04 mmol) and t-BuONa (173 mg, 1.64 mmol) in toluene (20 mL) was stirred at 100° C. for 12 h. The mixture was left to reach RT and filtered through a pad of Celite and the filter cake was washed with CH$_2$Cl$_2$ (30 mL). The combine filtrate was evaporated in vacuo and the residue was purified by flash column chromatography (20% to 40% EtOAc in petroleum ether) to afford 3-(2,3-dihydro-indol-1-yl)-3',4',5',6'-tetrahydro-2'H-[2,4']bipyridinyl-1'-carboxylic acid tert-butyl ester (95) (100 mg, 0.29 mmol, yield 32%).

ESI-MS (M+1): 380 calc. for C$_{23}$H$_{29}$N$_3$O$_2$ 379.

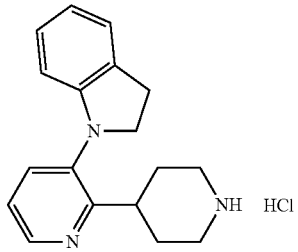

Step 2. 3-(2,3-Dihydro-Indol-1-Yl)-1',2',3',4',5',6'-Hexahydro-[2,4']Bipyridinyl Hydrochloride (96)

To 3-(2,3-dihydro-indol-1-yl)-3',4',5',6'-tetrahydro-2'H-[2,4']bipyridinyl-1'-carboxylic acid tert-butyl ester (95) (100 mg, 0.29 mmol) was added 4 M HCl in MeOH (20 mL). The reaction mixture was stirred at RT for 1 h. Then it was concentrated to give 3-(2,3-dihydro-indol-1-yl)-1',2',3',4',5',6'-hexahydro-[2,4']bipyridinyl hydrochloride (96) (0.083 g, 0.29 mmol, 100% yield) which was used in the next step without further purification.

ESI-MS (M+1): 280 calc. for C$_{18}$H$_{21}$N$_3$ 279.

Preparation 31

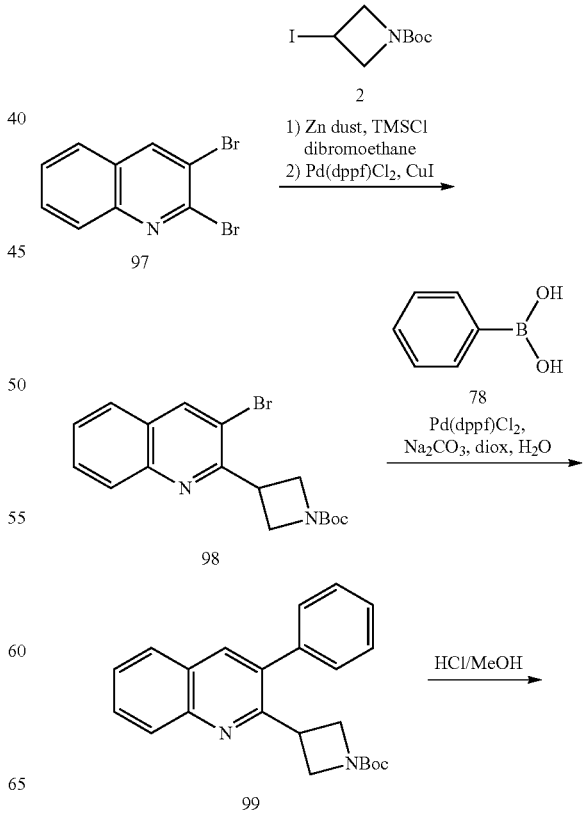

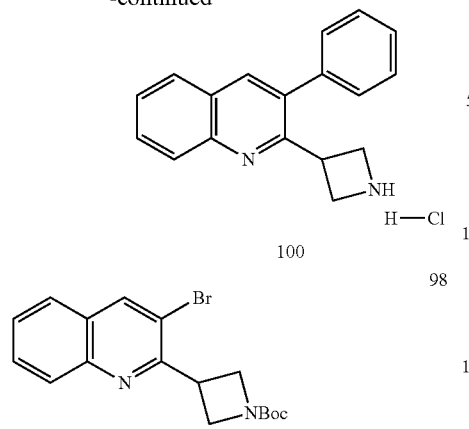

Step 1. 3-(3-Bromo-Quinolin-2-Yl)-Azetidine-1-Carboxylic Acid Tert-Butyl Ester (98)

A 100 mL 3-neck round bottom flask fitted with a magnetic stirrer and flushed with nitrogen was charged with zinc dust (813 mg, preactivated according to the above Preparation 1, 12.7 mmol, 2.0 eq.) and DMA (10 mL, anhydrous). 1,2-dibromoethane (236 mg, 1.27 mmol, 0.2 eq) was added slowly, followed by TMSCl (137 mg, 1.27 mmol, 0.2 eq). The reaction was stirred for 15 min at RT. A solution of N-Boc-3-iodoazetidine (2) (2.7 g, 9.5 mmol, 1.5 eq) in DMA (10 mL, anhydrous) was added dropwise. The suspension was stirred for 1 h at RT.

A 100 mL 3-neck round bottom flask fitted with a mechanical stirrer was charged with 2,3-dibromo-quinoline (97) (1.82 g, 6.4 mmol, 1.0 eq), PdCl$_2$(dppf) (446 mg, 0.64 mmol, 0.1 eq), CuI (121 mg, 0.64 mmol, 0.1 eq), and DMA (20 mL, anhydrous). The dark solution was degassed for 15 min. The clear zinc reagent solution above the residual solid zinc was transferred to the above 100 mL flask by cannulation. The dark solution was degassed and heated to 80° C. for 16 h. The reaction was diluted with brine and extracted with EtOAc (3×100 mL). The combined organics were washed with water (2×100 mL) and brine (100 mL), followed by drying over sodium sulfate. The solution was concentrated and the residue was purified by flash column chromatography (EtOAc:Petro ether=4:1) provides the title compound (98) (1.2 g, 3.30 mmol, 52% yield) as a light yellow solid.

ESI-MS (M+1): 363 calc. for C$_{17}$H$_{19}$BrN$_2$O$_2$ 362.

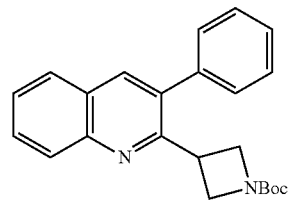

Step 2. 3-(3-Phenyl-Quinolin-2-Yl)-Azetidine-1-Carboxylic Acid Tert-Butyl Ester (99)

To a stirred solution of 3-(3-bromo-quinolin-2-yl)-azetidine-1-carboxylic acid tert-butyl ester (98) (174 mg, 0.48 mmol) in dioxane (10 mL) was added phenylboronic acid (78) (87 mg, 0.71 mmol), Na$_2$CO$_3$ (152 mg, 1.4 mmol) and H$_2$O (2 mL). The reaction mixture was degassed with N$_2$ and then PdCl$_2$(dppf) (35 mg, 0.05 mmol) was added. The reaction mixture was stirred at 80° C. for 12 h. The reaction mixture was left to reach RT and filtered through a pad of CELITE® and the filter cake was washed with CH$_2$Cl$_2$ (20 mL×3). The combined filtrates were evaporated in vacuo and the residue was purified by column chromatography ((EtOAc:Petrol ether=3:1) to give the desired compound (95) (154 mg, 0.42 mmol, 87% yield).

ESI-MS (M+1): 361 calc. for C$_{23}$H$_{24}$N$_2$O$_2$ 360.

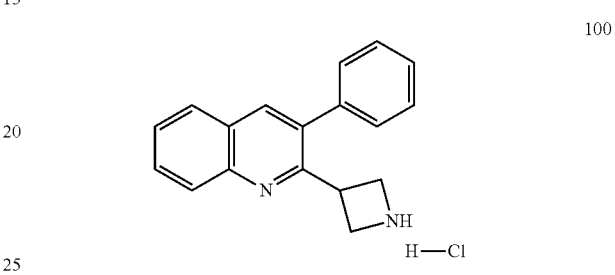

Step 3. 2-Azetidin-3-Yl-3-Phenyl-Quinoline Hydrochloride (100)

A mixture of 3-(3-phenyl-pyridin-2-yl)-azetidine-1-carboxylic acid tert-butyl ester (99) (216 mg, 0.60 mmol) in 4 M HCl/MeOH solution (10 mL) was stirred at RT. for 30 min. Then the solvent was evaporated at 40° C. to give 2-azetidin-3-yl-3-phenyl-pyridine (100) (177 mg, 100% yield) as a yellow solid.

ESI-MS (M+1): 261 calc. for C$_{18}$H$_{16}$N$_2$ 260.

Preparation 32

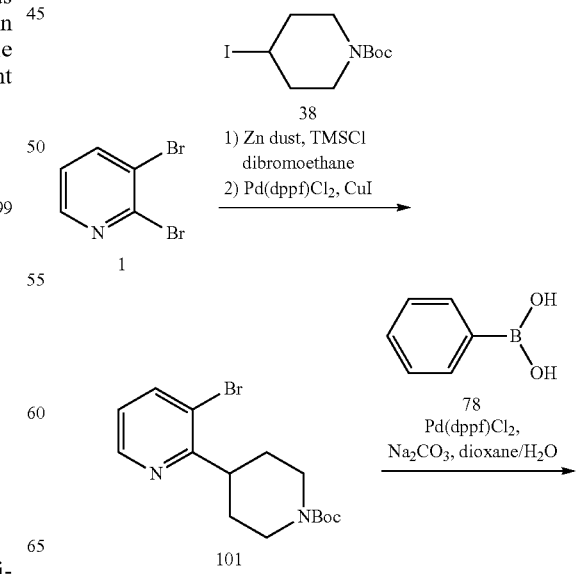

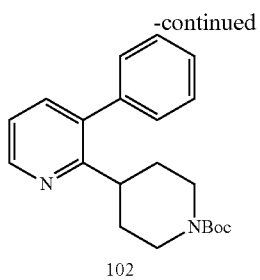

102

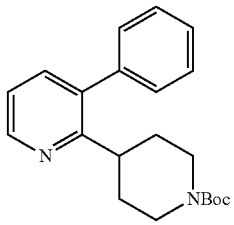

102

Step 2. 3-Phenyl-3',4',5',6'-Tetrahydro-2'H-[2,4']
Bipyridinyl-1'-Carboxylic Acid Tert-Butyl Ester
(102)

To a stirred solution of 3-bromo-3',4',5',6'-tetrahydro-2'H-[2,4']bipyridinyl-1'-carboxylic acid tert-butyl ester (101) (163 mg, 0.48 mmol) in dioxane (10 mL) was added phenylboronic acid (78) (87 mg, 0.71 mmol), $Na_2CO_3$ (152 mg, 1.4 mmol) and $H_2O$ (2 mL). The reaction mixture was degassed with $N_2$ and then $PdCl_2(dppf)$ (35 mg, 0.05 mmol) was added. The reaction mixture was stirred at 80° C. for 12 h. The reaction mixture was left to reach RT and filtered through a pad of CELITE® and the filter cake was washed with $CH_2Cl_2$ (20 mL×3). The combined filtrates were evaporated in vacuo and the residue was purified by column chromatography ((EtOAc:Petrol ether=4:1) to give the desired compound (102) (138 mg, 0.41 mmol, 85% yield).

ESI-MS (M+1): 339 calc. for $C_{21}H_{26}N_2O_2$ 338.

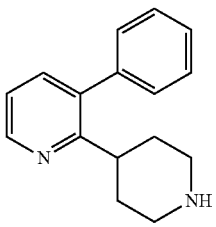

103  H—Cl
101

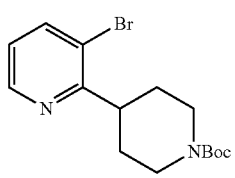

Step 1. 3-Bromo-3',4',5',6'-Tetrahydro-2'H-[2,4']
Bipyridinyl-1'-Carboxylic Acid Tert-Butyl Ester
(101)

A 100 mL 3-neck round bottom flask fitted with a magnetic stirrer and flushed with nitrogen was charged with zinc dust (813 mg, preactivated according to the above Preparation 1, 12.7 mmol, 2.0 eq.) and DMA (10 mL, anhydrous). 1,2-dibromoethane (236 mg, 1.27 mmol, 0.2 eq) was added slowly, followed by TMSCl (137 mg, 1.27 mmol, 0.2 eq). The reaction was stirred for 15 min at RT. A solution of 4-Iodo-piperidine-1-carboxylic acid tert-butyl ester (38) (2.95 g, 9.5 mmol, 1.5 eq) in DMA (10 mL, anhydrous) was added dropwise. The suspension was stirred for 1 h at RT.

A 100 mL 3-neck round bottom flask fitted with a mechanical stirrer was charged with 2,3-dibromo-pyridine (1) (1.5 g, 6.4 mmol, 1.0 eq), $PdCl_2(dppf)$ (446 mg, 0.64 mmol, 0.1 eq), CuI (121 mg, 0.64 mmol, 0.1 eq), and DMA (20 mL, anhydrous). The dark solution was degassed for 15 min. The clear zinc reagent solution above the residual solid zinc was transferred to the above 100 mL flask by cannulation. The dark solution was degassed and heated to 80° C. for 16 h. The reaction was diluted with brine and extracted with EtOAc (3×100 mL). The combined organics were washed with water (2×100 mL) and brine (100 mL), followed by drying over sodium sulfate. The solution was concentrated and the residue was purified by flash column chromatography (PE:EtOAc=2:1) provides the title compound (101) (761 mg, 2.3 mmol, 35% yield) as a light yellow solid.

ESI-MS (M+1): 341 calc. for $C_{15}H_{21}BrN_2O_2$ 340.

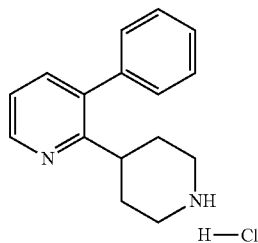

Step 3. 3-Phenyl-1',2',3',4',5',6'-Hexahydro-[2,4']
Bipyridinyl Hydrochloride (103)

A mixture of 3-phenyl-3',4',5',6'-tetrahydro-2'H-[2,4']bipyridinyl-1'-carboxylic acid tert-butyl ester (102) (202 mg, 0.60 mmol) in HCl/MeOH solution (5 mL) was stirred at RT. for 30 min. Then the solvent was evaporated at 40° C. to give 3-phenyl-1',2',3',4',5',6'-hexahydro-[2,4']bipyridinyl hydrochloride (103) (162 mg, 0.60 mmol, 100% yield) as a yellow solid.

ESI-MS (M+1): 239 calc. for $C_{16}H_{18}N_2$ 238.

Preparation 33

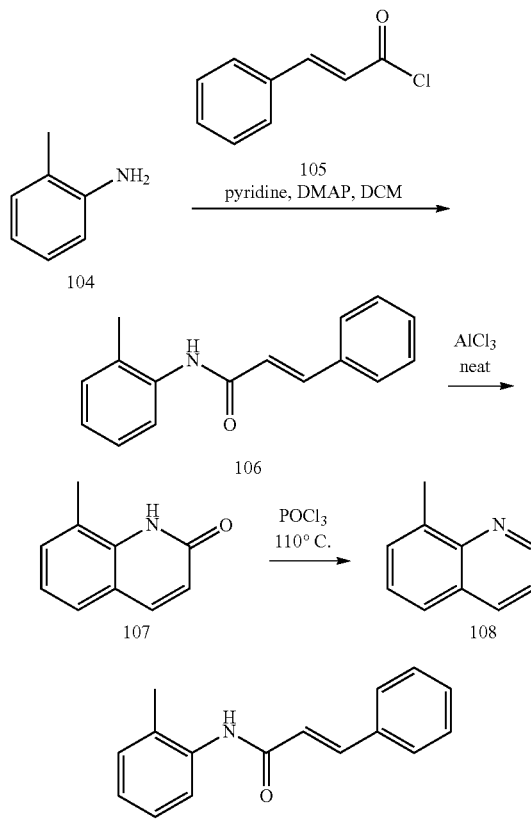

Step 1. 3-Phenyl-N—O-Tolyl-Acrylamide (106)

A solution of o-tolylamine (104) (5.3 g, 50.0 mmol) in DCM (50 mL) was added to a stirring mixture of pyridine (5 mL) and DMAP (0.61 g, 5.0 mmol) in DCM (20 mL) at 0° C. under $N_2$. The mixture was stirred for 15 min before a solution of cinnamoyl chloride (105) (8.3 g, 50.0 mmol) in DCM (50 mL) was added over 10 min. After being stirred for further 15 min, the mixture was allowed to warm to RT. The precipitate formed was collected, washed with cold DCM and dried to afford the title compound (106) (9.9 g, 42.0 mmol, 84% yield).

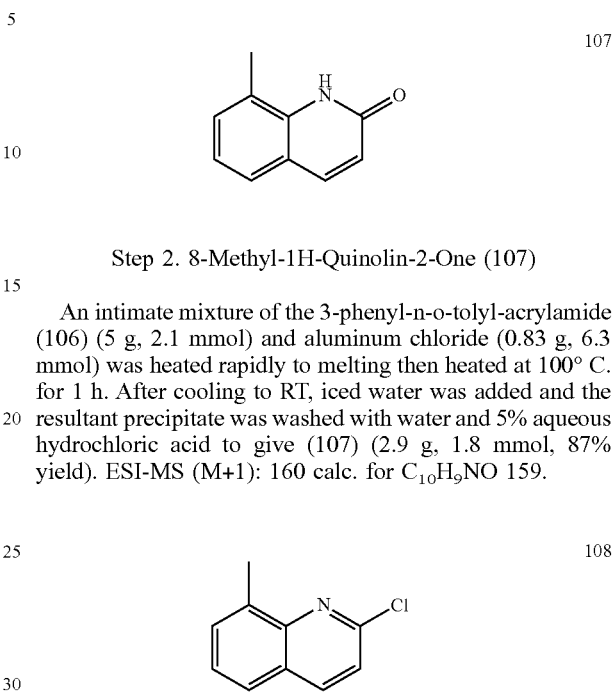

Step 2. 8-Methyl-1H-Quinolin-2-One (107)

An intimate mixture of the 3-phenyl-n-o-tolyl-acrylamide (106) (5 g, 2.1 mmol) and aluminum chloride (0.83 g, 6.3 mmol) was heated rapidly to melting then heated at 100° C. for 1 h. After cooling to RT, iced water was added and the resultant precipitate was washed with water and 5% aqueous hydrochloric acid to give (107) (2.9 g, 1.8 mmol, 87% yield). ESI-MS (M+1): 160 calc. for $C_{10}H_9NO$ 159.

Step 3. 2-Chloro-8-Methyl-Quinoline (108)

A mixture of 8-methyl-1H-quinolin-2-one (107) (580 mg, 3.6 mmol) and phosphorus oxychloride (5 mL) was stirred at 60° C. overnight. The mixture was then poured onto ice water and extracted with DCM (3×50 mL). The combined extracts were washed with water (2×100 mL) and dried with $Na_2SO_4$, and the solvent was removed. The residue was chromatographed on silica gel using 5% to 20% EtOAc in petroleum ether to give product (108) as small colorless crystals (400 mg, 2.3 mmol, 63% yield).

The following Table 10 lists compounds of Preparation P33.1 to P33.12, which were made analogous to Preparation 33 by using the appropriate materials.

TABLE 10

PREPARATION P33.1 TO P33.12

| Ex. # | Structure | Chemical Name | ESI-MS (M + 1) |
|---|---|---|---|
| P33.1 | 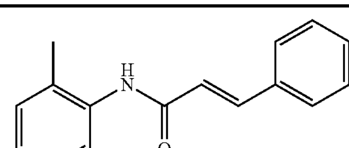 | N-(o-tolyl)cinnamamide | 238 |
| P33.2 | 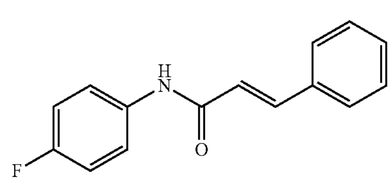 [SMILES: O=C(/C=C/c1ccccc1)Nc1ccc(F)cc1] | N-(4-fluorophenyl)cinnamamide | 242 |

TABLE 10-continued

PREPARATION P33.1 TO P33.12

| Ex. # | Structure | Chemical Name | ESI-MS (M + 1) |
|---|---|---|---|
| P33.3 | 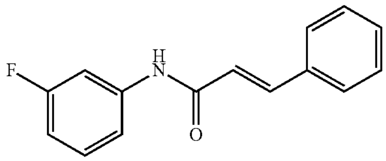 [SMILES: O=C(/C=C/c1ccccc1)Nc1cccc(F)c1] | N-(3-fluorophenyl)cinnamamide | 242 |
| P33.4 | 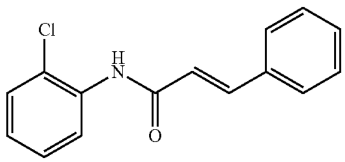 [SMILES: O=C(/C=C/c1ccccc1)Nc1ccccc1Cl] | N-(2-chlorophenyl)cinnamamide | 258 |
| P33.5 | 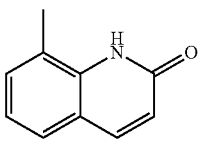 | 8-Methyl-1H-quinolin-2-one | 160 |
| P33.6 | 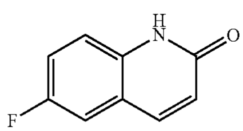 [SMILES: O=c1ccc2cc(F)ccc2[nH]1] | 6-Fluoro-1H-quinolin-2-one | 164 |
| P33.7 | 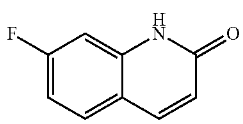 [SMILES: O=c1ccc2ccc(F)cc2[nH]1] | 7-Fluoro-1H-quinolin-2-one | 164 |
| P33.8 | 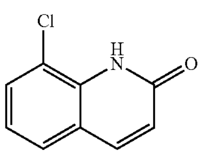 [SMILES: O=c1ccc2cccc(Cl)c2[nH]1] | 8-Chloro-1H-quinolin-2-one | 180 |
| P33.9 | 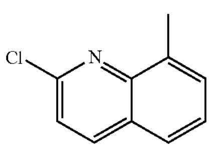 | 2-chloro-8-methylquinoline | 178 |
| P33.10 | 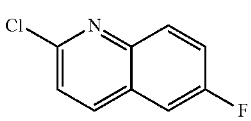 [SMILES: Fc1ccc2nc(Cl)ccc2c1] | 2-chloro-6-fluoroquinoline | 182 |
| P33.11 | 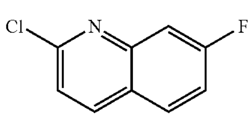 [SMILES: Fc1ccc2ccc(Cl)nc2c1] | 2-chloro-7-fluoroquinoline | 182 |
| P33.12 | 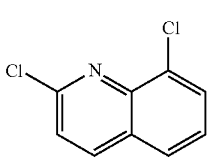 [SMILES: Clc1ccc2cccc(Cl)c2n1] | 2,8-dichloroquinoline | 198 |

Preparation 34

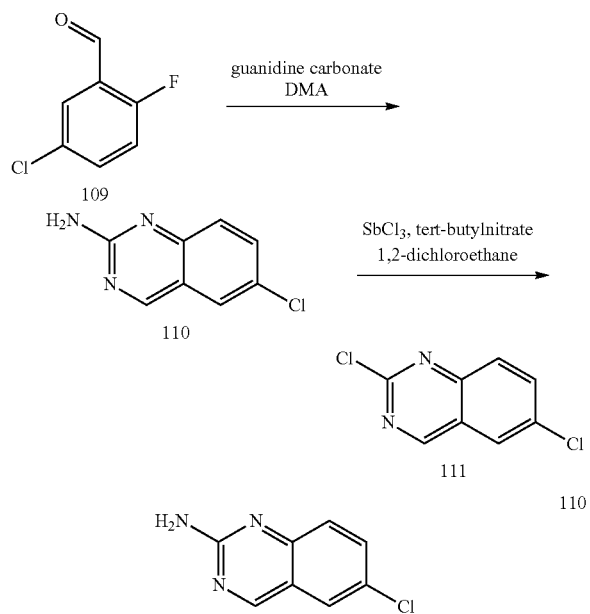

Step 1. 6-Chloroquinazolin-2-Amine (110)

A mixture of 5-chloro-2-fluoro-benzaldehyde (109) (5 g, 31.6 mmol) and guanidine carbonate (7.5 g, 41.1 mmol) was heated at 140° C. in DMA (50 mL) for 3 h. 100 ml water was added and after refrigeration, a solid was isolated by filtration, and dried under vacuum to give the product (110) (2.8 g, 15.8 mmol, 50% yield). ESI-MS (M+1): 180 calc. for $C_8H_6ClN_3$ 179.

Step 2. 2,6-Dichloro-Quinazoline (111)

To a suspension of 6-chloro-quinazolin-2-ylamine (110) (2.8 g, 15.8 mmol) and $SbCl_3$ (7.2 g, 32 mmol) in 1,2-dichloroethane (100 mL) was added tert-butylnitrate (6.2 ml, 52 mmol) and heated at 60° C. for 3 h under nitrogen atmosphere. To the mixture was added aqueous saturated $NaHCO_3$ and the mixture was filtered off and filtrate was extracted with $CHCl_3$. The organic layer was washed with brine, dried over $Na_2SO_4$, and evaporated. The residue was purified by silica gel column chromatography, using $CHCl_3$/EtOAc (9:1, v/v) as eluent to give 2,6-dichloro-quinazoline (111) (0.65 g, 3.12 mmol, 20% yield).

The following Table 11 lists compounds of Preparation P34.1 to P34.8, which were made analogous to Preparation 34 by using the appropriate materials.

TABLE 11

PREPARATION P34.1 TO P34.8

| Ex. # | Structure | Chemical Name | ESI-MS (M + 1) |
|---|---|---|---|
| P34.1 | 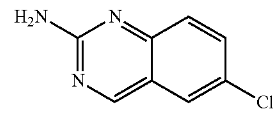 [SMILES: Nc1ncc2cc(Cl)ccc2n1] | 6-chloroquinazolin-2-amine | 180 |
| P34.2 | 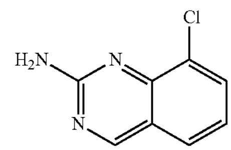 [SMILES: Nc1ncc2cccc(Cl)c2n1] | 8-chloroquinazolin-2-amine | 180 |
| P34.3 | 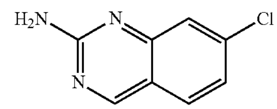 [SMILES: Nc1ncc2ccc(Cl)cc2n1] | 7-chloroquinazolin-2-amine | 180 |
| P34.4 | 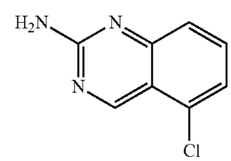 [SMILES: Nc1ncc2c(Cl)cccc2n1] | 5-chloroquinazolin-2-amine | 180 |
| P34.5 | 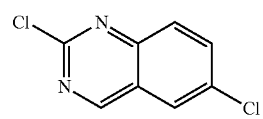 [SMILES: Clc1ccc2nc(Cl)ncc2c1] | 2,6-dichloroquinazoline | 199 |
| P34.6 | 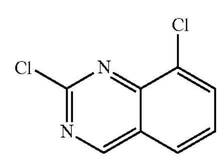 [SMILES: Clc1ncc2cccc(Cl)c2n1] | 2,8-dichloroquinazoline | 199 |
| P34.7 | 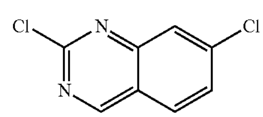 [SMILES: Clc1ccc2cnc(Cl)nc2c1] | 2,7-dichloroquinazoline | 199 |
| P34.8 | 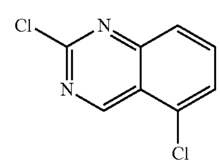 [SMILES: Clc1ncc2c(Cl)cccc2n1] | 2,5-dichloroquinazoline | 199 |

Preparation 35

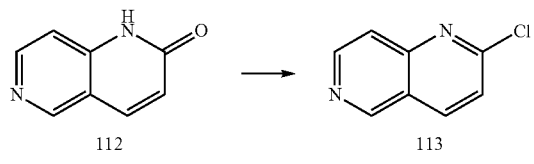 [SMILES: O=c1ccc2cnccc2[nH]1 ; Clc1ccc2cnccc2n1]

2-Chloro-1,6-Naphthyridine (113)

A mixture of phosphoryl trichloride (5.17 ml, 56.5 mmol) and 1,6-naphthyridin-2(1H)-one (112) (1.65 g, 11.29 mmol, Alfa Aesar) was stirred at 70° C. for 16 h. The reaction mixture was cooled to RT and was poured onto 150 g of ice carefully. EtOAc (50 mL) was added and the mixture was treated carefully with about 30 mL of 5 M NaOH until the final pH is persistently >10. The mixture was vigorously mixed, then transferred into a separatory funnel. The EtOAc layer was then separated and dried and re-suspended in 30 mL of DCM, the insoluble solids were filtered off. The filtrate was loaded onto a silica gel pad and flushed with 30% EtOAc in hexanes to give a solid after drying. The solid was initially white but changed color to yellow after drying on the high vacuum line over night. Yield; 1.19 g, 64%. The material (113) was used directly in the next step without any further purification.

Preparation 36 was stirred at RT overnight. Then the mixture reaction was poured into saturated aqueous $Na_2CO_3$ and extracted with DCM (50 mL×3), the organic layer was washed with brine, dried over $Na_2SO_4$ and concentrated to give the crude compound which was purified by ISCO silica gel column (10% to 80% EtOAc in petroleum ether) and followed by reverse phase prep. HPLC (10% to 80% water/MeCN) to afford pure (1H-benzoimidazol-2-yl)-[3-(3-chloro-pyrazin-2-yl)-azetidin-1-yl]-methanone (84) (50 mg, 0.16 mmol, yield 34%).

$^1$H-NMR (400 MHz, $d_6$-DMSO) δ (ppm) 8.67 (d, J=2.8 Hz, 1H); 8.43 (d, J=6.4 Hz, 1H); 7.63 (br, 2H); 7.25 (s, 2H); 5.10-5.08 (m, 1H); 4.97-4.93 (m, 1H); 4.51-4.39 (m, 3H).

ESI-MS (M+1): 314 calc. for $C_{15}H_{12}ClN_5O$ 313.

The following Table 12 lists compound of Preparation P36.1, which was made analogous to Preparation 36 by using the appropriate materials.

TABLE 12

PREPARATION P36.1

| Ex. # | Structure | Chemical Name | ESI-MS (M + 1) |
|---|---|---|---|
| P36.1 | 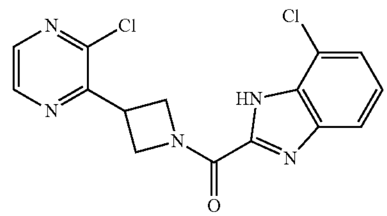 [SMILES: O=C(c1nc2cccc(Cl)c2[nH]1)N1CC(c2nccnc2Cl)C1] | (7-chloro-1H-benzo[d]imidazol-2-yl)(3-(3-chloropyrazin-2-yl)azetidin-1-yl)methanone | 348 |

Preparation 37

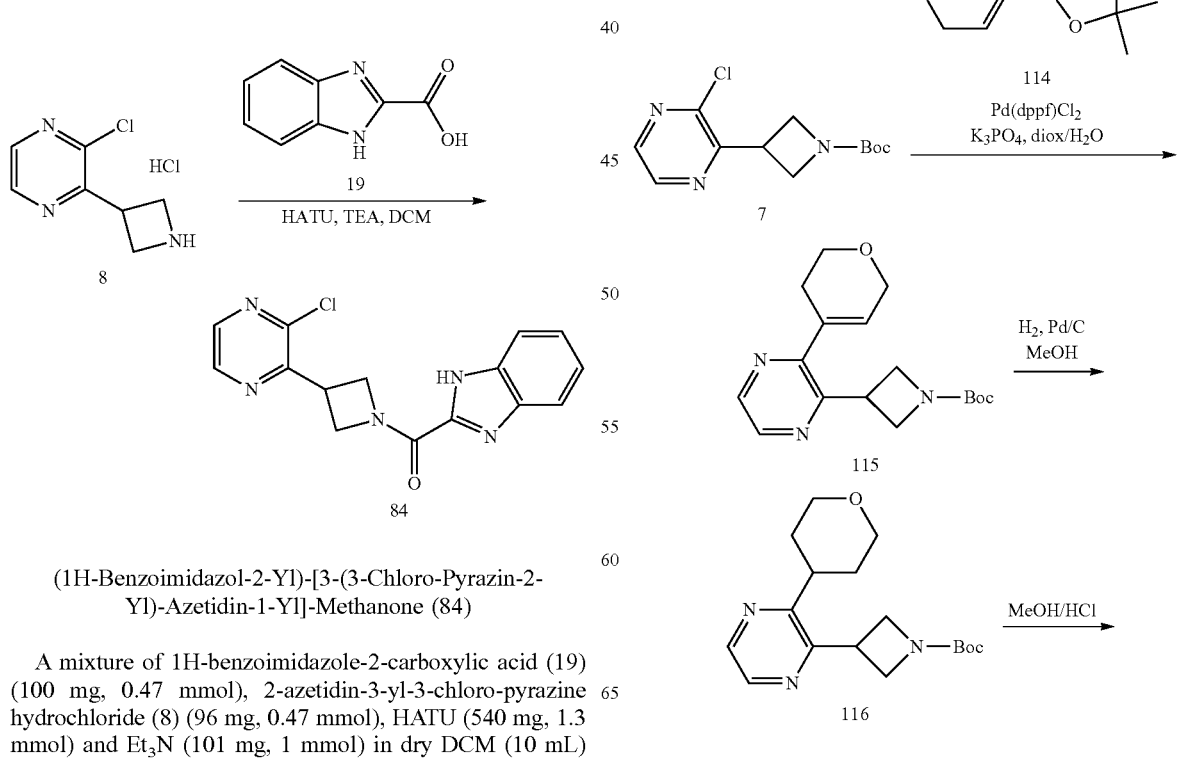

(1H-Benzoimidazol-2-Yl)-[3-(3-Chloro-Pyrazin-2-Yl)-Azetidin-1-Yl]-Methanone (84)

A mixture of 1H-benzoimidazole-2-carboxylic acid (19) (100 mg, 0.47 mmol), 2-azetidin-3-yl-3-chloro-pyrazine hydrochloride (8) (96 mg, 0.47 mmol), HATU (540 mg, 1.3 mmol) and $Et_3N$ (101 mg, 1 mmol) in dry DCM (10 mL)

Step 3. 2-Azetidin-3-Yl-3-(Tetrahydro-Pyran-4-Yl)-Pyrazine Hydrochloride (117)

To a solution of 4 N HCl in MeOH (10 mL) was added 3-[3-(Tetrahydro-pyran-4-yl)-pyrazin-2-yl]-azetidine-1-carboxylic acid tert-butyl ester (116) (897 mg, 2.81 mmol) at 0° C. and the resulting mixture was stirred at RT for 1 h. The mixture was concentrated under reduced pressure to give 2-azetidin-3-yl-3-(tetrahydro-pyran-4-yl)-pyrazine hydrochloride (117) (716 mg, yield 100%) which was used for the next step without further purification. ESI-MS (M+1): 220 calc. for $C_{12}H_{17}N_3O$ 219.

Preparation 38

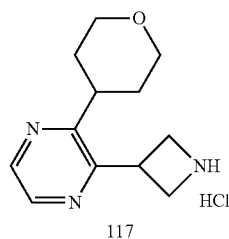

117

Step 1. 3-[3-(3,6-Dihydro-2H-Pyran-4-Yl)-Pyrazin-2-Yl]-Azetidine-1-Carboxylic Acid Tert-Butyl Ester (115)

To a solution of 3-(3-chloro-pyrazin-2-yl)-azetidine-1-carboxylic acid tert-butyl ester (7) (1.0 g, 3.7 mmol) in dioxane (16 mL) was added a solution of $Na_2CO_3$ (780 mg, 6.4 mmol) in 5 mL water, followed by additional of 4-(4,4,5,5-tetramethyl-[1,3,2]dioxaborolan-2-yl)-3,6-dihydro-2H-pyran (114) (purchased from WUXI APPTEC) (840 mg 4.0 mmol) and $Pd(dppf)Cl_2$ (80 mg). The resulting mixture was heated to reflux overnight under $N_2$ atmosphere. TLC showed that the staring material was consumed completely. The solution was filtered and the filtrate was concentrated to give the residue which was purified by ISCO silica gel column (10% to 80% EtOAc in petroleum ether) to give the product 3-[3-(3,6-dihydro-2H-pyran-4-yl)-pyrazin-2-yl]-azetidine-1-carboxylic acid tert-butyl ester (115) (938 mg, 2.96 mmol, yield 80%) as solid. ESI-MS (M+1): 318 calc. for $C_{17}H_{23}N_3O_3$ 317.

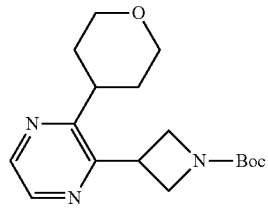

116

Step 2: 3-[3-(Tetrahydro-Pyran-4-Yl)-Pyrazin-2-Yl]-Azetidine-1-Carboxylic Acid Tert-Butyl Ester (116)

A mixture of (115) (938 mg, 2.96 mmol) and wet Pd—C (50%, 400 mg) in MeOH (30 mL) was stirred under $H_2$ (40 psi) at 30° C. overnight. Then the reaction mixture was filtered through CELITE® and washed with MeOH. The filtrate was concentrated to give the desired compound (116) (897 mg, 2.81 mmol, yield 95%). ESI-MS (M+1): 320 calc. for $C_{17}H_{25}N_3O_3$ 319.

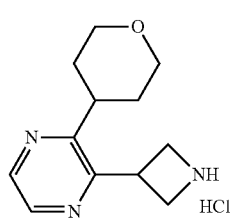

117

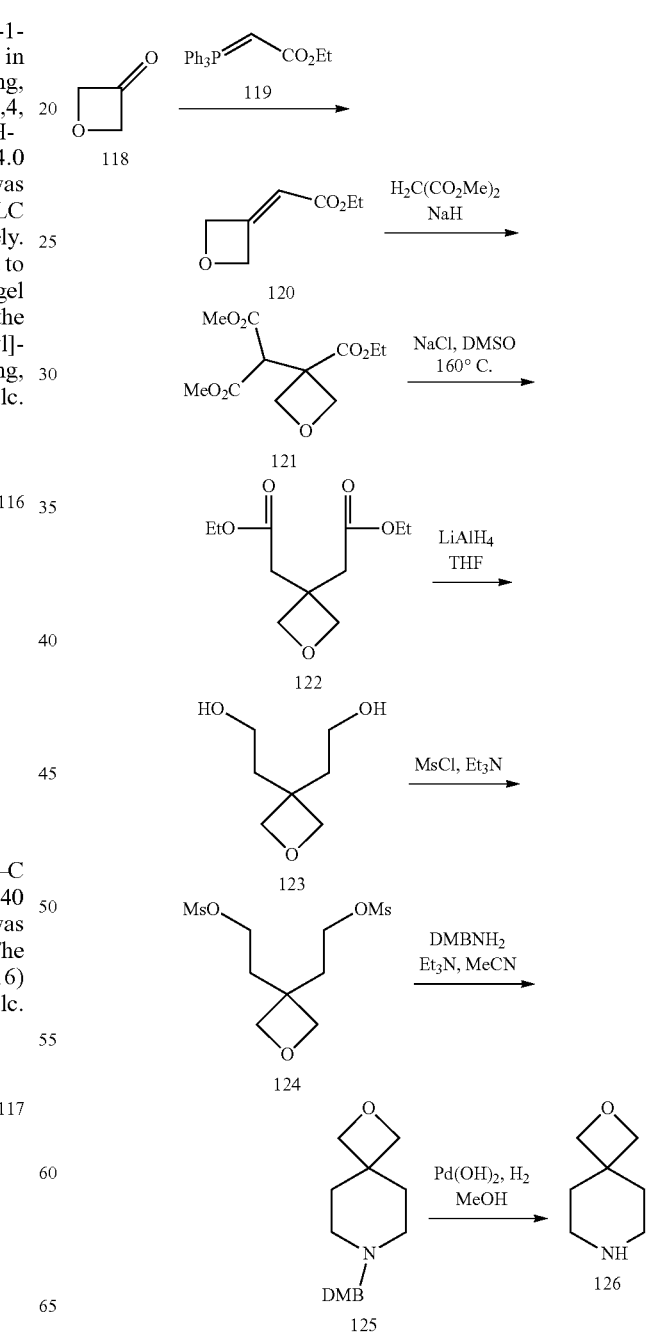

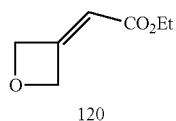

120

Step 1. Oxetan-3-Ylidene-Acetic Acid Ethyl Ester (120)

To a solution of oxetan-3-one (118) (5 g, 69.4 mmol) in CH$_2$Cl$_2$ (50 mL) at 0° C. was added ethyl 2-triphenylphosphoranylideneacetate (119) (26.6 g, 76.3 mmol). The solution was allowed to warm to RT and stirred for 15 min. The reaction mixture was then filtered through a pad of silica (washing with 30 percent EtOAc:Petrol ether), and the solvent removed under reduced pressure to give ethyl 2-(oxetan-3-ylidene)acetate (120) as a colourless viscous oil (8.15 g, 57.4 mmol, yield: 79%). ESI-MS (M+1): 142 calc. for C$_7$H$_{10}$O$_3$ 142.

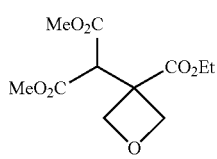

121

Step 2. 2-(3-Ethoxycarbonyl-Oxetan-3-Yl)-Malonic Acid Dimethyl Ester (121)

To a solution of oxetan-3-ylidene-acetic acid ethyl ester (120) (5.0 g, 35.2 mmol) in DMF (30 mL) at RT was added sodium hydride (60% wt in mineral oil) (4.2 g, 106 mmol). The mixture was stirred at RT for 60 min and malonic acid dimethyl ester (4.7 g, 35.2 mmol) was added. The reaction mixture was stirred at RT for 4 h. Then the reaction mixture was neutralized with saturated NH$_4$Cl (10 mL), diluted with EtOAc (30 mL) and water (30 mL). The aqueous phase was extracted with EtOAc (3×80 mL) and the combined organic extracts were washed with brine (100 mL), dried over MgSO$_4$, filtered, and concentrated to give the product (121) (8.0 g, 30.8 mmol, yield: 87%). ESI-MS (M+1): 261 calc. for C$_{11}$H$_{16}$O$_7$ 260.

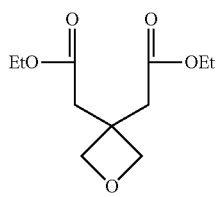

122

Step 3. (3-Ethoxycarbonylmethyl-Oxetan-3-Yl)-Acetic Acid Ethyl Ester (122)

To a solution of 2-(3-Ethoxycarbonyl-oxetan-3-yl)-malonic acid dimethyl ester (121) (5.0 g, 21.7 mmol) in DMSO (25 mL) was added NaCl (3.8 g, 65.1 mmol). The solution was heated at 160° C. for 3 h. The reaction mixture was diluted with EtOAc (30 mL) and water (30 mL). The aqueous phase was extracted with EtOAc (3×100 mL) and the combined organic extracts were washed with brine (100 mL), dried over MgSO$_4$, filtered, and concentrated to give the product (122) (2.3 g, 10 mmol, yield: 46%). ESI-MS (M+1): 231 calc. for C$_{11}$H$_{18}$O$_5$ 230.

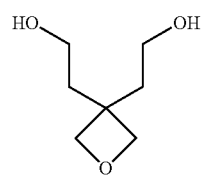

123

Step 4. 2-[3-(2-Hydroxy-Ethyl)-Oxetan-3-Yl]-Ethanol (123)

(3-Ethoxycarbonylmethyl-oxetan-3-yl)-acetic acid ethyl ester (122) (2.3 g, 10 mmol) was dissolved in 20 ml of THF. This solution was cooled down to 0° C. using an ice bath and AlLiH$_4$ (1.1 g, 30 mmol) was added by portions. The reaction mixture was stirred for 4 h at ambient temperature, and then saturated aqueous solution of ammonium chloride (20 mL) was added. THF was evaporated off under reduced pressure, then the reaction mixture was taken up in ethyl acetate. The organic phase was separated from the aqueous phase. This extraction was repeated one more time and then the organic phases were combined and washed with brine (100 mL), dried over MgSO$_4$, filtered, and concentrated to give the product (123) (1.3 g, 8.9 mmol, yield: 89%). ESI-MS (M+1): 147 calc. for C$_7$H$_{14}$O$_3$ 146.

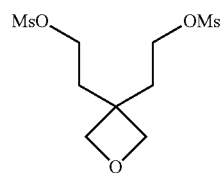

124

Step 5. Methanesulfonic Acid 2-[3-(2-Methanesulfonyloxy-Ethyl)-Oxetan-3-Yl]-Ethyl Ester (124)

To a solution of 2-[3-(2-Hydroxy-ethyl)-oxetan-3-yl]-ethanol (123) (1.3 g, 8.9 mmol) in CH$_2$Cl$_2$ (20 mL) at 0° C. was added Et$_3$N (2.7 g, 26.7 mmol) and methanesulfonyl chloride (2.0 g, 17.8 mmol). The solution was allowed to warm to RT and stirred for 15 min. The reaction mixture was diluted with water (80 mL). The aqueous phase was extracted with CH$_2$Cl$_2$ (3×50 mL) and the combined organic extracts were washed with brine (100 mL), dried over MgSO$_4$, filtered, and concentrated to give the product (124) (2.0 g, 6.6 mmol, yield: 74%). ESI-MS (M+1): 303 calc. for C$_9$H$_{18}$O$_7$S$_2$ 302.

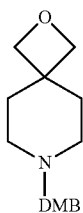

Step 6. 7-(2,4-Dimethoxy-Benzyl)-2-Oxa-7-Aza-Spiro[3.5]Nonane (125)

To a solution of (124) (2.0 g, 6.6 mmol) in MeCN (20 mL) were added 2,4-dimethoxy-benzylamine (1.2 g, 7.3 mmol) and Et$_3$N (2.0 g, 19.8 mmol). The solution was allowed to heat at reflux for 12 h. The reaction mixture was then filtered through a pad of silica (washing with 30 percent EtOAc: Petrol ether), and the solvent removed under reduced pressure to give the product (125) (1.2 g, 4.3 mmol, yield: 65%). ESI-MS (M+1): 278 calc. for $C_{16}H_{23}NO_3$ 277.

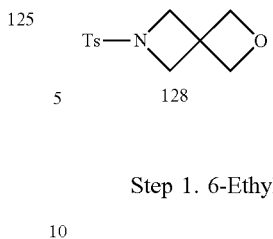

Step 7. 2-Oxa-7-Aza-Spiro[3.5]Nonane (126)

To a solution of 7-(2,4-Dimethoxy-benzyl)-2-oxa-7-aza-spiro[3.5]nonane (125) (300 mg, 1.1 mmol) in MeOH (10 mL) was added Pd(OH)$_2$ (300 mg). The reaction solution was stirred at RT overnight under H$_2$ atmosphere. LCMS showed that most of the staring material was consumed. The mixture was filtered and concentrated to give the product (126) (112 mg, 0.88 mmol, yield: 80%). ESI-MS (M+1): 128 calc. for $C_7H_{13}NO$ 127.

Preparation 39

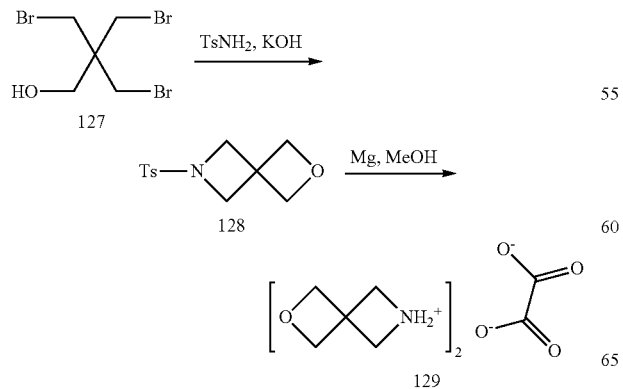

Step 1. 6-Ethyl-2-Oxa-6-Aza-Spiro[3.3]Heptanes (128)

To a solution of 3-bromo-2,2-bis(bromomethyl)propanol (127) (3.25 g, 10 mmol) and potassium hydroxide (1.12 g, 20 mmol, in 10 mL water) in EtOH (20 mL) were added toluene-4-sulfonamide (3.76 g, 22 mmol). The reaction mixture was refluxed for 2 h, evaporated to remove EtOH then diluted with EAOAc (20 mL), washed with H$_2$O (20 mL). The organic layer was washed with brine (20 mL), dried over Na$_2$SO$_4$, and filtered, evaporated to give the product to give 6-(toluene-4-sulfonyl)-2-oxa-6-aza-spiro [3.3]heptane (128) (1.6 g, 6.3 mmol, yield: 63%).

ESI-MS (M+1): 128 calc. for $C_7H_{13}NO$ 127.

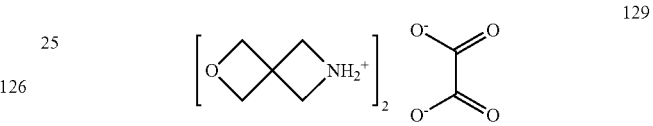

Step 2. 2-Oxa-6-Aza-Spiro[3.3]Heptane Oxalate Salt (129)

A mixture of 6-(toluene-4-sulfonyl)-2-oxa-6-aza-spiro [3.3]heptane (128) (1.27 g, 5 mmol) in MeOH (10 mL) was added magnesium chips. The mixture was reacted using ultrasound at RT for 20 mins. Oxalic acid was added and the mixture was stirred for 15 min, then concentrated to give oxalate salt (129) (1.06 g, 3.68 mmol, yield: 73.6%).

$^1$H NMR: (D$_2$O, 400 MHz): δ (ppm) 4.76 (s, 4H), 4.23 (s, 4H). ESI-MS (M+1): 101 calc. for $C_5H_9NO$ 100.

Preparation 40

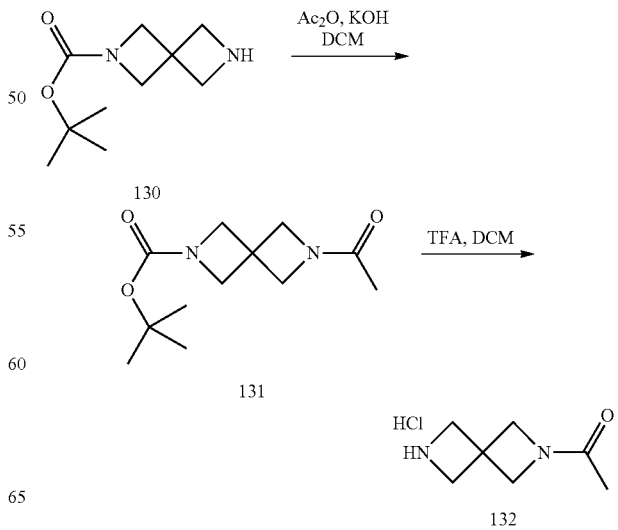

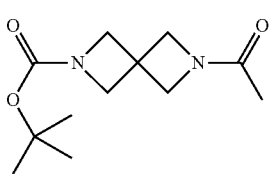

131

Step 1.
6-Acetyl-2,6-Diaza-Spiro[3.3]Heptane-2-Carboxylic Acid Tert-Butyl Ester (131)

To a solution of 2,6-diaza-spiro[3.3]heptane-2-carboxylic acid tert-butyl ester (130) (purchased from WUXI APPTEC®) ((500 mg, 2.73 mmol) in CH$_2$Cl$_2$ (10 mL) were added KOH (459 mg, 8.19 mmol) and Ac$_2$O (279 mg, 2.73 mmol). The reaction mixture was stirred at RT for 1 h, then diluted with CH$_2$Cl$_2$ (20 mL), washed with H$_2$O (20 mL). The organic layer was washed with brine (20 mL), dried over Na$_2$SO$_4$, and filtered, evaporated to give the product (131) (510 mg, 2.13 mmol, yield: 78%). ESI-MS (M+1): 241 calc. for C$_{12}$H$_{20}$N$_2$O$_3$ 240.

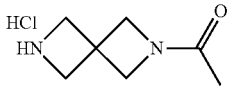

132

Step 2. 1-(2,6-Diaza-Spiro[3.3]Hept-2-Yl)-Ethanone Hydrochloride (132)

To a solution of 6-Acetyl-2,6-diaza-spiro[3.3]heptane-2-carboxylic acid tert-butyl ester (131) (300 mg, 1.33 mmol) in CH$_2$Cl$_2$ (10 mL) were added TFA (388 mg, 4.0 mmol). The reaction mixture was stirred at RT for 1 h, then diluted with CH$_2$Cl$_2$ (20 mL), washed with H$_2$O (20 mL). The organic layer was washed with brine (20 mL), dried over Na$_2$SO$_4$, and filtered, evaporated to give the product (132) (176 mg, 1.0 mmol, yield: 75%). ESI-MS (M+1): 141 calc. for C$_7$H$_{12}$N$_2$O 140.

Preparation 41

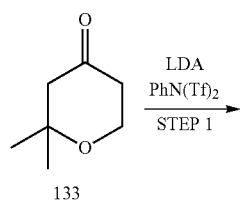

133

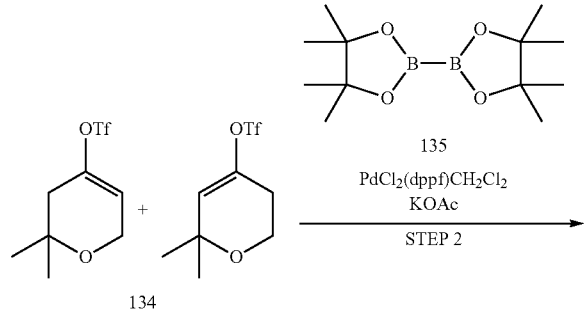

134

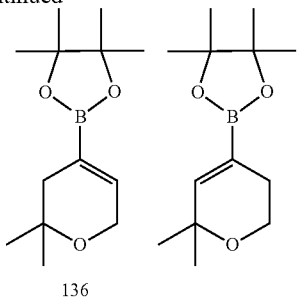

136 ratio: 80.4:19.6

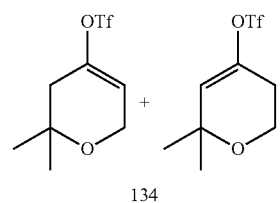

134

Step 1. 2,2-Dimethyl-3,6-Dihydro-2H-Pyran-4-Yl Trifluoromethanesulfonate and 6,6-Dimethyl-3,6-Dihydro-2H-Pyran-4-Yl Trifluoromethanesulfonate (134)

A solution of 2,2-dimethyltetrahydropyran-4-one (133) (115 g, 0.9 mol, 1.0 eq.) in anhydrous THF (600 mL) was cooled to −78° C. and to it was added LDA (2.0 M, 538 mL, 1.08 mol, 1.2 eq.) drop wise under N$_2$ keeping the internal temperature below −65° C. The resulting solution was stirred at −78° C. for 20 min. A solution of N-phenyl-bis(trifluoromethanesulfonimide) (353 g, 0.99 mol, 1.1 eq.) in anhydrous THF (1900 mL) was added to the above solution slowly keeping the internal temperature below −65° C. The reaction mixture was warmed to room temperature slowly and stirred overnight. The reaction was quenched with saturated aqueous sodium bicarbonate solution, and extracted with MTBE (2 L×2). The combined organic layers was washed with 10% aqueous NaOH solution (1 L×2), brine (500 mL×2), dried over Na$_2$SO$_4$, filtered and concentrated to give crude title triflate product mixture as dark brown oil. The crude product was extracted with hexanes (2 L×5) and the combined hexanes extracts was purified by column chromatography (directly loaded onto silica gel, Hexanes→15% ethyl acetate in hexanes, R$_f$=0.6, visualized with KMnO$_4$ stain) to give 200 g of the triflate product mixture (134) (a mixture of 2,2-dimethyl-3,6-dihydro-2H-pyran-4-yl trifluoromethanesulfonate and 6,6-dimethyl-3,6-dihydro-2H-pyran-4-yl trifluoromethanesulfonate ratio=80.6:19.4 by GCMS) as a light yellow liquid (~90% purity by GC-MS and $^1$H NMR). This was taken to the next step without further purification.

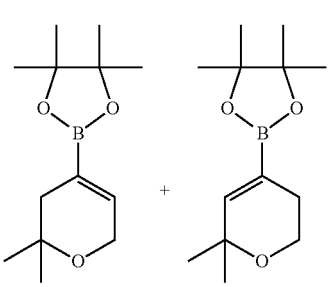

136

Step 2. 2-(2,2-Dimethyl-3,6-Dihydro-2H-Pyran-4-Yl)-4,4,5,5-Tetramethyl-1,3,2-Dioxaborolane and 2-(6,6-Dimethyl-3,6-Dihydro-2H-Pyran-4-Yl)-4,4,5,5-Tetramethyl-1,3,2-Dioxaborolane (136)

A mixture of compound 2,2-dimethyl-3,6-dihydro-2H-pyran-4-yl trifluoromethanesulfonate and 6,6-dimethyl-3,6-dihydro-2H-pyran-4-yl trifluoromethanesulfonate (134) (200 g, 0.77 mol, 1.0 eq.), bis(pinacolato)diboron (135) (195 g, 0.77 mol, 1.0 eq.), and potassium acetate (151 g, 1.54 mol, 2.0 eq.) in dioxane (2 L) was degassed for 15 min, to it was added 1,1'-bis(diphenylphosphino)ferrocene-palladium(II) dichloride dichloromethane complex (19 g, 0.023 mol, 0.03 eq.) and the reaction mixture was degassed again for 15 min. The reaction mixture was heated to 80° C. overnight, cooled, filtered through a medium fritted funnel, and washed with MTBE (300 mL×4). The organic extracts were combined and concentrated under reduced pressure. The crude product mixture (136) was cooled using an ice bath, stirred with an overhead stirrer and to it was added aqueous 2M NaOH solution (2 L) keeping the internal temperature below 15° C. The basic aqueous solution was extracted with MTBE (250 mL×3), and the organic extracts were discarded. The aqueous phase was cooled using an ice bath and the pH was adjusted to 3 to 5 with concentrated HCl keeping the internal temperature below 10° C. The heterogeneous solution (off-white solid precipitated out at pH 3-5) was extracted with EtOAc (3 L and 1.5 L). The combined organic layer was washed with water (1 L), brine (1 L), dried over $Na_2SO_4$, filtered and concentrated. The crude product mixture (136) was purified by column chromatography (Hexanes→15% ethyl acetate in hexanes, $R_f$=0.5, visualized on $KMnO_4$) to give 125 g of 2-(2,2-dimethyl-3,6-dihydro-2H-pyran-4-yl)-4,4,5,5-tetramethyl-1,3,2-dioxaborolane and 2-(6,6-dimethyl-3,6-dihydro-2H-pyran-4-yl)-4,4,5,5-tetramethyl-1,3,2-dioxaborolane mixture (136) as a white solid (58% overall yield, >97% purity by GCMS and $^1$H NMR, The ratio of regioisomers was found to be 80.4:19.6).

GCMS: >97%
$^1$H NMR (300 MHz, $CDCl_3$) δ 6.46-6.43 (m, 1H), 4.06 (q, 2H, J=3.0 Hz), 1.96-1.94 (m, 2H), 1.20 (s, 12H), 1.09 (s, 6H)
GCMS: 239 (M+1); calcd for $C_{13}H_{23}BO_3$: 238.13

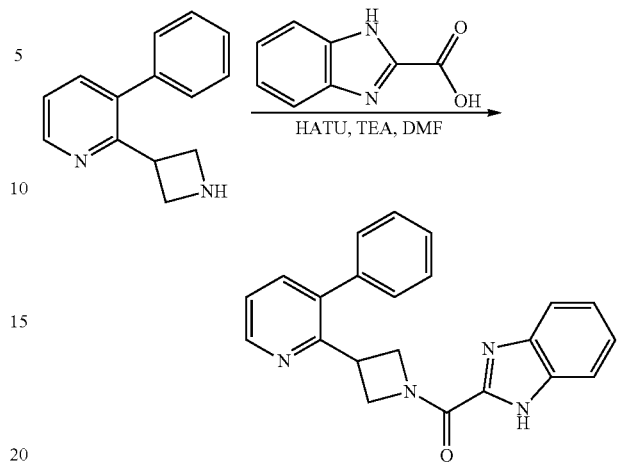

SCHEME 1

Example 1.1: (1H-Benzoimidazol-2-Yl)-[3-(3-Phenyl-Pyridin-2-Yl)-Azetidin-1-Yl]-Methanone To a mixture of 1H-benzoimidazole-2-carboxylic acid (124 mg, 0.76 mmol) in DMF (5 mL) was added TEA (152 mg, 1.5 mmol) and HATU (347 mg, 0.92 mmol). The reaction mixture was stirred for 5 min and 2-azetidin-3-yl-3-phenyl-pyridine hydrochloride (100 mg, 0.76 mmol) was added. The reaction mixture was stirred at RT overnight. The mixture was diluted with water (10 mL), and extracted with EtOAc (2×20 mL). The combined organic extracts were washed with water (5 mL) and brine (5 mL), dried over $Na_2SO_4$, and filtered. The filtrate was evaporated in vacuo and the residue was purified by column chromatography to give (1H-benzoimidazol-2-yl)-[3-(3-phenyl-pyridin-2-yl)-azetidin-1-yl]-methanone (100 mg, 0.28 mmol, 59% yield) as a light yellow solid.

The following Table 13A lists compounds of Examples 1.1 to 1.17, which were made analogous to Scheme 1 by using the appropriate materials and reaction conditions, which are listed in Table 13B. The NMR of the Examples are listed in Table 13C.

TABLE 13A

EXAMPLES 1.1 TO 1.17

| Ex. # | Structure | Chemical Name | ESI-MS (M + 1) | $IC_{50}$ (uM) |
|---|---|---|---|---|
| 1.1 | 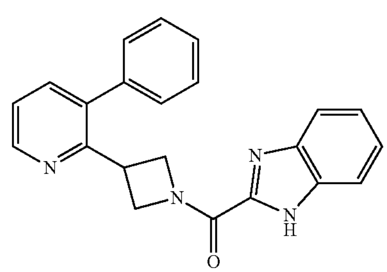 | (1H-Benzoimidazol-2-yl)-[3-(3-phenyl-pyridin-2-yl)-azetidin-1-yl]-methanone | 355 | 0.0219 |

TABLE 13A-continued

EXAMPLES 1.1 TO 1.17

| Ex. # | Structure | Chemical Name | ESI-MS (M + 1) | IC$_{50}$ (uM) |
|---|---|---|---|---|
| 1.2 | 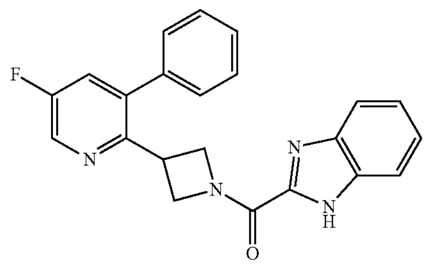 [SMILES: O=C(c1nc2ccccc2[nH]1)N1CC(c2ncc(F)cc2-c2ccccc2)C1] | (1H-Benzoimidazol-2-yl)[3-(5-fluoro-3-phenyl-pyridin-2-yl)-azetidin-1-yl]-methanone | 373 | 0.843 |
| 1.3 | 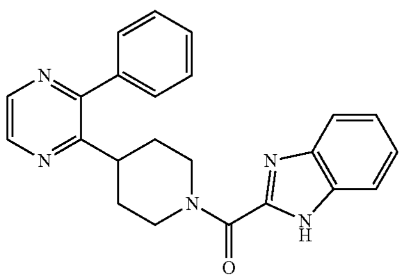 [SMILES: O=C(c1nc2ccccc2[nH]1)N1CCC(c2nccnc2-c2ccccc2)CC1] | (1H-benzoimidazol-2-yl)-[4-(3-phenyl-pyrazin-2-yl)-piperidin-1-yl]-methanone | 384 | 0.092 |
| 1.4 | 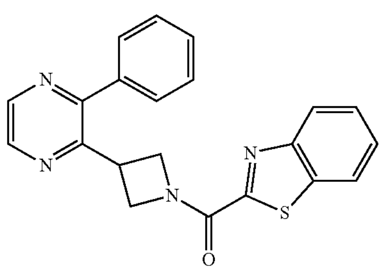 [SMILES: O=C(c1nc2ccccc2s1)N1CC(c2nccnc2-c2ccccc2)C1] | Benzothiazol-2-yl-[3-(3-phenyl-pyrazin-2-yl)-azetidin-1-yl]-methanone | 373 | 0.446 |
| 1.5 | 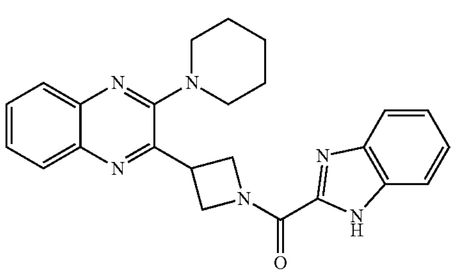 [SMILES: O=C(c1nc2ccccc2[nH]1)N1CC(c2nc3ccccc3nc2N2CCCCC2)C1] | (1H-Benzoimidazol-2-yl)-[3-(3-piperidin-1-yl-quinoxalin-2-yl)-azetidin-1-yl]-methanone | 413 | 0.0271 |
| 1.6 | 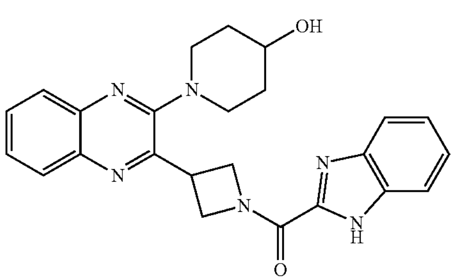 [SMILES: O=C(c1nc2ccccc2[nH]1)N1CC(c2nc3ccccc3nc2N2CCC(O)CC2)C1] | (1H-Benzoimidazol-2-yl)-{3-[3-(4-hydroxy-piperidin-1-yl)-quinoxalin-2-yl]-azetidin-1-yl}-methanone | 429 | 0.0115 |

TABLE 13A-continued

EXAMPLES 1.1 TO 1.17

| Ex. # | Structure | Chemical Name | ESI-MS (M + 1) | IC$_{50}$ (uM) |
|---|---|---|---|---|
| 1.7 | 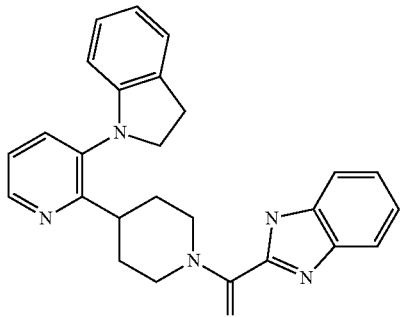 | (1H-Benzoimidazol-2-yl)-[3-(2,3-dihydro-indol-1-yl)-3',4',5',6'-tetrahydro-2'H-[2,4']bipyridinyl-1'-yl]-methanone | 424 | 0.92 |
| 1.8 | 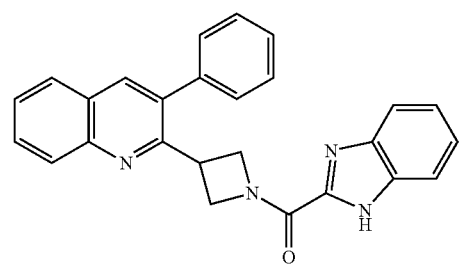 [SMILES: O=C(c1nc2ccccc2[nH]1)N1CC(c2nc3ccccc3cc2-c2ccccc2)C1] | (1H-Benzoimidazol-2-yl)-[3-(3-phenyl-quinolin-2-yl)-azetidin-1-yl]-methanone | 405 | 0.0834 |
| 1.9 | 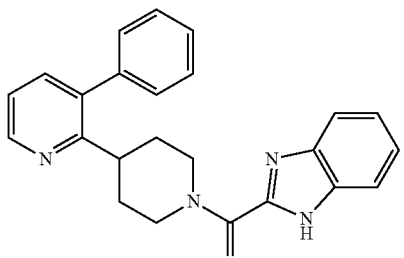 | (1H-Benzoimidazol-2-yl)-(3-phenyl-3',4',5',6'-tetrahydro-2'H-[2,4]bipyridinyl-1'-yl)-methanone | 383 | 0.0217 |
| 1.10 | 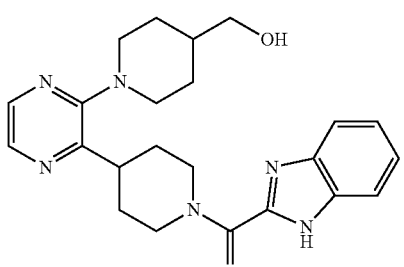 | (1H-Benzoimidazol-2-yl)-{4-[3-(4-hydroxymethyl-piperidin-1-yl)-pyrazin-2-yl]-piperidin-1-yl}-methanone | 421 | 0.0098 |
| 1.11 | 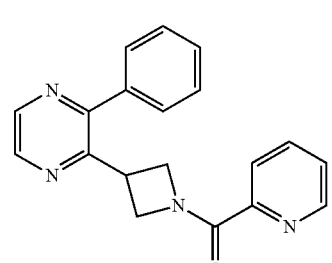 | (3-(3-phenylpyrazin-2-yl)azetidin-1-yl)(pyridin-2-yl)methanone | 317 | 0.828 |

TABLE 13A-continued

EXAMPLES 1.1 TO 1.17

| Ex. # | Structure | Chemical Name | ESI-MS (M + 1) | IC$_{50}$ (uM) |
|---|---|---|---|---|
| 1.12 | 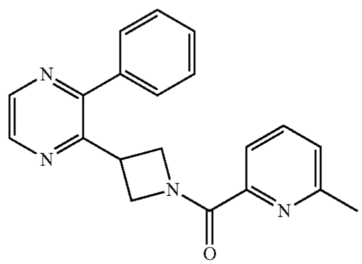 [SMILES: Cc1cccc(C(=O)N2CC(c3nccnc3-c3ccccc3)C2)n1] | (6-methylpyridin-2-yl)(3-(3-phenylpyrazin-2-yl)azetidin-1-yl)methanone | 331 | 3.67 |
| 1.13 | 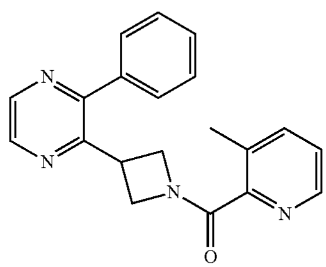 [SMILES: Cc1cccnc1C(=O)N1CC(c2nccnc2-c2ccccc2)C1] | (3-methylpyridin-2-yl)(3-(3-phenylpyrazin-2-yl)azetidin-1-yl)methanone | 331 | 11.9 |
| 1.14 | 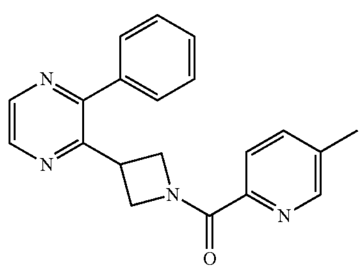 [SMILES: Cc1ccc(C(=O)N2CC(c3nccnc3-c3ccccc3)C2)nc1] | (5-methylpyridin-2-yl)(3-(3-phenylpyrazin-2-yl)azetidin-1-yl)methanone | 331 | 2.03 |
| 1.15 | 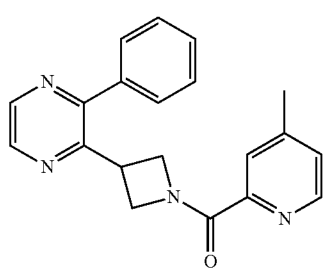 [SMILES: Cc1ccnc(C(=O)N2CC(c3nccnc3-c3ccccc3)C2)c1] | (4-methylpyridin-2-yl)(3-(3-phenylpyrazin-2-yl)azetidin-1-yl)methanone | 331 | 4.71 |
| 1.16 | 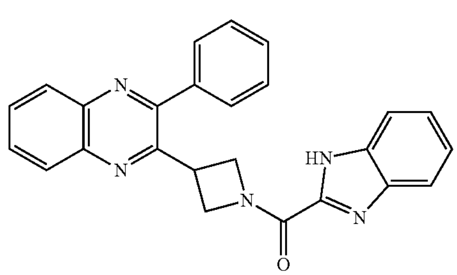 [SMILES: O=C(c1nc2ccccc2[nH]1)N1CC(c2nc3ccccc3nc2-c2ccccc2)C1] | (1H-Benzoimidazol-2-yl)-[3-(3-phenyl-quinoxalin-2-yl)-azetidin-1-yl]-methanone | 406 | 0.0335 |

TABLE 13A-continued

EXAMPLES 1.1 TO 1.17

| Ex. # | Structure | Chemical Name | ESI-MS (M + 1) | IC$_{50}$ (uM) |
|---|---|---|---|---|
| 1.17 | 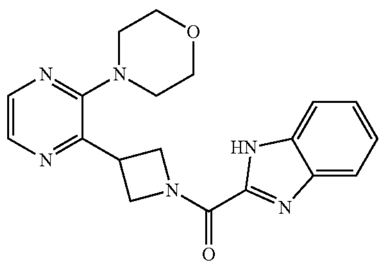 [SMILES: O=C(c1nc2ccccc2[nH]1)N1CC(c2nccnc2N2CCOCC2)C1] | (1H-Benzoimidazol-2-yl)-[3 (3-morpholin-4-yl-pyrazin-2-yl)-azetidin-1-yl]-methanone | 365 | 0.14 |

TABLE 13B

STARTING MATERIALS AND REACTION CONDITION FOR PREPARATION OF EXAMPLES 1.1 TO 1.17

| Ex. # | Starting Material 1 | Starting Material 2 | Reaction Condition |
|---|---|---|---|
| 1.1 | PREPARATION 24 | PREPARATION 6 | HATU, TEA, DMF |
| 1.2 | PREPARATION 27 | PREPARATION 6 | HATU, TEA, DMF |
| 1.3 | PREPARATION 28 | PREPARATION 6 | HATU, TEA, DMF |
| 1.4 | PREPARATION 7 | | HATU, TEA, DMF |

TABLE 13B-continued

STARTING MATERIALS AND REACTION CONDITION FOR
PREPARATION OF EXAMPLES 1.1 TO 1.17

| Ex. # | Starting Material 1 | Starting Material 2 | Reaction Condition |
|---|---|---|---|
| 1.5 | 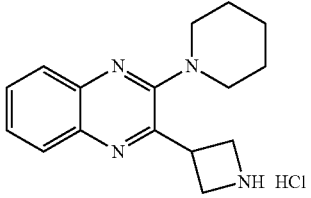<br>PREPARATION 29 | 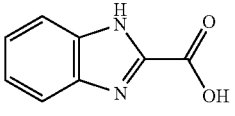<br>PREPARATION 6 | HATU, TEA, DMF |
| 1.6 | 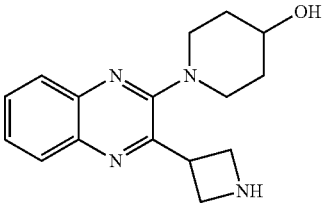<br>PREPARATION 29 | 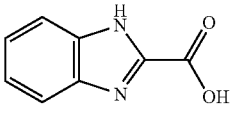<br>PREPARATION 6 | HATU, TEA, DMF |
| 1.7 | 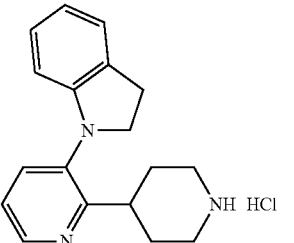<br>PREPARATION 30 | 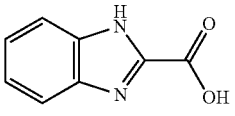<br>PREPARATION 6 | HATU, TEA, DMF |
| 1.8 | 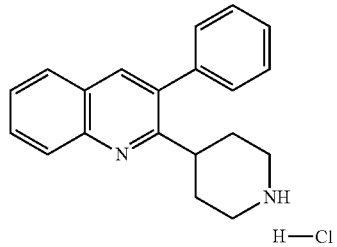<br>PREPARATION 31 | 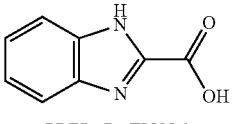<br>PREPARATION 6 | HATU, TEA, DMF |
| 1.9 | 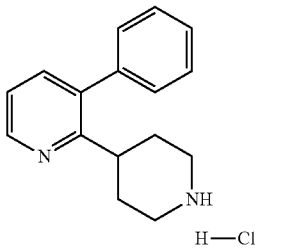<br>PREPARATION 32 | 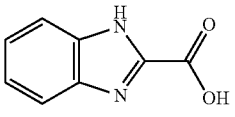<br>PREPARATION 6 | HATU, TEA, DMF |

US 9,718,803 B2

TABLE 13B-continued

STARTING MATERIALS AND REACTION CONDITION FOR
PREPARATION OF EXAMPLES 1.1 TO 1.17

| Ex. # | Starting Material 1 | Starting Material 2 | Reaction Condition |
|---|---|---|---|
| 1.10 | PREPARATION 12 | PREPARATION 6 | HATU, TEA, DMF |
| 1.11 | PREPARATION 7 | Alfa Aesar | HATU, TEA, THF |
| 1.12 | PREPARATION 7 | Alfa Aesar | HATU, TEA, THF |
| 1.13 | PREPARATION 7 | Alfa Aesar | HATU, TEA, THF |
| 1.14 | PREPARATION 7 | Alfa Aesar | HATU, TEA, THF |
| 1.15 | PREPARATION 7 | Alfa Aesar | HATU, TEA, THF |

TABLE 13B-continued

STARTING MATERIALS AND REACTION CONDITION FOR
PREPARATION OF EXAMPLES 1.1 TO 1.17

| Ex. # | Starting Material 1 | Starting Material 2 | Reaction Condition |
|---|---|---|---|
| 1.16 | PREPARATION 20 | PREPARATION 6 | HATU, TEA, DMF |
| 1.17 | PREPARATION 4 | PREPARATION 6 | HATU, TEA, DCM |

TABLE 13C

1H NMR δ (PPM) DATA FOR EXAMPLES 1.1 TO 1.17

| Ex. # | Structure | NMR |
|---|---|---|
| 1.1 | 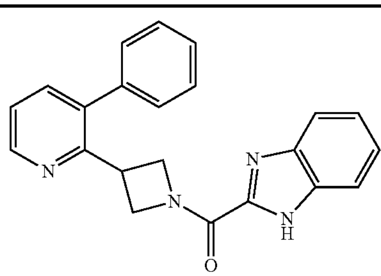 | (DMSO, 400 MHz): 8.61 (s, 1 H); 7.72-7.70 (m, 2 H); 7.66-7.20 (m, 10 H); 4.88-4.86 (m, 2 H); 4.20-4.13 (m, 3 H). |
| 1.2 | 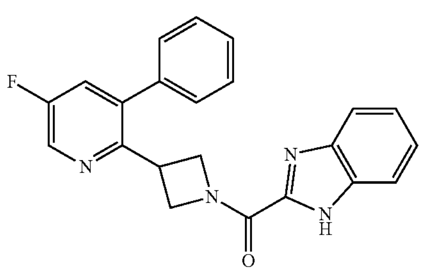 [SMILES: O=C(c1nc2ccccc2[nH]1)N1CC(c2ncc(F)cc2-c2ccccc2)C1] | (CDCl$_3$, 400 MHz): 8.49 (d, J = 2.4 Hz, 1H); 8.13-8.10 (m, 1H); 7.67-7.66 (m, 2H); 7.55-7.50 (m, 3H); 7.45-7.43 (m, 2H); 7.37-7.35 (m, 2H); 4.99-4.95 (m, 1H); 4.78-4.74 (m, 1H); 4.39-4.37 (m, 1 H); 3.34-4.25 (m, 1H); 4.17-4.13 (m, 1H). |
| 1.3 | 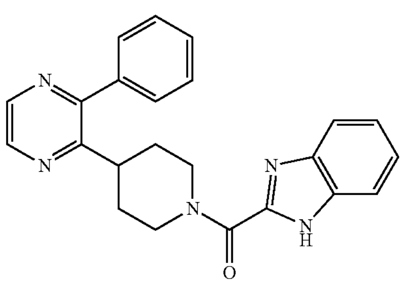 [SMILES: O=C(c1nc2ccccc2[nH]1)N1CCC(c2nccnc2-c2ccccc2)CC1] | (CDCl$_3$, 400 MHz): 8.50 (s, 2H); 7.70-7.67 (m, 2H); 7.56-7.51 (m, 5H); 7.37-7.26 (m, 2H); 6.06-6.03 (m, 1H); 4.91-4.88 (m, 1H); 3.39-3.28 (m, 2H); 2.90-2.84 (m, 1H); 2.17-2.11 (m, 2H); 2.01-1.90 (m, 2H). |

TABLE 13C-continued

1H NMR δ (PPM) DATA FOR EXAMPLES 1.1 TO 1.17

| Ex. # | Structure | NMR |
|---|---|---|
| 1.4 | 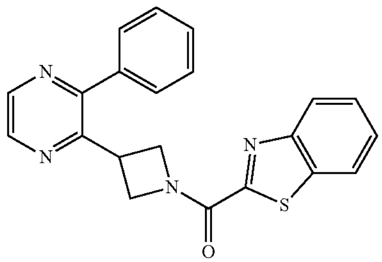 [SMILES: O=C(c1nc2ccccc2s1)N1CC(c2nccnc2-c2ccccc2)C1] | (CDCl$_3$, 400 MHz): 8.60 (dd, J = 2.4, 17.2 Hz, 2H); 8.06 (d, J = 7.6 Hz, 1H); 7.96 (d, J = 7.2 Hz, 1H); 7.56-7.45 (m, 7H); 5.15-5.06 (m, 2H); 4.53-4.42 (m, 2H); 4.39-4.32 (m, 1H). |
| 1.5 | 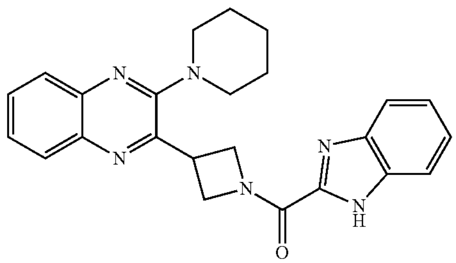 [SMILES: O=C(c1nc2ccccc2[nH]1)N1CC(c2nc3ccccc3nc2N2CCCCC2)C1] | (DMSO, 400 MHz): 7.93-7.91 (m, 1H); 7.77-7.70 (m, 2H); 7.63-7.61 (m, 1H); 7.55-7.49 (m, 2H); 7.28-7.22 (m, 2H); 5.13-5.11 (m, 1H); 5.01-5.00 (m, 1H); 4.54-4.53 (m, 1H); 4.42-4.40 (m, 2H); 3.18-3.16 (m, 4H); 1.71-1.68 (m, 4H); 1.61-1.59 (m, 2H). |
| 1.6 | 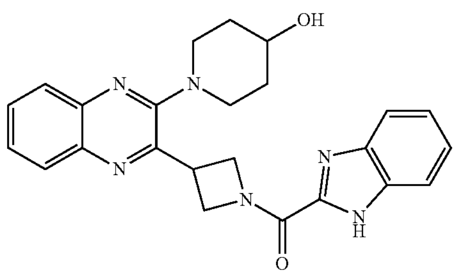 [SMILES: O=C(c1nc2ccccc2[nH]1)N1CC(c2nc3ccccc3nc2N2CCC(O)CC2)C1] | (DMSO, 400 MHz): 7.92 (d, J = 7.6 Hz, 1H); 7.77-7.71 (m, 2H); 7.65-7.63 (m, 1H); 7.55-7.50 (m, 2H); 7.30-7.20 (m, 2H); 5.13-5.10 (m, 1H); 4.73 (d, J = 4.0 Hz, 1H); 4.54-4.48 (m, 1H); 4.46-4.41 (m, 2H); 3.70-3.69 (m, 3H); 3.49-3.44 (m, 2H); 2.99-2.95 (m, 2H); 1.95-1.91 (m, 2H); 1.63-1.58 (m, 2H). |
| 1.7 | 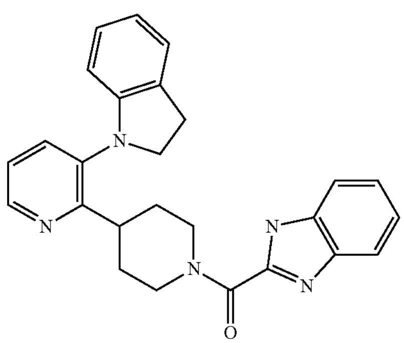 [SMILES: O=C(c1nc2ccccc2[nH]1)N1CCC(c2ncccc2N2CCc3ccccc32)CC1] | (CDCl$_3$, 400 MHz): 8.53 (d, J = 4.8 Hz, 1H); 8.30 (d, J = 8.4, 1H); 7.78-7.68 (m, 3H); 7.52-7.45 (m, 2H); 7.37-7.31 (m, 1H); 7.10-7.03 (m, 1H); 6.91-6.87 (m, 1H); 6.34 (d, J = 7.6 Hz, 1H); 4.89-4.86 (m, 1H); 4.30-4.27 (m, 1H); 3.82-3.73 (m, 3H); 3.50-3.38 (m, 1H); 3.34-3.25 (m, 2H); 2.95-2.89 (m, 1H); 2.53-2.43 (m, 1H); 2.33-2.29 (m, 1H); 1.96-1.94 (m, 1H); 1.89-1.85 (m, 1H). |
| 1.8 | 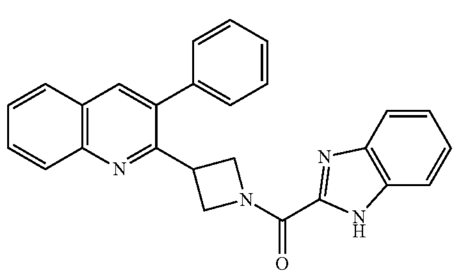 [SMILES: O=C(c1nc2ccccc2[nH]1)N1CC(c2nc3ccccc3cc2-c2ccccc2)C1] | (DMSO, 400 MHz): 8.22 (s, 1); 8.06 (d, J = 8.8 Hz, 1H); 7.99 (d, J = 8.0 Hz, 1H); 7.74-7.69 (m, 2H); 7.60-7.45 (m, 8H); 7.27-7.21 (m, 2H); 5.08-5.06 (m, 1H); 4.88-4.86 (m, 1H); 4.35-4.33 (m, 2H); 4.14-4.13 (m, 1H). |

TABLE 13C-continued

1H NMR δ (PPM) DATA FOR EXAMPLES 1.1 TO 1.17

| Ex. # | Structure | NMR |
|---|---|---|
| 1.9 | 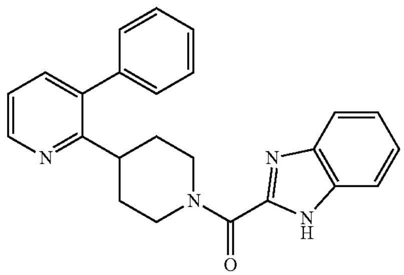 [SMILES: O=C(c1nc2ccccc2[nH]1)N1CCC(c2ncccc2-c2ccccc2)CC1] | (CD$_3$OD, 400 MHz): 8.73-8.71 (m, 1H); 8.35-8.33 (m, 1H); 7.91-7.88 (m, 1H); 7.68-7.88 (m, 1H); 7.58-7.54 (m, 3H); 7.45-7.43 (m, 2H); 7.40-7.37 (m, 2H); 5.07-5.02 (m, 1H); 4.80-4.71 (m, 1H); 3.48-3.45 (m, 1H); 3.28-3.25 (m, 1H); 2.90-2.80 (m, 1H); 2.15-2.00 (m, 4H). |
| 1.10 | 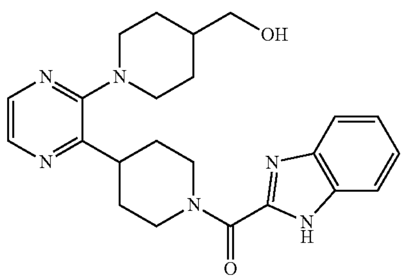 [SMILES: O=C(c1nc2ccccc2[nH]1)N1CCC(c2nccnc2N2CCC(CO)CC2)CC1] | (CD$_3$OD, 400 MHz): 8.14-8.12 (m, 1H); 8.10-8.08 (m, 1H); 7.76-7.74 (m, 2H); 7.50-7.48 (m, 2H); 4.35 (d, J = 6.8 Hz, 1H); 3.50 (d, J = 6.4 Hz, 2H); 3.46-3.43 (m, 4H); 3.31-3.30 (m, 2H); 3.15 (s, 1H); 2.92-2.89 (m, 2H); 1.99-1.98 (m, 3H); 1.89 (d, J = 12.8 Hz, 3H); 1.71-1.48 (m, 2H). |
| 1.11 | 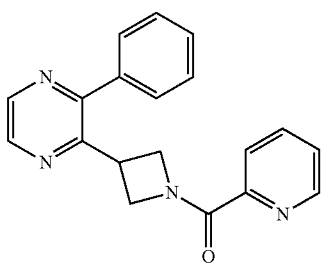 [SMILES: O=C(c1ccccn1)N1CC(c2nccnc2-c2ccccc2)C1] | (CD$_3$OD, 400 MHz): 8.65 (d, J = 2.4 Hz, 1H), 8.53 (d, J = 2.4 Hz, 2H), 7.98-7.89 (m, 2H), 7.52-7.47 (m, 6H), 4.90-4.86 (m, 2H), 4.39-4.26 (m, 3H). |
| 1.12 | 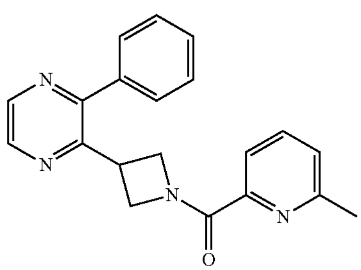 [SMILES: Cc1cccc(C(=O)N2CC(c3nccnc3-c3ccccc3)C2)n1] | (CD$_3$OD, 400 MHz): 8.64 (d, J = 2.4 Hz, 1H), 8.53 (d, J = 2.8 Hz, 1H), 7.91-7.87 (m, 1H), 7.80 (d, J = 8 Hz, 1H), 7.51-7.46 (m, 6H), 4.85-4.83 (m, 2H), 4.37-4.31 (m, 3H), 2.54 (s, 3H). |
| 1.13 | 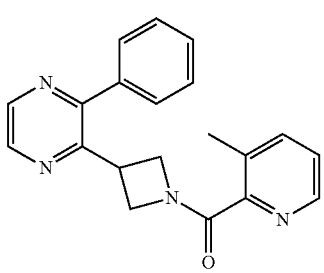 [SMILES: Cc1cccnc1C(=O)N1CC(c2nccnc2-c2ccccc2)C1] | (CD$_3$OD, 400 MHz): 8.53 (d, J = 2.4 Hz, 1H), 8.42 (d, J = 4.8 Hz, 1H), 8.40 (s, 1H), 7.91-7.89 (m, 1H), 7.51-7.43 (m, 6H), 4.39-4.29 (m, 5H), 2.45 (s, 3H). |

TABLE 13C-continued
1H NMR δ (PPM) DATA FOR EXAMPLES 1.1 TO 1.17
| Ex. # | Structure | NMR |
|---|---|---|
| 1.14 | 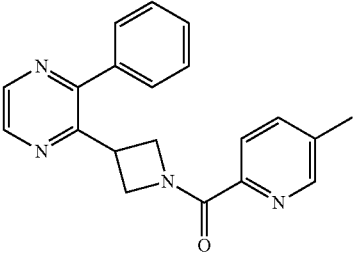 [SMILES: Cc1ccc(C(=O)N2CC(c3nccnc3-c3ccccc3)C2)nc1] | (CD$_3$OD, 400 MHz): 8.63 (d, J = 2.4 Hz, 1H), 8.52 (d, J = 2.8 Hz, 1H), 8.41 (s, 1H), 7.87 (d, J = 8.4 Hz, 1H), 7.76-7.73 (m, 1H), 7.50-7.46 (m, 5H), 4.85-4.84 (m, 2H), 4.37-4.26 (m, 3H), 2.36 (s, 3H). |
| 1.15 | 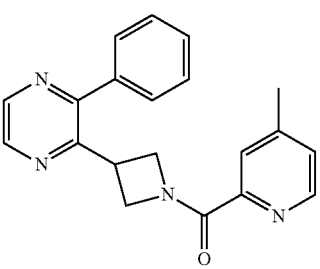 [SMILES: Cc1ccnc(C(=O)N2CC(c3nccnc3-c3ccccc3)C2)c1] | (CD$_3$OD, 400 MHz): 9.48 (d, J = 2.4 Hz, 1H), 9.42 (d, J = 2.8 Hz, 1H), 9.22 (d, J = 5.2 Hz, 1H), 8.58-8.57 (m, 1H), 8.31 (s, 5H), 8.14-8.12 (m, 1H), 5.61-5.52 (m, 2H), 5.04-4.97 (m, 3H), 3.15 (s, 3H). |
| 1.16 | 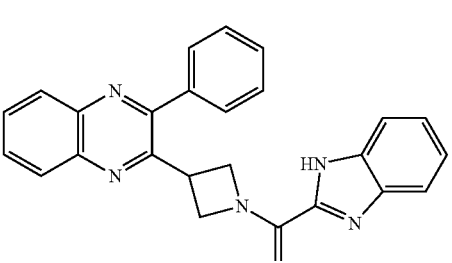 | (d-DMSO, 400 MHz): 8.17-8.11 (m, 2H); 7.86-7.85 (m, 2H); 7.67-7.48 (m, 7H); 7.27-7.26 (m, 2H); 5.11-5.07 (m, 1H); 4.98-4.94 (m, 1H); 4.51-4.49 (m, 1H); 4.39-4.35 (m, 1H); 4.27-4.22 (m, 1H). |
| 1.17 | 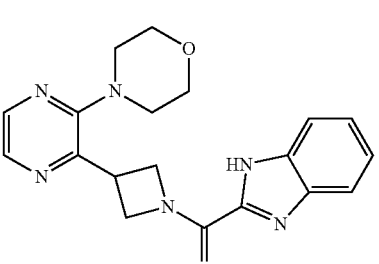 | (CDCl$_3$, 400 MHz): 8.23-8.22 (m, 1H); 8.16-8.15 (m, 1H); 7.71-7.69 (m, 2H); 7.36-7.34 (m, 2H); 5.33 (t, J = 10.0 Hz, 1H); 5.10-5.06 (m, 1H); 4.65-4.59 (m, 2H); 4.35-4.25 (m, 1H); 3.88-3.89 (m, 4H); 3.17-3.14 (m, 4H) |
SCHEME 2
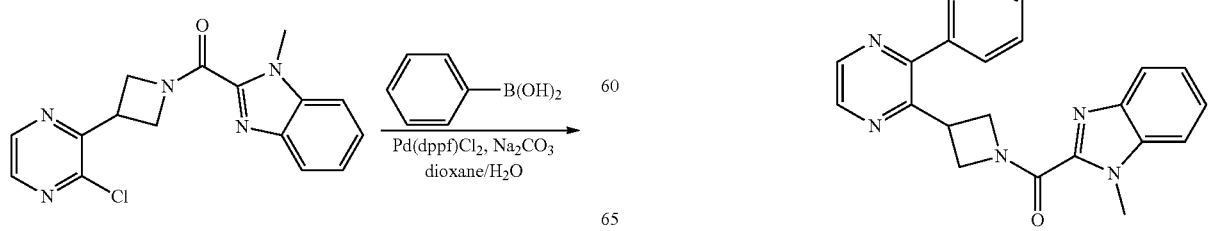

Example 2.1: (1-Methyl-1H-Benzoimidazol-2-Yl)-[3-(3-Phenyl-Pyrazin-2-Yl)-Azetidin-1-Yl]-Methanone To a stirred solution of [3-(3-chloro-pyrazin-2-yl)-azetidin-1-yl]-(1-methyl-1H-benzoimidazol-2-yl)-methanone (100 mg, 0.30 mmol) in dioxane (10 mL) was added phenylboronic acid (87 mg, 0.71 mmol), $Na_2CO_3$ (152 mg, 1.4 mmol) and $H_2O$ (2 mL). The reaction mixture was degassed with $N_2$ and then $PdCl_2(dppf)$ (35 mg, 0.05 mmol) was added. The reaction mixture was stirred at 80° C. for 12 h. The reaction mixture was left to reach RT and filtered through a pad of CELITE® and the filter cake was washed with $CH_2Cl_2$ (20 mL×3). The combined filtrates were evaporated in vacuo and the residue was purified by column chromatography to give the desired compound (60 mg, 0.17 mmol, yield 70%)

The following Table 14A lists compounds of Examples 2.1 to 2.30, which were made analogous to Scheme 2 by using the appropriate materials and reaction conditions, which are listed in Table 14B. The NMR data of the Examples are listed in Table 14C.

TABLE 14A

EXAMPLES 2.1 TO 2.30

| Ex. # | Structure | Chemical Name | ESI-MS (M + 1) | $IC_{50}$ (uM) |
|---|---|---|---|---|
| 2.1 | 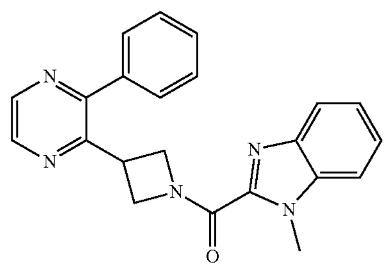 [SMILES: Cn1c(C(=O)N2CC(c3nccnc3-c3ccccc3)C2)nc2ccccc21] | (1-Methyl-1H-benzoimidazol-2-yl)-[3-(3-phenyl-pyrazin-2-yl)-azetidin-1-yl]-methanone | 370 | 0.181 |
| 2.2 | 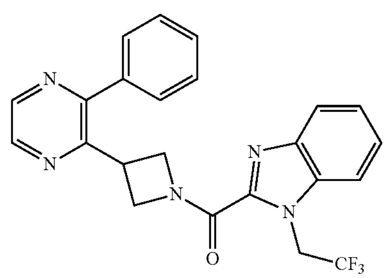 [SMILES: O=C(c1nc2ccccc2n1CC(F)(F)F)N1CC(c2nccnc2-c2ccccc2)C1] | [3-(3-Phenyl-pyrazin-2-yl)-azetidin-1-yl]-[1-(2,2,2-trifluoro-ethyl)-1H-benzoimidazol-2-yl]-methanone | 438 | 0.893 |
| 2.3 | 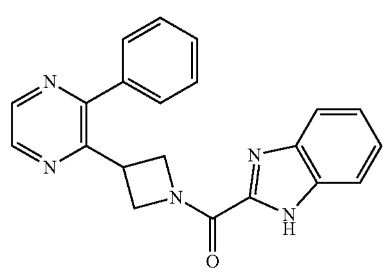 [SMILES: O=C(c1nc2ccccc2[nH]1)N1CC(c2nccnc2-c2ccccc2)C1] | (1H-Benzoimidazol-2-yl)-[3-(3-phenyl-pyrazin-2-yl)-azetidin-1-yl]-methanone | 356 | 0.0248 |
| 2.4 | 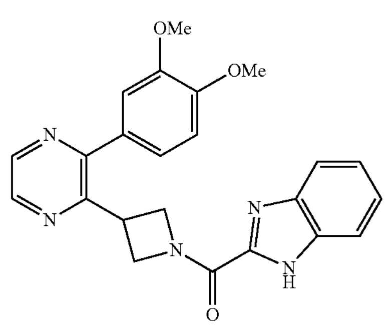 [SMILES: COc1ccc(-c2nccnc2C2CN(C(=O)c3nc4ccccc4[nH]3)C2)cc1OC] | (1H-Benzoimidazol-2-yl)-{3-[3-(3,4-dimethoxy-phenyl)-pyrazin-2-yl]-azetidin-1-yl}-methanone | 416 | 0.0188 |

TABLE 14A-continued

EXAMPLES 2.1 TO 2.30

| Ex. # | Structure | Chemical Name | ESI-MS (M + 1) | IC$_{50}$ (uM) |
|---|---|---|---|---|
| 2.5 | 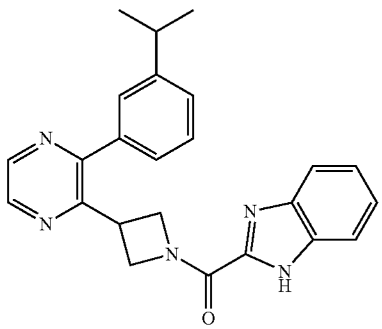 [SMILES: CC(C)c1cccc(-c2nccnc2C2CN(C(=O)c3nc4ccccc4[nH]3)C2)c1] | (1H-Benzoimidazol-2-yl)-{3-[3-(3-isopropyl-phenyl)-pyrazin-2-yl]-azetidin-1-yl}-methanone | 398 | 0.049 |
| 2.6 | 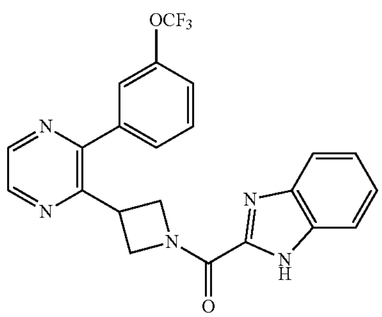 [SMILES: O=C(c1nc2ccccc2[nH]1)N1CC(c2nccnc2-c2cccc(OC(F)(F)F)c2)C1] | (1H-Benzoimidazol-2-yl)-{3-[3-(3-trifluoromethoxy-phenyl)-pyrazin-2-yl]-azetidin-1-yl}-methanone | 440 | 0.0357 |
| 2.7 | 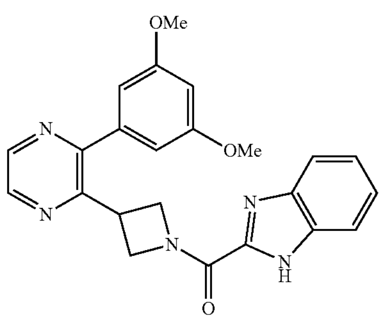 [SMILES: COc1cc(OC)cc(-c2nccnc2C2CN(C(=O)c3nc4ccccc4[nH]3)C2)c1] | 1H-Benzoimidazol-2-yl)-{3-[3-(3,5-dimethoxy-phenyl)-pyrazin-2-yl]-azetidin-1-yl}-methanone | 416 | 0.056 |
| 2.8 | 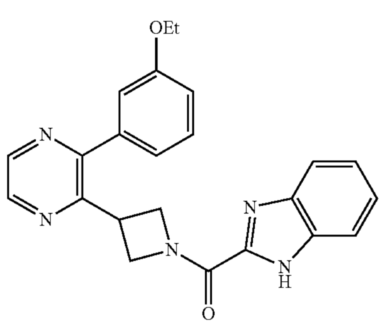 [SMILES: CCOc1cccc(-c2nccnc2C2CN(C(=O)c3nc4ccccc4[nH]3)C2)c1] | (1H-Benzoimidazol-2-yl)-{3-[3-(3-ethoxy-phenyl)-pyrazin-2-yl]-azetidin-1-yl}-methanone | 400 | 0.0299 |

TABLE 14A-continued

EXAMPLES 2.1 TO 2.30

| Ex. # | Structure | Chemical Name | ESI-MS (M + 1) | IC$_{50}$ (uM) |
|---|---|---|---|---|
| 2.9 | 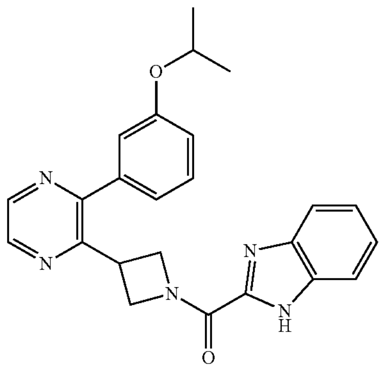 [SMILES: CC(C)Oc1cccc(-c2nccnc2C2CN(C(=O)c3nc4ccccc4[nH]3)C2)c1] | (1H-Benzoimidazol-2-yl)-{3-[3-(3-isopropoxy-phenyl)-pyrazin-2-yl]-azetidin-1-yl}-methanone | 414 | 0.0352 |
| 2.10 | 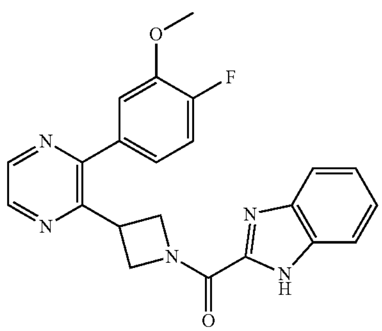 [SMILES: COc1cc(-c2nccnc2C2CN(C(=O)c3nc4ccccc4[nH]3)C2)ccc1F] | (1H-Benzoimidazol-2-yl)-{3-[3-(3-fluoro-5-methoxy-phenyl)-pyrazin-2-yl]-azetidin-1-yl}-methanone | 404 | 0.0424 |
| 2.11 | 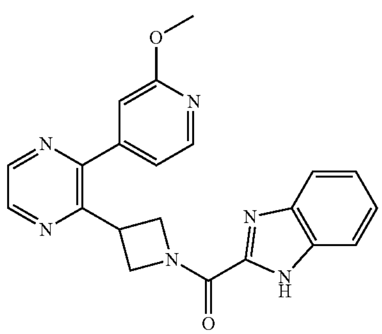 [SMILES: COc1cc(-c2nccnc2C2CN(C(=O)c3nc4ccccc4[nH]3)C2)ccn1] | (1H-Benzoimidazol-2-yl)-{3-[3-(2-methoxy-pyridin-4-yl)-pyrazin-2-yl]-azetidin-1-yl}-methanone | 387 | 0.093 |
| 2.12 | 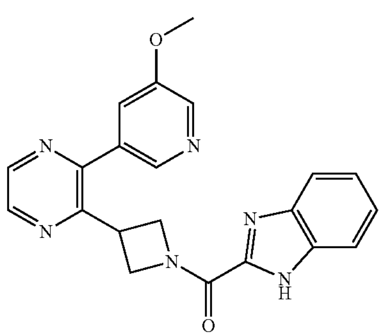 [SMILES: COc1cncc(-c2nccnc2C2CN(C(=O)c3nc4ccccc4[nH]3)C2)c1] | (1H-Benzoimidazol-2-yl)-{3-[3-(5-methoxy-pyridin-3-yl)-pyrazin-2-yl]-azetidin-1-yl}-methanone | 387 | 0.640 |

TABLE 14A-continued

EXAMPLES 2.1 TO 2.30

| Ex. # | Structure | Chemical Name | ESI-MS (M + 1) | IC$_{50}$ (uM) |
|---|---|---|---|---|
| 2.13 | 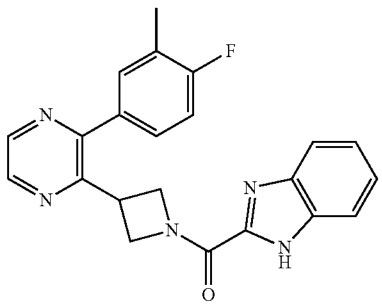 [SMILES: Cc1cc(-c2nccnc2C2CN(C(=O)c3nc4ccccc4[nH]3)C2)ccc1F] | (1H-benzo[d]imidazol-2-yl)(3-(3-(4-fluoro-3-methylphenyl)pyrazin-2-yl)azetidin-1-yl)methanone | 388 | 0.013 |
| 2.14 | 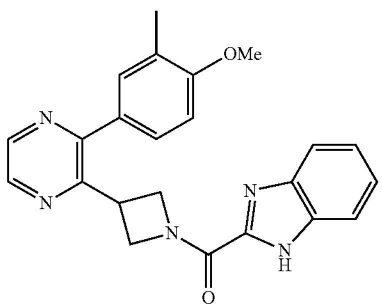 [SMILES: COc1ccc(-c2nccnc2C2CN(C(=O)c3nc4ccccc4[nH]3)C2)cc1C] | (1H-Benzoimidazol-2-yl)-{3-[3-(4-methoxy-3-methyl-phenyl)-pyrazin-2-yl]-azetidin-1-yl}-methanone | 400 | 0.0201 |
| 2.15 | 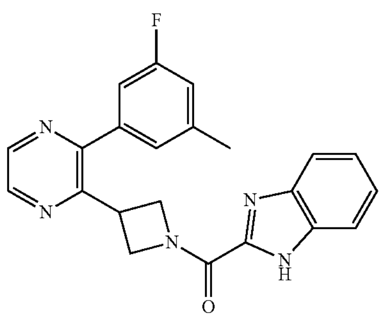 [SMILES: Cc1cc(F)cc(-c2nccnc2C2CN(C(=O)c3nc4ccccc4[nH]3)C2)c1] | (1H-Benzoimidazol-2-yl)-{3-[3-(3-fluoro-5-methyl-phenyl)-pyrazin-2-yl]-azetidin-1-yl}-methanone | 388 | 0.0393 |
| 2.16 | 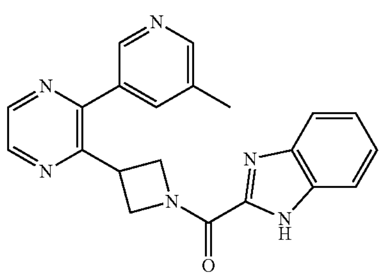 [SMILES: Cc1cncc(-c2nccnc2C2CN(C(=O)c3nc4ccccc4[nH]3)C2)c1] | (1H-Benzoimidazol-2-yl)-{3-[3-(5-methyl-pyridin-3-yl)-pyrazin-2-yl]-azetidin-1-yl}-methanone | 371 | 0.195 |
| 2.17 | 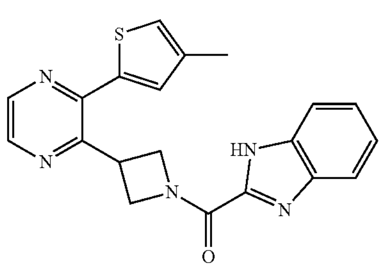 [SMILES: Cc1csc(-c2nccnc2C2CN(C(=O)c3nc4ccccc4[nH]3)C2)c1] | (1H-Benzoimidazol-2-yl)-{3-[3-(4-methyl-thiophen-2-yl)-pyrazin-2-yl]-azetidin-1-yl}-methanone | 376 | 0.013 |

TABLE 14A-continued

EXAMPLES 2.1 TO 2.30

| Ex. # | Structure | Chemical Name | ESI-MS (M + 1) | IC$_{50}$ (uM) |
|---|---|---|---|---|
| 2.18 | 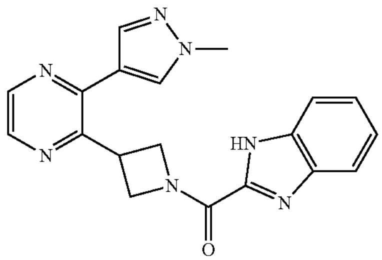 [SMILES: Cn1cc(-c2nccnc2C2CN(C(=O)c3nc4ccccc4[nH]3)C2)cn1] | (1H-Benzoimidazol-2-yl)-{3-[3-(1-methyl-1H-pyrazol-4-yl)-pyrazin-2-yl]-azetidin-1-yl}-methanone | 360 | 0.216 |
| 2.19 | 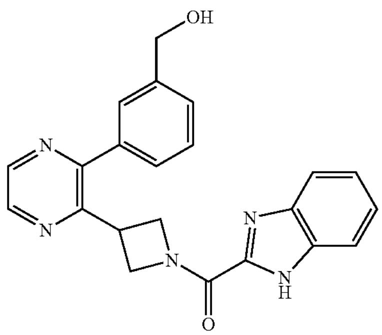 [SMILES: O=C(c1nc2ccccc2[nH]1)N1CC(c2nccnc2-c2cccc(CO)c2)C1] | (1H-Benzoimidazol-2-yl)-{3-[3-(3-hydroxymethyl-phenyl)-pyrazin-2-yl]-azetidin-1-yl}-methanone | 386 | 0.0336 |
| 2.20 | 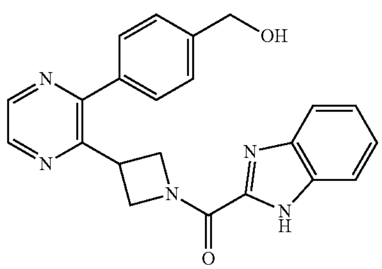 [SMILES: O=C(c1nc2ccccc2[nH]1)N1CC(c2nccnc2-c2ccc(CO)cc2)C1] | (1H-Benzoimidazol-2-yl)-{3-[3-(4-hydroxymethyl-phenyl)-pyrazin-2-yl]-azetidin-1-yl}-methanone | 386 | 0.0398 |
| 2.21 | 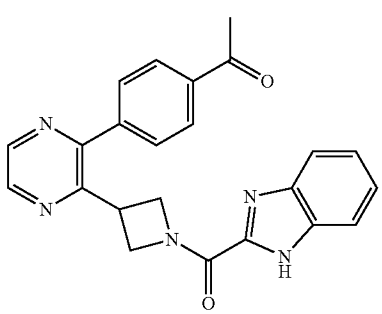 [SMILES: CC(=O)c1ccc(-c2nccnc2C2CN(C(=O)c3nc4ccccc4[nH]3)C2)cc1] | 1-(4-{3-[1-(1H-Benzoimidazole-2-carbonyl)-azetidin-3-yl]-pyrazin-2-yl}-phenyl)-ethanone | 398 | 0.0247 |
| 2.22 | 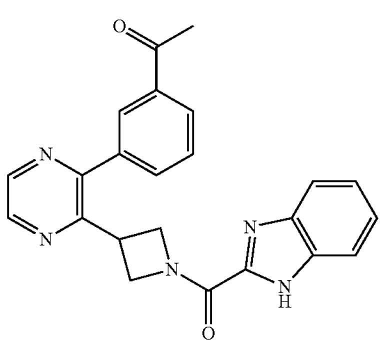 [SMILES: CC(=O)c1cccc(-c2nccnc2C2CN(C(=O)c3nc4ccccc4[nH]3)C2)c1] | 1-(3-{3-[1-(1H-Benzoimidazole-2-carbonyl)-azetidin-3-yl]-pyrazin-2-yl}-phenyl)-ethanone | 398 | 0.0151 |

TABLE 14A-continued

EXAMPLES 2.1 TO 2.30

| Ex. # | Structure | Chemical Name | ESI-MS (M + 1) | IC$_{50}$ (uM) |
|---|---|---|---|---|
| 2.23 | 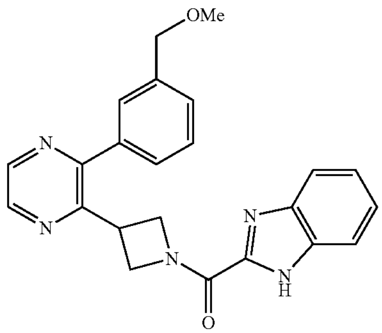 [SMILES: COCc1cccc(-c2nccnc2C2CN(C(=O)c3nc4ccccc4[nH]3)C2)c1] | (1H-Benzoimidazol-2-yl)-{3-[3-(3-methoxymethyl-phenyl)-pyrazin-2-yl]-azetidin-1-yl}-methanone | 400 | 0.0449 |
| 2.24 | 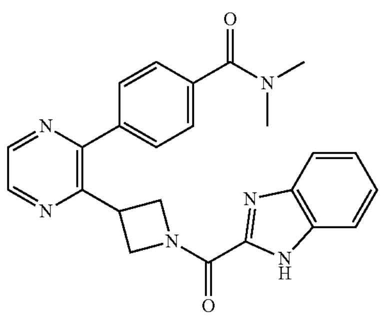 [SMILES: CN(C)C(=O)c1ccc(-c2nccnc2C2CN(C(=O)c3nc4ccccc4[nH]3)C2)cc1] | 4-{3-[1-(1H-Benzoimidazole-2-carbonyl)-azetidin-3-yl]-pyrazin-2-yl}-N,N-dimethyl-benzamide | 427 | 0.026 |
| 2.25 | 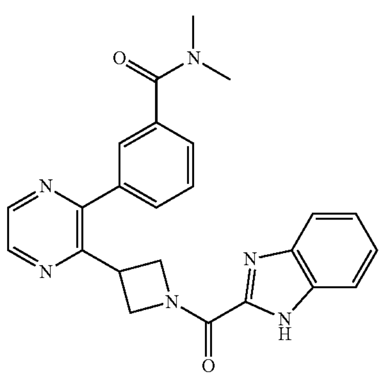 [SMILES: CN(C)C(=O)c1cccc(-c2nccnc2C2CN(C(=O)c3nc4ccccc4[nH]3)C2)c1] | 3-{3-[1-(1H-Benzoimidazole-2-carbonyl)-azetidin-3-yl]-pyrazin-2-yl}-N,N-dimethyl-benzamide | 427 | 0.537 |
| 2.26 | 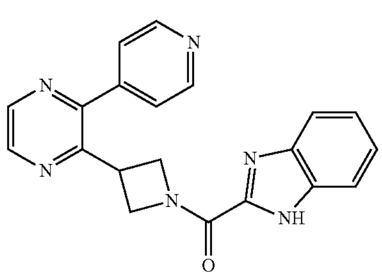 [SMILES: O=C(c1nc2ccccc2[nH]1)N1CC(c2nccnc2-c2ccncc2)C1] | (1H-benzo[d]imidazol-2-yl)(3-(3-(pyridin-4-yl)pyrazin-2-yl)azetidin-1-yl)methanone | 357 | 0.25 |

TABLE 14A-continued

EXAMPLES 2.1 TO 2.30

| Ex. # | Structure | Chemical Name | ESI-MS (M + 1) | IC$_{50}$ (uM) |
|---|---|---|---|---|
| 2.27 | 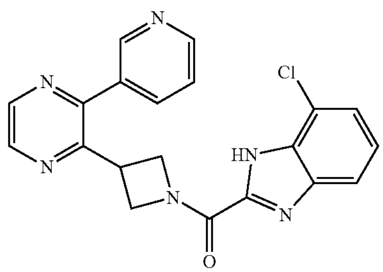 [SMILES: O=C(c1nc2cccc(Cl)c2[nH]1)N1CC(c2nccnc2-c2cccnc2)C1] | (7-chloro-1H-benzo[d]imidazol-2-yl)(3-(3-(pyridin-3-yl)pyrazin-2-yl)azetidin-1-yl)methanone | 391 | 0.587 |
| 2.28 | 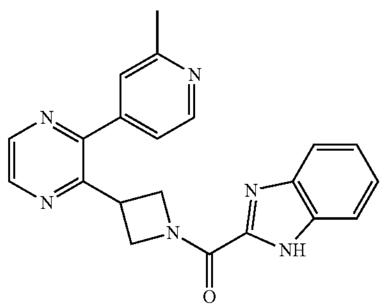 [SMILES: Cc1cc(-c2nccnc2C2CN(C(=O)c3nc4ccccc4[nH]3)C2)ccn1] | (1H-benzo[d]imidazol-2-yl)(3-(3-(2-methylpyridin-4-yl)pyrazin-2-yl)azetidin-1-yl)methanone | 371 | 0.037 |
| 2.29 | 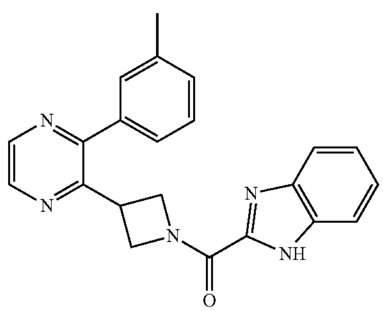 | (1H-benzo[d]imidazol-2-yl)(3-(3-(m-tolyl)pyrazin-2-yl)azetidin-1-yl)methanone | 370 | 0.0148 |
| 2.30 | 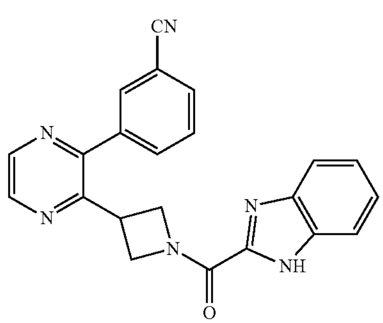 [SMILES: N#Cc1cccc(-c2nccnc2C2CN(C(=O)c3nc4ccccc4[nH]3)C2)c1] | 3-(3-(1-(1H-benzo[d]imidazole-2-carbonyl)azetidin-3-yl)pyrazin-2-yl)benzonitrile | 381 | 0.226 |

TABLE 14B

STARTING MATERIALS AND REACTION CONDITION FOR
PREPARATION OF EXAMPLES 2.1 TO 2.30

| Ex. # | Structure | NMR |
|---|---|---|
| 2.1 | 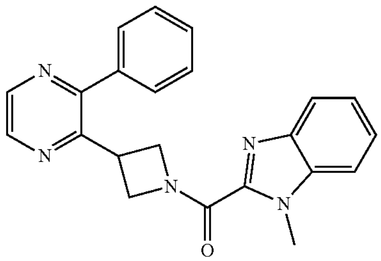 [SMILES: Cn1c(C(=O)N2CC(c3nccnc3-c3ccccc3)C2)nc2ccccc21] | (CD$_3$OD, 400 MHz): 8.65 (d, J = 2.4 Hz, 1 H); 8.53 (d, J = 2.4, 1 H); 7.70-7.67 (m, 1 H); 7.59-7.58 (m, 1 H); 7.53-7.40 (m, 5 H); 7.38-7.35 (m, 1 H); 7.34-7.31 (m, 1 H); 4.81-4.80 (m, 2 H); 4.41-4.32 (m, 1 H); 4.07 (s, 3 H). |
| 2.2 | 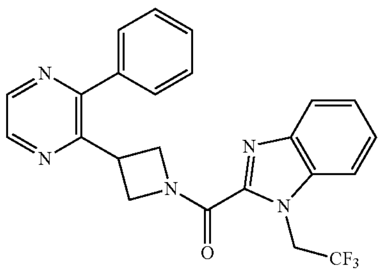 | (CD$_3$OD, 400 MHz): 8.67-8.66 (m, 1 H); 8.53-8.52 (m, 1 H); 7.74-7.72 (m, 1 H); 7.63-7.61 (m, 1 H); 7.53-7.48 (m, 5 H); 7.45-7.41 (m, 1 H); 7.37-7.33 (m, 1 H); 5.60-5.56 (m, 2 H); 4.94-4.92 (m, 2 H); 4.41-4.34 (m, 3 H). |
| 2.3 | 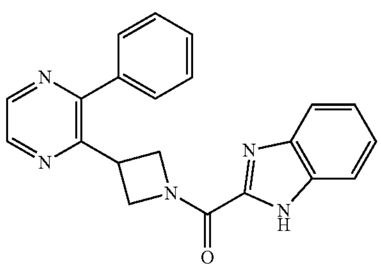 [SMILES: O=C(c1nc2ccccc2[nH]1)N1CC(c2nccnc2-c2ccccc2)C1] | (CDCl$_3$, 400 MHz): 8.62-8.60 (m, 2H); 7.69-7.68 (m, 2H); 7.58-7.44 (m, 5H); 7.43-7.32 (m, 2H); 5.22-5.12 (m, 2H); 4.64-4.62 (m, 1H); 4.52-4.34 (m, 1H). |
| 2.4 | 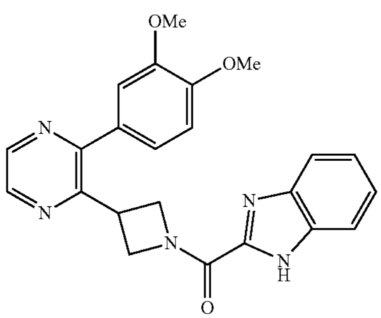 [SMILES: COc1ccc(-c2nccnc2C2CN(C(=O)c3nc4ccccc4[nH]3)C2)cc1OC] | (CDCl$_3$, 400 MHz): 8.51-8.48 (m, 2 H); 7.72 (br, 1H); 7.47 (br, 1H); 7.24 (brs, 2H); 7.05 (s, 1 H); 6.93 (s, 2 H); 5.15-5.16 (m, 2H); 4.58-4.54 (m, 1 H); 4.46-4.44 (m, 1H); 4.38-4.30 (m, 1 H); 3.90 (s, 6 H) |
| 2.5 | 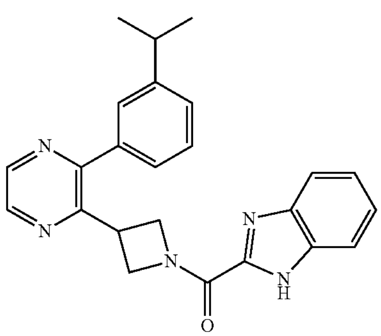 [SMILES: CC(C)c1cccc(-c2nccnc2C2CN(C(=O)c3nc4ccccc4[nH]3)C2)c1] | (CDCl$_3$, 400 MHz): 8.60-8.57 (m, 2 H); 7.67 (brs, 2H); 7.46-7.44 (m, 1H); 7.38-7.37 (m, 2 H); 7.31-7.26 (m, 3 H); 5.17-5.16 (m, 2H); 4.63-4.62 (m, 1H); 4.51-4.50 (m, 1 H); 4.36-4.33 (m, 1 H); 3.05-2.99 (m, 2H); 1.33 (d, J = 6.8 Hz, 6H). |

TABLE 14B-continued

STARTING MATERIALS AND REACTION CONDITION FOR
PREPARATION OF EXAMPLES 2.1 TO 2.30

| Ex. # | Structure | NMR |
|---|---|---|
| 2.6 | 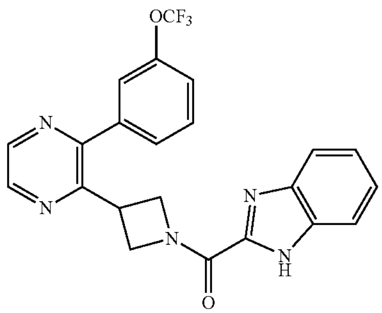 [SMILES: O=C(c1nc2ccccc2[nH]1)N1CC(c2nccnc2-c2cccc(OC(F)(F)F)c2)C1] | (DMSO, 400 MHz): 8.75-8.74 (m, 1 H); 8.67-8.66 (m, 1H); 7.69-7.54 (m, 6H); 7.27-7.25 (m, 2H); 4.95-4.92 (m, 2H); 4.31-4.25 (m, 3H). |
| 2.7 | 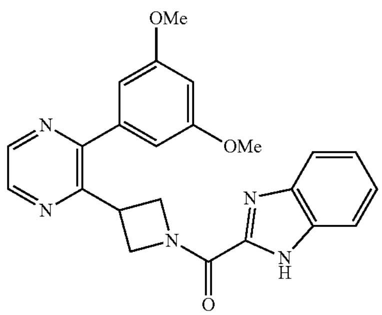 [SMILES: COc1cc(OC)cc(-c2nccnc2C2CN(C(=O)c3nc4ccccc4[nH]3)C2)c1] | (CDCl$_3$, 400 MHz): 8.60 (d, J = 2.4 Hz, 1H); 8.56 (d, J = 2.4 Hz, 1H); 7.67 (br, 2H); 7.43-7.40 (m, 1H); 7.32-7.30 (m, 2H); 7.02-6.98 (m, 3H); 5.17-5.16 (m, 2H); 4.66-4.60 (m, 2H); 4.54-4.49 (m, 1H); 4.40-4.36 (m, 1H); 1.38 (d, J = 6.0 Hz, 6H). |
| 2.8 | 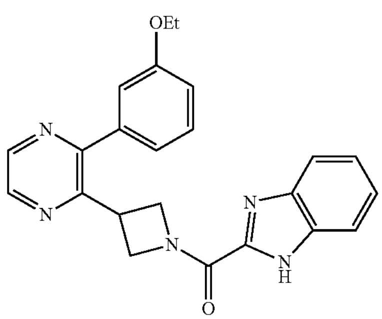 [SMILES: CCOc1cccc(-c2nccnc2C2CN(C(=O)c3nc4ccccc4[nH]3)C2)c1] | (CDCl$_3$, 400 MHz): 8.63-8.59 (m, 2 H); 7.70 (br, 2 H); 7.44-7.28 (m, 3 H); 7.06-7.01 (m, 3 H); 5.20-5.18 (m, 2 H); 4.63-4.53 (m, 2 H); 4.41-4.40 (m, 1 H); 4.15-4.10 (m, 2 H); 1.49-1.45 (m, 3 H). |
| 2.9 | 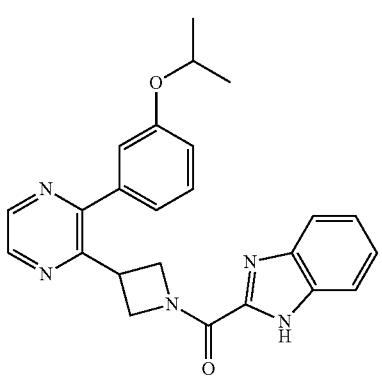 [SMILES: CC(C)Oc1cccc(-c2nccnc2C2CN(C(=O)c3nc4ccccc4[nH]3)C2)c1] | (DMSO, 400 MHz): 8.70 (d, J = 2.4 Hz, 1H); 8.64 (d, J = 2.4 Hz, 1H); 7.71 (brs, 1H); 7.50-7.41 (m, 5 H); 7.26 (brs, 2H); 5.32-5.29 (m, 1H); 4.98-4.93 (m, 2H); 4.61-4.59 (m, 2H); 4.34-4.28 (m, 2H); 4.24-4.21 (m, 1H). |

//

TABLE 14B-continued

STARTING MATERIALS AND REACTION CONDITION FOR
PREPARATION OF EXAMPLES 2.1 TO 2.30

| Ex. # | Structure | NMR |
|---|---|---|
| 2.10 | 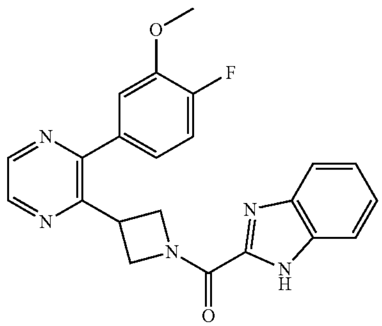 [SMILES: COc1cc(-c2nccnc2C2CN(C(=O)c3nc4ccccc4[nH]3)C2)ccc1F] | (CDCl$_3$, 400 MHz): 8.62 (d, J = 2.4 Hz, 1H); 8.57 (d, J = 2.4 Hz, 1H); 7.69-7.67 (m, 2H); 7.34-7.32 (m, 2H); 7.26-7.15 (m, 2H); 6.96-6.92 (m, 1H); 5.19-5.14 (m, 2H); 4.62 (t, J = 6.0 Hz, 1H); 4.51 (t, J = 9.2 Hz, 1H); 4.37-4.34 (m, 1H); 3.97 (s, 3H) |
| 2.11 | 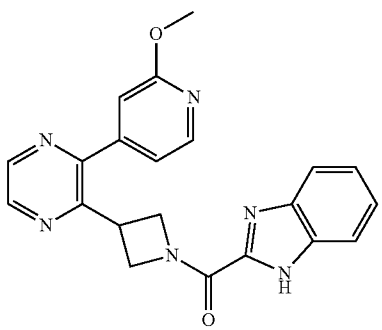 [SMILES: COc1cc(-c2nccnc2C2CN(C(=O)c3nc4ccccc4[nH]3)C2)ccn1] | (CDCl$_3$, 400 MHz): 8.70-8.69 (m, 1H); 8.63-8.62 (m, 1 H); 8.43-8.42 (m, 1 H); 7.74-7.72 (m, 2 H); 7.43-7.41 (m, 2H); 7.12-7.11 (m, 1 H); 7.01 (s, 1 H); 5.15-5.11 (m, 2 H); 4.56-4.52 (m, 2 H); 4.32-4.31 (m, 1 H); 4.06 (s, 3 H). |
| 2.12 | 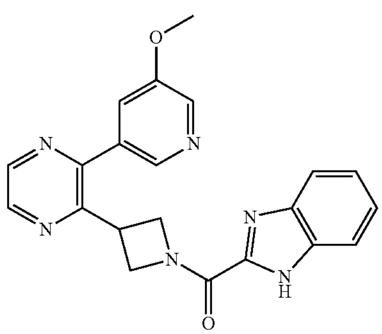 [SMILES: COc1cncc(-c2nccnc2C2CN(C(=O)c3nc4ccccc4[nH]3)C2)c1] | (CDCl$_3$, 400 MHz): 8.66-8.65 (m, 1H); 8.57-8.56 (m, 2H); 8.50 (s, 1H); 7.96 (s, 1H); 7.66-7.64 (m, 2H); 7.36-7.34 (m, 2H); 5.09-5.00 (m, 2H); 4.59-4.46 (m, 2H); 4.29-4.27 (m, 1H); 4.00 (s, 3H) |
| 2.13 | 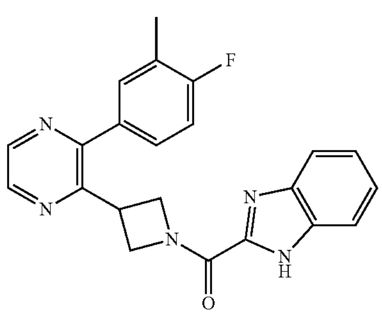 [SMILES: Cc1cc(-c2nccnc2C2CN(C(=O)c3nc4ccccc4[nH]3)C2)ccc1F] | (CDCl$_3$, 400 MHz): 8.54 (d, J = 1.6 Hz, 1H); 8.49 (d, J = 2.4 Hz, 1H); 7.62 (s, 2H); 7.33-7.26 (m, 3H); 7.19 (s, 1H); 7.09 (t, J = 8.8 Hz, 1H); 5.13-5.10 (m, 2H); 4.29-4.18 (m, 1H); 2.62 (s, 3H). |

TABLE 14B-continued

STARTING MATERIALS AND REACTION CONDITION FOR
PREPARATION OF EXAMPLES 2.1 TO 2.30

| Ex. # | Structure | NMR |
|---|---|---|
| 2.14 | 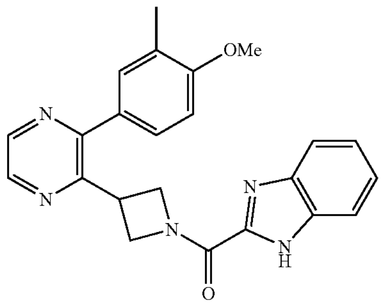 [SMILES: COc1ccc(-c2nccnc2C2CN(C(=O)c3nc4ccccc4[nH]3)C2)cc1C] | (CDCl$_3$, 400 MHz): 8.56 (s, 2H); 7.69 (brs, 2H); 7.34-7.24 (m, 4 H); 6.96-6.94 (m, 1H); 5.21-5.15 (m, 2H); 4.60-4.40 (m, 3H); 3.90 (s, 3H); 2.30 (s, 3H). |
| 2.15 | 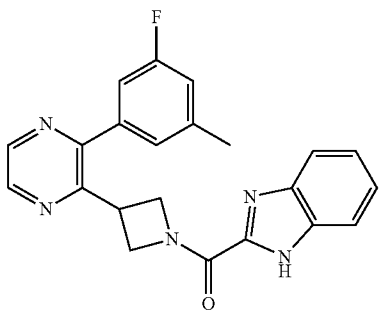 [SMILES: Cc1cc(F)cc(-c2nccnc2C2CN(C(=O)c3nc4ccccc4[nH]3)C2)c1] | (CDCl$_3$, 400 MHz): 8.62-8.57 (m, 2H); 7.67-7.67 (m, 2H); 7.30 (brs, 2 H); 7.05-7.03 (m, 3 H); 5.17-5.15 (m, 2H); 4.62-4.48 (m, 2H); 4.35-4.33 (m, 1 H); 2.46 (s, 3 H). |
| 2.16 | 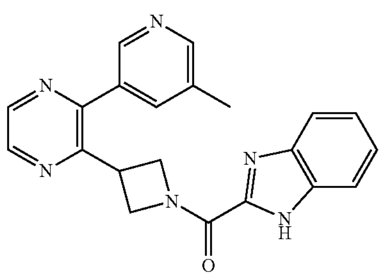 [SMILES: Cc1cncc(-c2nccnc2C2CN(C(=O)c3nc4ccccc4[nH]3)C2)c1] | (CDCl$_3$, 400 MHz): 8.83 (s, 1H); 8.67 (s, 1H); 8.65 (d, J = 2.0 Hz, 1H); 8.56 (d, J = 2.0 Hz, 1H); 8.31 (s, 1H); 7.65-7.62 (m, 2H); 7.33-7.31 (m, 2H); 5.11-5.07 (m, 1H); 5.03-5.00 (m, 1H); 4.29-4.25 (m, 1H); 2.57 (s, 3H). |
| 2.17 | 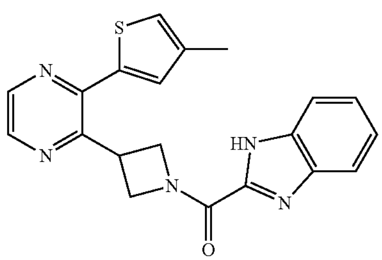 [SMILES: Cc1csc(-c2nccnc2C2CN(C(=O)c3nc4ccccc4[nH]3)C2)c1] | (CDCl$_3$, 400 MHz): 8.58-8.54 (m, 2 H); 7.61 (br, 2 H); 7.40-7.38 (m, 2 H); 7.27-7.25 (m, 2 H); 5.15-5.13 (m, 1 H); 4.96-4.92 (m, 1 H); 4.58-4.53 (m, 2 H); 4.38-4.36 (m, 1H); 2.29 (s, 3H). |
| 2.18 | 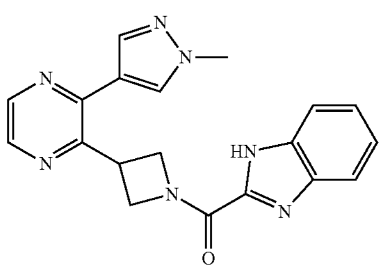 [SMILES: Cn1cc(-c2nccnc2C2CN(C(=O)c3nc4ccccc4[nH]3)C2)cn1] | (CDCl$_3$, 400 MHz): 8.50-8.49 (m, 2 H); 7.87 (brs, 2H); 7.72 (br, 2 H); 7.41-7.40 (m, 2H); 5.30-5.29 (m, 1H); 5.08-5.07(m, 1 H); 4.65-4.61 (m, 2H); 4.49-4.48 (m, 1H); 4.03 (s, 3H). |

TABLE 14B-continued

STARTING MATERIALS AND REACTION CONDITION FOR
PREPARATION OF EXAMPLES 2.1 TO 2.30

| Ex. # | Structure | NMR |
|---|---|---|
| 2.19 | 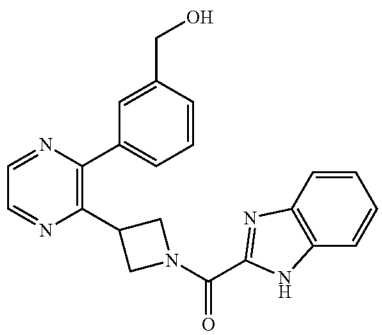 [SMILES: O=C(c1nc2ccccc2[nH]1)N1CC(c2nccnc2-c2cccc(CO)c2)C1] | (DMSO, 400 MHz): 8.70 (d, J = 2.4 Hz, 1H); 8.64 (d, J = 2.4 Hz, 1H); 7.71 (brs, 1H); 7.50-7.41 (m, 5 H); 7.26 (brs, 2H); 5.32-5.29 (m, 1H); 4.98-4.93 (m, 2H); 4.61-4.59 (m, 2H); 4.34-4.28 (m, 2H); 4.24-4.21 (m, 1H). |
| 2.20 | 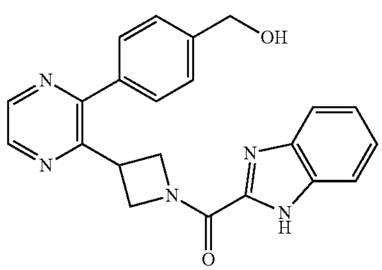 [SMILES: O=C(c1nc2ccccc2[nH]1)N1CC(c2nccnc2-c2ccc(CO)cc2)C1] | (DMSO, 400 MHz): 8.69 (d, J = 2.4 Hz, 1H); 8.63 (d, J = 2.4 Hz, 1H); 7.53-7.47 (m, 5 H); 7.71 (br, 2H); 4.97-4.88 (m, 2H); 4.59 (s, 2 H); 4.33-4.21 (m, 3H). |
| 2.21 | 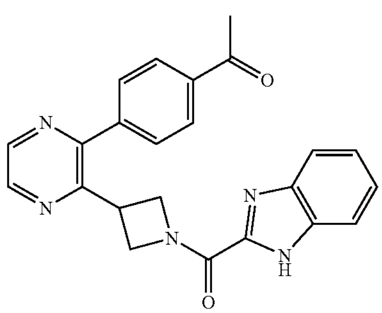 [SMILES: CC(=O)c1ccc(-c2nccnc2C2CN(C(=O)c3nc4ccccc4[nH]3)C2)cc1] | (CDCl$_3$, 400 MHz): 8.65-8.61 (m, 2 H); 8.12-8.10 (m, 2 H); 7.70-7.68 (m, 2 H); 7.59-7.57 (m, 2 H); 7.36-7.34 (m, 2 H); 5.21-5.10 (m, 2 H); 4.64-4.61 (m, 1 H); ; 4.51-4.50 (m, 1 H); 4.32-4.29 (m, 1 H); 2.68 (s, 3 H). |
| 2.22 | 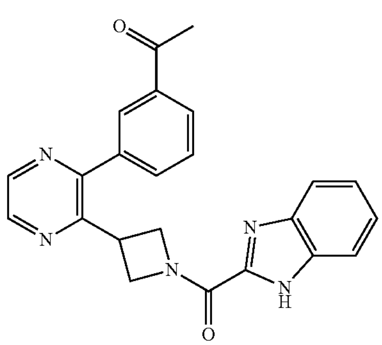 [SMILES: CC(=O)c1cccc(-c2nccnc2C2CN(C(=O)c3nc4ccccc4[nH]3)C2)c1] | (CDCl$_3$, 400 MHz): 8.63-8.59 (m, 2 H); 8.09-8.07 (m, 2H); 7.64-7.62 (m, 4H); 7.34-7.31 (m, 2H); 5.15-5.14 (m, 2H); 4.60-4.58 (m, 1H); 4.51-4.49 (m, 1H); 4.32-4.30 (m, 1H); 2.66 (s, 3H). |

TABLE 14B-continued

STARTING MATERIALS AND REACTION CONDITION FOR PREPARATION OF EXAMPLES 2.1 TO 2.30

| Ex. # | Structure | NMR |
|---|---|---|
| 2.23 | 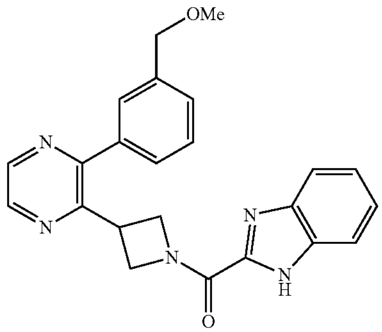 [SMILES: COCc1cccc(-c2nccnc2C2CN(C(=O)c3nc4ccccc4[nH]3)C2)c1] | (CDCl$_3$, 400 MHz): 8.63-8.59 (m, 2 H); 7.70-7.68 (m, 2H); 7.54-7.47 (m, 3H); 7.38-7.34 (m, 3H); 7.02-7.00 (m, 4H); 5.16-5.12 (m, 2H); 4.61-4.60 (m, 1H); 4.58-4.51 (m, 2H); 4.48-4.46 (m, 1H); 4.39-4.33 (m, 1H); 3.44 (s, 3H). |
| 2.24 | 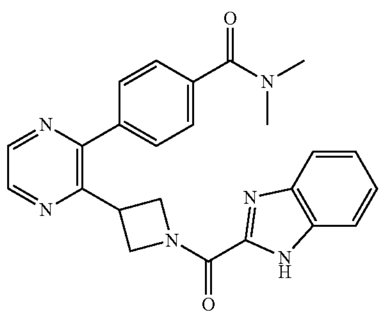 [SMILES: CN(C)C(=O)c1ccc(-c2nccnc2C2CN(C(=O)c3nc4ccccc4[nH]3)C2)cc1] | (CDCl$_3$, 400 MHz): 8.58-8.54 (m, 2 H); 7.67-7.66 (m, 2 H); 7.57-7.54 (m, 2 H); 7.49-7.47 (m, 2H); 7.34-7.32 (m, 2 H); 5.10-5.00 (m, 2H); 4.52-4.51 (m, 1H); 4.41-4.40 (m, 1H); 4.27-4.21 (m, 1H); 3.15 (s, 3 H); 3.02 (s, 3 H). |
| 2.25 | 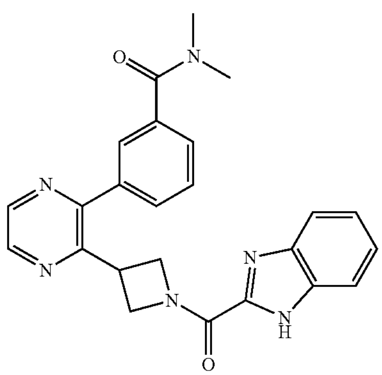 [SMILES: CN(C)C(=O)c1cccc(-c2nccnc2C2CN(C(=O)c3nc4ccccc4[nH]3)C2)c1] | (CDCl$_3$, 400 MHz): 8.60-8.55 (m, 2 H); 7.66 (brs, 2H); 7.57-7.50 (m, 4H); 7.30-7.29 (m, 2H); 5.10 (brs, 2H); 4.56-4.55 (m, 1H); 4.45-4.44 (m, 2H); 4.29-4.27 (m, 1H); 3.15 (s, 3H); 3.04 (s, 3H). |
| 2.26 | 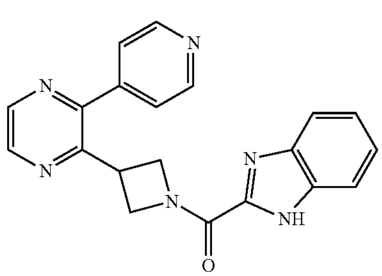 [SMILES: O=C(c1nc2ccccc2[nH]1)N1CC(c2nccnc2-c2ccncc2)C1] | (CDCl$_3$, 400 MHz): 8.90-8.80 (m, 2H); 8.70 (s, 1H); 8.60 (s, 1H); 7.85-7.72 (m, 2H); 7.67-7.62 (m, 2H); 7.46-7.45 (m, 2H); 5.24-5.13 (m, 2H); 4.66-4.62 (m, 1H); 4.54-4.49 (m, 1H); 4.30 (brs, 1H). |

| Ex. # | Structure | NMR |
|---|---|---|
| 2.27 | 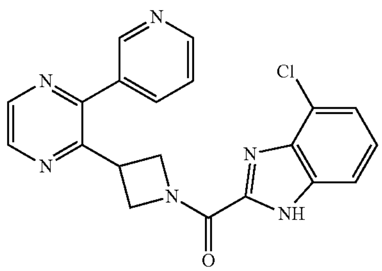 [SMILES: O=C(c1nc2c(Cl)cccc2[nH]1)N1CC(c2nccnc2-c2cccnc2)C1] | (CDCl₃, 400 MHz): 8.75-8.72 (m, 2H); 8.59 (s, 1H); 8.54 (s, 1H); 7.84-7.83 (m, 1H); 7.45-7.36 (m, 2H); 7.24-7.11 (m, 2H); 5.19-5.08 (m, 2H); 4.58-4.45 (m, 2H); 4.29-4.22 (m, 1H). |
| 2.28 | 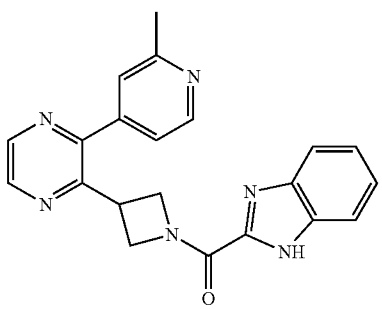 | (CDCl₃, 400 MHz): δ (ppm) 8.69-8.60 (m, 3H); 7.80 (d, J = 8.0 Hz, 1H); 7.55 (d, J = 8.0 Hz, 1H); 7.32-7.26 (m, 3H); 7.22-7.20 (m, 1H); 5.20-5.16 (m, 2H); 4.68-4.64 (m, 1H); 4.55-4.51 (m, 1H); 4.32-4.28 (m, 1H); 2.69 (s, 3H). |
| 2.29 | 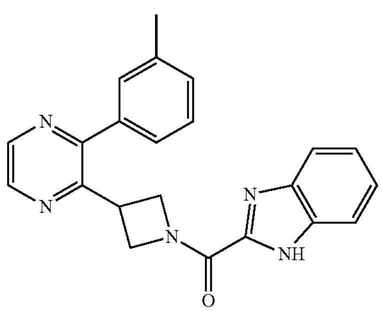 [SMILES: Cc1cccc(-c2nccnc2C2CN(C(=O)c3nc4ccccc4[nH]3)C2)c1] | (CDCl₃, 400 MHz): 8.60-8.57 (m, 2H); 7.81-7.79 (m, 1H); 7.55-7.40 (m, 1H); 7.34-7.26 (m, 6H); 5.18-5.17 (m, 2H); 4.66-4.62 (m, 1H); 4.52-4.48 (m, 1H); 4.38-4.34 (m, 1H); 2.46 (s, 3H). |
| 2.30 | 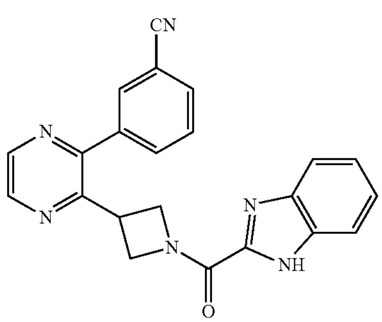 [SMILES: N#Cc1cccc(-c2nccnc2C2CN(C(=O)c3nc4ccccc4[nH]3)C2)c1] | (CDCl₃, 400 MHz): δ (ppm) 8.69-8.68 (m, 1H); 8.61-8.60 (m, 1H); 7.89 (s, 1H); 7.87-7.65 (m, 5H); 7.32-7.26 (m, 2H); 5.25-5.13 (m, 2H); 4.68-4.64 (m, 1H); 4.55-4.51 (m, 1H); 4.29-4.26 (m, 1H). |

TABLE 14C

STARTING MATERIALS AND REACTION CONDITION FOR
PREPARATION OF EXAMPLES 2.1 TO 2.30.
Unless otherwise stated, all starting materials are commercially available from common vendors.

| Ex. # | Starting Material 1 | Starting Material 2 | Reaction Condition |
|---|---|---|---|
| 2.1 | 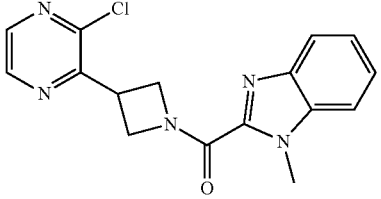<br>PREPARATION 25 | 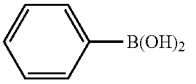 | PdCl$_2$(dppf), Na$_2$CO$_3$, dioxane/H$_2$O 80° C. |
| 2.2 | 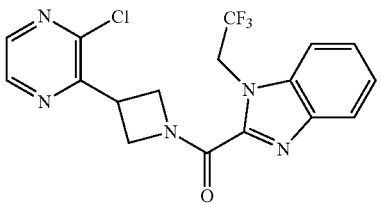<br>PREPARATION 26 | 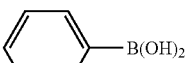 | PdCl$_2$(dppf), Na$_2$CO$_3$, dioxane/H$_2$O 80° C. |
| 2.3 | 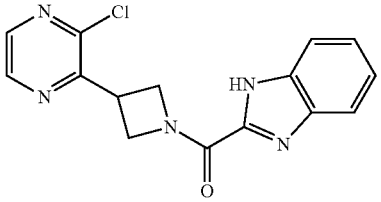<br>PREPARATION 36 | 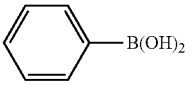 | PdCl$_2$(dppf), K$_3$PO$_4$, dioxane/H$_2$O 80° C. |
| 2.4 | 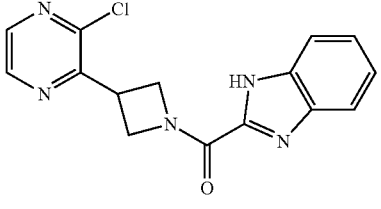<br>PREPARATION 36 | 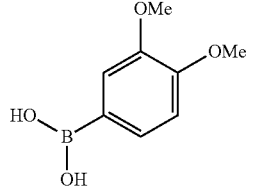 [SMILES: COc1ccc(B(O)O)cc1OC] | PdCl$_2$(dppf), K$_3$PO$_4$, dioxane/H$_2$O 80° C. |
| 2.5 | 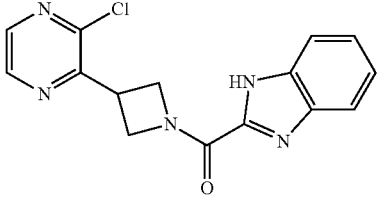<br>PREPARATION 36 | 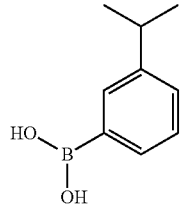 | PdCl$_2$(dppf), K$_3$PO$_4$, dioxane/H$_2$O 80° C. |
| 2.6 | 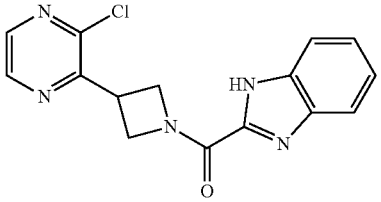<br>PREPARATION 36 | 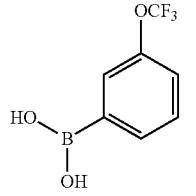 [SMILES: OB(O)c1cccc(OC(F)(F)F)c1] | PdCl$_2$(dppf), K$_3$PO$_4$, dioxane/H$_2$O 80° C. |

TABLE 14C-continued

STARTING MATERIALS AND REACTION CONDITION FOR
PREPARATION OF EXAMPLES 2.1 TO 2.30.
Unless otherwise stated, all starting materials are commercially available from common vendors.

| Ex. # | Starting Material 1 | Starting Material 2 | Reaction Condition |
|---|---|---|---|
| 2.7 | PREPARATION 36 | 3,5-dimethoxyphenylboronic acid | PdCl$_2$(dppf), K$_3$PO$_4$, dioxane/H$_2$O 80° C. |
| 2.8 | PREPARATION 36 | 3-ethoxyphenylboronic acid | PdCl$_2$(dppf), K$_3$PO$_4$, dioxane/H$_2$O 80° C. |
| 2.9 | PREPARATION 36 | 3-isopropoxyphenylboronic acid | PdCl$_2$(dppf), K$_3$PO$_4$, dioxane/H$_2$O 80° C. |
| 2.10 | PREPARATION 36 | 4-fluoro-3-methoxyphenylboronic acid | PdCl$_2$(dppf), K$_3$PO$_4$, dioxane/H$_2$O 80° C. |
| 2.11 | PREPARATION 36 | 2-methoxypyridin-4-ylboronic acid | PdCl$_2$(dppf), K$_3$PO$_4$, dioxane/H$_2$O 80° C. |
| 2.12 | PREPARATION 36 | 5-methoxypyridin-3-ylboronic acid | PdCl$_2$(dppf), K$_3$PO$_4$, dioxane/H$_2$O 80° C. |

TABLE 14C-continued

STARTING MATERIALS AND REACTION CONDITION FOR
PREPARATION OF EXAMPLES 2.1 TO 2.30.
Unless otherwise stated, all starting materials are commercially available from common vendors.

| Ex. # | Starting Material 1 | Starting Material 2 | Reaction Condition |
|---|---|---|---|
| 2.13 | PREPARATION 36 | 4-fluoro-3-methylphenylboronic acid | $PdCl_2(dppf)$, $K_3PO_4$, dioxane/$H_2O$ 80° C. |
| 2.14 | PREPARATION 36 | 4-methoxy-3-methylphenylboronic acid | $PdCl_2(dppf)$, $K_3PO_4$, dioxane/$H_2O$ 80° C. |
| 2.15 | PREPARATION 36 | 3-fluoro-5-methylphenylboronic acid | $PdCl_2(dppf)$, $K_3PO_4$, dioxane/$H_2O$ 80° C. |
| 2.16 | PREPARATION 36 | 5-methylpyridin-3-ylboronic acid | $PdCl_2(dppf)$, $K_3PO_4$, dioxane/$H_2O$ 80° C. |
| 2.17 | PREPARATION 36 | 4-methylthiophen-2-ylboronic acid | $PdCl_2(dppf)$, $K_3PO_4$, dioxane/$H_2O$ 80° C. |
| 2.18 | PREPARATION 36 | 1-methyl-1H-pyrazol-4-ylboronic acid | $PdCl_2(dppf)$, $K_3PO_4$, dioxane/$H_2O$ 80° C. |

TABLE 14C-continued

STARTING MATERIALS AND REACTION CONDITION FOR
PREPARATION OF EXAMPLES 2.1 TO 2.30.
Unless otherwise stated, all starting materials are commercially available from common vendors.

| Ex. # | Starting Material 1 | Starting Material 2 | Reaction Condition |
|---|---|---|---|
| 2.19 | 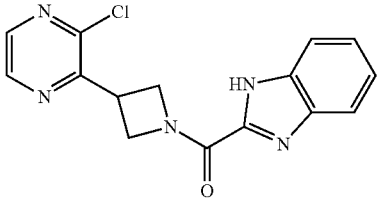 PREPARATION 36 | 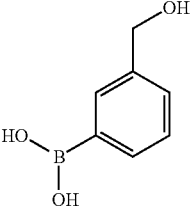 | PdCl$_2$(dppf), K$_3$PO$_4$, dioxane/H$_2$O 80° C. |
| 2.20 | 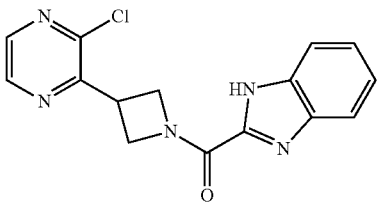 PREPARATION 36 | 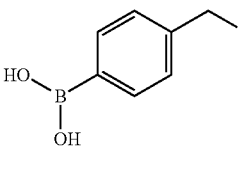 | PdCl$_2$(dppf), K$_3$PO$_4$, dioxane/H$_2$O 80° C. |
| 2.21 | 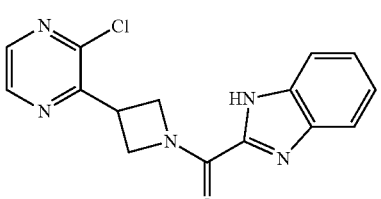 PREPARATION 36 | 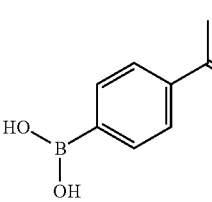 | PdCl$_2$(dppf), K$_3$PO$_4$, dioxane/H$_2$O 80° C. |
| 2.22 | 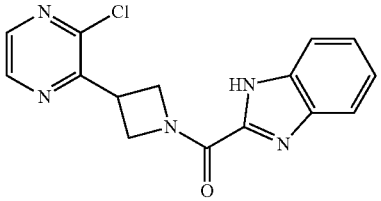 PREPARATION 36 | 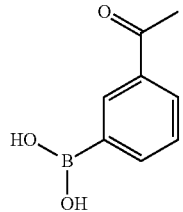 | PdCl$_2$(dppf), K$_3$PO$_4$, dioxane/H$_2$O 80° C. |
| 2.23 | 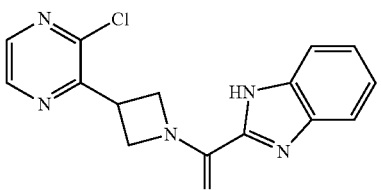 PREPARATION 36 | 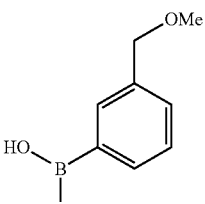 | PdCl$_2$(dppf), K$_3$PO$_4$, dioxane/H$_2$O 80° C. |
| 2.24 | 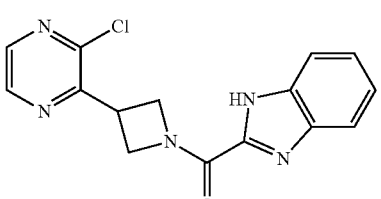 PREPARATION 36 | 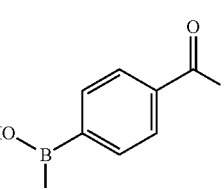 | PdCl$_2$(dppf), K$_3$PO$_4$, dioxane/H$_2$O 80° C. |

TABLE 14C-continued

STARTING MATERIALS AND REACTION CONDITION FOR
PREPARATION OF EXAMPLES 2.1 TO 2.30.
Unless otherwise stated, all starting materials are commercially available from common vendors.

| Ex. # | Starting Material 1 | Starting Material 2 | Reaction Condition |
|---|---|---|---|
| 2.25 | 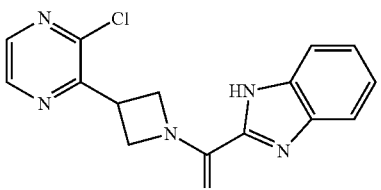<br>PREPARATION 36 | 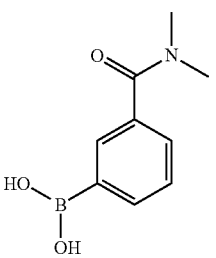 | PdCl$_2$(dppf), K$_3$PO$_4$, dioxane/H$_2$O<br>80° C. |
| 2.26 | 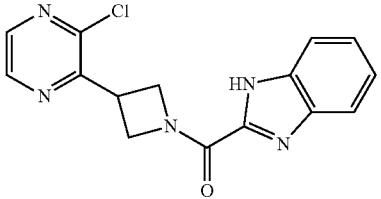<br>PREPARATION 36 | 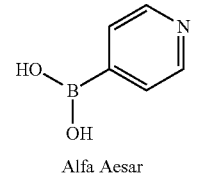<br>Alfa Aesar | PdCl$_2$(dppf), K$_3$PO$_4$, dioxane/H$_2$O<br>reflux |
| 2.27 | 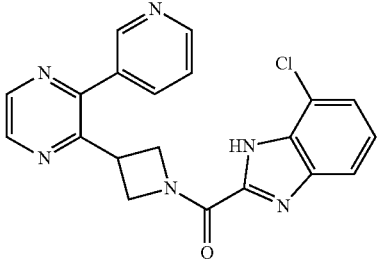<br>PREPARATION 36 | 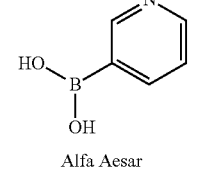<br>Alfa Aesar | PdCl$_2$(dppf), K$_3$PO$_4$, dioxane/H$_2$O<br>reflux |
| 2.28 | 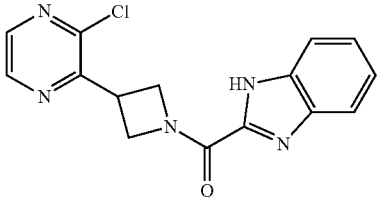<br>PREPARATION 36 | 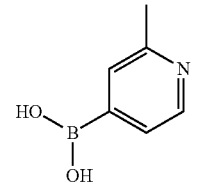<br>Alfa Aesar | PdCl$_2$(dppf), K$_2$CO$_3$, dioxane/H$_2$O<br>reflux |
| 2.29 | 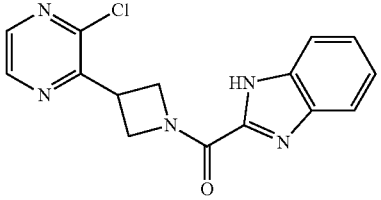<br>PREPARATION 36 | 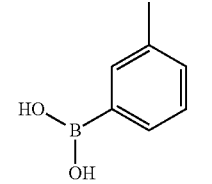<br>Alfa Aesar | PdCl$_2$(dppf), K$_2$CO$_3$, dioxane/H$_2$O<br>reflux |

TABLE 14C-continued

STARTING MATERIALS AND REACTION CONDITION FOR
PREPARATION OF EXAMPLES 2.1 TO 2.30.
Unless otherwise stated, all starting materials are commercially available from common vendors.

| Ex. # | Starting Material 1 | Starting Material 2 | Reaction Condition |
|---|---|---|---|
| 2.30 | PREPARATION 36 | Alfa Aesar | $PdCl_2(dppf)$, $K_2CO_3$, dioxane/$H_2O$ reflux |

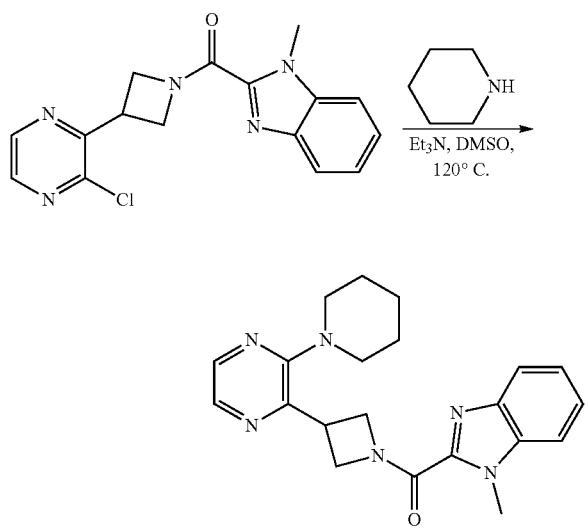

SCHEME 3

Example 3.1: (1-Methyl-1H-Benzoimidazol-2-Yl)-[3-(3-Piperidin-1-Yl-Pyrazin-2-Yl)-Azetidin-1-Yl]-Methanone To a mixture of [3-(3-chloro-pyrazin-2-yl)-azetidin-1-yl]-(1-methyl-1H-benzoimidazol-2-yl)-methanone (0.10 g, 0.30 mmol), piperidine (0.052 g, 0.60 mmol) and triethylamine (0.091 g, 0.90 mmol) was added DMSO (4 mL). The solution was heated to 120° C. for 5 h. Then the mixture was diluted with water (10 mL) and extracted with EtOAc (2×20 mL). The combined organic extracts were washed with water (10 mL), brine (10 mL), dried over $Na_2SO_4$ and filtered. The filtrate was evaporated in vacuo and the residue was purified by flash column chromatography on silica gel (20% to 50% EtOAc in petroleum ether) to give (1-methyl-1H-benzoimidazol-2-yl)-[3-(3-piperidin-1-yl-pyrazin-2-yl)-azetidin-1-yl]-methanone (0.072 g, 0.19 mmol, 63% yield) as white solid.

The following Table 15A lists compounds of Examples 3.1 to 3.54, which were made analogous to Scheme 3 by using the appropriate materials and reaction conditions, which are listed in Table 15B. The NMR data of the Examples are listed in Table 15C.

TABLE 15A

EXAMPLES 3.1 TO 3.54

| Ex. # | Structure | Chemical Name | ESI-MS (M + 1) | $IC_{50}$ (uM) |
|---|---|---|---|---|
| 3.1 | 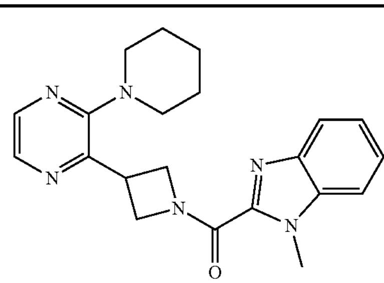 | (1-Methyl-1H-benzoimidazol-2-yl)-[3-(3-piperidin-1-yl-pyrazin-2-yl)-azetidin-1-yl]-methanone | 377 | 0.136 |

TABLE 15A-continued

EXAMPLES 3.1 TO 3.54

| Ex. # | Structure | Chemical Name | ESI-MS (M + 1) | IC$_{50}$ (uM) |
|---|---|---|---|---|
| 3.2 | 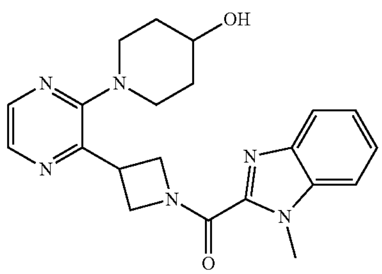 [SMILES: Cn1c(C(=O)N2CC(c3nccnc3N3CCC(O)CC3)C2)nc2ccccc21] | {3-[3-(4-Hydroxy-piperidin-1-yl)-pyrazin-2-yl]-azetidin-1-yl}-(1-methyl-1H-benzoimidazol-2-yl)-methanone | 393 | 0.351 |
| 3.3 | 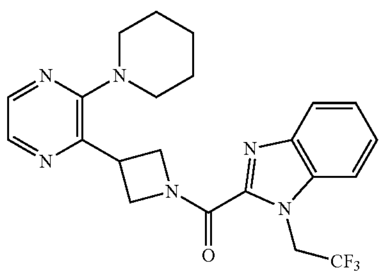 [SMILES: O=C(c1nc2ccccc2n1CC(F)(F)F)N1CC(c2nccnc2N2CCCCC2)C1] | [3-(3-Piperidin-1-yl-pyrazin-2-yl)-azetidin-1-yl]-[1-(2,2,2-trifluoro-ethyl)-1H-benzoimidazol-2-yl]-methanone | 445 | 0.575 |
| 3.4 | 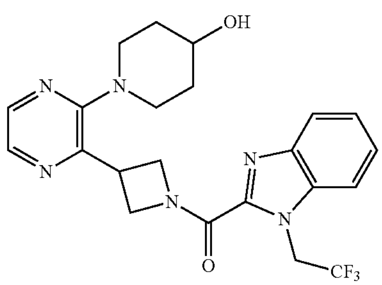 [SMILES: O=C(c1nc2ccccc2n1CC(F)(F)F)N1CC(c2nccnc2N2CCC(O)CC2)C1] | {3-[3-(4-Hydroxy-piperidin-1-yl)-pyrazin-2-yl]-azetidin-1-yl}-[1-(2,2,2-trifluoro-ethyl)-1H-benzoimidazol-2-yl]-methanone | 461 | 0.963 |
| 3.5 | 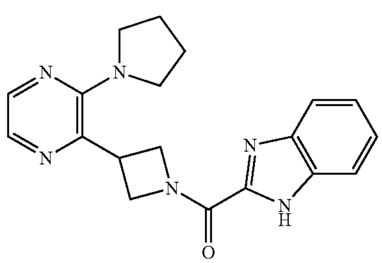 [SMILES: O=C(c1nc2ccccc2[nH]1)N1CC(c2nccnc2N2CCCC2)C1] | (1H-Benzoimidazol-2-yl)-[3-(3-pyrrolidin-1-yl-pyrazin-2-yl)-azetidin-1-yl]-methanone | 349 | 0.0217 |
| 3.6 | 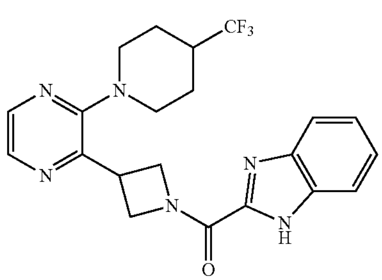 [SMILES: O=C(c1nc2ccccc2[nH]1)N1CC(c2nccnc2N2CCC(C(F)(F)F)CC2)C1] | (1H-Benzoimidazol-2-yl)-{3-[3-(4-trifluoromethyl-piperidin-1-yl)-pyrazin-2-yl]-azetidin-1-yl}-methanone | 431 | 0.0205 |

TABLE 15A-continued

EXAMPLES 3.1 TO 3.54

| Ex. # | Structure | Chemical Name | ESI-MS (M + 1) | IC$_{50}$ (uM) |
|---|---|---|---|---|
| 3.7 | 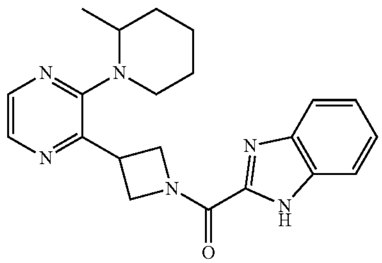 [SMILES: CC1CCCCN1c1nccnc1C1CN(C(=O)c2nc3ccccc3[nH]2)C1] | (R & S)-(1H-Benzoimidazol-2-yl)-{3-[3-(2-methyl-piperidin-1-yl)-pyrazin-2-yl]-azetidin-1-yl}-methanone | 377 | 0.0636 |
| 3.8 | 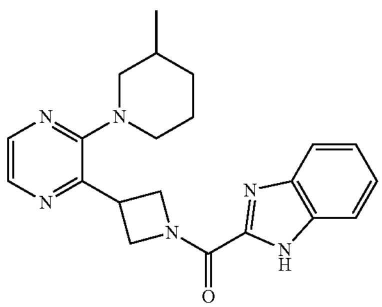 [SMILES: CC1CCCN(c2nccnc2C2CN(C(=O)c3nc4ccccc4[nH]3)C2)C1] | (1H-Benzoimidazol-2-yl)-{3-[3-(3-methyl-piperidin-1-yl)-pyrazin-2-yl]-azetidin-1-yl}-methanone | 377 | 0.016 |
| 3.9 | 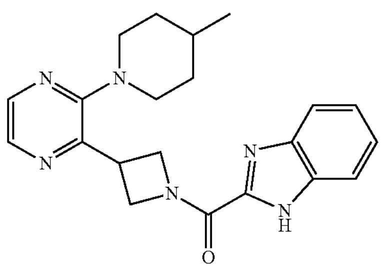 [SMILES: CC1CCN(c2nccnc2C2CN(C(=O)c3nc4ccccc4[nH]3)C2)CC1] | (1H-Benzoimidazol-2-yl)-{3-[3-(4-methyl-piperidin-1-yl)-pyrazin-2-yl]-azetidin-1-yl}-methanone | 377 | 0.0272 |
| 3.10 | 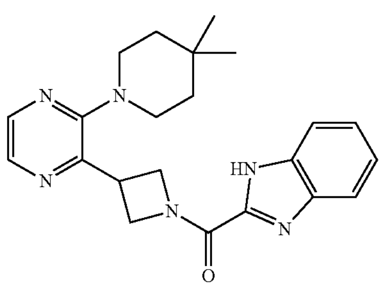 [SMILES: CC1(C)CCN(c2nccnc2C2CN(C(=O)c3nc4ccccc4[nH]3)C2)CC1] | (1H-Benzoimidazol-2-yl)-{3-[3-(4,4-dimethyl-piperidin-1-yl)-pyrazin-2-yl]-azetidin-1-yl}-methanone | 391 | 0.0481 |
| 3.11 | 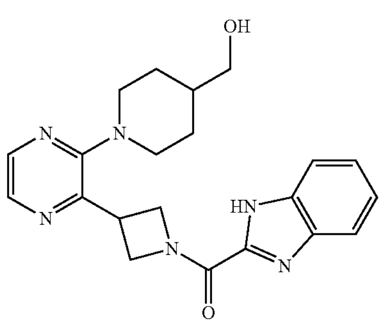 [SMILES: O=C(c1nc2ccccc2[nH]1)N1CC(c2nccnc2N2CCC(CO)CC2)C1] | (1H-Benzoimidazol-2-yl)-{3-[3-(4-hydroxymethyl-piperidin-1-yl)-pyrazin-2-yl]-azetidin-1-yl}-methanone | 393 | 0.0072 |

TABLE 15A-continued

EXAMPLES 3.1 TO 3.54

| Ex. # | Structure | Chemical Name | ESI-MS (M + 1) | IC$_{50}$ (uM) |
|---|---|---|---|---|
| 3.12 | 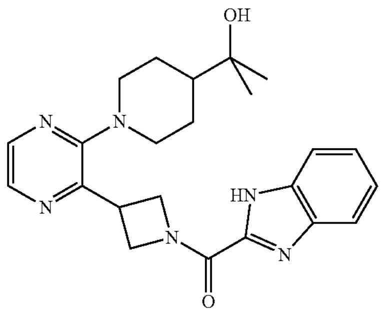 [SMILES: CC(C)(O)C1CCN(c2nccnc2C2CN(C(=O)c3nc4ccccc4[nH]3)C2)CC1] | (1H-Benzoimidazol-2-yl)-(3-{3-[4-(1-hydroxy-1-methyl-ethyl)-piperidin-1-yl]-pyrazin-2-yl}-azetidin-1-yl)-methanone | 421 | 0.0563 |
| 3.13 | 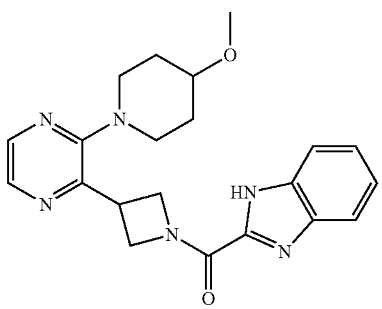 [SMILES: COC1CCN(c2nccnc2C2CN(C(=O)c3nc4ccccc4[nH]3)C2)CC1] | (1H-Benzoimidazol-2-yl)-(3-{3-[4-(1-hydroxy-1-methyl-ethyl)-piperidin-1-yl]-pyrazin-2-yl}-azetidin-1-yl)-methanone | 393 | 0.0381 |
| 3.14 | 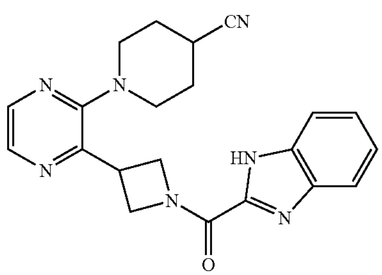 [SMILES: N#CC1CCN(c2nccnc2C2CN(C(=O)c3nc4ccccc4[nH]3)C2)CC1] | 1-{3-[1-(1H-Benzoimidazole-2-carbonyl)-azetidin-3-yl]-pyrazin-2-yl}-piperidine-4-carbonitrile | 388 | 0.00529 |
| 3.15 | 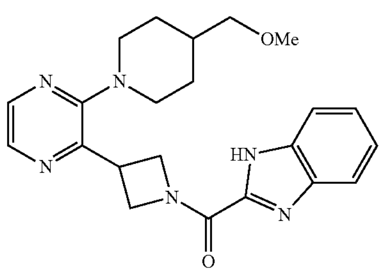 [SMILES: COCC1CCN(c2nccnc2C2CN(C(=O)c3nc4ccccc4[nH]3)C2)CC1] | (1H-Benzoimidazol-2-yl)-{3-[3-(4-methoxymethyl-piperidin-1-yl)-pyrazin-2-yl]-azetidin-1-yl}-methanone | 407 | 0.0185 |
| 3.16 | 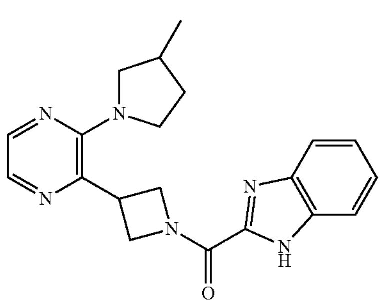 [SMILES: CC1CCN(c2nccnc2C2CN(C(=O)c3nc4ccccc4[nH]3)C2)C1] | (R & S)-(1H-Benzoimidazol-2-yl)-{3-[3-(3-methyl-pyrrolidin-1-yl)-pyrazin-2-yl]-azetidin-1-yl}-methanone | 363 | 0.00892 |

TABLE 15A-continued

EXAMPLES 3.1 TO 3.54

| Ex. # | Structure | Chemical Name | ESI-MS (M + 1) | IC$_{50}$ (uM) |
|---|---|---|---|---|
| 3.17 | 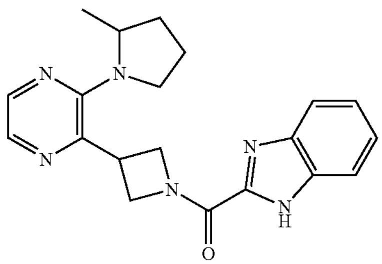 [SMILES: CC1CCCN1c1nccnc1C1CN(C(=O)c2nc3ccccc3[nH]2)C1] | (R & S)-(1H-Benzoimidazol-2-yl)-{3-[3-(2-methyl-pyrrolidin-1-yl)-pyrazin-2-yl]-azetidin-1-yl}-methanone | 363 | 0.0149 |
| 3.18 | 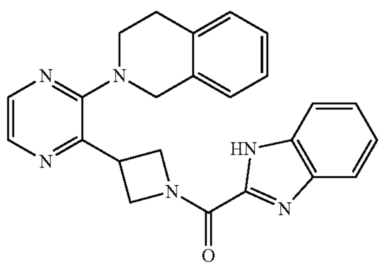 [SMILES: O=C(c1nc2ccccc2[nH]1)N1CC(c2nccnc2N2CCc3ccccc3C2)C1] | (1H-Benzoimidazol-2-yl)-{3-[3-(3,4-dihydro-1H-isoquinolin-2-yl)-pyrazin-2-yl]-azetidin-1-yl}-methanone | 411 | 0.00676 |
| 3.19 | 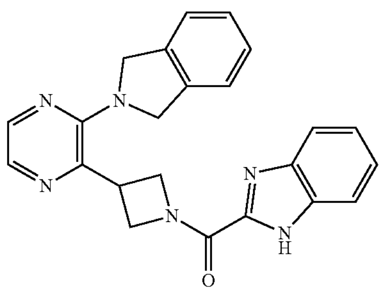 [SMILES: O=C(c1nc2ccccc2[nH]1)N1CC(c2nccnc2N2Cc3ccccc3C2)C1] | (1H-Benzoimidazol-2-yl)-{3-[3-(1,3-dihydro-isoindol-2-yl)-pyrazin-2-yl]-azetidin-1-yl}-methanone | 397 | 0.043 |
| 3.20 | 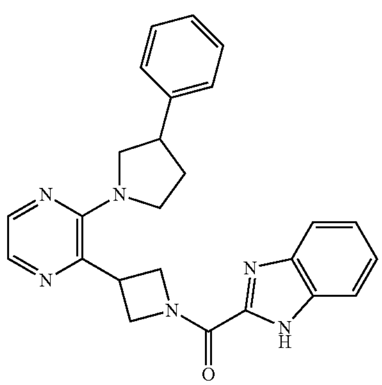 [SMILES: O=C(c1nc2ccccc2[nH]1)N1CC(c2nccnc2N2CCC(c3ccccc3)C2)C1] | (R & S)-(1H-Benzoimidazol-2-yl)-{3-[3-(3-phenyl-pyrrolidin-1-yl)-pyrazin-2-yl]-azetidin-1-yl}-methanone | 425 | 0.0468 |
| 3.21 | 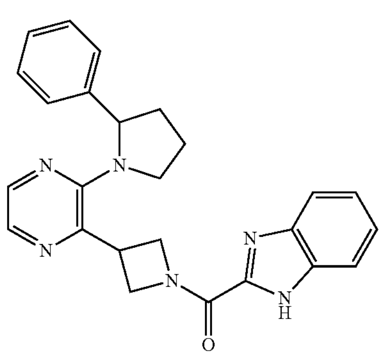 [SMILES: O=C(c1nc2ccccc2[nH]1)N1CC(c2nccnc2N2CCCC2c2ccccc2)C1] | (R & S)-(1H-Benzoimidazol-2-yl)-{3-[3-(2-phenyl-pyrrolidin-1-yl)-pyrazin-2-yl]-azetidin-1-yl}-methanone | 425 | 0.163 |

TABLE 15A-continued

EXAMPLES 3.1 TO 3.54

| Ex. # | Structure | Chemical Name | ESI-MS (M + 1) | IC$_{50}$ (uM) |
|---|---|---|---|---|
| 3.22 | 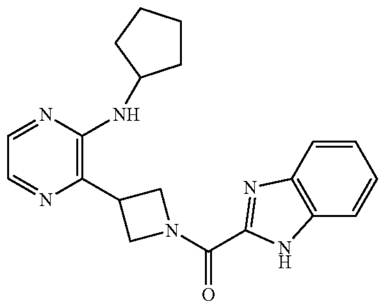 [SMILES: O=C(c1nc2ccccc2[nH]1)N1CC(c2nccnc2NC2CCCC2)C1] | (1H-Benzoimidazol-2-yl)-[3-(3-cyclopentylamino-pyrazin-2-yl)-azetidin-1-yl]-methanone | 363 | 0.0363 |
| 3.23 | 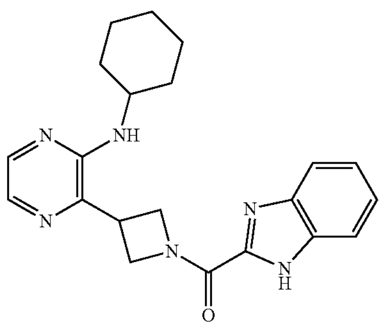 [SMILES: O=C(c1nc2ccccc2[nH]1)N1CC(c2nccnc2NC2CCCCC2)C1] | (1H-Benzoimidazol-2-yl)-[3-(3-cyclohexylamino-pyrazin-2-yl)-azetidin-1-yl]-methanone | 377 | 0.0389 |
| 3.24 | 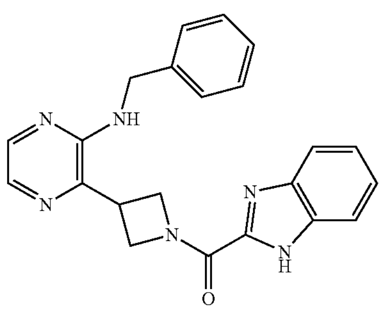 [SMILES: O=C(c1nc2ccccc2[nH]1)N1CC(c2nccnc2NCc2ccccc2)C1] | (1H-Benzoimidazol-2-yl)-[3-(3-benzylamino-pyrazin-2-yl)-azetidin-1-yl]-methanone | 385 | 0.171 |
| 3.25 | 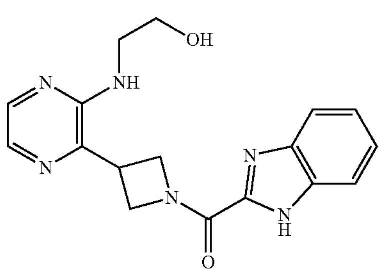 [SMILES: O=C(c1nc2ccccc2[nH]1)N1CC(c2nccnc2NCCO)C1] | (1H-Benzoimidazol-2-yl)-{3-[3-(2-hydroxy-ethylamino)-pyrazin-2-yl]-azetidin-1-yl}-methanone | 339 | 0.74 |
| 3.26 | 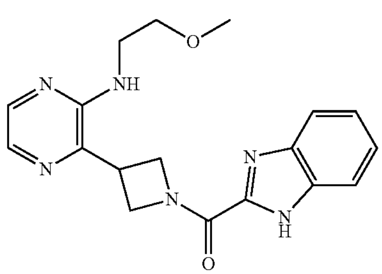 [SMILES: COCCNc1nccnc1C1CN(C(=O)c2nc3ccccc3[nH]2)C1] | (1H-benzo[d]imidazol-2-yl)(3-(3-((2-methoxyethyl)amino)pyrazin-2-yl)azetidin-1-yl)methanone | 353 | 0.0586 |

TABLE 15A-continued

EXAMPLES 3.1 TO 3.54

| Ex. # | Structure | Chemical Name | ESI-MS (M + 1) | IC$_{50}$ (uM) |
|---|---|---|---|---|
| 3.27 | 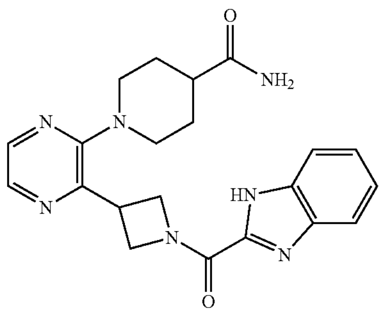 [SMILES: NC(=O)C1CCN(c2nccnc2C2CN(C(=O)c3nc4ccccc4[nH]3)C2)CC1] | 1-{3-[1-(1H-Benzoimidazole-2-carbonyl)-azetidin-3-yl]-pyrazin-2-yl}-piperidine-4-carboxylic acid amide | 406 | 0.00312 |
| 3.28 | 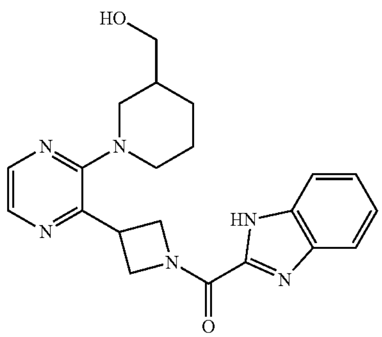 [SMILES: O=C(c1nc2ccccc2[nH]1)N1CC(c2nccnc2N2CCCC(CO)C2)C1] | (R & S)-(1H-Benzoimidazol-2-yl)-{3-[3-(3-hydroxymethyl-piperidin-1-yl)-pyrazin-2-yl]-azetidin-1-yl}-methanone | 393 | 0.0206 |
| 3.29 | 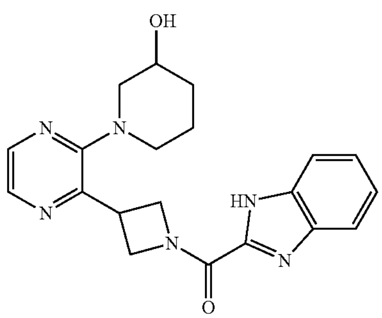 [SMILES: O=C(c1nc2ccccc2[nH]1)N1CC(c2nccnc2N2CCCC(O)C2)C1] | (1H-Benzoimidazol-2-yl)-{3-[3-(3-hydroxy-piperidin-1-yl)-pyrazin-2-yl]-azetidin-1-yl}-methanone | 379 | 0.0352 |
| 3.30 | 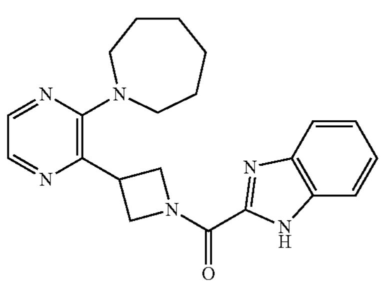 | [3-(3-Azepan-1-yl-pyrazin-2-yl)-azetidin-1-yl]-(1H-benzoimidazol-2-yl)-methanone | 379 | 0.0342 |
| 3.31 | 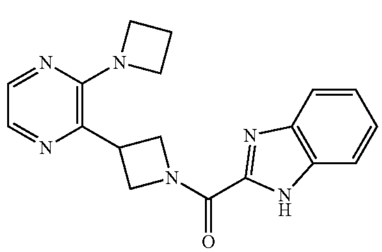 [SMILES: O=C(c1nc2ccccc2[nH]1)N1CC(c2nccnc2N2CCC2)C1] | [3-(3-Azetidin-1-yl-pyrazin-2-yl)-azetidin-1-yl]-(1H-benzoimidazol-2-yl)-methanone | 335 | 0.0882 |

TABLE 15A-continued

EXAMPLES 3.1 TO 3.54

| Ex. # | Structure | Chemical Name | ESI-MS (M + 1) | IC$_{50}$ (uM) |
|---|---|---|---|---|
| 3.32 | 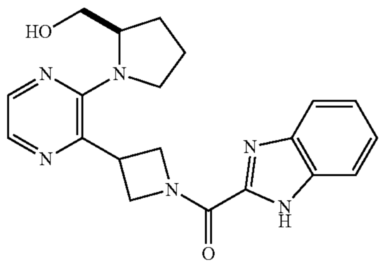 [SMILES: O=C(c1nc2ccccc2[nH]1)N1CC(c2nccnc2N2CCC[C@@H]2CO)C1] | (R)-(1H-Benzoimidazol-2-yl)-{3-[3-(2-hydroxymethyl-pyrrolidin-1-yl)-pyrazin-2-yl]-azetidin-1-yl}-methanone | 379 | 0.104 |
| 3.33 | 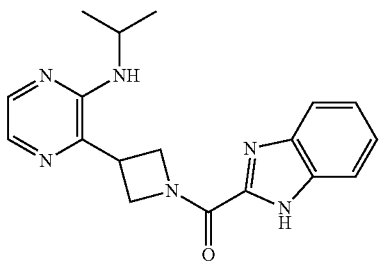 [SMILES: CC(C)Nc1nccnc1C1CN(C(=O)c2nc3ccccc3[nH]2)C1] | (1H-Benzoimidazol-2-yl)-[3-(3-isopropylamino-pyrazin-2-yl)-azetidin-1-yl]-methanone | 337 | 0.133 |
| 3.34 | 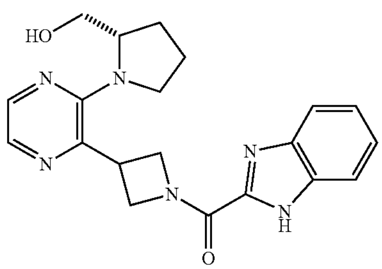 [SMILES: O=C(c1nc2ccccc2[nH]1)N1CC(c2nccnc2N2CCC[C@H]2CO)C1] | (S)-(1H-Benzoimidazol-2-yl)-{3-[3-(2-hydroxymethyl-pyrrolidin-1-yl)-pyrazin-2-yl]-azetidin-1-yl}-methanone | 379 | 0.917 |
| 3.35 | 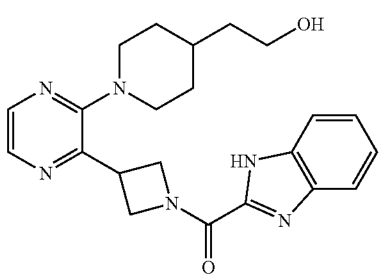 [SMILES: O=C(c1nc2ccccc2[nH]1)N1CC(c2nccnc2N2CCC(CCO)CC2)C1] | (1H-Benzoimidazol-2-yl)-(3-{3-[4-(2-hydroxy-ethyl)-piperidin-1-yl]-pyrazin-2-yl}-azetidin-1-yl)-methanone | 407 | 0.0094 |
| 3.36 | 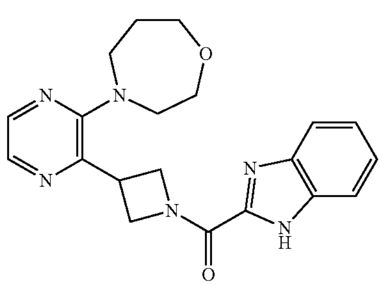 [SMILES: O=C(c1nc2ccccc2[nH]1)N1CC(c2nccnc2N2CCCOCC2)C1] | (1H-Benzoimidazol-2-yl)-[3-(3-[1,4]oxazepan-4-yl-pyrazin-2-yl)-azetidin-1-yl]-methanone | 379 | 0.0627 |

TABLE 15A-continued

EXAMPLES 3.1 TO 3.54

| Ex. # | Structure | Chemical Name | ESI-MS (M + 1) | IC$_{50}$ (uM) |
|---|---|---|---|---|
| 3.37 | 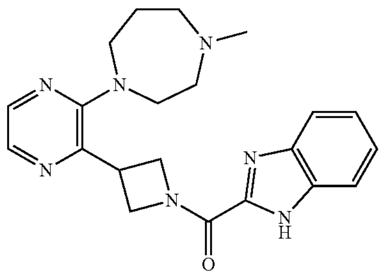 [SMILES: CN1CCCN(c2nccnc2C2CN(C(=O)c3nc4ccccc4[nH]3)C2)CC1] | (1H-Benzoimidazol-2-yl)-{3-[3-(4-methyl-[1,4]diazepan-1-yl)-pyrazin-2-yl]-azetidin-1-yl}-methanone | 392 | 4.28 |
| 3.38 | 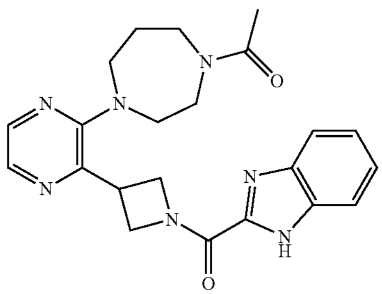 [SMILES: CC(=O)N1CCCN(c2nccnc2C2CN(C(=O)c3nc4ccccc4[nH]3)C2)CC1] | 1-(4-{3-[1-(1H-Benzoimidazole-2-carbonyl)-azetidin-3-yl]-pyrazin-2-yl}-[1,4]diazepan-1-yl)-ethanone | 420 | 0.0859 |
| 3.39 | 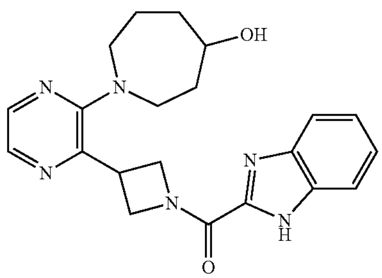 [SMILES: O=C(c1nc2ccccc2[nH]1)N1CC(c2nccnc2N2CCCC(O)CC2)C1] | (1H-Benzoimidazol-2-yl)-{3-[3-(4-hydroxy-azepan-1-yl)-pyrazin-2-yl]-azetidin-1-yl}-methanone | 393 | 0.0368 |
| 3.40 | 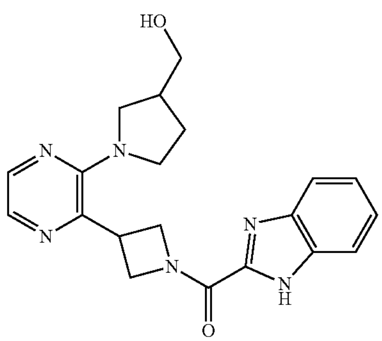 [SMILES: O=C(c1nc2ccccc2[nH]1)N1CC(c2nccnc2N2CCC(CO)C2)C1] | (R & S)-(1H-Benzoimidazol-2-yl)-{3-[3-(3-hydroxymethyl-pyrrolidin-1-yl)-pyrazin-2-yl]-azetidin-1-yl}-methanone | 379 | 0.0665 |
| 3.41 | 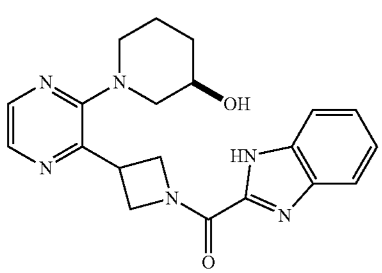 [SMILES: O=C(c1nc2ccccc2[nH]1)N1CC(c2nccnc2N2CCC[C@@H](O)C2)C1] | (R)-(1H-Benzoimidazol-2-yl)-{3-[3-(3-hydroxy-piperidin-1-yl)-pyrazin-2-yl]-azetidin-1-yl}-methanone | 379 | 0.0709 |

TABLE 15A-continued

EXAMPLES 3.1 TO 3.54

| Ex. # | Structure | Chemical Name | ESI-MS (M + 1) | IC$_{50}$ (uM) |
|---|---|---|---|---|
| 3.42 | 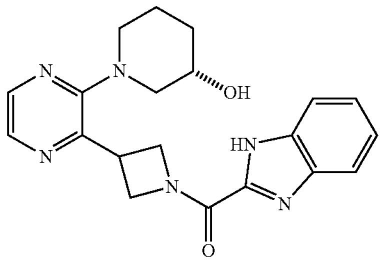 [SMILES: O=C(c1nc2ccccc2[nH]1)N1CC(c2nccnc2N2CCC[C@H](O)C2)C1] | (S)-(1H-Benzoimidazol-2-yl)-{3-[3-(3-hydroxy-piperidin-1-yl)-pyrazin-2-yl]-azetidin-1-yl}-methanone | 379 | 0.170 |
| 3.43 | 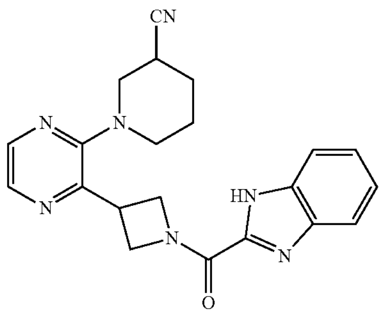 | (R & S)-1-{3-[1-(1H-Benzoimidazole-2-carbonyl)-azetidin-3-yl]-pyrazin-2-yl}-piperidine-3-carbonitrile | 388 | 0.0868 |
| 3.44 | 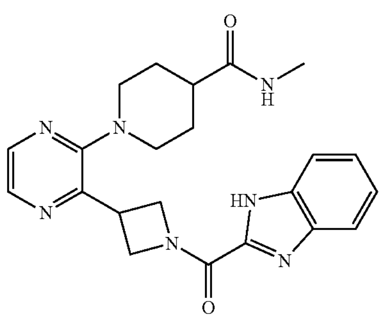 | 1-{3-[1-(1H-Benzoimidazole-2-carbonyl)-azetidin-3-yl]-pyrazin-2-yl}-piperidine-4-carboxylic acid methylamide | 420 | 0.016 |
| 3.45 | 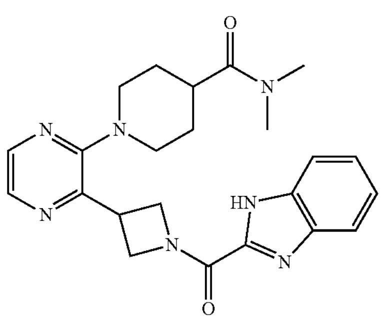 [SMILES: CN(C)C(=O)C1CCN(c2nccnc2C2CN(C(=O)c3nc4ccccc4[nH]3)C2)CC1] | 1-{3-[1-(1H-Benzoimidazole-2-carbonyl)-azetidin-3-yl]-pyrazin-2-yl}-piperidine-4-carboxylic acid dimethylamide | 434 | 0.0166 |
| 3.46 | 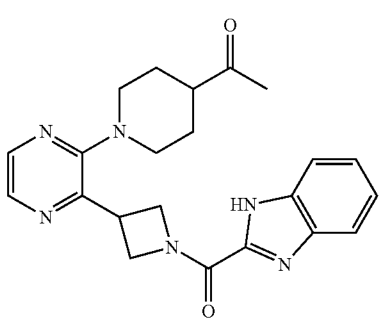 | 1-(1-(3-(1-(1H-benzo[d]imidazole-2-carbonyl)azetidin-3-yl)pyrazin-2-yl)piperidin-4-yl)ethanone | 405 | 0.0119 |

TABLE 15A-continued

EXAMPLES 3.1 TO 3.54

| Ex. # | Structure | Chemical Name | ESI-MS (M + 1) | IC$_{50}$ (uM) |
|---|---|---|---|---|
| 3.47 | 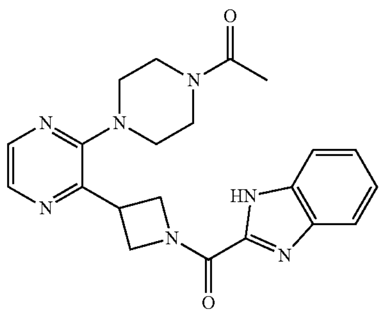 [SMILES: CC(=O)N1CCN(c2nccnc2C2CN(C(=O)c3nc4ccccc4[nH]3)C2)CC1] | 1-(4-(3-(1-(1H-benzo[d]imidazole-2-carbonyl)azetidin-3-yl)pyrazin-2-yl)piperazin-1-yl)ethanone | 406 | 0.192 |
| 3.48 | 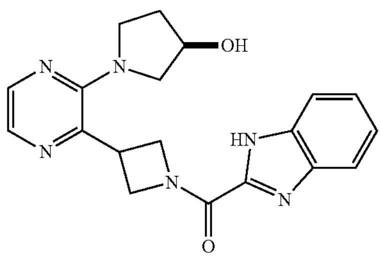 [SMILES: O=C(c1nc2ccccc2[nH]1)N1CC(c2nccnc2N2CC[C@@H](O)C2)C1] | (R)-(1H-benzo[d]imidazol-2-yl)(3-(3-(3-hydroxypyrrolidin-1-yl)pyrazin-2-yl)azetidin-1-yl)methanone | 365 | 0.0718 |
| 3.49 | 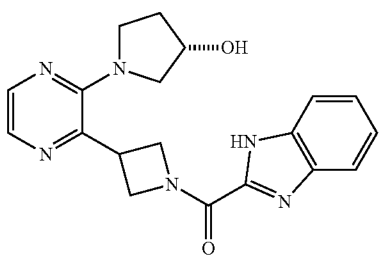 [SMILES: O=C(c1nc2ccccc2[nH]1)N1CC(c2nccnc2N2CC[C@H](O)C2)C1] | (S)-(1H-benzo[d]imidazol-2-yl)(3-(3-(3-hydroxypyrrolidin-1-yl)pyrazin-2-yl)azetidin-1-yl)methanone | 365 | 0.0632 |
| 3.50 | 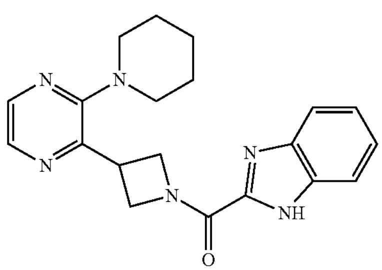 [SMILES: O=C(c1nc2ccccc2[nH]1)N1CC(c2nccnc2N2CCCCC2)C1] | (1H-benzo[d]imidazol-2-yl)(3-(3-(piperidin-1-yl)pyrazin-2-yl)azetidin-1-yl)methanone | 363 | 0.0107 |
| 3.51 | 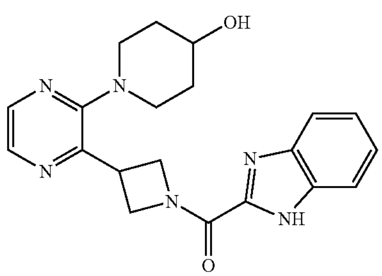 [SMILES: O=C(c1nc2ccccc2[nH]1)N1CC(c2nccnc2N2CCC(O)CC2)C1] | (1H-benzo[d]imidazol-2-yl)(3-(3-(4-hydroxypiperidin-1-yl)pyrazin-2-yl)azetidin-1-yl)methanone | 379 | 0.0233 |

TABLE 15A-continued

EXAMPLES 3.1 TO 3.54

| Ex. # | Structure | Chemical Name | ESI-MS (M + 1) | IC$_{50}$ (uM) |
|---|---|---|---|---|
| 3.52 | 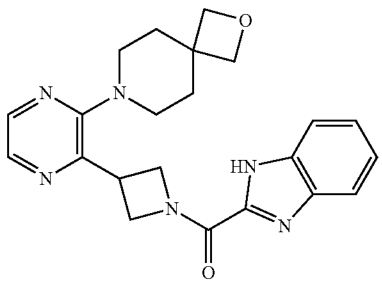 [SMILES: O=C(c1nc2ccccc2[nH]1)N1CC(c2nccnc2N2CCC3(CC2)COC3)C1] | (1H-Benzoimidazol-2-yl)-{3-[3-(2-oxa-7-aza-spiro[3.5]non-7-yl)-pyrazin-2-yl]-azetidin-1-yl}-methanone | 405 | 0.0276 |
| 3.53 | 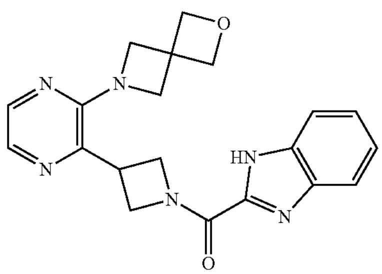 [SMILES: O=C(c1nc2ccccc2[nH]1)N1CC(c2nccnc2N2CC3(COC3)C2)C1] | (1H-Benzoimidazol-2-yl)-{3-[3-(2-oxa-6-aza-spiro[3.3]hept-6-yl)-pyrazin-2-yl]-azetidin-1-yl}-methanone | 377 | 0.1320 |
| 3.54 | 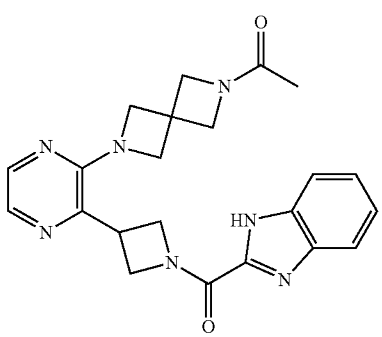 [SMILES: CC(=O)N1CC2(C1)CN(c1nccnc1C1CN(C(=O)c3nc4ccccc4[nH]3)C1)C2] | 1-(6-{3-[1-(1H-Benzoimida-zole-2-carbonyl)-azetidin-3-yl]-pyrazin-2-yl}-2,6-diaza-spiro[3.3]hept-2-yl)-ethanone | 418 | 0.4900 |

TABLE 15B

STARTING MATERIALS AND REACTION CONDITION FOR
PREPARATION OF EXAMPLES 3.1 TO 3.54.
Unless otherwise stated, all starting materials are commercially available from common vendors.

| Ex. # | Starting Material 1 | Starting Material 2 | Reaction Condition |
|---|---|---|---|
| 3.1 | PREPARATION 25 | | TEA, DMSO 120° C. |

TABLE 15B-continued

STARTING MATERIALS AND REACTION CONDITION FOR
PREPARATION OF EXAMPLES 3.1 TO 3.54.
Unless otherwise stated, all starting materials are commercially available from common vendors.

| Ex. # | Starting Material 1 | Starting Material 2 | Reaction Condition |
|---|---|---|---|
| 3.2 | 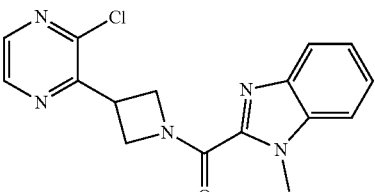<br>PREPARATION 25 | 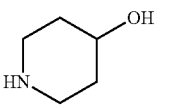 | TEA, DMSO<br>120° C. |
| 3.3 | 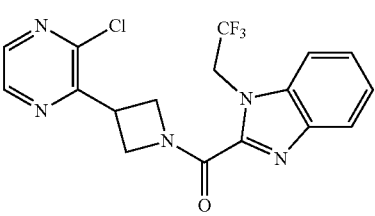<br>PREPARATION 26 |  | TEA, DMSO<br>120° C. |
| 3.4 | 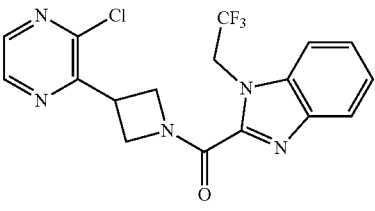<br>PREPARATION 26 | 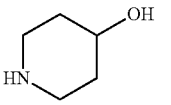 | TEA, DMSO<br>120° C. |
| 3.5 | 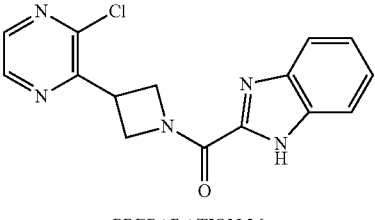<br>PREPARATION 36 |  | TEA, DMSO<br>120° C. |
| 3.6 | 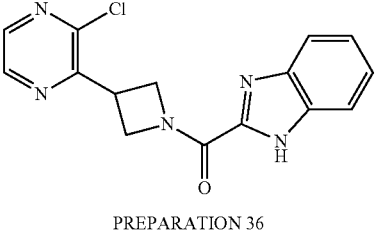 [SMILES: O=C(c1nc2ccccc2[nH]1)N1CC(c2nccnc2Cl)C1]<br>PREPARATION 36 | 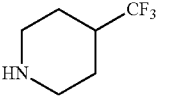 | TEA, DMSO<br>120° C. |
| 3.7 | 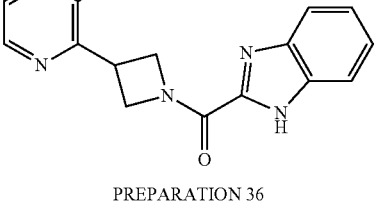<br>PREPARATION 36 | 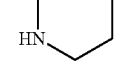 | TEA, DMSO<br>120° C. |

TABLE 15B-continued

STARTING MATERIALS AND REACTION CONDITION FOR
PREPARATION OF EXAMPLES 3.1 TO 3.54.
Unless otherwise stated, all starting materials are commercially available from common vendors.

| Ex. # | Starting Material 1 | Starting Material 2 | Reaction Condition |
|---|---|---|---|
| 3.8 | 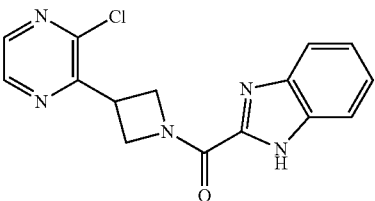<br>PREPARATION 36 | 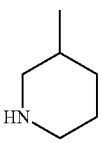 | TEA, DMSO<br>120° C. |
| 3.9 | 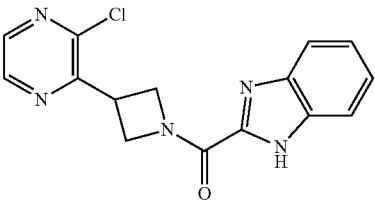<br>PREPARATION 36 | 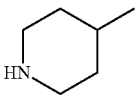 | TEA, DMSO<br>120° C. |
| 3.10 | 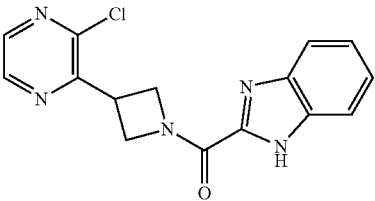<br>PREPARATION 36 | 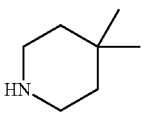 | TEA, DMSO<br>120° C. |
| 3.11 | 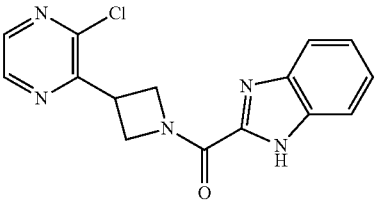<br>PREPARATION 36 | 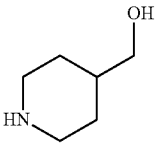 | TEA, DMSO<br>120° C. |
| 3.12 | 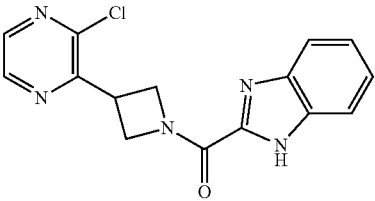<br>PREPARATION 36 | 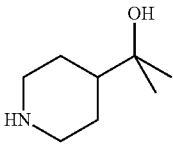 | TEA, DMSO<br>120° C. |
| 3.13 | 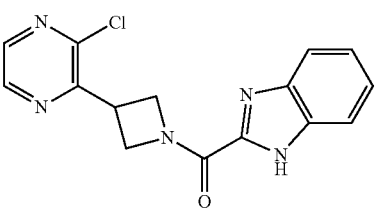<br>PREPARATION 36 | 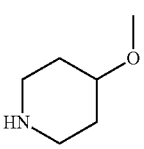 | TEA, DMSO<br>120° C. |

TABLE 15B-continued

STARTING MATERIALS AND REACTION CONDITION FOR
PREPARATION OF EXAMPLES 3.1 TO 3.54.
Unless otherwise stated, all starting materials are commercially available from common vendors.

| Ex. # | Starting Material 1 | Starting Material 2 | Reaction Condition |
|---|---|---|---|
| 3.14 | PREPARATION 36 | piperidine-4-carbonitrile | TEA, DMSO 120° C. |
| 3.15 | PREPARATION 36 | 4-(methoxymethyl)piperidine | TEA, DMSO 120° C. |
| 3.16 | PREPARATION 36 | 3-methylpyrrolidine | TEA, DMSO 120° C. |
| 3.17 | PREPARATION 36 | 2-methylpyrrolidine | TEA, DMSO 120° C. |
| 3.18 | PREPARATION 36 | 1,2,3,4-tetrahydroisoquinoline | TEA, DMSO 120° C. |
| 3.19 | PREPARATION 36 | isoindoline | TEA, DMSO 120° C. |

TABLE 15B-continued

STARTING MATERIALS AND REACTION CONDITION FOR
PREPARATION OF EXAMPLES 3.1 TO 3.54.
Unless otherwise stated, all starting materials are commercially available from common vendors.

| Ex. # | Starting Material 1 | Starting Material 2 | Reaction Condition |
|---|---|---|---|
| 3.20 | 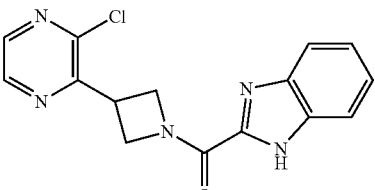<br>PREPARATION 36 | 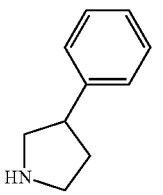 [SMILES: c1ccc(C2CCNC2)cc1] | TEA, DMSO<br>120° C. |
| 3.21 | 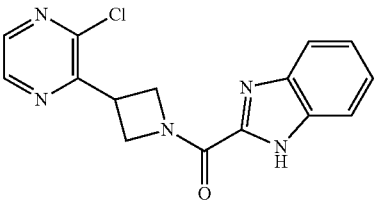<br>PREPARATION 36 | 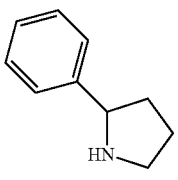 [SMILES: c1ccc(C2CCCN2)cc1] | TEA, DMSO<br>120° C. |
| 3.22 | 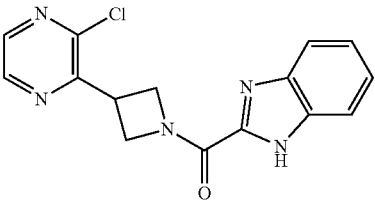<br>PREPARATION 36 | 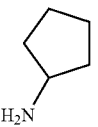 | TEA, DMSO<br>120° C. |
| 3.23 | 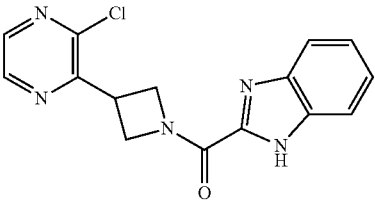<br>PREPARATION 36 |  | TEA, DMSO<br>120° C. |
| 3.24 | 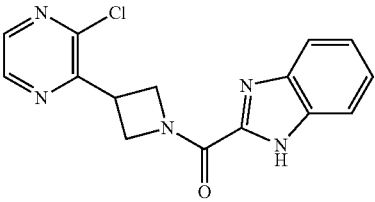<br>PREPARATION 36 | 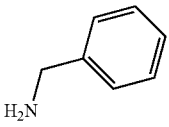 | TEA, DMSO<br>120° C. |
| 3.25 | 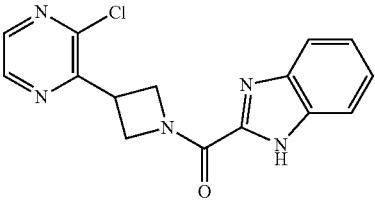<br>PREPARATION 36 | 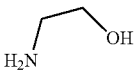 | TEA, DMSO<br>120° C. |

TABLE 15B-continued

STARTING MATERIALS AND REACTION CONDITION FOR
PREPARATION OF EXAMPLES 3.1 TO 3.54.
Unless otherwise stated, all starting materials are commercially available from common vendors.

| Ex. # | Starting Material 1 | Starting Material 2 | Reaction Condition |
|---|---|---|---|
| 3.26 | PREPARATION 36 | H₂N-CH₂CH₂-O-CH₃ | TEA, DMSO 120° C. |
| 3.27 | PREPARATION 36 | piperidine-4-carboxamide | TEA, DMSO 120° C. |
| 3.28 | PREPARATION 36 | 3-(hydroxymethyl)piperidine | TEA, DMSO 120° C. |
| 3.29 | PREPARATION 36 | 3-hydroxypiperidine | TEA, DMSO 120° C. |
| 3.30 | PREPARATION 36 | azepane | TEA, DMSO 120° C. |
| 3.31 | PREPARATION 36 | azetidine | TEA, DMSO 120° C. |

TABLE 15B-continued

STARTING MATERIALS AND REACTION CONDITION FOR
PREPARATION OF EXAMPLES 3.1 TO 3.54.
Unless otherwise stated, all starting materials are commercially available from common vendors.

| Ex. # | Starting Material 1 | Starting Material 2 | Reaction Condition |
|---|---|---|---|
| 3.32 | PREPARATION 36 | (S)-prolinol | TEA, DMSO 120° C. |
| 3.33 | PREPARATION 36 | isopropylamine | TEA, DMSO 120° C. |
| 3.34 | PREPARATION 36 | (R)-prolinol | TEA, DMSO 120° C. |
| 3.35 | PREPARATION 36 | 2-(piperidin-4-yl)ethanol | TEA, DMSO 120° C. |
| 3.36 | PREPARATION 36 | 1,4-oxazepane | TEA, DMSO 120° C. |
| 3.37 | PREPARATION 36 | 1-methyl-1,4-diazepane | TEA, DMSO 120° C. |

TABLE 15B-continued

STARTING MATERIALS AND REACTION CONDITION FOR
PREPARATION OF EXAMPLES 3.1 TO 3.54.
Unless otherwise stated, all starting materials are commercially available from common vendors.

| Ex. # | Starting Material 1 | Starting Material 2 | Reaction Condition |
|---|---|---|---|
| 3.38 | PREPARATION 36 | 1-acetyl-1,4-diazepane | TEA, DMSO 120° C. |
| 3.39 | PREPARATION 36 | azepan-4-ol | TEA, DMSO 120° C. |
| 3.40 | PREPARATION 36 | pyrrolidin-3-ylmethanol | TEA, DMSO 120° C. |
| 3.41 | PREPARATION 36 | (R)-piperidin-3-ol | TEA, DMSO 120° C. |
| 3.42 | PREPARATION 36 | (S)-piperidin-3-ol | TEA, DMSO 120° C. |
| 3.43 | PREPARATION 36 | piperidine-3-carbonitrile | TEA, DMSO 120° C. |

TABLE 15B-continued

STARTING MATERIALS AND REACTION CONDITION FOR
PREPARATION OF EXAMPLES 3.1 TO 3.54.
Unless otherwise stated, all starting materials are commercially available from common vendors.

| Ex. # | Starting Material 1 | Starting Material 2 | Reaction Condition |
|---|---|---|---|
| 3.44 | PREPARATION 36 | PREPARATION 19 | TEA, DMSO 120° C. |
| 3.45 | PREPARATION 36 | PREPARATION 19 | TEA, DMSO 120° C. |
| 3.46 | PREPARATION 36 | WuXi Apptec | TEA, DMSO 120° C. |
| 3.47 | PREPARATION 36 | | 36.1 μW, 145° C. 36.2 Et$_3$N, Ac$_2$O, DCM |
| 3.48 | PREPARATION 36 | Alfa Aesar | K$_2$CO$_3$, iPrOH, H$_2$O, 160° C. μW |
| 3.49 | PREPARATION 36 | Alfa Aesar | K$_2$CO$_3$, iPrOH, H$_2$O, 160° C. μW |

TABLE 15B-continued

STARTING MATERIALS AND REACTION CONDITION FOR
PREPARATION OF EXAMPLES 3.1 TO 3.54.
Unless otherwise stated, all starting materials are commercially available from common vendors.

| Ex. # | Starting Material 1 | Starting Material 2 | Reaction Condition |
|---|---|---|---|
| 3.50 | PREPARATION 36 | piperidine | $K_2CO_3$, i-PrOH, $H_2O$, μW, 160° C. |
| 3.51 | PREPARATION 36 | 4-hydroxypiperidine | $K_2CO_3$, i-PrOH, $H_2O$, μW, 160° C. |
| 3.52 | PREPARATION 36 | PREPARATION 38 | TEA, DMSO 120° C. |
| 3.53 | PREPARATION 36 | PREPARATION 39 | TEA, DMSO 120° C. |
| 3.54 | PREPARATION 36 | PREPARATION 40 | TEA, DMSO 120° C. |

TABLE 15C

1H NMR (PPM) DATA FOR EXAMPLES 3.1 TO 3.54

| Ex. # | Structure | NMR |
|---|---|---|
| 3.1 | 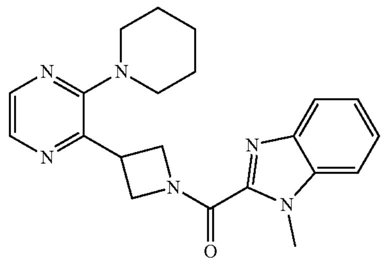 [SMILES: Cn1c(C(=O)N2CC(c3nccnc3N3CCCCC3)C2)nc2ccccc21] | (CD$_3$OD, 400 MHz): 8.11 (d, J = 2.4 Hz, 1 H); 8.30 (d, J = 2.4 Hz, 1 H); 7.68-7.66 (m, 1 H); 7.51-7.49 (m, 1 H); 7.37-7.33 (m, 1 H); 7.29-7.25 (m, 1 H); 5.03-4.98 (m, 1 H); 4.79-4.76 (m, 1 H); 4.53-4.49 (m, 1 H); 4.41-4.39 (m, 1 H); 4.26-4.23 (m, 1 H); 4.05 (s, 3 H); 3.03-3.00 (m, 4 H); 1.72-1.67 (m, 4 H); 1.61-1.57 (m, 2 H). |
| 3.2 | 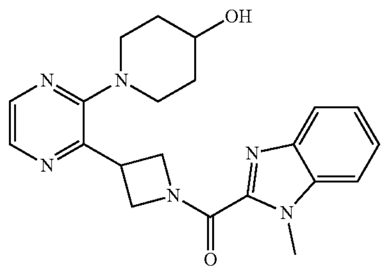 [SMILES: Cn1c(C(=O)N2CC(c3nccnc3N3CCC(O)CC3)C2)nc2ccccc21] | (CD$_3$OD, 400 MHz): 8.17-8.16 (m, 1 H); 8.10-8.09 (m, 1 H); 7.71-7.69 (m, 1 H); 7.58-7.55 (m, 1 H); 7.41-7.39 (m, 1 H); 7.37-7.29 (m, 1H); 5.04-5.01 (m, 1 H); 4.79-4.76 (m, 1 H); 4.57-4.54 (m, 1 H); 4.46-4.45 (m, 1 H); 4.31-4.26 (m, 1 H); 4.09 (s, 3 H); 3.38-3.34 (m, 1 H); 2.95-2.89 (m, 2 H); 1.99-1.97 (m, 2 H); 1.69-1.67 (m, 2 H). |
| 3.3 | 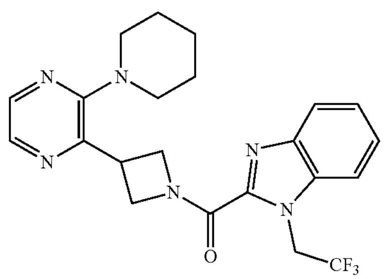 [SMILES: O=C(c1nc2ccccc2n1CC(F)(F)F)N1CC(c2nccnc2N2CCCCC2)C1] | (CD$_3$OD, 400 MHz): 8.14 (d, J = 2.4 Hz, 1 H); 8.08 (d, J = 2.4 Hz, 1 H); 7.75-7.73 (m, 1 H); 7.63-7.61 (m, 1 H); 7.44-7.40 (m, 1 H); 7.36-7.33 (m, 1 H); 5.63-5.58 (m, 2 H); 5.12-5.07 (m, 1 H); 4.92-4.90 (m, 1 H); 4.54-4.52 (m, 1 H); 4.44-4.40 (m, 1 H); 4.31-4.28 (m, 1 H); 3.06-3.03 (m, 4 H); 1.75-1.69 (m, 4 H); 1.64-1.59 (m, 2 H). |
| 3.4 | 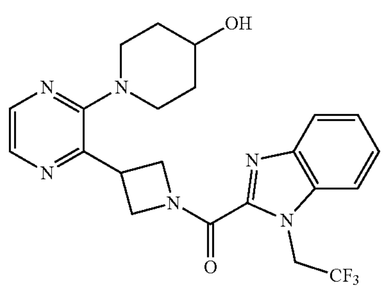 [SMILES: O=C(c1nc2ccccc2n1CC(F)(F)F)N1CC(c2nccnc2N2CCC(O)CC2)C1] | (CD$_3$OD, 400 MHz): 8.16 (d, J = 2.8 Hz, 1 H); 8.09 (d, J = 2.8 Hz, 1 H); 7.76-7.74 (m, 1 H); 7.64-7.62 (m, 1 H); 7.45-7.43 (m, 1 H); 7.37-7.33 (m, 1 H); 5.64-5.58 (m, 2 H); 5.10-5.08 (m, 1 H); 4.93-4.89 (m, 1 H); 4.56-4.53 (m, 1 H); 4.45-4.41 (m, 1 H); 4.38-4.31 (m, 1 H); 3.78-3.76 (m, 4 H); 3.38-3.36 (m, 2 H); 2.95-2.90 (m, 2 H); 2.00-1.96 (m, 2 H); 1.70-1.67 (m, 2 H) |
| 3.5 | 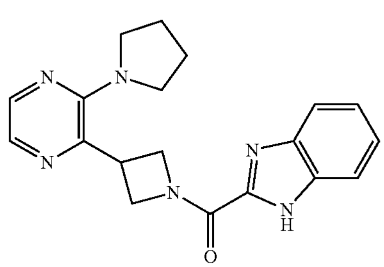 [SMILES: O=C(c1nc2ccccc2[nH]1)N1CC(c2nccnc2N2CCCC2)C1] | (CDCl$_3$, 400 MHz): 7.98-7.96 (m, 2 H); 7.74-7.64 (m, 2 H); 7.31-7.26 (m, 2 H); 5.25-5.12 (m, 2 H); 4.80-4.76 (m, 1 H); 4.60-4.55 (m, 1 H); 4.35-4.29 (m, 1 H); 3.51-3.49 (m, 4 H); 2.04-1.99 (m, 4 H). |

TABLE 15C-continued

1H NMR (PPM) DATA FOR EXAMPLES 3.1 TO 3.54

| Ex. # | Structure | NMR |
|---|---|---|
| 3.6 | 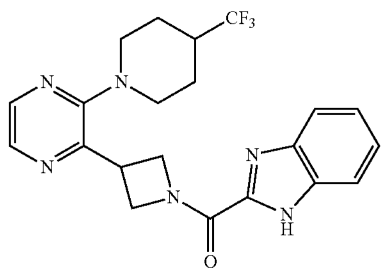 [SMILES: O=C(c1nc2ccccc2[nH]1)N1CC(c2nccnc2N2CCC(C(F)(F)F)CC2)C1] | (CDCl$_3$, 400 MHz): 8.21 (d, J = 2.4 Hz, 1H); 8.12 (d, J = 2.4, 1H); 7.67 (br, 2H); 7.33-7.31 (m, 2H); 5.32-5.27 (m, 1H); 5.10-5.06 (m, 1H); 4.63-4.61 (m, 2H); 4.30-4.26 (m, 1H); 3.45 (s, 2H); 2.93-2.81 (m, 2H); 2.26-2.19 (m, 1H); 1.99-1.98 (m, 2H); 1.87-1.74 (m, 2H). |
| 3.7 | 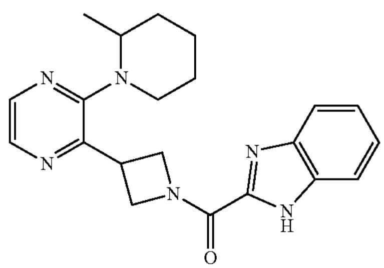 [SMILES: CC1CCCCN1c1nccnc1C1CN(C(=O)c2nc3ccccc3[nH]2)C1] | (CDCl$_3$, 400 MHz): 8.26-8.23 (m, 2H); 7.73-7.71 (m, 2H); 7.38-7.35 (m, 2H); 5.32-5.23 (m, 1H); 5.07-5.00 (m, 1H); 4.60-4.45 (m, 2H); 4.49-4.47 (m, 3H); 3.51-3.48 (m, 1H); 3.12-3.08 (m, 1H); 3.03-2.91 (m, 1H); 1.88-1.73 (m, 4H); 1.57-1.55 (m, 2H); 1.01-0.99 (m, 1H); 1.51-1.47 (m, 3H) |
| 3.8 | 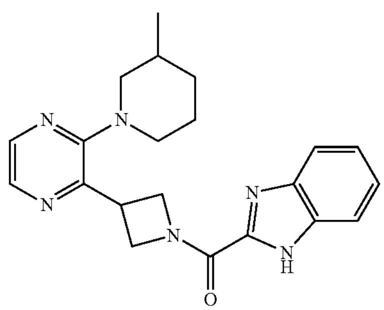 [SMILES: CC1CCCN(c2nccnc2C2CN(C(=O)c3nc4ccccc4[nH]3)C2)C1] | (CDCl$_3$, 400 MHz): 8.10-8.04 (m, 2H); 7.75-7.74 (m, 1H); 7.51-7.50 (m, 1H); 7.29-7.19 (m, 1H); 5.24-5.18 (m, 1H); 5.07-5.04 (m, 1H); 4.57-4.56 (m, 2H); 4.25-4.21 (m, 1H); 3.25-3.22 (m, 2H); 2.75-2.70 (m, 1H); 2.48-2.39 (m, 1H); 1.83-1.65 (m, 4H); 1.07-1.03 (m, 1H); 0.91 (d, J = 6.4 Hz, 3H). |
| 3.9 | 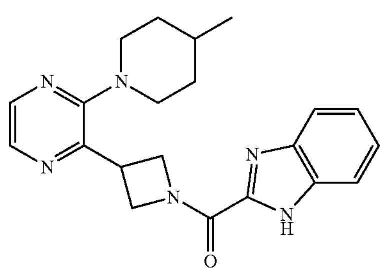 [SMILES: CC1CCN(c2nccnc2C2CN(C(=O)c3nc4ccccc4[nH]3)C2)CC1] | (CDCl$_3$, 400 MHz): 8.11-8.05 (m, 2H); 7.75-7.74 (m, 1H); 7.51-7.50 (m, 1H); 7.25-7.19 (m, 2H); 5.26-5.21 (m, 1H); 5.07-5.04 (m, 1H); 4.57-4.56 (m, 2H); 4.26-4.23 (m, 1H); 3.34-3.29 (m, 2H); 2.78-2.74 (m, 2H); 1.75-1.72 (m, 2H); 1.55-1.53 (m, 1H); 1.38-1.31 (m, 2H); 0.97 (d, J = 6.4 Hz, 3H). |
| 3.10 | 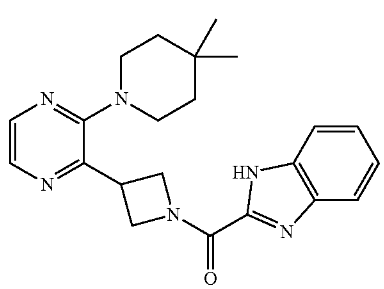 [SMILES: CC1(C)CCN(c2nccnc2C2CN(C(=O)c3nc4ccccc4[nH]3)C2)CC1] | (CDCl$_3$, 400 MHz): 8.14-8.10 (m, 2H); 7.70-7.68 (m, 2H); 7.32-7.24 (m, 2H); 5.30-5.26 (m, 1H); 5.08-5.03 (m, 1H); 4.62-4.60 (m, 2H); 4.29-4.25 (m, 1H); 3.10-3.08 (m, 4H); 1.55-1.53 (m, 4H); 1.01 (s, 6H). |

TABLE 15C-continued

1H NMR □ (PPM) DATA FOR EXAMPLES 3.1 TO 3.54

| Ex. # | Structure | NMR |
|---|---|---|
| 3.11 | 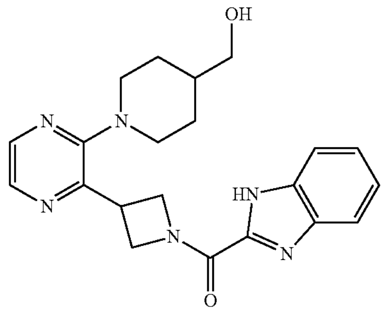 [SMILES: O=C(c1nc2ccccc2[nH]1)N1CC(c2nccnc2N2CCC(CO)CC2)C1] | (CDCl₃, 400 MHz): 8.14-8.13 (m, 1H); 8.08-8.07 (m, 1H); 7.77-7.75 (m, 1H); 7.55-7.52 (m, 1H); 7.30-7.22 (m, 2H); 5.27-5.21 (m, 1H); 5.07-5.04 (m, 1H); 4.60-4.58 (m, 2H); 4.25-4.21 (m, 1H); 3.58-3.55 (m, 2H); 3.40-3.34 (m, 1H); 2.89-2.77 (m, 2H); 2.41 (br, 1H); 1.87-1.84 (m, 1H); 1.69-1.68 (m, 1H); 1.49-1.40 (m, 2H). |
| 3.12 | 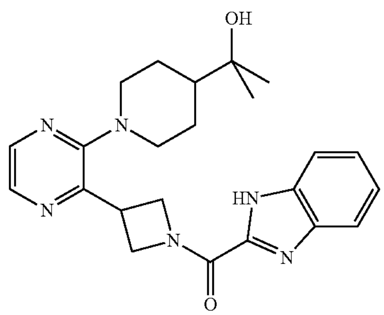 [SMILES: CC(C)(O)C1CCN(c2nccnc2C2CN(C(=O)c3nc4ccccc4[nH]3)C2)CC1] | (CD₃OD, 400 MHz): 8.16 (d, J = 2.4 Hz, 1H); 8.09 (d, J = 2.4 Hz, 1H); 7.63 (brs, 2H); 7.30-7.28 (m, 2H); 5.20-5.16 (m, 1H); 4.98-4.93 (m, 1H); 4.60-4.56 (m, 1H); 4.47-4.43 (m, 1H); 4.37-4.35 (m, 1H); 3.46 (d, J = 12.4 Hz, 2H); 2.83-2.78 (m, 2H); 1.89-1.86 (m, 2H); 1.56-1.46 (m, 3H); 1.19 (s, 6H) |
| 3.13 | 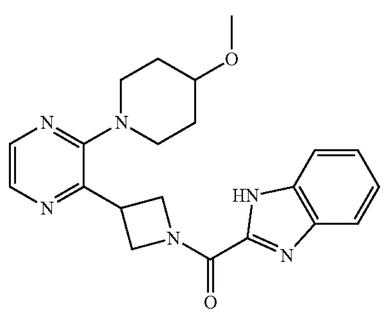 [SMILES: COC1CCN(c2nccnc2C2CN(C(=O)c3nc4ccccc4[nH]3)C2)CC1] | (CDCl₃, 400 MHz): 8.12 (d, J = 2.4 Hz, 1H); 8.04 (d, J = 2.4 Hz, 1H); 7.79 (br, 1H); 7.51 (br, 1H); 7.19 (br, 2H); 5.25-5.20 (m, 1H); 5.04-5.00 (m, 1H); 4.58-4.56 (m, 2H); 4.24-4.21 (m, 1H); 3.38-3.35 (m, 1H); 3.31 (s, 3H); 3.30-3.27 (m, 2H); 2.94-2.89 (m, 2H); 2.02-1.98 (m, 2H); 1.73-1.68 (m, 2H). |
| 3.14 | 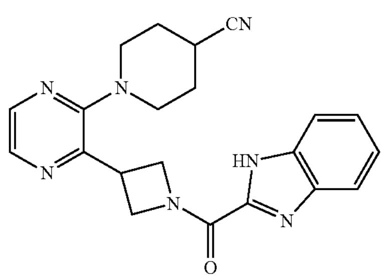 [SMILES: N#CC1CCN(c2nccnc2C2CN(C(=O)c3nc4ccccc4[nH]3)C2)CC1] | (CDCl₃, 400 MHz): 8.20 (d, J = 42.4 Hz, 1H); 8.13 (d, J = 2.4 Hz, 1H); 7.70-7.68 (m, 2H); 7.35-7.32 (m, 2H); 5.32-5.27 (m, 1H); 5.03-4.99 (m, 1H); 4.64-4.56 (m, 2H); 4.29-4.23 (m, 1H); 3.34-3.29 (m, 2H); 3.09-3.02 (m, 2H); 2.86-2.82 (m, 1H); 2.12-1.97 (m, 4H). |
| 3.15 | 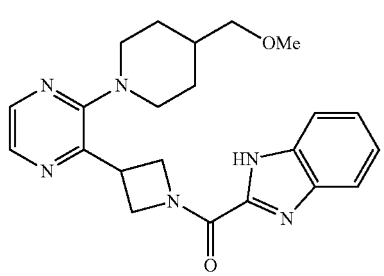 [SMILES: COCC1CCN(c2nccnc2C2CN(C(=O)c3nc4ccccc4[nH]3)C2)CC1] | (CDCl₃, 400 MHz): 8.15-8.06 (m, 2H); 7.376-7.74 (m, 1H); 7.52-7.50 (m, 1H); 7.28-7.24 (m, 2H); 5.27-5.22 (m, 1H); 5.07-5.04 (m, 1H); 4.61-4.58 (m, 2H); 4.27-4.24 (m, 1H); 3.36-3.27 (m, 7H); 2.89-2.78 (m, 2H); 1.92-1.78 (m, 3H); 1.49-1.40 (m, 2H). |

TABLE 15C-continued

1H NMR δ (PPM) DATA FOR EXAMPLES 3.1 TO 3.54

| Ex. # | Structure | NMR |
|---|---|---|
| 3.16 | 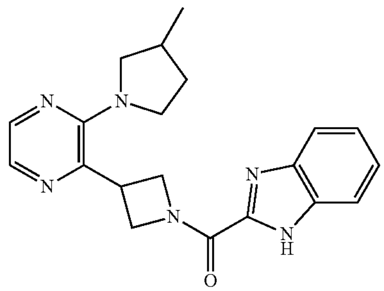 [SMILES: CC1CCN(c2nccnc2C2CN(C(=O)c3nc4ccccc4[nH]3)C2)C1] | (CDCl$_3$, 400 MHz): 7.95-7.93 (m, 2H); 7.67 (brs, 2H); 7.32-7.24 (m, 2H); 5.25-5.12 (m, 2H); 4.72-4.70 (m, 1H); 4.62-4.48 (m, 1H); 4.31-4.27 (m, 1H); 3.63-3.48 (m, 3H); 3.19-3.12 (m, 1H); 2.34-2.32 (m, 1H); 2.12-2.09 (m, 1H); 1.61-1.58 (m, 1H); 1.14-1.12 (m, 3H). |
| 3.17 | 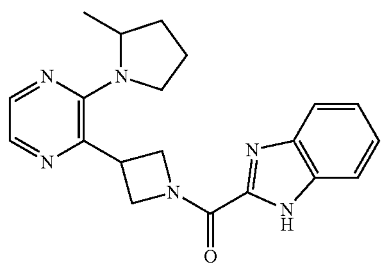 [SMILES: CC1CCCN1c1nccnc1C1CN(C(=O)c2nc3ccccc3[nH]2)C1] | (CDCl$_3$, 400 MHz): 7.98-7.96 (m, 2H); 7.75-7.59 (m, 2H); 7.26-7.24 (m, 2H); 5.31-5.08 (m, 2H); 4.69-4.47 (m, 2H); 4.21-4.19 (m, 2H); 3.70-3.68 (m, 1H); 3.13-3.11 (m, 1H); 2.16-2.15 (m, 1H); 1.95-1.94 (m, 1H); 1.77-1.76 (m, 1H); 1.63-1.62 (m, 1H); 1.18 (s, 3H) |
| 3.18 | 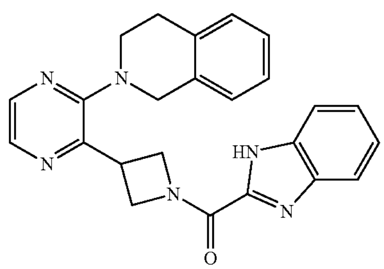 [SMILES: O=C(c1nc2ccccc2[nH]1)N1CC(c2nccnc2N2CCc3ccccc3C2)C1] | (CDCl$_3$, 400 MHz): 8.20-8.13 (m, 2H); 7.68 (brs, 2H); 7.33-7.32 (m, 2H); 7.24-7.16 (m, 4H); 5.34-5.29 (m, 1H); 5.15-5.11 (m, 1H); 4.68-4.59 (m, 2H); 4.46-4.31 (m, 3H); 3.42-3.40 (m, 2H); 3.16-3.05 (m, 2H). |
| 3.19 | 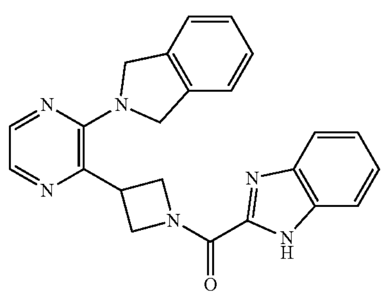 [SMILES: O=C(c1nc2ccccc2[nH]1)N1CC(c2nccnc2N2Cc3ccccc3C2)C1] | (CDCl$_3$, 400 MHz): 8.07-8.06 (m, 1H); 8.00-7.99 (m, 1H); 7.70-7.48 (m, 1H); 7.39-7.37 (m, 2H); 7.29-7.17 (m, 4H); 5.07-5.05 (m, 1H); 5.00-4.90 (m, 6H); 4.52-4.46 (m, 2H). |
| 3.20 | 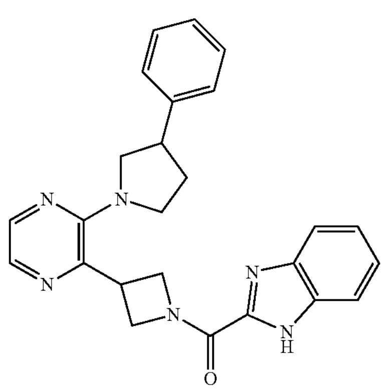 [SMILES: O=C(c1nc2ccccc2[nH]1)N1CC(c2nccnc2N2CCC(c3ccccc3)C2)C1] | (CDCl$_3$, 400 MHz): 7.98-7.96 (m, 2H); 7.69-7.68 (m, 2H); 7.35-7.30 (m, 4H); 7.28-7.15 (m, 3H); 5.27-5.23 (m, 1H); 5.13-5.07 (m, 1H); 4.67-4.63 (m, 1H); 4.55-4.43 (m, 1H); 4.34-4.32 (m, 1H); 3.83-3.75 (m, 2H); 3.70-3.65 (m, 2H); 3.48-3.46 (m, 1H); 2.41-2.39 (m, 1H); 2.14-2.12 (m, 1H). |

TABLE 15C-continued

1H NMR (PPM) DATA FOR EXAMPLES 3.1 TO 3.54

| Ex. # | Structure | NMR |
|---|---|---|
| 3.21 | 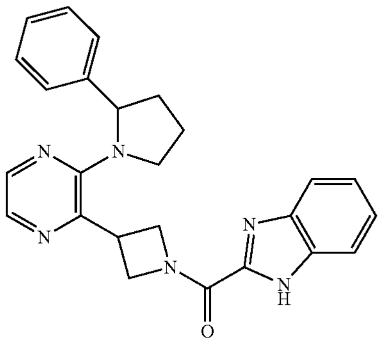 [SMILES: O=C(c1nc2ccccc2[nH]1)N1CC(c2nccnc2N2CCCC2c2ccccc2)C1] | (CDCl₃, 400 MHz): 7.93-7.89 (m, 2H); 7.67 (brs, 2H); 7.50-7.24 (m, 6H); 7.17-7.15 (m, 1H); 5.23-5.05 (m, 3H); 4.65-4.63 (m, 1H); 4.53-4.51 (m, 1H); 4.27-4.26 (m, 1H); 3.97-3.95 (m, 1H); 3.42-3.40 (m, 1H); 2.42-2.41 (m, 1H); 2.07-2.06 (m, 1H); 2.00-1.84 (m, 2H). |
| 3.22 | 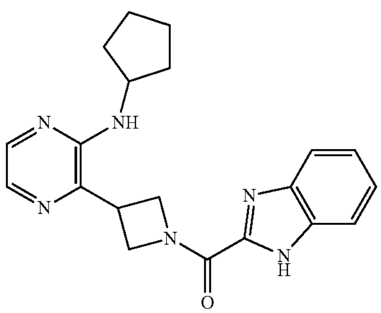 [SMILES: O=C(c1nc2ccccc2[nH]1)N1CC(c2nccnc2NC2CCCC2)C1] | (CDCl₃, 400 MHz): 7.98 (d, J = 2.8 Hz, 1H); 7.80 (d, J = 2.8 Hz, 1H); 7.69 (brs, 2H); 7.34-7.30 (m, 2H); 5.31-5.26 (m, 1H); 5.16-5.12 (m, 1H); 4.78-4.74 (m, 1H); 4.65-4.60 (m, 1H); 4.35-4.33 (m, 1H); 4.11-4.10 (m, 1H); 3.95-3.88 (m, 1H); 2.17-2.09 (m, 2H); 1.79-1.66 (m, 4H); 1.51-1.43 (m, 2H). |
| 3.23 | 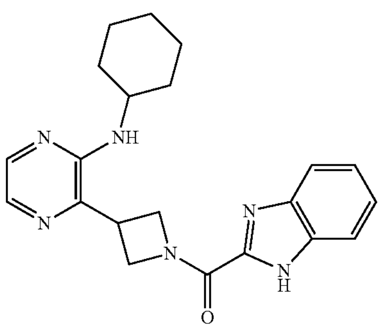 [SMILES: O=C(c1nc2ccccc2[nH]1)N1CC(c2nccnc2NC2CCCCC2)C1] | (CDCl₃, 400 MHz): 7.89-7.72 (m, 2H); 7.62 (brs, 2H); 7.30-7.26 (m, 2H); 5.25-5.20 (m, 1H); 5.11-5.08 (m, 1H); 4.66-4.53 (m, 2H); 3.95-3.84 (m, 2H); 2.02-1.99 (m, 1H); 1.73-1.35 (m, 6H); 1.21-1.16 (m, 3H). |
| 3.24 | 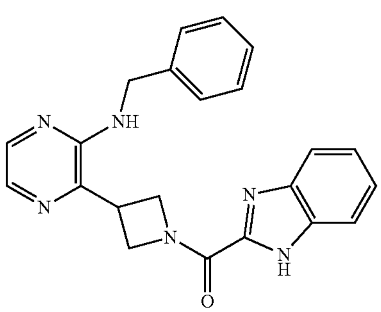 [SMILES: O=C(c1nc2ccccc2[nH]1)N1CC(c2nccnc2NCc2ccccc2)C1] | (CD₃OD, 400 MHz): 7.83-7.81 (m, 2H); 7.70-7.68 (m, 2H); 7.39-7.21 (m, 7H); 5.19-5.13 (m, 1H); 5.10-5.06 (m, 1H); 4.67 (s, 2H); 4.63-4.54 (m, 2H); 4.25-4.21 (m, 1H). |
| 3.25 | 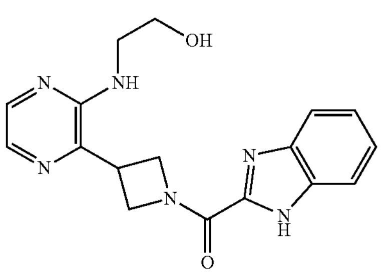 [SMILES: O=C(c1nc2ccccc2[nH]1)N1CC(c2nccnc2NCCO)C1] | (CD₃OD, 400 MHz): 7.89-7.88 (m, 1 H); 7.80-7.79 (m, 1 H); 7.69-7.66 (m, 2 H); 7.37-7.35 (m, 2 H); 5.19-5.18 (m, 1 H); 5.06-5.08 (m, 1 H); 4.62-4.55 (m, 2 H); 4.24-4.20 (m, 1H); 3.80-3.79 (m, 2 H); 3.63-3.61 (m, 2 H). |

TABLE 15C-continued

1H NMR (PPM) DATA FOR EXAMPLES 3.1 TO 3.54

| Ex. # | Structure | NMR |
|---|---|---|
| 3.26 | 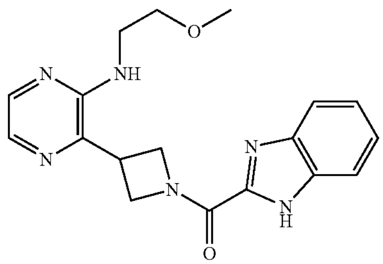 [SMILES: COCCNc1nccnc1C1CN(C(=O)c2nc3ccccc3[nH]2)C1] | (CDCl₃, 400 MHz): 7.94 (d, J = 2.4 Hz, 1H); 7.82 (d, J = 2.4 Hz, 1H); 7.78-7.60 (m, 2H); 7.32-7.31 (m, 2H); 5.29-5.28 (m, 1H); 5.16-5.14 (m, 1H); 4.76-4.73 (m, 2H); 4.65-4.63 (m, 1H); 4.00-3.95 (m, 1H); 3.71-3.61 (m, 4H); 3.43 (s, 3H). |
| 3.27 | 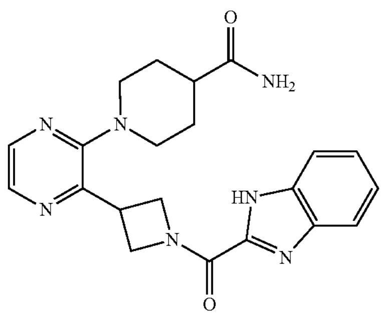 [SMILES: NC(=O)C1CCN(c2nccnc2C2CN(C(=O)c3nc4ccccc4[nH]3)C2)CC1] | (CDCl₃, 400 MHz): 8.22-8.16 (m, 2 H); 7.65 (br, 2 H); 7.62-7.54 (m, 4H); 5.11-5.07 (m, 1 H); 4.89-4.85 (m, 1H); 4.51-4.49 (m, 1H); 4.29-4.25 (m, 2H); 3.45-3.43 (m, 2 H); 2.83-2.73 (m, 1H); 2.52-2.51 (m, 1 H); 1.82-1.71 (m, 4 H). |
| 3.28 | 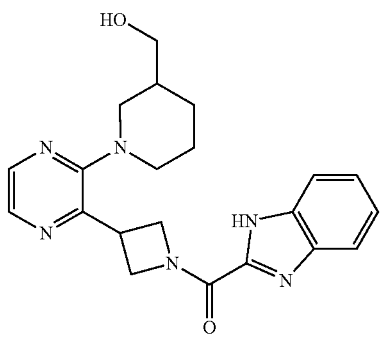 [SMILES: O=C(c1nc2ccccc2[nH]1)N1CC(c2nccnc2N2CCCC(CO)C2)C1] | (CD₃OD, 400 MHz): 8.18 (d, J = 2.4 Hz, 1H); 8.11 (d, J = 2.4 Hz, 1H); 7.68-7.65 (m, 2H); 7.35-7.32 (m, 2H); 5.21-5.17 (m, 1H); 5.02-4.95 (m, 1H); 4.65-4.59 (m, 1H); 4.47-4.36 (m, 2H); 3.57-3.53 (m, 1H); 3.48-3.34 (m, 3H); 2.86-2.84 (m, 1H); 2.64-2.58 (m, 1H); 1.96-1.94 (m, 1H); 1.85-1.76 (m, 3H); 1.21-1.18 (m, 1H). |
| 3.29 | 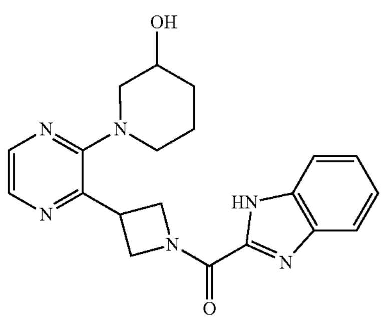 | (CD₃OD, 400 MHz): 8.17 (d, J = 2.4 Hz, 1H); 8.10 (d, J = 2.4 Hz, 1H); 7.63 (brs, 2H); 7.28-7.20 (m, 2H); 5.20-5.14 (m, 1H); 4.97-4.92 (m, 1H); 4.58-4.53 (m, 1H); 4.47-4.42 (m, 1H); 4.38-4.32 (m, 1H); 3.89-3.85 (m, 1H); 3.41-3.37 (m, 1H); 3.34-3.20 (m, 1H); 2.88-2.77 (m, 2H); 2.02-1.98 (m, 1H); 1.91-1.88 (m, 1H); 1.71-1.67 (m, 1H); 1.49-1.46 (m, 1H). |
| 3.30 | 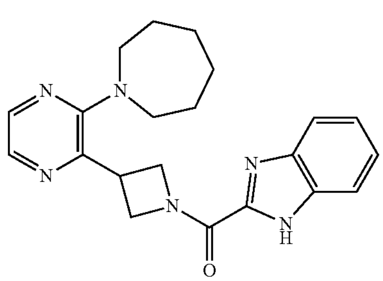 [SMILES: O=C(c1nc2ccccc2[nH]1)N1CC(c2nccnc2N2CCCCCC2)C1] | (CDCl₃, 400 MHz): 8.04-8.00 (m, 2H); 7.73-7.70 (m, 2H); 7.38-7.36 (m, 2H); 5.27-5.22 (m, 1H); 5.03-4.99 (m, 1H); 4.60-4.53 (m, 2H); 4.27-4.23 (m, 1H); 3.45-3.42 (m, 4H); 1.83 (brs, 4H) 1.65-1.63 (m, 6H). |

TABLE 15C-continued

1H NMR (PPM) DATA FOR EXAMPLES 3.1 TO 3.54

| Ex. # | Structure | NMR |
|---|---|---|
| 3.31 | 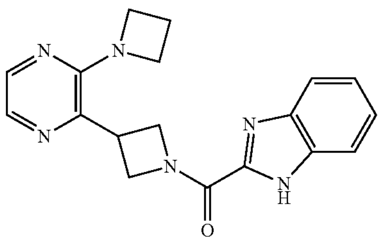 [SMILES: O=C(c1nc2ccccc2[nH]1)N1CC(c2nccnc2N2CCC2)C1] | (CD$_3$OD, 400 MHz): 7.97-7.92 (m, 2H); 7.76-7.74 (m, 1 H); 7.59-7.58 (m, 1 H); 7.32 (br, 2 H); 5.15-5.13 (m, 1H); 5.04-5.01 (m, 1H); 4.57-4.50 (m, 2H); 4.20-4.14 (m, 5H); 2.45-2.37 (m, 1H). |
| 3.32 | 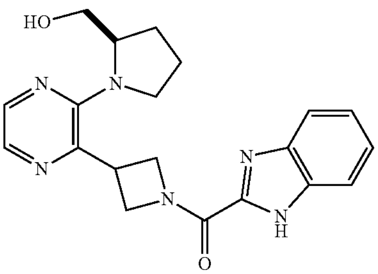 [SMILES: O=C(c1nc2ccccc2[nH]1)N1CC(c2nccnc2N2CCC[C@@H]2CO)C1] | (CDCl$_3$, 400 MHz): 7.97-7.94 (m, 1 H); 7.84-7.81 (m, 1 H); 7.71-7.65 (m, 2H); 7.22 (brs, 2H); 5.27-5.23 (m, 1H); 5.01-5.02 (m, 1H); 4.62-4.56 (m, 2H); 4.39-4.36 (m, 1H); 4.20-4.15 (m, 1H); 3.77-3.60 (m, 3H); 3.20-3.15 (m, 1H); 2.09 (s, 3H); 1.95-1.92 (m, 1H); 1.77-1.75 (m, 2 H). |
| 3.33 | 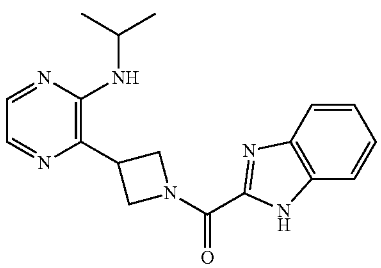 [SMILES: CC(C)Nc1nccnc1C1CN(C(=O)c2nc3ccccc3[nH]2)C1] | (CD$_3$OD, 400 MHz): 7.88-7.81 (m, 2H); 7.68-7.66 (m, 2H); 7.35-7.33 (m, 2H); 5.20-5.15 (m, 1H); 5.03-4.99 (m, 1H); 4.62-4.50 (m, 2H); 4.28-4.17 (m, 1H); 4.15-4.10 (m, 1H); 1.33-1.30 (m, 6H). |
| 3.34 | 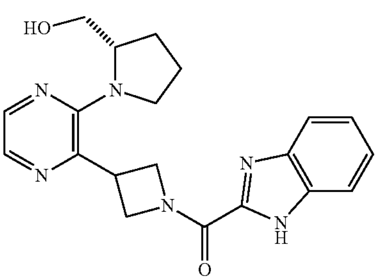 [SMILES: O=C(c1nc2ccccc2[nH]1)N1CC(c2nccnc2N2CCC[C@H]2CO)C1] | (CDCl$_3$, 400 MHz): 7.96-7.94 (m, 1 H); 7.83-7.81 (m, 1 H); 7.70-7.60 (m, 2H); 7.22 (brs, 2H); 5.26-5.24 (m, 1H); 5.011-5.02 (m, 1H); 4.61-4.56 (m, 2H); 4.38-4.36 (m, 1H); 4.18-4.16 (m, 1H); 3.76-3.59 (m, 3H); 3.15-3.13 (m, 1H); 2.08 (s, 3H); 1.94-1.92 (m, 1H); 1.76-1.73 (m, 2 H). |
| 3.35 | 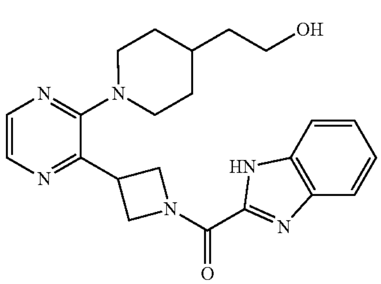 [SMILES: O=C(c1nc2ccccc2[nH]1)N1CC(c2nccnc2N2CCC(CCO)CC2)C1] | (CDCl$_3$, 400 MHz): 8.20-8.17 (m, 2H); 7.75-7.72 (m, 2 H); 7.43-7.40 (m, 2H); 5.33-5.32 (m, 1H); 505-5.02 (m, 1H); 4.63-4.61 (m, 2H); 4.57-4.55 (m, 1H); 4.36-4.34 (m, 1H); 3.79-3.77 (m, 1H); 3.42-3.36 (m, 2H); 2.95-2.90 (m, 2 H); 1.89-1.79 (m, 3 H); 1.65-1.67 (m, 2 H); 1.47-1.45 (m, 2H). |

TABLE 15C-continued

1H NMR (PPM) DATA FOR EXAMPLES 3.1 TO 3.54

| Ex. # | Structure | NMR |
|---|---|---|
| 3.36 | 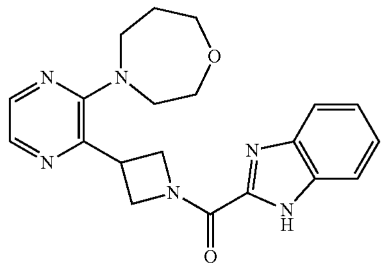 [SMILES: O=C(c1nc2ccccc2[nH]1)N1CC(c2nccnc2N2CCCOCC2)C1] | (CD$_3$OD, 400 MHz): 8.11-8.06 (m, 2 H); 7.72-7.70 (m, 2H); 7.43-7.40 (m, 2H); 5.16-5.11 (m, 1H); 5.00-4.98 (m, 1 H); 4.59-4.52 (m, 2 H); 4.34-4.33 (m, 1 H); 3.89-3.82 (m, 4 H); 2.06-2.03 (m, 2 H). |
| 3.37 | 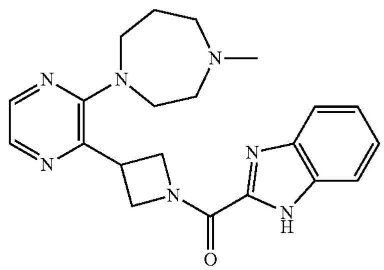 | (CD$_3$OD, 400 MHz): 8.17-8.16 (m, 1 H); 8.08-8.07 (m, 1 H); 7.68-7.66 (m, 2 H); 7.36-7.34 (m, 2 H); 5.17-5.14 (m, 1 H); 4.95-4.94 (m, 1 H); 4.59-4.52 (m, 2 H); 4.35-4.27 (m, 1 H); 3.76-3.57 (m, 6 H); 3.37-3.31 (m, 2 H); 3.30 (s, 3 H); 2.26-2.24 (m, 2 H). |
| 3.38 | 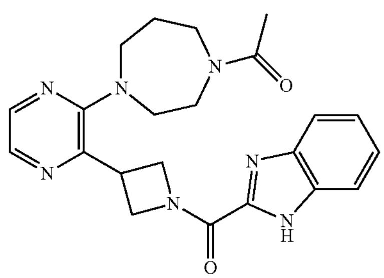 [SMILES: CC(=O)N1CCCN(c2nccnc2C2CN(C(=O)c3nc4ccccc4[nH]3)C2)CC1] | (CDCl$_3$, 400 MHz): 8.13-8.07 (m, 2H); 7.73-7.70 (m, 2H); 7.44-7.41 (m, 2 H); 5.12-5.09 (m, 1 H); 4.95.4.94 (m, 1 H); 4.62-4.51 (m, 2 H); 4.33-4.30 (m, 1H); 3.79-3.76 (m, 2 H); 3.66-3.60 (m, 3 H); 3.48-3.45 (m, 2 H); 3.42-3.40 (m, 1 H); 2.11 (s, 3 H); 2.05-2.02 (m, 1 H); 1.94-1.88 (m, 1 H). |
| 3.39 | 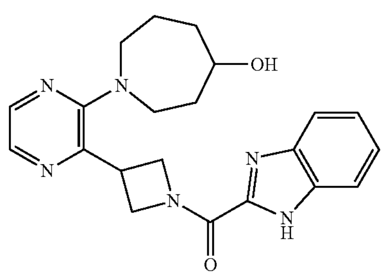 [SMILES: O=C(c1nc2ccccc2[nH]1)N1CC(c2nccnc2N2CCCC(O)CC2)C1] | (CD$_3$OD, 400 MHz): 8.05-8.00 (m, 2 H); 7.70-7.68 (m, 2 H); 7.39-7.36 (m, 2 H); 5.15-5.13 (m, 1H); 4.99-4.98 (m, 1 H); 4.56-4.50 (m, 2H); 4.33-4.30 (m, 1 H); 3.92-3.90 (m, 1 H); 3.57-3.54 (m, 1 H); 3.47-3.41 (m, 3 H); 2.14-2.11 (m, 1 H); 1.99-1.69 (m, 5 H). |
| 3.40 | 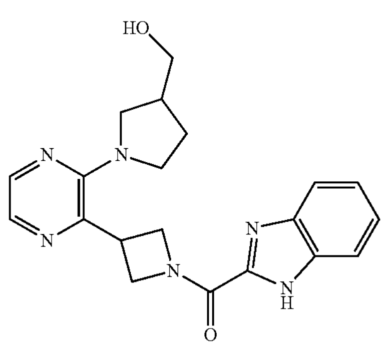 [SMILES: O=C(c1nc2ccccc2[nH]1)N1CC(c2nccnc2N2CCC(CO)C2)C1] | (CD$_3$OD, 400 MHz): 7.98-7.97 (m, 1 H); 7.88-7.87 (m, 1 H); 7.69-7.66 (m, 2 H); 7.37-7.34 (m, 2H); 5.15-5.07 (m, 1 H); 4.58-4.44 (m, 2H); 3.66-3.60 (m, 5 H); 3.45-3.43 (m, 1 H); 3.65 (s, 2 H); 2.55-2.51 (m, 1 H); 2.16-2.11 (m, 1 H); 1.85-1.80 (m, 1 H). |

TABLE 15C-continued

1H NMR ☐ (PPM) DATA FOR EXAMPLES 3.1 TO 3.54

| Ex. # | Structure | NMR |
|---|---|---|
| 3.41 | 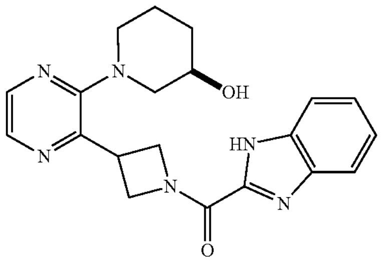 [SMILES: O=C(c1nc2ccccc2[nH]1)N1CC(c2nccnc2N2CCC[C@@H](O)C2)C1] | (CDCl$_3$, 400 MHz): 8.19 (d, J = 2.8 Hz, 1H); 8.11 (d, J = 2.8, 1H); 7.67-7.64 (m, 2H); 7.33-7.30 (m, 2H); 5.20-5.18 (m, 1H); 4.98-4.96 (m, 1H); 4.58-4.56 (m, 1H); 4.48-4.45 (m, 1H); 4.40-4.38 (m, 1H); 3.89-3.86 (m, 1H); 3.42-3.39 (m, 1H); 3.22-3.18 (m, 1H); 2.90-2.89 (m, 1H); 2.84-2.80 (m, 1H); 2.02-2.00 (m, 1H); 1.93-1.90 (m, 1H); 1.74-1.70 (m, 1H); 1.50-1.48 (m, 1H). |
| 3.42 | 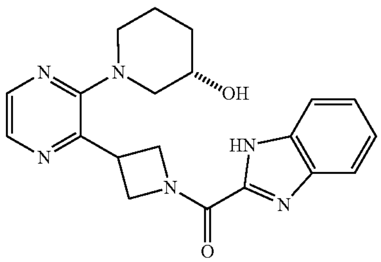 [SMILES: O=C(c1nc2ccccc2[nH]1)N1CC(c2nccnc2N2CCC[C@H](O)C2)C1] | (CDCl$_3$, 400 MHz): 8.20 (d, J = 2.8 Hz, 1H); 8.12 (d, J = 2.8, 1H); 7.66 (br, 2H); 7.34-7.31 (m, 2H); 5.21-5.19 (m, 1H); 4.97-4.96 (m, 1H); 4.61-4.54 (m, 1H); 4.48-4.38 (m, 2H); 3.89-3.85 (m, 1H); 3.42-3.41 (m, 1H); 3.23-3.20 (m, 1H); 2.91-2.88 (m, 1H); 2.84-2.79 (m, 1H); 2.04-2.00 (m, 1H); 1.95-1.90 (m, 1H); 1.74-1.70 (m, 1H); 1.51-1.47 (m, 1H). |
| 3.43 | 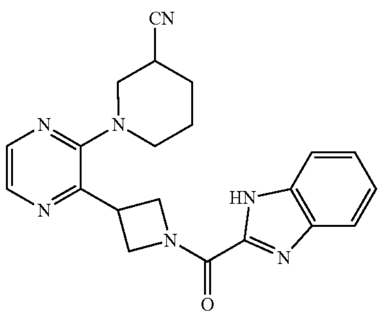 [SMILES: N#CC1CCCN(c2nccnc2C2CN(C(=O)c3nc4ccccc4[nH]3)C2)C1] | (CDCl$_3$, 400 MHz): 8.22 (m, 1H); 8.11 (m, 1H); 7.68-7.65 (m, 2H); 7.35-7.31 (m, 2H); 5.30 (m, 1H); 5.02 (m, 1H); 4.60 (d, J = 6.4 Hz, 2H); 4.37-4.34 (m, 1H); 3.34-3.28 (m, 2H); 3.08-2.93 (m, 3H); 1.98-1.90 (m, 3H); 1.74-1.72 (m, 1H). |
| 3.44 | 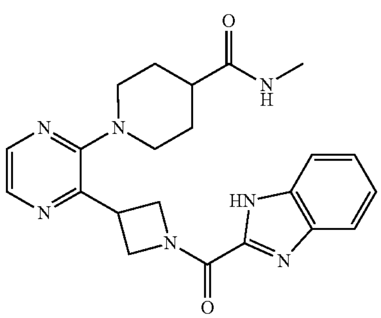 [SMILES: CNC(=O)C1CCN(c2nccnc2C2CN(C(=O)c3nc4ccccc4[nH]3)C2)CC1] | (CDCl$_3$, 400 MHz): 8.18 (d, J = 2.0 Hz, 1H); 8.12 (d, J = 2.4 Hz, 1H); 7.74-7.71 (m, 2H); 7.40-7.38 (m, 2H); 5.31 (t, J = 9.6 Hz, 1H); 5.04-5.00 (m, 1H); 4.62-4.58 (m, 2H); 4.34-4.27 (m, 1H); 3.40 (t, J = 12.0 Hz, 2H); 2.91 (d, J = 12.8 Hz, 1H); 2.86 (d, J = 4.4 Hz, 4H); 2.37-2.31 (m, 1H); 2.07-1.87 (m, 4H). |
| 3.45 | 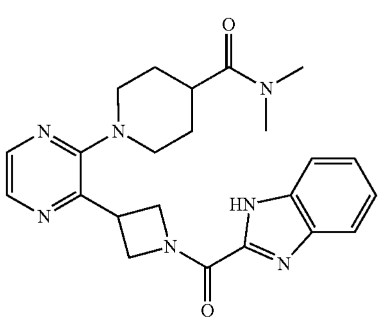 [SMILES: CN(C)C(=O)C1CCN(c2nccnc2C2CN(C(=O)c3nc4ccccc4[nH]3)C2)CC1] | (CDCl$_3$, 400 MHz): 8.14 (d, J = 2.4 Hz, 1H); 8.07 (d, J = 2.8 Hz, 1H); 7.67-7.65 (m, 2H); 5.22 (t, J = 10.0 Hz, 1H); 5.03-4.99 (m, 1H); 4.54 (d, J = 7.2 Hz, 2H); 4.28-4.24 (m, 1H); 3.37 (t, J = 12.8 Hz, 2H); 3.07 (s, 3H); 2.94 (s, 3H); 2.92-2.80 (m, 2H); 2.71-2.65 (m, 1H); 2.02-1.93 (m, 2H); 1.80 (d, J = 8.4 Hz, 2H). |

TABLE 15C-continued

1H NMR (PPM) DATA FOR EXAMPLES 3.1 TO 3.54

| Ex. # | Structure | NMR |
|---|---|---|
| 3.46 | 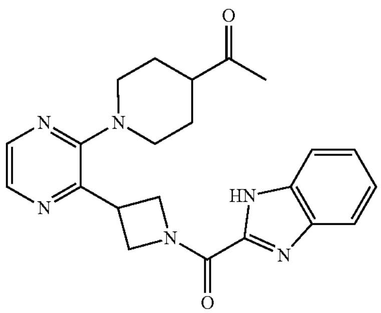 [SMILES: CC(=O)C1CCN(c2nccnc2C2CN(C(=O)c3nc4ccccc4[nH]3)C2)CC1] | (CDCl$_3$, 400 MHz): 8.15-8.14 (m, 1H); 8.06-8.05 (m, 1H); 7.07-7.06 (m, 1H); 7.47-7.46 (m, 1H); 7.28-7.18 (m, 2H); 5.23-5.21 (m, 1H); 5.04-5.02 (m, 1H); 4.56-5.54 (m, 2H); 4.23-4.21 (m, 1H); 3.38-3.36 (m, 2H); 2.89-2.80 (m, 2H); 2.48-2.45 (m, 1H); 2.16 (s, 3H); 1.98-1.96 (m, 2H); 1.82-1.79 (m, 2H). |
| 3.47 | 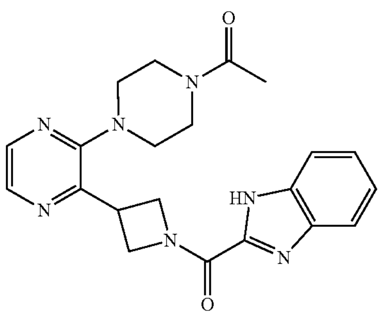 | (CDCl$_3$, 400 MHz): 8.20 (d, J = 2.4 Hz, 1H); 8.10 (d, J = 2.4 Hz, 1H); 7.66-7.64 (m, 2H); 7.32-7.29 (m, 2H); 5.26 (t, J = 8.0 Hz, 1H); 5.03-5.00 (m, 1H); 4.60-4.54 (m, 2H); 4.28-4.25 (m, 1H); 3.81-3.71 (m, 2H); 3.63-3.61 (m, 2H); 3.15-3.14 (m, 2H); 3.07-3.05 (m, 2H); 2.14 (s, 3H). |
| 3.48 | 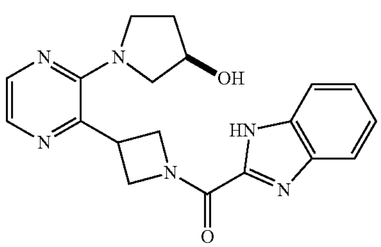 [SMILES: O=C(c1nc2ccccc2[nH]1)N1CC(c2nccnc2N2CC[C@@H](O)C2)C1] | (MeOD, 400 MHz): 8.00-7.97 (m, 1H); 7.92-7.88 (m, 1H); 7.68 (brs, 2H); 7.36-7.35 (m, 2H); 5.18-5.05 (m, 2H); 4.61-4.46 (m, 4H); 3.87-3.79 (m, 2H); 3.56-3.52 (m, 1H); 3.41-3.39 (m, 1H); 2.13-1.93 (m, 2H). |
| 3.49 | 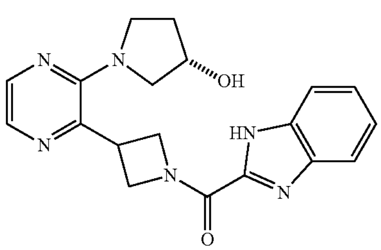 [SMILES: O=C(c1nc2ccccc2[nH]1)N1CC(c2nccnc2N2CC[C@H](O)C2)C1] | (MeOD, 400 MHz): 7.96-7.92 (m, 1H); 7.91-7.89 (m, 1H); 7.68 (brs, 2H); 7.35-7.33 (m, 2H); 5.21-4.88 (m, 2H); 4.63-4.41 (m, 4H); 3.86-3.80 (m, 2H); 3.55-3.50 (m, 1H); 3.37-3.40 (m, 1H); 2.13-2.00 (m, 2H). |
| 3.50 | 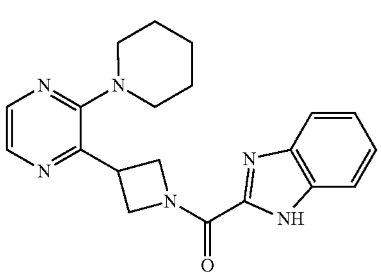 [SMILES: O=C(c1nc2ccccc2[nH]1)N1CC(c2nccnc2N2CCCCC2)C1] | (CDCl$_3$, 400 MHz): 8.16 (d, J = 2.4 Hz, 1H); 8.11 (d, J = 2.4 Hz, 1H); 7.71-7.69 (m, 2H); 7.32-7.30 (m, 2H); 5.33-5.28 (m, 1H); 5.11-5.07 (m, 1H); 4.67-4.65 (m, 2H); 4.32-4.29 (m, 1H); 3.11-3.08 (m, 4H); 1.78-1.74 (m, 4H); 1.68-1.64 (m, 2H). |

TABLE 15C-continued
1H NMR δ (PPM) DATA FOR EXAMPLES 3.1 TO 3.54
| Ex. # | Structure | NMR |
|---|---|---|
| 3.51 | 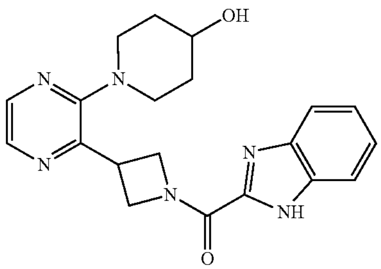 [SMILES: O=C(c1nc2ccccc2[nH]1)N1CC(c2nccnc2N2CCC(O)CC2)C1] | (MeOD, 400 MHz): 8.17 (d, J = 2.8 Hz, 1H); 8.10 (d, J = 2.8 Hz, 1H); 7.71-7.68 (m, 2H); 7.42-7.39 (m, 2H); 5.13-5.15 (m, 1H); 4.94-4.93 (m, 1H); 4.61-4.59 (m, 1H); 4.46-4.50 (m, 1H); 4.39-4.35 (m, 1H); 3.80-3.76 (m, 1H); 3.39-3.35 (m, 2H); 2.98-2.92 (m, 2H); 2.01-1.97 (m, 2H); 1.71-1.68 (m, 2H). |
| 3.52 | 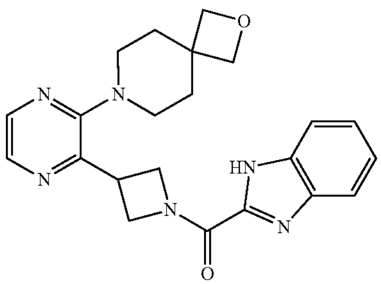 [SMILES: O=C(c1nc2ccccc2[nH]1)N1CC(c2nccnc2N2CCC3(CC2)COC3)C1] | (CDCl$_3$, 400 MHz): 8.19 (d, J = 2.4 Hz, 1H), 8.10 (d, J = 2.4 Hz, 1H), 7.81-7.65 (m, 1H), 7.56-7.50 (m, 1H), 7.32 (s, 2H), 5.30-5.24 (m, 1H), 5.09-5.05 (m, 1H), 4.61 (d, J = 16 Hz, 2H), 4.49 (s, 4H), 4.32-4.24 (m, 1H), 3.04-3.01 (m, 4H), 2.07-2.03 (m, 4H). |
| 3.53 | 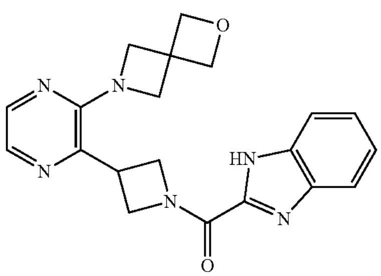 [SMILES: O=C(c1nc2ccccc2[nH]1)N1CC(c2nccnc2N2CC3(COC3)C2)C1] | (CDCl$_3$, 400 MHz): 8.00 (d, J = 4.0 Hz, 2H), 7.76-7.59 (m, 2H), 7.31-7.29 (m, 2H), 5.24-5.19 (m, 1H), 5.12-5.08 (m, 1H), 4.87 (s, 4H), 4.81-7.76 (m, 1H), 4.61-4.54 (m, 1H), 4.27 (s, 4H), 4.04-4.00 (m, 1H) |
| 3.54 | 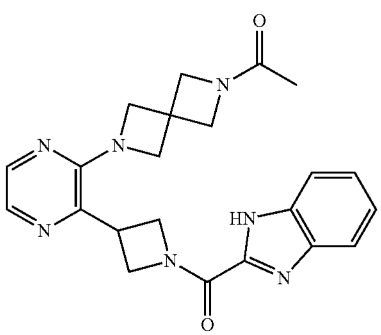 [SMILES: CC(=O)N1CC2(C1)CN(c1nccnc1C1CN(C(=O)c3nc4ccccc4[nH]3)C1)C2] | (MeOD, 400 MHz): 7.99 (dd, J = 2.8 Hz, 7.6 Hz, 2H), 7.66-7.62 (m, 2H), 7.33-7.30 (m, 2H), 5.17-5.12 (m, 1H), 5.02-4.98 (m, 1H), 4.61-4.50 (m, 2H), 4.41 (s, 2H), 4.28 (s, 4H), 4.19-4.12 (m, 3H), 1.88 (s, 3H). |
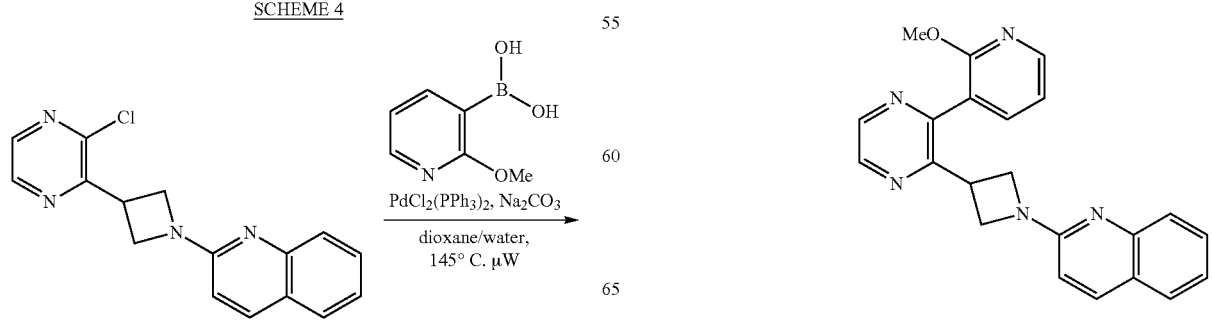
SCHEME 4

Example 4.1: 2-(3-(3-(2-Methoxypyridin-3-Yl)Pyrazin-2-Yl)Azetidin-1-Yl)Quinoline A glass microwave reaction vessel was charged with 2-(3-(3-chloropyrazin-2-yl)azetidin-1-yl)quinoline (0.160 g, 0.539 mmol), sodium carbonate (0.300 g, 2.83 mmol, JT Baker), 2-methoxy-3-pyridineboronic acid (0.150 g, 0.981 mmol, Aldrich) and trans-dichlorobis(triphenylphosphine)palladium (ii) (0.030 g, 0.043 mmol, Strem). Dioxane (3 mL) and water (1 mL) were added and the reaction mixture was sealed under argon and heated in an Initiator microwave reactor (Personal Chemistry, Biotage AB, Inc., Upssala, Sweden) at 145° C. for 15 min. The reaction mixture was partitioned between EtOAc/water and the aqueous layer was extracted with EtOAc (3×). The combined organic layers were evaporated to dryness and the residue was dissolved in MeOH and purified by reverse-phase HPLC (Gilson; Gemini-NX 10 m C18 110A AXIA, 100×50 mm column) eluting with 0.1% TFA-$H_2O$:0.1% TFA $CH_3CN$ (9:1→1:9). The fractions containing the desired product were combined and concentrated in vacuo. The residue was dissolved in MeOH and loaded onto an SCX II cartridge eluting with MeOH then 2M $NH_3$ in MeOH to give 145 mg (73%) of an off-white amorphous solid.

The following Table 16A lists compounds of Examples 4.1 to 4.45, which were made analogous to Scheme 4 by using the appropriate materials and reaction conditions, which are listed in Table 16B. The NMR data of the Examples are listed in Table 16C.

TABLE 16A

EXAMPLES 4.1 TO 4.45

| Ex. # | Structure | Chemical Name | ESI-MS (M + 1) | $IC_{50}$ (nM) |
|---|---|---|---|---|
| 4.1 | 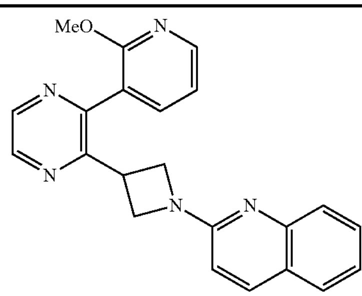 | 2-(3-(3-(2-methoxypyridin-3-yl)pyrazin-2-yl)azetidin-1-yl)quinoline | 370.0 | 0.00234 |
| 4.2 | 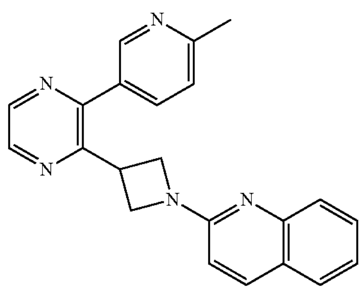 [SMILES: Cc1ccc(-c2nccnc2C2CN(c3ccc4ccccc4n3)C2)cn1] | 2-(3-(3-(6-methylpyridin-3-yl)pyrazin-2-yl)azetidin-1-yl)quinoline | 354 | 0.00279 |
| 4.3 | 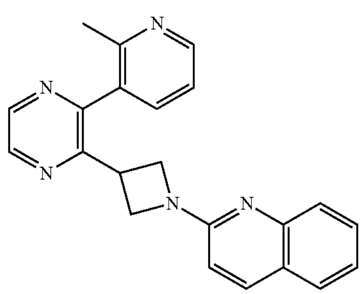 [SMILES: Cc1ncccc1-c1nccnc1C1CN(c2ccc3ccccc3n2)C1] | 2-(3-(3-(2-methylpyridin-3-yl)pyrazin-2-yl)azetidin-1-yl)quinoline | 354.20 | 0.00648 |
| 4.4 | 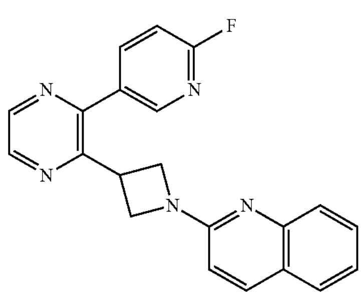 [SMILES: Fc1ccc(-c2nccnc2C2CN(c3ccc4ccccc4n3)C2)cn1] | 2-(3-(3-(6-fluoropyridin-3-yl)pyrazin-2-yl)azetidin-1-yl)quinoline | 358.0 | 0.00418 |

TABLE 16A-continued

EXAMPLES 4.1 TO 4.45

| Ex. # | Structure | Chemical Name | ESI-MS (M + 1) | IC$_{50}$ (nM) |
|---|---|---|---|---|
| 4.5 | 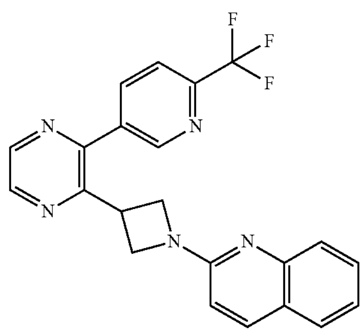 [SMILES: FC(F)(F)c1ccc(-c2nccnc2C2CN(c3ccc4ccccc4n3)C2)cn1] | 2-(3-(3-(6-(trifluoromethyl)pyridin-3-yl)pyrazin-2-yl)azetidin-1-yl)quinoline | 408.0 | 0.0142 |
| 4.6 | 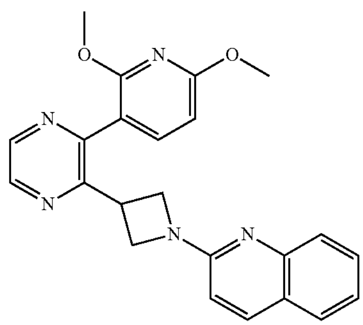 [SMILES: COc1ccc(-c2nccnc2C2CN(c3ccc4ccccc4n3)C2)c(OC)n1] | 2-(3-(3-(2,6-dimethoxypyridin-3-yl)pyrazin-2-yl)azetidin-1-yl)quinoline | 400.20 | 0.00135 |
| 4.7 | 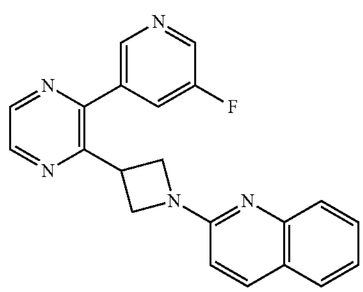 [SMILES: Fc1cncc(-c2nccnc2C2CN(c3ccc4ccccc4n3)C2)c1] | 2-(3-(3-(5-fluoropyridin-3-yl)pyrazin-2-yl)azetidin-1-yl)quinoline | 358.20 | 0.0123 |
| 4.8 | 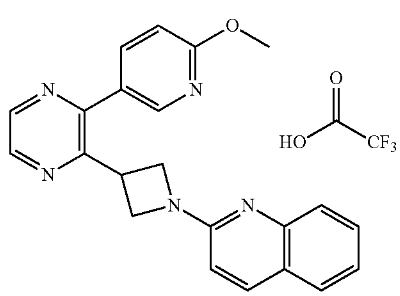 [SMILES: COc1ccc(-c2nccnc2C2CN(c3ccc4ccccc4n3)C2)cn1 ; O=C(O)C(F)(F)F] | 2-(3-(3-(6-methoxypyridin-3-yl)pyrazin-2-yl)azetidin-1-yl)quinoline 2,2,2-trifluoroacetate | 370.2 | 0.00787 |
| 4.9 | 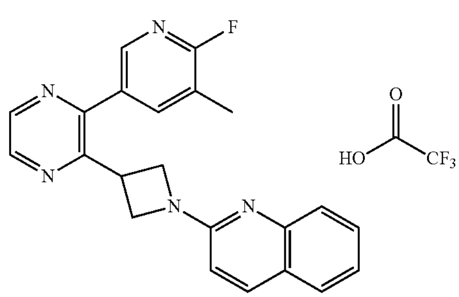 [SMILES: Cc1cc(-c2nccnc2C2CN(c3ccc4ccccc4n3)C2)cnc1F ; O=C(O)C(F)(F)F] | 2-(3-(3-(6-fluoro-5-methylpyridin-3-yl)pyrazin-2-yl)azetidin-1-yl)quinoline 2,2,2-trifluoroacetate | 372.20 | 0.0122 |

TABLE 16A-continued

EXAMPLES 4.1 TO 4.45

| Ex. # | Structure | Chemical Name | ESI-MS (M + 1) | IC$_{50}$ (nM) |
|---|---|---|---|---|
| 4.10 | 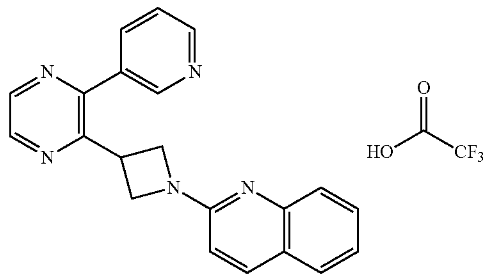 [SMILES: c1cncc(-c2nccnc2C2CN(c3ccc4ccccc4n3)C2)c1 ; O=C(O)C(F)(F)F] | 2-(3-(3-(pyridin-3-yl)pyrazin-2-yl)azetidin-1-yl)quinoline 2,2,2-trifluoroacetate | 340.20 | 0.00787 |
| 4.11 | 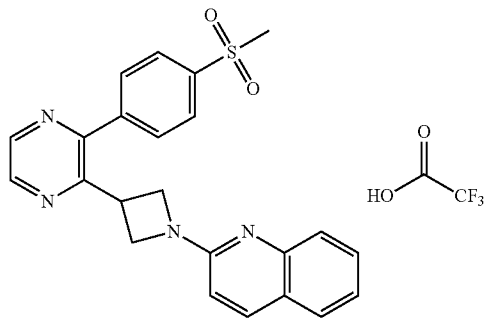 [SMILES: CS(=O)(=O)c1ccc(-c2nccnc2C2CN(c3ccc4ccccc4n3)C2)cc1 ; O=C(O)C(F)(F)F] | 2-(3-(3-(4-(methylsulfonyl)phenyl)pyrazin-2-yl)azetidin-1-yl)quinoline 2,2,2-trifluoroacetate | 417.2 | 0.00262 |
| 4.12 | 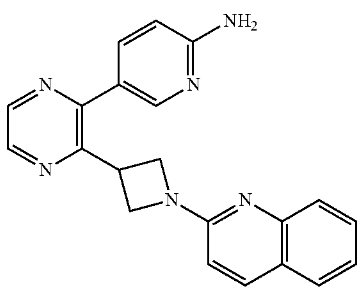 [SMILES: Nc1ccc(-c2nccnc2C2CN(c3ccc4ccccc4n3)C2)cn1] | 5-(3-(1-(quinolin-2-yl)azetidin-3-yl)pyrazin-2-yl)pyridin-2-amine | 355.20 | 0.00278 |
| 4.13 | 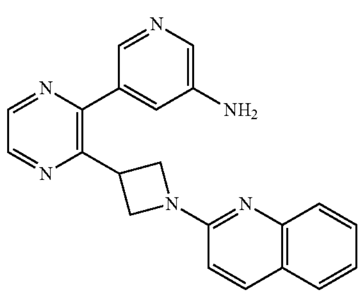 [SMILES: Nc1cncc(-c2nccnc2C2CN(c3ccc4ccccc4n3)C2)c1] | 5-(3-(1-(quinolin-2-yl)azetidin-3-yl)pyrazin-2-yl)pyridin-3-amine | 355.0 | 0.00376 |
| 4.14 | 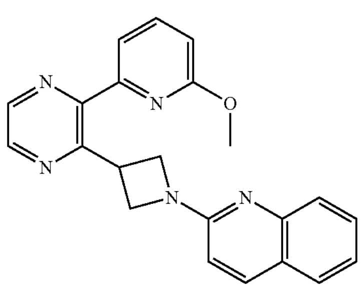 [SMILES: COc1cccc(-c2nccnc2C2CN(c3ccc4ccccc4n3)C2)n1] | 2-(3-(3-(6-methoxypyridin-2-yl)pyrazin-2-yl)azetidin-1-yl)quinoline | 370.20 | 0.0012 |

TABLE 16A-continued

EXAMPLES 4.1 TO 4.45

| Ex. # | Structure | Chemical Name | ESI-MS (M + 1) | IC$_{50}$ (nM) |
|---|---|---|---|---|
| 4.15 | 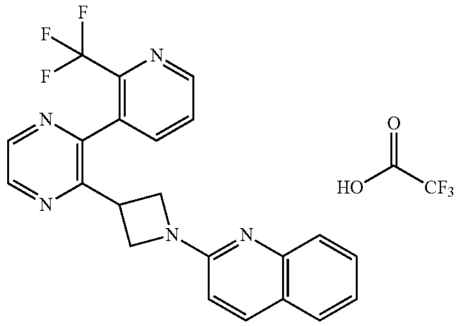 [SMILES: FC(F)(F)c1ncccc1-c1nccnc1C1CN(c2ccc3ccccc3n2)C1 ; O=C(O)C(F)(F)F] | 2-(3-(3-(2-(trifluoromethyl)pyridin-3-yl)pyrazin-2-yl)azetidin-1-yl)quinoline 2,2,2-trifluoroacetate | 408.0 | 0.12360 |
| 4.16 | 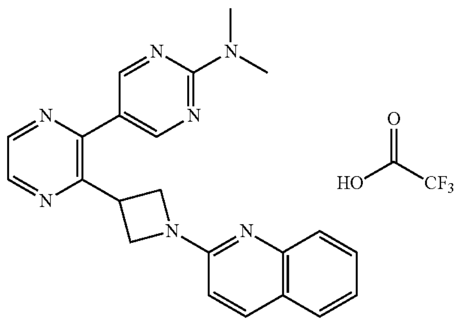 [SMILES: CN(C)c1ncc(-c2nccnc2C2CN(c3ccc4ccccc4n3)C2)cn1 ; O=C(O)C(F)(F)F] | N,N-dimethyl-5-(3-(1-(quinolin-2-yl)azetidin-3-yl)pyrazin-2-yl)pyrimidin-2-amine 2,2,2-trifluoroacetate | 384.0 | 0.02279 |
| 4.17 | 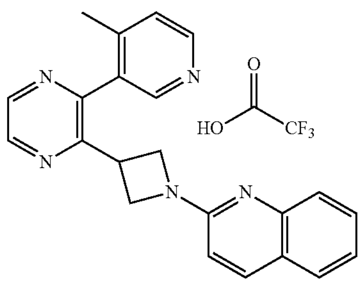 | 2-(3-(3-(4-methylpyridin-3-yl)pyrazin-2-yl)azetidin-1-yl)quinoline 2,2,2-trifluoroacetate | 354.0 | 0.02626 |
| 4.18 | 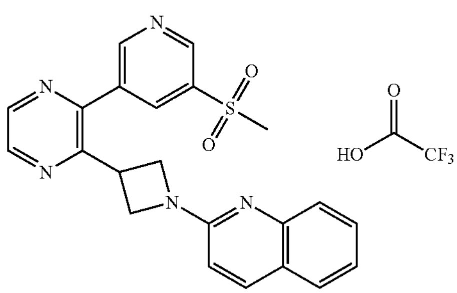 [SMILES: CS(=O)(=O)c1cncc(-c2nccnc2C2CN(c3ccc4ccccc4n3)C2)c1 ; O=C(O)C(F)(F)F] | 2-(3-(3-(5-(methylsulfonyl)pyridin-3-yl)pyrazin-2-yl)azetidin-1-yl)quinoline 2,2,2-trifluoroacetate | 418.0 | |
| 4.19 | 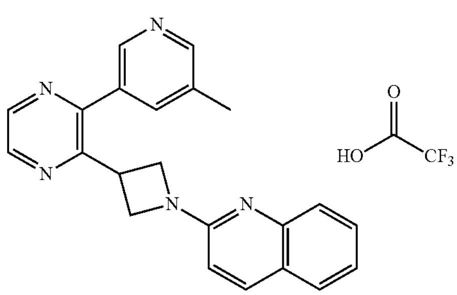 [SMILES: Cc1cncc(-c2nccnc2C2CN(c3ccc4ccccc4n3)C2)c1 ; O=C(O)C(F)(F)F] | 2-(3-(3-(5-methylpyridin-3-yl)pyrazin-2-yl)azetidin-1-yl)quinoline 2,2,2-trifluoroacetate | 354.0 | 0.01625 |

TABLE 16A-continued

EXAMPLES 4.1 TO 4.45

| Ex. # | Structure | Chemical Name | ESI-MS (M + 1) | IC$_{50}$ (nM) |
|---|---|---|---|---|
| 4.20 | 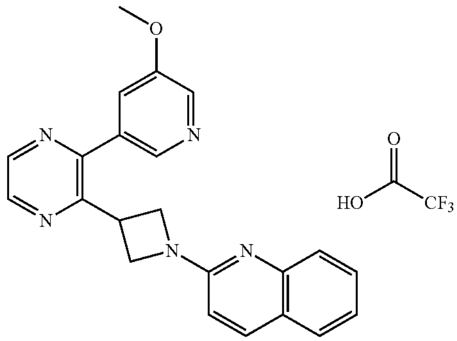 [SMILES: COc1cncc(-c2nccnc2C2CN(c3ccc4ccccc4n3)C2)c1 ; O=C(O)C(F)(F)F] | 2-(3-(3-(5-methoxypyridin-3-yl)pyrazin-2-yl)azetidin-1-yl)quinoline 2,2,2-trifluoroacetate | 370.1 | 0.02472 |
| 4.21 | 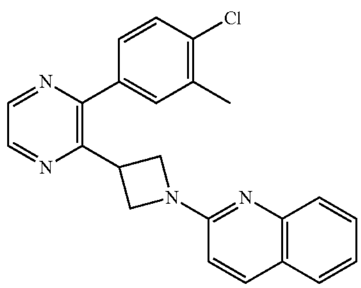 | 2-(3-(3-(4-chloro-3-methylphenyl)pyrazin-2-yl)azetidin-1-yl)quinoline | 387.1 | 0.0023 |
| 4.22 | 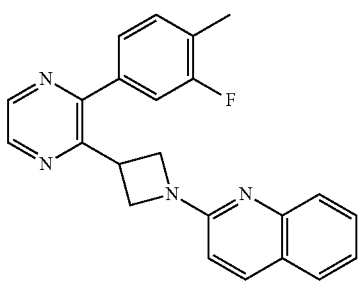 [SMILES: Cc1ccc(-c2nccnc2C2CN(c3ccc4ccccc4n3)C2)cc1F] | 2-(3-(3-(3-fluoro-4-methylphenyl)pyrazin-2-yl)azetidin-1-yl)quinoline | 371.2 | 0.0042 |
| 4.23 | 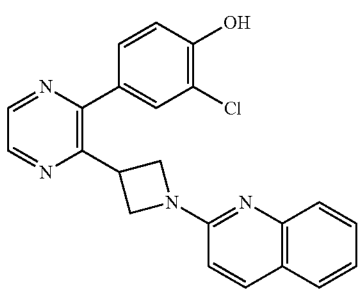 | 2-chloro-4-(3-(1-(quinolin-2-yl)azetidin-3-yl)pyrazin-2-yl)phenol | 389.0 | 0.0023 |
| 4.24 | 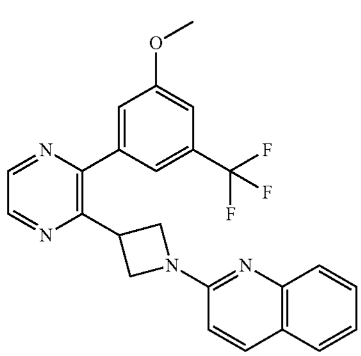 [SMILES: COc1cc(-c2nccnc2C2CN(c3ccc4ccccc4n3)C2)cc(C(F)(F)F)c1] | 2-(3-(3-(3-methoxy-5-(trifluoromethyl)phenyl)pyrazin-2-yl)azetidin-1-yl)quinoline | 437.2 | 0.0149 |

TABLE 16A-continued

EXAMPLES 4.1 TO 4.45

| Ex. # | Structure | Chemical Name | ESI-MS (M + 1) | IC$_{50}$ (nM) |
|---|---|---|---|---|
| 4.25 | 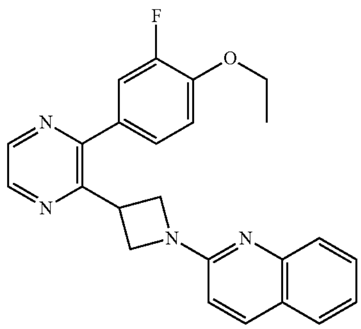 [SMILES: CCOc1ccc(-c2nccnc2C2CN(c3ccc4ccccc4n3)C2)cc1F] | 2-(3-(3-(4-ethoxy-3-fluorophenyl)pyrazin-2-yl)azetidin-1-yl)quinoline | 401.2 | 0.0062 |
| 4.26 | 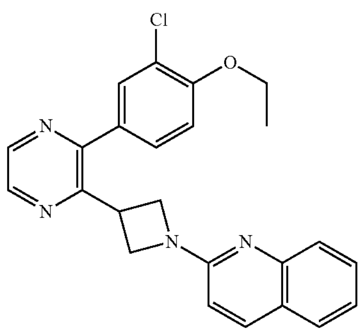 [SMILES: CCOc1ccc(-c2nccnc2C2CN(c3ccc4ccccc4n3)C2)cc1Cl] | 2-(3-(3-(3-chloro-4-ethoxyphenyl)pyrazin-2-yl)azetidin-1-yl)quinoline | 417.00 | 0.0106 |
| 4.27 | 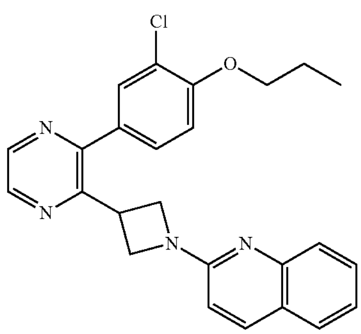 [SMILES: CCCOc1ccc(-c2nccnc2C2CN(c3ccc4ccccc4n3)C2)cc1Cl] | 2-(3-(3-(3-chloro-4-propoxyphenyl)pyrazin-2-yl)azetidin-1-yl)quinoline | 432.2 | 0.0171 |
| 4.28 | 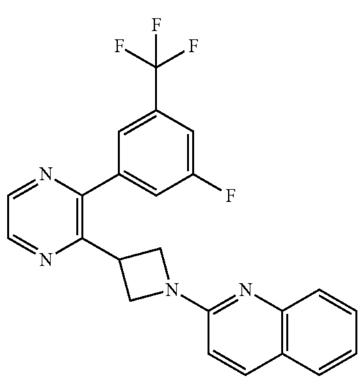 [SMILES: Fc1cc(-c2nccnc2C2CN(c3ccc4ccccc4n3)C2)cc(C(F)(F)F)c1] | 2-(3-(3-(3-fluoro-5-(trifluoromethyl)phenyl)pyrazin-2-yl)azetidin-1-yl)quinoline | 425.20 | 0.0122 |

TABLE 16A-continued

EXAMPLES 4.1 TO 4.45

| Ex. # | Structure | Chemical Name | ESI-MS (M + 1) | IC$_{50}$ (nM) |
|---|---|---|---|---|
| 4.29 | 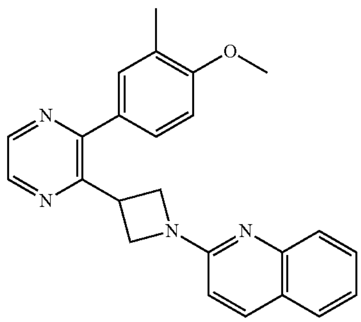 [SMILES: COc1ccc(-c2nccnc2C2CN(c3ccc4ccccc4n3)C2)cc1C] | 2-(3-(3-(4-methoxy-3-methylphenyl)pyrazin-2-yl)azetidin-1-yl)quinoline | 383.20 | 0.0035 |
| 4.30 | 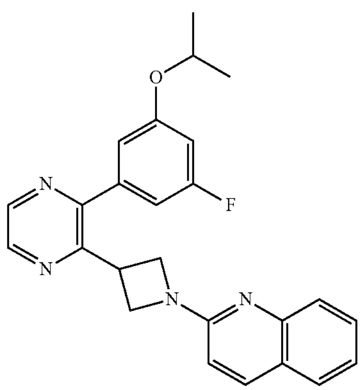 [SMILES: CC(C)Oc1cc(F)cc(-c2nccnc2C2CN(c3ccc4ccccc4n3)C2)c1] | 2-(3-(3-(3-fluoro-5-isopropoxyphenyl)pyrazin-2-yl)azetidin-1-yl)quinoline | 415.20 | 0.0110 |
| 4.31 | 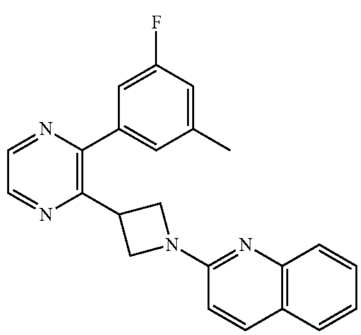 | 2-(3-(3-(3-fluoro-5-methylphenyl)pyrazin-2-yl)azetidin-1-yl)quinoline | 371.20 | 0.0051 |
| 4.32 | 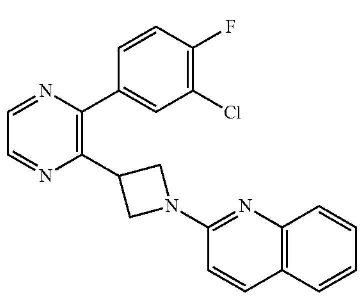 [SMILES: Fc1ccc(-c2nccnc2C2CN(c3ccc4ccccc4n3)C2)cc1Cl] | 2-(3-(3-(3-chloro-4-fluorophenyl)pyrazin-2-yl)azetidin-1-yl)quinoline | 392.20 | 0.0041 |

TABLE 16A-continued

EXAMPLES 4.1 TO 4.45

| Ex. # | Structure | Chemical Name | ESI-MS (M + 1) | IC$_{50}$ (nM) |
|---|---|---|---|---|
| 4.33 | 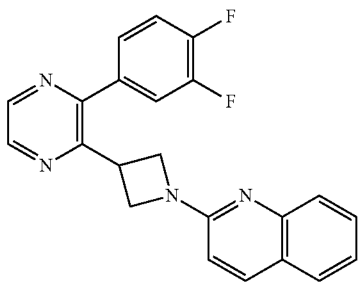 | 2-(3-(3-(3,4-difluorophenyl)pyrazin-2-yl)azetidin-1-yl)quinoline | 375.20 | 0.0099 |
| 4.34 | 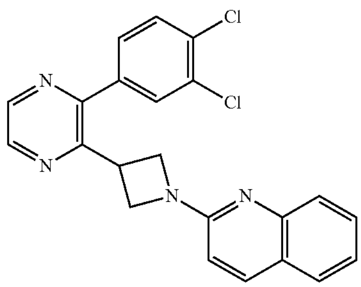 | 2-(3-(3-(3,4-dichlorophenyl)pyrazin-2-yl)azetidin-1-yl)quinoline | 407.0 | 0.0084 |
| 4.35 | 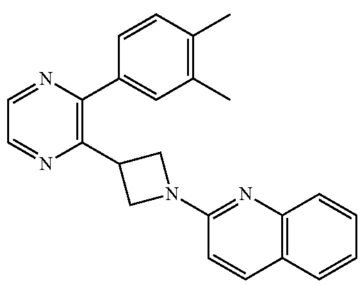 | 2-(3-(3-(3,4-dimethylphenyl)pyrazin-2-yl)azetidin-1-yl)quinoline | 367.20 | 0.0055 |
| 4.36 | 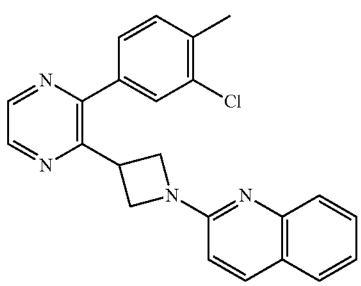 | 2-(3-(3-(3-chloro-4-methylphenyl)pyrazin-2-yl)azetidin-1-yl)quinoline | 388.2 | 0.0067 |
| 4.37 | 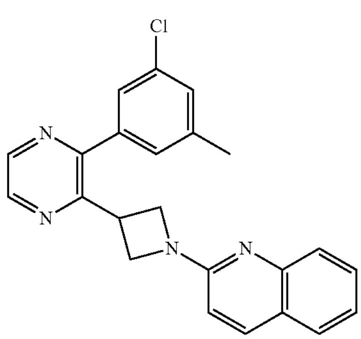 | 2-(3-(3-(3-chloro-5-methylphenyl)pyrazin-2-yl)azetidin-1-yl)quinoline | 387.0 | 0.0072 |

TABLE 16A-continued

EXAMPLES 4.1 TO 4.45

| Ex. # | Structure | Chemical Name | ESI-MS (M + 1) | IC$_{50}$ (nM) |
|---|---|---|---|---|
| 4.38 | 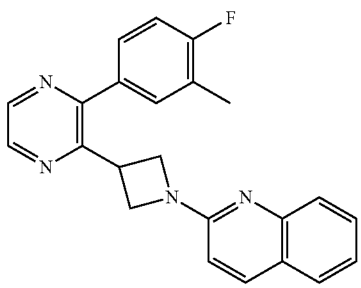 [SMILES: Cc1cc(-c2nccnc2C2CN(c3ccc4ccccc4n3)C2)ccc1F] | 2-(3-(3-(4-fluoro-3-methylphenyl)pyrazin-2-yl)azetidin-1-yl)quinoline | 371.0 | 0.0064 |
| 4.39 | 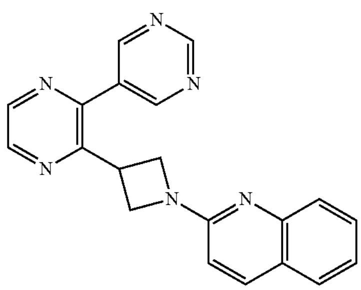 [SMILES: c1ccc2nc(N3CC(c4nccnc4-c4cncnc4)C3)ccc2c1] | 2-(3-(3-(pyrimidin-5-yl)pyrazin-2-yl)azetidin-1-yl)quinoline | 341.20 | 0.0887 |
| 4.40 | 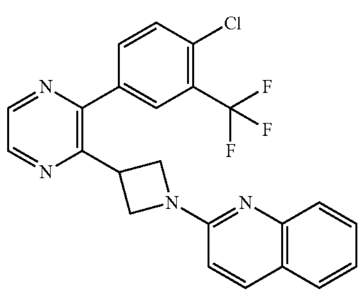 [SMILES: FC(F)(F)c1cc(-c2nccnc2C2CN(c3ccc4ccccc4n3)C2)ccc1Cl] | 2-(3-(3-(4-chloro-3-(trifluoromethyl)phenyl)pyrazin-2-yl)azetidin-1-yl)quinoline | 441.0 | 0.0091 |
| 4.41 | 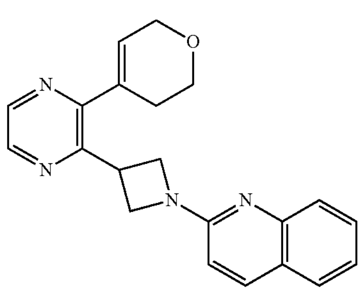 | 2-(3-(3-(3,6-dihydro-2H-pyran-4-yl)pyrazin-2-yl)azetidin-1-yl)quinoline | 345 | 0.0011 |

TABLE 16A-continued
EXAMPLES 4.1 TO 4.45
| Ex. # | Structure | Chemical Name | ESI-MS (M + 1) | IC$_{50}$ (nM) |
|---|---|---|---|---|
| 4.42 | 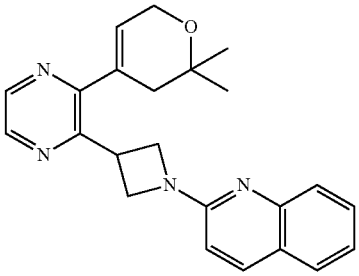 and 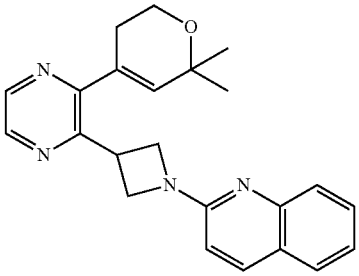 | 2-(3-(3-(2,2-dimethyl-3,6-dihydro-2H-pyran-4-yl)pyrazin-2-yl)azetidin-1-yl)quinoline and 2-(3-(3-(6,6-dimethyl-3,6-dihydro-2H-pyran-4-yl)pyrazin-2-yl)azetidin-1-yl)quinoline | 373 | 0.001 |
| 4.43 | 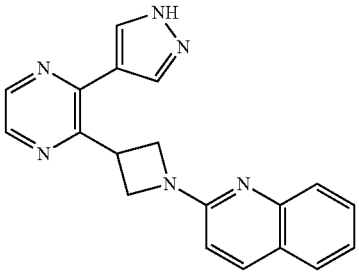 [SMILES: c1ccc2nc(N3CC(c4nccnc4-c4cn[nH]c4)C3)ccc2c1] | 2-(3-(3-(1H-pyrazol-4-yl)pyrazin-2-yl)azetidin-1-yl)quinoline | 329 | 0.007 |
| 4.44 | 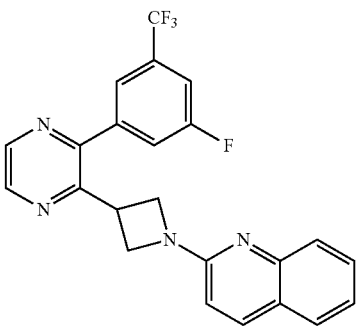 [SMILES: Fc1cc(-c2nccnc2C2CN(c3ccc4ccccc4n3)C2)cc(C(F)(F)F)c1] | 2-(3-(3-(3-fluoro-5-(trifluoromethyl)phenyl)pyrazin-2-yl)azetidin-1-yl)quinoline | 425.20 | 0.0122 |

TABLE 16A-continued

EXAMPLES 4.1 TO 4.45

| Ex. # | Structure | Chemical Name | ESI-MS (M + 1) | IC$_{50}$ (nM) |
|---|---|---|---|---|
| 4.45 | 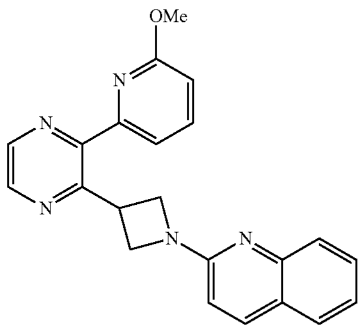 [SMILES: COc1cccc(-c2nccnc2C2CN(c3ccc4ccccc4n3)C2)n1] | 2-(3-(3-(6-methoxypyridin-2-yl)pyrazin-2-yl)azetidin-1-yl)quinoline | 370.20 | 0.0012 |

TABLE 16B

STARTING MATERIALS AND REACTION CONDITION FOR PREPARATION OF EXAMPLES 4.1 TO 4.45.
Unless otherwise stated, all starting materials are commercially available from common vendors.

| Ex. # | Key Starting Material(s) | Key Starting Material(s) | Reaction Condition | Purification Method* |
|---|---|---|---|---|
| 4.1 | Aldrich | PREPARATION 2 | PdCl$_2$(PPh$_3$)$_2$, Na$_2$CO$_3$ Dioxane/water, 145° C., μW | A |
| 4.2 | Combi-Blocks | PREPARATION 2 | PdCl$_2$(PPh$_3$)$_2$, Na$_2$CO$_3$ Dioxane/water, 145° C., μW | A |
| 4.3 | Combi-Blocks | PREPARATION 2 | PdCl$_2$(PPh$_3$)$_2$, Na$_2$CO$_3$ Dioxane/water, 145° C., μW | B |
| 4.4 | Acros | | PdCl$_2$(PPh$_3$)$_2$, Na$_2$CO$_3$ Dioxane/water, 145° C., μW | B |

TABLE 16B-continued

STARTING MATERIALS AND REACTION CONDITION FOR
PREPARATION OF EXAMPLES 4.1 TO 4.45.
Unless otherwise stated, all starting materials are commercially available from common vendors.

| Ex. # | Key Starting Material(s) | Key Starting Material(s) | Reaction Condition | Purification Method* |
|---|---|---|---|---|
| | | PREPARATION 2 | | |
| 4.5 | 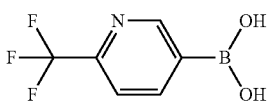<br>Combi-Blocks | 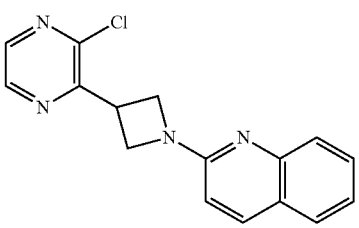<br>PREPARATION 2 | PdCl$_2$(PPh$_3$)$_2$, Na$_2$CO$_3$ Dioxane/water, 145° C., μW | B |
| 4.6 | 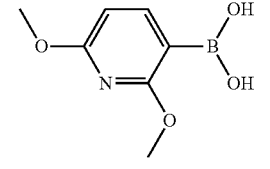<br>Alfa Aesar | 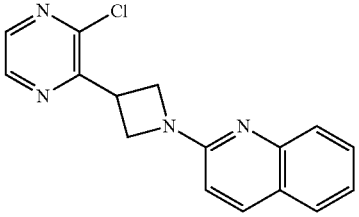 [SMILES: Clc1nccnc1C1CN(c2ccc3ccccc3n2)C1]<br>PREPARATION 2 | PdCl$_2$(PPh$_3$)$_2$, Na$_2$CO$_3$ Dioxane/water, 145° C., μW | B |
| 4.7 | 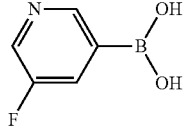<br>Combi-Blocks | 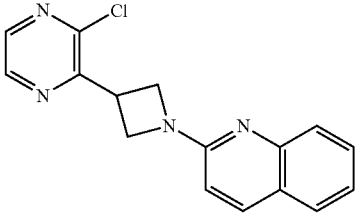 [SMILES: Clc1nccnc1C1CN(c2ccc3ccccc3n2)C1]<br>PREPARATION 2 | PdCl$_2$(PPh$_3$)$_2$, Na$_2$CO$_3$ Dioxane/water, 145° C., μW | B |
| 4.8 | 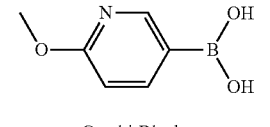<br>Combi-Blocks | 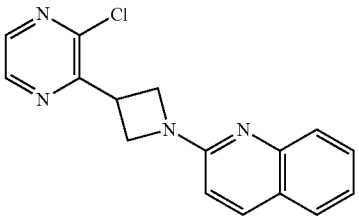<br>PREPARATION 2 | PdCl$_2$(PPh$_3$)$_2$, Na$_2$CO$_3$ Dioxane/water, 145° C., μW | E |
| 4.9 | 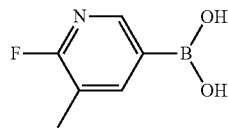<br>Boron Molecular | 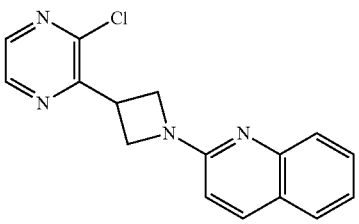<br>PREPARATION 2 | PdCl$_2$(PPh$_3$)$_2$, Na$_2$CO$_3$ Dioxane/water, 145° C., μW | E |

TABLE 16B-continued

STARTING MATERIALS AND REACTION CONDITION FOR
PREPARATION OF EXAMPLES 4.1 TO 4.45.
Unless otherwise stated, all starting materials are commercially available from common vendors.

| Ex. # | Key Starting Material(s) | Key Starting Material(s) | Reaction Condition | Purification Method* |
|---|---|---|---|---|
| 4.10 | 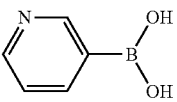<br>Boron Molecular | 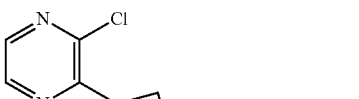<br>PREPARATION 2 | PdCl$_2$(PPh$_3$)$_2$, Na$_2$CO$_3$ Dioxane/water, 145° C., μW | E |
| 4.11 | 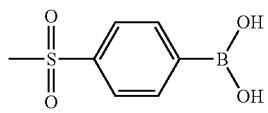<br>Alfa Aesar | 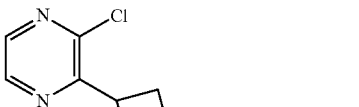<br>PREPARATION 2 | PdCl$_2$(PPh$_3$)$_2$, Na$_2$CO$_3$ Dioxane/water, 145° C., μW | E |
| 4.12 | 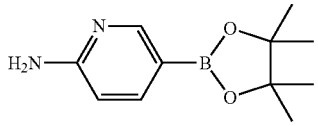 [SMILES: CC1(C)OB(c2ccc(N)nc2)OC1(C)C]<br>Boron Molecular | 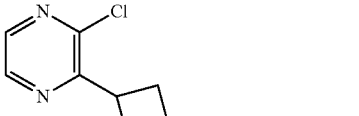<br>PREPARATION 2 | PdCl$_2$(PPh$_3$)$_2$, Na$_2$CO$_3$ Dioxane/water, 145° C., μW | D |
| 4.13 | 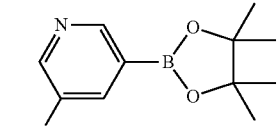<br>Boron Molecular | 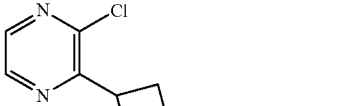<br>PREPARATION 2 | PdCl$_2$(PPh$_3$)$_2$, Na$_2$CO$_3$ Dioxane/water, 145° C., μW | D |
| 4.14 | 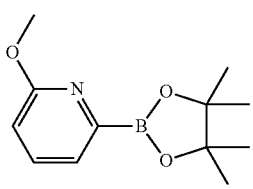 [SMILES: COc1cccc(B2OC(C)(C)C(C)(C)O2)n1]<br>Combi-Blocks | 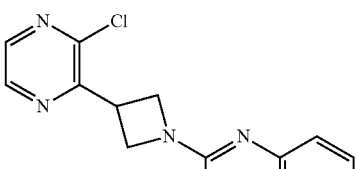<br>PREPARATION 2 | PdCl$_2$(PPh$_3$)$_2$, Na$_2$CO$_3$ Dioxane/water, 145° C., μW | D |
| 4.15 | 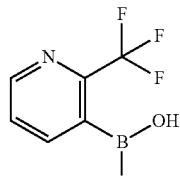<br>Frontier Scientific | 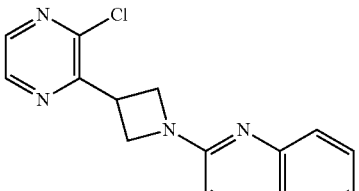<br>PREPARATION 2 | PdCl$_2$(PPh$_3$)$_2$, Na$_2$CO$_3$ Dioxane/water, 145° C., μW | C |

TABLE 16B-continued

STARTING MATERIALS AND REACTION CONDITION FOR
PREPARATION OF EXAMPLES 4.1 TO 4.45.
Unless otherwise stated, all starting materials are commercially available from common vendors.

| Ex. # | Key Starting Material(s) | Key Starting Material(s) | Reaction Condition | Purification Method* |
|---|---|---|---|---|
| 4.16 | Frontier Scientific | PREPARATION 2 | $PdCl_2(PPh_3)_2$, $Na_2CO_3$ Dioxane/water, 145° C., μW | C |
| 4.17 | Combi-Blocks | PREPARATION 2 | $PdCl_2(PPh_3)_2$, $Na_2CO_3$ Dioxane/water, 145° C., μW | C |
| 4.18 | Combi-Blocks | PREPARATION 2 | $PdCl_2(PPh_3)_2$, $Na_2CO_3$ Dioxane/water, 145° C., μW | C |
| 4.19 | Combi-Blocks | PREPARATION 2 | $PdCl_2(PPh_3)_2$, $Na_2CO_3$ Dioxane/water, 145° C., μW | C |
| 4.20 | Combi-Blocks | PREPARATION 2 | $PdCl_2(PPh_3)_2$, $Na_2CO_3$ Dioxane/water, 145° C., μW | C |
| 4.21 | Combi-Blocks | | $PdCl_2(PPh_3)_2$, $Na_2CO_3$ Dioxane/water, 145° C., μW | D |

TABLE 16B-continued

STARTING MATERIALS AND REACTION CONDITION FOR
PREPARATION OF EXAMPLES 4.1 TO 4.45.
Unless otherwise stated, all starting materials are commercially available from common vendors.

| Ex. # | Key Starting Material(s) | Key Starting Material(s) | Reaction Condition | Purification Method* |
|---|---|---|---|---|
| 4.22 | 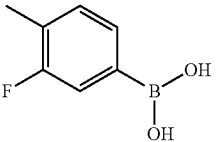 Combi-Blocks | 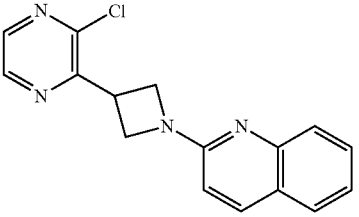 PREPARATION 2 | PdCl$_2$(PPh$_3$)$_2$, Na$_2$CO$_3$ Dioxane/water, 145° C., μW | D |
| 4.23 | 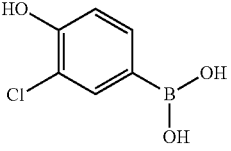 [SMILES: OB(O)c1ccc(O)c(Cl)c1] Combi-Blocks | 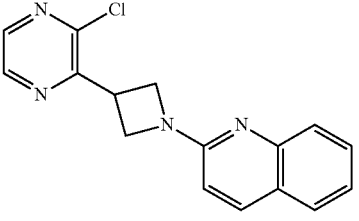 PREPARATION 2 | PdCl$_2$(PPh$_3$)$_2$, Na$_2$CO$_3$ Dioxane/water, 145° C., μW | D |
| 4.24 | 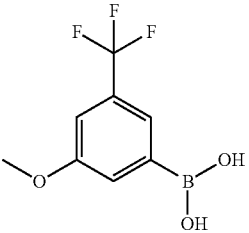 Combi-Blocks | 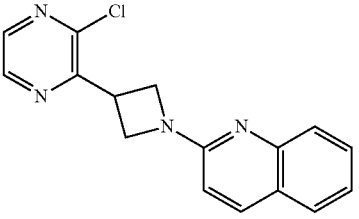 PREPARATION 2 | PdCl$_2$(PPh$_3$)$_2$, Na$_2$CO$_3$ Dioxane/water, 145° C., μW | D |
| 4.25 | 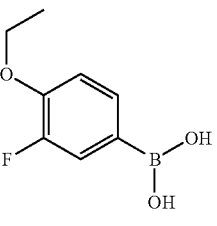 Combi-Blocks | 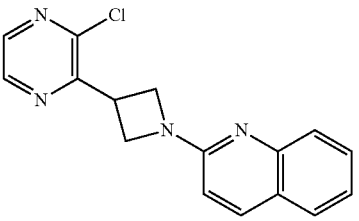 [SMILES: Clc1nccnc1C1CN(c2ccc3ccccc3n2)C1] PREPARATION 2 | PdCl$_2$(PPh$_3$)$_2$, Na$_2$CO$_3$ Dioxane/water, 145° C., μW | D |
| 4.26 | 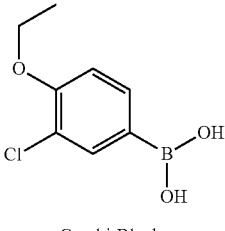 Combi-Blocks | 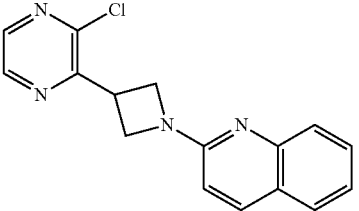 [SMILES: Clc1nccnc1C1CN(c2ccc3ccccc3n2)C1] PREPARATION 2 | PdCl$_2$(PPh$_3$)$_2$, Na$_2$CO$_3$ Dioxane/water, 145° C., μW | D |

TABLE 16B-continued

STARTING MATERIALS AND REACTION CONDITION FOR
PREPARATION OF EXAMPLES 4.1 TO 4.45.
Unless otherwise stated, all starting materials are commercially available from common vendors.

| Ex. # | Key Starting Material(s) | Key Starting Material(s) | Reaction Condition | Purification Method* |
|---|---|---|---|---|
| 4.27 | [structure: 3-chloro-4-propoxyphenylboronic acid], Combi-Blocks | [structure: PREPARATION 2] | $PdCl_2(PPh_3)_2$, $Na_2CO_3$ Dioxane/water, 145° C., μW | D |
| 4.28 | [structure: 3-fluoro-5-(trifluoromethyl)phenylboronic acid], Combi-Blocks | [structure: PREPARATION 2] | $PdCl_2(PPh_3)_2$, $Na_2CO_3$ Dioxane/water, 145° C., μW | D |
| 4.29 | [structure: 4-methoxy-3-methylphenylboronic acid], ASDI | [structure: PREPARATION 2] | $PdCl_2(PPh_3)_2$, $Na_2CO_3$ Dioxane/water, 145° C., μW | D |
| 4.30 | [structure: 3-fluoro-5-isopropoxyphenylboronic acid], ASDI | [structure: PREPARATION 2] | $PdCl_2(PPh_3)_2$, $Na_2CO_3$ Dioxane/water, 145° C., μW | D |
| 4.31 | [structure: 3-fluoro-5-methylphenylboronic acid], ASDI | [structure: PREPARATION 2] | $PdCl_2(PPh_3)_2$, $Na_2CO_3$ Dioxane/water, 145° C., μW | D |

TABLE 16B-continued

STARTING MATERIALS AND REACTION CONDITION FOR
PREPARATION OF EXAMPLES 4.1 TO 4.45.
Unless otherwise stated, all starting materials are commercially available from common vendors.

| Ex. # | Key Starting Material(s) | Key Starting Material(s) | Reaction Condition | Purification Method* |
|---|---|---|---|---|
| 4.32 | ASDI | PREPARATION 2 | PdCl$_2$(PPh$_3$)$_2$, Na$_2$CO$_3$ Dioxane/water, 145° C., μW | D |
| 4.33 | Aldrich | PREPARATION 2 | PdCl$_2$(PPh$_3$)$_2$, Na$_2$CO$_3$ Dioxane/water, 145° C., μW | D |
| 4.34 | Frontier Scientific | PREPARATION 2 | PdCl$_2$(PPh$_3$)$_2$, Na$_2$CO$_3$ Dioxane/water, 145° C., μW | D |
| 4.35 | Maybridge | PREPARATION 2 | PdCl$_2$(PPh$_3$)$_2$, Na$_2$CO$_3$ Dioxane/water, 145° C., μW | D |
| 4.36 | Combi-Blocks | PREPARATION 2 | PdCl$_2$(PPh$_3$)$_2$, Na$_2$CO$_3$ Dioxane/water, 145° C., μW | D |
| 4.37 | Combi-Blocks | PREPARATION 2 | PdCl$_2$(PPh$_3$)$_2$, Na$_2$CO$_3$ Dioxane/water, 145° C., μW | D |

TABLE 16B-continued

STARTING MATERIALS AND REACTION CONDITION FOR
PREPARATION OF EXAMPLES 4.1 TO 4.45.
Unless otherwise stated, all starting materials are commercially available from common vendors.

| Ex. # | Key Starting Material(s) | Key Starting Material(s) | Reaction Condition | Purification Method* |
|---|---|---|---|---|
| 4.38 | [structure: 4-fluoro-3-methylphenylboronic acid] Aldrich | [structure: 3-chloro-2-(1-(quinolin-2-yl)azetidin-3-yl)pyrazine] PREPARATION 2 | $PdCl_2(PPh_3)_2$, $Na_2CO_3$ Dioxane/water, 145° C., μW | D |
| 4.39 | [structure: pyrimidin-5-yl boronic acid pinacol ester] Asymchem | [structure: 3-chloro-2-(1-(quinolin-2-yl)azetidin-3-yl)pyrazine] PREPARATION 2 | $PdCl_2(PPh_3)_2$, $Na_2CO_3$ Dioxane/water, 145° C., μW | D |
| 4.40 | [structure: 4-chloro-3-(trifluoromethyl)phenylboronic acid] Combi-Blocks | [structure: 3-chloro-2-(1-(quinolin-2-yl)azetidin-3-yl)pyrazine] PREPARATION 2 | $PdCl_2(PPh_3)_2$, $Na_2CO_3$ Dioxane/water, 145° C., μW | D |
| 4.41 | [structure: 3,6-dihydro-2H-pyran-4-yl boronic acid pinacol ester] Combi-Blocks | [structure: 3-chloro-2-(1-(quinolin-2-yl)azetidin-3-yl)pyrazine] PREPARATION 2 | $Pd(tBu_3P)_2$, KOAc Dioxane/water, 125° C., μW, 30 min | E |
| 4.42 | [structures: two boronic ester isomers] 136 PREPARATION 41 | [structure: 3-chloro-2-(1-(quinolin-2-yl)azetidin-3-yl)pyrazine] PREPARATION 2 | $Pd(tBu_3P)_2$, KOAc Dioxane/water, 135° C., μW, 30 min | E |

TABLE 16B-continued

STARTING MATERIALS AND REACTION CONDITION FOR
PREPARATION OF EXAMPLES 4.1 TO 4.45.
Unless otherwise stated, all starting materials are commercially available from common vendors.

| Ex. # | Key Starting Material(s) | Key Starting Material(s) | Reaction Condition | Purification Method* |
|---|---|---|---|---|
| 4.43 | [pyrazole boronic acid pinacol ester] MAYBRIDGE | [chloropyrazine-azetidine-quinoline] PREPARATION 2 | Pd(tBu$_3$P)$_2$, KOAc Dioxane/water, 135° C., μW, 30 min | F |
| 4.44 | [3-fluoro-5-(trifluoromethyl)phenylboronic acid] Combi-Blocks | [chloropyrazine-azetidine-quinoline] PREPARATION 2 | PdCl$_2$(PPh$_3$)$_2$, Na$_2$CO$_3$ Dioxane/water, 145° C., μW | D |
| 4.45 | [6-methoxypyridine-2-boronic acid pinacol ester] Combi-Blocks | [chloropyrazine-azetidine-quinoline] PREPARATION 2 | PdCl$_2$(PPh$_3$)$_2$, Na$_2$CO$_3$ Dioxane/water, 145° C., μW | D |

*Purification Methods:
Method A-reverse-phase HPLC (Gilson; Gemini-NX 10m C18 110A AXIA, 100 × 50 mm column) eluting with 0.1% TFA-H$_2$O:0.1% TFA CH$_3$CN (9:1→1:9). The fractions containing the desired product were combined and concentrated in vacuo. The residue was dissolved in MeOH and loaded onto an SCX II cartridge eluting with MeOH then 2M NH$_3$ in MeOH.
Method B-reverse-phase HPLC (Instrumentation: MS-Waters SQ; UV-Waters 2487 or Waters PD; Solvents: A: Water w/ 0.1% NH$_4$OH B: Acetonitrile w/ 0.1% NH4OH; Column: Phenomenex Gemini-NX C18 110A 5um 21 × 100; Flow Rate: 44 mL/min. 10 min Method, variable gradient over 8 mins.
Method C-reverse-phase HPLC (Gilson; Gemini-NX 10m C18 110A AXIA, 100 × 50 mm column) eluting with 0.1% TFA-H$_2$O:0.1% TFA CH$_3$CN (9:1→1:9). The fractions containing the desired product were combined and concentrated in vacuo.
Method D-reverse-phase HPLC (Instrument: Waters Autopurificaton system; Column: Xbridge 19 × 100 mm, 10 um; Flow rate: 40 ml/min; Mobile phase: 0.1% NH$_4$OH in acetonitrile (B) and water (A)).
Method E-reverse-phase HPLC (Instrument: Waters Autopurificaton system; Column: Xbridge 19 × 100 mm, 10 um; Flow rate: 40 ml/min; Mobile phase: 0.1% TFA in acetonitrile (B) and water (A)).
Method E-purification by silicagel chromatography eluting with a gradient of EtOAc in hexane.
Method F-purification by silica gel chromatography eluting with a gradient of MeOH in DCM.

TABLE 16C

1H NMR δ (PPM) DATA FOR EXAMPLES 4.1 TO 4.45

| Ex. # | Structure | NMR |
|---|---|---|
| 4.1 | [MeO-pyridine-pyrazine-azetidine-quinoline structure] | (300 MHz, DMSO-d$_6$) 2.59 (s, 3 H) 4.21-4.50 (m, 5 H) 6.75 (d, J = 8.77 Hz, 1 H) 7.21 (ddd, J = 8.00, 6.47, 1.61 Hz, 1 H) 7.45 (d, J = 8.04 Hz, 1 H) 7.48-7.60 (m, 2 H) 7.70 (d, J = 7.60 Hz, 1 H) 7.93 (dd, J = 7.97, 2.41 Hz, 1 H) 8.02 (d, J = 8.77 Hz, 1 H) 8.63-8.74 (m, 3 H). |

TABLE 16C-continued

1H NMR δ (PPM) DATA FOR EXAMPLES 4.1 TO 4.45

| Ex. # | Structure | NMR |
|---|---|---|
| 4.2 | 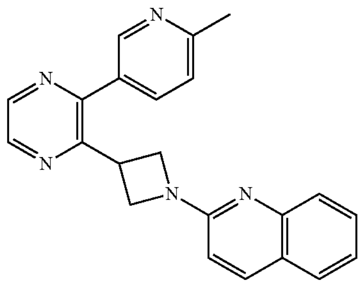 [SMILES: Cc1ccc(-c2nccnc2C2CN(c3ccc4ccccc4n3)C2)cn1] | (300 MHz, DMSO-$d_6$) 2.59 (s, 3 H) 4.21-4.50 (m, 5 H) 6.75 (d, J = 8.77 Hz, 1 H) 7.21 (ddd, J = 8.00, 6.47, 1.61 Hz, 1 H) 7.45 (d, J = 8.04 Hz, 1 H) 7.48-7.60 (m, 2 H) 7.70 (d, J = 7.60 Hz, 1 H) 7.93 (dd, J = 7.97, 2.41 Hz, 1 H) 8.02 (d, J = 8.77 Hz, 1 H) 8.63-8.74 (m, 3 H) |
| 4.3 | 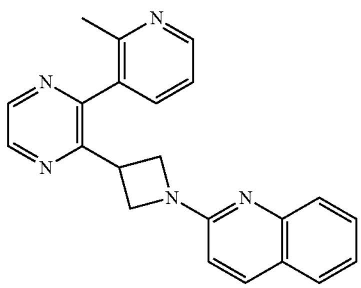 [SMILES: Cc1ncccc1-c1nccnc1C1CN(c2ccc3ccccc3n2)C1] | (400 MHz, DMSO-$d_6$) 8.74 (d, J = 2.35 Hz, 1 H) 8.67 (d, J = 2.35 Hz, 1 H) 8.61 (dd, J = 4.69, 1.56 Hz, 1 H) 8.02 (d, J = 9.00 Hz, 1 H) 7.66-7.78 (m, 2 H) 7.47-7.58 (m, 2 H) 7.41 (dd, J = 7.63, 4.89 Hz, 1 H) 7.21 (t, J = 7.24 Hz, 1 H) 6.74 (d, J = 8.61 Hz, 1 H) 4.24-4.31 (m, 2 H) 4.17-4.24 (m, 2 H) 3.93-4.07 (m, 1 H) 2.28 (s, 3 H). |
| 4.4 | 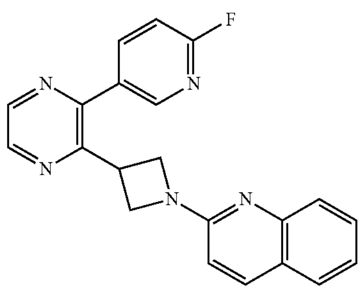 [SMILES: Fc1ccc(-c2nccnc2C2CN(c3ccc4ccccc4n3)C2)cn1] | (400 MHz, DMSO-$d_6$) 8.74 (d, J = 2.35 Hz, 1 H) 8.68 (d, J = 2.35 Hz, 1 H) 8.49 (d, J = 2.35 Hz, 1 H) 8.25 (td, J = 8.12, 2.54 Hz, 1 H) 8.02 (d, J = 8.61 Hz, 1 H) 7.70 (d, J = 7.43 Hz, 1 H) 7.46-7.61 (m, 2 H) 7.40 (dd, J = 8.61, 2.74 Hz, 1 H) 7.14-7.27 (m, 1 H) 6.75 (d, J = 8.61 Hz, 1 H) 4.37-4.49 (m, 1 H) 4.23-4.37 (m, 4H). |
| 4.5 | 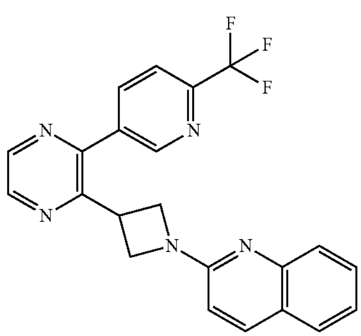 [SMILES: FC(F)(F)c1ccc(-c2nccnc2C2CN(c3ccc4ccccc4n3)C2)cn1] | (400 MHz, DMSO-$d_6$) 8.74 (d, J = 2.35 Hz, 1 H) 8.68 (d, J = 2.35 Hz, 1 H) 8.49 (d, J = 2.35 Hz, 1 H) 8.25 (td, J = 8.12, 2.54 Hz, 1 H) 8.02 (d, J = 8.61 Hz, 1 H) 7.70 (d, J = 7.43 Hz, 1 H) 7.46-7.61 (m, 2 H) 7.40 (dd, J = 8.61, 2.74 Hz, 1 H) 7.14-7.27 (m, 1 H) 6.75 (d, J = 8.61 Hz, 1 H) 4.37-4.49 (m, 1 H) 4.23-4.37 (m, 4H). |
| 4.6 | 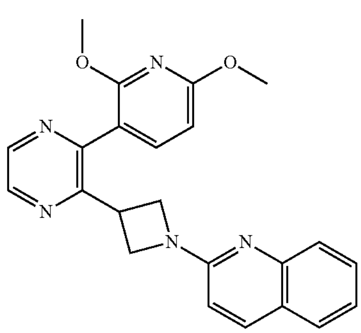 [SMILES: COc1ccc(-c2nccnc2C2CN(c3ccc4ccccc4n3)C2)c(OC)n1] | (400 MHz, DMSO-$d_6$) 8.64 (d, J = 2.35 Hz, 1 H) 8.60 (d, J = 1.96 Hz, 1 H) 8.02 (d, J = 9.00 Hz, 1 H) 7.78 (d, J = 8.22 Hz, 1 H) 7.70 (d, J = 7.82 Hz, 1 H) 7.43-7.62 (m, 2 H) 7.21 (t, J = 7.04 Hz, 1 H) 6.76 (d, J = 9.00 Hz, 1 H) 6.59 (d, J = 8.22 Hz, 1 H) 4.31 (br. s., 1 H) 4.23 (t, J = 6.65 Hz, 2 H) 4.00-4.14 (m, 2 H) 3.97 (s, 3 H) 3.94 (s, 3 H). |

TABLE 16C-continued

1H NMR δ (PPM) DATA FOR EXAMPLES 4.1 TO 4.45

| Ex. # | Structure | NMR |
|---|---|---|
| 4.7 | 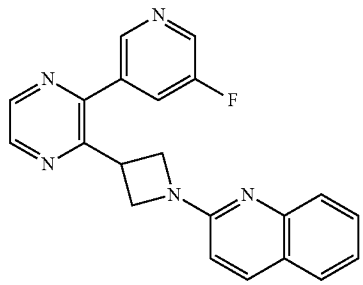 [SMILES: Fc1cncc(-c2nccnc2C2CN(c3ccc4ccccc4n3)C2)c1] | (400 MHz, DMSO-$d_6$) 8.77 (d, J = 2.3 Hz, 2 H), 8.70 (d, J = 2.3 Hz, 1 H), 8.69 (s, 1 H), 8.07-7.97 (m, 2 H), 7.70 (d, J = 8.2 Hz, 1 H), 7.59-7.47 (m, 2 H), 7.26-7.16 (m, 1 H), 6.76 (d, J = 9.0 Hz, 1 H), 4.50-4.40 (m, 1 H), 4.37-4.23 (m, 4 H) |
| 4.8 | 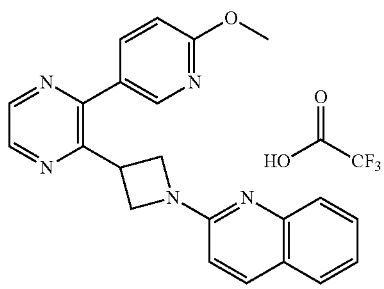 | (500 MHz, DMSO-$d_6$) 8.68-8.79 (m, 2 H) 8.43 (d, J = 2.29 Hz, 1 H) 8.38 (d, J = 9.28 Hz, 1 H) 8.00 (dd, J = 8.59, 2.41 Hz, 1 H) 7.93 (d, J = 7.90 Hz, 1 H) 7.77 (d, J = 3.55 Hz, 2 H) 7.49 (dd, J = 8.08, 4.07 Hz, 1 H) 7.03 (d, J = 8.59 Hz, 1 H) 7.05 (d, J = 9.74 Hz, 1 H) 4.66 (br. s., 2 H) 4.45-4.64 (m, 2 H) 3.96 (s, 3 H). |
| 4.9 | 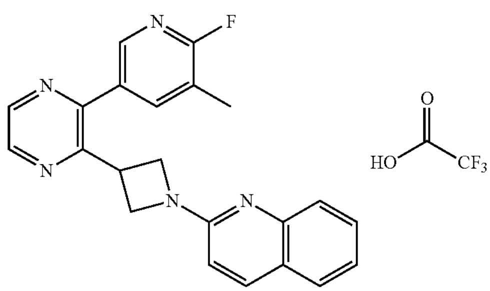 [SMILES: Cc1cc(-c2nccnc2C2CN(c3ccc4ccccc4n3)C2)cnc1F ; O=C(O)C(F)(F)F] | (500 MHz, DMSO-$d_6$) 8.78 (d, J = 2.41 Hz, 1 H) 8.71-8.76 (m, 1 H) 8.39 (d, J = 9.51 Hz, 1 H) 8.30 (s, 1 H) 8.11 (d, J = 9.51 Hz, 1 H) 7.93 (d, J = 7.90 Hz, 1 H) 7.78 (d, J = 3.55 Hz, 2 H) 7.44-7.52 (m, 1 H) 7.05 (d, J = 9.28 Hz, 1 H) 4.52-4.72 (m, 5 H) 2.37 (s, 3 H). |
| 4.10 | 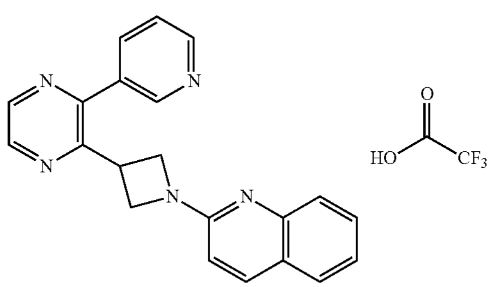 [SMILES: c1cncc(-c2nccnc2C2CN(c3ccc4ccccc4n3)C2)c1 ; O=C(O)C(F)(F)F] | (500 MHz, DMSO-$d_6$) 8.83 (s, 1 H) 8.79 (d, J = 2.29 Hz, 1 H) 8.76 (s, 2 H) 8.39 (d, J = 9.39 Hz, 1 H) 8.09 (d, J = 7.90 Hz, 1 H) 7.93 (d, J = 7.90 Hz, 1 H) 7.77 (br. s, 2 H) 7.64 (dd, J = 7.73, 4.75 Hz, 1 H) 7.50 (d, J = 8.02 Hz, 1 H) 7.05 (d, J = 9.39 Hz, 1 H) 4.67 (br. s., 2 H) 4.60 (br. s., 3 H). |
| 4.11 | 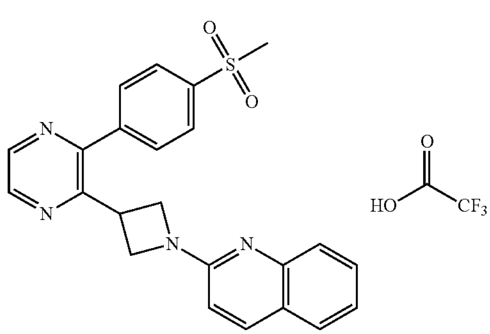 [SMILES: CS(=O)(=O)c1ccc(-c2nccnc2C2CN(c3ccc4ccccc4n3)C2)cc1 ; O=C(O)C(F)(F)F] | (600 MHz, DMSO-$d_6$) 8.80 (s, 1 H), 8.77-8.71 (m, 1 H), 8.37 (d, J = 9.3 Hz, 1 H), 8.18-8.08 (m, J = 8.1 Hz, 2H), 7.92 (d, J = 7.9 Hz, 1 H), 7.91-7.87 (m, J = 8.1 Hz, 2 H), 7.78 (br. s, 2H), 7.48 (t, J = 5.7 Hz, 1 H), 7.02 (d, J = 9.3 Hz, 1 H), 4.70-4.54 (m, 6 H) |

TABLE 16C-continued

1H NMR δ (PPM) DATA FOR EXAMPLES 4.1 TO 4.45

| Ex. # | Structure | NMR |
|---|---|---|
| 4.12 | 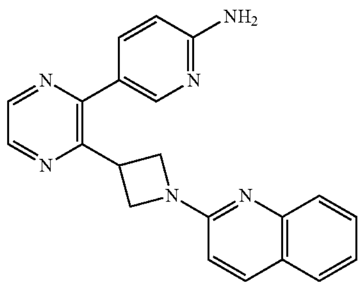 [SMILES: Nc1ccc(-c2nccnc2C2CN(c3ccc4ccccc4n3)C2)cn1] | (500 MHz, DMSO-$d_6$) 8.57 (s, 2 H) 8.17 (s, 1 H) 8.03 (d, J = 9.05 Hz, 1 H) 7.70 (d, J = 7.90 Hz, 1 H) 7.65 (dd, J = 8.59, 2.29 Hz, 1 H) 7.57 (d, J = 8.36 Hz, 1 H) 7.52 (t, J = 7.56 Hz, 1 H) 7.21 (t, J = 7.33 Hz, 1 H) 6.76 (d, J = 8.94 Hz, 1 H) 6.60 (d, J = 8.59 Hz, 1 H) 6.35 (s, 2 H) 4.47 (q, J = 7.48 Hz, 1 H) 4.37 (t, J = 8.08 Hz, 2 H) 4.22-4.30 (m, 2 H). |
| 4.13 | 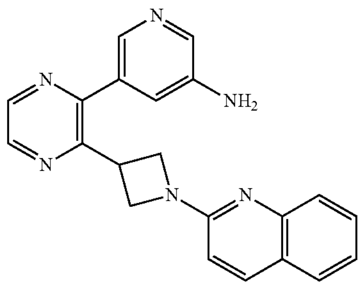 [SMILES: Nc1cncc(-c2nccnc2C2CN(c3ccc4ccccc4n3)C2)c1] | (500 MHz, DMSO-$d_6$) 8.67 (d, J = 2.29 Hz, 1 H) 8.63 (d, J = 2.29 Hz, 1 H) 8.08 (d, J = 2.52 Hz, 1 H) 8.02 (d, J = 8.94 Hz, 1 H) 7.89-7.96 (m, 1 H) 7.70 (d, J = 8.02 Hz, 1 H) 7.54-7.63 (m, 1 H) 7.45-7.54 (m, 1 H) 7.21 (t, J = 7.33 Hz, 1 H) 7.11 (d, J = 1.95 Hz, 1 H) 6.75 (d, J = 8.94 Hz, 1 H) 5.57 (br. s., 1H) 4.31-4.45 (m, 3 H) 4.20-4.31 (m, 2 H). |
| 4.14 | 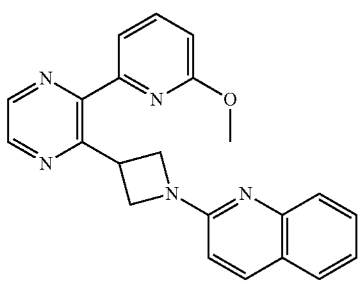 [SMILES: COc1cccc(-c2nccnc2C2CN(c3ccc4ccccc4n3)C2)n1] | (500 MHz, DMSO-$d_6$) 8.72 (d, J = 2.29 Hz, 1 H) 8.65 (d, J = 2.29 Hz, 1 H) 8.01 (d, J = 8.94 Hz, 1 H) 7.93 (t, J = 7.85 Hz, 1 H) 7.69 (d, J = 7.90 Hz, 1 H) 7.63 (d, J = 7.33 Hz, 1 H) 7.55 (d, J = 8.48 Hz, 1 H) 7.51 (t, J = 7.56 Hz, 1 H) 7.20 (t, J = 7.27 Hz, 1 H) 6.98 (d, J = 8.25 Hz, 1 H) 6.76 (d, J = 8.94 Hz, 1 H) 4.81-4.95 (m, 1 H) 4.40 (t, J = 8.25 Hz, 2 H) 4.21-4.33 (m, 2 H) 4.00 (s, 3 H). |
| 4.15 | 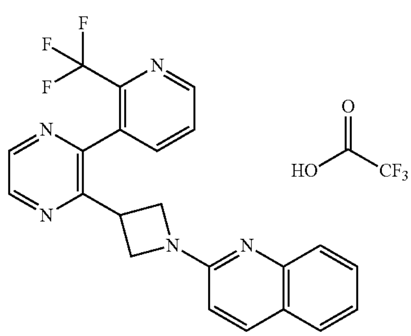 [SMILES: FC(F)(F)c1ncccc1-c1nccnc1C1CN(c2ccc3ccccc3n2)C1 ; O=C(O)C(F)(F)F] | (400 MHz, CD$_3$OD) 8.94 (d, J = 4.69 Hz, 1 H) 8.88 (d, J = 2.35 Hz, 1 H) 8.72 (d, J = 2.35 Hz, 1 H) 8.38 (d, J = 9.39 Hz, 1 H) 8.06 (d, J = 7.04 Hz, 1 H) 7.94 (d, J = 7.82 Hz, 1 H) 7.90 (dd, J = 7.92, 4.79 Hz, 1 H) 7.75-7.87 (m, 2 H) 7.49-7.65 (m, 1 H) 7.00 (d, J = 9.39 Hz, 1 H) 4.62-4.84 (m, 4 H) 4.14 (quin, J = 7.34 Hz, 1 H). |
| 4.16 | 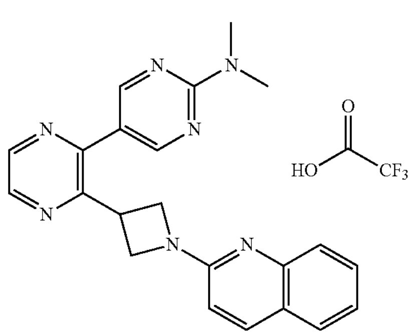 [SMILES: CN(C)c1ncc(-c2nccnc2C2CN(c3ccc4ccccc4n3)C2)cn1 ; O=C(O)C(F)(F)F] | (400 MHz, CD$_3$OD) 8.67-8.70 (m, 1 H) 8.65-8.67 (m, 1 H) 8.63 (s, 2 H) 8.38 (d, J = 9.39 Hz, 1 H) 7.94 (d, J = 7.63 Hz, 1 H) 7.75-7.88 (m, 2 H) 7.51-7.61 (m, 1 H) 7.02 (d, J = 9.59 Hz, 1 H) 4.67-4.85 (m, 5 H) 3.32 (s, 6 H). |

TABLE 16C-continued

| 1H NMR δ (PPM) DATA FOR EXAMPLES 4.1 TO 4.45 |||
| --- | --- | --- |
| Ex. # | Structure | NMR |
| 4.17 | | (400 MHz, CD$_3$OD) 8.86 (d, J = 2.35 Hz, 1 H) 8.76 (d, J = 2.54 Hz, 1 H) 8.68 (d, J = 5.28 Hz, 1 H) 8.55 (s, 1 H) 8.38 (d, J = 9.59 Hz, 1 H) 7.94 (d, J = 8.02 Hz, 1 H) 7.75-7.89 (m, 2 H) 7.70 (d, J = 5.48 Hz, 1 H) 7.56 (td, J = 7.48, 1.27 Hz, 1 H) 7.00 (d, J = 9.39 Hz, 1 H) 4.75-4.83 (m, 2 H) 4.63-4.75 (m, 2 H) 4.19-4.37 (m, 1 H) 2.34 (s, 3 H). |
| 4.18 | | (300 MHz, CD$_3$OD) 9.31 (d, J = 2.19 Hz, 1 H) 9.16 (d, J = 2.05 Hz, 1 H) 8.85 (d, J = 2.34 Hz, 1 H) 8.78 (d, J = 2.34 Hz, 1 H) 8.62 (t, J = 2.12 Hz, 1 H) 8.38 (d, J = 9.50 Hz, 1 H) 7.94 (d, J = 8.04 Hz, 1 H) 7.73-7.89 (m, 2 H) 7.56 (td, J = 7.38, 1.46 Hz, 1 H) 7.02 (d, J = 9.35 Hz, 1 H) 4.76-4.84 (m, 4 H) 4.56-4.73 (m, 1 H) 3.36 (s, 3 H). |
| 4.19 | | (300 MHz, CD$_3$OD) 8.80 (d, J = 2.48 Hz, 1 H) 8.73 (d, J = 2.48 Hz, 1 H) 8.60-8.69 (m, 2 H) 8.37 (d, J = 9.35 Hz, 1 H) 8.01-8.11 (m, 1 H) 7.93 (d, J = 7.89 Hz, 1 H) 7.72-7.89 (m, 2 H) 7.48-7.62 (m, 1 H) 7.00 (d, J = 9.50 Hz, 1 H) 4.73-4.83 (m, 4 H) 4.58-4.72 (m, 1 H) 2.56 (s, 3 H). |
| 4.20 | | (300 MHz, CD$_3$OD) 8.80 (d, J = 2.34 Hz, 1 H) 8.73 (d, J = 2.48 Hz, 1 H) 8.48 (d, J = 2.78 Hz, 1 H) 8.31-8.43 (m, 2 H) 7.93 (d, J = 7.89 Hz, 1 H) 7.74-7.88 (m, 2 H) 7.71 (dd, J = 2.78, 1.75 Hz, 1 H) 7.55 (ddd, J = 8.00, 6.76, 1.46 Hz, 1 H) 7.00 (d, J = 9.50 Hz, 1 H) 4.73-4.82 (m, 4 H) 4.60-4.73 (m, 1 H) 4.03 (s, 3 H). |
| 4.21 | | (500 MHz, DMSO-d$_6$) 8.68 (d, J = 2.41 Hz, 1 H) 8.63 (d, J = 2.41 Hz, 1 H) 8.01 (d, J = 8.82 Hz, 1 H) 7.69 (d, J = 7.67 Hz, 1 H) 7.53-7.63 (m, 3 H) 7.47-7.53 (m, 1 H) 7.43 (dd, J = 8.19, 2.00 Hz, 1 H) 7.14-7.26 (m, 1 H) 6.74 (d, J = 8.94 Hz, 1 H) 4.36-4.46 (m, 1 H) 4.32 (t, J = 7.96 Hz, 2 H) 4.20-4.29 (m, 2 H) 2.45 (s, 3 H). |

TABLE 16C-continued

1H NMR δ (PPM) DATA FOR EXAMPLES 4.1 TO 4.45

| Ex. # | Structure | NMR |
|---|---|---|
| 4.22 | 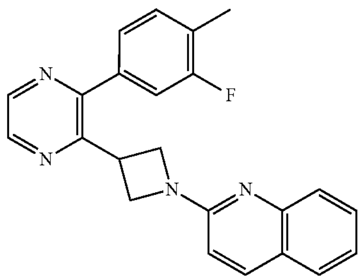 [SMILES: Cc1ccc(-c2nccnc2C2CN(c3ccc4ccccc4n3)C2)cc1F] | (500 MHz, DMSO-$d_6$) 8.68 (d, J = 2.41 Hz, 1 H) 8.63 (d, J = 2.41 Hz, 1 H) 8.04 (d, J = 8.82 Hz, 1 H) 7.71 (d, J = 7.68 Hz, 1 H) 7.50-7.62 (m, 2 H) 7.48 (t, J = 7.85 Hz, 1 H) 7.39 (d, J = 10.65 Hz, 1 H) 7.33 (dd, J = 7.73, 1.55 Hz, 1 H) 7.22 (t, J = 7.39 Hz, 1 H) 6.76 (d, J = 9.05 Hz, 1 H) 4.39-4.51 (m, 1 H) 4.21-4.39 (m, 4 H) 2.35 (s, 3 H). |
| 4.23 | 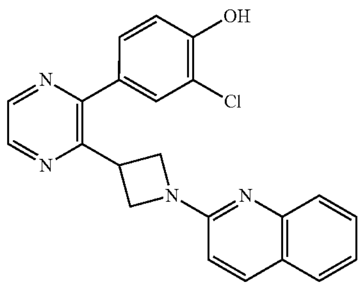 [SMILES: Oc1ccc(-c2nccnc2C2CN(c3ccc4ccccc4n3)C2)cc1Cl] | (500 MHz, DMSO-$d_6$) 8.62 (d, J = 2.41 Hz, 1 H) 8.59 (d, J = 2.29 Hz, 1 H) 8.01 (d, J = 8.82 Hz, 1 H) 7.70 (d, J = 7.22 Hz, 1 H) 7.59 (d, J = 2.06 Hz, 1 H) 7.54-7.58 (m, 1 H) 7.47-7.54 (m, 1 H) 7.39 (dd, J = 8.42, 2.12 Hz, 1 H) 7.17-7.25 (m, 1 H) 7.14 (d, J = 8.36 Hz, 1 H) 6.75 (d, J = 8.82 Hz, 1 H) 4.40-4.51 (m, 1 H) 4.33 (t, J = 8.13 Hz, 2 H) 4.19-4.29 (m, 2 H). |
| 4.24 | 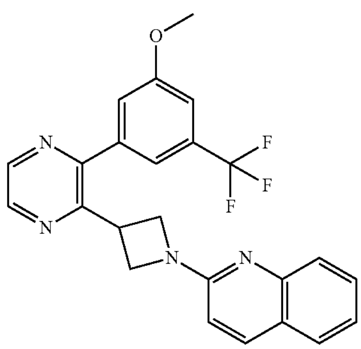 [SMILES: COc1cc(-c2nccnc2C2CN(c3ccc4ccccc4n3)C2)cc(C(F)(F)F)c1] | (500 MHz, DMSO-$d_6$) 8.73 (d, J = 2.41 Hz, 1 H) 8.66 (d, J = 2.41 Hz, 1 H) 8.02 (d, J = 8.94 Hz, 1 H) 7.70 (d, J = 7.79 Hz, 1 H) 7.54-7.60 (m, 1 H) 7.46-7.54 (m, 2 H) 7.43 (d, J = 9.39 Hz, 2 H) 7.14-7.28 (m, 1 H) 6.75 (d, J = 8.82 Hz, 1 H) 4.36-4.47 (m, 1 H) 4.24-4.36 (m, 4 H) 3.94 (s, 3 H). |
| 4.25 | 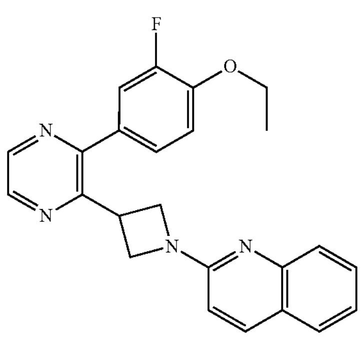 [SMILES: CCOc1ccc(-c2nccnc2C2CN(c3ccc4ccccc4n3)C2)cc1F] | (500 MHz, DMSO-$d_6$) 8.64 (d, J = 2.41 Hz, 1 H) 8.60 (d, J = 2.41 Hz, 1 H) 8.01 (d, J = 8.82 Hz, 1 H) 7.69 (d, J = 7.33 Hz, 1 H) 7.53-7.58 (m, 1 H) 7.45-7.53 (m, 2 H) 7.37 (dd, J = 8.53, 1.78 Hz, 1 H) 7.31 (t, J = 8.53 Hz, 1 H) 7.15-7.25 (m, 1 H) 6.74 (d, J = 8.94 Hz, 1 H) 4.41-4.55 (m, 1 H) 4.32 (t, J = 8.13 Hz, 2 H) 4.13-4.28 (m, 4 H) 1.41 (t, J = 6.99 Hz, 3 H). |
| 4.26 | 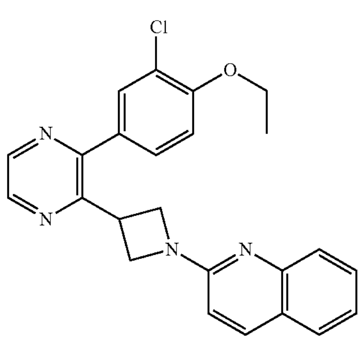 [SMILES: CCOc1ccc(-c2nccnc2C2CN(c3ccc4ccccc4n3)C2)cc1Cl] | (500 MHz, DMSO-$d_6$) 8.65 (d, J = 2.41 Hz, 1 H) 8.61 (d, J = 2.41 Hz, 1 H) 8.02 (d, J = 8.93 Hz, 1 H) 7.70 (d, J = 7.56 Hz, 1 H) 7.68 (d, J = 2.18 Hz, 1 H) 7.44-7.62 (m, 3 H) 7.30 (d, J = 8.59 Hz, 1 H) 7.14-7.25 (m, 1 H) 6.75 (d, J = 8.94 Hz, 1 H) 4.39-4.56 (m, 1 H) 4.32 (t, J = 8.13 Hz, 2 H) 4.06-4.29 (m, 4 H) 1.42 (t, J = 6.93 Hz, 3 H). |

TABLE 16C-continued

1H NMR δ (PPM) DATA FOR EXAMPLES 4.1 TO 4.45

| Ex. # | Structure | NMR |
|---|---|---|
| 4.27 | 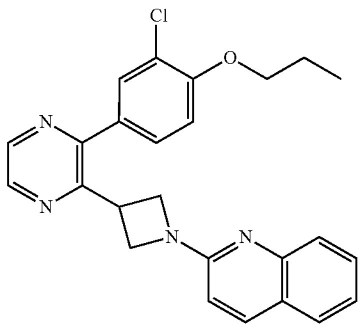 [SMILES: CCCOc1ccc(-c2nccnc2C2CN(c3ccc4ccccc4n3)C2)cc1Cl] | (500 MHz, DMSO-$d_6$) 8.65 (d, J = 2.41 Hz, 1 H) 8.61 (d, J = 2.41 Hz, 1 H) 8.02 (d, J = 8.94 Hz, 1 H) 7.70 (d, J = 7.45 Hz, 1 H) 7.67 (d, J = 2.18 Hz, 1 H) 7.46-7.61 (m, 3 H) 7.30 (d, J = 8.59 Hz, 1 H) 7.16-7.25 (m, 1 H) 6.75 (d, J = 8.82 Hz, 1 H) 4.40-4.52 (m, 1 H) 4.32 (t, J = 8.13 Hz, 2 H) 4.21-4.29 (m, 2 H) 4.13 (t, J = 6.42 Hz, 2 H) 1.82 (sxt, J = 6.99 Hz, 2 H) 1.05 (t, J = 7.39 Hz, 3 H). |
| 4.28 | 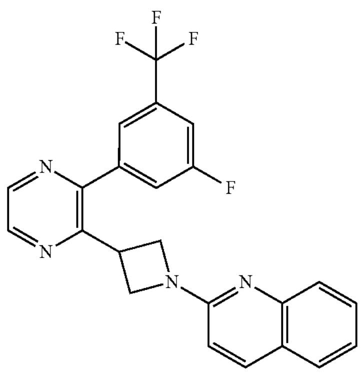 [SMILES: Fc1cc(-c2nccnc2C2CN(c3ccc4ccccc4n3)C2)cc(C(F)(F)F)c1] | (500 MHz, DMSO-$d_6$) 8.76 (d, J = 2.41 Hz, 1 H) 8.68 (d, J = 2.29 Hz, 1 H) 8.02 (d, J = 8.82 Hz, 1 H) 7.88 (d, J = 8.59 Hz, 1 H) 7.77-7.85 (m, 2 H) 7.70 (d, J = 7.90 Hz, 1 H) 7.54-7.61 (m, 1 H) 7.44-7.54 (m, 1 H) 7.12-7.29 (m, 1 H) 6.75 (d, J = 8.82 Hz, 1 H) 4.42 (quin, J = 7.25 Hz, 1 H) 4.30 (d, J = 7.22 Hz, 4 H). |
| 4.29 | 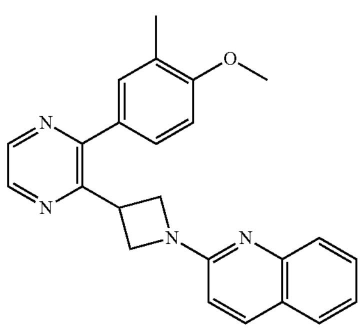 [SMILES: COc1ccc(-c2nccnc2C2CN(c3ccc4ccccc4n3)C2)cc1C] | (500 MHz, DMSO-$d_6$) 8.59-8.63 (m, 1 H) 8.54-8.59 (m, 1 H) 8.01 (d, J = 8.93 Hz, 1 H) 7.69 (d, J = 7.68 Hz, 1 H) 7.53-7.59 (m, 1 H) 7.47-7.53 (m, 1 H) 7.33-7.46 (m, 2 H) 7.14-7.28 (m, 1 H) 7.10 (d, J = 8.36 Hz, 1 H) 6.74 (d, J = 8.94 Hz, 1 H) 4.39-4.52 (m, 1 H) 4.33 (t, J = 8.13 Hz, 2 H) 4.18-4.29 (m, 2 H) 3.88 (s, 3 H) 2.26 (s, 3 H). |
| 4.30 | 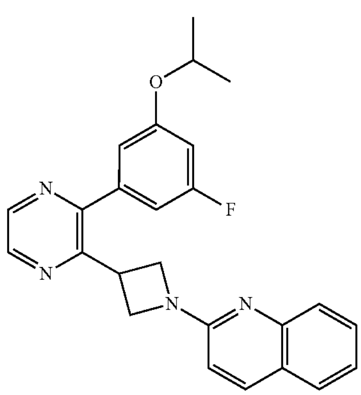 [SMILES: CC(C)Oc1cc(F)cc(-c2nccnc2C2CN(c3ccc4ccccc4n3)C2)c1] | (500 MHz, DMSO-$d_6$) 8.70 (d, J = 2.41 Hz, 1 H) 8.63 (d, J = 2.41 Hz, 1 H) 8.02 (d, J = 8.93 Hz, 1 H) 7.70 (d, J = 7.67 Hz, 1 H) 7.48-7.60 (m, 2 H) 7.10-7.31 (m, 1 H) 6.85-7.06 (m, 3 H) 6.75 (d, J = 8.82 Hz, 1 H) 4.75 (dt, J = 12.03, 6.01 Hz, 1 H) 4.36-4.50 (m, 1 H) 4.18-4.35 (m, 4 H) 1.32 (d, J = 5.96 Hz, 6 H). |

TABLE 16C-continued

1H NMR δ (PPM) DATA FOR EXAMPLES 4.1 TO 4.45

| Ex. # | Structure | NMR |
|---|---|---|
| 4.31 | 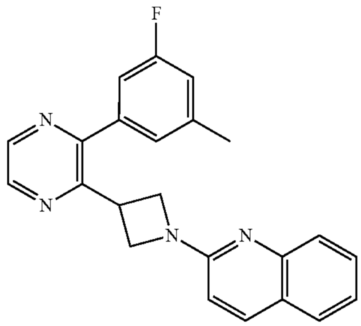 [SMILES: Cc1cc(F)cc(-c2nccnc2C2CN(c3ccc4ccccc4n3)C2)c1] | (500 MHz, DMSO-$d_6$) 8.69 (d, J = 2.41 Hz, 1 H) 8.63 (d, J = 2.41 Hz, 1 H) 8.02 (d, J = 8.94 Hz, 1 H) 7.70 (d, J = 7.56 Hz, 1 H) 7.54-7.58 (m, 1 H) 7.48-7.54 (m, 1 H) 7.14-7.31 (m, 4 H) 6.75 (d, J = 8.82 Hz, 1 H) 4.37-4.50 (m, 1 H) 4.20-4.36 (m, 4 H) 2.44 (s, 3 H). |
| 4.32 | 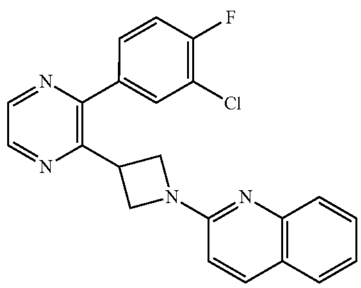 [SMILES: Fc1ccc(-c2nccnc2C2CN(c3ccc4ccccc4n3)C2)cc1Cl] | (500 MHz, DMSO-$d_6$) 8.71 (d, J = 2.41 Hz, 1 H) 8.64 (d, J = 2.41 Hz, 1 H) 8.02 (d, J = 8.93 Hz, 1 H) 7.80-7.87 (m, 1 H) 7.70 (d, J = 7.67 Hz, 1 H) 7.54-7.65 (m, 3 H) 7.48-7.54 (m, 1 H) 7.17-7.24 (m, 1 H) 6.75 (d, J = 8.94 Hz, 1 H) 4.37-4.47 (m, 1 H) 4.22-4.36 (m, 4 H). |
| 4.33 | 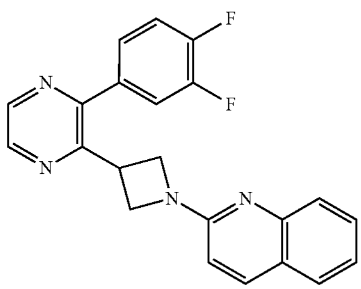 [SMILES: Fc1ccc(-c2nccnc2C2CN(c3ccc4ccccc4n3)C2)cc1F] | (500 MHz, DMSO-$d_6$) 8.70 (d, J = 2.41 Hz, 1 H) 8.64 (d, J = 2.41 Hz, 1 H) 8.01 (d, J = 8.82 Hz, 1 H) 7.66-7.74 (m, 2 H) 7.58-7.66 (m, 1 H) 7.53-7.58 (m, 1 H) 7.48-7.53 (m, 1 H) 7.41-7.48 (m, 1 H) 7.12-7.26 (m, 1 H) 6.74 (d, J = 8.94 Hz, 1 H) 4.38-4.48 (m, 1 H) 4.31 (t, J = 8.08 Hz, 2 H) 4.21-4.29 (m, 2 H). |
| 4.34 | 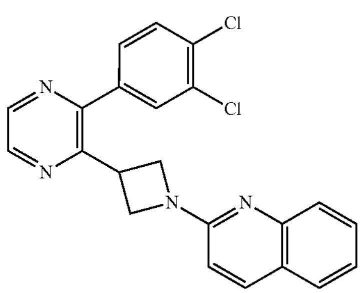 [SMILES: Clc1ccc(-c2nccnc2C2CN(c3ccc4ccccc4n3)C2)cc1Cl] | (500 MHz, DMSO-$d_6$) 8.72 (d, J = 2.41 Hz, 1 H) 8.65 (d, J = 2.41 Hz, 1 H) 8.02 (d, J = 8.93 Hz, 1 H) 7.87 (d, J = 1.95 Hz, 1 H) 7.82 (d, J = 8.25 Hz, 1 H) 7.70 (d, J = 7.45 Hz, 1 H) 7.60 (dd, J = 8.31, 2.00 Hz, 1 H) 7.54-7.58 (m, 1 H) 7.48-7.54 (m, 1 H) 7.16-7.27 (m, 1 H) 6.76 (d, J = 8.82 Hz, 1 H) 4.37-4.47 (m, 1 H) 4.32 (t, J = 8.02 Hz, 2 H) 4.24-4.30 (m, 2 H). |
| 4.35 | 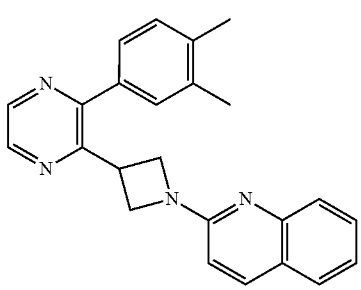 [SMILES: Cc1ccc(-c2nccnc2C2CN(c3ccc4ccccc4n3)C2)cc1C] | (500 MHz, DMSO-$d_6$) 8.63 (d, J = 2.41 Hz, 1 H) 8.60 (d, J = 2.41 Hz, 1 H) 8.02 (d, J = 8.82 Hz, 1 H) 7.70 (d, J = 7.56 Hz, 1 H) 7.53-7.58 (m, 1 H) 7.48-7.53 (m, 1 H) 7.36 (s, 1 H) 7.26-7.34 (m, 2 H) 7.17-7.24 (m, 1 H) 6.75 (d, J = 8.94 Hz, 1 H) 4.36-4.47 (m, 1 H) 4.32 (t, J = 8.02 Hz, 2 H) 4.21-4.29 (m, 2 H) 2.34 (s, 3 H) 2.33 (s, 3 H). |

TABLE 16C-continued

1H NMR δ (PPM) DATA FOR EXAMPLES 4.1 TO 4.45

| Ex. # | Structure | NMR |
|---|---|---|
| 4.36 | 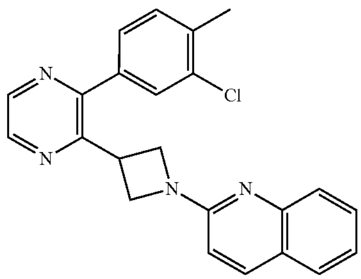 [SMILES: Cc1ccc(-c2nccnc2C2CN(c3ccc4ccccc4n3)C2)cc1Cl] | (500 MHz, DMSO-$d_6$) 8.68 (d, J = 2.29 Hz, 1 H) 8.63 (d, J = 2.41 Hz, 1 H) 8.01 (d, J = 8.82 Hz, 1 H) 7.69 (d, J = 7.56 Hz, 1 H) 7.64 (d, J = 1.49 Hz, 1 H) 7.48-7.59 (m, 3 H) 7.46 (dd, J = 7.79, 1.60 Hz, 1 H) 7.13-7.28 (m, 1 H) 6.75 (d, J = 8.82 Hz, 1 H) 4.37-4.48 (m, 1 H) 4.19-4.36 (m, 4 H) 2.44 (s, 3 H). |
| 4.37 | 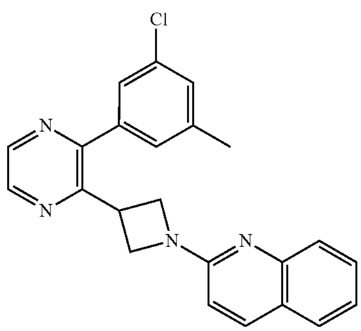 [SMILES: Cc1cc(Cl)cc(-c2nccnc2C2CN(c3ccc4ccccc4n3)C2)c1] | (500 MHz, DMSO-$d_6$) 8.70 (d, J = 2.41 Hz, 1 H) 8.63 (d, J = 2.41 Hz, 1 H) 8.02 (d, J = 8.82 Hz, 1 H) 7.70 (d, J = 7.67 Hz, 1 H) 7.54-7.59 (m, 1 H) 7.49-7.54 (m, 1 H) 7.45 (s, 2 H) 7.35 (s, 1 H) 7.12-7.27 (m, 1 H) 6.76 (d, J = 8.82 Hz, 1 H) 4.36-4.47 (m, 1 H) 4.20-4.36 (m, 4 H) 2.44 (s, 3 H). |
| 4.38 | 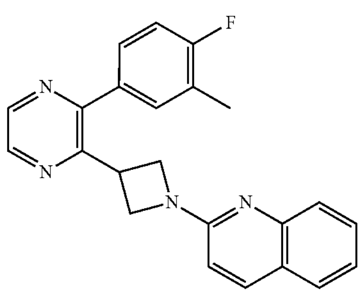 [SMILES: Cc1cc(-c2nccnc2C2CN(c3ccc4ccccc4n3)C2)ccc1F] | (500 MHz, DMSO-$d_6$) 8.66 (d, J = 2.41 Hz, 1 H) 8.61 (d, J = 2.41 Hz, 1 H) 8.01 (d, J = 8.94 Hz, 1 H) 7.70 (d, J = 7.56 Hz, 1 H) 7.54-7.58 (m, 1 H) 7.48-7.54 (m, 2 H) 7.41-7.47 (m, 1 H) 7.31 (t, J = 9.11 Hz, 1 H) 7.17-7.25 (m, 1 H) 6.74 (d, J = 8.82 Hz, 1 H) 4.37-4.45 (m, 1 H) 4.32 (t, J = 8.02 Hz, 2 H) 4.21-4.29 (m, 2 H) 2.26-2.42 (m, 3 H). |
| 4.39 | 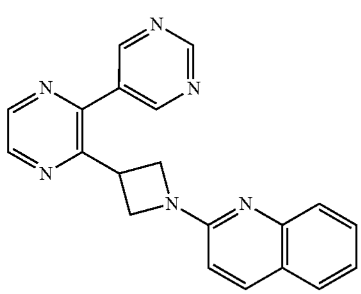 [SMILES: c1ccc2nc(N3CC(c4nccnc4-c4cncnc4)C3)ccc2c1] | (500 MHz, DMSO-$d_6$) 9.36 (s, 1 H) 9.08 (s, 2 H) 8.78 (d, J = 2.41 Hz, 1 H) 8.73 (d, J = 2.29 Hz, 1 H) 8.03 (d, J = 8.82 Hz, 1 H) 7.71 (d, J = 8.02 Hz, 1 H) 7.48-7.60 (m, 2 H) 7.22 (t, J = 7.33 Hz, 1 H) 6.76 (d, J = 8.82 Hz, 1 H) 4.41-4.52 (m, 1 H) 4.23-4.39 (m, 4 H). |
| 4.40 | 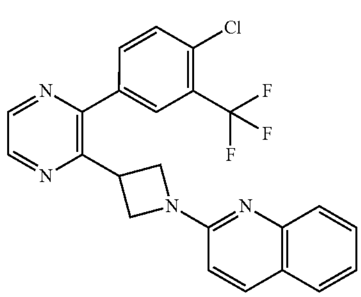 [SMILES: FC(F)(F)c1cc(-c2nccnc2C2CN(c3ccc4ccccc4n3)C2)ccc1Cl] | (500 MHz, DMSO-$d_6$) 8.74 (d, J = 2.41 Hz, 1 H) 8.67 (d, J = 2.41 Hz, 1 H) 8.06 (s, 1 H) 8.02 (d, J = 8.94 Hz, 1 H) 7.93 (s, 2 H) 7.70 (d, J = 7.67 Hz, 1 H) 7.54-7.60 (m, 1 H) 7.48-7.54 (m, 1 H) 7.16-7.27 (m, 1 H) 6.76 (d, J = 8.94 Hz, 1 H) 4.36-4.45 (m, 1 H) 4.26-4.36 (m, 4 H). |

TABLE 16C-continued

1H NMR δ (PPM) DATA FOR EXAMPLES 4.1 TO 4.45

| Ex. # | Structure | NMR |
|---|---|---|
| 4.41 | 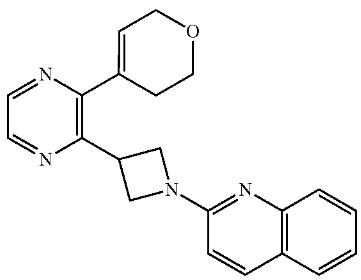 [SMILES: C1=C(c2nccnc2C2CN(c3ccc4ccccc4n3)C2)CCOC1] | (300 MHz, MeOH) 8.57 (1 H, d, J = 2.5 Hz), 8.48 (1 H, d, J = 2.3 Hz), 8.03 (1 H, d, J = 9.1 Hz), 7.70 (2 H, m), 7.54 (1 H, m), 7.23-7.30 (1 H, m), 6.78 (1 H, d, J = 8.9 Hz), 5.99 (1 H, br. s), 4.38-4.66 (3 H, m), 4.02 (4 H, m), 3.32-3.37 (2 H, m), 2.61 (2H, m) |
| 4.42 | and | (300 MHz, MeOH) 8.57 (1 H, d, J = 2.3 Hz), 8.48 (1 H, d, J = 2.5 Hz), 8.04 (1 H, d, J = 8.9 Hz), 7.71 (2 H, d, J = 1.1 Hz), 7.58 (1 H, t, J = 7.7 Hz), 7.22-7.34 (1 H, m), 6.79 (1 H, d, J = 8.9 Hz), 5.99 (1 H, s), 4.50-4.70 (3 H, m), 4.39-4.50 (3 H, m), 2.46-2.58 (2 H, m), 1.45 (1 H, s), 1.39(6 H, s) |
| 4.43 | 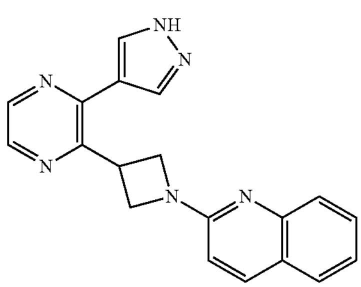 [SMILES: c1ccc2nc(N3CC(c4nccnc4-c4cn[nH]c4)C3)ccc2c1] | (300 MHz, DMSO-$d_6$) 13.31 (1 H, br. s.), 8.50 (1 H, d, J = 2.2 Hz), 8.54 (1 H, d, J = 2.3 Hz), 8.29 (1 H, s), 7.97-8.08 (2 H, m), 7.71 (1 H, d, J = 7.9 Hz), 7.47-7.61 (2 H, m), 7.22 (1 H, t, J = 6.7 Hz), 6.79 (1 H, d, J = 8.9 Hz), 4.42-4.71 (3 H, m), 4.21-4.42 (2 H, m) |
| 4.44 | 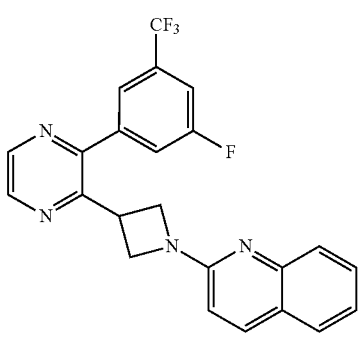 [SMILES: Fc1cc(-c2nccnc2C2CN(c3ccc4ccccc4n3)C2)cc(C(F)(F)F)c1] | (500 MHz, DMSO-$d_6$) 8.76 (d, J = 2.41 Hz, 1 H) 8.68 (d, J = 2.29 Hz, 1 H) 8.02 (d, J = 8.82 Hz, 1 H) 7.88 (d, J = 8.59 Hz, 1 H) 7.77-7.85 (m, 2 H) 7.70 (d, J = 7.90 Hz, 1 H) 7.54-7.61 (m, 1H) 7.44-7.54 (m, 1 H) 7.12-7.29 (m, 1 H) 6.75 (d, J = 8.82 Hz, 1 H) 4.42 (quin, J = 7.25 Hz, 1 H) 4.30 (d, J = 7.22 Hz, 4 H). |

TABLE 16C-continued

1H NMR δ (PPM) DATA FOR EXAMPLES 4.1 TO 4.45

| Ex. # | Structure | NMR |
|---|---|---|
| 4.45 | (structure with OMe-phenyl pyrazine azetidinyl quinoline) | (500 MHz, DMSO-d$_6$) 8.72 (d, J = 2.29 Hz, 1 H) 8.65 (d, J = 2.29 Hz, 1 H) 8.01 (d, J = 8.94 Hz, 1 H) 7.93 (t, J = 7.85 Hz, 1 H) 7.69 (d, J = 7.90 Hz, 1 H) 7.63 (d, J = 7.33 Hz, 1 H) 7.55 (d, J = 8.48 Hz, 1 H) 7.51 (t, J = 7.56 Hz, 1 H) 7.20 (t, J = 7.27 Hz, 1 H) 6.98 (d, J = 8.25 Hz, 1 H) 6.76 (d, J = 8.94 Hz, 1 H) 4.81-4.95 (m, 1 H) 4.40 (t, J = 8.25 Hz, 2 H) 4.21-4.33 (m, 2 H) 4.00 (s, 3 H). |

SCHEME 5

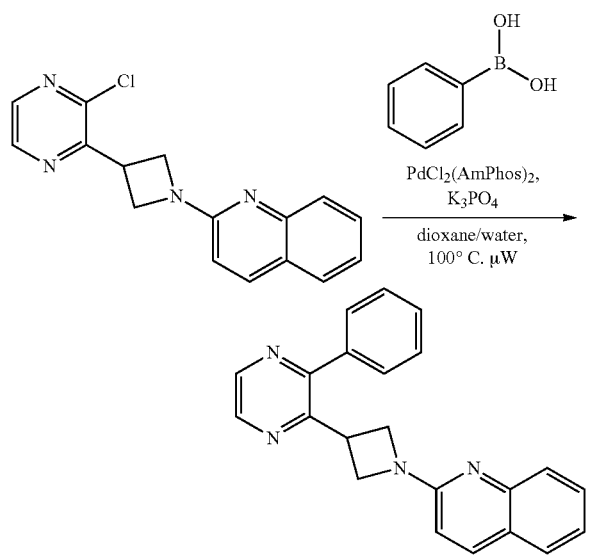

Example 5.1: 2-(3-(3-Phenylpyrazin-2-Yl)Azetidin-1-Yl)Quinoline

A glass microwave reaction vessel was charged with 2-(3-(3-chloropyrazin-2-yl)azetidin-1-yl)quinoline (0.085 g, 0.286 mmol), phenylboronic acid (0.070 g, 0.573 mmol, Aldrich), potassium phosphate (0.152 g, 0.716 mmol, Alfa Aesar), bis(di-tert-butyl(4-dimethylaminophenyl)phosphine)dichloropalladium (II) (0.020 g, 0.029 mmol, Aldrich), water (0.400 mL) and dioxane (1.6 mL). The mixture was purged with Argon gas and heated in an Initiator microwave reactor (Personal Chemistry, Biotage AB, Inc., Upssala, Sweden) at 100° C. for 30 min. LCMS showed the product. The mixture was diluted with EtOAc and washed with Na$_2$CO$_3$ and brine. The organic layer was dried over Na$_2$SO$_4$ and concentrated in vacuo. The crude was purified by silica gel chromatography (12 g, 10%-100% EtOAc-Hexane). The product was obtained as a white solid (85 mg, 88%).

The following Table 17A lists compounds of Examples 5.1 to 5.43, which were made analogous to Scheme 5 by using the appropriate materials and reaction conditions, which are listed in Table 17B. The NMR data of the Examples are listed in Table 17C.

TABLE 17A

EXAMPLES 5.1 TO 5.43

| Ex. # | Structure | Chemical Name | ESI-MS (M + 1) | IC$_{50}$ (µM) |
|---|---|---|---|---|
| 5.1 | (structure of phenylpyrazinyl-azetidinyl-quinoline) | 2-(3-(3-phenylpyrazin-2-yl)azetidin-1-yl)quinoline | 339 | 0.0012 |

TABLE 17A-continued

EXAMPLES 5.1 TO 5.43

| Ex. # | Structure | Chemical Name | ESI-MS (M + 1) | IC$_{50}$ (μM) |
|---|---|---|---|---|
| 5.2 | 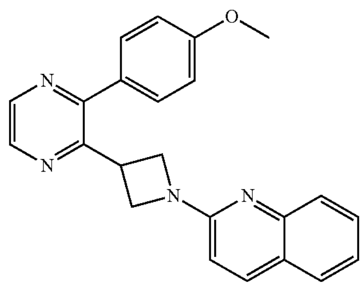 [SMILES: COc1ccc(-c2nccnc2C2CN(c3ccc4ccccc4n3)C2)cc1] | 2-(3-(3-(4-methoxyphenyl)pyrazin-2-yl)azetidin-1-yl)quinoline | 369 | 0.002 |
| 5.3 | 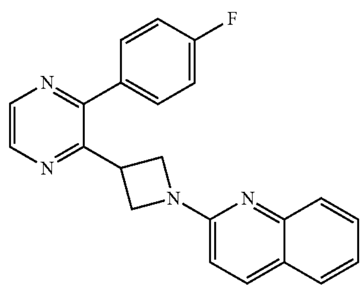 [SMILES: Fc1ccc(-c2nccnc2C2CN(c3ccc4ccccc4n3)C2)cc1] | 2-(3-(3-(4-fluorophenyl)pyrazin-2-yl)azetidin-1-yl)quinoline | 357 | 0.002 |
| 5.4 | 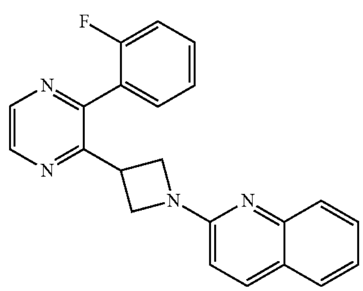 [SMILES: Fc1ccccc1-c1nccnc1C1CN(c2ccc3ccccc3n2)C1] | 2-(3-(3-(2-fluorophenyl)pyrazin-2-yl)azetidin-1-yl)quinoline | 357 | 0.01 |
| 5.5 | 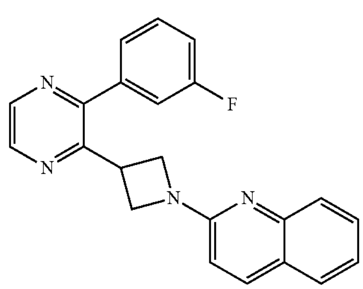 | 2-(3-(3-(3-fluorophenyl)pyrazin-2-yl)azetidin-1-yl)quinoline | 357 | 0.004 |
| 5.6 | 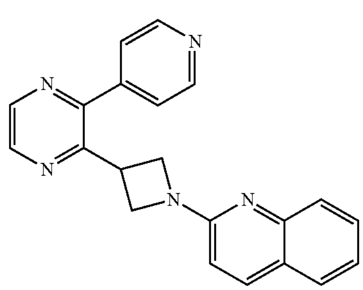 [SMILES: c1ccc2nc(N3CC(c4nccnc4-c4ccncc4)C3)ccc2c1] | 2-(3-(3-(pyridin-4-yl)pyrazin-2-yl)azetidin-1-yl)quinoline | 340 | 0.004 |

TABLE 17A-continued

EXAMPLES 5.1 TO 5.43

| Ex. # | Structure | Chemical Name | ESI-MS (M + 1) | IC$_{50}$ (μM) |
|---|---|---|---|---|
| 5.7 | 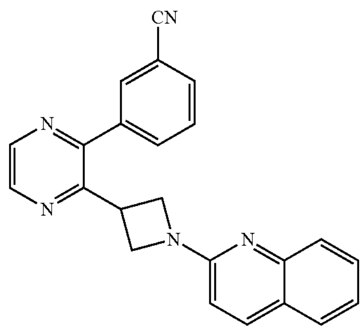 [SMILES: N#Cc1cccc(-c2nccnc2C2CN(c3ccc4ccccc4n3)C2)c1] | 3-(3-(1-(quinolin-2-yl)azetidin-3-yl)pyrazin-2-yl)benzonitrile | 364 | 0.003 |
| 5.8 | 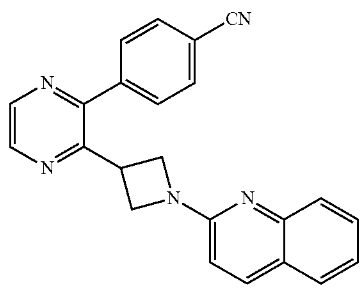 [SMILES: N#Cc1ccc(-c2nccnc2C2CN(c3ccc4ccccc4n3)C2)cc1] | 4-(3-(1-(quinolin-2-yl)azetidin-3-yl)pyrazin-2-yl)benzonitrile | 364 | 0.003 |
| 5.9 | 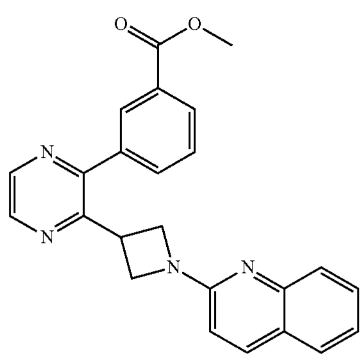 [SMILES: COC(=O)c1cccc(-c2nccnc2C2CN(c3ccc4ccccc4n3)C2)c1] | methyl 3-(3-(1-(quinolin-2-yl)azetidin-3-yl)pyrazin-2-yl)benzoate | 397 | 0.0002 |
| 5.10 | 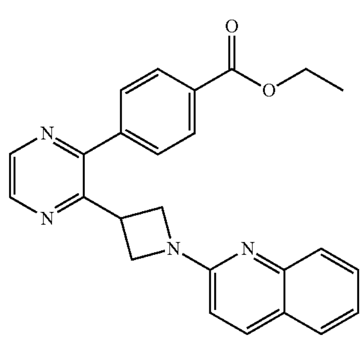 [SMILES: CCOC(=O)c1ccc(-c2nccnc2C2CN(c3ccc4ccccc4n3)C2)cc1] | ethyl 4-(3-(1-(quinolin-2-yl)azetidin-3-yl)pyrazin-2-yl)benzoate | 411 | 0.002 |

TABLE 17A-continued

EXAMPLES 5.1 TO 5.43

| Ex. # | Structure | Chemical Name | ESI-MS (M + 1) | IC$_{50}$ (μM) |
|---|---|---|---|---|
| 5.11 | 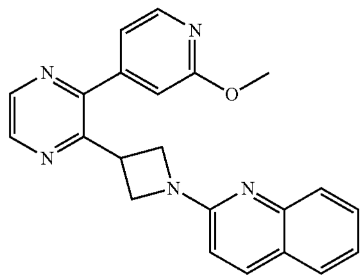 [SMILES: COc1cc(-c2nccnc2C2CN(c3ccc4ccccc4n3)C2)ccn1] | 2-(3-(3-(2-methoxypyridin-4-yl)pyrazin-2-yl)azetidin-1-yl)quinoline | 370 | 0.002 |
| 5.12 | 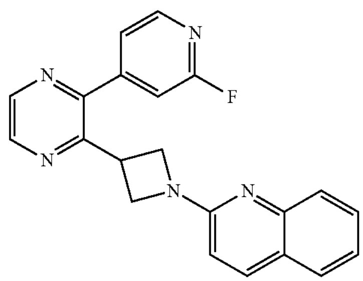 [SMILES: Fc1cc(-c2nccnc2C2CN(c3ccc4ccccc4n3)C2)ccn1] | 2-(3-(3-(2-fluoropyridin-4-yl)pyrazin-2-yl)azetidin-1-yl)quinoline | 358 | 0.01 |
| 5.13 | 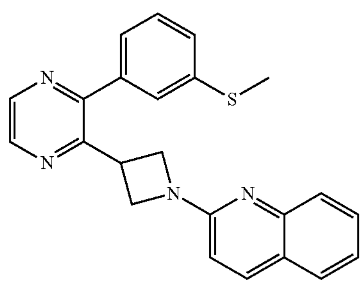 [SMILES: CSc1cccc(-c2nccnc2C2CN(c3ccc4ccccc4n3)C2)c1] | 2-(3-(3-(3-(methylthio)phenyl)pyrazin-2-yl)azetidin-1-yl)quinoline | 385 | 0.004 |
| 5.14 | 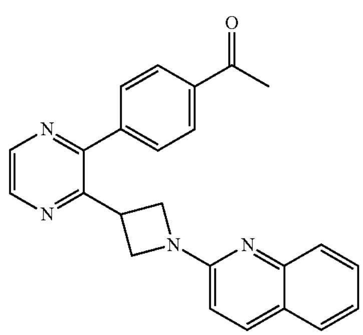 [SMILES: CC(=O)c1ccc(-c2nccnc2C2CN(c3ccc4ccccc4n3)C2)cc1] | 1-(4-(3-(1-(quinolin-2-yl)azetidin-3-yl)pyrazin-2-yl)phenyl)ethanone | 381 | 0.003 |
| 5.15 | 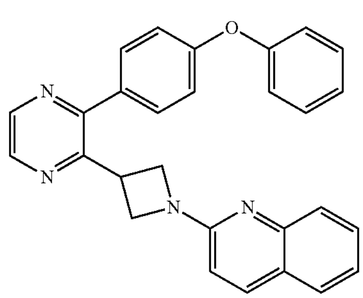 [SMILES: c1ccc(Oc2ccc(-c3nccnc3C3CN(c4ccc5ccccc5n4)C3)cc2)cc1] | 2-(3-(3-(4-phenoxyphenyl)pyrazin-2-yl)azetidin-1-yl)quinoline | 431 | 0.034 |

TABLE 17A-continued

EXAMPLES 5.1 TO 5.43

| Ex. # | Structure | Chemical Name | ESI-MS (M + 1) | IC$_{50}$ (μM) |
|---|---|---|---|---|
| 5.16 | 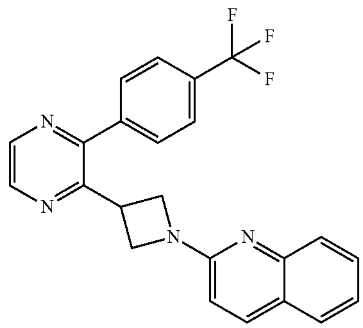 [SMILES: FC(F)(F)c1ccc(-c2nccnc2C2CN(c3ccc4ccccc4n3)C2)cc1] | 2-(3-(3-(4-(trifluoromethyl)phenyl)pyrazin-2-yl)azetidin-1-yl)quinoline | 407 | 0.027 |
| 5.17 | 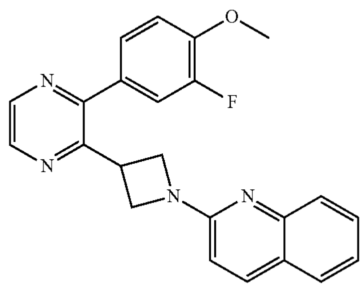 [SMILES: COc1ccc(-c2nccnc2C2CN(c3ccc4ccccc4n3)C2)cc1F] | 2-(3-(3-(3-fluoro-4-methoxyphenyl)pyrazin-2-yl)azetidin-1-yl)quinoline | 387 | 0.003 |
| 5.18 | 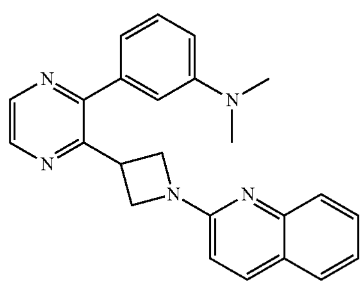 [SMILES: CN(C)c1cccc(-c2nccnc2C2CN(c3ccc4ccccc4n3)C2)c1] | N,N-dimethyl-3-(3-(1-(quinolin-2-yl)azetidin-3-yl)pyrazin-2-yl)aniline | 382 | 0.002 |
| 5.19 | 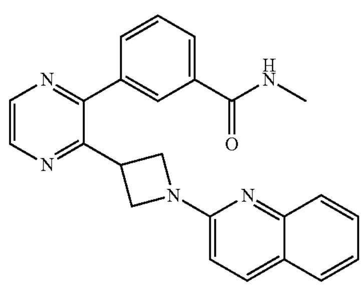 [SMILES: CNC(=O)c1cccc(-c2nccnc2C2CN(c3ccc4ccccc4n3)C2)c1] | N-methyl-3-(3-(1-(quinolin-2-yl)azetidin-3-yl)pyrazin-2-yl)benzamide | 396 | 0.0007 |
| 5.20 | 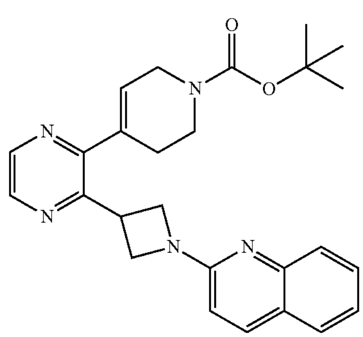 [SMILES: CC(C)(C)OC(=O)N1CC=C(c2nccnc2C2CN(c3ccc4ccccc4n3)C2)CC1] | tert-butyl 4-(3-(1-(quinolin-2-yl)azetidin-3-yl)pyrazin-2-yl)-5,6-dihydropyridine-1(2H)-carboxylate | 444 | 0.0007 |

TABLE 17A-continued

EXAMPLES 5.1 TO 5.43

| Ex. # | Structure | Chemical Name | ESI-MS (M + 1) | IC$_{50}$ (μM) |
|---|---|---|---|---|
| 5.21 | 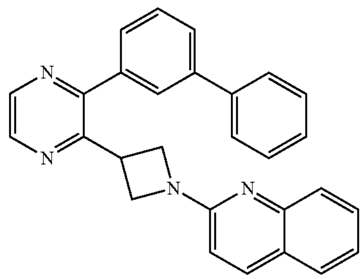 [SMILES: c1ccc(-c2cccc(-c3nccnc3C3CN(c4ccc5ccccc5n4)C3)c2)cc1] | 2-(3-(3-([1,1'-biphenyl]-3-yl)pyrazin-2-yl)azetidin-1-yl)quinoline | 415 | 0.002 |
| 5.22 | 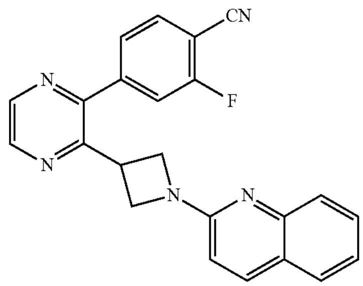 [SMILES: N#Cc1ccc(-c2nccnc2C2CN(c3ccc4ccccc4n3)C2)cc1F] | 2-fluoro-4-(3-(1-(quinolin-2-yl)azetidin-3-yl)pyrazin-2-yl)benzonitrile | 382 | 0.006 |
| 5.23 | 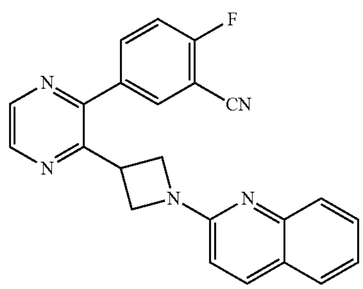 [SMILES: N#Cc1cc(-c2nccnc2C2CN(c3ccc4ccccc4n3)C2)ccc1F] | 2-fluoro-5-(3-(1-(quinolin-2-yl)azetidin-3-yl)pyrazin-2-yl)benzonitrile | 382 | 0.007 |
| 5.24 | 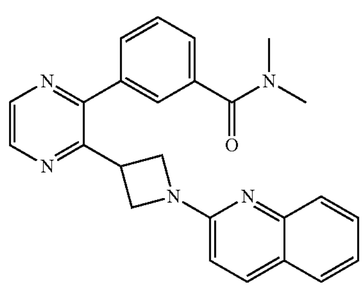 [SMILES: CN(C)C(=O)c1cccc(-c2nccnc2C2CN(c3ccc4ccccc4n3)C2)c1] | N,N-dimethyl-3-(3-(1-(quinolin-2-yl)azetidin-3-yl)pyrazin-2-yl)benzamide | 410 | 0.018 |
| 5.25 | 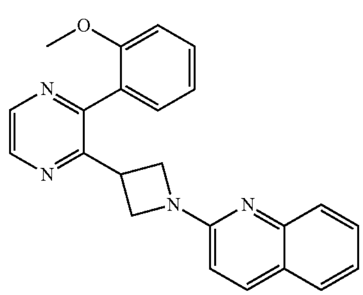 [SMILES: COc1ccccc1-c1nccnc1C1CN(c2ccc3ccccc3n2)C1] | 2-(3-(3-(2-methoxyphenyl)pyrazin-2-yl)azetidin-1-yl)quinoline | 369 | 0.002 |

TABLE 17A-continued

EXAMPLES 5.1 TO 5.43

| Ex. # | Structure | Chemical Name | ESI-MS (M + 1) | IC$_{50}$ (μM) |
|---|---|---|---|---|
| 5.26 | 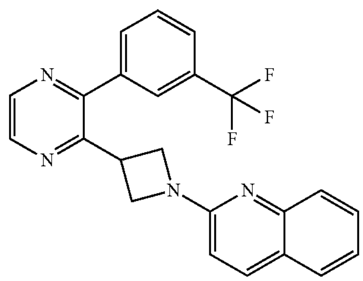 [SMILES: FC(F)(F)c1cccc(-c2nccnc2C2CN(c3ccc4ccccc4n3)C2)c1] | 2-(3-(3-(3-(trifluoromethyl)phenyl)pyrazin-2-yl)azetidin-1-yl)quinoline | 407 | 0.01344 |
| 5.27 | 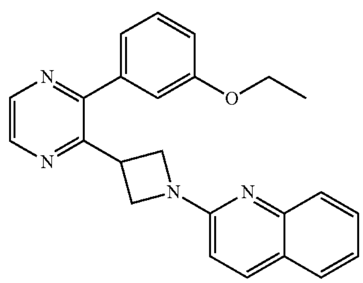 [SMILES: CCOc1cccc(-c2nccnc2C2CN(c3ccc4ccccc4n3)C2)c1] | 2-(3-(3-(3-ethoxyphenyl)pyrazin-2-yl)azetidin-1-yl)quinoline | 383 | 0.00388 |
| 5.28 | 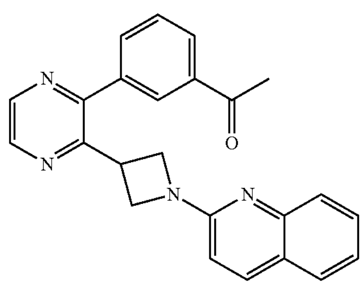 [SMILES: CC(=O)c1cccc(-c2nccnc2C2CN(c3ccc4ccccc4n3)C2)c1] | 1-(3-(3-(1-(quinolin-2-yl)azetidin-3-yl)pyrazin-2-yl)phenyl)ethanone | 381 | 0.00124 |
| 5.29 | 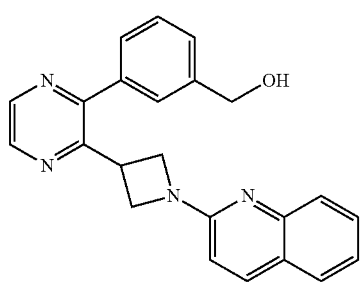 [SMILES: OCc1cccc(-c2nccnc2C2CN(c3ccc4ccccc4n3)C2)c1] | (3-(3-(1-(quinolin-2-yl)azetidin-3-yl)pyrazin-2-yl)phenyl)methanol | 369 | 0.00676 |
| 5.30 | 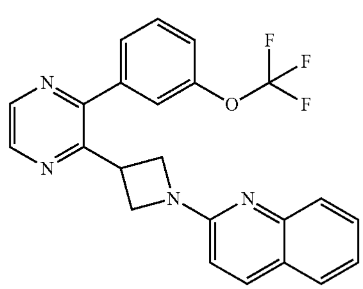 [SMILES: FC(F)(F)Oc1cccc(-c2nccnc2C2CN(c3ccc4ccccc4n3)C2)c1] | 2-(3-(3-(3-(trifluoromethoxy)phenyl)pyrazin-2-yl)azetidin-1-yl)quinoline | 423 | 0.00665 |

TABLE 17A-continued

EXAMPLES 5.1 TO 5.43

| Ex. # | Structure | Chemical Name | ESI-MS (M + 1) | IC$_{50}$ (μM) |
|---|---|---|---|---|
| 5.31 | 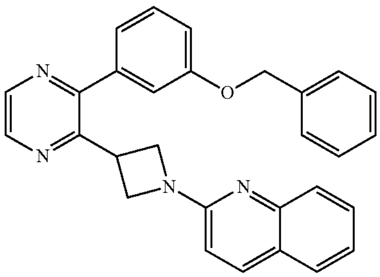 [SMILES: c1ccc(COc2cccc(-c3nccnc3C3CN(c4ccc5ccccc5n4)C3)c2)cc1] | 2-(3-(3-(3-(benzyloxy)phenyl)pyrazin-2-yl)azetidin-1-yl)quinoline | 445 | 0.01077 |
| 5.32 | 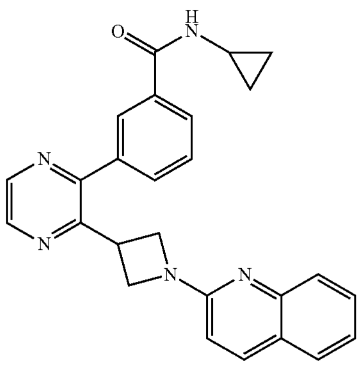 [SMILES: O=C(NC1CC1)c1cccc(-c2nccnc2C2CN(c3ccc4ccccc4n3)C2)c1] | N-cyclopropyl-3-(3-(1-(quinolin-2-yl)azetidin-3-yl)pyrazin-2-yl)benzamide | 422 | 0.00337 |
| 5.33 | 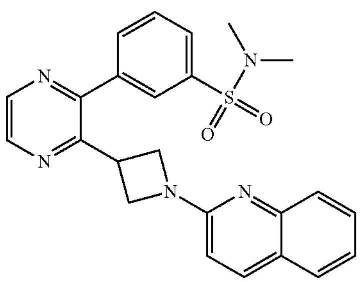 [SMILES: CN(C)S(=O)(=O)c1cccc(-c2nccnc2C2CN(c3ccc4ccccc4n3)C2)c1] | N,N-dimethyl-3-(3-(1-(quinolin-2-yl)azetidin-3-yl)pyrazin-2-yl)benzenesulfonamide | 446 | 0.01703 |
| 5.34 | 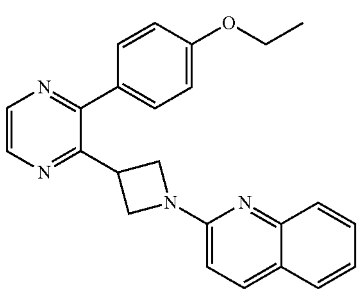 [SMILES: CCOc1ccc(-c2nccnc2C2CN(c3ccc4ccccc4n3)C2)cc1] | 2-(3-(3-(4-ethoxyphenyl)pyrazin-2-yl])azetidin-1-yl)quinoline | 383 | 0.01717 |
| 5.35 | 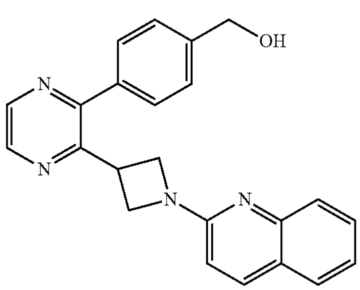 [SMILES: OCc1ccc(-c2nccnc2C2CN(c3ccc4ccccc4n3)C2)cc1] | (4-(3-(1-(quinolin-2-yl)azetidin-3-yl)pyrazin-2-yl)phenyl)methanol | 369 | 0.00519 |

TABLE 17A-continued

EXAMPLES 5.1 TO 5.43

| Ex. # | Structure | Chemical Name | ESI-MS (M + 1) | IC$_{50}$ (μM) |
|---|---|---|---|---|
| 5.36 | 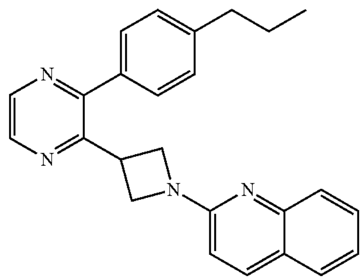 [SMILES: CCCc1ccc(-c2nccnc2C2CN(c3ccc4ccccc4n3)C2)cc1] | 2-(3-(3-(4-propylphenyl)pyrazin-2-yl)azetidin-1-yl)quinoline | 381 | 0.00995 |
| 5.37 | 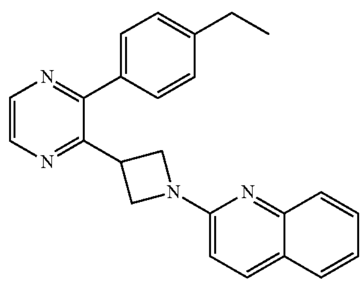 [SMILES: CCc1ccc(-c2nccnc2C2CN(c3ccc4ccccc4n3)C2)cc1] | 2-(3-(3-(4-ethylphenyl)pyrazin-2-yl)azetidin-1-yl)quinoline | 367 | 0.00609 |
| 5.38 | 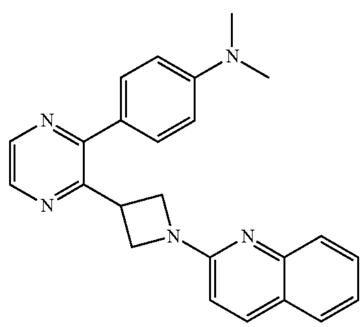 [SMILES: CN(C)c1ccc(-c2nccnc2C2CN(c3ccc4ccccc4n3)C2)cc1] | N,N-dimethyl-4-(3-(1-(quinolin-2-yl)azetidin-3-yl)pyrazin-2-yl)aniline | 382 | 0.01217 |
| 5.39 | 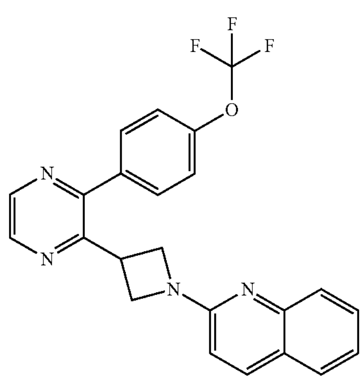 [SMILES: FC(F)(F)Oc1ccc(-c2nccnc2C2CN(c3ccc4ccccc4n3)C2)cc1] | 2-(3-(3-(4-(trifluoromethoxy)phenyl)pyrazin-2-yl)azetidin-1-yl)quinoline | 423 | 0.01747 |
| 5.40 | 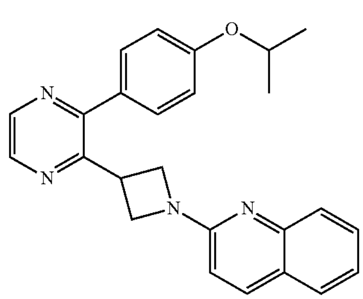 [SMILES: CC(C)Oc1ccc(-c2nccnc2C2CN(c3ccc4ccccc4n3)C2)cc1] | 2-(3-(3-(4-isopropoxyphenyl)pyrazin-2-yl)azetidin-1-yl)quinoline | 397 | 0.00723 |

TABLE 17A-continued

EXAMPLES 5.1 TO 5.43

| Ex. # | Structure | Chemical Name | ESI-MS (M + 1) | IC$_{50}$ (μM) |
|---|---|---|---|---|
| 5.41 | 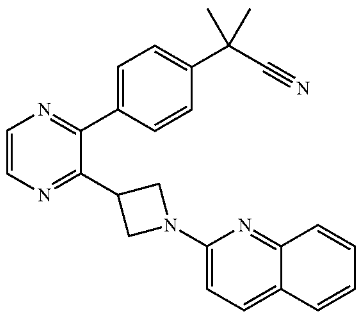 [SMILES: CC(C)(C#N)c1ccc(-c2nccnc2C2CN(c3ccc4ccccc4n3)C2)cc1] | 2-methyl-2-(4-(3-(1-(quinolin-2-yl)azetidin-3-yl)pyrazin-2-yl)phenyl)propanenitrile | 406 | 0.00737 |
| 5.42 | 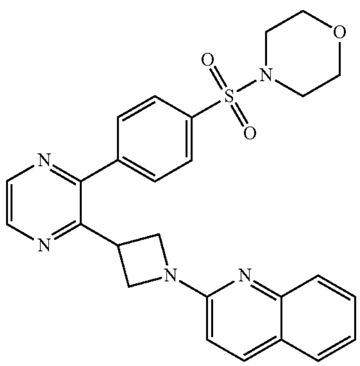 | 4-((4-(3-(1-(quinolin-2-yl)azetidin-3-yl)pyrazin-2-yl)phenyl)sulfonyl)morpholine | 488 | 0.03337 |
| 5.43 | 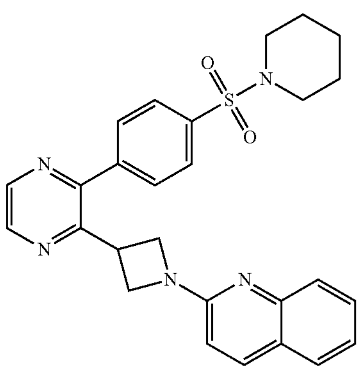 [SMILES: O=S(=O)(c1ccc(-c2nccnc2C2CN(c3ccc4ccccc4n3)C2)cc1)N1CCCCC1] | 2-(3-(3-(4-(piperidin-1-ylsulfonyl)phenyl)pyrazin-2-yl)azetidin-1-yl)quinoline | 486 | 0.02119 |

TABLE 17B

STARTING MATERIALS AND REACTION CONDITION FOR PREPARATION OF EXAMPLES 5.1 TO 5.43.
Unless otherwise stated, all starting materials are commercially available from common vendors.

| EX # | Key Starting Material(s) | Key Starting Material(s) | Reaction Condition | Purification Method* |
|---|---|---|---|---|
| 5.1 | Aldrich | PREPARATION 2 | Dioxane/water, 100° C., μW | A |

TABLE 17B-continued

STARTING MATERIALS AND REACTION CONDITION FOR
PREPARATION OF EXAMPLES 5.1 TO 5.43.
Unless otherwise stated, all starting materials are commercially available from common vendors.

| EX # | Key Starting Material(s) | Key Starting Material(s) | Reaction Condition | Purification Method* |
|---|---|---|---|---|
| 5.2 | 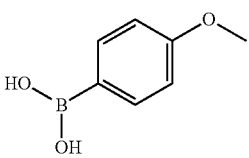<br>Aldrich | 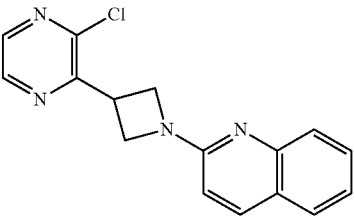<br>PREPARATION 2 | Dioxane/water, 100° C., μW | A |
| 5.3 | 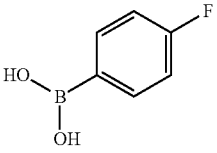<br>Aldrich | 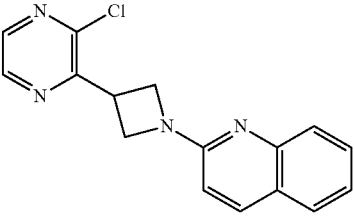 [SMILES: Clc1nccnc1C1CN(c2ccc3ccccc3n2)C1]<br>PREPARATION 2 | Dioxane/water, 100° C., μW | A |
| 5.4 | 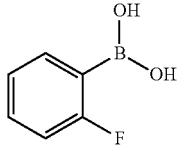<br>Aldrich | 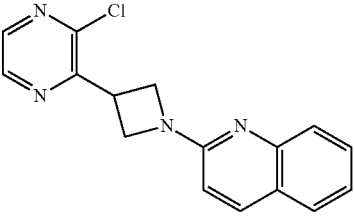 [SMILES: Clc1nccnc1C1CN(c2ccc3ccccc3n2)C1]<br>PREPARATION 2 | Dioxane/water, 100° C., μW | A |
| 5.5 | 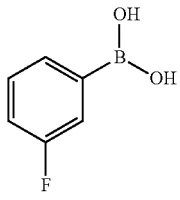<br>Alfa Aesar | 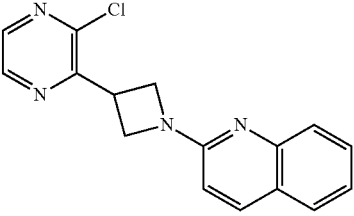 [SMILES: Clc1nccnc1C1CN(c2ccc3ccccc3n2)C1]<br>PREPARATION 2 | Dioxane/water, 100° C., μW | A |
| 5.6 | 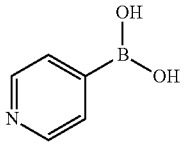<br>Combi-blocks | 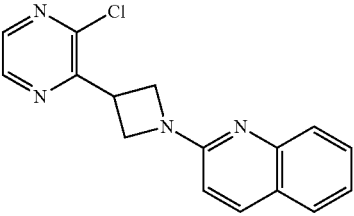<br>PREPARATION 2 | Dioxane/water, 100° C., μW | B |

TABLE 17B-continued

STARTING MATERIALS AND REACTION CONDITION FOR
PREPARATION OF EXAMPLES 5.1 TO 5.43.
Unless otherwise stated, all starting materials are commercially available from common vendors.

| EX # | Key Starting Material(s) | Key Starting Material(s) | Reaction Condition | Purification Method* |
|---|---|---|---|---|
| 5.7 | 3-cyanophenylboronic acid<br>Boron Molecular Ltd | PREPARATION 2 | Dioxane/water, 100° C., μW | A |
| 5.8 | 4-cyanophenylboronic acid<br>Aldrich | PREPARATION 2 | Dioxane/water, 100° C., μW | A |
| 5.9 | 3-(methoxycarbonyl)phenylboronic acid<br>Combi-blocks | PREPARATION 2 | Dioxane/water, 100° C., μW | A |
| 5.10 | 4-(ethoxycarbonyl)phenylboronic acid<br>Aldrich | PREPARATION 2 | Dioxane/water, 100° C., μW | A |
| 5.11 | 2-methoxypyridin-4-ylboronic acid<br>Combi-blocks | PREPARATION 2 | Dioxane/water, 100° C., μW | C |

US 9,718,803 B2

TABLE 17B-continued

STARTING MATERIALS AND REACTION CONDITION FOR
PREPARATION OF EXAMPLES 5.1 TO 5.43.
Unless otherwise stated, all starting materials are commercially available from common vendors.

| EX # | Key Starting Material(s) | Key Starting Material(s) | Reaction Condition | Purification Method* |
|---|---|---|---|---|
| 5.12 | 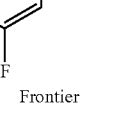<br>Frontier | 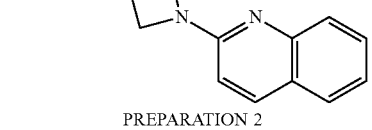<br>PREPARATION 2 | Dioxane/water, 100° C., μW | C |
| 5.13 | 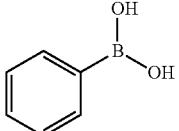<br>ASDI | 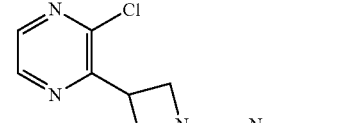<br>PREPARATION 2 | Dioxane/water, 100° C., μW | A |
| 5.14 | 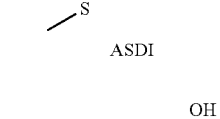<br>Alfa Aesar | 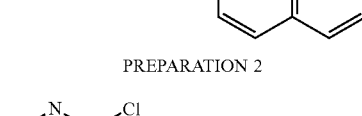<br>PREPARATION 2 | Dioxane/water, 100° C., μW | A |
| 5.15 | 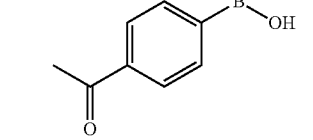<br>Frontier | 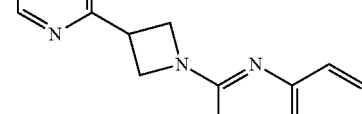<br>PREPARATION 2 | Dioxane/water, 100° C., μW | A |
| 5.16 | 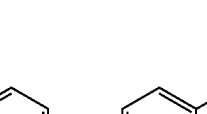<br>Aldrich | 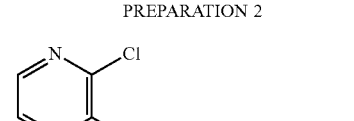<br>PREPARATION 2 | Dioxane/water, 100° C. | A |
| 5.17 | 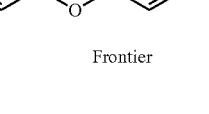<br>Aldrich | 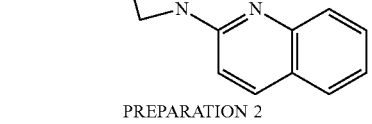<br>PREPARATION 2 | Dioxane/water, 100° C. | A |

TABLE 17B-continued

STARTING MATERIALS AND REACTION CONDITION FOR
PREPARATION OF EXAMPLES 5.1 TO 5.43.
Unless otherwise stated, all starting materials are commercially available from common vendors.

| EX # | Key Starting Material(s) | Key Starting Material(s) | Reaction Condition | Purification Method* |
|---|---|---|---|---|
| 5.18 | 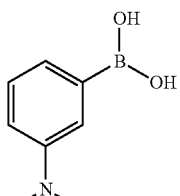 Frontier | 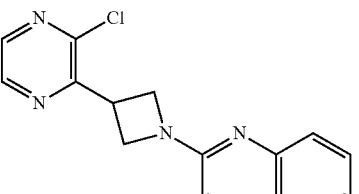 PREPARATION 2 | Dioxane/water, 100° C. | A |
| 5.19 | 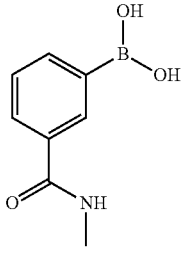 Combi-blocks | 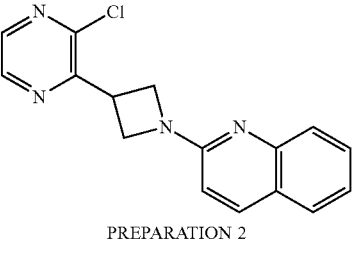 PREPARATION 2 | Dioxane/water, 100° C. | A |
| 5.20 | 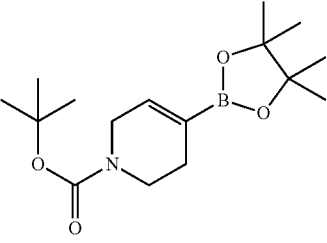 [SMILES: CC(C)(C)OC(=O)N1CC=C(B2OC(C)(C)C(C)(C)O2)CC1] Boron Molecular | 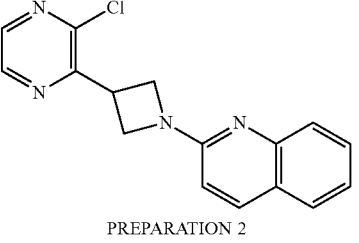 PREPARATION 2 | Dioxane/water, 100° C. | A |
| 5.21 | 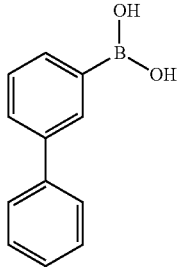 [SMILES: OB(O)c1cccc(-c2ccccc2)c1] Aldrich | 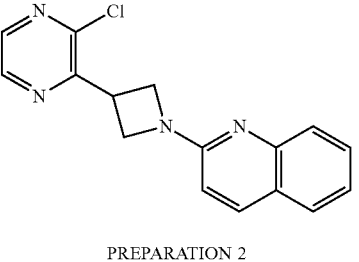 PREPARATION 2 | Dioxane/water, 100° C. | A |
| 5.22 | 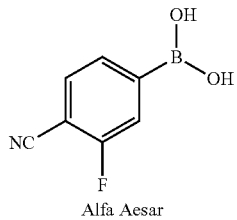 Alfa Aesar | 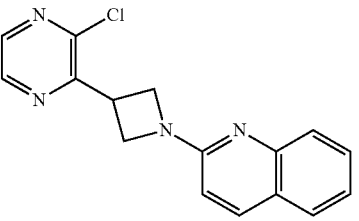 PREPARATION 2 | Dioxane/water, 100° C. | A |

TABLE 17B-continued

STARTING MATERIALS AND REACTION CONDITION FOR
PREPARATION OF EXAMPLES 5.1 TO 5.43.
Unless otherwise stated, all starting materials are commercially available from common vendors.

| EX # | Key Starting Material(s) | Key Starting Material(s) | Reaction Condition | Purification Method* |
|---|---|---|---|---|
| 5.23 | 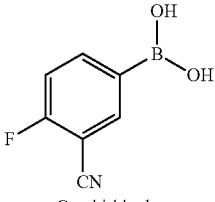<br>Combi-blocks | 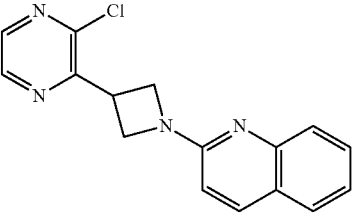 [SMILES: Clc1nccnc1C1CN(c2ccc3ccccc3n2)C1]<br>PREPARATION 2 | Dioxane/water, 100° C. | A |
| 5.24 | 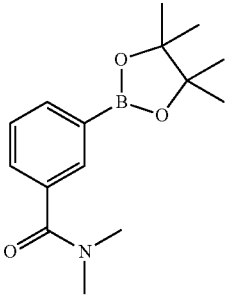 [SMILES: CN(C)C(=O)c1cccc(B2OC(C)(C)C(C)(C)O2)c1]<br>Boron Molecules | 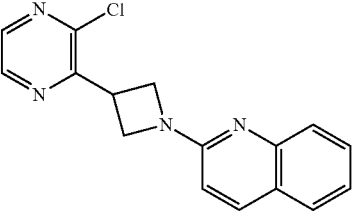<br>PREPARATION 2 | Dioxane/water, 100° C. | C |
| 5.25 | 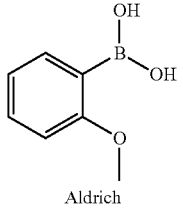<br>Aldrich | 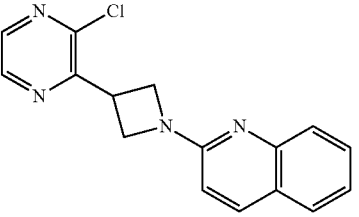 [SMILES: Clc1nccnc1C1CN(c2ccc3ccccc3n2)C1]<br>PREPARATION 2 | Dioxane/water, 100° C. | A |
| 5.26 | 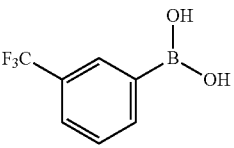 [SMILES: OB(O)c1cccc(C(F)(F)F)c1]<br>ASDI | 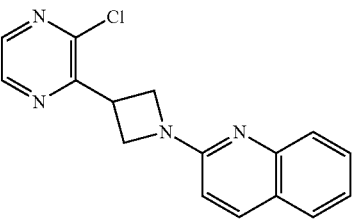 [SMILES: Clc1nccnc1C1CN(c2ccc3ccccc3n2)C1]<br>PREPARATION 2 | Dioxane/water, 100° C. | D |
| 5.27 | 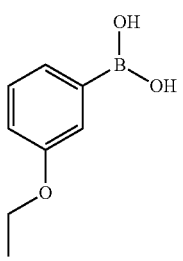<br>ASDI | 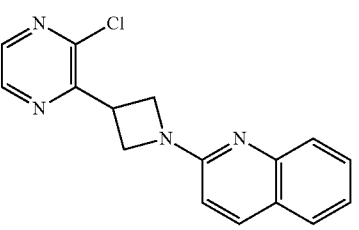<br>PREPARATION 2 | Dioxane/water, 100° C. | D |

TABLE 17B-continued

STARTING MATERIALS AND REACTION CONDITION FOR
PREPARATION OF EXAMPLES 5.1 TO 5.43.
Unless otherwise stated, all starting materials are commercially available from common vendors.

| EX # | Key Starting Material(s) | Key Starting Material(s) | Reaction Condition | Purification Method* |
|---|---|---|---|---|
| 5.28 | (3-acetylphenyl)boronic acid — ASDI | PREPARATION 2 | Dioxane/water, 100° C. | D |
| 5.29 | (3-(hydroxymethyl)phenyl)boronic acid — ASDI | PREPARATION 2 | Dioxane/water, 100° C. | D |
| 5.30 | (3-(trifluoromethoxy)phenyl)boronic acid — ASDI | PREPARATION 2 | Dioxane/water, 100° C. | D |
| 5.31 | (3-(benzyloxy)phenyl)boronic acid — ASDI | PREPARATION 2 | Dioxane/water, 100° C. | D |
| 5.32 | (3-(cyclopropylcarbamoyl)phenyl)boronic acid — ASDI | PREPARATION 2 | Dioxane/water, 100° C. | D |

TABLE 17B-continued

STARTING MATERIALS AND REACTION CONDITION FOR
PREPARATION OF EXAMPLES 5.1 TO 5.43.
Unless otherwise stated, all starting materials are commercially available from common vendors.

| EX # | Key Starting Material(s) | Key Starting Material(s) | Reaction Condition | Purification Method* |
|---|---|---|---|---|
| 5.33 | (3-(N,N-dimethylsulfamoyl)phenyl)boronic acid, ASDI | 3-chloro-2-(1-(quinolin-2-yl)azetidin-3-yl)pyrazine, PREPARATION 2 | Dioxane/water, 100° C. | D |
| 5.34 | (4-ethoxyphenyl)boronic acid, ASDI | 3-chloro-2-(1-(quinolin-2-yl)azetidin-3-yl)pyrazine, PREPARATION 2 | Dioxane/water, 100° C. | D |
| 5.35 | (4-(hydroxymethyl)phenyl)boronic acid, ASDI | 3-chloro-2-(1-(quinolin-2-yl)azetidin-3-yl)pyrazine, PREPARATION 2 | Dioxane/water, 100° C. | D |
| 5.36 | (4-propylphenyl)boronic acid, ASDI | 3-chloro-2-(1-(quinolin-2-yl)azetidin-3-yl)pyrazine, PREPARATION 2 | Dioxane/water, 100° C. | D |
| 5.37 | (4-ethylphenyl)boronic acid, ASDI | 3-chloro-2-(1-(quinolin-2-yl)azetidin-3-yl)pyrazine, PREPARATION 2 | Dioxane/water, 100° C. | D |
| 5.38 | (4-(dimethylamino)phenyl)boronic acid, ASDI | 3-chloro-2-(1-(quinolin-2-yl)azetidin-3-yl)pyrazine, PREPARATION 2 | Dioxane/water, 100° C. | D |

TABLE 17B-continued

STARTING MATERIALS AND REACTION CONDITION FOR
PREPARATION OF EXAMPLES 5.1 TO 5.43.
Unless otherwise stated, all starting materials are commercially available from common vendors.

| EX # | Key Starting Material(s) | Key Starting Material(s) | Reaction Condition | Purification Method* |
|---|---|---|---|---|
| 5.39 | 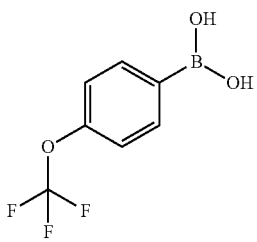 ASDI | 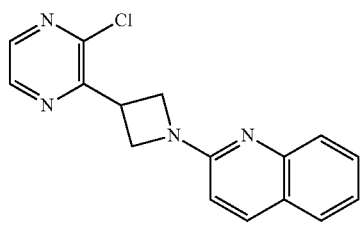 PREPARATION 2 | Dioxane/water, 100° C. | D |
| 5.40 | 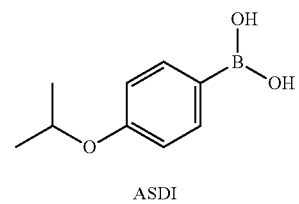 ASDI | 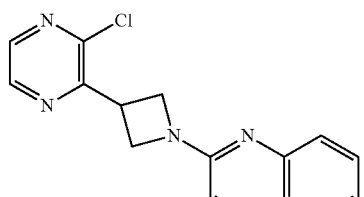 PREPARATION 2 | Dioxane/water, 100° C. | D |
| 5.41 | 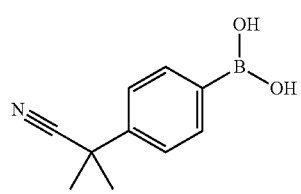 ASDI | 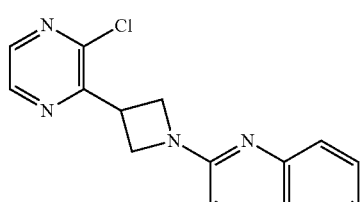 PREPARATION 2 | Dioxane/water, 100° C. | D |
| 5.42 | 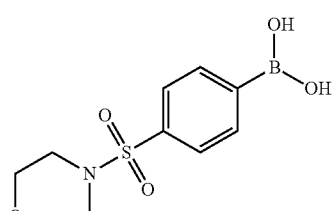 ASDI | 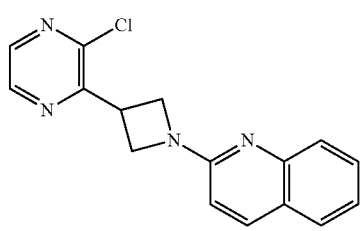 [SMILES: Clc1nccnc1C1CN(c2ccc3ccccc3n2)C1] PREPARATION 2 | Dioxane/water, 100° C. | D |

TABLE 17B-continued

STARTING MATERIALS AND REACTION CONDITION FOR PREPARATION OF EXAMPLES 5.1 TO 5.43.

Unless otherwise stated, all starting materials are commercially available from common vendors.

| EX # | Key Starting Material(s) | Key Starting Material(s) | Reaction Condition | Purification Method* |
|---|---|---|---|---|
| 5.43 | 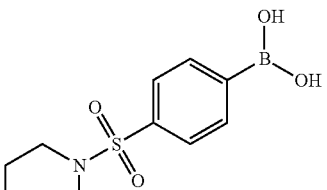 ASDI | 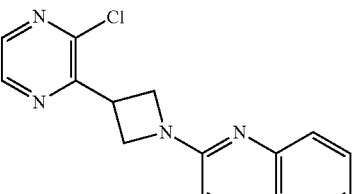 PREPARATION 2 | Dioxane/water, 100° C. | D |

*PURIFICATION CONDITIONS:

METHOD A-purification by silica gel chromatography: (ISCO 12 g RediSep-silica column, eluting with a gradient of 10% to 100% EtOAc in hexane).

METHOD B-purification by silica gel chromatography: (ISCO 12 g RediSep-silica column, eluting with a gradient of 0% to 10% MeOH in $CH_2Cl_2$).

METHOD C-reverse-phase HPLC (Shimazu; Gemini 10 μM C18 110A AXIA, 100 × 50 mm column) eluting with 0.1% TFA-$H_2O$:0.1% TFA $CH_3CN$ (10% → 55%). The fractions containing the desired product were combined, neutralized with $Na_2CO_3$, and extracted with a mixed solvent of $CHCl_3$: i-PrOH (3:1) three times. The organic phase was dried over $Na_2SO_4$ and concentrated in vacuo.

METHOD D-reverse phase purification using the following conditions:

(Instrumentation: MS-Waters SQ; UV-Waters 2487 or Waters PD;

Solvents:

A: Water w/ 0.1% $NH_4OH$

B: Acetonitrile w/ 0.1% $NH_4OH$;

Column: Phenomenex Gemini-NX C18 110A 5 um 21 × 100;

Flow Rate: 44 mL/min. 10 min Method, variable gradient over 8 min).

TABLE 17C

1H NMR δ (PPM) DATA FOR EXAMPLES 5.1 TO 5.43

| Ex. # | Structure | NMR |
|---|---|---|
| 5.1 | 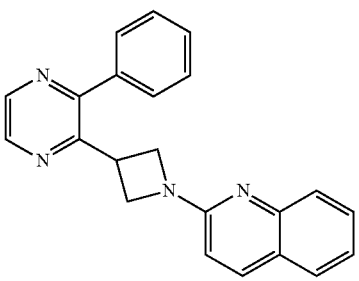 [SMILES: c1ccc(-c2nccnc2C2CN(c3ccc4ccccc4n3)C2)cc1] | (400 MHz, CHLOROFORM-d) 4.32-4.53 (m, 5 H) 6.61 (d, J = 9.00 Hz, 1 H) 7.18-7.23 (m, 1 H) 7.46-7.55 (m, 6 H) 7.59 (d, J = 8.02 Hz, 1 H) 7.72 (d, J = 8.41 Hz, 1 H) 7.85 (d, J = 9.00 Hz, 1 H) 8.55 (dd, J = 15.16, 2.45 Hz, 2 H). |
| 5.2 | 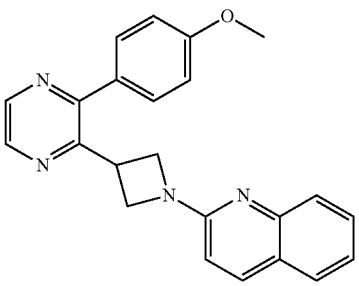 [SMILES: COc1ccc(-c2nccnc2C2CN(c3ccc4ccccc4n3)C2)cc1] | (400 MHz, CHLOROFORM-d) 3.90 (s, 3 H) 4.38-4.52 (m, 5 H) 6.62 (d, J = 8.80 Hz, 1 H) 7.04 (d, J = 8.61 Hz, 2 H) 7.21 (t, J = 7.43 Hz, 1 H) 7.44-7.55 (m, 3 H) 7.60 (d, J = 7.83 Hz, 1 H) 7.72 (d, J = 8.41 Hz, 1 H) 7.86 (d, J = 8.80 Hz, 1 H) 8.49-8.55 (m, 2 H). |

TABLE 17C-continued

1H NMR δ (PPM) DATA FOR EXAMPLES 5.1 TO 5.43

| Ex. # | Structure | NMR |
|---|---|---|
| 5.3 | 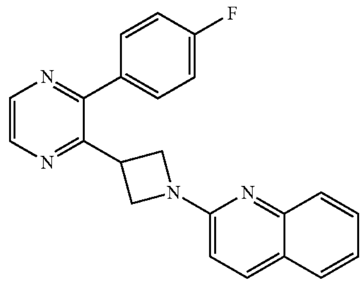 [SMILES: Fc1ccc(-c2nccnc2C2CN(c3ccc4ccccc4n3)C2)cc1] | (400 MHz, CHLOROFORM-d) 4.30-4.53 (m, 5 H) 6.63 (d, J = 8.80 Hz, 1 H) 7.18-7.25 (m, 3 H) 7.49-7.56 (m, 3 H) 7.60 (d, J = 8.02 Hz, 1 H) 7.72 (d, J = 8.41 Hz, 1 H) 7.87 (d, J = 8.80 Hz, 1 H) 8.47-8.63 (m, 2 H). |
| 5.4 | 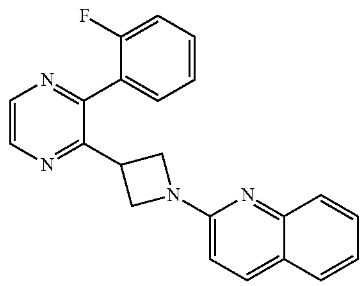 [SMILES: Fc1ccccc1-c1nccnc1C1CN(c2ccc3ccccc3n2)C1] | (400 MHz, CHLOROFORM-d) 4.12-4.25 (m, 1 H) 4.34-4.49 (m, 4 H) 6.62 (d, J = 8.80 Hz, 1 H) 7.16-7.25 (m, 2 H) 7.30-7.38 (m, 1 H) 7.45-7.56 (m, 3 H) 7.59 (d, J = 8.02 Hz, 1 H) 7.72 (d, J = 8.41 Hz, 1 H) 7.86 (d, J = 8.80 Hz, 1 H) 8.57 (d, J = 2.54 Hz, 1 H) 8.64 (d, J = 2.54 Hz, 1 H). |
| 5.5 | 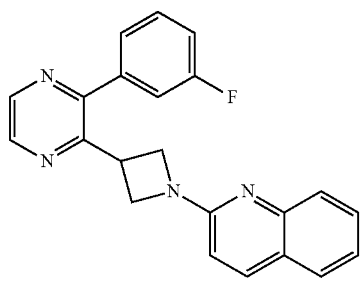 | (400 MHz, CHLOROFORM-d) 4.32-4.54 (m, 5 H) 6.63 (d, J = 9.00 Hz, 1 H) 7.16-7.33 (m, 4 H) 7.45-7.57 (m, 2 H) 7.60 (d, J = 7.82 Hz, 1 H) 7.72 (d, J = 8.41 Hz, 1 H) 7.87 (d, J = 9.00 Hz, 1 H) 8.54 (d, J = 2.35 Hz, 1 H) 8.61 (d, J = 2.35 Hz, 1 H). |
| 5.6 | 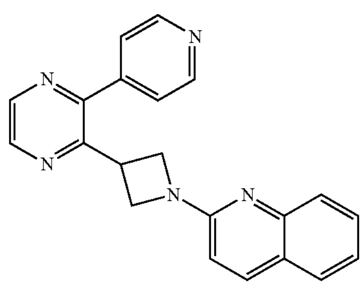 [SMILES: c1ccc2nc(N3CC(c4nccnc4-c4ccncc4)C3)ccc2c1] | (400 MHz, CHLOROFORM-d) 4.30-4.39 (m, 1 H) 4.41-4.52 (m, 4 H) 6.63 (d, J = 8.80 Hz, 1 H) 7.23 (t, J = 7.53 Hz, 1 H) 7.44-7.49 (m, 2 H) 7.51-7.57 (m, 1 H) 7.61 (d, J = 7.82 Hz, 1 H) 7.73 (d, J = 8.41 Hz, 1 H) 7.88 (d, J = 8.80 Hz, 1 H) 8.58 (d, J = 2.35 Hz, 1 H) 8.66 (d, J = 2.35 Hz, 1 H) 8.78-8.83 (m, 2 H). |
| 5.7 | 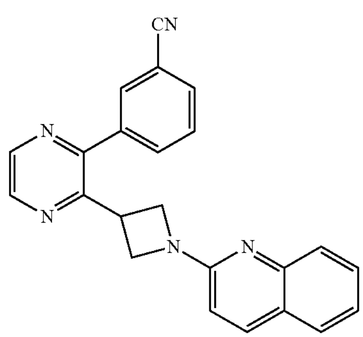 [SMILES: N#Cc1cccc(-c2nccnc2C2CN(c3ccc4ccccc4n3)C2)c1] | (400 MHz, CHLOROFORM-d) 4.28-4.38 (m, 1 H) 4.40-4.51 (m, 4 H) 6.64 (d, J = 8.80 Hz, 1 H) 7.20-7.25 (m, 1 H) 7.50-7.57 (m, 1 H) 7.59-7.84 (m, 5 H) 7.85-7.92 (m, 2 H) 8.57 (d, J = 2.35 Hz, 1 H) 8.65 (d, J = 2.35 Hz, 1 H). |

TABLE 17C-continued

1H NMR δ (PPM) DATA FOR EXAMPLES 5.1 TO 5.43

| Ex. # | Structure | NMR |
|---|---|---|
| 5.8 | 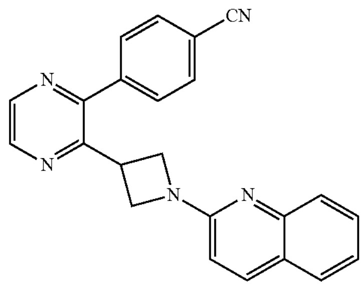 [SMILES: N#Cc1ccc(-c2nccnc2C2CN(c3ccc4ccccc4n3)C2)cc1] | (400 MHz, CHLOROFORM-d) 4.28-4.37 (m, 1 H) 4.39-4.50 (m, 4 H) 6.63 (d, J = 8.80 Hz, 1 H) 7.19-7.25 (m, 1 H) 7.50-7.57 (m, 1 H) 7.61 (d, J = 7.82 Hz, 1 H) 7.66 (d, J = 8.41 Hz, 2 H) 7.72 (d, J = 8.41 Hz, 1 H) 7.84 (d, J = 8.41 Hz, 2 H) 7.89 (d, J = 8.80 Hz, 1 H) 8.57 (d, J = 2.54 Hz, 1 H) 8.65 (d, J = 2.35 Hz, 1 H). |
| 5.9 | 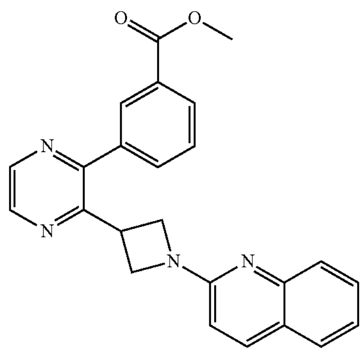 [SMILES: COC(=O)c1cccc(-c2nccnc2C2CN(c3ccc4ccccc4n3)C2)c1] | (400 MHz, CHLOROFORM-d) 3.97 (s, 3 H) 4.34-4.60 (m, 5 H) 6.63 (d, J = 8.80 Hz, 1 H) 7.18-7.25 (m, 1 H) 7.49-7.57 (m, 1 H) 7.58-7.68 (m, 2 H) 7.69-7.80 (m, 2 H) 7.87 (d, J = 9.00 Hz, 1 H) 8.17-8.24 (m, 2 H) 8.54-8.58 (m, 1 H) 8.61 (d, J = 2.35 Hz, 1 H). |
| 5.10 | 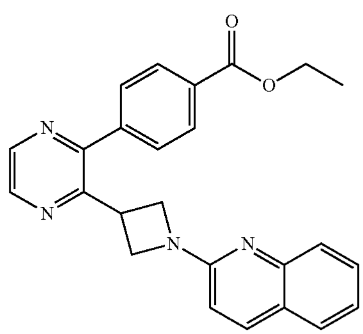 [SMILES: CCOC(=O)c1ccc(-c2nccnc2C2CN(c3ccc4ccccc4n3)C2)cc1] | $^1$H NMR (400 MHz, CHLOROFORM-d) δ ppm 1.45 (t, J = 7.14 Hz, 3 H) 4.27-4.55 (m, 7 H) 6.62 (d, J = 8.80 Hz, 1 H) 7.17-7.24 (m, 1 H) 7.49-7.64 (m, 4 H) 7.72 (d, J = 8.22 Hz, 1 H) 7.87 (d, J = 9.00 Hz, 1 H) 8.21 (d, J = 8.41 Hz, 2 H) 8.56 (d, J = 2.35 Hz, 1 H) 8.62 (d, J = 2.35 Hz, 1 H). |
| 5.11 | 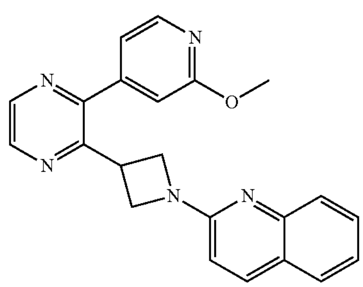 [SMILES: COc1cc(-c2nccnc2C2CN(c3ccc4ccccc4n3)C2)ccn1] | (400 MHz, CHLOROFORM-d) 4.02 (s, 3 H) 4.29-4.53 (m, 5 H) 6.63 (d, J = 9.00 Hz, 1 H) 6.87 (s, 1 H) 7.03 (dd, J = 5.28, 1.37 Hz, 1 H) 7.19-7.25 (m, 1 H) 7.50-7.56 (m, 1 H) 7.61 (d, J = 8.02 Hz, 1 H) 7.73 (d, J = 8.41 Hz, 1 H) 7.88 (d, J = 8.80 Hz, 1 H) 8.33 (d, J = 5.28 Hz, 1 H) 8.56 (d, J = 2.35 Hz, 1 H) 8.64 (d, J = 2.35 Hz, 1 H). |
| 5.12 | 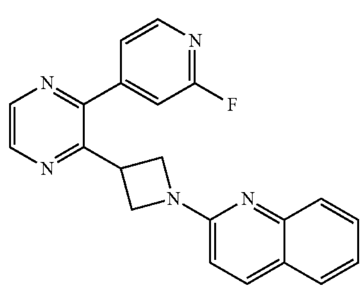 [SMILES: Fc1cc(-c2nccnc2C2CN(c3ccc4ccccc4n3)C2)ccn1] | (400 MHz, CHLOROFORM-d) 4.28-4.39 (m, 1 H) 4.41-4.53 (m, 4 H) 6.64 (d, J = 8.80 Hz, 1 H) 7.14 (s, 1 H) 7.20-7.26 (m, 1 H) 7.35 (d, J = 5.09 Hz, 1 H) 7.51-7.57 (m, 1 H) 7.61 (d, J = 7.82 Hz, 1 H) 7.73 (d, J = 8.41 Hz, 1 H) 7.90 (d, J = 8.80 Hz, 1 H) 8 41 (d, J = 5.28 Hz, 1 H) 8.59 (d, J = 2.35 Hz, 1 H) 8.69 (d, J = 2.35 Hz, 1 H). |

TABLE 17C-continued

1H NMR δ (PPM) DATA FOR EXAMPLES 5.1 TO 5.43

| Ex. # | Structure | NMR |
|---|---|---|
| 5.13 | 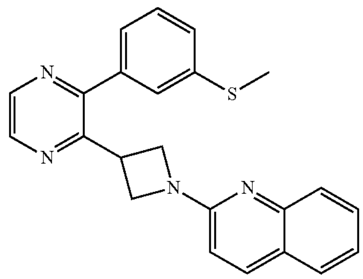 [SMILES: CSc1cccc(-c2nccnc2C2CN(c3ccc4ccccc4n3)C2)c1] | (400 MHz, CHLOROFORM-d) 2.55 (s, 3 H) 4.34-4.52 (m, 5 H) 6.63 (d, J = 8.80 Hz, 1 H) 7.18-7.25 (m, 2 H) 7.35-7.47 (m, 3 H) 7.50-7.56 (m, 1 H) 7.60 (d, J = 7.82 Hz, 1 H) 7.72 (d, J = 8.41 Hz, 1 H) 7.87 (d, J = 9.00 Hz, 1 H) 8.54 (d, J = 2.35 Hz, 1 H) 8.59 (d, J = 2.35 Hz, 1 H). |
| 5.14 | 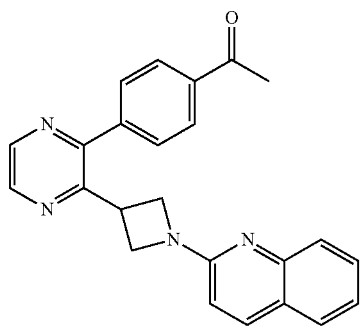 [SMILES: CC(=O)c1ccc(-c2nccnc2C2CN(c3ccc4ccccc4n3)C2)cc1] | (400 MHz, CHLOROFORM-d) 2.69 (s, 3 H) 4.30-4.54 (m, 5 H) 6.62 (d, J = 8.80 Hz, 1 H) 7.22 (t, J = 7.43 Hz, 1 H) 7.50-7.56 (m, 1 H) 7.60 (d, J = 8.02 Hz, 1 H) 7.64 (d, J = 8.41 Hz, 2 H) 7.72 (d, J = 8.41 Hz, 1 H) 7.87 (d, J = 8.80 Hz, 1 H) 8.12 (d, J = 8.41 Hz, 2 H) 8.57 (d, J = 2.35 Hz, 1 H) 8.62 (d, J = 2.35 Hz, 1 H). |
| 5.15 | 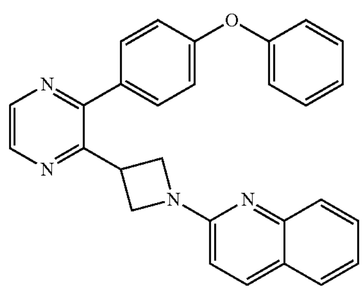 [SMILES: c1ccc(Oc2ccc(-c3nccnc3C3CN(c4ccc5ccccc5n4)C3)cc2)cc1] | (400 MHz, CHLOROFORM-d) 4 38-4.54 (m, 5 H) 6.63 (d, J = 8.80 Hz, 1 H) 7.08-7.24 (m, 6 H) 7.36-7.44 (m, 2 H) 7.46-7.56 (m, 3 H) 7.60 (d, J = 8.02 Hz, 1 H) 7.72 (d, J = 8.41 Hz, 1 H) 7.87 (d, J = 8.80 Hz, 1 H) 8.52 (d, J = 2.35 Hz, 1 H) 8.56 (d, J = 2.35 Hz, 1 H). |
| 5.16 | 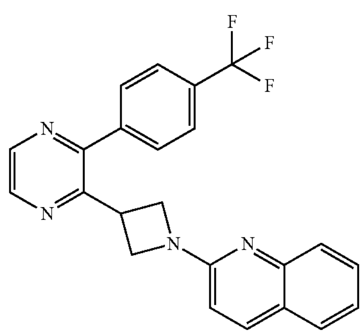 [SMILES: FC(F)(F)c1ccc(-c2nccnc2C2CN(c3ccc4ccccc4n3)C2)cc1] | (400 MHz, CHLOROFORM-d) 4.28-4.56 (m, 5 H) 6.63 (d, J = 9.00 Hz, 1 H) 7.19-7.25 (m, 1 H) 7.54 (t, J = 7.63 Hz, 1 H) 7.61 (d, J = 8.02 Hz, 1 H) 7.66 (d, J = 8.02 Hz, 2 H) 7.73 (d, J = 8.41 Hz, 1 H) 7.80 (d, J = 8.22 Hz, 2 H) 7.88 (d, J = 8.80 Hz, 1 H) 8.57 (d, J = 2.35 Hz, 1 H) 8.64 (d, J = 2.35 Hz, 1 H). |
| 5.17 | 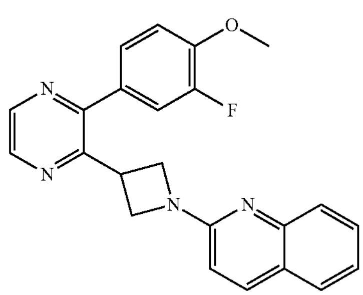 [SMILES: COc1ccc(-c2nccnc2C2CN(c3ccc4ccccc4n3)C2)cc1F] | (400 MHz, CHLOROFORM-d) 3.99 (s, 3 H) 4.38-4.51 (m, 5 H) 6.63 (d, J = 8.80 Hz, 1 H) 7.05-7.14 (m, 1 H) 7.18-7.25 (m, 2 H) 7.33 (dd, J = 11.74, 1.96 Hz, 1 H) 7.53 (t, J = 7.63 Hz, 1 H) 7.60 (d, J = 8.02 Hz, 1 H) 7.72 (d, J = 8.41 Hz, 1 H) 7.88 (d, J = 8.80 Hz, 1 H) 8.52 (d, J = 2.15 Hz, 1 H) 8.56 (d, J = 2.35 Hz, 1 H). |

TABLE 17C-continued

1H NMR δ (PPM) DATA FOR EXAMPLES 5.1 TO 5.43

| Ex. # | Structure | NMR |
|---|---|---|
| 5.18 | 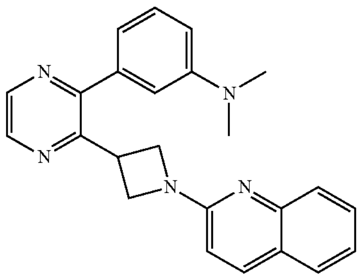 [SMILES: CN(C)c1cccc(-c2nccnc2C2CN(c3ccc4ccccc4n3)C2)c1] | (400 MHz, CHLOROFORM-d) 3.03 (s, 6 H) 4.34-4.55 (m, 5 H) 6.63 (d, J = 8.80 Hz, 1 H) 6.76-6.88 (m, 3 H) 7.18-7.24 (m, 1 H) 7.36 (t, J = 7.92 Hz, 1 H) 7.49-7.56 (m, 1 H) 7.60 (d, J = 7.82 Hz, 1 H) 7.72 (d, J = 8.41 Hz, 1 H) 7.86 (d, J = 9.00 Hz, 1 H) 8.52 (d, J = 2.35 Hz, 1 H) 8.56 (d, J = 2.35, 1 H). |
| 5.19 | 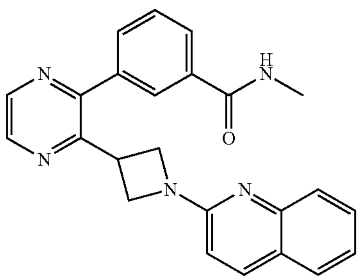 [SMILES: CNC(=O)c1cccc(-c2nccnc2C2CN(c3ccc4ccccc4n3)C2)c1] | (400 MHz, CHLOROFORM-d) 3.06 (d, J = 4.89 Hz, 3 H) 4.32-4.53 (m, 5 H) 6.27 (br. s., 1 H) 6.62 (d, J = 9.00 Hz, 1 H) 7.22 (t, J = 7.43 Hz, 1 H) 7.48-7.78 (m, 5 H) 7.83-8.06 (m, 3 H) 8.55 (d, J = 2.35 Hz, 1 H) 8.61 (d, J = 2.35 Hz, 1 H). |
| 5.20 | 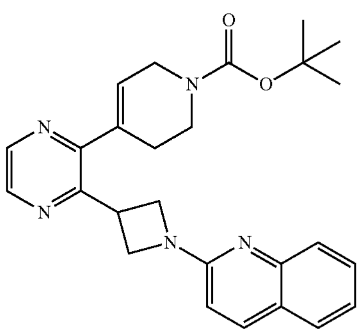 [SMILES: CC(C)(C)OC(=O)N1CC=C(c2nccnc2C2CN(c3ccc4ccccc4n3)C2)CC1] | (400 MHz, DMSO-d$_6$) 1.46 (s, 9 H) 3.31 (br. s., 2 H) 3.59 (t, J = 5.28 Hz, 2 H) 4.08 (br. s., 2 H) 4.20-4.32 (m, 2 H) 4.38-4.59 (m, 3 H) 5.92 (br. s., 1 H) 6.78 (d, J = 9.00 Hz, 1 H) 7.21 (t, J = 6.75 Hz, 1 H) 7.46-7.61 (m, 2 H) 7.71 (d, J = 7.82 Hz, 1 H) 8.04 (d, J = 8.80 Hz, 1 H) 8.52 (d, J = 2.35 Hz, 1 H) 8.56 (d, J = 2.35 Hz, 1 H). |
| 5.21 | 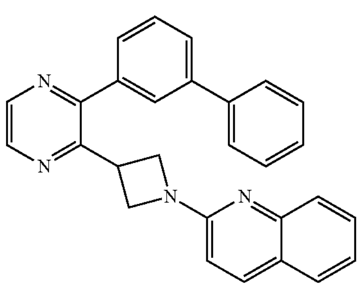 [SMILES: c1ccc(-c2cccc(-c3nccnc3C3CN(c4ccc5ccccc5n4)C3)c2)cc1] | (400 MHz, CHLOROFORM-d) 4.38-4.54 (m, 5 H) 6.63 (d, J = 9.00 Hz, 1 H) 7.19-7.24 (m, 1 H) 7.36-7.42 (m, 1 H) 7.44-7.55 (m, 4 H) 7.57-7.63 (m, 2 H) 7.66 (d, J = 7.63 Hz, 2 H) 7.69-7.77 (m, 3 H) 7.87 (d, J = 8.80 Hz, 1 H) 8.56 (d, J = 2.54 Hz, 1 H) 8.60 (d, J = 2.35 Hz, 1 H). |
| 5.22 | 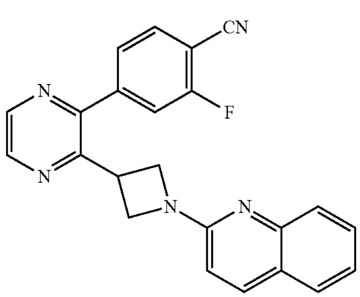 [SMILES: N#Cc1ccc(-c2nccnc2C2CN(c3ccc4ccccc4n3)C2)cc1F] | (400 MHz, CHLOROFORM-d) 4.26-4.38 (m, 1 H) 4.41-4.54 (m, 4 H) 6.64 (d, J = 9.00 Hz, 1 H) 7.20-7.25 (m, 1 H) 7.41-7.49 (m, 2 H) 7.51-7.58 (m, 1 H) 7.62 (d, J = 7.82 Hz, 1 H) 7.73 (d, J = 8.41 Hz, 1 H) 7.80 (t, J = 7.34 Hz, 1 H) 7.90 (d, J = 8.80 Hz, 1 H) 8.58 (d, J = 2.15 Hz, 1 H) 8.67 (d, J = 2.15 Hz, 1 H). |

TABLE 17C-continued

1H NMR δ (PPM) DATA FOR EXAMPLES 5.1 TO 5.43

| Ex. # | Structure | NMR |
|---|---|---|
| 5.23 | 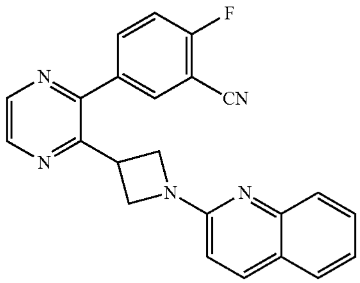 [SMILES: N#Cc1cc(-c2nccnc2C2CN(c3ccc4ccccc4n3)C2)ccc1F] | (400 MHz, CHLOROFORM-d) 4.26-4.37 (m, 1 H) 4.40-4.53 (m, 4 H) 6.65 (s, 1 H) 7.20-7.25 (m, 1 H) 7.40 (t, J = 8.51 Hz, 1 H) 7.51-7.58 (m, 1 H) 7.62 (d, J = 7.82 Hz, 1 H) 7.73 (d, J = 8.41 Hz, 1 H) 7.75-7.81 (m, 1 H) 7.86 (dd, J = 5.97, 2.25 Hz, 1 H) 7.90 (d, J = 8.80 Hz, 1 H) 8.56 (d, J = 2.35 Hz, 1 H) 8.65 (d, J = 2.15 Hz, 1 H). |
| 5.24 | 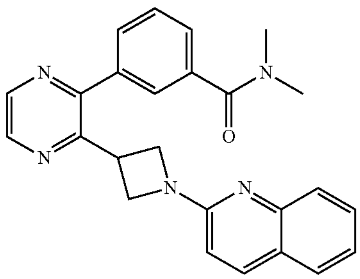 [SMILES: CN(C)C(=O)c1cccc(-c2nccnc2C2CN(c3ccc4ccccc4n3)C2)c1] | (400 MHz, CHLOROFORM-d) 2.98-3.22 (m, 6 H) 4.30-4.54 (m, 5 H) 6.63 (d, J = 8.80 Hz, 1 H) 7.22 (t, J = 7.14 Hz, 1 H) 7.49-7.64 (m, 6 H) 7.72 (d, J = 8.41 Hz, 1 H) 7.87 (d, J = 9.00 Hz, 1 H) 8.55 (d, J = 2.35 Hz, 1 H) 8.61 (d, J = 2.35 Hz, 1 H). |
| 5.25 | 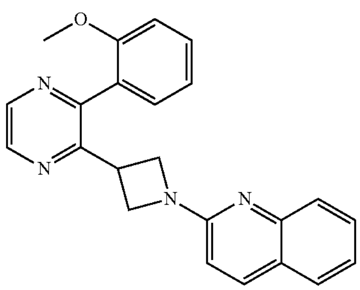 [SMILES: COc1ccccc1-c1nccnc1C1CN(c2ccc3ccccc3n2)C1] | (400 MHz, CHLOROFORM-d) 3.82 (s, 3 H) 4.04-4.56 (m, 5 H) 6.61 (d, J = 8.80 Hz, 1 H) 7.02 (d, J = 8.41 Hz, 1 H) 7.12 (t, J = 7.43 Hz, 1 H) 7.21 (t, J = 7.43 Hz, 1 H) 7.37 (dd, J = 7.53, 1.47 Hz, 1 H) 7.43-7.55 (m, 2 H) 7.59 (d, J = 7.82 Hz, 1 H) 7.72 (d, J = 8.41 Hz, 1 H) 7.85 (d, J = 8.80 Hz, 1 H) 8.53 (d, J = 2.54 Hz, 1 H) 8.58 (d, J = 2.35 Hz, 1 H). |
| 5.26 | 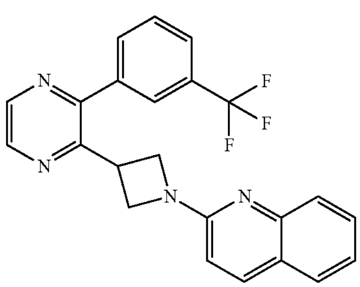 [SMILES: FC(F)(F)c1cccc(-c2nccnc2C2CN(c3ccc4ccccc4n3)C2)c1] | (400 MHz, DMSO-$d_6$) 4.22-4.45 (m, 5 H) 6.76 (d, J = 8.61 Hz, 1 H) 7.22 (t, J = 6.85 Hz, 1 H) 7.46-7.60 (m, 2 H) 7.71 (d, J = 7.82 Hz, 1 H) 7.78-7.85 (m, 1 H) 7.89-7.98 (m, 3 H) 8.03 (d, J = 9.00 Hz, 1 H) 8.68 (d, J = 2.35 Hz, 1 H) 8.74 (d, J = 2.35 Hz, 1 H). |
| 5.27 | 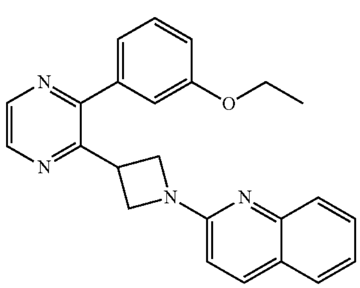 [SMILES: CCOc1cccc(-c2nccnc2C2CN(c3ccc4ccccc4n3)C2)c1] | (400 MHz, DMSO-$d_6$) 1-37 (t, J = 6.85 Hz, 3 H) 4.12 (q, J = 7.04 Hz, 2 H) 4.23-4.52 (m, 5 H) 6.77 (d, J = 9.00 Hz, 1 H) 7.06-7.15 (m, 3 H) 7.19-7.27 (m, 1 H) 7.42-7.61 (m, 3 H) 7.71 (d, J = 7.82 Hz, 1 H) 8.04 (d, J = 8.61 Hz, 1 H) 8.63 (d, J = 2.35 Hz, 1 H) 8.68 (d, J = 2.35 Hz, 1 H). |

TABLE 17C-continued

1H NMR δ (PPM) DATA FOR EXAMPLES 5.1 TO 5.43

| Ex. # | Structure | NMR |
|---|---|---|
| 5.28 | 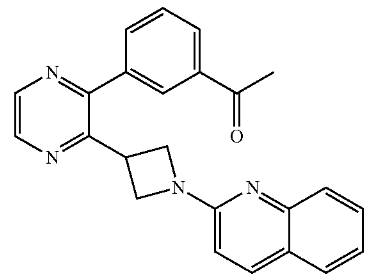 [SMILES: CC(=O)c1cccc(-c2nccnc2C2CN(c3ccc4ccccc4n3)C2)c1] | (400 MHz, DMSO-$d_6$) 2.68 (s, 3 H) 4.23-4.47 (m, 5 H) 6.75 (d, J = 9.00 Hz, 1 H) 7.17-7.24 (m, 1 H) 7.47-7.59 (m, 2 H) 7.67-7.78 (m, 2 H) 7.87 (d, J = 7.43 Hz, 1 H) 8.02 (d, J = 9.00 Hz, 1 H) 8.09-8.16 (m, 2 H) 8.67 (d, J = 2.35 Hz, 1 H) 8.72 (d, J = 2.35 Hz, 1 H) |
| 5.29 | 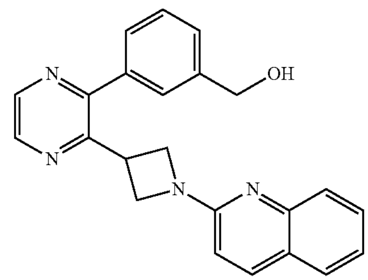 [SMILES: OCc1cccc(-c2nccnc2C2CN(c3ccc4ccccc4n3)C2)c1] | (400 MHz, DMSO-$d_6$) 4.20-4.45 (m, 5 H) 4.62 (d, J = 5.48 Hz, 2 H) 5.35 (t, J = 5.67 Hz, 1 H) 6.75 (d, J = 9.00 Hz, 1 H) 7.21 (t, J = 7.24 Hz, 1 H) 7.42-7.60 (m, 6 H) 7.70 (d, J = 8.22 Hz, 1 H) 8.03 (d, J = 8.61 Hz, 1 H) 8.63 (d, J = 2.35 Hz, 1 H) 8.67 (d, J = 2.35 Hz, 1 H). |
| 5.30 | 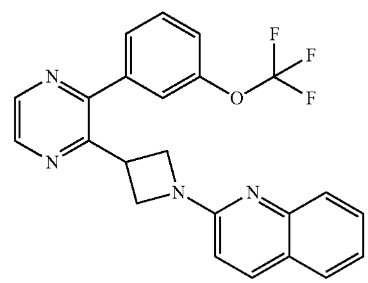 [SMILES: FC(F)(F)Oc1cccc(-c2nccnc2C2CN(c3ccc4ccccc4n3)C2)c1] | (400 MHz, DMSO-$d_6$) 4.23-4.47 (m, 5 H) 6.76 (d, J = 9.00 Hz, 1 H) 7.23 (t, J = 7.24 Hz, 1 H) 7.48-7.66 (m, 5 H) 7.67-7.75 (m, 2 H) 8.01-8.09 (m, 1 H) 8.65-8.68 (m, 1 H) 8.71-8.75 (m, 1 H). |
| 5.31 | 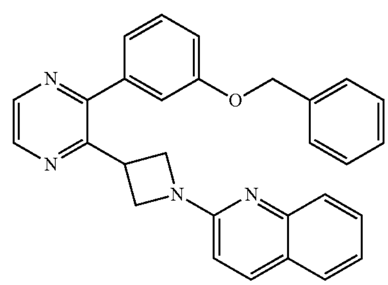 [SMILES: c1ccc(COc2cccc(-c3nccnc3C3CN(c4ccc5ccccc5n4)C3)c2)cc1] | (400 MHz, DMSO-$d_6$) 4.15-4.44 (m, 5 H) 5.21 (s, 2 H) 6.73 (d, J = 9.00 Hz, 1 H) 7.11-7.25 (m, 4 H) 7.28-7.34 (m, 1 H) 7.41 (t, J = 7.63 Hz, 2 H) 7.45-7.59 (m, 5 H) 7.70 (d, J = 7.82 Hz, 1 H) 8.02 (d, J = 9.00 Hz, 1 H) 8.63 (d, J = 2.35 Hz, 1 H) 8.67 (d, J = 2.35 Hz, 1 H) |
| 5.32 | 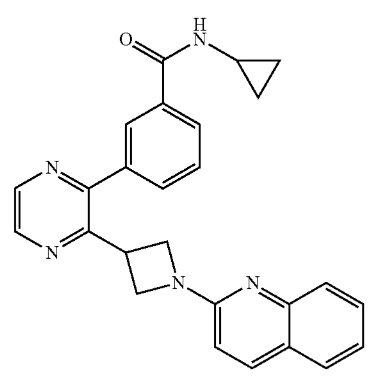 [SMILES: O=C(NC1CC1)c1cccc(-c2nccnc2C2CN(c3ccc4ccccc4n3)C2)c1] | (400 MHz, DMSO-$d_6$) 0.57-0.64 (m, 2 H) 0.69-0.77 (m, 2 H) 2.89 (tq, J = 7.34, 3.98 Hz, 1 H) 4.22-4.45 (m, 5 H) 6.75 (d, J = 9.00 Hz, 1 H) 7.21 (t, J = 7.43 Hz, 1 H) 7.47-7.59 (m, 2 H) 7.61-7.67 (m, 1 H) 7.72 (dd, J = 14.87, 7.82 Hz, 2 H) 7.93-8.08 (m, 3 H) 8.57 (d, J = 3.91 Hz, 1 H) 8.66 (d, J = 2.35 Hz, 1 H) 8.71 (d, J = 2.35 Hz, 1 H) |

TABLE 17C-continued

1H NMR δ (PPM) DATA FOR EXAMPLES 5.1 TO 5.43

| Ex. # | Structure | NMR |
|---|---|---|
| 5.33 | 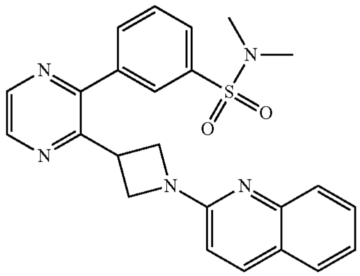 [SMILES: CN(C)S(=O)(=O)c1cccc(-c2nccnc2C2CN(c3ccc4ccccc4n3)C2)c1] | (400 MHz, DMSO-$d_6$) 2.70 (s, 6 H) 4.25-4.43 (m, 5 H) 6.72-6.78 (m, 1 H) 7.17-7.25 (m, 1 H) 7.47-7.59 (m, 2 H) 7.70 (d, J = 7.82 Hz, 1 H) 7.82-7.88 (m, 1 H) 7.90-7.98 (m, 3 H) 8.03 (d, J = 8.61 Hz, 1 H) 8.68 (d, J = 2.35 Hz, 1 H) 8.74 (d, J = 2.74 Hz, 1 H) |
| 5.34 | 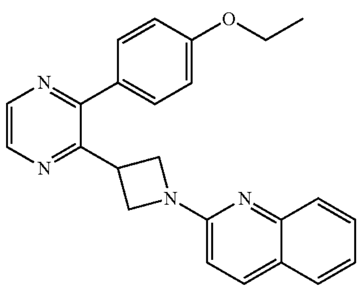 [SMILES: CCOc1ccc(-c2nccnc2C2CN(c3ccc4ccccc4n3)C2)cc1] | (400 MHz, DMSO-$d_6$) 1.38 (t, J = 7.04 Hz, 3 H) 4.13 (q, J = 6.78 Hz, 2 H) 4.22-4.29 (m, 2 H) 4.35 (t, J = 8.02 Hz, 2 H) 4.41-4.51 (m, 1 H) 6.76 (d, J = 9.00 Hz, 1 H) 7.05-7.12 (m, 2 H) 7.19-7.25 (m, 1 H) 7.48-7.59 (m, 4 H) 7.71 (d, J = 7.82 Hz, 1 H) 8.04 (d, J = 9.00 Hz, 1 H) 8.59-8.61 (m, 1 H) 8.61-8.63 (m, 1 H) |
| 5.35 | 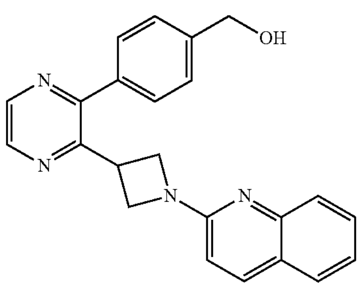 [SMILES: OCc1ccc(-c2nccnc2C2CN(c3ccc4ccccc4n3)C2)cc1] | (400 MHz, DMSO-$d_6$) 4.19-4.47 (m, 5 H) 4.62 (d, J = 5.87 Hz, 2 H) 5.33 (t, J = 5.67 Hz, 1 H) 6.75 (d, J = 9.00 Hz, 1 H) 7.21 (t, J = 7.04 Hz, 1 H) 7.47-7.59 (m, 6 H) 7.70 (d, J = 7.82 Hz, 1 H) 8.03 (d, J = 9.00 Hz, 1 H) 8.63 (d, J = 2.74 Hz, 1 H) 8.66 (d, J = 2.74 Hz, 1 H) |
| 5.36 | 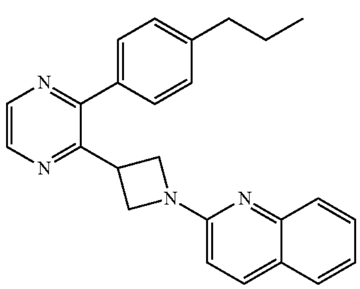 [SMILES: CCCc1ccc(-c2nccnc2C2CN(c3ccc4ccccc4n3)C2)cc1] | (400 MHz, DMSO-$d_6$) 0.95 (t, J = 7.43 Hz, 3 H) 1.67 (sxt, J = 7.43 Hz, 2 H) 2.66 (t, J = 7.63 Hz, 2 H) 4.23-4.47 (m, 5 H) 6.76 (d, J = 9.00 Hz, 1 H) 7.20-7.26 (m, 1 H) 7.38 (d, J = 7.82 Hz, 2 H) 7.47-7.61 (m, 4 H) 7.72 (d, J = 7.43 Hz, 1 H) 8.05 (d, J = 9.00 Hz, 1 H) 8.62 (d, J = 2.35 Hz, 1 H) 8.65 (d, J = 2.35 Hz, 1 H) |
| 5.37 | 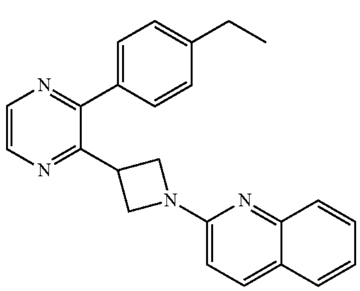 [SMILES: CCc1ccc(-c2nccnc2C2CN(c3ccc4ccccc4n3)C2)cc1] | (400 MHz, DMSO-$d_6$) 1.26 (t, J = 7.43 Hz, 3 H) 2.72 (q, J = 7.56 Hz, 2 H) 4.22-4.50 (m, 5 H) 6.76 (d, J = 9.00 Hz, 1 H) 7.18-7.27 (m, 1 H) 7.40 (d, J = 8.22 Hz, 2 H) 7.47-7.61 (m, 4 H) 7.71 (d, J = 7.82 Hz, 1 H) 8.04 (d, J = 9.00 Hz, 1 H) 8.62 (d, J = 2.35 Hz, 1 H) 8.65 (d, J = 2.74 Hz, 1 H) |

TABLE 17C-continued

1H NMR δ (PPM) DATA FOR EXAMPLES 5.1 TO 5.43

| Ex. # | Structure | NMR |
|---|---|---|
| 5.38 | 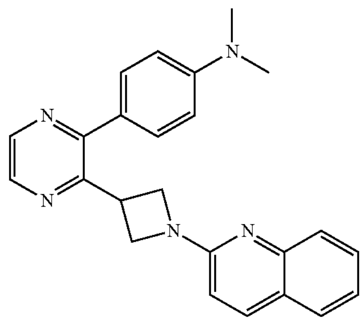 [SMILES: CN(C)c1ccc(-c2nccnc2C2CN(c3ccc4ccccc4n3)C2)cc1] | (400 MHz, DMSO-$d_6$) 3.01 (s, 6 H) 4.17-4.55 (m, 5 H) 6.76 (d, J = 9.00 Hz, 1 H) 6.86 (d, J = 9.00 Hz, 2 H) 7.16-7.25 (m, 1 H) 7.42-7.61 (m, 4 H) 7.70 (d, J = 7.43 Hz, 1 H) 8.02 (d, J = 9.00 Hz, 1 H) 8.51-8.58 (m, 2 H) |
| 5.39 | 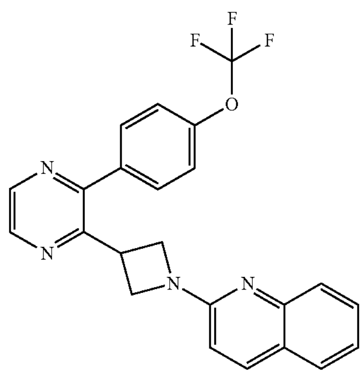 [SMILES: FC(F)(F)Oc1ccc(-c2nccnc2C2CN(c3ccc4ccccc4n3)C2)cc1] | (400 MHz, DMSO-$d_6$) 4.28-4.48 (m, 5 H) 6.80 (d, J = 9.00 Hz, 1 H) 7.22-7.30 (m, 1 H) 7.52-7.62 (m, 4 H) 7.74 (d, J = 9.00 Hz, 3 H) 8.09 (d, J = 8.61 Hz, 1 H) 8 66 (d, J = 2.35 Hz, 1 H) 8.72 (d, J = 2.35 Hz, 1 H) |
| 5.40 | 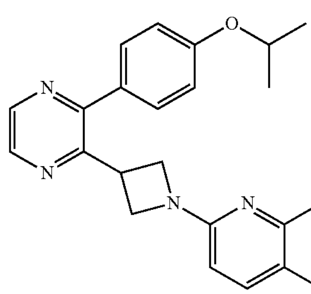 | (400 MHz, DMSO-$d_6$) 1.33 (d, J = 6.26 Hz, 6 H) 4.20-4.52 (m, 5 H) 4.73 (dt, J = 12.03, 5.92 Hz, 1 H) 6.78 (d, J = 9.00 Hz, 1 H) 7.08 (d, J = 8.61 Hz, 2 H) 7.24 (t, J = 6.85 Hz, 1 H) 7.46-7.62 (m, 4 H) 7.72 (d, J = 8.22 Hz, 1 H) 8.06 (d, J = 9.00 Hz, 1 H) 8.59-8.61 (m, 1 H) 8.61-8.63 (m, 1 H) |
| 5.41 | 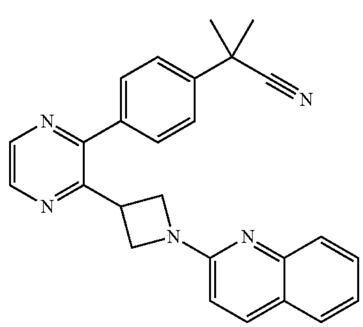 [SMILES: CC(C)(C#N)c1ccc(-c2nccnc2C2CN(c3ccc4ccccc4n3)C2)cc1] | (400 MHz, DMSO-$d_6$) 1.77 (s, 6 H) 4.23-4.46 (m, 5 H) 6.75 (d, J = 9.00 Hz, 1 H) 7.21 (t, J = 7.24 Hz, 1 H) 7.48-7.59 (m, 2 H) 7.62-7.76 (m, 5 H) 8.03 (d, J = 8.61 Hz, 1 H) 8.65 (d, J = 2.35 Hz, 1 H) 8.69 (d, J = 2.35 Hz, 1 H) |

TABLE 17C-continued

1H NMR δ (PPM) DATA FOR EXAMPLES 5.1 TO 5.43

| Ex. # | Structure | NMR |
|---|---|---|
| 5.42 | 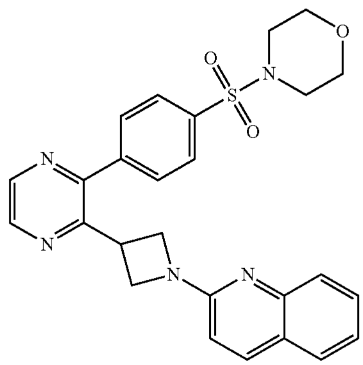 [SMILES: O=S(=O)(c1ccc(-c2nccnc2C2CN(c3ccc4ccccc4n3)C2)cc1)N1CCOCC1] | (400 MHz, DMSO-$d_6$) 2.89-3.02 (m, 4 H) 3.61-3.75 (m, 4 H) 4.22-4.48 (m, 5 H) 6.74 (d, J = 8.61 Hz, 1 H) 7.17-7.24 (m, 1 H) 7.47-7.61 (m, 2 H) 7.70 (d, J = 7.82 Hz, 1 H) 7.84-7.97 (m, 4 H) 8.02 (d, J = 9.00 Hz, 1 H) 8.69 (d, J = 2.35 Hz, 1 H) 8.75 (d, J = 2.35 Hz, 1 H) |
| 5.43 | 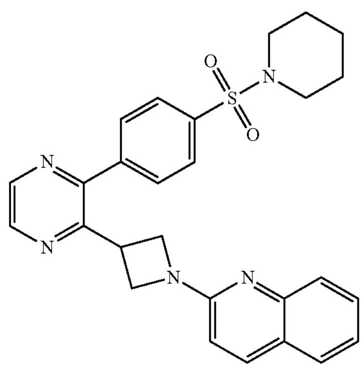 [SMILES: O=S(=O)(c1ccc(-c2nccnc2C2CN(c3ccc4ccccc4n3)C2)cc1)N1CCCCC1] | (400 MHz, DMSO-$d_6$) 1.41 (d, J = 3.91 Hz, 2 H) 1.57 (d, J = 4.69 Hz, 4 H) 2.99 (t, J = 5.28 Hz, 4 H) 4.20-4.47 (m, 5 H) 6.74 (d, J = 9.00 Hz, 1 H) 7.18-7.25 (m, 1 H) 7.48-7.58 (m, 2 H) 7.70 (d, J = 7.82 Hz, 1 H) 7.81-7.88 (m, 2 H) 7.88-7.95 (m, 2 H) 8.02 (d, J = 9.00 Hz, 1 H) 8.68 (d, J = 2.35 Hz, 1 H) 8.74 (d, J = 2.35 Hz, 1 H) |

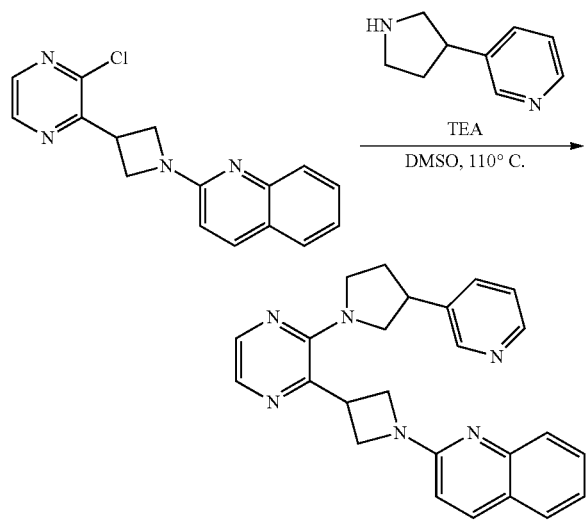

SCHEME 6

Example 6.1: (R— & S—)-2-(3-(3-(3-(Pyridin-3-Yl)Pyrrolidin-1-Yl)Pyrazin-2-Yl)Azetidin-1-Yl)Quinoline To a 3 mL vial was added 2-(3-(3-chloropyrazin-2-yl)azetidin-1-yl)quinoline (0.04000 g, 0.135 mmol), 3-(pyrrolidin-3-yl)pyridine (commerically available at Array Biopharma, 0.040 g, 0.270 mmol), and triethylamine (commerically available at Sigma Aldrich, 0.038 ml, 0.270 mmol) in DMSO (Solvent Volume: 0.449 ml) and the reaction was stirred at 110° C. overnight. Upon completion, the reaction was filtered into a 24 well plate and purified by reverse phase purification using the following conditions: (Instrumentation: MS—Waters SQ; UV—Waters 2487 or Waters PD; Solvents: A: Water w/0.1% NH$_4$OH B: Acetonitrile w/0.1% NH$_4$OH; Column: Phenomenex Gemini-NX C18 110A 5 um 21×100; Flow Rate: 44 mL/min. 10 min Method, variable gradient over 8 mins.)

The following Table 18A lists compounds of Examples 6.1 to 6.60, which were made analogous to Scheme 6 by using the appropriate materials and reaction conditions, which are listed in Table 18B. The NMR data of the Examples are listed in Table 18C.

TABLE 18A

EXAMPLES 6.1 TO 6.60

| Ex. # | Structure | Chemical Name | ESI-MS (M + 1) | IC$_{50}$ (μM) |
|---|---|---|---|---|
| 6.1 | 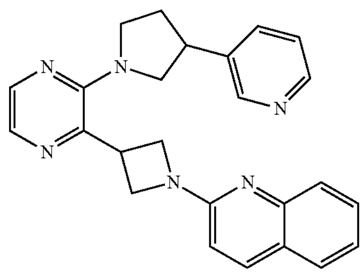 [SMILES: c1cncc(C2CCN(c3nccnc3C3CN(c4ccc5ccccc5n4)C3)C2)c1] | (R- & S-)-2-(3-(3-(3-(pyridin-3-yl)pyrrolidin-1-yl)pyrazin-2-yl)azetidin-1-yl)quinoline | 409.0 | 0.001 |
| 6.2 | 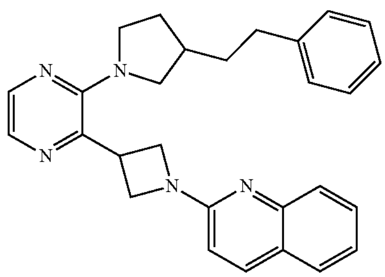 [SMILES: c1ccc(CCC2CCN(c3nccnc3C3CN(c4ccc5ccccc5n4)C3)C2)cc1] | (R- & S-)-2-(3-(3-(3-phenethylpyrrolidin-1-yl)pyrazin-2-yl)azetidin-1-yl)quinoline | 436 | 0.010 |
| 6.3 | 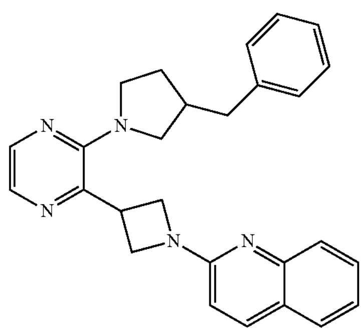 [SMILES: c1ccc(CC2CCN(c3nccnc3C3CN(c4ccc5ccccc5n4)C3)C2)cc1] | (R- & S-)-2-(3-(3-(3-benzylpyrrolidin-1-yl)pyrazin-2-yl)azetidin-1-yl)quinoline | 422 | 0.005 |
| 6.4 | 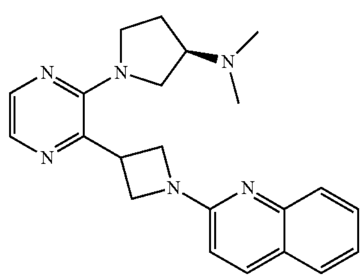 [SMILES: CN(C)[C@@H]1CCN(c2nccnc2C2CN(c3ccc4ccccc4n3)C2)C1] | (R)-N,N-dimethyl-1-(3-(1-(quinolin-2-yl)azetidin-3-yl)pyrazin-2-yl)pyrrolidin-3-amine | 375 | 0.097 |
| 6.5 | 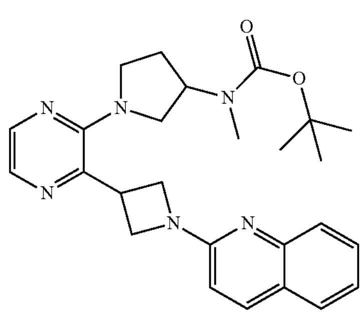 [SMILES: CN(C(=O)OC(C)(C)C)C1CCN(c2nccnc2C2CN(c3ccc4ccccc4n3)C2)C1] | (R- & S-)-tert-butyl methyl(1-(3-(1-(quinolin-2-yl)azetidin-3-yl)pyrazin-2-yl)pyrrolidin-3-yl)carbamate | 461 | 0.002 |

TABLE 18A-continued

EXAMPLES 6.1 TO 6.60

| Ex. # | Structure | Chemical Name | ESI-MS (M + 1) | IC$_{50}$ (μM) |
|---|---|---|---|---|
| 6.6 | 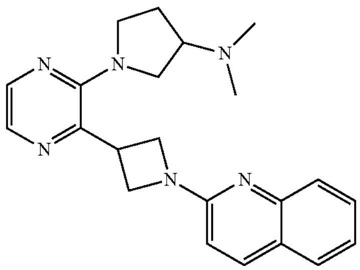 [SMILES: CN(C)C1CCN(c2nccnc2C2CN(c3ccc4ccccc4n3)C2)C1] | (R- & S-)-N,N-dimethyl-1-(3-(1-(quinolin-2-yl)azetidin-3-yl)pyrazin-2-yl)pyrrolidin-3-amine | 375 | 0.061 |
| 6.7 | 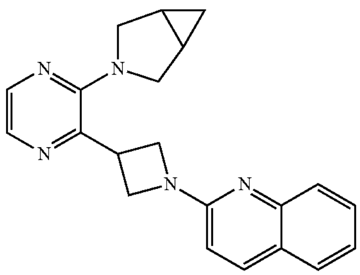 [SMILES: c1ccc2nc(N3CC(c4nccnc4N4CC5CC5C4)C3)ccc2c1] | 2-(3-(3-(3-azabicyclo[3.1.0]hexan-3-yl)pyrazin-2-yl)azetidin-1-yl)quinoline | 344 | 0.003 |
| 6.8 | 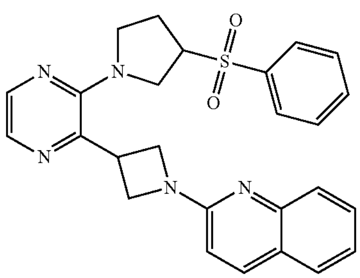 [SMILES: O=S(=O)(c1ccccc1)C1CCN(c2nccnc2C2CN(c3ccc4ccccc4n3)C2)C1] | (R- & S-)-2-(3-(3-(3-(phenylsulfonyl)pyrrolidin-1-yl)pyrazin-2-yl)azetidin-1-yl)quinoline | 472 | 0.008 |
| 6.9 | 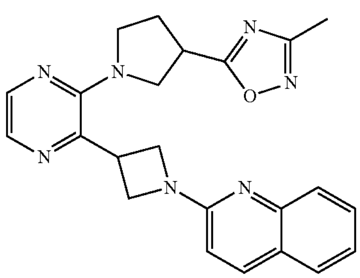 [SMILES: Cc1noc(C2CCN(c3nccnc3C3CN(c4ccc5ccccc5n4)C3)C2)n1] | (R- & S-)-3-methyl-5-(1-(3-(1-(quinolin-2-yl)azetidin-3-yl)pyrazin-2-yl)pyrrolidin-3-yl)-1,2,4-oxadiazole | 414 | 0.001 |
| 6.10 | 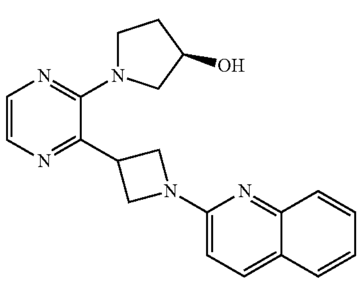 [SMILES: O[C@@H]1CCN(c2nccnc2C2CN(c3ccc4ccccc4n3)C2)C1] | (R)-1-(3-(1-(quinolin-2-yl)azetidin-3-yl)pyrazin-2-yl)pyrrolidin-3-ol | 348 | 0.007 |

TABLE 18A-continued

EXAMPLES 6.1 TO 6.60

| Ex. # | Structure | Chemical Name | ESI-MS (M + 1) | IC$_{50}$ (μM) |
|---|---|---|---|---|
| 6.11 | 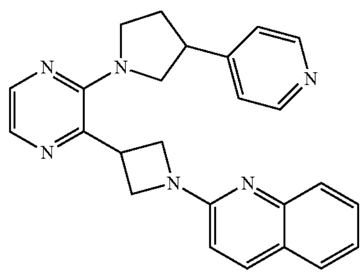 [SMILES: c1ccc2nc(N3CC(c4nccnc4N4CCC(c5ccncc5)C4)C3)ccc2c1] | (R- & S-)-2-(3-(3-(3-(pyridin-4-yl)pyrrolidin-1-yl)pyrazin-2-yl)azetidin-1-yl)quinoline | 409 | 0.001 |
| 6.12 | 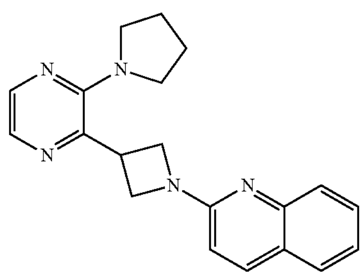 [SMILES: c1ccc2nc(N3CC(c4nccnc4N4CCCC4)C3)ccc2c1] | 2-(3-(3-(pyrrolidin-1-yl)pyrazin-2-yl)azetidin-1-yl)quinoline | 332 | 0.003 |
| 6.13 | 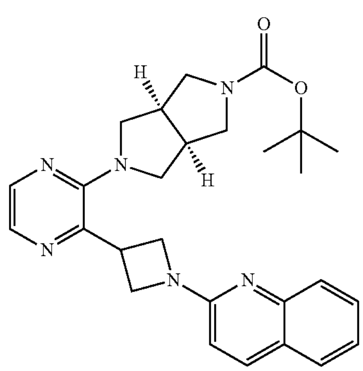 [SMILES: CC(C)(C)OC(=O)N1C[C@@H]2CN(c3nccnc3C3CN(c4ccc5ccccc5n4)C3)C[C@@H]2C1] | (3aR,6aS)-tert-butyl 5-(3-(1-(quinolin-2-yl)azetidin-3-yl)pyrazin-2-yl)hexahydropyrrolo[3,4-c]pyrrole-2(1H)-carboxylate | 473 | 0.001 |
| 6.14 | 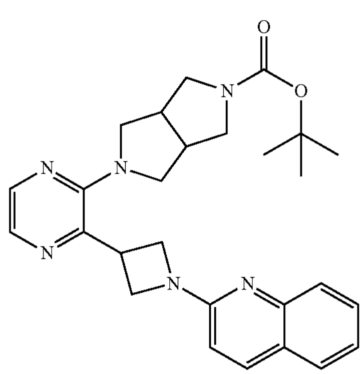 [SMILES: CC(C)(C)OC(=O)N1CC2CN(c3nccnc3C3CN(c4ccc5ccccc5n4)C3)CC2C1] | tert-butyl 5-(3-(1-(quinolin-2-yl)azetidin-3-yl)pyrazin-2-yl)hexahydropyrrolo[3,4-c]pyrrole-2(1H)-carboxylate | 473 | 0.003 |

TABLE 18A-continued

EXAMPLES 6.1 TO 6.60

| Ex. # | Structure | Chemical Name | ESI-MS (M + 1) | IC$_{50}$ (μM) |
|---|---|---|---|---|
| 6.15 | 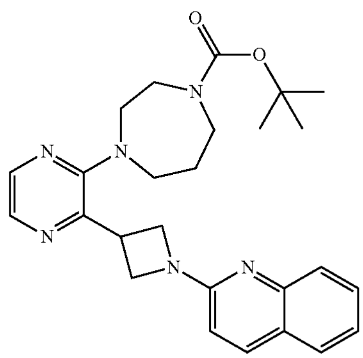 [SMILES: CC(C)(C)OC(=O)N1CCCN(c2nccnc2C2CN(c3ccc4ccccc4n3)C2)CC1] | tert-butyl 4-(3-(1-(quinolin-2-yl)azetidin-3-yl)pyrazin-2-yl)-1,4-diazepane-1-carboxylate | 461.1 | 0.225 |
| 6.16 | 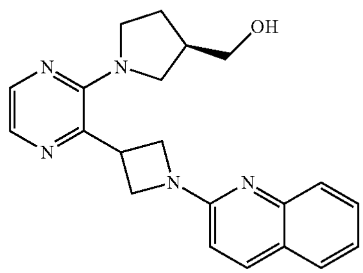 [SMILES: OC[C@@H]1CCN(c2nccnc2C2CN(c3ccc4ccccc4n3)C2)C1] | (R)-(1-(3-(1-(quinolin-2-yl)azetidin-3-yl)pyrazin-2-yl)pyrrolidin-3-yl)methanol | 362 | 0.006 |
| 6.17 | 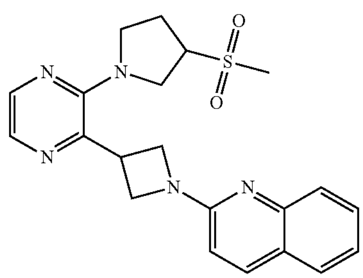 [SMILES: CS(=O)(=O)C1CCN(c2nccnc2C2CN(c3ccc4ccccc4n3)C2)C1] | (R- & S-)-2-(3-(3-(3-(methylsulfonyl)pyrrolidin-1-yl)pyrazin-2-yl)azetidin-1-yl)quinoline | 410 | 0.033 |
| 6.18 | 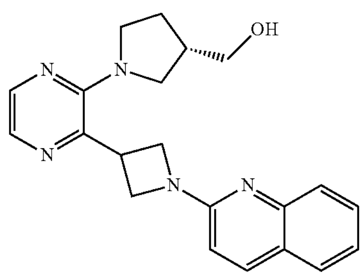 [SMILES: OC[C@H]1CCN(c2nccnc2C2CN(c3ccc4ccccc4n3)C2)C1] | (S)-(1-(3-(1-(quinolin-2-yl)azetidin-3-yl)pyrazin-2-yl)pyrrolidin-3-yl)methanol | 362 | 0.006 |
| 6.19 | 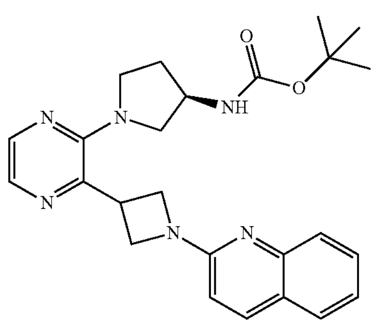 [SMILES: CC(C)(C)OC(=O)N[C@@H]1CCN(c2nccnc2C2CN(c3ccc4ccccc4n3)C2)C1] | (R)-tert-butyl 1-(3-(1-(quinolin-2-yl)azetidin-3-yl)pyrazin-2-yl)pyrrolidin-3-ylcarbamate | 447.0 | 0.021 |

TABLE 18A-continued

EXAMPLES 6.1 TO 6.60

| Ex. # | Structure | Chemical Name | ESI-MS (M + 1) | IC$_{50}$ (μM) |
|---|---|---|---|---|
| 6.20 | 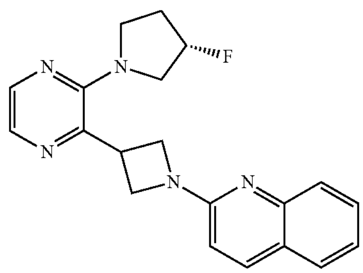 [SMILES: F[C@H]1CCN(c2nccnc2C2CN(c3ccc4ccccc4n3)C2)C1] | (S)-2-(3-(3-(3-fluoropyrrolidin-1-yl)pyrazin-2-yl)azetidin-1-yl)quinoline | 350.0 | 0.023 |
| 6.21 | 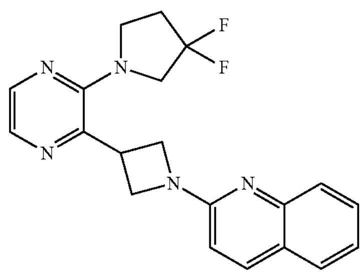 [SMILES: FC1(F)CCN(c2nccnc2C2CN(c3ccc4ccccc4n3)C2)C1] | 2-(3-(3-(3,3-difluoropyrrolidin-1-yl)pyrazin-2-yl)azetidin-1-yl)quinoline | 368 | 0.01575 |
| 6.22 | 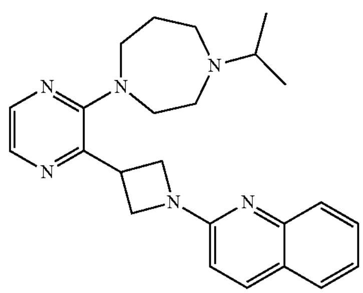 [SMILES: CC(C)N1CCCN(c2nccnc2C2CN(c3ccc4ccccc4n3)C2)CC1] | 2-(3-(3-(4-isopropyl-1,4-diazepan-1-yl)pyrazin-2-yl)azetidin-1-yl)quinoline | 403 | 0.655 |
| 6.23 | 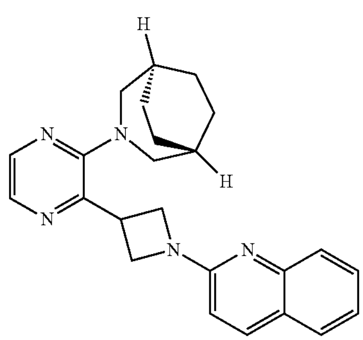 [SMILES: c1ccc2nc(N3CC(c4nccnc4N4C[C@H]5CC[C@@H](CC5)C4)C3)ccc2c1] | (1R,5R)-3-(3-(1-(quinolin-2-yl)azetidin-3-yl)pyrazin-2-yl)-3-azabicyclo[3.2.2]nonane | 386 | 0.035 |
| 6.24 | 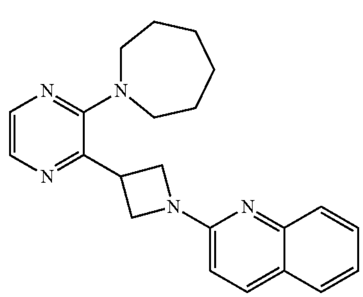 [SMILES: c1ccc2nc(N3CC(c4nccnc4N4CCCCCC4)C3)ccc2c1] | 2-(3-(3-(azepan-1-yl)pyrazin-2-yl)azetidin-1-yl)quinoline | 360 | 0.003 |

TABLE 18A-continued

EXAMPLES 6.1 TO 6.60

| Ex. # | Structure | Chemical Name | ESI-MS (M + 1) | IC$_{50}$ (µM) |
|---|---|---|---|---|
| 6.25 | 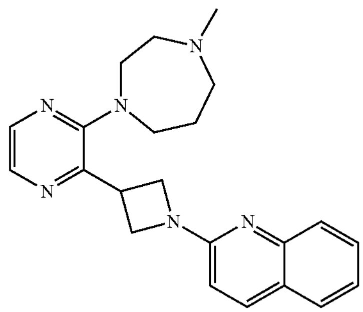 [SMILES: CN1CCCN(c2nccnc2C2CN(c3ccc4ccccc4n3)C2)CC1] | 2-(3-(3-(4-methyl-1,4-diazepan-1-yl)pyrazin-2-yl)azetidin-1-yl)quinoline | 375 | 0.233 |
| 6.26 | 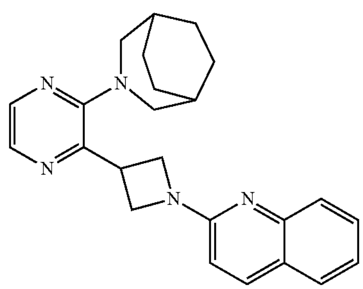 [SMILES: c1ccc2nc(N3CC(c4nccnc4N4CC5CCC(CC5)C4)C3)ccc2c1] | 3-(3-(1-(quinolin-2-yl)azetidin-3-yl)pyrazin-2-yl)-3-azabicyclo[3.2.2]nonane | 386 | 0.035 |
| 6.27 | 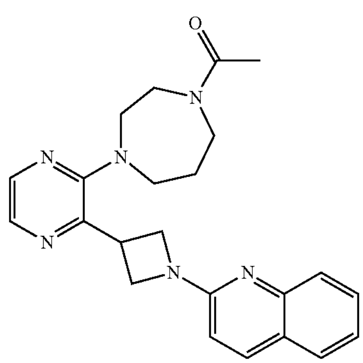 [SMILES: CC(=O)N1CCCN(c2nccnc2C2CN(c3ccc4ccccc4n3)C2)CC1] | 1-(4-(3-(1-(quinolin-2-yl)azetidin-3-yl)pyrazin-2-yl)-1,4-diazepan-1-yl)ethanone | 403 | 0.01607 |
| 6.28 | 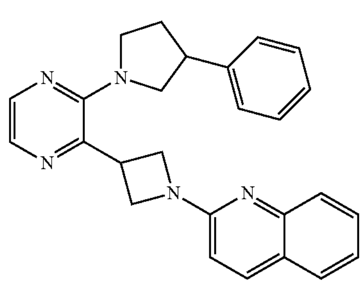 [SMILES: c1ccc(C2CCN(c3nccnc3C3CN(c4ccc5ccccc5n4)C3)C2)cc1] | (R- & S-)-2-(3-(3-(3-phenylpyrrolidin-1-yl)pyrazin-2-yl)azetidin-1-yl)quinoline | 408 | 0.0050 |

TABLE 18A-continued

EXAMPLES 6.1 TO 6.60

| Ex. # | Structure | Chemical Name | ESI-MS (M + 1) | IC$_{50}$ (μM) |
|---|---|---|---|---|
| 6.29 | 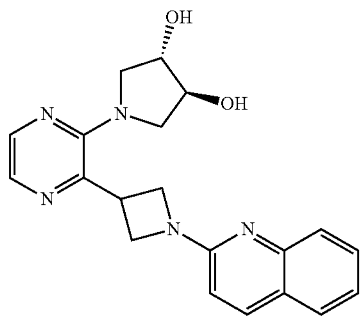 [SMILES: O[C@H]1CN(c2nccnc2C2CN(c3ccc4ccccc4n3)C2)C[C@@H]1O] | (3S,4S)-1-(3-(1-(quinolin-2-yl)azetidin-3-yl)pyrazin-2-yl)pyrrolidine-3,4-diol | 364 | 0.085 |
| 6.30 | 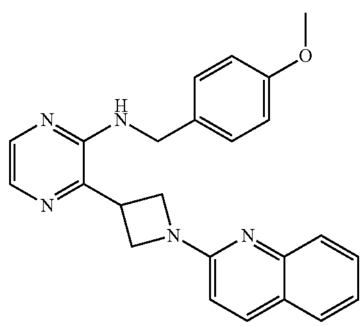 [SMILES: COc1ccc(CNc2nccnc2C2CN(c3ccc4ccccc4n3)C2)cc1] | N-(4-methoxybenzyl)-3-(1-(quinolin-2-yl)azetidin-3-yl)pyrazin-2-amine | 398 | 0.189 |
| 6.31 | 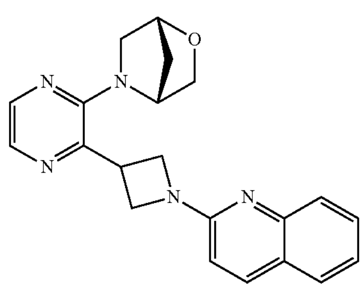 [SMILES: c1ccc2nc(N3CC(c4nccnc4N4C[C@H]5C[C@@H]4CO5)C3)ccc2c1] | (1R,4R)-5-(3-(1-(quinolin-2-yl)azetidin-3-yl)pyrazin-2-yl)-2-oxa-5-azabicyclo[2.2.1]heptane | 360 | 0.01545 |
| 6.32 | 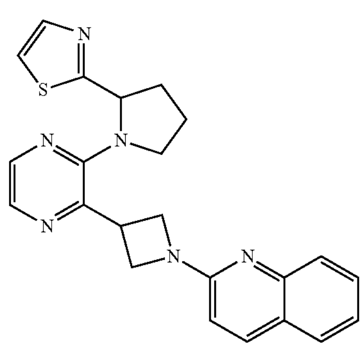 [SMILES: c1ccc2nc(N3CC(c4nccnc4N4CCCC4c4nccs4)C3)ccc2c1] | (R- & S-)-2-(1-(3-(1-(quinolin-2-yl)azetidin-3-yl)pyrazin-2-yl)pyrrolidin-3-yl)thiazole | 415 | 0.0871 |

TABLE 18A-continued

EXAMPLES 6.1 TO 6.60

| Ex. # | Structure | Chemical Name | ESI-MS (M + 1) | IC$_{50}$ (μM) |
|---|---|---|---|---|
| 6.33 | 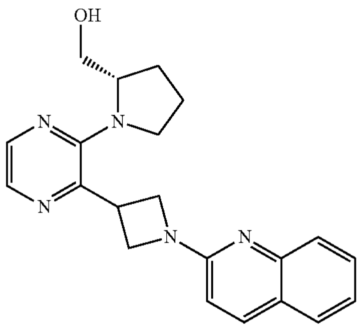 [SMILES: OC[C@@H]1CCCN1c1nccnc1C1CN(c2ccc3ccccc3n2)C1] | (S)-(1-(3-(1-(quinolin-2-yl)azetidin-3-yl)pyrazin-2-yl)pyrrolidin-2-yl)methanol | 362 | 0.01457 |
| 6.34 | 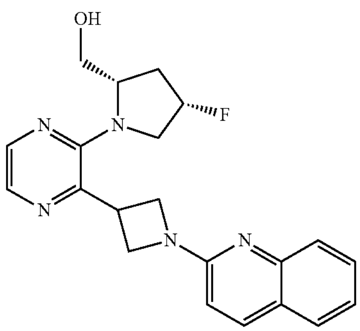 [SMILES: OC[C@@H]1C[C@H](F)CN1c1nccnc1C1CN(c2ccc3ccccc3n2)C1] | ((2S,4S)-4-fluoro-1-(3-(1-(quinolin-2-yl)azetidin-3-yl)pyrazin-2-yl)pyrrolidin-2-yl)methanol | 380 | 0.02989 |
| 6.35 | 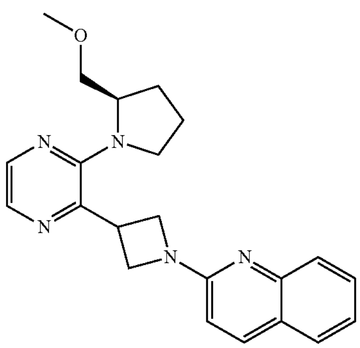 [SMILES: COC[C@H]1CCCN1c1nccnc1C1CN(c2ccc3ccccc3n2)C1] | (R)-2-(3-(3-(2-(methoxymethyl)pyrrolidin-1-yl)pyrazin-2-yl)azetidin-1-yl)quinoline | 362 | 0.81150 |
| 6.36 | 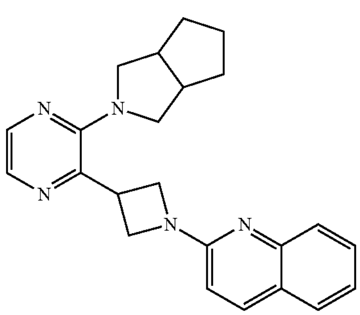 [SMILES: c1ccc2nc(N3CC(c4nccnc4N4CC5CCCC5C4)C3)ccc2c1] | 2-(3-(3-(hexahydrocyclopenta[c]pyrrol-2(1H)-yl)pyrazin-2-yl)azetidin-1-yl)quinoline | 372 | 0.00396 |

TABLE 18A-continued

EXAMPLES 6.1 TO 6.60

| Ex. # | Structure | Chemical Name | ESI-MS (M + 1) | IC$_{50}$ (μM) |
|---|---|---|---|---|
| 6.37 | 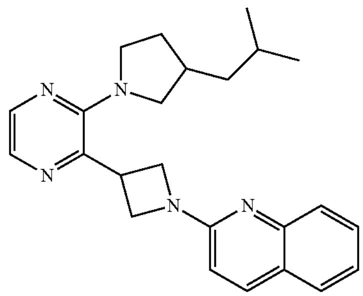 [SMILES: CC(C)CC1CCN(c2nccnc2C2CN(c3ccc4ccccc4n3)C2)C1] | (R- & S-)-2-(3-(3-(3-isobutylpyrrolidin-1-yl)pyrazin-2-yl)azetidin-1-yl)quinoline | 388 | 0.02193 |
| 6.38 | 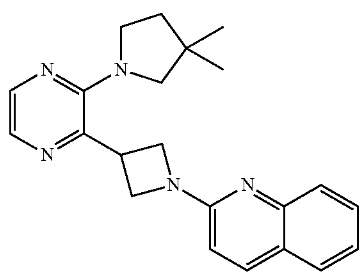 [SMILES: CC1(C)CCN(c2nccnc2C2CN(c3ccc4ccccc4n3)C2)C1] | 2-(3-(3-(3,3-dimethylpyrrolidin-1-yl)pyrazin-2-yl)azetidin-1-yl)quinoline | 360 | 0.01275 |
| 6.39 | 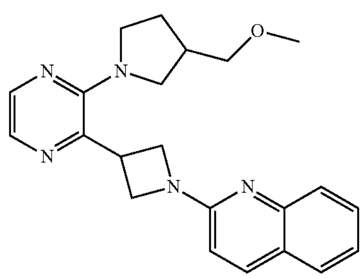 [SMILES: COCC1CCN(c2nccnc2C2CN(c3ccc4ccccc4n3)C2)C1] | (R- & S-)-2-(3-(3-(3-(methoxymethyl)pyrrolidin-1-yl)pyrazin-2-yl)azetidin-1-yl)quinoline | 376 | 0.00666 |
| 6.40 | 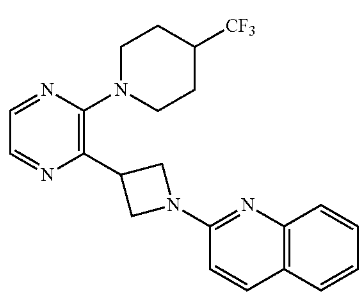 [SMILES: FC(F)(F)C1CCN(c2nccnc2C2CN(c3ccc4ccccc4n3)C2)CC1] | 2-(3-(3-(4-(trifluoromethyl)piperidin-1-yl)pyrazin-2-yl)azetidin-1-yl)quinoline | 414 | 0.0065 |
| 6.41 | 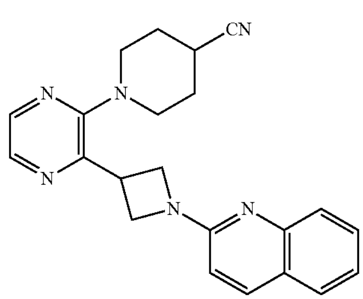 [SMILES: N#CC1CCN(c2nccnc2C2CN(c3ccc4ccccc4n3)C2)CC1] | 1-(3-(1-(quinolin-2-yl)azetidin-3-yl)pyrazin-2-yl)piperidine-4-carbonitrile | 371 | 0.00013 |

TABLE 18A-continued

EXAMPLES 6.1 TO 6.60

| Ex. # | Structure | Chemical Name | ESI-MS (M + 1) | IC$_{50}$ (μM) |
|---|---|---|---|---|
| 6.42 | 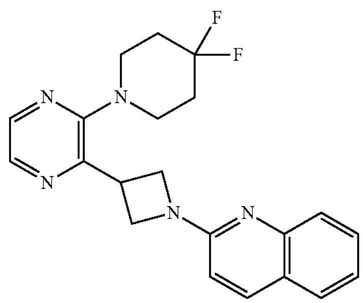 [SMILES: FC1(F)CCN(c2nccnc2C2CN(c3ccc4ccccc4n3)C2)CC1] | 2-(3-(3-(4,4-difluoropiperidin-1-yl)pyrazin-2-yl)azetidin-1-yl)quinoline | 382 | 0.0086 |
| 6.43 | 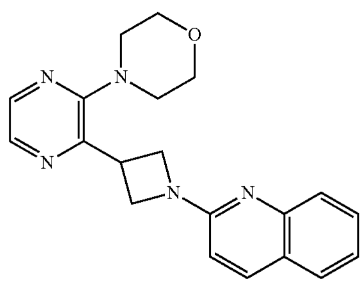 [SMILES: c1ccc2nc(N3CC(c4nccnc4N4CCOCC4)C3)ccc2c1] | 4-(3-(1-(quinolin-2-yl)azetidin-3-yl)pyrazin-2-yl)morpholine | 348 | 0.0147 |
| 6.44 | 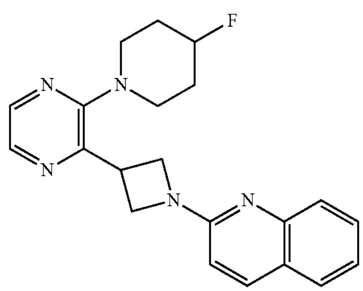 [SMILES: FC1CCN(c2nccnc2C2CN(c3ccc4ccccc4n3)C2)CC1] | 2-(3-(3-(4-fluoropiperidin-1-yl)pyrazin-2-yl)azetidin-1-yl)quinoline | 364 | 0.0014 |
| 6.45 | 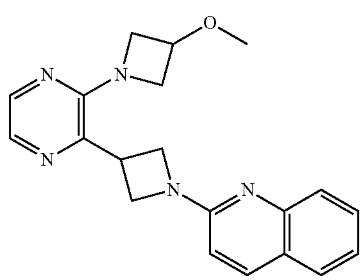 [SMILES: COC1CN(c2nccnc2C2CN(c3ccc4ccccc4n3)C2)C1] | 2-(3-(3-(3-methoxyazetidin-1-yl)pyrazin-2-yl)azetidin-1-yl)quinoline | 348 | 0.021 |
| 6.46 | 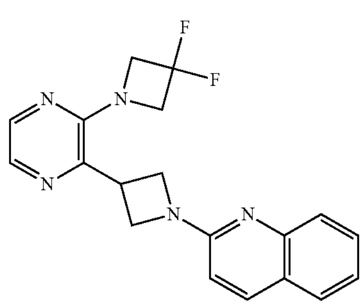 [SMILES: FC1(F)CN(c2nccnc2C2CN(c3ccc4ccccc4n3)C2)C1] | 2-(3-(3-(3,3-difluoroazetidin-1-yl)pyrazin-2-yl)azetidin-1-yl)quinoline | 354 | 0.027 |

TABLE 18A-continued

EXAMPLES 6.1 TO 6.60

| Ex. # | Structure | Chemical Name | ESI-MS (M + 1) | IC$_{50}$ (µM) |
|---|---|---|---|---|
| 6.47 | 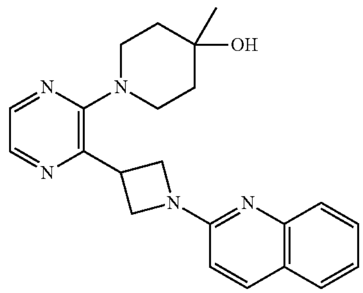 [SMILES: CC1(O)CCN(c2nccnc2C2CN(c3ccc4ccccc4n3)C2)CC1] | 4-methyl-1-(3-(1-(quinolin-2-yl)azetidin-3-yl)pyrazin-2-yl)piperidin-4-ol | 376 | 0.0097 |
| 6.48 | 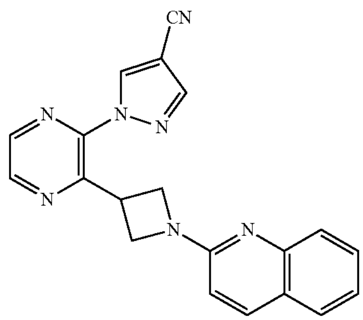 [SMILES: N#Cc1cnn(-c2nccnc2C2CN(c3ccc4ccccc4n3)C2)c1] | 1-(3-(1-(quinolin-2-yl)azetidin-3-yl)pyrazin-2-yl)-1H-pyrazole-4-carbonitrile | 354 | 0.066 |
| 6.49 | 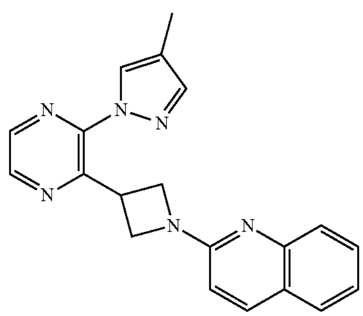 [SMILES: Cc1cnn(-c2nccnc2C2CN(c3ccc4ccccc4n3)C2)c1] | 2-(3-(3-(4-methyl-1H-pyrazol-1-yl)pyrazin-2-yl)azetidin-1-yl)quinoline | 343 | 0.020 |
| 6.50 | 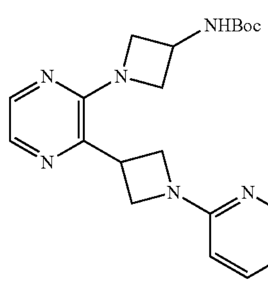 | tert-butyl (1-(3-(1-(quinolin-2-yl)azetidin-3-yl)pyrazin-2-yl)azetidin-3-yl)carbamate | 433 | 0.0056 |
| 6.51 | 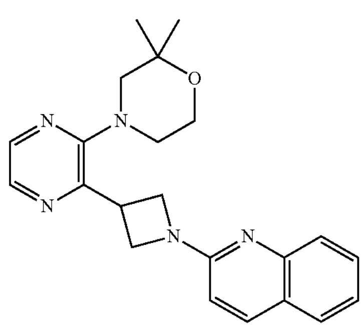 [SMILES: CC1(C)CN(c2nccnc2C2CN(c3ccc4ccccc4n3)C2)CCO1] | 2,2-dimethyl-4-(3-(1-(quinolin-2-yl)azetidin-3-yl)pyrazin-2-yl)morpholine | 376 | 0.006 |

TABLE 18A-continued

EXAMPLES 6.1 TO 6.60

| Ex. # | Structure | Chemical Name | ESI-MS (M + 1) | IC$_{50}$ (μM) |
|---|---|---|---|---|
| 6.52 | 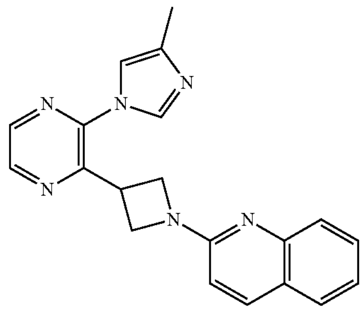 [SMILES: Cc1cn(-c2nccnc2C2CN(c3ccc4ccccc4n3)C2)cn1] | 2-(3-(3-(4-methyl-1H-imidazol-1-yl)pyrazin-2-yl)azetidin-1-yl)quinoline | 343 | 0.005 |
| 6.53 | 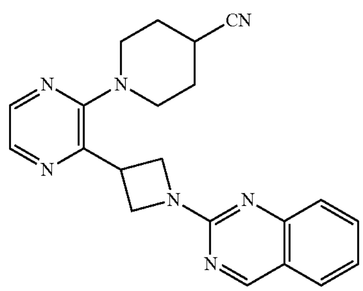 [SMILES: N#CC1CCN(c2nccnc2C2CN(c3ncc4ccccc4n3)C2)CC1] | 1-(3-(1-(quinazolin-2-yl)azetidin-3-yl)pyrazin-2-yl)piperidine-4-carbonitrile | 372 | 0.0015 |
| 6.54 | 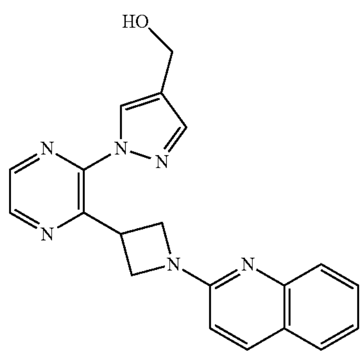 [SMILES: OCc1cnn(-c2nccnc2C2CN(c3ccc4ccccc4n3)C2)c1] | (1-(3-(1-(quinolin-2-yl)azetidin-3-yl)pyrazin-2-yl)-1H-pyrazol-4-yl)methanol | 359 | 0.091 |
| 6.55 | 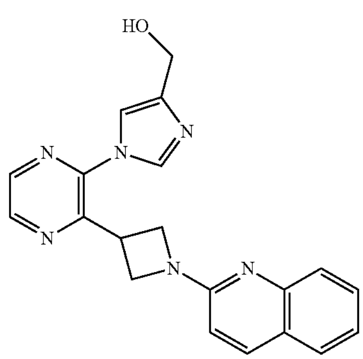 [SMILES: OCc1cn(-c2nccnc2C2CN(c3ccc4ccccc4n3)C2)cn1] | (1-(3-(1-(quinolin-2-yl)azetidin-3-yl)pyrazin-2-yl)-1H-imidazol-4-yl)methanol | 359 | 0.270 |

TABLE 18A-continued

EXAMPLES 6.1 TO 6.60

| Ex. # | Structure | Chemical Name | ESI-MS (M + 1) | IC$_{50}$ (μM) |
|---|---|---|---|---|
| 6.56 | 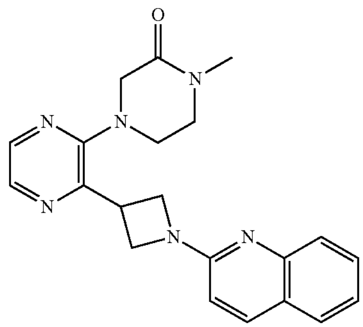 [SMILES: CN1CCN(c2nccnc2C2CN(c3ccc4ccccc4n3)C2)CC1=O] | 1-methyl-4-(3-(1-(quinolin-2-yl)azetidin-3-yl)pyrazin-2-yl)piperazin-2-one | 375 | 0.0022 |
| 6.57 | 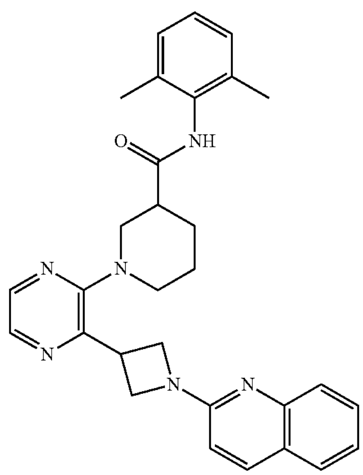 [SMILES: Cc1cccc(C)c1NC(=O)C1CCCN(c2nccnc2C2CN(c3ccc4ccccc4n3)C2)C1] | N-(2,6-dimethylphenyl)-1-(3-(1-(quinolin-2-yl)azetidin-3-yl)pyrazin-2-yl)piperidine-3-carboxamide | 493 | 0.010 |
| 6.58 | 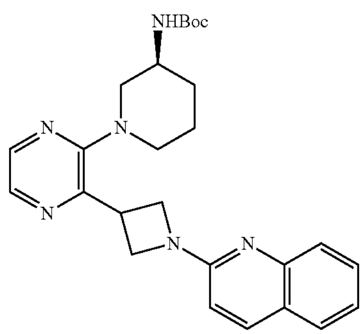 [SMILES: CC(C)(C)OC(=O)N[C@H]1CCCN(c2nccnc2C2CN(c3ccc4ccccc4n3)C2)C1] | (S)-tert-butyl (1-(3-(1-(quinolin-2-yl)azetidin-3-yl)pyrazin-2-yl)piperidin-3-yl)carbamate | 461 | 0.013 |
| 6.59 | 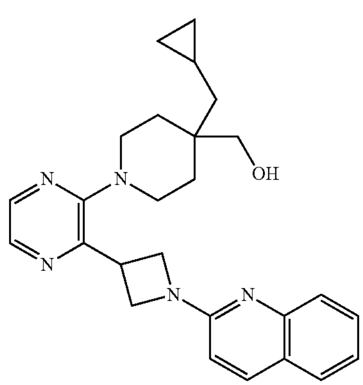 [SMILES: OCC1(CC2CC2)CCN(c2nccnc2C2CN(c3ccc4ccccc4n3)C2)CC1] | (4-(cyclopropylmethyl)-1-(3-(1-(quinolin-2-yl)azetidin-3-yl)pyrazin-2-yl)piperidin-4-yl)methanol | 430 | 0.004 |

TABLE 18A-continued

EXAMPLES 6.1 TO 6.60

| Ex. # | Structure | Chemical Name | ESI-MS (M + 1) | IC$_{50}$ (μM) |
|---|---|---|---|---|
| 6.60 | 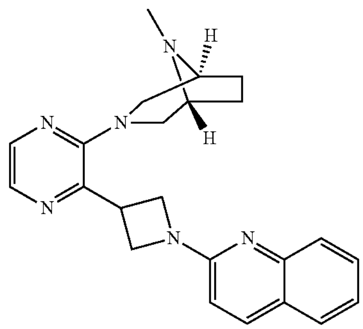 [SMILES: CN1[C@@H]2CC[C@H]1CN(c1nccnc1C1CN(c3ccc4ccccc4n3)C1)C2] | 2-(3-(3-((1R,5S)-8-methyl-3,8-diazabicyclo[3.2.1]octan-3-yl)pyrazin-2-yl)azetidin-1-yl)quinoline | 378 | >10 |

TABLE 18B

STARTING MATERIALS AND REACTION CONDITION FOR PREPARATION OF EXAMPLES 6.1 TO 6.60.
Unless otherwise stated, all starting materials are commerically available from common vendors.

| Ex. # | Key Starting Material(s) | Key Starting Material(s) | Reaction Condition | Purification Condition* |
|---|---|---|---|---|
| 6.1 | Array Biopharma | PREPARATION 2 | TEA, DMSO, 110° C. | A |
| 6.2 | Array Biopharma | PREPARATION 2 | TEA, DMSO, 110° C. | A |
| 6.3 | Array Biopharma | PREPARATION 2 | TEA, DMSO, 110° C. | A |

TABLE 18B-continued

STARTING MATERIALS AND REACTION CONDITION FOR PREPARATION OF EXAMPLES 6.1 TO 6.60.
Unless otherwise stated, all starting materials are commerically available from common vendors.

| Ex. # | Key Starting Material(s) | Key Starting Material(s) | Reaction Condition | Purification Condition* |
|---|---|---|---|---|
| 6.4 | (structure) TCI America | (structure) PREPARATION 2 | TEA, DMSO, 110° C. | A |
| 6.5 | (structure) TCI | (structure) PREPARATION 2 | TEA, DMSO, 110° C. | A |
| 6.6 | (structure) TCI | (structure) PREPARATION 2 | TEA, DMSO, 110° C. | A |
| 6.7 | (structure) ASDI | (structure) PREPARATION 2 | TEA, DMSO, 110° C. | A |
| 6.8 | (structure) ASDI | (structure) PREPARATION 2 | TEA, DMSO, 110° C. | A |

TABLE 18B-continued

STARTING MATERIALS AND REACTION CONDITION FOR PREPARATION OF EXAMPLES 6.1 TO 6.60.
Unless otherwise stated, all starting materials are commerically available from common vendors.

| Ex. # | Key Starting Material(s) | Key Starting Material(s) | Reaction Condition | Purification Condition* |
|---|---|---|---|---|
| 6.9 | 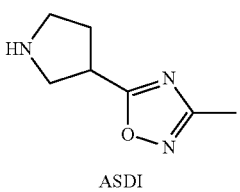<br>ASDI | 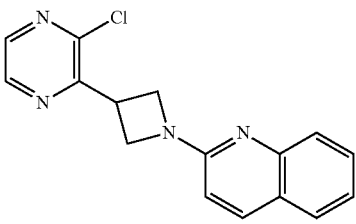<br>PREPARATION 2 | TEA, DMSO, 110° C. | A |
| 6.10 | 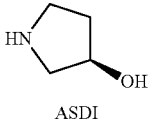<br>ASDI | 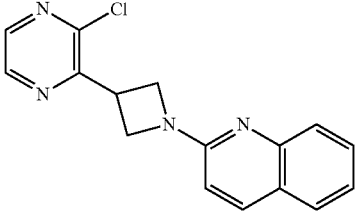<br>PREPARATION 2 | TEA, DMSO, 110° C. | A |
| 6.11 | 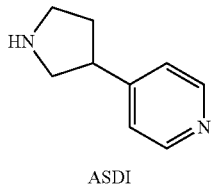 [SMILES: c1cc(C2CCNC2)ccn1]<br>ASDI | 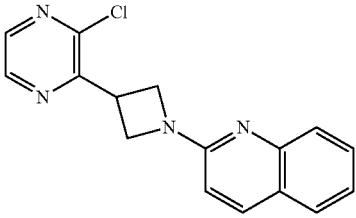<br>PREPARATION 2 | TEA, DMSO, 110° C. | A |
| 6.12 | 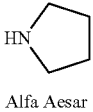<br>Alfa Aesar | 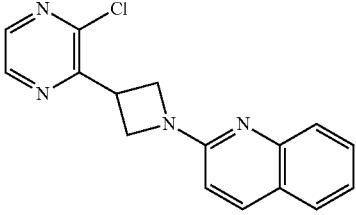<br>PREPARATION 2 | TEA, DMSO, 110° C. | A |
| 6.13 | 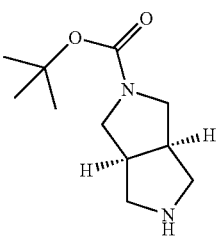<br>Tyger Scientific | 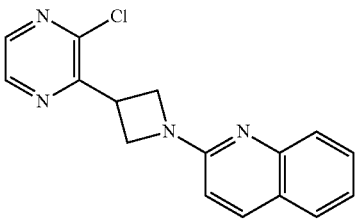<br>PREPARATION 2 | TEA, DMSO, 110° C. | A |

TABLE 18B-continued

STARTING MATERIALS AND REACTION CONDITION FOR PREPARATION OF EXAMPLES 6.1 TO 6.60.
Unless otherwise stated, all starting materials are commerically available from common vendors.

| Ex. # | Key Starting Material(s) | Key Starting Material(s) | Reaction Condition | Purification Condition* |
|---|---|---|---|---|
| 6.14 | 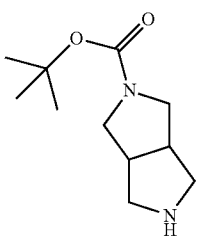<br>J & W PharmLab | 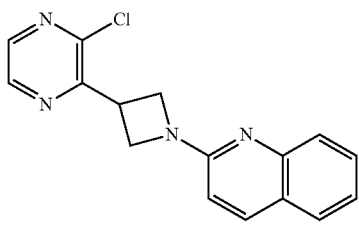<br>PREPARATION 2 | TEA, DMSO, 110° C. | A |
| 6.15 | 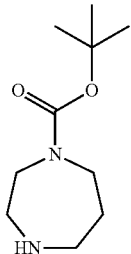<br>Aldrich | 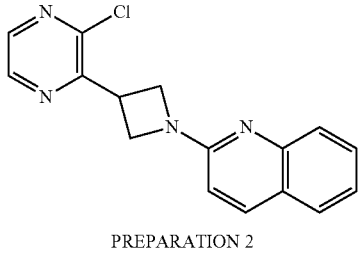 [SMILES: Clc1nccnc1C1CN(c2ccc3ccccc3n2)C1]<br>PREPARATION 2 | TEA, DMSO, 110° C. | A |
| 6.16 | 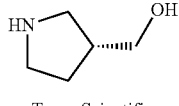<br>Tyger Scientific | 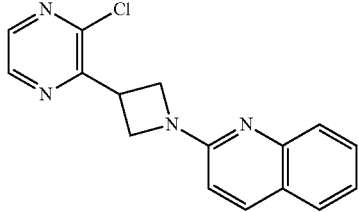<br>PREPARATION 2 | TEA, DMSO, 110° C., | D |
| 6.17 | 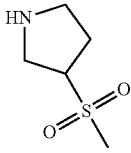<br>Pharma Tech | 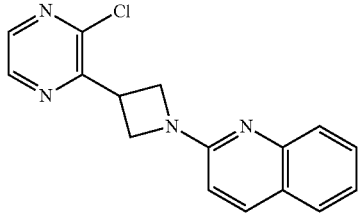<br>PREPARATION 2 | TEA, DMSO, 110° C. | A |
| 6.18 | 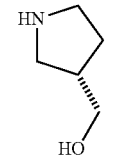<br>Tyger Scientific | 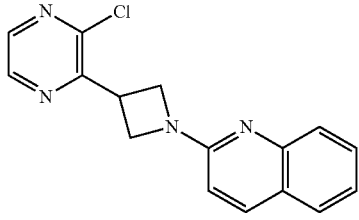<br>PREPARATION 2 | TEA, DMSO, 110° C. | A |

TABLE 18B-continued

STARTING MATERIALS AND REACTION CONDITION FOR PREPARATION OF EXAMPLES 6.1 TO 6.60.
Unless otherwise stated, all starting materials are commerically available from common vendors.

| Ex. # | Key Starting Material(s) | Key Starting Material(s) | Reaction Condition | Purification Condition* |
|---|---|---|---|---|
| 6.19 | 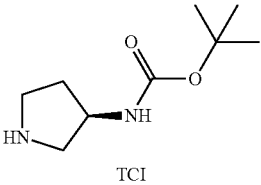 TCI | 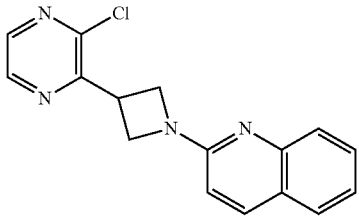 PREPARATION 2 | TEA, DMSO, 110° C. | A |
| 6.20 | 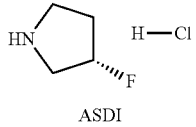 ASDI | 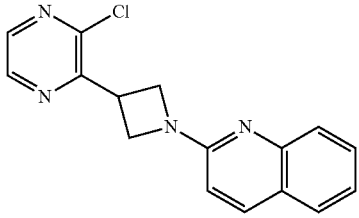 PREPARATION 2 | $K_2CO_3$, DMSO, 110° C. | A |
| 6.21 | 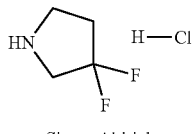 Sigma Aldrich | 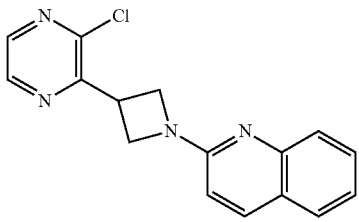 PREPARATION 2 | $K_2CO_3$, DMSO, 110° C. | B |
| 6.22 | 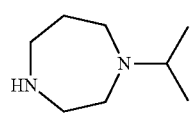 ASDI | 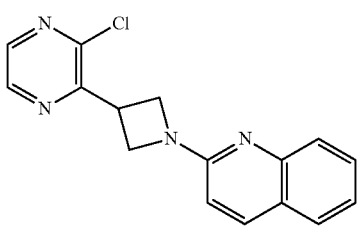 PREPARATION 2 | $K_2CO_3$, DMSO, 110° C. | A |
| 6.23 | 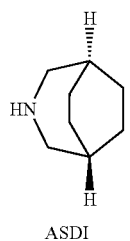 ASDI | 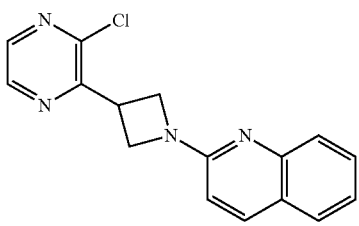 PREPARATION 2 | $K_2CO_3$, DMSO, 110° C. | A |

TABLE 18B-continued

STARTING MATERIALS AND REACTION CONDITION FOR PREPARATION OF EXAMPLES 6.1 TO 6.60.
Unless otherwise stated, all starting materials are commerically available from common vendors.

| Ex. # | Key Starting Material(s) | Key Starting Material(s) | Reaction Condition | Purification Condition* |
|---|---|---|---|---|
| 6.24 | 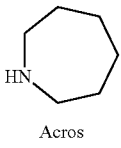 Acros | 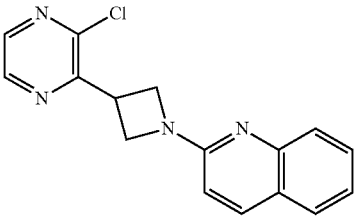 PREPARATION 2 | $K_2CO_3$, DMSO, 110° C. | A |
| 6.25 | 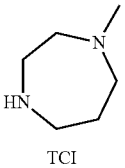 TCI | 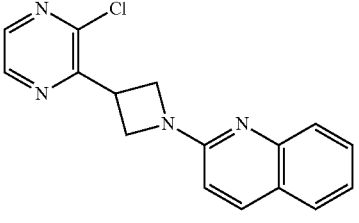 PREPARATION 2 | $K_2CO_3$, DMSO, 110° C. | A |
| 6.26 | 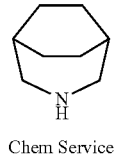 Chem Service | 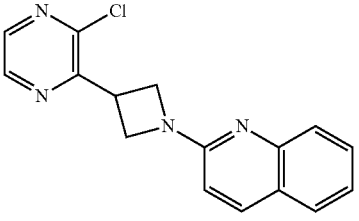 PREPARATION 2 | $K_2CO_3$, DMSO, 110° C. | A |
| 6.27 | 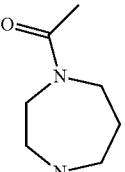 Alfa Aesar | 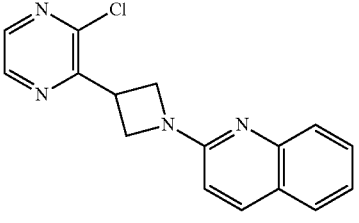 PREPARATION 2 | $K_2CO_3$, DMSO, 110° C. | A |
| 6.28 | 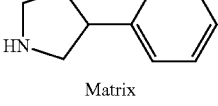 Matrix | 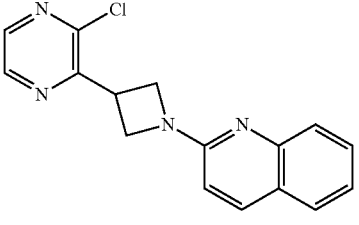 PREPARATION 2 | $K_2CO_3$, DMSO, 110° C. | A |

TABLE 18B-continued

STARTING MATERIALS AND REACTION CONDITION FOR PREPARATION OF EXAMPLES 6.1 TO 6.60.
Unless otherwise stated, all starting materials are commerically available from common vendors.

| Ex. # | Key Starting Material(s) | Key Starting Material(s) | Reaction Condition | Purification Condition* |
|---|---|---|---|---|
| 6.29 | 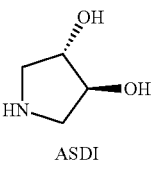<br>ASDI | 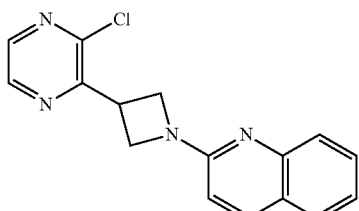<br>PREPARATION 2 | $K_2CO_3$, DMSO, 110° C. | A |
| 6.30 | 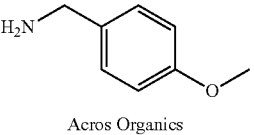<br>Acros Organics | 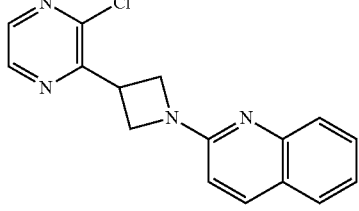<br>PREPARATION 2 | $K_2CO_3$, DMSO, 110° C. | C |
| 6.31 | 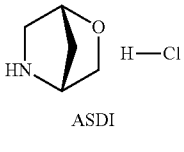<br>ASDI | 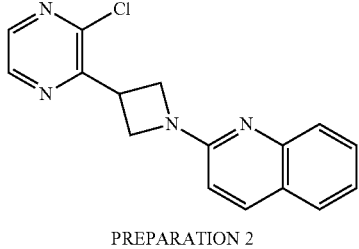 [SMILES: Clc1nccnc1C1CN(c2ccc3ccccc3n2)C1]<br>PREPARATION 2 | $K_2CO_3$, DMSO, 110° C. | A |
| 6.32 | 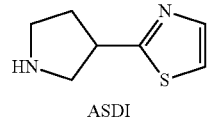<br>ASDI | 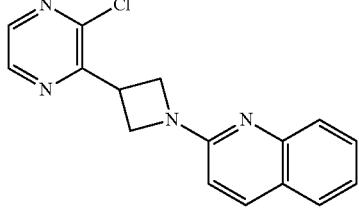<br>PREPARATION 2 | $K_2CO_3$, DMSO, 110° C. | A |
| 6.33 | 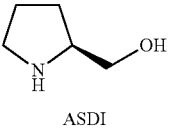<br>ASDI | 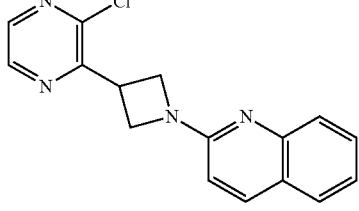<br>PREPARATION 2 | $K_2CO_3$, DMSO, 110° C. | A |

TABLE 18B-continued

STARTING MATERIALS AND REACTION CONDITION FOR PREPARATION OF EXAMPLES 6.1 TO 6.60.
Unless otherwise stated, all starting materials are commerically available from common vendors.

| Ex. # | Key Starting Material(s) | Key Starting Material(s) | Reaction Condition | Purification Condition* |
|---|---|---|---|---|
| 6.34 | ASDI | PREPARATION 2 | $K_2CO_3$, DMSO, 110° C. | A |
| 6.35 | ASDI | PREPARATION 2 | $K_2CO_3$, DMSO, 110° C. | A |
| 6.36 | Beta Pharma | PREPARATION 2 | $K_2CO_3$, DMSO, 110° C. | A |
| 6.37 | ChemBridge | PREPARATION 2 | $K_2CO_3$, DMSO, 110° C. | A |
| 6.38 | ChemBridge | PREPARATION 2 | $K_2CO_3$, DMSO, 110° C. | A |

TABLE 18B-continued

STARTING MATERIALS AND REACTION CONDITION FOR PREPARATION OF EXAMPLES 6.1 TO 6.60.
Unless otherwise stated, all starting materials are commerically available from common vendors.

| Ex. # | Key Starting Material(s) | Key Starting Material(s) | Reaction Condition | Purification Condition* |
|---|---|---|---|---|
| 6.39 | 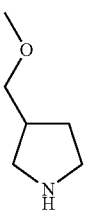<br>ChemBridge | 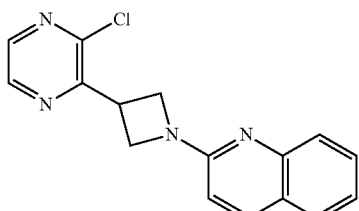<br>PREPARATION 2 | K$_2$CO$_3$, DMSO, 110° C. | A |
| 6.40 | 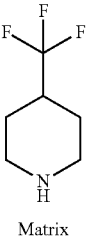<br>Matrix | 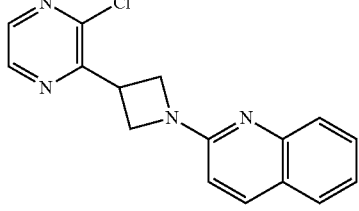<br>PREPARATION 2 | TEA, DMSO, 110° C. | B |
| 6.41 | 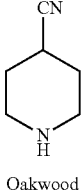<br>Oakwood | 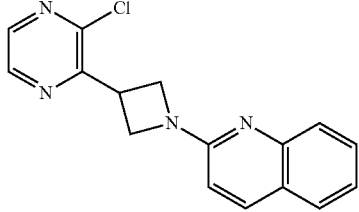<br>PREPARATION 2 | TEA, DMSO, 110° C. | B |
| 6.42 | 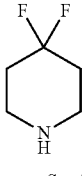<br>Lancaster Synthesis | 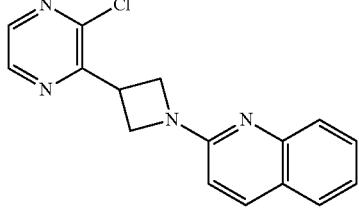<br>PREPARATION 2 | TEA, DMSO, 110° C. | B |
| 6.43 | 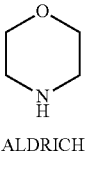<br>ALDRICH | 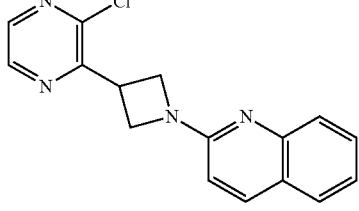<br>PREPARATION 2 | TEA, DMSO, 110° C. | B |

TABLE 18B-continued

STARTING MATERIALS AND REACTION CONDITION FOR PREPARATION OF EXAMPLES 6.1 TO 6.60.
Unless otherwise stated, all starting materials are commerically available from common vendors.

| Ex. # | Key Starting Material(s) | Key Starting Material(s) | Reaction Condition | Purification Condition* |
|---|---|---|---|---|
| 6.44 | 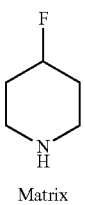 Matrix | 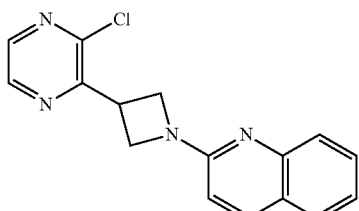 PREPARATION 2 | TEA, DMSO, 110° C. | B |
| 6.45 | 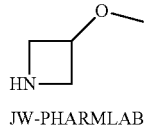 JW-PHARMLAB | 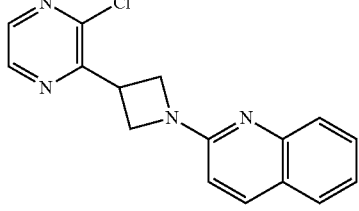 PREPARATION 2 | TEA, DMSO, 110° C. | B |
| 6.46 | 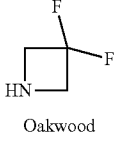 Oakwood | 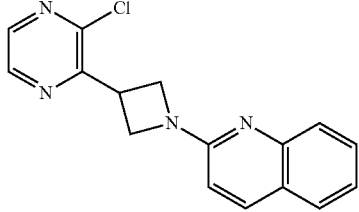 PREPARATION 2 | TEA, DMSO, 110° C. | B |
| 6.47 | 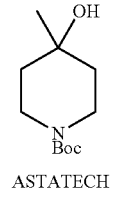 ASTATECH | 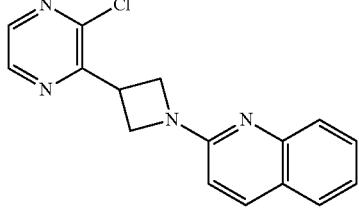 PREPARATION 2 | 1. HCl<br>2. Et$_3$N, DMSO, 110° C. | B |
| 6.48 | 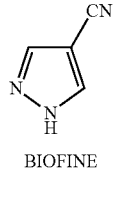 BIOFINE | 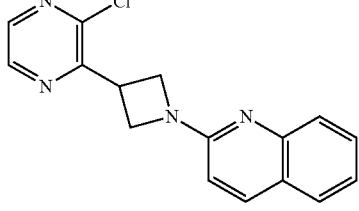 PREPARATION 2 | Cs$_2$CO$_3$, DMSO, 110° C. | B |

TABLE 18B-continued

STARTING MATERIALS AND REACTION CONDITION FOR PREPARATION OF EXAMPLES 6.1 TO 6.60.
Unless otherwise stated, all starting materials are commerically available from common vendors.

| Ex. # | Key Starting Material(s) | Key Starting Material(s) | Reaction Condition | Purification Condition* |
|---|---|---|---|---|
| 6.49 | 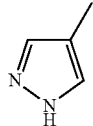 ALDRICH | 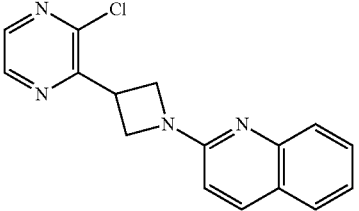 PREPARATION 2 | CsCO₃, DMSO, 110° C. | B |
| 6.50 | 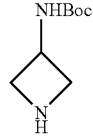 OAKWOOD | 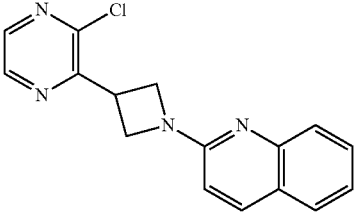 PREPARATION 2 | TEA, DMSO, 110° C. | B |
| 6.51 | 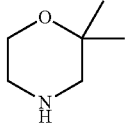 CHEMBRIDGE | 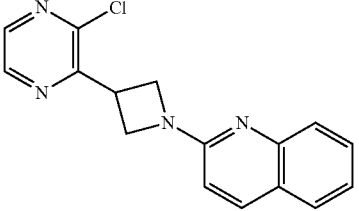 PREPARATION 2 | TEA, DMSO, 110° C. | B |
| 6.52 | 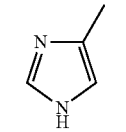 ALFA AESAR | 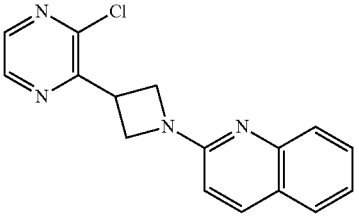 PREPARATION 2 | CsCO₃, DMSO, 110° C. | B |
| 6.53 | 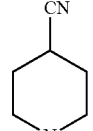 Oakwood | 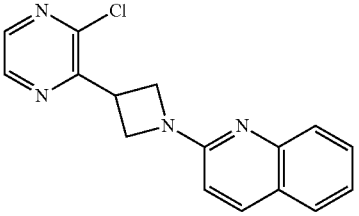 PREPARATION 2 | TEA, DMSO, 110° C. | B |

TABLE 18B-continued

STARTING MATERIALS AND REACTION CONDITION FOR PREPARATION OF EXAMPLES 6.1 TO 6.60.
Unless otherwise stated, all starting materials are commerically available from common vendors.

| Ex. # | Key Starting Material(s) | Key Starting Material(s) | Reaction Condition | Purification Condition* |
|---|---|---|---|---|
| 6.54 | BIOFINE | PREPARATION 2 | allylchloro[1,3-bis(2,6-di-i-propylphenyl)-4,5-dihydroimidazol-2-ylidene]palladium(II), $Cs_2CO_3$, Dioxane, 135° C., µW, 30 min | E |
| 6.55 | ALDRICH | PREPARATION 2 | TEA, DMSO, 110° C. | B |
| 6.56 | CHINGLU PHARM. | PREPARATION 2 | TEA, DMSO, 110° C. | B |
| 6.57 | ASDI | PREPARATION 2 | TEA, DMSO, 110° C. | B |
| 6.58 | ASDI | PREPARATION 2 | TEA, DMSO, 110° C. | B |

TABLE 18B-continued

STARTING MATERIALS AND REACTION CONDITION FOR PREPARATION OF EXAMPLES 6.1 TO 6.60.
Unless otherwise stated, all starting materials are commerically available from common vendors.

| Ex. # | Key Starting Material(s) | Key Starting Material(s) | Reaction Condition | Purification Condition* |
|---|---|---|---|---|
| 6.59 | ASDI | PREPARATION 2 | TEA, DMSO, 110° C. | B |
| 6.60 | J & W PharmLab | PREPARATION 2 | $K_2CO_3$, DMSO, 110° C. | C |

*Purification Conditions:
Method A- reverse phase purification using the following conditions: (Instrumentation: MS-Waters SQ; UV-Waters 2487 or Waters PD; Solvents: A:Water w/ 0.1% $NH_4OH$ B: Acetonitrile w/ 0.1% $NH_4OH$; Column: Phenomenex Gemini-NX C18 110A 5 um 21 × 100; Flow Rate: 44 mL/min. 10 min Method, variable gradient over 8 mins).
Method B- purification by silica gel chromatography: (Biotage 50 g SNAP HP-silica column, eluting with a gradient of EtOAc in hexane).
Method C- reverse-phase HPLC (Gilson; Gemini-NX 10m C18 110A AXIA, 100 × 50 mm column) eluting with 0.1% TFA-$H_2O$:0.1% TFA $CH_3CN$ (9:1 → 1:9). The fractions containing the desired product were combined and concentrated in vacuo. The residue was dissolved in DCM and loaded onto a Si-Carbonate cartridge (Silicycle) eluting with DCM.
Method D- Product precipitated out of solution.
Method E-purification by silica gel chromatography eluting with a gradient of MeOH in DCM.

TABLE 18C

1H NMR δ (PPM) DATA FOR EXAMPLES 6.1 TO 6.60

| Ex. # | Structure | NMR |
|---|---|---|
| 6.1 | 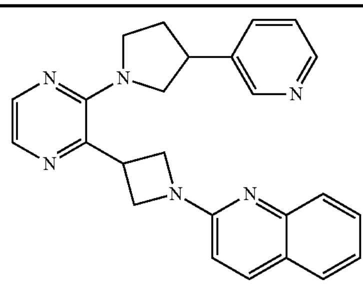 | (400 MHz, DMSO-$d_6$) 2.09 (quin, J = 9.88 Hz, 1 H) 2.38 (td, J = 5.87, 2.35 Hz, 1 H) 3.44-3.56 (m, 1 H) 3.55-3.66 (m, 2 H) 3.76 (td, J = 9.78, 6.65 Hz, 1 H) 3.85 (dd, J = 9.78, 7.43 Hz, 1 H) 4.27-4.49 (m, 5 H) 6.78 (d, J = 9.00 Hz, 1 H) 7.16-7.25 (m, 1 H) 7.39 (dd, J = 7.82, 4.69 Hz, 1 H) 7.46-7.59 (m, 2 H) 7.70 (d, J = 7.82 Hz, 1 H) 7.77-7.85 (m, 1 H) 7.93-8.06 (m, 3 H) 8.48 (dd, J = 4.69, 1.56 Hz, 1 H) 8.60 (d, J = 2.35 Hz, 1 H) |
| 6.2 | 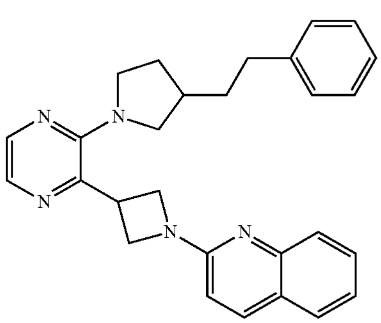 [SMILES: c1ccc(CCC2CCN(c3nccnc3C3CN(c4ccc5ccccc5n4)C3)C2)cc1] | (400 MHz, DMSO-$d_6$) 1.54-1.68 (m, 1 H) 1.76 (q, J = 6.91 Hz, 2 H) 2.02-2.24 (m, 2 H) 2.68 (t, J = 7.63 Hz, 2 H) 3.24 (t, J = 9.19 Hz, 1 H) 3.42-3.60 (m, 3 H) 4.34 (s, 4 H) 4.45 (s, 1 H) 6.78 (d, J = 9.00 Hz, 1 H) 7.13-7.34 (m, 6 H) 7.47-7.59 (m, 2 H) 7.71 (d, J = 8.22 Hz, 1 H) 7.91 (d, J = 2.74 Hz, 1 H) 7.97 (d, J = 2.74 Hz, 1 H) 8.03 (d, J = 9.00 Hz, 1 H) |

TABLE 18C-continued

1H NMR δ (PPM) DATA FOR EXAMPLES 6.1 TO 6.60

| Ex. # | Structure | NMR |
|---|---|---|
| 6.3 | 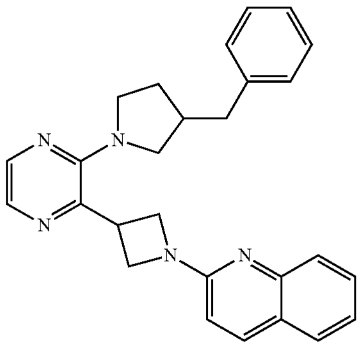 [SMILES: c1ccc(CC2CCN(c3nccnc3C3CN(c4ccc5ccccc5n4)C3)C2)cc1] | (400 MHz, DMSO-$d_6$) 1.60-1.72 (m, 1 H) 1.99 (dd, J = 10.56 Hz, 1 H) 2.75 (dd, J = 7.24, 2.54 Hz, 2 H) 3.23-3.30 (m, 1 H) 3.45 (dd, J = 10.17, 7.04 Hz, 1 H) 3.50-3.59 (m, 2 H) 4.25-4.44 (m, 5 H) 6.77 (d, J = 8.61 Hz, 1 H), 7.15-7.25 (m, 2 H) 7.24-7.29 (m, 2 H) 7.29-7.36 (m, 2 H) 7.47-7.60 (m, 2 H) 7.70 (d, J = 7.82 Hz, 1 H) 7.90 (d, J = 2.35 Hz, 1 H) 7.96 (d, J = 2.74 Hz, 1 H) 8.03 (d, J = 9.00 Hz, 1 H) |
| 6.4 | 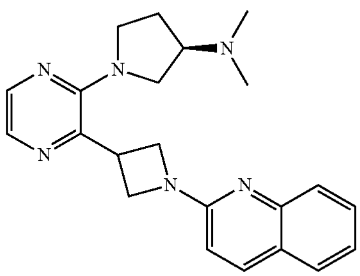 [SMILES: CN(C)[C@@H]1CCN(c2nccnc2C2CN(c3ccc4ccccc4n3)C2)C1] | (400 MHz, DMSO-$d_6$) 2.02-2.18 (m, 1 H) 2.38 (qd, J = 6.00, 3.91 Hz, 1 H) 2.45-2.54 (m, 3 H) 3.45-3.58 (m, 1 H) 3.57-3.67 (m, 2 H) 3.76 (td, J = 9.78, 6.65 Hz, 1 H) 3.86 (dd, J = 9.78, 7.43 Hz, 1 H) 4.30-4.50 (m, 5 H) 6.78 (d, J = 9.00 Hz, 1 H) 7.16-7.25 (m, 1 H) 7.39 (dd, J = 7.82, 4.69 Hz, 1 H) 7.47-7.59 (m, 2 H) 7.70 (d, J = 7.82 Hz, 1 H) 7.82 (d, J = 7.82 Hz, 1 H) 7.95-8.06 (m, 3 H) 8.48 (dd, J = 4.69, 1.56 Hz, 1 H) 8.61 (d, J = 2.35 Hz, 1 H) |
| 6.5 | 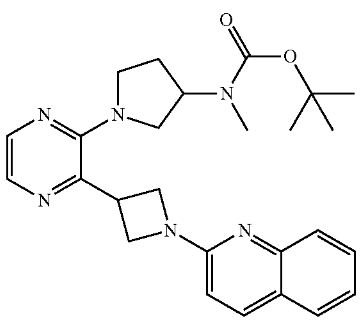 [SMILES: CN(C(=O)OC(C)(C)C)C1CCN(c2nccnc2C2CN(c3ccc4ccccc4n3)C2)C1] | (400 MHz, DMSO-$d_6$) 1.43 (s, 8 H) 2.01-2.13 (m, 2 H) 2.47-2.54 (m, 3 H) 2.81 (s, 3 H) 3.46-3.60 (m, 4 H) 4.29-4.40 (m, 4 H) 4.40-4.49 (m, 1 H) 6.79 (d, J = 8.61 Hz, 1 H) 7.16-7.25 (m, 1 H) 7.47-7.60 (m, 2 H) 7.71 (d, J = 7.82 Hz, 1 H) 7.95-8.06 (m, 2 H) |
| 6.6 | 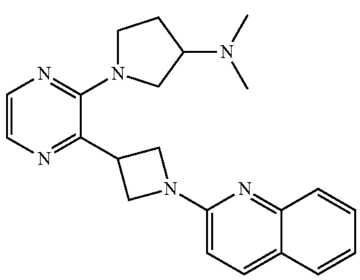 [SMILES: CN(C)C1CCN(c2nccnc2C2CN(c3ccc4ccccc4n3)C2)C1] | (400 MHz, DMSO-$d_6$) 1.76 (quin, J = 10.07 Hz, 1 H) 2.07-2.17 (m, 1 H) 2.22 (s, 5 H) 2.64-2.77 (m, 1 H) 3.17 (br. s., 1 H) 3.41 (s, 1 H) 3.44-3.67 (m, 3 H) 4.35 (dt, J = 8.70, 4.45 Hz, 3 H) 4.41-4.51 (m, 1 H) 6.79 (d, J = 9.00 Hz, 1 H) 7.17-7.25 (m, 1 H) 7.47-7.60 (m, 2 H) 7.71 (d, J = 7.43 Hz, 1 H) 7.96 (dd, J = 18.78, 2.74 Hz, 2 H) 8.03 (d, J = 9.00 Hz, 1 H) |
| 6.7 | 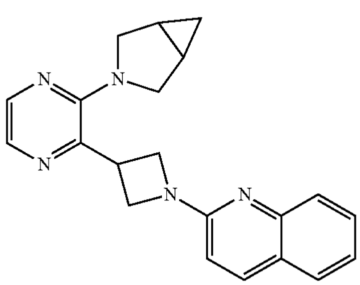 [SMILES: c1ccc2nc(N3CC(c4nccnc4N4CC5CC5C4)C3)ccc2c1] | (400 MHz, DMSO-$d_6$) 0.30 (q, J = 4.30 Hz, 1 H) 0.66 (td, J = 7.63, 4.69 Hz, 1 H) 1.59-1.70 (m, 2 H) 3.46 (d, J = 10.17 Hz, 2 H) 3.73 (d, J = 10.17 Hz, 2 H) 4.23-4.35 (m, 3 H) 4.36-4.46 (m, 2 H) 6.78 (d, J = 9.00 Hz, 1 H) 7.17-7.26 (m, 1 H) 7.48-7.60 (m, 2 H) 7.71 (d, J = 7.43 Hz, 1 H) 7.97 (d, J = 2.35 Hz, 1 H) 8.00 (d, J = 2.35 Hz, 1H) 8.03 (d, J = 9.00 Hz, 1 H) |

TABLE 18C-continued

1H NMR δ (PPM) DATA FOR EXAMPLES 6.1 TO 6.60

| Ex. # | Structure | NMR |
|---|---|---|
| 6.8 | 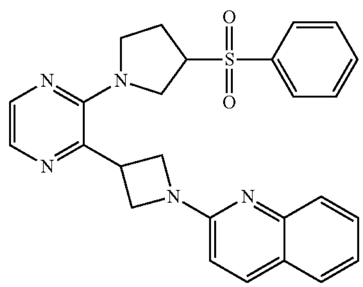 [SMILES: O=S(=O)(c1ccccc1)C1CCN(c2nccnc2C2CN(c3ccc4ccccc4n3)C2)C1] | (400 MHz, DMSO-$d_6$) 2.21-2.37 (m, 2 H) 3.46-3.61 (m, 2 H) 3.63-3.72 (m, 1 H) 3.80 (dd, J = 11.74, 5.87 Hz, 1 H) 4.18-4.40 (m, 6 H) 6.77 (d, J = 9.00 Hz, 1 H) 7.18-7.26 (m, 1 H) 7.48-7.56 (m, 1 H) 7.55-7.61 (m, 1 H) 7.67-7.75 (m, 3 H) 7.77-7.86 (m, 1 H) 7.93-7.99 (m, 2 H) 8.00-8.07 (m, 3 H) |
| 6.9 | 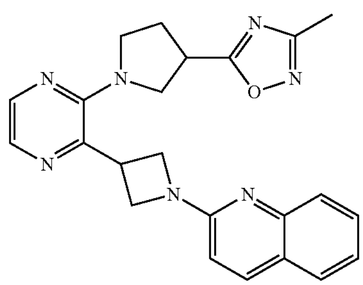 [SMILES: Cc1noc(C2CCN(c3nccnc3C3CN(c4ccc5ccccc5n4)C3)C2)n1] | (400 MHz, DMSO-$d_6$) 2.23-2.35 (m, 1 H) 2.38 (s, 3 H) 2.43-2.51 (m, 1 H) 3.61-3.74 (m, 2 H) 3.79-3.88 (m, 1 H) 3.88-3.99 (m, 2 H) 4.33-4.48 (m, 5 H) 6.81 (d, J = 9.00 Hz, 1 H) 7.24 (ddd, J = 7.92, 6.55, 1.56 Hz, 1 H) 7.52-7.63 (m, 2 H) 7.74 (d, J = 7.43 Hz, 1 H) 8.02-8.04 (m, 1 H) 8.04-8.08 (m, 2 H) |
| 6.10 | 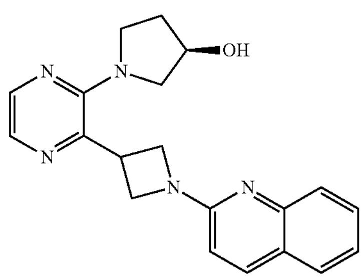 [SMILES: O[C@@H]1CCN(c2nccnc2C2CN(c3ccc4ccccc4n3)C2)C1] | (400 MHz, DMSO-$d_6$) 1.88 (d, J = 3.52 Hz, 1 H) 1.92-2.04 (m, 1 H) 3.25 (d, J = 10.95 Hz, 1 H) 3.40-3.50 (m, 1 H) 3.64-3.76 (m, 2 H) 4.29-4.42 (m, 5 H) 4.42-4.51 (m, 1 H) 4.97 (d, J = 3.13 Hz, 1 H) 6.79 (d, J = 9.00 Hz, 1 H) 7.21 (t, J = 7.43 Hz, 1 H) 7.48-7.60 (m, 2 H) 7.71 (d, J = 7.43 Hz, 1 H) 7.91 (d, J = 2.74 Hz, 1 H) 7.97 (d, J = 2.35 Hz, 1 H) 8.03 (d, J = 9.00 Hz, 1 H) |
| 6.11 | 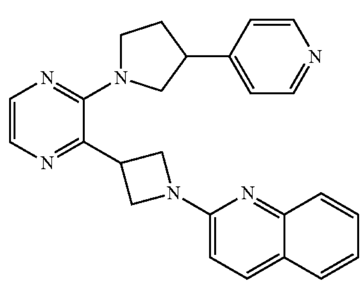 [SMILES: c1ccc2nc(N3CC(c4nccnc4N4CCC(c5ccncc5)C4)C3)ccc2c1] | (400 MHz, DMSO-$d_6$) 1.97-2.13 (m, 1 H) 2.38 (dq, J = 8.95, 6.15 Hz, 1 H) 3.44-3.56 (m, 1 H) 3.56-3.68 (m, 1 H) 3.74 (td, J = 9.59, 7.04 Hz, 1 H) 3.85 (dd, J = 9.98, 7.24 Hz, 1 H) 4.29-4.49 (m, 1 H) 6.78 (d, J = 9.00 Hz, 1 H) 7.16-7.25 (m, 1 H) 7.36-7.44 (m, 1 H) 7.46-7.60 (m, 1 H) 7.70 (d, J = 7.40 Hz, 1 H) 7.97 (d, J = 2.74 Hz, 1 H) 7.99-8.06 (m, 1 H) 8.49-8.56 (m, 1 H) |
| 6.12 | 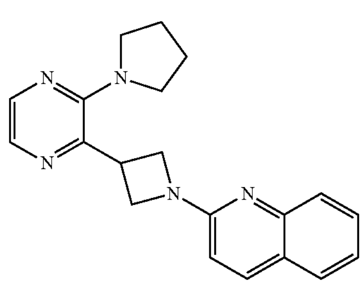 [SMILES: c1ccc2nc(N3CC(c4nccnc4N4CCCC4)C3)ccc2c1] | (400 MHz, DMSO-$d_6$) 1.91 (dt, J = 6.16, 3.37 Hz, 1 H) 3.43-3.53 (m, 1 H) 4.31-4.44 (m, 1 H) 6.78 (d, J = 9.00 Hz, 1 H) 7.17-7.24 (m, 1 H) 7.48-7.59 (m, 1 H) 7.70 (d, J = 7.82 Hz, 1 H) 7.91 (d, J = 2.35 Hz, 1 H) 7.97 (d, J = 2.35 Hz, 1 H) 8.03 (d, J = 9.00 Hz, 1 H) |

TABLE 18C-continued

1H NMR δ (PPM) DATA FOR EXAMPLES 6.1 TO 6.60

| Ex. # | Structure | NMR |
|---|---|---|
| 6.13 | 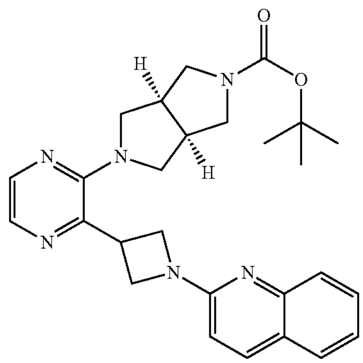 [SMILES: CC(C)(C)OC(=O)N1C[C@@H]2CN(c3nccnc3C3CN(c4ccc5ccccc5n4)C3)C[C@@H]2C1] | (400 MHz, DMSO-$d_6$) 1.41 (s, 9 H) 2.95 (br. s., 2 H) 3.17 (d, J = 5.09 Hz, 1 H) 3.40 (d, J = 3.91 Hz, 2 H) 3.52 (br. s., 2 H) 3.68 (dd, J = 10.37, 7.24 Hz, 2 H) 4.10 (q, J = 5.09 Hz, 1 H) 4.30-4.46 (m, 5 H) 6.77 (d, J = 9.00 Hz, 1 H) 7.16-7.26 (m, 1 H) 7.46-7.59 (m, 2 H) 7.70 (d, J = 7.82 Hz, 1 H) 7.93-8.06 (m, 3 H) |
| 6.14 | 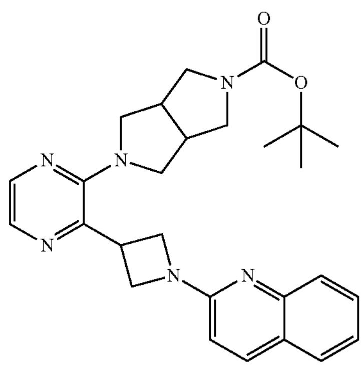 [SMILES: CC(C)(C)OC(=O)N1CC2CN(c3nccnc3C3CN(c4ccc5ccccc5n4)C3)CC2C1] | (400 MHz, DMSO-$d_6$) 1.41 (s, 8 H) 2.95 (br. s., 2 H) 3.17 (d, J = 5.09 Hz, 1 H) 3.23 (d, J = 10.17 Hz, 2 H) 3.40 (d, J = 3.91 Hz, 1 H) 3.52 (br. s., 2 H) 3.68 (dd, J = 10.56, 7.43 Hz, 2 H) 4.10 (q, J = 4.96 Hz, 1 H) 4.31-4.47 (m, 5 H) 6.77 (d, J = 9.00 Hz, 1 H) 7.17-7.25 (m, 1 H) 7.47-7.59 (m, 2 H) 7.71 (d, J = 7.43 Hz, 1 H) 7.95-8.06 (m, 3 H) |
| 6.15 | 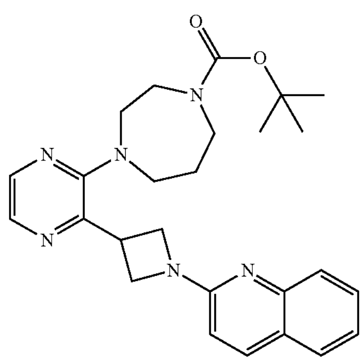 [SMILES: CC(C)(C)OC(=O)N1CCCN(c2nccnc2C2CN(c3ccc4ccccc4n3)C2)CC1] | (400 MHz, DMSO-$d_6$) 1.36 (d, J = 19.56 Hz, 9 H) 1.86-1.97 (m, 2 H) 3.42 (dd, J = 11.35, 5.67 Hz, 4 H) 3.53 (br. s., 4 H) 4.20-4.35 (m, 3 H) 4.42-4.50 (m, 2 H) 6.81 (d, J = 8.80 Hz, 1 H) 7.19-7.27 (m, 1 H) 7.55 (dd, J = 6.65, 1.37 Hz, 1 H) 7.58 (s, 1 H) 7.73 (d, J = 7.43 Hz, 1 H) 8.02-8.12 (m, 3 H) |
| 6.16 | 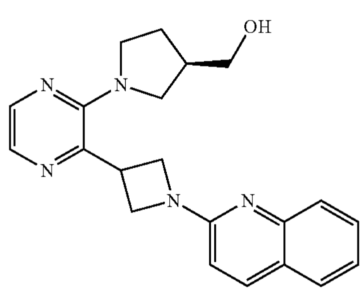 [SMILES: OC[C@@H]1CCN(c2nccnc2C2CN(c3ccc4ccccc4n3)C2)C1] | (400 MHz, DMSO-$d_6$) 1.69 (dq, J = 12.18, 7.81 Hz, 1 H) 1.99 (dq, J = 12.10, 6.01 Hz, 1 H) 2.29-2.42 (m, 1 H) 3.32-3.37 (m, 1 H) 3.38-3.56 (m, 5 H) 4.29-4.38 (m, 4 H) 4.39-4.47 (m, 1 H) 4.70 (t, J = 5.38 Hz, 1 H) 6.78 (d, J = 8.80 Hz, 1 H) 7.16-7.25 (m, 1 H) 7.47-7.54 (m, 1 H) 7.54-7.59 (m, 1 H) 7.70 (d, J = 7.63 Hz, 1 H) 7.91 (d, J = 2.54 Hz, 1 H) 7.97 (d, J = 2.54 Hz, 1 H) 8.03 (d, J = 8.80 Hz, 1 H) |

TABLE 18C-continued

1H NMR δ (PPM) DATA FOR EXAMPLES 6.1 TO 6.60

| Ex. # | Structure | NMR |
|---|---|---|
| 6.17 | 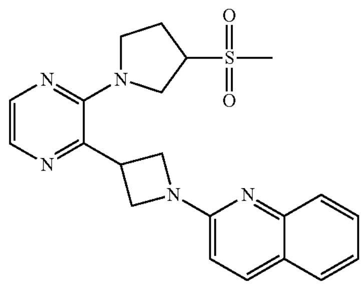 [SMILES: CS(=O)(=O)C1CCN(c2nccnc2C2CN(c3ccc4ccccc4n3)C2)C1] | (400 MHz, DMSO-$d_6$) 2.34-2.45 (m, 1 H) 2.95 (s, 3 H) 3.51-3.61 (m, 1 H) 3.63-3.73 (m, 1 H) 3.80-3.92 (m, 2 H) 4.29-4.40 (m, 1 H) 4.40-4.53 (m, 3 H) 6.74 (d, J = 9.00 Hz, 1 H) 7.21-7.29 (m, 1 H) 7.52-7.59 (m, 1 H) 7.60-7.65 (m, 1 H) 7.66-7.72 (m, 1 H) 7.96-8.05 (m, 2 H) |
| 6.18 | 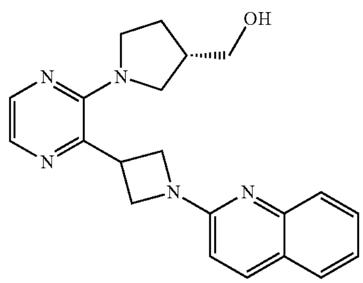 [SMILES: OC[C@H]1CCN(c2nccnc2C2CN(c3ccc4ccccc4n3)C2)C1] | (400 MHz, ACETONITRILE-$d_3$) 1.66-1.79 (m, 1 H) 1.96-2.09 (m, 1 H) 2.43 (dt, J = 14.23, 7.07 Hz, 1 H) 3.35 (dd, J = 10.17, 7.04 Hz, 1 H) 3.48-3.61 (m, 3 H) 4.31-4.55 (m, 3 H) 6.74 (d, J = 9.00 Hz, 1 H) 7.21-7.30 (m, 1 H) 7.52-7.59 (m, 1 H) 7.60-7.66 (m, 1 H) 7.66-7.73 (m, 1 H) 7.89 (d, J = 2.54 Hz, 1 H) 7.93 (d, J = 2.54 Hz, 1 H) 7.99 (d, J = 9.00 Hz, 1 H) |
| 6.19 | 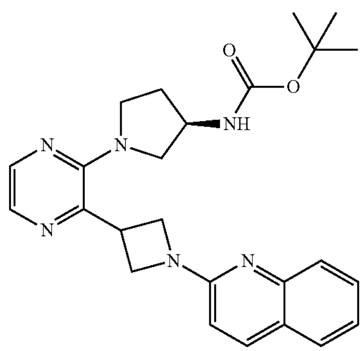 [SMILES: CC(C)(C)OC(=O)N[C@@H]1CCN(c2nccnc2C2CN(c3ccc4ccccc4n3)C2)C1] | (400 MHz, DMSO-$d_6$) 1.41 (s, 9 H) 1.86 (dq, J = 12.47, 6.41 Hz, 1 H) 2.09 (dq, J = 12.62, 6.49 Hz, 1 H) 3.17 (d, J = 5.09 Hz, 1 H) 3.45-3.55 (m, 1 H) 3.55-3.62 (m, 1 H) 3.62-3.71 (m, 1 H) 4.03-4.14 (m, 1 H) 4.28-4.45 (m, 5 H) 6.78 (d, J = 9.00 Hz, 1 H) 7.14-7.25 (m, 2 H) 7.48-7.60 (m, 2 H) 7.71 (d, J = 7.43 Hz, 1 H) 7.91-8.00 (m, 2 H) 8.04 (d, J = 9.00 Hz, 1 H) |
| 6.20 | 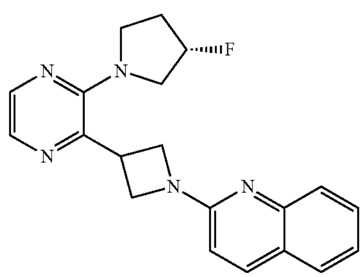 [SMILES: F[C@H]1CCN(c2nccnc2C2CN(c3ccc4ccccc4n3)C2)C1] | (400 MHz, DMSO-$d_6$) 1.99-2.30 (m, 2 H) 3.48-3.64 (m, 2 H) 3.71-3.96 (m, 2 H) 4.30-4.42 (m, 4 H) 4.45-4.55 (m, 1 H) 5.32-5.52 (m, 1 H) 6.78 (d, J = 9.00 Hz, 1 H) 7.17-7.25 (m, 1 H) 7.48-7.60 (m, 2 H) 7.70 (d, J = 7.43 Hz, 1 H) 7.95-8.06 (m, 3 H) |
| 6.21 | 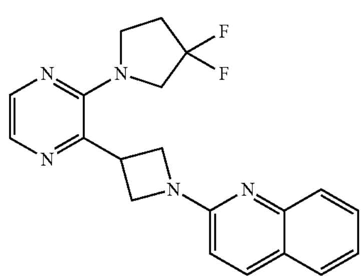 [SMILES: FC1(F)CCN(c2nccnc2C2CN(c3ccc4ccccc4n3)C2)C1] | (400 MHz, ACETONITRILE-$d_3$) (tt, J = 14.08, 7.24 Hz, 2 H) 3.75 (t, J = 7.24 Hz, 2 H) 3.89 (t, J = 13.20 Hz, 2 H) 4.27-4.38 (m, 1 H) 4.40-4.54 (m, 4 H) 6.77 (d, J = 8.80 Hz, 1 H) 7.22-7.30 (m, 1 H) 7.53-7.60 (m, 1 H) 7.60-7.65 (m, 1 H) 7.67-7.74 (m, 1 H) 8.00 (d, J = 8.80 Hz, 1 H) 8.07 (dd, J = 16.63, 2.54 Hz, 2 H) |

TABLE 18C-continued

1H NMR δ (PPM) DATA FOR EXAMPLES 6.1 TO 6.60

| Ex. # | Structure | NMR |
|---|---|---|
| 6.22 | 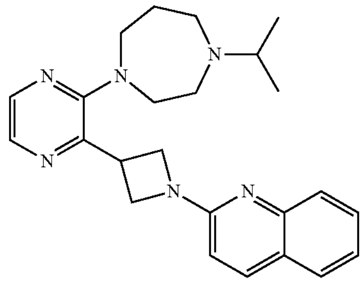 [SMILES: CC(C)N1CCCN(c2nccnc2C2CN(c3ccc4ccccc4n3)C2)CC1] | (400 MHz, DMSO-$d_6$) 0.96 (d, J = 6.65 Hz, 6 H) 1.79-1.91 (m, 2 H) 2.45-2.54 (m, 1 H) 2.58-2.65 (m, 2 H) 2.70-2.77 (m, 2 H) 2.86 (quin, J = 6.55 Hz, 1 H) 3.42-3.50 (m, 4 H) 4.16-4.33 (m, 3 H) 4.37-4.47 (m, 2 H) 6.78 (d, J = 8.61 Hz, 1 H) 7.16-7.26 (m, 1 H) 7.46-7.60 (m, 2 H) 7.70 (d, J = 7.43 Hz, 1 H) 7.98-8.06 (m, 3 H) |
| 6.23 | 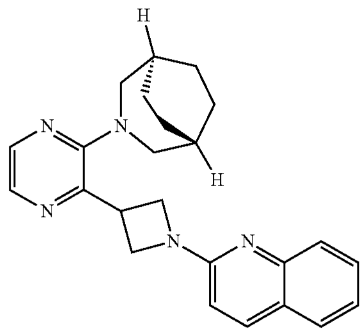 [SMILES: c1ccc2nc(N3CC(c4nccnc4N4C[C@H]5CC[C@@H](CC5)C4)C3)ccc2c1] | (400 MHz, DMSO-$d_6$) 1.67 (d, J = 9.78 Hz, 1 H) 1.83 (d, J = 7.82 Hz, 1 H) 2.11 (br. s., 1 H) 3.31 (d, J = 4.69 Hz, 1 H) 4.26-4.33 (m, 1 H) 4.32-4.42 (m, 1 H) 4.43-4.51 (m, 1 H) 6.79 (d, J = 9.00 Hz, 1 H) 7.17-7.25 (m, 1 H) 7.48-7.60 (m, 1 H) 7.71 (d, J = 7.43 Hz, 1 H) 8.04 (d, J = 9.00 Hz, 1 H) 8.11 (d, J = 2.35 Hz, 1 H) 8.15 (d, J = 2.35 Hz, 1 H) |
| 6.24 | 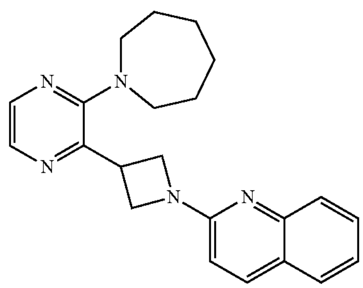 [SMILES: c1ccc2nc(N3CC(c4nccnc4N4CCCCCC4)C3)ccc2c1] | (400 MHz, DMSO-$d_6$) 1.53-1.62 (m, 4 H) 1.79 (br. s., 4 H) 3.42-3.48 (m, 5 H) 4.20-4.31 (m, 1 H) 4.39 (t, J = 7.04 Hz, 2 H) 4.46-4.55 (m, 2 H) 6.85 (d, J = 9.00 Hz, 1 H) 7.28 (t, J = 6.85 Hz, 1 H) 7.54-7.65 (m, 2 H) 7.76 (d, J = 7.82 Hz, 1 H) 8.03 (q, J = 2.35 Hz, 2 H) 8.12 (d, J = 9.00 Hz, 1 H) |
| 6.25 | 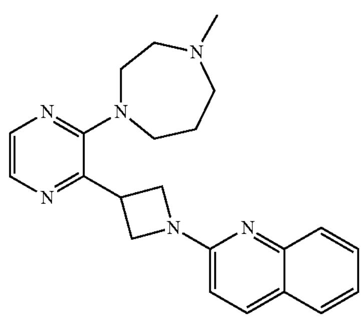 [SMILES: CN1CCCN(c2nccnc2C2CN(c3ccc4ccccc4n3)C2)CC1] | (400 MHz, DMSO-$d_6$) 1.89-2.01 (m, 1 H) 2.35 (s, 1 H) 2.60-2.69 (m, 1 H) 2.80 (d, J = 3.52 Hz, 1 H) 3.48 (br. s., 2 H) 3.50-3.56 (m, 1 H) 4.18-4.34 (m, 1 H) 4.37-4.47 (m, 1 H) 6.78 (d, J = 8.61 Hz, 1 H) 7.17-7.26 (m, 1 H) 7.47-7.60 (m, 1 H) 7.71 (d, J = 7.43 Hz, 1 H) 7.99-8.07 (m, 1 H) |
| 6.26 | 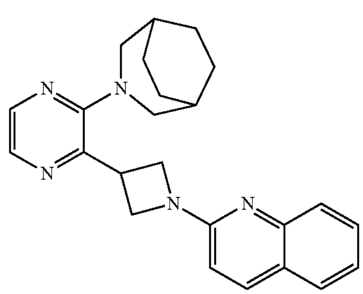 [SMILES: c1ccc2nc(N3CC(c4nccnc4N4CC5CCC(CC5)C4)C3)ccc2c1] | (400 MHz, DMSO-$d_6$) 1.66 (d, J = 9.78 Hz, 1 H) 1.83 (d, J = 7.43 Hz, 1 H) 2.11 (br. s., 1 H) 3.31 (d, J = 4.30 Hz, 1 H) 4.26-4.33 (m, 1 H) 4.33-4.42 (m, 1 H) 4.43-4.52 (m, 1 H) 6.79 (d, J = 9.00 Hz, 1 H) 7.18-7.26 (m, 1 H) 7.48-7.61 (m, 1 H) 7.71 (d, J = 7.82 Hz, 1 H) 8.04 (d, J = 9.00 Hz, 1 H) 8.11 (d, J = 2.35 Hz, 1 H) 8.15 (d, J = 2.35 Hz, 1 H) |

TABLE 18C-continued

1H NMR δ (PPM) DATA FOR EXAMPLES 6.1 TO 6.60

| Ex. # | Structure | NMR |
|---|---|---|
| 6.27 | 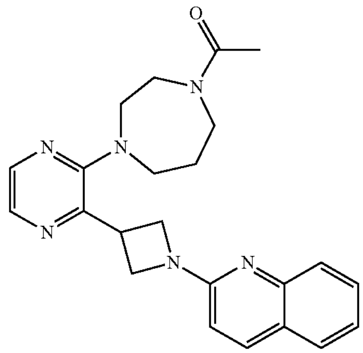 [SMILES: CC(=O)N1CCCN(c2nccnc2C2CN(c3ccc4ccccc4n3)C2)CC1] | (400 MHz, DMSO-$d_6$) 1.77-1.88 (m, 1 H) 1.96 (s, 2 H) 3.12-3.30 (m, 5 H) 3.40-3.61 (m, 6 H) 3.66 (br. s., 1 H) 4.18-4.36 (m, 2 H) 4.41-4.52 (m, 1 H) 6.76-6.84 (m, 1 H) 7.23 (t, J = 7.43 Hz, 1 H) 7.48-7.62 (m, 1 H) 7.72 (d, J = 7.82 Hz, 1 H) 8.01-8.14 (m, 2 H) |
| 6.28 | 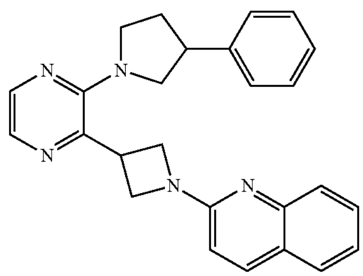 [SMILES: c1ccc(C2CCN(c3nccnc3C3CN(c4ccc5ccccc5n4)C3)C2)cc1] | (400 MHz, DMSO-$d_6$) 2.05 (quin, J = 9.98 Hz, 1 H) 2.34 (qd, J = 5.93, 4.11 Hz, 1 H) 3.40-3.52 (m, 1 H) 3.53-3.65 (m, 2 H) 3.68-3.86 (m, 2 H) 4.29-4.49 (m, 5 H) 6.77 (d, J = 8.61 Hz, 1 H) 7.16-7.29 (m, 2 H) 7.30-7.41 (m, 4 H) 7.47-7.59 (m, 2 H) 7.70 (d, J = 7.43 Hz, 1 H) 7.91-8.06 (m, 3 H) |
| 6.29 | 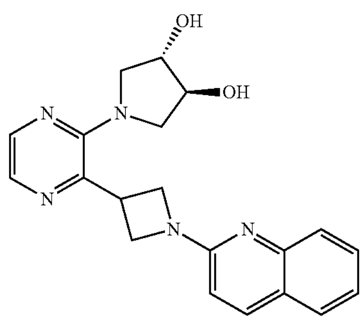 [SMILES: O[C@H]1CN(c2nccnc2C2CN(c3ccc4ccccc4n3)C2)C[C@@H]1O] | (400 MHz, DMSO-$d_6$) 3.22 (d, J = 11.35 Hz, 2 H) 3.85 (dd, J = 11.15, 3.72 Hz, 2 H) 4.02 (br. s., 2 H) 4.26-4.42 (m, 4 H) 4.50 (t, J = 6.06 Hz, 1 H) $^1$H NMR (400 MHz, DMSO-$d_6$) δ 5.15 (d, J = 2.35 Hz, 2 H) 6.78 (d, J = 9.00 Hz, 1 H) 7.16-7.25 (m, 1 H) 7.48-7.55 (m, 1 H) 7.55-7.60 (m, 1 H) 7.71 (d, J = 7.82 Hz, 1 H) 7.90 (d, J = 2.35 Hz, 1 H) 7.96 (d, J = 2.74 Hz, 1 H) 8.03 (d, J = 9.00 Hz, 1 H) |
| 6.30 | 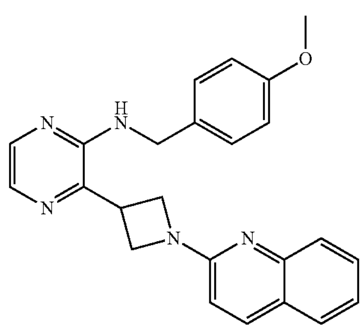 [SMILES: COc1ccc(CNc2nccnc2C2CN(c3ccc4ccccc4n3)C2)cc1] | (400 MHz, DMSO-$d_6$) 3.74 (s, 3 H) 4.18-4.27 (m, 1 H) 4.28-4.36 (m, 2 H) 4.47-4.57 (m, 3 H) 6.82 (d, J = 8.80 Hz, 1 H) 6.89 (d, J = 8.61 Hz, 2 H) 7.06 (t, J = 5.97 Hz, 1 H) 7.19-7.31 (m, 3 H) 7.50-7.57 (m, 1 H) 7.57-7.62 (m, 1 H) 7.69-7.76 (m, 2 H) 7.88 (d, J = 2.74 Hz, 1 H) 8.05 (d, J = 8.80 Hz, 1 H) |
| 6.31 | 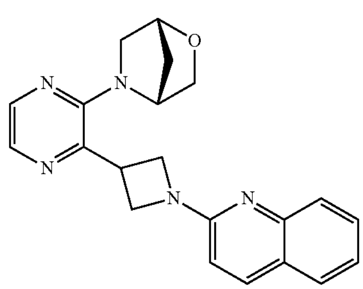 [SMILES: c1ccc2nc(N3CC(c4nccnc4N4C[C@H]5C[C@@H]4CO5)C3)ccc2c1] | (400 MHz, DMSO-$d_6$) 1.81-1.88 (m, 1 H) 1.88-1.94 (m, 1 H) 3.21 (d, J = 9.39 Hz, 1 H) 3.73 (dd, J = 9.19, 1.37 Hz, 1 H) 3.80 (dd, J = 7.63, 1.37 Hz, 1 H) 3.86- $^1$H NMR (400 MHz, DMSO-$d_6$) δ 3.92 (m, 1 H) 4.17-4.27 (m, 1 H) 4.28-4.39 (m, 3 H) 4.43-4.51 (m, 2 H) 4.63 (s, 1 H) 4.69 (s, 1 H) 6.78 (d, J = 9.00 Hz, 1 H) 7.17-7.25 (m, 1 H) 7.48-7.60 (m, 2 H) 7.70 (d, J = 7.43 Hz, 1 H) 7.98-8.06 (m, 3 H) |

TABLE 18C-continued

1H NMR δ (PPM) DATA FOR EXAMPLES 6.1 TO 6.60

| Ex. # | Structure | NMR |
|---|---|---|
| 6.32 | 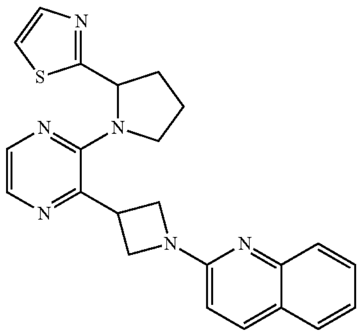 [SMILES: c1ccc2nc(N3CC(c4nccnc4N4CCCC4c4nccs4)C3)ccc2c1] | (400 MHz, DMSO-d$_6$) 1.92-2.11 (m, 3 H) 3.40 (dd, J = 8.61, 3.52 Hz, 2 H) 3.94-4.04 (m, 1 H) 4.36-4.48 (m, 4 H) 4.50-4.58 (m, 1 H) 5.68 (t, J = 7.04 Hz, 1 H) 6.80 (d, J = 9.00 Hz, 1 H) 7.17-7.25 (m, 1 H) 7.48 (d, J = 3.13 Hz, 1 H) 7.50-7.56 (m, 1 H) 7.56-7.61 (m, 1 H) 7.68 (d, J = 3.13 Hz, 1 H) 7.71 (d, J = 7.04 Hz, 1 H) 7.98 (d, J = 2.74 Hz, 1 H) 8.02-8.08 (m, 2 H) |
| 6.33 | 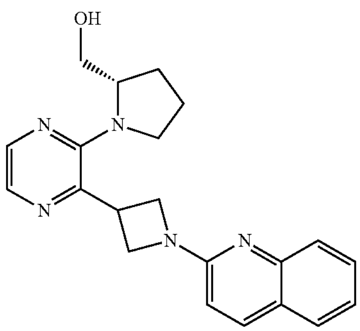 [SMILES: OC[C@@H]1CCCN1c1nccnc1C1CN(c2ccc3ccccc3n2)C1] | (400 MHz, DMSO-d$_6$) 1.66-1.81 (m, 1 H) 1.88 (d, J = 7.43 Hz, 1 H) 1.94 (ddd, J = 13.89, 7.04, 3.33 Hz, 1 H) 2.00-2.10 (m, 1 H) 3.21 (t, J = 7.24 Hz, 1 H) 3.47-3.56 (m, 1 H) 3.56-3.76 (m, 1 H) 4.25-4.37 (m, 5 H) 4.47-4.56 (m, 1 H) 4.62 (t, J = 5.67 Hz, 1 H) 6.77 (d, J = 9.00 Hz, 1 H) 7.16-7.24 (m, 1 H) 7.52 (dd, J = 6.85, 1.37 Hz, 1 H) 7.54-7.59 (m, 1 H) 7.70 (d, J = 7.43 Hz, 1 H) 7.94-7.97 (m, 1 H) 7.97-8.00 (m, 1 H) 8.02 (d, J = 9.00 Hz, 1 H) |
| 6.34 | 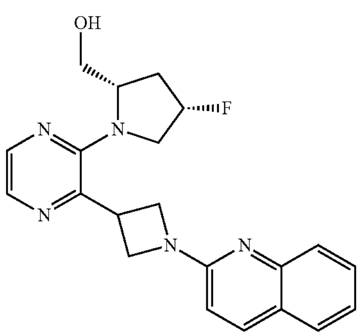 [SMILES: OC[C@@H]1C[C@H](F)CN1c1nccnc1C1CN(c2ccc3ccccc3n2)C1] | (400 MHz, DMSO-d$_6$) 2.17-2.38 (m, 2 H) 3.33-3.40 (m, 1 H) 3.47-3.63 (m, 2 H) 3.95 (t, J = 13.11 Hz, 1 H) 4.26-4.41 (m, 3 H) 4.45-4.57 (m, 2 H) 4.77 (t, J = 5.48 Hz, 1 H) 5.27-5.48 (m, 1 H) 6.78 (d, J = 9.00 Hz, 1 H) 7.22 (t, J = 7.24 Hz, 1 H) 7.53 (d, J = 6.65 Hz, 1 H) 7.55-7.61 (m, 1 H) 7.71 (d, J = 7.82 Hz, 1 H) 8.00-8.09 (m, 2 H) |
| 6.35 | 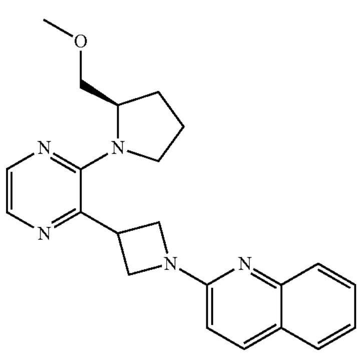 [SMILES: COC[C@H]1CCCN1c1nccnc1C1CN(c2ccc3ccccc3n2)C1] | (400 MHz, DMSO-d$_6$) ppm 1.67-1.86 (m, 2 H) 1.90-2.00 (m, 1 H) 2.05-2.15 (m, 1 H) 3.15-3.26 (m, 4 H) 3.47 (dd, J = 9.39, 3.91 Hz, 1 H) 3.65-3.75 (m, 1 H) 4.22-4.36 (m, 4 H) 4.44 (dd, J = 6.85, 4.11 Hz, 1 H) 4.47-4.56 (m, 1 H) 6.76 (d, J = 9.00 Hz, 1 H) 7.17-7.24 (m, 1 H) 7.47-7.54 (m, 1 H) 7.55 (s, 1 H) 7.70 (d, J = 7.82 Hz, 1 H) 7.96-8.06 (m, 2 H) |

TABLE 18C-continued

1H NMR δ (PPM) DATA FOR EXAMPLES 6.1 TO 6.60

| Ex. # | Structure | NMR |
|---|---|---|
| 6.36 | 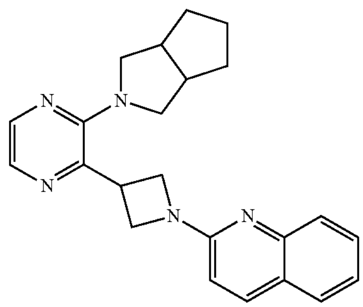 [SMILES: c1ccc2nc(N3CC(c4nccnc4N4CC5CCCC5C4)C3)ccc2c1] | (400 MHz, DMSO-$d_6$) 1.45-1.62 (m, 1 H) 1.68-1.84 (m, 1 H) 2.72 (br. s., 1 H) 3.15 (dd, J = 10.17, 3.52 Hz, 1 H) 3.41 (br. s., 1 H) 3.55 (dd, J = 10.76, 7.63 Hz, 1 H) 4.33 (d, J = 2.35 Hz, 2 H) 4.44 (s, 1 H) 6.79 (d, J = 9.00 Hz, 1 H) 7.21 (t, J = 7.04 Hz, 1 H) 7.48-7.59 (m, 1 H) 7.71 (d, J = 7.82 Hz, 1 H) 7.97-8.06 (m, 2 H) |
| 6.37 | 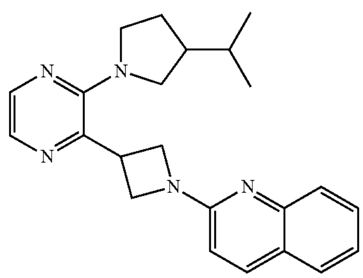 [SMILES: CC(C)C1CCN(c2nccnc2C2CN(c3ccc4ccccc4n3)C2)C1] | (400 MHz, DMSO-$d_6$) 0.92 (dd, J = 6.46, 2.93 Hz, 4 H) 1.33 (t, J = 6.94 Hz, 1 H) 1.52 (quin, J = 9.93 Hz, 1 H) 1.58-1.70 (m, 1 H) 2.01-2.12 (m, 1 H) 2.19-2.31 (m, 1 H) 3.13-3.22 (m, 1 H) 3.40-3.49 (m, 1 H) 3.49-3.64 (m, 1 H) 4.29-4.39 (m, 3 H) 4.45 (s, 1 H) 6.78 (d, J = 8.80 Hz, 1 H) 7.21 (t, J = 6.75 Hz, 1 H) 7.57-7.60 (m, 1 H) 7.70 (d, J = 7.82 Hz, 1 H) 7.91 (d, J = 2.35 Hz, 1 H) 7.96 (d, J = 2.35 Hz, 1 H) 8.03 (d, J = 8.80 Hz, 1 H) |
| 6.38 | 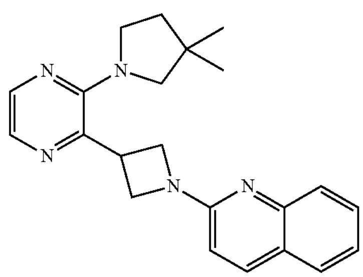 [SMILES: CC1(C)CCN(c2nccnc2C2CN(c3ccc4ccccc4n3)C2)C1] | (400 MHz, DMSO-$d_6$) 1.11 (s, 5 H) 1.73 (t, J = 7.04 Hz, 2 H) 3.24 (s, 2 H) 3.59 (t, J = 6.85 Hz, 2 H) 4.30-4.45 (m, 5 H) 6.78 (d, J = 9.00 Hz, 1 H) 7.17-7.25 (m, 1 H) 7.47-7.60 (m, 2 H) 7.70 (d, J = 7.82 Hz, 1 H) 7.90 (d, J = 2.74 Hz, 1 H) 7.96 (d, J = 2.35 Hz, 1 H) 8.03 (d, J = 8.61 Hz, 1 H) |
| 6.39 | 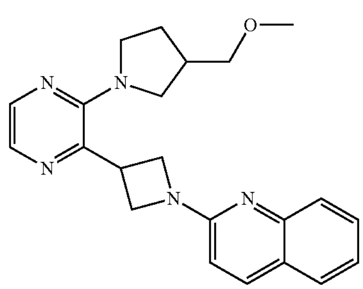 [SMILES: COCC1CCN(c2nccnc2C2CN(c3ccc4ccccc4n3)C2)C1] | (400 MHz, DMSO-$d_6$) 1.62-1.74 (m, 1 H) 2.02 (dd, J = 11.74, 5.09 Hz, 1 H) 3.25-3.32 (m, 4 H) 3.37-3.43 (m, 2 H) 3.46-3.59 (m, 3 H) 4.30-4.46 (m, 5 H) 6.78 (d, J = 9.00 Hz, 1 H) 7.16-7.24 (m, 1 H) 7.48-7.60 (m, 2 H) 7.70 (d, J = 7.82 Hz, 1 H) 7.92 (d, J = 2.35 Hz, 1 H) 7.97 (d, J = 2.74 Hz, 1 H) 8.03 (d, J = 9.00 Hz, 1 H) |
| 6.40 | 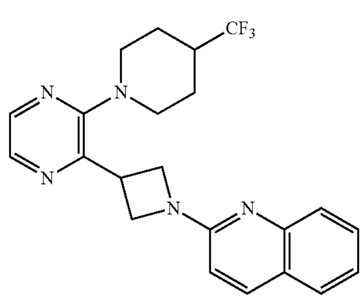 | (300 MHz, MeOH) 8.22 (1 H, d, J = 2.6 Hz), 8.15 (1 H, d, J = 2.5 Hz), 8.01 (1 H, d, J = 8.9 Hz), 7.64-7.74 (2 H, m), 7.55 (1 H, td, J = 7.7, 1.4 Hz), 7.18-7.30 (1 H, m), 6.77 (1 H, d, J = 8.9 Hz), 4.54-4.67 (2 H, m), 4.38-4.49 (3 H, m), 3.57 (2 H, d, J = 12.9 Hz), 2.76-3.03 (2 H, m), 2.42 (1 H, m), 1.96-2.13 (2 H, m), 1.66-1.96 (2 H, m). |

TABLE 18C-continued

1H NMR δ (PPM) DATA FOR EXAMPLES 6.1 TO 6.60

| Ex. # | Structure | NMR |
|---|---|---|
| 6.41 | 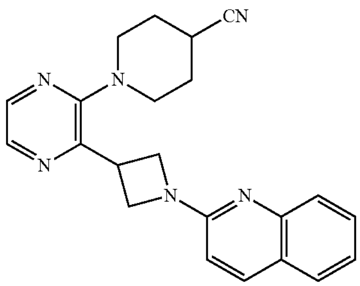 | (300 MHz, MeOH) 8.22 (1 H, d, J = 2.6 Hz), 8.15 (1 H, d, J = 2.5 Hz), 8.01 (1 H, d, J = 8.9 Hz), 7.64-7.74 (2 H, m), 7.55 (1 H, td, J = 7.7, 1.4 Hz), 7.18-7.30 (1 H, m), 6.77 (1 H, d, J = 8.9 Hz), 4.54-4.67 (2 H, m), 4.38-4.49 (3 H, m), 3.31-3-36 (2 H, m), 3.00-3.16 (3 H, m), 1.99-2.22 (4H, m) |
| 6.42 | 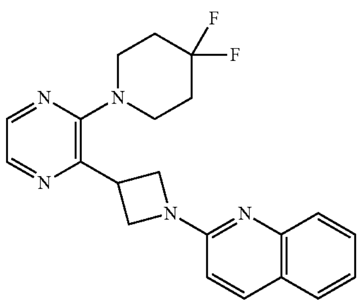 [SMILES: FC1(F)CCN(c2nccnc2C2CN(c3ccc4ccccc4n3)C2)CC1] | (300 MHz, MeOH) 8.22 (1 H, d, J = 2.6 Hz), 8.15 (1 H, d, J = 2.5 Hz), 8.01 (1 H, d, J = 8.9 Hz), 7.64-7.74 (2 H, m), 7.55 (1 H, td, J = 7.7, 1.4 Hz), 7.18-7.30 (1 H, m), 6.77 (1 H, d, J = 8.9 Hz), 4.54-4.67 (2 H, m), 4.38-4.49 (3 H, m), 3.31-3.36 (4 H, m), 2.13-2.27 (4H, m) |
| 6.43 | 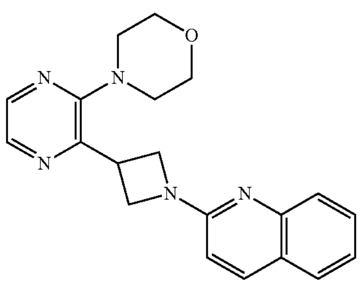 | (300 MHz, MeOH) 8.22 (1 H, d, J = 2.6 Hz), 8.15 (1 H, d, J = 2.5 Hz), 8.01 (1 H, d, J = 8.9 Hz), 7.64-7.74 (2 H, m), 7.55 (1 H, td, J = 7.7, 1.4 Hz), 7.18-7.30 (1 H, m), 6.77 (1 H, d, J = 8.9 Hz), 4.54-4.67 (2 H, m), 4.38-4.49 (3 H, m), 3.83-3.99 (4 H, m), 3.06-3.27 (4H, m) |
| 6.44 | 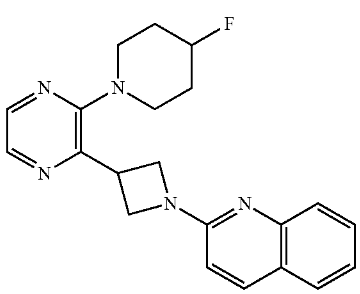 [SMILES: FC1CCN(c2nccnc2C2CN(c3ccc4ccccc4n3)C2)CC1] | (300 MHz, MeOH) 8.20 (1 H, d, J = 2.5 Hz), 8.14 (1 H, d, J = 2.6 Hz), 8.01 (1 H, d, J = 8.9 Hz), 7.64-7.74 (2 H, m), 7.49-7.60 (1 H, m), 7.20-7.30 (1 H, m), 6.77 (1 H, d, J = 8.9 Hz), 4.94 (1 H, dt, J = 6.6, 3.3 Hz), 4.78 (1 H, dt, J = 6.7, 3.3 Hz), 4.54-4.67 (2 H, m), 4.35-4.52 (3 H, m), 3.24-3.45 (1 H, m), 3.05-3.22 (2 H, m), 1.90-2.25 (4 H, m) |
| 6.45 | 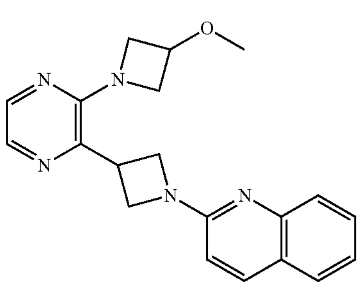 | (300 MHz, MeOH) 7.93-8.04 (3 H, m), 7.64-7.73 (2 H, m), 7.55 (1 H, ddd, J = 8.4, 7.0, 1.4 Hz), 7.19-7.30 (1 H, m), 6.76 (1 H, d, J = 8.9 Hz), 4.45-4.57 (4 H, m), 4.30-4.44 (3 H, m), 4.10-4.26 (1 H, m), 3.93-4.08 (2 H, m), 3.38 (3 H, s) |

TABLE 18C-continued

1H NMR δ (PPM) DATA FOR EXAMPLES 6.1 TO 6.60

| Ex. # | Structure | NMR |
|---|---|---|
| 6.46 | 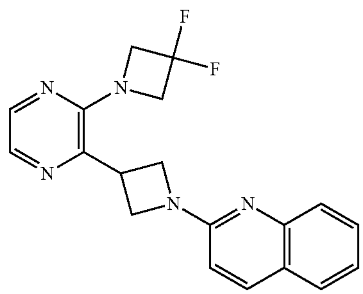 [SMILES: FC1(F)CN(c2nccnc2C2CN(c3ccc4ccccc4n3)C2)C1] | (300 MHz, MeOH) 8.09 (2 H, q, J = 2.6 Hz), 8.01 (1 H, d, J = 8.9 Hz), 7.64-7.73 (2 H, m), 7.55 (1 H, ddd, J = 8.5, 6.9, 1.4 Hz), 7.25 (1 H, td, J = 7.5, 1.0 Hz), 6.77 (1 H, d, J = 9.1 Hz), 4.45-4.61 (8 H, m), 4.10-4.27 (1 H, m) |
| 6.47 | 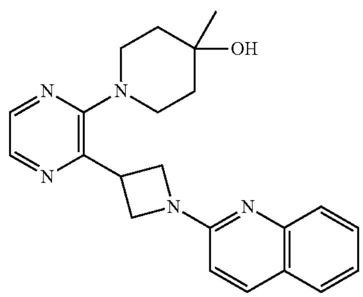 [SMILES: CC1(O)CCN(c2nccnc2C2CN(c3ccc4ccccc4n3)C2)CC1] | (300 MHz, MeOH) 8.17 (1 H, d, J = 2.5 Hz), 8.12 (1 H, d, J = 2.6 Hz), 8.01 (1 H, d, J = 8.9 Hz), 7.69 (2 H, dd, J = 8.0, 5.2 Hz), 7.55 (1 H, td, J = 7.7, 1.5 Hz), 7.20-7.30 (1 H, m), 6.77 (1 H, d, J = 8.9 Hz), 4.51-4.65 (2 H, m), 4.36-4.49 (3 H, m), 3.09-3.38 (4 H, m), 1.69-1.93 (4 H, m), 1.32 (3 H, s) |
| 6.48 | 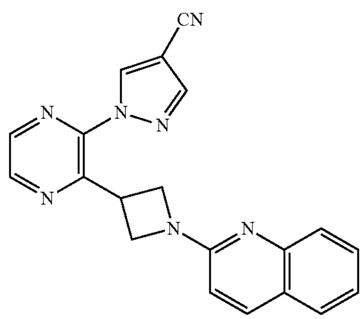 [SMILES: N#Cc1cnn(-c2nccnc2C2CN(c3ccc4ccccc4n3)C2)c1] | (300 MHz, MeOH) 9.08-9.13 (1 H, m), 8.77 (1 H, d, J = 2.5 Hz), 8.50 (1 H, d, J = 2.3 Hz), 8.28 (1 H, s), 8.01 (1 H, d, J = 9.1 Hz), 7.63-7.72 (2 H, m), 7.50-7.59 (1 H, m), 7.24 (1 H, td, J = 7.5, 1.0 Hz), 6.75 (1 H, d, J = 8.9 Hz), 4.74 (1 H, quin, J = 7.2 Hz), 4.46-4.60 (4 H, m) |
| 6.49 | 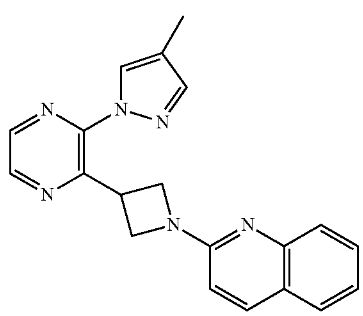 [SMILES: Cc1cnn(-c2nccnc2C2CN(c3ccc4ccccc4n3)C2)c1] | (300 MHz, MeOH) 8.60 (1 H, d, J = 2.5 Hz), 8.40 (1 H, d, J = 2.5 Hz), 8.24 (1 H, s), 7.99 (1 H, d, J = 8.9 Hz), 7.62-7.74 (3 H, m), 7.54 (1 H, ddd, J = 8.5, 7.0, 1.5 Hz), 7.23 (1 H, td, J = 7.5, 1.0 Hz), 6.73 (1 H, d, J = 9.1 Hz), 4.74-4.84 (1 H, m), 4.38-4.59 (4 H, m), 2.22 (3 H, s) |
| 6.50 | 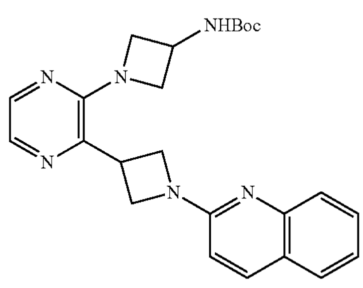 | (300 MHz, DMSO-d$_6$) 8.03 (2 H, dd, J = 5.7, 3.1 Hz), 7.96 (1 H, d, J = 2.6 Hz), 7.71 (1 H, d, J = 7.6 Hz), 7.46-7.62 (3 H, m), 7.21 (1 H, ddd, J = 8.0, 6.5, 1.6 Hz), 6.78 (1 H, d, J = 8.8 Hz), 4.25-4.52 (7 H, m), 3.97-4.18 (1 H, m), 3.92 (2 H, dd, J = 8.1, 5.6 Hz), 1.40 (9 H, s) |

TABLE 18C-continued

1H NMR δ (PPM) DATA FOR EXAMPLES 6.1 TO 6.60

| Ex. # | Structure | NMR |
|---|---|---|
| 6.51 | 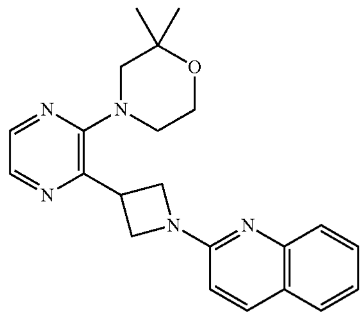 [SMILES: CC1(C)CN(c2nccnc2C2CN(c3ccc4ccccc4n3)C2)CCO1] | (300 MHz, DMSO-$d_6$) 8.25 (1 H, d, J = 2.5 Hz), 8.20 (1 H, d, J = 2.5 Hz), 8.04 (1 H, d, J = 8.9 Hz), 7.71 (1 H, d, J = 8.2 Hz), 7.48-7.63 (2 H, m), 7.14-7.28 (1 H, m), 6.80 (1 H, d, J = 8.9 Hz), 4.44-4.56 (2 H, m), 4.23-4.44 (3 H, m), 3.78-3.89 (2 H, m), 2.99-3.12 (2 H, m), 2.89 (2 H, s), 1.30 (6 H, s) |
| 6.52 | 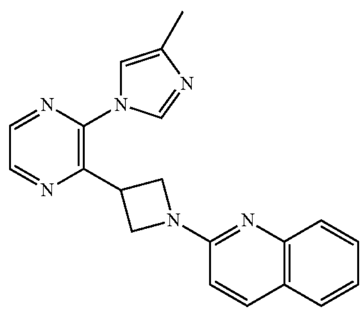 [SMILES: Cc1cn(-c2nccnc2C2CN(c3ccc4ccccc4n3)C2)cn1] | (300 MHz, DMSO-$d_6$) 8.76 (1 H, d, J = 2.5 Hz), 8.56 (1 H, d, J = 2.5 Hz), 7.96-8.07 (2 H, m), 7.71 (1 H, d, J = 7.6 Hz), 7.46-7.60 (2 H, m), 7.35 (1 H, s), 7.22 (1 H, ddd, J = 7.9, 6.5, 1.5 Hz), 6.76 (1 H, d, J = 8.9 Hz), 4.35-4.51 (2 H, m), 4.24-4.31 (3 H, m), 2.20 (3 H, s). |
| 6.53 | 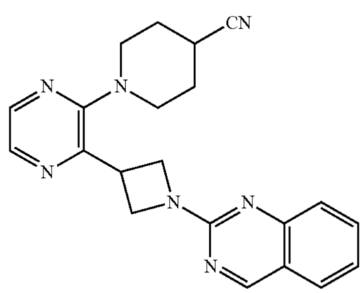 | (400 MHz, MeOH) 9.03 (1 H, s), 8.12 (1 H, d, J = 2.5 Hz), 8.05 (1 H, d, J = 2.5 Hz), 7.73 (1 H, d, J = 7.6 Hz), 7.60-7.69 (1 H, m), 7.51 (1 H, d, J = 8.6 Hz), 7.21 (1 H, t, J = 7.5 Hz), 4.50-4.58 (2 H, m), 4.24-4.42 (3 H, m), 3.22-3.32 (2 H, m), 2.86-3.06 (3 H, m), 2.00-2.12 (2 H, m), 1.87-2.00 (2 H, m) |
| 6.54 | 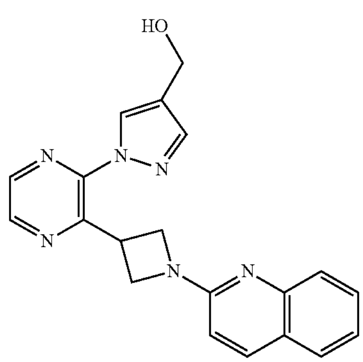 [SMILES: OCc1cnn(-c2nccnc2C2CN(c3ccc4ccccc4n3)C2)c1] | (400 MHz, MeOH) 8.52 (1 H, d, J = 2.3 Hz), 8.32 (2 H, s), 7.88 (1H, d, J = 8.8 Hz), 7.75 (1 H, s), 7.56 (2 H, dd, J = 7.8, 4.1 Hz), 7.43 (1 H, t, J = 7.7 Hz), 7.12 (1 H, t, J = 7.5 Hz), 6.63 (1 H, d, J = 9.0 Hz), 4.65-4.73 (1 H, m), 4.54 (2 H, s), 4.33-4.46 (4 H, m) |

TABLE 18C-continued

1H NMR δ (PPM) DATA FOR EXAMPLES 6.1 TO 6.60

| Ex. # | Structure | NMR |
|---|---|---|
| 6.55 | 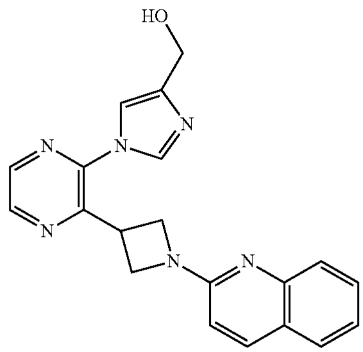 [SMILES: OCc1cn(-c2nccnc2C2CN(c3ccc4ccccc4n3)C2)cn1] | (300 MHz, DMSO-$d_6$) 8.78 (2 H, d, J = 2.5 Hz), 8.57 (2 H, d, J = 2.3 Hz), 8.03 (3 H, dd, J = 5.1, 3.8 Hz), 7.71 (2 H, d, J = 7.6 Hz), 7.43-7.62 (5 H, m), 7.22 (2 H, ddd, J = 7.9, 6.6, 1.5 Hz), 6.76 (2 H, d, J = 8.9 Hz), 5.06 (2 H, t, J = 5.6 Hz), 4.48 (2H, m), 4.28-4.31 (3H, m), 4.26 (2 H, d, J = 5.6 Hz). |
| 6.56 | 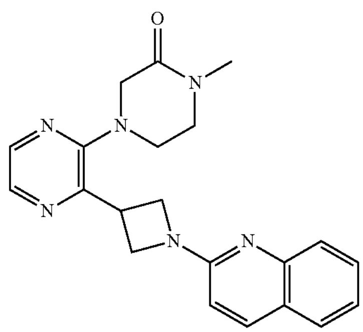 [SMILES: CN1CCN(c2nccnc2C2CN(c3ccc4ccccc4n3)C2)CC1=O] | (400 MHz, MeOH) 8.17 (1 H, d, J = 2.5 Hz), 8.07 (1 H, d, J = 2.5 Hz), 7.90 (1 H, d, J = 8.8 Hz), 7.57 (2 H, dd, J = 8.0, 3.7 Hz), 7.40-7.48 (1 H, m), 7.13 (1 H, t, J = 7.1 Hz), 6.66 (1 H, d, J = 8.8 Hz), 4.41-4.56 (2 H, m), 4.28-4.41 (3 H, m), 3.81 (2 H, s), 3.41 (4 H, s), 2.92 (3 H, s) |
| 6.57 | 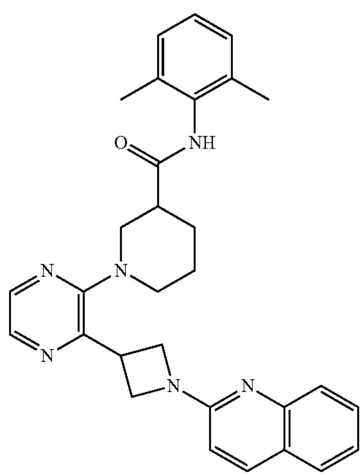 [SMILES: Cc1cccc(C)c1NC(=O)C1CCCN(c2nccnc2C2CN(c3ccc4ccccc4n3)C2)C1] | (400 MHz, MeOH) 8.11 (1 H, d, J = 2.5 Hz), 8.05 (1 H, d, J = 2.5 Hz), 7.91 (1 H, d, J = 9.0 Hz), 7.58 (2 H, dd, J = 7.7, 4.4 Hz), 7.40-7.47 (1 H, m), 7.14 (1 H, t, J = 7.5 Hz), 6.99 (3 H, s), 6.6 (1 H, d, J = 9.0 Hz), 4.43-4.57 (2 H, m), 4.27-4.43 (3 H, m), 3.58 (1 H, d, J = 11.0 Hz), 3.35 (1 H, d, J = 12.7 Hz), 3.05-3.15 (1 H, m), 2.77-2.96 (2 H, m), 2.02-2.31 (7 H, m), 1.70-1.94 (3 H, m) |
| 6.58 | 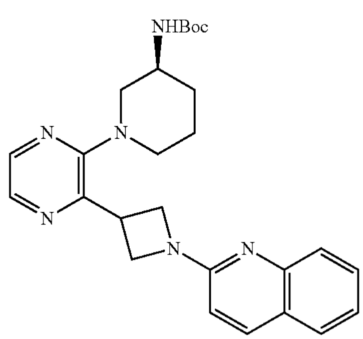 [SMILES: CC(C)(C)OC(=O)N[C@H]1CCCN(c2nccnc2C2CN(c3ccc4ccccc4n3)C2)C1] | (400 MHz, MeOH) 8.21 (1 H, d, J = 2.5 Hz), 8.13 (1 H, d, J = 2.5 Hz), 8.02 (1 H, d, J = 8.8 Hz), 7.69 (2 H, dd, J = 7.6, 4.9 Hz), 7.56 (1 H, t, J = 7.6 Hz), 7.25 (1 H, t, J = 7.4 Hz), 6.77 (1 H, d, J = 8.8 Hz), 4.56-4.73 (2 H, m), 4.36-4.52 (3 H, m), 3.69-3.83 (1 H, m), 3.39 (1H, m), 2.97 (1H, t, J = 8.9 Hz), 2.76 (1 H, dd, J = 12.1, 8.6 Hz), 1.91-2.02 (2 H, m), 1.82 (1 H, m), 1.40-1.59 (10 H, m), 1.29-1.40 (1 H, m) |

TABLE 18C-continued

1H NMR δ (PPM) DATA FOR EXAMPLES 6.1 TO 6.60

| Ex. # | Structure | NMR |
|---|---|---|
| 6.59 | 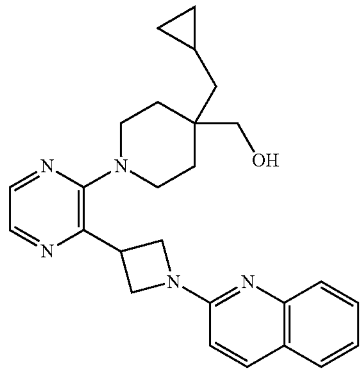 [SMILES: OCC1(CC2CC2)CCN(c2nccnc2C2CN(c3ccc4ccccc4n3)C2)CC1] | (300 MHz, MeOH) 8.56 (1 H, d, J = 2.5 Hz), 8.44 (1 H, d, J = 2.5 Hz), 7.69 (2 H, dd, J = 7.7, 5.6 Hz), 7.56 (1 H, t, J = 7.7 Hz), 7.25 (1 H, t, J = 7.5 Hz), 6.78 (1 H, d, J = 8.8 Hz), 4.54-4.72 (2 H, m), 4.34-4.54 (3 H, m), 3.64 (2 H, s), 3.09-3.28 (4 H, m), 1.68-1.86 (4 H, m), 1.31 (1 H, m), 0.84-1.01 (1 H, m), 0.77 (1 H, t, J = 6.8 Hz), 0.38-0.59 (2 H, m), 0.07-0.19 (2 H, m) |
| 6.60 | 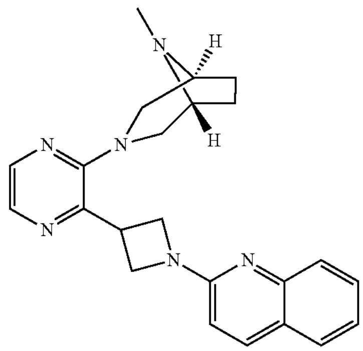 [SMILES: CN1[C@@H]2CC[C@H]1CN(c1nccnc1C1CN(c3ccc4ccccc4n3)C1)C2] | (400 MHz, DMSO-$d_6$) 1.61-1.78 (m, 1 H) 1.89 (br. s., 1 H) 2.18 (s, 2 H) 2.98-3.16 (m, 3 H) 3.20 (d, J = 11.15 Hz, 1 H) 3.36-3.55 (m, 1 H) 3.67 (d, J = 13.30 Hz, 1 H) 4.06 (t, J = 11.05 Hz, 1 H) 4.33 (d, J = 11.74 Hz, 1 H) 6.58 (d, J = 9.39 Hz, 1 H) 7.17 (t, J = 7.34 Hz, 1 H) 7.37-7.44 (m, 1 H) 7.44-7.53 (m, 1 H) 7.56 (d, J = 7.43 Hz, 1 H) 8.21 (d, J = 2.54 Hz, 1 H) 8.24 (d, J = 2.54 Hz, 1 H) |

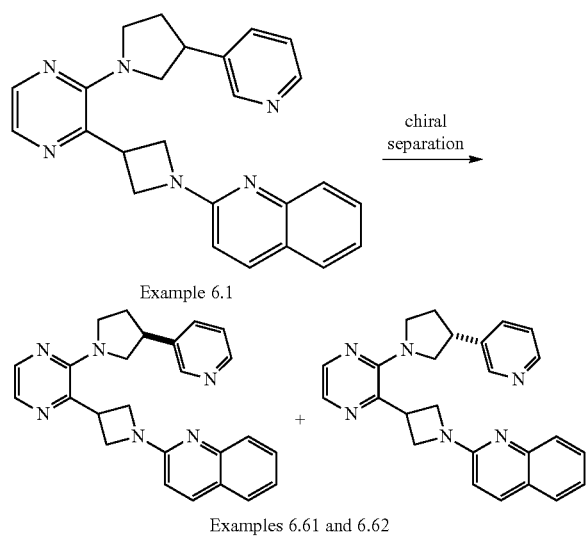

SCHEME 6b

Examples 6.61 and 6.62

Examples 6.61 and 6.62: Separated Stereoisomers of Example 6.1

Note: the absolute stereochemistry of each separated isomer was not further determined. 2-(3-(3-(3-(pyridin-3-yl)pyrrolidin-1-yl)pyrazin-2-yl)azetidin-1-yl)quinoline (SCHEME 6, Example 6.1) was chirally separated by using a Chiralpak ASH (150×4.6 mm i.d.), mobile phase 85% liquid $CO_2$/15% methanol containing 0.2% DEA (Flow rate: 4 ml/min, column temp: 40° C., outlet pressure: 100 Bar, wavelength: 248 nm)

Separated isomer Example 6.61: ESI-MS (M+1): 409. PDE10 $IC_{50}$ (uM): 0.0115.

$^1$H NMR δ (ppm) (400 MHz, DMSO-$d_6$) δ ppm 2.00-2.16 (m, 1H) 2.31-2.44 (m, 1H) 3.46-3.57 (m, 1H) 3.57-3.68 (m, 2H) 3.68-3.81 (m, 1H) 3.81-3.90 (m, 1H) 4.30-4.52 (m, 4H) 6.79 (d, J=9.00 Hz, 1H) 7.21 (t, J=7.24 Hz, 1H) 7.39 (dd, J=7.82, 4.69 Hz, 1H) 7.45-7.61 (m, 2H) 7.71 (d, J=8.02 Hz, 1H) 7.82 (d, J=7.83 Hz, 1H) 7.94-8.08 (m, 3H) 8.49 (d, J=4.50 Hz, 1H) 8.61 (s, 1H) Separated isomer Example 6.62: ESI-MS (M+1): 409. PDE10 $IC_{50}$ (uM): 0.0022.

$^1$H NMR δ (ppm) (400 MHz, DMSO-$d_6$) δ ppm 2.10 (quin, J=9.93 Hz, 1H) 2.30-2.44 (m, 1H) 3.46-3.58 (m, 1H) 3.58-3.68 (m, 2H) 3.70-3.81 (m, 1H) 3.86 (dd, J=9.59, 7.43 Hz, 1H) 4.30-4.51 (m, 5H) 6.79 (d, J=9.00 Hz, 1H) 7.22 (t, J=6.75 Hz, 1H) 7.39 (dd, J=7.82, 4.69 Hz, 1H) 7.47-7.61 (m, 2H) 7.71 (d, J=7.82 Hz, 1H) 7.82 (d, J=7.83 Hz, 1H) 7.95-8.07 (m, 3H) 8.49 (d, J=3.52 Hz, 1H) 8.61 (d, J=1.76 Hz, 1H)

SCHEME 7

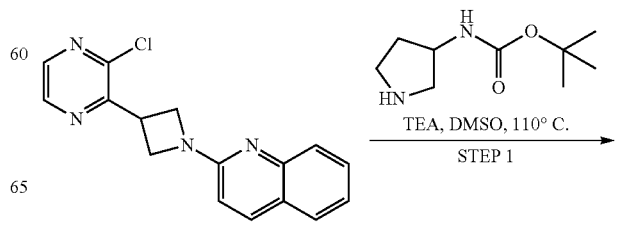

STEP 1

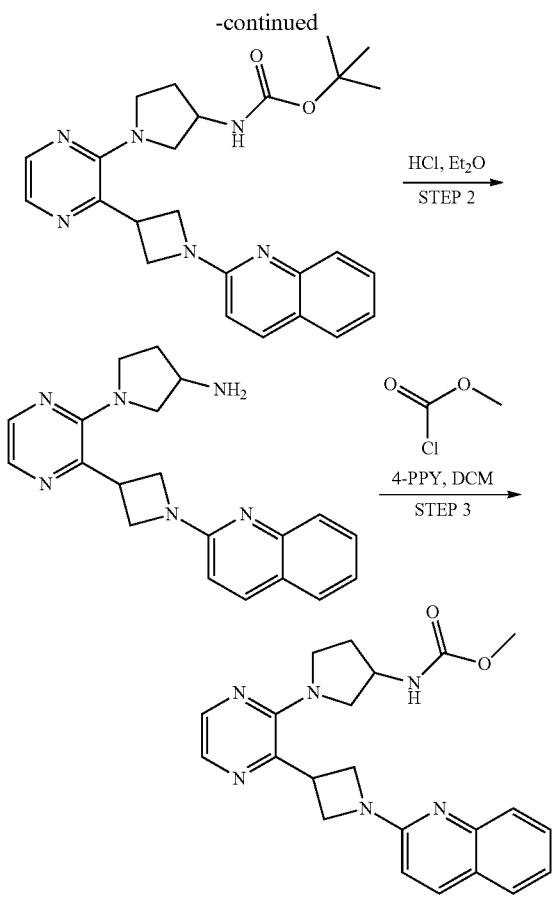

Example 7: Methyl (1-(3-(1-(Quinolin-2-Yl)Azetidin-3-Yl)Pyrazin-2-Yl)Pyrrolidin-3-Yl)Carbamate Step 1. tert-Butyl (1-(3-(1-(quinolin-2-yl)azetidin-3-yl)pyrazin-2-yl)pyrrolidin-3-yl)carbamate: To a round bottomed flask was added 2-(3-(3-chloropyrazin-2-yl)azetidin-1-yl)quinoline (1.0337 g, 3.48 mmol), tert-butyl pyrrolidin-3-ylcarbamate (commercially available from TCI, 1.298 g, 6.97 mmol), and triethylamine (commercially available from Aldrich, 0.971 ml, 6.97 mmol) in DMSO (11.61 ml) to stir at 110° C. overnight.

The reaction mixture was diluted with water and extracted with $CH_2Cl_2$. The organic extract was washed with water, saturated NaCl, dried over $MgSO_4$, filtered and concentrated in vacuo. The crude product was adsorbed onto a plug of silica gel and chromatographed through a Biotage 50 g SNAP HP-silica column, eluting with a gradient of 10% to 100% EtOAc in hexane, to provide tert-butyl (1-(3-(1-(quinolin-2-yl)azetidin-3-yl)pyrazin-2-yl)pyrrolidin-3-yl)carbamate (1.3145 g, 2.94 mmol, 85% yield). $^1$H NMR (400 MHz, DMSO-$d_6$) δ ppm 1.41 (s, 9H) 1.86 (dq, J=12.35, 6.32 Hz, 1H) 2.01-2.15 (m, 1H) 3.34 (d, J=4.89 Hz, 1H) 3.44-3.54 (m, 1H) 3.54-3.62 (m, 1H) 3.61-3.71 (m, 1H) 4.08 (d, J=5.67 Hz, 1H) 4.27-4.45 (m, 3H) 6.78 (d, J=8.80 Hz, 1H) 7.15-7.26 (m, 1H) 7.47-7.60 (m, 1H) 7.71 (d, J=7.82 Hz, 1H) 7.93 (d, J=2.54 Hz, 1H) 7.98 (d, J=2.35 Hz, 1H) 8.03 (d, J=8.80 Hz, 1H) ESI (M+1) 447.0; calc for $C_{25}H_{30}N_6O_2$ 446.

Step 2. 1-(3-(1-(Quinolin-2-Yl)Azetidin-3-Yl)Pyrazin-2-Yl)Pyrrolidin-3-Amine

To a round bottomed flask was added tert-butyl (1-(3-(1-(quinolin-2-yl)azetidin-3-yl)pyrazin-2-yl)pyrrolidin-3-yl)carbamate (1.3145 g, 2.94 mmol) and hydrogen chloride, 1M in diethyl ether (0.089 ml, 2.94 mmol) to stir. Solvent was evaporated. The reaction mixture was diluted with saturated sodium bicarbonate and extracted with $CH_2Cl_2$. The organic extract was washed with water, saturated $Na_2CO_3$, saturated NaCl, dried over $MgSO_4$, filtered and concentrated in vacuo to give 1-(3-(1-(quinolin-2-yl)azetidin-3-yl)pyrazin-2-yl)pyrrolidin-3-amine (0.696 g, 2.009 mmol, 68.2% yield).

Step 3. Methyl (1-(3-(1-(Quinolin-2-Yl)Azetidin-3-Yl)Pyrazin-2-Yl)Pyrrolidin-3-Yl)Carbamate To a round bottomed flask was added 1-(3-(1-(quinolin-2-yl)azetidin-3-yl)pyrazin-2-yl)pyrrolidin-3-amine (0.0974 g, 0.281 mmol), pyridine (commercially available through Aldrich, 0.045 ml, 0.562 mmol), and 4-(pyrrolidin-1-yl)pyridine (PPY) (commercially available through Alfa Aesar, 0.042 g, 0.281 mmol) to stir at RT in DCM (0.937 ml). Methyl carbonochloridate (commercially available through Aldrich, 0.027 ml, 0.422 mmol) was added and allowed to stir overnight. The crude product was adsorbed onto a plug of silica gel and chromatographed through a Biotage 50 g SNAP HP-silica column, eluting with a gradient of 1% to 6% MeOH in $CH_2Cl_2$, to provide methyl (1-(3-(1-(quinolin-2-yl)azetidin-3-yl)pyrazin-2-yl)pyrrolidin-3-yl)carbamate.

The following Table 19A lists compounds of Examples 7.1 to 7.5, which were made analogous to Scheme 7, Steps 2 and 3, by using the appropriate materials and reaction conditions, which are listed in Table 19B. The NMR data of the Examples are listed in Table 19C.

TABLE 19A

EXAMPLES 7.1 TO 7.5

| Ex. # | Structure | Chemical Name | ESI-MS (M + 1) | IC$_{50}$ (µM) |
|---|---|---|---|---|
| 7.1 | 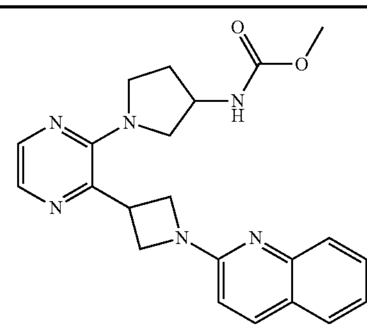 | (R- & S-)-methyl (1-(3-(1-(quinolin-2-yl)azetidin-3-yl)pyrazin-2-yl)pyrrolidin-3-yl)carbamate | 405.1 | 0.002 |

TABLE 19A-continued

EXAMPLES 7.1 TO 7.5

| Ex. # | Structure | Chemical Name | ESI-MS (M + 1) | IC$_{50}$ (μM) |
|---|---|---|---|---|
| 7.2 | 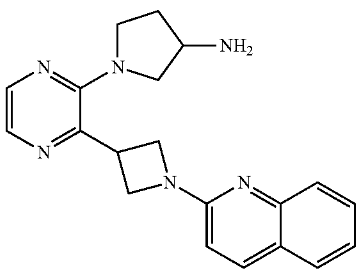 [SMILES: NC1CCN(c2nccnc2C2CN(c3ccc4ccccc4n3)C2)C1] | 1-(3-(1-(quinolin-2-yl)azetidin-3-yl)pyrazin-2-yl)pyrrolidin-3-amine | 347.1 | 0.038 |
| 7.3 | 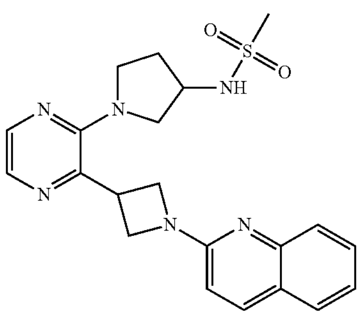 [SMILES: CS(=O)(=O)NC1CCN(c2nccnc2C2CN(c3ccc4ccccc4n3)C2)C1] | (R- & S-)-N-(1-(3-(1-(quinolin-2-yl)azetidin-3-yl)pyrazin-2-yl)pyrrolidin-3-yl)methanesulfonamide | 425 | 0.011 |
| 7.4 | 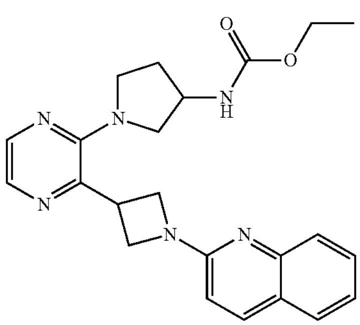 [SMILES: CCOC(=O)NC1CCN(c2nccnc2C2CN(c3ccc4ccccc4n3)C2)C1] | (R- & S-)-2-ethyl (1-(3-(1-(quinolin-2-yl)azetidin-3-yl)pyrazin-2-yl)pyrrolidin-3-yl)carbamate | 419 | 0.001 |
| 7.5 | 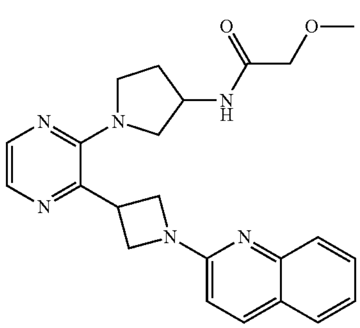 [SMILES: COCC(=O)NC1CCN(c2nccnc2C2CN(c3ccc4ccccc4n3)C2)C1] | (R- & S-)-2-methoxy-N-(1-(3-(1-(quinolin-2-yl)azetidin-3-yl)pyrazin-2-yl)pyrrolidin-3-yl)acetamide | 419 | 0.0044 |

TABLE 19B

STARTING MATERIALS AND REACTION CONDITION FOR PREPARATION OF EXAMPLES 7.3 TO 7.5.
Examples 7.1 to 7.2 are prepared as described in Scheme 7.
Unless otherwise stated, all starting materials are commercially available from common vendors

| Ex. # | Key Starting Material(s) | Key Starting Material(s) | Reaction Condition | Purification Condition* |
|---|---|---|---|---|
| 7.3 | 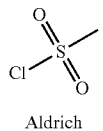 Aldrich | 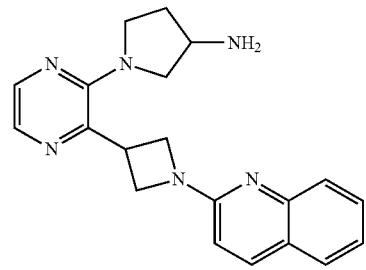 SCHEME 7 | 4-PPY, Py, DCM, RT | A |
| 7.4 | 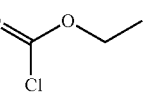 Lancaster | 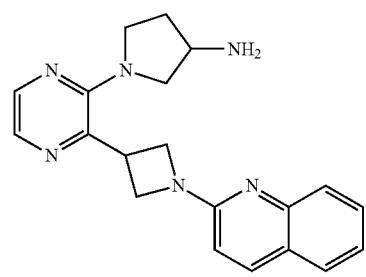 SCHEME 7 | 4-PPY, Py, DCM, RT | A |
| 7.5 | 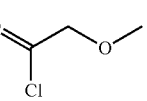 Aldrich | 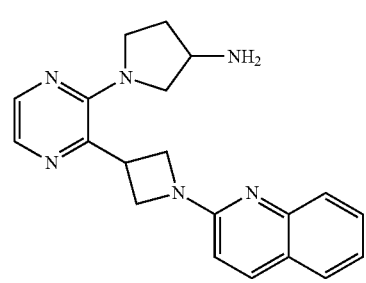 [SMILES: NC1CCN(c2nccnc2C2CN(c3ccc4ccccc4n3)C2)C1] SCHEME 7 | 4-PPY, Py, DCM, RT | A |

*Purification Method A: purification by silica gel chromatography: (Biotage 50 g SNAP HP-silica column, eluting with a gradient of 1% to 6% MeOH in $CH_2Cl_2$).

TABLE 19C

1H NMR δ (PPM) DATA FOR EXAMPLES 7.1 TO 7.5

| Ex. # | Structure | NMR |
|---|---|---|
| 7.1 | 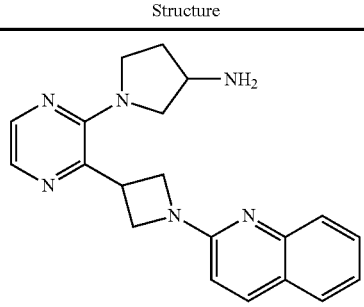 | (400 MHz, DMSO-$d_6$) 0.83-0.94 (m, 1 H) 1.20-1.40 (m, 1 H) 1.70 (dq, J = 12.37, 6.31 Hz, 1 H) 1.86 (br. s., 1 H) 1.96-2.09 (m, 1 H) 3.17 (dd, J = 9.98, 4.69 Hz, 1 H) 3.44-3.59 (m, 2 H) 3.59-3.71 (m, 2 H) 4.30-4.48 (m, 4 H) 6.80 (d, J = 9.00 Hz, 1 H) 7.23 (t, J = 6.85 Hz, 1 H) 7.48-7.62 (m, 2 H) 7.72 (d, J = 7.82 Hz, 1 H) 7.92 (d, J = 2.35 Hz, 1 H) 7.98 (d, J = 2.35 Hz, 1 H) 8.05 (d, J = 9.00 Hz, 1 H) |

TABLE 19C-continued

1H NMR δ (PPM) DATA FOR EXAMPLES 7.1 TO 7.5

| Ex. # | Structure | NMR |
|---|---|---|
| 7.2 | 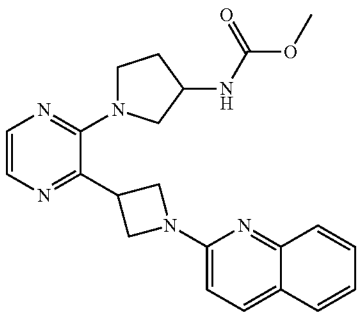 [SMILES: COC(=O)NC1CCN(c2nccnc2C2CN(c3ccc4ccccc4n3)C2)C1] | (400 MHz, DMSO-$d_6$) 1.88 (dq, J = 12.52, 6.39 Hz, 1 H) 2.04-2.17 (m, 3 H) 3.35 (dd, J = 10.56, 4.89 Hz, 1 H) 3.47-3.65 (m, 4 H) 3.68 (dd, J = 10.56, 6.26 Hz, 1 H) 4.07-4.17 (m, 1 H) 4.29-4.44 (m, 4 H) 6.78 (d, J = 8.80 Hz, 1 H) 7.16-7.25 (m, 1 H) 7.45-7.59 (m, 2 H) 7.70 (d, J = 7.63 Hz, 1 H) 7.93 (d, J = 2.35 Hz, 1 H) 7.98 (d, J = 2.54 Hz, 1 H) 8.03 (d, J = 9.00 Hz, 1 H) |
| 7.3 | 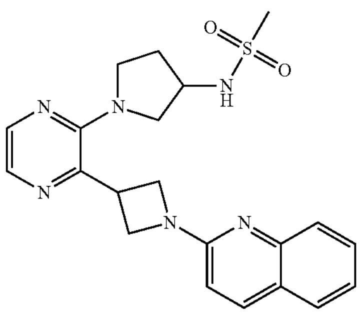 [SMILES: CS(=O)(=O)NC1CCN(c2nccnc2C2CN(c3ccc4ccccc4n3)C2)C1] | (400 MHz, DMSO-$d_6$) 1.86-1.99 (m, 1 H) 2.12-2.26 (m, 1 H) 3.00 (s, 2H) 3.41 (dd, J = 10.56, 5.67 Hz, 1 H) 3.49-3.65 (m, 1 H) 3.72 (dd, J = 10.37, 6.46 Hz, 1 H) 4.00 (br. s., 1 H) 4.28-4.46 (m, 3 H) 6.79 (d, J = 8.80 Hz, 1 H) 7.21 (t, J = 7.24 Hz, 1 H) 7.42 (br. s., 1 H) 7.46-7.61 (m, 1 H) 7.71 (d, J = 8.02 Hz, 1 H) 7.96 (d, J = 2.35 Hz, 1 H) 8.00 (d, J = 2.54 Hz, 1 H) 8.04 (d, J = 8.80 Hz, 1 H) |
| 7.4 | 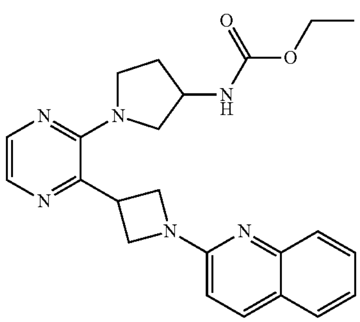 [SMILES: CCOC(=O)NC1CCN(c2nccnc2C2CN(c3ccc4ccccc4n3)C2)C1] | (400 MHz, DMSO-$d_6$) 1.19 (t, J = 7.04 Hz, 3 H) 1.90 (dq, J = 12.57, 6.57 Hz, 1 H) 2.06-2.19 (m, 1 H) 3.36 (dd, J = 10.56, 4.89 Hz, 1 H) 3.48-3.57 (m, 1 H) 3.58-3.67 (m, 1 H) 3.70 (dd, J = 10.47, 6.16 Hz, 1 H) 4.03 (q, J = 7.04 Hz, 2 H) 4.08-4.20 (m, 1 H) 4.32-4.52 (m, 4 H) 6.85 (d, J = 8.61 Hz, 1 H) 7.27 (t, J = 7.04 Hz, 1 H) 7.47 (d, J = 6.26 Hz, 1 H) 7.53-7.67 (m, 2 H) 7.76 (d, J = 7.82 Hz, 1 H) 7.96 (d, J = 2.54 Hz, 1 H) 8.01 (d, J = 2.54 Hz, 1 H) 8.11 (d, J = 8.41 Hz, 1 H) |
| 7.5 | 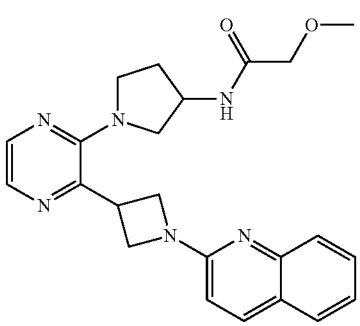 [SMILES: COCC(=O)NC1CCN(c2nccnc2C2CN(c3ccc4ccccc4n3)C2)C1] | (400 MHz, DMSO-$d_6$) 1.88-2.01 (m, 1 H) 2.04-2.19 (m, 1 H) 3.31 (s, 3 H) 3.44 (dd, J = 10.37, 5.48 Hz, 1 H) 3.48-3.63 (m, 2 H) 3.68 (dd, J = 10.27, 6.55 Hz, 1 H) 3.83 (s, 2 H) 4.29-4.44 (m, 5 H) 6.78 (d, J = 9.00 Hz, 1 H) 7.21 (t, J = 7.34 Hz, 1 H) 7.47-7.59 (m, 2 H) 7.70 (d, J = 8.02 Hz, 1 H) 7.94 (d, J = 2.54 Hz, 1 H) 7.99 (d, J = 2.54 Hz, 1 H) 8.03 (d, J = 8.80 Hz, 2 H) |

SCHEME 8

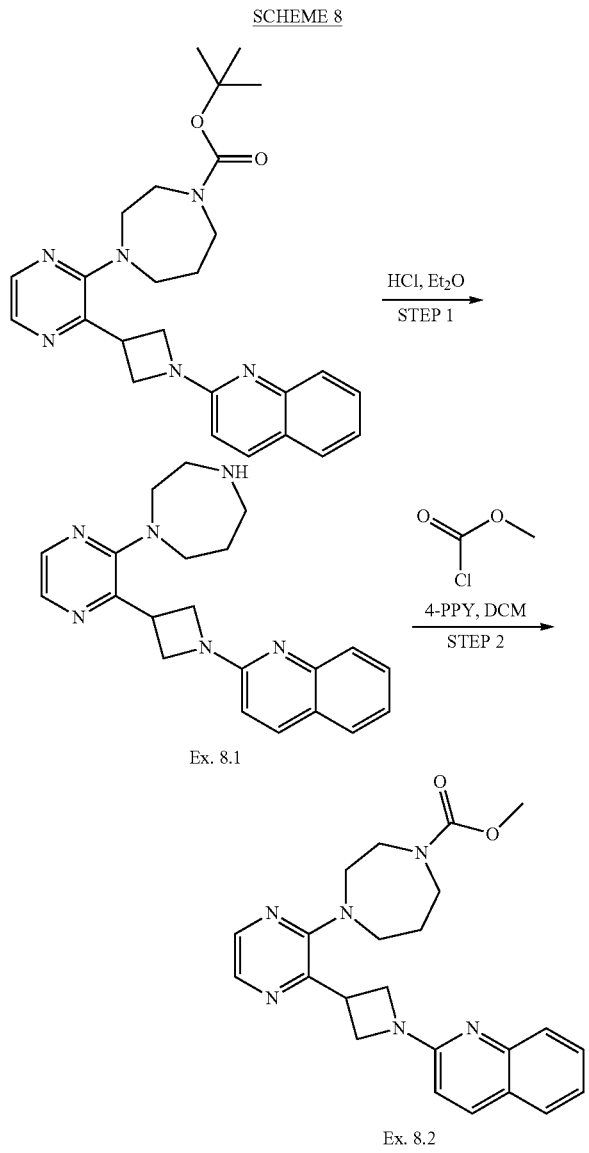

Ex. 8.1

Ex. 8.2

Examples 8.1 and 8.2

Example 8.1: 2-(3-(3-(1,4-Diazepan-1-Yl)Pyrazin-2-Yl)Azetidin-1-Yl)Quinoline To a round bottomed flask was added tert-butyl 4-(3-(1-(quinolin-2-yl)azetidin-3-yl)pyrazin-2-yl)-1,4-diazepane-1-carboxylate (0.5340 g, 1.159 mmol, SCHEME 6, Example 6.15) and HCl, (1.0 M solution in diethyl ether (1.159 ml, 1.159 mmol)) and the reaction was allowed to stir at RT. After 1 h, the reaction mixture was concentrated, then diluted with saturated $Na_2CO_3$ and extracted with $CH_2Cl_2$. The organic extract was washed with saturated $Na_2CO_3$, saturated NaCl, dried over $MgSO_4$, filtered and concentrated in vacuo to give 2-(3-(3-(1,4-diazepan-1-yl)pyrazin-2-yl)azetidin-1-yl)quinoline (0.3627 g, 1.006 mmol, 87% yield).

ESI-MS (M+1): 361.1. PDE10 $IC_{50}$ (μM): 0.050.

Example 8.2: Methyl 4-(3-(1-(Quinolin-2-Yl)Azetidin-3-Yl)Pyrazin-2-Yl)-1,4-Diazepane-1-Carboxylate To a round bottomed flask was added 2-(3-(3-(1,4-diazepan-1-yl)pyrazin-2-yl)azetidin-1-yl)quinoline (0.0772 g, 0.214 mmol), pyridine (commercially available through Aldrich, 0.035 ml, 0.428 mmol), and 4-(pyrrolidin-1-yl)pyridine (commercially available through Alfa Aesar, 0.032 g, 0.214 mmol) and the reaction was allowed to stir at RT in DCM (0.714 ml). Methyl carbonochloridate (commercially available through Aldrich, 0.021 ml, 0.321 mmol) was added and allowed to stir overnight. Upon completion, the solvent was evaporated. The crude product was adsorbed onto a plug of silica gel and chromatographed through a Biotage 50 g SNAP HP-silica column, eluting with a gradient of 0.5% to 5% MeOH in $CH_2CL_2$, to provide methyl 4-(3-(1-(quinolin-2-yl)azetidin-3-yl)pyrazin-2-yl)-1,4-diazepane-1-carboxylate (0.0632 g, 0.151 mmol, 70.5% yield). ESI-MS (M+1): 419.0. PDE10 $IC_{50}$ (μM): 0.0046.

The following Table 20 lists NMR data of Examples 8.1 to 8.2, which were made as described in the above Scheme 8.

TABLE 20

1H NMR δ (PPM) DATA FOR EXAMPLES 8.1 TO 8.2

| Ex. # | Structure | NMR |
|---|---|---|
| 8.1 | 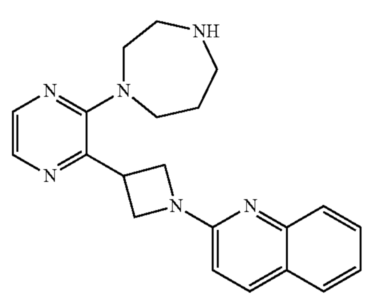 [SMILES: c1ccc2nc(N3CC(c4nccnc4N4CCCNCC4)C3)ccc2c1] | (400 MHz, DMSO-$d_6$) 1.86 (t, J = 5.58 Hz, 1 H) 2.85 (t, J = 5.77 Hz, 1 H) 2.93-3.03 (m, 1 H) 3.41-3.53 (m, 2 H) 4.19-4.34 (m, 2 H) 4.38-4.47 (m, 2 H) 6.79 (d, J = 8.80 Hz, 1 H) 7.21 (t, J = 7.34 Hz, 1 H) 7.46-7.61 (m, 1 H) 7.71 (d, J = 7.82 Hz, 1 H) 8.03 (d, J = 2.54 Hz, 2 H) |

TABLE 20-continued

1H NMR δ (PPM) DATA FOR EXAMPLES 8.1 TO 8.2

| Ex. # | Structure | NMR |
|---|---|---|
| 8.2 | 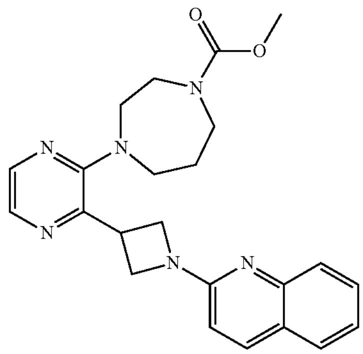 [SMILES: COC(=O)N1CCCN(c2nccnc2C2CN(c3ccc4ccccc4n3)C2)CC1] | (400 MHz, DMSO-d$_6$) 1.93 (br. s., 2 H) 3.42 (br. s., 2 H) 3.48 (br. s., 2 H) 3.53 (d, J = 4.69 Hz, 2 H) 3.56-3.65 (m, 5 H) 4.21-4.35 (m, 3 H) 4.41-4.51 (m, 2 H) 6.81 (d, J = 9.00 Hz, 1 H) 7.19-7.27 (m, 1 H) 7.49-7.62 (m, 2 H) 7.73 (d, J = 7.82 Hz, 1 H) 8.05 (d, J = 8.80 Hz, 1 H) 8.11 (dd, J = 12.52, 2.54 Hz, 2 H) |

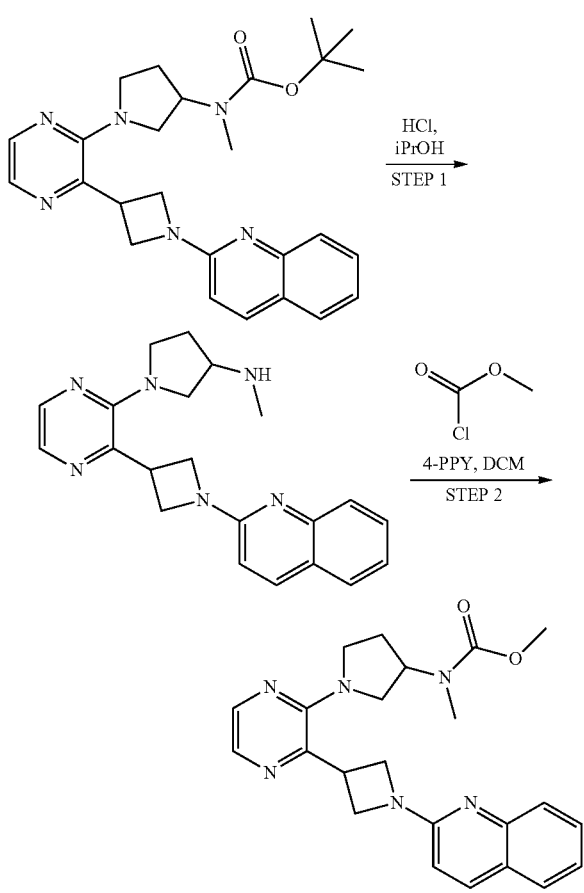

Example 9.1: N-Methyl-Methyl(1-(3-(1-(Quinolin-2-Yl)Azetidin-3-Yl)Pyrazin-2-Yl)Pyrrolidin-3-Yl) Carbamate Step 1. N-Methyl-1-(3-(1-(Quinolin-2-Yl)Azetidin-3-Yl)Pyrazin-2-Yl)Pyrrolidin-3-Amine To a round bottomed flask was added tert-butyl methyl (1-(3-(1-(quinolin-2-yl)azetidin-3-yl)pyrazin-2-yl)pyrrolidin-3-yl)carbamate (3.0 g, 6.51 mmol) and hydrogen chloride, 5-6N in isopropanol (0.237 g, 6.51 mmol) to stir overnight. Solvent was evaporated and the reaction mixture was diluted with water and extracted with EtOAc. The organic extract was washed with water, saturated Na$_2$CO$_3$, saturated NaCl, and dried over MgSO4, filtered and concentrated in vacuo to give N-methyl-1-(3-(1-(quinolin-2-yl)azetidin-3-yl)pyrazin-2-yl)pyrrolidin-3-amine (1.0339 g, 2.87 mmol, 44.0% yield). $^1$H NMR (400 MHz, DMSO-d$_6$) δ ppm 1.71-1.83 (m, 1H) 2.02 (dt, J=12.18, 5.94 Hz, 1H) 2.32 (s, 2H) 3.16-3.28 (m, 1H) 3.32 (br. s., 1H) 3.42-3.52 (m, 1H) 3.54-3.67 (m, 1H) 4.29-4.45 (m, 4H) 6.78 (d, J=8.80 Hz, 1H) 7.17-7.25 (m, 1H) 7.48-7.59 (m, 2H) 7.71 (d, J=7.83 Hz, 1H) 7.91 (d, J=2.54 Hz, 1H) 7.97 (d, J=2.35 Hz, 1H) 8.03 (d, J=8.80 Hz, 1H)

Step 2. N-Methyl-Methyl(1-(3-(1-(Quinolin-2-Yl) Azetidin-3-Yl)Pyrazin-2-Yl)Pyrrolidin-3-Yl)Carbamate 14 Mar. 2011 To a round bottomed flask was added N-methyl-1-(3-(1-(quinolin-2-yl)azetidin-3-yl)pyrazin-2-yl)pyrrolidin-3-amine (0.0999 g, 0.277 mmol), pyridine (0.045 ml, 0.554 mmol), and 4-(pyrrolidin-1-yl)pyridine (0.041 g, 0.277 mmol) to stir at RT in DCM (0.924 ml). Methyl carbonochloridate (0.027 ml, 0.416 mmol) was added and allowed to stir for 2 h. Solvent was evaporated and the crude product was adsorbed onto a plug of silica gel and chromatographed through a Biotage 50 g SNAP HP-silica column, eluting with a gradient of 1% to 4% MeOH in CH$_2$Cl$_2$, to provide methyl methyl(1-(3-(1-(quinolin-2-yl)azetidin-3-yl)pyrazin-2-yl)pyrrolidin-3-yl)carbamate (0.0307 g, 0.073 mmol, 26.5% yield).

The following Table 21A lists compounds of Examples 9.1 to 9.3, which were made analogous to Scheme 9 by using the appropriate materials and reaction conditions, which are listed in Table 21B. The NMR data of the Examples are listed in Table 21C.

TABLE 21A

EXAMPLES 9.1 TO 9.3

| Ex. # | Structure | Chemical Name | ESI-MS (M + 1) | IC$_{50}$ (uM) |
|---|---|---|---|---|
| 9.1 | 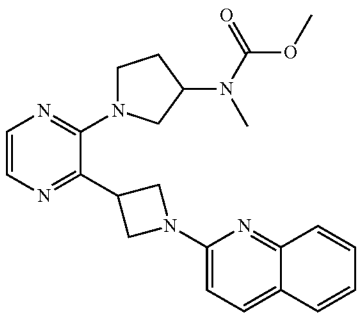 [SMILES: COC(=O)N(C)C1CCN(c2nccnc2C2CN(c3ccc4ccccc4n3)C2)C1] | N-methyl-methyl (1-(3-(1-(quinolin-2-yl)azetidin-3-yl)pyrazin-2-yl)pyrrolidin-3-yl)carbamate | 419.0 | 0.00052 |
| 9.2 | 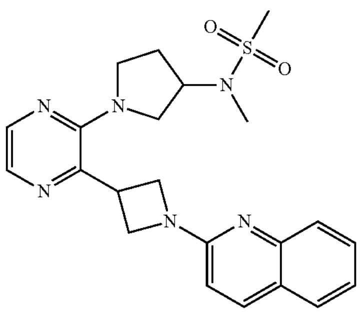 [SMILES: CN(C1CCN(c2nccnc2C2CN(c3ccc4ccccc4n3)C2)C1)S(C)(=O)=O] | N-methyl-N-(1-(3-(1-(quinolin-2-yl)azetidin-3-yl)pyrazin-2-yl)pyrrolidin-3-yl)methanesulfonamide | 439.0 | 0.00568 |
| 9.3 | 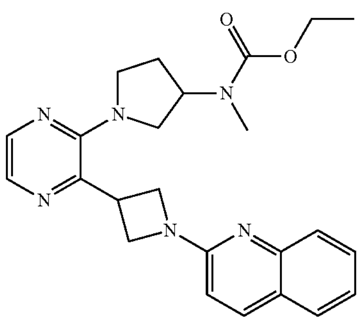 [SMILES: CCOC(=O)N(C)C1CCN(c2nccnc2C2CN(c3ccc4ccccc4n3)C2)C1] | Ethyl methyl(1-(3-(1-(quinolin-2-yl)azetidin-3-yl)pyrazin-2-yl)pyrrolidin-3-yl)carbamate | 433.1 | 0.002 |

TABLE 21B

STARTING MATERIALS AND REACTION CONDITION FOR PREPARATION OF EXAMPLES 9.1 TO 9.3.
Unless otherwise stated, all starting materials are commercially available from common vendors.

| Ex. # | Starting Material 1 | Starting Material 2 | Reaction Condition | Purification Condition* |
|---|---|---|---|---|
| 9.1 | | Aldrich | 4-PPY, Py, DCM | A |

TABLE 21B-continued

STARTING MATERIALS AND REACTION CONDITION FOR PREPARATION OF EXAMPLES 9.1 TO 9.3.
Unless otherwise stated, all starting materials are commercially available from common vendors.

| Ex. # | Starting Material 1 | Starting Material 2 | Reaction Condition | Purification Condition* |
|---|---|---|---|---|
| 9.2 | 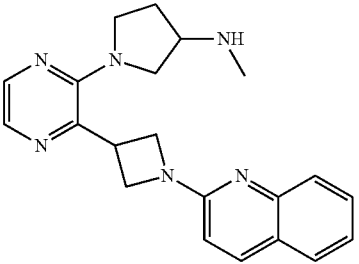 [SMILES: CNC1CCN(c2nccnc2C2CN(c3ccc4ccccc4n3)C2)C1] | 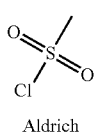  Aldrich | 4-PPY, Py, DCM | A |
| 9.3 | 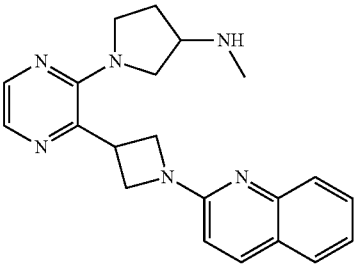 [SMILES: CNC1CCN(c2nccnc2C2CN(c3ccc4ccccc4n3)C2)C1] | 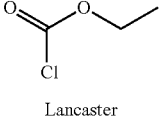  Lancaster | 4-PPY, Py, DCM | A |

*Purification condition: Method A: flash column chromatography on silica gel using Biotage 50 g SNAP HP-silica column, eluting with a gradient of 1% to 4% MeOH in $CH_2Cl_2$

TABLE 21C

1H NMR δ (PPM) DATA FOR EXAMPLES 9.1 TO 9.3

| Ex. # | Structure | NMR |
|---|---|---|
| 9.1 | 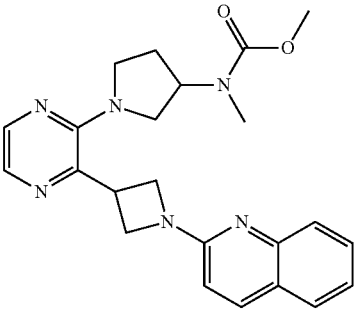 [SMILES: COC(=O)N(C)C1CCN(c2nccnc2C2CN(c3ccc4ccccc4n3)C2)C1] | (400 MHz, DMSO-$d_6$) 2.09 (q, J = 6.91 Hz, 2 H) 2.86 (s, 3 H) 3.49-3.61 (m, 4 H) 3.64 (s, 3 H) 4.31-4.41 (m, 4 H) 4.41-4.51 (m, 1 H) 6.79 (d, J = 8.80 Hz, 1 H) 7.22 (t, J = 6.85 Hz, 1 H) 7.48-7.60 (m, 2 H) 7.71 (d, J = 7.82 Hz, 1 H) 7.96-8.07 (m, 3 H) |
| 9.2 | 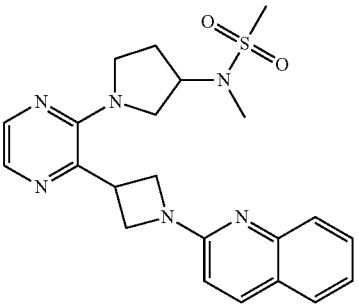 [SMILES: CN(C1CCN(c2nccnc2C2CN(c3ccc4ccccc4n3)C2)C1)S(C)(=O)=O] | (400 MHz, DMSO-$d_6$) 2.03-2.20 (m, 1 H) 2.83 (s, 2 H) 2.99 (s, 2 H) 3.49-3.61 (m, 2 H) 4.31-4.51 (m, 3 H) 6.79 (d, J = 9.00 Hz, 1 H) 7.21 (t, J = 6.85 Hz, 1 H) 7.46-7.60 (m, 1 H) 7.71 (d, J = 7.82 Hz, 1 H) 7.96-8.06 (m, 2 H) |

TABLE 21C-continued

1H NMR δ (PPM) DATA FOR EXAMPLES 9.1 TO 9.3

| Ex. # | Structure | NMR |
|---|---|---|
| 9.3 | (structure) | (400 MHz, DMSO-$d_6$) 1.21 (t, J = 7.14 Hz, 2 H) 2.08 (q, J = 7.50 Hz, 1 H) 2.85 (s, 2 H) 3.48-3.61 (m, 2 H) 4.08 (q, J = 7.04 Hz, 1 H) 4.29-4.40 (m, 2 H) 4.40-4.49 (m, 1 H) 4.72 (br. s., 1 H) 6.79 (d, J = 9.00 Hz, 1 H) 7.21 (t, J = 7.24 Hz, 1 H) 7.47-7.60 (m, 1 H) 7.70 (d, J = 7.82 Hz, 1 H) 7.95-8.06 (m, 2 H) |

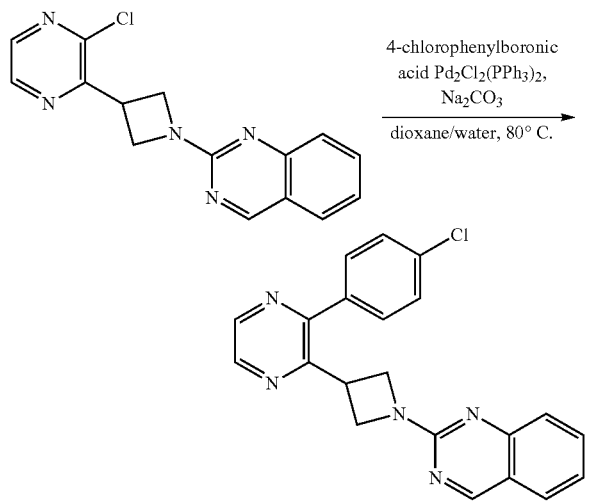

SCHEME 10

Example 10.1: 2-(3-(3-(4-Chlorophenyl)Pyrazin-2-Yl)Azetidin-1-Yl)Quinazoline 2M aqueous sodium carbonate (0.378 mL, 0.756 mmol, J. T. Baker) was added to a stirred mixture of 2-(3-(3-chloropyrazin-2-yl)azetidin-1-yl)quinazoline (0.075 g, 0.252 mmol, Preparation 1), trans-dichlorobis(triphenylphosphine)palladium (ii) (0.009 g, 0.013 mmol, Strem), and 4-chlorophenylboronic acid (0.047 g, 0.302 mmol, ASDI) in 1,4-dioxane (1 mL) in a sealed tube under an argon atmosphere. The reaction mixture was stirred at 80° C. for 17 h. The reaction mixture was concentrated in vacuo and diluted with DCM. The resulting suspension was filtered, and the filtrate was concentrated in vacuo. The resulting crude material was purified via reverse phase HPLC (Column: Xbridge 19×100 mm, 5 m, 1771302301) eluting with 0.1% NH$_4$OH in acetonitrile/water to give 0.060 g (64%) of a yellow amorphous solid. $^1$HNMR (500 MHz, DMSO-$d_6$) δ ppm 4.28-4.38 (m, 5H) 7.25-7.30 (m, 1H) 7.52 (d, J=8.48 Hz, 1H) 7.62 (s, 4H) 7.70-7.75 (m, 1H) 7.84 (br. d, J=7.80 Hz, 1H) 8.64 (d, J=2.41 Hz, 1H) 8.70 (d, J=2.41 Hz, 1H) 9.18 (s, 1H). ESI (M+1) 374.0; calc for $C_{21}H_{16}ClN_5$ 373.

The following Table 22A lists compounds of Examples 10.1 to 10.20, which were made analogous to Scheme 10 by using the appropriate materials and reaction conditions, which are listed in Table 22B. The NMR data of the Examples are listed in Table 22C.

TABLE 22A

EXAMPLES 10.1 TO 10.20

| Ex. # | Structure | Chemical Name | ESI-MS (M + 1) | IC$_{50}$ (μM) |
|---|---|---|---|---|
| 10.1 | (structure) | 2-(3-(3-(4-chlorophenyl)pyrazin-2-yl)azetidin-1-yl)quinazoline | 374.0 | 0.00482 |

TABLE 22A-continued

EXAMPLES 10.1 TO 10.20

| Ex. # | Structure | Chemical Name | ESI-MS (M + 1) | IC$_{50}$ (µM) |
|---|---|---|---|---|
| 10.2 | 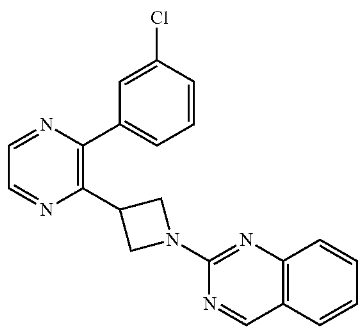 [SMILES: Clc1cccc(-c2nccnc2C2CN(c3ncc4ccccc4n3)C2)c1] | 2-(3-(3-(3-chlorophenyl)pyrazin-2-yl)azetidin-1-yl)quinazoline | 374.0 | 0.00615 |
| 10.3 | 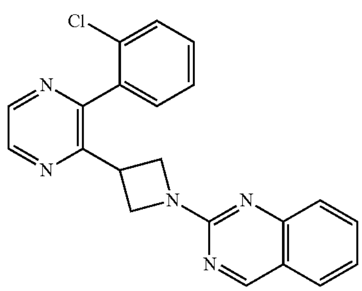 [SMILES: Clc1ccccc1-c1nccnc1C1CN(c2ncc3ccccc3n2)C1] | 2-(3-(3-(2-chlorophenyl)pyrazin-2-yl)azetidin-1-yl)quinazoline | 374.0 | 0.0309 |
| 10.4 | 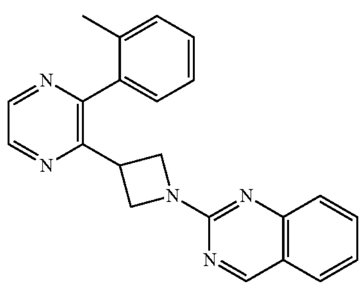 [SMILES: Cc1ccccc1-c1nccnc1C1CN(c2ncc3ccccc3n2)C1] | 2-(3-(3-(o-tolyl)pyrazin-2-yl)azetidin-1-yl)quinazoline | 354.2 | 0.0178 |
| 10.5 | 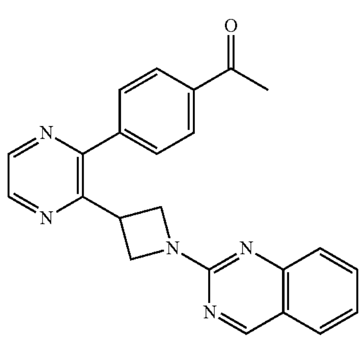 [SMILES: CC(=O)c1ccc(-c2nccnc2C2CN(c3ncc4ccccc4n3)C2)cc1] | 1-(4-(3-(1-(quinazolin-2-yl)azetidin-3-yl)pyrazin-2-yl)phenyl)ethanone | 382.2 | 0.00738 |

TABLE 22A-continued

EXAMPLES 10.1 TO 10.20

| Ex. # | Structure | Chemical Name | ESI-MS (M + 1) | IC$_{50}$ (μM) |
|---|---|---|---|---|
| 10.6 | 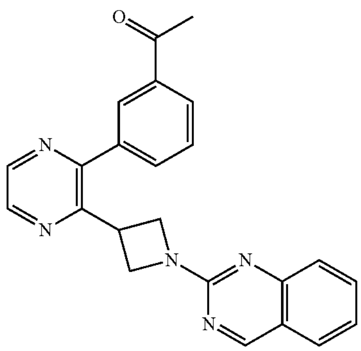 [SMILES: CC(=O)c1cccc(-c2nccnc2C2CN(c3ncc4ccccc4n3)C2)c1] | 1-(3-(3-(1-(quinazolin-2-yl)azetidin-3-yl)pyrazin-2-yl)phenyl)ethanone | 382.2 | 0.00136 |
| 10.7 | 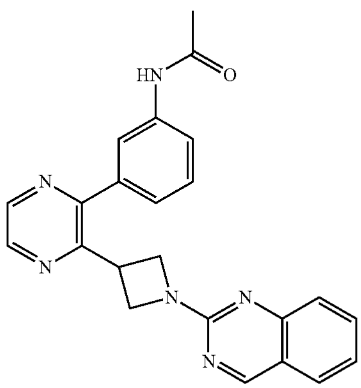 [SMILES: CC(=O)Nc1cccc(-c2nccnc2C2CN(c3ncc4ccccc4n3)C2)c1] | N-(3-(3-(1-(quinazolin-2-yl)azetidin-3-yl)pyrazin-2-yl)phenyl)acetamide | 397.2 | 0.000635 |
| 10.8 | 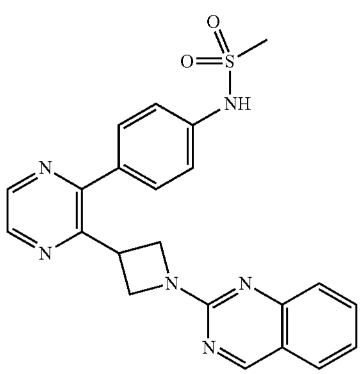 [SMILES: CS(=O)(=O)Nc1ccc(-c2nccnc2C2CN(c3ncc4ccccc4n3)C2)cc1] | N-(4-(3-(1-(quinazolin-2-yl)azetidin-3-yl)pyrazin-2-yl)phenyl)methanesulfonamide | 433.2 | 0.00336 |
| 10.9 | 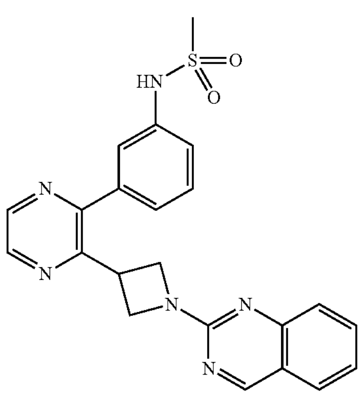 [SMILES: CS(=O)(=O)Nc1cccc(-c2nccnc2C2CN(c3ncc4ccccc4n3)C2)c1] | N-(3-(3-(1-(quinazolin-2-yl)azetidin-3-yl)pyrazin-2-yl)phenyl)methanesulfonamide | 433.2 | 0.00959 |

TABLE 22A-continued
EXAMPLES 10.1 TO 10.20
| Ex. # | Structure | Chemical Name | ESI-MS (M + 1) | IC$_{50}$ (μM) |
|---|---|---|---|---|
| 10.10 | 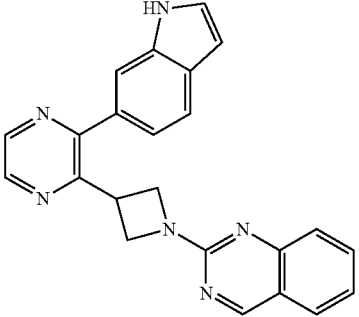 [SMILES: c1ccc2nc(N3CC(c4nccnc4-c4ccc5cc[nH]c5c4)C3)ncc2c1] | 2-(3-(3-(1H-indol-6-yl)pyrazin-2-yl)azetidin-1-yl)quinazoline | 379.2 | 0.00525 |
| 10.11 | 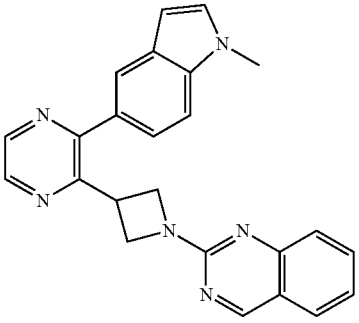 [SMILES: Cn1ccc2cc(-c3nccnc3C3CN(c4ncc5ccccc5n4)C3)ccc21] | 2-(3-(3-(1-methyl-1H-indol-5-yl)pyrazin-2-yl)azetidin-1-yl)quinazoline | 393.2 | 0.00595 |
| 10.12 | 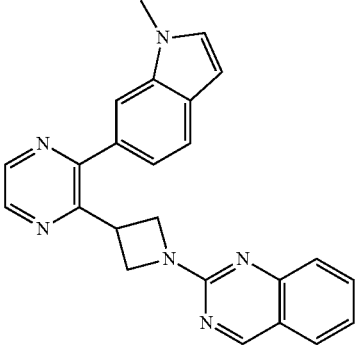 [SMILES: Cn1ccc2ccc(-c3nccnc3C3CN(c4ncc5ccccc5n4)C3)cc21] | 2-(3-(3-(1-methyl-1H-indol-6-yl)pyrazin-2-yl)azetidin-1-yl)quinazoline | 393.2 | 0.00298 |
| 10.13 | 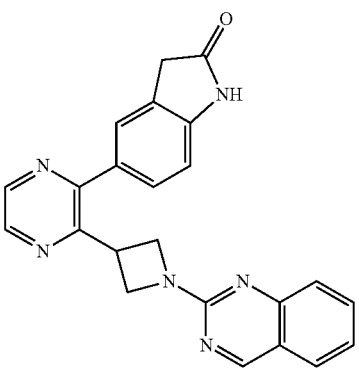 [SMILES: O=C1Cc2cc(-c3nccnc3C3CN(c4ncc5ccccc5n4)C3)ccc2N1] | 5-(3-(1-(quinazolin-2-yl)azetidin-3-yl)pyrazin-2-yl)indolin-2-one | 395.2 | 0.00946 |

TABLE 22A-continued

EXAMPLES 10.1 TO 10.20

| Ex. # | Structure | Chemical Name | ESI-MS (M + 1) | IC$_{50}$ (μM) |
|---|---|---|---|---|
| 10.14 | 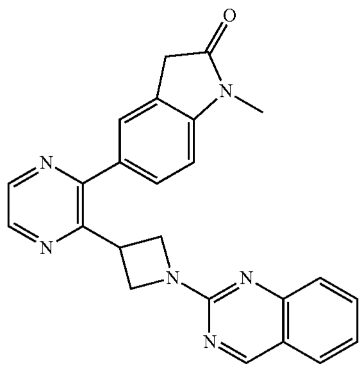 [SMILES: CN1C(=O)Cc2cc(-c3nccnc3C3CN(c4ncc5ccccc5n4)C3)ccc21] | 1-methyl-5-(3-(1-(quinazolin-2-yl)azetidin-3-yl)pyrazin-2-yl)indolin-2-one | 409.2 | 0.018 |
| 10.15 | 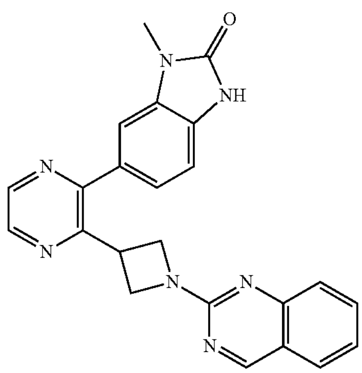 [SMILES: Cn1c(=O)[nH]c2ccc(-c3nccnc3C3CN(c4ncc5ccccc5n4)C3)cc21] | 1-methyl-6-(3-(1-(quinazolin-2-yl)azetidin-3-yl)pyrazin-2-yl)-1H-benzo[d]imidazol-2(3H)-one | 410.2 | 0.0042 |
| 10.16 | 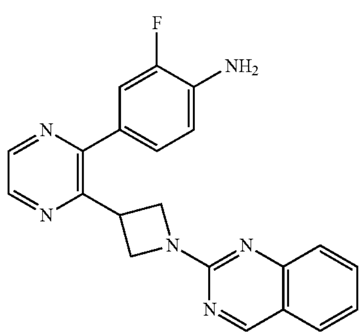 [SMILES: Nc1ccc(-c2nccnc2C2CN(c3ncc4ccccc4n3)C2)cc1F] | 2-fluoro-4-(3-(1-(quinazolin-2-yl)azetidin-3-yl)pyrazin-2-yl)aniline | 373.1 | 0.00682 |
| 10.17 | 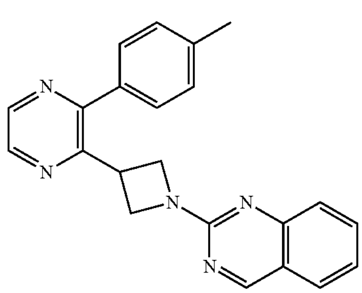 [SMILES: Cc1ccc(-c2nccnc2C2CN(c3ncc4ccccc4n3)C2)cc1] | 2-(3-(3-(p-tolyl)pyrazin-2-yl)azetidin-1-yl)quinazoline | 354.2 | 0.00708 |

TABLE 22A-continued

EXAMPLES 10.1 TO 10.20

| Ex. # | Structure | Chemical Name | ESI-MS (M + 1) | IC$_{50}$ (μM) |
|---|---|---|---|---|
| 10.18 | 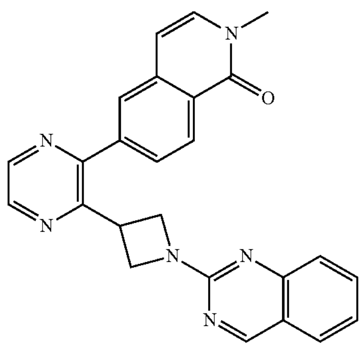 [SMILES: Cn1ccc2cc(-c3nccnc3C3CN(c4ncc5ccccc5n4)C3)ccc2c1=O] | 2-methyl-6-(3-(1-(quinazolin-2-yl)azetidin-3-yl)pyrazin-2-yl)isoquinolin-1(2H)-one | 421.1 | 0.01739 |
| 10.19 | 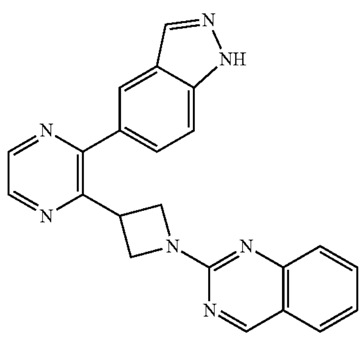 [SMILES: c1ccc2nc(N3CC(c4nccnc4-c4ccc5[nH]ncc5c4)C3)ncc2c1] | 2-(3-(3-(1H-indazol-5-yl)pyrazin-2-yl)azetidin-1-yl)quinazoline | 380.1 | 0.01216 |
| 10.20 | 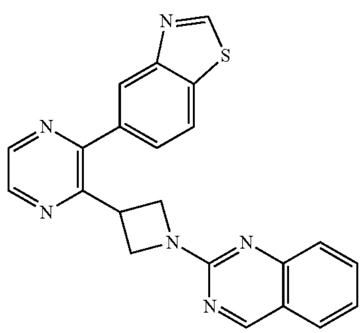 [SMILES: c1ccc2nc(N3CC(c4nccnc4-c4ccc5scnc5c4)C3)ncc2c1] | 5-(3-(1-(quinazolin-2-yl)azetidin-3-yl)pyrazin-2-yl)benzo[d]thiazole | 397.1 | 0.0044 |

TABLE 22B

STARTING MATERIALS AND REACTION CONDITION
FOR PREPARATION OF EXAMPLES 10.1 TO 10.20.
Unless otherwise stated, all starting materials are commercially available from common vendors.

| Ex. | Key Starting Material(s) | Key Starting Material(s) | Reaction Condition | Purification Method* |
|---|---|---|---|---|
| 10.1 | ASDI | PREPARATION 3 | Dioxane/water, 80° C., 17 h | A |

TABLE 22B-continued

STARTING MATERIALS AND REACTION CONDITION
FOR PREPARATION OF EXAMPLES 10.1 TO 10.20.
Unless otherwise stated, all starting materials are commercially available from common vendors.

| Ex. | Key Starting Material(s) | Key Starting Material(s) | Reaction Condition | Purification Method* |
|---|---|---|---|---|
| 10.2 | 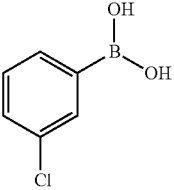 ASDI | 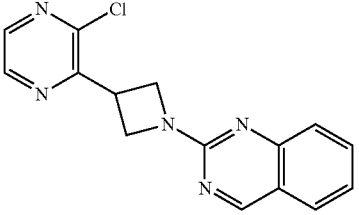 [SMILES: Clc1nccnc1C1CN(c2ncc3ccccc3n2)C1] PREPARATION 3 | Dioxane/water, 80° C., 17 h | A |
| 10.3 | 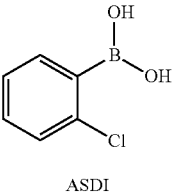 ASDI | 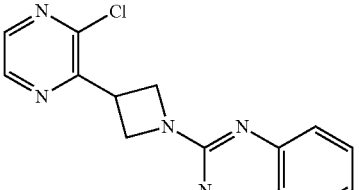 PREPARATION 3 | Dioxane/water, 80° C., 17 h | A |
| 10.4 | 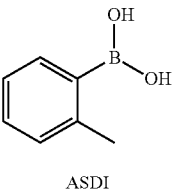 ASDI | 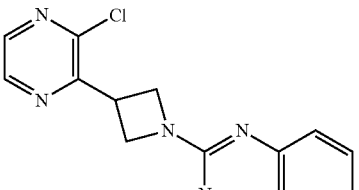 PREPARATION 3 | Dioxane/water, 80° C., 17 h | A |
| 10.5 | 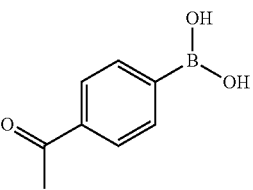 ASDI | 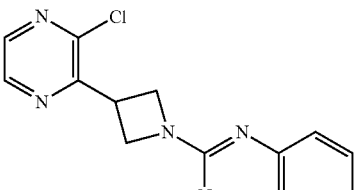 PREPARATION 3 | Dioxane/water, 80° C., 17 h | A |
| 10.6 | 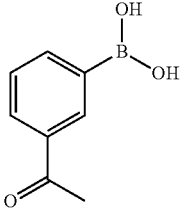 ASDI | 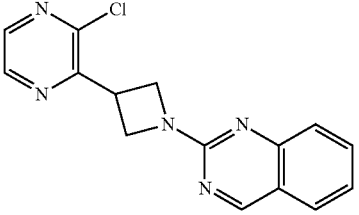 [SMILES: Clc1nccnc1C1CN(c2ncc3ccccc3n2)C1] PREPARATION 3 | Dioxane/water, 80° C., 17 h | A |

TABLE 22B-continued

STARTING MATERIALS AND REACTION CONDITION
FOR PREPARATION OF EXAMPLES 10.1 TO 10.20.
Unless otherwise stated, all starting materials are commercially available from common vendors.

| Ex. | Key Starting Material(s) | Key Starting Material(s) | Reaction Condition | Purification Method* |
|---|---|---|---|---|
| 10.7 | ASDI | PREPARATION 3 | Dioxane/water, 80° C., 17 h | A |
| 10.8 | Boron Molecular | PREPARATION 3 | Dioxane/water, 80° C., 17 h | A |
| 10.9 | Combi-blocks | PREPARATION 3 | Dioxane/water, 80° C., 17 h | A |
| 10.10 | Aldrich | PREPARATION 3 | Dioxane/water, 80° C., 17 h | A |
| 10.11 | Frontier Scientific | PREPARATION 3 | Dioxane/water, 80° C., 17 h | A |

TABLE 22B-continued

STARTING MATERIALS AND REACTION CONDITION
FOR PREPARATION OF EXAMPLES 10.1 TO 10.20.
Unless otherwise stated, all starting materials are commercially available from common vendors.

| Ex. | Key Starting Material(s) | Key Starting Material(s) | Reaction Condition | Purification Method* |
|---|---|---|---|---|
| 10.12 | 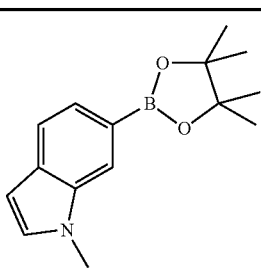<br>Maybridge | 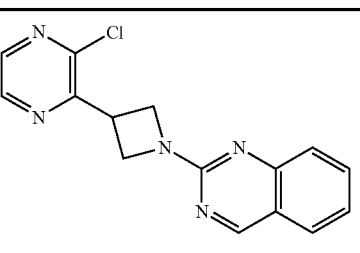<br>PREPARATION 3 | Dioxane/water, 80° C., 15 h | A |
| 10.13 | 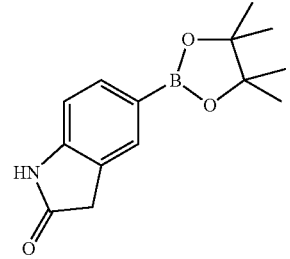 [SMILES: CC1(C)OB(c2ccc3c(c2)CC(=O)N3)OC1(C)C]<br>ASDI | 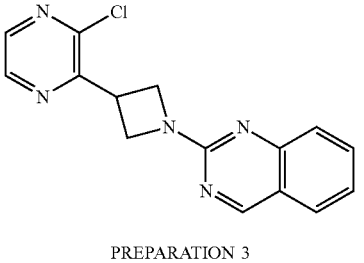<br>PREPARATION 3 | Dioxane/water, 80° C., 15 h | A |
| 10.14 | 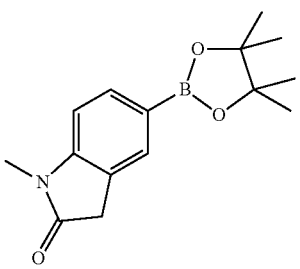<br>ASDI | 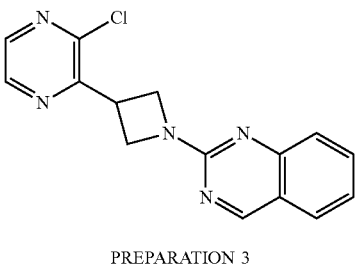<br>PREPARATION 3 | Dioxane/water, 80° C., 15 h | A |
| 10.15 | 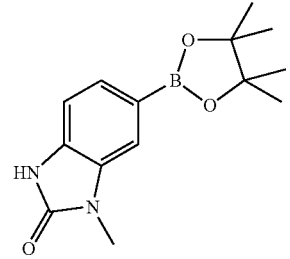 [SMILES: Cn1c(=O)[nH]c2ccc(B3OC(C)(C)C(C)(C)O3)cc21]<br>ASDI | 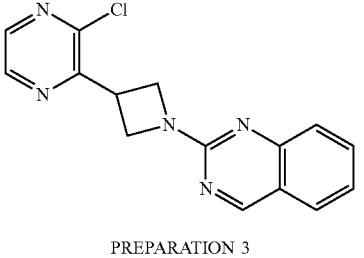<br>PREPARATION 3 | Dioxane/water, 80° C., 15 h | A |
| 10.16 | 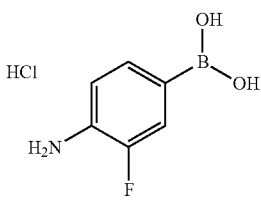 [SMILES: Cl ; Nc1ccc(B(O)O)cc1F]<br>Aldrich | 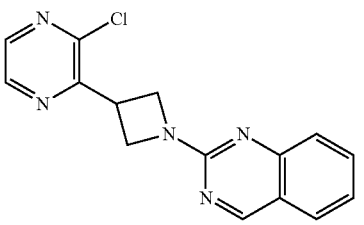 [SMILES: Clc1nccnc1C1CN(c2ncc3ccccc3n2)C1]<br>PREPARATION 3 | $Pd_2Cl_2(PPh_3)_2$, $Na_2CO_3$, (4 equiv), Dioxane/water, 80° C., 17 h | B |

TABLE 22B-continued

STARTING MATERIALS AND REACTION CONDITION
FOR PREPARATION OF EXAMPLES 10.1 TO 10.20.
Unless otherwise stated, all starting materials are commercially available from common vendors.

| Ex. | Key Starting Material(s) | Key Starting Material(s) | Reaction Condition | Purification Method* |
|---|---|---|---|---|
| 10.17 | 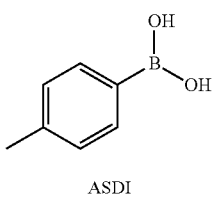 ASDI | 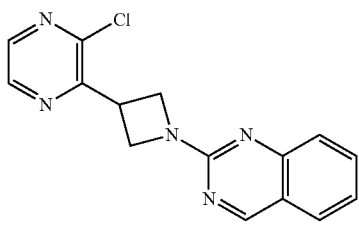 [SMILES: Clc1nccnc1C1CN(c2ncc3ccccc3n2)C1] PREPARATION 3 | $Pd_2Cl_2(PPh_3)_2$, $Na_2CO_3$, Dioxane/water, 80° C., 17 h | B |
| 10.18 | 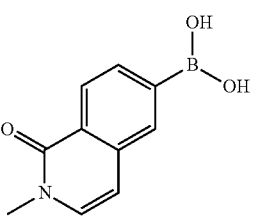 ASDI | 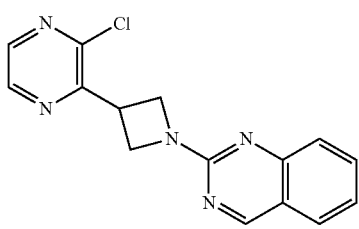 [SMILES: Clc1nccnc1C1CN(c2ncc3ccccc3n2)C1] PREPARATION 3 | $Pd_2Cl_2(PPh_3)_2$, $Na_2CO_3$, Dioxane/water, 80° C., 17 h | B |
| 10.19 | 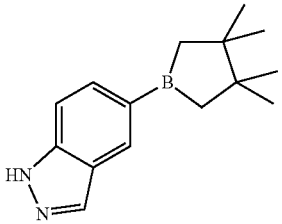 ASDI | 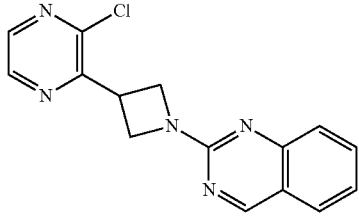 [SMILES: Clc1nccnc1C1CN(c2ncc3ccccc3n2)C1] PREPARATION 3 | $Pd_2Cl_2(PPh_3)_2$, $Na_2CO_3$, Dioxane/water, 80° C., 17 h | B |
| 10.20 | 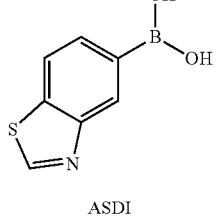 ASDI | 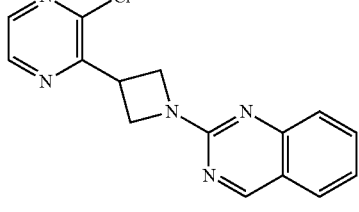 PREPARATION 3 | $Pd_2Cl_2(PPh_3)_2$, $Na_2CO_3$, Dioxane/water, 80° C., 17 h | A, B |

*Purification Methods: Method A- reverse phase HPLC (Column: Xbridge 19 × 100 mm, 5 μm, 1771302301) eluting with 0.1% $NH_4OH$ in acetonitrile/water. Method B- silica gel flash column chromatography eluting with 0% to 75% EtOAc in hexanes

TABLE 22C

1H NMR δ (PPM) DATA FOR EXAMPLES 10.1 TO 10.20

| Ex. # | Structure | NMR |
|---|---|---|
| 10.1 | 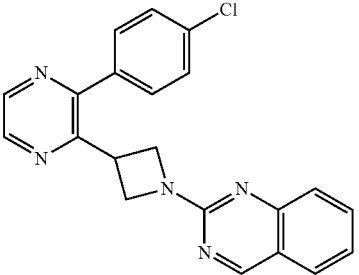 | (500 MHz, DMSO-$d_6$) 4.28-4.38 (m, 5H) 7.25-7.30 (m, 1H) 7.52 (d, J = 8.48 Hz, 1H) 7.62 (s, 4H) 7.70-7.75 (m, 1H) 7.84 (br. d, J = 7.80 Hz, 1H) 8.64 (d, J = 2.41 Hz, 1H) 8.70 (d, J = 2.41 Hz, 1H) 9.18 (s, 1H) |
| 10.2 | 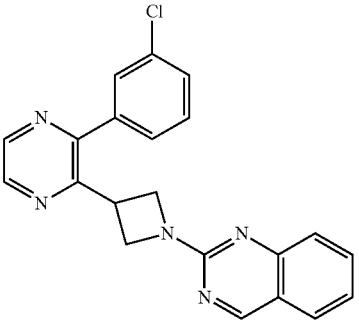 [SMILES: Clc1cccc(-c2nccnc2C2CN(c3ncc4ccccc4n3)C2)c1] | (500 MHz, DMSO-$d_6$) 4.28-4.40 (m, 5H) 7.28 (t, J = 7.40 Hz, 1H) 7.50-7.62 (m, 4H) 7.66 (s, 1H) 7.70-7.75 (m, 1H) 7.84 (d, J = 7.79 Hz, 1H) 8.64 (d, J = 2.40 Hz, 1H) 8.71 (d, J = 2.40 Hz, 1H) 9.18 (s, 1H) |
| 10.3 | 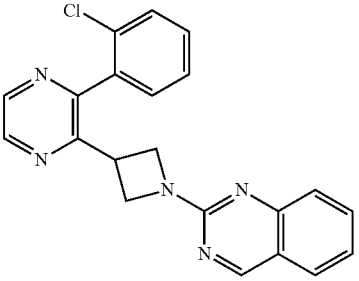 [SMILES: Clc1ccccc1-c1nccnc1C1CN(c2ncc3ccccc3n2)C1] | (500 MHz, DMSO-$d_6$) 3.96 (quin, J = 7.30 Hz, 1H) 4.33 (m, 4H) 7.28 (t, J = 7.39 Hz, 1H) 7.50-7.59 (m, 4H) 7.66 (br. d, J = 7.45 Hz, 1H) 7.70-7.75 (m, 1H) 7.84 (d, J = 7.56 Hz, 1H) 8.67 (d, J = 2.41 Hz, 1H) 8.76 (d, J = 2.52 Hz, 1H) 9.18 (s, 1H) |
| 10.4 | 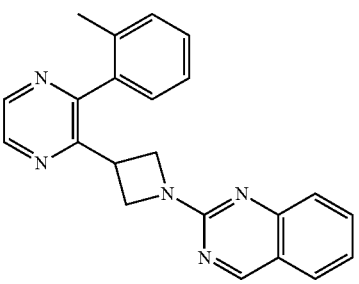 [SMILES: Cc1ccccc1-c1nccnc1C1CN(c2ncc3ccccc3n2)C1] | (500 MHz, DMSO-$d_6$) 2.07 (s, 3H) 3.94-4.01 (m, 1H) 4.22 (t, J = 8.36 Hz, 2H) 4.28-4.33 (m, 2H) 7.23-7.30 (m, 2H) 7.32-7.37 (m, 1H) 7.37-7.44 (m, 2H) 7.51 (d, J = 8.48 Hz, 1H) 7.70-7.74 (m, 1H) 7.84 (d, J = 7.56 Hz, 1H) 8.63 (d, J = 2.52 Hz, 1H) 8.70 (d, J = 2.41 Hz, 1H) 9.17 (s, 1H) |
| 10.5 | 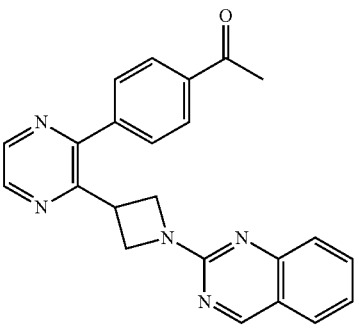 [SMILES: CC(=O)c1ccc(-c2nccnc2C2CN(c3ncc4ccccc4n3)C2)cc1] | (500 MHz, DMSO-$d_6$) 2.67 (s, 3H) 4.29-4.39 (m, 5H) 7.28 (br. t, J = 7.40, 7.40 Hz, 1H) 7.51 (d, J = 8.25 Hz, 1H) 7.71-7.77 (m, 3H) 7.85 (br. d, J = 8.00 Hz, 1H) 8.13 (d, J = 8.36 Hz, 2H) 8.68 (d, J = 2.41 Hz, 1H) 8.73 (d, J = 2.41 Hz, 1H) 9.18 (s, 1H) |

TABLE 22C-continued
1H NMR δ (PPM) DATA FOR EXAMPLES 10.1 TO 10.20
| Ex. # | Structure | NMR |
|---|---|---|
| 10.6 | 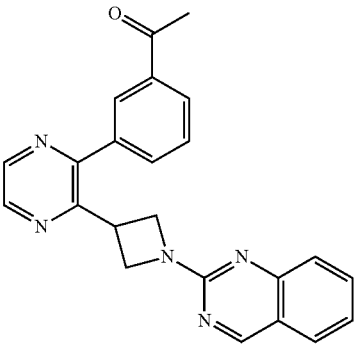 [SMILES: CC(=O)c1cccc(-c2nccnc2C2CN(c3ncc4ccccc4n3)C2)c1] | (500 MHz, DMSO-$d_6$) 2.67 (s, 3H) 4.30-4.40 (m, 5H) 7.27 (t, J = 7.39 Hz, 1H) 7.51 (d, J = 8.48 Hz, 1H) 7.71 (t, J = 7.68 Hz, 2H) 7.83 (d, J = 8.02 Hz, 1H) 7.86 (d, J = 7.68 Hz, 1H) 8.10 (d, J = 7.79 Hz, 1H) 8.13 (s, 1H) 8.66 (d, J = 2.29 Hz, 1H) 8.72 (d, J = 2.29 Hz, 1H) 9.17 (s, 1H) |
| 10.7 | 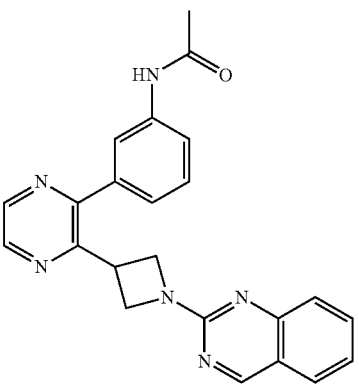 [SMILES: CC(=O)Nc1cccc(-c2nccnc2C2CN(c3ncc4ccccc4n3)C2)c1] | (500 MHz, DMSO-$d_6$) 2.09 (s, 3H) 4.29-4.45 (m, 5H) 7.26-7.30 (m, 2H) 7.48 (t, J = 7.85 Hz, 1H) 7.53 (d, J = 8.48 Hz, 1H) 7.67 (br. d, J = 8.00 Hz, 1H) 7.71-7.75 (m, 1H) 7.83-7.87 (m, 2H) 8.63 (d, J = 2.41 Hz, 1H) 8.68 (d, J = 2.41 Hz, 1H) 9.19 (s, 1H) 10.13 (s, 1H) |
| 10.8 | 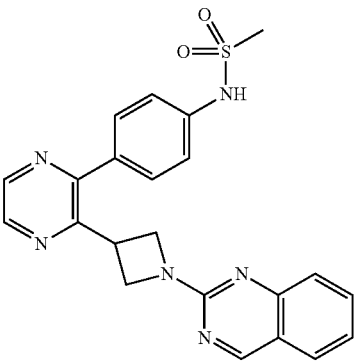 [SMILES: CS(=O)(=O)Nc1ccc(-c2nccnc2C2CN(c3ncc4ccccc4n3)C2)cc1] | (500 MHz, DMSO-$d_6$) 3.10 (s, 3H) 4.27-4.32 (m, 2H) 4.36-4.42 (m, 3H) 7.28 (br. t, J = 7.40, 7.40 Hz, 1H) 7.38 (d, J = 8.59 Hz, 2H) 7.52 (d, J = 8.48 Hz, 1H) 7.57 (d, J = 8.59 Hz, 2H) 7.71-7.75 (m, 1H) 7.85 (br. d, J = 8.00 Hz, 1H) 8.61 (d, J = 2.40 Hz, 1H) 8.65 (d, J = 2.41 Hz, 1H) 9.18 (s, 1H) 10.05 (s, 1H) |
| 10.9 | 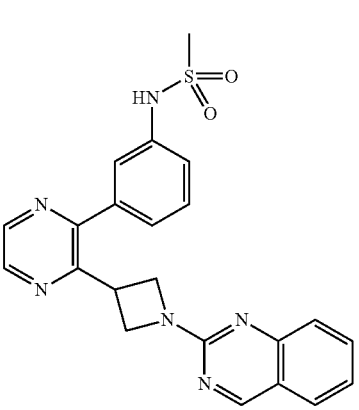 [SMILES: CS(=O)(=O)Nc1cccc(-c2nccnc2C2CN(c3ncc4ccccc4n3)C2)c1] | (500 MHz, DMSO-$d_6$) 3.07 (s, 3H) 4.30-4.37 (m, 3H) 4.38-4.44 (m, 2H) 7.29 (br. t, J = 7.50, 7.50 Hz, 1H) 7.33-7.39 (m, 3H) 7.51-7.55 (m, 2H) 7.71-7.75 (m, 1H) 7.86 (br. d, J = 8.10 Hz, 1H) 8.64 (d, J = 2.41 Hz, 1H) 8.70 (d, J = 2.41 Hz, 1H) 9.19 (s, 1H) 9.97 (s, 1H) |

TABLE 22C-continued

1H NMR δ (PPM) DATA FOR EXAMPLES 10.1 TO 10.20

| Ex. # | Structure | NMR |
|---|---|---|
| 10.10 | 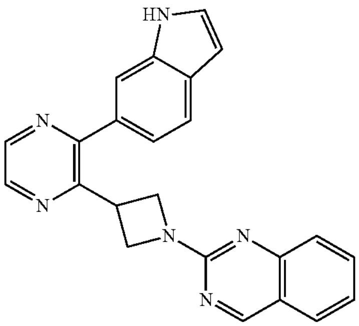 [SMILES: c1ccc2nc(N3CC(c4nccnc4-c4ccc5cc[nH]c5c4)C3)ncc2c1] | (500 MHz, DMSO-$d_6$) 4.30-4.40 (m, 4H) 4.42-4.49 (m, 1H) 6.52-6.54 (m, 1H) 7.24 (dd, J = 8.25, 1.49 Hz, 1H) 7.27 (m, J = 7.80, 7.80 Hz, 1H) 7.49 (t, J = 2.75 Hz, 1H) 7.51 (d, J = 8.48 Hz, 1H) 7.61 (s, 1H) 7.68-7.74 (m, 2H) 7.82-7.86 (m, 1H) 8.62 (d, J = 2.40 Hz, 1H) 8.63 (d, J = 2.40 Hz, 1H) 9.17 (s, 1H) 11.30 (br. s., 1H) |
| 10.11 | 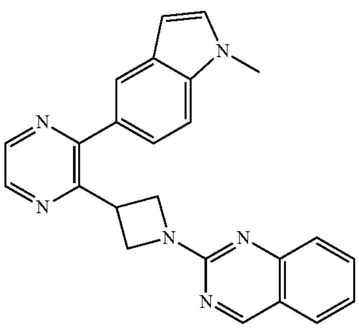 [SMILES: Cn1ccc2cc(-c3nccnc3C3CN(c4ncc5ccccc5n4)C3)ccc21] | (500 MHz, DMSO-$d_6$) 3.87 (s, 3H) 4.25-4.36 (m, 4H) 4.45-4.52 (m, 1H) 6.57 (d, J = 2.86 Hz, 1H) 7.27 (br. t, J = 7.40, 7.40 Hz, 1H) 7.39 (dd, J = 8.42, 1.55 Hz, 1H) 7.44 (d, J = 2.98 Hz, 1H) 7.50 (d, J = 8.59 Hz, 1H) 7.60 (d, J = 8.48 Hz, 1H) 7.69-7.73 (m, 1H) 7.77 (d, J = 1.26 Hz, 1H) 7.83 (br. d, J = 7.10 Hz, 1H) 8.60-8.63 (m, 2H) 9.16 (s, 1H) |
| 10.12 | 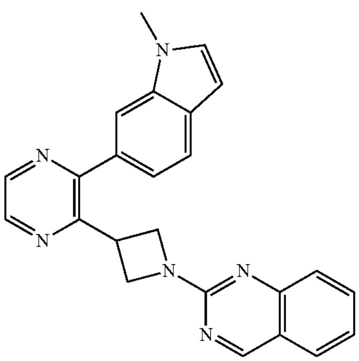 [SMILES: Cn1ccc2ccc(-c3nccnc3C3CN(c4ncc5ccccc5n4)C3)cc21] | (500 MHz, DMSO-$d_6$) 3.88 (s, 3H) 4.28-4.38 (m, 4H) 4.47-4.54 (m, 1H) 6.53 (d, J = 2.86 Hz, 1H) 7.24-7.29 (m, 2H) 7.47 (d, J = 3.09 Hz, 1H) 7.51 (d, J = 8.48 Hz, 1H) 7.64 (s, 1H) 7.70 (m, J = 8.40 Hz, 2H) 7.83 (br. d, J = 7.80 Hz, 1H) 8.63 (d, J = 2.40 Hz, 1H) 8.65 (d, J = 2.40 Hz, 1H) 9.16 (s, 1H) |
| 10.13 | 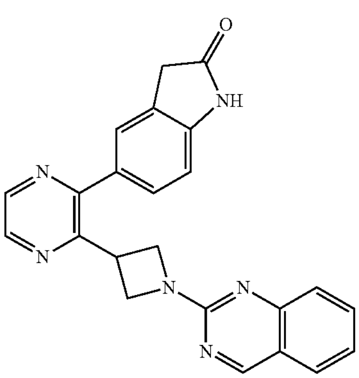 [SMILES: O=C1Cc2cc(-c3nccnc3C3CN(c4ncc5ccccc5n4)C3)ccc2N1] | (500 MHz, DMSO-$d_6$) 3.60 (s, 2H) 4.26-4.31 (m, 2H) 4.36-4.45 (m, 3H) 6.98 (d, J = 8.02 Hz, 1H) 7.26-7.30 (m, 1H) 7.41 (d, J = 8.02 Hz, 1H) 7.44 (s, 1H) 7.51 (d, J = 8.48 Hz, 1H) 7.70-7.75 (m, 1H) 7.85 (br. d, J = 7.20 Hz, 1H) 8.59 (d, J = 2.29 Hz, 1H) 8.62 (d, J = 2.41 Hz, 1H) 9.18 (s, 1H) 10.57 (s, 1H) |

TABLE 22C-continued

1H NMR δ (PPM) DATA FOR EXAMPLES 10.1 TO 10.20

| Ex. # | Structure | NMR |
|---|---|---|
| 10.14 | 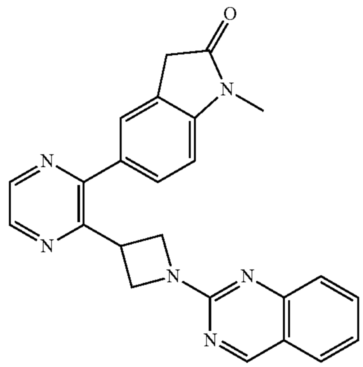 [SMILES: CN1C(=O)Cc2cc(-c3nccnc3C3CN(c4ncc5ccccc5n4)C3)ccc21] | (500 MHz, DMSO-$d_6$) 3.20 (s, 3H) 3.68 (s, 2H) 4.27-4.32 (m, 2H) 4.35-4.41 (m, 2H) 4.41-4.48 (m, 1H) 7.14 (d, J = 7.90 Hz, 1H) 7.28 (br. t, J = 7.50, 7.50 Hz, 1H) 7.49-7.53 (m, 3H) 7.70-7.75 (m, 1H) 7.85 (br. d, J = 7.20 Hz, 1H) 8.60 (d, J = 2.41 Hz, 1H) 8.63 (d, J = 2.41 Hz, 1H) 9.18 (s, 1H) |
| 10.15 | 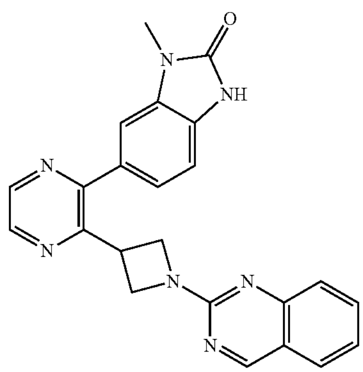 [SMILES: Cn1c(=O)[nH]c2ccc(-c3nccnc3C3CN(c4ncc5ccccc5n4)C3)cc21] | (500 MHz, DMSO-$d_6$) 3.35 (s, 3H) 4.27-4.32 (m, 2H) 4.34-4.40 (m, 2H) 4.43-4.50 (m, 1H) 7.14 (d, J = 7.90 Hz, 1H) 7.21 (dd, J = 8.00, 1.50 Hz, 1H) 7.28 (t, J = 7.45 Hz, 1H) 7.30 (s, 1H) 7.51 (d, J = 8.48 Hz, 1H) 7.70-7.74 (m, 1H) 7.84 (br. d, J = 7.90 Hz, 1H) 8.61 (d, J = 2.41 Hz, 1H) 8.64 (d, J = 2.40 Hz, 1H) 9.18 (s, 1H) 11.05 (s, 1H) |
| 10.16 | 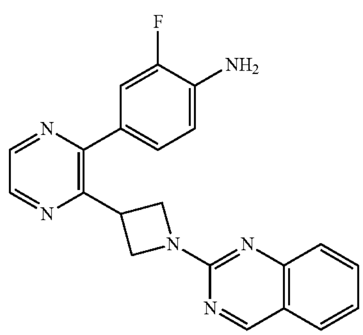 [SMILES: Nc1ccc(-c2nccnc2C2CN(c3ncc4ccccc4n3)C2)cc1F] | (500 MHz, d-CHLOROFORM) 3.98 (br. s., 2H) 4.41 (quin, J = 7.20 Hz, 1H) 4.53 (d, J = 7.20 Hz, 4H) 6.88 (t, J = 8.61 Hz, 1H) 7.11 (br. d, J = 8.00 Hz, 1H) 7.20-7.27 (m, 2H) 7.60-7.70 (m, 3H) 8.49 (d, J = 2.15 Hz, 1H) 8.52 (d, J = 2.15 Hz, 1H) 9.02 (s, 1H) |
| 10.17 | 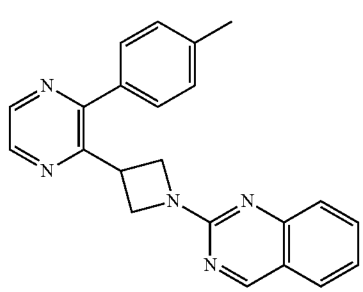 [SMILES: Cc1ccc(-c2nccnc2C2CN(c3ncc4ccccc4n3)C2)cc1] | (500 MHz, d-CHLOROFORM) 2.45 (s, 3H) 4.37 (quin, J = 7.20 Hz, 1H) 4.45-4.57 (m, 4H) 7.23 (t, J = 7.34 Hz, 1H) 7.32 (d, 1H NMR (500 MHz, d-CHLOROFORM) δ J = 8.02 Hz, 2H) 7.41 (d, J = 8.00 Hz, 2H) 7.60-7.70 (m, 3H) 8.52 (d, J = 2.20 Hz, 1H) 8.56 (d, J = 2.15 Hz, 1H) 9.01 (s, 1H) |

TABLE 22C-continued
1H NMR δ (PPM) DATA FOR EXAMPLES 10.1 TO 10.20
| Ex. # | Structure | NMR |
|---|---|---|
| 10.18 | 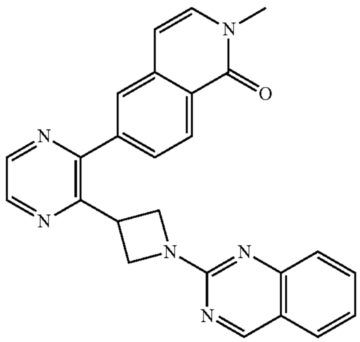 [SMILES: Cn1ccc2cc(-c3nccnc3C3CN(c4ncc5ccccc5n4)C3)ccc2c1=O] | (500 MHz, d-CHLOROFORM) 3.66 (s, 3H) 4.36 (quin, J = 7.40 Hz, 1H) 4.46-4.59 (m, 4H) 6.55 (d, J = 7.43 Hz, 1H) 7.16 (d, J = 7.43 Hz, 1H) 7.24 (t, J = 7.40 Hz, 1H) 7.59-7.71 (m, 5H) 8.56-8.60 (m, 2H) 8.65 (d, J = 2.15 Hz, 1H) 9.01 (s, 1H) |
| 10.19 | 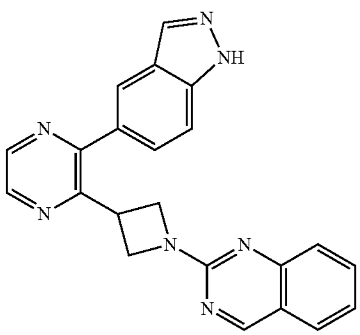 [SMILES: c1ccc2nc(N3CC(c4nccnc4-c4ccc5[nH]ncc5c4)C3)ncc2c1] | (500 MHz, d-CHLOROFORM) 4.40-4.59 (m, 5H) 7.21-7.25 (m, 1H) 7.54-7.70 (m, 5H) 7.90 (s, 1H) 8.17 (s, 1H) 8.56 (d, J = 2.30 Hz, 1H) 8.60 (d, J = 2.35 Hz, 1H) 9.01 (s, 1H) 10.53 (br. s, 1H) |
| 10.20 | 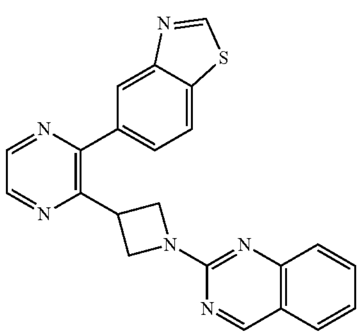 [SMILES: c1ccc2nc(N3CC(c4nccnc4-c4ccc5scnc5c4)C3)ncc2c1] | (400 MHz, d-CHLOROFORM) 4.42-4.59 (m, 5H) 7.23 (t, J = 7.43 Hz, 1H) 7.59-7.71 (m, 4H) 8.13 (d, J = 8.41 Hz, 1H) 8.29 (d, J = 0.78 Hz, 1H) 8.59 (d, J = 2.35 Hz, 1H) 8.64 (d, J = 2.35 Hz, 1H) 9.01 (s, 1H) 9.11 (s, 1H) |
SCHEME 11
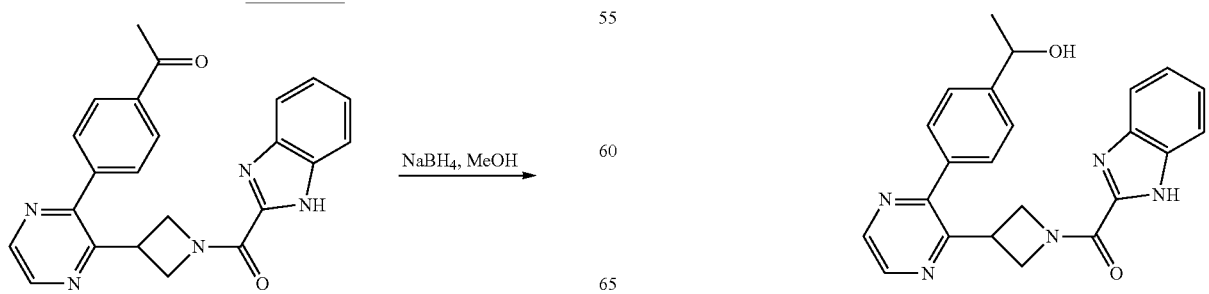

Example 11.1: (1H-Benzoimidazol-2-Yl)-(3-{3-[4-(1-Hydroxy-Ethyl)-Phenyl]-Pyrazin-2-Yl}-Azetidin-1-Yl)-Methanone 1-(4-{3-[1-(1H-benzoimidazole-2-carbonyl)-azetidin-3-yl]-pyrazin-2-yl}-phenyl)-ethanone (100 mg, 0.25 mmol, Scheme 2, Example 2.21) was dissolved in 10 ml of methanol. This solution was cooled down to 0° C. using an ice bath and sodium tetraborohydride (19 mg, 0.50 mmol) was added by portions. The reaction mixture was stirred for 4 h at ambient temperature, then saturated aqueous solution of ammonium chloride (5 mL) was added. The methanol was evaporated off under reduced pressure then the reaction mixture was taken up in ethyl acetate. The organic phase was separated from the aqueous phase. This extraction was repeated one more time and then the organic phases were combined and dried over magnesium sulphate, followed by concentrating under reduced pressure. The residue was purified by column chromatography to give the title compound (75 mg, 0.19 mmol, 75% yield).

The following Table 23A lists compounds of Examples 11.1 to 11.3, which were made analogous to Scheme 11 by using the appropriate materials and reaction conditions, which are listed in Table 23B. The NMR data of the Examples are listed in Table 23C.

TABLE 23A

EXAMPLES 11.1 TO 11.3

| Ex. # | Structure | Chemical Name | ESI-MS (M + 1) | IC$_{50}$ (uM) |
|---|---|---|---|---|
| 11.1 | 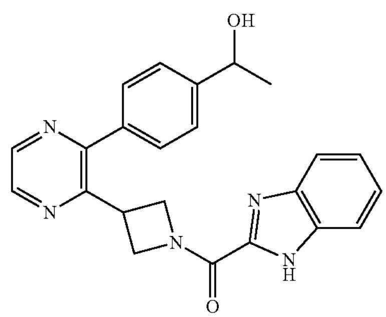 [SMILES: CC(O)c1ccc(-c2nccnc2C2CN(C(=O)c3nc4ccccc4[nH]3)C2)cc1] | (R & S)-(1H-Benzoimidazol-2-yl)-(3-{3-[4-(1-hydroxy-ethyl)-phenyl]-pyrazin-2-yl}-azetidin-1-yl)-methanone | 400 | 0.0288 |
| 11.2 | 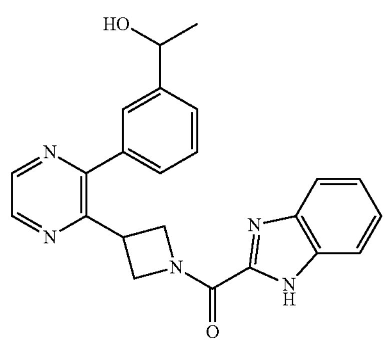 [SMILES: CC(O)c1cccc(-c2nccnc2C2CN(C(=O)c3nc4ccccc4[nH]3)C2)c1] | (R & S)-(1H-Benzoimidazol-2-yl)-(3-{3-[3-(1-hydroxy-ethyl)-phenyl]-pyrazin-2-yl}-azetidin-1-yl)-methanone | 400 | 0.0778 |
| 11.3 | 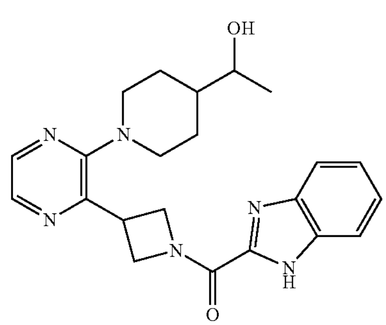 [SMILES: CC(O)C1CCN(c2nccnc2C2CN(C(=O)c3nc4ccccc4[nH]3)C2)CC1] | (R & S)-(1H-Benzoimidazol-2-yl)-(3-{3-[4-(1-hydroxy-ethyl)-piperidin-1-yl]-pyrazin-2-yl}-azetidin-1-yl)-methanone | 407 | 0.056 |

TABLE 23B

STARTING MATERIALS AND REACTION CONDITION FOR PREPARATION OF EXAMPLES 11.1 TO 11.3. Unless otherwise stated, all starting materials are commerically available from common vendors.

| Ex. # | Starting Material 1 | Reaction Condition |
|---|---|---|
| 11.1 | (4-acetylphenyl pyrazine azetidine benzimidazole carbonyl structure) SCHEME 2 | $NaBH_4$, MeOH 0° C. |
| 11.2 | (3-acetylphenyl pyrazine azetidine benzimidazole carbonyl structure) SCHEME 2 | $NaBH_4$, MeOH 0° C. |
| 11.3 | (4-acetylpiperidinyl pyrazine azetidine benzimidazole carbonyl structure) SCHEME 3, Ex. 3.46 | $NaBH_4$, MeOH 0° C. |

TABLE 23C

1H NMR δ (PPM) DATA FOR EXAMPLES 11.1 TO 11.3

| Ex. # | Structure | NMR |
|---|---|---|
| 11.1 | 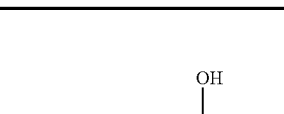 | (DMSO, 400 MHz): 8.65 (d, J = 2.4 Hz, 1H); 8.54 (d, J = 2.4 Hz, 1H); 7.67-7.65 (m, 2 H); 7.56-7.54 (m, 2H); 7.49-7.47 (m, 2H); 7.37-7.34 (m, 2H); 4.99-4.98 (m, 2H); 4.91-4.90 (m, 1H); 4.42-4.39 (m, 3H); 1.49 (d, J = 6.4 Hz, 3H). |

TABLE 23C-continued
1H NMR δ (PPM) DATA FOR EXAMPLES 11.1 TO 11.3
| Ex. # | Structure | NMR |
|---|---|---|
| 11.2 | 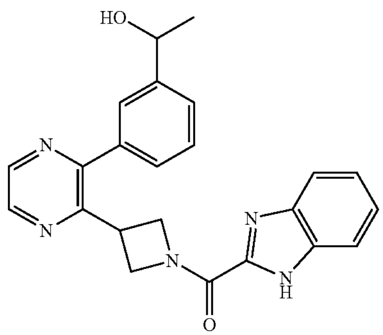 [SMILES: CC(O)c1cccc(-c2nccnc2C2CN(C(=O)c3nc4ccccc4[nH]3)C2)c1] | (CDCl$_3$, 400 MHz): 8.44 (s, 2 H); 7.51 (brs, 2H); 7.36-7.35 (m, 3H); 7.23-7.19 (m, 3H); 4.91-4.90 (m, 3H); 4.39-4.13 (m, 3H); 1.43 (d, J = 6.0 Hz, 3H). |
| 11.3 | 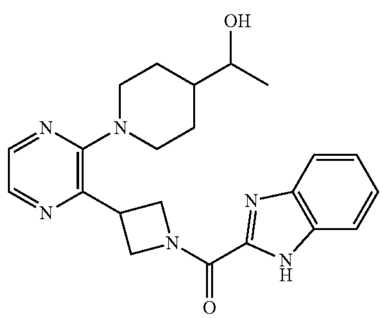 [SMILES: CC(O)C1CCN(c2nccnc2C2CN(C(=O)c3nc4ccccc4[nH]3)C2)CC1] | (CD$_3$OD, 400 MHz): 8.17 (d, J = 2.4 Hz, 1H); 8.11 (d, J = 2.4 Hz, 1H); 7.67 (m, 2H), 7.26 (m, 2H); 5.18 (t, J = 7.6, 1H); 4.96 (m, 1H); 4.62 (t, J = 8.0 Hz, 1H); 4.46-4.40 (m, 1H); 4.42-4.36 (m, 1H); 3.61-3.53 (m, 1H); 3.45 (d, J = 8.4 Hz, 2H); 2.2.89-2.79 (m, 1H); 2.01-1.75 (m, 2H); 1.61-1.42 (m, 2H) 1.38 (d, J = 6.4 Hz, 1H); 1.19 (d, J = 6.4 Hz, 3H). |
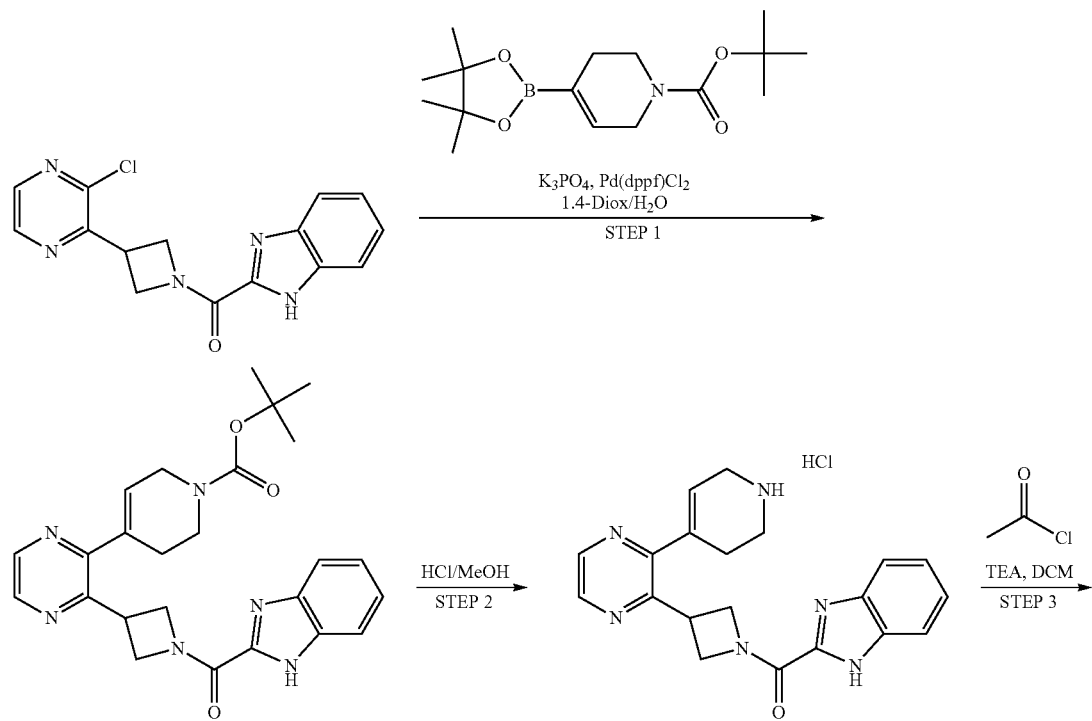
SCHEME 12

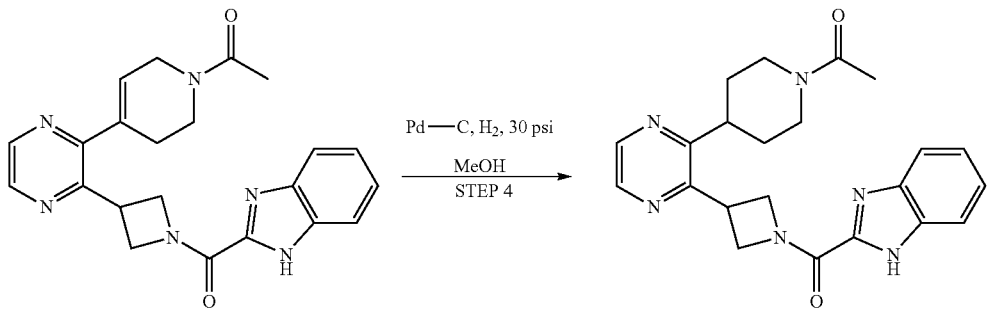

Example 12.1: 1-(4-{3-[1-(1H-Benzoimidazole-2-Carbonyl)-Azetidin-3-Yl]-Pyrazin-2-Yl}-Piperidin-1-Yl)-Ethanone Step 1. 4-{3-[1-(1H-Benzoimidazole-2-Carbonyl)-Azetidin-3-Yl]-Pyrazin-2-Yl}-3,6-Dihydro-2H-Pyridine-1-Carboxylic Acid Tert-Butyl Ester To a mixture of (1H-Benzoimidazol-2-yl)-[3-(3-chloro-pyrazin-2-yl)-azetidin-1-yl]-methanone (188 mg, 0.6 mmol) in 1,4-dioxane/water (5:1, 12 mL) was added 4-(4,4,5,5-tetramethyl-[1,3,2]dioxaborolan-2-yl)-3,6-dihydro-2H-pyridine-1-carboxylic acid tert-butyl ester (278 mg, 0.9 mmol), $K_3PO_4$ (254 mg, 1.2 mmol) and Pd(dppf)Cl$_2$ (44 mg, 0.06 mmol). The mixture was refluxed overnight. The reaction mixture was filtered and concentrated. The residue was purified by ISCO silica gel column (10% to 80% EtOAc in petroleum ether) to give 4-{3-[1-(1H-benzoimidazole-2-carbonyl)-azetidin-3-yl]-pyrazin-2-yl}-3,6-dihydro-2H-pyridine-1-carboxylic acid tert-butyl ester (221 mg, 0.48 mmol, yield 80%). ESI-MS (M+1): 461 calc. for $C_{25}H_{28}N_6O_3$ 460.

Step 2. (1H-Benzoimidazol-2-Yl)-{3-[3-(1,2,3,6-Tetrahydro-Pyridin-4-Yl)-Pyrazin-2-Yl]-Azetidin-1-Yl}-Methanone Hydrochloride To 4-{3-[1-(1H-Benzoimidazole-2-carbonyl)-azetidin-3-yl]-pyrazin-2-yl}-3,6-dihydro-2H-pyridine-1-carboxylic acid tert-butyl ester (217 mg, 0.47 mmol) was added 4 M HCl in MeOH (100 mL). The solution was stirred at RT for 2 h. The solvent was removed under reduced pressure to give (1H-benzoimidazol-2-yl)-{3-[3-(1,2,3,6-tetrahydro-pyridin-4-yl)-pyrazin-2-yl]-azetidin-1-yl}-methanone hydrochloride (187 mg, 0.47 mmol, yield 100%). ESI-MS (M+1): 361 calc. for $C_{20}H_{20}N_6O$ 360.

Step 3. 1-(4-{3-[1-(1H-Benzoimidazole-2-Carbonyl)-Azetidin-3-Yl]-Pyrazin-2-Yl}-3,6-Dihydro-2H-Pyridin-1-Yl)-Ethanone To a solution of (1H-benzoimidazol-2-yl)-{3-[3-(1,2,3,6-tetrahydro-pyridin-4-yl)-pyrazin-2-yl]-azetidin-1-yl}-methanone hydrochloride (187 mg, 0.47 mmol) in dry CH$_2$Cl$_2$ (10 mL) was added Et$_3$N (1 mL). The reaction mixture was cooled to 0° C. with an ice bath, and acetyl chloride (39 mg, 0.50 mmol) was added dropwise. After 1 h, the reaction mixture was warmed to RT, and stirred overnight. Then the reaction mixture was washed with brine, dried over Na$_2$SO$_4$, filtered, and concentrated under vacuum to give the crude product (170 mg, 0.42 mmol, 90% yield). ESI-MS (M+1): 403 calc. for $C_{22}H_{22}N_6O_2$ 402.

Step 4. 1-(4-{3-[1-(1H-Benzoimidazole-2-Carbonyl)-Azetidin-3-Yl]-Pyrazin-2-Yl}-Piperidin-1-Yl)-Ethanone A mixture of 1-(4-{3-[1-(1H-benzoimidazole-2-carbonyl)-azetidin-3-yl]-pyrazin-2-yl}-3,6-dihydro-2H-pyridin-1-yl)-ethanone (170 mg, 0.42 mmol) and wet Pd—C (50%, 50 mg) in MeOH (30 mL) was stirred under H$_2$ (30 psi) at RT for 2 h then the reaction mixture was filtered through CELITE® and washed with MeOH. The filtrate was concentrated in vacuo and the residue was purified by ISCO silica gel column (10% to 50% EtOAc in petroleum ether) to give 1-(4-{3-[1-(1H-benzoimidazole-2-carbonyl)-azetidin-3-yl]-pyrazin-2-yl}-piperidin-1-yl)-ethanone (101 mg, 0.25 mmol, 60% yield).

$^1$H NMR (CDCl$_3$, 400 MHz): δ (ppm) 8.44 (dd, J=2.4, 4.0 Hz, 2H); 7.23-7.22 (m, 2H); 7.39-7.37 (m, 2H); 5.36-5.34 (m, 1H); 5.08-5.05 (m, 1H); 4.81-4.62 (m, 3H); 4.41-4.38 (m, 1H); 4.01 (d, J=13.2 Hz, 1H); 3.28-3.26 (m, 1H); 3.06-3.01 (m, 1H); 2.79-2.77 (m, 1H); 2.20 (s, 3H); 2.04-2.01 (m, 1H); 1.88-1.75 (m, 3H).

ESI-MS (M+1): 405. PDE10 IC$_{50}$ (uM): 0.427.

SCHEME 13

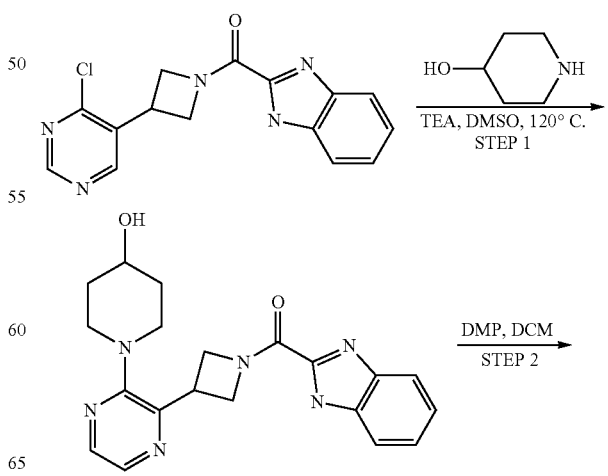

-continued

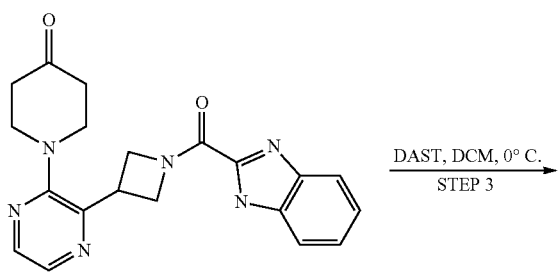

Example 13.1

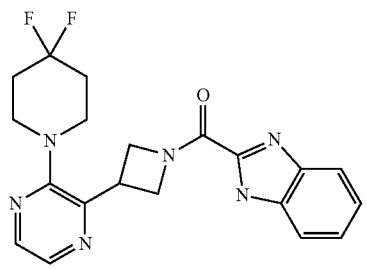

Example 13.2

Examples 13.1 and 13.2

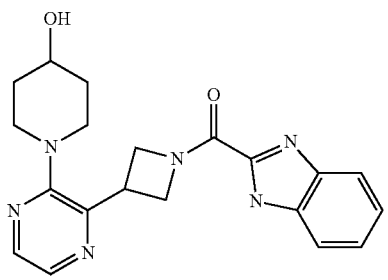 [SMILES: O=C(c1nc2ccccc2[nH]1)N1CC(c2nccnc2N2CCC(O)CC2)C1]

Step 1. (1H-Benzoimidazol-2-Yl)-{3-[3-(4-Hydroxy-Piperidin-1-Yl)-Pyrazin-2-Yl]-Azetidin-1-Yl}-Methanone To a mixture of (1H-benzoimidazol-2-yl)-[3-(3-chloro-pyrazin-2-yl)-azetidin-1-yl]-methanone (0.170 g, 0.50 mmol) and piperidin-4-ol (0.101 g, 1.0 mmol) was added triethylamine (0.10 g, 1.0 mmol) and DMSO (4 mL). The solution was heated to 120° C. for 4 h. Then the mixture was diluted with water (10 mL) and extracted with EtOAc (2×20 mL). The combined organic extracts were washed with water (10 mL) and brine (10 mL), dried over $Na_2SO_4$ and filtered. The filtrate was evaporated in vacuo and the residue was purified by flash column chromatography on silica gel (20% to 50% EtOAc in petroleum ether) to give (1H-benzoimidazol-2-yl)-{3-[3-(4-hydroxy-piperidin-1-yl)-pyrazin-2-yl]-azetidin-1-yl}-methanone (0.16 g, 0.42 mmol, 85% yield) as a white solid.

ESI-MS (M+1): 379 calc. for $C_{20}H_{22}N_6O_2$ 378.

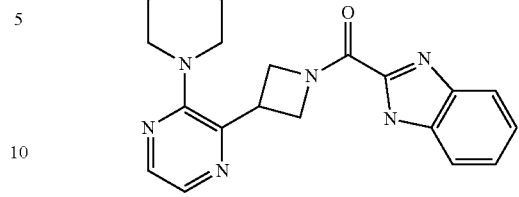

Step 2. 1-{3-[1-(1H-Benzoimidazole-2-Carbonyl)-Azetidin-3-Yl]-Pyrazin-2-Yl}-Piperidin-4-One (1H-Benzoimidazol-2-yl)-{3-[3-(4-hydroxy-piperidin-1-yl)-pyrazin-2-yl]-azetidin-1-yl}-methanone (0.16 g, 0.42 mmol) was dissolved in anhydrous $CH_2Cl_2$ (20 mL), treated with Dess-Martin Periodinane (DMP) (195 mg, 0.46 mmol, 1.1 equiv) and stirred at RT until complete conversion controlled by TLC (Petro ether:EtOAc=1:1). The organic layer was washed with an aqueous solution of $NaHCO_3$/$Na_2S_2O_3$ (3×10 mL)), dried over $Na_2SO_4$, filtered and evaporated. The resulting residue was purified by flash chromatography (20% to 40% EtOAc in petroleum ether) to give 1-{3-[1-(1H-benzoimidazole-2-carbonyl)-azetidin-3-yl]-pyrazin-2-yl}-piperidin-4-one (0.134 g, 0.36 mmol, 85% yield) as a white solid.

$^1$H NMR (CDCl$_3$, 400 MHz): δ (ppm) 8.24-8.14 (m, 2H); 7.71-7.68 (m, 2H); 7.35-7.24 (m, 2H); 5.34-5.30 (m, 1H); 5.08-5.04 (m, 1H); 4.69-4.60 (m, 2H); 4.39-4.31 (m, 1H); 3.55-3.44 (m, 4H); 2.67-2.57 (m, 4H).

ESI-MS (M+1): 377 calc. for $C_{20}H_{20}N_6O_2$ 376.

PDE10 IC$_{50}$ (uM): 0.0956.

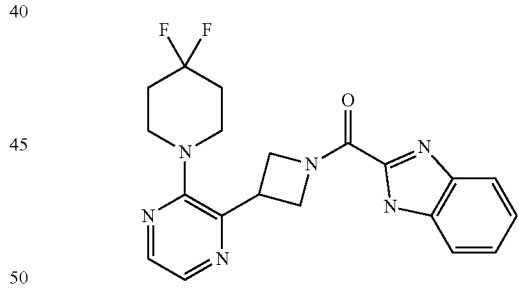

Step 3. (1H-Benzoimidazol-2-Yl)-{3-[3-(4,4-Difluoro-Piperidin-1-Yl)-Pyrazin-2-Yl]-Azetidin-1-Yl}-Methanone In a 50 mL flask, 1-{3-[1-(1H-benzoimidazole-2-carbonyl)-azetidin-3-yl]-pyrazin-2-yl}-piperidin-4-one (0.134 g, 0.36 mmol) was dissolved in anhydrous $CH_2Cl_2$ (15 mL). The solution was cooled to −10° C. under nitrogen atmosphere and DAST (0.12 g, 0.72 mmol) was added dropwise. The reaction mixture was allowed to warm to RT and stirred for 2 h. The mixture was poured into cold water (10 mL). The separated aqueous phase was extracted twice with $CH_2Cl_2$ (20 mL), and the combined organic phases were dried over MgSO₄. After filtration, the solvent was evaporated in vacuo, and the concentrate was purified via flash chromatography on silica gel (20% to 45% EtOAc in petroleum ether) to give (1H-benzoimidazol-2-yl)-{3-[3-(4,4-difluoro-piperidin-1-yl)-pyrazin-2-yl]-azetidin-1-yl}-methanone (0.114 g, 0.29 mmol, 80% yield) as a white solid.

¹H NMR (CDCl₃, 400 MHz): δ (ppm) 8.15 (d, J=1.6 Hz, 1H); 8.07 (d, J=2.4, 1H); 7.64-7.62 (m, 2H); 7.29-7.26 (m, 2H); 5.26-5.22 (m, 1H); 5.00-4.96 (m, 1H); 4.56-4.54 (m, 2H); 4.23-4.19 (m, 1H); 3.23-3.20 (m, 4H); 2.12-2.04 (m, 4H).

ESI-MS (M+1): 399 calc. for $C_{20}H_{20}F_2N_6O$ 398.

PDE10 IC₅₀ (uM): 0.0765.

SCHEME 14

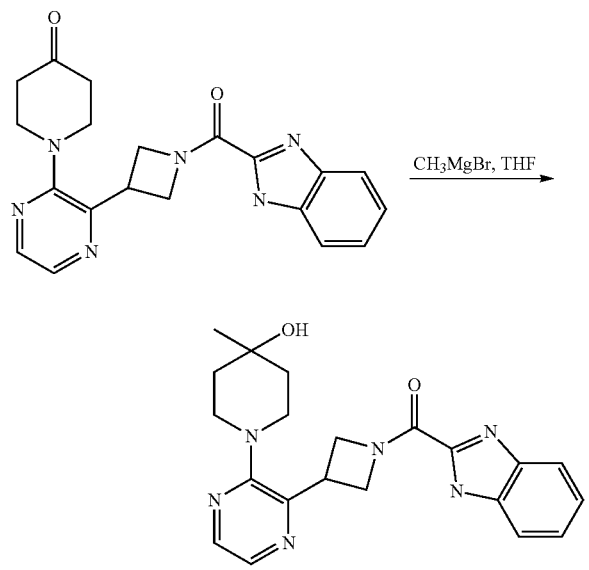

Example 14.1: (1H-Benzoimidazol-2-Yl)-{3-[3-(4-Hydroxy-4-Methyl-Piperidin-1-Yl)-Pyrazin-2-Yl]-Azetidin-1-Yl}-Methanone To a solution of 1-{3-[1-(1H-benzoimidazole-2-carbonyl)-azetidin-3-yl]-pyrazin-2-yl}-piperidin-4-one (150 mg, 0.40 mol, SCHEME 13, Ex. 13.1) in 20 mL of THF was added CH₃MgBr (0.60 mol, 3 M in ether) dropwise at 0° C. The mixture was stirred for 1 h at RT and then quenched with saturated aqueous NH₄Cl. The resulting mixture was extracted with EtOAc (2×20 mL) and the combined organic layers were dried over anhydrous Na₂SO₄, filtered and concentrated to give crude product which was purified by prep. TLC (EtOAc:Petrol ether=1:1) to give (1H-benzoimidazol-2-yl)-{3-[3-(4-hydroxy-4-methyl-piperidin-1-yl)-pyrazin-2-yl]-azetidin-1-yl}-methanone (0.109 g, 0.28 mmol, 70% yield) as a white solid.

¹H NMR (CD₃OD, 400 MHz): δ (ppm) 8.12 (d, J=2.8 Hz, 1H); 8.05 (d, J=2.8 Hz, 1H); 7.63-7.56 (m, 2H); 7.29-7.26 (m, 2H); 5.21-5.16 (m, 1H); 4.57-4.54 (m, 2H); 3.28-3.20 (m, 2H); 3.11-3.08 (m, 2H); 1.81-1.70 (m, 4H); 1.27 (s, 3H).

ESI-MS (M+1): 393. PDE10 IC₅₀ (uM): 0.131.

SCHEME 15

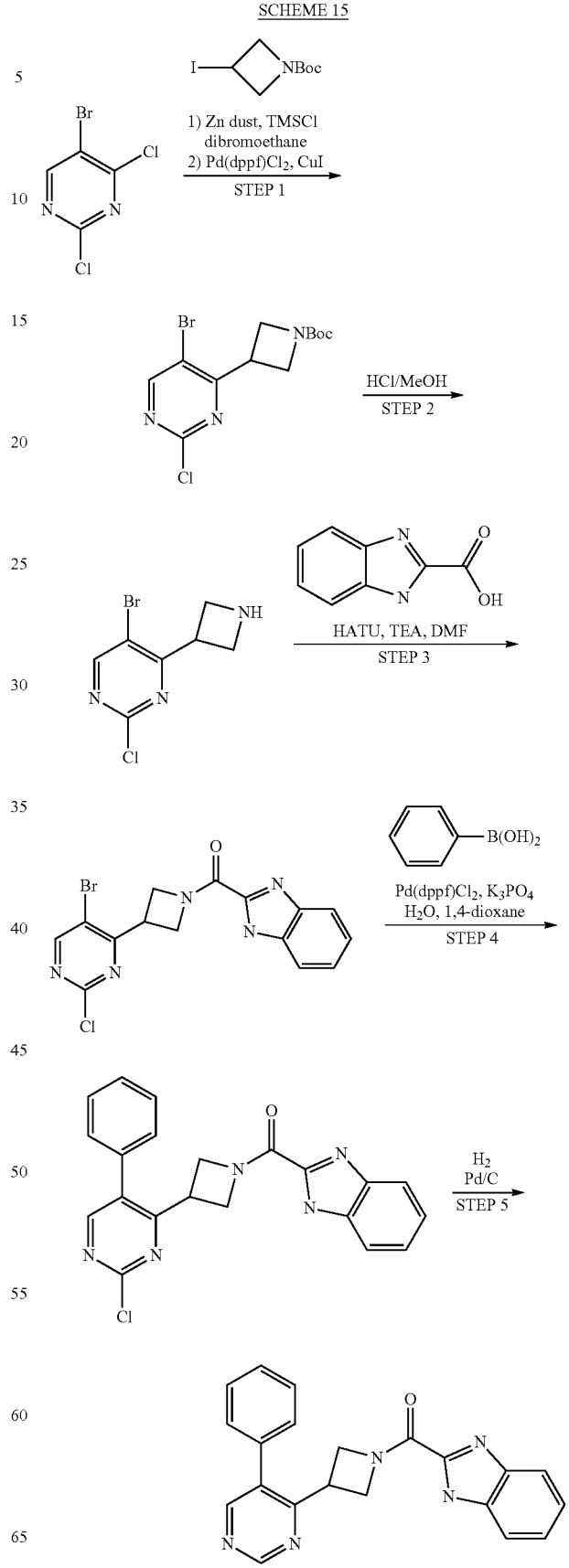

Example 15.1: (1H-Benzoimidazol-2-Yl)-[3-(5-Phenyl-Pyrimidin-4-Yl)-Azetidin-1-Yl]-Methanone

Step 1. 3-(5-Bromo-2-Chloro-Pyrimidin-4-Yl)-Azetidine-1-Carboxylic Acid Tert-Butyl Ester A 100 mL 3-neck round bottom flask fitted with a magnetic stirrer and flushed with nitrogen was charged with zinc dust (813 mg, preactivated according to the above Preparation 1, 12.7 mmol) and DMA (10 mL, anhydrous). 1,2-dibromoethane (236 mg, 1.27 mmol) was added slowly, followed by TMSCl (137 mg, 1.27 mmol). The reaction was stirred for 15 minutes at RT. A solution of N-Boc-3-iodo-azetidine (2.7 g, 9.5 mmol) in DMA (10 mL, anhydrous) was added dropwise. The suspension was stirred for 1 h at RT.

A 100 mL 3-neck round bottom flask fitted with a mechanical stirrer was charged with 5-bromo-2,4-dichloro-pyrimidine (2 g, 4.42 mmol), Pd(dppf)Cl$_2$ (324 mg, 0.442 mmol), CuI (84 mg, 0.442 mmol), and DMA (20 mL, anhydrous). The dark solution was degassed for 15 minutes. The clear zinc reagent solution above the residual solid zinc was transferred to the above 100 mL flask by cannulation. The dark solution was degassed and heated to 80° C. for 16 h. The reaction was diluted with brine and extracted with EtOAc (3×100 mL). The combined organics were washed with water (2×100 mL) and brine (100 mL), followed by drying over sodium sulfate. The solution was concentrated and the residue was purified by flash column chromatography provides the title compound (0.7 g, 2.0 mmol, yield: 46%). ESI-MS (M+1): 348 calc. for $C_{12}H_{15}BrClN_3O_2$ 347.

Step 2. 4-Azetidin-3-Yl-5-Bromo-2-Chloro-Pyrimidine Hydrochloride

The mixture of 3-(5-bromo-2-chloro-pyrimidin-4-yl)-azetidine-1-carboxylic acid tert-butyl ester (0.7 g, 2.0 mmol) in HCl/MeOH (10 mL) was stirred at RT for 1 h. Then it was concentrated to give 4-azetidin-3-yl-5-bromo-2-chloro-pyrimidine hydrochloride (0.57 g, 2.0 mmol, yield 100%) which was used in the next step without further purification. ESI-MS (M+1): 248 calc. for $C_7H_7BrClN_3$ 247.

Step 3. (1H-Benzoimidazol-2-Yl)-[3-(5-Bromo-2-Chloro-Pyrimidin-4-Yl)-Azetidin-1-Yl]-Methanone To a solution of 4-azetidin-3-yl-5-bromo-2-chloro-pyrimidine hydrochloride (0.57 mg, 2.0 mmol) in DCM (20 mL) were added HATU (1.5 g, 4.0 mmol), TEA (404 mg, 4 mmol) and 1H-benzoimidazole-2-carboxylic acid (398 mg, 2.4 mmol). The reaction mixture was stirred at RT for 12 h. TLC showed that most of starting materials were consumed completely. Then the solution was washed with aqueous HCl (1 mol/L) (50 mL×3), saturated aqueous NaHCO$_3$ (50 mL×3) and brine, dried over MgSO$_4$. The solution was evaporated, the residue was purified by column chromatography to give the product (206 mg, 0.53 mmol, yield: 27%). ESI-MS (M+1): 392 calc. for $C_{15}H_{11}BrClN_5O$ 391.

Step 4. (1H-Benzoimidazol-2-Yl)-[3-(2-Chloro-5-Phenyl-Pyrimidin-4-Yl)-Azetidin-1-Yl]-Methanone A solution of (1H-benzoimidazol-2-yl)-[3-(5-bromo-2-chloro-pyrimidin-4-yl)-azetidin-1-yl]-methanone (206 mg, 0.53 mmol) in dioxane (15 mL) was treated with Na$_2$CO$_3$ (112 mg, 1.1 mmol dissolved 1 mL of H$_2$O), followed by additional of phenylboronic acid (78 mg 0.64 mmol) and Pd(dppf)Cl$_2$ (37 mg, 0.05 mmol). The resulting mixture was heated at refluxing overnight under N$_2$ atmosphere. TLC showed that most of the staring materials were consumed completely. The solution was filtered, and the filter was concentrated. And the residue was purified by silica gel chromatography to give the product (102 mg, 0.28 mmol, yield: 53%). ESI-MS (M+1): 362 calc. for $C_{21}H_{16}ClN_5O$ 361.

Step 5. (1H-Benzoimidazol-2-Yl)-[3-(5-Phenyl-Pyrimidin-4-Yl)-Azetidin-1-Yl]-Methanone To a solution of (1H-Benzoimidazol-2-yl)-[3-(2-chloro-5-phenyl-pyrimidin-4-yl)-azetidin-1-yl]-methanone (102 mg, 0.28 mmol) in MeOH (10 mL) was added Pd/C (100 mg). The reaction solution was stirred at RT overnight under H$_2$ atmosphere. The mixture was filtered and concentrated to give the product (51 mg, 0.16 mmol, yield: 55%).
$^1$H NMR: (CDCl$_3$, 400 MHz): δ (ppm) 9.19 (s, 1H), 8.61 (s, 1H), 7.61-7.57 (m, 2H), 7.49-7.41 (m, 5H), 7.31-7.18 (m, 2H), 5.07 (d, J=6.8 Hz, 2H), 4.59-4.57 (m, 1H), 4.39-4.34 (m, 1H), 4.18-4.14 (m, 1H).
ESI-MS (M+1): 328.
PDE10 IC$_{50}$ (uM): 0.0291.

SCHEME 16

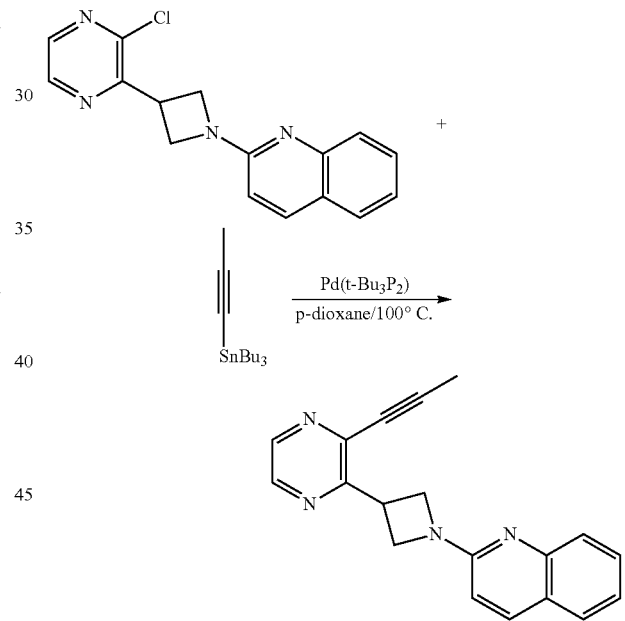

Example 16.1: 2-(3-(3-(Prop-1-Yn-1-Yl)Pyrazin-2-Yl)Azetidin-1-Yl)Quinoline

A mixture of 2-(3-(3-chloropyrazin-2-yl)azetidin-1-yl)quinoline (0.200 g, 0.674 mmol), tributyl(prop-1-yn-1-yl)stannane (0.266 g, 0.809 mmol), and bis(tri-t-butylphosphine)palladium (o) (0.017 g, 0.034 mmol) in p-dioxane (4 mL) was heated at 100° C. in 16 h. The reaction mixture was cooled, concentrated, and purified by ISCO (0-60% EtOAc/Hexanes) to give the title compound (128 mg, 68%).
$^1$H NMR (300 MHz, MeOH) 8.56 (1H, d, J=2.5 Hz), 8.44 (1H, d, J=2.5 Hz), 8.04 (1H, d, J=9.1 Hz), 7.71 (2H, dd, J=7.8, 5.6 Hz), 7.58 (1H, td, J=7.7, 1.3 Hz), 7.27 (1H, t, J=7.5 Hz), 6.80 (1H, d, J=8.9 Hz), 4.51-4.66 (5H, m), 2.21 (3H, s).
ESI-MS (M+1): 601. PDE10 IC$_{50}$ (μM): 0.077.

SCHEME 17

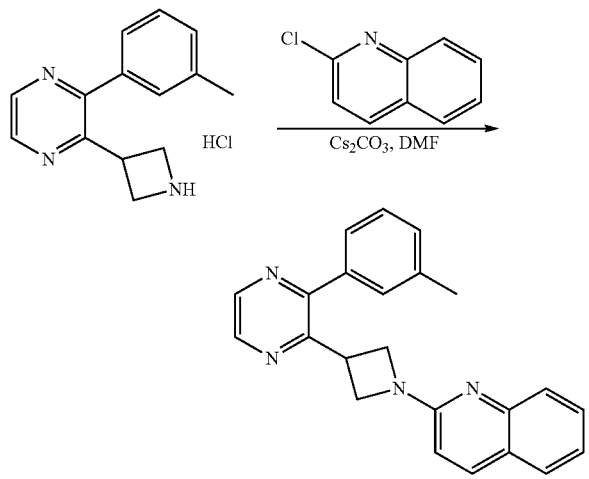

Example 17.1: 2-[3-(3-M-Tolyl-Pyrazin-2-Yl)-Azetidin-1-Yl]-Quinoline

To a solution of 2-azetidin-3-yl-3-m-tolyl-pyrazine hydrochloride (131 mg, 0.05 mmol) and 2-chloro-quinoline (82 mg, 0.05 mmol) in DMF (10 mL) was added $Cs_2CO_3$ (325 mg, 1.0 mmol). The reaction mixture was stirred at 100° C. overnight. The reaction mixture was diluted with water, extracted with EtOAc (30 mL×2). The combined organic extracts were washed with water (30 mL) and brine (30 mL), dried over $Na_2SO_4$ and filtered. The filtrate was evaporated in vacuo and the residue was purified by flash column chromatography on silica gel (20% to 40% EtOAc in petroleum ether) to give 2-[3-(3-m-tolyl-pyrazin-2-yl)-azetidin-1-yl]-quinoline (44 mg, 0.13 mmol, 25%).

The following Table 24A lists compounds of Examples 17.1 to 17.6, which were made analogous to Scheme 17 by using the appropriate materials and reaction conditions, which are listed in Table 24B. The NMR data of the Examples are listed in Table 24C.

TABLE 24A

EXAMPLES 17.1 TO 17.6

| Ex. # | Structure | Chemical Name | ESI-MS (M + 1) | $IC_{50}$ (uM) |
|---|---|---|---|---|
| 17.1 | 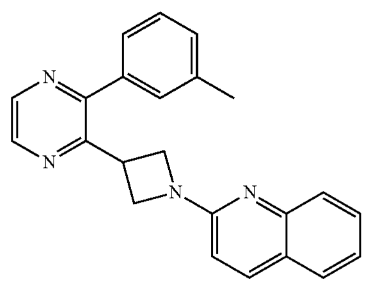 | 2-[3-(3-m-Tolyl-pyrazin-2-yl)-azetidin-1-yl]-quinoline | 353 | 0.00178 |
| 17.2 | 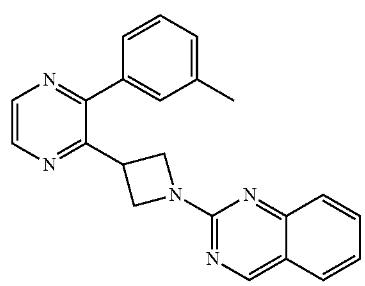 | 2-[3-(3-m-Tolyl-pyrazin-2-yl)-azetidin-1-yl]-quinazoline | 354 | 0.012 |
| 17.3 | 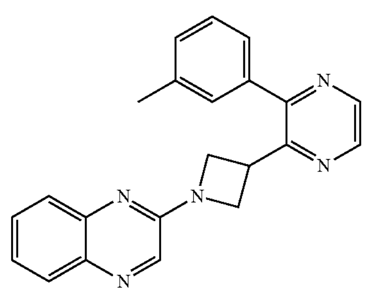 [SMILES: Cc1cccc(-c2nccnc2C2CN(c3cnc4ccccc4n3)C2)c1] | 2-[3-(3-m-Tolyl-pyrazin-2-yl)-azetidin-1-yl]-quinoxaline | 354 | 0.0209 |

TABLE 24A-continued

EXAMPLES 17.1 TO 17.6

| Ex. # | Structure | Chemical Name | ESI-MS (M + 1) | IC$_{50}$ (uM) |
|---|---|---|---|---|
| 17.4 | 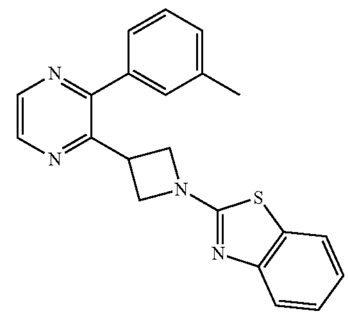 [SMILES: Cc1cccc(-c2nccnc2C2CN(c3nc4ccccc4s3)C2)c1] | 2-[3-(3-m-Tolyl-pyrazin-2-yl)-azetidin-1-yl]-benzothiazole | 359 | 0.0319 |
| 17.5 | 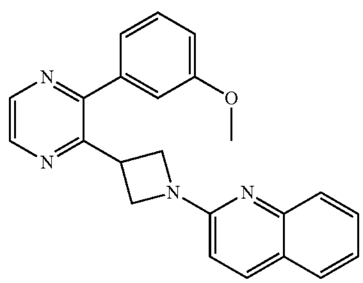 [SMILES: COc1cccc(-c2nccnc2C2CN(c3ccc4ccccc4n3)C2)c1] | 2-{3-[3-(3-Methoxy-phenyl)-pyrazin-2-yl]-azetidin-1-yl}-quinoline | 369 | 0.00299 |
| 17.6 | 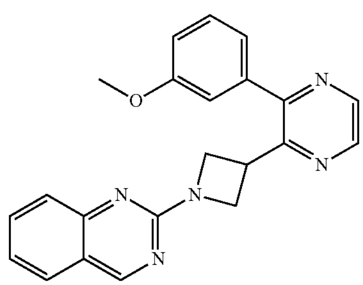 [SMILES: COc1cccc(-c2nccnc2C2CN(c3ncc4ccccc4n3)C2)c1] | 2-{3-[3-(3-Methoxy-phenyl)-pyrazin-2-yl]-azetidin-1-yl}-quinazoline | 370 | 0.00929 |

TABLE 24B

STARTING MATERIALS AND REACTION CONDITION FOR PREPARATION OF EXAMPLES 17.1 TO 17.6.
Unless otherwise stated, all starting materials are commercially available from common vendors.

| Ex. # | Starting Material 1 | Starting Material 2 | Reaction Condition |
|---|---|---|---|
| 17.1 | 31 PREPARATION 9 | | Cs$_2$CO$_3$, DMF, 100° C. |
| 17.2 | 31 PREPARATION 9 | | Cs$_2$CO$_3$, DMF, 100° C. |

TABLE 24B-continued

STARTING MATERIALS AND REACTION CONDITION FOR
PREPARATION OF EXAMPLES 17.1 TO 17.6.
Unless otherwise stated, all starting materials are commercially available from common vendors.

| Ex. # | Starting Material 1 | Starting Material 2 | Reaction Condition |
|---|---|---|---|
| 17.3 | 31 PREPARATION 9 | (2-chloroquinoxaline) | $Cs_2CO_3$, DMF, 100° C. |
| 17.4 | 31 PREPARATION 9 | (2-chlorobenzothiazole) ALDRICH | $Cs_2CO_3$, DMF, 100° C. |
| 17.5 | 34 PREPARATION 10 | (2-chlorobenzothiazole) | $Cs_2CO_3$, DMF, 100° C. |
| 17.6 | 34 PREPARATION 10 | (2-chloroquinazoline) | $Cs_2CO_3$, DMF, 100° C. |

TABLE 24C

1H NMR δ (PPM) DATA FOR EXAMPLES 17.1 TO 17.6

| Ex. # | Structure | NMR |
|---|---|---|
| 17.1 | 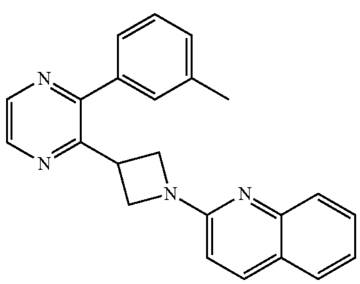 | (CDCl$_3$, 400 MHz): 8.53-8.49 (m, 2H); 7.99 (d, J = 8.4 Hz, 1H); 7.92 (d, J = 8.4 Hz, 1H); 7.60 (t, J = 6.4 Hz, 2H); 7.33 (dd, J = 2.4, 7.6 Hz, 2H); 7.24 (d, J = 7.6 Hz, 1H); 7.19 (s, 1H); 7.12 (d, J = 7.6 Hz, 1H); 7.19 (s, 1H); 7.12 (d, J = 7.6 Hz, 1H); 6.53 (d, J = 9.2 Hz, 1H); 4.89 (br s, 1H); 4.72-4.68 (m, 2H); 4.48-4.42 (m, 2H); 2.37 (s, 3H) |
| 17.2 | 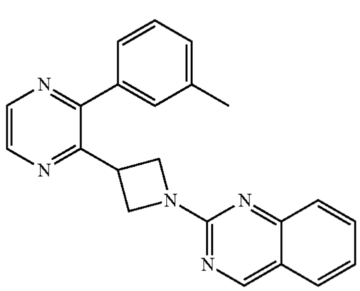 | CD$_3$OD, 400 MHz): 9.04 (s, 1H); 8.12 (d, J = 1.2 Hz, 1H); 8.49 (d, J = 1.2 Hz, 1H); 7.71-7.67 (m, 2H); 7.54-7.52 (m, 1H); 7.41 (t, J = 7.6 Hz, 1H); 7.33-7.26 (m, 2H); 7.285-7.23 (m, 2H); 4.38-4.36 (m, 5H); 2.43 (s, 3H) |

TABLE 24C-continued
1H NMR δ (PPM) DATA FOR EXAMPLES 17.1 TO 17.6
| Ex. # | Structure | NMR |
|---|---|---|
| 17.3 | 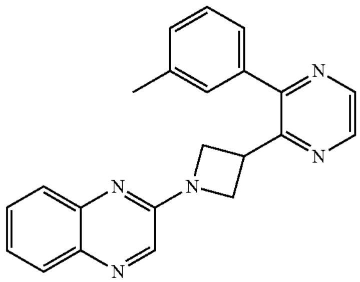 [SMILES: Cc1cccc(-c2nccnc2C2CN(c3cnc4ccccc4n3)C2)c1] | (CD$_3$OD, 400 MHz): 8.62 (d, J = 2.4 Hz, 1H); 8.52 (d, J = 2.4 Hz, 1H); 8.17 (s, 1H); 7.79-7.76 (m, 1H); 7.61 (dd, J = 1.6, 8.8 Hz, 1H); 7.57-7.52 (m, 1H); 7.43 (t, J = 7.6 Hz, 1H); 7.37-7.33 (m, 3H); 7.29 (d, J = 7.6 Hz, 1H); 4.44-4.39 (m, 5H); 2.45(s, 3H). |
| 17.4 | 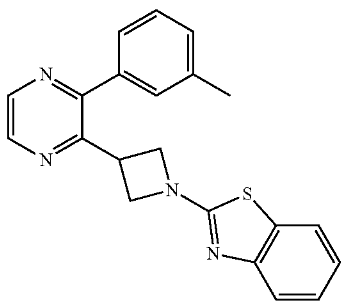 [SMILES: Cc1cccc(-c2nccnc2C2CN(c3nc4ccccc4s3)C2)c1] | (CD$_3$OD, 400 MHz): 8.63 (d, J = 1.2 Hz, 1H); 8.51 (d, J = 1.6 Hz, 1H); 7.60 (d, J = 8.0 Hz, 1H); 7.44-7.39 (m, 2H); 7.34-7.30 (m, 2H); 7.27-7.22 (m, 2H); 7.06-7.02 (m, 1H); 4.44-4.40 (m, 1H); 4.35-4.25 (m, 4H); 2.43 (s, 3H). |
| 17.5 | 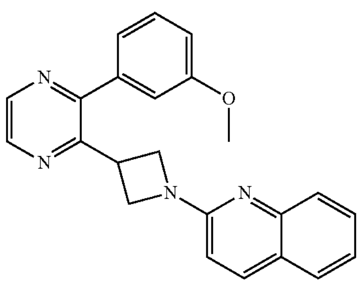 [SMILES: COc1cccc(-c2nccnc2C2CN(c3ccc4ccccc4n3)C2)c1] | (CD$_3$OD, 400 MHz): 8.54 (s, 1H); 8.50 (d, J = 0.8 Hz, 1H); 7.83 (d, J = 8.8 Hz, 1H); 7.71 (d, J = 8.4 Hz, 1H); 7.57 (d, J = 8.0 Hz, 1H); 7.50 (t, J = 7.2 Hz, 1H); 7.40 (t, J = 8.0 Hz, 1H); 7.18 (t, J = 7.2 Hz, 1H); 7.05-7.00 (m, 3H); 6.60 (d, J = 8.8 Hz, 1H); 4.47-4.38 (m, 5H); 3.86 (s, 3H). |
| 17.6 | 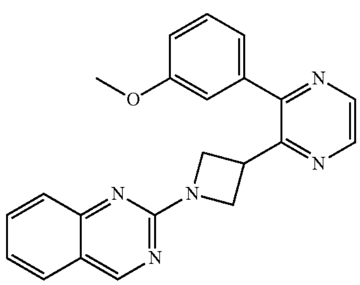 [SMILES: COc1cccc(-c2nccnc2C2CN(c3ncc4ccccc4n3)C2)c1] | (CDCl3, 400 MHz): 8.96 (s, 1H); 8.53 (d, J = 2.8 Hz, 1H); 8.46 (d, J = 2.4 Hz, 1H); 7.62-7.55 (m, 3H); 7.38-7.33 (m, 1H); 7.16-7.13 (m, 1H); 7.01-6.95 (m, 3H); 4.51-4.41 (m, 4H); 4.35-4.29 (m, 1H); 3.80 (s, 3H). |
SCHEME 18
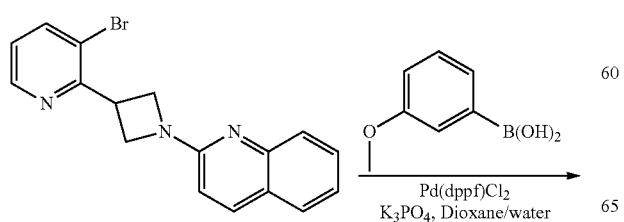
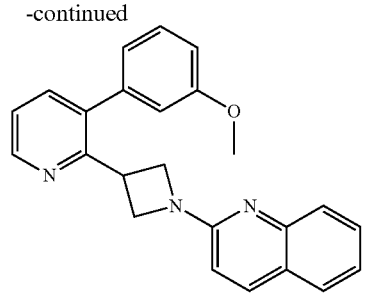
-continued

Example 18.1: 2-{3-[3-(3-Methoxy-Phenyl)-Pyridin-2-Yl]-Azetidin-1-Yl}-Quinoline To a solution of 2-[3-(3-bromo-pyridin-2-yl)-azetidin-1-yl]-quinoline (339 mg, 1 mmol), 3-methoxy-phenylboronic acid (167.2 mg, 1.1 mmol), $K_3PO_4$ (414 mg, 2.0 mmol) in dioxane (20 mL) and water (2 mL) was added Pd(dppf)Cl$_2$ (36.6 mg, 0.05 mmol) then the reaction mixture was stirred at 90° C. under nitrogen atmosphere overnight. The reaction mixture was filtered through CELITE® and washed with EtOAc (50 mL). The filtrate was concentrated and the crude product was purified by ISCO silica gel column (10% to 80% EtOAc in petroleum ether) to give 2-{3-[3-(3-methoxy-phenyl)-pyridin-2-yl]-azetidin-1-yl}-quinoline (132 mg, 0.36 mmol, yield 36%).

The following Table 25A lists compounds of Examples 18.1 to 18.2, which were made analogous to Scheme 18 by using the appropriate materials and reaction conditions, which are listed in Table 25B. The NMR data of the Examples are listed in Table 25C.

TABLE 25A

EXAMPLES 18.1 TO 18.2

| Ex. # | Structure | Chemical Name | ESI-MS (M + 1) | IC$_{50}$ (uM) |
|---|---|---|---|---|
| 18.1 | 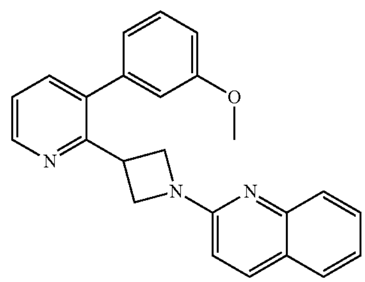 [SMILES: COc1cccc(-c2cccnc2C2CN(c3ccc4ccccc4n3)C2)c1] | 2-{3-[3-(3-Methoxy-phenyl)-pyridin-2-yl]-azetidin-1-yl}-quinoline | 368 | 0.00493 |
| 18.2 | 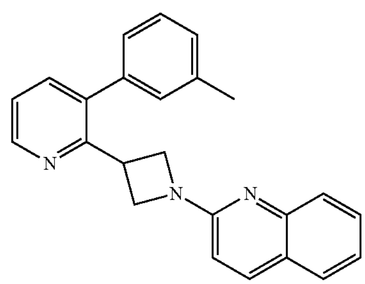 [SMILES: Cc1cccc(-c2cccnc2C2CN(c3ccc4ccccc4n3)C2)c1] | 2-[3-(3-m-Tolyl-pyridin-2-yl)-azetidin-1-yl]-quinoline | 352 | 0.00609 |

TABLE 25B

STARTING MATERIALS AND REACTION CONDITION FOR
PREPARATION OF EXAMPLES 18.1 TO 18.2.

Unless otherwise stated, all starting materials are commercially available from common vendors.

| Ex. # | Starting Material 1 | Starting Material 2 | Reaction Condition |
|---|---|---|---|
| 18.1 | | | Pd(dppf)Cl$_2$, $K_3PO_4$, Dioxane/water |

PREPARATION 1

TABLE 25B-continued

STARTING MATERIALS AND REACTION CONDITION FOR
PREPARATION OF EXAMPLES 18.1 TO 18.2.
Unless otherwise stated, all starting materials are commercially available from common vendors.

| Ex. # | Starting Material 1 | Starting Material 2 | Reaction Condition |
|---|---|---|---|
| 18.2 | [3-bromo-2-(1-(quinolin-2-yl)azetidin-3-yl)pyridine] PREPARATION 1 | [3-methylphenylboronic acid] | Pd(dppf)Cl$_2$, K$_3$PO$_4$, Dioxane/water |

TABLE 25C

1H NMR δ (PPM) DATA FOR EXAMPLES 18.1 TO 18.2

| Ex. # | Structure | NMR |
|---|---|---|
| 18.1 | [structure] | (CDCl$_3$, 400 MHz): 8.79 (s, 1H); 8.03 (d, J = 9.2 Hz, 1H): 7.93 (d, J = 8.0 Hz, 1H); 7.78 (d, J = 8.8 Hz, 1H); 7.66-7.62 (m, 2H); 7.59-7.56 (m, 1H); 7.40-7.35 (m, 2H); 6.99-6.97 (m, 1H); 6.75 (t, J = 8.4 Hz, 2H); 6.57 (d, J = 9.2 Hz, 1H); 4.75 (s, 3H); 4.54-4.52 (m, 2H); 3.79 (s, 3H). |
| 18.2 | [structure] | (CDCl$_3$, 400 MHz); 8.65 (s, 1H); 7.99 (d, J = 9.2 Hz, 1H); 7.88 (d, J = 8.4 Hz, 1H); 7.67-7.59 (m, 3H); 7.35-7.30 (m, 3H); 7.22-7.19 (m, 1H); 6.95 (d, J = 11.6 Hz, 2H); 6.54 (d, J = 5.2 Hz, 1H); 4.74 (s, 3H); 4.33 (s, 2H); 2.37 (s, 3H). |

SCHEME 19

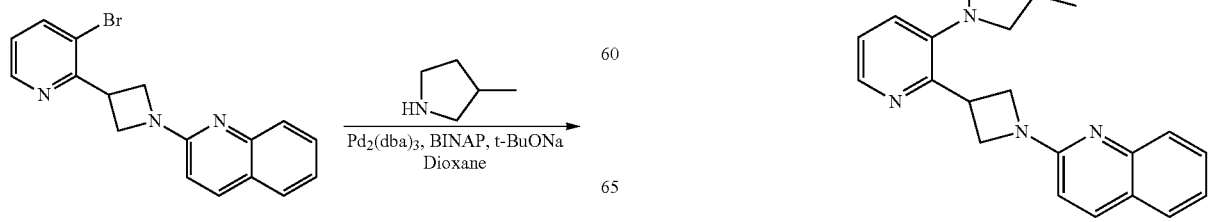

Example 19.1: (R & S)-2-{3-[3-(3-Methyl-Pyrrolidin-1-Yl)-Pyridin-2-Yl]-Azetidin-1-Yl}-Quinoline To a solution of 2-[3-(3-bromo-pyridin-2-yl)-azetidin-1-yl]-quinoline (339 mg, 1 mmol), 3-methyl-pyrrolidine (93.5 mg, 1.1 mmol), BINAP (31.1 mg, 0.05 mmol), t-BuONa (196 mg, 2 mmol) in dioxane (25 mL) was added $Pd_2(dba)_3$ (45.75 mg, 0.05 mmol) then the reaction mixture was stirred at 90° C. under nitrogen atmosphere overnight. The reaction mixture was filtered through CELITE® and washed with EtOAc (50 mL). The filtrate was concentrated and the crude product was purified by ISCO silica gel column (10% to 80% EtOAc in petroleum ether) to give 2-{3-[3-(3-methyl-pyrrolidin-1-yl)-pyridin-2-yl]-azetidin-1-yl} -quinoline (64 mg, 0.19 mmol, yield 19%).

The following Table 26A lists compounds of Examples 19.1 to 19.2, which were made analogous to Scheme 19 by using the appropriate materials and reaction conditions, which are listed in Table 26B. The NMR data of the Examples are listed in Table 26C.

TABLE 26A

EXAMPLES 19.1 TO 19.2

| Ex. # | Structure | Chemical Name | ESI-MS (M + 1) | $IC_{50}$ (uM) |
|---|---|---|---|---|
| 19.1 | 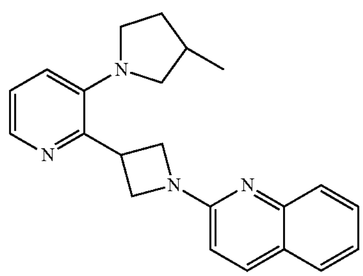 [SMILES: CC1CCN(c2cccnc2C2CN(c3ccc4ccccc4n3)C2)C1] | (R & S)-2-{3-[3-(3-Methyl-pyrrolidin-1-yl)-pyridin-2-yl]-azetidin-1-yl}-quinoline | 345 | 0.864 |
| 19.2 | 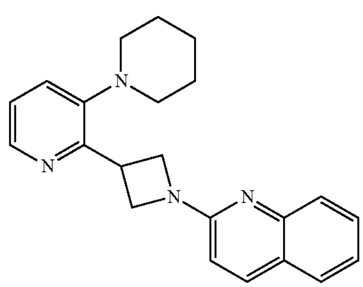 | 4-Methyl-2'-(1-quinolin-2-yl-azetidin-3-yl)-3,4,5,6-tetrahydro-2H-[1,3']bipyridinyl | 345 | 0.00522 |

TABLE 26B

STARTING MATERIALS AND REACTION CONDITION FOR PREPARATION OF EXAMPLES 19.1 TO 19.2.
Unless otherwise stated, all starting materials are commercially available from common vendors.

| Ex. # | Starting Material 1 | Starting Material 2 | Reaction Condition |
|---|---|---|---|
| 19.1 | PREPARATION 1 | | $Pd_2(dba)_3$, BINAP, t-BuONa, dioxane |

TABLE 26B-continued

STARTING MATERIALS AND REACTION CONDITION FOR
PREPARATION OF EXAMPLES 19.1 TO 19.2.
Unless otherwise stated, all starting materials are commercially available from common vendors.

| Ex. # | Starting Material 1 | Starting Material 2 | Reaction Condition |
|---|---|---|---|
| 19.2 | <br>PREPARATION 1 | 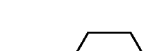 | Pd$_2$(dba)$_3$, BINAP, t-BuONa, dioxane |

TABLE 26C

1H NMR δ (PPM) DATA FOR EXAMPLES 19.1 TO 19.2

| Ex. # | Structure | NMR |
|---|---|---|
| 19.1 | 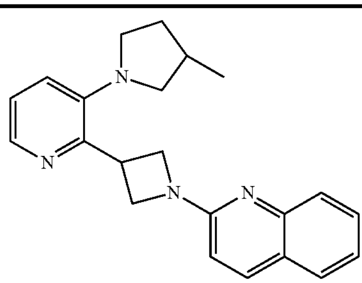 | (CDCl$_3$, 400 MHz): 8.22 (s, 1H); 8.02 (d, J = 9.2 Hz, 1H); 7.96 (d, J = 8.4, 1H); 7.67-7.62 (m, 2H); 7.40-7.31 (m, 3H); 6.62 (d, J = 9.2 Hz, 1H); 5.04-4.74 (m, 3H); 4.60-4.57 (m, 1H); 3.42 (s, 1H); 3.41-3.32 (m, 1H); 3.27-3.18 (m, 1H); 2.91-2.86 (m, 1H); 2.39-2.33 (m, 1H); 2.14-2.09 (m, 1H); 1.62-1.57 (m, 1H); 1.19 (s, 1H); 1.09 (d, J = 2.4 Hz, 3H). |
| 19.2 | 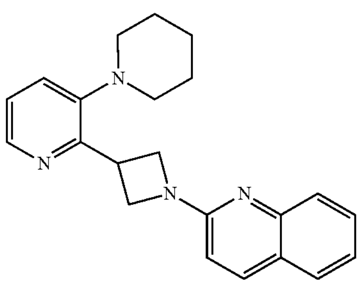 | (CDCl$_3$, 400 MHz): 8.32-8.31 (m, 1H); 7.85 (d, J = 8.8 Hz, 1H); 7.73 (d, J = 8.4 Hz, 1H), 7.60-7.58 (m, 1H); 7.53-7.51 (m, 1H); 7.34-7.32 (m, 1H); 7.26-7.21 (m, 1H); 7.19-7.10 (m, 1H); 6.66 (d, J = 8.8 Hz, 1H); 4.59-4.52 (m, 3H); 4.51-4.47 (m, 2H); 2.81 (m, 4H); 1.79-1.68 (m, 4H); 1.62-1.56 (m, 2H). |

SCHEME 20

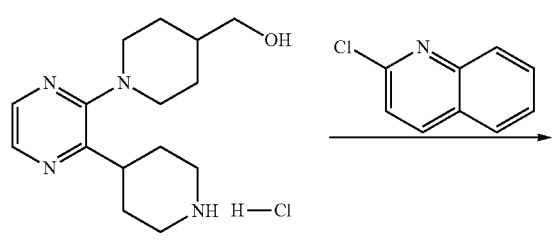

-continued

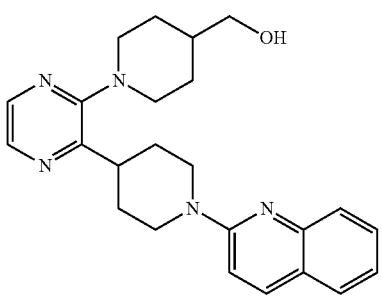 [SMILES: OCC1CCN(c2nccnc2C2CCN(c3ccc4ccccc4n3)CC2)CC1]

Example 20.1: {1-[3-(1-Quinolin-2-Yl-Piperidin-4-Yl)-Pyrazin-2-Yl]-Piperidin-4-Yl}-Methanol To a solution of [1-(3-piperidin-4-yl-pyrazin-2-yl)-piperidin-4-yl]-methanol hydrochloride (156 mg, 0.5 mmol) and 2-chloro-quinoline (81.5 mg 0.5 mmol) in DMF (5 mL) was added $Cs_2CO_3$ (325 mg, 1 mmol). The reaction mixture was stirred at 100° C. overnight. The reaction mixture was diluted with water, extracted with EtOAc (2×20 mL). The combined organic extracts were washed with water (15 mL) and brine (15 mL), dried over $Na_2SO_4$ and filtered. The filtrate was evaporated in vacuo and the residue was purified by flash column chromatography on silica gel to give {1-[3-(1-quinolin-2-yl-piperidin-4-yl)-pyrazin-2-yl]-piperidin-4-yl}-methanol (142 mg, 0.35 mmol, yield 70.47%).

The following Table 27A lists compounds of Examples 20.1 to 20.10, which were made analogous to Scheme 20 by using the appropriate materials and reaction conditions, which are listed in Table 27B. The NMR data of the Examples are listed in Table 27C.

TABLE 27A

EXAMPLES 20.1 TO 20.10

| Ex. # | Structure | Chemical Name | ESI-MS (M + 1) | IC$_{50}$ (uM) |
|---|---|---|---|---|
| 20.1 | 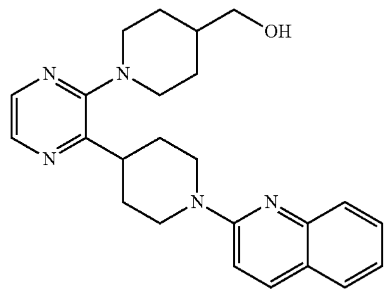 | {1-[3-(1-Quinolin-2-yl-piperidin-4-yl)-pyrazin-2-yl]-piperidin-4-yl}-methanol | 404 | 0.00172 |
| 20.2 | 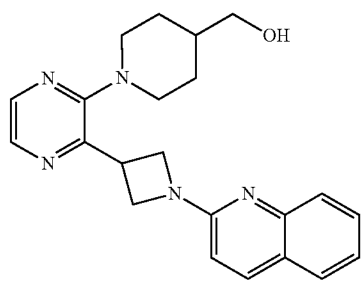 | {1-[3-(1-Quinolin-2-yl-azetidin-3-yl)-pyrazin-2-yl]-piperidin-4-yl}-methanol | 376 | 0.00114 |
| 20.3 | 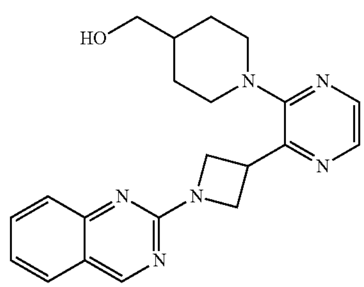 [SMILES: OCC1CCN(c2nccnc2C2CN(c3ncc4ccccc4n3)C2)CC1] | {1-[3-(1-Quinazolin-2-yl-azetidin-3-yl)-pyrazin-2-yl]-piperidin-4-yl}-methanol | 377 | 0.00256 |
| 20.4 | 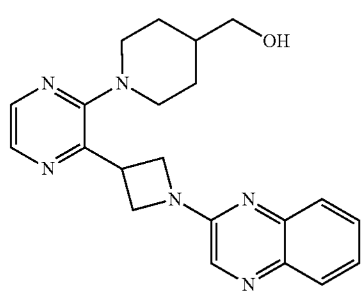 [SMILES: OCC1CCN(c2nccnc2C2CN(c3cnc4ccccc4n3)C2)CC1] | 4-[3-(1-Quinolin-2-yl-azetidin-3-yl)-pyrazin-2-yl]-phenylamine | 377 | >10 |

TABLE 27A-continued

EXAMPLES 20.1 TO 20.10

| Ex. # | Structure | Chemical Name | ESI-MS (M + 1) | IC$_{50}$ (uM) |
|---|---|---|---|---|
| 20.5 | 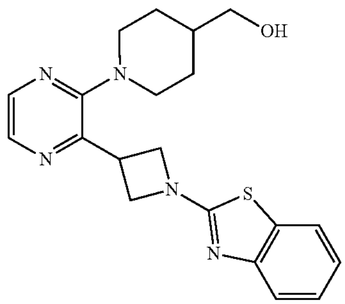 | {1-[3-(1-Benzothiazol-2-yl-azetidin-3-yl)-pyrazin-2-yl]-piperidin-4-yl}-methanol | 382 | 0.0323 |
| 20.6 | 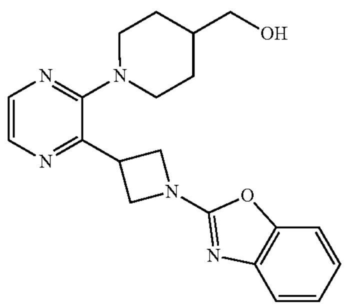 [SMILES: OCC1CCN(c2nccnc2C2CN(c3nc4ccccc4o3)C2)CC1] | {1-[3-(1-Benzooxazol-2-yl-azetidin-3-yl)-pyrazin-2-yl]-piperidin-4-yl}-methanol | 366 | 2.170 |
| 20.7 | 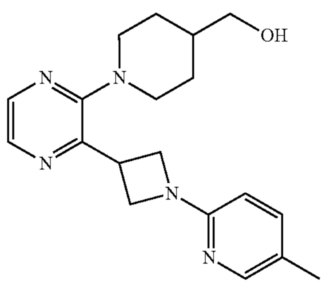 [SMILES: Cc1ccc(N2CC(c3nccnc3N3CCC(CO)CC3)C2)nc1] | (1-{3-[1-(5-Methyl-pyridin-2-yl)-azetidin-3-yl]-pyrazin-2-yl}-piperidin-4-yl)-methanol | 340 | 0.583 |
| 20.8 | 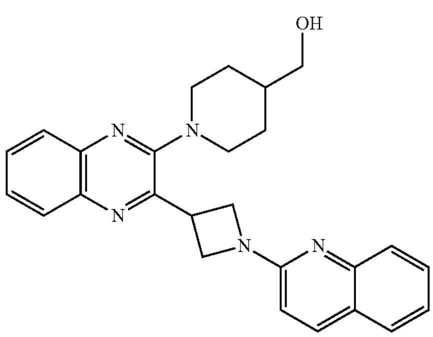 [SMILES: OCC1CCN(c2nc3ccccc3nc2C2CN(c3ccc4ccccc4n3)C2)CC1] | 2-(4-benzylpiperidin-1-yl)-3-(1-(quinolin-2-yl)azetidin-3-yl)quinoxaline | 426 | 0.00243 |
| 20.9 | 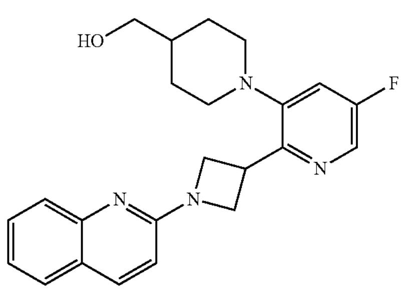 [SMILES: OCC1CCN(c2cc(F)cnc2C2CN(c3ccc4ccccc4n3)C2)CC1] | [5'-Fluoro-2'-(1-quinolin-2-yl-azetidin-3-yl)-3,4,5,6-tetrahydro-2H-[1,3']bipyridinyl-4-yl]-methanol | 393 | 0.181 |

TABLE 27A-continued

EXAMPLES 20.1 TO 20.10

| Ex. # | Structure | Chemical Name | ESI-MS (M + 1) | IC$_{50}$ (uM) |
|---|---|---|---|---|
| 20.10 | 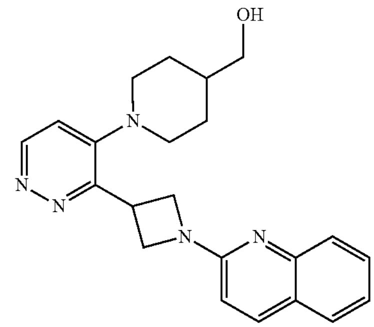 [SMILES: OCC1CCN(c2ccnnc2C2CN(c3ccc4ccccc4n3)C2)CC1] | {1-[3-(1-Quinolin-2-yl-azetidin-3-yl)-pyridazin-4-yl]-piperidin-4-yl}-methanol | 376 | 0.0322 |

TABLE 27B

STARTING MATERIALS AND REACTION CONDITION FOR
PREPARATION OF EXAMPLES 20.1 TO 20.10.
Unless otherwise stated, all starting materials are commercially available from common vendors.

| Ex. # | Starting Material 1 | Starting Material 2 | Reaction Condition |
|---|---|---|---|
| 20.1 | PREPARATION 12 | | Cs$_2$CO$_3$, DMF; 100° C. |
| 20.2 | PREPARATION 11 | | Cs$_2$CO$_3$, DMF; 100° C. |
| 20.3 | PREPARATION 11 | | Cs$_2$CO$_3$, DMF; 100° C. |
| 20.4 | PREPARATION 11 | | Cs$_2$CO$_3$, DMF; 100° C. |

TABLE 27B-continued

STARTING MATERIALS AND REACTION CONDITION FOR
PREPARATION OF EXAMPLES 20.1 TO 20.10.
Unless otherwise stated, all starting materials are commercially available from common vendors.

| Ex. # | Starting Material 1 | Starting Material 2 | Reaction Condition |
|---|---|---|---|
| 20.5 | PREPARATION 11 | 2-chlorobenzothiazole (ALDRICH) | $Cs_2CO_3$, DMF; 100° C. |
| 20.6 | PREPARATION 11 | 2-chlorobenzoxazole | $Cs_2CO_3$, DMF; 100° C. |
| 20.7 | PREPARATION 11 | 2-chloro-5-methylpyridine (ALDRICH) | $Cs_2CO_3$, DMF; 100° C. |
| 20.8 | PREPARATION 15 | 2-chloroquinoline | $Cs_2CO_3$, DMF; 100° C. |
| 20.9 | PREPARATION 23 | 2-chloroquinoline | $Cs_2CO_3$, DMF; 100° C. |

TABLE 27B-continued

STARTING MATERIALS AND REACTION CONDITION FOR
PREPARATION OF EXAMPLES 20.1 TO 20.10.
Unless otherwise stated, all starting materials are commercially available from common vendors.

| Ex. # | Starting Material 1 | Starting Material 2 | Reaction Condition |
|---|---|---|---|
| 20.10 | 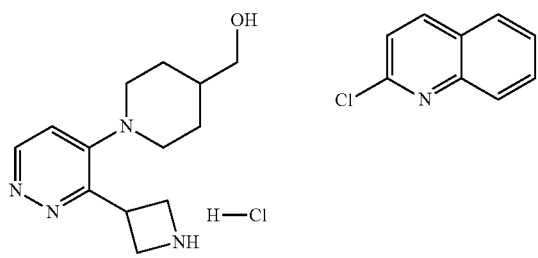<br>PREPARATION 18 |  | $Cs_2CO_3$, DMF; 100° C. |

TABLE 27C

1H NMR δ (PPM) DATA FOR EXAMPLES 20.1 TO 20.10

| Ex. # | Structure | NMR |
|---|---|---|
| 20.1 | 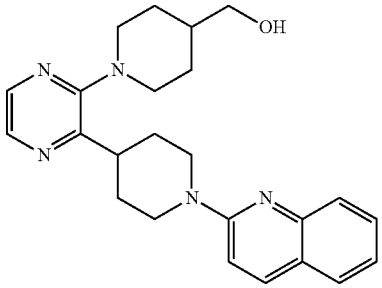 [SMILES: OCC1CCN(c2nccnc2C2CCN(c3ccc4ccccc4n3)CC2)CC1] | (CDCl$_3$, 400 MHz): 8.28-8.15 (m, 4H); 7.80-7.69 (m, 2H); 7.52-7.44 (m, 1H); 7.14 (d, J = 8.0 Hz, 1H); 4.62 (s, 2H); 4.30 (d, J = 6.4 Hz, 1H); 3.64 (d, J = 29.4 Hz, 3H); 3.44 (d, J = 7.6 Hz, 3H); 2.97-2.91 (m, 2H); 2.10 (s, 4H); 1.90 (d, J = 6.4 Hz, 2H); 1.74 (s, 1H); 1.55 (d, J = 9.6 Hz, 2H). |
| 20.2 | 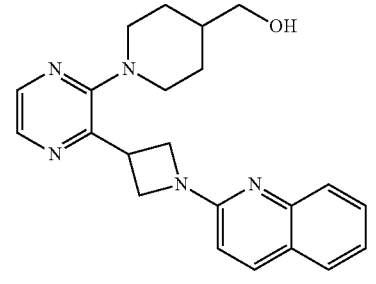 [SMILES: OCC1CCN(c2nccnc2C2CN(c3ccc4ccccc4n3)C2)CC1] | (CDCl$_3$, 400 MHz): 8.15 (d, J = 2.4 Hz, 1H); 8.07 (d, J = 2.0 Hz, 1H); 7.87 (d, J = 8.4 Hz, 1H); 7.74 (d, J = 8.4 Hz, 1H); 7.60 (d, J = 7.6 Hz, 1H); 7.53 (t, J = 7.2 Hz, 1H); 7.23-7.19(m, 1H); 6.65 (d, J = 8.8 Hz, 1H); 4.55 (t, J = 8.0 Hz, 2H); 4.46 (t, J = 6.4 Hz, 2H); 4.34-4.28 (m, 1H); 3.58 (d, J = 6.0 Hz, 2H); 3.44 (d, J = 12.8 Hz, 2H); 2.89-2.82 (m, 2H); 2.06 (s, 1H); 1.87 (d, J = 12.0 Hz, 1H); 1.74-1.68 (m, 1H); 1.52-1.41 (m, 2H). |
| 20.3 | 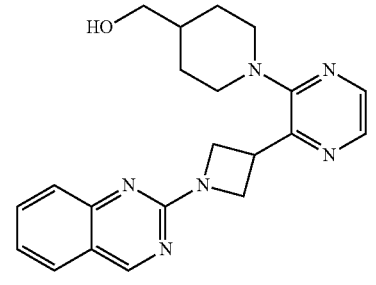 [SMILES: OCC1CCN(c2nccnc2C2CN(c3ncc4ccccc4n3)C2)CC1] | (CD$_3$OD, 400 MHz): 9.01 (s, 1H); 8.06 (d, J = 2.8 Hz, 1H); 8.01 (d, J = 2.4 Hz, 1H); 7.71 (dd, J = 2.4, 8.0 Hz, 1H); 7.67-7.63 (m, 1H); 7.49 (d, J = 8.4 Hz, 1H); 7.22-7.18 (m, 1H); 4.52 (t, J = 8.0 Hz, 2H); 4.36-4.30 (m, 2H); 4.28-4.26 (m, 1H); 3.40 (d, J = 6.4 Hz, 4H); 3.37 (s, 1H); 2.81-2.74 (m, 2H); 1.81-1.78 (m, 2H); 1.61-1.54(m, 1H); 1.43-1.39 (m, 2H). |

TABLE 27C-continued

1H NMR δ (PPM) DATA FOR EXAMPLES 20.1 TO 20.10

| Ex. # | Structure | NMR |
|---|---|---|
| 20.4 | 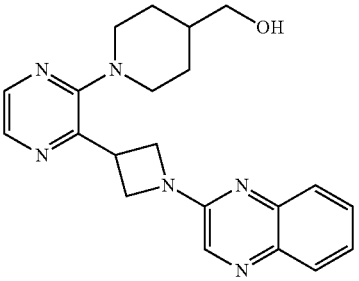 [SMILES: OCC1CCN(c2nccnc2C2CN(c3cnc4ccccc4n3)C2)CC1] | (CD$_3$OD, 400 MHz): 8.91 (dd, J = 2.4, 7.2 Hz, 1H); 8.64 (dd, J = 0.8, 2.4 Hz, 1H); 8.31 (s, 1H); 7.82 (d, J = 8.4 Hz, 1H); 7.67 (m, 1H); 7.66-7.59 (m, 1H); 7.44-7.40 (m, 1H); 4.73-4.72 (m, 1H); 4.31-4.25 (m, 4H); 4.17-4.16 (m, 1H); 4.08-4.05 (m, 1H); 3.83-3.75 (m, 3H); 3.52 (d, J = 6.4 Hz, 2H); 2.11-1.96 (m, 4H). |
| 20.5 | 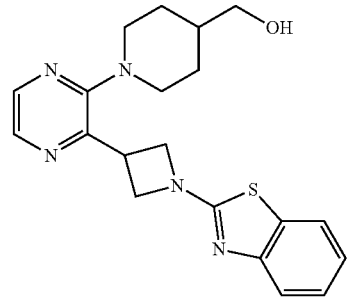 | (CD$_3$OD, 400 MHz): 8.22-8.20 (m, 1H); 8.17-8.15 (dd, J = 2.4, 8.4 Hz, 1H); 7.87 (d, J = 8.0 Hz, 1H); 7.62-7.58 (m, 2H); 7.49-7.44 (m, 1H); 4.62 (m, 1H); 4.54 (m, 1H); 4.32 (d, J = 6.8 Hz, 1H); 4.05-4.01 (m, 2H); 3.94-3.89 (m, 1H); 3.54-3.51 (m, 1H); 3.47 (d, J = 10.4 Hz, 2H); 3.02-2.90 (m, 2H); 1.93-1.86 (m, 2H); 1.58-1.45 (m, 3H). |
| 20.6 | 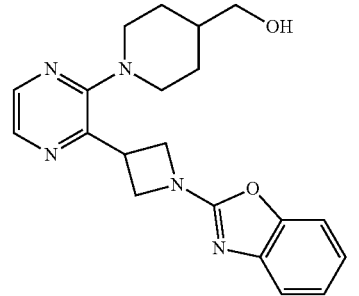 [SMILES: OCC1CCN(c2nccnc2C2CN(c3nc4ccccc4o3)C2)CC1] | (CD$_3$OD, 400 MHz): 8.91 (d, J = 2.8 Hz, 1H); 8.66 (dd, J = 1.2, 2.8 Hz, 1H); 7.33-7.30 (m, 2H); 7.20 (m, 1H); 7.10 (dd, J = 1.2, 4.0 Hz, 1H); 4.25-4.10 (m, 5H); 3.96-3.91 (m, 1H); 3.83-3.74 (m, 3H); 3.65 (d, J = 1.6 Hz, 2H); 2.14-1.89 (m, 5H). |
| 20.7 | 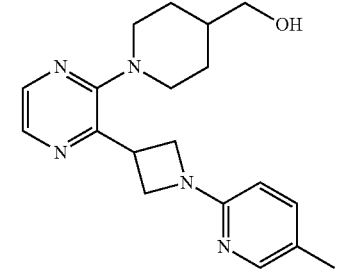 [SMILES: Cc1ccc(N2CC(c3nccnc3N3CCC(CO)CC3)C2)nc1] | (CD$_3$OD, 400 MHz): 8.12 (d, J = 2.4 Hz, 1H); 8.07 (d, J = 2.4 Hz, 1H); 7.83 (s, 1H); 7.43-7.40 (m, 1H); 6.42 (d, J = 8.8 Hz, 1H); 4.39-4.34 (m, 3H); 4.18-4.15 (m, 2H); 3.48-3.43 (m, 4H); 2.87-2.80 (m, 2H); 2.18 (s, 3H); 1.88-1.84 (m, 2H); 1.68-1.62 (m, 1H); 1.49-1.42 (m, 2H). |
| 20.8 | 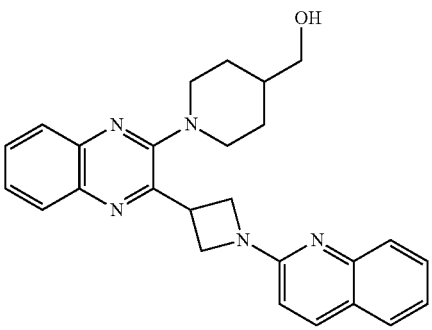 [SMILES: OCC1CCN(c2nc3ccccc3nc2C2CN(c3ccc4ccccc4n3)C2)CC1] | (CD$_3$OD, 400 MHz): 8.34 (d, J = 8.0 Hz, 1H); 7.89 (s, 1H); 7.88 (t, J = 1.2 Hz, 1H); 7.86 (t, J = 1.2 Hz, 1H); 7.81-7.78 (m, 2H); 7.70-7.66 (m, 1H); 7.61-7.57 (m, 1H); 7.54-7.50 (m, 1H); 7.03 (d, J = 9.2 Hz, 1H); 4.97-4.90 (m, 6H); 3.67 (d, J = 12.4 Hz, 2H); 3.54 (d, J = 6.0 Hz, 2H); 3.05-2.99 (m, 2H); 1.98-1.94 (m, 2H); 1.76-1.73 (m, 2H). |

TABLE 27C-continued
1H NMR δ (PPM) DATA FOR EXAMPLES 20.1 TO 20.10
| Ex. # | Structure | NMR |
|---|---|---|
| 20.9 | 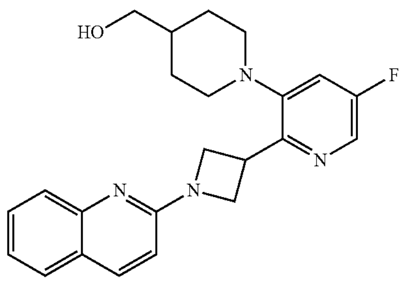 [SMILES: OCC1CCN(c2cc(F)cnc2C2CN(c3ccc4ccccc4n3)C2)CC1] | (CD$_3$OD, 400 MHz): 8.19-8.16 (m, 2H); 7.82 (d, J = 7.6 Hz, 1H); 7.77-7.71 (m, 2H); 7.45 (t, J = 7.6 Hz, 1H); 7.37 (d, J = 10.4 Hz, 1H); 7.04 (d, J = 9.2 Hz, 1H); 6.04 (s, 1H); 5.74 (s, 1H); 4.72 (s, 2H); 3.47-3.43 (m, 4H); 2.67 (t, J = 10.8 Hz, 2H); 1.83-1.80 (m, 2H); 1.60-1.57 (m, 1H); 1.43-1.31 (m, 3H). |
| 20.10 | 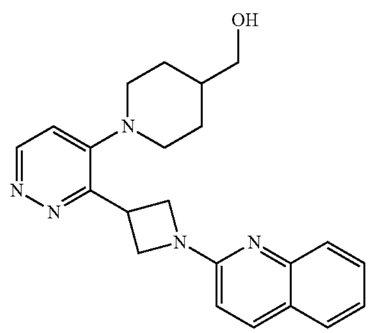 [SMILES: OCC1CCN(c2ccnnc2C2CN(c3ccc4ccccc4n3)C2)CC1] | (CDCl$_3$, 400 MHz): 8.77 (s, 1H); 7.82 (d, J = 8.8 Hz, 1H); 7.66 (s, 1H); 7.54 (d, J = 7.6 Hz, 1H); 7.46 (t, J = 7.6 Hz, 1H); 7.15 (t, J = 8.0 Hz, 1H); 6.81 (t, J = 2.0 Hz, 1H); 6.61 (d, J = 8.8 Hz, 1H); 4.60-4.58 (m, 4H); 4.41-4.16 (m, 1H); 3.55 (s, 2H); 3.23 (d, J = 12.4 Hz, 2H); 2.70-2.68 (m, 2H); 1.86 (d, J = 12.0 Hz, 2H); 1.64 (s, 2H); 1.51-1.37 (m, 1H) |
SCHEME 21
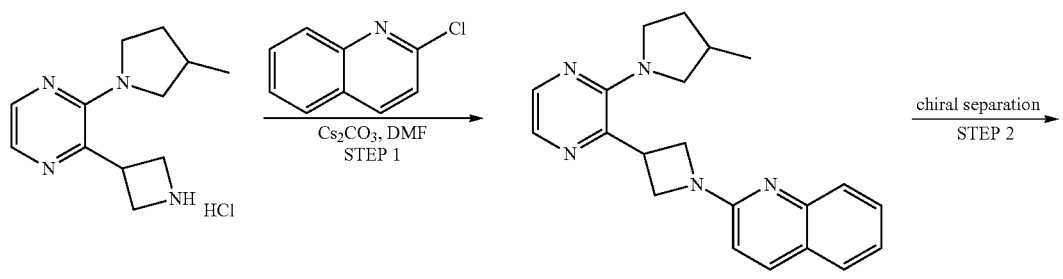
Example 21.1
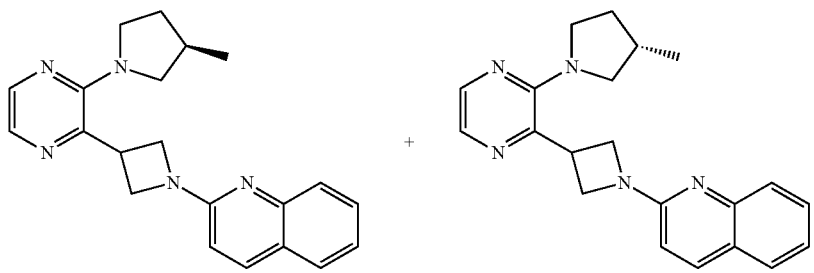
Examples 21.1 and 21.3

Examples 21.2, 21.2 and 21.3: Racemic Mixture and Separated Enantiomers, Wherein the Absolute Stereospecificity were not Determined

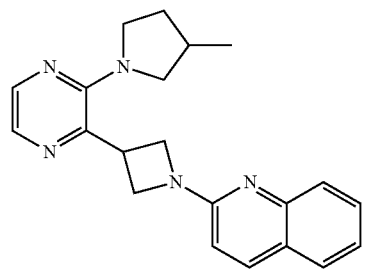 [SMILES: CC1CCN(c2nccnc2C2CN(c3ccc4ccccc4n3)C2)C1]

Step 1. (R & S)-2-{3-[3-(3-Methyl-Pyrrolidin-1-Yl)-Pyrazin-2-Yl]-Azetidin-1-Yl}-Quinoline To a solution of 2-Azetidin-3-yl-3-(3-methyl-pyrrolidin-1-yl)-pyrazine hydrochloride (44) (127 mg, 0.5 mmol, PREPARATION 13) and 2-chloro-quinoline (81.5 mg 0.5 mmol) in DMF (5 mL) was added $Cs_2CO_3$ (325 mg, 1 mmol). The reaction mixture was stirred at 100° C. overnight. The reaction mixture was diluted with water, extracted with EtOAc (2×20 mL). The combined organic extracts were washed with water (15 mL) and brine (15 mL), dried over $Na_2SO_4$ and filtered. The filtrate was evaporated in vacuo and the residue was purified by flash column chromatography on silica gel to give (rac)-2-{3-[3-(3-methyl-pyrrolidin-1-yl)-pyrazin-2-yl]-azetidin-1-yl}-quinoline (127.65 mg, 0.37 mmol, yield 74%). ESI-MS (M+1): 346. PDE10 $IC_{50}$ (uM): 0.00465.

($CDCl_3$, 400 MHz): 8.05 (d, J=8.4 Hz, 1H); 8.00 (d, J=9.2 Hz, 1H); 7.93 (d, J=2.4 Hz, 1H); 7.84 (d, J=2.4 Hz, 1H); 7.66-7.60 (m, 2H); 7.35 (t, J=7.6 Hz, 1H); 6.58 (d, J=9.6 Hz, 1H); 4.94-4.51 (m, 4H); 4.48-4.34 (m, 1H); 3.45 (s, 3H); 3.08 (s, 1H); 2.31-2.25 (m, 1H); 2.09-2.02 (m, 1H); 1.58-1.51 (m, 1H); 1.07 (d, J=6.8 Hz, 3H).

Step 2. (R or S)-2-{3-[3-(3-Methyl-Pyrrolidin-1-Yl)-Pyrazin-2-Yl]-Azetidin-1-Yl}-Quinoline The racemic 2-{3-[3-(3-methyl-pyrrolidin-1-yl)-pyrazin-2-yl]-azetidin-1-yl}-quinoline obtained above (450 mg, 1.3 mmol) was separated by chiral prep. HPLC (Column: Chiralcel OD-H 250*30 mm, 5 u; Mobile phase: 85% hexane in EtOH (0.05% diethyl amine); Flow rate: 30 mL/minute) to give their separated stereoisomers (187 mg, 0.54 mmol, 42% yield) and (175 mg, 0.50 mmol, 38.5% yield). The absolute stereospecificity was not determined. Separated isomer Example 21.2: ESI-MS (M+1): 346. PDE10 $IC_{50}$ (uM): 0.00367.

($CDCl_3$, 400 MHz): 7.97-7.93 (m, 2H); 7.87 (d, J=8.8 Hz, 1H); 7.73 (d, J=8.4 Hz, 1H); 7.60 (d, J=8.0 Hz, 1H); 7.53 (t, J=8.4 Hz, 1H); 7.22 (t, J=7.6 Hz, 1H); 6.66 (d, J=9.2 Hz, 1H); 4.59-4.53 (m, 3H); 4.43 (t, J=8.0 Hz, 1H); 4.33-4.26 (m, 1H); 3.66-3.48 (m, 3H); 3.18 (t, J=8.8 Hz, 1H); 2.37-2.30 (m, 1H); 2.13-2.09 (m, 1H); 1.65-1.55 (m, 1H); 1.22 (d, J=6.8 Hz, 3H). Separated isomer Example 21.3: ESI-MS (M+1): 346. PDE10 $IC_{50}$ (uM): 0.00367.

($CDCl_3$, 400 MHz): 7.86-7.83 (m, 2H); 7.76 (d, J=8.8 Hz, 1H); 7.64 (d, J=8.4 Hz, 1H); 7.50 (d, J=7.6 Hz, 1H); 7.45-7.42 (m, 1H); 7.12 (t, J=8.4 Hz, 1H); 6.55 (d, J=8.8 Hz, 1H); 4.48-4.43 (m, 3H); 4.18 (t, J=8.4 Hz, 1H); 4.20-4.17 (m, 1H); 3.55-3.38 (m, 3H); 3.10-3.06 (m, 1H); 2.25-2.24 (m, 1H); 2.03-1.99 (m, 1H); 1.52-1.47 (m, 1H); 1.05-1.04 (d, J=6.8 Hz, 3H).

SCHEME 22

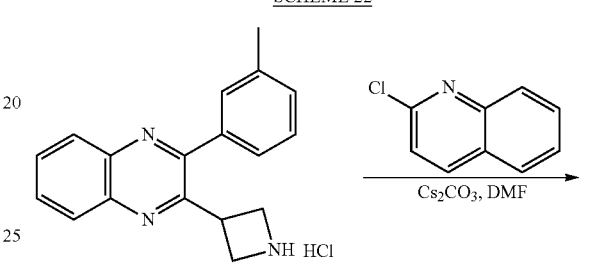

Example 22.1: 2-(1-Quinolin-2-Yl-Azetidin-3-Yl)-3-M-Tolyl-Quinoxaline

To a solution of 2-azetidin-3-yl-3-m-tolyl-quinoxaline hydrochloride (311 mg, 1 mmol) and 2-chloro-quinoline (163 mg, 1.0 mmol) in DMF (6 mL) was added $Cs_2CO_3$ (650 mg, 2 mmol). The reaction mixture was stirred at 100° C. overnight. The reaction mixture was diluted with water, extracted with EtOAc (2×30 mL). The combined organic extracts were washed with water (20 mL) and brine (20 mL), dried over $Na_2SO_4$ and filtered. The filtrate was evaporated in vacuo and the residue was purified by flash column chromatography on silica gel to give 2-(1-quinolin-2-yl-azetidin-3-yl)-3-m-tolyl-quinoxaline (256 mg, 0.64 mmol yield 63.7%).

The following Table 28A lists compounds of Examples 22.1 to 22.4, which were made analogous to Scheme 22 by using the appropriate materials and reaction conditions, which are listed in Table 28B. The NMR data of the Examples are listed in Table 28C.

TABLE 28A

EXAMPLES 22.1 TO 22.4

| Ex. # | Structure | Chemical Name | ESI-MS (M + 1) | IC$_{50}$ (uM) |
|---|---|---|---|---|
| 22.1 | 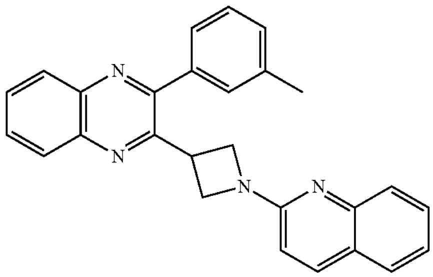 [SMILES: Cc1cccc(-c2nc3ccccc3nc2C2CN(c3ccc4ccccc4n3)C2)c1] | 2-(1-Quinolin-2-yl-azetidin-3-yl)-3-m-tolyl-quinoxaline | 403 | 0.00399 |
| 22.2 | 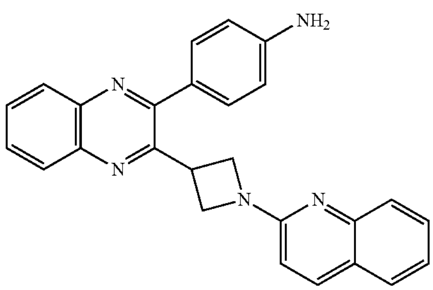 [SMILES: Nc1ccc(-c2nc3ccccc3nc2C2CN(c3ccc4ccccc4n3)C2)cc1] | 4-[3-(1-Quinolin-2-yl-azetidin-3-yl)-quinoxalin-2-yl]-phenylamine | 404 | 0.00156 |
| 22.3 | 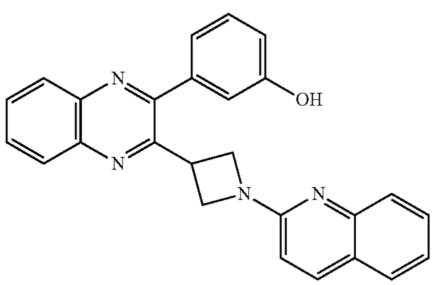 [SMILES: Oc1cccc(-c2nc3ccccc3nc2C2CN(c3ccc4ccccc4n3)C2)c1] | 3-[3-(1-Quinolin-2-yl-azetidin-3-yl)-quinoxalin-2-yl]-phenol | 405 | 0.00099 |
| 22.4 | 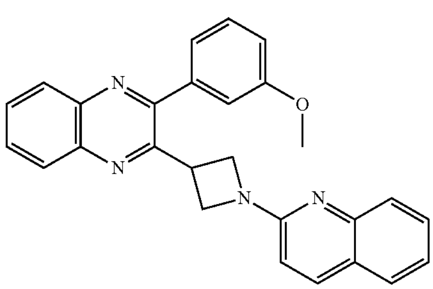 [SMILES: COc1cccc(-c2nc3ccccc3nc2C2CN(c3ccc4ccccc4n3)C2)c1] | 2-(3-Methoxy-phenyl)-3-(1-quinolin-2-yl-azetidin-3-yl)-quinoxaline | 419 | 0.00222 |

TABLE 28B

STARTING MATERIALS AND REACTION CONDITION FOR
PREPARATION OF EXAMPLES 22.1 TO 22.4.
Unless otherwise stated, all starting materials are commercially available from common vendors.

| Ex. # | Starting Material 1 | Starting Material 2 | Reaction Condition |
|---|---|---|---|
| 22.1 | [quinoxaline with 3-methylphenyl and azetidine-NH·HCl] PREPARATION 20 | 2-chloroquinoline | $Cs_2CO_3$, DMF, 100° C. |
| 22.2 | [quinoxaline with 4-aminophenyl and azetidine-NH·HCl] PREPARATION 20 | 2-chloroquinoline | $Cs_2CO_3$, DMF, 100° C. |
| 22.3 | [quinoxaline with 3-hydroxyphenyl and azetidine-NH·HCl] PREPARATION 20 | 2-chloroquinoline | $Cs_2CO_3$, DMF, 100° C. |
| 22.4 | [quinoxaline with 3-methoxyphenyl and azetidine-NH·HCl] PREPARATION 20 | 2-chloroquinoline | $Cs_2CO_3$, DMF, 100° C. |

TABLE 28C

1H NMR δ (PPM) DATA FOR EXAMPLES 22.1 TO 22.4

| Ex. # | Structure | NMR |
|---|---|---|
| 22.1 | [quinoxaline with 3-methylphenyl and azetidine-N-quinoline] | (DMSO, 400 MHz): 8.15-8.08 (m, 2H); 8.01 (d, J = 8.0 Hz, 1H); 7.84-7.82 (m, 2H); 7.68 (d, J = 7.6 Hz, 1H); 7.53-7.47 (m, 4H); 7.39-7.31 (m, 2H); 7.21-7.17 (m, 1H); 6.75 (d, J = 8.8 Hz, 1H); 4.58-4.54 (m, 1H); 4.39 (t, J = 8.0 Hz, 2H); 4.26 (t, J = 8.4 Hz, 2H); 2.38 (s, 3H). |

TABLE 28C-continued

1H NMR δ (PPM) DATA FOR EXAMPLES 22.1 TO 22.4

| Ex. # | Structure | NMR |
|---|---|---|
| 22.2 | 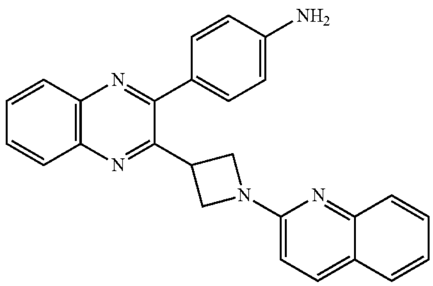 [SMILES: Nc1ccc(-c2nc3ccccc3nc2C2CN(c3ccc4ccccc4n3)C2)cc1] | (CD₃OD, 400 MHz): 8.89 (d, J = 8.8 Hz, 1H); 8.11-8.08 (m, 2H); 7.86-7.82 (m, 3H); 7.75-7.72 (m, 4H); 7.49-7.42 (m, 3H); 6.92 (d, J = 9.2 Hz, 1H); 4.85-4.68 (m, 5H). |
| 22.3 | 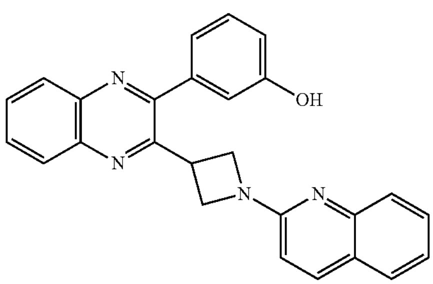 [SMILES: Oc1cccc(-c2nc3ccccc3nc2C2CN(c3ccc4ccccc4n3)C2)c1] | (CD₃OD, 400 MHz): 8.29 (d, J = 9.2 Hz, 1H); 8.15-8.09 (m, 2H); 7.87-7.83 (m, 3H); 7.78-7.73 (m, 2H); 7.50-7.40 (m, 2H); 7.10-6.99 (m, 3H); 6.94 (d, J = 9.2 Hz, 1H); 4.81-4.67 (m, 5H). |
| 22.4 | 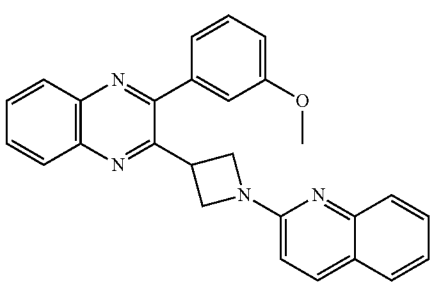 [SMILES: COc1cccc(-c2nc3ccccc3nc2C2CN(c3ccc4ccccc4n3)C2)c1] | (CD₃OD, 400 MHz): 8.27 (d, J = 8.0 Hz, 1H); 8.25-8.28 (m, 2H); 7.86-7.82 (m, 3H); 7.77-7.71 (m, 2H); 7.53-7.46 (m, 2H); 7.21-7.13 (m, 3H); 6.93 (d, J = 9.2 Hz, 1H); 4.81-4.66 (m, 5H); 3.88 (s, 3H). |

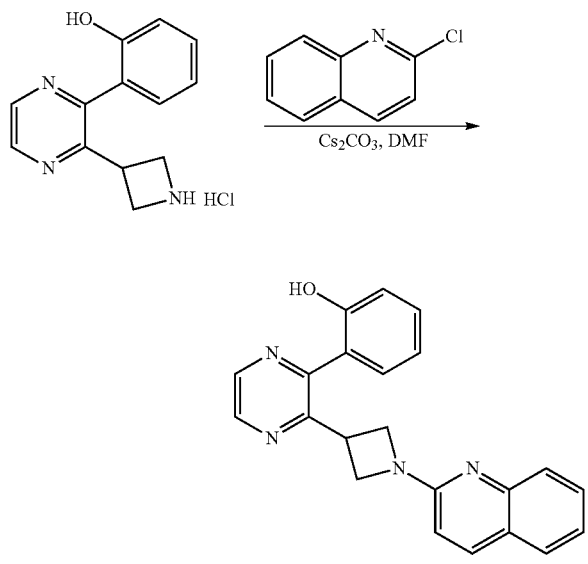

SCHEME 23

Example 23.1: 2-[3-(1-Quinolin-2-Yl-Azetidin-3-Yl)-Pyrazin-2-Yl]-Phenol

To a solution of 2-(3-azetidin-3-yl-pyrazin-2-yl)-phenol hydrochloride (275 mg, 1 mmol) and 2-chloro-quinoline (163 mg, 1 mmol) in DMF (10 mL) was added Cs₂CO₃ (650 mg, 2 mmol). The reaction mixture was stirred at 100° C. overnight. The reaction mixture was diluted with water, extracted with EtOAc (30 mL×2). The combined organic extracts were washed with water (30 mL) and brine (30 mL), dried over Na₂SO₄ and filtered. The filtrate was evaporated in vacuo and the residue was purified by ISCO silica gel column (10% to 80% EtOAc in petroleum ether) to give 2-[3-(1-quinolin-2-yl-azetidin-3-yl)-pyrazin-2-yl]-phenol (56 mg, 0.16 mmol, yield 16%).

The following Table 29A lists compounds of Examples 23.1 to 23.8, which were made analogous to Scheme 23 by using the appropriate materials and reaction conditions, which are listed in Table 29B. The NMR data of the Examples are listed in Table 29C.

TABLE 29A

EXAMPLES 23.1 TO 23.8

| Ex. # | Structure | Chemical Name | ESI-MS (M + 1) | IC$_{50}$ (uM) |
|---|---|---|---|---|
| 23.1 | 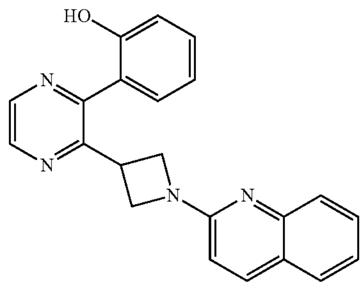 [SMILES: Oc1ccccc1-c1nccnc1C1CN(c2ccc3ccccc3n2)C1] | 2-[3-(1-Quinolin-2-yl-azetidin-3-yl)-pyrazin-2-yl]-phenol | 355 | 0.0339 |
| 23.2 | 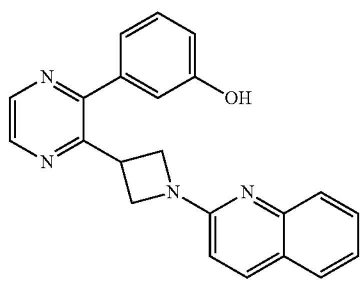 [SMILES: Oc1cccc(-c2nccnc2C2CN(c3ccc4ccccc4n3)C2)c1] | 3-[3-(1-Quinolin-2-yl-azetidin-3-yl)-pyrazin-2-yl]-phenol | 355 | 0.00465 |
| 23.3 | 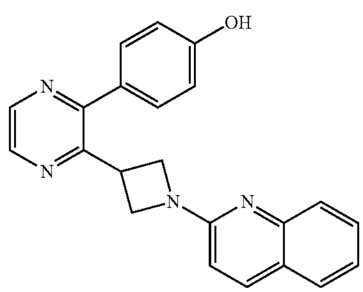 | 4-[3-(1-Quinolin-2-yl-azetidin-3-yl)-pyrazin-2-yl]-phenol | 355 | 0.00442 |
| 23.4 | 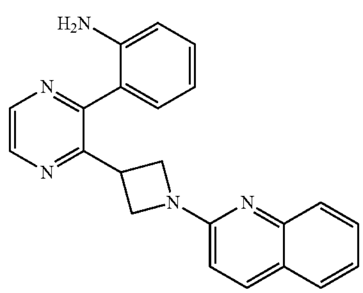 [SMILES: Nc1ccccc1-c1nccnc1C1CN(c2ccc3ccccc3n2)C1] | 2-[3-(1-Quinolin-2-yl-azetidin-3-yl)-pyrazin-2-yl]-phenylamine | 354 | 0.133 |
| 23.5 | 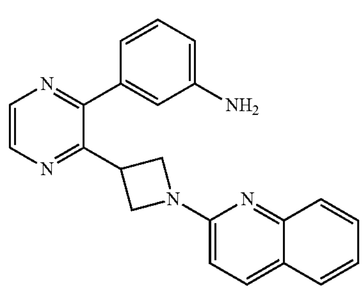 | 3-[3-(1-Quinolin-2-yl-azetidin-3-yl)-prazin-2-yl]-phenylamine | 354 | 0.0111 |

TABLE 29A-continued

EXAMPLES 23.1 TO 23.8

| Ex. # | Structure | Chemical Name | ESI-MS (M + 1) | IC$_{50}$ (uM) |
|---|---|---|---|---|
| 23.6 | 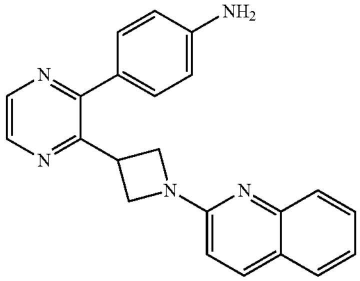 | 4-[3-(1-Quinolin-2-yl-azetidin-3-yl)-pyrazin-2-yl]-phenylamine | 354 | 0.00522 |
| 23.7 | 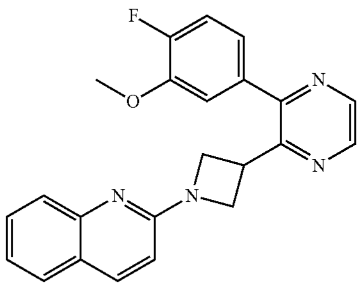 [SMILES: COc1cc(-c2nccnc2C2CN(c3ccc4ccccc4n3)C2)ccc1F] | 2-{3-[3-(4-Fluoro-3-methoxy-phenyl)-pyrazin-2-yl]-azetidin-1-yl}-quinoline | 387 | 0.00298 |
| 23.8 | 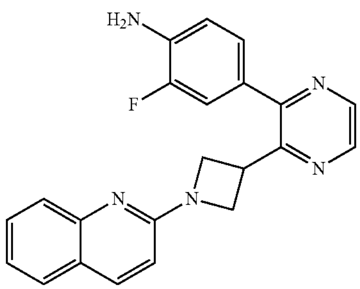 [SMILES: Nc1ccc(-c2nccnc2C2CN(c3ccc4ccccc4n3)C2)cc1F] | 2-Fluoro-4-[3-(1-quinolin-2-yl-azetidin-3-yl)-pyrazin-2-yl]-phenylamine | 372 | 0.00437 |

TABLE 29B

STARTING MATERIALS AND REACTION CONDITION FOR PREPARATION OF EXAMPLES 23.1 TO 23.8.
Unless otherwise stated, all starting materials are commercially available from common vendors

| Ex. # | Starting Material 1 | Starting Material 2 | Reaction Condition |
|---|---|---|---|
| 23.1 | PREPARATION 21 | | Cs$_2$CO$_3$, DMF, 100° C. |

TABLE 29B-continued

STARTING MATERIALS AND REACTION CONDITION FOR
PREPARATION OF EXAMPLES 23.1 TO 23.8.
Unless otherwise stated, all starting materials are commercially available from common vendors

| Ex. # | Starting Material 1 | Starting Material 2 | Reaction Condition |
|---|---|---|---|
| 23.2 | 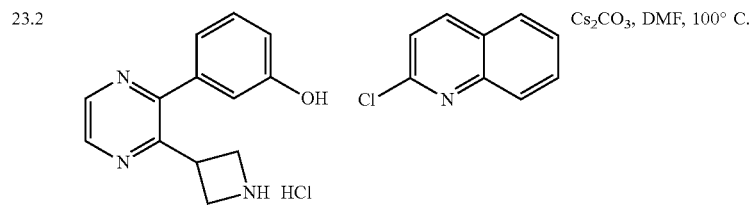 PREPARATION 21 | | $Cs_2CO_3$, DMF, 100° C. |
| 23.3 | 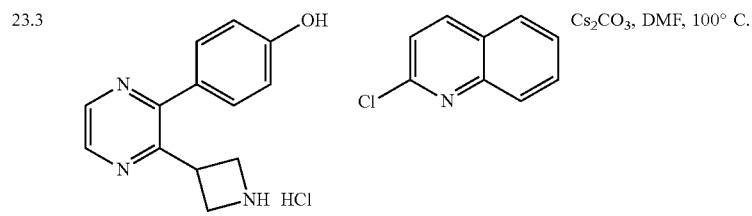 PREPARATION 21 | | $Cs_2CO_3$, DMF, 100° C. |
| 23.4 | 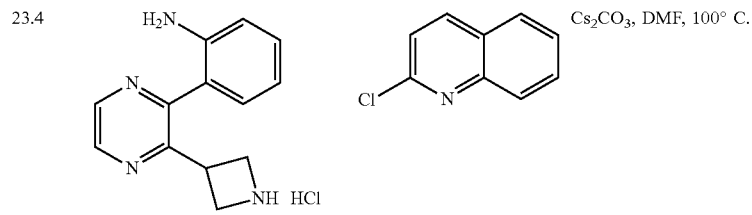 PREPARATION 21 | | $Cs_2CO_3$, DMF, 100° C. |
| 23.5 | 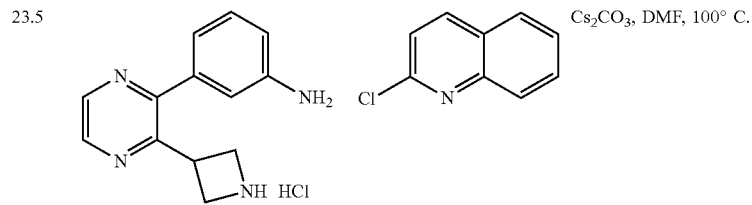 PREPARATION 21 | | $Cs_2CO_3$, DMF, 100° C. |
| 23.6 | 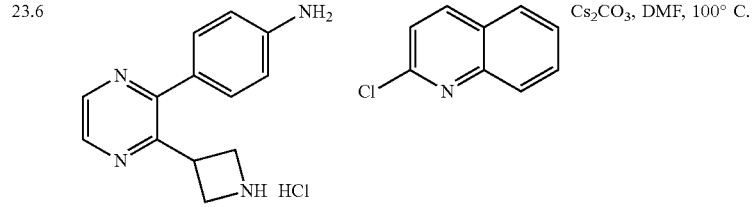 PREPARATION 21 | | $Cs_2CO_3$, DMF, 100° C. |

TABLE 29B-continued

STARTING MATERIALS AND REACTION CONDITION FOR
PREPARATION OF EXAMPLES 23.1 TO 23.8.
Unless otherwise stated, all starting materials are commercially available from common vendors

| Ex. # | Starting Material 1 | Starting Material 2 | Reaction Condition |
|---|---|---|---|
| 23.7 | [structure: methoxy-fluorophenyl pyrazine azetidine·HCl] PREPARATION 21 | [2-chloroquinoline] | $Cs_2CO_3$, DMF, 100° C. |
| 23.8 | [structure: fluoro-amino-phenyl pyrazine azetidine·HCl] PREPARATION 21 | [2-chloroquinoline] | $Cs_2CO_3$, DMF, 100° C. |

TABLE 29C

1H NMR δ (PPM) DATA FOR EXAMPLES 23.1 TO 23.8

| Ex. # | Structure | NMR |
|---|---|---|
| 23.1 | [structure: 2-hydroxyphenyl pyrazine, azetidine-N-quinolinyl] | (CDCl$_3$, 400 MHz): 8.57 (s, 2H); 8.06 (d, J = 9.6 Hz, 1H); 7.94 (d, J = 8.4 Hz, 1H); 7.73-7.68 (m, 2H); 7.45-7.41 (m, 1H); 7.35-7.31 (m, 1H); 7.29-7.28 (m, 1H); 7.06 (d, J = 8.4 Hz, 1H); 7.02-6.98 (m, 1H); 6.62 (d, J = 9.6 Hz, 1H); 5.07 (s, 1H); 4.88-4.72 (m, 3H); 4.55 (s, 1H); 4.33 (s, 1H) |
| 23.2 | [structure: 3-hydroxyphenyl pyrazine, azetidine-N-quinolinyl] | (CD$_3$OD, 400 MHz): 8.68 (m, 1H); 8.52 (m, 1H); 8.49 (m, 1H); 8.28 (d, J = 7.2 Hz, 1H); 7.79-7.71 (m, 2H); 7.51-7.47 (m, 1H); 7.39-7.35 (m, 1H); 6.99-6.91 (m, 4H); 4.86-4.61 (m, 5H) |

TABLE 29C-continued

1H NMR δ (PPM) DATA FOR EXAMPLES 23.1 TO 23.8

| Ex. # | Structure | NMR |
|---|---|---|
| 23.3 | 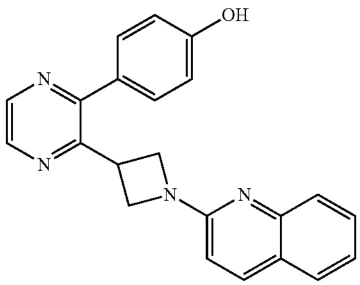 [SMILES: Oc1ccc(-c2nccnc2C2CN(c3ccc4ccccc4n3)C2)cc1] | (CDCl$_3$, 400 MHz): 8.56-8.52 (m, 2H); 7.82 (d, J = 8.8 Hz, 1H); 7.95 (d, J = 8.4 Hz, 1H); 7.73-7.67 (m, 2H); 7.42(t, J = 8.0 Hz, 1H); 7.19 (d, J = 8.0 Hz, 2H); 6.88 (d, J = 8.8 Hz, 2H); 6.62 (d, J = 9.2 Hz, 1H); 4.73 (m, 2H); 4.36 (m, 1H); 4.19 (s, 2H). |
| 23.4 | 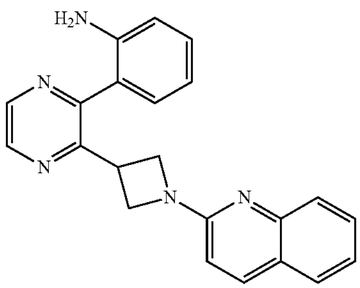 [SMILES: Nc1ccccc1-c1nccnc1C1CN(c2ccc3ccccc3n2)C1] | (CDCl$_3$, 400 MHz): 8.49 (s, 1H); 8.41 (s, 1H); 7.65 (d, J = 8.8 Hz, 1H); 7.51 (d, J = 8.0 Hz, 1H); 7.46 (d, J = 1.2 Hz, 1H); 7.45-7.42 (m, 1H); 7.12-7.10 (m, 2H); 6.94 (dd, J = 7.6 Hz, 1H); 6.81-6.75 (m, 2H); 6.52 (d, J = 8.8 Hz, 1H); 4.37-4.21 (m, 5H); 4.13 (s, 2H) |
| 23.5 | 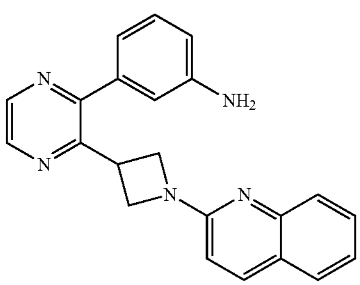 [SMILES: Nc1cccc(-c2nccnc2C2CN(c3ccc4ccccc4n3)C2)c1] | (CDCl$_3$, 400 MHz): 8.61-8.52 (m, 2H); 8.05 (d, J = 9.6 Hz, 1H); 8.00 (d, J = 8.4 Hz, 1H); 7.69-7.69 (m, 2H); 7.41-7.26 (m, 2H); 7.02-6.98 (m, 2H); 6.91-6.90 (m, 1H); 6.62 (d, J = 9.2 Hz, 1H); 4.85-4.31 (m, 5H). |
| 23.6 | 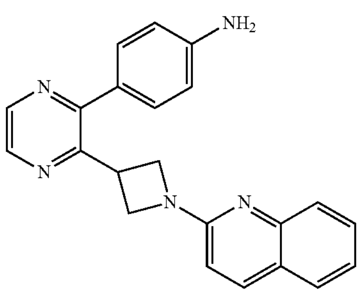 [SMILES: Nc1ccc(-c2nccnc2C2CN(c3ccc4ccccc4n3)C2)cc1] | (CD$_3$OD, 400 MHz): 8.63 (d, J = 2.4 Hz, 1H); 8.56 (d, J = 2.4 Hz, 1H); 8.31 (d, J = 9.2 Hz, 1H); 7.89 (d, J = 8.4 Hz, 1H); 7.78-7.75(m, 2H); 7.50 (m, 1H); 7.45 (d, J = 8.4 Hz, 2H); 7.06 (d, J = 8.4 Hz, 2H); 6.94 (d, J = 9.6 Hz, 1H); 4.70 (s, 5H). |
| 23.7 | 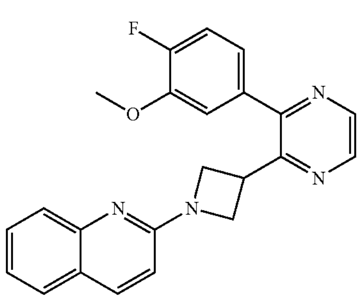 [SMILES: COc1cc(-c2nccnc2C2CN(c3ccc4ccccc4n3)C2)ccc1F] | (CDCl3, 400 MHz): 8.63 (d, J = 2.4 Hz, 1H); 8.57 (d, J = 2.0 Hz, 1H); 7.90 (d, J = 8.0 Hz, 1H); 7.76 (d, J = 9.2 Hz, 1H); 7.64 (dd, J = 1.2, 8.0 Hz, 1H); 7.59-7.55 (m, 1H); 7.28-7.20 (m, 3H); 7.06-7.03 (m, 1H); 6.67 (d, J = 8.8 Hz, 1H); 4.49-4.45 (m, 5H); 4.01 (s, 3H) |

TABLE 29C-continued

1H NMR δ (PPM) DATA FOR EXAMPLES 23.1 TO 23.8

| Ex. # | Structure | NMR |
|---|---|---|
| 23.8 | (structure) | (CDCl3, 400 MHz): 8.43 (d, J = 2.0 Hz, 1H); 8.41 (d, J = 2.0 Hz, 1H); 7.80 (d, J = 8.8 Hz, 1H); 7.66 (d, J = 8.4 Hz, 1H); 7.53 (dd, J = 1.2, 8.0 Hz, 1H); 7.48-7.44 (m, 1H); 7.17-7.13 (m, 2H); 7.06-7.03 (m, 1H); 6.81 (t, J = 8.8 Hz, 1H); 6.55 (d, J = 8.8 Hz, 1H); 4.38-4.35 (m, 5H); 4.01 (s, 2H) |

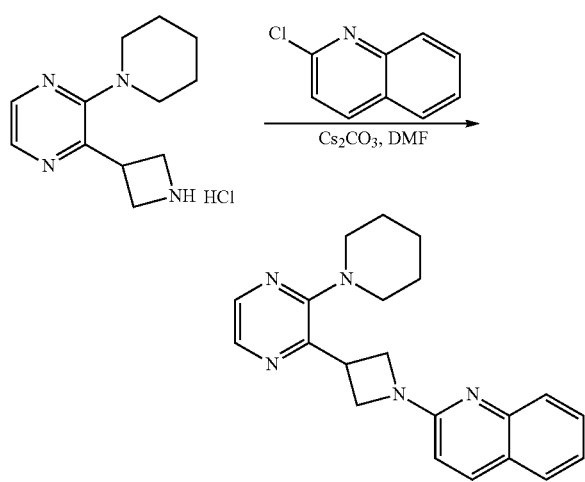

SCHEME 24

Example 24.1: 2-[3-(3-Piperidin-1-Yl-Pyrazin-2-Yl)-Azetidin-1-Yl]-Quinoline

To a solution of 2-azetidin-3-yl-3-piperidin-1-yl-pyrazine hydrochloride (127 mg, 0.5 mmol) and 2-chloro-quinoline (81.5 mg 0.5 mmol) in DMF (5 mL) was added $Cs_2CO_3$ (325 mg, 1 mmol). The reaction mixture was stirred at 100° C. overnight. The reaction mixture was diluted with water, extracted with EtOAc (2×20 mL). The combined organic extracts were washed with water (15 mL) and brine (15 mL), dried over $Na_2SO_4$ and filtered. The filtrate was evaporated in vacuo and the residue was purified by ISCO silica gel column (10% to 80% EtOAc in petroleum ether) to give 2-[3-(3-piperidin-1-yl-pyrazin-2-yl)-azetidin-1-yl]-quinoline (58 mg, 0.17 mmol yield 17%).

The following Table 30A lists compounds of Examples 24.1 to 24.7, which were made analogous to Scheme 24 by using the appropriate materials and reaction conditions, which are listed in Table 30B. The NMR data of the Examples are listed in Table 30C.

TABLE 30A

EXAMPLES 24.1 TO 24.7

| Ex. # | Structure | Chemical Name | ESI-MS (M + 1) | IC$_{50}$ (uM) |
|---|---|---|---|---|
| 24.1 | (structure) | 2-[3-(3-Piperidin-1-yl-pyrazin-2-yl)-azetidin-1-yl]-quinoline | 346 | 0.00393 |

TABLE 30A-continued

EXAMPLES 24.1 TO 24.7

| Ex. # | Structure | Chemical Name | ESI-MS (M + 1) | IC$_{50}$ (uM) |
|---|---|---|---|---|
| 24.2 | 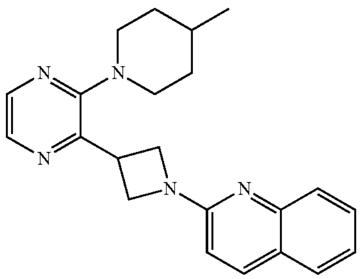 [SMILES: CC1CCN(c2nccnc2C2CN(c3ccc4ccccc4n3)C2)CC1] | 2-{3-[3-(4-Methyl-piperidin-1-yl)-pyrazin-2-yl]-azetidin-1-yl}-quinoline | 368 | 0.000803 |
| 24.3 | 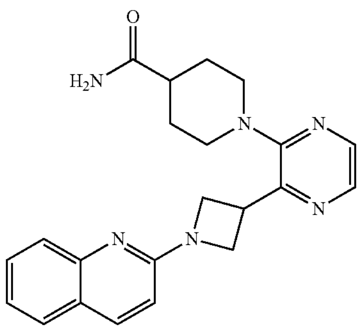 [SMILES: NC(=O)C1CCN(c2nccnc2C2CN(c3ccc4ccccc4n3)C2)CC1] | 1-[3-(1-Quinolin-2-yl-azetidin-3-yl)-pyrazin-2-yl]-piperidine-4-carboxylic acid amide | 389 | 0.00048 |
| 24.4 | 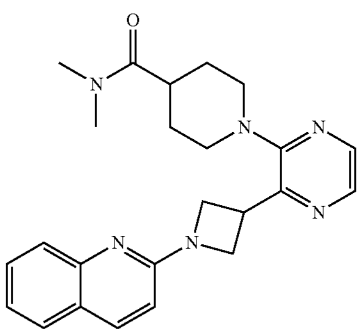 [SMILES: CN(C)C(=O)C1CCN(c2nccnc2C2CN(c3ccc4ccccc4n3)C2)CC1] | 1-[3-(1-Quinolin-2-yl-azetidin-3-yl)-pyrazin-2-yl]-piperidine-4-carboxylic acid dimethylamide | 417 | 0.00355 |
| 24.5 | 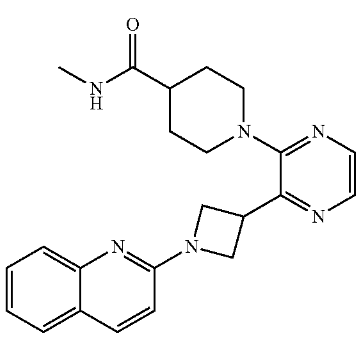 [SMILES: CNC(=O)C1CCN(c2nccnc2C2CN(c3ccc4ccccc4n3)C2)CC1] | 1-[3-(1-Quinolin-2-yl-azetidin-3-yl)-pyrazin-2-yl]-piperidine-4-carboxylic acid methylamide | 403 | 0.00251 |

TABLE 30A-continued

EXAMPLES 24.1 TO 24.7

| Ex. # | Structure | Chemical Name | ESI-MS (M + 1) | IC$_{50}$ (uM) |
|---|---|---|---|---|
| 24.6 | 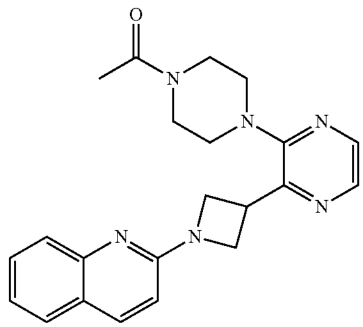 [SMILES: CC(=O)N1CCN(c2nccnc2C2CN(c3ccc4ccccc4n3)C2)CC1] | 1-[3'-(1-Quinolin-2-yl-azetidin-3-yl)-2,3,5,6-tetrahydro-[1,2']bipyrazinyl-4-yl]-ethanone | 389 | 0.029 |
| 24.7 | 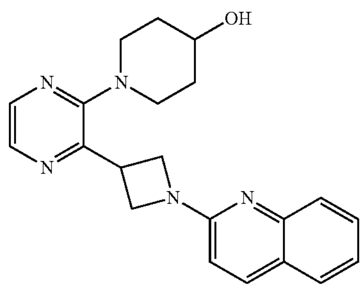 [SMILES: OC1CCN(c2nccnc2C2CN(c3ccc4ccccc4n3)C2)CC1] | 1-[3-(1-Quinolin-2-yl-azetidin-3-yl)-pyrazin-2-yl]-piperidin-4-ol | 362 | 0.00497 |

TABLE 30B

STARTING MATERIALS AND REACTION CONDITION FOR
PREPARATION OF EXAMPLES 24.1 TO 24.7.
Unless otherwise stated, all starting materials are commercially available from common vendors.

| Ex. # | Starting Material 1 | Starting Material 2 | Reaction Condition |
|---|---|---|---|
| 24.1 | PREPARATION 22 | | Cs$_2$CO$_3$, DMF, 100° C. |
| 24.2 | PREPARATION 22 | | Cs$_2$CO$_3$, DMF, 100° C. |

TABLE 30B-continued

STARTING MATERIALS AND REACTION CONDITION FOR
PREPARATION OF EXAMPLES 24.1 TO 24.7.
Unless otherwise stated, all starting materials are commercially available from common vendors.

| Ex. # | Starting Material 1 | Starting Material 2 | Reaction Condition |
|---|---|---|---|
| 24.3 | PREPARATION 22 | | Cs₂CO₃, DMF, 100° C. |
| 24.4 | PREPARATION 22 | | Cs₂CO₃, DMF, 100° C. |
| 24.5 | PREPARATION 22 | | Cs₂CO₃, DMF, 100° C. |
| 24.6 | PREPARATION 22 | | Cs₂CO₃, DMF, 100° C. |
| 24.7 | PREPARATION 2 | | Cs₂CO₃, DMF, 100° C. |

TABLE 30C

1H NMR δ (PPM) DATA FOR EXAMPLES 24.1 TO 24.7

| Ex. # | Structure | NMR |
|---|---|---|
| 24.1 | 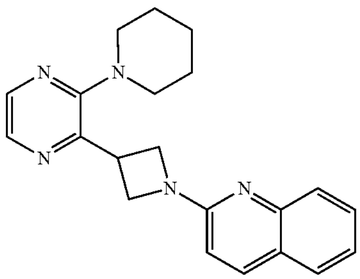 | (CDCl$_3$, 400 MHz): 8.12 (s, 2H); 8.05 (d, J = 20.8 Hz, 1H); 7.96 (d, J = 8.4 Hz, 1H); 7.67-7.63 (m, 2H); 7.40-7.36 (m, 1H); 6.62 (d, J = 9.2 Hz, 1H); 5.07 (s, 1H); 4.75-4.71 (m, 3H); 4.39-4.36 (m, 1H); 3.06-3.04 (m, 4H); 1.75-1.69 (m, 4H); 1.64-1.62 (m, 2H). |
| 24.2 | 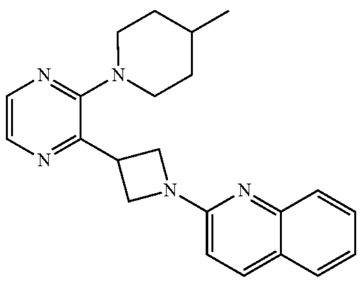 [SMILES: CC1CCN(c2nccnc2C2CN(c3ccc4ccccc4n3)C2)CC1] | (CDCl$_3$, 400 MHz): 8.12 (d, J = 2.4 Hz, 1H); 8.06 (d, J = 2.4 Hz, 1H); 7.85 (d, J = 8.8 Hz, 1H); 7.74 (d, J = 8.4 Hz, 1H); 7.58 (d, J = 8.0 Hz, 1H); 7.50 (t, J = 2.8 Hz, 2H); 7.20-7.18 (m, 1H); 6.64 (d, J = 8.8 Hz, 1H); 4.56-4.52 (m, 2H); 4.47-4.43 (m, 2H); 4.33-4.26 (m, 1H); 3.38 (d, J = 12.8 Hz, 2H); 2.83 (t, J = 12.0 Hz, 2H); 1.77 (d, J = 12.4 Hz, 2H); 1.57 (s, 1H); 1.44-1.35 (m, 2H); 1.01 (d, J = 6.4 Hz, 3H). |
| 24.3 | 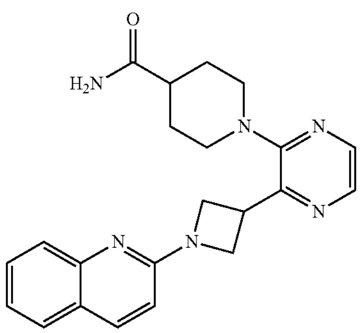 [SMILES: NC(=O)C1CCN(c2nccnc2C2CN(c3ccc4ccccc4n3)C2)CC1] | (CDCl3, 400 MHz): 8.21 (m, 2H); 8.19 (dd, J = 2.4, 7.2 Hz, 2H); 8.09 (d, J = 9.2 Hz, 1H); 8.06 (d, J = 8.4 Hz, 1H); 7.75-7.69 (s, 1H); 6.68-6.66 (d, J = 9.2 Hz, 1H); 5.84 (s, 1H); 4.98 (s, 1H); 4.69 (m, 2H); 4.47-4.43 (m, 1H); 3.45 (d, J = 12.4 Hz, 2H); 2.89 (m, 2H); 2.42-2.41 (m, 1H); 2.06-2.04 (m, 4H) |
| 24.4 | 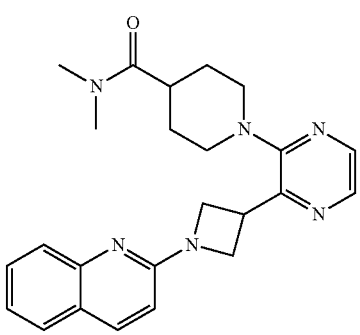 [SMILES: CN(C)C(=O)C1CCN(c2nccnc2C2CN(c3ccc4ccccc4n3)C2)CC1] | (CD$_3$OD), 400 MHz): 8.31 (d, J = 9.6 Hz, 1H); 8.20 (dd, J = 2.4, 15.6 Hz, 2H); 7.87 (d, J = 8.0 Hz, 1H); 7.80-7.74 (m, 2H); 7.51-7.47 (m, 1H); 6.98 (d, J = 9.6 Hz, 1H); 4.90 (t, J = 9.2 Hz, 2H); 4.73 (t, J = 7.8 Hz, 2H); 4.60-4.57 (m, 1H); 3.49 (d, J = 12.8 Hz, 2H); 3.14 (s, 3H); 3.01-2.91 (m, 5H); 2.43-2.38 (m, 1H); 1.94-1.85 (m, 4H). |
| 24.5 | 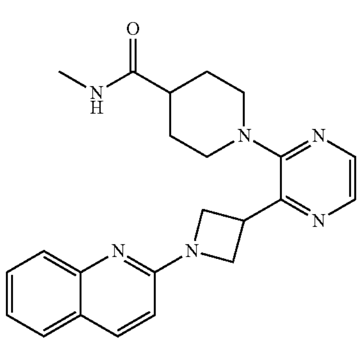 [SMILES: CNC(=O)C1CCN(c2nccnc2C2CN(c3ccc4ccccc4n3)C2)CC1] | (CD$_3$OD, 400 MHz): 8.33 (d, J = 9.6 Hz, 1H); 8.23 (d, J = 2.4 Hz, 1H); 8.19 (d, J = 2.4 Hz, 1H); 7.89 (d, J = 7.6 Hz, 1H); 7.79-7.76 (m, 2H); 7.53-7.49 (m, 1H); 7.00 (d, J = 9.6 Hz, 1H); 4.93-4.89 (m, 2H); 4.74 (t, J = 6.4 Hz, 2H); 4.60-4.56 (m, 1H); 3.50-3.47 (d, J = 12.8 Hz, 2H); 2.93-2.91 (m, 2H); 2.75 (s, 3H); 2.43-2.38 (m, 1H); 1.93-1.98 (m, 4H). |

TABLE 30C-continued

1H NMR δ (PPM) DATA FOR EXAMPLES 24.1 TO 24.7

| Ex. # | Structure | NMR |
|---|---|---|
| 24.6 | 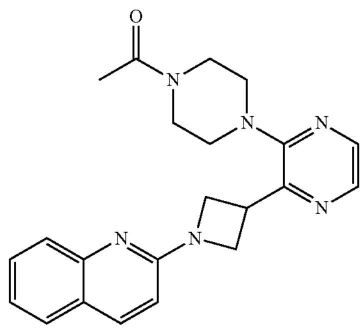 | (MeOD, 400 MHz): 8.32 (d, J = 9.6 Hz, 1H); 8.28 (d, J = 2.4 Hz, 1H); 8.22 (d, J = 2.4 Hz, 1H); 7.88 (d, J = 8.0 Hz, 1H); 7.80-7.74 (m, 2H); 7.52-7.48 (m, 1H); 6.99 (d, J = 9.6 Hz, 1H); 4.91 (d, J = 9.2 Hz, 2H); 4.75 (s, 2H); 4.63-4.59 (m, 1H); 3.79-3.73 (m, 4H); 3.23 (t, J = 5.2 Hz, 2H); 3.14 (t, J = 5.2 Hz, 2H); 2.15 (s, 3H). |
| 24.7 | 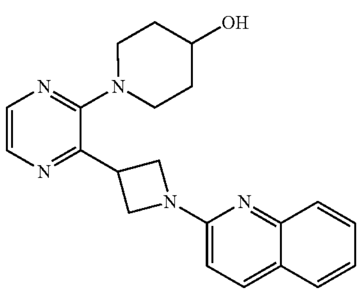 [SMILES: OC1CCN(c2nccnc2C2CN(c3ccc4ccccc4n3)C2)CC1] | (MeOD, 400 MHz): 8.07-8.02 (m, 2H); 7.94 (d, J = 9.2 Hz, 1H); 7.59 (d, J = 8.8 Hz, 2H); 7.47 (t, J = 6.4 Hz, 1H); 7.16 (t, J = 6.0 Hz, 1H); 6.69 (d, J = 9.2 Hz, 1H); 4.52 (s, 2H); 4.35-3.34 (m, 3H); 3.75-3.68 (m, 1H); 3.37-3.29 (m, 2H); 2.89 (m, 2H); 1.95-1.89 (m, 2H); 1.69-1.65 (m, 2H). |

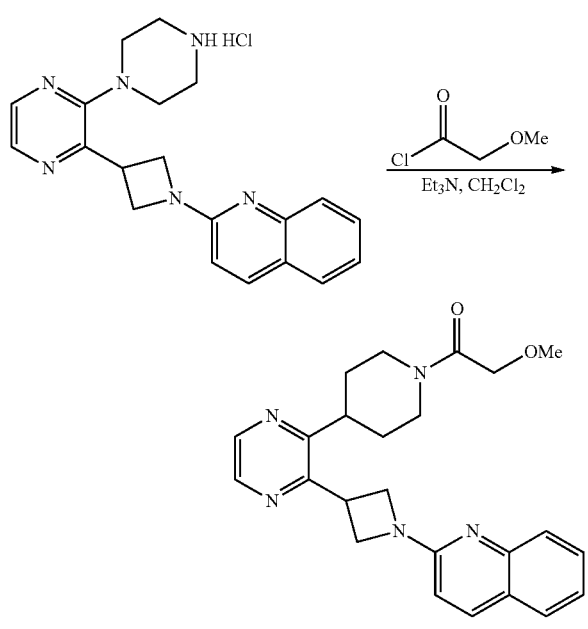

SCHEME 25

Example 25.1: 2-Methoxy-1-{4-[3-(1-Quinolin-2-Yl-Azetidin-3-Yl)-Pyrazin-2-Yl]-Piperidin-1-Yl}-Ethanone A solution of 2-azetidin-3-yl-3-chloro-pyrazine hydrochloride (190 mg, 0.5 mmol) and Et₃N (101 mg, 1 mL,) in DCM (15 mL) was added methoxy-acetyl chloride (purchased from ALDRICH) (81 mg, 0.75 mmol). The reaction was stirred at RT for 2 h. The reaction mixture was concentrated and purified by ISCO silica gel column (10% to 80% EtOAc in petroleum ether) give the product 2-methoxy-1-{4-[3-(1-quinolin-2-yl-azetidin-3-yl)-pyrazin-2-yl]-piperidin-1-yl}-ethanone (82 mg, 0.20 mmol, 39% yield).

The following Table 31A lists compounds of Examples 25.1 to 25.4, which were made analogous to Scheme 25 by using the appropriate materials and reaction conditions, which are listed in Table 31B. The NMR data of the Examples are listed in Table 31C.

TABLE 31A
EXAMPLES 25.1 TO 25.4
| Ex. # | Structure | Chemical Name | ESI-MS (M + 1) | IC$_{50}$ (uM) |
|---|---|---|---|---|
| 25.1 | 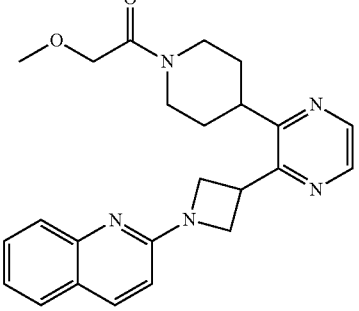 | 2-Methoxy-1-{4-[3-(1-quinolin-2-yl-azetidin-3-yl)-pyrazin-2-yl]-piperidin-1-yl}-ethanone | 418 | 0.0636 |
| 25.2 | 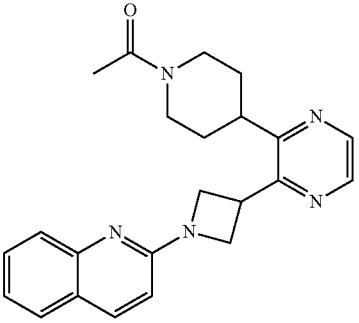 | 1-{4-[3-(1-Quinolin-2-yl-azetidin-3-yl)-pyrazin-2-yl]-piperidin-1-yl}-ethanone | 388 | 0.0342 |
| 25.3 | 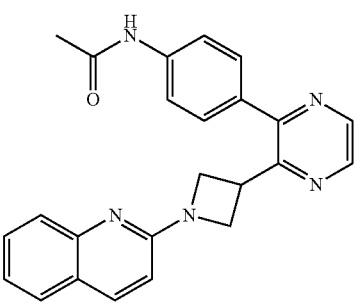 [SMILES: CC(=O)Nc1ccc(-c2nccnc2C2CN(c3ccc4ccccc4n3)C2)cc1] | N-{4-[3-(1-Quinolin-2-yl-azetidin-3-yl)-pyrazin-2-yl]-phenyl}-acetamide | 396 | 0.00236 |
| 25.4 | 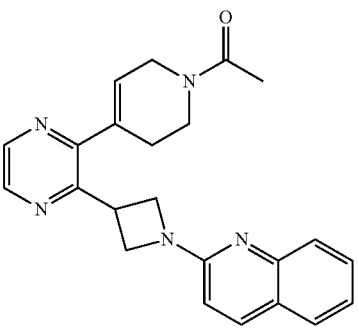 [SMILES: CC(=O)N1CC=C(c2nccnc2C2CN(c3ccc4ccccc4n3)C2)CC1] | 1-(4-(3-(1-(quinolin-2-yl)azetidin-3-yl)pyrazin-2-yl)-5,6-dihydropyridin-1(2H)-yl)ethanone | 386 | 0.0006 |

TABLE 31B
STARTING MATERIALS AND REACTION CONDITION FOR
PREPARATION OF EXAMPLES 25.1 TO 25.4.
Unless otherwise stated, all starting materials are commercially available from common vendors.
| Ex. # | Starting Material 1 | Starting Material 2 | Reaction Condition |
|---|---|---|---|
| 25.1 | 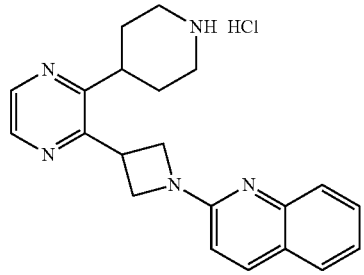<br>54<br>PREPARATION 16 | 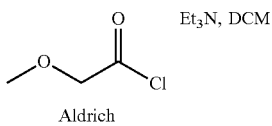<br>Aldrich | Et₃N, DCM |
| 25.2 | 54<br>PREPARATION 16 | 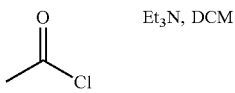 | Et₃N, DCM |
| 25.3 | 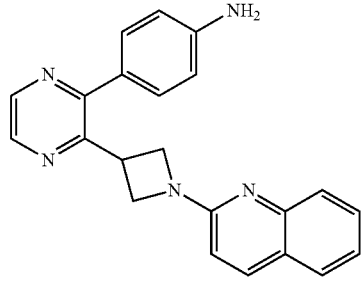<br>SCHEME 23 | 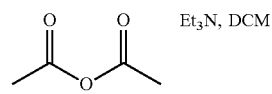 | Et₃N, DCM |
| 25.4 | 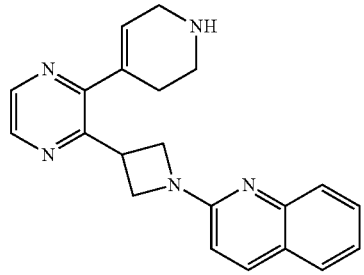<br>SCHEME 32 | 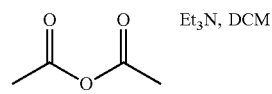 | Et₃N, DCM |

TABLE 31C

1H NMR δ (PPM) DATA FOR EXAMPLES 25.1 TO 25.4

| Ex. # | Structure | NMR |
|---|---|---|
| 25.1 | 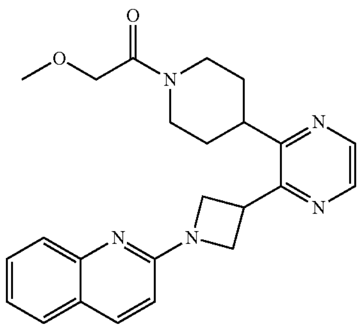 [SMILES: COCC(=O)N1CCC(c2nccnc2C2CN(c3ccc4ccccc4n3)C2)CC1] | (CD$_3$OD, 400 MHz): 8.41-8.38 (m, 2H); 7.97 (t, J = 7.6 Hz, 1H); 7.64 (t, J = 8.8 Hz, 2H); 7.54-7.50 (m, 1H); 7.24-7.19 (m, 1H); 6.72 (t, J = 8.8 Hz, 1H); 4.64-4.44 (m, 6H); 4.22-4.11 (m, 2H); 3.97 (d, J = 13.2 Hz, 1H); 3.42 (s, 3H); 3.30-3.15 (m, 2H); 2.84-2.82 (m, 1H); 1.82-1.78 (m, 4H) |
| 25.2 | 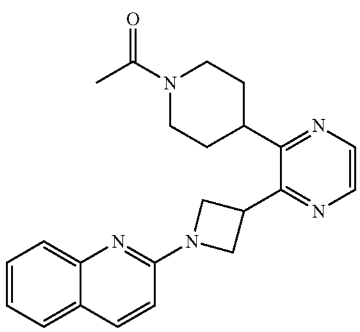 [SMILES: CC(=O)N1CCC(c2nccnc2C2CN(c3ccc4ccccc4n3)C2)CC1] | (CDCl$_3$, 400 MHz): 8.35-8.33 (m, 2H); 7.85 (d, J = 8.8 Hz, 1H); 7.72 (d, J = 8.4 Hz, 1H); 7.55 (dd, J = 1.2, 8.0 Hz, 1H); 7.51-7.47 (m, 1H); 7.21-7.17 (m, 1H); 6.61 (d, J = 8.8 Hz, 1H); 4.73 (d, J = 12.4 Hz, 1H); 4.60-4.47 (m, 4H); 4.36-4.32 (m, 1H); 3.94-3.91 (m, 1H); 3.19-3.13 (m, 1H); 2.95-2.88 (m, 1H); 2.64-3.63 (m, 1H); 2.07 (s, 3H); 2.03-2.00 (m, 1H); 1.77-1.71 (m, 3H). |
| 25.3 | 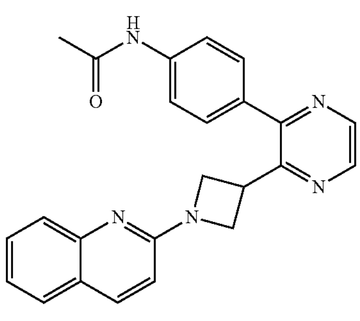 [SMILES: CC(=O)Nc1ccc(-c2nccnc2C2CN(c3ccc4ccccc4n3)C2)cc1] | (CD$_3$OD, 400 MHz): 8.53-8.44 (m, 2H); 7.94 (d, J = 9.2 Hz, 1H); 7.69 (d, J = 8.4 Hz, 2H); 7.60-7.56 (m, 2H); 7.47-7.42 (m, 3H); 7.18 (t, J = 7.6 Hz, 1H); 6.64 (d, J = 9.2 Hz, 1H); 4.39-4.33 (m, 5H); 2.08 (s, 3H). |
| 25.4 | 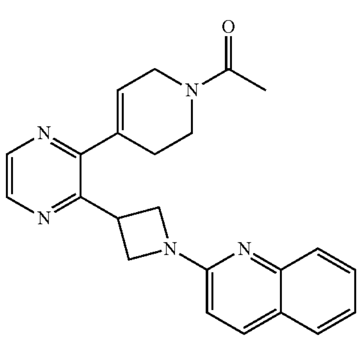 [SMILES: CC(=O)N1CC=C(c2nccnc2C2CN(c3ccc4ccccc4n3)C2)CC1] | (400 MHz, chloroform-d) 2.19 (d, J = 5.87 Hz, 3 H) 2.69 (br. S., 2 H) 3.72 (t, J = 5.58 Hz, 1H) 3.89 (t, J = 5.58 Hz, 1H) 4.19 (d, J = 2.54 Hz, 1 H) 4.31 (d, J = 2.54 Hz, 1 H) 4.36-4.56 (m, 5 H) 5.77-5.88 (m, 1 H) 6.65 (dd, J = 8.90, 2.25 Hz, 1 H) 7.22 (t, J = 7.43 Hz, 1 H) 7.53 (t, J = 7.63 Hz, 1 H) 7.61 (d, J = 8.02 Hz, 1 H) 7.74 (d, J = 8.41 Hz, 1 H) 7.89 (dd, J = 8.90, 3.03 Hz, 1 H) 8.42 (t, J = 2.93 Hz, 1 H) 8.49 (d, J = 2.54 Hz, 1 H). |

SCHEME 26

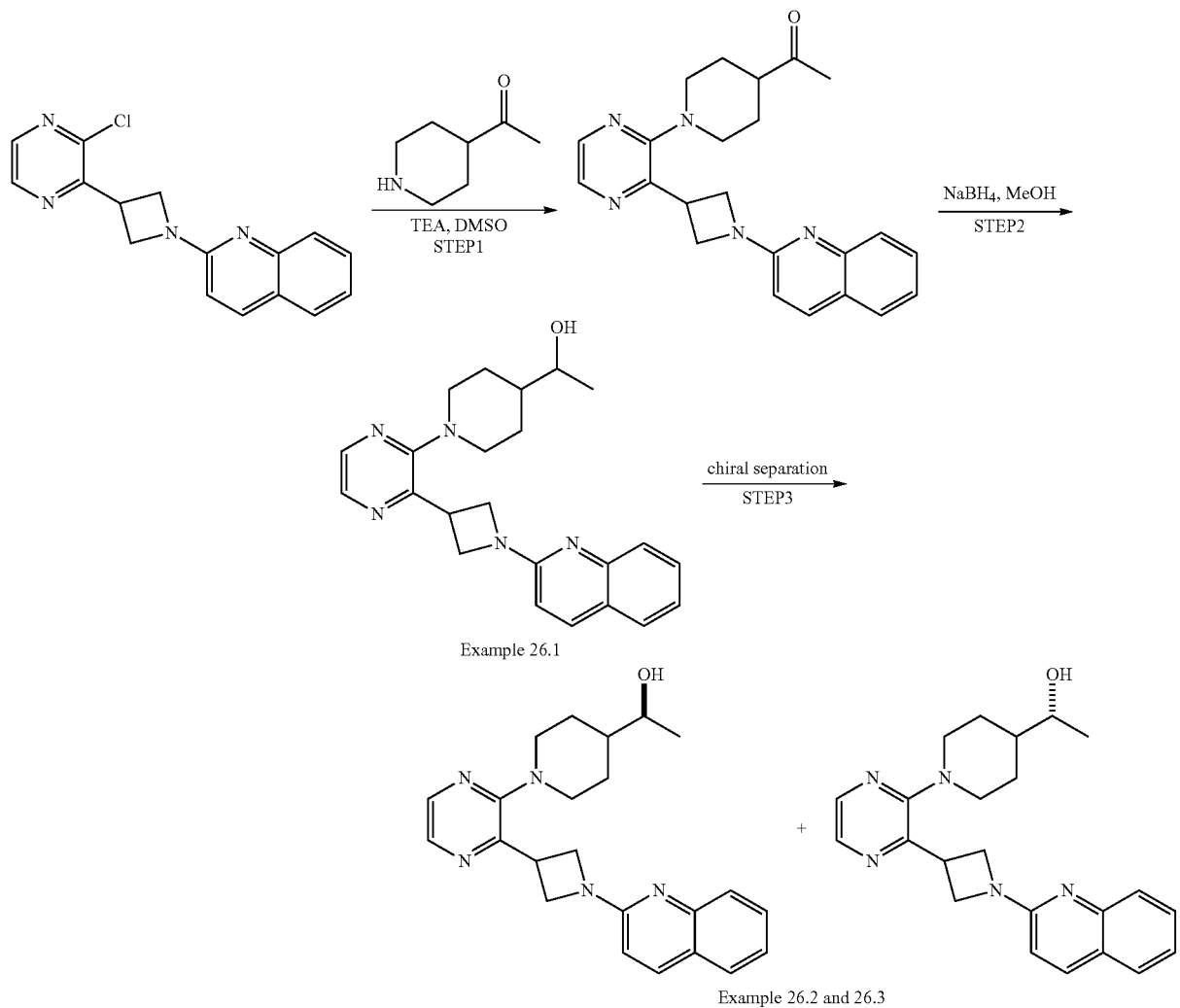

Examples 26.1, 26.2, and 26.3: Racemic Mixtures and Separated Enantiomers, Absolute Stereochemistry not Further Determined Step 1. 1-{1-[3-(1-Quinolin-2-Yl-Azetidin-3-Yl)-Pyrazin-2-Yl]-Piperidin-4-Yl}-Ethanone To a solution of 2-[3-(3-chloro-pyrazin-2-yl)-azetidin-1-yl]-quinoline (80 mg, 0.27 mmol) and 1-piperidin-4-yl-ethanone (WUXI APPTEC) (34.3 mg, 0.27 mmol) in DMSO (5 mL) was added Et₃N (54.5 mg, 0.54 mmol). The reaction mixture was stirred at 100° C. overnight. The reaction mixture was diluted with water, extracted with EtOAc (20 mL×3). The combined organic extracts were washed with water (30 mL) and brine (30 mL), dried over Na₂SO₄ and filtered. The filtrate was evaporated in vacuo and the residue was purified by flash column chromatography on silica gel to give 1-{1-[3-(1-quinolin-2-yl-azetidin-3-yl)-pyrazin-2-yl]-piperidin-4-yl}-ethanone (65.8 mg, 0.17 mmol, yield 62.9%).

ESI-MS (M+1): 388 calc. for $C_{23}H_{25}N_5O$ 387.

Step 2. (S & R)-1-{1-[3-(1-Quinolin-2-Yl-Azetidin-3-Yl)-Pyrazin-2-Yl]-Piperidin-4-Yl}-Ethanol A solution of 1-{1-[3-(1-quinolin-2-yl-azetidin-3-yl)-pyrazin-2-yl]-piperidin-4-yl}-ethanone (96.75 mg, 0.25 mmol) in MeOH (10 mL) was added NaBH₄ (37 mg, 1 mmol). The mixture was stirred at RT for 2 h. The reaction mixture was concentrated to give the product (racemic)-1-

{1-[3-(1-quinolin-2-yl-azetidin-3-yl)-pyrazin-2-yl]-piperidin-4-yl}-ethanol (76 mg, 0.20 mmol, yield 78%).

ESI-MS (M+1): 390. PDE10 IC$_{50}$ (uM): 0.00805.

(CD$_3$OD, 400 MHz): 8.31 (d, J=9.2 Hz, 1H); 8.22-8.16 (m, 2H); 7.88 (d, J=7.6 Hz, 1H); 7.78-7.75 (m, 2H); 7.52-7.48 (m, 1H); 6.98 (d, J=9.6 Hz, 1H); 4.89 (d, J=7.2 Hz, 1H); 4.72 (t, J=7.2 Hz, 2H); 4.56-4.55 (m, 1H); 3.60-3.57 (m, 1H); 3.47 (d, J=12.8 Hz, 2H); 2.87-2.84 (m, 2H); 1.98-1.97 (m, 1H); 1.77-1.76 (m, 1H); 1.56-1.48 (m, 3H); 1.47 (d, J=3.2 Hz, 1H); 1.20 (d, J=6.4 Hz, 3H).

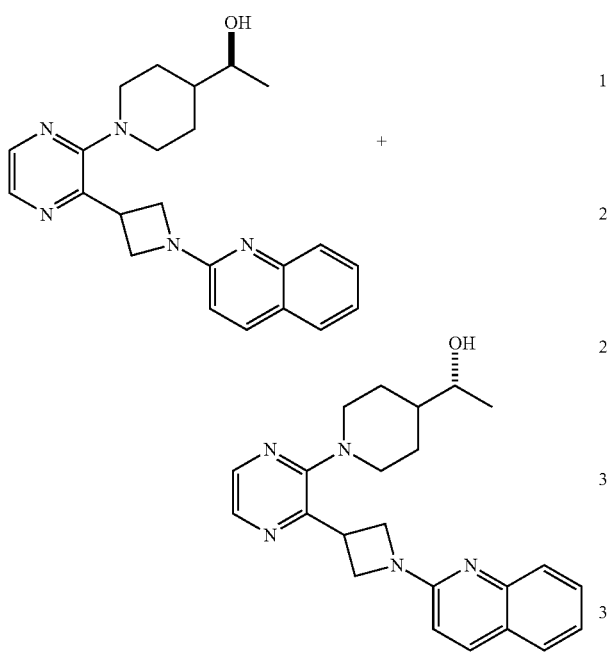

Examples 26.2 and 26.3

Step 3. Separated R and S-1-{1-[3-(1-Quinolin-2-Yl-Azetidin-3-Yl)-Pyrazin-2-Yl]-Piperidin-4-Yl}-Ethanol The racemic mixture of 1-{1-[3-(1-quinolin-2-yl-azetidin-3-yl)-pyrazin-2-yl]-piperidin-4-yl}-ethanol (450 mg, 1.16 mmol) was separated by chiral prep. HPLC (Column: Chiralpak AD-H 250*30 mm, 5 u; Mobile phase: 70% hexane in EtOH (0.05% diethyl amine); Flow rate: 20 mL/minute) to give their separated enantiomers (152 mg, 0.41 mmol, 34% yield) and 182 mg, 0.47 mmol, 41% yield).

Separated isomer Example 26.2: ESI-MS (M+1): 390. PDE10 IC$_{50}$ (uM): 0.00237.

1H NMR δ (ppm) (CDCl$_3$, 400 MHz): 8.16-8.08 (m, 2H); 7.88 (d, J=8.8 Hz, 1H); 7.73 (d, J=8.4 Hz, 1H); 7.62-7.59 (m, 1H); 7.55-7.51 (m, 1H); 7.24-7.20 (m, 1H); 6.66 (d, J=8.8 Hz, 1H); 4.57-4.53 (m, 2H); 4.48-4.45 (m, 2H); 4.34-4.32 (m, 1H); 3.70-3.68 (m, 1H); 3.50-3.46 (m, 2H); 2.88-2.81 (m, 2H); 2.02-1.99 (m, 1H); 1.79-1.76 (m, 1H); 1.58-1.49 (m, 3H); 1.25 (d, J=6.4 Hz, 3H).

Separated isomer Example 26.3: ESI-MS (M+1): 390. PDE10 IC$_{50}$ (uM): 0.00262.

1H NMR δ (ppm) (CDCl$_3$, 400 MHz): 8.15-8.08 (m, 2H); 7.88 (d, J=8.8 Hz, 1H); 7.73 (d, J=8.4 Hz, 1H); 7.61-7.55 (m, 1H); 7.53-7.51 (m, 1H); 7.23-7.19 (m, 1H); 6.66 (d, J=9.2 Hz, 1H); 4.57-4.53 (m, 2H); 4.48-4.44 (m, 2H); 4.35-4.29 (m, 1H); 3.69-3.67 (m, 1H); 3.49-3.46 (m, 2H); 2.87-2.81 (m, 2H); 2.02-1.99 (m, 1H); 1.79-1.76 (m, 1H); 1.57-1.51 (m, 3H); 1.25 (d, J=6.4 Hz, 3H).

SCHEME 27

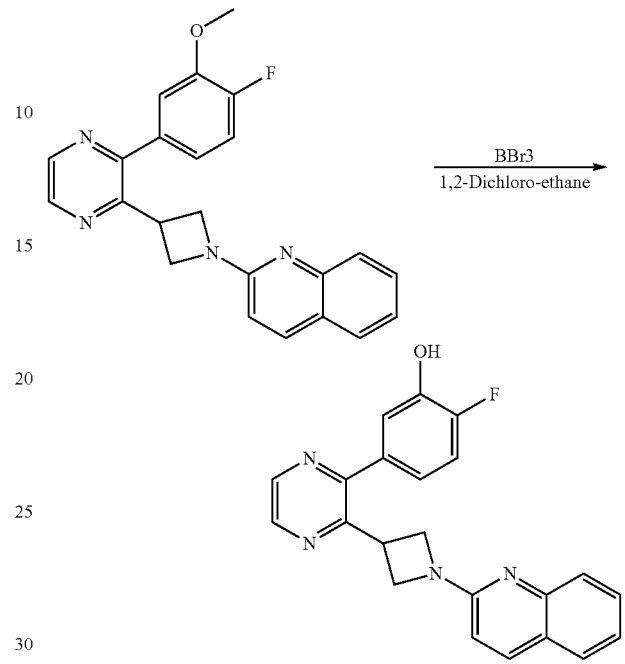

Example 27.1: 2-Fluoro-5-[3-(1-Quinolin-2-Yl-Azetidin-3-Yl)-Pyrazin-2-Yl]-Phenol To a solution of 2-{3-[3-(4-fluoro-3-methoxy-phenyl)-pyrazin-2-yl]-azetidin-1-yl}-quinoline (193 mg, 0.5 mmol) in 1,2-dichloro-ethane (5 mL) was added BBr$_3$ (250 mg, 1.0 mmol). The reaction mixture was stirred at RT for 2 h. The reaction mixture was diluted with water, extracted with DCM (2×30 mL). The combined organic extracts were washed with water (20 mL) and brine (20 mL), dried over Na$_2$SO$_4$ and filtered. The filtrate was evaporated in vacuo and the residue was purified by flash column chromatography on silica gel to give 2-fluoro-5-[3-(1-quinolin-2-yl-azetidin-3-yl)-pyrazin-2-yl]-phenol (111 mg, 0.31 mmol yield 62%).

ESI-MS (M+1): 373. PDE10 IC$_{50}$ (uM): 0.00284.

1H NMR δ (ppm) (CD$_3$OD, 400 MHz): 8.63-8.57 (m, 2H); 8.29 (d, J=8.0 Hz, 1H); 7.87 (d, J=8.0 Hz, 1H); 7.79-7.72 (m, 2H); 7.52-7.48 (m, 1H); 7.26-7.21 (m, 1H); 7.15-7.13 (m, 1H); 7.00-6.96 (m, 1H); 6.93 (d, J=9.2 Hz, 1H); 4.68-4.64 (m, 5H).

SCHEME 28

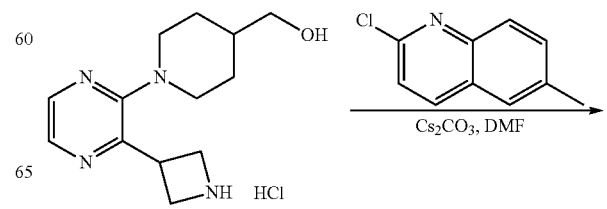

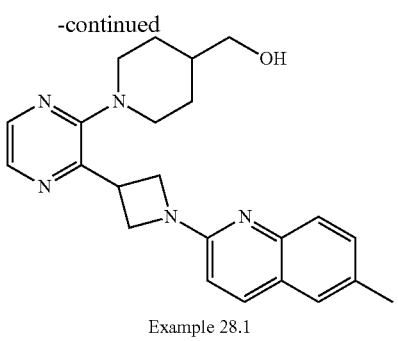

Example 28.1

Example 28.1: (1-{3-[1-(6-Methyl-Quinolin-2-Yl)-Azetidin-3-Yl]-Pyrazin-2-Yl}-Piperidin-4-Yl)-Methanol To a solution of [1-(3-azetidin-3-yl-pyrazin-2-yl)-piperidin-4-yl]-methanol hydrochloride (284 mg, 1.0 mmol) and 2-chloro-6-methyl-quinoline (purchased from ALDRICH) (177 mg, 1.0 mmol) in DMF (15 mL) was added $Cs_2CO_3$ (650 mg, 2.0 mmol). The reaction mixture was stirred at 100° C. overnight. The reaction mixture was diluted with water, extracted with EtOAc (2×30 mL). The combined organic extracts were washed with water (20 mL) and brine (20 mL), dried over $Na_2SO_4$ and filtered. The filtrate was evaporated in vacuo and the residue was purified by flash column chromatography (EtOAc:Petrol ether=5:1) on silica gel to give (1-{3-[1-(6-methyl-quinolin-2-yl)-azetidin-3-yl]-pyrazin-2-yl}-piperidin-4-yl)-methanol (102 mg, 0.26 mmol 26%).

The following Table 32A lists compounds of Examples 28.1 to 28.18, which were made analogous to Scheme 28 by using the appropriate materials and reaction conditions, which are listed in Table 32B. The NMR data of the Examples are listed in Table 32C.

TABLE 32A

EXAMPLES 28.1 TO 28.18

| Ex. # | Structure | Chemical Name | ESI-MS (M + 1) | $IC_{50}$ (uM) |
|---|---|---|---|---|
| 28.1 | 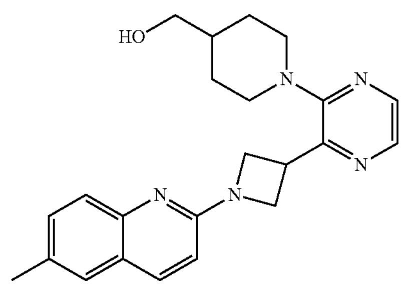 [SMILES: Cc1ccc2nc(N3CC(c4nccnc4N4CCC(CO)CC4)C3)ccc2c1] | (1-{3-[1-(6-Methyl-quinolin-2-yl)-azetidin-3-yl]-pyrazin-2-yl}-piperidin-4-yl)-methanol | 390 | 0.00117 |
| 28.2 | 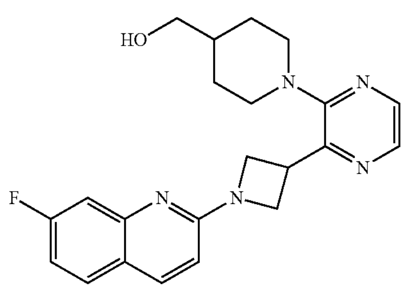 [SMILES: OCC1CCN(c2nccnc2C2CN(c3ccc4ccc(F)cc4n3)C2)CC1] | (1-{3-[1-(7-Fluoro-quinolin-2-yl)-azetidin-3-yl]-pyrazin-2-yl}-piperidin-4-yl)-methanol | 394 | 0.0001 |
| 28.3 | 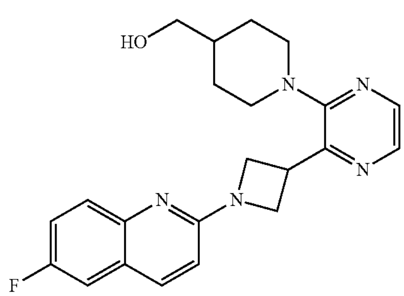 [SMILES: OCC1CCN(c2nccnc2C2CN(c3ccc4cc(F)ccc4n3)C2)CC1] | (1-{3-[1-(6-Fluoro-quinolin-2-yl)-azetidin-3-yl]-pyrazin-2-yl}-piperidin-4-yl)-methanol | 394 | 0.0037 |

TABLE 32A-continued

EXAMPLES 28.1 TO 28.18

| Ex. # | Structure | Chemical Name | ESI-MS (M + 1) | IC$_{50}$ (uM) |
|---|---|---|---|---|
| 28.4 | 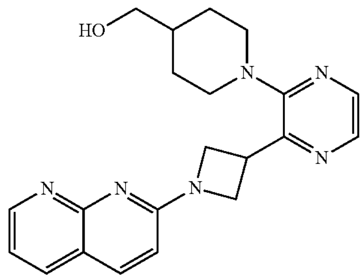 [SMILES: OCC1CCN(c2nccnc2C2CN(c3ccc4cccnc4n3)C2)CC1] | {1-[3-(1-[1,8]Naphthyridin-2-yl-azetidin-3-yl)-pyrazin-2-yl]-piperidin-4-yl}-methanol | 377 | 0.0419 |
| 28.5 | 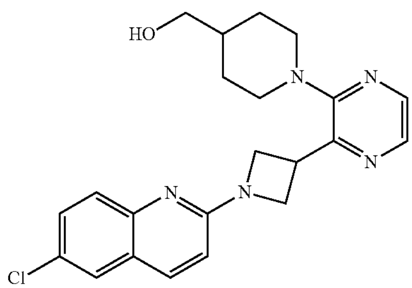 [SMILES: OCC1CCN(c2nccnc2C2CN(c3ccc4cc(Cl)ccc4n3)C2)CC1] | (1-{3-[1-(6-Chloro-quinolin-2-yl)-azetidin-3-yl]-pyrazin-2-yl}-piperidin-4-yl)-methanol | 410 | 0.00116 |
| 28.6 | 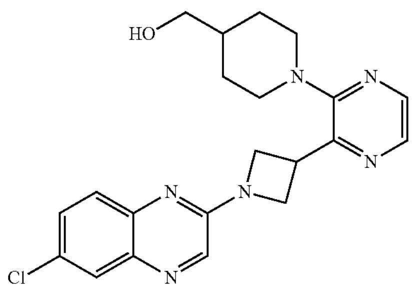 | (1-{3-[1-(6-Chloro-quinoxalin-2-yl)-azetidin-3-yl]-pyrazin-2-yl}-piperidin-4-yl)-methanol | 411 | 0.0144 |
| 28.7 | 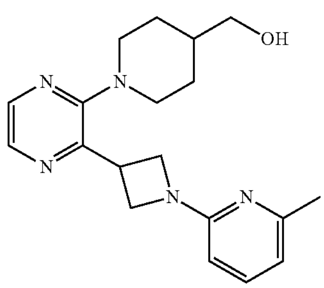 [SMILES: Cc1cccc(N2CC(c3nccnc3N3CCC(CO)CC3)C2)n1] | (1-{3-[1-(6-Methyl-pyridin-2-yl)-azetidin-3-yl]-pyrazin-2-yl}-piperidin-4-yl)-methanol | 340 | 0.217 |
| 28.8 | 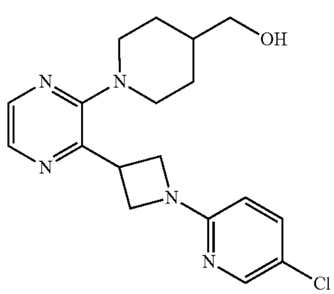 [SMILES: OCC1CCN(c2nccnc2C2CN(c3ccc(Cl)cn3)C2)CC1] | (1-{3-[1-(5-Chloro-pyridin-2-yl)-azetidin-3-yl]-pyrazin-2-yl}-piperidin-4-yl)-methanol | 360 | 0.490 |

TABLE 32A-continued

EXAMPLES 28.1 TO 28.18

| Ex. # | Structure | Chemical Name | ESI-MS (M + 1) | IC$_{50}$ (uM) |
|---|---|---|---|---|
| 28.9 | 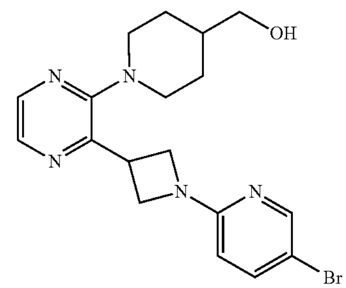 [SMILES: OCC1CCN(c2nccnc2C2CN(c3ccc(Br)cn3)C2)CC1] | (1-(3-(1-(5-bromopyridin-2-yl)azetidin-3-yl)pyrazin-2-yl)piperidin-4-yl)methanol | 404 | 0.466 |
| 28.10 | 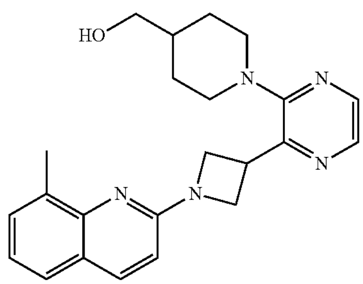 | (1-(3-(1-(8-methylquinolin-2-yl)azetidin-3-yl)pyrazin-2-yl)piperidin-4-yl)methanol | 390 | 0.446 |
| 28.11 | 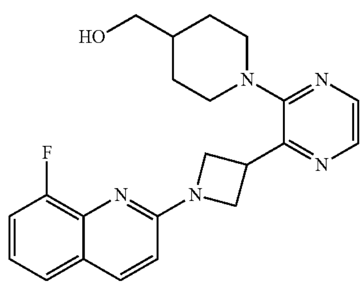 [SMILES: OCC1CCN(c2nccnc2C2CN(c3ccc4cccc(F)c4n3)C2)CC1] | (1-{3-[1-(8-Fluoro-quinolin-2-yl)-azetidin-3-yl]-pyrazin-2-yl}-piperidin-4-yl)-methanol | 394 | 0.00228 |
| 28.12 | 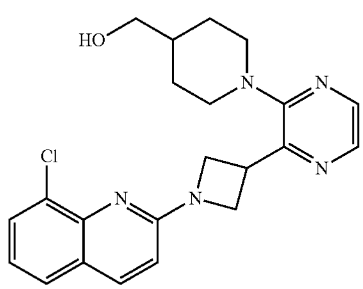 | (1-(3-(1-(8-chloroquinolin-2-yl)azetidin-3-yl)pyrazin-2-yl)piperidin-4-yl)methanol | 410 | 0.0233 |
| 28.13 | 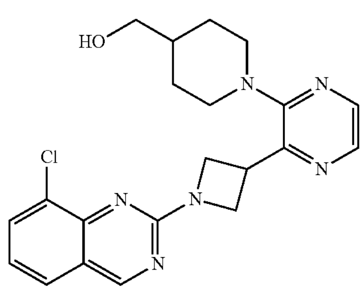 [SMILES: OCC1CCN(c2nccnc2C2CN(c3ncc4cccc(Cl)c4n3)C2)CC1] | (1-{3-[1-(8-Chloro-quinazolin-2-yl)-azetidin-3-yl]-pyrazin-2-yl}-piperidin-4-yl)-methanol | 411 | 0.0117 |

TABLE 32A-continued

EXAMPLES 28.1 TO 28.18

| Ex. # | Structure | Chemical Name | ESI-MS (M + 1) | IC$_{50}$ (uM) |
|---|---|---|---|---|
| 28.14 | 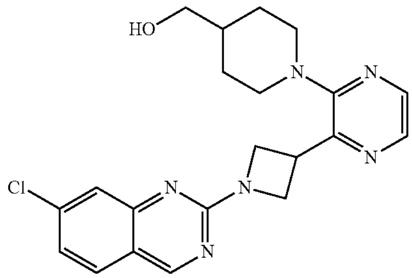 [SMILES: OCC1CCN(c2nccnc2C2CN(c3ncc4ccc(Cl)cc4n3)C2)CC1] | (1-{3-[1-(7-Chloro-quinazolin-2-yl)-azetidin-3-yl]-pyrazin-2-yl}-piperidin-4-yl)-methanol | 411 | 0.0001 |
| 28.15 | 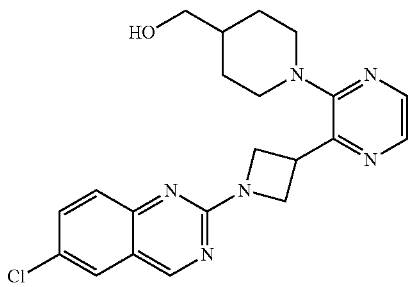 [SMILES: OCC1CCN(c2nccnc2C2CN(c3ncc4cc(Cl)ccc4n3)C2)CC1] | (1-{3-[1-(6-Chloro-quinazolin-2-yl)-azetidin-3-yl]-pyrazin-2-yl}-piperidin-4-yl)-methanol | 411 | 0.0068 |
| 28.16 | 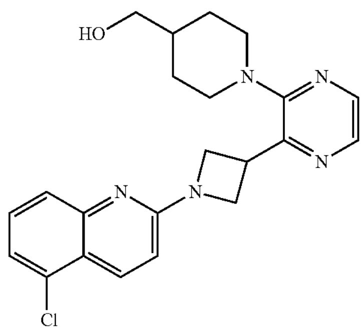 [SMILES: OCC1CCN(c2nccnc2C2CN(c3ccc4c(Cl)cccc4n3)C2)CC1] | (1-{3-[1-(5-Chloro-quinazolin-2-yl)-azetidin-3-yl]-pyrazin-2-yl}-piperidin-4-yl)-methanol | 411 | |
| 28.17 | 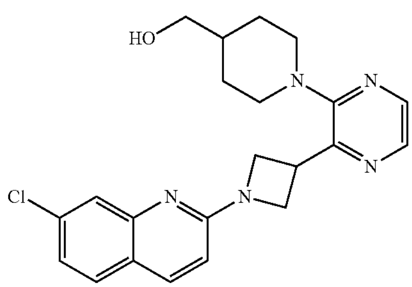 [SMILES: OCC1CCN(c2nccnc2C2CN(c3ccc4ccc(Cl)cc4n3)C2)CC1] | (1-{3-[1-(7-Chloro-quinoxalin-2-yl)-azetidin-3-yl]-pyrazin-2-yl}-piperidin-4-yl)-methanol | 411 | 0.0005 |
| 28.18 | 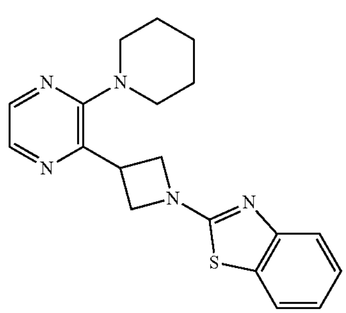 [SMILES: c1ccc2sc(N3CC(c4nccnc4N4CCCCC4)C3)nc2c1] | 2-[3-(3-Piperidin-1-yl-pyrazin-2-yl)-azetidin-1-yl]-benzothiazole | 352 | >10 |

TABLE 32B

STARTING MATERIALS AND REACTION CONDITION FOR
PREPARATION OF EXAMPLES 28.1 TO 28.18.
Unless otherwise stated, all starting materials are commercially available from common vendors.

| Ex. # | Starting Material 1 | Starting Material 2 | Reaction Condition |
|---|---|---|---|
| 28.1 | PREPARATION 11 (piperidine-pyrazine-azetidine-CH2OH·HCl) | 2-chloro-6-methylquinoline, Combi-Blocks | $Cs_2CO_3$, DMF, 100° C. |
| 28.2 | 37 PREPARATION 11 | 2-chloro-6-fluoroquinoline, PREPARATION 33 | $Cs_2CO_3$, DMF, 100° C. |
| 28.3 | 37 PREPARATION 11 | 2-chloro-7-fluoroquinoline, PREPARATION 33 | $Cs_2CO_3$, DMF, 100° C. |
| 28.4 | 37 PREPARATION 11 | 2-chloro-1,8-naphthyridine, ANICHEM | $Cs_2CO_3$, DMF, 100° C. |
| 28.5 | 37 PREPARATION 11 | 2,6-dichloroquinoline, ALDRICH | $Cs_2CO_3$, DMF, 100° C. |
| 28.6 | 37 PREPARATION 11 | 2,6-dichloroquinoxaline, ALDRICH | $Cs_2CO_3$, DMF, 100° C. |
| 28.7 | 37 PREPARATION 11 | 2-chloro-6-methylpyridine, Alfa Aesar | $Cs_2CO_3$, DMF, 100° C. |
| 28.8 | 37 PREPARATION 11 | 2,5-dichloropyridine, Alfa Aesar | $Cs_2CO_3$, DMF, 100° C. |
| 28.9 | 37 PREPARATION 11 | 5-bromo-2-chloropyridine, Alfa Aesar | $Cs_2CO_3$, DMF, 100° C. |

TABLE 32B-continued

STARTING MATERIALS AND REACTION CONDITION FOR
PREPARATION OF EXAMPLES 28.1 TO 28.18.
Unless otherwise stated, all starting materials are commercially available from common vendors.

| Ex. # | Starting Material 1 | Starting Material 2 | Reaction Condition |
|---|---|---|---|
| 28.10 | 37<br>PREPARATION 11 | 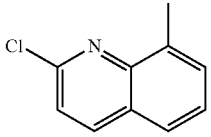<br>PREPARATION 33 | Cs$_2$CO$_3$, DMF, 100° C. |
| 28.11 | 37<br>PREPARATION 11 | 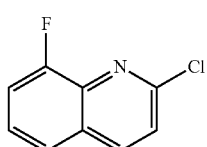<br>Combi-Blocks | Cs$_2$CO$_3$, DMF, 100° C. |
| 28.12 | 37<br>PREPARATION 11 | 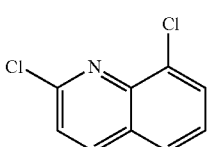<br>PREPARATION 33.12 | Cs$_2$CO$_3$, DMF, 100° C. |
| 28.13 | 37<br>PREPARATION 11 | 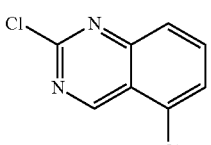<br>PREPARATION 34 | Cs$_2$CO$_3$, DMF, 100° C. |
| 28.14 | 37<br>PREPARATION 11 | 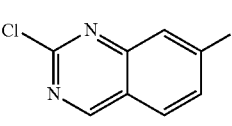<br>PREPARATION 34 | Cs$_2$CO$_3$, DMF, 100° C. |
| 28.15 | 37<br>PREPARATION 11 | 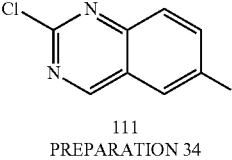<br>111<br>PREPARATION 34 | Cs$_2$CO$_3$, DMF, 100° C. |
| 28.16 | 37<br>PREPARATION 11 | 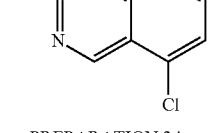<br>PREPARATION 34 | Cs$_2$CO$_3$, DMF, 100° C. |
| 28.17 | 37<br>PREPARATION 11 | 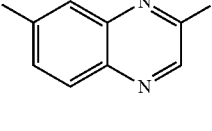 | Cs$_2$CO$_3$, DMF, 100° C. |

TABLE 32B-continued

STARTING MATERIALS AND REACTION CONDITION FOR
PREPARATION OF EXAMPLES 28.1 TO 28.18.
Unless otherwise stated, all starting materials are commercially available from common vendors.

| Ex. # | Starting Material 1 | Starting Material 2 | Reaction Condition |
|---|---|---|---|
| 28.18 | 75 PREPARATION 22 | | $K_2CO_3$, iPrOH/$H_2O$ 160° C., μW |

TABLE 32C

1H NMR δ (PPM) DATA FOR EXAMPLES 28.1 TO 28.18

| Ex. # | Structure | NMR |
|---|---|---|
| 28.1 | 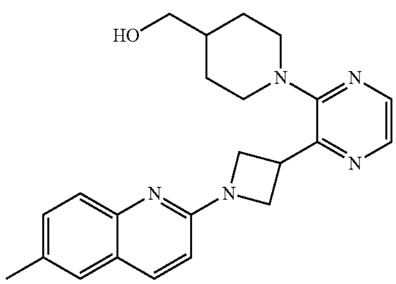 [SMILES: Cc1ccc2nc(N3CC(c4nccnc4N4CCC(CO)CC4)C3)ccc2c1] | (CDCl$_3$, 400 MHz): 8.14-8.06 (m, 2H); 7.79 (d, J = 8.8 Hz, 1H); 7.64 (d, J = 9.2 Hz, 1H); 7.37-7.35 (m, 2H); 6.62 (d, J = 9.2 Hz, 1H); 4.54-4.50 (m, 2H); 4.45-4.41 (m, 2H); 4.33-4.25 (m, 1H); 3.58-3.56 (m, 2H); 3.45-3.42 (m, 2H); 2.88-2.81 (m, 2H); 2.43 (s, 3H); 1.89-1.85 (m, 2H); 1.75-1.65 (m, 1H); 1.50-1.46 (m, 2H). |
| 28.2 | 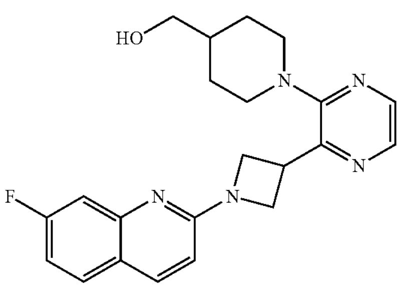 [SMILES: OCC1CCN(c2nccnc2C2CN(c3ccc4ccc(F)cc4n3)C2)CC1] | (CDCl$_3$, 400 MHz): 8.10-8.09 (m, 1H); 8.03-8.02 (m, 1H); 7.77 (d, J = 8.8 Hz, 1H); 7.51-7.47 (m, 1H); 7.30-7.27 (m, 1H); 6.93-6.88 (m, 1H); 6.54-6.51 (m, 1H); 4.50-4.46 (m, 2H); 4.41-4.37 (m, 2H); 4.28-4.23 (m, 1H); 3.54-3.53 (m, 2H); 3.38 (d, J = 12.8 Hz, 2H); 1.85-1.82 (m, 2H); 1.69-1.64 (m, 1H); 1.53-1.37 (m, 1H) |
| 28.3 | 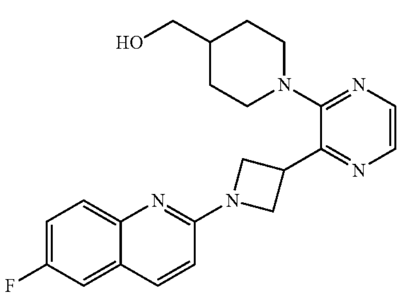 [SMILES: OCC1CCN(c2nccnc2C2CN(c3ccc4cc(F)ccc4n3)C2)CC1] | (CDCl$_3$, 400 MHz): 8.16-8.09 (m, 2H); 7.82 (d, J = 8.8 Hz, 1H); 7.73-7.69 (m, 1H); 7.33-7.28 (m, 1H); 7.27-7.23 (m, 1H); 6.69 (d, J = 8.8 Hz, 1H); 4.56-4.52 (m, 2H); 4.46-4.43 (m, 2H); 4.36-4.30 (m, 1H); 3.60 (d, J = 6.4 Hz, 2H); 3.47-3.44 (m, 2H); 2.91-2.84 (m, 2H); 1.92-1.88 (m, 2H); 1.75-1.69 (m, 1H); 1.53-1.43 (m, 2H). |

TABLE 32C-continued

1H NMR δ (PPM) DATA FOR EXAMPLES 28.1 TO 28.18

| Ex. # | Structure | NMR |
|---|---|---|
| 28.4 | 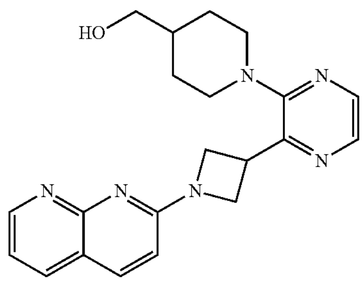 [SMILES: OCC1CCN(c2nccnc2C2CN(c3ccc4cccnc4n3)C2)CC1] | (CD3OD, 400 MHz): 8.07 (s, 1H); 8.16-8.14 (m, 2H); 8.10 (d, J = 2.4 Hz, 1H); 8.02 (d, J = 9.2 Hz, 1H); 7.26-7.23 (m, 1H); 6.83 1(d, J = 9.2 Hz, 1H); 4.55 (m, 2H); 4.37 (m, 3H); 3.50-3.43 (m, 4H); 2.89-2.83 (m, 2H); 1.89-1.86 (m, 2H); 1.68-1.64 (m, 1H); 1.50-1.40 (m, 2H). |
| 28.5 | 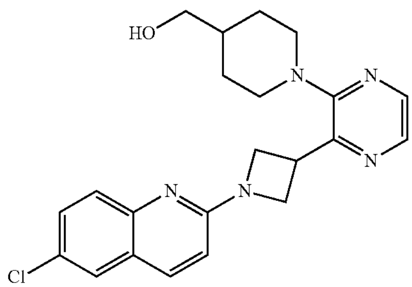 [SMILES: OCC1CCN(c2nccnc2C2CN(c3ccc4cc(Cl)ccc4n3)C2)CC1] | (CDCl$_3$, 400 MHz): 8.18-8.10 (m, 2H); 7.80 (d, J = 4.8 Hz, 1H); 7.67 (d, J = 5.2 Hz, 1H); 7.59 (s, 1H); 7.49-7.46 (m, 1H); 6.68 (d, J = 8.8 Hz, 1H); 4.58-4.54 (m, 2H); 4.49-4.46 (m, 2H); 4.37-4.30 (m, 1H); 3.62 (d, J = 6.4 Hz, 2H); 3.46 (d, J = 12.8 Hz, 2H); 2.92-2.86 (m, 2H); 1.93-1.90 (m, 2H); 1.76-1.69 (m, 1H); 1.54-1.44 (m, 2H). |
| 28.6 | 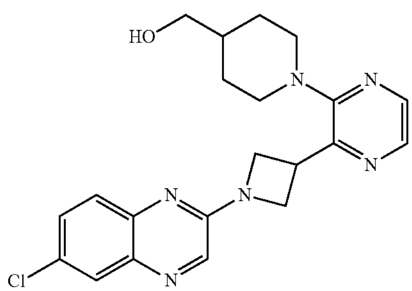 [SMILES: OCC1CCN(c2nccnc2C2CN(c3cnc4cc(Cl)ccc4n3)C2)CC1] | (CDCl$_3$, 400 MHz): 8.20-8.13 (m, 2H); 8.13 (t, J = 2.4 Hz, 1H); 7.89 (d, J = 2.4 Hz, 1H); 7.65 (d, J = 8.8 Hz, 1H); 7.54-7.51 (m, 1H); 4.67-4.62 (m, 2H); 4.59-4.55 (m, 2H); 4.44-4.37 (m, 1H); 3.61 (d, J = 6.0 Hz, 2H); 3.46 (d, J = 12.8 Hz, 2H); 2.94-2.87(m, 2H); 1.94-1.91 (m, 2H); 1.81-1.71 (m, 1H); 1.55-1.48 (m, 2H). |
| 28.7 | 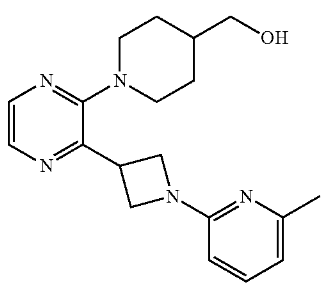 [SMILES: Cc1cccc(N2CC(c3nccnc3N3CCC(CO)CC3)C2)n1] | (CDCl$_3$, 400 MHz): 8.09 (s, 1H); 8.00 (s, 1H); 7.30-7.26 (m, 1H); 6.42-6.40 (m, 1H); 6.12-6.10 (m, 1H); 4.32(s, 2H); 4.21-4.20 (m, 3H); 3.53-3.51 (m, 2H); 3.39-3.36 (m, 2H); 2.81-2.75 (m, 2H); 2.33 (s, 3H); 1.82-1.79 (m, 2H); 1.65-1.63 (m, 1H); 1.45-1.34 (m, 2H); 1.18-1.17 (m, 1H). |
| 28.8 | 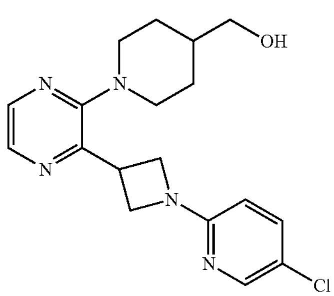 [SMILES: OCC1CCN(c2nccnc2C2CN(c3ccc(Cl)cn3)C2)CC1] | (CDCl$_3$, 400 MHz): 8.10-8.09 (m, 1H); 8.02-8.01 (m, 2H); 7.35-7.32 (m, 1H); 6.24 (d, J = 8.8 Hz, 1H); 4.33-4.29 (m, 2H); 4.25-4.19 (m, 3H); 3.51 (d, J = 6.0 Hz, 2H); 3.35 (d, J = 12.4 Hz, 2H); 2.81-2.75 (m, 2H); 1.83-1.80 (m, 2H); 1.70-1.59 (m, 1H); 1.43-1.36 (m, 2H). |

TABLE 32C-continued

1H NMR δ (PPM) DATA FOR EXAMPLES 28.1 TO 28.18

| Ex. # | Structure | NMR |
|---|---|---|
| 28.9 | 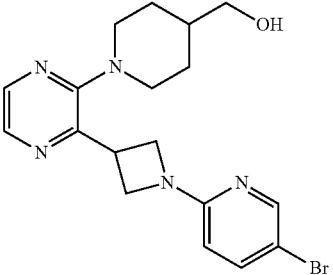 [SMILES: OCC1CCN(c2nccnc2C2CN(c3ccc(Br)cn3)C2)CC1] | (CDCl$_3$, 400 MHz): 8.16 (s, 2H); 8.08 (d, J = 3.2 Hz, 1H); 6.27 (d, J = 8.8 Hz, 1H); 4.39-4.35 (m, 2H); 4.32-4.27 (m, 3H); 3.58 (s, 2H); 3.43-3.40 (m, 3H); 2.88-2.82 (m, 2H); 2.05-2.00 (m, 1H); 1.89-1.86 (m, 2H); 1.74-1.68 (m, 1H); 1.50-1.40 (m, 1H). |
| 28.10 | 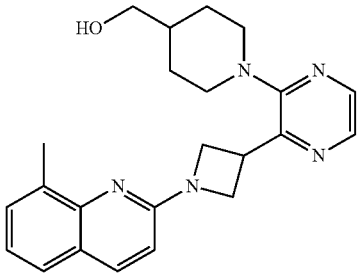 | (CDCl$_3$, 400 MHz): 8.19-8.11 (m, 2H); 7.89 (d, J = 8.8 Hz, 1H); 7.49 (d, J = 8.0 Hz, 1H); 7.43 (d, J = 6.8, 1H); 7.15 (t, J = 7.6 Hz, 1H); 6.69 (d, J = 8.8 Hz, 1H); 4.57-4.53 (m, 2H); 4.47-4.43 (m, 2H); 4.38-4.31 (m, 1H); 3.63-3.61 (m, 2H); 3.51-3.48 (m, 2H); 2.93-2.87 (m, 2H); 2.67 (s, 3H); 1.94-1.91 (m, 2H); 1.82-1.62 (m, 1H); 1.55-1.45 (m, 2H). |
| 28.11 | 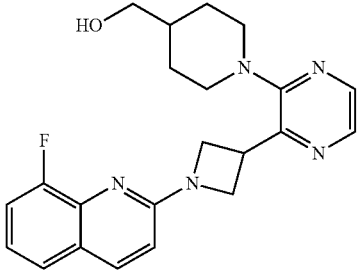 | (CDCl$_3$, 400 MHz): 8.09-8.02 (m, 2H); 7.82-7.83 (m, 1H); 7.32 (d, J = 8.0 Hz, 1H); 7.21-7.16 (m, 1H); 7.07-7.02 (m, 1H); 6.63 (d, J = 8.8 Hz, 1H); 4.53-4.49 (m, 2H); 4.45-4.41 (m, 2H); 4.29-4.23 (m, 1H); 3.53 (d, J = 6.4 Hz, 2H); 3.39 (d, J = 12.8 Hz, 2H); 2.84-2.77 (m, 2H); 1.85-1.81 (m, 2H); 1.68-1.64 (m, 1H). 1.63-1.36 (m, 2H) |
| 28.12 | 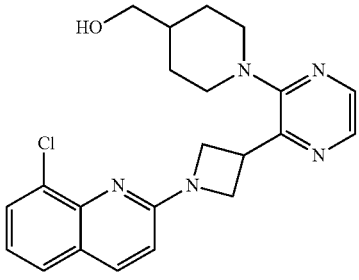 [SMILES: OCC1CCN(c2nccnc2C2CN(c3ccc4cccc(F)c4n3)C2)CC1] | (CDCl$_3$, 400 MHz): 8.09-8.02 (m, 2H); 7.80 (d, J = 8.8 Hz, 1H); 7.60-7.58 (m, 1H); 7.44-7.43 (m, 1H); 7.04 (t, J = 7.6 Hz, 1H); 6.63 (d, J = 8.8 Hz, 1H); 4.53-4.49 (m, 2H); 4.45-4.41 (m, 2H); 4.28-4.23 (m, 1H); 3.54 (d, J = 6.4 Hz, 2H); 3.39 (d, J = 12.0 Hz, 2H); 2.81 (m, 2H); 1.86-1.83 (m, 2H); 1.71-1.63 (m, 1H); 1.46-1.36 (m, 2H). |
| 28.13 | 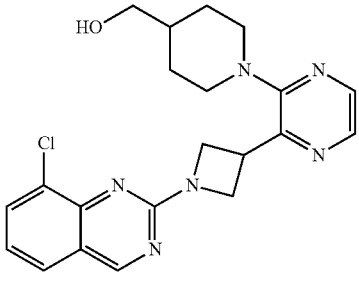 [SMILES: OCC1CCN(c2nccnc2C2CN(c3ncc4cccc(Cl)c4n3)C2)CC1] | (CDCl$_3$, 400 MHz): 8.99 (s, 1H); 8.16-8.15 (m, 1H); 8.08-8.07 (m, 1H); 7.76-7.74 (m, 1H); 7.58-7.56 (m, 1H); 7.13-7.09 (m, 1H); 4.64-4.57 (m, 4H); 4.31-4.27 (m, 1H); 3.58-3.55 (m, 2H); 3.45-3.41 (m, 2H); 2.88-2.82 (m, 2H); 2.33 (s, 1H); 1.89-1.86 (m, 2H); 1.73-1.66 (m, 1H); 1.50-1.40 (m, 2H) |

TABLE 32C-continued
1H NMR δ (PPM) DATA FOR EXAMPLES 28.1 TO 28.18
| Ex. # | Structure | NMR |
|---|---|---|
| 28.14 | 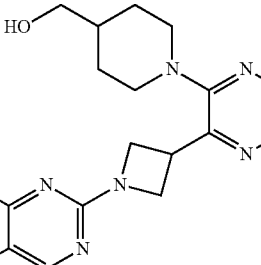 | (CDCl$_3$, 400 MHz): 8.91 (s, 1H); 8.10 (d, J = 2.8 Hz, 1H); 8.03 (d, J = 2.8 Hz, 1H); 7.56-7.51 (m, 2H); 7.11-7.09 (m, 1H); 4.57-4.52 (m, 2H); 4.49-4.45 (m, 2H); 4.27-4.19 (m, 1H); 3.53 (d, J = 6.4 Hz, 2H); 3.38 (d, J = 12.4 Hz, 2H); 2.84-2.78 (m, 2H); 1.84-1.81 (m, 2H); 1.71-1.62 (m, 1H); 1.47-1.43 (m, 2H) |
| 28.15 | 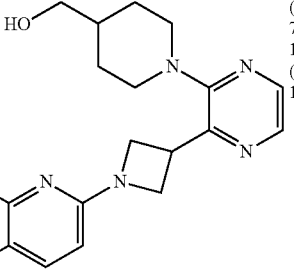 | (CDCl$_3$, 400 MHz): 8.96 (s, 1H); 8.18-8.09 (m, 2H); 7.66-7.58 (m, 3H); 4.61-4.54 (m, 4H); 4.35-4.25 (m, 1H); 3.61-3.59 (m, 2H); 3.46-3.43 (m, 2H); 2.92-2.85 (m, 2H); 1.91-1.89 (m, 2H); 1.75-1.71 (m, 1H); 1.52-1.47 (m, 2H). |
| 28.16 | 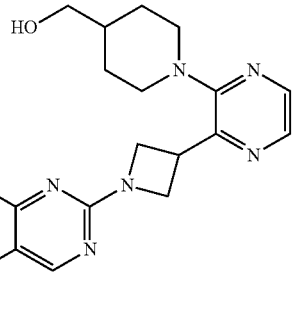 | (CDCl$_3$, 400 MHz): 9.42 (s, 1H); 8.20 (d, J = 2.8 Hz, 1H); 8.12 (d, J = 2.4 Hz, 1H); 7.57-7.54 (m, 2H); 7.25-7.23 (m, 1H); 4.67-4.63 (m, 2H); 4.59-4.55 (m, 2H); 4.35-4.31 (m, 1H); 3.64-3.62 (m, 2H); 3.48-3.45 (m, 2H); 2.93-2.86 (m, 2H); 193-1.90 (m, 2H); 1.78-1.72 (m, 1H); 1.56-1.42 (m, 3H). |
| 28.17 | 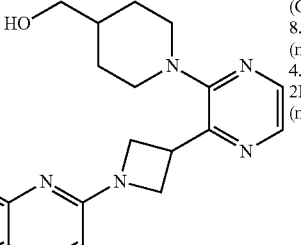 | (CDCl$_3$, 400 MHz): 8.14 (s, 1H); 8.12-8.11 (m, 1H); 8.06-8.05 (m, 1H); 7.73 (d, J = 8.8 Hz, 1H); 7.63-7.62 (m, 1H); 7.26-7.24 (m, 1H); 4.58-4.51 (m, 2H); 4.49-4.47 (m, 2H); 4.36-4.28 (m, 1H); 3.54 (d, J = 4.4 Hz, 2H); 3.38-3.35 (m, 2H); 2.86-2.79 (m, 2H); 1.85-1.83 (m, 2H); 1.73-1.62 (m, 1H); 1.47-1.37 (m, 2H) |
| 28.18 | 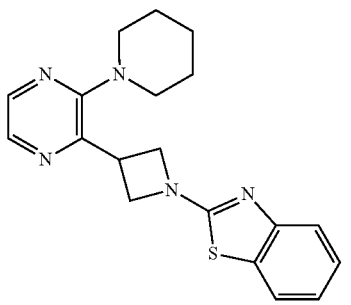 [SMILES: c1ccc2sc(N3CC(c4nccnc4N4CCCCC4)C3)nc2c1] | (CDCl$_3$, 400 MHz): 8.70-8.69 (m, 1H); 8.42-8.41 (m, 1 H); 7.57-7.55 (m, 1H); 7.47-7.45 (m, 1 H); 7.38-7.34 (m, 1 H); 7.26-7.22 (m, 1 H); 5.21-5.18 (m, 1H); 4.72-4.70 (m, 1 H); 4.30-4.16 (m, 2H); 4.06-3.95 (m, 3 H); 3.83-3.80 (m, 1 H); 3.46-3.41 (m, 1 H); 2.27-2.12 (m, 1 H); 2.08-1.94 (m, 4 H); 1.61-1.58 (m, 1 H). |

SCHEME 29

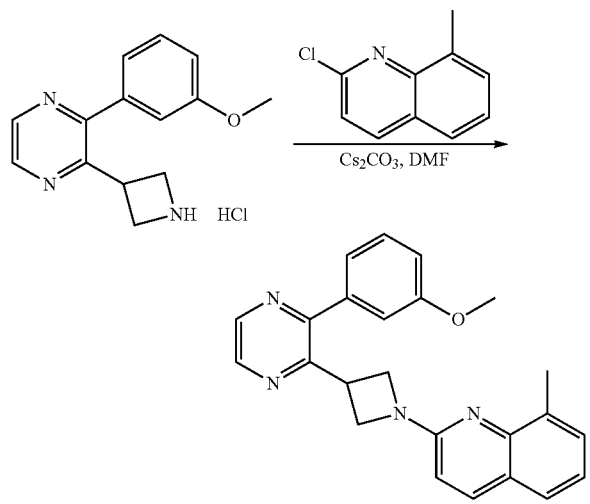

Example 29.1: 2-{3-[3-(3-Methoxy-Phenyl)-Pyrazin-2-Yl]-Azetidin-1-Yl}-8-Methyl-Quinoline To a solution of 2-azetidin-3-yl-3-(3-methoxy-phenyl)-pyrazine hydrochloride (138 mg, 0.50 mmol) and 2-chloro-quinoline (84 mg, 0.50 mmol) in DMF (6 mL) was added $Cs_2CO_3$ (325 mg, 1.0 mmol). The reaction mixture was stirred at 110° C. overnight. The reaction mixture was diluted with water, extracted with EtOAc (30 mL×2). The combined organic extracts were washed with water (30 mL) and brine (30 mL), dried over $Na_2SO_4$ and filtered. The filtrate was evaporated in vacuo and the residue was purified by flash column chromatography on silica gel (20% to 40% EtOAc in petroleum ether) to give 2-{3-[3-(3-methoxy-phenyl)-pyrazin-2-yl]-azetidin-1-yl}-8-methyl-quinoline (118 mg, 0.31 mmol, 63.35%).

The following Table 33A lists compounds of Examples 29.1 to 29.18, which were made analogous to Scheme 29 by using the appropriate materials and reaction conditions, which are listed in Table 33B. The NMR data of the Examples are listed in Table 33C.

TABLE 33A

EXAMPLES 29.1 TO 29.18

| Ex. # | Structure | Chemical Name | ESI-MS (M + 1) | $IC_{50}$ (uM) |
|---|---|---|---|---|
| 29.1 | 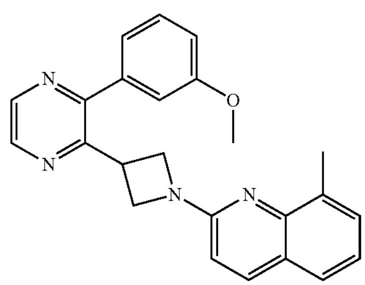 [SMILES: COc1cccc(-c2nccnc2C2CN(c3ccc4cccc(C)c4n3)C2)c1] | 2-(3-(3-(3-methoxyphenyl)pyrazin-2-yl)azetidin-1-yl)-8-methylquinoline | 383 | 0.997 |
| 29.2 | 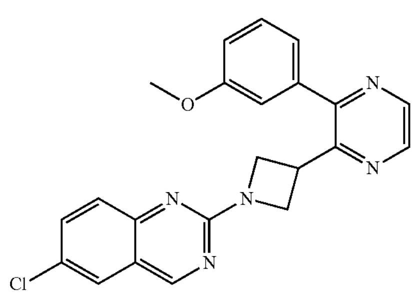 [SMILES: COc1cccc(-c2nccnc2C2CN(c3ncc4cc(Cl)ccc4n3)C2)c1] | 6-Chloro-2-{3-[3-(3-methoxy-phenyl)-pyrazin-2-yl]-azetidin-1-yl}-quinazoline | 404 | 0.0750 |
| 29.3 | 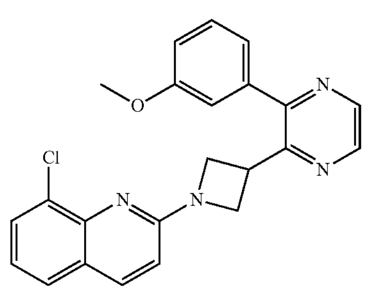 [SMILES: COc1cccc(-c2nccnc2C2CN(c3ccc4cccc(Cl)c4n3)C2)c1] | 8-Chloro-2-{3-[3-(3-methoxy-phenyl)-pyrazin-2-yl]-azetidin-1-yl}-quinoline | 403 | 0.111 |

TABLE 33A-continued

EXAMPLES 29.1 TO 29.18

| Ex. # | Structure | Chemical Name | ESI-MS (M + 1) | IC$_{50}$ (uM) |
|---|---|---|---|---|
| 29.4 | 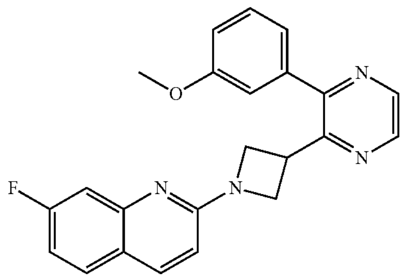 [SMILES: COc1cccc(-c2nccnc2C2CN(c3ccc4ccc(F)cc4n3)C2)c1] | 7-Fluoro-2-{3-[3-(3-methoxy-phenyl)-pyrazin-2-yl]-azetidin-1-yl}-quinoline | 387 | 0.00122 |
| 29.5 | 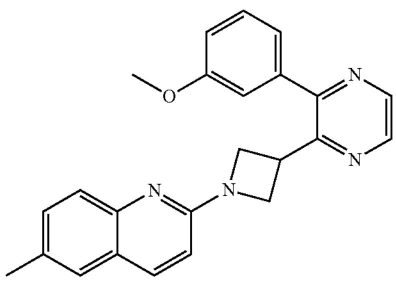 [SMILES: COc1cccc(-c2nccnc2C2CN(c3ccc4cc(C)ccc4n3)C2)c1] | 2-{3-[3-(3-Methoxy-phenyl)-pyrazin-2-yl]-azetidin-1-yl}-6-methyl-quinoline | 383 | 0.0061- |
| 29.6 | 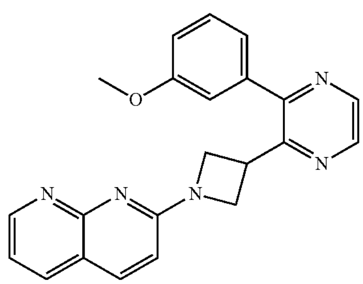 [SMILES: COc1cccc(-c2nccnc2C2CN(c3ccc4cccnc4n3)C2)c1] | 2-{3-[3-(3-Methoxy-phenyl)-pyrazin-2-yl]-azetidin-1-yl}-[1,8]naphthyridine | 370 | 0.0794 |
| 29.7 | 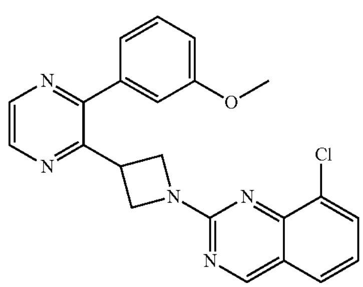 [SMILES: COc1cccc(-c2nccnc2C2CN(c3ncc4cccc(Cl)c4n3)C2)c1] | 8-Chloro-2-{3-[3-(3-methoxy-phenyl)-pyrazin-2-yl]-azetidin-1-yl}-quinazoline | 404 | |
| 29.8 | 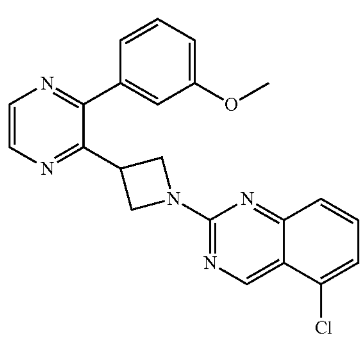 [SMILES: COc1cccc(-c2nccnc2C2CN(c3ncc4c(Cl)cccc4n3)C2)c1] | 5-Chloro-2-{3-[3-(3-methoxy-phenyl)-pyrazin-2-yl]-azetidin-1-yl}-quinazoline | 404 | |

TABLE 33A-continued

EXAMPLES 29.1 TO 29.18

| Ex. # | Structure | Chemical Name | ESI-MS (M + 1) | IC$_{50}$ (uM) |
|---|---|---|---|---|
| 29.9 | 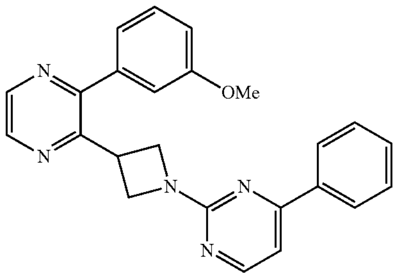 [SMILES: COc1cccc(-c2nccnc2C2CN(c3nccc(-c4ccccc4)n3)C2)c1] | 2-(3-(3-(3-methoxyphenyl)pyrazin-2-yl)azetidin-1-yl)-4-phenylpyrimidine | 396 | 4.3 |
| 29.10 | 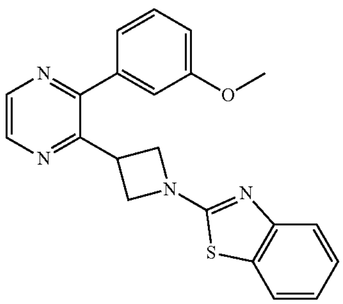 [SMILES: COc1cccc(-c2nccnc2C2CN(c3nc4ccccc4s3)C2)c1] | 2-(3-(3-(3-methoxyphenyl)pyrazin-2-yl)azetidin-1-yl)benzo[d]thiazole | 375 | 0.016 |
| 29.11 | 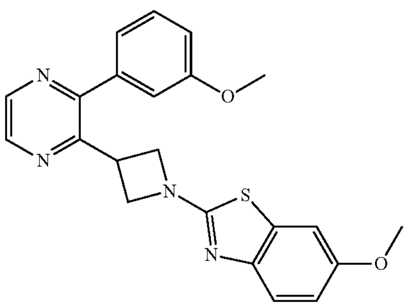 [SMILES: COc1cccc(-c2nccnc2C2CN(c3nc4ccc(OC)cc4s3)C2)c1] | 6-methoxy-2-(3-(3-(3-methoxyphenyl)pyrazin-2-yl)azetidin-1-yl)benzo[d]thiazole | 405 | 0.010 |
| 29.12 | 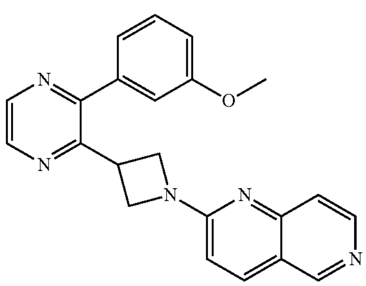 [SMILES: COc1cccc(-c2nccnc2C2CN(c3ccc4cnccc4n3)C2)c1] | 2-(3-(3-(3-methoxyphenyl)pyrazin-2-yl)azetidin-1-yl)-1,6-naphthyridine | 370 | 0.008 |
| 29.13 | 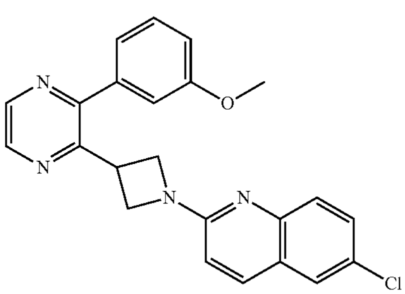 [SMILES: COc1cccc(-c2nccnc2C2CN(c3ccc4cc(Cl)ccc4n3)C2)c1] | 6-Chloro-2-(3-(3-(3-methoxyphenyl)pyrazin-2-yl)azetidin-1-yl)quinoline | 403 | 0.0049 |

TABLE 33A-continued

EXAMPLES 29.1 TO 29.18

| Ex. # | Structure | Chemical Name | ESI-MS (M + 1) | IC$_{50}$ (uM) |
|---|---|---|---|---|
| 29.13 | 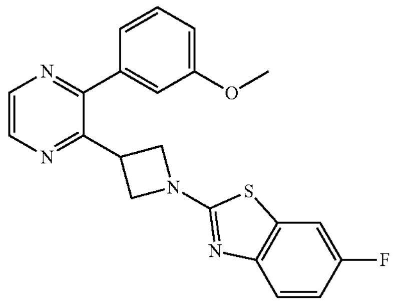 [SMILES: COc1cccc(-c2nccnc2C2CN(c3nc4ccc(F)cc4s3)C2)c1] | 6-fluoro-2-(3-(3-(3-methoxyphenyl)pyrazin-2-yl)azetidin-1-yl)benzo[d]thiazole | 393 | 0.029 |
| 29.14 | 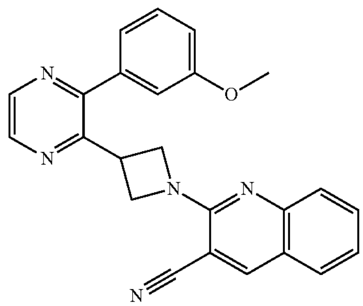 [SMILES: COc1cccc(-c2nccnc2C2CN(c3nc4ccccc4cc3C#N)C2)c1] | 2-(3-(3-(3-methoxyphenyl)pyrazin-2-yl)azetidin-1-yl)quinoline-3-carbonitrile | 394 | 0.0062 |
| 29.15 | 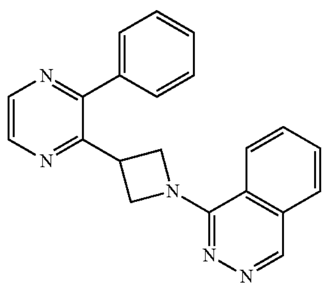 [SMILES: c1ccc(-c2nccnc2C2CN(c3nncc4ccccc34)C2)cc1] | 1-[3-(3-Phenyl-pyrazin-2-yl)-azetidin-1-yl]-phthalazine | 340 | 1.9100 |
| 29.16 | 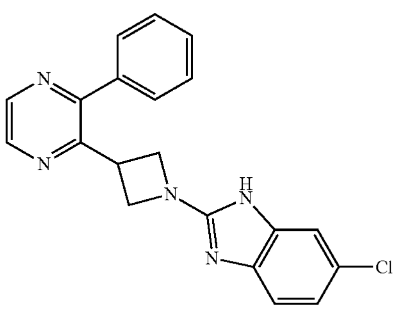 [SMILES: Clc1ccc2nc(N3CC(c4nccnc4-c4ccccc4)C3)[nH]c2c1] | 6-chloro-2-(3-(3-phenylpyrazin-2-yl)azetidin-1-yl)-1H-benzo[d]imidazole | 362 | 0.0504 |
| 29.17 | 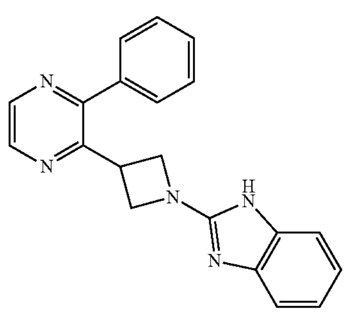 [SMILES: c1ccc(-c2nccnc2C2CN(c3nc4ccccc4[nH]3)C2)cc1] | 2-(3-(3-phenylpyrazin-2-yl)azetidin-1-yl)-1H-benzo[d]imidazole | 327 | 0.191 |

TABLE 33A-continued

EXAMPLES 29.1 TO 29.18

| Ex. # | Structure | Chemical Name | ESI-MS (M + 1) | IC$_{50}$ (uM) |
|---|---|---|---|---|
| 29.18 | 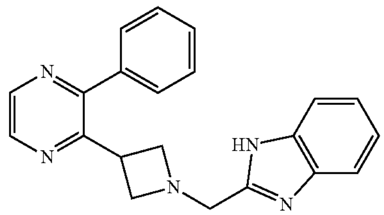 [SMILES: c1ccc(-c2nccnc2C2CN(Cc3nc4ccccc4[nH]3)C2)cc1] | 2-((3-(3-phenylpyrazin-2-yl)azetidin-1-yl)methyl)-1H-benzo[d]imidazole | 342 | 1.07 |

TABLE 33B

STARTING MATERIALS AND REACTION CONDITION FOR
PREPARATION OF EXAMPLES 29.1 TO 29.18.
Unless otherwise stated, all starting materials are commercially available from common vendors.

| Ex. # | Starting Material 1 | Starting Material 2 | Reaction Condition |
|---|---|---|---|
| 29.1 | 34 PREPARATION 10 | PREPARATION 33 | Cs$_2$CO$_3$, DMF, 100° C. |
| 29.2 | 34 PREPARATION 10 | PREPARATION 34 | Cs$_2$CO$_3$, DMF, 100° C. |
| 29.3 | 34 PREPARATION 10 | PREPARATION 33 | Cs$_2$CO$_3$, DMF, 100° C. |
| 29.4 | 34 PREPARATION 10 | PREPARATION 33 | Cs$_2$CO$_3$, DMF, 100° C. |
| 29.5 | 34 PREPARATION 10 | ALDRICH | Cs$_2$CO$_3$, DMF, 100° C. |

TABLE 33B-continued

STARTING MATERIALS AND REACTION CONDITION FOR
PREPARATION OF EXAMPLES 29.1 TO 29.18.
Unless otherwise stated, all starting materials are commercially available from common vendors.

| Ex. # | Starting Material 1 | Starting Material 2 | Reaction Condition |
|---|---|---|---|
| 29.6 | 34 PREPARATION 10 | [1,8-naphthyridine, 2-chloro] ANICHEM | Cs$_2$CO$_3$, DMF, 100° C. |
| 29.7 | 34 PREPARATION 10 | [2,8-dichloroquinazoline] PREPARATION 34 | Cs$_2$CO$_3$, DMF, 100° C. |
| 29.8 | 34 PREPARATION 10 | [2,5-dichloroquinazoline] PREPARATION 34 | Cs$_2$CO$_3$, DMF, 100° C. |
| 29.9 | 34 PREPARATION 10 | [2-chloro-4-phenylpyrimidine] Combi-Blocks | DMSO, 130-145° C., μW |
| 29.10 | 34 PREPARATION 10 | [2-chlorobenzothiazole] Alfa Aesar | DMSO, 130-145° C., μW |
| 29.11 | 34 PREPARATION 10 | [2-chloro-6-methoxybenzothiazole] TCI America | DMSO, 130-145° C., μW |
| 29.12 | 34 PREPARATION 10 | [2-chloro-1,6-naphthyridine] PREPARATION 35 | DMSO, 145-155° C., μW |
| 29.13 | 34 PREPARATION 10 | [2,6-dichloroquinoline] Aldrich | DMSO, 145-155° C., μW |

TABLE 33B-continued

STARTING MATERIALS AND REACTION CONDITION FOR
PREPARATION OF EXAMPLES 29.1 TO 29.18.
Unless otherwise stated, all starting materials are commercially available from common vendors.

| Ex. # | Starting Material 1 | Starting Material 2 | Reaction Condition |
|---|---|---|---|
| 29.13 | 34 PREPARATION 10 | 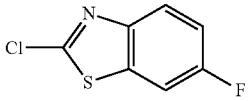 [SMILES: Fc1ccc2nc(Cl)sc2c1]<br>Aldrich | DMSO, 145-155° C., μW |
| 29.14 | 34 PREPARATION 10 | 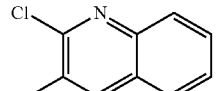<br>Aldrich | DMSO, 100° C., μW |
| 29.15 | PREPARATION 7 | 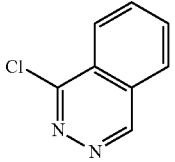 [SMILES: Clc1nncc2ccccc12] | $Cs_2CO_3$, DMF 120° C. |
| 29.16 | 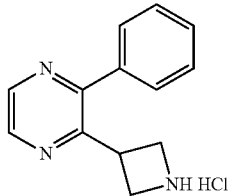<br>PREPARATION 7 | 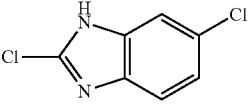 [SMILES: Clc1ccc2nc(Cl)[nH]c2c1]<br>WUXI APPTEC | $K_2CO_3$, i-PrOH, $H_2O$, MW, 160° C. |
| 29.17 | 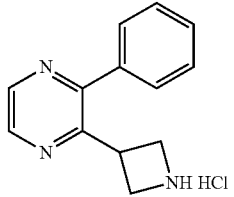<br>PREPARATION 7 | 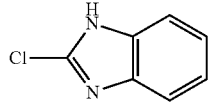<br>WUXI APPTEC | $K_2CO_3$, i-PrOH, $H_2O$, MW, 160° C. |
| 29.18 | 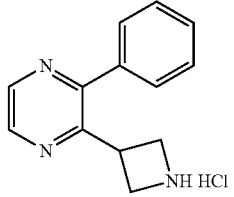<br>PREPARATION 7 | 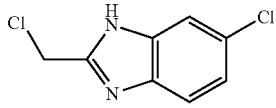 [SMILES: ClCc1nc2ccc(Cl)cc2[nH]1]<br>WUXI APPTEC | $K_2CO_3$, i-PrOH, $H_2O$, MW, 160° C. |

TABLE 33C

1H NMR δ (PPM) DATA FOR EXAMPLES 29.1 TO 29.18

| Ex. # | Structure | NMR |
|---|---|---|
| 29.1 | 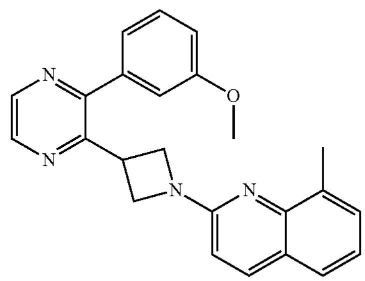 [SMILES: COc1cccc(-c2nccnc2C2CN(c3ccc4cccc(C)c4n3)C2)c1] | (CDCl₃, 400 MHz): 8.59-8.53 (m, 2H); 7.85 (d, J = 8.8 Hz, 1H); 7.47-7.40 (m, 3H); 7.14-7.10 (m, 1H); 7.08-7.03 (m, 3H); 6.62 (d, J = 8.8 Hz, 1H); 4.44-4.37 (m, 5H); 3.90 (s, 3H); 2.64 (s, 3H). |
| 29.2 | 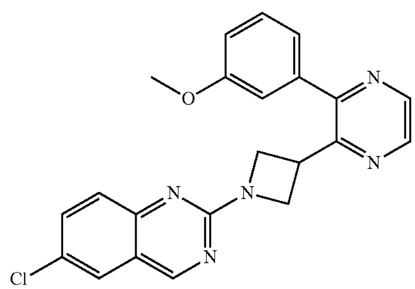 [SMILES: COc1cccc(-c2nccnc2C2CN(c3ncc4cc(Cl)ccc4n3)C2)c1] | (CDCl₃, 400 MHz): 9.07 (s, 1H); 8.60-8.59 (m, 2H); 7.88-7.86 (m, 1H); 7.78-7.74 (m, 2H); 7.43-7.41 (m, 1H); 7.05-6.98 (m, 3H); 4.75-4.74 (m, 4H); 4.45-4.43 (m, 1H); 3.87 (s, 3H). |
| 29.3 | 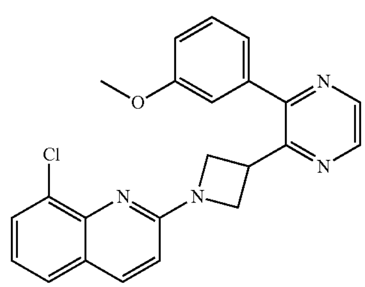 [SMILES: COc1cccc(-c2nccnc2C2CN(c3ccc4cccc(Cl)c4n3)C2)c1] | (CDCl₃, 400MHz): 8.61 (s, 1H); 8.56 (s, 1H); 7.87 (d, J = 8.8 Hz, 1H); 7.67 (d, J = 7.6 Hz, 1H); 7.53 (d, J = 8.0 Hz, 1H); 7.48-7.44 (m, 1H); 7.15-7.11 (m, 1H); 7.09-7.06 (m, 3H) 6.68 (d, J = 8.8 Hz, 1H); 4.55-4.42 (m, 5H); 3.92 (s, 3H) |
| 29.4 | 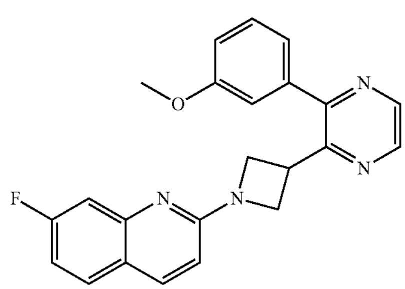 [SMILES: COc1cccc(-c2nccnc2C2CN(c3ccc4ccc(F)cc4n3)C2)c1] | (CDCl₃, 400 MHz): 8.61-8.56 (m, 2H); 7.86-7.83 (m, 1H); 7.59-7.55 (m, 1H); 7.47-7.43 (m, 1H); 7.38-7.35 (m, 1H); 7.09-7.05 (m, 3H); 7.01-6.91 (m, 1H); 6.58-6.65 (m, 1H); 4.48-4.43 (m, 5H); 3.91 (s, 3H). |
| 29.5 | 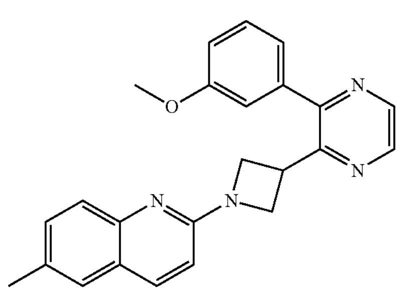 [SMILES: COc1cccc(-c2nccnc2C2CN(c3ccc4cc(C)ccc4n3)C2)c1] | (CDCl₃, 400 MHz): 8.60-8.55 (m, 2H); 7.82 (d, J = 8.8 Hz, 1H); 7.71-7.69 (m, 1H); 7.47-7.43 (m, 1H); 7.41-7.39 (m, 2H); 7.09-7.04 (m, 3H); 6.62 (d, J = 8.8 Hz, 1H); 4.49-4.43 (m, 5H); 3.91 (s, 3H); 2.46 (s, 3H). |

TABLE 33C-continued

1H NMR δ (PPM) DATA FOR EXAMPLES 29.1 TO 29.18

| Ex. # | Structure | NMR |
|---|---|---|
| 29.6 | 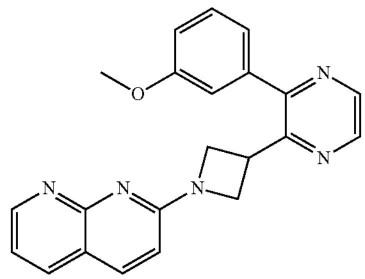 [SMILES: COc1cccc(-c2nccnc2C2CN(c3ccc4cccnc4n3)C2)c1] | (CDCl$_3$, 400 MHz): 8.59-8.54 (m, 2H); 7.77 (d, J = 8.8 Hz, 1H); 7.64 (d, J = 9.2 Hz, 1H); 7.57-7.56 (m, 1H); 7.47-7.41 (m, 2H); 7.07-7.03 (m, 3H); 6.62 (d, J = 8.8 Hz, 1H); 4.46-4.40 (m, 5H); 3.89 (s, 3H). |
| 29.7 | 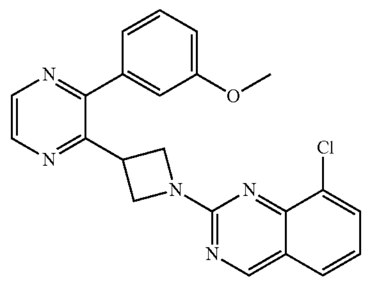 [SMILES: COc1cccc(-c2nccnc2C2CN(c3ncc4cccc(Cl)c4n3)C2)c1] | (CDCl$_3$, 400 MHz): 9.00-8.99 (m, 1H); 8.61-8.50 (m, 2H); 7.77-7.74 (m, 1H); 7.59-7.56 (m, 1H); 7.43-7.40 (m, 1H); 7.14-7.10 (m, 1H); 7.07-7.01 (m, 3H); 4.58-4.50 (m, 4H); 4.39-4.36 (m, 1H); 3.87 (s, 3H). |
| 29.8 | 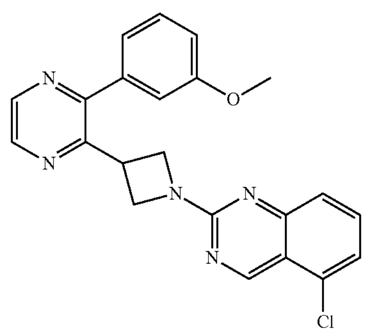 [SMILES: COc1cccc(-c2nccnc2C2CN(c3ncc4c(Cl)cccc4n3)C2)c1] | (CDCl$_3$, 400 MHz): 9.54 (s, 1H); 8.65-8.63 (m, 2H); 7.83-7.80 (m, 2H); 7.48-7.44 (m, 2H); 7.08-6.99 (m, 3H); 4.82-4.81 (m, 4H); 4.50-4.47 (m,1H); 3.89 (s, 3H). |
| 29.9 | 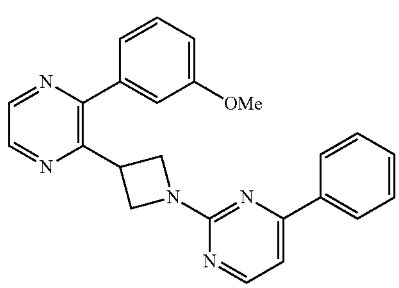 [SMILES: COc1cccc(-c2nccnc2C2CN(c3nccc(-c4ccccc4)n3)C2)c1] | (400 MHz, DMSO-d$_6$) 3.78-3.92 (m, 3 H) 4.16-4.50 (m, 5 H) 7.06-7.17 (m, 3 H) 7.26 (d, J = 5.09 Hz, 1 H) 7.42-7.56 (m, 4 H) 8.06-8.16 (m, 2 H) 8.42 (d, J = 5.09 Hz, 1 H) 8.64 (d, J = 2.15 Hz, 1 H) 8.70 (d, J = 2.35 Hz, 1 H). |
| 29.10 | 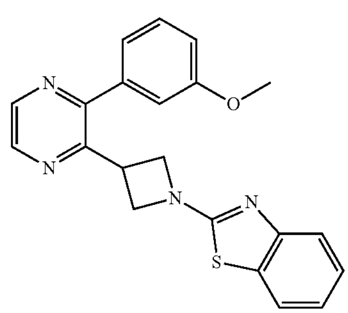 [SMILES: COc1cccc(-c2nccnc2C2CN(c3nc4ccccc4s3)C2)c1] | (400 MHz, DMSO-d$_6$) 3.84 (s, 3 H) 4.24-4.41 (m, 4 H) 4.44-4.57 (m, 1 H) 7.01-7.17 (m, 4 H) 7.24-7.33 (m, 1 H) 7.42-7.52 (m, 2 H) 7.78 (d, J = 7.82 Hz, 1 H) 8.66 (d, J = 2.35 Hz, 1 H) 8.72 (d, J = 2.35 Hz, 1 H) |

TABLE 33C-continued

1H NMR δ (PPM) DATA FOR EXAMPLES 29.1 TO 29.18

| Ex. # | Structure | NMR |
|---|---|---|
| 29.11 | 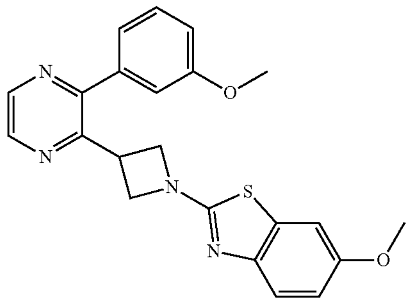 [SMILES: COc1cccc(-c2nccnc2C2CN(c3nc4ccc(OC)cc4s3)C2)c1] | (400 MHz, DMSO-$d_6$) 3.71-3.79 (m, 3 H) 3.84 (s, 3 H) 4.21-4.35 (m, 4 H) 4.43-4.55 (m, 1 H) 6.89 (dd, J = 8.80, 2.54 Hz, 1 H) 7.04-7.15 (m, 3 H) 7.34-7.43 (m, 2 H) 7.44-7.51 (m, 1 H) 8.65 (d, J = 2.35 Hz, 1 H) 8.71 (d, J = 2.35 Hz, 1 H) |
| 29.12 | 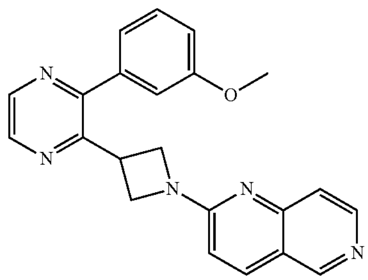 [SMILES: COc1cccc(-c2nccnc2C2CN(c3ccc4cnccc4n3)C2)c1] | (400 MHz, DMSO-$d_6$) 3.87 (s, 3H) 4.28-4.49 (m, 5 H) 6.83 (d, J = 9.00 Hz, 1 H) 7.06-7.19 (m, 3 H) 7.38 (d, J = 5.87 Hz, 1 H) 7.49 (t, J = 8.02 Hz, 1 H) 8.13 (d, J = 9.00 Hz, 1 H) 8.42 (d, J = 5.67 Hz, 1 H) 8.66 (d, J = 2.35 Hz, 1 H) 8.71 (d, J = 2.15 Hz, 1 H) 8.93 (s, 1 H) |
| 29.13 | | (400 MHz, DMSO-$d_6$) 8.69 (d, J = 2.35 Hz, 1H), 8.64 (d, J = 2.35 Hz, 1H), 8.01 (d, J = 9.00 Hz, 1H), 7.82 (d, J = 2.15 Hz, 1H), 7.42-7.60 (m, 3H), 7.06-7.19 (m, 3H), 6.81 (d, J = 9.00 Hz, 1H), 4.36-4.47 (m, 1H), 4.20-4.36 (m, 4H), 3.85 (s, 3H) |
| 29.13 | | (400 MHz, DMSO-$d_6$) 8.71 (d, J = 2.54 Hz, 1H), 8.65 (d, J = 2.35 Hz, 1H), 7.71 (dd, J = 2.74, 8.80 Hz, 1H), 7.41-7.49 (m, 2H), 7.05-7.17 (m, 4H), 4.49 (s, 1H), 4.23-4.38 (m, 4H), 3.83 (s, 3H) |
| 29.14 | 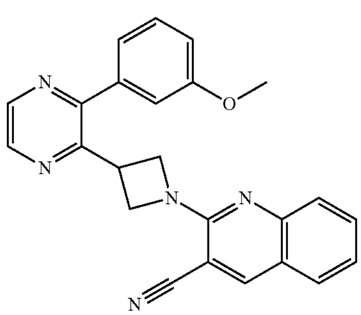 [SMILES: COc1cccc(-c2nccnc2C2CN(c3nc4ccccc4cc3C#N)C2)c1] | (400 MHz, DMSO-$d_6$) 8.73 (s, 1H), 8.67 (d, J = 2.35 Hz, 1H), 8.61 (d, J = 2.35 Hz, 1H), 7.77 (d, J = 8.02 Hz, 1H), 7.63-7.69 (m, 1H), 7.54-7.59 (m, 1H), 7.41-7.47 (m, 1H), 7.30 (t, J = 7.43 Hz, 1H), 7.04-7.13 (m, 3H), 4.43-4.55 (m, 4H), 4.33-4.42 (m, 1H), 3.81 (s, 3H) |

TABLE 33C-continued
1H NMR δ (PPM) DATA FOR EXAMPLES 29.1 TO 29.18
| Ex. # | Structure | NMR |
|---|---|---|
| 29.15 | 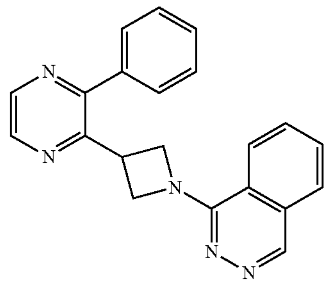 [SMILES: c1ccc(-c2nccnc2C2CN(c3nncc4ccccc34)C2)cc1] | (CD$_3$OD, 400 MHz): 8.84 (S, 1h); 8.65 (d, J = 2.4 Hz, 1H); 8.53 (d, J = 2.4 Hz, 1H); 8.03-8.00 (m, 1H); 7.92-7.80 (m, 3H); 7.57-7 50 (m, 5H); 4.77-4.71 (m, 4H); 4.49-4.46 (m, 1H). |
| 29.16 | 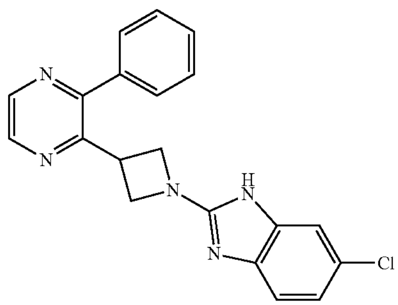 [SMILES: Clc1ccc2nc(N3CC(c4nccnc4-c4ccccc4)C3)[nH]c2c1] | (CDCl$_3$, 400 MHz): 8.54-8.53 (m, 1H); 8.42 (s, 1H); 7.54-7.53 (m, 3H); 7.35-7.32 (m, 2H); 7.26-7.20 (m, 1H); 7.11-7.09 (m, 1H); 6.97-6.95 (m, 1H); 4.46-4.42 (m, 2H); 4 18-4.15 (m, 2H); 4.03-4.00 (m, 1H). |
| 29.17 | 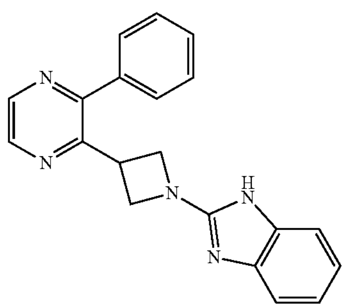 [SMILES: c1ccc(-c2nccnc2C2CN(c3nc4ccccc4[nH]3)C2)cc1] | (MeOD, 400 MHz): 8.66-8.65 (m, 1H); 8.55-8.54 (m, 1H); 7.58-7.52 (m, 5H); 7.22-7.19 (m, 2H); 7.01-6.98 (m, 2H); 4.51-4.45 (m, 1H), 4.38-4.30 (m, 4H). |
| 29.18 | 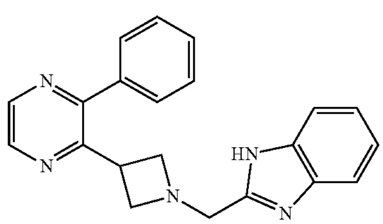 [SMILES: c1ccc(-c2nccnc2C2CN(Cc3nc4ccccc4[nH]3)C2)cc1] | (MeOD, 400 MHz): 8.67-8.65 (m, 1H); 8.60-8.58 (m, 1H); 7.67-7.63 (m, 2H); 7.55-7.47 (m, 5H); 7.39-7.36 (m, 2H); 4.81 (s, 2H); 4.55-4.48 (m, 5H). |
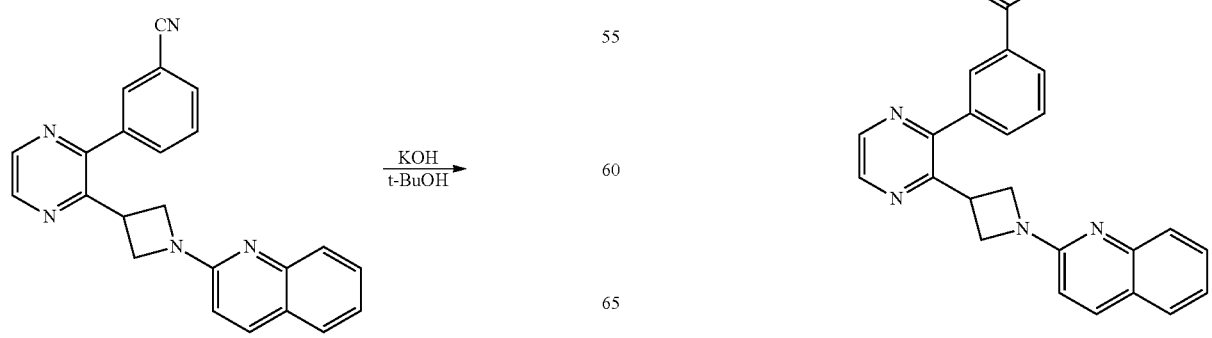
SCHEME 30

Example 30.1: 3-(3-(1-(Quinolin-2-Yl)Azetidin-3-Yl)Pyrazin-2-Yl)Benzamide

A mixture of 3-(3-(1-(quinolin-2-yl)azetidin-3-yl)pyrazin-2-yl)benzonitrile (0.072 g, 0.198 mmol), potassium hydroxide (0.111 g, 1.981 mmol, v/w) and t-BuOH (2 mL, Acros) was heated at 80° C. overnight. LCMS showed the product. The mixture was diluted with water and extracted with a mixture of CHCl$_3$:i-PrOH (3:1) three times. The combined organic layers were dried over Na$_2$SO$_4$ and concentrated in vacuo. The product was obtained as a white solid (75 mg, 99%).

The following Table 34A lists compounds of Examples 30.1 to 30.4, which were made analogous to Scheme 30 by using the appropriate materials and reaction conditions, which are listed in Table 34B. The NMR data of the Examples are listed in Table 34C.

TABLE 34A

EXAMPLES 30.1 TO 30.4

| Ex. # | Structure | Chemical Name | ESI-MS (M + 1) | IC$_{50}$ (μM) |
|---|---|---|---|---|
| 30.1 | 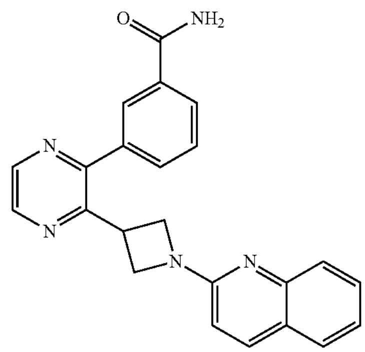 [SMILES: NC(=O)c1cccc(-c2nccnc2C2CN(c3ccc4ccccc4n3)C2)c1] | 3-(3-(1-(quinolin-2-yl)azetidin-3-yl)pyrazin-2-yl)benzamide | 382 | 0.0008 |
| 30.2 | 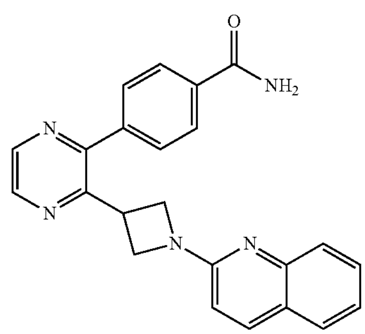 | 4-(3-(1-(quinolin-2-yl)azetidin-3-yl)pyrazin-2-yl)benzamide | 382 | 0.0013 |
| 30.3 | 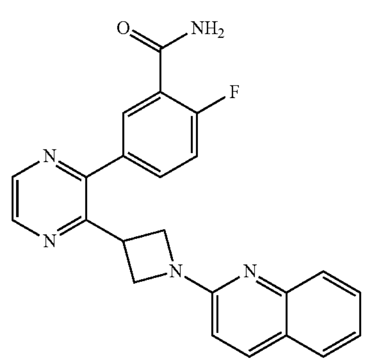 [SMILES: NC(=O)c1cc(-c2nccnc2C2CN(c3ccc4ccccc4n3)C2)ccc1F] | 2-fluoro-5-(3-(1-(quinolin-2-yl)azetidin-3-yl)pyrazin-2-yl)benzamide | 400 | 0.0006 |

TABLE 34A-continued

EXAMPLES 30.1 TO 30.4

| Ex. # | Structure | Chemical Name | ESI-MS (M + 1) | IC$_{50}$ (μM) |
|---|---|---|---|---|
| 30.4 | 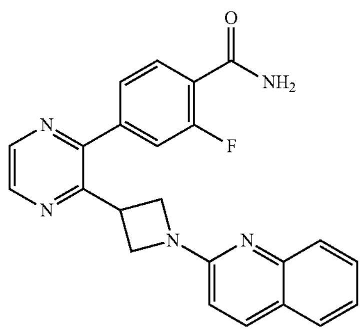 [SMILES: NC(=O)c1ccc(-c2nccnc2C2CN(c3ccc4ccccc4n3)C2)cc1F] | 2-fluoro-4-(3-(1-(quinolin-2-yl)azetidin-3-yl)pyrazin-2-yl)benzamide | 400 | 0.002 |

TABLE 34B

STARTING MATERIALS AND REACTION CONDITION FOR
PREPARATION OF EXAMPLES 30.1 TO 30.4.

Unless otherwise stated, all starting materials are commercially available from common vendors.

| Ex. # | Key starting Material(s)/Source | Reaction Condition |
|---|---|---|
| 30.1 | 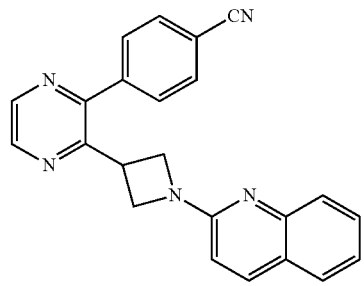 [SMILES: N#Cc1ccc(-c2nccnc2C2CN(c3ccc4ccccc4n3)C2)cc1]<br>SCHEME 5 | KOH, t-BuOH, 80° C. |
| 30.2 | SCHEME 5 | KOH, t-BuOH, 80° C. |

TABLE 34B-continued

STARTING MATERIALS AND REACTION CONDITION FOR
PREPARATION OF EXAMPLES 30.1 TO 30.4.

Unless otherwise stated, all starting materials are commercially available from common vendors.

| Ex. # | Key starting Material(s)/Source | Reaction Condition |
|---|---|---|
| 30.3 | [structure] SCHEME 5 | EtOH/DMSO NaOH/H$_2$O$_2$ |
| 30.4 | [structure] SCHEME 5 | EtOH/DMSO NaOH/H$_2$O$_2$ |

TABLE 34C

1H NMR δ (PPM) DATA FOR EXAMPLES 30.1 TO 30.4

| Ex. # | Structure | $^1$H NMR |
|---|---|---|
| 30.1 | [structure] | (400 MHz, DMSO-d$_6$) 4.24-4.35 (m, 4 H) 4.37-4.46 (m, 1 H) 6.75 (d, J = 8.80 Hz, 1 H) 7.21 (t, J = 7.34 Hz, 1 H) 7.45-7.59 (m, 3 H) 7.62-7.81 (m, 3 H) 7.99-8.17 (m, 4 H) 8.67 (d, J = 2.35 Hz, 1 H) 8.71 (d, J = 2.35 Hz, 1 H) |

TABLE 34C-continued

1H NMR δ (PPM) DATA FOR EXAMPLES 30.1 TO 30.4

| Ex. # | Structure | ¹H NMR |
|---|---|---|
| 30.2 | 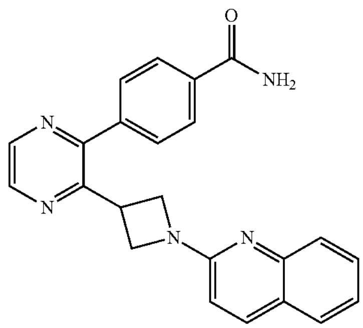 [SMILES: NC(=O)c1ccc(-c2nccnc2C2CN(c3ccc4ccccc4n3)C2)cc1] | (400 MHz, DMSO-$d_6$) 4.20-4.35 (m, 4 H) 4.38-4.49 (m, 1 H) 6.75 (d, J = 9.00 Hz, 1 H) 7.16-7.28 (m, 1 H) 7.45-7.59 (m, 3 H) 7.64-7.74 (m, 3 H) 7.98-8.20 (m, 4 H) 8.66 (d, J = 2.35 Hz, 1 H) 8.71 (d, J = 2.35 Hz, 1 H) |
| 30.3 | 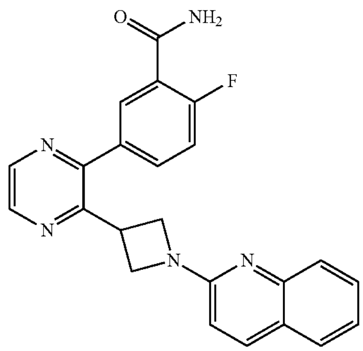 [SMILES: NC(=O)c1cc(-c2nccnc2C2CN(c3ccc4ccccc4n3)C2)ccc1F] | (400 MHz, chloroform-d) 4.34-4.51 (m, 5 H) 5.94 (br. s., 1 H) 6.64 (d, J = 9.00 Hz, 1 H) 6.77 (d, J = 10.17 Hz, 1 H) 7.19-7.25 (m, 1 H) 7.34 (dd, J = 11.35, 8.61 Hz, 1 H) 7.49-7.56 (m, 1 H) 7.60 (d, J = 7.82 Hz, 1 H) 7.72 (d, J = 8.41 Hz, 1 H) 7.77 (ddd, J = 8.17, 5.14, 2.54 Hz, 1 H) 7.88 (d, J = 8.80 Hz, 1 H) 8.30 (dd, J = 7.43, 2.54 Hz, 1 H) 8.55 (d, J = 2.35 Hz, 1 H) 8.62 (d, J = 2.35 Hz, 1 H). |
| 30.4 | 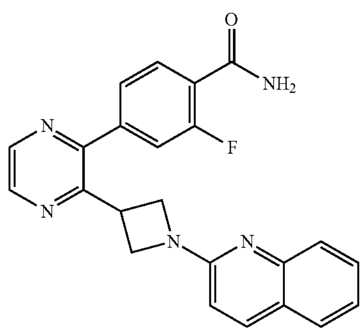 [SMILES: NC(=O)c1ccc(-c2nccnc2C2CN(c3ccc4ccccc4n3)C2)cc1F] | (400 MHz, chloroform-d) 4.33-4.52 (m, 5 H) 5.89 (br. s., 1 H) 6.64 (d, J = 9.00 Hz, 1 H) 6.76 (d, J = 11.35 Hz, 1 H) 7.20-7.26 (m, 1 H) 7.36-7.47 (m, 2 H) 7.54 (t, J = 7.73 Hz, 1 H) 7.61 (d, J = 8.02 Hz, 1 H) 7.73 (d, J = 8.41 Hz, 1 H) 7.89 (d, J = 9.00 Hz, 1 H) 8.30 (t, J = 8.02 Hz, 1 H) 8.58 (d, J = 2.35 Hz, 1 H) 8.65 (d, J = 2.35 Hz, 1 H). |

SCHEME 31

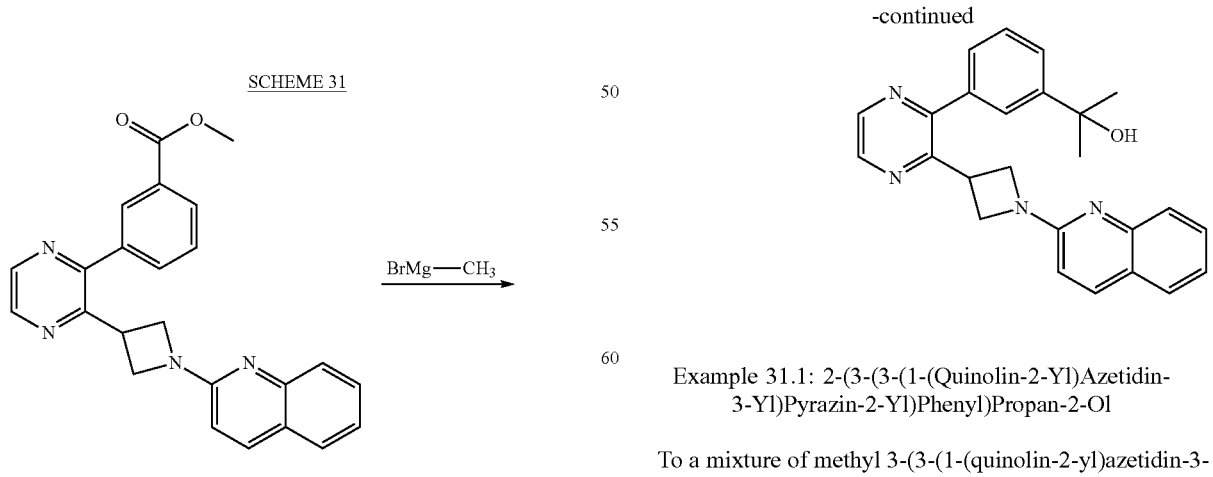

Example 31.1: 2-(3-(3-(1-(Quinolin-2-Yl)Azetidin-3-Yl)Pyrazin-2-Yl)Phenyl)Propan-2-Ol To a mixture of methyl 3-(3-(1-(quinolin-2-yl)azetidin-3-yl)pyrazin-2-yl)benzoate (0.044 g, 0.110 mmol) and THF (1 mL) was added methylmagnesium bromide (0.110 mL, 0.331 mmol). The mixture was stirred at RT for 2 h. LCMS showed the product. The mixture was diluted with saturated NH$_4$Cl and extracted with EtOAc. The organic layer was dried over Na$_2$SO$_4$ and concentrated in vacuo. The crude was purified by silica gel chromatography (12 g, 10%-100% EtOAc-Hexane). The product was obtained as a white solid (44 mg, 100%). $^1$H NMR (400 MHz, chloroform-d) δ ppm 1.66 (s, 6H) 1.88 (br. s., 1H) 4.29-4.63 (m, 5H) 6.62 (d, J=8.80 Hz, 1H) 7.22 (t, J=7.43 Hz, 1H) 7.39 (d, J=7.63 Hz, 1H) 7.51 (dt, J=11.79, 7.70 Hz, 2H) 7.57-7.65 (m, 2H) 7.66-7.76 (m, 2H) 7.87 (d, J=8.80 Hz, 1H) 8.54 (d, J=2.35 Hz, 1H) 8.58 (d, J=2.15 Hz, 1H). ESI (M+1) 397; calc for C$_{25}$H$_{24}$N$_4$ 396.

The following Table 35A lists compounds of Examples 31.1 to 31.2, which were made analogous to Scheme 31 by using the appropriate materials and reaction conditions, which are listed in Table 35B. The NMR data of the Examples are listed in Table 35C.

TABLE 35A

EXAMPLES 31.1 TO 31.2

| Ex. # | Structure | Chemical Name | ESI-MS (M + 1) | IC$_{50}$ (μm) |
|---|---|---|---|---|
| 31.1 | 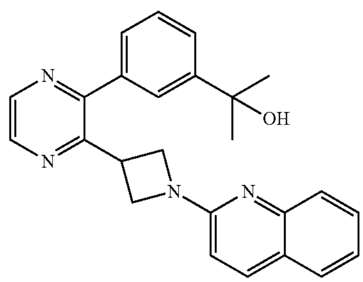 [SMILES: CC(C)(O)c1cccc(-c2nccnc2C2CN(c3ccc4ccccc4n3)C2)c1] | 2-(3-(3-(1-(quinolin-2-yl)azetidin-3-yl)pyrazin-2-yl)phenyl)propan-2-ol | 397 | 0.0034 |
| 31.2 | 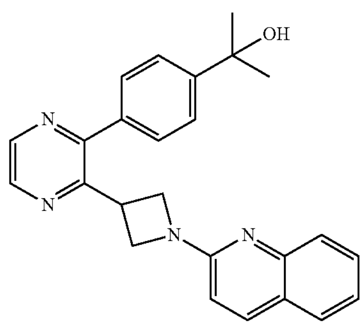 [SMILES: CC(C)(O)c1ccc(-c2nccnc2C2CN(c3ccc4ccccc4n3)C2)cc1] | 2-(4-(3-(1-(quinolin-2-yl)azetidin-3-yl)pyrazin-2-yl)phenyl)propan-2-ol | 397 | 0.0042 |

TABLE 35B

STARTING MATERIALS AND REACTION CONDITION FOR
PREPARATION OF EXAMPLES 31.1 TO 31.2.
Unless otherwise stated, all starting materials are commercially available from common vendors.

| Ex. # | Key Starting Material(s)/Source | Reaction Condition |
|---|---|---|
| 31.1 | | CH$_3$MgBr, THF, RT |

SCHEME 5

TABLE 35B-continued

STARTING MATERIALS AND REACTION CONDITION FOR
PREPARATION OF EXAMPLES 31.1 TO 31.2.

Unless otherwise stated, all starting materials are commercially available from common vendors.

| Ex. # | Key Starting Material(s)/Source | Reaction Condition |
|---|---|---|
| 31.2 | 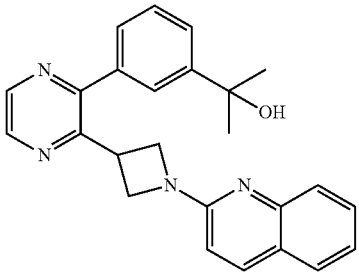 [SMILES: CC(C)(O)c1cccc(-c2nccnc2C2CN(c3ccc4ccccc4n3)C2)c1] | CH₃MgBr, THF, RT |

SCHEME 5

TABLE 35C

1H NMR δ (PPM) DATA FOR EXAMPLES 31.1 TO 31.2

| Ex. # | Structure | NMR |
|---|---|---|
| 31.1 | 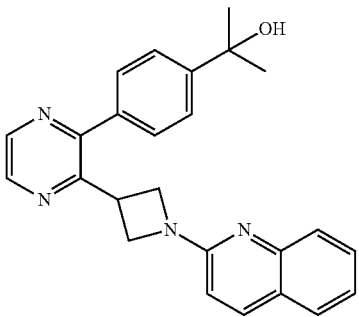 [SMILES: CC(C)(O)c1ccc(-c2nccnc2C2CN(c3ccc4ccccc4n3)C2)cc1] | (400 MHz, chloroform-d) 1.66 (s, 6 H) 1.88 (br. s., 1 H) 4.29-4.63 (m, 5 H) 6.62 (d, J = 8.80 Hz, 1 H) 7.22 (t, J = 7.43 Hz, 1 H) 7.39 (d, J = 7.63 Hz, 1 H) 7.51 (dt, J = 11.79, 7.70 Hz, 2 H) 7.57-7.65 (m, 2 H) 7.66-7.76 (m, 2 H) 7.87 (d, J = 8.80 Hz, 1 H) 8.54 (d, J = 2.35 Hz, 1 H) 8.58 (d, J = 2.15 Hz, 1 H). |
| 31.2 | 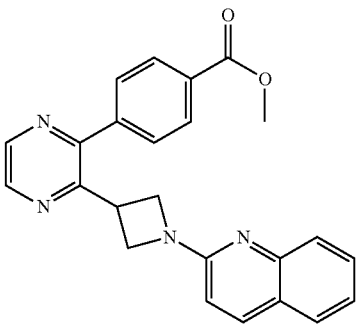 | (400 MHz, chloroform-d) 1.65 (s, 6 H) 1.80 (s, 1 H) 4.38-4.53 (m, 5 H) 6.63 (d, J = 8.80 Hz, 1 H) 7.22 (t, J = 7.43 Hz, 1 H) 7.47-7.56 (m, 3 H) 7.60 (d, J = 7.63 Hz, 1 H) 7.65 (d, J = 8.41 Hz, 2 H) 7.72 (d, J = 8.41 Hz, 1 H) 7.87 (d, J = 9.00 Hz, 1 H) 8.53 (d, J = 2.35 Hz, 1 H) 8.57 (d, J = 2.54 Hz, 1 H). |

SCHEME 32

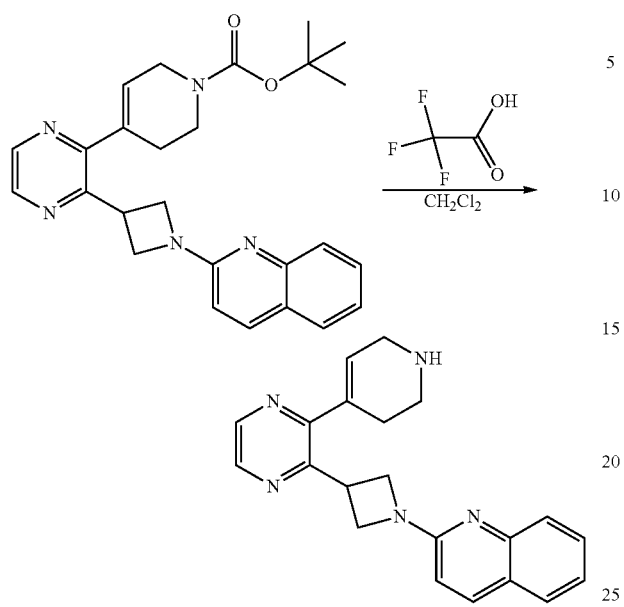

Example 32.1: 2-(3-(3-(1,2,3,6-Tetrahydropyridin-4-Yl)Pyrazin-2-Yl)Azetidin-1-Yl)Quinoline A mixture of tert-butyl 4-(3-(1-(quinolin-2-yl)azetidin-3-yl)pyrazin-2-yl)-5,6-dihydropyridine-1(2H)-carboxylate (0.100 g, 0.225 mmol, SCHEME 5), CH$_2$Cl$_2$ (1 mL) and TFA (0.174 mL, 2.255 mmol) was stirred at RT for 1 h. LCMS showed the product and no more starting material was present. The mixture was concentrated in vacuo and neutralized with Na$_2$CO$_3$. The mixture was extracted with a mixture of CHCl$_3$:i-PrOH (3:1) three times. The organic layer was dried over Na$_2$SO$_4$ and concentrated in vacuo. The product was obtained as a white solid (77 mg, 99%).

ESI-MS (M+1): 344. PDE10 IC$_{50}$ (μM): 0.013.

$^1$H NMR δ (ppm): (400 MHz, chloroform-d) 2.53 (d, J=1.76 Hz, 2H) 3.18 (t, J=5.67 Hz, 2H) 3.61 (d, J=2.74 Hz, 2H) 4.38-4.59 (m, 5H) 5.86 (br. s., 1H) 6.66 (d, J=8.80 Hz, 1H) 7.22 (t, J=7.43 Hz, 1H) 7.49-7.57 (m, 1H) 7.61 (d, J=7.83 Hz, 1H) 7.74 (d, J=8.41 Hz, 1H) 7.89 (d, J=9.00 Hz, 1H) 8.42 (d, J=2.35 Hz, 1H) 8.47 (d, J=2.35 Hz, 1H).

SCHEME 33

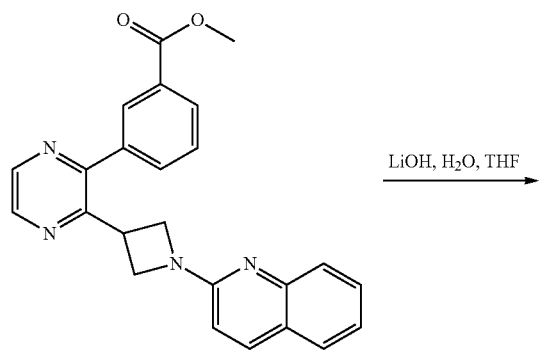

LiOH, H$_2$O, THF

-continued

Example 33.1: Lithium 3-(3-(1-(Quinolin-2-Yl)Azetidin-3-Yl)Pyrazin-2-Yl)Benzoate A mixture of methyl 3-(3-(1-(quinolin-2-yl)azetidin-3-yl)pyrazin-2-yl)benzoate (0.079 g, 0.198 mmol, SCHEME 5), lithium hydroxide hydrate (0.017 g, 0.397 mmol), water (0.4 mL) and THF (1.2 mL) was stirred at RT overnight. The mixture was concentrated in vacuo. The product was obtained as an off-white solid (83 mg, 108%).

ESI-MS (M+1): 383. PDE10 IC$_{50}$ (μM): 0.0016.

$^1$H NMR δ (ppm): (400 MHz, DMSO-d$_6$) 4.20-4.45 (m, 5H) 6.76 (d, J=9.00 Hz, 1H) 7.21 (t, J=7.04 Hz, 1H) 7.42-7.61 (m, 4H) 7.70 (d, J=7.82 Hz, 1H) 7.97-8.04 (m, 2H) 8.08 (s, 1H) 8.64 (dd, J=9.39, 2.35 Hz, 2H).

SCHEME 34

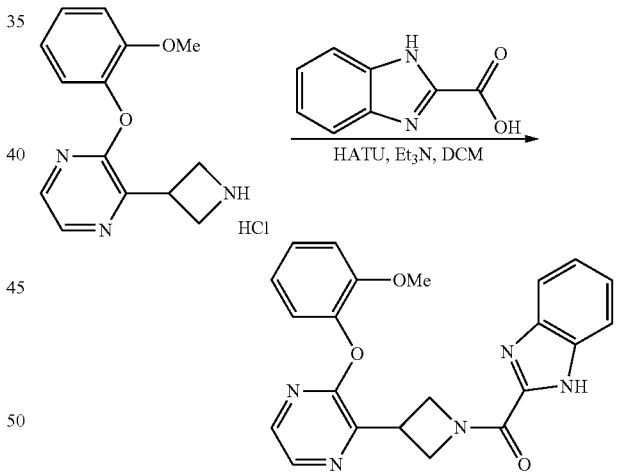

Example 34.1: (1H-Benzoimidazol-2-Yl)-{3-[3-(2-Methoxy-Phenoxy)-Pyrazin-2-Yl]-Azetidin-1-Yl}-Methanone The mixture of 2-azetidin-3-yl-3-(2-methoxy-phenoxy)-pyrazine hydrochloride (108 mg, 0.37 mmol), HATU (280 mg, 0.74 mmol) and TEA (130 mg, 1.3 mmol) in dry DCM (10 mL) was stirred at RT for 30 min, then 1H-benzoimidazole-2-carboxylic acid was added to the solution. The solution was heated to 80° C. overnight. The mixture was poured into saturated aqueous Na$_2$CO$_3$ and extracted with DCM (50 mL×2). The organic layer was washed with brine, dried over Na$_2$SO$_4$ and concentrated to give the crude compound, which was purified by ISCO silica gel column (10% to 80% EtOAc in petroleum ether) and followed by reverse phase prep. HPLC (10% to 80% water/MeCN) to give (1H-benzoimidazol-2-yl)-{3-[3-(2-methoxy-phenoxy)-pyrazin-2-yl]-azetidin-1-yl}-methanone (40 mg, 0.11 mmol, yield 27%).

The following Table 36A lists compounds of Examples 34.1 to 34.2, which were made analogous to Scheme 34 by using the appropriate materials and reaction conditions, which are listed in Table 36B. The NMR data of the Examples are listed in Table 36C.

TABLE 36A

EXAMPLES 34.1 TO 34.2

| Ex. # | Structure | Chemical Name | ESI-MS (M + 1) | IC$_{50}$ (uM) |
|---|---|---|---|---|
| 34.1 | 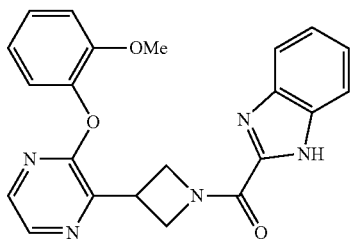 [SMILES: COc1ccccc1Oc1nccnc1C1CN(C(=O)c2nc3ccccc3[nH]2)C1] | (1H-Benzoimidazol-2-yl)-{3-[3-(2-methoxy-phenoxy)-pyrazin-2-yl]-azetidin-1-yl}-methanone | 402 | 1.74 |
| 34.2 | 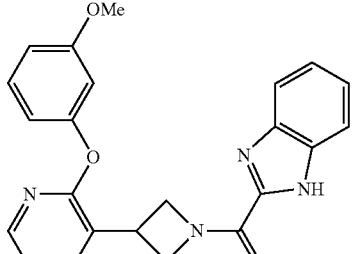 | (1H-Benzoimidazol-2-yl)-{3-[3-(3-methoxy-phenoxy)-pyrazin-2-yl]-azetidin-1-yl}-melhanone | 402 | 0.78 |
| 34.3 | 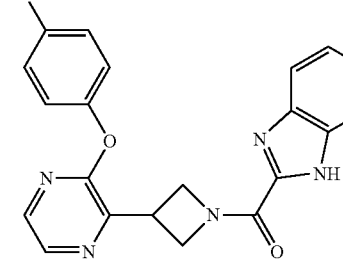 | (1H-benzoimidazol-2-yl)-{3-[3-(4-methoxy-phenoxy)-pyrazin-2-yl]-azetidin-1-yl}-methanone | 402 | 2.04 |
| 34.4 | 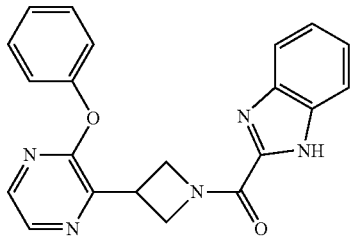 [SMILES: O=C(c1nc2ccccc2[nH]1)N1CC(c2nccnc2Oc2ccccc2)C1] | (1H-Benzoimidazol-2-yl)-[3-(3-phenoxy-pyrazin-2-yl)-azetidin-1-yl]-methanone | 372 | 0.73 |
| 34.5 | 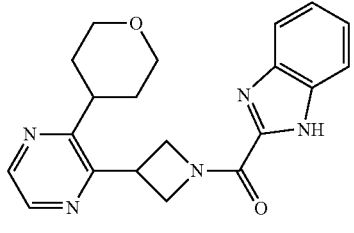 [SMILES: O=C(c1nc2ccccc2[nH]1)N1CC(c2nccnc2C2CCOCC2)C1] | (1H-benzoimidazol-2-yl)-{3-[3-(tetrahydro-pyran-4-yl)-pyrazin-2-yl]-azetidin-1-yl}-methanone | 364 | 0.124 |

TABLE 36A-continued

EXAMPLES 34.1 TO 34.2

| Ex. # | Structure | Chemical Name | ESI-MS (M + 1) | IC$_{50}$ (uM) |
|---|---|---|---|---|
| 34.6 | 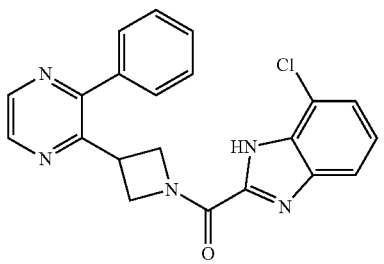 [SMILES: O=C(c1nc2cccc(Cl)c2[nH]1)N1CC(c2nccnc2-c2ccccc2)C1] | (7-Chloro-1H-benzoimidazol-2-yl)-[3-(3-phenyl-pyrazin-2-yl)-azetidin-1-yl]-methanone | 390 | 0.131 |
| 34.7 | 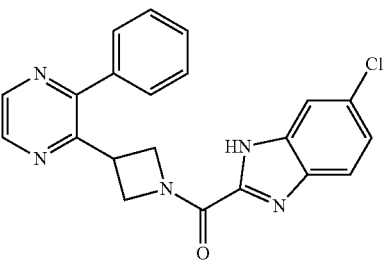 [SMILES: O=C(c1nc2ccc(Cl)cc2[nH]1)N1CC(c2nccnc2-c2ccccc2)C1] | (6-Chloro-1H-benzoimidazol-2-yl)-[3-(3-phenyl-pyrazin-2-yl)-azetidin-1-yl]-methanone | 390 | 0.0692 |
| 34.8 | 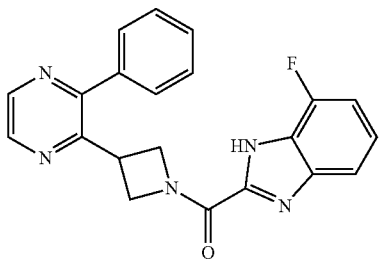 | (7-Fluoro-1H-benzoimidazol-2-yl)-[3-(3-phenyl-pyrazin-2-yl)-azetidin-1-yl]-methanone | 374 | 0.0438 |
| 34.9 | 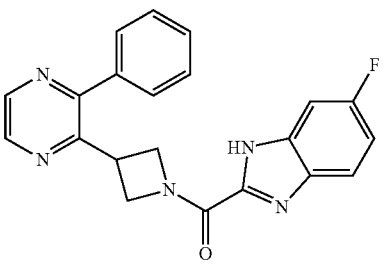 [SMILES: O=C(c1nc2ccc(F)cc2[nH]1)N1CC(c2nccnc2-c2ccccc2)C1] | (6-Fluoro-1H-benzoimidazol-2-yl)-[3-(3-phenyl-pyrazin-2-yl)-azetidin-1-yl]-methanone | 374 | 0.0373 |
| 34.10 | 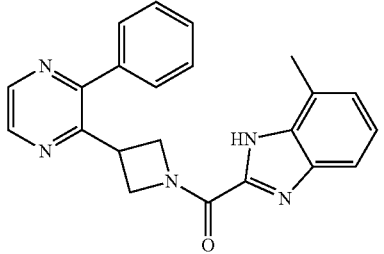 [SMILES: Cc1cccc2nc(C(=O)N3CC(c4nccnc4-c4ccccc4)C3)[nH]c12] | (6-methyl-1H-benzoimidazol-2-yl)-[3-(3-phenyl-pyrazin-2-yl)-azetidin-1-yl]-methanone | 370 | 0.0687 |

TABLE 36A-continued

EXAMPLES 34.1 TO 34.2

| Ex. # | Structure | Chemical Name | ESI-MS (M + 1) | IC$_{50}$ (uM) |
|---|---|---|---|---|
| 34.11 | 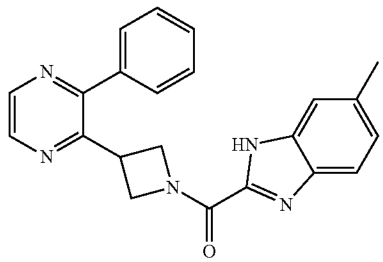 [SMILES: Cc1ccc2nc(C(=O)N3CC(c4nccnc4-c4ccccc4)C3)[nH]c2c1] | (6-methyl-1H-benzoimidazol-2-yl)-[3-(3-phenyl-pyrazin-2-yl)-azetidin-1-yl]-methanone | 370 | 0.0219 |
| 34.12 | 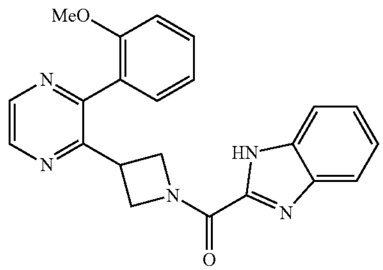 [SMILES: COc1ccccc1-c1nccnc1C1CN(C(=O)c2nc3ccccc3[nH]2)C1] | (1H-benzoimidazol-2-yl)-{3-[3-(2-methoxy-phenyl)-pyrazin-2-yl]-azetidin-1-yl}-methanone | 386 | 0.0978 |
| 34.13 | 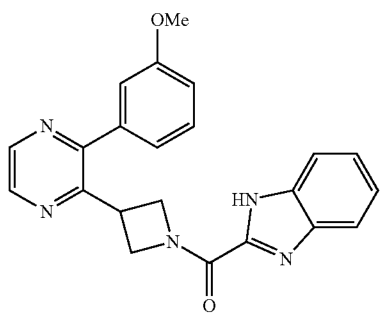 [SMILES: COc1cccc(-c2nccnc2C2CN(C(=O)c3nc4ccccc4[nH]3)C2)c1] | (1H-benzoimidazol-2-yl)-{3-[3-(3-methoxy-phenyl)-pyrazin-2-yl]-azetidin-1-yl}-methanone | 386 | 0.087 |
| 34.14 | | (1H-Benzoimidazol-2-yl)-{3-[3-(4-methoxy-phenyl)-pyrazin-2-yl]-azetidin-1-yl}-methanone | 386 | 0.0322 |
| 34.14 | | (1H-benzoimidazol-2-yl)-[3-(2-phenyl-pyridin-3-yl)-azetidin-1-yl]-methanone | 355 | 0.515 |

TABLE 36B

STARTING MATERIALS AND REACTION CONDITION FOR
PREPARATION OF EXAMPLES 34.1 TO 34.2.
Unless otherwise stated, all starting materials are commercially available from common vendors.

| Ex. # | Starting Material 1 | Starting Material 2 | Reaction Condition |
|---|---|---|---|
| 34.1 | PREPARATION 5 | PREPARATION 6 | HATU, TEA, DCM, 80° C. |
| 34.2 | PREPARATION 5 | PREPARATION 6 | HATU, TEA, DCM, 80° C. |
| 34.3 | PREPARATION 5 | PREPARATION 6 | HATU, TEA, DCM, 80° C. |
| 34.4 | PREPARATION 5 | PREPARATION 6 | HATU, TEA, DCM, 80° C. |
| 34.5 | PREPARATION 37 | PREPARATION 6 | HATU, TEA, THF |

TABLE 36B-continued

STARTING MATERIALS AND REACTION CONDITION FOR
PREPARATION OF EXAMPLES 34.1 TO 34.2.
Unless otherwise stated, all starting materials are commercially available from common vendors.

| Ex. # | Starting Material 1 | Starting Material 2 | Reaction Condition |
|---|---|---|---|
| 34.6 | 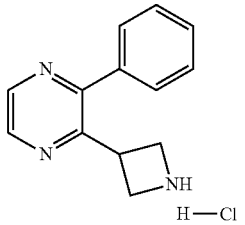<br>PREPARATION 7 | 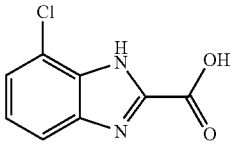 [SMILES: O=C(O)c1nc2cccc(Cl)c2[nH]1]<br>PREPARATION 6 | HATU, TEA, DCM,<br>0° C. to RT |
| 34.7 | 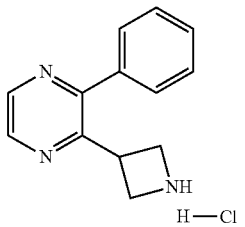<br>PREPARATION 7 | 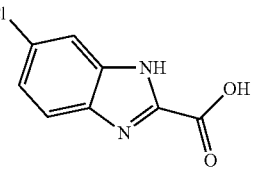<br>PREPARATION 6 | HATU, TEA, DCM,<br>0° C. to RT |
| 34.8 | 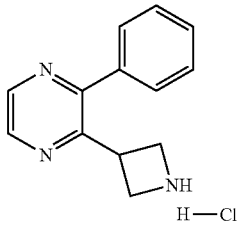<br>PREPARATION 7 | 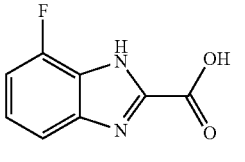 [SMILES: O=C(O)c1nc2cccc(F)c2[nH]1]<br>PREPARATION 6 | HATU, TEA, DCM,<br>0° C. to RT |
| 34.9 | 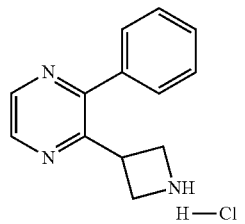<br>PREPARATION 7 | 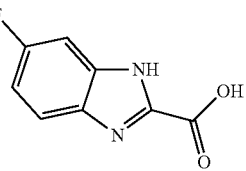<br>PREPARATION 6 | HATU, TEA, DCM,<br>0° C. to RT |
| 34.10 | 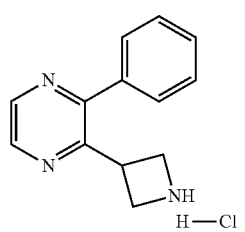<br>PREPARATION 7 | 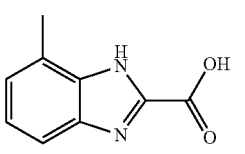<br>PREPARATION 6 | HATU, TEA, DCM,<br>0° C. to RT |

TABLE 36B-continued

STARTING MATERIALS AND REACTION CONDITION FOR
PREPARATION OF EXAMPLES 34.1 TO 34.2.
Unless otherwise stated, all starting materials are commercially available from common vendors.

| Ex. # | Starting Material 1 | Starting Material 2 | Reaction Condition |
|---|---|---|---|
| 34.11 | PREPARATION 7 | PREPARATION 6 | HATU, TEA, DCM, 0° C. to RT |
| 34.12 | PREPARATION 7 | PREPARATION 6 | HATU, TEA, DCM, RT |
| 34.13 | PREPARATION 10 | PREPARATION 6 | HATU, TEA, DCM, RT |
| 34.14 | PREPARATION 7 | PREPARATION 6 | HATU, TEA, DCM, RT |
| 34.14 | PREPARATION 8 | PREPARATION 6 | HATU, TEA, DCM, RT |

US 9,718,803 B2

TABLE 36C

1H NMR δ (PPM) DATA FOR EXAMPLES 34.1 TO 34.2

| Ex. # | Structure | NMR |
|---|---|---|
| 34.1 | 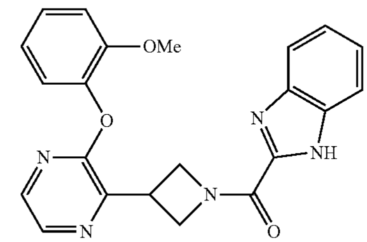 [SMILES: COc1ccccc1Oc1nccnc1C1CN(C(=O)c2nc3ccccc3[nH]2)C1] | (CD$_3$OD, 400 MHz): 8.19 (d, J = 2.4 Hz, 1H); 7.93 (d, J = 2.8 Hz, 1H); 7.74-7.70 (m, 2H); 7.37-7.33 (m, 2H); 7.26-7.15 (m, 1H); 7.02-6.97 (m, 3H); 5.38-5.29 (m, 2H); 4.85-4.71 (m, 2H); 4.53-4.10 (m, 1H); 3.69 (s, 3H). |
| 34.2 | 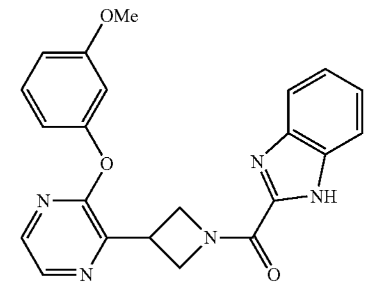 [SMILES: COc1cccc(Oc2nccnc2C2CN(C(=O)c3nc4ccccc4[nH]3)C2)c1] | (CD$_3$OD, 400 MHz): 8.18 (d, J = 2.4 Hz, 1H); 7.95 (d, J = 2.8 Hz, 1H); 7.70-7.68 (m, 2H); 7.35-7.33 (m, 2H); 7.28-7.24 (m, 1H); 6.76-6.73 (m, 1H); 6.66-6.64 (m, 2H); 5.32-5.27 (m, 1H); 5.21-5.17 (m, 1H); 4.36-4.63 (m, 2H); 4.49-4.43 (m, 1H); 3.74 (s, 3H). |
| 34.3 | 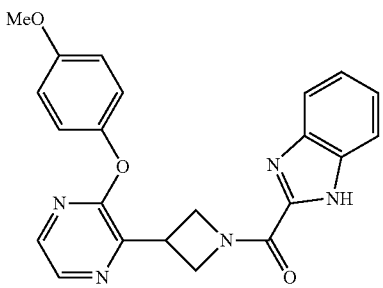 [SMILES: COc1ccc(Oc2nccnc2C2CN(C(=O)c3nc4ccccc4[nH]3)C2)cc1] | (CD$_3$OD 400 MHz): 8.27-8.26 (m, 1 H); 7.99-7.98 (m, 1 H); 7.85-7.83 (m, 2 H); 7.67-7.64 (m, 2 H); 7.08-7.06 (m, 2 H); 6.96-6.94 (m, 2 H); 5.15-5.13 (m, 2 H); 4.76-7.74 (m, 2 H); 4.56-4.53 (m, 1 H); 3.79 (s, 3 H). |
| 34.4 | 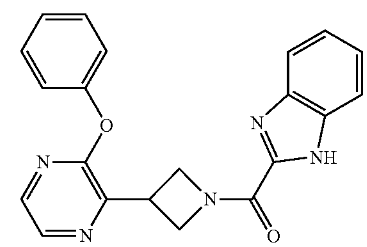 [SMILES: O=C(c1nc2ccccc2[nH]1)N1CC(c2nccnc2Oc2ccccc2)C1] | (CD$_3$OD, 400 MHz): 8.29 (d, J = 2.8 Hz, 1H); 8.00-7.99 (m, 1H); 7.75-7.73 (m, 2H); 7.49-7.47 (m, 2H); 7.43-7.39 (m, 2H); 7.25-7.23 (m, 1H); 7.17-7.14 (m, 2H); 5.22-5.13 (m, 2H); 4.73-4.68 (m, 2H); 4.58-4.51 (m, 1H) |
| 34.5 | 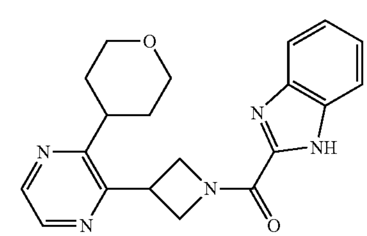 [SMILES: O=C(c1nc2ccccc2[nH]1)N1CC(c2nccnc2C2CCOCC2)C1] | (CD$_3$OD, 400 MHz): 8.48-8.45 (m, 2 H); 7.74-7.72 (m, 2 H); 7.47-7.44 (m, 2 H); 5.15-5.12 (m, 1 H); 5.03-5.01 (m, 1 H); 4.64-4.56 (m, 3 H); 4.09-4.02 (m, 2 H); 3.65-3.59 (m, 2 H); 3.17-3.13 (m, 1 H); 2.05-2.03 (m, 2 H); 1.66-1.63 (m, 2 H) |
| 34.6 | 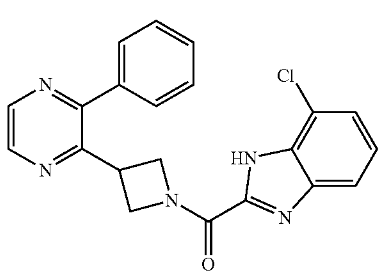 | (CDCl$_3$, 400 MHz) 8.62-8.58 (m, 2H), 7.54-7.49 (m, 6H); 7.31-7.20 (m, 2H); 5.16 (br, 2H); 4.63-4.59 (m, 1H); 4.50-4.46 (m, 1H); 4.40-4.33 (m, 1H). |

TABLE 36C-continued

1H NMR δ (PPM) DATA FOR EXAMPLES 34.1 TO 34.2

| Ex. # | Structure | NMR |
|---|---|---|
| 34.7 | 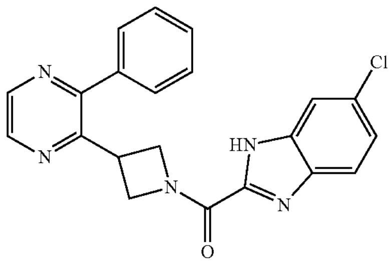 [SMILES: O=C(c1nc2ccc(Cl)cc2[nH]1)N1CC(c2nccnc2-c2ccccc2)C1] | (CDCl$_3$, 400 MHz): 8.55-8.51 (m, 2H); 7.47-7.41 (m, 7H); 7.24 (s, 1H); 5.06 (m, 2H); 4.53-4.50 (m, 1H); 4.42-4.37 (m, 1H); 4.30-4.28 (m, 1H). |
| 34.8 | 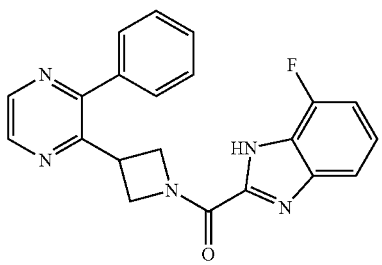 | (CDCl$_3$, 400 MHz): 8.68-8.59 (m, 2H); 7.62-7.49 (m, 5H); 7.45-7.41 (m, 1H); 7.38-7.20 (m, 1H); 7.05-6.96 (m, 1H); 5.25-5.14 (m, 2H); 4.64-4.60 (m, 1H), 4.52-4.49 (m, 1H); 4.47-4.33 (m, 1H). |
| 34.9 | 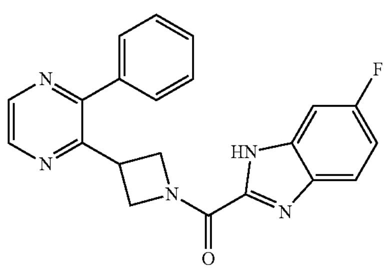 [SMILES: O=C(c1nc2ccc(F)cc2[nH]1)N1CC(c2nccnc2-c2ccccc2)C1] | (MeOD, 400 MHz): 8.62-8.61 (m, 1H); 8.55-8.54 (m, 1H); 7.68-7.52 (m, 6H); 7.35-7.31 (m, 1H); 7.11-7.08 (m, 1H); 5.06-5.00 (m, 2H); 4.46-4.36 (m, 3H). |
| 34.10 | 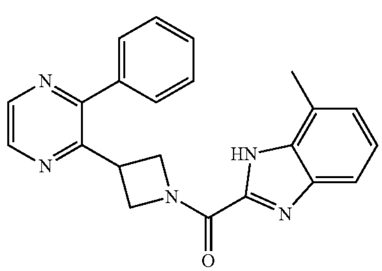 | (CDCl$_3$ 400 MHz): 8.64-8.63 (m, 1H); 8.61-8.60 (m, 1H); 7.56-7.52 (m, 4H); 7.47-7.45 (m, 2H); 7.28-7.26 (m, 1H); 7.17-7.15 (m, 1H); 5.17-5.10 (m, 2H); 4.56-4.54 (m, 1H); 4.41-4.36 (m, 2H); 2.59 (s, 3H). |
| 34.11 | 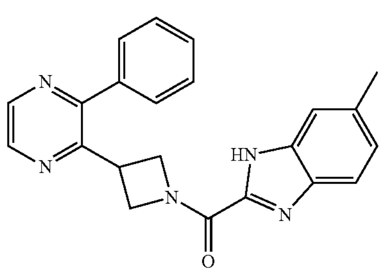 [SMILES: Cc1ccc2nc(C(=O)N3CC(c4nccnc4-c4ccccc4)C3)[nH]c2c1] | (CDCl$_3$, 400 MHz); 8.54-8.53 (m, 1H); 8.51-8.50 (m, 1H); 7.45-7.43 (m, 6H); 7.18 (brs, 1H); 7.06-7.04 (m, 1H); 5.10-5.06 (m, 2H); 4.55-4.53 (m, 1H); 4.43-4.38 (m, 1H); 4.29-4.27 (m, 1H); 2.14 (s, 3H) |

TABLE 36C-continued
1H NMR δ (PPM) DATA FOR EXAMPLES 34.1 TO 34.2
| Ex. # | Structure | NMR |
|---|---|---|
| 34.12 | 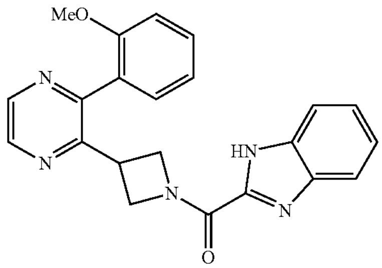 [SMILES: COc1ccccc1-c1nccnc1C1CN(C(=O)c2nc3ccccc3[nH]2)C1] | (CDCl₃ 400 MHz): 8.69-8.68 (m, 1H); 8.56-8.55 (m, 1H); 7.74-7.72 (m, 2H); 7.53-7.45 (m, 3H); 7.36-7.34 (m, 1H); 7.17-7.12(m, 2H); 5.01-4.95 (m, 2H); 4.50-4.91 (m, 2H); 4.15-4.09 (m. 1H); 3.81 (s, 3H). |
| 34.13 | 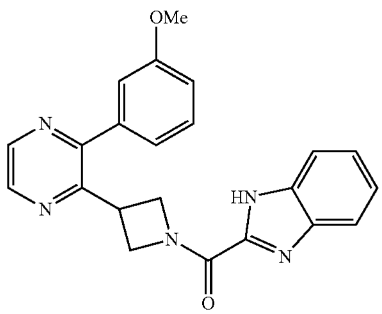 [SMILES: COc1cccc(-c2nccnc2C2CN(C(=O)c3nc4ccccc4[nH]3)C2)c1] | (CDCl₃, 400 MHz): 8.62-8.57 (m, 2H); 7.69-7.67 (m, 2H); 7.46-7.42 (m, 1H); 7.34-7.32 (m, 2H); 7.06-7.01(m, 3H); 5.19-5.15 (m, 2H); 4.68-4.31 (m, 3H); 3.88 (s, 3H). |
| 34.14 | | (CDCl₃, 400 MHz): 8.86 (d, J = 2.8 Hz, 2H), 7.73-7.71 (m, 2H); 7.45-7.43 (m, 2H); 7.40-7.37 (m, 2H); 7.07-7.05 (m, 2H); 5.24-5.22 (m, 1H); 5.13-5.12 (m, 1H); 4.59-4.57 (m, 1H); 4.48-4.40 (m, 2H); 3.89 (s, 3H). |
| 34.14 | | (CDCl₃, 400 MHz): 8.87-8.86 (m, 1 H); 8.58-8.56 (m, 1 H); 7.86-7.81 (m, 1 H); 7.70-7.68 (m, 2 H); 7.58-7.56 (m, 3 H); 7.45-7.38 (m, 4 H); 5.17-5.15 (m, 1 H); 4.98-4.96 (m, 1 H); 4.51-4.47 (m, 1 H); 4.28-4.15 (m, 2 H). |
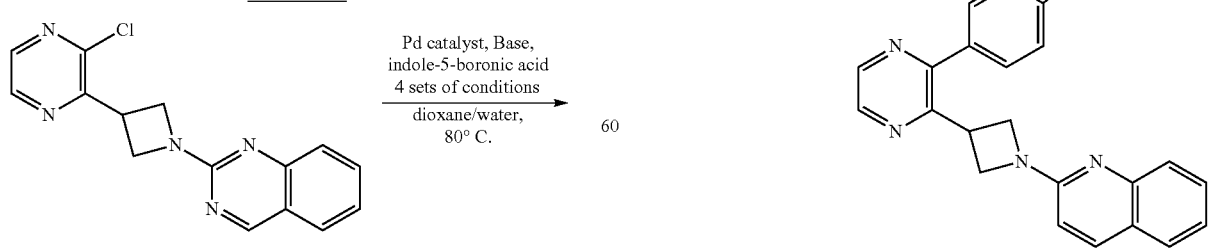
SCHEME 35
Pd catalyst, Base, indole-5-boronic acid
4 sets of conditions
⎯⎯⎯⎯⎯⎯⎯⎯→
dioxane/water, 80° C.
-continued

Example 35.1: 2-(3-(3-(1H-Indol-5-Yl)Pyrazin-2-Yl)Azetidin-1-Yl)Quinazoline

The above example was run in four different flasks under four different sets of reaction conditions. All four flasks were then combined before work up and purified to give the product.

Reaction condition (1): 2M aqueous sodium carbonate (0.252 mL, 0.504 mmol, J. T. Baker) was added to a stirred mixture of 2-(3-(3-chloropyrazin-2-yl)azetidin-1-yl)quinazoline (0.050 g, 0.168 mmol, Preparation 1), indole-5-boronic acid (0.032 g, 0.202 mmol, Frontier Scientific), and trans-dichlorobis(triphenylphosphine)palladium (ii) (0.006 mg, 0.008 mmol, Strem) in 1,4-dioxane (0.7 mL) in a sealed tube under an argon atmosphere. The reaction mixture was stirred at 80° C. for 17 h before being cooled to RT and combined with the other three crude reactions.

Reaction condition (2) 2M aqueous sodium carbonate (0.252 mL, 0.504 mmol, J. T. Baker) was added to a stirred mixture of 2-(3-(3-chloropyrazin-2-yl)azetidin-1-yl)quinazoline (0.050 g, 0.168 mmol, Preparation 1), indole-5-boronic acid (0.032 g, 0.202 mmol, Frontier), and tetrakis(triphenylphosphine)palladium (0.010 g, 0.008 mmol, Strem) in 1,4-dioxane (0.7 mL) in a sealed tube under an argon atmosphere. The reaction mixture was stirred at 80° C. for 17 h before being cooled to RT and combined with the other three crude reactions.

Reaction condition (3) 2-(3-(3-Chloropyrazin-2-yl)azetidin-1-yl)quinazoline (0.050 g, 0.168 mmol, Preparation 1), indole-5-boronic acid (0.032 g, 0.202 mmol, Frontier Scientific), dichloro 1,1'-bis(diphenylphosphino)ferrocene palladium (ii) (0.007 g, 0.008 mmol, Strem), and potassium phosphate (0.035 mL, 0.420 mmol, Aldrich) were mixed in 1,4-dioxane (1.5 mL) and water (0.3 mL) in a sealed tube under an argon atmosphere. The reaction mixture was stirred at 80° C. for 17 h before being cooled to RT and combined with the other three crude reactions Reaction condition (4) 2-(3-(3-Chloropyrazin-2-yl)azetidin-1-yl)quinazoline (0.050 g, 0.168 mmol, Preparation 1), indole-5-boronic acid (0.032 g, 0.202 mmol, Frontier Scientific), bis(di-tert-butyl(4-dimethylaminophenyl)phosphine)dichloropalladium (ii) (0.006 g, 0.008 mmol, Strem), and potassium phosphate (0.089 g, 0.420 mmol, Aldrich) were mixed in 1,4-dioxane (0.8 mL) and water (0.2 mL) in a sealed tube under an argon atmosphere. The reaction mixture was stirred at 80° C. for 17 h before being cooled to RT and combined with the other three crude reactions.

The combined reaction mixtures were diluted with water and extracted with DCM (1×). The organic extract was dried over magnesium sulfate, filtered, and concentrated in vacuo. The resulting crude material was purified via silica gel flash column chromatography eluting with 0% to 100% EtOAc in hexanes to give 0.217 g (85%) of a yellow amorphous solid.

ESI-MS (M+1): 379.1. PDE10 $IC_{50}$ (µM): 0.009.

1H NMR δ (ppm): (400 MHz, d-chloroform) 4.44-4.60 (m, 5H) 6.63 (s, 1H) 7.22 (t, J=7.20 Hz, 1H) 7.30 (d, J=2.00 Hz, 1H) 7.35 (d, J=8.41 Hz, 1H) 7.50 (d, J=8.41 Hz, 1H) 7.59-7.70 (m, 3H) 7.77 (s, 1H) 8.47-8.57 (m, 3H) 9.01 (s, 1H).

The following Table 37 lists compounds of Examples 36.1 to 36.190, which can be made according to the above schemes and preparations.

TABLE 37

Examples 36.1 to 36.190

| Ex. # | Structure | Chemical Name |
|---|---|---|
| 36.1 | 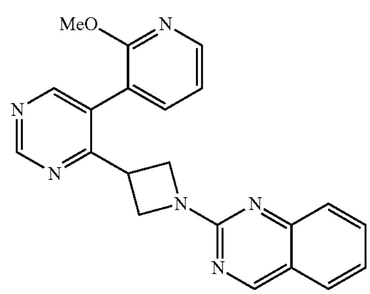 [SMILES: COc1ncccc1-c1cncnc1C1CN(c2ncc3ccccc3n2)C1] | 2-(3-(5-(2-methoxypyridin-3-yl)pyrimidin-4-yl)azetidin-1-yl)quinazoline |
| 36.2 | 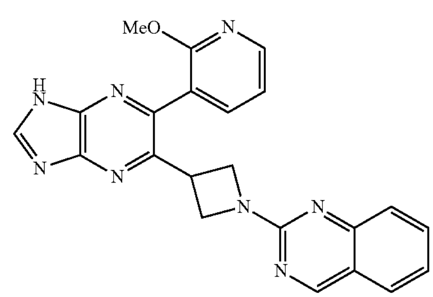 [SMILES: COc1ncccc1-c1nc2[nH]cnc2nc1C1CN(c2ncc3ccccc3n2)C1] | 2-(3-(6-(2-methoxypyridin-3-yl)-1H-imidazo[4,5-b]pyrazin-5-yl)azetidin-1-yl)quinazoline |

TABLE 37-continued

Examples 36.1 to 36.190

| Ex. # | Structure | Chemical Name |
|---|---|---|
| 36.3 | 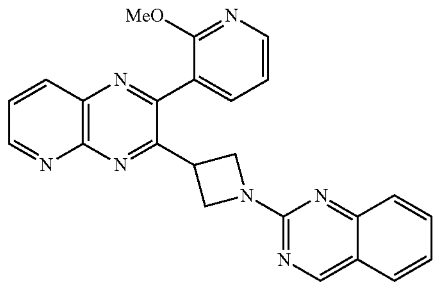 [SMILES: COc1ncccc1-c1nc2cccnc2nc1C1CN(c2ncc3ccccc3n2)C1] | 2-(2-methoxypyridin-3-yl)-3-(1-(quinazolin-2-yl)azetidin-3-yl)pyrido[2,3-b]pyrazine |
| 36.4 | 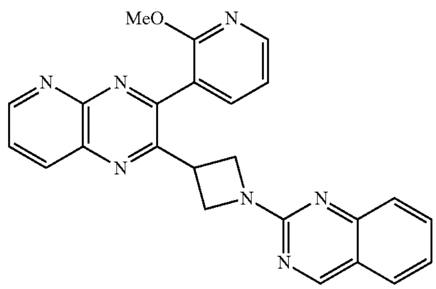 [SMILES: COc1ncccc1-c1nc2ncccc2nc1C1CN(c2ncc3ccccc3n2)C1] | 3-(2-methoxypyridin-3-yl)-2-(1-(quinazolin-2-yl)azetidin-3-yl)pyrido[2,3-b]pyrazine |
| 36.5 | 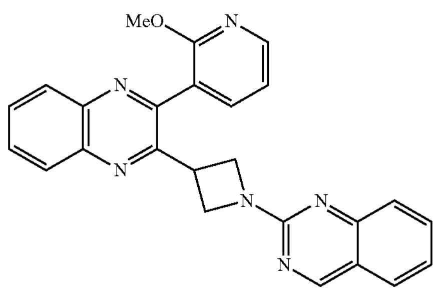 [SMILES: COc1ncccc1-c1nc2ccccc2nc1C1CN(c2ncc3ccccc3n2)C1] | 2-(3-(3-(2-methoxypyridin-3-yl)quinoxalin-2-yl)azetidin-1-yl)quinazoline |
| 36.6 | 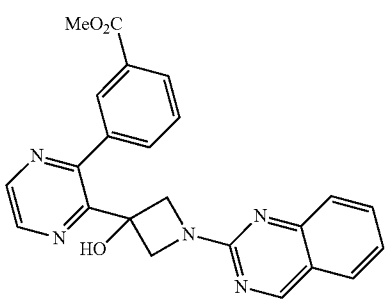 [SMILES: COC(=O)c1cccc(-c2nccnc2C2(O)CN(c3ncc4ccccc4n3)C2)c1] | methyl 3-(3-(3-hydroxy-1-(quinazolin-2-yl)azetidin-3-yl)pyrazin-2-yl)benzoate |
| 36.7 | 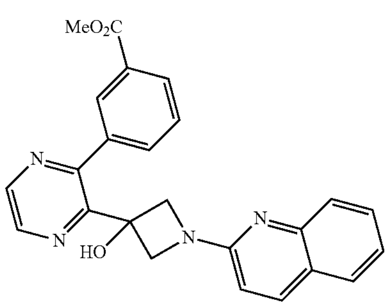 [SMILES: COC(=O)c1cccc(-c2nccnc2C2(O)CN(c3ccc4ccccc4n3)C2)c1] | methyl 3-(3-(3-hydroxy-1-(quinolin-2-yl)azetidin-3-yl)pyrazin-2-yl)benzoate |

TABLE 37-continued

Examples 36.1 to 36.190

| Ex. # | Structure | Chemical Name |
|---|---|---|
| 36.8 | 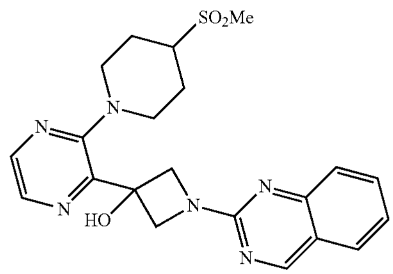 [SMILES: CS(=O)(=O)C1CCN(c2nccnc2C2(O)CN(c3ncc4ccccc4n3)C2)CC1] | 3-(3-(4-(methylsulphonyl)piperidin-1-yl)pyrazin-2-yl)-1-(quinazolin-2-yl)azetidin-3-ol |
| 36.9 | 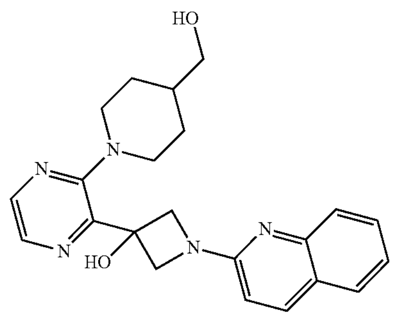 | 3-(3-(4-(hydroxymethyl)piperidin-1-yl)pyrazin-2-yl)-1-(quinolin-2-yl)azetidin-3-ol |
| 36.10 | 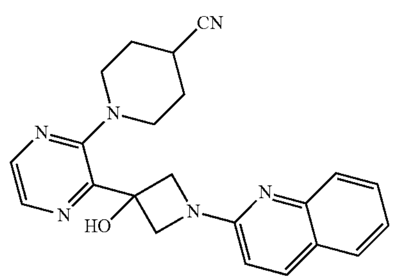 [SMILES: N#CC1CCN(c2nccnc2C2(O)CN(c3ccc4ccccc4n3)C2)CC1] | 1-(3-(3-hydroxy-1-(quinolin-2-yl)azetidin-3-yl)pyrazin-2-yl)piperidine-4-carbonitrile |
| 36.11 | 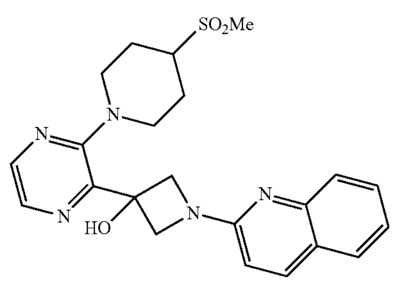 [SMILES: CS(=O)(=O)C1CCN(c2nccnc2C2(O)CN(c3ccc4ccccc4n3)C2)CC1] | 3-(3-(4-(methylsulfonyl)piperidin-1-yl)pyrazin-2-yl)-1-(quinolin-2-yl)azetidin-3-ol |
| 36.12 | 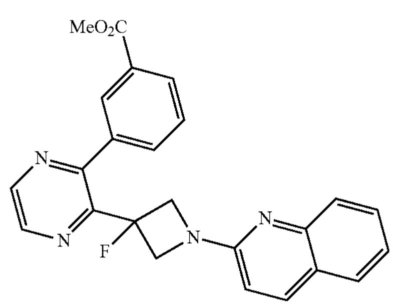 [SMILES: COC(=O)c1cccc(-c2nccnc2C2(F)CN(c3ccc4ccccc4n3)C2)c1] | methyl 3-(3-(3-fluoro-1-(quinolin-2-yl)azetidin-3-yl)pyrazin-2-yl)benzoate |

TABLE 37-continued

Examples 36.1 to 36.190

| Ex. # | Structure | Chemical Name |
|---|---|---|
| 36.13 | 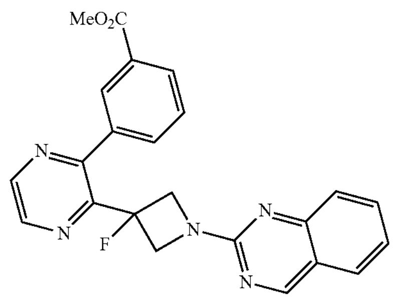 [SMILES: COC(=O)c1cccc(-c2nccnc2C2(F)CN(c3ncc4ccccc4n3)C2)c1] | methyl 3-(3-(3-fluoro-1-(quinazolin-2-yl)azetidin-3-yl)pyrazin-2-yl)benzoate |
| 36.14 | 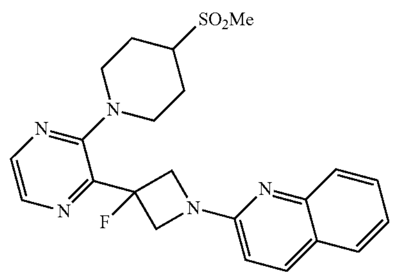 [SMILES: CS(=O)(=O)C1CCN(c2nccnc2C2(F)CN(c3ccc4ccccc4n3)C2)CC1] | 2-(3-fluoro-3-(3-(4-(methylsulfonyl)piperidin-1-yl)pyrazin-2-yl)azetidin-1-yl)quinoline |
| 36.15 | 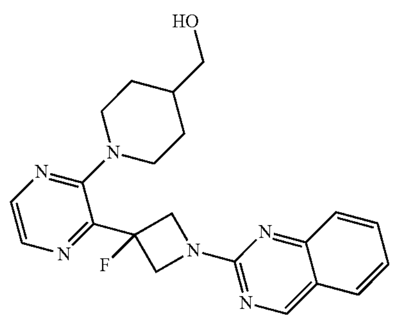 [SMILES: OCC1CCN(c2nccnc2C2(F)CN(c3ncc4ccccc4n3)C2)CC1] | (1-(3-(3-fluoro-1-(quinazolin-2-yl)azetidin-3-yl)pyrazin-2-yl)piperidin-4-yl)methanol |
| 36.16 | 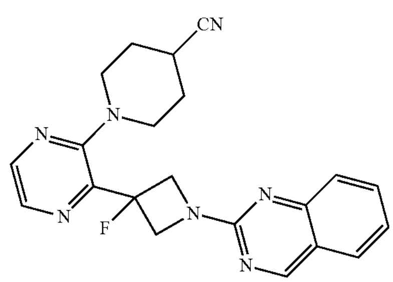 [SMILES: N#CC1CCN(c2nccnc2C2(F)CN(c3ncc4ccccc4n3)C2)CC1] | 1-(3-(3-fluoro-1-(quinazolin-2-yl)azetidin-3-yl)pyrazin-2-yl)piperidine-4-carbonitrile |
| 36.17 | 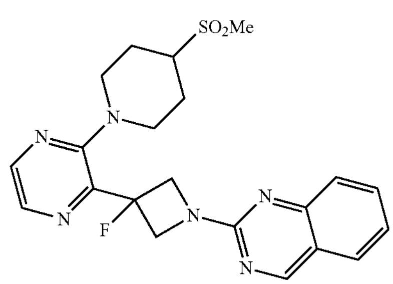 [SMILES: CS(=O)(=O)C1CCN(c2nccnc2C2(F)CN(c3ncc4ccccc4n3)C2)CC1] | 2-(3-fluoro-3-(3-(4-(methylsulfonyl)piperidin-1-yl)pyrazin-2-yl)azetidin-1-yl)quinazoline |

TABLE 37-continued

Examples 36.1 to 36.190

| Ex. # | Structure | Chemical Name |
|---|---|---|
| 36.18 | 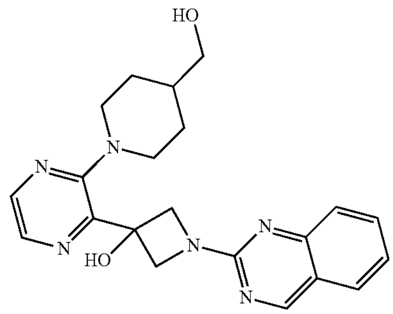 [SMILES: OCC1CCN(c2nccnc2C2(O)CN(c3ncc4ccccc4n3)C2)CC1] | 3-(3-(4-(hydroxymethyl)piperidin-1-yl)pyrazin-2-yl)-1-(quinazolin-2-yl)azetidin-3-ol |
| 36.19 | 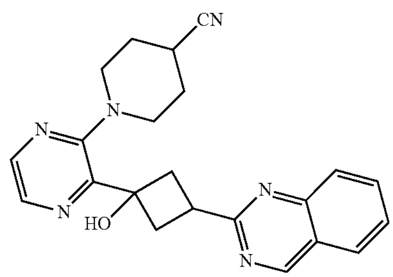 [SMILES: N#CC1CCN(c2nccnc2C2(O)CC(c3ncc4ccccc4n3)C2)CC1] | 1-(3-(1-hydroxy-3-(quinazolin-2-yl)cyclobutyl)pyrazin-2-yl)piperidine-4-carbonitrile |
| 36.20 | 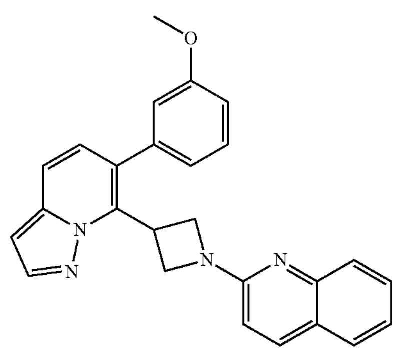 [SMILES: COc1cccc(-c2ccc3ccnn3c2C2CN(c3ccc4ccccc4n3)C2)c1] | 2-(3-(6-(3-methoxyphenyl)pyrazolo[1,5-a]pyridin-7-yl)azetidin-1-yl)quinoline |
| 36.21 | 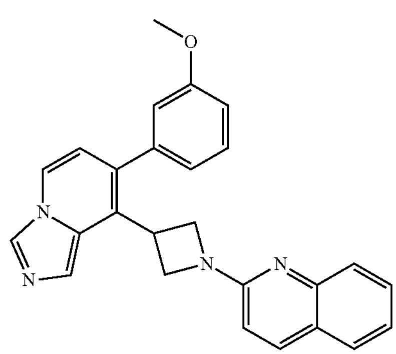 [SMILES: COc1cccc(-c2ccn3cncc3c2C2CN(c3ccc4ccccc4n3)C2)c1] | 2-(3-(7-(3-methoxyphenyl)imidazo[1,5-a]pyridin-8-yl)azetidin-1-yl)quinoline |

TABLE 37-continued

Examples 36.1 to 36.190

| Ex. # | Structure | Chemical Name |
|---|---|---|
| 36.22 | 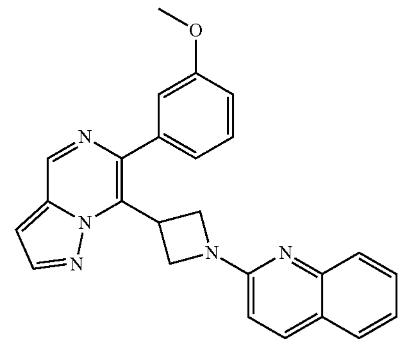 [SMILES: COc1cccc(-c2ncc3ccnn3c2C2CN(c3ccc4ccccc4n3)C2)c1] | 2-(3-(6-(3-methoxyphenyl)pyrazolo(1,5-a]pyrazin-7-yl)azetidin-1-yl)quinoline |
| 36.23 | 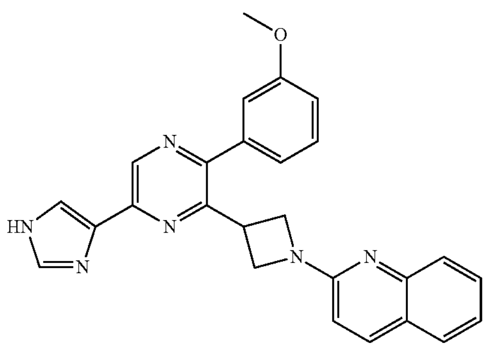 [SMILES: COc1cccc(-c2ncc(-c3c[nH]cn3)nc2C2CN(c3ccc4ccccc4n3)C2)c1] | 2-(3-(6-(1H-imidazol-4-yl)-3-(3-methoxyphenyl)pyrazin-2-yl)azetidin-1-yl)quinoline |
| 36.24 | 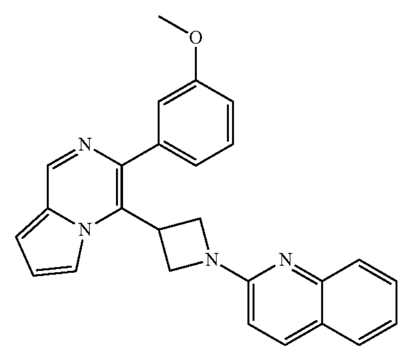 | 2-(3-(3-(3-methoxyphenyl)pyrrolo[1,2-a]pyrazin-4-yl)azetidin-1-yl)quinoline |
| 36.25 | 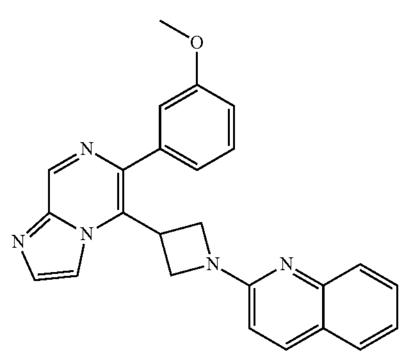 [SMILES: COc1cccc(-c2ncc3nccn3c2C2CN(c3ccc4ccccc4n3)C2)c1] | 2-(3-(6-(3-methoxyphenyl)imidazo[1,2-a]pyrazin-5-yl)azetidin-1-yl)quinoline |

TABLE 37-continued

Examples 36.1 to 36.190

| Ex. # | Structure | Chemical Name |
|---|---|---|
| 36.26 | 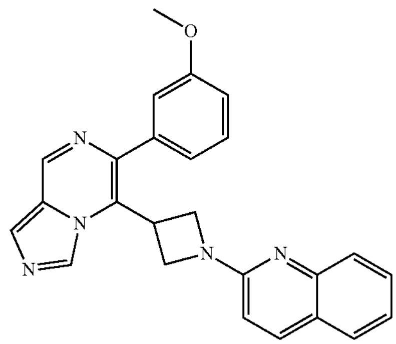 [SMILES: COc1cccc(-c2ncc3cncn3c2C2CN(c3ccc4ccccc4n3)C2)c1] | 2-(3-(6-(3-methoxyphenyl)imidazo[1,5-a]pyrazin-5-yl)azetidin-1-yl)quinoline |
| 36.27 | 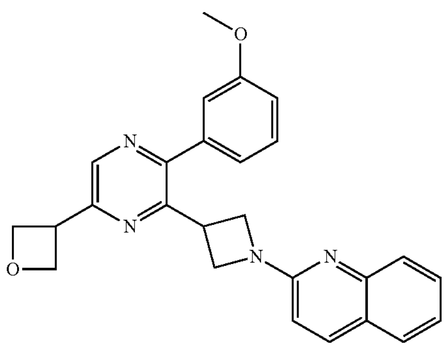 [SMILES: COc1cccc(-c2ncc(C3COC3)nc2C2CN(c3ccc4ccccc4n3)C2)c1] | 2-(3-(3-(3-methoxyphenyl)-6-(oxetan-3-yl)pyrazin-2-yl)azetidin-1-yl)quinoline |
| 36.28 | 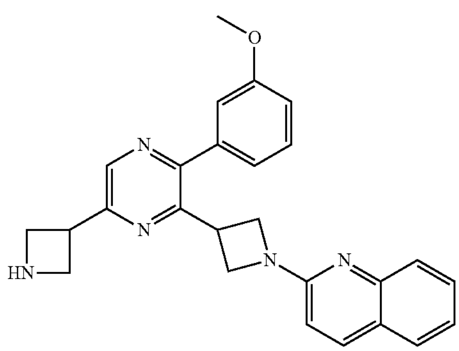 [SMILES: COc1cccc(-c2ncc(C3CNC3)nc2C2CN(c3ccc4ccccc4n3)C2)c1] | 2-(3-(6-(azetidin-3-yl)-3-(3-methoxyphenyl)pyrazin-2-yl)azetidin-1-yl)quinoline |
| 36.29 | 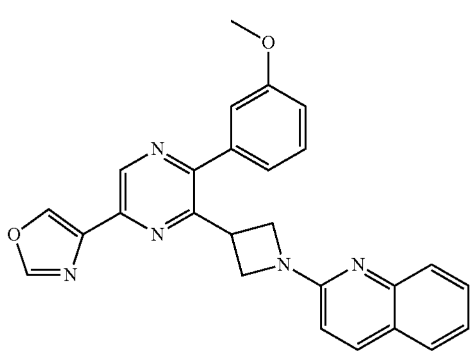 [SMILES: COc1cccc(-c2ncc(-c3cocn3)nc2C2CN(c3ccc4ccccc4n3)C2)c1] | 4-(5-(3-methoxyphenyl)-6-(1-(quinolin-2-yl)azetidin-3-yl)pyrazin-2-yl)oxazole |

TABLE 37-continued

Examples 36.1 to 36.190

| Ex. # | Structure | Chemical Name |
|---|---|---|
| 36.30 | 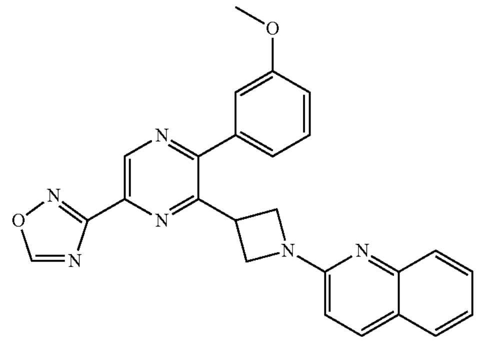 [SMILES: COc1cccc(-c2ncc(-c3ncon3)nc2C2CN(c3ccc4ccccc4n3)C2)c1] | 3-(5-(3-methoxyphenyl)-6-(1-(quinolin-2-yl)azetidin-3-yl)pyrazin-2-yl)-1,2,4-oxadiazole |
| 36.31 | 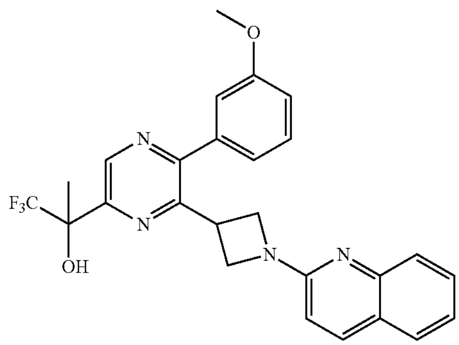 [SMILES: COc1cccc(-c2ncc(C(C)(O)C(F)(F)F)nc2C2CN(c3ccc4ccccc4n3)C2)c1] | 1,1,1-trifluoro-2-(5-(3-methoxyphenyl)-6-(1-(quinolin-2-yl)azetidin-3-yl)pyrazin-2-yl)propan-2-ol |
| 36.32 | 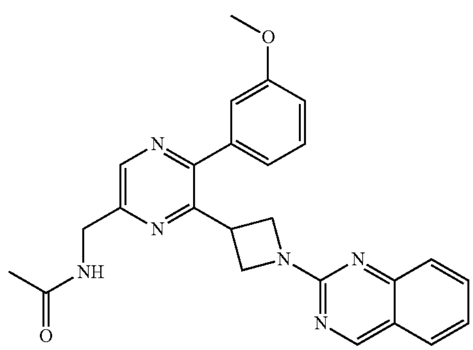 [SMILES: COc1cccc(-c2ncc(CNC(C)=O)nc2C2CN(c3ncc4ccccc4n3)C2)c1] | N-((5-(3-methoxyphenyl)-6-(1-(quinazolin-2-yl)azetidin-3-yl)pyrazin-2-yl)methyl)acetamide |
| 36.33 | 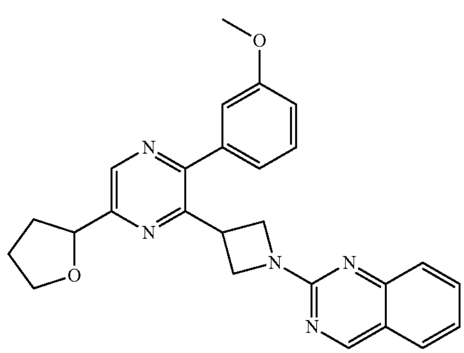 [SMILES: COc1cccc(-c2ncc(C3CCCO3)nc2C2CN(c3ncc4ccccc4n3)C2)c1] | 2-(3-(3-(3-methoxyphenyl)-6-(tetrahydrofuran-2-yl)pyrazin-2-yl)azetidin-1-yl)quinazoline |

TABLE 37-continued

Examples 36.1 to 36.190

| Ex. # | Structure | Chemical Name |
|---|---|---|
| 36.34 | 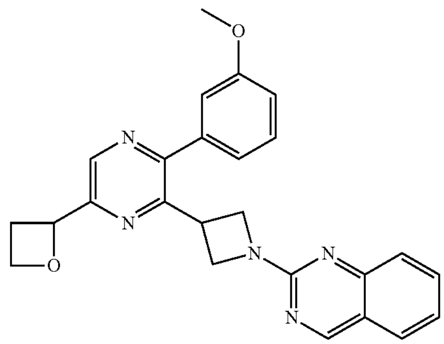 [SMILES: COc1cccc(-c2ncc(C3CCO3)nc2C2CN(c3ncc4ccccc4n3)C2)c1] | 2-(3-(3-(3-methoxyphenyl)-6-(oxetan-2-yl)pyrazin-2-yl)azetidinyl)quinazoline |
| 36.35 | 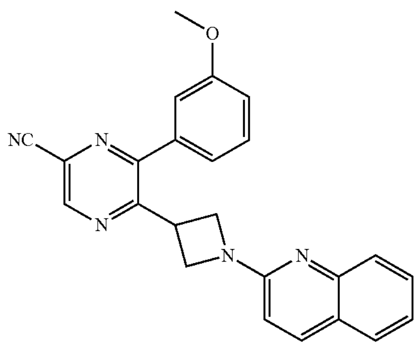 [SMILES: COc1cccc(-c2nc(C#N)cnc2C2CN(c3ccc4ccccc4n3)C2)c1] | 6-(3-methoxyphenyl)-5-(1-(quinolin-2-yl)azetidin-3-yl)pyrazine-2-carbonitrile |
| 36.36 | 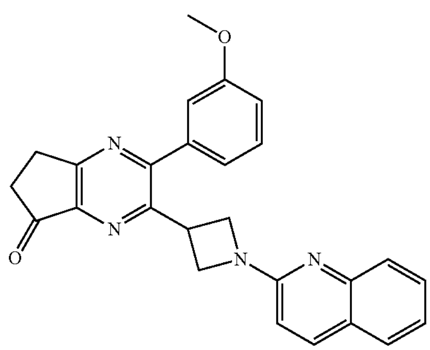 [SMILES: COc1cccc(-c2nc3c(nc2C2CN(c4ccc5ccccc5n4)C2)C(=O)CC3)c1] | 2-(3-methoxyphenyl)-3-(1-(quinolin-2-yl)azetidin-3-yl)-6,7-dihydro-5H-cyclopenta[b]pyrazin-5-one |
| 36.37 | 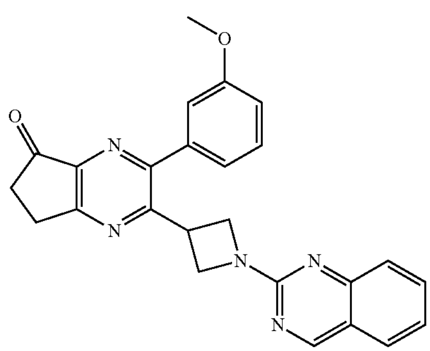 [SMILES: COc1cccc(-c2nc3c(nc2C2CN(c4ncc5ccccc5n4)C2)CCC3=O)c1] | 3-(3-methoxyphenyl)-2-(1-(quinazolin-2-yl)azetidin-3-yl)-6,7-dihydro-5H-cyclopenta[b]pyrazin-5-one |

TABLE 37-continued

Examples 36.1 to 36.190

| Ex. # | Structure | Chemical Name |
|---|---|---|
| 36.38 | 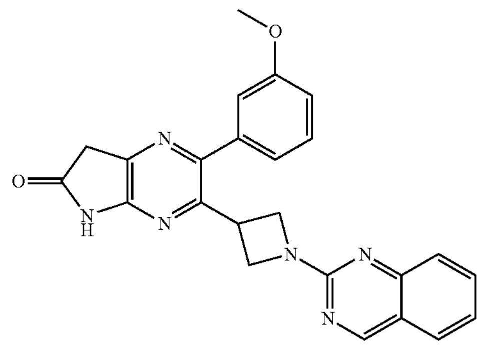 [SMILES: COc1cccc(-c2nc3c(nc2C2CN(c4ncc5ccccc5n4)C2)NC(=O)C3)c1] | 2-(3-methoxyphenyl)-3-(1-(quinazolin-2-yl)azetidin-3-yl)-5H-pyrrolo[2,3-b]pyrazin-6(7H)-one |
| 36.39 | 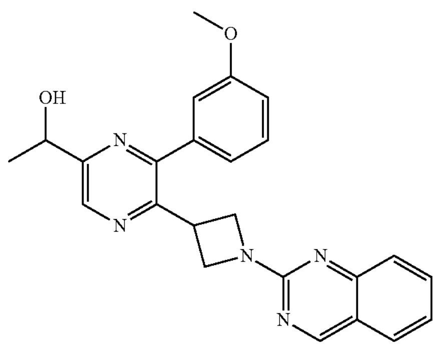 [SMILES: COc1cccc(-c2nc(C(C)O)cnc2C2CN(c3ncc4ccccc4n3)C2)c1] | 1-(6-(3-methoxyphenyl)-5-(1-(quinazolin-2-yl)azetidin-3-yl)pyrazin-2-yl)ethanol |
| 36.40 | 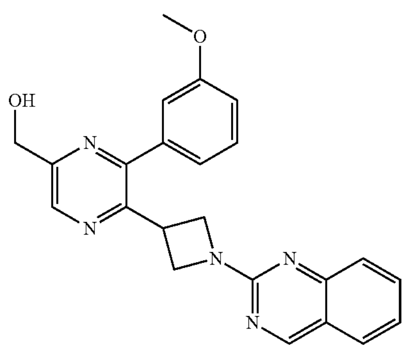 [SMILES: COc1cccc(-c2nc(CO)cnc2C2CN(c3ncc4ccccc4n3)C2)c1] | (6-(3-methoxyphenyl)-5-(1-(quinazolin-2-yl)azetidin-3-yl)pyrazin-2-yl)methanol |
| 36.41 | 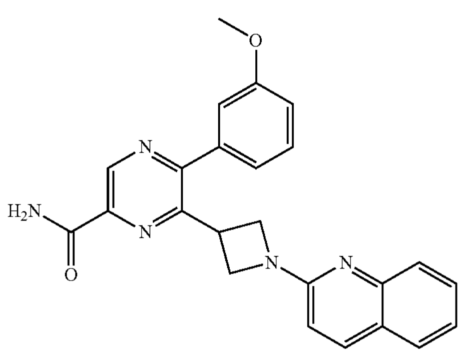 [SMILES: COc1cccc(-c2ncc(C(N)=O)nc2C2CN(c3ccc4ccccc4n3)C2)c1] | 5-(3-methoxyphenyl)-6-(1-(quinolin-2-yl)azetidin-3-yl)pyrazine-2-carboxamide |

TABLE 37-continued

Examples 36.1 to 36.190

| Ex. # | Structure | Chemical Name |
|---|---|---|
| 36.42 | 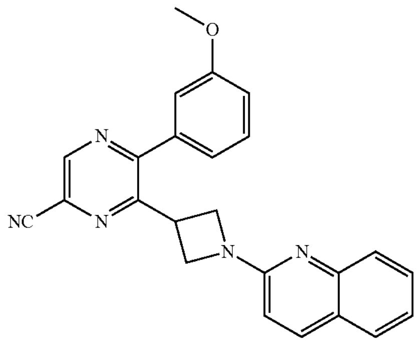 [SMILES: COc1cccc(-c2ncc(C#N)nc2C2CN(c3ccc4ccccc4n3)C2)c1] | 5-(3-methoxyphenyl)-6-(1-(quinolin-2-yl)azetidin-3-yl)pyrazine-2-carbonitrile |
| 36.43 | 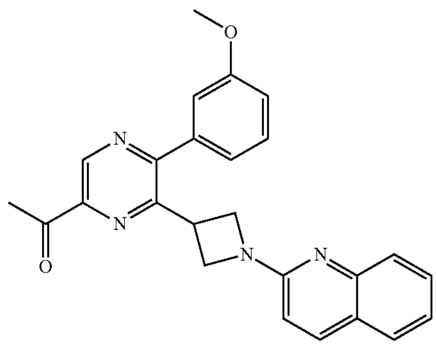 | 1-(5-(3-methoxyphenyl)-6-(1-(quinolin-2-yl)azetidin-3-yl)pyrazin-2-yl)ethanone |
| 36.44 | 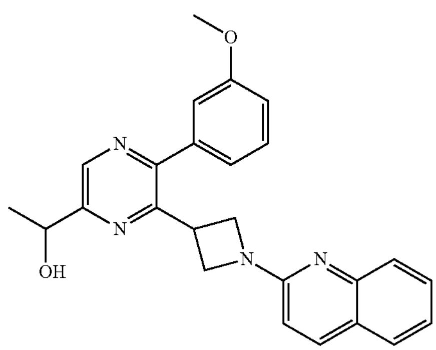 [SMILES: COc1cccc(-c2ncc(C(C)O)nc2C2CN(c3ccc4ccccc4n3)C2)c1] | 1-(5-(3-methoxyphenyl)-6-(1-(quinolin-2-yl)azetidin-3-yl)pyrazin-2-yl)ethanol |
| 36.45 | 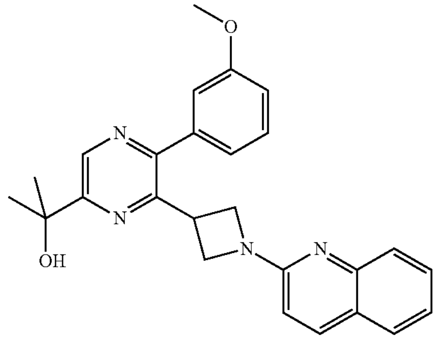 [SMILES: COc1cccc(-c2ncc(C(C)(C)O)nc2C2CN(c3ccc4ccccc4n3)C2)c1] | 2-(5-(3-methoxyphenyl)-6-(1-(quinolin-2-yl)azetidin-3-yl)pyrazin-2-yl)propan-2-ol |

TABLE 37-continued

Examples 36.1 to 36.190

| Ex. # | Structure | Chemical Name |
|---|---|---|
| 36.46 | 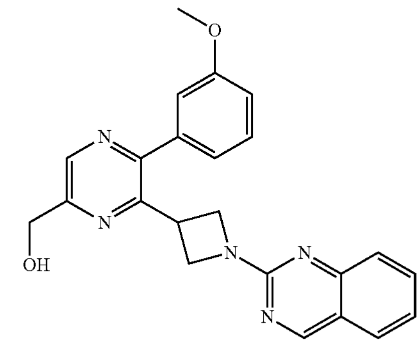 [SMILES: COc1cccc(-c2ncc(CO)nc2C2CN(c3ncc4ccccc4n3)C2)c1] | (5-(3-methoxyphenyl)-6-(1-(quinazolin-2-yl)azetidin-3-yl)pyrazin-2-yl)methanol |
| 36.47 | 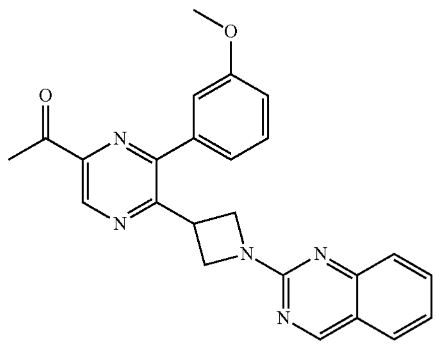 [SMILES: COc1cccc(-c2nc(C(C)=O)cnc2C2CN(c3ncc4ccccc4n3)C2)c1] | 1-(6-(3-methoxyphenyl)-5-(1-(quinazolin-2-yl)azetidin-3-yl)pyrazin-2-yl)ethanone |
| 36.48 | 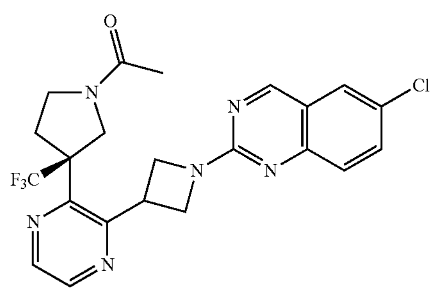 [SMILES: CC(=O)N1CC[C@](c2nccnc2C2CN(c3ccc4cc(Cl)ccc4n3)C2)(C(F)(F)F)C1] | (S)-1-(3-(3-(1-(6-chloroquinazolin-2-yl)azetidin-3-yl)pyrazin-2-yl)-3-(trifluoromethyl)pyrrolidin-1-yl)ethanone |
| 36.49 | 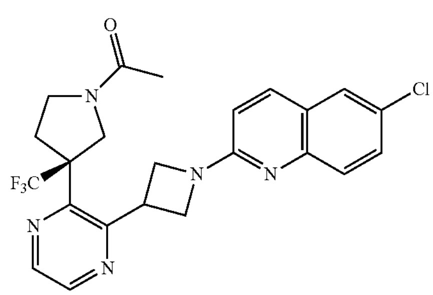 | (S)-1-(3-(3-(1-(6-chloroquinolin-2-yl)azetidin-3-yl)pyrazin-2-yl)-3-(trifluoromethyl)pyrrolidin-1-yl)ethanone |
| 36.50 | 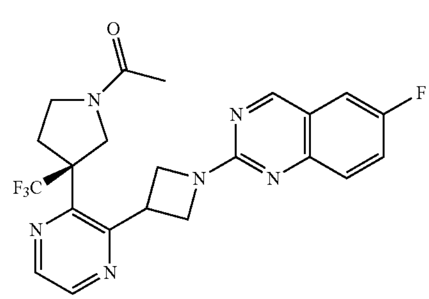 | (S)-1-(3-(3-(1-(6-fluoroquinazolin-2-yl)azetidin-3-yl)pyrazin-2-yl)-3-(trifluoromethyl)pyrrolidin-1-yl)ethanone |

TABLE 37-continued

Examples 36.1 to 36.190

| Ex. # | Structure | Chemical Name |
|---|---|---|
| 36.51 | 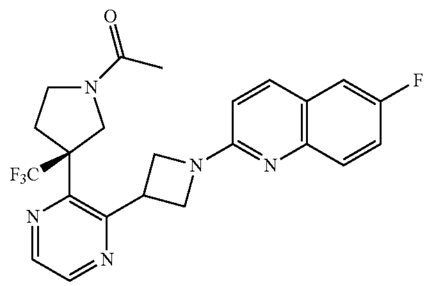 [SMILES: CC(=O)N1CC[C@](c2nccnc2C2CN(c3ncc4cc(F)ccc4n3)C2)(C(F)(F)F)C1] | (S)-1-(3-(3-(1-(6-fluoroquinolin-2-yl)azetidin-3-yl)pyrazin-2-yl)-3-(trifluoromethyl)pyrrolidin-1-yl)ethanone |
| 36.52 | 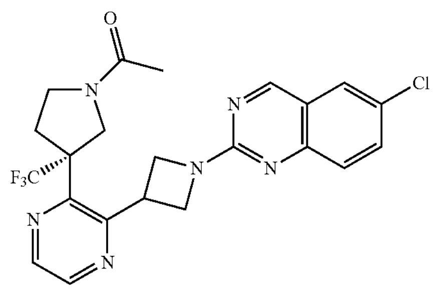 [SMILES: CC(=O)N1CC[C@@](c2nccnc2C2CN(c3ncc4cc(Cl)ccc4n3)C2)(C(F)(F)F)C1] | (R)-1-(3-(3-(1-(6-chloroquinazolin-2-yl)azetidin-3-yl)pyrazin-2-yl)-3-(trifluoromethyl)pyrrolidin-1-yl)ethanone |
| 36.53 | 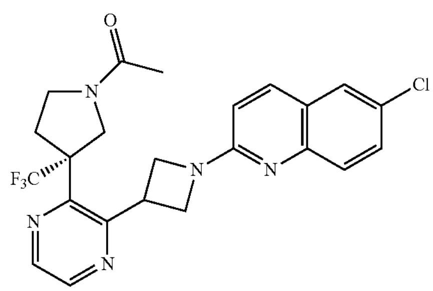 [SMILES: CC(=O)N1CC[C@@](c2nccnc2C2CN(c3ccc4cc(Cl)ccc4n3)C2)(C(F)(F)F)C1] | (R)-1-(3-(3-(1-(6-chloroquinolin-2-yl)azetidin-3-yl)pyrazin-2-yl)-3-(trifluoromethyl)pyrrolidin-1-yl)ethanone |
| 36.54 | 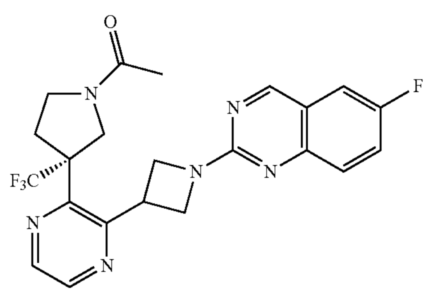 [SMILES: CC(=O)N1CC[C@@](c2nccnc2C2CN(c3ncc4cc(F)ccc4n3)C2)(C(F)(F)F)C1] | (R)-1-(3-(3-(1-(6-fluoroquinazolin-2-yl)azetidin-3-yl)pyrazin-2-yl)-3-(trifluoromethyl)pyrrolidin-1-yl)ethanone |
| 36.55 | 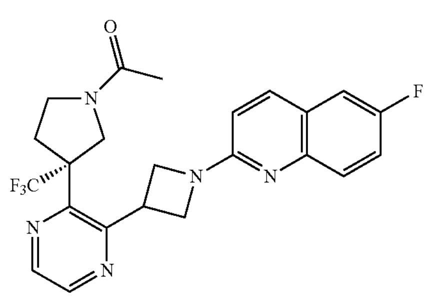 | (R)-1-(3-(3-(1-(6-fluoroquinolin-2-yl)azetidin-3-yl)pyrazin-2-yl)-3-(trifluoromethyl)pyrrolidin-1-yl)ethanone |

TABLE 37-continued

Examples 36.1 to 36.190

| Ex. # | Structure | Chemical Name |
|---|---|---|
| 36.56 | 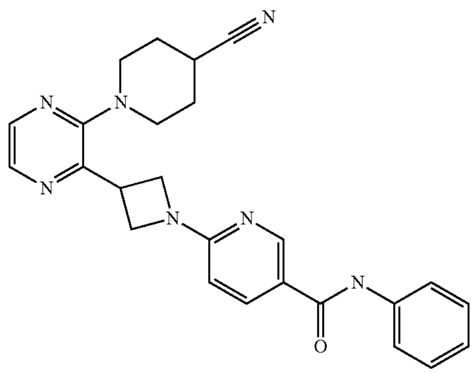 [SMILES: N#CC1CCN(c2nccnc2C2CN(c3ccc(C(=O)Nc4ccccc4)cn3)C2)CC1] | 6-(3-(3-(4-cyanopiperidin-1-yl)pyrazin-2-yl)azetidin-1-yl)-N-phenylnicotinamide |
| 36.57 | 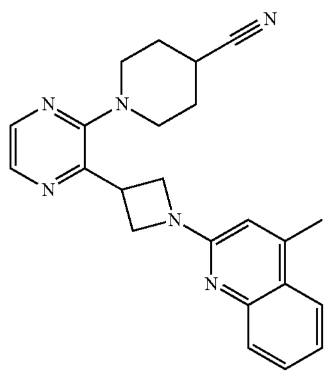 [SMILES: Cc1cc(N2CC(c3nccnc3N3CCC(C#N)CC3)C2)nc2ccccc12] | 1-(3-(1-(4-methylquinolin-2-yl)azetidin-3-yl)pyrazin-2-yl)piperidine-4-carbonitrile |
| 36.58 | 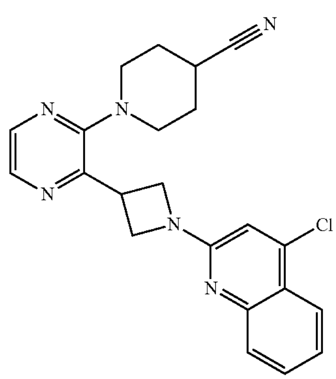 [SMILES: N#CC1CCN(c2nccnc2C2CN(c3cc(Cl)c4ccccc4n3)C2)CC1] | 1-(3-(1-(4-chloroquinolin-2-yl)azetidin-3-yl)pyrazin-2-yl)piperidine-4-carbonitrile |
| 36.59 | 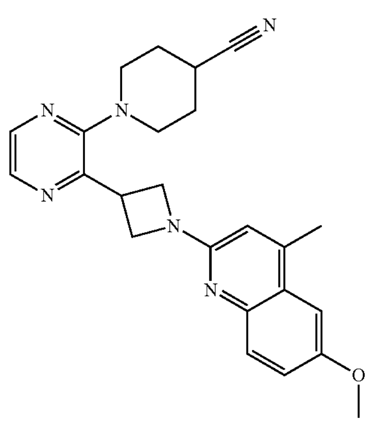 [SMILES: COc1ccc2nc(N3CC(c4nccnc4N4CCC(C#N)CC4)C3)cc(C)c2c1] | 1-(3-(1-(6-methoxy-4-methylquinolin-2-yl)azetidin-3-yl)pyrazin-2-yl)piperidine-4-carbonitrile |

TABLE 37-continued

Examples 36.1 to 36.190

| Ex. # | Structure | Chemical Name |
|---|---|---|
| 36.60 | 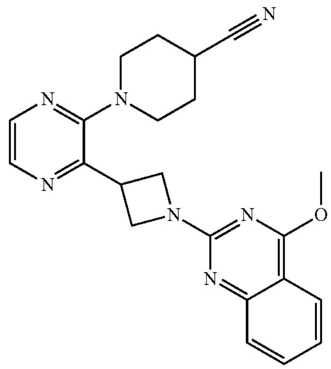 [SMILES: COc1nc(N2CC(c3nccnc3N3CCC(C#N)CC3)C2)nc2ccccc12] | 1-(3-(1-(4-methoxyquinazolin-2-yl)azetidin-3-yl)pyrazin-2-yl)piperidine-4-carbonitrile |
| 36.61 | 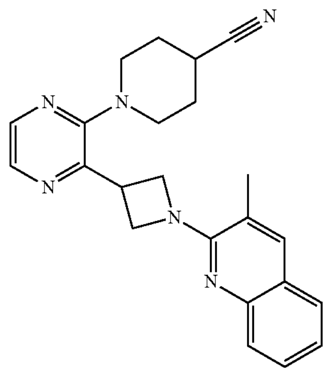 [SMILES: Cc1cc2ccccc2nc1N1CC(c2nccnc2N2CCC(C#N)CC2)C1] | 1-(3-(1-(3-methylquinolin-2-yl)azetidin-3-yl)pyrazin-2-yl)piperidine-4-carbonitrile |
| 36.62 | 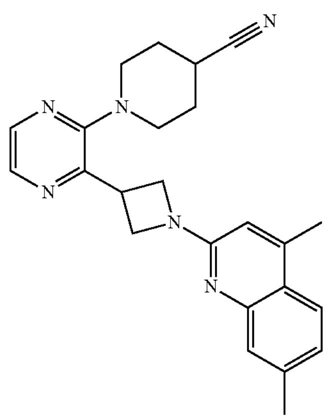 [SMILES: Cc1ccc2c(C)cc(N3CC(c4nccnc4N4CCC(C#N)CC4)C3)nc2c1] | 1-(3-(1-(4,7-dimethylquinolin-2-yl)azetidin-3-yl)pyrazin-2-yl)piperidine-4-carbonitrile |
| 36.63 | 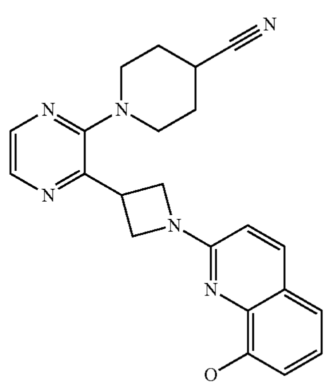 [SMILES: N#CC1CCN(c2nccnc2C2CN(c3ccc4cccc(O)c4n3)C2)CC1] | 1-(3-(1-(8-hydroxyquinolin-2-yl)azetidin-3-yl)pyrazin-2-yl)piperidine-4-carbonitrile |

TABLE 37-continued

Examples 36.1 to 36.190

| Ex. # | Structure | Chemical Name |
|---|---|---|
| 36.64 | 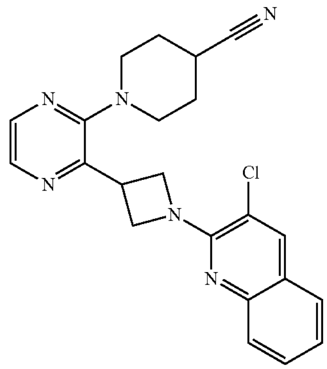 [SMILES: N#CC1CCN(c2nccnc2C2CN(c3nc4ccccc4cc3Cl)C2)CC1] | 1-(3-(1-(3-chloroquinolin-2-yl)azetidin-3-yl)pyrazin-2-yl)piperidine-4-carbonitrile |
| 36.65 | 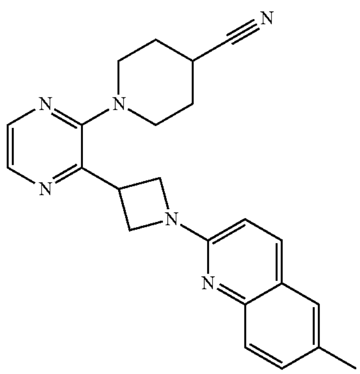 [SMILES: Cc1ccc2nc(N3CC(c4nccnc4N4CCC(C#N)CC4)C3)ccc2c1] | 1-(3-(1-(6-methylquinolin-yl)azetidin-3-yl)pyrazin-2-yl)piperidine-4-carbonitrile |
| 36.66 | 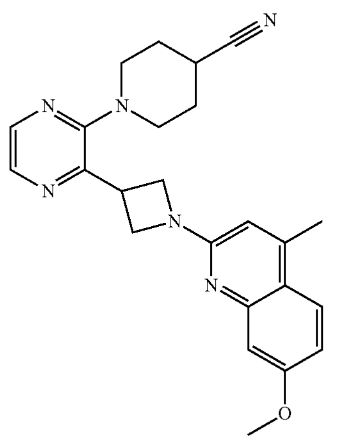 [SMILES: COc1ccc2c(C)cc(N3CC(c4nccnc4N4CCC(C#N)CC4)C3)nc2c1] | 1-(3-(1-(7-methoxy-4-methylquinolin-2-yl)azetidin-3-yl)pyrazin-2-yl)piperidine-4-carbonitrile |
| 36.67 | 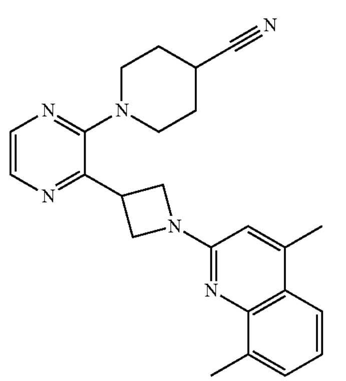 [SMILES: Cc1cc(N2CC(c3nccnc3N3CCC(C#N)CC3)C2)nc2c(C)cccc12] | 1-(3-(1-(4,8-dimethylquinolin-2-yl)azetidin-3-yl)pyrazin-2-yl)piperidine-4-carbonitrile |

TABLE 37-continued

Examples 36.1 to 36.190

| Ex. # | Structure | Chemical Name |
|---|---|---|
| 36.68 | 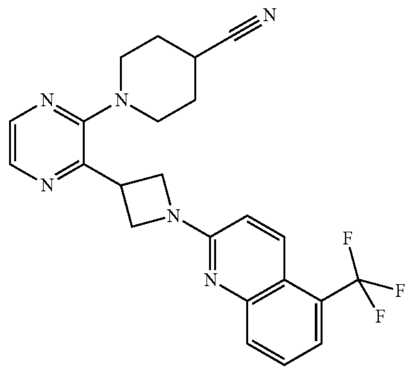 [SMILES: N#CC1CCN(c2nccnc2C2CN(c3ccc4c(C(F)(F)F)cccc4n3)C2)CC1] | 1-(3-(1-(5-(trifluoromethyl)quinolin-2-yl)azetidin-3-yl)pyrazin-2-yl)piperidine-4-carbonitrile |
| 36.69 | 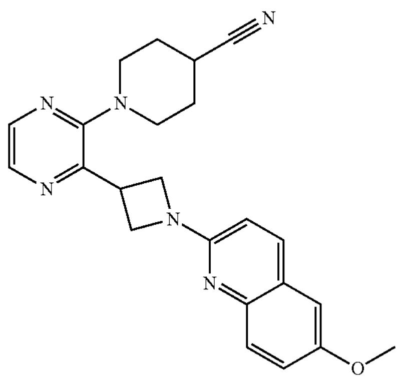 [SMILES: COc1ccc2nc(N3CC(c4nccnc4N4CCC(C#N)CC4)C3)ccc2c1] | 1-(3-(1-(6-methoxyquinolin-2-yl)azetidin-3-yl)pyrazin-2-yl)piperidine-4-carbonitrile |
| 36.70 | 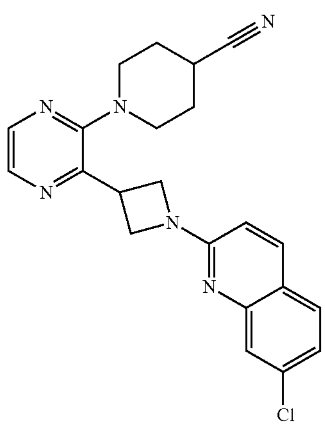 [SMILES: N#CC1CCN(c2nccnc2C2CN(c3ccc4ccc(Cl)cc4n3)C2)CC1] | 1-(3-(1-(7-chloroquinolin-2-yl)azetidin-3-yl)pyrazin-2-yl)piperidine-4-carbonitrile |
| 36.71 | 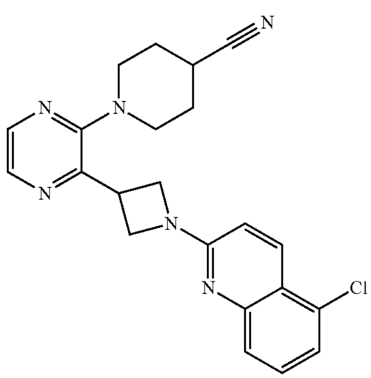 [SMILES: N#CC1CCN(c2nccnc2C2CN(c3ccc4c(Cl)cccc4n3)C2)CC1] | 1-(3-(1-(5-chloroquinolin-2-yl)azetidin-3-yl)pyrazin-2-yl)piperidine-4-carbonitrile |

TABLE 37-continued

Examples 36.1 to 36.190

| Ex. # | Structure | Chemical Name |
|---|---|---|
| 36.72 | 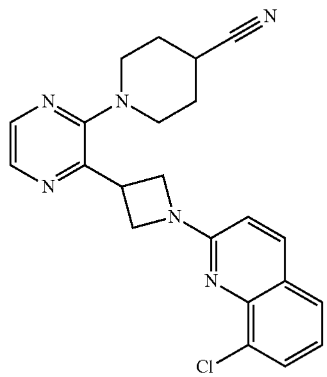 [SMILES: N#CC1CCN(c2nccnc2C2CN(c3ccc4cccc(Cl)c4n3)C2)CC1] | 1-(3-(1-(8-chloroquinolin-2-yl)azetidin-3-yl)pyrazin-2-yl)piperidine-4-carbonitrile |
| 36.73 | 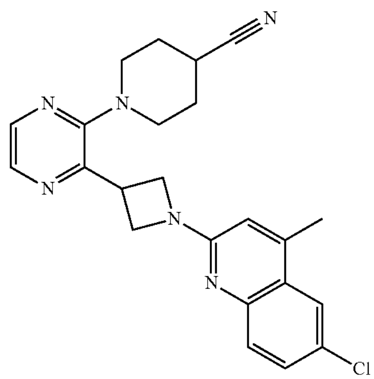 [SMILES: Cc1cc(N2CC(c3nccnc3N3CCC(C#N)CC3)C2)nc2ccc(Cl)cc12] | 1-(3-(1-(6-chloro-4-methylquinolin-2-yl)azetidin-3-yl)pyrazin-2-yl)piperidine-4-carbonitrile |
| 36.74 | 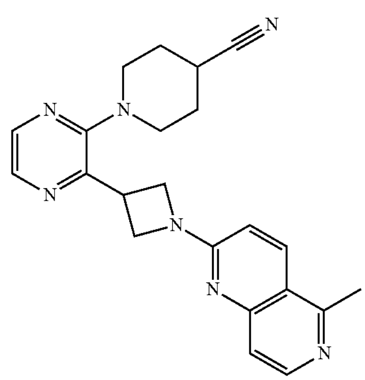 [SMILES: Cc1nccc2nc(N3CC(c4nccnc4N4CCC(C#N)CC4)C3)ccc12] | 1-(3-(1-(5-methyl-1,6-naphthyridin-2-yl)azetidin-3-yl)pyrazin-2-yl)piperidine-4-carbonitrile |
| 36.75 | 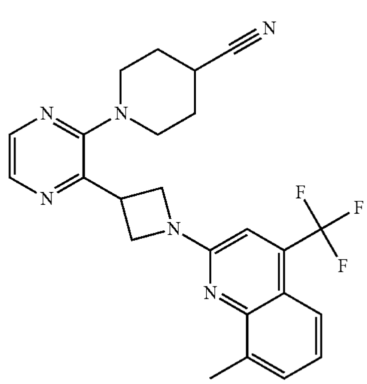 [SMILES: Cc1cccc2c(C(F)(F)F)cc(N3CC(c4nccnc4N4CCC(C#N)CC4)C3)nc12] | 1-(3-(1-(8-methyl-4-(trifluoromethyl)quinolin-2-yl)azetidin-3-yl)pyrazin-2-yl)piperidine-4-carbonitrile |

TABLE 37-continued
Examples 36.1 to 36.190
| Ex. # | Structure | Chemical Name |
|---|---|---|
| 36.76 | 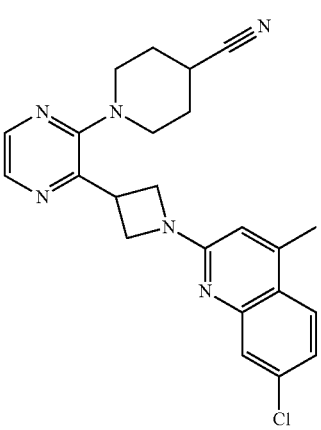 [SMILES: Cc1cc(N2CC(c3nccnc3N3CCC(C#N)CC3)C2)nc2cc(Cl)ccc12] | 1-(3-(1-(7-chloro-4-methylquinolin-2-yl)azetidin-3-yl)pyrazin-2-yl)piperidine-4-carbonitrile |
| 36.77 | 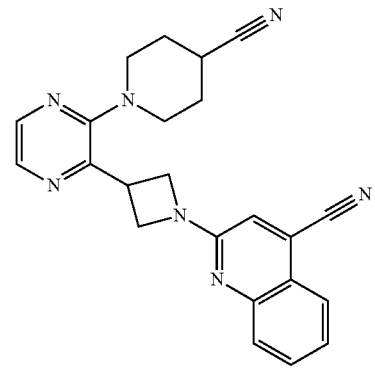 [SMILES: N#Cc1cc(N2CC(c3nccnc3N3CCC(C#N)CC3)C2)nc2ccccc12] | 2-(3-(3-(4-cyanopiperidin-1-yl)pyrazin-2-yl)azetidin-1-yl)quinoline-4-carbonitrile |
| 36.78 | 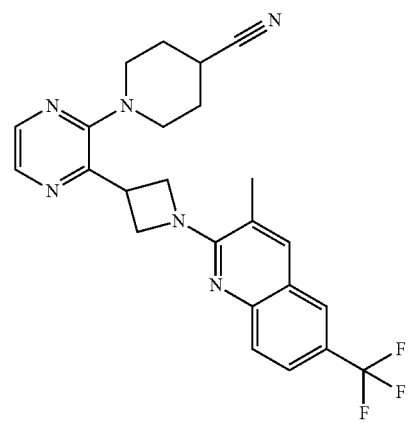 [SMILES: Cc1cc2cc(C(F)(F)F)ccc2nc1N1CC(c2nccnc2N2CCC(C#N)CC2)C1] | 1-(3-(1-(3-methyl-6-(trifluoromethyl)quinolin-2-yl)azetidin-3-yl)pyrazin-2-yl)piperidine-4-carbonitrile |

TABLE 37-continued

Examples 36.1 to 36.190

| Ex. # | Structure | Chemical Name |
|---|---|---|
| 36.79 | 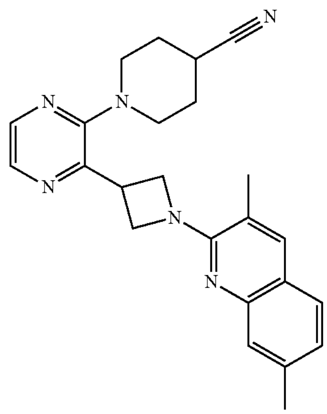 [SMILES: Cc1ccc2cc(C)c(N3CC(c4nccnc4N4CCC(C#N)CC4)C3)nc2c1] | 1-(3-(1-(3,7-dimethylquinolin-2-yl)azetidin-3-yl)pyrazin-2-yl)piperidine-4-carbonitrile |
| 36.80 | 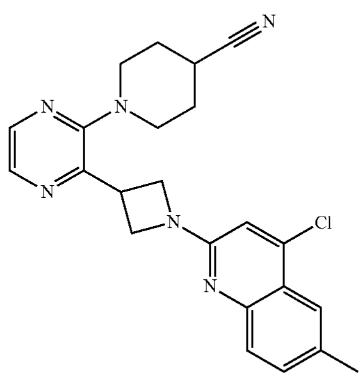 [SMILES: Cc1ccc2nc(N3CC(c4nccnc4N4CCC(C#N)CC4)C3)cc(Cl)c2c1] | 1-(3-(1-(4-chloro-6-methylquinolin-2-yl)azetidin-3-yl)pyrazin-2-yl)piperidine-4-carbonitrile |
| 36.81 | 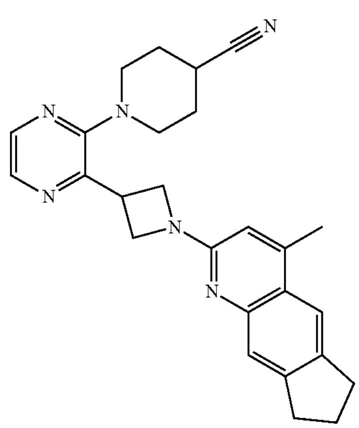 [SMILES: Cc1cc(N2CC(c3nccnc3N3CCC(C#N)CC3)C2)nc2cc3c(cc12)CCC3] | 1-(3-(1-(4-methyl-7,8-dihydro-6H-cyclopenta[g]quinolin-2-yl)azetidin-3-yl)pyrazin-2-yl)piperidine-4-carbonitrile |

TABLE 37-continued

Examples 36.1 to 36.190

| Ex. # | Structure | Chemical Name |
|---|---|---|
| 36.82 | 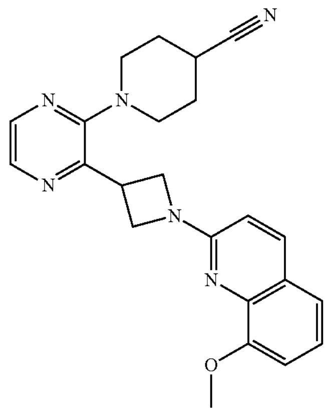 [SMILES: COc1cccc2ccc(N3CC(c4nccnc4N4CCC(C#N)CC4)C3)nc12] | 1-(3-(1-(8-methoxyquinolin-2-yl)azetidin-3-yl)pyrazin-2-yl)piperidine-4-carbonitrile |
| 36.83 | 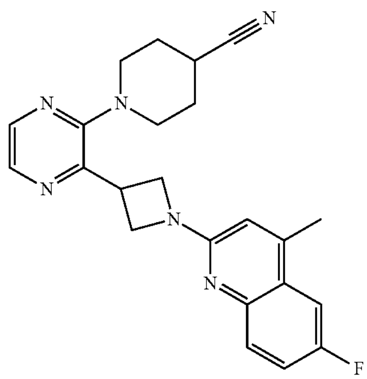 [SMILES: Cc1cc(N2CC(c3nccnc3N3CCC(C#N)CC3)C2)nc2ccc(F)cc12] | 1-(3-(1-(6-fluoro-4-methylquinolin-2-yl)azetidin-3-yl)pyrazin-2-yl)piperidine-4-carbonitrile |
| 36.84 | 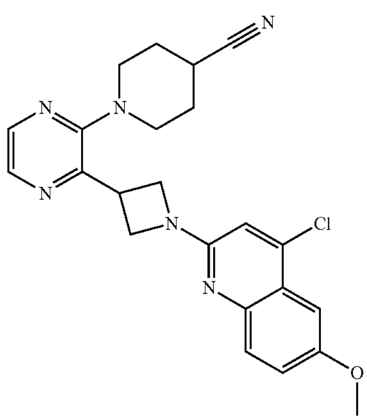 [SMILES: COc1ccc2nc(N3CC(c4nccnc4N4CCC(C#N)CC4)C3)cc(Cl)c2c1] | 1-(3-(1-(4-chloro-6-methoxyquinolin-2-yl)azetidin-3-yl)pyrazin-2-yl)piperidine-4-carbonitrile |
| 36.85 | 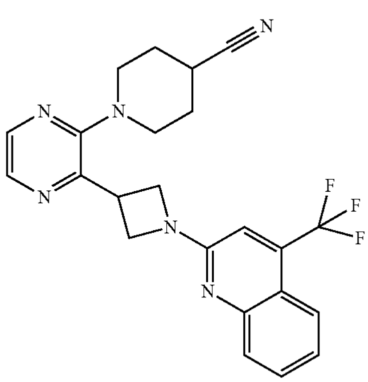 [SMILES: N#CC1CCN(c2nccnc2C2CN(c3cc(C(F)(F)F)c4ccccc4n3)C2)CC1] | 1-(3-(1-(4-(trifluoromethyl)quinolin-2-yl)azetidin-3-yl)pyrazin-2-yl)piperidine-4-carbonitrile |

TABLE 37-continued
Examples 36.1 to 36.190
| Ex. # | Structure | Chemical Name |
|---|---|---|
| 36.86 | 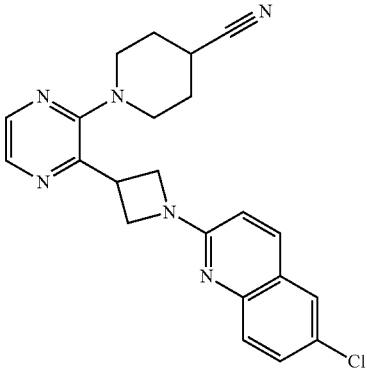 [SMILES: N#CC1CCN(c2nccnc2C2CN(c3ccc4cc(Cl)ccc4n3)C2)CC1] | 1-(3-(1-(6-chloroquinolin-2-yl)azetidin-3-yl)pyrazin-2-yl)piperidine-4-carbonitrile |
| 36.87 | 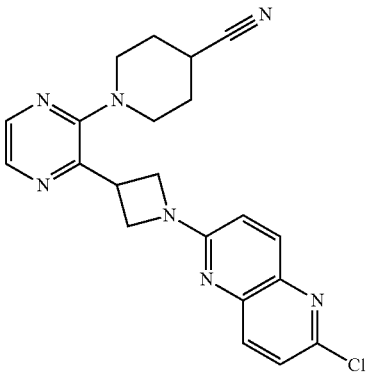 [SMILES: N#CC1CCN(c2nccnc2C2CN(c3ccc4nc(Cl)ccc4n3)C2)CC1] | 1-(3-(1-(6-chloro-1,5-naphthyridin-2-yl)azetidin-3-yl)pyrazin-2-yl)piperidine-4-carbonitrile |
| 36.88 | 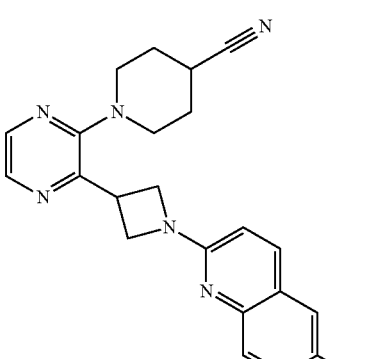 | 1-(3-(1-(6-bromoquinolin-2-yl)azetidin-3-yl)pyrazin-2-yl)piperidine-4-carbonitrile |
| 36.89 | 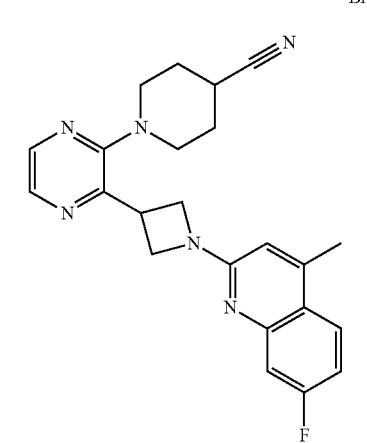 | 1-(3-(1-(7-fluoro-4-methylquinolin-2-yl)azetidin-3-yl)pyrazin-2-yl)piperidine-4-carbonitrile |

TABLE 37-continued
Examples 36.1 to 36.190
| Ex. # | Structure | Chemical Name |
|---|---|---|
| 36.90 | 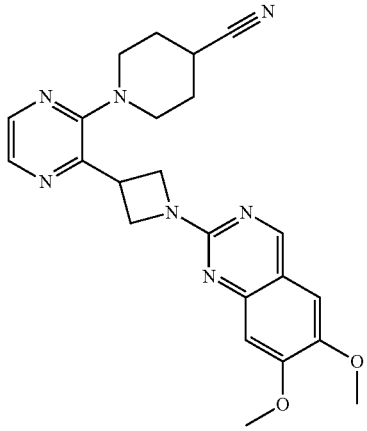 [SMILES: COc1cc2cnc(N3CC(c4nccnc4N4CCC(C#N)CC4)C3)nc2cc1OC] | 1-(3-(1-(6,7-dimethoxyquinazolin-2-yl)azetidin-3-yl)pyrazin-2-yl)piperidine-4-carbonitrile |
| 36.91 | 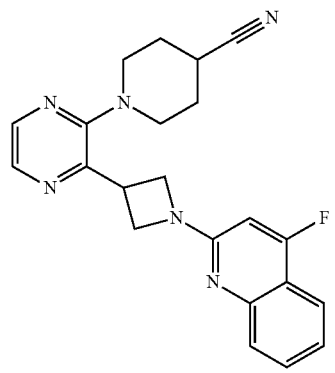 [SMILES: N#CC1CCN(c2nccnc2C2CN(c3cc(F)c4ccccc4n3)C2)CC1] | 1-(3-(1-(4-fluoroquinolin-2-yl)azetidin-3-yl)pyrazin-2-yl)piperidine-4-carbonitrile |
| 36.92 | 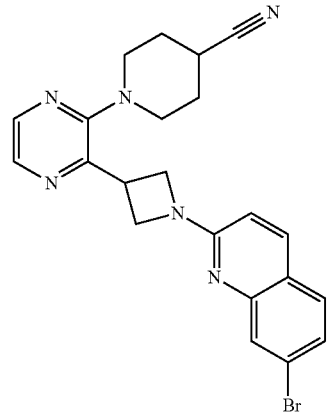 [SMILES: N#CC1CCN(c2nccnc2C2CN(c3ccc4ccc(Br)cc4n3)C2)CC1] | 1-(3-(1-(7-bromoquinolin-2-yl)azetidin-3-yl)pyrazin-2-yl)piperidine-4-carbonitrile |

TABLE 37-continued
Examples 36.1 to 36.190
| Ex. # | Structure | Chemical Name |
|---|---|---|
| 36.93 | 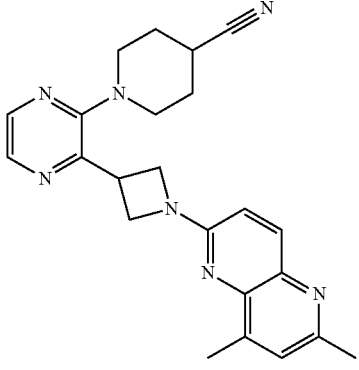 [SMILES: Cc1cc(C)c2nc(N3CC(c4nccnc4N4CCC(C#N)CC4)C3)ccc2n1] | 1-(3-(1-(6,8-dimethyl-1,5-naphthyridin-2-yl)azetidin-3-yl)pyrazin-2-yl)piperidine-4-carbonitrile |
| 36.94 | 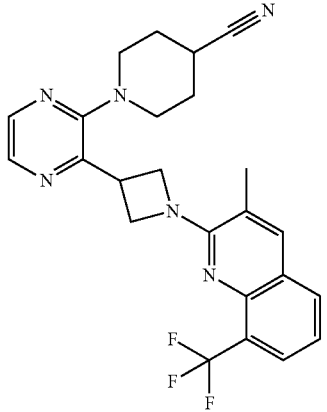 [SMILES: Cc1cc2cccc(C(F)(F)F)c2nc1N1CC(c2nccnc2N2CCC(C#N)CC2)C1] | 1-(3-(1-(3-methyl-8-(trifluoromethyl)quinolin-2-yl)azetidin-3-yl)pyrazin-2-yl)piperidine-4-carbonitrile |
| 36.95 | 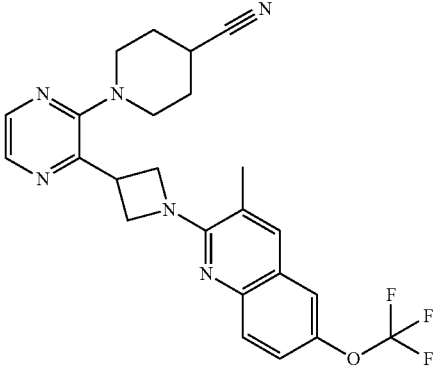 [SMILES: Cc1cc2cc(OC(F)(F)F)ccc2nc1N1CC(c2nccnc2N2CCC(C#N)CC2)C1] | 1-(3-(1-(3-methyl-6-(trifluoromethoxy)quinolin-2-yl)azetidin-3-yl)pyrazin-2-yl)piperidine-4-carbonitrile |

TABLE 37-continued

Examples 36.1 to 36.190

| Ex. # | Structure | Chemical Name |
|---|---|---|
| 36.96 | 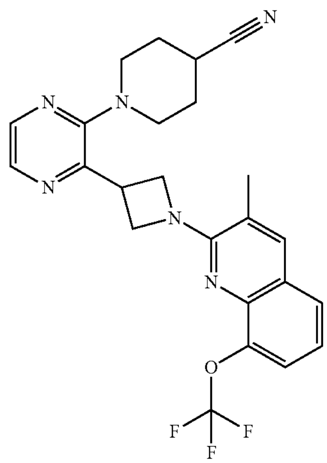 [SMILES: Cc1cc2cccc(OC(F)(F)F)c2nc1N1CC(c2nccnc2N2CCC(C#N)CC2)C1] | 1-(3-(1-(3-methyl-8-(trifluoromethoxy)quinolin-2-yl)azetidin-3-yl)pyrazin-2-yl)piperidine-4-carbonitrile |
| 36.97 | 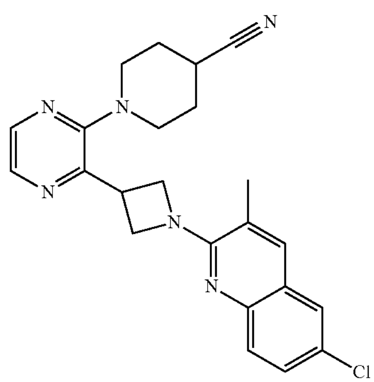 [SMILES: Cc1cc2cc(Cl)ccc2nc1N1CC(c2nccnc2N2CCC(C#N)CC2)C1] | 1-(3-(1-(6-chloro-3-methylquinolin-2-yl)azetidin-3-yl)pyrazin-2-yl)piperidine-4-carbonitrile |
| 36.98 | 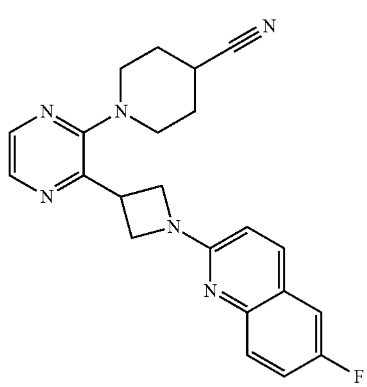 [SMILES: N#CC1CCN(c2nccnc2C2CN(c3ccc4cc(F)ccc4n3)C2)CC1] | 1-(3-(1-(6-fluoroquinolin-2-yl)azetidin-3-yl)pyrazin-2-yl)piperidine-4-carbonitrile |

TABLE 37-continued

Examples 36.1 to 36.190

| Ex. # | Structure | Chemical Name |
|---|---|---|
| 36.99 | 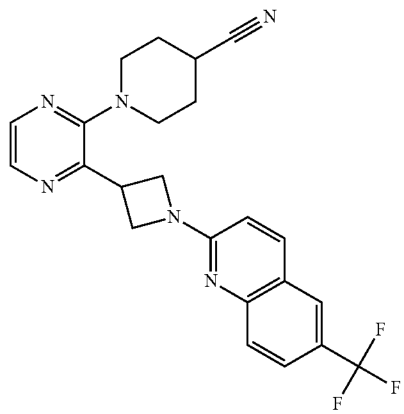 [SMILES: N#CC1CCN(c2nccnc2C2CN(c3ccc4cc(C(F)(F)F)ccc4n3)C2)CC1] | 1-(3-(1-(6-(trifluoromethyl)quinolin-2-yl)azetidin-3-yl)pyrazin-2-yl)piperidine-4-carbonitrile |
| 36.100 | 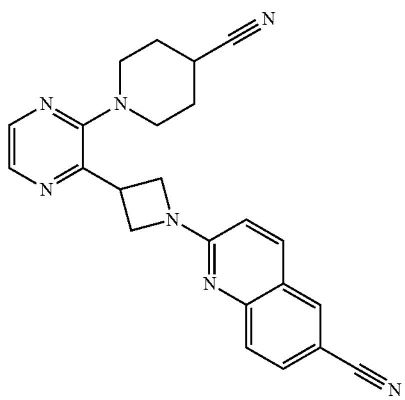 [SMILES: N#Cc1ccc2nc(N3CC(c4nccnc4N4CCC(C#N)CC4)C3)ccc2c1] | 2-(3-(3-(4-cyanopiperidin-1-yl)pyrazin-2-yl)azetidin-1-yl)quinoline-6-carbonitrile |
| 36.101 | 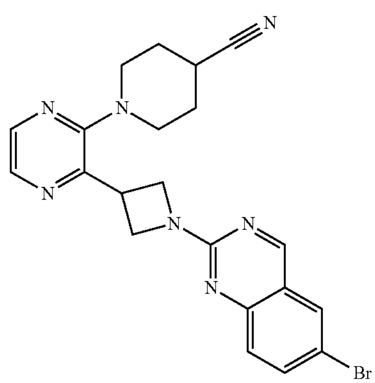 [SMILES: N#CC1CCN(c2nccnc2C2CN(c3ncc4cc(Br)ccc4n3)C2)CC1] | 1-(3-(1-(6-bromoquinazolin-2-yl)azetidin-3-yl)pyrazin-2-yl)piperidine-4-carbonitrile |

TABLE 37-continued

Examples 36.1 to 36.190

| Ex. # | Structure | Chemical Name |
|---|---|---|
| 36.102 | 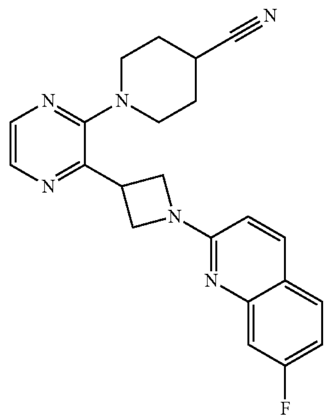 [SMILES: N#CC1CCN(c2nccnc2C2CN(c3ccc4ccc(F)cc4n3)C2)CC1] | 1-(3-(1-(7-fluoroquinolin-2-yl)azetidin-3-yl)pyrazin-2-yl)piperidine-4-carbonitrile |
| 36.103 | 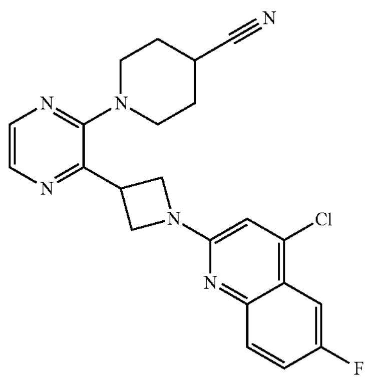 [SMILES: N#CC1CCN(c2nccnc2C2CN(c3cc(Cl)c4cc(F)ccc4n3)C2)CC1] | 1-(3-(1-(4-chloro-6-fluoroquinolin-2-yl)azetidin-3-yl)pyrazin-2-yl)piperidine-4-carbonitrile |
| 36.104 | 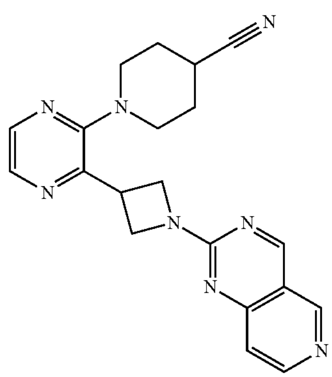 [SMILES: N#CC1CCN(c2nccnc2C2CN(c3ncc4cnccc4n3)C2)CC1] | 1-(3-(1-(pyrido[4,3-d]pyrimidin-2-yl)azetidin-3-yl)pyrazin-2-yl)piperidine-4-carbonitrile |
| 36.105 | 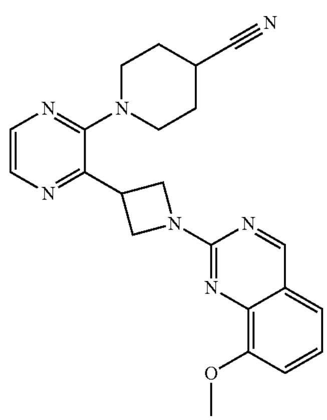 [SMILES: COc1cccc2cnc(N3CC(c4nccnc4N4CCC(C#N)CC4)C3)nc12] | 1-(3-(1-(8-methoxyquinazolin-2-yl)azetidin-3-yl)pyrazin-2-yl)piperidine-4-carbonitrile |

TABLE 37-continued

Examples 36.1 to 36.190

| Ex. # | Structure | Chemical Name |
|---|---|---|
| 36.106 | 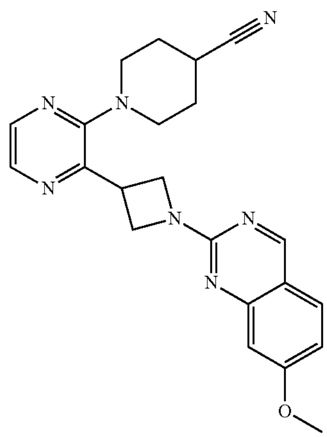 [SMILES: COc1ccc2cnc(N3CC(c4nccnc4N4CCC(C#N)CC4)C3)nc2c1] | 1-(3-(1-(7-methoxyquinazolin-2-yl)azetidin-3-yl)pyrazin-2-yl)piperidine-4-carbonitrile |
| 36.107 | 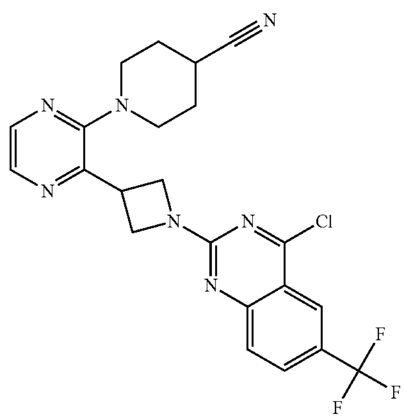 [SMILES: N#CC1CCN(c2nccnc2C2CN(c3nc(Cl)c4cc(C(F)(F)F)ccc4n3)C2)CC1] | 1-(3-(1-(4-chloro-6-(trifluoromethyl)quinazolin-2-yl)azetidin-3-yl)pyrazin-2-yl)piperidine-4-carbonitrile |
| 36.108 | 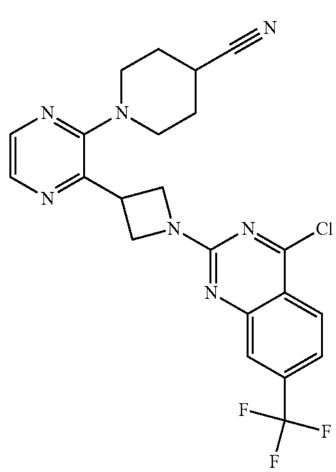 [SMILES: N#CC1CCN(c2nccnc2C2CN(c3nc(Cl)c4ccc(C(F)(F)F)cc4n3)C2)CC1] | 1-(3-(1-(4-chloro-7-(trifluoromethyl)quinazolin-2-yl)azetidin-3-yl)pyrazin-2-yl)piperidine-4-carbonitrile |

TABLE 37-continued

Examples 36.1 to 36.190

| Ex. # | Structure | Chemical Name |
|---|---|---|
| 36.109 | 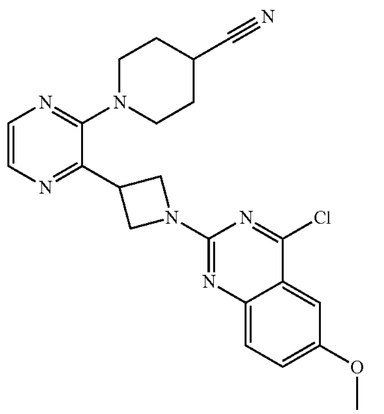 [SMILES: COc1ccc2nc(N3CC(c4nccnc4N4CCC(C#N)CC4)C3)nc(Cl)c2c1] | 1-(3-(1-(4-chloro-6-methoxyquinazolin-2-yl)azetidin-3-yl)pyrazin-2-yl)piperidine-4-carbonitrile |
| 36.110 | 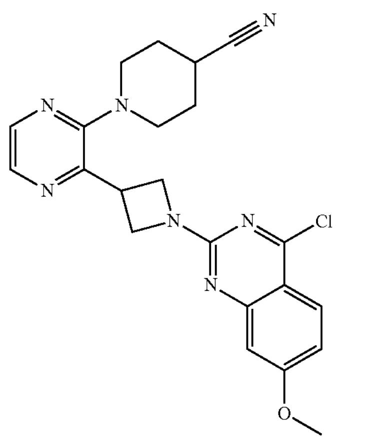 [SMILES: COc1ccc2c(Cl)nc(N3CC(c4nccnc4N4CCC(C#N)CC4)C3)nc2c1] | 1-(3-(1-(4-chloro-7-methoxyquinazolin-2-yl)azetidin-3-yl)pyrazin-2-yl)piperidine-4-carbonitrile |
| 36.111 | 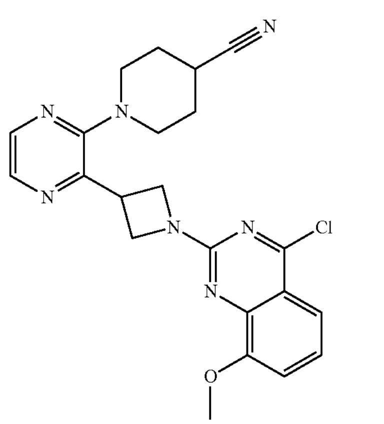 [SMILES: COc1cccc2c(Cl)nc(N3CC(c4nccnc4N4CCC(C#N)CC4)C3)nc12] | 1-(3-(1-(4-chloro-8-methoxyquinazolin-2-yl)azetidin-3-yl)pyrazin-2-yl)piperidine-4-carbonitrile |

TABLE 37-continued

Examples 36.1 to 36.190

| Ex. # | Structure | Chemical Name |
|---|---|---|
| 36.112 | 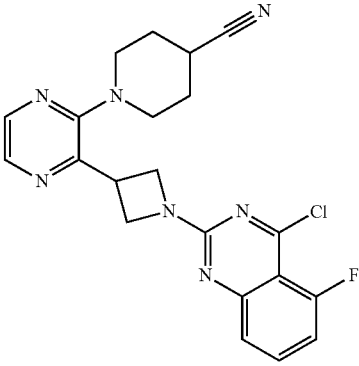 [SMILES: N#CC1CCN(c2nccnc2C2CN(c3nc(Cl)c4c(F)cccc4n3)C2)CC1] | 1-(3-(1-(4-chloro-5-fluoroquinazolin-2-yl)azetidin-3-yl)pyrazin-2-yl)piperidine-4-carbonitrile |
| 36.113 | 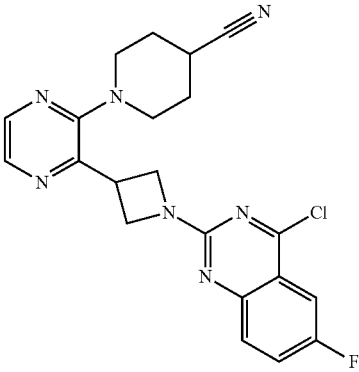 [SMILES: N#CC1CCN(c2nccnc2C2CN(c3nc(Cl)c4cc(F)ccc4n3)C2)CC1] | 1-(3-(1-(4-chloro-6-fluoroquinazolin-2-yl)azetidin-3-yl)pyrazin-2-yl)piperidine-4-carbonitrile |
| 36.114 | 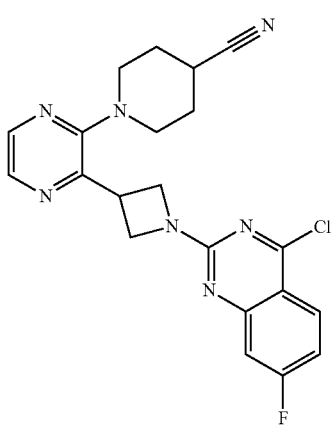 | 1-(3-(1-(4-chloro-7-fluoroquinazolin-2-yl)azetidin-3-yl)pyrazin-2-yl)piperidine-4-carbonitrile |
| 36.115 | 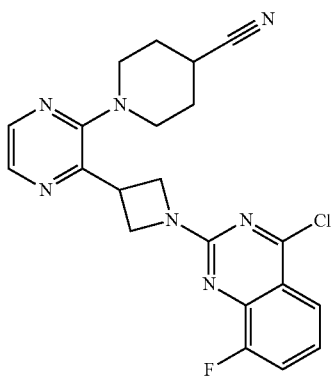 [SMILES: N#CC1CCN(c2nccnc2C2CN(c3nc(Cl)c4cccc(F)c4n3)C2)CC1] | 1-(3-(1-(4-chloro-8-fluoroquinazolin-2-yl)azetidin-3-yl)pyrazin-2-yl)piperidine-4-carbonitrile |

TABLE 37-continued

Examples 36.1 to 36.190

| Ex. # | Structure | Chemical Name |
|---|---|---|
| 36.116 | 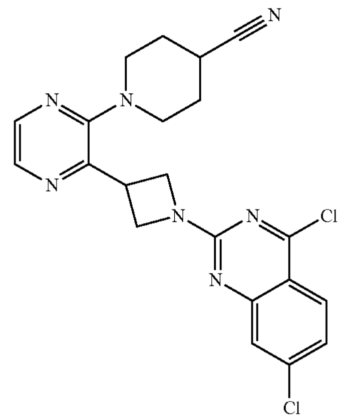 [SMILES: N#CC1CCN(c2nccnc2C2CN(c3nc(Cl)c4ccc(Cl)cc4n3)C2)CC1] | 1-(3-(1-(4,7-dichloroquinazolin-2-yl)azetidin-3-yl)pyrazin-2-yl)piperidine-4-carbonitrile |
| 36.117 | 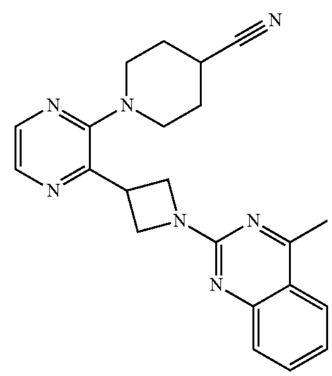 [SMILES: Cc1nc(N2CC(c3nccnc3N3CCC(C#N)CC3)C2)nc2ccccc12] | 1-(3-(1-(4-methylquinazolin-2-yl)azetidin-3-yl)pyrazin-2-yl)piperidine-4-carbonitrile |
| 36.118 | 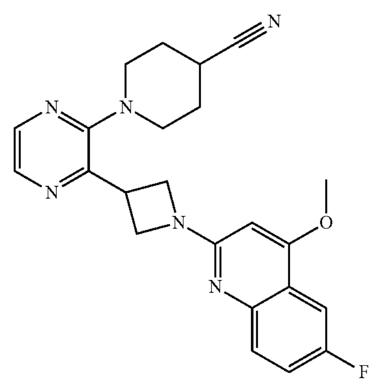 [SMILES: COc1cc(N2CC(c3nccnc3N3CCC(C#N)CC3)C2)nc2ccc(F)cc12] | 1-(3-(1-(6-fluoro-4-methoxyquinol-2-yl)azetidin-3-yl)pyrazin-2-yl)piperidine-4-carbonitrile |
| 36.119 | 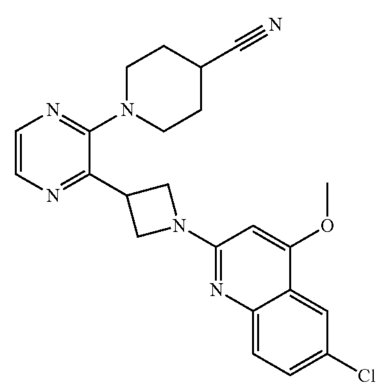 [SMILES: COc1cc(N2CC(c3nccnc3N3CCC(C#N)CC3)C2)nc2ccc(Cl)cc12] | 1-(3-(1-(6-chloro-4-methoxyquinolin-2-yl)azetidin-3-yl)pyrazin-2-yl)piperidine-4-carbonitrile |

TABLE 37-continued

Examples 36.1 to 36.190

| Ex. # | Structure | Chemical Name |
|---|---|---|
| 36.120 | 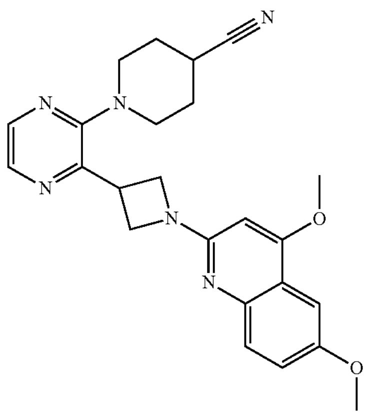 [SMILES: COc1ccc2nc(N3CC(c4nccnc4N4CCC(C#N)CC4)C3)cc(OC)c2c1] | 1-(3-(1-(4,6-dimethoxyquinolin-2-yl)azetidin-3-yl)pyrazin-2-yl)piperidine-4-carbonitrile |
| 36.121 | 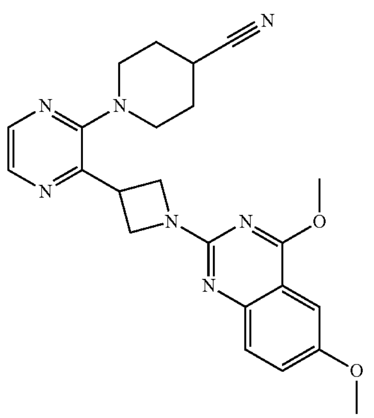 [SMILES: COc1ccc2nc(N3CC(c4nccnc4N4CCC(C#N)CC4)C3)nc(OC)c2c1] | 1-(3-(1-(4,6-dimethoxyquinazolin-2-yl)azetidin-3-yl)pyrazin-2-yl)piperidine-4-carbonitrile |
| 36.122 | 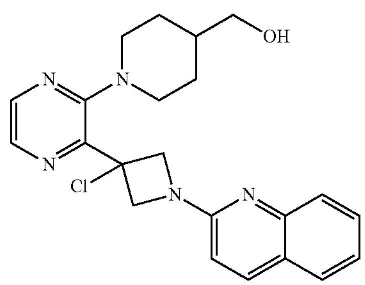 [SMILES: OCC1CCN(c2nccnc2C2(Cl)CN(c3ccc4ccccc4n3)C2)CC1] | 1-(3-(1-(4-methyl-6-(trifluoromethoxy)quinolin-2-yl)azetidin-3-yl)pyrazin-2-yl)piperidine-4-carbonitrile |
| 36.123 | 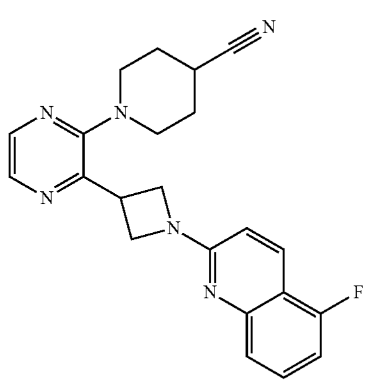 [SMILES: N#CC1CCN(c2nccnc2C2CN(c3ccc4c(F)cccc4n3)C2)CC1] | 1-(3-(1-(5-fluoroquinolin-2-yl)azetidin-3-yl)pyrazin-2-yl)piperidine-4-carbonitrile |

TABLE 37-continued

Examples 36.1 to 36.190

| Ex. # | Structure | Chemical Name |
|---|---|---|
| 36.124 | 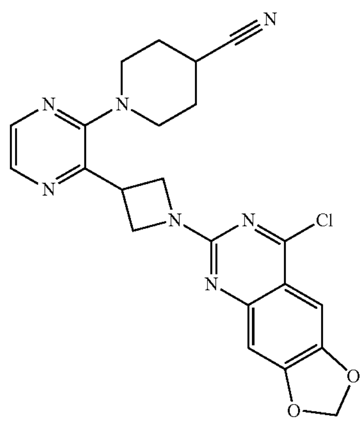 [SMILES: N#CC1CCN(c2nccnc2C2CN(c3nc(Cl)c4cc5c(cc4n3)OCO5)C2)CC1] | 1-(3-(1-(8-chloro-[1,3]dioxolo[4,5-g]quinazolin-6-yl)azetidin-3-yl)pyrazin-2-yl)piperidine-4-carbonitrile |
| 36.125 | 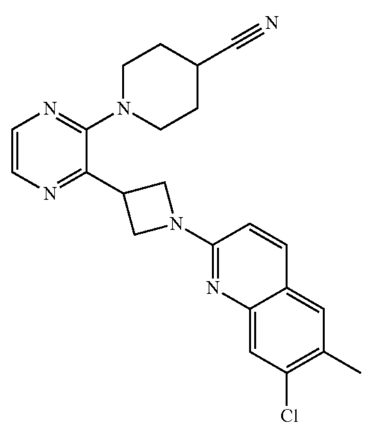 [SMILES: Cc1cc2ccc(N3CC(c4nccnc4N4CCC(C#N)CC4)C3)nc2cc1Cl] | 1-(3-(1-(7-chloro-6-methylquinolin-2-yl)azetidin-3-yl)pyrazin-2-yl)piperidine-4-carbonitrile |
| 36.126 | 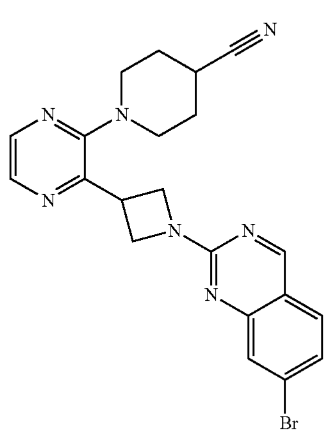 [SMILES: N#CC1CCN(c2nccnc2C2CN(c3ncc4ccc(Br)cc4n3)C2)CC1] | 1-(3-(1-(7-bromoquinazolin-2-yl)azetidin-3-yl)pyrazin-2-yl)piperidine-4-carbonitrile |

TABLE 37-continued
Examples 36.1 to 36.190
| Ex. # | Structure | Chemical Name |
|---|---|---|
| 36.127 | 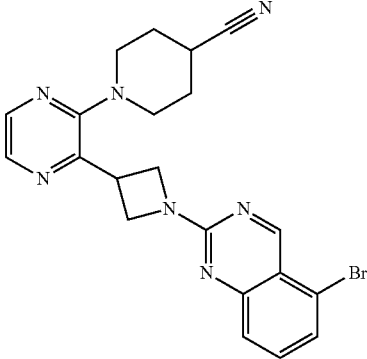 [SMILES: N#CC1CCN(c2nccnc2C2CN(c3ncc4c(Br)cccc4n3)C2)CC1] | 1-(3-(1-(5-bromoquinazolin-2-yl)azetidin-3-yl)pyrazin-2-yl)piperidine-4-carbonitrile |
| 36.128 | 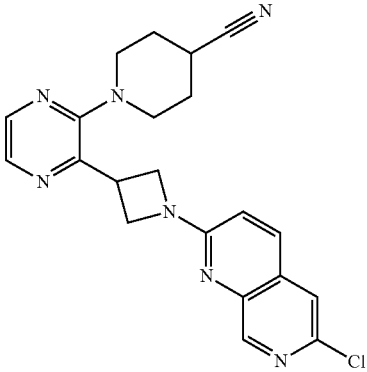 [SMILES: N#CC1CCN(c2nccnc2C2CN(c3ccc4cc(Cl)ncc4n3)C2)CC1] | 1-(3-(1-(6-chloro-1,7-naphthyridin-yl)azetidin-3-yl)pyrazin-2-yl)piperidine-4-carbonitrile |
| 36.129 | 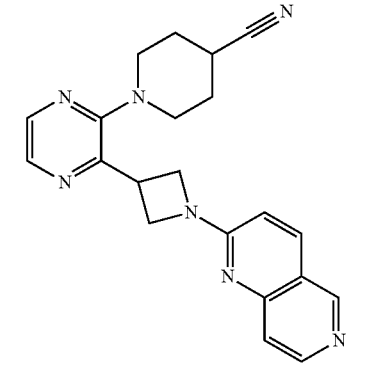 [SMILES: N#CC1CCN(c2nccnc2C2CN(c3ccc4cnccc4n3)C2)CC1] | 1-(3-(1-(1,6-naphthyridin-2-yl)azetidin-3-yl)pyrazin-2-yl)piperidine-4-carbonitrile |
| 36.130 | 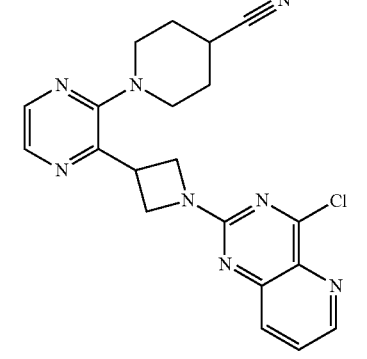 | 1-(3-(1-(4-chloropyrido[3,2-d]pyrimidin-2-yl)azetidin-3-yl)pyrazin-2-yl)piperidine-4-carbonitrile |

TABLE 37-continued
Examples 36.1 to 36.190
| Ex. # | Structure | Chemical Name |
|---|---|---|
| 36.131 | 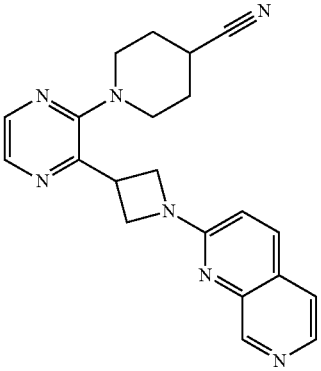 [SMILES: N#CC1CCN(c2nccnc2C2CN(c3ccc4ccncc4n3)C2)CC1] | 1-(3-(1-(1,7-naphthyridin-2-yl)azetidin-3-yl)pyrazin-2-yl)piperidine-4-carbonitrile |
| 36.132 | 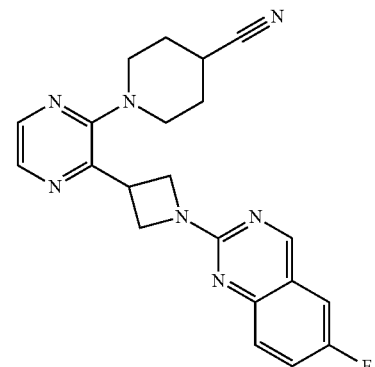 | 1-(3-(1-(6-fluoroquinazolin-2-yl)azetidin-3-yl)pyrazin-2-yl)piperidine-4-carbonitrile |
| 36.133 | 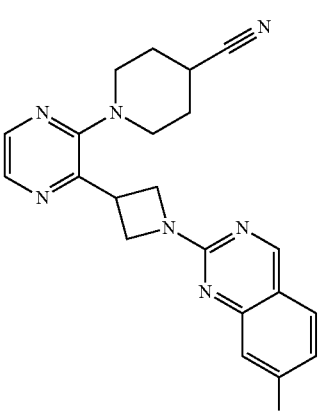 | 1-(3-(1-(7-fluoroquinazolin-2-yl)azetidin-3-yl)pyrazin-2-yl)piperidine-4-carbonitrile |
| 36.134 | 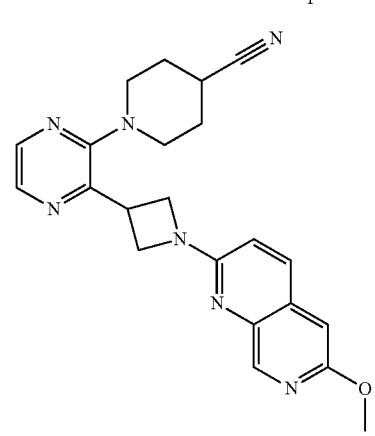 | 1-(3-(1-(6-methoxy-1,7-naphthyridin-2-yl)azetidin-3-yl)pyrazin-2-yl)piperidine-4-carbonitrile |

TABLE 37-continued

Examples 36.1 to 36.190

| Ex. # | Structure | Chemical Name |
|---|---|---|
| 36.135 | 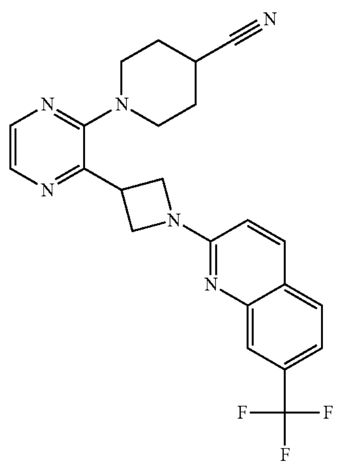 [SMILES: N#CC1CCN(c2nccnc2C2CN(c3ccc4ccc(C(F)(F)F)cc4n3)C2)CC1] | 1-(3-(1-(7-(trifluoromethyl)quinolin-2-yl)azetidin-3-yl)pyrazin-2-yl)piperidine-4-carbonitrile |
| 36.136 | 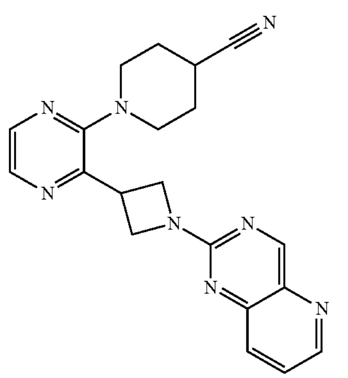 [SMILES: N#CC1CCN(c2nccnc2C2CN(c3ncc4ncccc4n3)C2)CC1] | 1-(3-(1-(pyrido[3,2-d]pyrimidin-2-yl)azetidin-3-yl)pyrazin-2-yl)piperidine-4-carbonitrile |
| 36.137 | 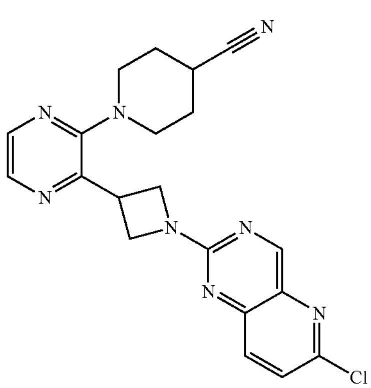 [SMILES: N#CC1CCN(c2nccnc2C2CN(c3ncc4nc(Cl)ccc4n3)C2)CC1] | 1-(3-(1-(6-chloropyrido[3,2-d]pyrimidin-2-yl)azetidin-3-yl)pyrazin-2-yl)piperidine-4-carbonitrile |

TABLE 37-continued

Examples 36.1 to 36.190

| Ex. # | Structure | Chemical Name |
|---|---|---|
| 36.138 | 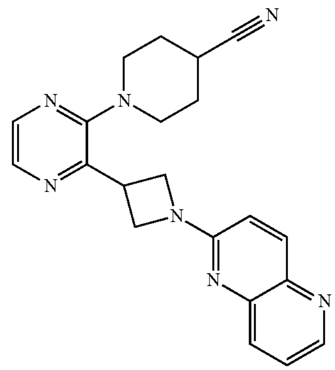 [SMILES: N#CC1CCN(c2nccnc2C2CN(c3ccc4ncccc4n3)C2)CC1] | 1-(3-(1-(1,5-naphthyridin-2-yl)azetidin-3-yl)pyrazin-2-yl)piperidine-4-carbonitrile |
| 36.139 | 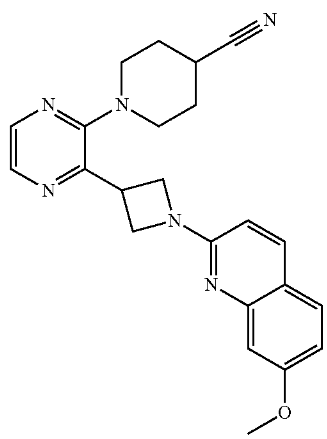 [SMILES: COc1ccc2ccc(N3CC(c4nccnc4N4CCC(C#N)CC4)C3)nc2c1] | 1-(3-(1-(7-methoxyquinolin-2-yl)azetidin-3-yl)pyrazin-2-yl)piperidine-4-carbonitrile |
| 36.140 | 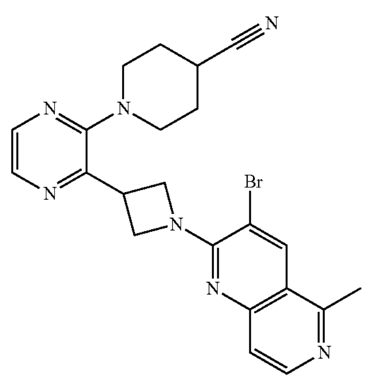 [SMILES: Cc1nccc2nc(N3CC(c4nccnc4N4CCC(C#N)CC4)C3)c(Br)cc12] | 1-(3-(1-(3-bromo-5-methyl-1,6-naphthyridin-2-yl)azetidin-3-yl)pyrazin-2-yl)piperidine-4-carbonitrile |
| 36.141 | 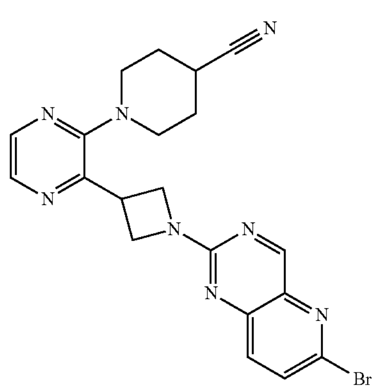 [SMILES: N#CC1CCN(c2nccnc2C2CN(c3ncc4nc(Br)ccc4n3)C2)CC1] | 1-(3-(1-(6-bromopyrido[3,2-d]pyrimidin-2-yl)azetidin-3-yl)pyrazin-2-yl)piperidine-4-carbonitrile |

TABLE 37-continued
Examples 36.1 to 36.190
| Ex. # | Structure | Chemical Name |
|---|---|---|
| 36.142 | 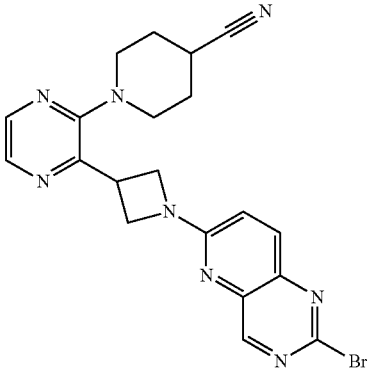 [SMILES: N#CC1CCN(c2nccnc2C2CN(c3ccc4nc(Br)ncc4n3)C2)CC1] | 1-(3-(1-(2-bromopyrido[3,2-d]pyrimidin-6-yl)azetidin-3-yl)pyrazin-2-yl)piperidine-4-carbonitrile |
| 36.143 | 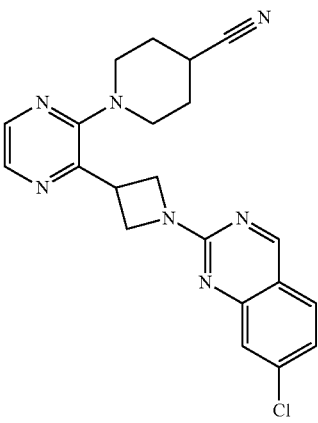 | 1-(3-(1-(7-chloroquinazolin-2-yl)azetidin-3-yl)pyrazin-2-yl)piperidine-4-carbonitrile |
| 36.144 | 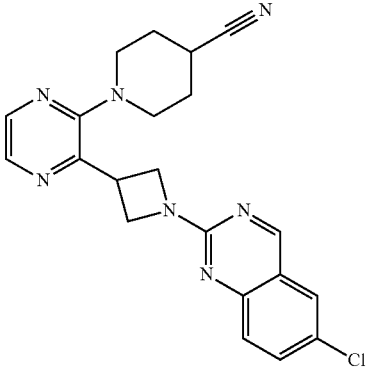 [SMILES: N#CC1CCN(c2nccnc2C2CN(c3ncc4cc(Cl)ccc4n3)C2)CC1] | 1-(3-(1-(6-chloroquinazolin-2-yl)azetidin-3-yl)pyrazin-2-yl)piperidine-4-carbonitrile |
| 36.145 | 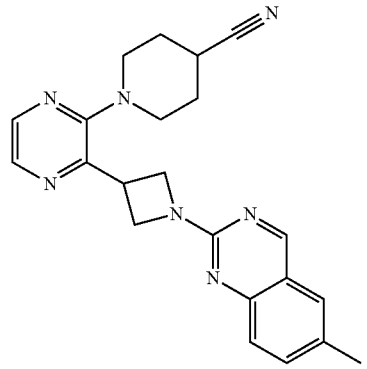 [SMILES: Cc1ccc2nc(N3CC(c4nccnc4N4CCC(C#N)CC4)C3)ncc2c1] | 1-(3-(1-(6-methylquinazolin-2-yl)azetidin-3-yl)pyrazin-2-yl)piperidine-4-carbonitrile |

TABLE 37-continued

Examples 36.1 to 36.190

| Ex. # | Structure | Chemical Name |
|---|---|---|
| 36.146 | 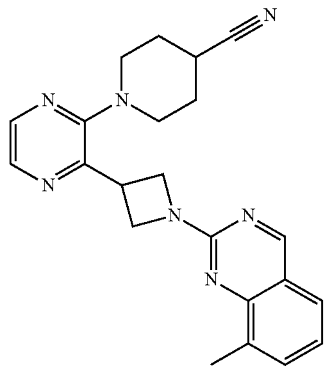 [SMILES: Cc1cccc2cnc(N3CC(c4nccnc4N4CCC(C#N)CC4)C3)nc12] | 1-(3-(1-(8-methylquinazolin-2-yl)azetidin-3-yl)pyrazin-2-yl)piperidine-4-carbonitrile |
| 36.147 | 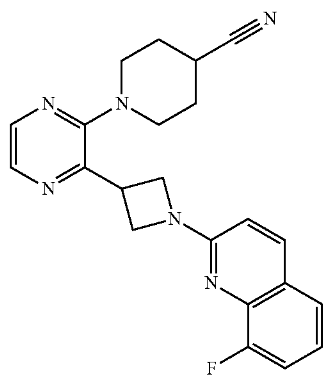 [SMILES: N#CC1CCN(c2nccnc2C2CN(c3ccc4cccc(F)c4n3)C2)CC1] | 1-(3-(1-(8-fluoroquinolin-2-yl)azetidin-3-yl)pyrazin-2-yl)piperidine-4-carbonitrile |
| 36.148 | 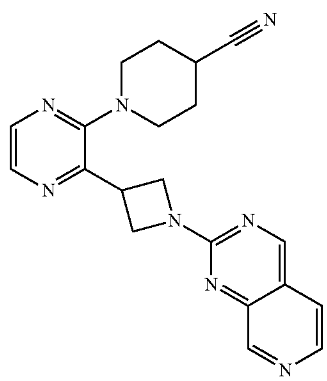 [SMILES: N#CC1CCN(c2nccnc2C2CN(c3ncc4ccncc4n3)C2)CC1] | 1-(3-(1-(pyrido[3,4-d]pyrimidin-2-yl)azetidin-3-yl)pyrazin-2-yl)piperidine-4-carbonitrile |
| 36.149 | 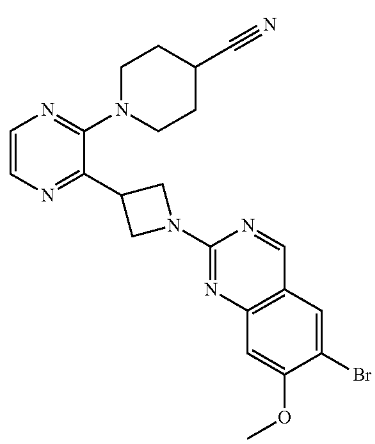 [SMILES: COc1cc2nc(N3CC(c4nccnc4N4CCC(C#N)CC4)C3)ncc2cc1Br] | 1-(3-(1-(6-bromo-7-methoxyquinazolin-2-yl)azetidin-3-yl)pyrazin-2-yl)piperidine-4-carbonitrile |

TABLE 37-continued

Examples 36.1 to 36.190

| Ex. # | Structure | Chemical Name |
|---|---|---|
| 36.150 | 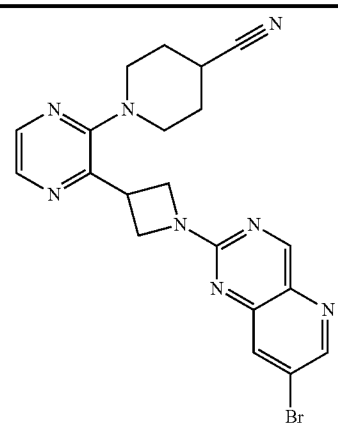 | 1-(3-(1-(7-bromopyrido[3,2-d]pyrimidin-2-yl)azetidin-3-yl)pyrazin-2-yl)piperidine-4-carbonitrile |
| 36.151 | 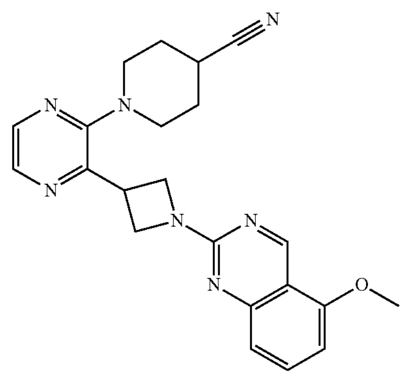 [SMILES: COc1cccc2nc(N3CC(c4nccnc4N4CCC(C#N)CC4)C3)ncc12] | 1-(3-(1-(5-methoxyquinazolin-2-yl)azetidin-3-yl)pyrazin-2-yl)piperidine-4-carbonitrile |
| 36.152 | 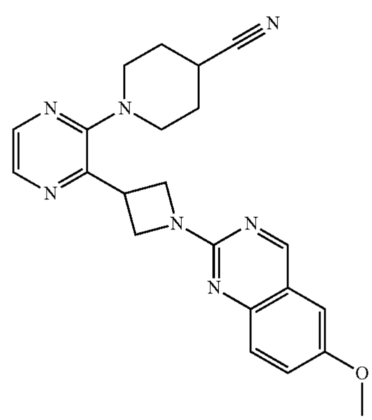 [SMILES: COc1ccc2nc(N3CC(c4nccnc4N4CCC(C#N)CC4)C3)ncc2c1] | 1-(3-(1-(6-methoxyquinazolin-2-yl)azetidin-3-yl)pyrazin-2-yl)piperidine-4-carbonitrile |
| 36.153 | 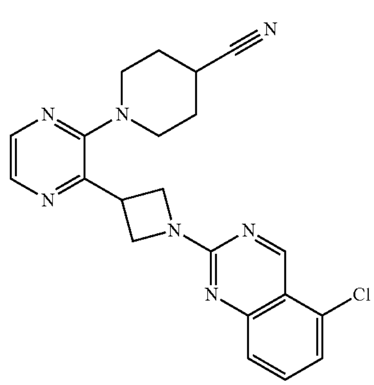 [SMILES: N#CC1CCN(c2nccnc2C2CN(c3ncc4c(Cl)cccc4n3)C2)CC1] | 1-(3-(1-(5-chloroquinazolin-2-yl)azetidin-3-yl)pyrazin-2-yl)piperidine-4-carbonitrile |

TABLE 37-continued

Examples 36.1 to 36.190

| Ex. # | Structure | Chemical Name |
|---|---|---|
| 36.154 | 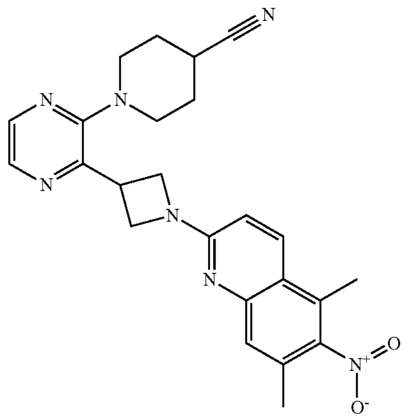 [SMILES: Cc1cc2nc(N3CC(c4nccnc4N4CCC(C#N)CC4)C3)ccc2c(C)c1[N+](=O)[O-]] | 1-(3-(1-(5,7-dimethyl-6-nitroquinolin-2-yl)azetidin-3-yl)pyrazin-2-yl)piperidine-4-carbonitrile |
| 36.155 | 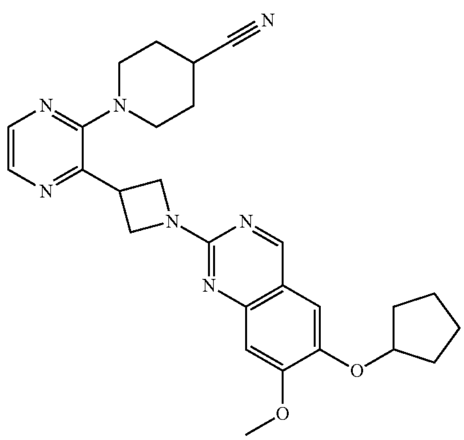 [SMILES: COc1cc2nc(N3CC(c4nccnc4N4CCC(C#N)CC4)C3)ncc2cc1OC1CCCC1] | 1-(3-(1-(6-(cyclopentyloxy)-7-methoxyquinazolin-2-yl)azetidin-3-yl)pyrazin-2-yl)piperidine-4-carbonitrile |
| 36.156 | 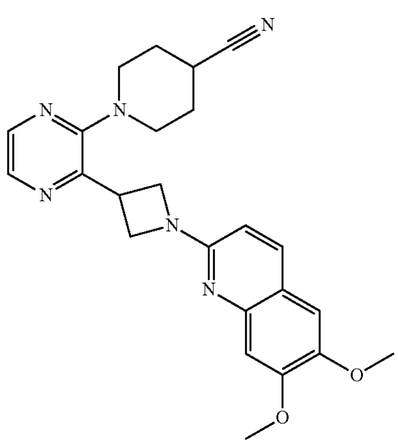 [SMILES: COc1cc2ccc(N3CC(c4nccnc4N4CCC(C#N)CC4)C3)nc2cc1OC] | 1-(3-(1-(6,7-dimethoxyquinolin-2-yl)azetidin-3-yl)pyrazin-2-yl)piperidine-4-carbonitrile |

TABLE 37-continued

Examples 36.1 to 36.190

| Ex. # | Structure | Chemical Name |
|---|---|---|
| 36.157 | 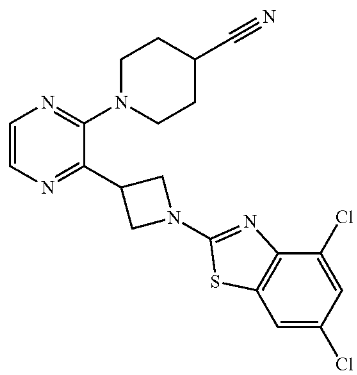 [SMILES: N#CC1CCN(c2nccnc2C2CN(c3nc4c(Cl)cc(Cl)cc4s3)C2)CC1] | 1-(3-(1-(4,6-dichlorobenzo[d]thiazol-2-yl)azetidin-3-yl)pyrazin-2-yl)piperidine-4-carbonitrile |
| 36.158 | 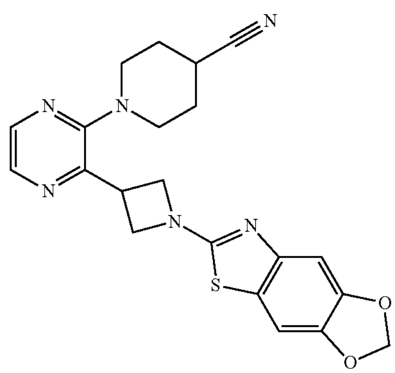 [SMILES: N#CC1CCN(c2nccnc2C2CN(c3nc4cc5c(cc4s3)OCO5)C2)CC1] | 1-(3-(1-([1,3]dioxolo[4',5':4,5]benzo[1,2-d]thiazol-6-yl)azetidin-3-yl)pyrazin-2-yl)piperidine-4-carbonitrile |
| 36.159 | 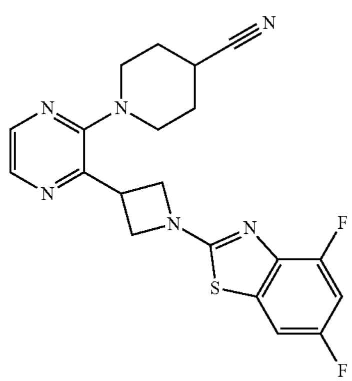 [SMILES: N#CC1CCN(c2nccnc2C2CN(c3nc4c(F)cc(F)cc4s3)C2)CC1] | 1-(3-(1-(4,6-difluorobenzo[d]thiazol-2-yl)azetidin-3-yl)pyrazin-2-yl)piperidine-4-carbonitrile |
| 36.160 | 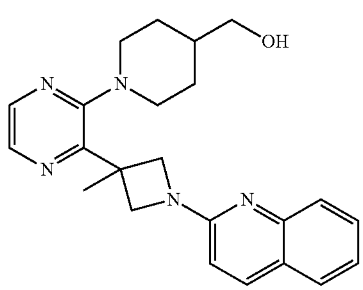 [SMILES: CC1(c2nccnc2N2CCC(CO)CC2)CN(c2ccc3ccccc3n2)C1] | (1-(3-(3-methyl-1-(quinolin-2-yl)azetidin-3-yl)pyrazin-2-yl)piperidin-4-yl)methanol |

TABLE 37-continued

Examples 36.1 to 36.190

| Ex. # | Structure | Chemical Name |
|---|---|---|
| 36.161 | 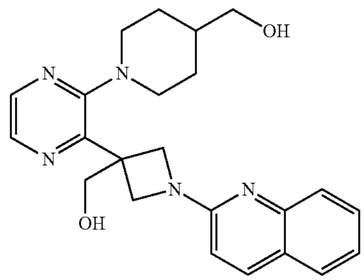 [SMILES: OCC1CCN(c2nccnc2C2(CO)CN(c3ccc4ccccc4n3)C2)CC1] | (1-(3-(3-(hydroxymethyl)-1-(quinolin-2-yl)azetidin-3-yl)pyrazin-2-yl)piperidin-4-yl)methanol |
| 36.162 | 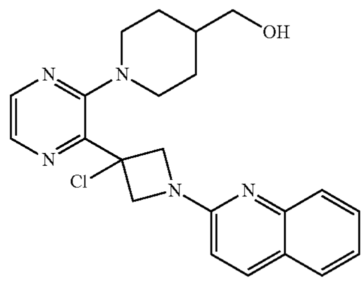 | (1-(3-(3-chloro-1-(quinolin-2-yl)azetidin-3-yl)pyrazin-2-yl)piperidin-4-yl)methanol |
| 36.163 | 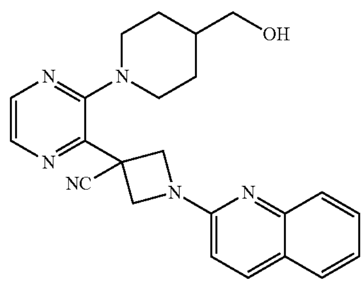 [SMILES: N#CC1(c2nccnc2N2CCC(CO)CC2)CN(c2ccc3ccccc3n2)C1] | 3-(3-(4-(hydroxymethyl)piperidin-1-yl)pyrazin-2-yl)-1-(quinolin-2-yl)azetidine-3-carbonitrile |
| 36.164 | 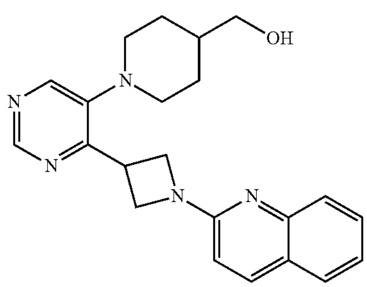 [SMILES: OCC1CCN(c2cncnc2C2CN(c3ccc4ccccc4n3)C2)CC1] | (1-(4-(1-(quinolin-2-yl)azetidin-3-yl)pyrimidin-5-yl)piperidin-4-yl)methanol |
| 36.165 | 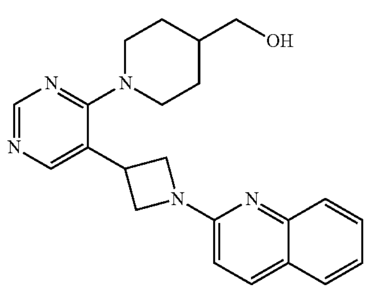 | (1-(5-(1-(quinolin-2-yl)azetidin-3-yl)pyrimidin-4-yl)piperidin-4-yl)methanol |

TABLE 37-continued

Examples 36.1 to 36.190

| Ex. # | Structure | Chemical Name |
|---|---|---|
| 36.166 | 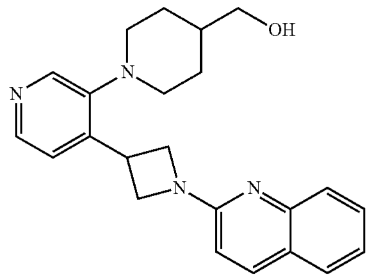 [SMILES: OCC1CCN(c2cnccc2C2CN(c3ccc4ccccc4n3)C2)CC1] | (1-(4-(1-(quinolin-2-yl)azetidin-3-yl)pyridin-3-yl)piperidin-4-yl)methanol |
| 36.167 | 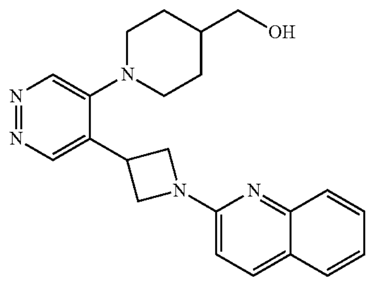 | (1-(5-(1-(quinolin-2-yl)azetidin-3-yl)pyridazin-4-yl)piperidin-4-yl)methanol |
| 36.168 | 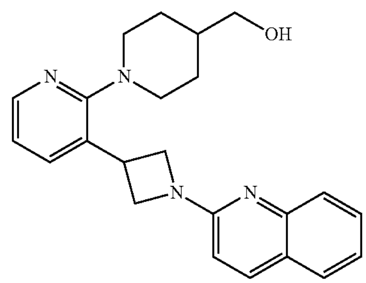 [SMILES: OCC1CCN(c2ncccc2C2CN(c3ccc4ccccc4n3)C2)CC1] | (1-(3-(1-(quinolin-2-yl)azetidin-3-yl)pyridin-2-yl)piperidin-4-yl)methanol |
| 36.169 | 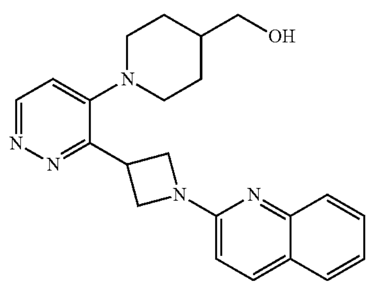 | (1-(3-(1-(quinolin-2-yl)azetidin-3-yl)pyridazin-4-yl)piperidin-4-yl)methanol |
| 36.170 | 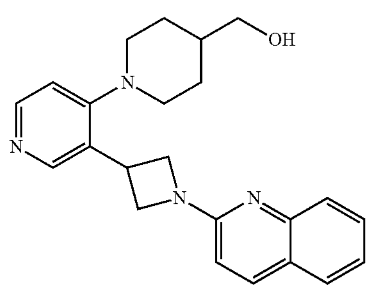 [SMILES: OCC1CCN(c2ccncc2C2CN(c3ccc4ccccc4n3)C2)CC1] | (1-(3-(1-(quinolin-2-yl)azetidin-3-yl)pyridin-4-yl)piperidin-4-yl)methanol |

TABLE 37-continued

Examples 36.1 to 36.190

| Ex. # | Structure | Chemical Name |
|---|---|---|
| 36.171 | 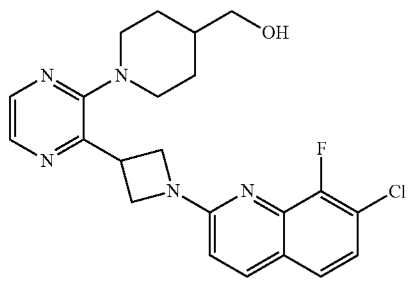 [SMILES: OCC1CCN(c2nccnc2C2CN(c3ccc4ccc(Cl)c(F)c4n3)C2)CC1] | (1-(3-(1-(7-chloro-8-fluoroquinolin-2-yl)azetidin-3-yl)pyrazin-2-yl)-piperidin-1-yl)methanol |
| 36.172 | 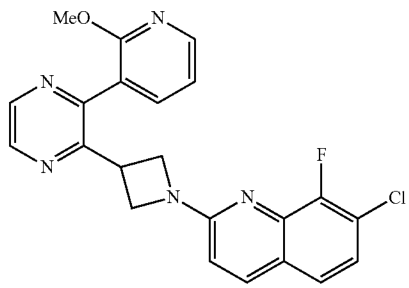 [SMILES: COc1ncccc1-c1nccnc1C1CN(c2ccc3ccc(Cl)c(F)c3n2)C1] | 7-chloro-8-fluoro-2-(3-(3-(2-methoxypyridin-3-yl)pyrazin-2-yl)azetidin-1-yl)quinoline |
| 36.173 | 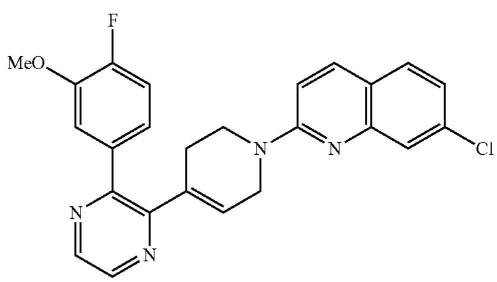 [SMILES: COc1cc(-c2nccnc2C2=CCN(c3ccc4ccc(Cl)cc4n3)CC2)ccc1F] | 7-chloro-2-(4-(3-(4-fluoro-3-methoxyphenyl)pyrazin-2-yl)-5,6-dihydropyridin-1(2H)-yl)quinoline |
| 36.174 | 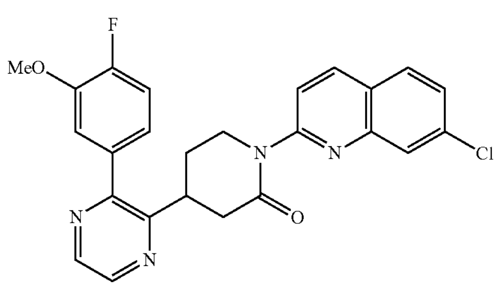 [SMILES: COc1cc(-c2nccnc2C2CCN(c3ccc4ccc(Cl)cc4n3)C(=O)C2)ccc1F] | 1-(7-chloroquinolin-2-yl)-4-(3-(4-fluoro-3-methoxyphenyl)pyrazin-2-yl)piperidin-2-one |
| 36.175 | 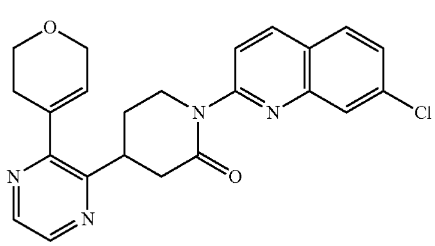 [SMILES: O=C1CC(c2nccnc2C2=CCOCC2)CCN1c1ccc2ccc(Cl)cc2n1] | 1-(7-chloroquinolin-2-yl)-4-(3-(3,6-dihydro-2H-pyran-4-yl)pyrazin-2-yl)piperidin-2-one |

TABLE 37-continued

Examples 36.1 to 36.190

| Ex. # | Structure | Chemical Name |
|---|---|---|
| 36.176 | 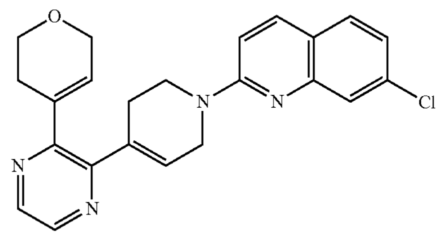 [SMILES: Clc1ccc2ccc(N3CC=C(c4nccnc4C4=CCOCC4)CC3)nc2c1] | 7-chloro-2-(4-(3-(3,6-dihydro-2H-pyran-4-yl)pyrazin-2-yl)-5,6-dihydropyridin-1(2H)-yl)quinoline |
| 36.177 | 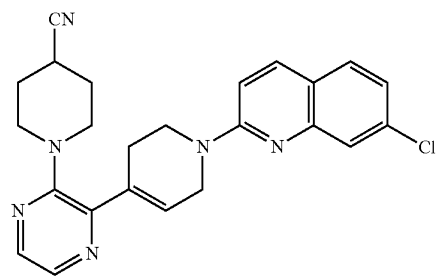 [SMILES: N#CC1CCN(c2nccnc2C2=CCN(c3ccc4ccc(Cl)cc4n3)CC2)CC1] | 1-(3-(1-(7-chloroquinolin-2-yl)-1,2,3,6-tetrahydropyridin-4-yl)pyrazin-2-yl)piperidine-4-carbonitrile |
| 36.178 | 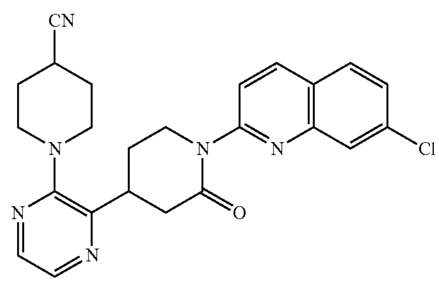 [SMILES: N#CC1CCN(c2nccnc2C2CCN(c3ccc4ccc(Cl)cc4n3)C(=O)C2)CC1] | 1-(3-(1-(7-chloroquinolin-2-yl)-2-oxopiperidin-4-yl)pyrazin-2-yl)piperidine-4-carbonitrile |
| 36.179 | 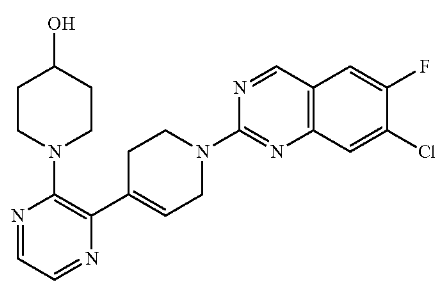 [SMILES: OC1CCN(c2nccnc2C2=CCN(c3ncc4cc(F)c(Cl)cc4n3)CC2)CC1] | 1-(3-(1-(7-chloro-6-fluoroquinazolin-2-yl)-1,2,3,6-tetrahydropyridin-4-yl)pyrazin-2-yl)piperidin-4-ol |
| 36.180 | 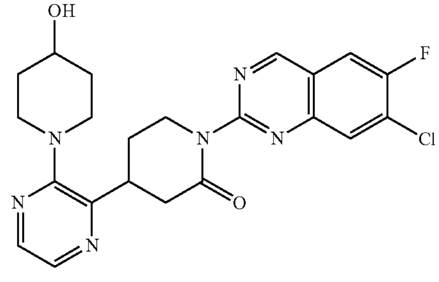 [SMILES: O=C1CC(c2nccnc2N2CCC(O)CC2)CCN1c1ncc2cc(F)c(Cl)cc2n1] | 1-(7-chloro-6-fluoroquinazolin-2-yl)-4-(3-(4-hydroxypiperidin-1-yl)pyrazin-2-yl)piperidin-2-one |

TABLE 37-continued

Examples 36.1 to 36.190

| Ex. # | Structure | Chemical Name |
| --- | --- | --- |
| 36.181 | 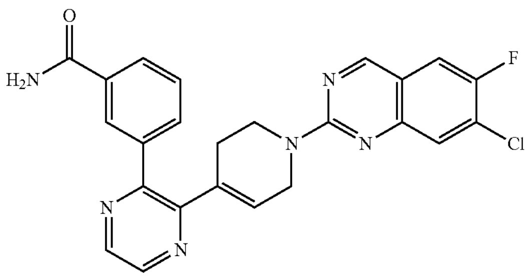 [SMILES: NC(=O)c1cccc(-c2nccnc2C2=CCN(c3ncc4cc(F)c(Cl)cc4n3)CC2)c1] | 3-(3-(1-(7-chloro-6-fluoroquinazolin-2-yl)-1,2,3,6-tetrahydropyridin-4-yl)pyrazin-2-yl)benzamide |
| 36.182 | 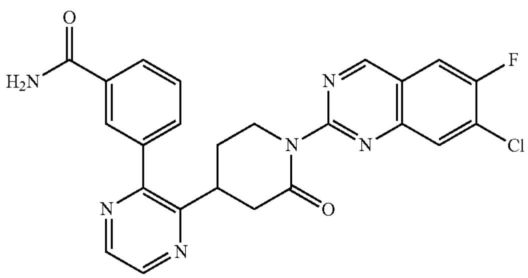 [SMILES: NC(=O)c1cccc(-c2nccnc2C2CCN(c3ncc4cc(F)c(Cl)cc4n3)C(=O)C2)c1] | 3-(3-(1-(7-chloro-6-fluoroquinazolin-2-yl)-2-oxopiperidin-4-yl)pyrazin-2-yl)benzamide |
| 36.183 | 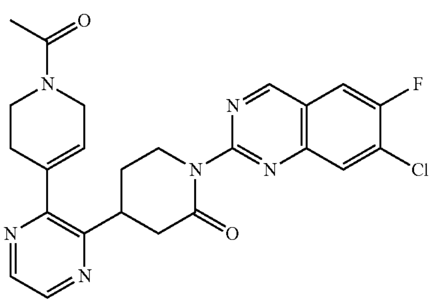 [SMILES: CC(=O)N1CC=C(c2nccnc2C2CCN(c3ncc4cc(F)c(Cl)cc4n3)C(=O)C2)CC1] | 4-(3-(1-acetyl-1,2,3,6-tetrahydropyridin-4-yl)pyrazin-2-yl)-1-(7-chloro-6-fluoroquinazolin-2-yl)piperidin-2-one |
| 36.184 | 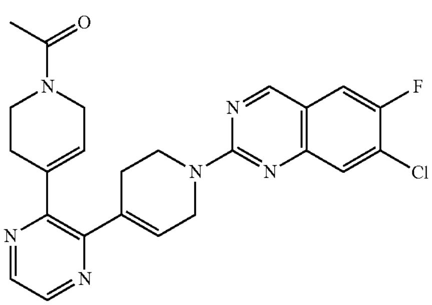 [SMILES: CC(=O)N1CC=C(c2nccnc2C2=CCN(c3ncc4cc(F)c(Cl)cc4n3)CC2)CC1] | 1-(4-(3-(1-(7-chloro-6-fluoroquinazolin-2-yl)-1,2,3,6-tetrahydropyridin-4-yl)pyrazin-2-yl)5,6-dihydropyridin-1(2H)-yl)ethanone |
| 36.185 | 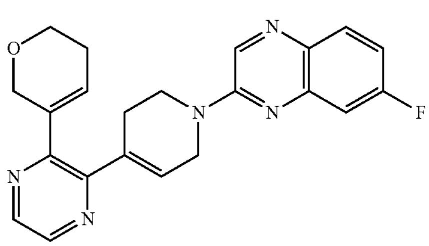 [SMILES: Fc1ccc2ncc(N3CC=C(c4nccnc4C4=CCCOC4)CC3)nc2c1] | 2-(4-(3-(5,6-dihydro-2H-pyran-3-yl)pyrazin-2-yl)-5,6-dihydropyridin-1(2H)-yl)-7-fluoroquinoxaline |

TABLE 37-continued

Examples 36.1 to 36.190

| Ex. # | Structure | Chemical Name |
|---|---|---|
| 36.186 | 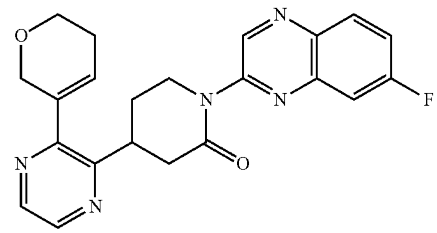 [SMILES: O=C1CC(c2nccnc2C2=CCCOC2)CCN1c1cnc2ccc(F)cc2n1] | 4-(3-(5,6-dihydro-2H-pyran-3-yl)pyrazin-2-yl)-1-(7-fluoroquinoxalin-2-yl)piperidin-2-one |
| 36.187 | 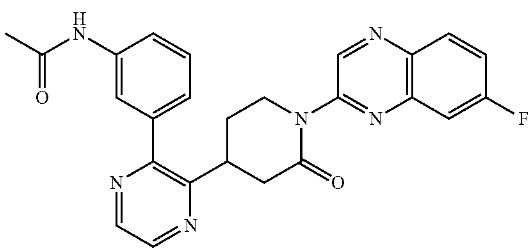 [SMILES: CC(=O)Nc1cccc(-c2nccnc2C2CCN(c3cnc4ccc(F)cc4n3)C(=O)C2)c1] | N-(3-(3-(1-(7-fluoroquinoxalin-2-yl)-2-oxopiperidin-4-yl)pyrazin-2-yl)phenyl)acetamide |
| 36.188 | 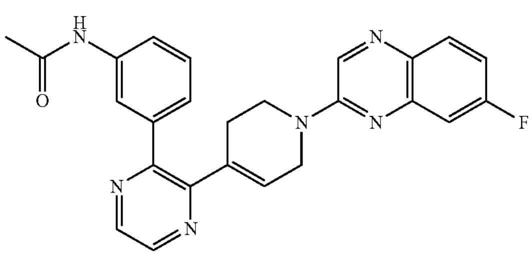 [SMILES: CC(=O)Nc1cccc(-c2nccnc2C2=CCN(c3cnc4ccc(F)cc4n3)CC2)c1] | N-(3-(3-(1-(7-fluoroquinoxalin-2-yl)-1,2,3,6-tetrahydropyridin-4-yl)pyrazin-2-yl)phenyl)acetamide |
| 36.189 | 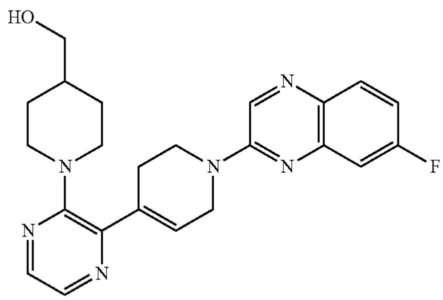 [SMILES: OCC1CCN(c2nccnc2C2=CCN(c3cnc4ccc(F)cc4n3)CC2)CC1] | (1-(3-(1-(7-fluoroquinoxalin-2-yl)-1,2,3,6-tetrahydropyridin-4-yl)pyrazin-2-yl)piperidin-4-yl)methanol |
| 36.190 | 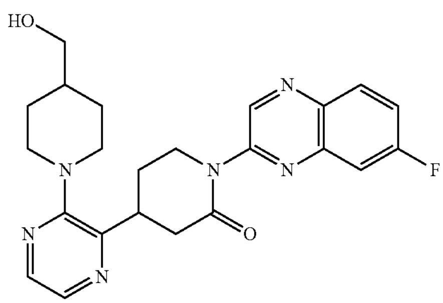 [SMILES: O=C1CC(c2nccnc2N2CCC(CO)CC2)CCN1c1cnc2ccc(F)cc2n1] | 1-(7-fluoroquinoxalin-2-yl)-4-(3-(4-(hydroxymethyl)piperidin-1-yl)pyrazin-2-yl)piperidin-2-one |

BIOLOGICAL EXAMPLES

The above PDE10 $IC_{50}$ data were obtained by using the following assays.

Example A

MPDE10A7 Enzyme Activity and Inhibition

Enzyme Activity. An IMAP TR-FRET assay was used to analyze the enzyme activity (Molecular Devices Corp., Sunnyvale Calif.). 5 L of serial diluted PDE10A (BPS Bioscience, San Diego, Calif.) or tissue homogenate was incubated with equal volumes of diluted fluorescein labeled cAMP or cGMP for 60 min in 384-well polystyrene assay plates (Corning, Corning, N.Y.) at room temperature. After incubation, the reaction was stopped by adding 60 L of diluted binding reagents and was incubated for 3 hours to overnight at room temperature. The plates were read on an Envision (Perkin Elmer, Waltham, Mass.) for time resolved fluorescence resonance energy transfer. The data were analyzed with GraphPad Prism (La Jolla, Calif.).

Enzyme Inhibition. To check the inhibition profile, 5 µL of serial diluted compounds were incubated with 5 µL of diluted PDE10 enzyme (BPS Bioscience, San Diego, Calif.) or tissue homogenate in a 384-well polystyrene assay plate (Corning, Corning, N.Y.) for 30 min at room temperature. After incubation, 10 L of diluted fluorescein labeled cAMP or cGMP substrate were added and incubated for 60 min at room temperature. The reaction was stopped by adding 60 µL of diluted binding reagents and plates were read on an Envision (Perkin Elmer, Waltham, Mass.) for time resolved fluorescence resonance energy transfer. The data were analyzed with GraphPad Prism (La Jolla, Calif.).

Example B

Apomorphine Induced Deficits in Prepulse Inhibition of the Startle Response in Rats, an In Vivo Test for Antipsychotic Activity The thought disorders that are characteristic of schizophrenia may result from an inability to filter, or gate, sensorimotor information. The ability to gate sensorimotor information can be tested in many animals as well as in humans. A test that is commonly used is the reversal of apomorphine-induced deficits in the prepulse inhibition of the startle response. The startle response is a reflex to a sudden intense stimulus such as a burst of noise. In this example, rats can be exposed to a sudden burst of noise, at a level of 120 db for 40 msec, e.g., the reflex activity of the rats can be measured. The reflex of the rats to the burst of noise may be attenuated by preceding the startle stimulus with a stimulus of lower intensity, at 3 db to 12 db above background (65 db), which attenuates the startle reflex by 20% to 80%.

The prepulse inhibition of the startle reflex, described above, may be attenuated by drugs that affect receptor signaling pathways in the CNS. One commonly used drug is the dopamine receptor agonist apomorphine. Administration of apomorphine reduces the inhibition of the startle reflex produced by the prepulse. Antipsychotic drugs such as haloperidol prevents apomorphine from reducing the prepulse inhibition of the startle reflex. This assay can be used to test the antipsychotic efficacy of PDE10 inhibitors, as they reduce the apomorphine-induced deficit in the prepulse inhibition of startle.

Example C

Conditioned Avoidance Responding (Car) in Rats, an In Vivo Test for Antipsychotic Activity Conditioned avoidance responding (CAR) occurs, for instance, when an animal learns that a tone and light predict the onset of a mild foot shock. The subject learns that when the tone and light are on, it must leave the chamber and enter a safe area. All known antipsychotic drugs reduce this avoidance response at doses which do not cause sedation. Examining the ability of test compounds to suppress the conditioned avoidance has been widely used for close to fifty years to screen for drugs with useful antipsychotic properties.

In this example, an animal can be placed in a two-chambered shuttle box and presented with a neutral conditioned stimulus (CS) consisting of a light and tone, followed by an aversive unconditioned stimulus (US) consisting of a mild foot shock through a floor grid in the shuttle box chamber. The animal can be free to escape the US by running from one chamber to the other, where the grid is not electrified. After several presentations of the CS-US pair, the animal typically learns to leave the chamber during the presentation of the CS and avoid the US altogether. Animals treated with clinically-relevant doses of antipsychotic drugs have a suppression of their rate of avoidances in the presence of the CS even though their escape response to the shock itself is unaffected.

Specifically, conditioned avoidance training can be conducted using a shuttle box (Med Associates, St. Albans, Vt.). The shuttle box is typically divided into 2 equal compartments that each contain a light source, a speaker that emits an 85 dB tone when activated and an electrified grid that can deliver a scrambled foot shock. Sessions can consist of 20 trials per day (intertrial interval of 25-40 sec) during which a 10 sec illumination and a concurrent 10 sec tone signals the subsequent delivery of a 0.5 mA shock applied for a maximum of 10 sec. Active avoidance, defined as the crossing into the opposite compartment during the 10 sec conditioning stimuli (light and tone) prevents the delivery of the shock. Crossing over to the other compartment after the delivery of the shock terminates shock delivery and may be recorded as an escape response. If an animal does not leave the conditioning chamber during the delivery of the shock it is recorded as an escape failure. Training can be continued daily until the avoidance of 16 or more shocks out of 20 trials (80% avoidance) on 2 consecutive days is achieved. After this criterion is reached the rats may be given one day of pharmacological testing. On test day, rats can be randomly assigned to experimental groups, weighed and injected intraperitoneally (i.p.) (1 cc tuberculin syringe, 26⅜ gauge needle) or per os (p.o.) (18 gauge feeding needle) with either control or compound solutions. Compounds can be injected at 1.0 ml/kg for i.p. and 10 mL/kg for p.o. administration. Compounds can be administered either acutely or chronically. For testing, each rat may be placed in the shuttle box, and given 20 trials with the same parameters as described above for training trials. The number of avoidances, escapes, and escape failures can be recorded.

Example D

PCP-Induced Hyperactivity (PCP-LMA)

Equipment Used: 4×8 home cage photobeam activity system (PAS) frame from San Diego Instruments. Open PAS program and prepare an experimental session using the following variables:

Multiphase Experiment
300 sec/interval (5 min)
12 intervals (1 h)
Individual on screen switches.
Start recording after first beam break.
End session after end of interval.

Cage Preparation:

Techniplast™ rat cage with filter top, but no wire lid. Place ~400 mL bedding and one food pellet in cage and place 250 mL techniplast water bottle in holder on filter top. Place the prepped cage in the PAS frame. Make sure bedding or pellet doesn't block the photobeams.

Animal Preparation:

Mark rats and record their weights. Bring rats to testing room.

Phase I: Habituation

Start the experiment session. Place the rat in the enclosure. The computer should start recording when it detects the rat breaking the beam. The computer will record for 1 h. During the habituation phase, prepare risperidone (positive control): Measure out risperidone, calculate final volume at 1 mg/mL concentration and add 1% glacial acetic acid of the final volume to dissolve risperidone. When risperidone is dissolved, add saline to final volume to make a concentration of 1 mg/mL. Fill syringes (3 mL syringes with 23 g ½ needle or oral gavage needle) with Amgen compound solution (5 mL/kg) or risperidone (1 mL syringe with 23 g ½ needle) control (1 mL/kg) s.c.

Phase II: Compound Pre-Treatment

Make sure Phase I has ended. Remove rat from enclosure, start the next phase using on-screen individual switch, administer compound p.o or i.p. and control s.c. and place rat back in the enclosure. The computer should start recording when it detects the rat breaking the beam. The computer will record for 1 h.

During phase II, prepare pcp: Dissolve pcp in saline to a concentration of 5 mg/mL.

Fill syringes (1 mL syringes with 26 g ⅜ needle) with pcp solution (1 mL/kg).

Phase III: PCP Administration.

Make sure phase II is ended. Remove rat from enclosure, start the next phase using on-screen individual switch, administer pcp s.c. and place rat back in the enclosure. The computer will record for 1 h.

Clean-Up:

End-session to terminate experiment and so that computer will compile data. Export raw data to spreadsheet file for data analysis. Euthanize rats and take necessary tissue/sample for PK.

Data Generation:

Export raw data to spreadsheet file for data analysis. Total time of movement is recorded as the number of photobeam breaks by the computer. Total time of movement (seconds) is combined into 5 minute bins and averaged for each treatment group for an N of 7-10 animals. Data are analyzed for statistical significance using a two-way ANOVA followed by a Bonferroni's post-hoc test for multiple comparisons.

The foregoing is merely illustrative of the invention and is not intended to limit the invention to the disclosed compounds. Variations and changes which are obvious to one skilled in the art are intended to be within the scope and nature of the invention which are defined in the appended claims. All patents, patent applications, and other publications recited herein are hereby incorporated by reference in their entirety.

What is claimed is:
1. A compound of formula I:

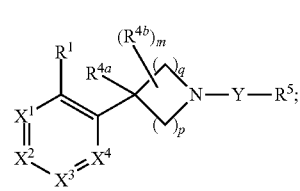

or a pharmaceutically acceptable salt thereof, wherein: the group

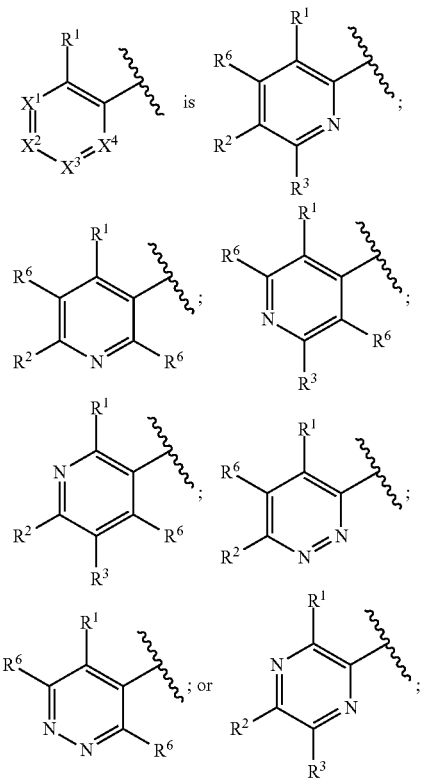

$R^1$ is $L^1$ or $C_{1-4}$alk-$L^1$;
Y is a bond or —C(=O);
each $R^2$ and $R^3$ is independently H, halo, CN, OH, —O$C_{1-4}$alk, $C_{1-4}$alk, $C_{1-4}$haloalk, —$C_{1-6}$alkOR$^a$, —C(=O)$C_{1-4}$alk, —C(=O)NR$^a$R$^a$, or —$C_{0-4}$alkNH—C(=O)R$^a$;
$R^{4a}$ is H, OH, halo, $C_{1-4}$alk, or $C_{1-4}$haloalk;
$R^{4b}$ is halo, CN, OH, O$C_{1-4}$alk, $C_{1-4}$alk, $C_{1-4}$haloalk, or oxo;
$R^5$ is 5- to 6-membered heteroaryl or unsaturated 9- to 10-membered bicyclo-heterocyclic ring; wherein each $R^5$ ring is substituted by 0, 1, 2, 3, or 4 $R^8$ groups;
$R^6$ is independently H, halo, CN, OH, O$C_{1-4}$alk, $C_{1-4}$alk or $C_{1-4}$haloalk;
m is 0;
each of p and q is independently 2; wherein the sum of p and q is 4;
the ring containing p and q contains 0 or 1 double bonds;

$R^a$ is independently H or $R^b$;

$R^b$ is independently phenyl, benzyl, or $C_{1-6}$alk, wherein said phenyl, benzyl, and $C_{1-6}$alk are substituted by 0, 1, 2 or 3 substituents which are, independently, halo, $C_{1-4}$alk, $C_{1-3}$haloalk, —OH, —$OC_{1-4}$alk, —$NH_2$, —$NHC_{1-4}$alk, —$OC(=O)C_{1-4}$alk, or —$N(C_{1-4}$alk)$C_{1-4}$alk;

$R^c$ is $L^2$ or $C_{1-4}$alk-$L^2$;

each $L^1$ is independently a carbon-linked or nitrogen-linked saturated, partially-saturated or unsaturated 3-, 4-, 5-, 6-, or 7-membered monocyclic ring or a saturated, partially-saturated or unsaturated 6-, 7-, 8-, 9-, 10-, 11-, or 12-membered bicyclic ring, said ring contains 0, 1, 2, 3, or 4 N atoms and 0, 1, or 2 atoms which are O or S; $L^1$ is independently substituted by 0, 1, 2 or 3 $R^9$ groups;

each $L^2$ is independently a carbon-linked or nitrogen-linked saturated, partially-saturated or unsaturated 3-, 4-, 5-, 6-, or 7-membered monocyclic ring or a saturated, partially-saturated or unsaturated 6-, 7-, 8-, 9-, 10-, 11-, or 12-membered bicyclic ring, said ring contains 0, 1, 2, 3, or 4 N atoms and 0, 1, or 2 atoms which are O or S; $L^2$ is independently substituted by 0, 1, 2 or 3 $R^{11}$ groups;

$R^8$ is halo, CN, OH, $C_{1-4}$alk, $C_{1-4}$haloalk, —$OC_{1-4}$haloalk, —$C(=O)R^b$, —$C(=O)R^c$, —$C(=O)NHR^b$, —$C(=O)NHR^c$, —$S(=O)_2R^b$, —$S(=O)_2R^c$, —$S(=O)_2NR^aR^a$, $R^b$, $R^c$, $NO_2$, $OR^b$, or $OR^c$;

$R^9$ is halo, $C_{1-6}$alk, $C_{1-4}$haloalk, —$OR^a$, —$OC_{1-4}$haloalk, CN, —$C(=O)R^b$, —$C(=O)OR^a$, —$C(=O)NR^aR^a$, —$C(=NR^a)NR^aR^a$, —$OC(=O)R^b$, —$OC(=O)NR^aR^a$, —$OC_{1-6}$alkNR^aR^a$, —$OC_{1-6}$alkOR^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{1-6}$alkNR^aR^a$, —$NR^aC_{1-6}$alkOR^a$, —$C_{1-6}$alkNR^aR^a$, —$C_{1-6}$alkOR^a$, —$C_{1-6}$alkN(R^a)C(=O)R^b$, —$C_{1-6}$alkOC(=O)R^b$, —$C_{1-6}$alkC(=O)NR^aR^a$, —$C_{1-6}$alkC(=O)OR^a$, oxo, or $R^c$; and $R^{11}$ is halo, $C_{1-6}$alk, $C_{1-4}$haloalk, —$OR^a$, —$OC_{1-4}$haloalk, CN, —$C(=O)R^b$, —$C(=O)OR^a$, —$C(=O)NR^aR^a$, —$C(=NR^a)NR^aR^a$, —$OC(=O)R^b$, —$OC(=O)NR^aR^a$, —$OC_{1-6}$alkNR^aR^a$, —$OC_{1-6}$alkOR^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{1-6}$alkNR^aR^a$, —$NR^aC_{1-6}$alkOR^a$, —$C_{1-6}$alkNR^aR^a$, —$C_{1-6}$alkOR^a$, —$C_{1-6}$alkN(R^a)C(=O)R^b$, —$C_{1-6}$alkOC(=O)R^b$, —$C_{1-6}$alkC(=O)NR^aR^a$, —$C_{1-6}$alkC(=O)OR^a$, or oxo.

2. The compound according to claim 1, or a pharmaceutically acceptable salt thereof, wherein Y is a bond.

3. The compound according to claim 1, or a pharmaceutically acceptable salt thereof, wherein the group

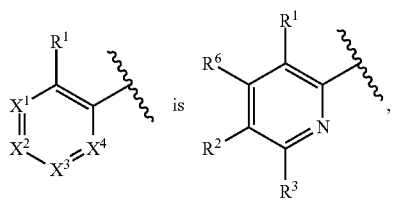

is

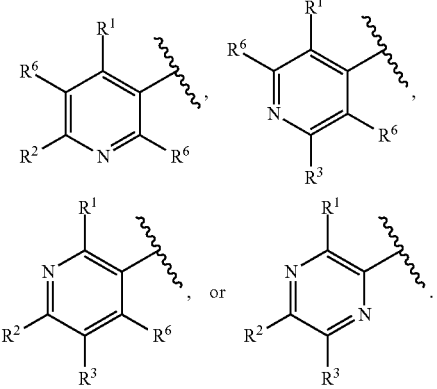

4. The compound according to claim 1, or a pharmaceutically acceptable salt thereof, wherein the ring containing p and q contains 0 double bond.

5. The compound according to claim 1, or a pharmaceutically acceptable salt thereof, wherein the ring containing p and q contains 1 double bond.

6. The compound according to claim 1, or a pharmaceutically acceptable salt thereof, wherein the group

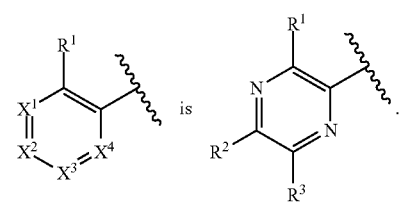

7. The compound according to claim 1, or a pharmaceutically acceptable salt thereof, wherein $R^1$ is $L^1$.

8. The compound according to claim 1, or a pharmaceutically acceptable salt thereof, wherein is a carbon-linked-unsaturated 5- to 6-membered monocyclic ring, wherein each said ring contains 0, 1, or 2 N atoms and 0 or 1 O atoms, and wherein each said $L^1$ substituted by 0, 1 or 2 $R^9$ groups which are F, Cl, Br, $C_{1-6}$alk, —$OR^a$, CN, —$C(=O)R^b$, —$C(=O)OR^a$, —$C(=O)NR^aR^a$, —$NR^aR^a$, —$N(R^a)C(=O)R^b$, —$N(R^a)C(=O)OR^b$, or —$N(R^a)C(=O)OR^b$.

9. The compound according to claim 1, or a pharmaceutically acceptable salt thereof, wherein is phenyl substituted by 0, 1 or 2 $R^9$ groups which are F, Cl, Br, $C_{1-6}$alk, —$OR^a$, CN, —$C(=O)R^b$, —$C(=O)OR^a$, —$C(=O)NR^aR^a$, —$NR^aR^a$, —$N(R^a)C(=O)R^b$, —$N(R^a)C(=O)OR^b$, or —$N(R^a)C(=O)OR^b$.

10. The compound according to claim 1, or a pharmaceutically acceptable salt thereof, wherein each $R^2$ and $R^3$ is independently H.

11. The compound according to claim 1, or a pharmaceutically acceptable salt thereof, wherein $R^8$ is halo.

12. The compound according to claim 1, or a pharmaceutically acceptable salt thereof, wherein $R^{4a}$ is H.

13. The compound according to claim 1, or a pharmaceutically acceptable salt thereof, wherein the group —Y—$R^5$ is:

wherein R⁵ is substituted by 1 or 2 R⁸ groups.

14. The compound according to claim 1, or a pharmaceutically acceptable salt thereof, wherein the group —Y—R⁵ is:

15. The compound according to claim 1, or a pharmaceutically acceptable salt thereof, wherein R⁸ is F, Cl, CF₃, methyl, or CN.

16. The compound according to claim 1, or a pharmaceutically acceptable salt thereof, wherein R⁸ is Cl.

17. The compound according to claim 1, or a pharmaceutically acceptable salt thereof, wherein R⁸ is F.

18. The compound according to claim 1, or a pharmaceutically acceptable salt thereof, which is:

(1H-benzoimidazol-2-yl)-[4-(3-phenyl-pyrazin-2-yl)-piperidin-1-yl]-methanone;
(1H-Benzoimidazol-2-yl)-[3-(2,3-dihydro-indol-1-yl)-3',4',5',6'-tetrahydro-2'H-[2,4']bipyridinyl-1'-yl]-methanone;
(1H-Benzoimidazol-2-yl)-(3-phenyl-3',4',5',6'-tetrahydro-2'H-[2,4']bipyridinyl-1'-yl)-methanone;
(1H-Benzoimidazol-2-yl)-{4-[3-(4-hydroxymethyl-piperidin-1-yl)-pyrazin-2-yl]-piperidin-1-yl}-methanone;
7-chloro-2-(4-(3-(4-fluoro-3-methoxyphenyl)pyrazin-2-yl)-5,6-dihydropyridin-1(2H)-yl)quinoline;
7-chloro-2-(4-(3-(3,6-dihydro-2H-pyran-4-yl)pyrazin-2-yl)-5,6-dihydropyridin-1(2H)-yl)quinoline;
1-(3-(1-(7-chloroquinolin-2-yl)-1,2,3,6-tetrahydropyridin-4-yl)pyrazin-2-yl)piperidine-4-carbonitrile;
1-(3-(1-(7-chloro-6-fluoroquinazolin-2-yl)-1,2,3,6-tetrahydropyridin-4-yl)pyrazin-2-yl)piperidin-4-ol;
3-(3-(1-(7-chloro-6-fluoroquinazolin-2-yl)-1,2,3,6-tetrahydropyridin-4-yl)pyrazin-2-yl)benzamide;
1-(4-(3-(1-(7-chloro-6-fluoroquinazolin-2-yl)-1,2,3,6-tetrahydropyridin-4-yl)pyrazin-2-yl)-5,6-dihydropyridin-1(2H)-yl)ethanone;
2-(4-(3-(5,6-dihydro-2H-pyran-3-yl)pyrazin-2-yl)-5,6-dihydropyridin-1(2H)-yl)-7-fluoroquinoxaline;
N-(3-(3-(1-(7-fluoroquinoxalin-2-yl)-1,2,3,6-tetrahydropyridin-4-yl)pyrazin-2-yl)phenyl)acetamide; or
(1-(3-(1-(7-fluoroquinoxalin-2-yl)-1,2,3,6-tetrahydropyridin-4-yl)pyrazin-2-yl)piperidin-4-yl)methanol.

19. A pharmaceutical composition comprising a compound according to claim 1, or a pharmaceutically acceptable salt thereof, and a pharmaceutically acceptable excipient.

* * * * *